United States Patent
Biber et al.

(10) Patent No.: US 10,722,501 B2
(45) Date of Patent: Jul. 28, 2020

(54) SUBSTITUTED 5,6,7,8-TETRAHYDRO[1,2,4]TRIAZOLO[4,3-A]PYRIDINE-3(2H)-ONES AND 2,5,6,7-TETRAHYDRO-3H-PYRROLO[2,1-C][1,2,4]TRIAZOL-3-ONES, AND USE THEREOF

(71) Applicants: BAYER AKTIENGESELLSCHAFT, Leverkusen (DE); BAYER PHARMA AKTIENGESELLSCHAFT, Berlin (DE)

(72) Inventors: Nicole Biber, Wuppertal (DE); Damian Brockschnieder, Haan (DE); Kersten Matthias Gericke, Wuppertal (DE); Florian Kölling, Wuppertal (DE); Klemens Lustig, Wuppertal (DE); Jörg Meding, Wuppertal (DE); Heinrich Meier, Wuppertal (DE); Thomas Neubauer, Wuppertal (DE); Martina Schäfer, Berlin (DE); Andreas Timmermann, Düsseldorf (DE); Dmitry Zubov, Remscheid (DE); Carsten Terjung, Bochum (DE); Niels Lindner, Wuppertal (DE); Volker Badock, Berlin (DE); Dieter Moosmayer, Berlin (DE); Hideki Miyatake Ondozabal, Berlin (DE); Stephen Moore, Sheffield (GB); Alexander Schulz, Hannover (DE)

(73) Assignees: BAYER AKTIENGESELLSCHAFT, Leverkusen (DE); BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/300,480

(22) PCT Filed: May 8, 2017

(86) PCT No.: PCT/EP2017/060900
§ 371 (c)(1),
(2) Date: Nov. 9, 2018

(87) PCT Pub. No.: WO2017/194459
PCT Pub. Date: Nov. 16, 2017

(65) Prior Publication Data
US 2019/0160048 A1 May 30, 2019

(30) Foreign Application Priority Data
May 9, 2016 (EP) .................................... 16168809

(51) Int. Cl.
| | | |
|---|---|---|
| A61K 31/437 | (2006.01) |
| A61K 31/506 | (2006.01) |
| C07D 471/04 | (2006.01) |
| A61K 31/4375 | (2006.01) |
| A61K 31/4709 | (2006.01) |
| A61K 31/497 | (2006.01) |
| C07D 519/00 | (2006.01) |

(Continued)

(52) U.S. Cl.
CPC ........ *A61K 31/437* (2013.01); *A61K 31/4375* (2013.01); *A61K 31/444* (2013.01); *A61K 31/4709* (2013.01); *A61K 31/497* (2013.01); *A61K 31/506* (2013.01); *A61K 45/06* (2013.01); *A61P 11/00* (2018.01); *A61P 29/00* (2018.01); *C07D 471/04* (2013.01); *C07D 519/00* (2013.01)

(58) Field of Classification Search
CPC ............................ C07D 471/04; C07D 519/00
See application file for complete search history.

(56) References Cited

U.S. PATENT DOCUMENTS

| | | |
|---|---|---|
| 3,966,781 A | 6/1976 | Atkinson et al. |
| 6,693,102 B2 | 2/2004 | Stasch et al. |

(Continued)

FOREIGN PATENT DOCUMENTS

| | | |
|---|---|---|
| CA | 2384417 | 3/2002 |
| WO | WO-97/07116 | 2/1997 |

(Continued)

OTHER PUBLICATIONS

Boswell-Smith (International Journal of COPD 2007:2(2) 121-129).*

(Continued)

*Primary Examiner* — Valerie Rodriguez-Garcia
(74) *Attorney, Agent, or Firm* — Morrison & Foerster LLP

(57) ABSTRACT

The present application relates to novel substituted 5,6,7,8-tetrahydro[1,2,4]triazolo[4,3-a]pyridin-3(2H)-ones and 2,5,6,7-tetrahydro-3H-pyrrolo[2,1-c][1,2,4]triazol-3-ones of formula (I), to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of lung inflammation disorders.

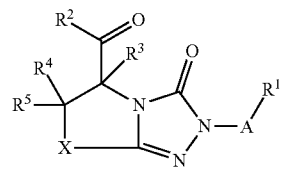

19 Claims, 4 Drawing Sheets

(51) Int. Cl.
    *A61K 45/06*     (2006.01)
    *A61K 31/444*     (2006.01)
    *A61P 11/00*     (2006.01)
    *A61P 29/00*     (2006.01)

(56) References Cited

U.S. PATENT DOCUMENTS

| | | |
|---|---|---|
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,087,644 B1 | 8/2006 | Alonso-Alija et al. |
| 7,173,037 B2 | 2/2007 | Alonso-Alija et al. |
| 7,618,983 B2 | 11/2009 | Lawson et al. |
| 7,674,825 B2 | 3/2010 | Alonso-Alija et al. |
| 8,420,656 B2 | 4/2013 | Follmann et al. |
| 9,096,592 B2 | 8/2015 | Follmann et al. |
| 9,216,978 B2 | 12/2015 | Follmann et al. |
| 9,309,239 B2 | 4/2016 | Follmann et al. |
| 2004/0082798 A1 | 4/2004 | Alonso-Alija |
| 2004/0176446 A1 | 9/2004 | Alonso-Alija |

FOREIGN PATENT DOCUMENTS

| | | |
|---|---|---|
| WO | WO-00/06568 | 2/2000 |
| WO | WO-00/06569 | 2/2000 |
| WO | WO-01/19355 | 3/2001 |
| WO | WO-01/19776 | 3/2001 |
| WO | WO-01/19778 | 3/2001 |
| WO | WO-01/19780 | 3/2001 |
| WO | WO-02/42301 | 3/2002 |
| WO | WO-02/070462 | 9/2002 |
| WO | WO-02/070510 | 9/2002 |
| WO | WO-03/095451 | 11/2003 |
| WO | WO-2006/052962 | 5/2006 |
| WO | WO-2008/144748 | 11/2008 |
| WO | WO-2011/062864 | 5/2011 |
| WO | WO-2011/147809 | 12/2011 |
| WO | WO-2012/004258 | 1/2012 |
| WO | WO-2012/028647 | 3/2012 |
| WO | WO-2012/059549 | 3/2012 |
| WO | WO-2012/112363 | 8/2013 |

OTHER PUBLICATIONS

Wells (American Journal of Respiratory and Critical Care Medicine, vol. 192, No. 8 (Oct. 2015) p. 934-942).*
Lauren Cahoon, Science vol. 322, p. 667-669 (Oct. 31, 2008).*
R. Eisenberg; J. Autoimmunity 32 (2009) 223-230.*
Mangialasche et al. (Lancet Neurol 2010; 9; 702-716).*
Merck Manual Professional Version, printed Aug. 2019.*
AAAS, printed Aug. 25, 2019.*
American Autoimmune Related Diseases Association, printed Aug. 2019.*
Anzueto, A. (2010) "Impact of exacerbations on COPD," *Eur Respir Rev*, 19(116):113-118.
Atzrodt, J., et al. (2007) "The Renaissance of H/D Exchange," *Angew. Chem. Int. Ed.*, 46:7744-7765.
Braber, S., et al. (2011) "CXCR2 antagonists block the N-Ac-PGP-induced neutrophil influx in the airways of mice, but not the production of the chemokine CXCL1," *Eur. J. Pharmacol.*, 668:443-449.
Braber, S., et al. (2011) "Cigarette smoke-induced lung emphysema in mice is associated with prolyl endopeptidase, an enzyme involved in collagen breakdown," *Am J Physiol Lung Cell Mol Physiol*, 300:L255-L265.
Bruno, N., et al. (2013) "Design and preparation of new palladium precatalysts for C—C and C—N cross-coupling reactionst," *Chem. Sci.*, 4:916-920.
Chandrasekhar, S., et al. (2011) "Flow chemistry approach for partial deuteration of alkynes: synthesis of deuterated taxol side chain," *Tetrahedron Letters* 52:3865-3867.

Emsley, P., et al. (Feb. 26, 2010) "Features and development of Coot," *Acta Cryst.*, D66:486-501.
Esaki, H., et al. (2007) "Efficient H/D Exchange Reactions of Alkyl-Substituted Benzene Derivatives by Means of the Pd/C—$H_2$—$D_2O$ System," *Chem. Eur. J.*, 13:4052-4063.
Esaki, H., et al. (2006) "General method of obtaining deuterium-labeled heterocyclic compounds using neutral $D_2O$ with heterogeneous Pd/C," *Tetrahedron*, 62:10954-10961.
Evans, P. (2006) "Scaling and assessment of data quality," *Acta Cryst.*, D62:72-82.
Ewig, S. (2013) "Akute Exazerbation der COPD Besonderheiten der Therapie und Prävention, " *klinikarzt*, 42(4):182-187.
Gaggar, A. (2008) "A Novel Proteolytic Cascade Generates an Extracellular Matrix-Derived Chemoattractant in Chronic Neutrophilic Inflammation[1,2]," *J Immunol*, 180:5662-5669.
Hahn, C. (Apr. 24, 2015) "The matrikine N-α-PGP couples extracellular matrix fragmentation to endothelial permeability," *Sci. Adv.*, pp. 1-10.
Ling, K.H., et al. (Apr. 28, 1989) "Deuterium Isotope Effects on Toluene Metabolism. Product Release as a Rate-Limiting Step in Cytochrome P-450 Catalysis," *Biochem. Biophys. Res. Commun.*, 160(2), 844-849.
Hanzlik, R., et al. (1990) "Active Site Dynamics of Toluene Hydroxylation by Cytochrome P-450[1]," *J. Org. Chem.*, 55(13):3992-3997.
Hassan, J. (2002) "Aryl-Aryl Bond Formation One Century after the Discovery of the Ullmann Reaction," *Chem. Rev.*, 102:1359-1469.
Rosman, K. (1998) "Isotopic Compositions of the Elements 1997," Technical Report, *Pure & Appl. Chem.*, 70(1):217-235.
International Search Report and Written Opinion dated Jul. 26, 2017 for International Application No. PCT/EP2017/060900, filed May 8, 2017, 14 pages.
Jarman, M. (1995) "The deuterium isotope effect for the α-hydroxylation of tamoxifen by rat liver microsomes accounts for the reduced genotoxicity of [$D_5$-ethyl]tamoxifen," *Carcinogenesis*, 16(4):683-688.
Khan, N. A. (1952) "Preparation of Deuterized Raney Nickel and Selective Deuteration of the Triple Bond[2]," *J. Am. Chem. Soc.*, 74(12):3018-3022.
de Kruijf, P., et al. (2010) "The collagen-breakdown product N-acetyl-Proline-Glycine-Proline (N-α-PGP) does not interact directly with human CXCR1 and CXCR2," *European Journal of Pharmacology*, 643:29-33.
Kushner, D.J., et al. (1999) "Pharmacological uses and perspectives of heavy water and deuterated compounds," 77(2):79-88.
Leis, H.J., et al. (1998) "Stable Isotope Labeled Target Compounds: Preparation and Use as Internal Standards in Quantitative Miss Spectrometry," *Curr. Org. Chem.*, 2:131-144.
Long, F., et al. (2008) "BALBES: a molecular-replacement pipeline," *Acta Cryst.* D64:125-132.
Maltais, F., et al. (2009) "In Vitro and In Vivo Isotope Effects with Hepatitis C Protease Inhibitors: Enhanced Plasma Exposure of Deuterated Telaprevir versus Telaprevir in Rats," *J. Med. Chem.*, 52:7993-8001.
Matoishi, K., et al. (2000) "The first synthesis of both enantiomers of [α-$^2$H]phenylacetic acid in high enantiomeric excess," *Chem. Commun.*, pp. 1519-1520.
Morandi, J.R., et al. (Jun. 1969) "Homogeneous Catalytic Deuteration of Olefinic Double Bonds[1]," *Journal of Organic Chemistry*, 34(6):1889-1891.
Moriyama, A., et al. (1988) "Porcine Muscle Prolyl Endopeptidase and Its Endogenous Substrates," *J. Biochem.*, 104:112-117.
Murshudov, G., et al. (1997) "Refinement of Macromolecular Structures by the Maximum-Likelihood Method," *Acta. Cryst.*, D53:240-255.
Mutlib, A., et al. (2000) "The Species-Dependent Metabolism of Efavirenz Produces a Nephrotoxic Glutathione Conjugate in Rats," *Toxicology and Applied Pharmacology*, 169:102-113.
O'Reilly, P., et al. (May 18, 2009) "N-α-PGP and PGP, potential biomarkers and therapeutic targets for COPD," *Respir. Res.*, 10(38)1-8.

(56) References Cited

OTHER PUBLICATIONS

Overbeek, S., et al. (2011) "N-acetylated Proline-Glycine-Proline induced G-protein dependent chemotaxis of neutrophils is independent of CXCL8 release," *Eur. J. Pharmacol.*, 668:428-434.

Perrin, C., et al. (2003) "β-Deuterium Isotope Effects on Amine Basicity, "Inductive" and Stereochemical," *J. Am. Chem. Soc.*, 125:15008-15009.

Perrin, C., et al. (2007) "Secondary Deuterium Isotope Effects on the Acidity of Carboxylic Acids and Phenols," *J. Am. Chem. Soc.*, 129:4490-4497.

Perrin, C. (2010) "Secondary equilibrium isotope effects on acidity," *Advances in Physical Organic Chemistry*, 44:123-146.

Perrin, C. (2005) "Stereochemistry of β-Deuterium Isotope Effects on Amine Basicity," *J. Am. Chem. Soc.*, 127:9641-9647.

Pfister, R., et al. (Aug. 1998) "Injection of Chemoattractants into Normal Cornea: A Model of Inflammation after Alkali Injury," IOVS, 39(9):1744-1750.

Reider, P., et al. (1987) "Synthesis of (R)-Serine-2-d and Its Conversion to the Broad Spectrum Antibiotic Fludalanine," *J. Org. Chem.*, 52:15:3326-3334.

Russell, D., et al. (Mar. 2016) "Disease phenotyping in chronic obstructive pulmonary disease: the neutrophilic endotype," *Curr. Opin. Pilm. Med.*, 22(2):91-99.

Salvi, S. (2014) "Tobacco Smoking and Environmental Risk Factors for Chronic Obstructive Pulmonary Disease," *Clin Chest Med*, 35:17-27.

Schneider, F., et al. (2006) "Enhanced Plasma Concentration by Selective Deuteration of Rofecoxib in Rats," *Arzneim.-Forsch./Drug Res.*, 56(4):295-300.

Sharma, A., et al. (Feb. 6, 2013) "Nevirapine Bioactivation and Covalent Binding in the Skin," *Chem. Res. Toxicol.*, 26:410-421.

Streitwieser, A., et al. (Sep. 20, 1963) "Isotope Effects on Acidity of Deuterated Formic, Acetic, Pivalic, and Benzoic Acids," *J. Am. Chem. Soc.*, 85:2759-2763.

Szul, T., et al. (Mar. 2016) "Toll-Like Receptor 4 Engagement Mediates Prolyl Endopeptidase Release from Airway Epithelia via Exosomes," *Am. J. Respir. Cell Mol. Biol.*, 54:359-369.

El Tayar, N., et al. (1984) "The lipophilicity of deuterium atoms. A comparison of shake-flask and HPLC methods," *Int. J. Pharm.*, 19(3):271-281 (Abstract Only).

Weathington, N., et al. (Mar. 2006) "A novel peptide CXCR ligand derived from extracellular matrix degradation during airway inflammation," *Nat. Med.*, 12(3):317-323.

Wells, J., et al. (Oct. 15, 2015) "A Randomized, Placebo-controlled Trial of Roflumilast," *Am. J. Respir. Crit. Care Med.*, 192(8):934-942.

Wenthur, C., et al. (May 29, 2013) "Discovery of (R)-(2-Fluoro-4-((-4-methoxyphenyl)ethynyl)phenyl) (3-Hydroxypiperidin-1-yl)methanone (ML337), An mGlu$_3$ Selective and CNS Penetrant Negative Allosteric Modulator (NAM)," *J. Med. Chem.*, 56:5208-5212.

\* cited by examiner

Figure 1, Example 237 in a complex with PREP (porcine)
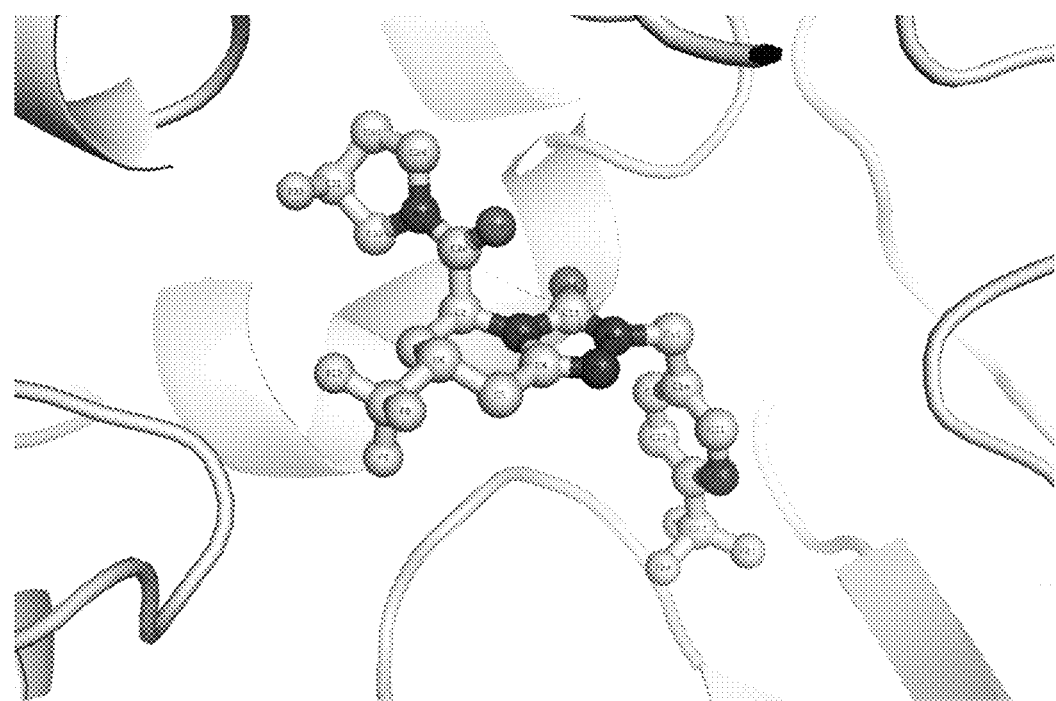
Figure 2, Example 358 in a complex with PREP (porcine)
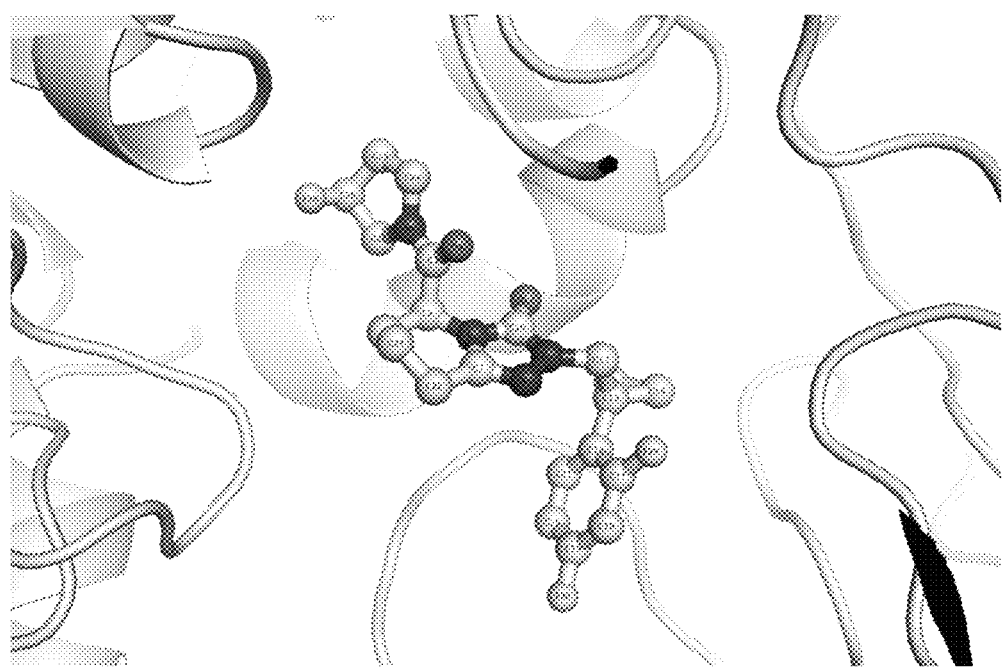

Figure 3, Example 454 in a complex with PREP (porcine)
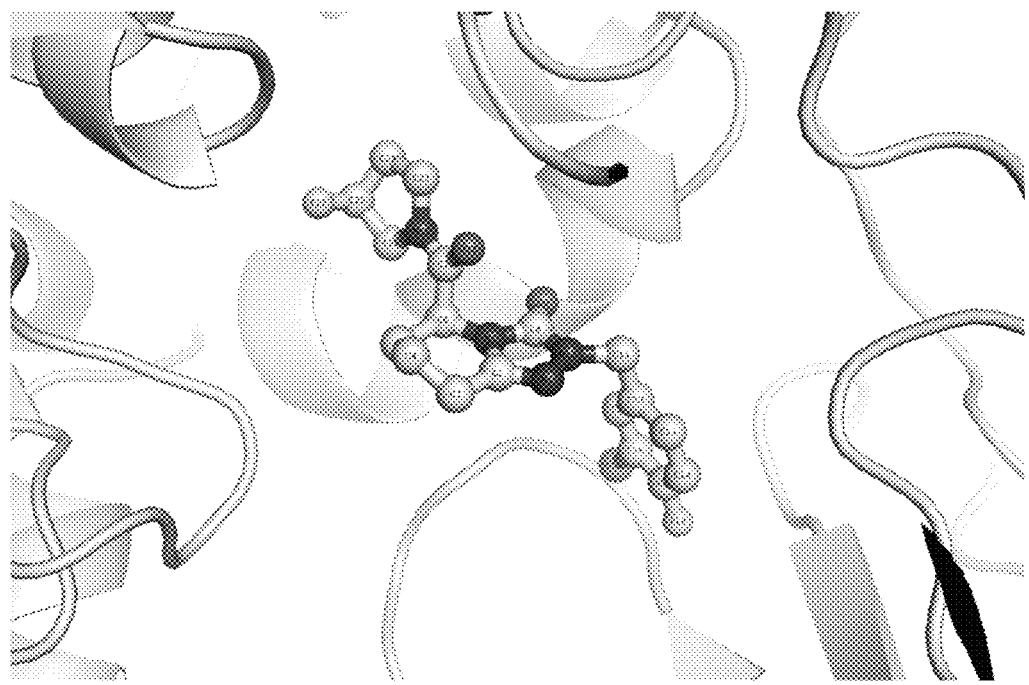
Figure 4, Example 108 in a complex with PREP (porcine)
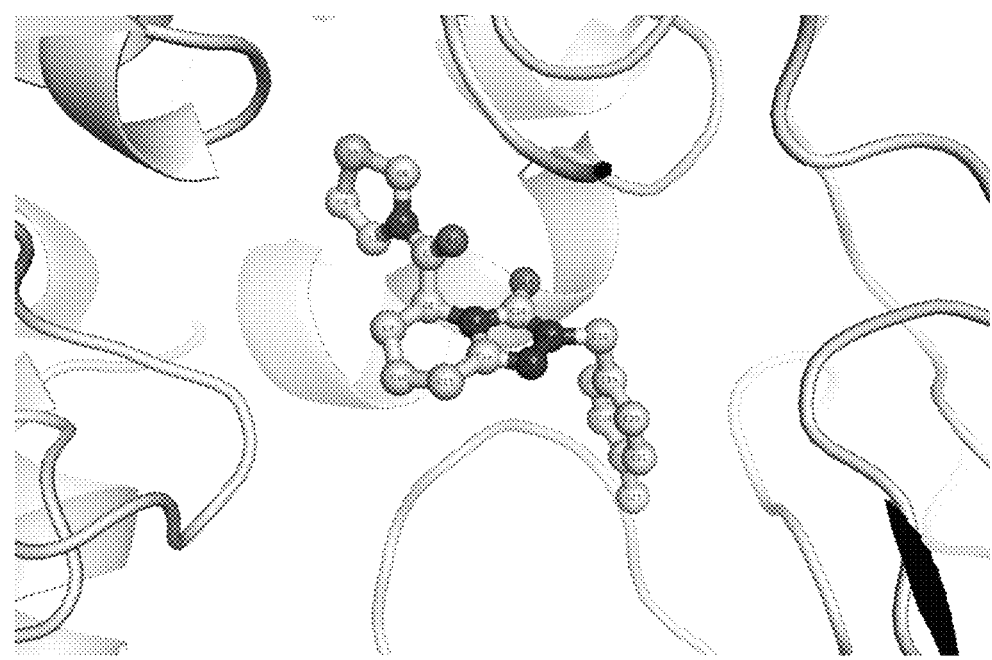

Figure 5, Example 113 in a complex with PREP (porcine)
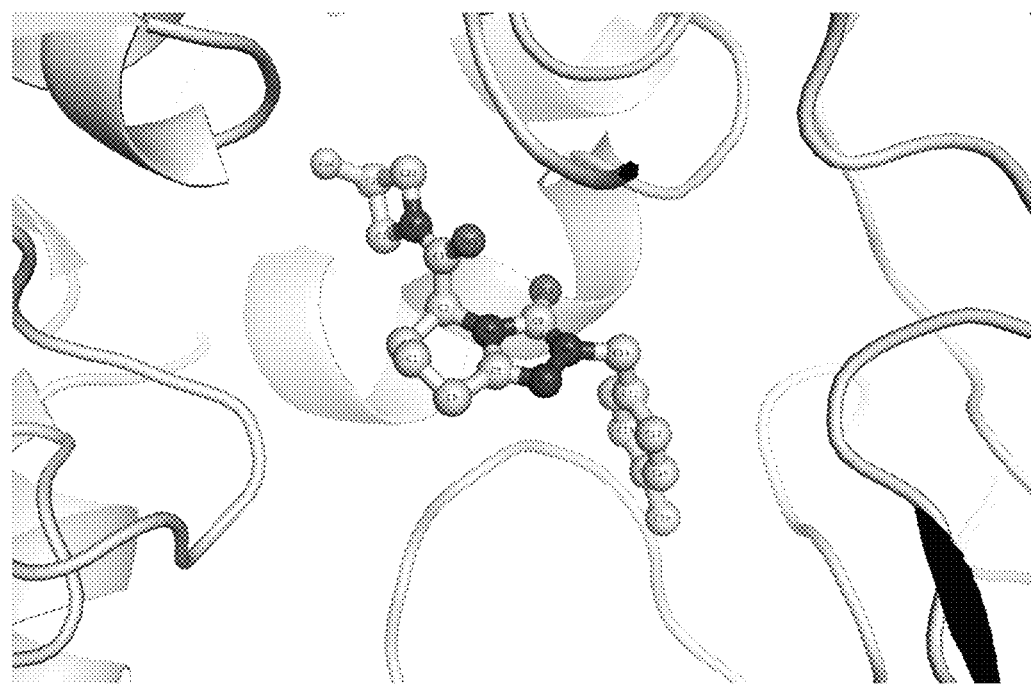
Figure 6, Example 157 in a complex with PREP (porcine)
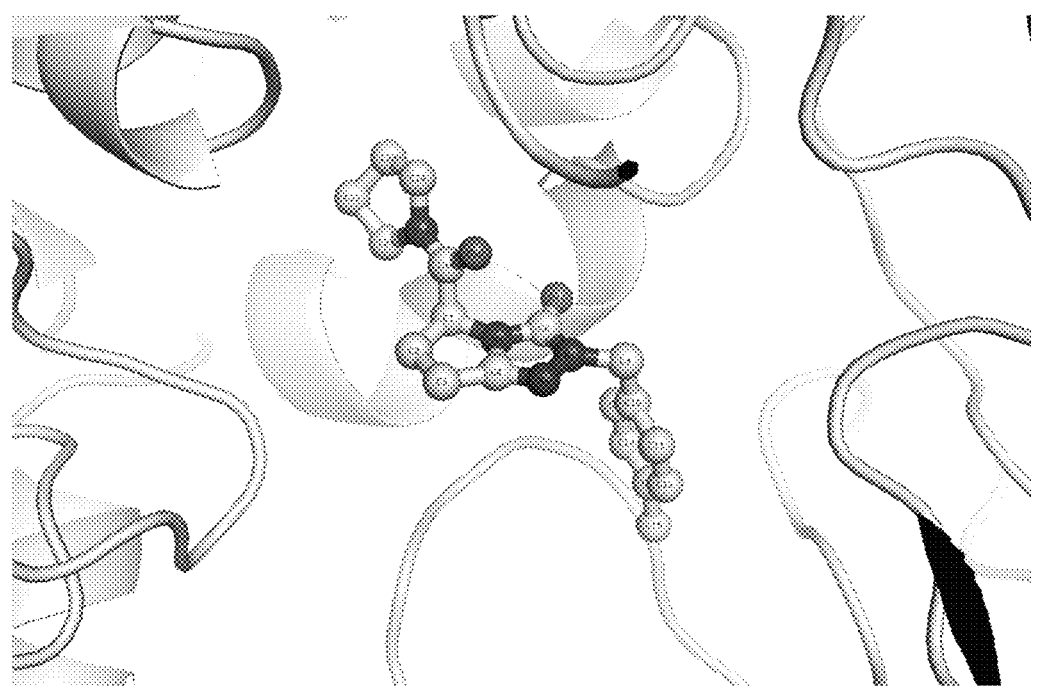

Figure 7, Example 26 in a complex with PREP (porcine)
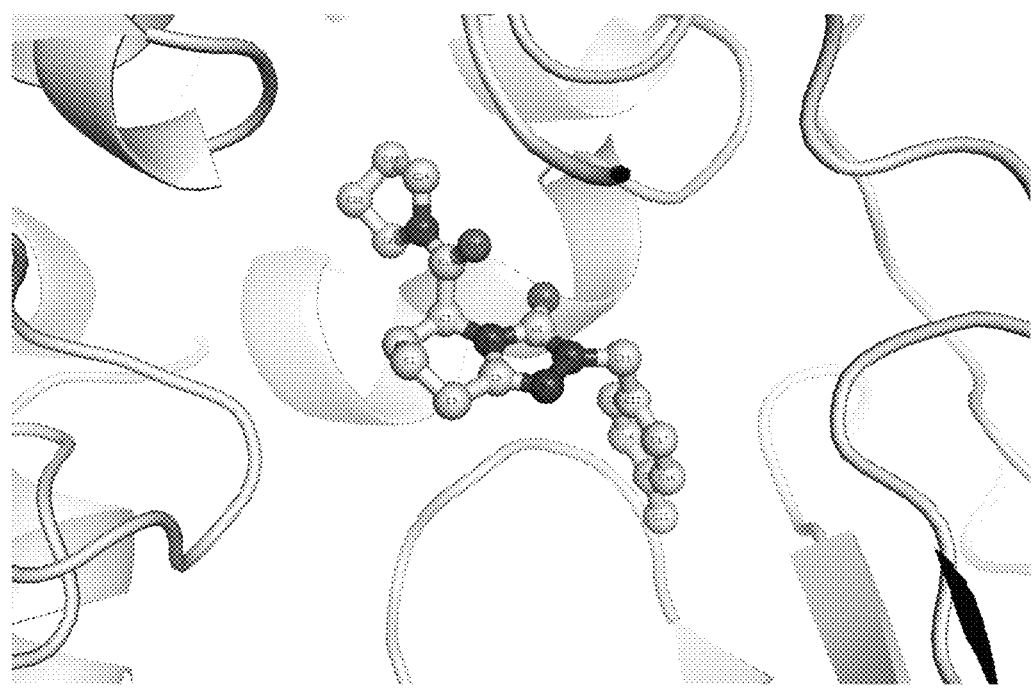

SUBSTITUTED 5,6,7,8-TETRAHYDRO[1,2,4]TRIAZOLO[4,3-A]PYRIDINE-3(2H)-ONES AND 2,5,6,7-TETRAHYDRO-3H-PYRROLO[2,1-C][1,2,4]TRIAZOL-3-ONES, AND USE THEREOF

CROSS REFERENCE TO RELATED APPLICATIONS

This application is a national phase application under 35 U.S.C. § 371 of International Application No. PCT/EP2017/060900, filed May 8, 2017, which claims priority benefit of European Application No. 16168809.8, filed May 9, 2016.

The present application relates to novel substituted 5,6,7,8-tetrahydro[1,2,4]triazolo[4,3-a]pyridin-3(2H)-ones and 2,5,6,7-tetrahydro-3H-pyrrolo[2,1-c][1,2,4]triazol-3-ones, to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of lung inflammation disorders.

The enzyme prolyl endopeptidase (PREP, prolyl oligopetidase, PE, POP) is a serine protease which cleaves peptides up to a length of 30 amino acids beyond the amino acid proline [Moriyama et al., *J. Biochem.* 1988, 104:112-117]. PREP is expressed and secreted constitutively in all organs and tissue, by cells including leucocytes and epithelial cells. Release is increased on contact with irritant, inflammatory substances [Szul et al., *Am. J. Respir. Cell Mol. Biol.* 2016, 54:359-369]. While PREP in the central nervous system is involved in the degradation of peptidic neurotransmitters, PREP in the entire periphery, including in the lung, is an enzyme which cleaves degradation products of collagen inter alia in degenerative and inflammatory processes. Because of the high content of proline and glycine in the amino acid sequence of collagen, tripeptides having the sequence proline-glycine-proline (PGP) are formed therein by the degradation of the collagen fragments [Weathington et al., *Nat. Med.* 2006, 12:317-323]. Significantly elevated PGP concentrations have been described in sputum from patients having chronic inflammatory lung disorders, such as chronic obstructive pulmonary disease (COPD) or cystic fibrosis (mucoviscidosis, CF) [O'Reilly et al., Respir. Res. 2009, 10:38 doi:10.1186/1465-9921-10-38; Gaggar et al., *J. Immunol.* 2008, 180:5662-5669]. PGP, which is produced by PREP, is a chemokine for neutrophil granulocytes (neutrophils for short), meaning that PGP leads to migration of neutrophils into tissue having elevated PGP concentrations. There are pointers that the mechanism of this attraction of neutrophils is based on direct stimulation of the neutrophils via PGP-sensitive receptors on the neutrophil cell membrane (e.g. CXCR1, CXCR2) or is brought about indirectly through the release of further chemokines, for example interleukins (e.g. interleukin-8, CXCL8), by other cell types (e.g. macrophages, epithelial cells). The chemokine effect of PGP on neutrophils has been repeatedly demonstrated in vitro and in vivo [Weathington et al., Nat. Med. 2006, 12:317-323; De Kruijf et al., *Eur. J. Pharmacol.* 2010, 643:29-33; Overbeek et al., *Eur. J. Pharmacol.* 2011, 668:428-434; Braber et al., *Eur. J. Pharmacol.* 2011, 668: 443-449]. In an animal experiment, the effect of PGP has been eliminated by the addition of a complementary tripeptide (threonine-arginine-threonine, RTR) and by the administration of a CXCR2 receptor blocker. It has been shown that repeated application of PGP to the lungs of mice can trigger lung emphysema. In addition, cigarette smoke increases the PGP concentration in the lungs of mice exposed to cigarette smoke. The simultaneous administration of PGP-neutralizing RTR can eliminate the abovementioned cigarette smoke-induced effects [Braber et al., *Eur J. Pharmacol.* 2011, 668:443-449; Braber et al., *Am. J. Physiol. Lung Cell Mol. Pysiol.* 2011, 300:L255-L265].

Chronic obstructive pulmonary disease (COPD) is a lung disease associated with chronic bronchitis, breathlessness, coughing and expectoration, and with the decline of lung tissue (emphysema). Lung function is increasingly restricted owing to the obstructive change in the bronchia and as a result of the loss of functional lung tissue as the disorder progresses. Hyperinflation of the lung is a common consequence of the hindered exhalation.

The most common cause of the occurrence of COPD is chronic inhalation of cigarette smoke. In addition, on a global scale, with regional differences, 10% to 40% of patients develop COPD which is not attributable to cigarette smoke but probably to exposure to environmental poisons, for example smoke from coal or wood fires or diesel exhaust gases [Salvi, *Clin. Chest Med.* 2014, 35:17-27].

At present, only treatment of the symptoms of COPD is possible. COPD patients primarily receive bronchia-widening medicaments which make it easier to breathe. The use of inflammation-inhibiting medicaments has been limited to date.

As well as the chronic symptoms described, COPD patients frequently suffer from acute onset of time-limited deteriorations in their state of health, which is impaired in any case, and these necessitate additional treatment [Ewig, *Klinikarzt* 2013, 42:182-187]. The treatment of these disease episodes, referred to as acute exacerbations, has today been restricted to the administration of oxygen and systemically administered corticosteroids.

In a clinical COPD study, it was shown that roflumilast (an anti-inflammatory PDE4 inhibitor) leads to a decrease in the concentration of PGP in the sputum and serum of the COPD patients treated [Wells et al., *Am. J. Respir. Crit. Care Med.* 2015, 192:934-942].

Elevated pro-inflammatory PGP concentrations have additionally been described, inter alia, in shock lung (acute respiratory syndrome, ARDS) and in corneal injury to the eye [Hahn et al., *Sci. Adv.* 2015, 1: e1500175; Pfister et al., *Invest. Ophthalmol. Vis. Sci.* 1998, 39:1744-1750]. Here too, a pro-inflammatory effect of PGP is formulated, which leads firstly to elevated permeability of vessels, and secondly, as already described above, to increasing recruitment of neutrophils (neutrophilia) and hence to increased inflammation. Since the formation of PGP in inflammatory processes is directly linked to the destruction of tissue, and PGP in turn promotes the inflammation, the involvement of PGP in self-sustaining chronic inflammation processes is probable. Particular mention should be made here of COPD and acute exacerbations of COPD (AE-COPD), which are based on chronic inflammation [Russell et al., *Curr Opin Pilm Med.* 2016, 22:91-99; Anzueto, *Eur. Respir. Rev.* 2010, 19:113-118]. But there are also other chronic inflammation disorders and wound-healing disorders of the lung and other tissues and organs, for example of the skin, the eye, the blood vessels, connective tissue, the skeleton and the musculature, that could also profit from a reduction in the PGP concentration as a result of the PREP inhibition.

Potential fields of use for PREP inhibitors are acute and chronic pathological processes involving PREP or substrates and products of PREP. Since this anti-inflammatory effect of the PREP inhibitors probably does not intervene directly in the function of the immune system, and therefore possibly no immunosuppressive effect is to be expected, one advantage of PREP inhibition could be that fewer side effects could occur in this regard in treated patients than with conventional immunomodulatory principles of action. Since PGP is formed from collagen fragments by means of the PREP enzyme which is expressed constitutively, i.e. is constantly present, and PGP production is therefore not controlled or regulated by the immune system, it is to be expected that the anti-inflammatory effect will also occur in patients where efficacy with respect to corticosteroids is reduced, for instance due to resistances. Corticosteroid resistances are described, particularly in COPD patients, in stable phases outside acute exacerbations. Furthermore, an additive or synergistic efficacy of the combination with corticosteroids is also to be expected in the event that corticosteroids are fully effective, and in the event that their effect is restricted or greatly reduced. A combination with all other inflammatory mechanisms of action is likewise possible.

Since PGP, the formation of which is prevented by PREP inhibition, probably plays a leading role in the inflammation process in all disorders with inflammatory components and the involvement of collagen or fragments thereof, PREP inhibition can have positive effects on many disorders such as autoimmune disorders, chronic inflammation disorders such as rheumatoid disorders, infection events, degenerative processes (skin, organs, bones, musculature).

The problem addressed by the present invention was that of identifying and providing novel compounds of low molecular weight that act as potent inhibitors of the enzyme prolyl endopeptidase (PREP, prolyl oligopeptidase, PE, POP), and, in the event of acute or chronic, pathological or inflammatory-degenerative processes, via the reduction in PREP-dependent PGP production, particularly reduce the recruitment of neutrophil granulocytes in organs, especially in the lung.

The application WO2006052962A2 describes bicyclic triazoles for controlling disorders that occur via integrin inhibition. 1,2-Dihydro-3H-indazol-3-ones as NOX inhibitors for controlling diseases such as COPD, Alzheimer's, inflammatory or fibrotic disorders are known from WO2011062864A2.

The present invention provides compounds of the general formula (I)

in which
A is $(C_1-C_4)$-alkylene or $CD_2$,
  where $(C_1-C_4)$-alkylene may be substituted by hydroxyl and $(C_1-C_4)$-alkoxy and up to pentasubstituted by fluorine,
or
is a group of the formula in which
n is 0 or 1,
p is 0 or 1,
q is 1 or 2,
where
$^1$ marks the bond to the nitrogen atom of the 5-oxo-4,5-dihydro-1H-1,2,4-triazol-1-yl ring,
* marks the bond to $R^1$,
X is $-CR^6R^7-$, $\#^2-CR^6R^7-CR^8R^9-$, $\#^2-CR^6=CR^8-$ or $\#^2-CR^6R^7-CR^8R^9-CR^{10}R^{11}-**$
where $\#^2$ marks the bond to the carbon atom of the $CR^4R^5-$ group,
where ** marks the bond to the carbon atom of the 5-oxo-4,5-dihydro-1H-1,2,4-triazol-1-yl ring,
where
$R^6$ is hydrogen, fluorine, $(C_1-C_4)$-alkyl, $(C_1-C_4)$-alkoxy, trifluoromethoxy, hydroxyl, mono-$(C_1-C_4)$-alkylamino or di-$(C_1-C_4)$-alkylamino,
  in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine,
$R^7$ is hydrogen, fluorine or $(C_1-C_4)$-alkyl,
  in which $(C_1-C_4)$-alkyl may be up to pentasubstituted by fluorine
or
$R^6$ and $R^7$ together with the carbon atom to which they are bonded form a carbonyl group,
or
$R^6$ and $R^7$ together with the carbon atom to which they are bonded form a cyclopropyl ring, cyclobutyl ring or cyclopentyl ring,
or
$R^6$ and $R^4$ together with the carbon atom to which they are bonded form a cyclopropyl ring, cyclobutyl ring or cyclopentyl ring,
$R^8$ is hydrogen, $(C_1-C_4)$-alkyl, $(C_1-C_4)$-alkoxy, fluorine, hydroxyl, mono-$(C_1-C_4)$-alkylamino or di-$(C_1-C_4)$-alkylamino,
  in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine,
$R^9$ is hydrogen, fluorine or $(C_1-C_4)$-alkyl,
  in which $(C_1-C_4)$-alkyl may be up to pentasubstituted by fluorine
or
$R^8$ and $R^9$ together with the carbon atom to which they are bonded form a cyclopropyl ring, cyclobutyl ring or cyclopentyl ring,
or
$R^7$ and $R^9$ together with the carbon atoms to which they are bonded form a cyclopropyl ring, cyclobutyl ring or cyclopentyl ring,
$R^{10}$ is hydrogen, $(C_1-C_4)$-alkyl, $(C_1-C_4)$-alkoxy, fluorine, hydroxyl, mono-$(C_1-C_4)$-alkylamino or di-$(C_1-C_4)$-alkylamino,
  in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine,
$R^{11}$ is hydrogen, fluorine or $(C_1-C_4)$-alkyl,
  in which $(C_1-C_4)$-alkyl may be up to pentasubstituted by fluorine or
R¹⁰ and R¹¹ together with the carbon atom to which they are bonded form a cyclopropyl ring, cyclobutyl ring or cyclopentyl ring, R¹ is $(C_3-C_7)$-cycloalkyl, phenyl or 5- to 10-membered heteroaryl, where $(C_3-C_7)$-cycloalkyl may be substituted by 1 to 3 substituents independently selected from the group of halogen, cyano, trifluoromethyl, $(C_1-C_4)$-alkyl and $(C_1-C_4)$-alkoxy,
in which $(C_1-C_4)$-alkyl may be up to pentasubstituted by fluorine, where phenyl is substituted by 1 to 4 substituents independently selected from the group of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, monofluoromethoxy, difluoromethoxy, trifluoromethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_5)$-cycloalkylaminocarbonyl, $(C_1-C_4)$-alkylsulphanyl, $(C_1-C_4)$-alkylsulphonyl, $(C_1-C_4)$-alkylsulphonimidoyl, $(C_1-C_4)$-cycloalkylsulphonyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino or di-$(C_1-C_4)$-alkylamino, or where phenyl may be fused to $(C_3-C_7)$-cycloalkyl, $(C_3-C_7)$-heterocyclyl or 5- to 6-membered heteroaryl,
in which phenyl may be substituted by methyl, ethyl, chlorine, fluorine or methoxy,
in which $(C_3-C_7)$-cycloalkyl, $(C_3-C_7)$-heterocyclyl and 5- to 6-membered heteroaryl may be substituted by 1 or 2 $(C_1-C_4)$-alkyl substituents,
in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine, or where 5- to 10-membered heteroaryl may be substituted by 1 to 4 substituents independently selected from the group of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, difluoromethoxy, trifluoromethoxy, 2,2,2-trifluoroethoxy, phenyl, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_5)$-cycloalkylaminocarbonyl, $(C_1-C_4)$-alkylsulphanyl, $(C_1-C_4)$-alkylsulphonyl, $(C_1-C_4)$-alkylsulphonimidoyl, $(C_1-C_4)$-cycloalkylsulphonyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino or di-$(C_1-C_4)$-alkylamino,
in which phenyl may be substituted by methyl, ethyl, chlorine, fluorine or methoxy, or where 5- to 10-membered heteroaryl may be fused to $(C_3-C_7)$-cycloalkyl or $(C_3-C_7)$-heterocyclyl,
where 5- to 10-membered heteroaryl may be substituted by methyl, ethyl, chlorine, fluorine or methoxy,
in which $(C_3-C_7)$-cycloalkyl and $(C_3-C_7)$-heterocyclyl may be substituted by 1 or 2 $(C_1-C_4)$-alkyl substituents,
in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine, R² is a group of the formula

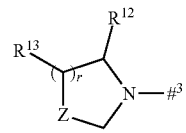

where
³ marks the bond to the carbonyl carbon atom,
r is 0 or 1,
Z is O, NR¹⁸, S, SO, SO₂ or $CR^{14A}R^{14B}$,
in which
$R^{14A}$ is hydrogen, halogen, cyano, $(C_1-C_4)$-alkyl, $(C_3-C_6)$-cycloalkyl, trifluoromethyl, difluoromethyl, fluoromethyl, hydroxyl, $(C_1-C_4)$-alkoxy, $(C_3-C_5)$-cycloalkoxy, difluoromethoxy, trifluoromethoxy or 2,2,2-trifluoroethoxy,
in which $(C_1-C_4)$-alkyl may be substituted by hydroxyl, amino, mono-$(C_1-C_4)$-alkylamino or di-$(C_1-C_4)$-alkylamino,
$R^{14B}$ is hydrogen, fluorine or $(C_1-C_4)$-alkyl,
in which $(C_1-C_4)$-alkyl may be up to pentasubstituted by fluorine or $R^{14A}$ and $R^{14B}$ together with the carbon atom to which they are bonded form a carbonyl group,
R¹⁸ is hydrogen or methyl,
R¹² is hydrogen, cyano, $(C_1-C_4)$-alkyl, acetyl or formyl,
in which $(C_1-C_4)$-alkyl may be substituted by hydroxyl or up to pentasubstituted by fluorine,
in which acetyl may be substituted by hydroxyl or up to trisubstituted by fluorine,
R¹³ is hydrogen, fluorine or $(C_1-C_4)$-alkyl, or R¹² and R¹³ together with the carbon atoms to which they are bonded form a cyclopropyl or cyclobutyl ring,
in which the cyclopropyl or cyclobutyl ring may be up to disubstituted by fluorine, or R¹³ and $R^{14A}$ together with the carbon atoms to which they are bonded form a cyclopropyl or cyclobutyl ring,
in which the cyclopropyl or cyclobutyl ring may be up to disubstituted by fluorine, or $R^{14A}$ and $R^{14B}$ together with the carbon atom to which they are bonded form a cyclopropyl or cyclobutyl ring,
in which the cyclopropyl or cyclobutyl ring may be up to disubstituted by fluorine,
where R¹³, $R^{14A}$ and $R^{14B}$ are hydrogen when R¹² is not hydrogen,
where R¹² is hydrogen when one of the R¹³, $R^{14A}$ and $R^{14B}$ substituents is not hydrogen, or is a group of the formula

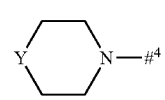

where
⁴ marks the bond to the carbonyl carbon atom,
Y is NR¹⁵, $CR^{16A}R^{16B}$, oxygen or sulphur, in which $R^{15}$ is hydrogen or methyl, $R^{16A}$ is hydrogen or methyl, $R^{16B}$ is hydrogen or methyl, $R^3$ is hydrogen or $(C_1-C_4)$-alkyl, $R^4$ is hydrogen, $(C_1-C_4)$-alkyl, $(C_1-C_4)$-alkoxy, fluorine, hydroxyl, mono-$(C_1-C_4)$-alkylamino or di-$(C_1-C_4)$-alkylamino, in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine, $R^5$ is hydrogen or $(C_1-C_4)$-alkyl, in which $(C_1-C_4)$-alkyl may be up to pentasubstituted by fluorine or $R^4$ and $R^5$ together with the carbon atom to which they are bonded form a carbonyl group, or $R^4$ and $R^5$ together with the carbon atom to which they are bonded form a cyclopropyl ring, cyclobutyl ring or cyclopentyl ring, and the salts, solvates and solvates of the salts of the compounds of the formula (I).

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for isolation or purification of the compounds of the invention.

Physiologically acceptable salts of the compounds of the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated in a known manner from such mixtures of enantiomers and/or diastereomers; preference is given to using chromatographic methods for this purpose, especially HPLC chromatography on an achiral or chiral phase. In the case of carboxylic acids as intermediates or end products, separation is alternatively also possible via diastereomeric salts using chiral amine bases.

If the compounds of the invention can occur in tautomeric forms, the present invention encompasses all the tautomeric forms.

The compounds of the general formula (I) may take the form of isotopic variants. The invention therefore encompasses one or more isotopic variants of the compounds of the general formula (I), especially deuterium-containing compounds of the general formula (I).

The term "isotopic variant" of a compound or reagent is defined as a compound with an unnatural proportion of one or more isotopes from which such a compound is formed.

The term "isotopic variant of the compound of the general formula (I)" is defined as a compound of the general formula (I) with an unnatural proportion of one or more isotopes from which such a compound is formed.

The expression "unnatural proportion" is understood to mean a proportion of such an isotope higher than its natural frequency. The natural frequencies of isotopes to be employed in this connection can be found in "Isotopic Compositions of the Elements 1997", Pure Appl. Chem., 70(1), 217-235, 1998.

Examples of such isotopes are stable and radioactive isotopes of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$.

With regard to the treatment and/or prophylaxis of the disorders specified here, the isotopic variant(s) of the compounds of the general formula (I) preferably contain deuterium ("deuterium-containing compounds of the general formula (I)"). Isotopic variants of the compounds of the general formula (I) into which one or more radioactive isotopes such as $^3H$ or $^{14}C$ have been incorporated are beneficial, for example, in medicament and/or substrate tissue distribution studies. Because of their easy incorporability and detectability, these isotopes are particularly preferred. It is possible to incorporate positron-emitting isotopes such as $^{18}F$ or $^{11}C$ into a compound of the general formula (I). These isotopic variants of the compounds of the general formula (I) are suitable for use in in vivo imaging applications. Deuterium-containing and $^{13}C$-containing compounds of the general formula (I) can be used within preclinical or clinical studies in mass spectrometry analyses.

Isotopic variants of the compounds of the general formula (I) can be prepared by processes known to those skilled in the art as described in the schemes and/or examples described here, by replacing a reagent with an isotopic variant of the reagent, preferably a deuterium-containing reagent. According to the desired deuteration sites, in some cases, deuterium from $D_2O$ can either be incorporated directly into the compounds or into reagents which can be used for the synthesis of such compounds. Another useful reagent for incorporation of deuterium into molecules is deuterium gas. A rapid route to the incorporation of deuterium is the catalytic deuteration of olefinic bonds and acetylenic bonds. For direct exchange of hydrogen for deuterium in hydrocarbons containing functional groups, it is also possible to use metal catalysts (i.e. Pd, Pt and Rh) in the presence of deuterium gas. Various deuterated reagents and synthesis units are commercially available from companies like, for example, C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of the general formula (I)" is defined as a compound of the general formula (I) in which one or more hydrogen atoms have been replaced by one or more deuterium atoms and in which the frequency of deuterium in every deuterated position in the compound of the general formula (I) is higher than the natural frequency of deuterium, which is about 0.015%. More particularly, in a deuterium-containing compound of the general formula (I), the frequency of deuterium in every deuterated position in the compound of the general formula (I) is higher than 10%, 20%, 30%, 40%, 50%, 60%, 70% or 80%, preferably higher than 90%, 95%, 96% or 97%, even further preferably higher than 98% or 99%, in this position or these positions. It will be apparent that the frequency of deuterium in every deuterated position is independent of the frequency of deuterium in other deuterated positions.

Through the selective incorporation of one or more deuterium atoms into a compound of the general formula (I), it is possible to alter the physicochemical properties (for example acidity [C. L. Perrin, et al., *J. Am. Chem. Soc.*, 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and cause changes in the ratio of parent compound to metabolites or the amounts of metabolites formed. Such changes may lead to particular therapeutic benefits and therefore be preferable under particular circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of the general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Examples of this deuterium effect are ML-337 (C. J. Wenthur et al., J. Med. Chem., 2013, 56, 5208) and odanacatib (K. Kassahun et al., WO2012/112363). Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

The present invention additionally also encompasses prodrugs of the compounds of the invention. The term "prodrugs" in this context refers to compounds which may themselves be biologically active or inactive but are reacted (for example metabolically or hydrolytically) to give compounds of the invention during their residence time in the body.

In the context of the present invention, unless specified otherwise, the substituents are defined as follows:

Alkyl in the context of the invention is a straight-chain or branched alkyl radical having the particular number of carbon atoms specified. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 1,4-dimethylpentyl, 4,4-dimethylpentyl and 1,4,4-trimethylpentyl.

Alkylcarbonyl in the context of the invention is a straight-chain or branched alkyl radical having the particular number of carbon atoms specified and a carbonyl group attached to the carbon atom. Preferred examples include: methylcarbonyl, ethylcarbonyl, n-propylcarbonyl, isopropylcarbonyl and tert-butylcarbonyl.

Alkoxy in the context of the invention is a straight-chain or branched alkoxy radical having the particular number of carbon atoms specified. Preferred examples include: methoxy, ethoxy, n-propoxy, isopropoxy, n-butoxy and tert-butoxy.

Cycloalkoxy in the context of the invention is a monocyclic saturated alkyl radical which has the particular number of ring carbon atoms specified and is joined via an oxygen atom. Preferred examples include: cyclopropyloxy, cyclobutyloxy, cyclopentyloxy and cyclohexyloxy.

Cycloalkyl or carbocycle in the context of the invention is a monocyclic saturated alkyl radical having the particular number of ring carbon atoms specified. Preferred examples include: cyclopropyl, cyclobutyl, cyclopentyl, cyclohexyl and cycloheptyl.

Cycloalkylcarbonyl in the context of the invention is a monocyclic saturated alkyl radical having the particular number of ring carbon atoms specified and a carbonyl group attached to the carbon atom. Preferred examples include: cyclopropylcarbonyl, cyclobutylcarbonyl, cyclopentylcarbonyl, cyclohexylcarbonyl and cycloheptylcarbonyl.

Alkoxycarbonyl in the context of the invention is a straight-chain or branched alkoxy radical having the particular number of carbon atoms specified and a carbonyl group attached to the oxygen atom. Preferred examples include: methoxycarbonyl, ethoxycarbonyl, n-propoxycarbonyl, isopropoxycarbonyl and tert-butoxycarbonyl.

Heterocycle or heterocyclyl in the context of the invention is a monocyclic or bicyclic, saturated heterocycle which has the particular number of ring atoms specified, contains one or two ring heteroatoms from the group of N, O, S, SO and SO$_2$ and is joined via a ring carbon atom or optionally a ring nitrogen atom. Preferred examples include: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Azaheterocyclyl in the context of the invention is a monocyclic or bicyclic, saturated or partly unsaturated heterocycle which has the particular number of ring atoms specified, contains a nitrogen atom and may additionally contain one or two further ring heteroatom(s) from the group of N, O, S, SO and/or SO$_2$, and is joined via a ring nitrogen atom. Preferred examples include: pyrrolidinyl, pyrazolidinyl, piperidinyl, piperazinyl, morpholinyl, thiomorpholinyl, 1,1-dioxothiomorpholinyl, hexahydroazepinyl, hexahydro-1,4-diazepinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl.

Heteroaryl in the context of the invention is a monocyclic or bicyclic aromatic heterocycle (heteroaromatic) which has the particular number of ring atoms specified, contains up to four identical or different ring heteroatoms from the group of N, O and S and is joined via a ring carbon atom or optionally via a ring nitrogen atom. Preferred examples include: furyl, pyrrolyl, thienyl, pyrazolyl, imidazolyl, quinolinyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl.

Monoalkylaminocarbonyl in the context of the invention is an amino group which is joined via a carbonyl group and has a straight-chain or branched alkyl substituent having the particular number of carbon atoms specified. Preferred examples include: methylaminocarbonyl, ethylaminocarbonyl, n-propylaminocarbonyl, isopropylaminocarbonyl, n-butylaminocarbonyl, tert-butylaminocarbonyl, n-pentylaminocarbonyl and n-hexylaminocarbonyl.

Dialkylaminocarbonyl in the context of the invention is an amino group which is joined via a carbonyl group and has two identical or different, straight-chain or branched alkyl substituents each having the particular number of carbon atoms specified. Preferred examples include: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl, N-tert-butyl-N-methylaminocarbonyl, N-n-pentyl-N-methylaminocarbonyl and N-n-hexyl-N-methylaminocarbonyl.

Monoalkylaminosulphonyl in the context of the invention is an amino group which is joined via a sulphonyl group and has a straight-chain or branched alkyl substituent having the particular number of carbon atoms specified. Preferred examples include: methylaminosulphonyl, ethylaminosulphonyl, n-propylaminosulphonyl, isopropylaminosulphonyl, n-butylaminosulphonyl, tert-butylaminosulphonyl, n-pentylaminosulphonyl and n-hexylaminosulphonyl.

Dialkylaminocarbonyl in the context of the invention is an amino group which is joined via a sulphonyl group and has two identical or different, straight-chain or branched alkyl substituents each having the particular number of carbon atoms specified. Preferred examples include: N,N-dimethylaminosulphonyl, N,N-diethylaminosulphonyl, N-ethyl-N-methylaminosulphonyl, N-methyl-N-n-propylaminosulphonyl, N-n-butyl-N-methylaminosulphonyl, N-tert-butyl-N-methylaminosulphonyl, N-n-pentyl-N-methylaminosulphonyl and N-n-hexyl-N-methylaminosulphonyl.

Monoalkylamino in the context of the invention is an amino group having a linear or branched alkyl substituent having the particular number of carbon atoms specified. Preferred examples include: methylamino, ethylamino, n-propylamino, isopropylamino, n-butylamino, tert-butylamino, n-pentylamino and n-hexylamino.

Dialkylamino in the context of the invention is an amino group having two identical or different, straight-chain or branched alkyl substituents each having the particular number of carbon atoms specified. Preferred examples include: N,N-dimethylamino, N,N-diethylamino, N-ethyl-N-methylamino, N-methyl-N-n-propylamino, N-n-butyl-N-methylamino, N-tert-butyl-N-methylamino, N-n-pentyl-N-methylamino and N-n-hexyl-N-methylamino.

Halogen in the context of the invention includes fluorine, chlorine, bromine and iodine. Preference is given to chlorine or fluorine.

An oxo group in the context of the invention is an oxygen atom attached to a carbon atom via a double bond.

In the formulae of the group that A, X and $R^2$ can represent, the end point of the line marked by a symbol #$^1$ or #$^2$ or #$^3$ or #$^4$ or #$^5$ or * or  or * does not represent a carbon atom or a CH$_2$ group, but is part of the bond to the respective atom to which A, X and $R^2$ are bonded.

When radicals in the compounds of the invention are substituted, the radicals may be mono- or polysubstituted, unless specified otherwise. In the context of the present invention, all radicals which occur more than once are defined independently of one another. Substitution by one or two identical or different substituents is preferred. Very particular preference is given to substitution by one substituent.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the general formula (I) in which
A is (C$_1$-C$_4$)-alkylene,
where (C$_1$-C$_4$)-alkylene may be substituted by hydroxyl and methoxy and may be up to trisubstituted by fluorine,
or
is a group of the formula

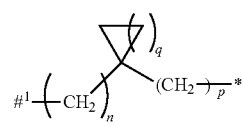

in which
n is 1,
p is 0,
q is 1,
where
$\#^1$ marks the bond to the nitrogen atom of the 5-oxo-4,5-dihydro-1H-1,2,4-triazol-1-yl ring,
* marks the bond to $R^1$,
X is —$CR^6R^7$— or $\#^2$—$CR^6R^7$—$CR^8R^9$—**,
    where $\#^2$ marks the bond to the carbon atom of the $CR^4R^5$— group,
    where ** marks the bond to the carbon atom of the 5-oxo-4,5-dihydro-1H-1,2,4-triazol-1-yl ring,
    where
    $R^6$ is hydrogen, fluorine, methyl, ethyl, methoxy, ethoxy, trifluoromethoxy, hydroxyl, mono-$(C_1-C_4)$-alkylamino or di-$(C_1-C_4)$-alkylamino,
        in which methyl and ethyl may be up to trisubstituted by fluorine,
    $R^7$ is hydrogen, fluorine or methyl,
        in which methyl may be up to trisubstituted by fluorine,
    or
    $R^6$ and $R^7$ together with the carbon atom to which they are bonded form a carbonyl group,
    or
    $R^6$ and $R^7$ together with the carbon atom to which they are bonded form a cyclopropyl or cyclobutyl ring,
    or
    $R^6$ and $R^4$ together with the carbon atoms to which they are bonded form a cyclopropyl or cyclobutyl ring,
    $R^8$ is hydrogen, fluorine, methyl, ethyl, methoxy, ethoxy, trifluoromethoxy, hydroxyl, mono-$(C_1-C_4)$-alkylamino or di-$(C_1-C_4)$-alkylamino,
        in which methyl and ethyl may be up to trisubstituted by fluorine,
    $R^9$ is hydrogen, fluorine or methyl,
        in which methyl may be up to trisubstituted by fluorine,
    or
    $R^8$ and $R^9$ together with the carbon atom to which they are bonded form a cyclopropyl or cyclobutyl ring,
$R^1$ is $(C_5-C_6)$-cycloalkyl, phenyl or 5- to 10-membered heteroaryl,
    in which $(C_5-C_6)$-cycloalkyl may be substituted by 1 to 3 substituents independently selected from the group of fluorine, cyano, trifluoromethyl, methyl, ethyl, methoxy and ethoxy,
        in which methyl and ethyl may be up to trisubstituted by fluorine,
    where phenyl is substituted by 1 to 4 substituents independently selected from the group of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, monofluoromethoxy, difluoromethoxy, trifluoromethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulphanyl, $(C_1-C_4)$-alkylsulphonyl, $(C_1-C_4)$-alkylsulphonimidoyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino or di-$(C_1-C_4)$-alkylamino,
    or
    where phenyl may be fused to cyclopentyl, cyclohexyl, 5- to 6-membered heterocyclyl or 5- to 6-membered heteroaryl,
        in which phenyl may be substituted by methyl, ethyl, chlorine, fluorine or methoxy, in which cyclopentyl, cyclohexyl, 5- to 6-membered heterocyclyl and 5- to 6-membered heteroaryl may be substituted by 1 or 2 methyl or ethyl substituents,
    in which methyl and ethyl may be substituted by methoxy, hydroxyl, monomethylamino or diethylamino and up to trisubstituted by fluorine,
or
where 5- to 10-membered heteroaryl may be substituted by 1 to 4 substituents independently selected from the group of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, difluoromethoxy, trifluoromethoxy, 2,2,2-trifluoroethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulphanyl, $(C_1-C_4)$-alkylsulphonyl, $(C_1-C_4)$-alkylsulphonimidoyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino or di-$(C_1-C_4)$-alkylamino,
or
where 5- to 10-membered heteroaryl may be fused to cyclopentyl, cyclohexyl or 5- to 6-membered heterocyclyl,
    where 5- to 10-membered heteroaryl may be substituted by methyl, ethyl, chlorine, fluorine or methoxy,
    in which cyclopentyl, cyclohexyl and 5- to 6-membered heterocyclyl may be substituted by 1 or 2 $(C_1-C_4)$-alkyl substituents,
        in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine,
$R^2$ is a group of the formula

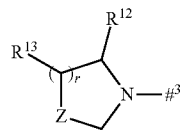

where
$\#^3$ marks the bond to the carbonyl carbon atom,
r is 0 or 1,
Z is S, SO, $SO_2$ or $CR^{14A}R^{14B}$,
    in which
    $R^{14A}$ is hydrogen, halogen, cyano, $(C_1-C_4)$-alkyl, cyclopropyl, trifluoromethyl, difluoromethyl, fluoromethyl, hydroxyl, methoxy, ethoxy, cyclopropoxy, difluoromethoxy, trifluoromethoxy, 2,2,2-trifluoroethoxy, hydroxycarbonyl, aminocarbonyl or amino,
        in which $(C_1-C_4)$-alkyl may be substituted by hydroxyl, amino, mono-$(C_1-C_4)$-alkylamino or di-$(C_1-C_4)$-alkylamino,
    $R^{14B}$ is hydrogen, fluorine, methyl or trifluoromethyl,
    or
    $R^{14A}$ and $R^{14B}$ together with the carbon atom to which they are bonded form a carbonyl group,
$R^{12}$ is hydrogen, cyano, methyl, ethyl, acetyl or formyl,
    in which methyl may be substituted by hydroxyl or up to pentasubstituted by fluorine,
    in which acetyl is substituted by hydroxyl or up to trisubstituted by fluorine, $R^{13}$ is hydrogen, fluorine or methyl,
or
$R^{12}$ and $R^{13}$ together with the carbon atoms to which they are bonded form a cyclopropyl ring,
in which the cyclopropyl ring may be up to disubstituted by fluorine,
or
$R^{13}$ and $R^{14A}$ together with the carbon atoms to which they are bonded form a cyclopropyl or cyclobutyl ring,
in which the cyclopropyl or cyclobutyl ring may be up to disubstituted by fluorine,
or
$R^{14A}$ and $R^{14B}$ together with the carbon atom to which they are bonded form a cyclopropyl or cyclobutyl ring,
in which the cyclopropyl or cyclobutyl ring may be up to disubstituted by fluorine,
where $R^{13}$, $R^{14A}$ and $R^{14B}$ are hydrogen when $R^{12}$ is not hydrogen,
where $R^{12}$ is hydrogen when one of the $R^{13}$, $R^{14A}$ and $R^{14B}$ substituents is not hydrogen,
or
is a group of the formula

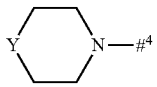

where
⁴ marks the bond to the carbonyl carbon atom,
Y is $NR^{15}$, $CR^{16A}R^{16B}$, oxygen or sulphur,
in which
$R^{15}$ is hydrogen or methyl,
$R^{16A}$ is hydrogen or methyl,
$R^{16B}$ is hydrogen or methyl,
$R^3$ is hydrogen or methyl,
$R^4$ is hydrogen, fluorine, methyl, ethyl, methoxy, ethoxy, trifluoromethoxy, hydroxyl, mono-$(C_1-C_4)$-alkylamino or di-$(C_1-C_4)$-alkylamino,
in which methyl and ethyl may be up to trisubstituted by fluorine,
$R^5$ is hydrogen, fluorine or methyl,
in which methyl may be up to trisubstituted by fluorine,
or
$R^4$ and $R^5$ together with the carbon atom to which they are bonded form a cyclopropyl ring, and the salts, solvates and solvates of the salts of the compounds of the formula (I).

Particular preference in the context of the present invention is given to compounds of the general formula (I) in which A is —$CH_2$—, —$CH(CH_3)$—, —$CH_2CH_2$—, #⁵—$CH_2CH(CH_3)$—*, #⁵—$CH_2C(CH_3)_2$—*, #⁵—$CH_2CHF$—* or #⁵—$CH_2CF_2$—*,
where #⁵ marks the bond to the nitrogen atom of the 5-oxo-4,5-dihydro-1H-1,2,4-triazol-1-yl ring,
where *** marks the bond to the $R^1$ group,
X is —#²—$CR^6R^7$—$CR^8R^9$—**,
where #² marks the bond to the carbon atom of the $CR^4R^5$— group,
where ** marks the bond to the carbon atom of the 5-oxo-4,5-dihydro-1H-1,2,4-triazol-1-yl ring,
where
$R^6$ is hydrogen, fluorine, methyl, trifluoromethyl or hydroxyl, $R^7$ is hydrogen, fluorine or methyl,
or
$R^6$ and $R^7$ together with the carbon atom to which they are bonded form a cyclopropyl ring,
$R^1$ is phenyl or 5- to 6-membered heteroaryl,
where phenyl is substituted by 1 to 3 substituents independently selected from the group of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl or methylsulphinyl,
or
where phenyl may be fused to cyclopentyl, cyclohexyl, 5- to 6-membered heterocyclyl or 5- to 6-membered heteroaryl,
in which cyclopentyl, cyclohexyl, $(C_5-C_6)$-heterocyclyl and 5- to 6-membered heteroaryl may be substituted by 1 or 2 methyl or ethyl substituents,
or
where 5- to 6-membered heteroaryl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl,
where 5- to 6-membered heteroaryl may be fused to cyclopentyl, cyclohexyl, 5- to 6-membered heterocyclyl, phenyl or 5- to 6-membered heteroaryl,
where 5- to 6-membered heteroaryl may be substituted by methyl, ethyl, chlorine, fluorine or methoxy,
in which cyclopentyl, cyclohexyl, 5- to 6-membered heterocyclyl, phenyl and 5- to 6-membered heteroaryl may be substituted by 1 or 2 $(C_1-C_4)$-alkyl substituents,
$R^2$ is a group of the formula

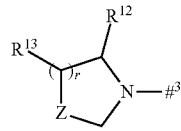

where
³ marks the bond to the carbonyl carbon atom,
r is 0 or 1,
Z is S or $CR^{14A}R^{14B}$ when r is 0,
Z is S, SO, $SO_2$ or $CR^{14A}R^{14B}$ when r is 1,
in each of which
$R^{14A}$ is hydrogen, fluorine, methyl, trifluoromethyl, difluoromethyl, fluoromethyl, hydroxyl, methoxy, difluoromethoxy or trifluoromethoxy,
$R^{14B}$ is hydrogen or fluorine,
or
$R^{14A}$ and $R^{14B}$ together with the carbon atom to which they are bonded form a carbonyl group,
$R^{12}$ is hydrogen, cyano, methyl, acetyl or formyl,
in which acetyl is substituted by hydroxyl or up to trisubstituted by fluorine,
$R^{13}$ is hydrogen, fluorine or methyl,
or
$R^{12}$ and $R^{13}$ together with the carbon atoms to which they are bonded form a cyclopropyl ring, or R$^{13}$ and R$^{14A}$ together with the carbon atom to which they are bonded form a cyclopropyl ring,
in which the cyclopropyl ring may be up to disubstituted by fluorine,
or R$^{14A}$ and R$^{14B}$ together with the carbon atom to which they are bonded form a cyclopropyl ring,
in which the cyclopropyl ring may be up to disubstituted by fluorine,
where R$^{13}$, R$^{14A}$ and R$^{14B}$ are hydrogen when R$^{12}$ is not hydrogen,
where R$^{12}$ is hydrogen when one of the R$^{13}$, R$^{14A}$ and R$^{14B}$ substituents is not hydrogen, R$^3$ is hydrogen,
R$^4$ is hydrogen, fluorine or methyl,
R$^5$ is hydrogen,
and the salts, solvates and solvates of the salts of the compounds of the formula (I).

Particular preference in the context of the present invention is given to compounds of the general formula (I) in which A is —CH$_2$—, —CH(CH$_3$)—, —CH$_2$CH$_2$—, #$^5$—CH$_2$CH(CH$_3$)—*, #$^5$—CH$_2$C(CH$_3$)$_2$—*, #$^5$—CH$_2$CHF—* or #$^5$—CH$_2$CF$_2$—*,
where #$^5$ marks the bond to the nitrogen atom of the 5-oxo-4,5-dihydro-1H-1,2,4-triazol-1-yl ring,
where * marks the bond to the R$^1$ group, X is —#$^2$—CR$^6$R$^7$—CR$^8$R$^9$—,
where #$^2$ marks the bond to the carbon atom of the CR$^4$R$^5$— group,
where ** marks the bond to the carbon atom of the 5-oxo-4,5-dihydro-1H-1,2,4-triazol-1-yl ring,
where
R$^6$ is hydrogen, fluorine, methyl, trifluoromethyl or hydroxyl,
R$^7$ is hydrogen, fluorine or methyl,
or
R$^6$ and R$^7$ together with the carbon atom to which they are bonded form a cyclopropyl ring,
R$^8$ is hydrogen, fluorine, methyl or trifluoromethyl,
R$^9$ is hydrogen, fluorine or methyl,
R$^1$ is phenyl or 5- to 6-membered heteroaryl,
where phenyl is substituted by 1 to 3 substituents independently selected from the group of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl or methylsulphinyl,
or
where phenyl may be fused to cyclopentyl, cyclohexyl, 5- to 6-membered heterocyclyl or 5- to 6-membered heteroaryl,
in which cyclopentyl, cyclohexyl, 5- to 6-membered heterocyclyl and 5- to 6-membered heteroaryl may be substituted by 1 or 2 methyl or ethyl substituents,
or
where 5- to 6-membered heteroaryl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl,
where 5- to 6-membered heteroaryl may be fused to cyclopentyl, cyclohexyl, 5- to 6-membered heterocyclyl, phenyl or 5- to 6-membered heteroaryl,
where 5- to 6-membered heteroaryl may be substituted by methyl, ethyl, chlorine, fluorine or methoxy,
in which cyclopentyl, cyclohexyl, 5- to 6-membered heterocyclyl, phenyl and 5- to 6-membered heteroaryl may be substituted by 1 or 2 (C$_1$-C$_4$)-alkyl substituents, R$^2$ is a group of the formula

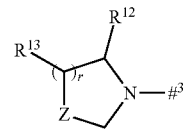

where
$^3$ marks the bond to the carbonyl carbon atom,
r is 0 or 1,
Z is S or CR$^{14A}$R$^{14B}$ when r is 0,
Z is S, SO, SO$_2$ or CR$^{14A}$R$^{14B}$ when r is 1,
in each of which
R$^{14A}$ is hydrogen, fluorine, methyl, trifluoromethyl, difluoromethyl, fluoromethyl, hydroxyl, methoxy, difluoromethoxy or trifluoromethoxy,
R$^{14B}$ is hydrogen or fluorine,
or
R$^{14A}$ and R$^{14B}$ together with the carbon atom to which they are bonded form a carbonyl group,
R$^{12}$ is hydrogen, cyano, methyl, acetyl or formyl,
in which acetyl is substituted by hydroxyl or up to trisubstituted by fluorine,
R$^{13}$ is hydrogen, fluorine or methyl,
or
R$^{12}$ and R$^{13}$ together with the carbon atoms to which they are bonded form a cyclopropyl ring,
or
R$^{13}$ and R$^{14A}$ together with the carbon atom to which they are bonded form a cyclopropyl ring,
in which the cyclopropyl ring may be up to disubstituted by fluorine,
or
R$^{14A}$ and R$^{14B}$ together with the carbon atom to which they are bonded form a cyclopropyl ring,
in which the cyclopropyl ring may be up to disubstituted by fluorine,
where R$^{13}$, R$^{14A}$ and R$^{14B}$ are hydrogen when R$^{12}$ is not hydrogen,
where R$^{12}$ is hydrogen when one of the R$^{13}$, R$^{14A}$ and R$^{14B}$ substituents is not hydrogen, R$^3$ is hydrogen,
R$^4$ is hydrogen, fluorine or methyl,
R$^5$ is hydrogen,
and the salts, solvates and solvates of the salts of the compounds of the formula (I).

Particular preference in the context of the present invention is given to compounds of the general formula (I) in which A is —CH$_2$—, —CH(CH$_3$)—, —CH$_2$CH$_2$—, #$^5$—CH$_2$CH(CH$_3$)—*, #$^5$—CH$_2$C(CH$_3$)$_2$—*, #$^5$—CH$_2$CHF—* or #$^5$—CH$_2$CF$_2$—*,
where #$^5$ marks the bond to the nitrogen atom of the 5-oxo-4,5-dihydro-1H-1,2,4-triazol-1-yl ring, where *** marks the bond to the $R^1$ group,
X is —#²—$CR^6R^7$—$CR^8R^9$—**,
  where #² marks the bond to the carbon atom of the $CR^4R^5$— group,
  where ** marks the bond to the carbon atom of the 5-oxo-4,5-dihydro-1H-1,2,4-triazol-1-yl ring,
  where
  $R^6$ is hydrogen, fluorine, methyl, trifluoromethyl or hydroxyl,
  $R^7$ is hydrogen, fluorine or methyl,
  or
  $R^6$ and $R^7$ together with the carbon atom to which they are bonded form a cyclopropyl ring,
  $R^8$ is hydrogen, fluorine, methyl or trifluoromethyl,
  $R^9$ is hydrogen, fluorine or methyl,
$R^1$ is phenyl, pyrazolyl, imidazolyl, thiazolyl, thiophenyl, oxazolyl, oxadiazolyl or pyridyl,
  where phenyl is substituted by 1 to 3 substituents independently selected from the group of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl or methylsulphinyl,
  or
  where phenyl may be fused to cyclopentyl, cyclohexyl, pyrazolyl or pyridyl,
    in which cyclopentyl, cyclohexyl, pyrazolyl or pyridyl may be substituted by 1 or 2 methyl or ethyl substituents,
  or
  where pyrazolyl, imidazolyl, thiazolyl, thiophenyl, oxazolyl, oxadiazolyl or pyridyl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl,
  where pyrazolyl, imidazolyl, thiazolyl, thiophenyl, oxazolyl, oxadiazolyl or pyridyl may be fused to cyclopentyl, cyclohexyl, phenyl or pyridyl,
    in which pyridyl may be substituted by methyl, ethyl, chlorine, fluorine or methoxy,
    in which cyclopentyl, cyclohexyl, phenyl and pyridyl may be substituted by 1 or 2 ($C_1$-$C_4$)-alkyl substituents,
$R^2$ is a group of the formula

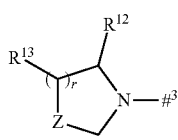

where
³ marks the bond to the carbonyl carbon atom,
r is 0 or 1,
Z is S or $CR^{14A}R^{14B}$ when r is 0,
Z is S, SO, $SO_2$ or $CR^{14A}R^{14B}$ when r is 1,
  in each of which
  $R^{14A}$ is hydrogen, fluorine, methyl, trifluoromethyl, difluoromethyl, fluoromethyl, hydroxyl, methoxy, difluoromethoxy or trifluoromethoxy, $R^{14B}$ is hydrogen or fluorine,
or
  $R^{14A}$ and $R^{14B}$ together with the carbon atom to which they are bonded form a carbonyl group,
$R^{12}$ is hydrogen, cyano, methyl, acetyl or formyl,
  in which acetyl is substituted by hydroxyl or up to trisubstituted by fluorine,
$R^{13}$ is hydrogen, fluorine or methyl,
or
  $R^{12}$ and $R^{13}$ together with the carbon atoms to which they are bonded form a cyclopropyl ring,
or
  $R^{13}$ and $R^{14A}$ together with the carbon atom to which they are bonded form a cyclopropyl ring,
    in which the cyclopropyl ring may be up to disubstituted by fluorine,
or
  $R^{14A}$ and $R^{14B}$ together with the carbon atom to which they are bonded form a cyclopropyl ring,
    in which the cyclopropyl ring may be up to disubstituted by fluorine,
  where $R^{13}$, $R^{14A}$ and $R^{14B}$ are hydrogen when $R^{12}$ is not hydrogen,
  where $R^{12}$ is hydrogen when one of the $R^{13}$, $R^{14A}$ and $R^{14B}$ substituents is not hydrogen,
$R^3$ is hydrogen,
$R^4$ is hydrogen, fluorine or methyl,
$R^5$ is hydrogen,
and the salts, solvates and solvates of the salts of the compounds of the formula (I).
In the context of the present invention, preference is also given to compounds of the formula (I) in which
A is —$CH_2$—, —$CH(CH_3)$—, —$CH_2CH_2$—, #⁵—$CH_2CH(CH_3)$—*, #⁵—$CH_2C(CH_3)_2$—*, #⁵—$CH_2CHF$—* or #⁵—$CH_2CF_2$—*
  where #⁵ marks the bond to the nitrogen atom of the 5-oxo-4,5-dihydro-1H-1,2,4-triazol-1-yl ring,
  where *** marks the bond to the $R^1$ group,
and the solvates, salts and solvates of the salts thereof.
Particular preference is given in the context of the present invention also to compounds of the formula (I) in which
A is —$CH_2$—, —$CH(CH_3)$— or —$CH_2CH_2$—,
and the solvates, salts and solvates of the salts thereof.
Particular preference is given in the context of the present invention also to compounds of the formula (I) in which
A is —$CH_2$—,
and the solvates, salts and solvates of the salts thereof.
In the context of the present invention, preference is also given to compounds of the formula (I) in which
X is —#²—$CR^6R^7$—$CR^8R^9$—**,
  where #² marks the bond to the carbon atom of the $CR^4R^5$— group,
  where ** marks the bond to the carbon atom of the 5-oxo-4,5-dihydro-1H-1,2,4-triazol-1-yl ring,
  where
  $R^6$ is hydrogen, fluorine, methyl, trifluoromethyl or hydroxyl,
  $R^7$ is hydrogen, fluorine or methyl,
  or
  $R^6$ and $R^7$ together with the carbon atom to which they are bonded form a cyclopropyl ring,
and the solvates, salts and solvates of the salts thereof.
In the context of the present invention, preference is also given to compounds of the formula (I) in which
X is -#²—$CR^6R^7$—$CR^8R^9$—**,
  where #² marks the bond to the carbon atom of the $CR^4R^5$— group, where ** marks the bond to the carbon atom of the 5-oxo-4,5-dihydro-1H-1,2,4-triazol-1-yl ring,
where
$R^6$ is hydrogen, fluorine, methyl, trifluoromethyl or hydroxyl,
$R^7$ is hydrogen, fluorine or methyl,
or
$R^6$ and $R^7$ together with the carbon atom to which they are bonded form a cyclopropyl ring,
$R^8$ is hydrogen, fluorine, methyl or trifluoromethyl,
$R^9$ is hydrogen, fluorine or methyl,
and the solvates, salts and solvates of the salts thereof.

Particular preference is given in the context of the present invention also to compounds of the formula (I) in which
X is -#²—$CR^6R^7$—$CR^8R^9$—**,
where #² marks the bond to the carbon atom of the $CR^4R^5$— group,
where ** marks the bond to the carbon atom of the 5-oxo-4,5-dihydro-1H-1,2,4-triazol-1-yl ring,
where
$R^6$ is hydrogen, fluorine, methyl or trifluoromethyl,
$R^7$ is hydrogen,
and the solvates, salts and solvates of the salts thereof.

Particular preference is given in the context of the present invention also to compounds of the formula (I) in which
X is -#²—$CR^6R^7$—$CR^8R^9$—**,
where #² marks the bond to the carbon atom of the $CR^4R^5$— group,
where ** marks the bond to the carbon atom of the 5-oxo-4,5-dihydro-1H-1,2,4-triazol-1-yl ring,
where
$R^6$ is trifluoromethyl,
$R^7$ is hydrogen,
$R^8$ is hydrogen,
$R^9$ is hydrogen,
and the solvates, salts and solvates of the salts thereof.

In the context of the present invention, preference is also given to compounds of the formula (I) in which
X is -#²—$CR^6R^7$—$CR^8R^9$—**,
where #² marks the bond to the carbon atom of the $CR^4R^5$— group,
where ** marks the bond to the carbon atom of the 5-oxo-4,5-dihydro-1H-1,2,4-triazol-1-yl ring,
where
$R^6$ is hydrogen,
$R^7$ is hydrogen,
$R^8$ is hydrogen, fluorine, methyl or trifluoromethyl,
$R^9$ is hydrogen, fluorine or methyl,
and the solvates, salts and solvates of the salts thereof.

Particular preference is given in the context of the present invention also to compounds of the formula (I) in which
X is -#²—$CR^6R^7$—$CR^8R^9$—**,
where #² marks the bond to the carbon atom of the $CR^4R^5$— group,
where ** marks the bond to the carbon atom of the 5-oxo-4,5-dihydro-1H-1,2,4-triazol-1-yl ring,
where
$R^6$ is hydrogen,
$R^7$ is hydrogen,
$R^8$ is fluorine,
$R^9$ is fluorine,
and the solvates, salts and solvates of the salts thereof.

Particular preference is given in the context of the present invention also to compounds of the formula (I) in which
X is -#²—$CR^6R^7$—$CR^9R^9$—**,
where #² marks the bond to the carbon atom of the $CR^4R^5$— group,
where ** marks the bond to the carbon atom of the 5-oxo-4,5-dihydro-1H-1,2,4-triazol-1-yl ring,
where
$R^6$ is hydrogen,
$R^7$ is hydrogen,
$R^8$ is hydrogen,
$R^9$ is hydrogen,
and the solvates, salts and solvates of the salts thereof.

In the context of the present invention, preference is also given to compounds of the formula (I) in which
$R^1$ is phenyl or 5- to 6-membered heteroaryl,
where phenyl is substituted by 1 to 3 substituents independently selected from the group of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl or methylsulphinyl,
or
where phenyl may be fused to cyclopentyl, cyclohexyl, 5- to 6-membered heterocyclyl or 5- to 6-membered heteroaryl,
in which cyclopentyl, cyclohexyl, ($C_5$-$C_6$)-heterocyclyl and 5- to 6-membered heteroaryl may be substituted by 1 or 2 methyl or ethyl substituents,
or
where 5- to 6-membered heteroaryl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl,
where 5- to 6-membered heteroaryl may be fused to cyclopentyl, cyclohexyl, 5- to 6-membered heterocyclyl, phenyl or 5- to 6-membered heteroaryl,
where 5- to 6-membered heteroaryl may be substituted by methyl, ethyl, chlorine, fluorine or methoxy,
in which cyclopentyl, cyclohexyl, 5- to 6-membered heterocyclyl, phenyl and 5- to 6-membered heteroaryl may be substituted by 1 or 2 ($C_1$-$C_4$)-alkyl substituents,
and the solvates, salts and solvates of the salts thereof.

In the context of the present invention, preference is also given to compounds of the formula (I) in which
$R^1$ is 5- to 6-membered heteroaryl,
where 5- to 6-membered heteroaryl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl,
where 5- to 6-membered heteroaryl may be fused to cyclopentyl, cyclohexyl, 5- to 6-membered heterocyclyl, phenyl or 5- to 6-membered heteroaryl,
where 5- to 6-membered heteroaryl may be substituted by methyl, ethyl, chlorine, fluorine or methoxy,
in which cyclopentyl, cyclohexyl, 5- to 6-membered heterocyclyl, phenyl and 5- to 6-membered heteroaryl may be substituted by 1 or 2 ($C_1$-$C_4$)-alkyl substituents,
and the solvates, salts and solvates of the salts thereof.

In the context of the present invention, preference is also given to compounds of the formula (I) in which $R^1$ is phenyl, pyrazolyl, imidazolyl, thiazolyl, thiophenyl, oxazolyl, oxadiazolyl or pyridyl, where phenyl is substituted by 1 to 3 substituents independently selected from the group of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl or methylsulphinyl, or where phenyl may be fused to cyclopentyl, cyclohexyl, pyrazolyl or pyridyl, in which cyclopentyl, cyclohexyl, pyrazolyl or pyridyl may be substituted by 1 or 2 methyl or ethyl substituents, or where pyrazolyl, imidazolyl, thiazolyl, thiophenyl, oxazolyl, oxadiazolyl or pyridyl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl, where pyrazolyl, imidazolyl, thiazolyl, thiophenyl, oxazolyl, oxadiazolyl or pyridyl may be fused to cyclopentyl, cyclohexyl, phenyl or pyridyl, in which pyridyl may be substituted by methyl, ethyl, chlorine, fluorine or methoxy, in which cyclopentyl, cyclohexyl, phenyl and pyridyl may be substituted by 1 or 2 ($C_1$-$C_4$)-alkyl substituents, and the solvates, salts and solvates of the salts thereof.

In the context of the present invention, preference is also given to compounds of the formula (I) in which
$R^1$ is phenyl, where phenyl is substituted by 1 to 3 substituents independently selected from the group of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl or methylsulphinyl, or where phenyl may be fused to cyclopentyl, cyclohexyl, pyrazolyl or pyridyl, in which cyclopentyl, cyclohexyl, pyrazolyl or pyridyl may be substituted by 1 or 2 methyl or ethyl substituents, and the solvates, salts and solvates of the salts thereof.

Particular preference is given in the context of the present invention also to compounds of the formula (I) in which
$R^1$ is pyrazolyl, imidazolyl, thiazolyl, thiophenyl, oxazolyl or oxadiazolyl, where phenyl may be fused to cyclopentyl, cyclohexyl, pyrazolyl or pyridyl, in which cyclopentyl, cyclohexyl, pyrazolyl or pyridyl may be substituted by 1 or 2 methyl or ethyl substituents, where pyrazolyl, imidazolyl, thiazolyl, thiophenyl, oxazolyl or oxadiazolyl may be substituted by 1 to 3 substituents independently selected from the group of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, dimethylaminocarbonyl, where pyrazolyl, imidazolyl, thiazolyl, thiophenyl, oxazolyl, oxadiazolyl or pyridyl may be fused to cyclopentyl, cyclohexyl, phenyl or pyridyl, in which pyridyl may be substituted by methyl, ethyl, chlorine, fluorine or methoxy, in which cyclopentyl, cyclohexyl, phenyl and pyridyl may be substituted by 1 or 2 ($C_1$-$C_4$)-alkyl substituents, and the solvates, salts and solvates of the salts thereof.

Particular preference is given in the context of the present invention also to compounds of the formula (I) in which
$R^1$ is pyridyl, where pyridyl may be substituted by 1 or 2 substituents independently of one another selected from the group consisting of fluorine, chlorine, trifluoromethyl and methoxy, and the solvates, salts and solvates of the salts thereof.

In the context of the present invention, preference is also given to compounds of the formula (I) in which
$R^2$ is a group of the formula

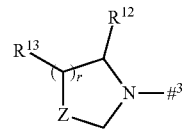

where
$^3$ marks the bond to the carbonyl carbon atom,
r is 0 or 1,
Z is S or $CR^{14A}R^{14B}$ when r is 0,
Z is S, SO, $SO_2$ or $CR^{14A}R^{14B}$ when r is 1,
in each of which
$R^{14A}$ is hydrogen, fluorine, methyl, trifluoromethyl, difluoromethyl, fluoromethyl, hydroxyl, methoxy, difluoromethoxy or trifluoromethoxy,
$R^{14B}$ is hydrogen or fluorine,
or
$R^{14A}$ and $R^{14B}$ together with the carbon atom to which they are bonded form a carbonyl group,
$R^{12}$ is hydrogen, cyano, methyl, acetyl or formyl,
in which acetyl is substituted by hydroxyl or up to trisubstituted by fluorine,
$R^{13}$ is hydrogen, fluorine or methyl,
or
$R^{12}$ and $R^{13}$ together with the carbon atoms to which they are bonded form a cyclopropyl ring,
or
$R^{13}$ and $R^{14A}$ together with the carbon atoms to which they are bonded form a cyclopropyl ring,
in which the cyclopropyl ring may be up to disubstituted by fluorine,
or
$R^{14A}$ and $R^{14B}$ together with the carbon atom to which they are bonded form a cyclopropyl ring,
in which the cyclopropyl ring may be up to disubstituted by fluorine,
where $R^{13}$, $R^{14A}$ and $R^{14B}$ are hydrogen when $R^{12}$ is not hydrogen,
where $R^{12}$ is hydrogen when one of the $R^{13}$, $R^{14A}$ and $R^{14B}$ substituents is not hydrogen,
and the solvates, salts and solvates of the salts thereof.

In the context of the present invention, preference is also given to compounds of the formula (I) in which $R^3$ is hydrogen, and the solvates, salts and solvates of the salts thereof.

In the context of the present invention, preference is also given to compounds of the formula (I) in which $R^4$ is hydrogen, fluorine or methyl, and the solvates, salts and solvates of the salts thereof.

In the context of the present invention, preference is also given to compounds of the formula (I) in which $R^5$ is hydrogen, and the solvates, salts and solvates of the salts thereof.

The invention further provides a process for preparing the inventive compounds of the formula (I), characterized in that

[A] a compound of the formula (II)

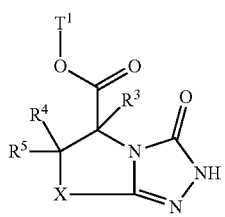

(II)

in which $A^1$, $R^1$, $R^3$, $R^4$, $R^5$ and X each have the definitions given above, and $T^1$ is $(C_1-C_4)$-alkyl or benzyl, is reacted in an inert solvent in the presence of a suitable base with a compound of the formula (III)

(III)

in which $A^1$ is —$CH_2$—, —$CH(CH_3)$—, —$CH_2CH_2$—, $\#^5$—$CH_2CH(CH_3)$—*, $\#^5$—$CH_2C(CH_3)_2$—*, $\#^5$—$CH_2CHF$—* or $\#^5$—$CH_2CF_2$—* where $\#^5$ marks the bond to the nitrogen atom of the 5-oxo-4,5-dihydro-1H-1,2,4-triazol-1-yl ring, where *** marks the bond to the $R^1$ group, $R^1$ has the definitions given above, and $X^1$ is a suitable leaving group, especially chlorine, bromine, iodine, mesylate {(methylsulphonyl)oxy}, triflate {[(trifluoromethyl)sulphonyl]oxy}, nonaflate {[(nonafluorobutyl)sulphonyl]oxy}, nosylate {[(4-nitrophenyl)sulphonyl]oxy} or tosylate {[(4-methylphenyl)sulphonyl]oxy}, to give a compound of the formula (IV)

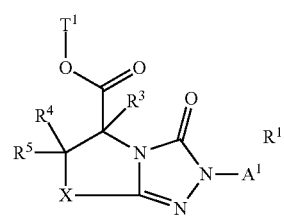

(IV)

in which $A^1$, $R^1$, $R^3$, $R^4$, $R^5$, X and $T^1$ each have the definitions given above, then the latter are converted by removing the "$T^1$" group in an inert solvent in the presence of a suitable base or acid to a compound of the formula (V)

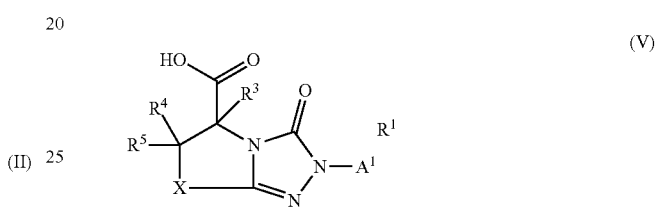

(V)

in which $A^1$, $R^1$, $R^3$, $R^4$, $R^5$ and X each have the definitions given above, and then the latter is reacted in an inert solvent under amide coupling conditions with an amine of the formula (VI-A) or (VI-B)

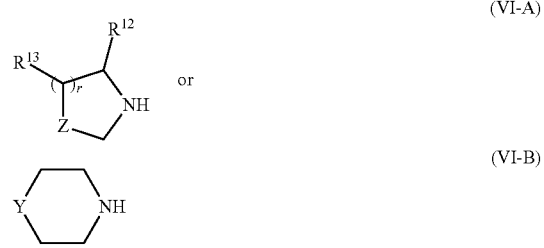

(VI-A)

(VI-B)

in which Y, Z, $R^{12}$ and $R^{13}$ each have the definitions given above, and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof, or

[B] a compound of the formula (II)

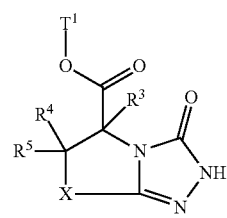

(II)

in which $A^1$, $R^1$, $R^3$, $R^4$, $R^5$ and X each have the definitions given above,
and
$T^1$ is ($C_1$-$C_4$)-alkyl or benzyl,
is reacted in an inert solvent in the presence of a suitable base with
an amine of the formula (VI-A) or (VI-B)

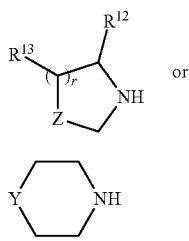

(VI-A)

or (VI-B)

in which Y, Z, $R^{12}$ and $R^{13}$ each have the definitions given above,
to give a compound of the formula (XXIII-A) or (XXIII-B)

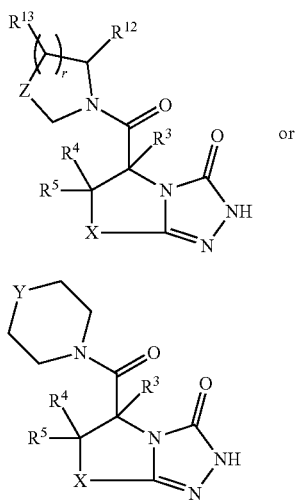

(XXIII-A)

or (XXIII-B)

in which $R^3$, $R^4$, $R^5$, $R^{12}$, $R^{13}$, X, Y and Z each have the definitions given above,
the latter is reacted in an inert solvent in the presence of a suitable base with a compound of the formula (III)

(III)

in which
$A^1$ is —$CH_2$—, —$CH(CH_3)$—, —$CH_2CH_2$—, #⁵—$CH_2CH(CH_3)$—*, #⁵—$CH_2C(CH_3)_2$—*, #⁵—$CH_2CHF$—* or #⁵—$CH_2CF_2$—*
where #⁵ marks the bond to the nitrogen atom of the 5-oxo-4,5-dihydro-1H-1,2,4-triazol-1-yl ring, where *** marks the bond to the $R^1$ group,
$R^1$ has the definitions given above,
and
$X^1$ is a suitable leaving group, especially chlorine, bromine, iodine, mesylate {(methylsulphonyl)oxy}, triflate {[(trifluoromethyl)sulphonyl]oxy}, nonaflate {[(nonafluorobutyl)sulphonyl]oxy}, nosylate {[(4-nitrophenyl)sulphonyl]oxy} or tosylate {[(4-methylphenyl)sulphonyl]oxy},
and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof,
or
[C] a compound of the formula (VII)

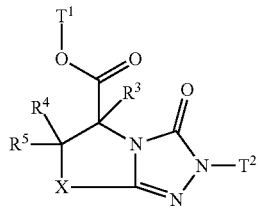

(VII)

in which $R^3$, $R^4$, $R^5$ and X each have the definitions given above and
$T^1$ is ($C_1$-$C_4$)-alkyl or benzyl,
$T^2$ is 4-methoxybenzyl, benzyl, allyl, β-(trimethylsilyl)ethoxymethyl (SEM), methoxymethyl (MOM) or benzyloxymethyl,
is converted by hydrolysis of the ester group in an inert solvent in the presence of a suitable base or acid to a compound of the formula (VIII)

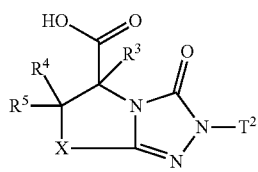

(VIII)

in which $R^3$, $R^4$, $R^5$, $T^2$ and X each have the definitions given above,
then the latter is reacted in an inert solvent under amide coupling conditions with an amine of the formula (VI-A)

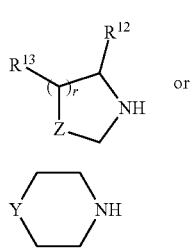

(VI-A)

or (VI-B)

in which Z, $R^{12}$ and $R^{13}$ each have the definitions given above, to give a compound of the formula (IX-A) or (IX-B)

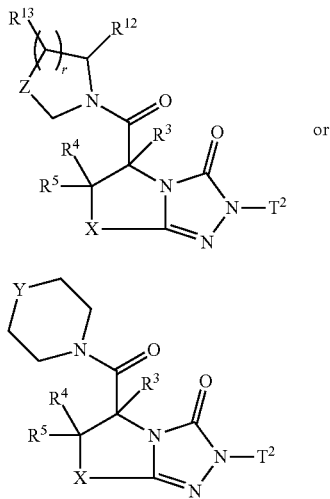

(IX-A)

(IX-B)

in which $R^3$, $R^4$, $R^5$, $R^{12}$, $R^{13}$, $T^2$, X, Y and Z each have the definitions given above, the protecting group "$T^2$" is removed in an inert solvent in the presence of a suitable base or acid or optionally in the presence of a suitable palladium catalyst and the resulting compound of the formula (X-A) or (X-B)

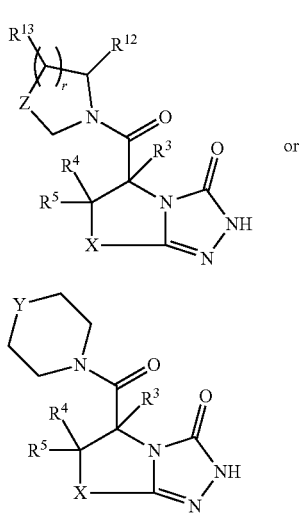

(X-A)

(X-B)

in which $R^3$, $R^4$, $R^5$, $R^{12}$, $R^{13}$, X, Y and Z each have the definitions given above, is reacted in an inert solvent in the presence of a suitable base with a compound of the formula (III)

(III)

in which
$A^1$ is —$CH_2$—, —$CH(CH_3)$—, —$CH_2CH_2$—, $\#^5$—$CH_2CH(CH_3)$—*, $\#^5$—$CH_2C(CH_3)_2$—*, $\#^5$—$CH_2CHF$—* or $\#^5$—$CH_2CF_2$—* where $\#^5$ marks the bond to the nitrogen atom of the 5-oxo-4,5-dihydro-1H-1,2,4-triazol-1-yl ring, where *** marks the bond to the $R^1$ group, $R^1$ has the definitions given above, and $X^1$ is a suitable leaving group, especially chlorine, bromine, iodine, mesylate {(methylsulphonyl)oxy}, triflate {[(trifluoromethyl)sulphonyl]oxy}, nonaflate {[(nonafluorobutyl)sulphonyl]oxy}, nosylate {[(4-nitrophenyl)sulphonyl]oxy} or tosylate {[(4-methylphenyl)sulphonyl]oxy}, and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof.

The compounds of the formulae (III), (VI-A) and (VI-B) are commercially available or known from the literature, or can be prepared in analogy to processes known from the literature.

Inert solvents for the process step (II)+(III)→(IV) or (X)+(III)→(I) are, for example, halohydrocarbons such as dichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, n-propanol, isopropanol, n-butanol, 2,2,2-trifluoroethanol, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is equally possible to use mixtures of the solvents mentioned. Preference is given to using dimethylformamide or acetonitrile.

Suitable bases for the process step (II)+(III)→(IV) or (X)+(III)→(I) are the customary inorganic or organic bases. These preferably include lithium, sodium, potassium, alkali metal hydroxides, for example lithium hydroxide, sodium hydroxide or potassium hydroxide, alkoxides such as potassium tert-butoxide, methoxide, ethoxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, or organic amines such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using caesium carbonate.

The reaction is generally conducted within a temperature range from 0° C. to +120° C., preferably at +20° C. to +80° C., most preferably at room temperature, optionally in a microwave. The reaction can be conducted at standard, elevated or reduced pressure (for example from 0.5 to 5 bar).

The hydrolysis of the esters in the compounds (IV) to compounds of the formula (V) or in the compounds (VII) to compounds of the formula (VIII) is effected by customary methods, by treating the esters in inert solvents with acids or bases, in which latter case the salts formed at first are converted to the free carboxylic acids by treating with acid.

In the case of the tert-butyl esters, the ester hydrolysis is preferably effected with acids.

Suitable inert solvents for these reactions are water or the organic solvents customary for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is equally possible to use mixtures of the solvents mentioned. In the case of a basic ester hydrolysis, preference is given to using mixtures of water with dioxane, tetrahydrofuran, methanol and/or ethanol and/or n-propanol. In the case of the reaction with trifluoroacetic acid, preference is given to using dichloromethane, and in the case of the reaction with hydrogen chloride preference is given to using tetrahydrofuran, diethyl ether, dioxane or water.

Suitable bases are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally effected within a temperature range from 0° C. to +100° C., preferably at +0° C. to +50° C., more preferably at room temperature.

These conversions can be performed at atmospheric, elevated or reduced pressure (for example from 0.5 to 5 bar). In general, standard pressure is employed in each case.

Inert solvents for the amide coupling (V)+(VI-A)→(I) or (V)+(VI-B)→(I) or (VIII)+(VI-A)→(IX-A) or (VIII)+(VI-B)→(IX-B) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable condensing agents for the amide formation v or (VIII)+(VI-A)→(IX-A) or (VIII)+(VI-B)→(IX-B) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N' ethylcarbodiimide hydrochloride (EDC), phosgene derivatives such as N,N'carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline or isobutyl chloroformate, propanephosphonic anhydride (T3P), 1-chloro-N,N,2-trimethylprop-1-ene-1-amine, diethyl cyanophosphonate, bis(2-oxo-3-oxazolidinyl)phosphoryl chloride, benzotriazol-1-yloxytris(dimethylamino) phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium hydrogencarbonate or potassium hydrogencarbonate, or organic bases such as trialkylamines, for example triethylamine, N-methylmorpholine, N-methylpiperidine or N,N-diisopropylethylamine. Preference is given to using HATU.

The condensation (V)+(VI-A)→(I) or (V)+(VI-B)→(I) or (VIII)+(VI-A)→(IX-A) or (VIII)+(VI-B)→(IX-B) is generally conducted within a temperature range from −20° C. to +100° C., preferably at 0° C. to +60° C. The conversion can be effected at standard, elevated or reduced pressure (for example from 0.5 to 5 bar). In general, standard pressure is employed.

Alternatively, the carboxylic acid of the formula (V) or (VIII) can also first be converted to the corresponding carbonyl chloride and the latter can then be reacted directly or in a separate reaction with an amine of the formula (VI) to the compounds of the invention. The formation of carbonyl chlorides from carboxylic acids is effected by the methods known to those skilled in the art, for example by treatment with thionyl chloride or oxalyl chloride, in the presence of a suitable base, for example in the presence of pyridine, and optionally with addition of dimethylformamide, optionally in a suitable inert solvent.

The detachment of the protecting group in the reaction step (IX)-(X) is effected here by standard methods known from protecting group chemistry, preferably by reaction with acid, for example trifluoroacetic acid in dichloromethane, by base, for example ammonia in methanol, hydrogenolysis in the presence of a palladium catalyst, for example palladium on activated charcoal, in an inert solvent, for example ethanol or ethyl acetate, 2,3-dichloro-5,6-dicyano-1,4-benzoquinone (DDQ) or ammonium cerium(IV) nitrate (CAN) [see also, for example, T. W. Greene and P. G. M. Wuts, *Protective Groups in Organic Synthesis*, Wiley, New York, 1999].

Inert solvents for the reaction (II)+(VI-A)→(XXIII-A) or (II)+(VI-B)→(XXIII-B) are, for example, pyrrolidine, toluene, acetonitrile, tetrahydrofuran or dichloromethane. Preference is given to using pyrrolidine.

Reaction (II)+(VI-A)→(XXIII-A) or (II)+(VI-B)→(XXIII-B) is generally conducted within a temperature range from 20° C. to +200° C., preferably at 80° C. to +200° C. The conversion can be effected at standard or elevated pressure (for example from 1 to 5 bar). In general, standard pressure is employed.

The compounds of the formula (II) in which X is #$^2$—$CR^6R^7$—$CR^8R^9$—** and $R^3$, $R^7$ and $R^9$ are hydrogen can be prepared by reacting a compound of the formula (XI)

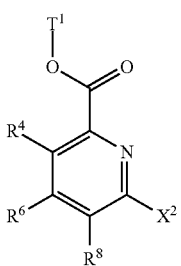

in which
T$^1$ is (C$_1$-C$_4$)-alkyl or benzyl,
X$^2$ is fluorine, chlorine, bromine or iodine,
and R$^4$, R$^6$ and R$^8$ each have the definitions given above,
in an inert solvent in the presence of a suitable base and optionally of a palladium catalyst with a compound of the formula XII

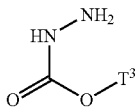
(XII)

in which
T$^3$ is benzyl or tert-butyl,
to give a compound of the formula (XIII)

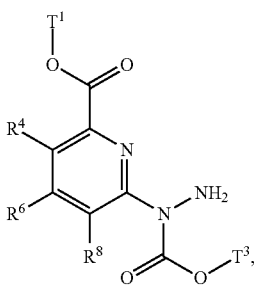
(XIII)

in which
R$^4$, R$^6$, R$^8$, T$^1$ and T$^3$ each have the definitions given above,
the protecting group T$^3$ is detached in a suitable inert solvent by hydrogenolysis in the presence of a palladium catalyst and the resulting compound of the formula (XIV)

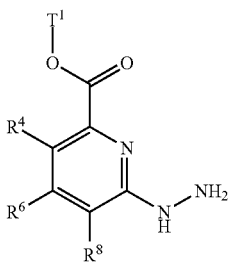
(XIV)

in which
R$^4$, R$^6$, R$^8$ and T$^1$ each have the definitions given above,
is cyclized in a suitable solvent with a phosgene derivative of the formula (XV)

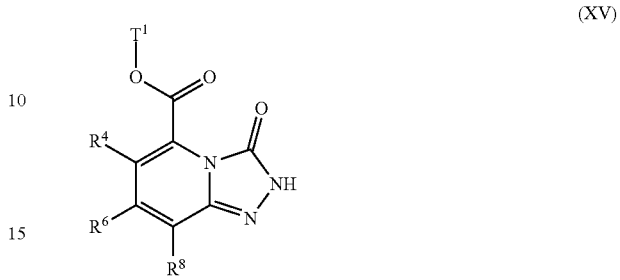
(XV)

in which R$^4$, R$^6$, R$^8$ and T$^1$ each have the definitions given above,
and then hydrogenated in a suitable solvent in the presence of a palladium catalyst in a hydrogen atmosphere,
and the resulting compounds of the formulae (II) are optionally converted with the appropriate (i) solvents and/or (ii) acids or bases to the solvates, salts and/or solvates of the salts thereof.

The compounds of the formula (II) or (IV) in which X is #$^2$—CR$^6$R$^7$—CR$^8$R$^9$—** can be prepared by reacting a compound of the formula (XVI)

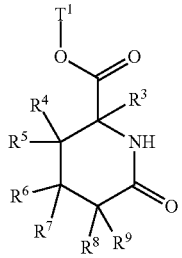
(XVI)

in which T$^1$ is (C$_1$-C$_4$)-alkyl or benzyl,
and R$^3$, R$^4$, R$^5$, R$^6$, R$^7$, R$^8$ and R$^9$ each have the definitions given above,
in a suitable solvent in the presence of trimethyloxonium tetrafluoroborate with a compound of the formula (XVII-A) or (XVII-B)

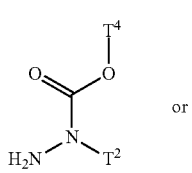
(XVII-A)

or

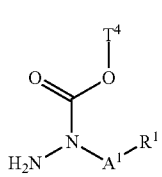
(XVII-B)

in which
T$^2$ is 4-methoxybenzyl,
T$^4$ is methyl or ethyl, and $A^1$ and $R^1$ each have the definitions given above,
to give a compound of the formula (XVIII-A) or (XVIII-B)

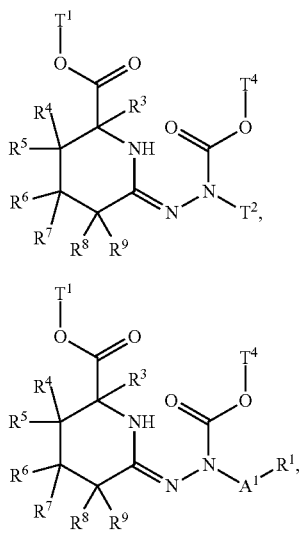

(XVIII-A)

(XVIII-B)

in which
$A^1$, $R^1$, $R^3$, $R^4$, $R^5$, $R^6$, $R^7$, $R^8$, $R^9$, $T^1$, $T^2$ and $T^4$ each have the definitions given above,
the latter are cyclized in a suitable solvent to give a compound of the formula (XIX-A) or (XIX-B)

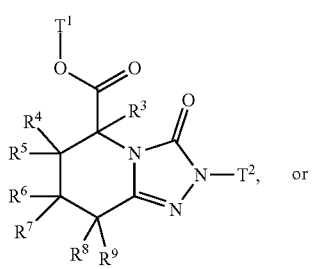

(XIX-A)

(XIX-B)

in which $A^1$, $R^1$, $R^3$, $R^4$, $R^5$, $R^6$, $R^7$, $R^8$, $R^9$, $T^1$ and $T^2$ each have the definitions given above,
and, for the compounds of the formula (XIX-A), the $T^2$ protecting group is then removed in an inert solvent in the presence of a suitable acid,
and the resulting compounds of the formulae (II) are optionally converted with the appropriate (i) solvents and/or (ii) acids or bases to the solvates, salts and/or solvates of the salts thereof.

The compounds of the formula (XIX-B) correspond to the compounds of the formula (IV) when, in formula (IV), X is $\#^2$—$CR^6R^7$—$CR^8R^9$—$**$.

The compounds of the formula (VII) correspond to the compounds of the formula (XIX) when, in formula (VII), X is $\#^2$—$CR^6R^7$—$CR^8R^9$—$**$.

The compounds of the formula (II) in which X is —$CR^6R^7$— can be prepared by reacting a compound of the formula (XX)

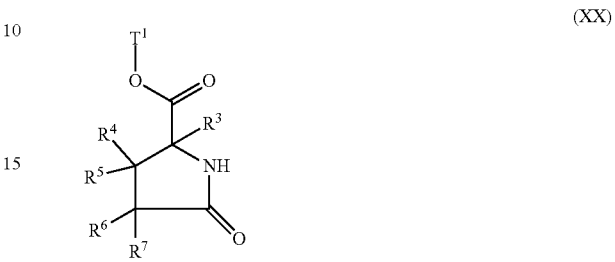

(XX)

in which $T^1$ is $(C_1$-$C_4)$-alkyl or benzyl,
and $R^3$, $R^4$, $R^5$, $R^6$ and $R^7$ each have the definitions given above,
in a suitable solvent, first in the presence of trimethyloxonium tetrafluoroborate and then with a compound of the formula (XXI)

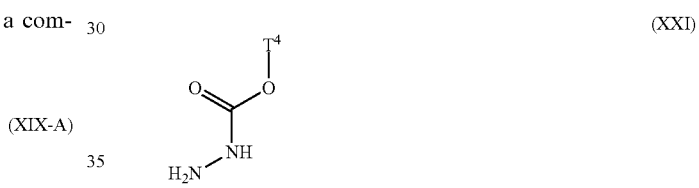

(XXI)

in which
$T^4$ is methyl, ethyl, tert-butyl or benzyl,
to give a compound of the formula (XXII)

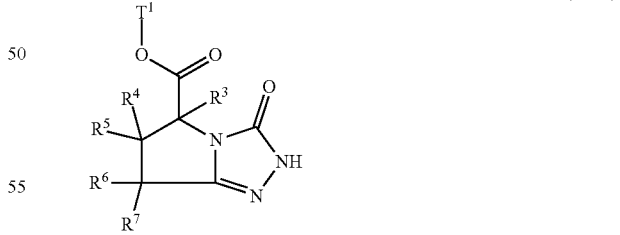

(XXII)

in which $R^3$, $R^4$, $R^5$, $R^6$, $R^7$ and $T^1$ each have the definitions given above.

The compounds of the formulae (XI), (XII), (XVII-A), (XVII-B), (XX) and (XXI) are commercially available or known from the literature, or can be prepared in analogy to literature processes.

The processes described are illustrated by way of example by the schemes below (Schemes 1-3):

Scheme 1

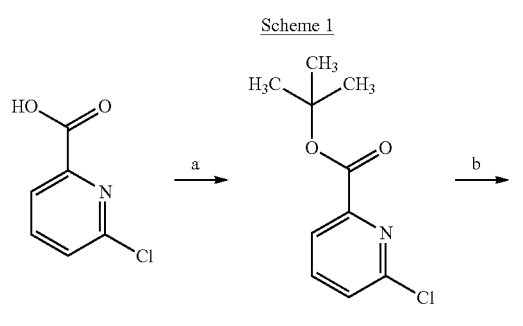

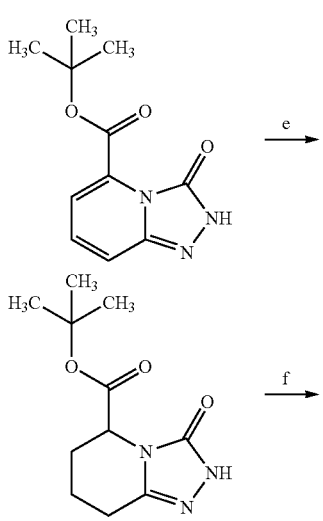

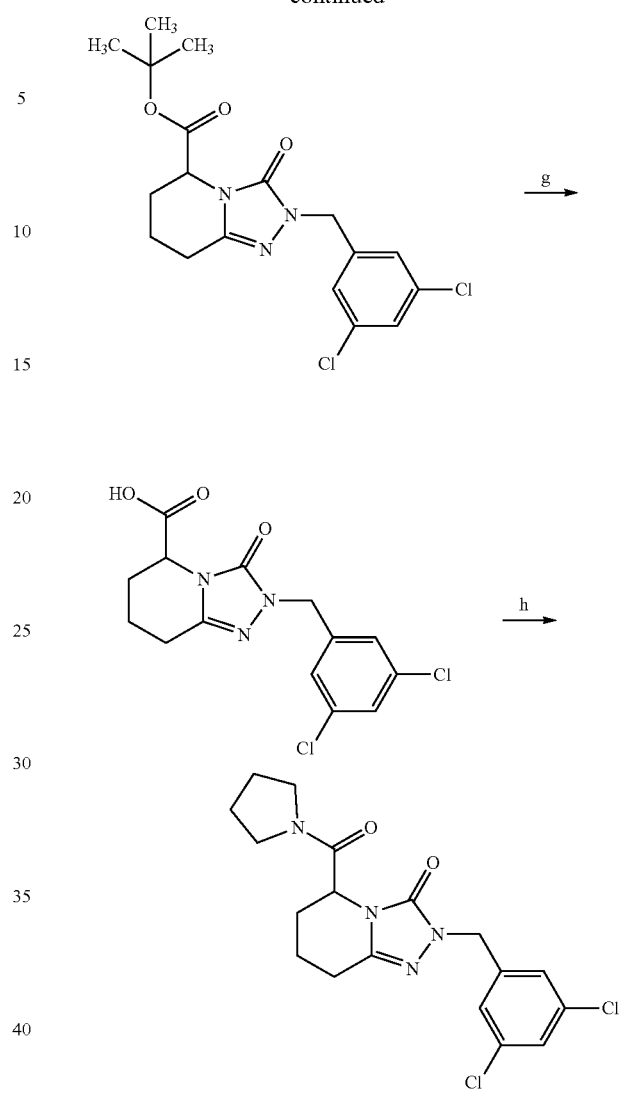

a) tert-butanol, pyridine, p-toluenesulphonyl chloride, RT; b) benzyl carbazate, caesium carbonate, 1,1'-bis(diphenylphosphino)ferrocene, bis(dibenzylideneacetone)palladium(0) in toluene 80° C.; c) Pd/C 5%, 1 bar H₂ in toluene/methanol, RT; d) carbonyldiimidazole, THF, RT; e) Pd/C 5%, 34.5 bar H₂ in toluene/methanol, RT; f) caesium carbonate, 1-(bromomethyl)-3,5-dichlorobenzene in acetonitrile, RT; g) HCl in 1,4-dioxane, RT; h) HATU, triethylamine, pyrrolidine in THF, RT.

Scheme 2

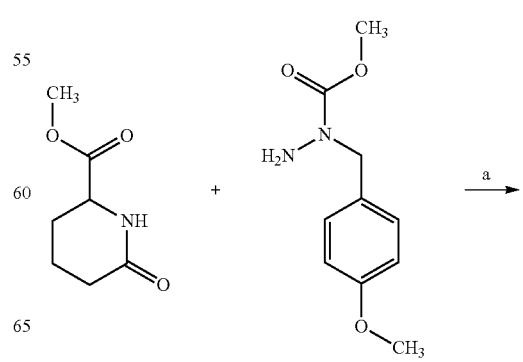

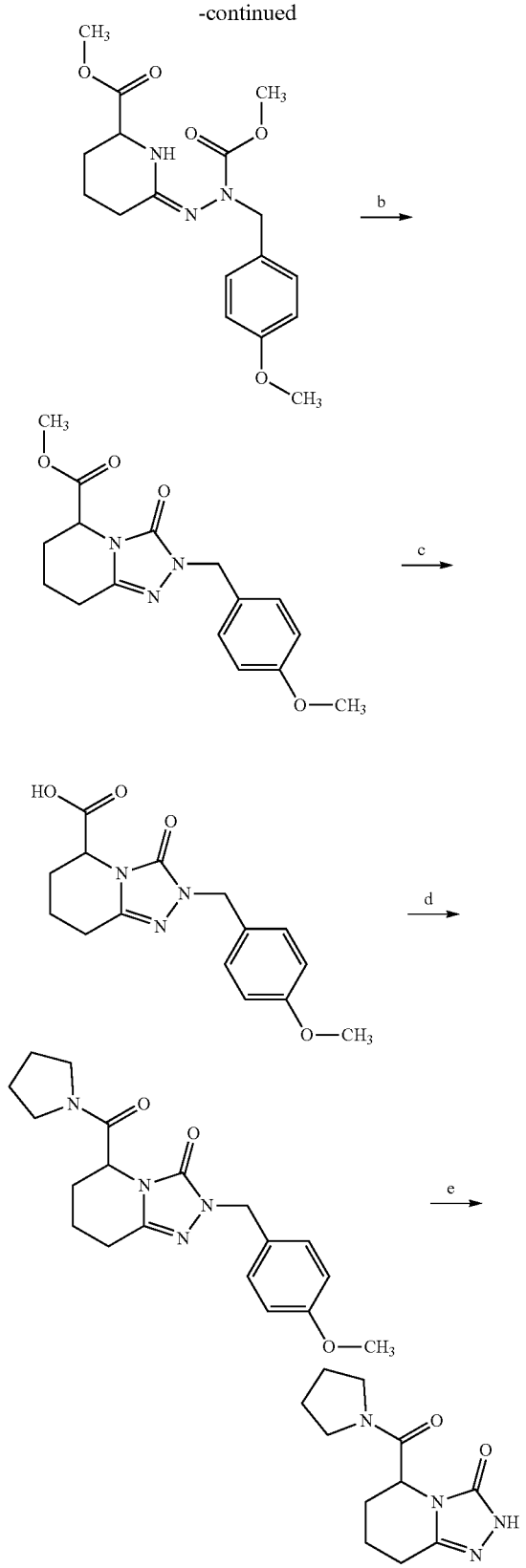

a) 1. methyl (5RS)-6-oxopiperidine-2-carboxylate, trimethyloxonium tetrafluoroborate, dichloromethane, RT; 2. methyl 1-(4-methoxybenzyl)hydrazinecarboxylate, dichloromethane, RT: b) DMF, 150° C.; c) lithium hydroxide, THF/water, RT; d) HATU, triethylamine, pyrrolidine in DMF, RT; e) trifluoroacetic acid, 150° C.

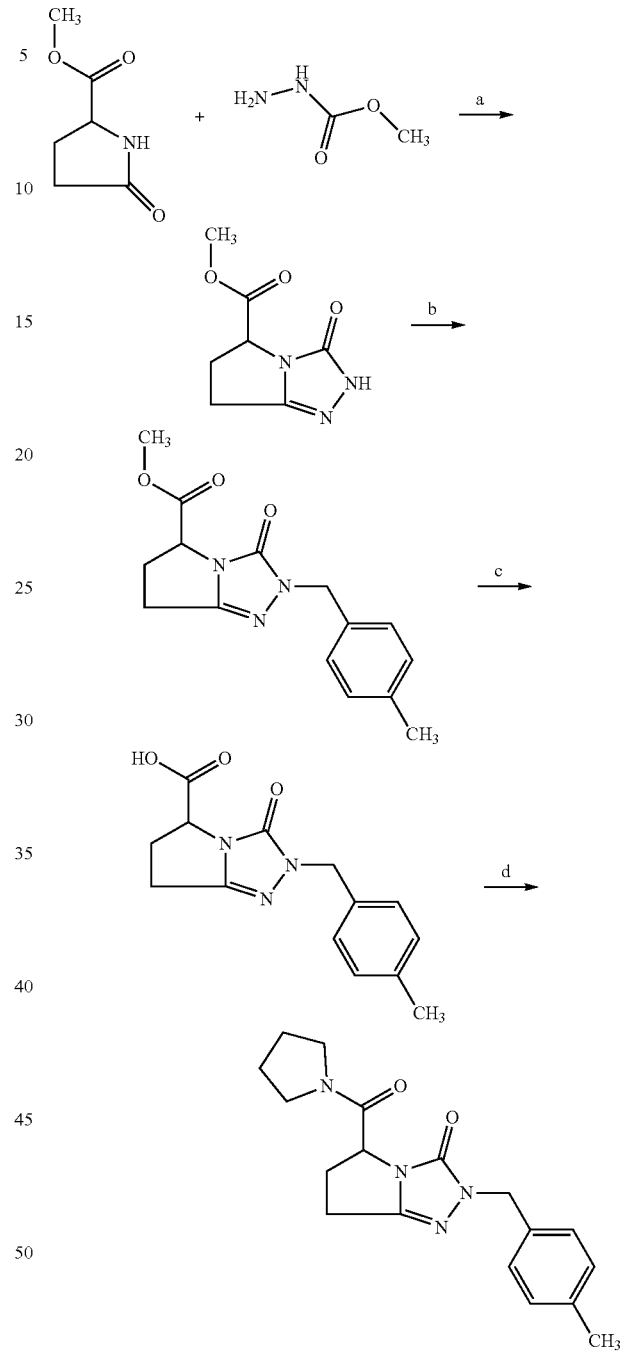

a) 1. trimethyloxonium tetrafluoroborate and methyl 5-oxo-L-prolinate in dichloromethane, RT; 2. methyl hydrazinoformate, RT; 3. DMF, 170° C.; b) caesium carbonate, 1-(bromomethyl)-4-methylbenzene in acetonitrile, RT; c) lithium hydroxide in water/THF, RT; d) HATU, diisopropylethylamine, pyrrolidine in DMF/dichloromethane, RT.

The process step (XI)+(XII)→(XIII) is effected in a solvent which is inert under the reaction conditions. Suitable solvents are, for example, ethers such as 1,4-dioxane, tetrahydrofuran, 2-methyltetrahydrofuran, diethyl ether, di-n-butyl ether, glycol dimethyl ether or diethylene glycol dimethyl ether, alcohols such as tert-butanol or amyl alcohols or other solvents such as dimethylformamide (DMF), dimethyl sulphoxide (DMSO), dimethylacetamide (DMA), toluene or acetonitrile. It is equally possible to use mixtures of the solvents mentioned. Preference is given to tert-butanol, 1,4-dioxane and toluene.

The process step (XI)+(XII)→(XIII) is effected in the presence of a suitable palladium catalyst. An example of a suitable palladium catalyst is palladium on activated charcoal, palladium(II) acetate, bis(dibenzylideneacetone)palladium(0), tetrakis(triphenylphosphine)palladium(0), bis(triphenylphosphine)palladium(II) chloride, bis(acetonitrile)palladium(II) chloride, [1,1'-bis(diphenylphosphino)ferrocene]dichloropalladium(II) and the corresponding dichloromethane complex, optionally in conjunction with additional phosphine ligands, for example 2,2'-bis(diphenylphosphino)-1,1'-binaphthyl (BINAP), (2-biphenyl)di-tert-butylphosphine, dicyclohexyl[2',4',6'-tris(1-methylethyl)biphenyl-2-yl]phosphine (XPhos), bis(2-phenylphosphinophenyl) ether (DPEphos) or 4,5-bis(diphenylphosphino)-9,9-dimethylxanthene (Xantphos) [cf., for example, Hassan J. et al., Chem. Rev. 2002, 102, 1359-1469], 2-(dicyclohexylphosphino)-3,6-dimethoxy-2',4',6'-triisopropyl-1,1'-biphenyl (BrettPhos), 2-dicyclohexylphosphino-2',6'-dimethoxybiphenyl (SPhos), 2-dicyclohexylphosphino-2',6'-diisopropoxybiphenyl (RuPhos), 2-(di-t-butylphosphino)-3-methoxy-6-methyl-2',4',6'-tri-i-propyl-1,1'-biphenyl (RockPhos) and 2-di-tert-butylphosphino-2',4',6'-triisopropylbiphenyl (tert-ButylXPhos). In addition, it is possible to use corresponding precatalysts such as chloro-[2-(dicyclohexylphosphino)-3,6-dimethoxy-2',4',6'-triisopropyl-1,1'-biphenyl][2-(2-aminoethyl)-phenyl]palladium(II) (BrettPhos precatalyst) [cf., for example, S. L. Buchwald et al., Chem. Sci. 2013, 4, 916], optionally in conjunction with additional phosphine ligands such as 2-(dicyclohexylphosphino)-3,6-dimethoxy-2',4',6'-triisopropyl-1,1'-biphenyl (BrettPhos). Preference is given to bis(dibenzylideneacetone)palladium(0) in combination with 4,5-bis(diphenylphosphino)-9,9-dimethylxanthene (Xantphos) and to chloro-[2-(dicyclohexylphosphino)-3,6-dimethoxy-2',4',6'-triisopropyl-1,1'-biphenyl][2-(2-aminoethyl)phenyl]palladium(II) (BrettPhos precatalyst).

The conversion (XI)+(XII)→(XIII) is effected in the presence of a suitable base. Suitable bases for this conversion are the customary inorganic or organic bases. These preferably include alkali metal or alkaline earth metal carbonates such as lithium carbonate, sodium carbonate, potassium carbonate, calcium carbonate or caesium carbonate, alkali metal or alkaline earth metal hydroxides such as sodium hydroxide, potassium hydroxide or barium hydroxide, alkali metal or alkaline earth metal phosphates such as potassium phosphate, alkali metal alkoxides such as sodium tert-butoxide or potassium tert-butoxide and sodium methoxide, alkali metal phenoxides such as sodium phenoxide, amides such as sodium amide, lithium bis(trimethylsilyl)amide, sodium bis(trimethylsilyl)amide or potassium bis(trimethylsilyl)amide or lithium diisopropylamide or organic amines such as 1,5-diazabicyclo[4.3.0]non-5-ene (DBN), 1,8-diazabicyclo[5.4.0]undec-7-ene (DBU). Preference is given to using caesium carbonate, potassium carbonate, sodium tert-butoxide or potassium tert-butoxide or lithium bis(trimethylsilyl)amide.

The process step (XI)+(XII)→(XIII) is generally conducted within a temperature range from 0° C. to +200° C., preferably at +10° C. to +150° C. The conversions can also be effected in closed vessels (microwave tubes) in the microwave. The conversion can be effected at standard, elevated or reduced pressure (for example from 0.5 to 5 bar). Operations generally take place at standard pressure or in closed vessels (microwave tubes) below or above the boiling point of the solvent used. Preference is given to reactions in closed vessels (microwave tubes), at temperatures above the boiling point of the solvent and under elevated pressure, with or without use of a microwave.

The detachment of the protecting group in the reaction step (XIII)-(XIV) is effected here by customary methods known from protecting group chemistry, preferably by reaction with acid, for example trifluoroacetic acid, hydrogenolysis in the presence of a palladium catalyst, for example palladium on activated charcoal, in an inert solvent, for example ethanol or ethyl acetate [see also, for example, T. W. Greene and P. G. M. Wuts, *Protective Groups in Organic Synthesis*, Wiley, New York, 1999].

Inert solvents for the process step (XIV)→(XV) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Examples of suitable phosgene derivatives used for the process step (XIV)-(XV) are, for example, N,N'-carbonyldiimidazole (CDI), trichloromethyl chlorocarbonate (diphosgene), bis(trichloromethyl) carbonate (triphosgene) or aryl chloroformate. Preference is given to using N,N'-carbonyldiimidazole (CDI).

The process step (XIV)-(XV) is generally conducted within a temperature range from −20° C. to +100° C., preferably at 0° C. to +60° C. The conversion can be effected at standard, elevated or reduced pressure (for example from 0.5 to 5 bar). In general, standard pressure is employed.

Inert solvents for the process step (XV)→(II) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, ethyl acetate, acetonitrile, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

The process step (XV)→(II) is generally conducted within a temperature range from −20° C. to +100° C., preferably at 0° C. to +60° C. The conversion can be effected at standard or elevated hydrogen pressure (for example from 1.0 to 100 bar). In general, elevated hydrogen pressure is employed.

Inert solvents for the process step (XVI)+(XVII-A)→(XVIII-A) or (XVI)+(XVII-B)→(XVIII-B) or (XXI)+(XXI)→(XXII) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane.

The process step (XVI)+(XVII-A)→(XVIII-A) or (XVI)+(XVII-B)→(XVIII-B) or (XXI)+(XXI)→(XXII) is generally conducted within a temperature range from −20° C. to +100° C., preferably at 0° C. to +60° C. The conversion can be effected at standard, elevated or reduced pressure (for example from 0.5 to 5 bar). In general, standard pressure is employed.

Inert solvents for the process step (XVI)+(XVII-A)→(XVIII-A) or (XVI)+(XVII-B)→(XVIII-B) or (XXI)+(XXI)→(XXII) are, for example, ethers such as dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to N,N-dimethylformamide.

The process step (XVI)+(XVII-A)→(XVIII-A) or (XVI)+(XVII-B)→(XVIII-B) is generally conducted within a temperature range from 20° C. to +100° C., preferably at 0° C. to +60° C. 20° C. to +250° C., preferably at 100° C. to +200° C. The conversion can be effected at standard, elevated or reduced pressure (for example from 0.5 to 5 bar). In general, standard pressure is employed.

Inert solvents for the process step (XVIII-A)→(XIX-A) or (XVIII-B)→(XIX-B) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N-dimethylpropyleneurea (DMPU) or N-methylpyrrolidone (NMP). It is likewise possible to use mixtures of the solvents mentioned. Preference is given to dichloromethane and acetonitrile.

The process step (XVIII-A)→(XIX-A) or (XVIII-B)→(XIX-B) is generally conducted within a temperature range from 20° C. to +250° C., preferably at 100° C. to +200° C. The conversion can be effected at standard, elevated or reduced pressure (for example from 0.5 to 5 bar). In general, standard pressure is employed.

Any hydroxyl, amino and/or amido groups present in the starting compounds of formulae (II) and (VII) can, if appropriate or necessary, also be used in temporarily protected form and then released again at the end of the particular reaction sequence [with regard to the suitability, introduction and removal of such protecting groups see, for example, T. W. Greene and P. G. M. Wuts, *Protective Groups in Organic Synthesis*, Wiley, New York, 1999].

Further compounds of the invention can optionally also be prepared by conversions of functional groups of individual substituents, especially those listed for $R^3$, $R^4$, $R^5$, $R^6$, $R^7$, $R^8$, $R^9$, proceeding from the compounds of the formula (I) obtained by above processes. These conversions are conducted by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether hydrolysis, formation of carbonamides, dehydrations, and introduction and removal of temporary protective groups.

Detailed procedures can also be found in the Experimental, in the section on the preparation of the starting compounds and intermediates.

ELUCIDATIONS FOR THE FIGURES

FIG. 1: Example 237 in a complex with pig PREP.
FIG. 2: Example 358 in a complex with pig PREP.
FIG. 3: Example 454 in a complex with pig PREP.
FIG. 4: Example 108 in a complex with pig PREP.
FIG. 5: Example 113 in a complex with pig PREP.
FIG. 6: Example 157 in a complex with pig PREP.
FIG. 7: Example 026 in a complex with pig PREP.

The compounds of the invention have valuable pharmacological properties and can be used for prevention and treatment of diseases in humans and animals.

The compounds of the invention are potent, chemically stable inhibitors of human prolyl endopeptidase (PREP, PE, prolyl oligopeptidase, POP) and are therefore suitable for treatment and/or prevention of disorders and pathological processes, especially those in which PREP or the PREP product PGP (proline-glycine-proline) is involved in the course of an infectious or non-infectious inflammation event and/or tissue or vessel reconstruction.

In the context of the present invention, these especially include disorders of the respiratory pathway and the lung, such as chronic obstructive pulmonary disease (COPD), cystic fibrosis (mucoviscidosis, CF), asthma and the group of interstitial lung diseases (ILDs), and disorders of the cardiovascular system such as arteriosclerosis and myocarditis.

The forms of COPD especially include pulmonary emphysema induced by cigarette smoke, chronic bronchitis (CB), pulmonary hypertension in COPD (PH-COPD), bronchiectasis (BE) and combinations thereof, especially in acute exacerbating stages of the disease (AE-COPD).

The forms of asthma include asthmatic disorders of different severity with intermittent or persistent character, such as refractory asthma, bronchial asthma, allergic asthma, intrinsic asthma, extrinsic asthma and medicament- or dust-induced asthma.

The group of interstitial lung diseases (ILDs) includes idiopathic pulmonary fibrosis (IPF), pulmonary sarcoidosis and acute interstitial pneumonia, non-specific interstitial pneumonia, lymphoid interstitial pneumonia, respiratory bronchiolitis with interstitial pulmonary disorder, cryptogenic organizing pneumonia, desquamative interstitial pneumonia and non-classifiable idiopathic interstitial pneumonia, and also granulomatous interstitial pulmonary disorders, interstitial pulmonary disorders of known cause and other interstitial pulmonary disorders of unknown cause.

The compounds of the invention can also be used for the treatment and/or prevention of further disorders of the respiratory pathways and of the lung, for example of pulmonary arterial hypertension (PAH) and other forms of pulmonary hypertension (PH), of bronchiolitis obliterans syndrome (BOS), of acute respiratory distress syndrome (ARDS), of acute lung damage (ALI), alpha-1 antitrypsin deficiency (AATD) and cystic fibrosis (CF), of various forms of bronchitis (chronic bronchitis, infectious bronchitis, eosinophilic bronchitis), of bronchiectasis, pneumonia, farmer's lung and related diseases, cough- and cold-type diseases having infectious and non-infectious causes (chronic inflammatory cough, iatrogenic cough), mucous membrane inflammation (including medicamentous rhinitis, vasomotor rhinitis and seasonally dependent allergic rhinitis, for example hay fever), and polyps.

The compounds of the invention can additionally be used for treatment and/or prevention of cardiovascular disorders, for example high blood pressure (hypertension), heart failure, coronary heart disorders, stable and unstable angina pectoris, renal hypertension, peripheral and cardiovascular disorders, arrhythmias, rhythm disorders of the atria and ventricles, and conduction disorders, for example atrioventricular blocks of degrees I-III, supraventricular tachycardia, atrial fibrillation, atrial flutter, ventricular fibrillation, ventricular flutter, ventricular tachycardia, Torsade de pointes tachycardia, atrial and ventricular extrasystoles, AV-junctional extrasystoles, sick sinus syndrome, syncopes, AV nodal reentrant tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, and also for treatment and/or prevention of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention can also be used for treatment of disorders of the female reproductive system, such as uterine myoma, endometriosis, dysmenorrhoea and premature contractions. In addition, they are suitable for prophylaxis or treatment of hirsutism or hypertrichosis.

In addition, the compounds of the invention have antiinflammatory action and can therefore be used as antiinflammatory agents for the treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, osteoarthritis, inflammatory disorders of the central nervous system, multiple sclerosis, infammatory skin disorders and inflammatory eye disorders.

The compounds of the invention are also suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphoea, keloids, hypertrophic scarring, naevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for ageing or keratinized skin.

The compounds of the invention can also be used for treatment and/or prevention of anaemias such as haemolytic anaemias, in particular haemoglobinopathies such as sickle cell anaemia and thalassaemias, megaloblastic anaemias, iron deficiency anaemias, anaemias owing to acute blood loss, displacement anaemias and aplastic anaemias.

Moreover, the compounds of the invention are suitable for treatment of cancers, for example skin cancer, brain tumours, breast cancer, bone marrow tumours, leukaemias, liposarcomas, carcinomas of the gastrointestinal tract, of the liver, the pancreas, the lung, the kidney, the ureter, the prostate and the genital tract and also of malignant tumours of the lymphoproliferative system, for example Hodgkin's and non-Hodgkin's lymphoma.

In addition, the compounds of the invention can be used for treatment and/or prevention of arteriosclerosis, impaired lipid metabolism and dyslipidaemias (hypolipoproteinaemia, hypertriglyceridaemias, hyperlipidaemia, combined hyperlipidaemias, hypercholesterolaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestation diabetes, hyperinsulinaemia, insulin resistance, glucose intolerance and diabetic sequelae, such as retinopathy, nephropathy and neuropathy), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, coeliac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, for example dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, for example HPV, HCMV, HIV, SARS), of disorders of the skeletal bone and the joints and also the skeletal muscle (various forms of arthritis, for example arthritis alcaptonurica, arthritis ankylosans, arthritis dysenterica, arthritis exsudativa, arthritis fungosa, arthritis gonorhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, haemophilic arthritis, juvenile chronic arthritis, rheumatoid arthritis and metastatic arthritis, and also Still syndrome, Felty syndrome, Sjörgen syndrome, Clutton syndrome, Poncet syndrome, Pott syndrome and Reiter syndrome, various forms of arthropathy, for example arthropathia deformans, arthropathia neuropathica, arthropathia ovaripriva, arthropathia psoriatica and arthropathia tabica, systemic scleroses, various forms of inflammatory myopathies, for example myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also Günther syndrome and Münchmeyer syndrome), of inflammatory changes to the arteries (various forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, lepra, Sezary syndrome and paraneoplastic syndrome, in the event of rejection reactions after organ transplants and for wound healing and angiogenesis particularly in the case of chronic wounds.

Because of their profile of biochemical and pharmacological properties, the compounds of the invention are especially suitable for treatment and/or prevention of inflammatory lung disorders, particularly of chronic-obstructive lung disease (COPD), of pulmonary emphysema, of chronic bronchitis, of bronchiectasis, of pulmonary hypertension in COPD (PH-COPD), of acute exacerbation in COPD, of cystic fibrosis (mucoviscidosis, CF), of asthma, and idiopathic pulmonary fibrosis (IPF), of bronchiolitis obliterans syndrome (BOS), of arteriosclerosis, of myocarditis, and of inflammatory skin and eye disorders or inflammatory disorders of the internal organs.

Because of their profile of biochemical and pharmacological properties, the compounds of the invention are very particularly suitable for treatment and/or prevention of inflammatory lung disorders, particularly of chronic-obstructive lung disease (COPD), of pulmonary emphysema, of chronic bronchitis, of bronchiectasis, of pulmonary hypertension in COPD (PH-COPD), of acute exacerbation in COPD, of cystic fibrosis (mucoviscidosis, CF), of asthma, and idiopathic pulmonary fibrosis (IPF) and of bronchiolitis obliterans syndrome (BOS).

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;

NO- and haem-independent activators of soluble guanylate cyclase (sGC), such as in particular the compounds described in WO 01/19355, WO 01/19776, WO 01/19778, WO 01/19780, WO 02/070462 and WO 02/070510;

NO-independent but haem-dependent stimulators of soluble guanylate cyclase (sGC), such as in particular riociguat and the compounds described in WO 00/06568, WO 00/06569, WO 02/42301, WO 03/095451, WO 2011/147809, WO 2012/004258, WO 2012/028647 and WO 2012/059549;

prostacyclin analogues and IP receptor agonists, by way of example and with preference iloprost, beraprost, treprostinil, epoprostenol or selexipag;

edothelin receptor antagonists, by way of example and with preference bosentan, darusentan, ambrisentan or sitaxsentan;

compounds which inhibit human neutrophil elastase (HNE), by way of example and with preference sivelestat or DX-890 (reltran);

compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptor, by way of example and with preference antagonists of the 5-HT$_{2B}$ receptor such as PRX-08066;

antagonists of growth factors, cytokines and chemokines, by way of example and with preference antagonists of TGF-β, CTGF, IL-1, IL-4, IL-5, IL-6, IL-8, IL-13 and integrins;

Rho kinase-inhibiting compounds, by way of example and with preference fasudil, Y-27632, SLx-2119, BF-66851, BF-66852, BF-66853, KI-23095 or BA-1049;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

anti-obstructive agents as used, for example, for treatment of chronic obstructive pulmonary disease (COPD) or bronchial asthma, by way of example and with preference from the group of the inhalatively or systemically administered agonists of the β-adrenergic receptor (β-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, pirfenidone or etanercept;

antifibrotic agents, by way of example and with preference adenosine A2b receptor antagonists, sphingosine-1-phosphate receptor 3 (S1P3) antagonists, autotaxin inhibitors, lysophosphatidic acid receptor 1 (LPA-1) and lysophosphatidic acid receptor 2 (LPA-2) antagonists, lysyl oxidase (LOX) inhibitors, lysyl oxidase-like 2 inhibitors, CTGF inhibitors, IL-13 antagonists, $α_vβ_6$-integrin antagonists, TGF-β antagonists, inhibitors of the Wnt signalling pathway or CCR2 antagonists;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, α-receptor blockers, β-receptor blockers, mineralocorticoid receptor antagonists and also the diuretics;

lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-α, PPAR-γ and/or PPAR-δ agonists, cholesterol absorption inhibitors, lipase inhibitors, polymeric bile acid adsorbents, bile acid reabsorption inhibitors and lipoprotein(a) antagonists; and/or chemotherapeutics like those employed, for example, for the therapy of neoplasms in the lung or other organs.

In a preferred embodiment of the invention, the compounds of the invention are administered in combination with a β-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, α-receptor blockers, β-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an $\alpha_1$-receptor blocker, by way of example and with preference prazosin.

In a preferred embodiment of the invention, the compounds of the invention are administered in combination with a β-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan, embursaran, irbesartan, olmesartan, eprosartan or azilsartan or a dual angiotensin AII antagonist/NEP inhibitor, for example and with preference LCZ696 (valsartan/sacubitril).

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-α, PPAR-γ and/or PPAR-δ agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-γ agonist, by way of example and with preference pioglitazone or rosiglitazone.

In a preferred embodiment of the invention, the compounds of the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of PDE 5 inhibitors, sGC activators, sGC stimulators, prostacyclin analogues, IP receptor agonists, endothelin antagonists, compounds that inhibit the signal transduction cascade and pirfenidone.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers, dosage aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and intrapulmonary (inhalative) administration.

The compounds of the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount is generally about 0.1 to 50 mg per inhalation.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

The present invention further provides medicaments pharmaceutical compositions which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, vaginal, dermal, transdermal, conjunctival or otic route, or as an implant or stent.

The compounds of the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous, intravitreal or intraperitoneal route). Administration forms suitable for parenteral administration include preparations for injection and infusion in the form of solutions, suspensions, emulsions, lyophilizates or sterile powders.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, eye drops, eye ointments, eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (for example patches), milk, pastes, foams, dusting powders, implants or stents.

The compounds of the invention can be converted to the administration forms mentioned. This can be accomplished in a manner known per se by mixing with pharmaceutically suitable excipients. These excipients include fillers and carriers (for example cellulose, microcrystalline cellulose, for example Avicel®, lactose, mannitol, starch, calcium phosphates, for example Di-Cafos®), ointment bases (for example vaseline, paraffins, triglycerides, waxes, wool wax, wool wax alcohols, lanolin, hydrophilic ointment, polyethylene glycols), suppository bases (for example polyethylene glycols, cocoa butter, hard fat), solvents (e.g. water, ethanol, isopropanol, glycerol, propylene glycol, mid-chain triglycerides, fatty oils, liquid polyethylene glycols, paraffins), surfactants, emulsifiers, dispersants or wetting agents (for example sodium dodecylsulphate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®), buffer substances, and also acids and bases (for example phosphates, carbonates, citric acid, acetic acid, hydrochloric acid, sodium hydroxide, ammonium carbonate, trometamol, triethanolamine), isotonizing agents (for example glucose, sodium chloride), adsorbents (for example finely divided silicas), viscosity-increasing agents, gel formers, thickeners or binders (for example polyvinylpyrrolidone, methyl cellulose, hydroxypropyl methyl cellulose, hydroxypropyl cellulose, carboxymethyl cellulose-sodium, starch, carbomers, polyacrylic acids, for example Carbopol®, alginates, gelatins), disintegrants (for example modified starch, carboxymethyl cellulose-sodium, sodium starch glycolate, for example Explotab®, crosslinked polyvinylpyrrolidone, croscarmellose-sodium, for example AcDiSol®), flow regulators, lubricants, glidants and mould release agents (for example magnesium stearate, stearic acid, talc, finely divided silicas, for example Aerosil®), coating agents (for example sugar, shellac) and film formers for films or diffusion membranes with fast or modified dissolution (for example by polyvinylpyrrolidones, for example Kollidon®, polyvinyl alcohol, hydroxypropyl methyl cellulose, hydroxypropyl cellulose, ethyl cellulose, hydroxypropyl methyl cellulose phthalate, cellulose acetate, cellulose acetate phthalate, polyacrylates, polymethacrylates, for example Eudragit®), capsule materials (e.g. gelatins, hydroxypropyl methyl cellulose), synthetic polymers (for example polylactides, polyglycolides, polyacrylates, polymethacrylates, for example Eudragit®, polyvinylpyrrolidones, for example Kollidon®, polyvinyl alcohols, polyvinyl acetates, polyethylene oxides, polyethylene glycols and the copolymers and block copolymers thereof), plasticizers (for example polyethylene glycols, propylene glycol, glycerol, triacetin, triacetyl citrate, dibutyl phthalate), penetration enhancers, stabilizers (e.g. antioxidants, for example ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), dyes (e.g. inorganic pigments, for example iron oxides, titanium dioxide), aromas, sweeteners, flavour and/or odour correctors.

Preference is given to oral or parenteral administration, especially oral administration.

The compounds of the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In the case of parenteral administration, it has generally been found to be advantageous to administer amounts of about 0.1 to 6 mg/kg to achieve effective results. In the case of oral administration, the dose is about 0.1 to 10 mg/kg of body weight.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

A. EXAMPLES

Abbreviations and Acronyms

| | |
|---|---|
| Ac | acetyl |
| aq. | aqueous, aqueous solution |
| boc | tert-butoxycarbonyl |
| br.d | broad doublet (NMR) |
| br.m | broad multiplet (NMR) |
| br.s | broad singlet (NMR) |
| br.t | broad triplet (NMR) |
| c | concentration |
| cat. | catalytic |
| d | doublet (NMR) |
| de | diastereomeric excess |
| TLC | thin layer chromatography |
| DCI | direct chemical ionization (in MS) |
| dd | doublet of doublets (NMR) |
| ddd | doublet of doublet of doublets (NMR) |
| dist. | distilled |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethyl sulphoxide |
| DSC | differential scanning calorimetry |
| dt | doublet of triplets (NMR) |
| EDC | N'-(3-dimethylaminopropyl)-N-ethylcarbodiimide hydrochloride |
| ee | enantiomeric excess |
| ent | enantiomerically pure, enantiomer |
| eq. | equivalent(s) |
| ESI | electrospray ionization (in MS) |
| Et | ethyl |
| GC-MS | gas chromatography-coupled mass spectrometry |
| h | hour(s) |
| HATU | O-(7-azabenzotriazol-1-yl)-N,N,N',N'-tetramethyluronium hexafluorophosphate |
| HBTU | O-(benzotriazol-1-yl)-N,N,N',N'-tetramethyluronium hexafluorophosphate |
| HOBt | 1-hydroxy-1H-benzotriazole hydrate |
| HPLC | high-pressure, high-performance liquid chromatography |
| ID | internal diameter |
| iPr | isopropyl |
| J | coupling constant (NMR) |
| conc. | concentrated |
| LC-MS | liquid chromatography-coupled mass spectrometry |
| m | multiplet (NMR) |
| Me | methyl |
| min | minute(s) |
| MPLC | medium-pressure liquid chromatography |
| MS | mass spectrometry |
| MTBE | methyl tert-butyl ether |
| NMR | nuclear magnetic resonance spectrometry |
| Pd/C | palladium on activated charcoal |
| Ph | phenyl |
| PyBOP | benzotriazol-1-yloxytris(pyrrolidino)phosphonium hexafluorophosphate |
| quant. | quantitative (in yield) |
| rac | racemic, racemate |
| RT | room temperature |
| $R_t$ | retention time (in HPLC) |
| mp | melting point |
| SFC | supercritical fluid chromatography |
| t | triplet (NMR) |
| tBu | tert-butyl |
| tert | tertiary |
| TFA | trifluoroacetic acid |
| TFAA | trifluoroacetic anhydride |
| THF | tetrahydrofuran |
| TPPO | triphenylphosphine oxide |
| UV | ultraviolet spectrometry |
| v/v | volume to volume ratio (of a solution) |

HPLC, GC-MS and LC-MS Methods

Method 1:

Instrument: Agilent MS Quad 6150; HPLC: Agilent 1290; column: Waters Acquity UPLC HSS T3 1.8µ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205305 nm.

Method 2:

Instrument: Thermo DFS, Trace GC Ultra; column: Restek RTX-35, 15 m×200 µm×0.33 µm; constant flow rate of helium: 1.20 ml/min; oven: 60° C.; inlet: 220° C.; gradient: 60° C., 30° C./min→300° C. (hold for 3.33 min).

Method 3:

MS instrument type: Thermo Scientific FT-MS; UHPLC+ instrument type: Thermo Scientific UltiMate 3000; column: Waters, HSST3, 2.1×75 mm, C18 1.8 µm; eluent A: 1 l of water+0.01% formic acid; eluent B: 1 l of acetonitrile+ 0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm Method 4:

Instrument: Waters ACQUITY SQD UPLC System; column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 5:

Instrument: HP 1100 Series with LC/MSD SL; column: CS MultoKrom 100-3 C18 60×4.6 mm; eluent A: 1 l water+10 ml 99% formic acid, eluent B: 1 l+10 ml 99% formic acid; gradient: 0.0 min 80% A→8.0 min 10% A→10.0 min 10% A; flow rate: 1.00 ml/min; DAD detection: 120-800 nm.

Method 6:

MS instrument: Waters (Micromass) Quattro Micro; Instrument Waters UPLC Acquity; column: Waters BEH C18 1.7µ 50×2.1 mm; eluent A: 1 l water+0.01 mol ammonium formate, eluent B: 1 of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm Method 7:

Instrument: Waters Acquity, Waters Acquity Autosampler; column: XBridge BEH C18 2.5 µm 2.1×50 mm (UPLC LG 500 nm); eluent A: 10 mM ammonium hydrogencarbonate pH 10, eluent B: acetonitrile; gradient: 2-98% B in 0.80 min, hold at 98% B for 1.30 min.

Method 8:

Instrument: Waters ACQUITY SQD UPLC System; column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 9:

MS instrument type: ThermoFisher Scientific LTQ-Orbitrap-XL; HPLC instrument type: Agilent 1200SL; column: Agilent, POROSHELL 120, 3×150 mm, SB-C18 2.7 µm; eluent A: 1 l water+0.1% trifluoroacetic acid; eluent B: 1 l acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm Method 10:

Instrument: Waters Prep LC/MS System, column: XBridge C18 5 µm 100×30 mm; eluent A: water, eluent B: acetonitrile, flow rate: 65 ml/min plus 5 ml 2% formic acid in water, room temperature, wavelength 200-400 nm, at-column injection (complete injection); gradient profile: between 0 and 2 min 10% eluent B, between 2 and 2.2 min to 20% eluent B, between 2.2 and 7 min to 60% eluent B, between 7 and 7.5 min to 92% eluent B, between 7.5 to 9 min at 92% B.

Method 11:

Instrument: Waters Prep LC/MS System, column: XBridge C18 5 µm 100×30 mm; eluent A: water, eluent B: acetonitrile, flow rate: 65 ml/min plus 5 ml 2% formic acid in water, room temperature, wavelength 200-400 nm, at-column injection (complete injection); gradient profile: between 0 and 2 min 7.5% eluent B, between 2 and 7 min to 35% eluent B, between 7 and 7.5 min to 92% eluent B, between 7.5 to 9 min at 92% B.

Method 12:

Instrument: Waters Prep LC/MS System, column: XBridge C18 5 µm 100×30 mm; eluent A: water, eluent B: acetonitrile, flow rate: 65 ml/min plus 5 ml 2% ammonia in water, room temperature, wavelength 200-400 nm, at-column injection (complete injection); gradient profile: between 0 and 2 min 7.5% eluent B, between 2 and 7 min to 35% eluent B, between 7 and 7.5 min to 92% eluent B, between 7.5 to 9 min at 92% B.

Method 13:

Instrument MS: Waters SQD2; Instrument HPLC: Waters UPLC; column: Zorbax SB-Aq (Agilent), 50 mm×2.1 mm, 1.8 µm; eluent A: water+0.025% formic acid, eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow rate: 0.600 ml/min; UV detection: DAD; 210 nm.

Method 14:

Instrument: Waters Prep LC/MS System, column: Phenomenex Kinetex C18 5 µm 100×30 mm; eluent A: water, eluent B: acetonitrile, flow rate: 65 ml/min plus 5 ml 2% formic acid in water, room temperature, wavelength 200-400 nm, at-column injection (complete injection); gradient profile: between 0 and 2 min 10% eluent B, between 2 and 2.2 min to 20% eluent B, between 2.2 and 7 min to 60% eluent B, between 7 and 7.5 min to 92% eluent B, between 7.5 to 9 min at 92% B.

Method 15:

Instrument: Waters Single Quad MS System; Instrument: Waters UPLC Acquity; column: Waters BEH C18 1.7 µm 50×2.1 mm; eluent A: 1 l water+1.0 ml (25% ammonia)/l, eluent B: 1 l acetonitrile; gradient: 0.0 min 92% A→0.1 min 92% A→1.8 min 5% A-3.5 min 5% A; oven: 50° C.; flow rate: 0.45 ml/min; UV detection: 210 nm (208-400 nm).

Further details:

In the case of purifications of compounds of the invention by chromatography, particularly by column chromatography, prepacked silica gel cartridges, for example Biotage SNAP cartridges, KP-Sil® or KP-NH®, are used in combination with a Biotage system (SP4® or Isolera Four®). Eluents employed are gradients of hexane/ethyl acetate or dichloromethane/methanol.

In the case of purifications of compounds of the invention by preparative HPLC by the above-described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Furthermore, amidines can be present as free compounds or partially (depending on the preparation if acetic acid is involved) as acetate salts or acetate solvates.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x hydrochloric acid, "×$CF_3COOH$", "×$Na^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Furthermore, the secondary amides according to the invention may be present as rotational isomers/isomer mixtures, in particular in NMR studies. Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

In all $^1$H NMR spectra data, the chemical shifts δ[ppm]= are stated in ppm.

The multiplicities of proton signals in $^1$H NMR spectra reported in the paragraphs which follow represent the signal form observed in each case and do not take account of any higher-order signal phenomena. In general, the stated chemical shift refers to the centre of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

Melting points and melting point ranges, if stated, are uncorrected.

The $^1$H NMR data of selected synthesis intermediates and working examples are stated in the form of $^1$H NMR peak lists. For each signal peak, first the δ[ppm]=value in ppm and then the signal intensity in round brackets are listed. The δ[ppm]=value/signal intensity number pairs for different signal peaks are listed with separation from one another by commas. The peak list for an example therefore takes the following form: δ[ppm]=$_1$ (intensity$_1$), δ[ppm]=$_2$ (intensity$_2$), . . . , δ[ppm]=$_i$ (intensity$_i$), . . . , δ[ppm]=$_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation. A detailed description of the presentation of NMR data in the form of peak lists can be found in the publication "Citation of NMR Peaklist Data within Patent Applications" (cf. Research Disclosure Database Number 605005, 2014, 1 Aug. 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "MinimumHeight" to values of <1%.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

In the intermediates and working examples described hereinafter, a "5RS" identifier in the IUPAC name of the example in question, in conjunction with the term "racemate", means that this is a racemic mixture of the 5R enantiomer (→1st letter after the position number in "5RS") with the corresponding 5S enantiomers (→2nd letter after the position number). The "5RS" identifier in conjunction with the statements "enantiomer 1" and "enantiomer 2" means that these are the two enantiomers in separate, isolated form, without having undertaken an assignment of the absolute configuration (5R or 5S) to these enantiomers. Similar identifiers such as "5SR" that arise from the altered priority and/or sequence of named constituents owing to the IUPAC nomenclature rules should be interpreted in an analogous manner according to these instructions.

In the intermediates and working examples described hereinafter, a "5RS,7RS" identifier in the IUPAC name of the example in question, in conjunction with the term "racemate", means that this is a racemic mixture of the 5R,7R enantiomer (→1st letter in each case after the position number in "5RS,7RS") with the corresponding 5S,7S enantiomer (→2nd letter in each case after the position number). The "5RS,7RS" identifier in conjunction with the statements "enantiomer 1" and "enantiomer 2" means that these are the two enantiomers in separate, isolated form, without having undertaken an assignment of the absolute configuration (5R,7R or 5S,7S) to these enantiomers. Similar identifiers such as "5SR,7SR" that arise from the altered priority and/or sequence of named constituents owing to the IUPAC nomenclature rules should be interpreted in an analogous manner according to these instructions.

The (5S) configuration was assigned on the basis of crystal structure elucidation for Example 26, 108, 113, 157, 237, 358 and 454. In analogy, the (5S) configuration was assigned for examples 183-188, 190-219, 275-279, 342-402, 404-415, 418-563.

Starting Compounds and Intermediates

Intermediate 1

Methyl 3-fluoro-2-(trifluoromethyl)isonicotinate

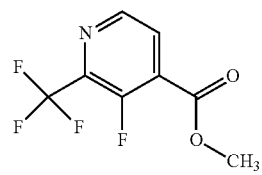

3-Fluoro-2-(trifluoromethyl)isonicotinic acid (1.00 g, 4.78 mmol) was dissolved in methanol (10 ml), and sulphuric acid (310 μl, 5.7 mmol) was added. The reaction mixture was heated to 60° C. for 30 minutes and then stirred at room temperature overnight. The reaction mixture was concentrated under reduced pressure and the residue was dissolved in ethyl acetate and washed with saturated sodium hydrogencarbonate solution. The organic phase was dried over sodium sulphate and filtered and the filtrate was concentrated. 890 mg (70% purity, 58% of theory) of the title compound were obtained.

LC-MS (Method 1): $R_t$=1.15 min; MS (ESIpos): m/z=224 [M+H]$^+$

Intermediate 2

[3-Fluoro-2-(trifluoromethyl)pyridin-4-yl]methanol

Methyl 3-fluoro-2-(trifluoromethyl)isonicotinate (890 mg, 70% purity, 3.99 mmol) was dissolved in methanol (5.0 ml), and sodium borohydride (166 mg, 4.39 mmol) was added in portions at 0° C. After stirring overnight, the reaction mixture was admixed at room temperature with saturated aqueous ammonium chloride solution and the methanol was removed under reduced pressure. The residue was admixed with ethyl acetate and water. The aqueous phase was extracted three times with ethyl acetate. The combined organic phases were dried over sodium sulphate and filtered, and the filtrate was concentrated. 420 mg (54% of theory) of the title compound were obtained. The compound was converted further directly.

Intermediate 3

4-(Chloromethyl)-3-fluoro-2-(trifluoromethyl)pyridine Hydrochloride

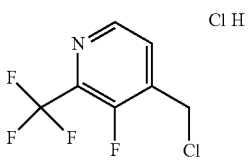

[3-Fluoro-2-(trifluoromethyl)pyridin-4-yl]methanol (420 mg, 2.15 mmol) was dissolved in dichloromethane (10 ml), and thionyl dichloride (310 µl, 4.3 mmol) was added at room temperature. After the reaction mixture had been stirred at room temperature overnight, thionyl dichloride (310 µl, 4.3 mmol) again and a drop of dimethylformamide were added. The reaction mixture was stirred at room temperature for one hour and then thionyl dichloride (620 µl, 8.6 mmol) and one drop of dimethylformamide were added again. After stirring at room temperature again for 2 hours, the solvent was removed under reduced pressure. 379 mg (70% of theory) of the title compound were obtained.

GC-MS (Method 2): $R_t$=2.74 min; MS (ESIpos): m/z=213 [M+H]$^+$

Intermediate 4

5-Chloro-4-(trifluoromethyl)pyridin-2-yl]methanol

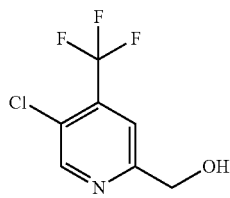 [SMILES: OCc1cc(C(F)(F)F)c(Cl)cn1]

Methyl 5-chloro-4-(trifluoromethyl)pyridine-2-carboxylate (412 mg, 1.72 mmol) was dissolved in methanol (20 ml), and sodium borohydride (78.1 mg, 2.06 mmol) was added in portions at 0° C. After at room temperature stirring overnight, the reaction mixture was admixed again with sodium borohydride (35 mg, 0.9 mmol). After stirring for 2 days at room temperature, the reaction mixture was admixed with saturated aqueous ammonium chloride solution and the methanol was removed under reduced pressure. The residue was admixed with ethyl acetate and water. The aqueous phase was extracted three times with ethyl acetate. The combined organic phases were dried over sodium sulphate and filtered, and the filtrate was concentrated. 295 mg (77% of theory) of the title compound were obtained.

LC-MS (Method 3): $R_t$=1.32 min; MS (ESIpos): m/z=212 [M+H]$^+$

Intermediate 5

5-Chloro-2-(chloromethyl)-4-(trifluoromethyl)pyridine Hydrochloride

[5-Chloro-4-(trifluoromethyl)pyridin-2-yl]methanol (295 mg, 1.39 mmol) was dissolved in dichloromethane (20 ml), and thionyl dichloride (200 µl, 2.8 mmol) was added at room temperature. After the reaction mixture had been stirred at room temperature for 72 hours, the solvent was removed under reduced pressure. 274 mg (85% purity, 63% of theory) of the title compound were obtained.

$^1$H-NMR (400 MHz, DMSO-d6) δ[ppm]: 0.008 (0.42), 3.937 (2.06), 4.644 (1.11), 4.903 (16.00), 7.839 (0.47), 8.078 (5.73), 8.296 (0.43), 8.857 (0.51), 8.957 (5.04), 9.102 (0.45).

Intermediate 6

4-(Chloromethyl)-2-(trifluoromethyl)quinoline Hydrochloride

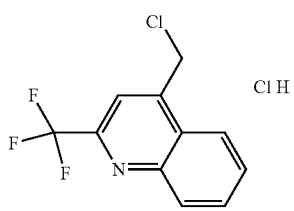

[2-(Trifluoromethyl)quinolin-4-yl]methanol (350 mg, 1.54 mmol) was dissolved in dichloromethane (10 ml), and thionyl dichloride (220 µl, 3.1 mmol) was added at 0° C. After the reaction mixture had been stirred at room temperature overnight, the solvent was removed under reduced pressure. The residue was purified via preparative HPLC (Chromatorex C18, 10 µm, 125 mm×30 mm; eluent: acetonitrile/water gradient). The product-containing fractions were concentrated under reduced pressure, and 336 mg (74% purity, 57% of theory) of the title compound were obtained.

LC-MS (Method 4): $R_t$=1.06 min; MS (ESIpos): m/z=246 [M+H]$^+$

Intermediate 7

4-(Chloromethyl)-2-(trifluoromethyl)pyrimidine Hydrochloride

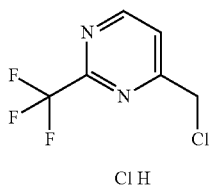 [SMILES: FC(F)(F)c1nccc(CCl)n1 ; "Cl H"]

[2-(Trifluoromethyl)pyrimidin-4-yl]methanol (313 mg, 1.76 mmol) was dissolved in dichloromethane (10 ml), and thionyl dichloride (260 µl, 3.5 mmol) was added at room temperature. After the reaction mixture had been stirred at room temperature for 4 hours, the solvent was removed under reduced pressure. 134 mg (61% purity, 20% of theory) of the title compound were obtained.

$^1$H-NMR (400 MHz, DMSO-d6) δ[ppm]: 3.678 (0.60), 4.946 (16.00), 5.366 (0.57), 7.993 (2.80), 8.006 (2.88), 9.129 (3.11), 9.142 (3.06).

Intermediate 8

Methyl 6-[1-(tert-butoxycarbonyl)hydrazino]pyridine-2-carboxylate

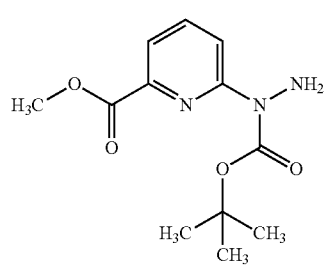 [SMILES: COC(=O)c1cccc(N(N)C(=O)OC(C)(C)C)n1]

Methyl 6-chloropyridine-2-carboxylate (32.5 g, 189 mmol), tert-butyl hydrazinecarboxylate (25.0 g, 189 mmol) and caesium carbonate (61.6 g, 189 mmol) in toluene (325 ml) were degassed with argon, before [1,1'-bis(diphenylphosphino)ferrocene]dichloropalladium(II) (6.9 g, 10 mmol) was added. The reaction mixture was stirred at 100° C. overnight. The reaction mixture was diluted with dichloromethane and filtered through kieselguhr. The filtrate was concentrated under reduced pressure and the residue was purified via column chromatography (silica gel, eluent: methanol/dichloromethane 4/96). The product-containing fractions were concentrated under reduced pressure and stirred with methyl tert-butyl ether. 28.8 g (57% of theory) of the title compound were obtained.

LC-MS (Method 5): $R_t$=3.45 min; MS (ESIpos): m/z=268 [M+H]$^+$

Intermediate 9

2-(Diazan-2-ium-1-yl)-6-(methoxycarbonyl)pyridinium Dichloride

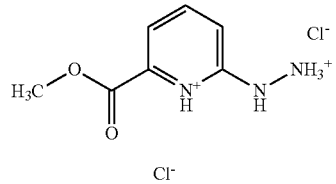

Methyl 6-{1-[(benzyloxy)carbonyl]hydrazino}pyridine-2-carboxylate (29.8 g, 112 mmol) was dissolved in dioxane (150 ml), and hydrochloric acid (112 ml, 446 mmol, 4 M in dioxane) was added. The reaction mixture was stirred at room temperature for 4 h and diluted with methyl tert-butyl ether (500 ml). After stirring for 1 h, the solids were filtered off, washed with methyl tert-butyl ether and dried. 28.8 g (>100%) of the title compound were obtained.

LC-MS (Method 5): $R_t$=0.88 min; MS (ESIpos): m/z=168 [M+H]$^+$

Intermediate 10

Methyl 3-oxo-2,3-dihydro[1,2,4]triazolo[4,3-a]pyridine-5-carboxylate

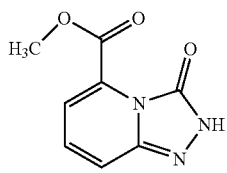

2-(Diazan-2-ium-1-yl)-6-(methoxycarbonyl)pyridinium dichloride (28.8 g, 112 mmol) was dissolved in THF (500 ml), and triethylamine (46 ml, 335 mmol) was added. The reaction mixture was stirred at room temperature for 15 min. Subsequently, 1,1-carbonyldiimidazole (19.9 g, 123 mmol) was added. The reaction mixture was stirred at 70° C. for 2 h. The reaction mixture was filtered and the filtrate was concentrated under reduced pressure. The residue was taken up in dilute aqueous hydrochloric acid and extracted with dichloromethane/methanol 9/1. The combined organic phases were dried over sodium sulphate and filtered, and the filtrate was concentrated. The residue was suspended in ethyl acetate and stirred overnight. After filtration and drying, 11.4 g (53% of theory) of the title compound were obtained.

LC-MS (Method 5): $R_t$=1.40 min; MS (ESIpos): m/z=194 [M+H]$^+$

Intermediate 11

Methyl (5RS)-3-oxo-2,3,5,6,7,8-hexahydro[1,2,4]triazolo[4,3-a]pyridine-5-carboxylate (Racemate)

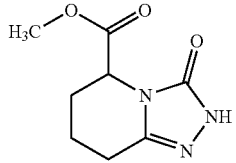

Methyl 3-oxo-2,3-dihydro[1,2,4]triazolo[4,3-a]pyridine-5-carboxylate (17.6 g, 91.1 mmol) and palladium on charcoal (1.0 g, 10%) were suspended in methanol (500 ml) and the mixture was stirred at room temperature in a hydrogen atmosphere (10 bar) overnight. The reaction mixture was filtered through kieselguhr. The filtrate was concentrated, and 17.8 g (99% of theory) of the title compound were obtained.

LC-MS (Method 5): $R_t$=1.35 min; MS (ESIpos): m/z=198 [M+H]$^+$ $^1$H-NMR (500 MHz, MeOD) δ [ppm]=1.64-1.74 (br, 1H), 1.89-1.97 (br, 1H), 2.15-2.29 (br, 2H), 2.60-2.69 (m, 1H), 2.77 (dt, 1H), 3.79 (s, 3H), 4.63 (dd, 1H).

Intermediate 12

Methyl (5RS)-3-oxo-2,3,5,6,7,8-hexahydro[1,2,4]triazolo[4,3-a]pyridine-5-carboxylate (Enantiomer 1)

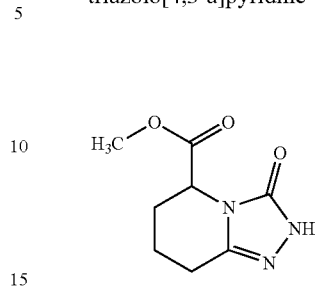

Methyl (5RS)-3-oxo-2,3,5,6,7,8-hexahydro[1,2,4]triazolo[4,3-a]pyridine-5-carboxylate (racemate) was separated by chiral preparative SFC [sample preparation: 33.20 g dissolved in 200 ml of methanol; injection volume: 4.0 ml; column: Daicel Chiralpak® IC 20 µm, 360×50 mm; eluent: CO$_2$/i-propanol 80/20; flow rate: 400 g/min; temperature 35° C.; UV detection: 210 nm]. After the separation, 15.7 g of enantiomer 1, which eluted first, and 15.8 g of enantiomer 2, which eluted later, were isolated.

Enantiomer 1

Analytical chiral SFC: $R_t$=2.76 min, d.e.=100% [column: Daicel Chiralpak® IC 50×4.6 mm; eluent: CO$_2$/i-propanol 80:20; flow rate: 3 ml/min; UV detection: 210 nm].

LC-MS (Method 3): $R_t$=0.54 min; MS (ESIpos): m/z=198 [M+H]$^+$ $^1$H-NMR (400 MHz, DMSO-d6) δ[ppm]=1.45-1.60 (m, 1H), 1.75-1.84 (m, 1H), 1.98-2.17 (m, 2H), 2.48-2.58 (m, 1H), 2.59-2.68 (m, 1H), 3.69 (s, 3H), 4.51 (dd, 1H), 11.42 (s, 1H).

Intermediate 13

Methyl (5RS)-3-oxo-2,3,5,6,7,8-hexahydro[1,2,4]triazolo[4,3-a]pyridine-5-carboxylate (Enantiomer 2)

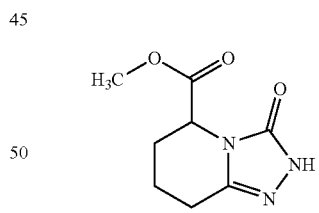

Methyl (5RS)-3-oxo-2,3,5,6,7,8-hexahydro[1,2,4]triazolo[4,3-a]pyridine-5-carboxylate (racemate) was separated by chiral preparative SFC [sample preparation: 33.20 g dissolved in 200 ml of methanol; injection volume: 4.0 ml; column: Daicel Chiralpak® IC 20 µm, 360×50 mm; eluent: CO$_2$/i-propanol 80/20; flow rate: 400 g/min; temperature 35° C.; UV detection: 210 nm]. After the separation, 15.7 g of enantiomer 1, which eluted first, and 15.8 g of enantiomer 2, which eluted later, were isolated.

Enantiomer 2

Analytical chiral SFC: $R_t$=3.90 min, d.e.=100% [column: Daicel Chiralpak® IC 50×4.6 mm; eluent: CO$_2$/i-propanol 80:20; flow rate: 3 ml/min; UV detection: 210 nm].

LC-MS (Method 3): R$_t$=0.54 min; MS (ESIpos): m/z=198 [M+H]$^+$ $^1$H-NMR (400 MHz, DMSO-d6) δ[ppm]=1.42-1.59 (m, 1H), 1.72-1.86 (m, 1H), 1.96-2.17 (m, 2H), 2.44-2.59 (m, 1H), 2.59-2.69 (m, 1H), 3.69 (s, 3H), 4.51 (dd, 1H), 11.42 (s, 1H).

The (5S) configuration was assigned on the basis of the crystal structure elucidation for Example 26, 108, 113, 157, 237, 358 and 454.

Methyl (5S)-3-oxo-2,3,5,6,7,8-hexahydro[1,2,4]triazolo[4,3-a]pyridine-5-carboxylate Intermediate 14

Methyl 1-(4-methoxybenzyl)hydrazinecarboxylate

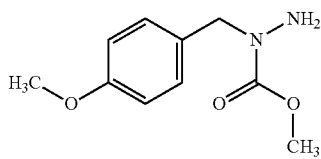

(4-Methoxybenzyl)hydrazine dihydrochloride (1.50 g, 80% purity, 5.33 mmol) was dissolved in dichloromethane (50 ml), triethylamine (2.6 ml, 19 mmol) was added, and the mixture was stirred at room temperature for 30 minutes. This mixture was subsequently cooled to 0° C., and methyl carbonochloridate (450 µl, 5.9 mmol), dissolved in dichloromethane (10 ml), was added. After stirring overnight, the reaction mixture was admixed at room temperature with water. The organic phase was removed, washed with saturated aqueous sodium chloride solution, dried over sodium sulphate and filtered, and the filtrate was concentrated. The residue was purified via column chromatography (silica gel, eluent: cyclohexane/ethyl acetate gradient). The product-containing fractions were concentrated under reduced pressure, and 1.04 g (92% purity, 85% of theory) of the title compound were obtained.

LC-MS (Method 3): R$_t$=1.08 min; MS (ESIpos): m/z=211 [M+H]$^+$ $^1$H-NMR (400 MHz, DMSO-d6) δ[ppm]: 1.988 (0.46), 3.314 (7.32), 3.541 (0.79), 3.622 (16.00), 4.397 (7.56), 4.553 (4.94), 6.861 (0.47), 6.868 (3.43), 6.873 (1.30), 6.885 (1.38), 6.890 (3.96), 6.897 (0.47), 7.161 (3.22), 7.182 (2.79).

Intermediate 15

Methyl (2S)-6-oxopiperidine-2-carboxylate (Enantiomer)

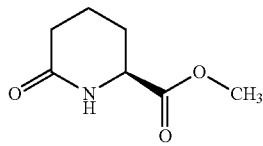

To an initial charge of methanol (15 ml) at 0° C. were added thionyl dichloride (560 µl, 7.7 mmol) and then, in portions, (2S)-6-oxopiperidine-2-carboxylic acid (1.00 g, 6.99 mmol). After stirring at room temperature overnight, the solvent was removed under reduced pressure, and the residue was admixed with toluene and triethylamine (1.9 ml, 14 mmol). The mixture was stirred at room temperature for 30 minutes, then filtered, and the filtrate was concentrated. 805 mg (70% of theory) of the title compound were obtained.

LC-MS (Method 4): R$_t$=0.26 min; MS (ESIpos): m/z=158 [M+H]$^+$ $^1$H-NMR (400 MHz, DMSO-d6) δ[ppm]: −0.008 (1.70), 0.008 (1.69), 1.541 (0.78), 1.550 (1.05), 1.560 (1.24), 1.566 (1.90), 1.575 (2.78), 1.584 (3.48), 1.591 (3.19), 1.594 (3.57), 1.600 (4.36), 1.610 (3.31), 1.619 (4.16), 1.628 (3.71), 1.636 (3.43), 1.644 (5.02), 1.652 (4.23), 1.660 (4.33), 1.668 (4.60), 1.676 (2.96), 1.684 (2.78), 1.693 (1.99), 1.702 (1.75), 1.708 (1.01), 1.717 (0.85), 1.745 (1.91), 1.754 (2.09), 1.759 (2.49), 1.768 (2.39), 1.778 (3.46), 1.787 (3.35), 1.793 (3.60), 1.802 (3.22), 1.810 (2.52), 1.819 (1.83), 1.901 (2.92), 1.910 (3.42), 1.916 (3.20), 1.925 (4.72), 1.935 (4.50), 1.941 (3.46), 1.949 (4.49), 1.959 (3.35), 1.968 (1.78), 1.974 (1.91), 1.983 (1.62), 2.097 (0.90), 2.113 (0.85), 2.128 (11.31), 2.141 (16.00), 2.148 (10.19), 2.156 (7.22), 2.164 (7.72), 2.188 (0.61), 2.192 (0.69), 2.208 (0.70), 2.289 (0.72), 2.306 (1.34), 2.324 (0.85), 2.523 (0.72), 3.168 (4.31), 3.311 (4.19), 3.409 (0.45), 3.480 (0.73), 3.581 (8.47), 3.635 (7.91), 3.849 (0.72), 4.049 (4.37), 4.055 (4.73), 4.063 (8.78), 4.069 (8.78), 4.077 (4.66), 4.083 (4.33), 7.542 (6.15).

Intermediate 16

Methyl (5S)-2-(4-methoxybenzyl)-3-oxo-2,3,5,6,7,8-hexahydro[1,2,4]triazolo[4,3-a]pyridine-5-carboxylate (Enantiomer)

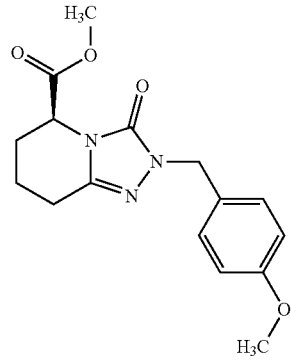 [SMILES: COC(=O)[C@@H]1CCCc2nn(Cc3ccc(OC)cc3)c(=O)n21]

Methyl (2S)-6-oxopiperidine-2-carboxylate (enantiomer) (300 mg, 1.91 mmol) was initially charged in dichloromethane (6.0 ml, 93 mmol) at room temperature and under argon. Subsequently, trimethyloxonium tetrafluoroborate (311 mg, 2.10 mmol) was added and the reaction mixture was stirred at room temperature for 2 days. The solvent was removed under reduced pressure and the residue was admixed with DMF (5 ml). Subsequently, methyl 1-(4-methoxybenzyl)hydrazinecarboxylate (401 mg, 1.91 mmol) was added and the reaction mixture was stirred at 170° C. for 4 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 156 mg (26% of theory) of the title compound were obtained.

LC-MS (Method 3): $R_t$=1.20 min; MS (ESIpos): m/z=318 [M+H]$^+$ $^1$H-NMR (400 MHz, DMSO-d6) δ[ppm]: −0.008 (1.02), 1.784 (0.43), 1.795 (0.46), 2.045 (0.41), 2.055 (0.68), 2.068 (0.64), 2.076 (0.62), 2.084 (0.47), 2.092 (0.40), 2.100 (0.48), 2.112 (0.44), 2.120 (0.47), 2.128 (0.45), 2.564 (0.76), 2.578 (0.61), 2.603 (0.56), 2.615 (1.06), 2.627 (0.59), 2.657 (0.47), 2.669 (0.42), 2.829 (0.43), 3.700 (14.01), 3.730 (16.00), 3.743 (0.70), 4.581 (0.93), 4.591 (1.04), 4.597 (1.20), 4.607 (0.91), 4.749 (6.71), 6.882 (3.25), 6.903 (3.86), 7.161 (3.37), 7.183 (2.94).

Intermediate 17

Methyl (5S)-3-oxo-2,3,5,6,7,8-hexahydro[1,2,4]triazolo[4,3-a]pyridine-5-carboxylate (Enantiomer)

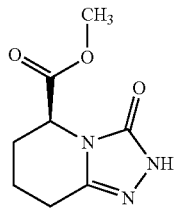

Methyl (5S)-2-(4-methoxybenzyl)-3-oxo-2,3,5,6,7,8-hexahydro[1,2,4]triazolo[4,3-a]pyridine-5-carboxylate (155 mg, 488 μmol) (enantiomer) was dissolved in trifluoroacetic acid (4.5 ml), and the mixture was stirred at 150° C. in a microwave apparatus for one hour. Saturated aqueous sodium chloride solution was added to the reaction mixture, and the solution was adjusted to pH 7 with saturated aqueous sodium hydrogencarbonate solution. Dichloromethane was added, and the aqueous phase was extracted three times with dichloromethane. The combined organic phases were dried over sodium sulphate and filtered, and the filtrate was concentrated. The residue was purified via column chromatography (silica gel, eluent: dichloromethane/methanol gradient). The product-containing fractions were concentrated under reduced pressure, admixed with ethyl acetate and filtered. The filtrate was concentrated down to one millilitre, and the product was crystallized with 10 ml of petroleum ether. The solids were filtered off and dried under reduced pressure. 53.1 mg (53% of theory) of the title compound were obtained with an ee of 88%.

The enantiomeric excess is determined via analytical chiral HPLC:

Comparative values for racemate:
Analytical chiral HPLC: enantiomer 1 $R_t$=3.40, enantiomer 2 $R_t$=4.09 min, ratio 1:1 [column: Daicel Chiraltek® AY-3 3 μm 50×4.6 mm; eluent: i-hexane/ethanol 1:1, flow rate: 1 ml/min; UV detection: 220 nm]

Enantiomer:
Analytical chiral HPLC: enantiomer 1 $R_t$=3.35, enantiomer 2 $R_t$=4.01 min, ratio 6:94 [column: Daicel Chiraltek® AY-3 3 μm 50×4.6 mm; eluent: i-hexane/ethanol 1:1, flow rate: 1 ml/min; UV detection: 220 nm]

$^1$H-NMR (400 MHz, DMSO-d6) δ[ppm]: 1.506 (0.41), 1.540 (0.44), 1.774 (0.50), 1.787 (0.56), 1.800 (0.48), 1.808 (0.40), 2.026 (0.49), 2.037 (0.75), 2.050 (0.70), 2.061 (0.71), 2.069 (0.52), 2.077 (0.48), 2.085 (0.55), 2.096 (0.54), 2.105 (0.55), 2.113 (0.53), 2.560 (0.95), 2.574 (0.73), 2.601 (0.65), 2.613 (1.22), 2.626 (0.67), 2.655 (0.55), 2.669 (0.46), 3.586 (0.54), 3.687 (16.00), 4.496 (1.07), 4.506 (1.20), 4.511 (1.37), 4.521 (1.06), 11.424 (1.40).

The (5S) configuration was assigned on the basis of the crystal structure elucidation for Example 26, 108, 113, 157, 237, 358 and 454.

Intermediate 18

Methyl (5RS)-2-(4-methoxybenzyl)-5-methyl-3-oxo-2,3,5,6,7,8-hexahydro[1,2,4]triazolo[4,3-a]pyridine-5-carboxylate (Racemate)

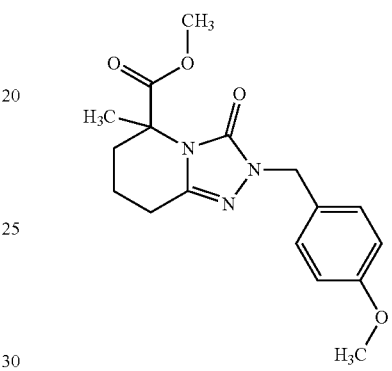

Methyl (5RS)-2-methyl-6-oxopiperidine-2-carboxylate (racemate) (500 mg, 93% purity, 2.72 mmol, CAS 89115-90-2) was initially charged in dichloromethane (10 ml) at room temperature and under argon. Subsequently, trimethyloxonium tetrafluoroborate (442 mg, 2.99 mmol) was added and the reaction mixture was stirred at room temperature for 2 days. The solvent was removed under reduced pressure and the residue was admixed with DMF (5 ml). Subsequently, methyl 1-(4-methoxybenzyl)hydrazinecarboxylate (571 mg, 2.72 mmol, 92% purity) was added and the reaction mixture was stirred at 170° C. for 8 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 186 mg (91% purity, 19% of theory) of the title compound were obtained.

LC-MS (Method 3): $R_t$=1.42 min; MS (ESIpos): m/z=332 [M+H]$^+$ $^1$H-NMR (400 MHz, DMSO-d6) δ[ppm]: 1.589 (0.43), 1.597 (0.42), 1.606 (0.51), 1.623 (0.42), 1.697 (11.51), 1.769 (0.47), 1.782 (0.56), 1.802 (0.43), 1.907 (0.40), 1.935 (0.74), 1.942 (0.63), 1.960 (0.63), 2.023 (0.59), 2.030 (0.65), 2.042 (0.59), 2.050 (0.53), 2.058 (0.40), 2.570 (2.79), 2.586 (1.50), 2.829 (3.14), 3.531 (0.70), 3.645 (0.69), 3.665 (13.44), 3.730 (16.00), 3.742 (4.13), 4.677 (0.71), 4.716 (2.98), 4.736 (2.97), 4.774 (0.71), 5.753 (5.67), 6.885 (3.42), 6.906 (4.16), 6.922 (0.90), 7.148 (3.49), 7.169 (3.14), 7.232 (0.92), 7.253 (0.84), 7.632 (0.93).

Intermediate 19

Methyl (5RS)-methyl-3-oxo-2,3,5,6,7,8-hexahydro[1,2,4]triazolo[4,3-a]pyridine-5-carboxylate (Racemate)

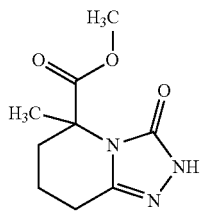

Methyl 2-(4-methoxybenzyl)-5-methyl-3-oxo-2,3,5,6,7,8-hexahydro[1,2,4]triazolo[4,3-a]pyridine-5-carboxylate (racemate) (186 mg, 560 µmol) was dissolved in trifluoroacetic acid (5.0 ml), and the mixture was stirred at 150° C. (microwave apparatus) for one hour. Saturated aqueous sodium chloride solution was added to the reaction mixture, and the solution was adjusted to pH 7 with saturated aqueous sodium hydrogencarbonate solution. Dichloromethane was added, and the aqueous phase was extracted three times with dichloromethane. The combined organic phases were dried over sodium sulphate and filtered, and the filtrate was concentrated. The residue was purified via column chromatography (silica gel, eluent: dichloromethane/methanol gradient). The product-containing fractions were concentrated under reduced pressure, and 40.5 mg (34% of theory) of the title compound were obtained.

LC-MS (Method 3): $R_t$=0.70 min; MS (ESIpos): m/z=212 [M+H]$^+$ $^1$H-NMR (400 MHz, DMSO-d6) δ [ppm]: −0.008 (0.64), 0.008 (0.61), 1.622 (0.54), 1.631 (0.51), 1.640 (0.78), 1.654 (15.63), 1.757 (0.51), 1.771 (0.63), 1.777 (0.57), 1.785 (0.46), 1.792 (0.52), 1.880 (0.46), 1.887 (0.52), 1.903 (0.40), 1.915 (0.92), 1.922 (0.83), 1.938 (0.81), 1.946 (0.65), 1.990 (0.78), 1.998 (0.84), 2.010 (0.73), 2.018 (0.68), 2.025 (0.49), 2.033 (0.43), 2.045 (0.43), 2.568 (3.91), 2.584 (1.91), 3.309 (16.00), 11.369 (1.45).

Intermediate 20 tert-Butyl 6-chloropyridine-2-carboxylate

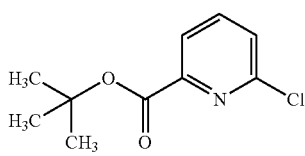

6-Chloropicolinic acid (80.0 g, 0.51 mol) was dissolved in pyridine (300 ml) and tert-butanol (1.60 l), then p-toluenesulphonyl chloride (194 g, 1.02 mol) was added in portions. The reaction mixture was stirred at room temperature overnight. After addition of saturated aqueous sodium hydrogencarbonate solution, the mixture was stirred at room temperature for 1 h. The reaction mixture was concentrated to a volume of 1.50 l and diluted with heptane (500 ml), ethyl acetate (500 ml) and water (500 ml). The organic phase was removed, washed with saturated aqueous sodium chloride solution, dried over magnesium sulphate and filtered, and the filtrate was concentrated. 104 g (96% of theory) of the title compound were obtained.

$^1$H-NMR (400 MHz, CDCl$_3$) δ [ppm]=1.61 (s, 9H), 7.45-7.48 (dd, 1H), 7.74-7.77 (t, 1H), 7.93-7.95 (dd, 1H).

Intermediate 21 tert-Butyl 6-{1-[(benzyloxy)carbonyl]hydrazino}pyridine-2-carboxylate

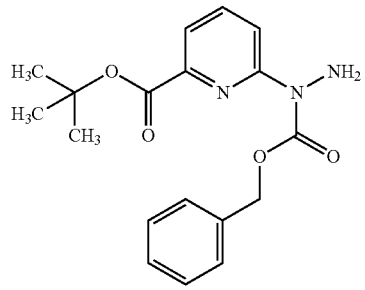 [SMILES: CC(C)(C)OC(=O)c1cccc(N(N)C(=O)OCc2ccccc2)n1]

tert-Butyl 6-chloropyridine-2-carboxylate (91.1 g, 0.43 mol), benzyl hydrazinecarboxylate (70.9 g, 0.43 mol), caesium carbonate (174 g, 0.53 mol) and 1,1'-bis(diphenylphosphino)ferrocene (17.1 g, 32.0 mmol) were suspended in toluene (1.00 l) under argon. Bis(dibenzylideneacetone)palladium(0) (9.76 g, 10.7 mmol) was added, and the reaction mixture was stirred at 80° C. for 3 h. The reaction mixture was admixed with water and ethyl acetate, filtered through kieselguhr and washed through with ethyl acetate. The organic phase was removed, washed with water and saturated aqueous sodium chloride solution, dried over magnesium sulphate and filtered. The filtrate was admixed with silica gel, stirred for 10 min, then filtered and washed through with ethyl acetate. The filtrate was concentrated and the residue was purified via column chromatography (silica gel, eluent: heptane/ethyl acetate 4/1, 2/1, 1/1). The product-containing fractions were concentrated under reduced pressure, and 112 g (77% of theory) of the title compound were obtained.

LC-MS (Method 7): $R_t$=0.81 min; MS (ESIpos): m/z=344 [M+H]$^+$ $^1$H-NMR (400 MHz, CDCl$_3$) δ [ppm]=1.59 (s, 9H), 5.30 (s, 2H), 7.31-7.39 (m, 3H), 7.42-7.45 (m, 2H), 7.76-7.78 (m, 2H), 7.98-8.12 (dd, 1H).

Intermediate 22 tert-Butyl 6-hydrazinopyridine-2-carboxylate

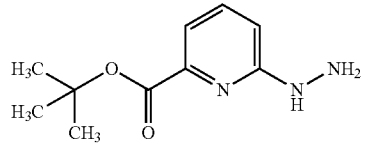

tert-Butyl 6-{1-[(benzyloxy)carbonyl]hydrazino}pyridine-2-carboxylate (112 g, 0.33 mol) and palladium on charcoal (11.2 g, 5%) were suspended in toluene (100 ml) and methanol (1.12 l), and the mixture was stirred at room temperature in a hydrogen atmosphere (1 bar) overnight. The reaction mixture was filtered through kieselguhr and washed with methanol. The solvent was removed under reduced pressure, and 79.9 g (>100%) of the title compound were obtained.

¹H-NMR (400 MHz, CDCl₃) δ [ppm]=1.61 (s, 9H), 6.92-6.95 (d, 1H), 7.38-7.41 (d, 1H), 7.53-7.58 (dd, 1H).

Intermediate 23 tert-Butyl 3-oxo-2,3-dihydro[1,2,4]triazolo[4,3-a]pyridine-5-carboxylate

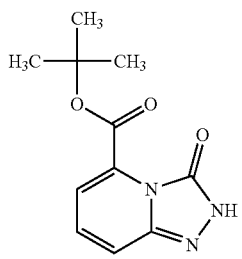 [SMILES: CC(C)(C)OC(=O)c1cccc2n[nH]c(=O)n12]

tert-Butyl 6-hydrazinopyridine-2-carboxylate (79.9 g, 0.33 mol) was dissolved in THF (1.40 l), and 1,1-carbonyldiimidazole (74.3 g, 0.46 mol) was added at room temperature while stirring. The reaction mixture was stirred at room temperature overnight. After addition of water (1.0 l), the mixture was stirred for 15 min and volatile solvents were removed under reduced pressure. The aqueous residue was saturated with sodium chloride and extracted with ethyl acetate. The combined organic phases were washed with saturated aqueous sodium chloride solution, dried over sodium sulphate and filtered, and the filtrate was concentrated. The organic phase was removed, dried over magnesium sulphate and silica gel, and filtered. The filtrate was concentrated and the residue was purified via column chromatography (SiO₂; eluent: heptane/ethyl acetate 4/1, 2/1, 1/1, 1/2). The product-containing fractions were concentrated under reduced pressure, and 62.4 g (80% of theory over two stages) of the title compound were obtained.

LC-MS (Method 7): R_t=0.50 min; MS (ESIpos): m/z=180 [M+H]⁺

¹H-NMR (400 MHz, CDCl₃) δ [ppm]=1.62 (s, 9H), 6.62-6.64 (dd, 1H), 7.00-7.06 (dd, 1H), 7.15-7.19 (dd, 1H), 10.86 (br s, 1H).

Intermediate 24 tert-Butyl (5RS)-3-oxo-2,3,5,6,7,8-hexahydro[1,2,4]triazolo[4,3-a]pyridine-5-carboxylate (Racemate)

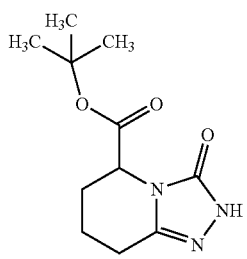 [SMILES: CC(C)(C)OC(=O)C1CCCc2n[nH]c(=O)n21]

tert-Butyl 3-oxo-2,3-dihydro[1,2,4]triazolo[4,3-a]pyridine-5-carboxylate (34.5 g, 0.15 mol) and palladium on charcoal (6.90 g, 5%) were suspended in toluene (60 ml) and methanol (500 ml), and the mixture was stirred at room temperature in a hydrogen atmosphere (34.5 bar) for 24 h. The reaction mixture was filtered through kieselguhr and washed with dichloromethane/methanol 9/1. The filtrate was concentrated and the residue was stirred with ethyl acetate for 30 min, then filtered and concentrated. 36.8 g (89% of theory) of the title compound were obtained.

LC-MS (Method 7): R_t=1.28 min; MS (ESIpos): m/z=240 [M+H]⁺

¹H-NMR (400 MHz, CDCl₃) δ [ppm]=0.53 (s, 9H), 0.74-0.91 (m, 1H), 1.01-1.13 (m, 1H), 1.21-1.32 (m, 1H), 1.47-1.56 (m, 1H), 1.88-2.00 (m, 1H), 2.17-2.26 (dt, 1H), 4.29-4.34 (dd, 1H), 11.9 (br s, 1H).

Intermediate 25 tert-Butyl (5RS)-3-oxo-2,3,5,6,7,8-hexahydro[1,2,4]triazolo[4,3-a]pyridine-5-carboxylate (Enantiomer 2)

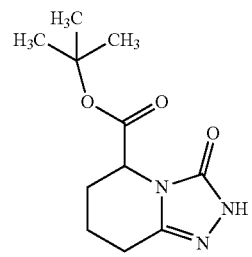 [SMILES: CC(C)(C)OC(=O)C1CCCc2n[nH]c(=O)n21]

tert-Butyl (5RS)-3-oxo-2,3,5,6,7,8-hexahydro[1,2,4]triazolo[4,3-a]pyridine-5-carboxylate (racemate) was separated by chiral preparative SFC [sample preparation: 6.00 g dissolved in 88 ml of methanol; injection volume: 4.5 ml; column: Daicel Chiralpak® IC 20 μm, 370×50 mm; eluent: CO₂/i-propanol: 0.0 min 35% i-propanol, flow rate: 200 g/min; 14.0 min 35% isopropanol, flow rate: 200 g/min; 15.0 min 60% i-propanol, flow rate: 115 g/min; 37.0 min 60% i-propanol, flow rate: 115 g/min; 38.0 min 35% i-propanol, flow rate: 200 g/min; 42.0 min 35% i-propanol, flow rate: 200 g/min; temperature 38° C.; UV detection: 210 nm]. After the separation, 2.78 g of enantiomer 1, which eluted first, and 2.79 g of enantiomer 2, which eluted later, were isolated.

Enantiomer 2

Analytical chiral SFC: R_t=4.20 min, d.e.=100% [column: Daicel Chiralpak® IC 50×4.6 mm; eluent: CO₂/i-propanol 70:30; flow rate: 3 ml/min; UV detection: 210 nm].

LC-MS (Method 4): R_t=0.60 min; MS (ESIpos): m/z=239 [M+H]⁺

¹H-NMR (400 MHz, DMSO-d6) δ[ppm]=1.41 (s, 9H), 1.49 (dq, 1H), 1.72-1.84 (m, 1H), 1.95-2.10 (m, 2H), 2.46-2.56 (m, 1H), 2.59-2.68 (m, 1H), 4.35 (t, 1H), 11.36 (s, 1H).

The (5S) configuration was assigned on the basis of the crystal structure elucidation for Example 26, 108, 113, 157, 237, 358 and 454.

tert-Butyl (5S)-3-oxo-2,3,5,6,7,8-hexahydro[1,2,4]triazolo[4,3-a]pyridine-5-carboxylate

Intermediate 26 tert-Butyl (5RS)3-oxo-2,3,5,6,7,8-hexahydro[1,2,4]triazolo[4,3-a]pyridine-5-carboxylate (Enantiomer 1)

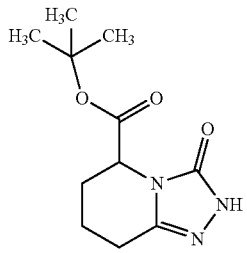 [SMILES: CC(C)(C)OC(=O)C1CCCc2n[nH]c(=O)n21]

tert-Butyl (5RS)-3-oxo-2,3,5,6,7,8-hexahydro[1,2,4]triazolo[4,3-a]pyridine-5-carboxylate (racemate) was separated by chiral preparative SFC [sample preparation: 6.00 g dissolved in 88 ml of methanol; injection volume: 4.5 ml; column: Daicel Chiralpak® IC 20 µm, 370×50 mm; eluent: CO$_2$/i-propanol: 0.0 min 35% i-propanol, flow rate: 200 g/min; 14.0 min 35% isopropanol, flow rate: 200 g/min; 15.0 min 60% i-propanol, flow rate: 115 g/min; 37.0 min 60% i-propanol, flow rate: 115 g/min; 38.0 min 35% i-propanol, flow rate: 200 g/min; 42.0 min 35% i-propanol, flow rate: 200 g/min; temperature 38° C.; UV detection: 210 nm]. After the separation, 2.78 g of enantiomer 1, which eluted first, and 2.79 g of enantiomer 2, which eluted later, were isolated.

Enantiomer 1

Analytical chiral SFC: R$_t$=1.67 min, d.e.=100% [column: Daicel Chiralpak® IC 50×4.6 mm; eluent: CO$_2$/i-propanol 70:30; flow rate: 3 ml/min; UV detection: 210 nm].

LC-MS (Method 4): R$_t$=0.60 min; MS (ESIpos): m/z=239 [M+H]$^+$ $^1$H-NMR (400 MHz, DMSO-d6) δ[ppm]=1.41 (s, 9H), 1.49 (dq, 1H), 1.81 (dt, 1H), 2.00-2.10 (m, 2H), 2.45-2.56 (m, 1H), 2.58-2.67 (m, 1H), 4.35 (t, 1H), 11.36 (s, 1H).

Intermediate 27 tert-Butyl 6-chloro-4-methylpyridine-2-carboxylate

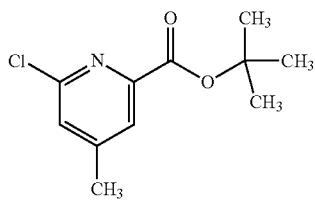

6-Chloro-4-methylpyridine-2-carboxylic acid (2.50 g, 14.6 mmol) was dissolved in pyridine (10 ml) and tert-butanol (50 ml, 520 mmol), and 4-methylbenzenesulphonyl chloride (5.56 g, 29.1 mmol) was added. The reaction mixture was stirred at room temperature overnight and diluted with saturated aqueous sodium hydrogencarbonate solution and cyclohexane/ethyl acetate 90/10. The organic phase was separated off and the aqueous phase was extracted with cyclohexane/ethyl acetate 90/10. The combined organic phases were washed with saturated aqueous sodium chloride solution, dried over sodium sulphate and filtered, and the filtrate was concentrated. 2.89 g (87% purity, 75% of theory) of the title compound were obtained.

$^1$H-NMR (400 MHz, DMSO-d6) δ [ppm]: 1.325 (0.86), 1.340 (0.86), 1.553 (16.00), 7.614 (0.68), 7.830 (0.80).

Intermediate 28 tert-Butyl 6-{1-[(benzyloxy)carbonyl]hydrazino}-4-methylpyridine-2-carboxylate

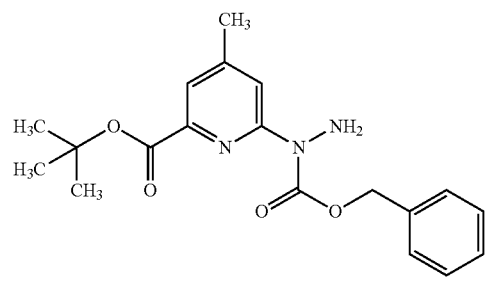 [SMILES: Cc1cc(C(=O)OC(C)(C)C)nc(N(N)C(=O)OCc2ccccc2)c1]

Under argon, tert-butyl 6-chloro-4-methylpyridine-2-carboxylate (2.89 g, 12.7 mmol) and benzyl hydrazinecarboxylate (2.32 g, 14.0 mmol) were dissolved in toluene (32 ml), and 1,1'-bis(diphenylphosphino)ferrocene (657 mg, 635 µmol), tris(dibenzylideneacetone)dipalladium-chloroform complex (704 mg, 1.27 mmol) and caesium carbonate (4.96 g, 15.2 mmol) were added. The reaction mixture was stirred at 80° C. for 4 h and then water and ethyl acetate were added. The organic phase was removed and the aqueous phase was extracted three times with ethyl acetate. The combined organic phases were washed with saturated aqueous sodium chloride solution, dried over magnesium sulphate and filtered, and the filtrate was concentrated. The residue was purified via column chromatography (silica gel; eluent: isocratic, methanol/dichloromethane 4/96). The product-containing fractions were concentrated under reduced pressure, and 4.25 g (86% purity, 81% of theory) of the title compound were obtained.

LC-MS (Method 3): R$_t$=1.96 min; MS (ESIpos): m/z=358 [M+H]

$^1$H-NMR (400 MHz, DMSO-d6) δ [ppm]: 1.317 (0.87), 1.329 (0.87), 1.549 (16.00), 2.387 (5.39), 5.192 (4.02), 5.277 (3.65), 7.314 (0.79), 7.331 (1.05), 7.344 (1.30), 7.360 (1.75), 7.380 (0.82), 7.421 (2.12), 7.440 (1.40), 7.618 (1.55), 7.649 (1.81).

Intermediate 29 tert-Butyl 7-methyl-3-oxo-2,3-dihydro[1,2,4]triazolo[4,3-a]pyridine-5-carboxylate

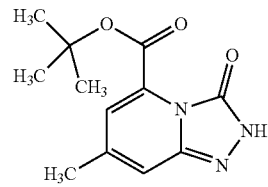 [SMILES: Cc1cc(C(=O)OC(C)(C)C)n2c(=O)[nH]nc2c1]

To an initial charge of palladium on charcoal (299 mg, 10%) under argon were added tert-butyl 6-{1-[(benzyloxy)carbonyl]hydrazino}-4-methylpyridine-2-carboxylate (1.80 g, 5.04 mmol) in methanol (20 ml). The reaction mixture was stirred in a hydrogen atmosphere (1 bar) at room temperature overnight. The suspension was diluted with methanol, filtered through kieselguhr and washed through with methanol. The reaction mixture was concentrated and converted further directly.

The residue was dissolved in THF (40 ml), and di-1H-imidazol-1-ylmethanone (980 mg, 6.04 mmol) was added. The reaction mixture was stirred at room temperature for 30 min. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 1.05 g (90% purity, 75% of theory) of the title compound were obtained.

LC-MS (Method 1): $R_t$=0.98 min; MS (ESIneg): m/z=248 [M−H]⁻

¹H-NMR (400 MHz, DMSO-d6) δ [ppm]: 1.536 (16.00), 1.553 (0.97), 2.218 (3.39), 3.318 (0.65), 6.597 (1.20), 7.051 (0.96), 12.345 (0.65).

Intermediate 30 tert-Butyl (5RS,7RS)-7-methyl-3-oxo-2,3,5,6,7,8-hexahydro[1,2,4]triazolo[4,3-a]pyridine-5-carboxylate (Diastereomer Mixture; 4 Isomers)

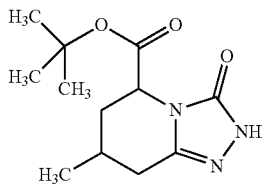

To an initial charge of palladium on charcoal (740 mg, 10%) under argon were added tert-butyl 7-methyl-3-oxo-2,3-dihydro[1,2,4]triazolo[4,3-a]pyridine-5-carboxylate (3.1 g, 12.44 mmol) in methanol (124 ml). The reaction mixture was stirred in a hydrogen atmosphere (1 bar) at room temperature overnight. The suspension was diluted with methanol and filtered through kieselguhr and washed through with methanol. The solvent was removed under reduced pressure. The residue was taken up in methanol (124 ml) and admixed with palladium on charcoal (740 mg, 10%). The reaction mixture was stirred in a hydrogen atmosphere (2 bar) at room temperature for 48 h. The suspension was diluted with methanol and filtered through kieselguhr and washed through with methanol. The solvent was removed under reduced pressure, and 2.71 g (86% of theory) of the title compound were obtained.

LC-MS (Method 3): $R_t$=1.24 min; MS (ESIpos): m/z=507 [2M+H]⁺

¹H-NMR (400 MHz, DMSO-d6) δ[ppm]: 1.015 (2.13), 1.032 (2.20), 1.400 (0.73), 1.405 (1.16), 1.416 (16.00), 1.432 (0.48), 2.181 (0.46), 2.209 (0.56), 4.184 (0.45), 4.195 (0.43), 11.342 (0.73).

Intermediate 31

Ethyl 6-{1-[(benzyloxy)carbonyl]hydrazino}-3-methylpyridine-2-carboxylate

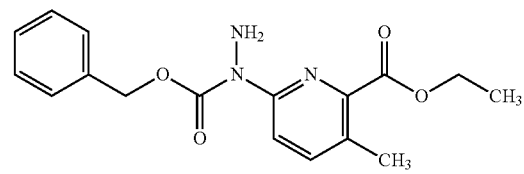 [SMILES: CCOC(=O)c1nc(N(N)C(=O)OCc2ccccc2)ccc1C]

Under argon, ethyl 6-chloro-3-methylpyridine-2-carboxylate (970 mg, 4.86 mmol) and benzyl hydrazinecarboxylate (969 mg, 5.83 mmol) were dissolved in toluene (9.7 ml), and tris(dibenzylideneacetone)dipalladium-chloroform complex (251 mg, 243 µmol), 1,1'-bis(diphenylphosphino)ferrocene (269 mg, 486 µmol) and caesium carbonate (1.90 g, 5.83 mmol) were added. The reaction mixture was stirred at 80° C. for 4 h and then water and ethyl acetate were added. The organic phase was removed and the aqueous phase was extracted three times with ethyl acetate. The combined organic phases were washed with saturated aqueous sodium chloride solution, dried over magnesium sulphate and filtered, and the filtrate was concentrated. The residue was purified via column chromatography (SiO₂; eluent: isocratic, methanol/dichloromethane 8/92). The product-containing fractions were concentrated under reduced pressure, and 1.89 g (47% purity, 55% of theory) of the title compound were obtained.

LC-MS (Method 4): $R_t$=0.89 min; MS (ESIpos): m/z=330 [M+H]

Intermediate 32

Ethyl 6-hydrazino-3-methylpyridine-2-carboxylate Dihydrochloride

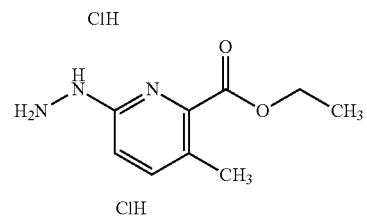

To an initial charge of palladium on charcoal (232 mg, 10%) under argon were added ethyl 6-{1-[(benzyloxy)carbonyl]hydrazino}-3-methylpyridine-2-carboxylate (1.89 g, 5.74 mmol) in methanol (60 ml). The reaction mixture was stirred in a hydrogen atmosphere (1 bar) at room temperature overnight. The suspension was diluted with methanol and filtered through kieselguhr and washed through with methanol. The solvent was removed under reduced pressure and the residue was taken up in dioxane and admixed with dioxane/hydrochloric acid (4M). The precipitated solids were filtered and washed with methyl tert-butyl ether and converted further directly.

Intermediate 33

Ethyl 6-methyl-3-oxo-2,3-dihydro[1,2,4]triazolo[4,3-a]pyridine-5-carboxylate

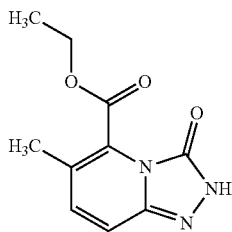

Ethyl 6-hydrazino-3-methylpyridine-2-carboxylate dihydrochloride (419 mg, 1.56 mmol) was taken up in THF (12 ml), and di-1H-imidazol-1-ylmethanone (261 mg, 1.61 mmol) was added. The reaction mixture was stirred at room temperature for 2 h. The reaction mixture was admixed with water and dichloromethane, and basified with saturated aqueous sodium hydrogencarbonate solution. The organic phase was removed and the aqueous phase was extracted three times with ethyl acetate. The combined organic phases were washed with saturated aqueous sodium chloride solution, dried over magnesium sulphate and filtered, and the filtrate was concentrated. 347 mg (89% purity, 104% of theory) of the title compound were obtained.

LC-MS (Method 1): $R_t$=0.77 min; MS (ESIneg): m/z=220 [M–H]⁻

¹H-NMR (400 MHz, DMSO-d6) δ[ppm]: 1.282 (5.00), 1.299 (10.60), 1.317 (5.79), 1.335 (0.84), 1.356 (2.69), 2.078 (16.00), 2.118 (0.45), 2.280 (0.45), 2.395 (0.71), 2.428 (0.75), 4.331 (1.67), 4.349 (4.92), 4.367 (4.80), 4.385 (1.58), 7.060 (2.57), 7.084 (3.35), 7.239 (3.24), 7.263 (2.51), 7.632 (0.45), 12.533 (1.43).

Intermediate 34

Ethyl (5RS,6RS)-6-methyl-3-oxo-2,3,5,6,7,8-hexahydro[1,2,4]triazolo[4,3-a]pyridine-5-carboxylate (Diastereomer Mixture; 4 Isomers)

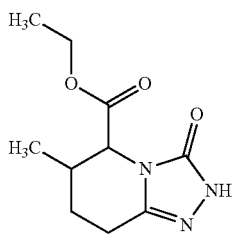

To an initial charge of palladium on charcoal (63 mg, 10%) under argon were added ethyl 6-methyl-3-oxo-2,3-dihydro[1,2,4]triazolo[4,3-a]pyridine-5-carboxylate (297 mg, 1.34 mmol) in methanol (10 ml), and the reaction mixture was stirred in a hydrogen atmosphere (1 bar) at room temperature overnight. The suspension was diluted with methanol and filtered through kieselguhr and washed through with methanol. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure.

The residue was dissolved in methanol (5.0 ml) and, after addition of palladium on charcoal (25 mg, 10%), the reaction mixture was stirred in a hydrogen atmosphere (1 bar) at room temperature overnight. The suspension was diluted with methanol and filtered through kieselguhr and washed through with methanol. The solvent was removed under reduced pressure, and 117 mg (39% of theory) of the title compound were obtained.

LC-MS (Method 3): $R_t$=0.93 min; MS (ESIpos): m/z=226 [M+H]⁺

¹H-NMR (400 MHz, DMSO-d6) δ[ppm]: 1.015 (11.82), 1.033 (12.24), 1.175 (7.82), 1.193 (16.00), 1.211 (8.16), 1.236 (0.40), 1.428 (0.40), 1.441 (0.50), 1.459 (1.16), 1.473 (1.29), 1.492 (1.47), 1.505 (1.43), 1.522 (0.71), 1.536 (0.62), 1.691 (1.35), 1.698 (1.45), 1.706 (1.50), 1.717 (0.89), 1.724 (1.18), 1.732 (1.11), 1.739 (1.07), 2.246 (0.67), 2.252 (0.78), 2.263 (1.08), 2.269 (1.18), 2.278 (1.20), 2.284 (1.18), 2.292 (1.12), 2.299 (1.03), 2.309 (0.72), 2.316 (0.63), 2.557 (1.30), 2.569 (1.98), 2.584 (1.68), 2.600 (1.66), 2.615 (1.39), 2.656 (1.71), 2.661 (2.10), 2.669 (2.15), 2.675 (1.92), 2.698 (0.96), 2.703 (1.08), 2.711 (1.03), 2.717 (0.80), 4.098 (0.91), 4.107 (1.22), 4.116 (1.20), 4.125 (4.30), 4.134 (1.05), 4.142 (6.35), 4.151 (1.07), 4.160 (4.32), 4.169 (1.26), 4.178 (1.27), 4.187 (0.95), 4.419 (4.25), 4.435 (4.22), 11.412 (1.99).

Intermediate 35

Ethyl 6-hydrazino-4-(trifluoromethyl)pyridine-2-carboxylate

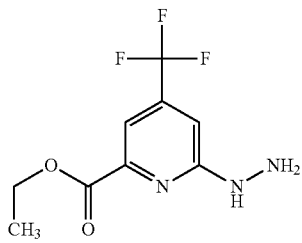 [SMILES: CCOC(=O)c1cc(C(F)(F)F)cc(NN)n1]

Under argon, ethyl 6-chloro-4-(trifluoromethyl)pyridine-2-carboxylate (1000 mg, 3.94 mmol) and benzyl hydrazinecarboxylate (721 mg, 4.34 mmol) were dissolved in toluene (10 ml), and tris(dibenzylideneacetone)dipalladium-chloroform complex (204 mg, 197 µmol), 1,1'-bis(diphenylphosphino)ferrocene (219 mg, 394 µmol) and caesium carbonate (1.54 g, 4.73 mmol) were added. The reaction mixture was stirred at 80° C. for 4 h and water and ethyl acetate were added. The organic phase was removed and the aqueous phase was extracted three times with ethyl acetate. The combined organic phases were washed with saturated aqueous sodium chloride solution, dried over magnesium sulphate and filtered, and the filtrate was concentrated. The residue was purified via column chromatography (SiO₂; eluent: isocratic, methanol/dichloromethane 8/92). The product-containing fractions were concentrated under reduced pressure and the residue obtained was converted further directly. The residue was dissolved in methanol (50 ml) under argon, and palladium on charcoal (223 mg, 10%) was added. The reaction mixture was stirred in a hydrogen atmosphere (1 bar) at room temperature overnight. Further palladium on charcoal (223 mg, 10%) was added, and the mixture was stirred in a hydrogen atmosphere (1 bar) at room temperature overnight. The suspension was diluted with methanol, filtered through kieselguhr and washed through with methanol. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 385 mg (93% purity, 38% of theory) of the title compound were obtained.

LC-MS (Method 1): $R_t$=0.91 min; MS (ESIpos): m/z=250 [M+H]$^+$

Intermediate 36

Ethyl 3-oxo-7-(trifluoromethyl)-2,3-dihydro[1,2,4]triazolo[4,3-a]pyridine-5-carboxylate

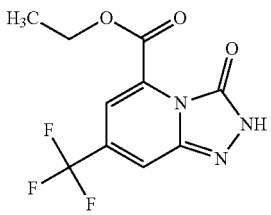 [SMILES: CCOC(=O)c1cc(C(F)(F)F)cc2n[nH]c(=O)n12]

Ethyl 6-hydrazino-4-(trifluoromethyl)pyridine-2-carboxylate (384 mg, 1.54 mmol) was initially charged in THF (19 ml), di-1H-imidazol-1-ylmethanone (300 mg, 1.85 mmol) was added, and the mixture was stirred at room temperature overnight. The reaction mixture was admixed with water and dichloromethane. The organic phase was removed and the aqueous phase was extracted three times with dichloromethane. The combined organic phases were washed with water and saturated aqueous sodium chloride solution, dried over magnesium sulphate and filtered, and the filtrate was concentrated. 391 mg (94% purity, 87% of theory) of the title compound were obtained.

LC-MS (Method 4): $R_t$=0.71 min; MS (ESIpos): m/z=276 [M+H]$^+$ $^1$H-NMR (400 MHz, DMSO-d6) δ [ppm]: 1.299 (7.46), 1.316 (16.00), 1.334 (7.58), 1.345 (0.42), 1.357 (1.20), 1.363 (0.66), 2.525 (0.47), 4.336 (2.37), 4.354 (7.32), 4.371 (7.27), 4.389 (2.27), 7.044 (4.79), 7.048 (4.79), 7.954 (2.71), 7.957 (3.98), 7.960 (2.90).

Intermediate 37

Ethyl (5RS,7RS)-3-oxo-7-(trifluoromethyl)-2,3,5,6,7,8-hexahydro[1,2,4]triazolo[4,3-a]pyridine-5-carboxylate (Diastereomer Mixture; 4 Isomers)

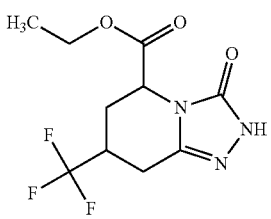 [SMILES: CCOC(=O)C1CC(C(F)(F)F)Cc2n[nH]c(=O)n21]

To an initial charge of palladium on charcoal (30 mg, 10%) under argon were added ethyl 3-oxo-7-(trifluoromethyl)-2,3-dihydro[1,2,4]triazolo[4,3-a]pyridine-5-carboxylate (100 mg, 363 μmol) in methanol (5.0 ml). The reaction mixture was stirred in a hydrogen atmosphere (1 bar) at room temperature for 40 h. The suspension was diluted with methanol and filtered through kieselguhr and washed through with methanol. The solvent was removed under reduced pressure, and 97.8 mg (87% purity, 84% of theory) of the title compound were obtained.

LC-MS (Method 4): $R_t$=0.64 min; MS (ESIpos): m/z=280 [M+H]$^+$ $^1$H-NMR (500 MHz, DMSO-d6) δ [ppm]: 1.042 (1.06), 1.056 (2.04), 1.070 (1.10), 1.199 (8.42), 1.214 (16.00), 1.228 (8.00), 1.305 (0.45), 1.356 (1.36), 1.738 (1.02), 1.763 (2.47), 1.787 (2.58), 1.812 (1.20), 2.696 (1.56), 2.721 (2.08), 2.728 (2.47), 2.752 (2.57), 2.869 (2.23), 2.896 (1.50), 2.901 (1.51), 3.057 (1.19), 3.064 (1.13), 3.072 (1.13), 3.165 (1.54), 3.174 (1.56), 3.429 (0.48), 3.439 (0.55), 3.452 (0.48), 4.141 (0.78), 4.149 (1.47), 4.156 (2.22), 4.163 (4.00), 4.170 (4.33), 4.177 (4.39), 4.184 (3.95), 4.191 (2.27), 4.198 (1.47), 4.205 (0.83), 4.319 (0.42), 4.331 (0.60), 4.432 (2.24), 4.444 (2.52), 4.455 (2.47), 4.466 (2.20), 7.628 (0.41), 11.601 (3.48).

Intermediate 38

Methyl (2RS)-6-[(4-methoxybenzyl)(m ethoxycarbonyl)hydrazono]piperidine-2-carboxylate (Racemate)

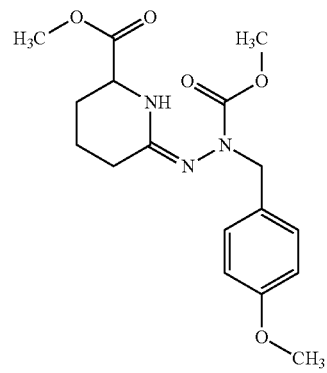

To methyl (2RS)-6-oxopiperidine-2-carboxylate (racemate) (685 mg, 4.36 mmol) in dichloromethane (15 ml) under argon was added trimethyloxonium tetrafluoroborate (678 mg, 95% purity, 4.36 mmol), and the reaction mixture was stirred at room temperature overnight. Then methyl 1-(4-methoxybenzyl)hydrazinecarboxylate (1.29 g, 71% purity, 4.36 mmol) was added and the mixture was stirred at room temperature with occasional checking of the conversion for several days. For workup, the volatile components were removed under reduced pressure. The remaining crude product (1.52 g, 100% of theory) was converted further without additional purification.

Intermediate 39

Methyl (5RS)-2-(4-methoxybenzyl)-3-oxo-2,3,5,6,7,8-hexahydro[1,2,4]triazolo[4,3-a]pyridine-5-carboxylate (Racemate)

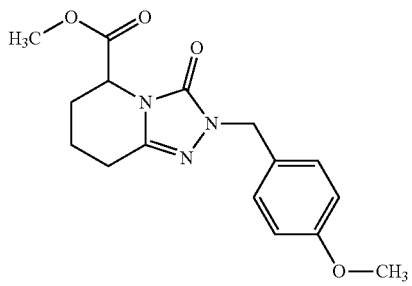

Methyl (2RS)-6-[(4-methoxybenzyl)(methoxycarbonyl)hydrazono]piperidine-2-carboxylate (racemate) (1.52 g, 4.35 mmol) in DMF (5 ml) was stirred at 150° C. overnight. For workup, the cooled mixture was added to about 50 ml of water, and the mixture was alkalized to about pH 9 with aqueous sodium hydroxide solution and extracted three times with 50 ml of dichloromethane. The combined organic phases were washed with saturated aqueous sodium chloride solution, dried over magnesium sulphate, filtered and concentrated under reduced pressure. The crude product thus obtained was purified by chromatography on silica gel (PuriFlash 50 g silica gel cartridge, dichloromethane 100%=>dichloromethane:MeOH 80:1). In this way, two fractions of the title compound were obtained: 327 mg in 60% purity (14% of theory) and 858 mg in 72% purity (45% of theory).

Analysis results for the second fraction:

LC-MS (Method 6): $R_t$=1.33 min; MS (ESIpos): m/z=318 [M+H]$^+$ $^1$H-NMR (400 MHz, DMSO-d6) δ [ppm]: 2.615 (0.90), 2.731 (9.35), 2.890 (12.58), 3.700 (13.65), 3.730 (16.00), 3.736 (6.83), 3.742 (2.33), 4.492 (1.54), 4.582 (0.85), 4.591 (0.94), 4.597 (1.08), 4.607 (0.82), 4.750 (5.88), 6.882 (3.29), 6.887 (2.11), 6.899 (1.66), 6.904 (4.11), 6.908 (1.73), 7.162 (3.09), 7.167 (1.04), 7.178 (1.35), 7.183 (3.40), 7.203 (1.01), 7.923 (0.79), 7.952 (1.25).

Intermediate 40

(5RS)-2-(4-Methoxybenzyl)-3-oxo-2,3,5,6,7,8-hexahydro[1,2,4]triazolo[4,3-a]pyridine-5-carboxylic Acid (Racemate)

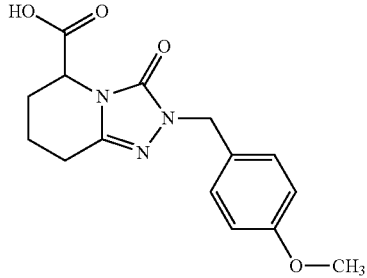 [SMILES: COc1ccc(Cn2nc3n(c2=O)C(C(=O)O)CCC3)cc1]

Methyl (5RS)-2-(4-methoxybenzyl)-3-oxo-2,3,5,6,7,8-hexahydro[1,2,4]triazolo[4,3-a]pyridine-5-carboxylate (racemate) (320 mg, 60% purity, 605 μmol) was dissolved in water/THF (5 ml/5 ml), lithium hydroxide (72.4 mg, 3.03 mmol) was added and the reaction mixture was stirred at room temperature over a weekend. For workup, water was added, the pH was adjusted to 3 with 1 N aqueous hydrochloric acid, and the mixture was saturated with sodium chloride and extracted three times with 30 ml each time of ethyl acetate. The combined organic phases were dried with magnesium sulphate, filtered, concentrated under reduced pressure and dried. 250 mg (71% purity, 97% of theory) of the title compound were obtained. The product thus obtained was used further without additional purification.

In a second batch conducted analogously, 850 mg of methyl (5RS)-2-(4-methoxybenzyl)-3-oxo-2,3,5,6,7,8-hexahydro[1,2,4]triazolo[4,3-a]pyridine-5-carboxylate (72% purity, 1.93 mmol) were used to obtain 625 mg of the title compound (89% purity, 95% of theory).

LC-MS (Method 3): $R_t$=1.00 min; MS (ESIpos): m/z=304 [M+H]$^+$

Intermediate 41

(5RS)-5-(Pyrrolidin-1-ylcarbonyl)-5,6,7,8-tetrahydro[1,2,4]triazolo[4,3-a]pyridin-3(2H)-one (Racemate)

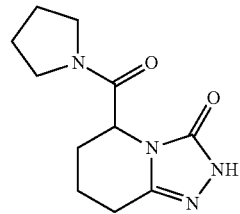 [SMILES: O=C(C1CCCc2n[nH]c(=O)n21)N1CCCC1]

Variant a)

(5RS)-2-(4-Methoxybenzyl)-5-(pyrrolidin-1-ylcarbonyl)-5,6,7,8-tetrahydro[1,2,4]triazolo[4,3-a]pyridin-3(2H)-one (racemate) (670 mg, 1.88 mmol) was dissolved in trifluoroacetic acid (15 ml) and stirred at 150° C. in a microwave apparatus for 1 h. For workup, the cooled mixture was concentrated and the residue was purified in 2 injections via preparative HPLC (column: Chromatorex C18, 250×40 mm 10 μm. Flow rate: 50 ml/min. Gradient (A=water+0.1% formic acid, B=acetonitrile): 0 min 10% B, 6 min 10% B, 27 min 95% B, 38 min 95% B, 40 min 10% B. Run time per separation 40 min. Detection: 210 nm). Product fractions were concentrated and lyophilized. In this way, 0.36 g (80% of theory) of the title compound was obtained.

Variant b)

Methyl (5RS)-3-oxo-2,3,5,6,7,8-hexahydro[1,2,4]triazolo[4,3-a]pyridine-5-carboxylate (racemate) (500 mg, 2.54 mmol) in a mixture with pyrrolidine (5.0 ml, 60 mmol) was stirred at 50° C. first for 2 h, then for a further 18 h, then at 60° C. for about a further 24 h (monitoring of conversion by HPLC/LC-MS). For workup, the mixture was admixed with water, diluted with ethyl acetate and extracted. The aqueous phase was extracted twice more with ethyl acetate. The organic phases were discarded after an LC-MS check. The product-containing aqueous phase was concentrated and dried under reduced pressure. By triturating the residue with ethyl acetate/methanol, concentrating the mother liquor and triturating again with the solvent mixture, two fractions of the title compound were obtained: 45.7 mg (8%) and 112 mg (19%).

Analysis data for the second fraction:

LC-MS (Method 6): $R_t$=0.80 min; MS (ESIpos): m/z=237 [M+H]$^+$ $^1$H-NMR (500 MHz, DMSO-d6) δ [ppm]: 1.147 (0.62), 1.662 (1.69), 1.673 (2.39), 1.682 (4.36), 1.690 (6.79), 1.700 (8.57), 1.710 (6.71), 1.720 (3.20), 1.757 (2.60), 1.771 (9.56), 1.784 (16.00), 1.798 (11.83), 1.812 (3.41), 1.894 (3.39), 1.907 (11.19), 1.921 (15.40), 1.935 (10.59), 1.948 (4.95), 1.956 (5.06), 1.965 (4.50), 1.972 (2.37), 1.978 (2.52), 1.990 (3.30), 1.999 (3.57), 2.007 (3.10), 2.019 (2.87), 2.036 (1.28), 2.049 (0.83), 2.472 (2.42), 2.518 (5.78), 2.524 (4.83), 2.571 (3.49), 2.580 (6.69), 2.590 (3.51), 2.604 (1.94), 2.613 (3.22), 2.623 (1.57), 2.636 (0.62), 3.013 (0.68), 3.027 (1.51), 3.041 (0.64), 3.225 (2.19), 3.238 (4.42), 3.248 (4.27), 3.262 (7.12), 3.276 (3.96), 3.288 (5.24), 3.324 (12.41), 3.333 (4.62), 3.338 (5.10), 3.347 (4.83), 3.362 (2.48), 3.375 (0.68), 3.437 (2.33), 3.451 (4.93), 3.457 (3.84), 3.465 (3.28), 3.471 (6.13), 3.485 (2.81), 3.579 (2.85), 3.593 (5.88), 3.599 (3.34), 3.606 (3.61), 3.612 (4.77), 3.626 (2.17), 4.637 (5.45), 4.644 (6.46), 4.650 (7.06), 4.657 (5.49), 11.270 (6.83).

Intermediate 42

Ethyl 2-isopropylidene-1-(4-methylbenzyl)hydrazinecarboxylate

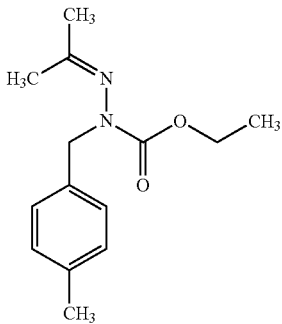

To ethyl 2-isopropylidenehydrazinecarboxylate (CAS 6637-60-1; 3.23 g, 22.4 mmol) in 55 ml of toluene were added, under argon, potassium hydroxide powder (4.11 g, 29.7 mmol) and tetra-n-butylammonium hydrogensulphate (734 mg, 2.16 mmol). For better stirrability, 10 ml of toluene were added. After heating to 50° C., a solution of 1-(bromomethyl)-4-methylbenzene (5.00 g, 27.0 mmol) in 15 ml of toluene was added dropwise, and the mixture was heated to 80° C. and stirred for a further 2.5 h. For workup, the mixture was admixed with water and the organic phase was removed after extraction. The organic phase was extracted twice more with water, then the combined organic phases were reextracted once with toluene. The organic phases were washed with saturated aqueous sodium chloride solution, dried over sodium sulphate, concentrated and dried under reduced pressure. The crude product obtained was purified by chromatography using silica gel (instrument: Isolera column: 340 g SNAP eluent: cyclohexane and EtOAc gradient: 0 min cyclohexane, 10 min cyclohexane, 35 min 30% EtOAc, 40 min 30% EtOAc). Product-containing fractions were combined, concentrated and dried. In this way, 3.76 g (56% of theory) of the title compound were obtained.

LC-MS (Method 4): $R_t$=0.96 min; MS (ESIpos): m/z=249 [M+H]$^+$

Intermediate 43

Ethyl 1-(4-methylbenzyl)hydrazinecarboxylate

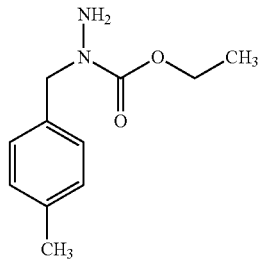

Ethyl 2-isopropylidene-1-(4-methylbenzyl)hydrazinecarboxylate (3.77 g, 15.2 mmol, according to LC-MS already partly hydrolysed to the title compound) was dissolved in ethanol/water (100 ml/66 ml), heated to reflux and stirred for 3 h. For workup, the mixture was then very substantially concentrated, and the residue was taken up in dichloromethane/water and extracted. After separation of the phases, the aqueous phase was extracted twice more with dichloromethane, and the combined organic phases were washed with saturated sodium chloride solution, dried over sodium sulphate, concentrated and dried under reduced pressure. In this way, 3.25 g (87% purity, 89% of theory) of the title compound were obtained, which was converted further without further purification.

LC-MS (Method 6): $R_t$=1.53 min; MS (ESIpos): m/z=209 [M+H]$^+$ $^1$H-NMR (400 MHz, DMSO-d6) δ[ppm]: 1.159 (0.80), 1.168 (1.91), 1.185 (3.86), 1.203 (1.95), 1.667 (1.33), 1.927 (1.25), 2.267 (1.24), 2.275 (9.41), 4.035 (1.18), 4.053 (3.64), 4.071 (3.59), 4.088 (1.13), 4.425 (5.48), 4.548 (3.26), 7.126 (16.00).

Intermediate 44

Methyl (2RS)-6-[(ethoxycarbonyl)(4-methylbenzyl)hydrazono]piperidine-2-carboxylate (Racemate)

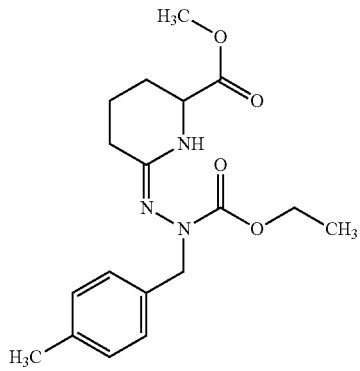 [SMILES: CCOC(=O)N(Cc1ccc(C)cc1)/N=C1/CCCC(C(=O)OC)N1]

To methyl (2RS)-6-oxopiperidine-2-carboxylate (racemate) (1.58 g, 10.1 mmol) in 20 ml of dichloromethane under argon was added trimethyloxonium tetrafluoroborate (1.57 g, 95% purity, 10.1 mmol), and the reaction mixture was stirred at room temperature for 18 h. Then ethyl 1-(4-methylbenzyl)hydrazinecarboxylate (2.41 g, 87% purity, 10.1 mmol), dissolved in 10 ml of dichloromethane, was added dropwise and the mixture was stirred at room temperature for 26 h. For workup, the volatile components were removed under reduced pressure and the residue was separated using silica gel. (Instrument: Isolera; column: 100 g SNAP cartridge, eluent: cyclohexane and EtOAc/EtOAc and MeOH Gradient: 0 min 30% EtOAc, 3 min 30% EtOAc, 13 min 100% EtOAc, 18 min 100% EtOAc, 18.01 min 10% MeOH, 33 min 10% MeOH). Product-containing fractions were combined, concentrated and dried under reduced pressure. This gave 1.46 g (88% purity, 37% of theory) of the title compound, which was converted further as such.

LC-MS (Method 3): $R_t$=0.98 min; MS (ESIpos): m/z=348 [M+H]$^+$ $^1$H-NMR (400 MHz, DMSO-d6) δ [ppm]: 1.055 (0.58), 1.149 (1.00), 1.157 (1.01), 1.167 (1.78), 1.175 (1.73), 1.184 (0.92), 1.192 (0.87), 1.644 (0.91), 1.908 (0.76), 1.988 (2.45), 2.128 (2.05), 2.141 (2.19), 2.144 (2.23), 2.148 (1.42), 2.156 (0.95), 2.164 (0.99), 2.274 (3.39), 2.279 (4.35), 3.162 (0.90), 3.175 (0.90), 3.538 (3.77), 3.578 (0.99), 3.585 (1.56), 3.638 (3.98), 3.667 (16.00), 3.675 (1.67), 3.684 (2.39), 3.701 (3.26), 4.021 (0.67), 4.038 (0.81), 4.049 (1.01), 4.056 (1.07), 4.063 (1.50), 4.069 (1.44), 4.775 (1.21), 7.127 (1.68), 7.134 (2.17), 7.174 (1.17).

Intermediate 45

Methyl (5RS)-2-(4-methylbenzyl)-3-oxo-2,3,5,6,7,8-hexahydro[1,2,4]triazolo[4,3-a]pyridine-5-carboxylate (Racemate)

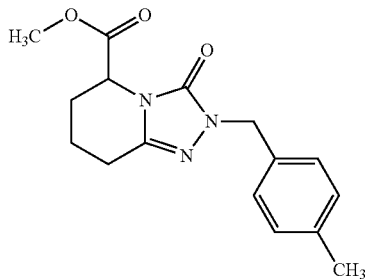

Methyl (2RS)-6-[(ethoxycarbonyl) (4-methylbenzyl)hydrazono]piperidine-2-carboxylate (racemate) (730 mg, 88% purity, 1.85 mmol) in DMF (15 ml) was stirred at 150° C. overnight. For workup, the mixture was added to water, alkalized with 3 N sodium hydroxide solution and extracted with dichloromethane. The aqueous phase was saturated with sodium chloride and extracted twice more with dichloromethane. The combined organic phases were washed with saturated aqueous sodium chloride solution, dried over sodium sulphate, filtered and concentrated under reduced pressure. This gave 288 mg (52% of theory) of the title compound.

LC-MS (Method 3): $R_t$=1.42 min; MS (ESIpos): m/z=302 [M+H]$^+$ $^1$H-NMR (400 MHz, DMSO-d6) δ[ppm]: 2.274 (12.04), 2.580 (0.80), 2.616 (1.19), 2.731 (10.86), 2.890 (12.92), 3.285 (1.12), 3.700 (16.00), 4.588 (1.05), 4.598 (1.19), 4.604 (1.34), 4.614 (1.04), 4.775 (6.63), 7.105 (0.94), 7.119 (1.09), 7.127 (7.35), 7.134 (6.83), 7.155 (1.02), 7.952 (1.56).

Alternative Synthesis:

Methyl (5RS)-3-oxo-2,3,5,6,7,8-hexahydro[1,2,4]triazolo[4,3-a]pyridine-5-carboxylate (500 mg, 2.54 mmol) was initially charged in acetonitrile (10 ml). Caesium carbonate (909 mg, 2.79 mmol) and 1-(bromomethyl)-4-methylbenzene (493 mg, 2.66 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 560 mg (73% of theory) of the title compound were obtained.

LC-MS (Method 1): $R_t$=1.05 min; MS (ESIpos): m/z=302 [M+H]$^+$ $^1$H-NMR (400 MHz, DMSO-d6) δ[ppm]: −0.008 (0.61), 0.008 (0.56), 1.787 (0.45), 1.798 (0.49), 1.812 (0.42), 2.050 (0.42), 2.060 (0.71), 2.072 (0.83), 2.080 (0.64), 2.088 (0.52), 2.096 (0.44), 2.104 (0.52), 2.108 (0.45), 2.116 (0.53), 2.124 (0.51), 2.132 (0.48), 2.274 (11.08), 2.523 (0.63), 2.566 (0.81), 2.580 (0.64), 2.605 (0.58), 2.616 (1.09), 2.629 (0.60), 2.659 (0.49), 3.701 (16.00), 4.588 (0.99), 4.598 (1.12), 4.604 (1.28), 4.614 (0.97), 4.775 (6.33), 7.106 (0.87), 7.127 (6.84), 7.134 (6.17), 7.154 (0.82).

Intermediate 46

Methyl (5RS)-2-(4-methylbenzyl)-3-oxo-2,3,5,6,7,8-hexahydro[1,2,4]triazolo[4,3-a]pyridine-5-carboxylate (Enantiomer 1)

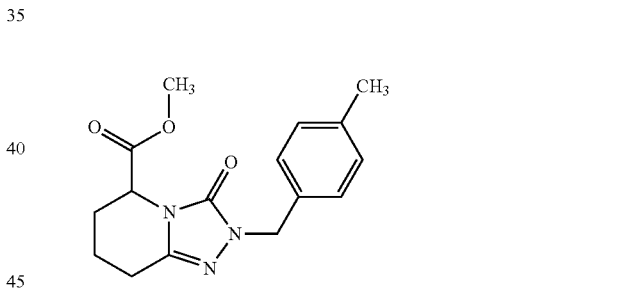

Methyl (5RS)-3-oxo-2,3,5,6,7,8-hexahydro[1,2,4]triazolo[4,3-a]pyridine-5-carboxylate (enantiomer 2) (700 mg, 3.55 mmol) was initially charged in acetonitrile (31 ml). Caesium carbonate (1.27 g, 3.90 mmol) and 1-(bromomethyl)-4-methylbenzene (690 mg, 3.73 mmol) were subsequently added. After stirring overnight, the reaction mixture was admixed at room temperature with water and ethyl acetate. The organic phase was removed and the aqueous phase was extracted twice with ethyl acetate. The combined organic phases were washed with saturated aqueous sodium chloride solution, dried over magnesium sulphate and filtered, and the filtrate was concentrated. 1.05 g (91% purity, 89% of theory) of the title compound were obtained.

LC-MS (Method 3): $R_t$=1.46 min; MS (ESIpos): m/z=302 [M+H]$^+$ $^1$H-NMR (400 MHz, DMSO-d6) δ[ppm]: 1.497 (0.40), 1.519 (0.42), 1.524 (0.43), 1.532 (0.43), 1.788 (0.50), 1.797 (0.54), 1.811 (0.47), 1.821 (0.43), 1.988 (0.48), 2.049 (0.50), 2.060 (0.81), 2.073 (0.80), 2.080 (0.72), 2.087 (0.59), 2.095 (0.51), 2.104 (0.58), 2.115 (0.59), 2.124 (0.56), 2.131 (0.52), 2.273 (12.47), 2.292 (0.91), 2.523 (0.62), 2.566 (0.84), 2.580 (0.68), 2.604 (0.64), 2.616 (1.20), 2.628 (0.66), 2.658 (0.55), 3.310 (16.00), 3.683 (0.71), 4.588 (1.13), 4.598 (1.28), 4.604 (1.44), 4.614 (1.10), 4.674 (0.43), 4.775 (6.90), 7.106 (1.01), 7.127 (8.08), 7.133 (7.29), 7.154 (1.06).

The (5S) configuration was assigned on the basis of the crystal structure elucidation for Example 26, 108, 113, 157, 237, 358 and 454.

Methyl (5S)-2-(4-methylbenzyl)-3-oxo-2,3,5,6,7,8-hexahydro[1,2,4]triazolo[4,3-a]pyridine-5-carboxylate Intermediate 47

Methyl (5S)-3-oxo-2,5,6,7-tetrahydro-3H-pyrrolo[2,1-c][1,2,4]triazole-5-carboxylate (Enantiomer)

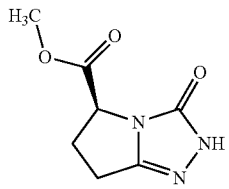

Methyl 5-oxo-L-prolinate (24.0 g, 168 mmol, CAS 4931-66-2) was initially charged in dichloromethane (210 ml) at room temperature. Subsequently, trimethyloxonium tetrafluoroborate (24.8 g, 168 mmol) was added and the reaction mixture was stirred at room temperature overnight. The solvent was removed under reduced pressure and the residue was admixed with DMF (240 ml). Subsequently, methyl hydrazinecarboxylate (15.1 g, 168 mmol) was added and the reaction mixture was stirred at 170° C. overnight. The reaction mixture was concentrated under reduced pressure and the residue was purified via column chromatography (silica gel, eluent: dichloromethane/methanol gradient). The product-containing fractions were concentrated under reduced pressure, and 7.57 g (25% of theory) of the title compound were obtained. The latter was converted further directly.

GC-MS (WUP-GC/MS): $R_t$=6.48 min; MS (ESIpos): m/z=183 [M+H]$^+$

Intermediate 48

Methyl (5S)-2-(4-methylbenzyl)-3-oxo-2,5,6,7-tetrahydro-3H-pyrrolo[2,1-c][1,2,4]triazole-5-carboxylate (Enantiomer)

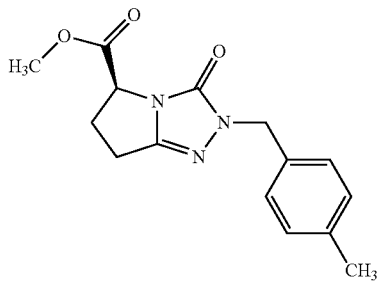

Methyl (5S)-3-oxo-2,5,6,7-tetrahydro-3H-pyrrolo[2,1-c][1,2,4]triazole-5-carboxylate (enantiomer) (250 mg, 1.36 mmol) was initially charged in acetonitrile (3.0 ml). Caesium carbonate (489 mg, 1.50 mmol) and 1-(bromomethyl)-4-methylbenzene (265 mg, 1.43 mmol, CAS 104-81-4) were subsequently added. After stirring overnight, the reaction mixture was admixed at room temperature with water and ethyl acetate. The organic phase was removed and the aqueous phase was extracted three times with dichloromethane. The combined organic phases were washed with saturated aqueous sodium chloride solution, dried over sodium sulphate and filtered, and the filtrate was concentrated. 412 mg (91% purity, 96% of theory) of the title compound were obtained.

LC-MS (Method 3): $R_t$=1.32 min; MS (ESIpos): m/z=288 [M+H]$^+$ $^1$H-NMR (400 MHz, DMSO-d6) δ [ppm]: 2.072 (1.11), 2.275 (9.70), 2.303 (0.99), 2.458 (0.51), 2.465 (0.54), 2.720 (1.21), 2.743 (1.93), 2.758 (1.66), 2.837 (0.42), 2.857 (0.41), 2.869 (0.51), 2.892 (0.49), 3.708 (1.25), 3.722 (12.20), 4.758 (2.95), 4.763 (3.01), 4.776 (1.05), 4.791 (1.07), 4.799 (0.95), 4.937 (0.40), 5.753 (0.46), 7.141 (16.00).

Intermediate 49

Methyl (5S)-2-[(6-chloropyridin-3-yl)methyl]-3-oxo-2,5,6,7-tetrahydro-3H-pyrrolo[2,1-c][1,2,4]triazole-5-carboxylate (Enantiomer)

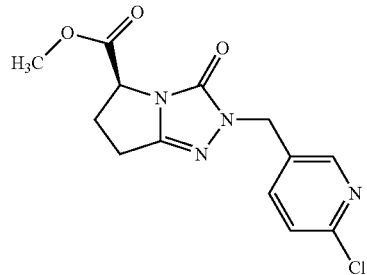 [SMILES: COC(=O)[C@@H]1CCc2nn(Cc3ccc(Cl)nc3)c(=O)n21]

Methyl (5S)-3-oxo-2,5,6,7-tetrahydro-3H-pyrrolo[2,1-c][1,2,4]triazole-5-carboxylate (enantiomer) (300 mg, 1.64 mmol) was initially charged in acetonitrile (10 ml). After stirring for 5 min, caesium carbonate (587 mg, 1.80 mmol) and 5-(bromomethyl)-2-chloropyridine (355 mg, 1.72 mmol, CAS 182924-36-3) were added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 430 mg (85% of theory) of the title compound were obtained.

Intermediate 50

Methyl (5S)-3-oxo-2-{[6-(trifluoromethyl)pyridin-3-yl]methyl}-2,5,6,7-tetrahydro-3H-pyrrlo[2,1-c][1,2,4]triazole-5-carboxylate (Enantiomer)

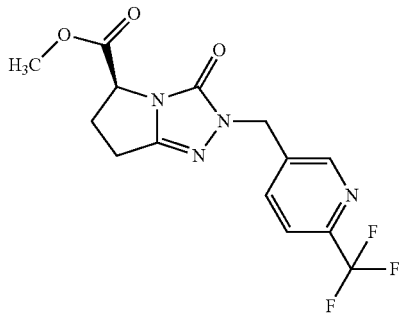 [SMILES: COC(=O)[C@@H]1CCc2nn(Cc3ccc(C(F)(F)F)nc3)c(=O)n21]

Methyl (5S)-3-oxo-2,5,6,7-tetrahydro-3H-pyrrolo[2,1-c][1,2,4]triazole-5-carboxylate (enantiomer) (300 mg, 1.64 mmol) was initially charged in acetonitrile (10 ml). Caesium carbonate (587 mg, 1.80 mmol) and 5-(bromomethyl)-2-(trifluoromethyl)pyridine (413 mg, 1.72 mmol, CAS 108274-33-5) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 441 mg (79% of theory) of the title compound were obtained.

LC-MS (Method 1): $R_t$=0.92 min; MS (ESIpos): m/z=343 [M+H]$^+$

Intermediate 51

Methyl (5S)-2-(3-chloro-4-fluorobenzyl)-3-oxo-2,5,6,7-tetrahydro-3H-pyrrolo[2,1-c][1,2,4]triazole-5-carboxylate (Enantiomer)

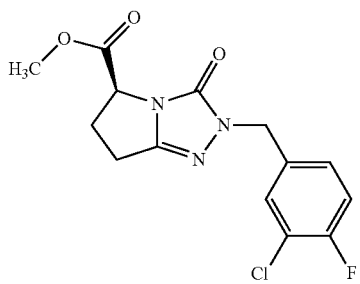 [SMILES: COC(=O)[C@@H]1CCc2nn(Cc3ccc(F)c(Cl)c3)c(=O)n21]

Methyl (5S)-3-oxo-2,5,6,7-tetrahydro-3H-pyrrolo[2,1-c][1,2,4]triazole-5-carboxylate (enantiomer) (300 mg, 1.64 mmol) was initially charged in acetonitrile (530 µl). After stirring for 5 min, caesium carbonate (587 mg, 1.80 mmol) and 4-(bromomethyl)-2-chloro-1-fluorobenzene (384 mg, 1.72 mmol, CAS 192702-01-5) were added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 460 mg (86% of theory) of the title compound were obtained.

LC-MS (Method 3): $R_t$=1.42 min; MS (ESIpos): m/z=326 [M+H]$^+$

Intermediate 52

Methyl (5S)-3-oxo-2-[3-(trifluoromethyl)benzyl]-2,5,6,7-tetrahydro-3H-pyrrolo[2,1-c][1,2,4]triazole-5-carboxylate (Enantiomer)

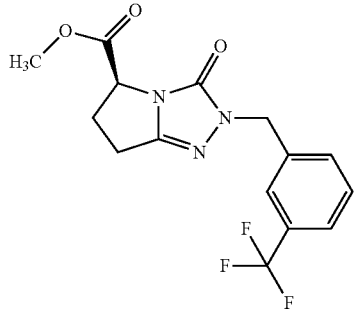 [SMILES: COC(=O)[C@@H]1CCc2nn(Cc3cccc(C(F)(F)F)c3)c(=O)n21]

Methyl (5S)-3-oxo-2,5,6,7-tetrahydro-3H-pyrrolo[2,1-c][1,2,4]triazole-5-carboxylate (enantiomer) (150 mg, 819 µmol) was initially charged in acetonitrile (8.0 ml). After stirring for 5 min, caesium carbonate (294 mg, 901 µmol) and 1-(bromomethyl)-3-(trifluoromethyl)benzene (206 mg, 860 µmol, CAS 402-23-3) were added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 150 mg (53% of theory) of the title compound were obtained.

LC-MS (Method 1): R$_t$=1.09 min; MS (ESIpos): m/z=342 [M+H]$^+$

Intermediate 53

Methyl (5S)-2-[(2-chloropyridin-4-yl)methyl]-3-oxo-2,5,6,7-tetrahydro-3H-pyrrolo[2,1-c][1,2,4]triazole-5-carboxylate (Enantiomer)

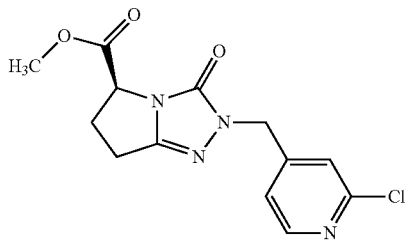 [SMILES: COC(=O)[C@@H]1CCc2nn(Cc3ccnc(Cl)c3)c(=O)n21]

Methyl (5S)-3-oxo-2,5,6,7-tetrahydro-3H-pyrrolo[2,1-c][1,2,4]triazole-5-carboxylate (enantiomer) (150 mg, 819 µmol) was initially charged in acetonitrile (7.0 ml). After stirring for 5 min, caesium carbonate (294 mg, 901 µmol) and 4-(bromomethyl)-2-chloropyridine (178 mg, 860 µmol, CAS 83004-15-3) were added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 250 mg (99% of theory) of the title compound were obtained.

LC-MS (Method 1): R$_t$=0.78 min; MS (ESIpos): m/z=309 [M+H]$^+$

Intermediate 54

Methyl (5RS)-2-(4-chlorobenzyl)-3-oxo-2,3,5,6,7,8-hexahydro[1,2,4]triazolo[4,3-a]pyridine-5-carboxylate (Racemate)

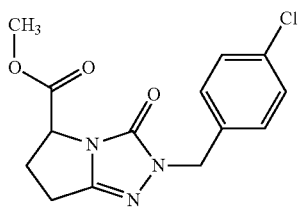 [SMILES: COC(=O)C1CCc2nn(Cc3ccc(Cl)cc3)c(=O)n21]

Methyl (2RS)-6-[(tert-butoxycarbonyl)hydrazono]piperidine-2-carboxylate (racemate) (2.20 g, 7.21 mmol) in DMF (15 ml) was stirred at 150° C. overnight. The reaction mixture (theoretical yield: 1.42 g) was divided into aliquots and used further directly. To the solution of an aliquot of the crude product methyl (5RS)-3-oxo-2,3,5,6,7,8-hexahydro[1,2,4]triazolo[4,3-a]pyridine-5-carboxylate (racemate) (calculated as 473 mg, 2.40 mmol) in 5 ml of DMF were added caesium carbonate (1.17 g, 3.60 mmol) and 1-(bromomethyl)-4-chlorobenzene (518 mg, 2.52 mmol). The reaction mixture was stirred at room temperature overnight. Then more 1-(bromomethyl)-4-chlorobenzene was added (493 mg, 2.40 mmol) and the mixture was stirred at 50° C. overnight. For workup, water was added, the mixture was extracted twice with 15 ml each time of ethyl acetate, and the combined organic phases were washed once with saturated aqueous sodium chloride solution, dried with magnesium sulphate, filtered and concentrated under reduced pressure. The residue was separated in 2 portions via preparative HPLC (column: Chromatorex, 125×40 mm 10 µm. Flow rate: 50 ml/min. Gradient (A=water+0.1% formic acid, B=acetonitrile): 0 min 10% B, 5 min 10% B, 27 min 98% B, 35 min 98% B, 35.01 min 10% B, 38 min 10% B. Run time per separation 38 min. Detection: 210 nm). Concentration of the product fractions gave 80 mg (96% purity, 9.6% of theory) of the title compound.

LC-MS (Method 3): R$_t$=1.78 min; MS (ESIpos): m/z=388 [M+H]$^+$

Intermediate 55 tert-Butyl (5RS)-2-(4-methylbenzyl)-3-oxo-2,3,5,6,7,8-hexahydro[1,2,4]triazolo[4,3-a]pyridine-5-carboxylate (Enantiomer 1)

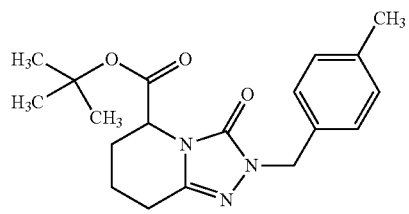 [SMILES: Cc1ccc(Cn2nc3n(c2=O)C(C(=O)OC(C)(C)C)CCC3)cc1]

tert-Butyl (5RS)-3-oxo-2,3,5,6,7,8-hexahydro[1,2,4]triazolo[4,3-a]pyridine-5-carboxylate (enantiomer 2) (1.77 g, 7.38 mmol) was initially charged in acetonitrile (71 ml). Caesium carbonate (2.40 g, 7.38 mmol) and 1-(bromomethyl)-4-methylbenzene (1.37 g, 7.38 mmol) were subsequently added. After stirring overnight, the reaction mixture was admixed at room temperature with water and ethyl acetate. The organic phase was removed and the aqueous phase was extracted with ethyl acetate. The combined organic phases were washed with saturated aqueous sodium chloride solution, dried over magnesium sulphate and filtered, and the filtrate was concentrated. 2.65 g (>100% of theory) of the title compound were obtained.

LC-MS (Method 4): $R_t$=0.97 min; MS (ESIpos): m/z=343 [M+H]$^+$

Intermediate 56 tert-Butyl (5RS)-2-[(5-chloropyridin-2-yl)methyl]-3-oxo-2,3,5,6,7,8-hexahydro[1,2,4]triazolo[4,3-a]pyridine-5-carboxylate (Racemate)

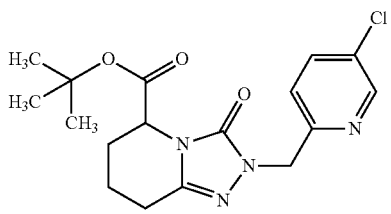 [SMILES: CC(C)(C)OC(=O)C1CCCc2nn(Cc3ccc(Cl)cn3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (613 mg, 1.88 mmol) and 2-(bromomethyl)-5-chloropyridine (272 mg, 1.32 mmol, CAS 605681-01-4) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 306 mg (65% of theory) of the title compound were obtained.

LC-MS (Method 3): $R_t$=1.61 min; MS (ESIpos): m/z=365 [M+H]$^+$ $^1$H-NMR (600 MHz, DMSO-d6) δ[ppm]: 1.410 (16.00), 2.078 (0.62), 2.085 (0.56), 2.637 (0.42), 4.453 (0.46), 4.459 (0.48), 4.463 (0.58), 4.469 (0.43), 4.932 (1.44), 4.947 (1.43), 7.232 (0.89), 7.246 (0.91), 7.928 (0.56), 7.932 (0.56), 7.942 (0.53), 7.946 (0.52), 8.578 (0.90), 8.582 (0.88).

Intermediate 57 tert-Butyl (5RS)-3-oxo-2-{[6-(trifluoromethyl)pyridin-3-yl]methyl}-2,3,5,6,7,8-hexahydro-[1,2,4]triazolo[4,3-a]pyridine-5-carboxylate (Racemate)

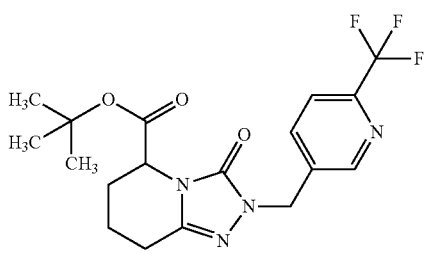 [SMILES: CC(C)(C)OC(=O)C1CCCc2nn(Cc3ccc(C(F)(F)F)nc3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (613 mg, 1.88 mmol) and 5-(bromomethyl)-2-(trifluoromethyl)pyridine (316 mg, 1.32 mmol, CAS 108274-33-5) were subsequently added. After stirring at room temperature for 48 h, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was suspended in diethyl ether and the solids were filtered off and dried under reduced pressure. 345 mg (66% of theory) of the title compound were obtained.

LC-MS (Method 4): $R_t$=0.92 min; MS (ESIpos): m/z=399 [M+H]$^+$ $^1$H-NMR (400 MHz, DMSO-d6) δ[ppm]: 1.383 (16.00), 1.404 (0.51), 2.069 (0.60), 2.081 (0.48), 4.457 (0.62), 5.036 (2.03), 7.923 (1.20), 7.933 (0.73), 7.937 (0.70), 8.665 (0.72).

Intermediate 58 tert-Butyl (5RS)-2-(3,5-dichlorobenzyl)-3-oxo-2,3,5,6,7,8-hexahydro[1,2,4]triazolo[4,3-a]pyridine-5-carboxylate (Racemate)

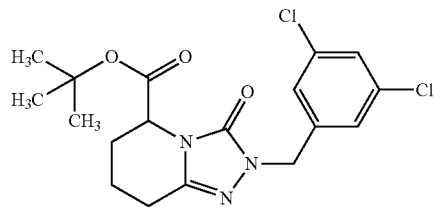 [SMILES: CC(C)(C)OC(=O)C1CCCc2nn(Cc3cc(Cl)cc(Cl)c3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (613 mg, 1.88 mmol) and 1-(bromomethyl)-3,5-dichlorobenzene (316 mg, 1.32 mmol, CAS 7778-01-0) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 445 mg (82% purity, 89% of theory) of the title compound were obtained.

LC-MS (Method 3): $R_t$=2.12 min; MS (ESIpos): m/z=342 [M+H]$^+$

Intermediate 59 tert-Butyl (5RS)-3-oxo-2-(pyridin-3-ylmethyl)-2,3,5,6,7,8-hexahydro[1,2,4]triazolo[4,3-a]pyridine-5-carboxylate (Racemate)

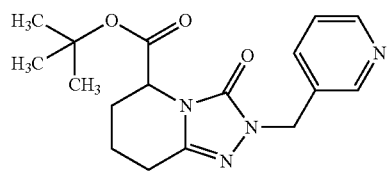 [SMILES: CC(C)(C)OC(=O)C1CCCc2nn(Cc3cccnc3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (1.02 g, 3.13 mmol) and 3-(bromomethyl)pyridine hydrobromide (333 mg, 1.32 mmol, CAS 4916-55-6) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 366 mg (88% of theory) of the title compound were obtained.

LC-MS (Method 4): $R_t$=0.58 min; MS (ESIpos): m/z=331 [M+H]$^+$ $^1$H-NMR (400 MHz, DMSO-d6) δ[ppm]: 1.390 (16.00), 1.405 (12.47), 2.037 (0.58), 2.050 (0.73), 2.060 (0.77), 2.070 (0.65), 2.523 (0.58), 2.617 (0.41), 2.627 (0.42), 4.348 (0.50), 4.444 (0.59), 4.526 (0.81), 4.896 (1.69), 7.359 (0.43), 7.371 (0.43), 7.378 (0.45), 7.391 (0.45), 7.642 (0.49), 7.661 (0.42), 8.483 (0.82), 8.500 (0.55), 8.504 (0.55), 8.513 (0.52).

Intermediate 60

Methyl (5RS)-2-[(5-methyl-1,2-oxazol-3-yl)methyl]-3-oxo-2,3,5,6,7,8-hexahydro[1,2,4]triazolo[4,3-a]pyridine-5-carboxylate (Racemate)

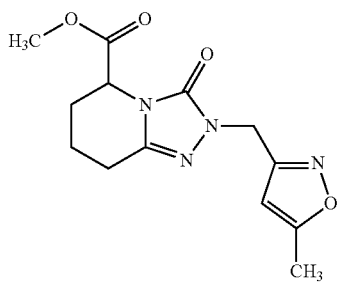 [SMILES: COC(=O)C1CCCc2nn(Cc3cc(C)on3)c(=O)n21]

Methyl (5RS)-3-oxo-2,3,5,6,7,8-hexahydro[1,2,4]triazolo[4,3-a]pyridine-5-carboxylate (racemate) (50.0 mg, 254 µmol) was initially charged in acetonitrile (3.6 ml). Caesium carbonate (124 mg, 380 µmol) and 3-(bromomethyl)-5-methyl-1,2-oxazole (46.9 mg, 266 µmol, CAS 130628-75-0) were subsequently added. After stirring at room temperature for 24 h, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 58.0 mg (93% purity, 73% of theory) of the title compound were obtained.

LC-MS (Method 1): $R_t$=0.78 min; MS (ESIpos): m/z=293 [M+H]$^+$ $^1$H-NMR (400 MHz, DMSO-d6) δ [ppm]: −0.008 (0.58), 0.008 (0.51), 1.527 (0.40), 1.532 (0.40), 1.540 (0.42), 1.798 (0.45), 1.806 (0.50), 1.820 (0.43), 2.055 (0.46), 2.072 (3.66), 2.084 (0.69), 2.092 (0.58), 2.100 (0.46), 2.108 (0.53), 2.113 (0.51), 2.120 (0.49), 2.129 (0.51), 2.136 (0.47), 2.206 (1.02), 2.376 (10.50), 2.518 (0.88), 2.560 (0.90), 2.575 (0.76), 2.587 (0.75), 2.601 (0.66), 2.624 (0.60), 2.636 (1.04), 2.648 (0.59), 2.678 (0.48), 3.687 (1.59), 3.703 (16.00), 4.591 (0.92), 4.600 (1.03), 4.607 (1.24), 4.616 (0.92), 4.854 (7.94), 4.981 (0.43), 6.065 (2.10).

Intermediate 61 tert-Butyl (5RS)-2-(3,4-difluorobenzyl)-3-oxo-2,3,5,6,7,8-hexahydro[1,2,4]triazolo[4,3-a]pyridine-5-carboxylate (Racemate)

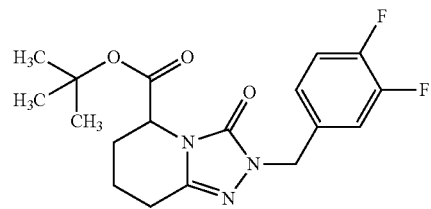 [SMILES: CC(C)(C)OC(=O)C1CCCc2nn(Cc3ccc(F)c(F)c3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (10 ml). Caesium carbonate (429 mg, 1.32 mmol) and 4-(bromomethyl)-1,2-difluorobenzene (273 mg, 1.32 mmol, CAS 85118-01-0) were subsequently added. The reaction mixture was stirred at room temperature overnight and at 90° C. for one hour. Water and ethyl acetate were then added to the reaction mixture. The organic phase was removed and the aqueous phase was extracted three times with ethyl acetate. The combined organic phases were washed with saturated aqueous sodium chloride solution, dried over sodium sulphate and filtered, and the filtrate was concentrated. 455 mg (99% of theory) of the title compound were obtained.

$^1$H-NMR (400 MHz, DMSO-d6) δ[ppm]: −0.008 (0.57), 0.008 (0.51), 1.393 (16.00), 1.404 (3.82), 1.908 (1.06), 1.988 (0.61), 2.064 (0.60), 2.074 (0.56), 2.523 (0.73), 4.433 (0.44), 4.443 (0.41), 4.448 (0.56), 4.699 (0.90), 4.847 (1.99), 7.400 (0.49), 7.428 (0.45).

Intermediate 62 tert-Butyl (5RS)-2-(3-chloro-4-fluorobenzyl)-3-oxo-2,3,5,6,7,8-hexahydro[1,2,4]triazolo[4,3-a]pyridine-5-carboxylate (Racemate)

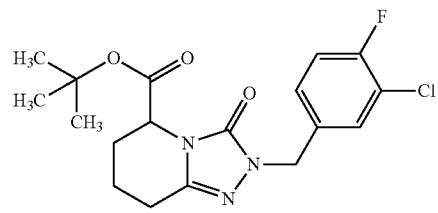 [SMILES: CC(C)(C)OC(=O)C1CCCc2nn(Cc3ccc(F)c(Cl)c3)c(=O)n21]

tert-Butyl (5RS)-3-oxo-2,3,5,6,7,8-hexahydro[1,2,4]triazolo[4,3-a]pyridine-5-carboxylate (racemate) (311 mg, 1.30 mmol) was initially charged in acetonitrile (10 ml). Caesium carbonate (445 mg, 1.36 mmol) and 4-(bromomethyl)-2-chloro-1-fluorobenzene (305 mg, 1.36 mmol, CAS 192702-01-5) were subsequently added. The reaction mixture was stirred at room temperature overnight and at 90° C. for one hour. Water and ethyl acetate were then added to the reaction mixture. The organic phase was removed and the aqueous phase was extracted three times with ethyl acetate. The combined organic phases were washed with saturated aqueous sodium chloride solution, dried over sodium sulphate and filtered, and the filtrate was concentrated. 491 mg (90% purity, 89% of theory) of the title compound were obtained.

LC-MS (Method 1): $R_t$=1.32 min; MS (ESIpos): m/z=326 [M−tBu+H]$^+$

Intermediate 63

Methyl (5RS)-2-(3-chlorobenzyl)-3-oxo-2,3,5,6,7,8-hexahydro[1,2,4]triazolo[4,3-a]pyridine-5-carboxylate (Racemate)

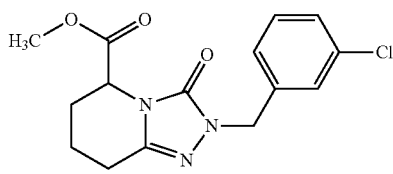 [SMILES: COC(=O)C1CCCc2nn(Cc3cccc(Cl)c3)c(=O)n21]

Methyl (5RS)-3-oxo-2,3,5,6,7,8-hexahydro[1,2,4]triazolo[4,3-a]pyridine-5-carboxylate (racemate) (50.0 mg, 254 μmol) was initially charged in acetonitrile (3.6 ml). Caesium carbonate (124 mg, 380 μmol) and 1-(bromomethyl)-3-chlorobenzene (54.7 mg, 266 μmol, CAS 766-80-3) were subsequently added. After stirring at room temperature for 24 h, the reaction mixture was admixed with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 66.0 mg (81% of theory) of the title compound were obtained.

LC-MS (Method 4): $R_t$=0.82 min; MS (ESIpos): m/z=322 [M+H]$^+$ $^1$H-NMR (400 MHz, DMSO-d6) δ [ppm]: −0.008 (1.42), 0.008 (1.25), 1.526 (0.41), 1.532 (0.41), 1.802 (0.49), 1.811 (0.51), 1.825 (0.45), 1.836 (0.42), 2.065 (0.46), 2.075 (0.77), 2.088 (0.74), 2.095 (0.70), 2.102 (0.56), 2.110 (0.46), 2.118 (0.54), 2.130 (0.51), 2.139 (0.53), 2.146 (0.50), 2.523 (1.49), 2.564 (1.03), 2.579 (0.83), 2.591 (0.83), 2.605 (0.68), 2.631 (0.63), 2.642 (1.16), 2.654 (0.67), 2.673 (0.53), 2.684 (0.51), 3.708 (16.00), 4.615 (1.04), 4.625 (1.16), 4.631 (1.33), 4.640 (1.01), 4.863 (5.05), 7.190 (1.12), 7.208 (1.43), 7.282 (1.86), 7.343 (0.46), 7.359 (1.33), 7.364 (2.10), 7.369 (2.85), 7.387 (1.85), 7.407 (0.62).

Intermediate 64 tert-Butyl (5RS)-2-[(2-methoxypyridin-4-yl)methyl]-3-oxo-2,3,5,6,7,8-hexahydro[1,2,4]triazolo[4,3-a]pyridine-5-carboxylate (Racemate)

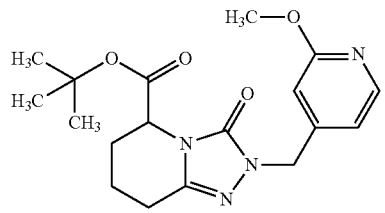 [SMILES: COc1cc(Cn2nc3n(c2=O)C(C(=O)OC(C)(C)C)CCC3)ccn1]

tert-Butyl (5RS)-3-oxo-2,3,5,6,7,8-hexahydro[1,2,4]triazolo[4,3-a]pyridine-5-carboxylate (racemate) (357 mg, 1.49 mmol) was initially charged in acetonitrile (10 ml). Caesium carbonate (510 mg, 1.57 mmol) and 4-(bromomethyl)-2-methoxypyridine (381 mg, 83% purity, 1.57 mmol, CAS 120277-15-8) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 144 mg (27% of theory) of the title compound were obtained.

LC-MS (Method 3): $R_t$=1.52 min; MS (ESIpos): m/z=361 [M+H]$^+$

Intermediate 65 tert-Butyl (5RS)-2-(3-fluorobenzyl)-3-oxo-2,3,5,6,7,8-hexahydro[1,2,4]triazolo[4,3-a]pyridine-5-carboxylate (Racemate)

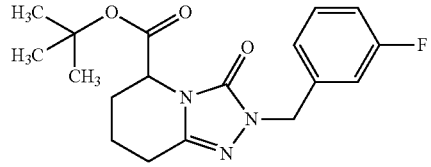 [SMILES: CC(C)(C)OC(=O)C1CCCc2nn(Cc3cccc(F)c3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (10 ml). Caesium carbonate (429 mg, 1.32 mmol) and 1-(bromomethyl)-3-fluorobenzene (249 mg, 1.32 mmol, CAS 456-41-7) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 297 mg (68% of theory) of the title compound were obtained.

LC-MS (Method 1): $R_t$=1.23 min; MS (ESIpos): m/z=291 [M+H]$^+$ $^1$H-NMR (400 MHz, DMSO-d6) δ [ppm]: −0.008 (1.11), 0.008 (0.97), 1.397 (16.00), 2.067 (0.49), 2.077 (0.52), 2.518 (1.08), 2.523 (0.83), 4.451 (0.57), 4.865 (1.75), 4.872 (1.37), 7.078 (0.48), 7.097 (0.65), 7.380 (0.40), 7.396 (0.42).

Intermediate 66 tert-Butyl (5RS)-2-(3-chloro-4-methoxybenzyl)-3-oxo-2,3,5,6,7,8-hexahydro[1,2,4]triazolo[4,3-a]pyridine-5-carboxylate (Racemate)

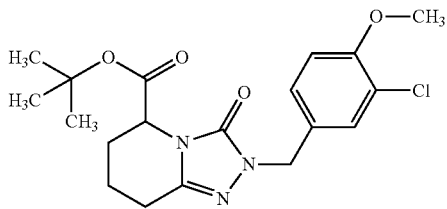 [SMILES: COc1ccc(Cn2nc3n(c2=O)C(C(=O)OC(C)(C)C)CCC3)cc1Cl]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (613 mg, 1.88 mmol) and 4-(bromomethyl)-2-chloro-1-methoxybenzene (314 mg, 99% purity, 1.32 mmol, CAS 320407-92-9) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 365 mg (74% of theory) of the title compound were obtained.

LC-MS (Method 4): $R_t$=0.96 min; MS (ESIpos): m/z=393 [M]

Intermediate 67 tert-Butyl (5RS)-3-oxo-2-[3-(trifluoromethyl)benzyl]-2,3,5,6,7,8-hexahydro[1,2,4]triazolo[4,3-a]pyridine-5-carboxylate (Racemate)

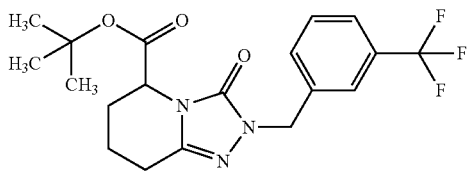 [SMILES: CC(C)(C)OC(=O)C1CCCc2nn(Cc3cccc(C(F)(F)F)c3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (613 mg, 1.88 mmol) and 1-(bromomethyl)-3-(trifluoromethyl)benzene (315 mg, 1.32 mmol, CAS 402-23-3) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was suspended in diethyl ether, and the solids were filtered off and dried under reduced pressure. 388 mg (75% of theory) of the title compound were obtained.

LC-MS (Method 1): $R_t$=1.35 min; MS (ESIpos): m/z=342 [M+H]$^+$

Intermediate 68 tert-Butyl (5RS)-2-(3-methoxybenzyl)-3-oxo-2,3,5,6,7,8-hexahydro[1,2,4]triazolo[4,3-a]pyridine-5-carboxylate (Racemate)

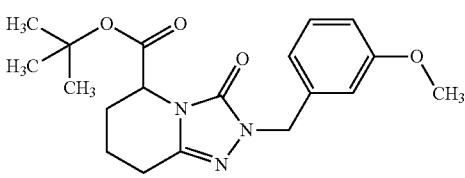 [SMILES: COc1cccc(Cn2nc3n(c2=O)C(C(=O)OC(C)(C)C)CCC3)c1]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (6.0 ml). Caesium carbonate (613 mg, 1.88 mmol) and 1-(bromomethyl)-3-methoxybenzene (265 mg, 1.32 mmol, CAS 874-98-6) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 340 mg (94% purity, 71% of theory) of the title compound were obtained.

LC-MS (Method 4): $R_t$=0.91 min; MS (ESIpos): m/z=360 [M+H]$^+$

Intermediate 69 tert-Butyl (5RS)-2-[(1-methyl-1H-pyrazol-3-yl)methyl]-3-oxo-2,3,5,6,7,8-hexahydro[1,2,4]triazolo[4,3-a]pyridine-5-carboxylate (Racemate)

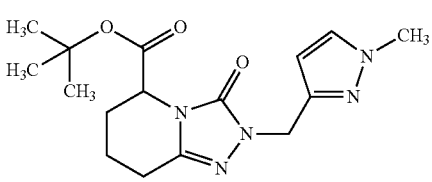 [SMILES: Cn1ccc(Cn2nc3n(c2=O)C(C(=O)OC(C)(C)C)CCC3)n1]

tert-Butyl (5RS)-3-oxo-2,3,5,6,7,8-hexahydro[1,2,4]triazolo[4,3-a]pyridine-5-carboxylate (racemate) (145 mg, 606 µmol) was initially charged in acetonitrile (6.0 ml). Caesium carbonate (207 mg, 636 µmol) and 3-(bromomethyl)-1-methyl-1H-pyrazole (106 mg, 606 µmol, CAS 102846-13-9) were subsequently added. The reaction mixture was stirred at room temperature overnight and then at 70° C. for 3 h. The reaction mixture was cooled to room temperature, and water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 150 mg (74% of theory) of the title compound were obtained.

LC-MS (Method 1): R$_t$=0.97 min; MS (ESIpos): m/z=278 [M−tBu+H]$^+$

Intermediate 70 tert-Butyl (5RS)-3-oxo-2-(5,6,7,8-tetrahydronaphthalen-2-ylmethyl)-2,3,5,6,7,8-hexahydro[1,2,4]triazolo[4,3-a]pyridine-5-carboxylate (Racemate)

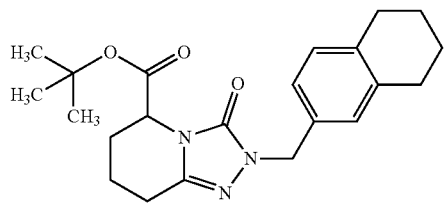 [SMILES: CC(C)(C)OC(=O)C1CCCc2nn(Cc3ccc4c(c3)CCCC4)c(=O)n21]

tert-Butyl (5RS)-3-oxo-2,3,5,6,7,8-hexahydro[1,2,4]triazolo[4,3-a]pyridine-5-carboxylate (racemate) (400 mg, 1.67 mmol) was initially charged in acetonitrile (10 ml). Caesium carbonate (572 mg, 1.76 mmol) and 6-(chloromethyl)-1,2,3,4-tetrahydronaphthalene (317 mg, 1.76 mmol, CAS 17450-63-4) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 280 mg (43% of theory) of the title compound were obtained.

LC-MS (Method 1): R$_t$=1.44 min; MS (ESIpos): m/z=328 [M−tBu+H]$^+$

Intermediate 71 tert-Butyl (5RS)-3-oxo-2-(2,4,5-trifluorobenzyl)-2,3,5,6,7,8-hexahydro[1,2,4]triazolo[4,3-a]pyridine-5-carboxylate (Racemate)

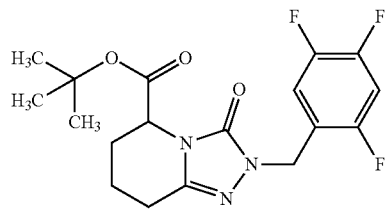 [SMILES: CC(C)(C)OC(=O)C1CCCc2nn(Cc3cc(F)c(F)cc3F)c(=O)n21]

tert-Butyl (5RS)-3-oxo-2,3,5,6,7,8-hexahydro[1,2,4]triazolo[4,3-a]pyridine-5-carboxylate (racemate) (400 mg, 1.67 mmol) was initially charged in acetonitrile (10 ml). Caesium carbonate (572 mg, 1.76 mmol) and 1-(chloromethyl)-2,4,5-trifluorobenzene (317 mg, 1.76 mmol, CAS 243139-71-1) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 390 mg (61% of theory) of the title compound were obtained.

LC-MS (Method 1): R$_t$=1.29 min; MS (ESIpos): m/z=328 [M−tBu+H]+

Intermediate 72 tert-Butyl (5RS)-2-[(2-chloropyridin-4-yl)methyl]-3-oxo-2,3,5,6,7,8-hexahydro[1,2,4]triazolo[4,3-a]pyridine-5-carboxylate (Racemate)

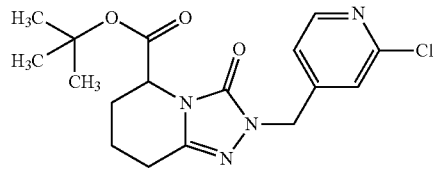 [SMILES: CC(C)(C)OC(=O)C1CCCc2nn(Cc3ccnc(Cl)c3)c(=O)n21]

tert-Butyl (5RS)-3-oxo-2,3,5,6,7,8-hexahydro[1,2,4]triazolo[4,3-a]pyridine-5-carboxylate (racemate) (370 mg, 1.54 mmol) was initially charged in acetonitrile (10 ml). Caesium carbonate (528 mg, 1.62 mmol) and 4-(bromomethyl)-2-chloropyridine (360 mg, 93% purity, 1.62 mmol, CAS 83004-15-3) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 490 mg (83% of theory) of the title compound were obtained.

LC-MS (Method 3): $R_t$=1.54 min; MS (ESIpos): m/z=365 [M+H]$^+$ $^1$H-NMR (400 MHz, DMSO-d6) δ[ppm]: −0.008 (1.57), 0.008 (1.54), 1.405 (16.00), 2.084 (0.54), 2.094 (0.44), 2.523 (0.99), 2.568 (0.41), 2.669 (0.51), 4.476 (0.54), 4.944 (1.40), 4.949 (1.35), 7.240 (0.51), 7.250 (0.53), 7.328 (0.82), 8.377 (0.75), 8.389 (0.75).

Intermediate 73 tert-Butyl (5RS)-2-[(5-chloro-2-thienyl)methyl]-3-oxo-2,3,5,6,7,8-hexahydro[1,2,4]triazolo[4,3-a]pyridine-5-carboxylate (Racemate)

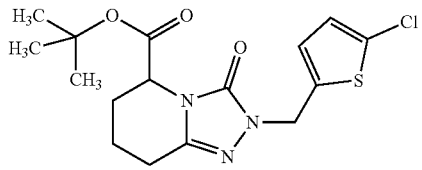 [SMILES: CC(C)(C)OC(=O)C1CCCc2nn(Cc3ccc(Cl)s3)c(=O)n21]

tert-Butyl (5RS)-3-oxo-2,3,5,6,7,8-hexahydro[1,2,4]triazolo[4,3-a]pyridine-5-carboxylate (racemate) (300 mg, 1.25 mmol) was initially charged in acetonitrile (10 ml). Caesium carbonate (429 mg, 1.32 mmol) and 2-chloro-5-(chloromethyl)thiophene (220 mg, 1.32 mmol, CAS 23784-96-5) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 414 mg (83% purity, 74% of theory) of the title compound were obtained.

LC-MS (Method 3): $R_t$=1.88 min; MS (ESIpos): m/z=313 [M+H]$^+$ $^1$H-NMR (400 MHz, DMSO-d6) δ [ppm]: 1.175 (0.45), 1.335 (0.71), 1.384 (16.00), 1.397 (0.99), 1.988 (0.79), 2.045 (0.50), 2.057 (0.51), 4.420 (0.56), 4.950 (2.59), 4.986 (2.46), 6.922 (0.61), 6.931 (0.84), 6.976 (1.11), 6.986 (0.79), 7.011 (0.48), 7.020 (0.65), 7.079 (0.51).

Intermediate 74

Methyl (5RS)-2-[(4-methyl-1,2,5-oxadiazol-3-yl)methyl]-3-oxo-2,3,5,6,7,8-hexahydro[1,2,4]triazolo[4,3-a]pyridine-5-carboxylate (Racemate)

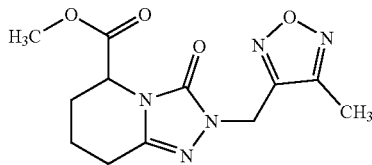

Methyl (5RS)-3-oxo-2,3,5,6,7,8-hexahydro[1,2,4]triazolo[4,3-a]pyridine-5-carboxylate (racemate) (300 mg, 1.52 mmol) was initially charged in acetonitrile (10 ml). Caesium carbonate (545 mg, 1.67 mmol) and 3-(bromomethyl)-4-methyl-1,2,5-oxadiazole (283 mg, 1.60 mmol, CAS 90507-32-7) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 281 mg (63% of theory) of the title compound were obtained.

LC-MS (Method 3): $R_t$=1.06 min; MS (ESIpos): m/z=294 [M+H]$^+$

Intermediate 75

Methyl (5RS)-2-[(6-methylpyridin-3-yl)methyl]-3-oxo-2,3,5,6,7,8-hexahydro[1,2,4]triazolo[4,3-a]pyridine-5-carboxylate (Racemate)

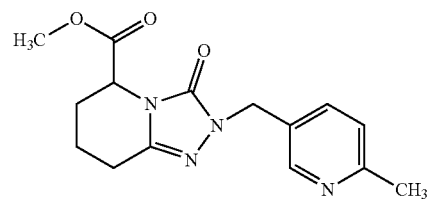

Methyl (5RS)-3-oxo-2,3,5,6,7,8-hexahydro[1,2,4]triazolo[4,3-a]pyridine-5-carboxylate (racemate) (300 mg, 1.52 mmol) was initially charged in acetonitrile (10 ml). Caesium carbonate (1.24 g, 3.80 mmol) and 5-(chloromethyl)-2-methylpyridine hydrochloride (298 mg, 1.67 mmol, CAS 106651-81-4) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 236 mg (51% of theory) of the title compound were obtained.

LC-MS (Method 4): $R_t$=0.26 min; MS (ESIpos): m/z=303 [M+H]$^+$ $^1$H-NMR (400 MHz, DMSO-d6) δ [ppm]: −0.008 (0.57), 0.008 (0.57), 1.511 (0.41), 1.517 (0.41), 1.525 (0.42), 1.787 (0.49), 1.798 (0.53), 1.812 (0.45), 1.822 (0.42), 2.051 (0.47), 2.061 (0.80), 2.073 (3.59), 2.086 (0.68), 2.095 (0.50), 2.103 (0.56), 2.107 (0.49), 2.115 (0.52), 2.123 (0.54), 2.131 (0.51), 2.439 (12.07), 2.523 (0.56), 2.557 (0.88), 2.569 (0.86), 2.583 (0.68), 2.609 (0.63), 2.621 (1.16), 2.633 (0.65), 2.663 (0.57), 3.700 (16.00), 4.594 (1.02), 4.603 (1.12), 4.610 (1.31), 4.619 (1.00), 4.835 (5.24), 7.216 (1.67), 7.236 (1.95), 7.506 (1.19), 7.512 (1.20), 7.526 (1.07), 7.532 (1.07), 8.337 (1.47), 8.342 (1.45).

Intermediate 76

Methyl (5RS)-2-[(6-methoxypyridin-3-yl)methyl]-3-oxo-2,3,5,6,7,8-hexahydro[1,2,4]triazolo[4,3-a]pyridine-5-carboxylate (Racemate)

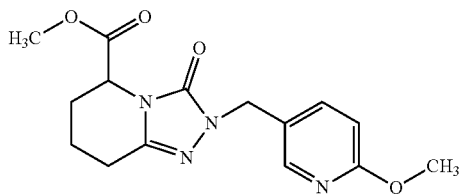

Methyl (5RS)-3-oxo-2,3,5,6,7,8-hexahydro[1,2,4]triazolo[4,3-a]pyridine-5-carboxylate (racemate) (300 mg, 1.52 mmol) was initially charged in acetonitrile (10 ml). Caesium carbonate (1.24 g, 3.80 mmol) and 5-(chloromethyl)-2-methoxypyridine hydrochloride (325 mg, 1.67 mmol, CAS 120276-36-0) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 206 mg (42% of theory) of the title compound were obtained.

LC-MS (Method 4): $R_t$=0.61 min; MS (ESIpos): m/z=319 [M+H]$^+$ $^1$H-NMR (400 MHz, DMSO-d6) δ [ppm]: −0.008 (1.39), 0.008 (1.28), 1.795 (0.43), 2.073 (5.67), 2.091 (0.40), 2.099 (0.45), 2.111 (0.42), 2.120 (0.44), 2.127 (0.41), 2.523 (0.87), 2.568 (0.68), 2.582 (0.55), 2.608 (0.50), 2.620 (0.92), 2.631 (0.52), 2.662 (0.50), 3.698 (13.67), 3.828 (16.00), 3.851 (0.46), 4.585 (0.90), 4.594 (0.95), 4.600 (1.13), 4.610 (0.82), 4.794 (5.64), 6.793 (1.69), 6.815 (1.80), 7.560 (1.13), 7.566 (1.15), 7.582 (1.09), 7.588 (1.11), 8.066 (1.53), 8.071 (1.49).

Intermediate 77

Methyl (5RS)-2-[2,5-bis(trifluoromethyl)benzyl]-3-oxo-2,3,5,6,7,8-hexahydro[1,2,4]triazolo[4,3-a]pyridine-5-carboxylate (Racemate)

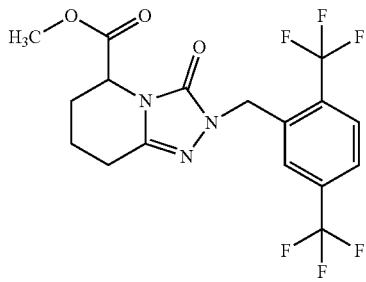 [SMILES: COC(=O)C1CCCc2nn(Cc3cc(C(F)(F)F)ccc3C(F)(F)F)c(=O)n21]

Methyl (5RS)-3-oxo-2,3,5,6,7,8-hexahydro[1,2,4]triazolo[4,3-a]pyridine-5-carboxylate (racemate) (300 mg, 1.52 mmol) was initially charged in acetonitrile (10 ml). Caesium carbonate (1.24 g, 3.80 mmol) and 2-(bromomethyl)-1,4-bis(trifluoromethyl)benzene (514 mg, 1.67 mmol, CAS 302911-98-4) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 649 mg (95% of theory) of the title compound were obtained.

LC-MS (Method 4): $R_t$=1.00 min; MS (ESIpos): m/z=424 [M+H]$^+$ $^1$H-NMR (400 MHz, DMSO-d6) δ[ppm]: −0.008 (0.90), 0.008 (0.79), 1.157 (0.56), 1.175 (1.14), 1.193 (0.59), 1.539 (0.40), 1.815 (0.51), 1.825 (0.49), 1.839 (0.42), 1.850 (0.43), 1.988 (2.13), 2.073 (0.47), 2.091 (0.47), 2.103 (0.89), 2.111 (1.07), 2.134 (0.56), 2.147 (0.48), 2.155 (0.51), 2.163 (0.47), 2.576 (0.89), 2.591 (0.71), 2.603 (0.74), 2.617 (0.61), 2.649 (0.57), 2.660 (1.10), 2.671 (0.76), 2.702 (0.47), 3.702 (16.00), 4.021 (0.51), 4.038 (0.50), 4.660 (1.05), 4.669 (1.11), 4.675 (1.37), 4.684 (1.00), 5.056 (0.60), 5.097 (1.96), 5.130 (2.04), 5.171 (0.61), 7.632 (2.12), 7.934 (0.89), 7.953 (1.38), 8.025 (1.90), 8.045 (1.28).

Intermediate 78

Methyl (5RS)-3-oxo-2-({5-[3-(trifluoromethyl)phenyl]-1,2,4-oxadiazol-3-yl}methyl)-2,3,5,6,7,8-hexahydro[1,2,4]triazolo[4,3-a]pyridine-5-carboxylate (Racemate)

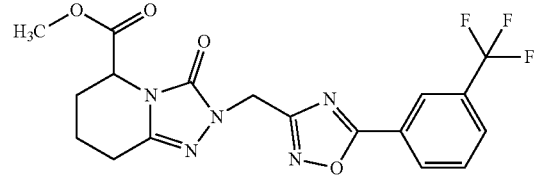 [SMILES: COC(=O)C1CCCc2nn(Cc3noc(-c4cccc(C(F)(F)F)c4)n3)c(=O)n21]

Methyl (5RS)-3-oxo-2,3,5,6,7,8-hexahydro[1,2,4]triazolo[4,3-a]pyridine-5-carboxylate (racemate) (300 mg, 1.52 mmol) was initially charged in acetonitrile (10 ml). Caesium carbonate (1.24 g, 3.80 mmol) and 3-(chloromethyl)-5-[3-(trifluoromethyl)phenyl]-1,2,4-oxadiazole (439 mg, 1.67 mmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 642 mg (90% purity, 90% of theory) of the title compound were obtained.

LC-MS (Method 3): $R_t$=1.68 min; MS (ESIpos): m/z=424 [M+H]$^+$ $^1$H-NMR (400 MHz, DMSO-d6) δ[ppm]: −0.008 (0.48), 0.008 (0.43), 1.158 (0.79), 1.175 (1.64), 1.193 (0.83), 1.530 (0.40), 1.563 (0.43), 1.802 (0.50), 1.814 (0.55), 1.828 (0.47), 1.989 (3.08), 2.067 (0.47), 2.077 (0.73), 2.090 (0.67), 2.105 (0.47), 2.113 (0.50), 2.121 (0.46), 2.129 (0.54), 2.141 (0.53), 2.149 (0.56), 2.157 (0.53), 2.577 (0.87), 2.592 (0.78), 2.603

(0.82), 2.617 (0.63), 2.640 (0.62), 2.652 (1.20), 2.665 (0.72), 2.695 (0.51), 3.311 (16.00), 3.701 (0.48), 4.021 (0.74), 4.039 (0.71), 4.632 (1.16), 4.641 (1.31), 4.647 (1.53), 4.657 (1.11), 5.001 (2.12), 5.074 (0.77), 5.115 (4.74), 5.128 (4.74), 5.168 (0.79), 7.878 (0.89), 7.897 (2.02), 7.917 (1.26), 8.101 (1.45), 8.120 (1.38), 8.334 (2.40), 8.391 (1.51), 8.410 (1.42).

Intermediate 79

Methyl (5RS)-2-(2-methylbenzyl)-3-oxo-2,3,5,6,7,8-hexahydro[1,2,4]triazolo[4,3-a]pyridine-5-carboxylate (Racemate)

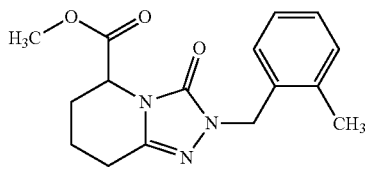

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (10 ml). Caesium carbonate (364 mg, 1.12 mmol) and 1-(bromomethyl)-2-methylbenzene (197 mg, 1.06 mmol, CAS 89-92-9) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 196 mg (93% purity, 60% of theory) of the title compound were obtained.

LC-MS (Method 1): $R_t$=1.04 min; MS (ESIpos): m/z=302 [M+H]$^+$

Intermediate 80

Methyl (5RS)-2-[4-fluoro-3-(trifluoromethyl)benzyl]-3-oxo-2,3,5,6,7,8-hexahydro[1,2,4]triazolo[4,3-a]pyridine-5-carboxylate (Racemate)

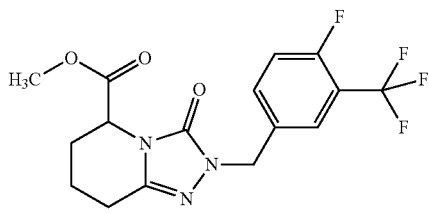 [SMILES: COC(=O)C1CCCc2nn(Cc3ccc(F)c(C(F)(F)F)c3)c(=O)n21]

Methyl (5RS)-3-oxo-2,3,5,6,7,8-hexahydro[1,2,4]triazolo[4,3-a]pyridine-5-carboxylate (racemate) (300 mg, 1.52 mmol) was initially charged in acetonitrile (10 ml). Caesium carbonate (1.24 g, 3.80 mmol) and 4-(bromomethyl)-1-fluoro-2-(trifluoromethyl)benzene (430 mg, 1.67 mmol, CAS 184970-26-1) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 569 mg (90% purity, 90% of theory) of the title compound were obtained.

LC-MS (Method 4): $R_t$=0.90 min; MS (ESIpos): m/z=374 [M+H]$^+$

Intermediate 81

Methyl (5RS)-2-[4-methoxy-3-(trifluoromethyl)benzyl]-3-oxo-2,3,5,6,7,8-hexahydro[1,2,4]triazolo[4,3-a]pyridine-5-carboxylate (Racemate)

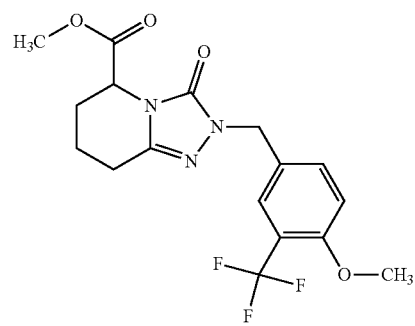

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (10 ml). Caesium carbonate (347 mg, 1.06 mmol) and 4-(bromomethyl)-1-methoxy-2-(trifluoromethyl)benzene (300 mg, 1.11 mmol, CAS 261951-89-7) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 316 mg (80% of theory) of the title compound were obtained.

LC-MS (Method 3): $R_t$=1.60 min; MS (ESIpos): m/z=386 [M+H]$^+$ $^1$H-NMR (400 MHz, DMSO-d6) δ[ppm]: −0.008 (0.97), 0.008 (0.99), 1.492 (0.42), 1.513 (0.43), 1.519 (0.45), 1.526 (0.45), 1.789 (0.53), 1.798 (0.55), 1.813 (0.47), 1.823 (0.45), 2.052 (0.49), 2.062 (0.82), 2.073 (0.90), 2.096 (0.50), 2.104 (0.57), 2.116 (0.52), 2.125 (0.55), 2.132 (0.51), 2.560 (0.84), 2.572 (0.84), 2.587 (0.67), 2.613 (0.64), 2.625 (1.19), 2.637 (0.68), 2.668 (0.66), 3.696 (15.68), 3.873 (16.00), 4.600 (1.06), 4.609 (1.20), 4.615 (1.38), 4.625 (1.04), 4.844 (4.92), 7.239 (1.72), 7.260 (2.01), 7.489 (1.35), 7.510 (1.41), 7.520 (2.68).

Intermediate 82

Methyl (5RS)-2-[(1-methyl-1H-indazol-5-yl)methyl]-3-oxo-2,3,5,6,7,8-hexahydro[1,2,4]triazolo[4,3-a]pyridine-5-carboxylate (Racemate)

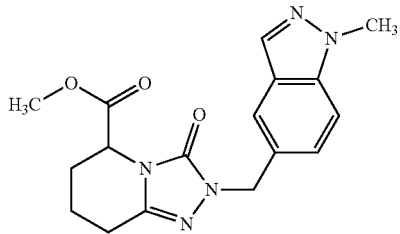

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (10 ml). Caesium carbonate (347 mg, 1.06 mmol) and 5-(bromomethyl)-1-methyl-1H-indazole (251 mg, 1.11 mmol, CAS 1092961-01-7) were subsequently added. After stirring at room temperature for 72 h, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 87.0 mg (25% of theory) of the title compound were obtained.

LC-MS (Method 3): $R_t$=1.10 min; MS (ESIpos): m/z=342 [M+H]$^+$ $^1$H-NMR (400 MHz, DMSO-d6) δ [ppm]: −0.008 (1.77), 0.008 (1.59), 1.447 (0.66), 1.456 (0.44), 1.783 (0.44), 1.794 (0.48), 1.808 (0.41), 2.049 (0.42), 2.060 (0.69), 2.073 (0.71), 2.080 (0.63), 2.087 (0.51), 2.095 (0.41), 2.103 (0.49), 2.115 (0.45), 2.123 (0.48), 2.131 (0.44), 2.563 (0.85), 2.578 (0.63), 2.602 (0.59), 2.613 (1.08), 2.626 (0.61), 2.656 (0.49), 2.669 (0.50), 3.706 (14.99), 4.024 (16.00), 4.597 (0.97), 4.607 (1.09), 4.613 (1.27), 4.623 (0.94), 4.922 (6.84), 7.285 (1.33), 7.307 (1.37), 7.310 (1.55), 7.593 (1.89), 7.614 (3.97), 8.019 (3.08).

Intermediate 83

Methyl (5RS)-2-[(1-ethyl-1H-imidazol-2-yl)methyl]-3-oxo-2,3,5,6,7,8-hexahydro[1,2,4]triazolo[4,3-a]pyridine-5-carboxylate (Racemate)

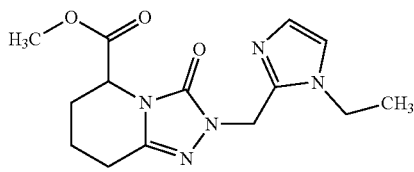 [SMILES: CCn1ccnc1Cn1nc2n(c1=O)C(C(=O)OC)CCC2]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (6.0 ml). Caesium carbonate (364 mg, 1.12 mmol) and 2-(chloromethyl)-1-ethyl-1H-imidazole (154 mg, 1.06 mmol, CAS 780722-30-7) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 54.0 mg (17% of theory) of the title compound were obtained.

LC-MS (Method 1): $R_t$=0.29 min; MS (ESIpos): m/z=306 [M+H]$^+$

Intermediate 84

Methyl (5RS)-2-[(1-methyl-1H-benzimidazol-2-yl)methyl]-3-oxo-2,3,5,6,7,8-hexahydro[1,2,4]triazolo[4,3-a]pyridine-5-carboxylate (Racemate)

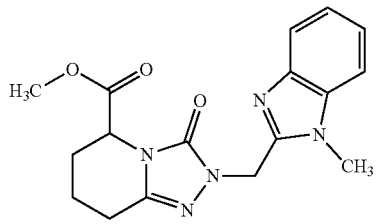 [SMILES: COC(=O)C1CCCc2nn(Cc3nc4ccccc4n3C)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (6.0 ml). Caesium carbonate (364 mg, 1.12 mmol) and 2-(bromomethyl)-1-methyl-1H-benzimidazole (240 mg, 1.06 mmol, CAS 136099-52-0) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 137 mg (40% of theory) of the title compound were obtained.

LC-MS (Method 1): $R_t$=0.73 min; MS (ESIpos): m/z=342 [M+H]

Intermediate 85

Methyl (5RS)-2-[3-chloro-4-(trifluoromethoxy)benzyl]-3-oxo-2,3,5,6,7,8-hexahydro[1,2,4]triazolo[4,3-a]pyridine-5-carboxylate (Racemate)

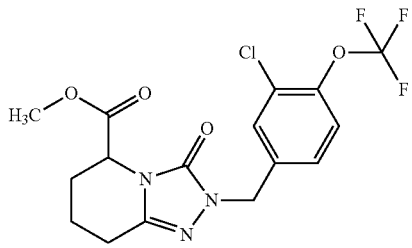 [SMILES: COC(=O)C1CCCc2nn(Cc3ccc(OC(F)(F)F)c(Cl)c3)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (10 ml). Caesium carbonate (347 mg, 1.06 mmol) and 4-(bromomethyl)-2-chlorophenyl trifluoromethyl ether (323 mg, 1.11 mmol, CAS 261763-18-2) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 302 mg (73% of theory) of the title compound were obtained.

LC-MS (Method 3): $R_t$=1.81 min; MS (ESIpos): m/z=406 [M+H]$^+$ $^1$H-NMR (400 MHz, DMSO-d6) δ[ppm]: −0.008 (0.94), 0.008 (0.87), 1.805 (0.43), 1.815 (0.45), 2.070 (0.41), 2.079 (0.69), 2.094 (0.77), 2.104 (0.63), 2.112 (0.43), 2.120 (0.49), 2.124 (0.42), 2.132 (0.44), 2.140 (0.47), 2.148 (0.44), 2.524 (0.61), 2.569 (0.83), 2.583 (0.70), 2.595 (0.73), 2.609 (0.58), 2.636 (0.54), 2.647 (1.01), 2.660 (0.61), 2.690 (0.45), 3.708 (16.00), 4.619 (0.97), 4.629 (1.06), 4.635 (1.29), 4.644 (0.95), 4.911 (5.85), 7.317 (1.07), 7.322 (1.12), 7.338 (1.27), 7.344 (1.31), 7.533 (2.04), 7.539 (1.93), 7.564 (1.23), 7.567 (1.21), 7.585 (1.04), 7.588 (1.02).

Intermediate 86

Methyl (5RS)-2-{[3-chloro-5-(trifluoromethyl)pyridin-2-yl]methyl}-3-oxo-2,3,5,6,7,8-hexahydro[1,2,4]triazolo[4,3-a]pyridine-5-carboxylate (Racemate)

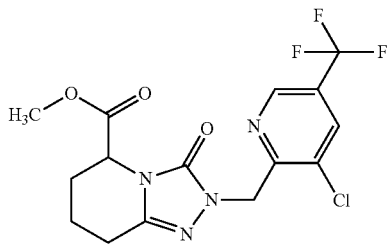 [SMILES: COC(=O)C1CCCc2nn(Cc3ncc(C(F)(F)F)cc3Cl)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (5.0 ml). Caesium carbonate (364 mg, 1.12 mmol) and 3-chloro-2-(chloromethyl)-5-(trifluoromethyl)pyridine (245 mg, 1.06 mmol, CAS 175277-52-8) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 293 mg (74% of theory) of the title compound were obtained.

LC-MS (Method 1): $R_t$=1.08 min; MS (ESIpos): m/z=391 [M+H]$^+$

Intermediate 87

Methyl (5RS)-2-[3-fluoro-4-(trifluoromethoxy)benzyl]-3-oxo-2,3,5,6,7,8-hexahydro[1,2,4]triazolo[4,3-a]pyridine-5-carboxylate (Racemate)

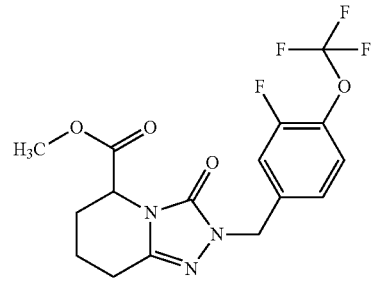 [SMILES: COC(=O)C1CCCc2nn(Cc3ccc(OC(F)(F)F)c(F)c3)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (6.0 ml). Caesium carbonate (364 mg, 1.12 mmol) and 4-(bromomethyl)-2-fluorophenyl trifluoromethyl ether (291 mg, 1.06 mmol, CAS 886499-04-3) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 263 mg (66% of theory) of the title compound were obtained.

LC-MS (Method 1): $R_t$=1.22 min; MS (ESIpos): m/z=390 [M+H]$^+$

Intermediate 88

Methyl (5RS)-2-{[2-methyl-4-(trifluoromethyl)-1,3-thiazol-5-yl]methyl}-3-oxo-2,3,5,6,7,8-hexahydro[1,2,4]triazolo[4,3-a]pyridine-5-carboxylate (Racemate)

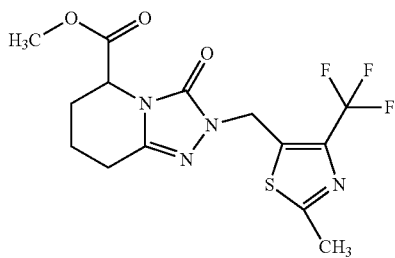 [SMILES: COC(=O)C1CCCc2nn(Cc3sc(C)nc3C(F)(F)F)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (10 ml). Caesium carbonate (347 mg, 1.06 mmol) and 5-(bromomethyl)-2-methyl-4-(trifluoromethyl)-1,3-thiazole (290 mg, 1.11 mmol, CAS 1000339-73-0) were subsequently added. After stirring at room temperature for 72 h, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 384 mg (99% of theory) of the title compound were obtained.

LC-MS (Method 3): $R_t$=1.33 min; MS (ESIpos): m/z=377 [M+H]$^+$ $^1$H-NMR (400 MHz, DMSO-d6) δ [ppm]: −0.008 (1.01), 0.008 (1.10), 1.157 (1.51), 1.175 (3.06), 1.193 (1.55), 1.793 (0.43), 1.804 (0.48), 1.818 (0.41), 1.988 (5.82), 2.051 (0.42), 2.062 (0.77), 2.073 (0.86), 2.086 (0.67), 2.094 (0.45), 2.102 (0.51), 2.114 (0.46), 2.122 (0.50), 2.130 (0.46), 2.524 (0.72), 2.568 (0.84), 2.583 (0.72), 2.594 (0.74), 2.608 (0.61), 2.639 (1.12), 2.651 (15.16), 2.668 (1.55), 2.679 (0.51), 2.687 (0.68), 3.697 (16.00), 4.003 (0.46), 4.021 (1.39), 4.038 (1.38), 4.056 (0.46), 4.594 (1.02), 4.603 (1.12), 4.609 (1.32), 4.619 (0.98), 5.171 (4.60).

Intermediate 89

Methyl (5RS)-2-[(3-methyl-1,2-oxazol-5-yl)methyl]-3-oxo-2,3,5,6,7,8-hexahydro[1,2,4]triazolo[4,3-a]pyridine-5-carboxylate (Racemate)

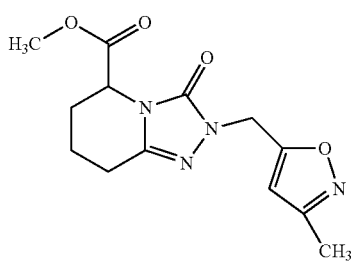 [SMILES: COC(=O)C1CCCc2nn(Cc3cc(C)no3)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (10 ml). Caesium carbonate (347 mg, 1.06 mmol) and 5-(bromomethyl)-3-methyl-1,2-oxazole (196 mg, 1.11 mmol, CAS 36958-61-9) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 259 mg (86% purity, 75% of theory) of the title compound were obtained.

LC-MS (Method 3): $R_t$=0.94 min; MS (ESIpos): m/z=293 [M+H]$^+$ $^1$H-NMR (400 MHz, DMSO-d6) δ[ppm]: −0.008 (0.44), 1.174 (0.64), 1.510 (0.40), 1.531 (0.43), 1.536 (0.43), 1.544 (0.42), 1.798 (0.49), 1.809 (0.54), 1.824 (0.47), 1.988 (1.18), 2.042 (0.41), 2.055 (0.52), 2.065 (0.75), 2.071 (0.80), 2.078 (0.73), 2.087 (0.86), 2.096 (0.58), 2.104 (0.53), 2.112 (0.61), 2.117 (0.52), 2.124 (0.64), 2.133 (0.58), 2.141 (0.55), 2.205 (15.12), 2.218 (2.90), 2.518 (0.41), 2.524 (0.52), 2.567 (0.86), 2.581 (0.78), 2.593 (0.80), 2.607 (0.67), 2.629 (0.63), 2.641 (1.15), 2.653 (0.66), 2.683 (0.47), 3.687 (1.47), 3.691 (0.75), 3.703 (16.00), 4.596 (1.03), 4.606 (1.14), 4.612 (1.28), 4.622 (0.98), 4.773 (1.74), 4.981 (6.40), 6.237 (3.04), 6.458 (0.50).

Intermediate 90

Methyl (5RS)-2-[(1-methyl-1H-1,2,4-triazol-3-yl)methyl]-3-oxo-2,3,5,6,7,8-hexahydro[1,2,4]triazolo[4,3-a]pyridine-5-carboxylate (Racemate)

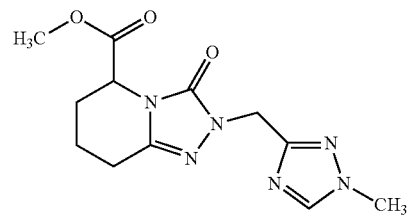

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (11 ml). Caesium carbonate (793 mg, 2.43 mmol) and 3-(chloromethyl)-1-methyl-1H-1,2,4-triazole hydrochloride (187 mg, 1.11 mmol, CAS 135206-76-7) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 178 mg (74% purity, 44% of theory) of the title compound were obtained.

LC-MS (Method 3): $R_t$=0.61 min; MS (ESIpos): m/z=293 [M+H]$^+$

Intermediate 91

Methyl (5RS)-2-[2-fluoro-3-(trifluoromethyl)benzyl]-3-oxo-2,3,5,6,7,8-hexahydro[1,2,4]triazolo[4,3-a]pyridine-5-carboxylate (Racemate)

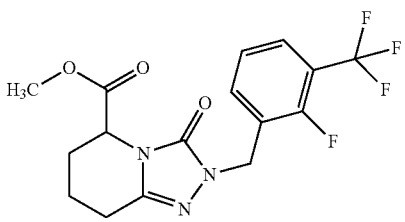 [SMILES: COC(=O)C1CCCc2nn(Cc3cccc(C(F)(F)F)c3F)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (5.0 ml). Caesium carbonate (364 mg, 1.12 mmol) and 1-(bromomethyl)-2-fluoro-3-(trifluoromethyl)benzene (274 mg, 1.06 mmol, CAS 184970-25-0) were added after stirring for 5 min. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 184 mg (49% of theory) of the title compound were obtained.

LC-MS (Method 1): $R_t$=1.16 min; MS (ESIpos): m/z=374 [M+H]$^+$

Intermediate 92

Methyl (5RS)-2-[3-fluoro-5-(trifluoromethyl)benzyl]-3-oxo-2,3,5,6,7,8-hexahydro[1,2,4]triazolo[4,3-a]pyridine-5-carboxylate (Racemate)

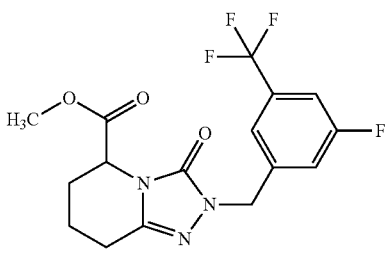 [SMILES: COC(=O)C1CCCc2nn(Cc3cc(F)cc(C(F)(F)F)c3)c(=O)n21]

Methyl (5RS)-3-oxo-2,3,5,6,7,8-hexahydro[1,2,4]triazolo[4,3-a]pyridine-5-carboxylate (racemate) (200 mg, 1.01 mmol) was initially charged in acetonitrile (5.0 ml). Caesium carbonate (364 mg, 1.12 mmol) and 1-(bromomethyl)-3-fluoro-5-(trifluoromethyl)benzene (274 mg, 1.06 mmol, CAS 239087-09-3) were added after stirring for 5 min. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 154 mg (41% of theory) of the title compound were obtained.

LC-MS (Method 1): $R_t$=1.19 min; MS (ESIpos): m/z=374 [M+H]$^+$

Intermediate 93

Methyl (5RS)-3-oxo-2-{[2-(trifluoromethyl)pyridin-4-yl]methyl}-2,3,5,6,7,8-hexahydro[1,2,4]triazolo[4,3-a]pyridine-5-carboxylate (Enantiomer 1)

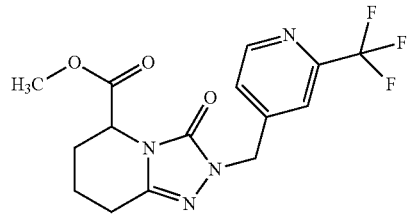 [SMILES: COC(=O)C1CCCc2nn(Cc3ccnc(C(F)(F)F)c3)c(=O)n21]

Methyl (5RS)-3-oxo-2,3,5,6,7,8-hexahydro[1,2,4]triazolo[4,3-a]pyridine-5-carboxylate (enantiomer 2) (200 mg, 1.01 mmol) was initially charged in acetonitrile (5.0 ml). Caesium carbonate (364 mg, 1.12 mmol) and 4-(chloromethyl)-2-(trifluoromethyl)pyridine hydrochloride (247 mg, 1.06 mmol) were added after stirring for 5 min. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 279 mg (77% of theory) of the title compound were obtained.

LC-MS (Method 4): $R_t$=0.71 min; MS (ESIpos): m/z=357 [M+H]$^+$

The (5S) configuration was assigned on the basis of the crystal structure elucidation for Example 26, 108, 113, 157, 237, 358 and 454.

121

Methyl (5S)-3-oxo-2-{[2-(trifluoromethyl)pyridin-4-yl]methyl}-2,3,5,6,7,8-hexahydro[1,2,4]triazolo[4,3-a]pyridine-5-carboxylate

Intermediate 94

Methyl (5RS)-2-{[3-fluoro-2-(trifluoromethyl)pyridin-4-yl]methyl}-3-oxo-2,3,5,6,7,8-hexahydro[1,2,4]triazolo[4,3-a]pyridine-5-carboxylate (Enantiomer 1)

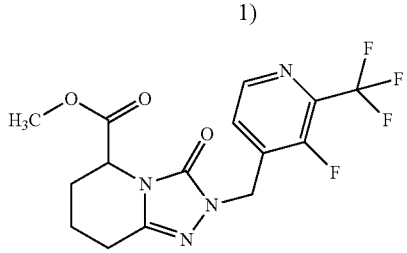

Methyl (5RS)-3-oxo-2,3,5,6,7,8-hexahydro[1,2,4]triazolo[4,3-a]pyridine-5-carboxylate (enantiomer 2) (200 mg, 1.01 mmol) was initially charged in acetonitrile (5.0 ml). Caesium carbonate (364 mg, 1.12 mmol) and 4-(chloromethyl)-3-fluoro-2-(trifluoromethyl)pyridine hydrochloride (266 mg, 1.06 mmol) were subsequently added. After stirring overnight, the reaction mixture was admixed again with caesium carbonate (199 mg, 0.61 mmol) and stirred at 60° C. for 2 hours. Subsequently, the reaction mixture was cooled to room temperature, and water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 181 mg (48% of theory) of the title compound were obtained.

LC-MS (Method 3): $R_t$=1.42 min; MS (ESIpos): m/z=375 [M+H]$^+$

The (5S) configuration was assigned on the basis of the crystal structure elucidation for Example 26, 108, 113, 157, 237, 358 and 454.

Methyl (5S)-2-{[3-fluoro-2-(trifluoromethyl)pyridin-4-yl]methyl}-3-oxo-2,3,5,6,7,8-hexahydro[1,2,4]triazolo[4,3-a]pyridine-5-carboxylate

Intermediate 95

Methyl (5RS)-2-{[5-chloro-4-(trifluoromethyl)pyridin-2-yl]methyl}-3-oxo-2,3,5,6,7,8-hexahydro[1,2,4]triazolo[4,3-a]pyridine-5-carboxylate (Enantiomer 1)

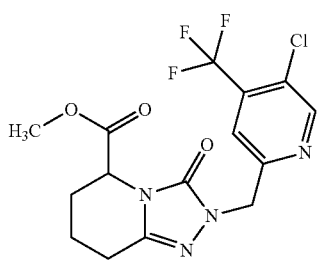 [SMILES: COC(=O)C1CCCc2nn(Cc3cc(C(F)(F)F)c(Cl)cn3)c(=O)n21]

122

Methyl (5RS)-3-oxo-2,3,5,6,7,8-hexahydro[1,2,4]triazolo[4,3-a]pyridine-5-carboxylate (enantiomer 2) (164 mg, 829 μmol) was initially charged in acetonitrile (4.0 ml). Caesium carbonate (594 mg, 1.82 mmol) and 5-chloro-2-(chloromethyl)-4-(trifluoromethyl)pyridine hydrochloride (274 mg, 85% purity, 871 μmol) were subsequently added. The reaction mixture was stirred at room temperature overnight, at 85° C. for 5 h, and again at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 269 mg (93% purity, 77% of theory) of the title compound were obtained.

LC-MS (Method 3): $R_t$=1.55 min; MS (ESIpos): m/z=391 [M+H]$^+$ $^1$H-NMR (400 MHz, DMSO-d6) δ[ppm]: −0.008 (0.42), 0.008 (0.46), 1.157 (1.75), 1.175 (3.60), 1.193 (1.82), 1.352 (0.61), 1.534 (0.40), 1.540 (0.41), 1.807 (0.47), 1.816 (0.49), 1.830 (0.41), 1.989 (6.73), 2.074 (0.58), 2.086 (0.74), 2.098 (0.77), 2.119 (0.46), 2.126 (0.53), 2.131 (0.46), 2.139 (0.47), 2.148 (0.52), 2.155 (0.46), 2.520 (0.80), 2.563 (0.87), 2.578 (0.72), 2.590 (0.72), 2.604 (0.62), 2.630 (0.57), 2.642 (1.01), 2.654 (0.60), 2.671 (0.40), 2.684 (0.45), 3.688 (1.91), 3.704 (16.00), 3.936 (0.71), 4.003 (0.54), 4.021 (1.59), 4.039 (1.58), 4.057 (0.52), 4.628 (1.01), 4.637 (1.55), 4.643 (1.37), 4.652 (1.42), 5.074 (7.18), 7.727 (3.53), 7.832 (0.45), 8.858 (0.45), 8.910 (3.33).

The (5S) configuration was assigned on the basis of the crystal structure elucidation for Example 26, 108, 113, 157, 237, 358 and 454.

Methyl (5S)-2-{[5-chloro-4-(trifluoromethyl)pyridin-2-yl]methyl}-3-oxo-2,3,5,6,7,8-hexahydro[1,2,4]triazolo[4,3-a]pyridine-5-carboxylate

Intermediate 96

Methyl (5RS)-3-oxo-2-{[2-(trifluoromethyl)quinolin-4-yl]methyl}-2,3,5,6,7,8-hexahydro[1,2,4]triazolo[4,3-a]pyridine-5-carboxylate (Enantiomer 1)

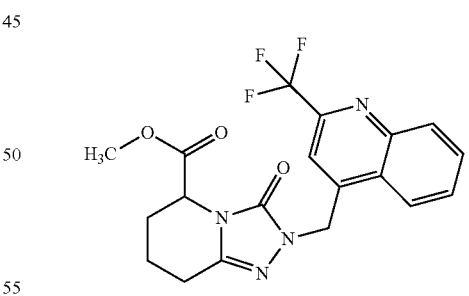

Methyl (5RS)-3-oxo-2,3,5,6,7,8-hexahydro[1,2,4]triazolo[4,3-a]pyridine-5-carboxylate (enantiomer 2) (166 mg, 839 μmol) was initially charged in acetonitrile (4.1 ml). Caesium carbonate (301 mg, 923 μmol) and 4-(chloromethyl)-2-(trifluoromethyl)quinoline hydrochloride (336 mg, 74% purity, 881 μmol) were added after stirring for 5 min. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 111 mg (33% of theory) of the title compound were obtained.

LC-MS (Method 1): $R_t$=1.19 min; MS (ESIpos): m/z=407 [M+H]$^+$

The (5S) configuration was assigned on the basis of the crystal structure elucidation for Example 26, 108, 113, 157, 237, 358 and 454.

Methyl (5S)-3-oxo-2-{[2-(trifluoromethyl)quinolin-4-yl]methyl}-2,3,5,6,7,8-hexahydro[1,2,4]triazolo[4,3-a]pyridine-5-carboxylate Intermediate 97

Methyl (5RS)-2-{[3-chloro-5-(trifluoromethyl)pyridin-2-yl]methyl}-3-oxo-2,3,5,6,7,8-hexahydro[1,2,4]triazolo[4,3-a]pyridine-5-carboxylate (Enantiomer 1)

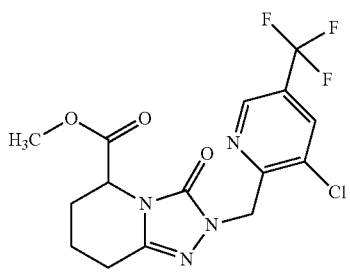 [SMILES: COC(=O)C1CCCc2nn(Cc3ncc(C(F)(F)F)cc3Cl)c(=O)n21]

Methyl (5RS)-3-oxo-2,3,5,6,7,8-hexahydro[1,2,4]triazolo[4,3-a]pyridine-5-carboxylate (enantiomer 2) (200 mg, 1.01 mmol) was initially charged in acetonitrile (5.0 ml). Caesium carbonate (364 mg, 1.12 mmol) and 3-chloro-2-(chloromethyl)-5-(trifluoromethyl)pyridine (245 mg, 1.06 mmol, CAS 175277-52-8) were added after stirring for 5 min. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 216 mg (55% of theory) of the title compound were obtained.

LC-MS (Method 3): $R_t$=1.49 min; MS (ESIpos): m/z=391 [M+H]$^+$

The (5S) configuration was assigned on the basis of the crystal structure elucidation for Example 26, 108, 113, 157, 237, 358 and 454.

Methyl (5S)-2-{[3-chloro-5-(trifluoromethyl)pyridin-2-yl]methyl}-3-oxo-2,3,5,6,7,8-hexahydro[1,2,4]triazolo[4,3-a]pyridine-5-carboxylate Intermediate 98

Methyl (5RS)-3-oxo-2-[(3,5,6-trimethylpyrazin-2-yl)methyl]-2,3,5,6,7,8-hexahydro[1,2,4]triazolo[4,3-a]pyridine-5-carboxylate (Enantiomer 1)

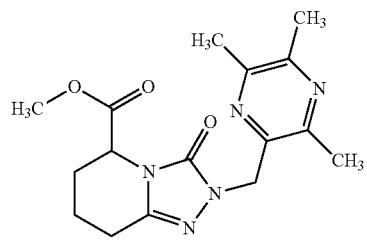

Methyl (5RS)-3-oxo-2,3,5,6,7,8-hexahydro[1,2,4]triazolo[4,3-a]pyridine-5-carboxylate (enantiomer 2) (250 mg, 1.27 mmol) was initially charged in acetonitrile (5.0 ml). Caesium carbonate (454 mg, 1.39 mmol) and 2-(bromomethyl)-3,5,6-trimethylpyrazine (286 mg, 1.33 mmol, CAS 79074-45-6) were added after stirring for 5 min. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 261 mg (62% of theory) of the title compound were obtained.

LC-MS (Method 3): $R_t$=1.02 min; MS (ESIpos): m/z=332 [M+H]$^+$

Intermediate 99

Methyl (5RS)-3-oxo-2-{[4-(trifluoromethyl)pyridin-2-yl]methyl}-2,3,5,6,7,8-hexahydro[1,2,4]triazolo[4,3-a]pyridine-5-carboxylate (Enantiomer 1)

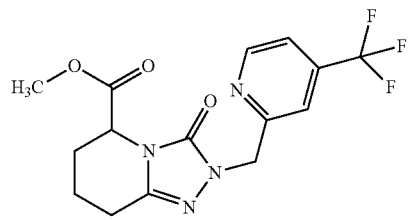 [SMILES: COC(=O)C1CCCc2nn(Cc3cc(C(F)(F)F)ccn3)c(=O)n21]

Methyl (5RS)-3-oxo-2,3,5,6,7,8-hexahydro[1,2,4]triazolo[4,3-a]pyridine-5-carboxylate (enantiomer 2) (300 mg, 1.52 mmol) was initially charged in acetonitrile (6.0 ml). Caesium carbonate (744 mg, 2.28 mmol) and 2-(chloromethyl)-4-(trifluoromethyl)pyridine hydrochloride (371 mg, 1.60 mmol, CAS 215867-87-1) were subsequently added. After stirring at room temperature for 4 hours, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 282 mg (52% of theory) of the title compound were obtained.

LC-MS (Method 3): $R_t$=1.35 min; MS (ESIpos): m/z=357 [M+H]$^+$ $^1$H-NMR (400 MHz, DMSO-d6) δ [ppm]: −0.008 (0.50), 1.811 (0.48), 1.821 (0.49), 1.835 (0.42), 2.073 (0.44), 2.079 (0.46), 2.090 (0.74), 2.103 (0.69), 2.110 (0.66), 2.118 (0.53), 2.126 (0.46), 2.133 (0.53), 2.138 (0.46), 2.146 (0.48), 2.154 (0.50), 2.162 (0.46), 2.519 (0.45), 2.570 (0.85), 2.585 (0.73), 2.597 (0.75), 2.611 (0.61), 2.636 (0.59), 2.647 (1.03), 2.660 (0.59), 2.690 (0.44), 3.706 (16.00), 4.636 (1.03), 4.646 (1.11), 4.652 (1.26), 4.661 (0.93), 5.075 (7.03), 7.551 (2.03), 7.713 (1.09), 7.724 (1.09), 8.822 (1.50), 8.834 (1.43).

The (5S) configuration was assigned on the basis of the crystal structure elucidation for Example 26, 108, 113, 157, 237, 358 and 454.

Methyl (5S)-3-oxo-2-{[4-(trifluoromethyl)pyridin-2-yl]methyl}-2,3,5,6,7,8-hexahydro[1,2,4]triazolo[4,3-a]pyridine-5-carboxylate Intermediate 100

Methyl (5RS)-3-oxo-2-{[2-(trifluoromethyl)pyrimidin-4-yl]methyl}-2,3,5,6,7,8-hexahydro[1,2,4]triazolo[4,3-a]pyridine-5-carboxylate (Enantiomer 1)

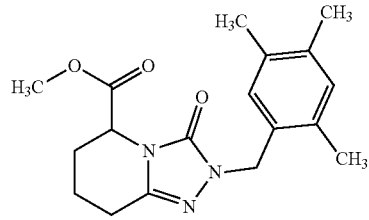

Methyl (5RS)-3-oxo-2,3,5,6,7,8-hexahydro[1,2,4]triazolo[4,3-a]pyridine-5-carboxylate (enantiomer 2) (108 mg, 548 µmol) was initially charged in acetonitrile (2.0 ml). Caesium carbonate (268 mg, 822 µmol) and 4-(chloromethyl)-2-(trifluoromethyl)pyrimidine hydrochloride (134 mg, 575 µmol) were subsequently added. After stirring at room temperature overnight and under reflux for a further 2 hours, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 49.3 mg (25% of theory) of the title compound were obtained.

LC-MS (Method 4): $R_t$=0.69 min; MS (ESIpos): m/z=358 [M+H]$^+$

The (5S) configuration was assigned on the basis of the crystal structure elucidation for Example 26, 108, 113, 157, 237, 358 and 454.

Methyl (5S)-3-oxo-2-{[2-(trifluoromethyl)pyrimidin-4-yl]methyl}-2,3,5,6,7,8-hexahydro[1,2,4]triazolo[4,3-a]pyridine-5-carboxylate Intermediate 101

Methyl (5RS)-3-oxo-2-(2,4,5-trimethylbenzyl)-2,3,5,6,7,8-hexahydro[1,2,4]triazolo[4,3-a]pyridine-5-carboxylate (Enantiomer 1)

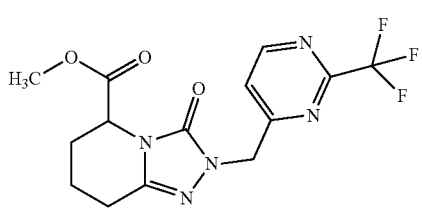 [SMILES: COC(=O)C1CCCc2nn(Cc3ccnc(C(F)(F)F)n3)c(=O)n21]

Methyl (5RS)-3-oxo-2,3,5,6,7,8-hexahydro[1,2,4]triazolo[4,3-a]pyridine-5-carboxylate (enantiomer 2) (200 mg, 1.01 mmol) was initially charged in acetonitrile (5.0 ml). Caesium carbonate (364 mg, 1.12 mmol) and 1-(bromomethyl)-2,4,5-trimethylbenzene (227 mg, 1.06 mmol, CAS 35509-98-9) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 198 mg (59% of theory) of the title compound were obtained.

LC-MS (Method 4): $R_t$=0.91 min; MS (ESIpos): m/z=330 [M+H]$^+$

The (5S) configuration was assigned on the basis of the crystal structure elucidation for Example 26, 108, 113, 157, 237, 358 and 454.

Methyl (5S)-3-oxo-2-(2,4,5-trimethylbenzyl)-2,3,5,6,7,8-hexahydro[1,2,4]triazolo[4,3-a]pyridine-5-carboxylate Intermediate 102

Methyl (5RS)-2-[4-(tert-butoxycarbonyl)benzyl]-3-oxo-2,3,5,6,7,8-hexahydro[1,2,4]triazolo[4,3-a]pyridine-5-carboxylate (Racemate)

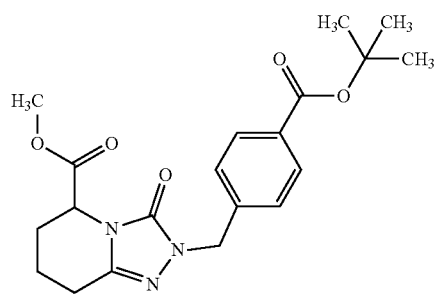 [SMILES: COC(=O)C1CCCc2nn(Cc3ccc(C(=O)OC(C)(C)C)cc3)c(=O)n21]

To methyl (5RS)-3-oxo-2,3,5,6,7,8-hexahydro[1,2,4]triazolo[4,3-a]pyridine-5-carboxylate (racemate) (300 mg, 1.52 mmol) and caesium carbonate (744 mg, 2.28 mmol) in 15 ml of acetonitrile was added tert-butyl 4-(bromomethyl)benzoate (433 mg, 1.60 mmol), then the reaction mixture was stirred at room temperature overnight. For workup, the precipitate present was filtered off, and the filtrate was admixed and extracted with ethyl acetate/water. The aqueous phase was extracted twice more with ethyl acetate. The combined organic phases were washed with saturated sodium chloride solution, dried with sodium sulphate, filtered, and concentrated and dried under reduced pressure. 676 mg (88% purity, 101% of theory) of the title compound were obtained, which was converted further as such.

LC-MS (Method 3): $R_t$=1.78 min; MS (ESIpos): m/z=388 [M+H]$^+$ $^1$H-NMR (400 MHz, DMSO-d6) δ [ppm]: −0.008 (1.08), 0.008 (1.04), 1.175 (0.71), 1.537 (16.00), 1.988 (1.29), 3.286 (1.03), 3.709 (5.39), 4.915 (1.64), 7.323 (0.99), 7.344 (1.09), 7.857 (1.29), 7.878 (1.18).

Intermediate 103 tert-Butyl (5RS)-2-(4-methylbenzyl)-3-oxo-2,3,5,6,7,8-hexahydro[1,2,4]triazolo[4,3-a]pyridine-5-carboxylate (Racemate)

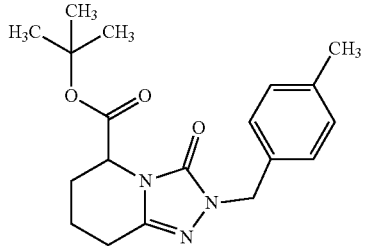 [SMILES: Cc1ccc(Cn2nc3n(c2=O)C(C(=O)OC(C)(C)C)CCC3)cc1]

To tert-butyl (5RS)-3-oxo-2,3,5,6,7,8-hexahydro[1,2,4]triazolo[4,3-a]pyridine-5-carboxylate (racemate) (5.00 g, 20.9 mmol) and caesium carbonate (10.2 g, 31.3 mmol) in 180 ml of acetonitrile was added 1-(bromomethyl)-4-methylbenzene (4.06 g, 21.9 mmol), then the reaction mixture was stirred at room temperature overnight. For workup, the precipitate present was filtered off, the filtrate was substantially concentrated on a rotary evaporator, and the residue was taken up and extracted with ethyl acetate/water. For better phase separation, saturated aqueous sodium chloride solution and a little methanol were added here. The aqueous phase was extracted twice more with ethyl acetate. The combined organic phases were washed with saturated aqueous sodium chloride solution, dried with sodium sulphate, filtered, and concentrated and dried under reduced pressure. 7.14 g (94% purity, 94% of theory) of the title compound were obtained, which was used further as such.

LC-MS (Method 6): $R_t$=1.80 min; MS (ESIpos): m/z=344 [M+H]$^+$ $^1$H-NMR (400 MHz, DMSO-d6) δ [ppm]: 1.396 (16.00), 1.402 (2.28), 2.270 (4.79), 4.771 (2.95), 7.129 (7.75).

Intermediate 104 tert-Butyl (5RS)-2-[(1 RS)-1-(4-chlorophenyl)ethyl]-3-oxo-2,3,5,6,7,8-hexahydro[1,2,4]triazolo[4,3-a]pyridine-5-carboxylate (Diastereomer Mixture; 4 Isomers)

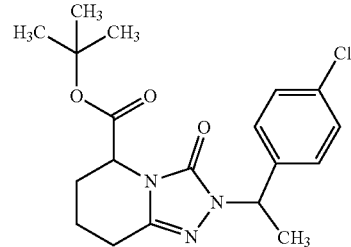 [SMILES: CC(c1ccc(Cl)cc1)n1nc2n(c1=O)C(C(=O)OC(C)(C)C)CCC2]

To tert-butyl (5RS)-3-oxo-2,3,5,6,7,8-hexahydro[1,2,4]triazolo[4,3-a]pyridine-5-carboxylate (racemate) (500 mg, 2.09 mmol) and caesium carbonate (1.02 g, 3.13 mmol) in 30 ml of acetonitrile was added 1-[(1 RS)-1-bromoethyl]-4-chlorobenzene (racemate) (550 mg, 2.51 mmol), then the reaction mixture was stirred at room temperature overnight. For workup, the precipitate present was filtered off, the filtrate was substantially concentrated on a rotary evaporator, and the residue was taken up and extracted with ethyl acetate/water. For better phase separation, saturated aqueous sodium chloride solution and a little methanol were added here. The aqueous phase was extracted twice more with ethyl acetate. The combined organic phases were washed with saturated sodium chloride solution, dried with sodium sulphate, filtered, and concentrated and dried under reduced pressure. 755 mg (87% purity, 83% of theory) of the title compound were obtained as a diastereomer mixture, which was converted further as such.

LC-MS (Method 8): $R_t$=3.28 min; MS (ESIpos): m/z=378 [M+H]$^+$; $R_t$=3.33 min; MS (ESIpos): m/z=378 [M+H]$^+$ $^1$H-NMR (400 MHz, DMSO-d6) δ [ppm]: −0.008 (1.98), 0.008 (1.51), 1.157 (0.78), 1.175 (1.54), 1.192 (0.85), 1.329 (15.89), 1.342 (1.34), 1.405 (16.00), 1.416 (1.42), 1.438 (1.47), 1.597 (2.79), 1.603 (2.55), 1.614 (2.71), 1.620 (2.46), 1.988 (2.92), 2.063 (1.04), 2.661 (0.78), 3.287 (1.01), 4.020 (0.72), 4.038 (0.70), 4.403 (0.81), 4.418 (0.94), 7.323 (1.58), 7.344 (3.21), 7.378 (2.24), 7.385 (2.41), 7.399 (1.19), 7.406 (1.69).

Intermediate 105 tert-Butyl (5R,S)-3-oxo-2-(4-sulphamoylbenzyl)-2,3,5,6,7,8-hexahydro[1,2,4]triazolo[4,3-a]pyridine-5-carboxylate (Racemate)

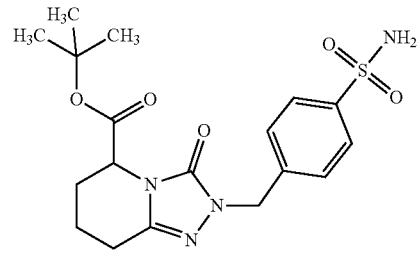 [SMILES: CC(C)(C)OC(=O)C1CCCc2nn(Cc3ccc(S(N)(=O)=O)cc3)c(=O)n21]

To tert-butyl (5RS)-3-oxo-2,3,5,6,7,8-hexahydro[1,2,4]triazolo[4,3-a]pyridine-5-carboxylate (racemate) (500 mg, 2.09 mmol) in 10 ml of acetonitrile were added caesium carbonate (1.02 g, 3.13 mmol) and 4-(bromomethyl)benzenesulphonamide (627 mg, 2.51 mmol), then the reaction mixture was twice stirred at room temperature under argon overnight. For workup, the mixture was admixed with water and extracted twice with dichloromethane. The combined organic phases were dried with magnesium sulphate, filtered and concentrated under reduced pressure. The remaining residue was purified via preparative HPLC (column: RP, Chromatorex C18, 250×40 mm 10 μm. Flow rate: 50 ml/min. Gradient (A=water+0.1% formic acid, B=acetonitrile): 0 min 10% B, 5 min 10% B, 27 min 98% B, 35 min 98% B, 35.01 min 10% B, 38 min 10% B. Run time per separation 38 min. Detection: 210 nm). 755 mg (87% purity, 83% of theory) were obtained. By concentrating the product fractions, 37 mg (4.3% of theory) of the title compound were obtained.

LC-MS (Method 6): $R_t$=1.35 min; MS (ESIneg): m/z=407 [M−H]$^-$ $^1$H-NMR (400 MHz, DMSO-d6) δ[ppm]: 1.404 (16.00), 2.072 (1.17), 4.451 (0.63), 4.920 (2.40), 7.331 (2.07), 7.401 (1.29), 7.422 (1.42), 7.772 (1.69), 7.793 (1.46).

Intermediate 106 tert-Butyl (5RS)-2-[4-(methylsulphanyl)benzyl]-3-oxo-2,3,5,6,7,8-hexahydro[1,2,4]triazolo[4,3-a]pyridine-5-carboxylate (Racemate)

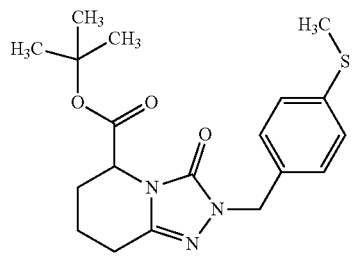 [SMILES: CSc1ccc(Cn2nc3n(c2=O)C(C(=O)OC(C)(C)C)CCC3)cc1]

To tert-butyl (5RS)-3-oxo-2,3,5,6,7,8-hexahydro[1,2,4]triazolo[4,3-a]pyridine-5-carboxylate (racemate) (500 mg, 2.09 mmol) and caesium carbonate (1.02 g, 3.13 mmol) in 18 ml of acetonitrile was added 1-(bromomethyl)-4-(methylsulphanyl)benzene (476 g, 2.19 mmol), then the reaction mixture was stirred at room temperature for 4 h. For workup, the precipitate present was filtered off, and the filtrate was admixed and extracted with ethyl acetate/water.

The aqueous phase was extracted twice more with ethyl acetate. The combined organic phases were washed with saturated sodium chloride solution, dried with sodium sulphate, filtered, and concentrated and dried under reduced pressure. 776 mg (92% purity, 91% of theory) of the title compound were obtained, which was converted further as such.

LC-MS (Method 3): $R_t$=1.88 min; MS (ESIpos): m/z=376 [M+H]$^+$ $^1$H-NMR (500 MHz, DMSO-d6) δ [ppm]: 1.395 (16.00), 1.403 (1.34), 1.988 (0.68), 2.452 (7.33), 4.783 (2.62), 7.181 (0.76), 7.198 (1.88), 7.221 (2.16), 7.238 (0.85).

Intermediate 107 tert-Butyl (5RS)-2-[(6-chloropyridin-3-yl)methyl]-3-oxo-2,3,5,6,7,8-hexahydro[1,2,4]triazolo[4,3-a]pyridine-5-carboxylate (Racemate)

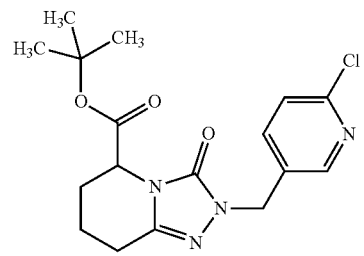 [SMILES: CC(C)(C)OC(=O)C1CCCc2nn(Cc3ccc(Cl)nc3)c(=O)n21]

To tert-butyl (5RS)-3-oxo-2,3,5,6,7,8-hexahydro[1,2,4]triazolo[4,3-a]pyridine-5-carboxylate (racemate) (1.00 g, 4.18 mmol) and caesium carbonate (2.04 g, 6.27 mmol) in 25 ml of acetonitrile was added 2-chloro-5-(chloromethyl)pyridine (711 g, 4.39 mmol), then the reaction mixture was stirred at room temperature overnight. For workup, the mixture was added to water and extracted twice with ethyl acetate. The combined organic phases were washed with saturated sodium chloride solution, dried with magnesium sulphate, filtered, and concentrated and dried under reduced pressure. 1.48 g (89% purity, 87% of theory) of the title compound were obtained, which was used further as such.

LC-MS (Method 4): $R_t$=0.84 min; MS (ESIpos): m/z=365 [M+H]$^+$ $^1$H-NMR (400 MHz, DMSO-d6) δ [ppm]: 1.369 (0.99), 1.387 (16.00), 1.405 (3.22), 1.988 (0.89), 2.060 (0.76), 2.496 (4.74), 2.501 (6.51), 2.505 (5.26), 4.443 (0.68), 4.910 (2.74), 7.510 (0.80), 7.530 (0.98), 8.313 (0.82), 8.319 (0.82).

Intermediate 108 tert-Butyl (5RS)-2-[(6-cyanopyridin-3-yl)methyl]-3-oxo-2,3,5,6,7,8-hexahydro[1,2,4]triazolo[4,3-a]pyridine-5-carboxylate (Racemate)

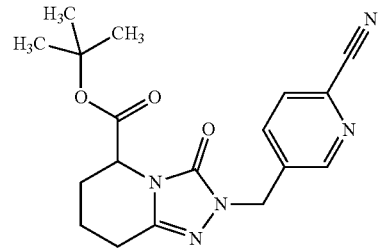 [SMILES: CC(C)(C)OC(=O)C1CCCc2nn(Cc3ccc(C#N)nc3)c(=O)n21]

To tert-butyl (5RS)-3-oxo-2,3,5,6,7,8-hexahydro[1,2,4]triazolo[4,3-a]pyridine-5-carboxylate (racemate) (200 mg, 836 μmol) and caesium carbonate (409 mg, 1.25 mmol) in 8.0 ml of acetonitrile was added 5-(bromomethyl)pyridine-2-carbonitrile (173 mg, 878 μmol), then the reaction mixture was stirred first for 2 h, then at room temperature overnight. Then 5-(bromomethyl)pyridine-2-carbonitrile (32.9 mg, 167 μmol) was added once again (monitoring of conversion by HPLC). For workup, after stirring at room temperature for a further 2 h, the precipitate present was filtered off, and the filtrate was admixed and extracted with ethyl acetate/water. The aqueous phase was extracted twice more with ethyl acetate. The combined organic phases were washed with saturated sodium chloride solution, dried with sodium sulphate, filtered, and concentrated and dried under reduced pressure. 303 mg (>100% of theory) of the title compound were obtained.

LC-MS (Method 4): $R_t$=0.79 min; MS (ESIpos): m/z=356 [M+H]$^+$ $^1$H-NMR (400 MHz, DMSO-d6) δ[ppm]: −0.008 (1.79), 0.008 (1.80), 1.175 (0.81), 1.394 (16.00), 1.406 (1.87), 1.988 (1.44), 3.287 (1.33), 4.459 (0.60), 5.033 (2.16), 8.034 (0.73), 8.037 (0.79).

Intermediate 109 tert-Butyl (5RS)-2-[4-chloro-3-(trifluoromethyl) benzyl]-3-oxo-2,3,5,6,7,8-hexahydro[1,2,4]triazolo [4,3-a]pyridine-5-carboxylate (Racemate)

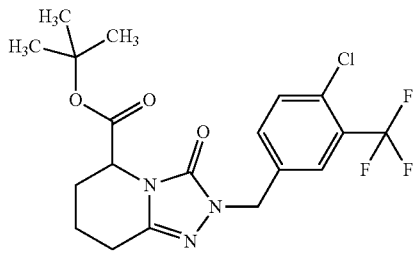 [SMILES: CC(C)(C)OC(=O)C1CCCc2nn(Cc3ccc(Cl)c(C(F)(F)F)c3)c(=O)n21]

To tert-butyl (5RS)-3-oxo-2,3,5,6,7,8-hexahydro[1,2,4] triazolo[4,3-a]pyridine-5-carboxylate (racemate) (200 mg, 836 μmol) and caesium carbonate (409 mg, 1.25 mmol) in 8.0 ml of acetonitrile was added 4-(bromomethyl)-1-chloro-2-(trifluoromethyl)benzene (274 mg, 1.00 mmol), then the reaction mixture was stirred first for 4 h, then at room temperature overnight (monitoring of conversion by HPLC). For workup, the precipitate present was filtered off, and the filtrate was admixed and extracted with ethyl acetate/water. The aqueous phase was extracted twice more with ethyl acetate. The combined organic phases were washed with saturated sodium chloride solution, dried with sodium sulphate, filtered, and concentrated and dried under reduced pressure. 323 mg (87% of theory) of the title compound were obtained, which was used further as such.

LC-MS (Method 3): $R_t$=2.12 min; MS (ESIpos): m/z=376 [M+H]$^+$ $^1$H-NMR (400 MHz, DMSO-d6) δ [ppm]: 1.377 (16.00), 4.946 (1.13), 4.962 (1.09).

Intermediate 110 tert-Butyl (5RS)-2-(3-chlorobenzyl)-3-oxo-2,3,5,6,7,8-hexahydro[1,2,4]triazolo[4,3-a]pyridine-5-carboxylate (Racemate)

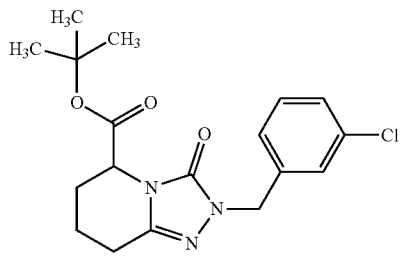 [SMILES: CC(C)(C)OC(=O)C1CCCc2nn(Cc3cccc(Cl)c3)c(=O)n21]

To tert-butyl (5RS)-3-oxo-2,3,5,6,7,8-hexahydro[1,2,4] triazolo[4,3-a]pyridine-5-carboxylate (racemate) (200 mg, 836 μmol) and caesium carbonate (409 mg, 1.25 mmol) in 8.0 ml of acetonitrile was added 1-(bromomethyl)-3-chlorobenzene (130 μl, 1.0 mmol), then the reaction mixture was stirred first for 4 h, then at room temperature overnight (monitoring of conversion by HPLC). For workup, the precipitate present was filtered off, and the filtrate was admixed and extracted with ethyl acetate/water. The aqueous phase was extracted twice more with ethyl acetate. The combined organic phases were washed with saturated sodium chloride solution, dried with sodium sulphate, filtered, and concentrated and dried under reduced pressure. 284 mg (84% purity, 78% of theory) of the title compound were obtained, which was converted further as such.

LC-MS (Method 3): $R_t$=1.91 min; MS (ESIpos): m/z=308 [M+H]$^+$ $^1$H-NMR (400 MHz, DMSO-d6) δ [ppm]: 1.395 (16.00), 1.406 (0.97), 1.988 (0.71), 4.856 (1.40), 4.862 (1.37), 7.360 (1.24), 7.379 (0.68).

Intermediate 111 tert-Butyl (5RS)-2-(3,4-dichlorobenzyl)-3-oxo-2,3,5, 6,7,8-hexahydro[1,2,4]triazolo[4,3-a]pyridine-5-carboxylate (Racemate)

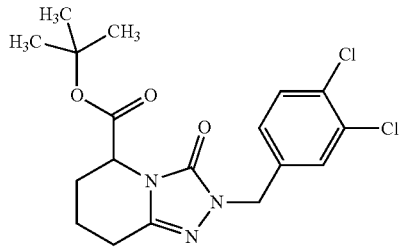 [SMILES: CC(C)(C)OC(=O)C1CCCc2nn(Cc3ccc(Cl)c(Cl)c3)c(=O)n21]

To tert-butyl (5RS)-3-oxo-2,3,5,6,7,8-hexahydro[1,2,4] triazolo[4,3-a]pyridine-5-carboxylate (racemate) (200 mg, 836 μmol) and caesium carbonate (409 mg, 1.25 mmol) in 8.0 ml of acetonitrile was added 4-(bromomethyl)-1,2-dichlorobenzene (241 mg, 1.00 mmol), then the reaction mixture was stirred at room temperature over a weekend. For workup, the precipitate present was filtered off, and the filtrate was admixed and extracted with ethyl acetate/water.

The aqueous phase was extracted twice more with ethyl acetate. The combined organic phases were washed with saturated sodium chloride solution, dried with sodium sulphate, filtered, and concentrated and dried under reduced pressure. 330 mg (78% purity, 77% of theory) of the title compound were obtained, which was converted further as such.

LC-MS (Method 4): R$_t$=1.08 min; MS (ESIpos): m/z=398 [M+H]$^+$ $^1$H-NMR (400 MHz, DMSO-d6) δ[ppm]: 1.392 (16.00), 4.867 (1.86), 7.503 (0.82), 7.508 (0.81), 7.610 (1.04), 7.631 (0.95).

Intermediate 112

Methyl (5RS)-methyl-2-(4-methylbenzyl)-3-oxo-2,3,5,6,7,8-hexahydro[1,2,4]triazolo[4,3-a]pyridine-5-carboxylate (Racemate)

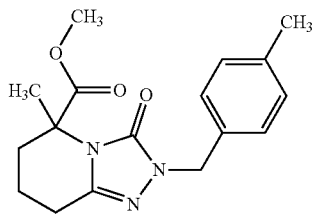 [SMILES: COC(=O)C1(C)CCCc2nn(Cc3ccc(C)cc3)c(=O)n21]

Methyl (5RS)-methyl-3-oxo-2,3,5,6,7,8-hexahydro[1,2,4]triazolo[4,3-a]pyridine-5-carboxylate (racemate) (40.0 mg, 189 µmol) was initially charged in acetonitrile (2.0 ml). Caesium carbonate (67.9 mg, 208 µmol) and 1-(bromomethyl)-4-methylbenzene (36.8 mg, 199 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 32.0 mg (54% of theory) of the title compound were obtained.

LC-MS (Method 3): R$_t$=1.59 min; MS (ESIpos): m/z=316 [M+H]$^+$

Intermediate 113 tert-Butyl (5RS,7RS)-7-methyl-3-oxo-2-{[6-(trifluoromethyl)pyridin-3-yl]methyl}-2,3,5,6,7,8-hexahydro[1,2,4]triazolo[4,3-a]pyridine-5-carboxylate (Diastereomer Mixture; 4 Isomers)

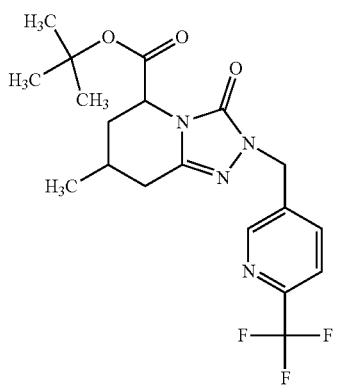 [SMILES: CC1Cc2nn(Cc3ccc(C(F)(F)F)nc3)c(=O)n2C(C(=O)OC(C)(C)C)C1]

tert-Butyl (5RS,7RS)-7-methyl-3-oxo-2,3,5,6,7,8-hexahydro[1,2,4]triazolo[4,3-a]pyridine-5-carboxylate (diastereomer mixture, 4 isomers) (238 mg, 940 µmol) was initially charged in acetonitrile (10 ml). Caesium carbonate (612 mg, 1.88 mmol) and 5-(bromomethyl)-2-(trifluoromethyl)pyridine (237 mg, 987 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over magnesium sulphate and filtered, and the filtrate was concentrated. 383 mg (92% purity, 91% of theory) of the title compound were obtained.

LC-MS (Method 1): R$_t$=1.30 min; MS (ESIpos): m/z=357 [M−tBu+H]$^+$ $^1$H-NMR (400 MHz, DMSO-d6) δ[ppm]: −0.008 (1.52), 0.008 (1.72), 1.012 (2.06), 1.028 (2.14), 1.371 (0.43), 1.406 (16.00), 2.217 (0.48), 2.230 (0.62), 2.258 (0.49), 4.295 (0.45), 4.305 (0.44), 4.835 (0.45), 5.019 (2.25), 7.922 (1.31), 7.936 (0.83), 8.668 (0.83).

Intermediate 114

Ethyl (5RS,6RS)-6-methyl-2-(4-methylbenzyl)-3-oxo-2,3,5,6,7,8-hexahydro[1,2,4]triazolo[4,3-a]pyridine-5-carboxylate (Diastereomer Mixture; 4 Isomers)

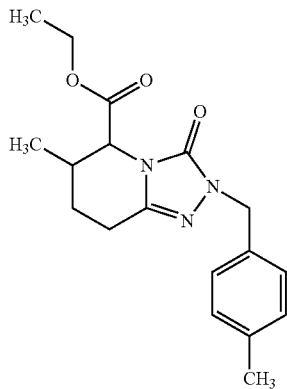 [SMILES: CCOC(=O)C1C(C)CCc2nn(Cc3ccc(C)cc3)c(=O)n21]

Ethyl (5RS,6RS)-6-methyl-3-oxo-2,3,5,6,7,8-hexahydro[1,2,4]triazolo[4,3-a]pyridine-5-carboxylate (diastereomer mixture, 4 isomers) (80.0 mg, 355 µmol) was initially charged in acetonitrile (3.0 ml). Caesium carbonate (174 mg, 533 µmol) and 1-(bromomethyl)-4-methylbenzene (69.0 mg, 373 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over magnesium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 108 mg (71% purity, 65% of theory) of the title compound were obtained.

Intermediate 115

Ethyl (5RS,7RS)-2-(4-methylbenzyl)-3-oxo-7-(trifluoromethyl)-2,3,5,6,7,8-hexahydro[1,2,4]triazolo[4,3-a]pyridine-5-carboxylate (Diastereomer Mixture; 4 Isomers)

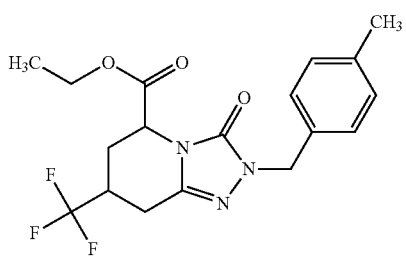 [SMILES: CCOC(=O)C1CC(C(F)(F)F)Cc2nn(Cc3ccc(C)cc3)c(=O)n21]

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (80.0 mg, 287 µmol) was initially charged in acetonitrile (3.5 ml). Caesium carbonate (140 mg, 430 µmol) and 1-(bromomethyl)-4-methylbenzene (55.7 mg, 301 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over magnesium sulphate and filtered, and the filtrate was concentrated. 102 mg (81% purity, 75% of theory) of the title compound were obtained.

LC-MS (Method 1): $R_t$=1.33 min; MS (ESIpos): m/z=384 [M+H]$^+$

Intermediate 116

Methyl ((5RS)-2-[2-(4-methylphenyl)ethyl]-3-oxo-2,3,5,6,7,8-hexahydro[1,2,4]triazolo[4,3-a]pyridine-5-carboxylate (Racemate)

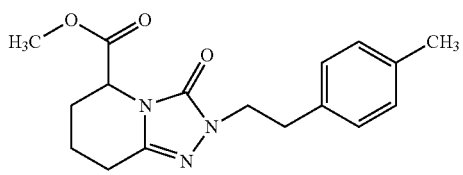

Methyl (5RS)-3-oxo-2,3,5,6,7,8-hexahydro[1,2,4]triazolo[4,3-a]pyridine-5-carboxylate (racemate) (180 mg, 913 µmol) was initially charged in acetonitrile (8.0 ml). Caesium carbonate (312 mg, 959 µmol) and 1-(2-bromoethyl)-4-methylbenzene (200 mg, 1.00 mmol, CAS 6529-51-7) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 88.0 mg (30% of theory) of the title compound were obtained.

LC-MS (Method 4): $R_t$=0.85 min; MS (ESIpos): m/z=316 [M+H]$^+$ $^1$H-NMR (500 MHz, DMSO-d6) δ [ppm]: 1.356 (0.66), 2.257 (8.94), 2.567 (0.54), 2.579 (0.46), 2.588 (0.48), 2.649 (0.66), 2.870 (0.95), 2.885 (1.81), 2.900 (1.02), 3.680 (12.74), 3.783 (0.71), 3.788 (0.75), 3.798 (1.46), 3.804 (1.47), 3.813 (0.68), 3.819 (0.66), 4.525 (0.70), 4.533 (0.78), 4.538 (0.88), 4.546 (0.69), 7.085 (16.00).

Intermediate 117 tert-Butyl (5RS)-3-oxo-2-{[4-(trifluoromethyl)cyclohexyl]methyl}-2,3,5,6,7,8-hexahydro[1,2,4]triazolo[4,3-a]pyridine-5-carboxylate (Diastereomer Mixture; 4 Isomers)

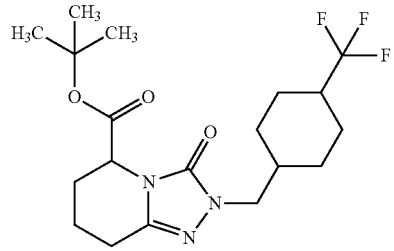 [SMILES: CC(C)(C)OC(=O)C1CCCc2nn(CC3CCC(C(F)(F)F)CC3)c(=O)n21]

To tert-butyl (5RS)-3-oxo-2,3,5,6,7,8-hexahydro[1,2,4]triazolo[4,3-a]pyridine-5-carboxylate (racemate) (250 mg, 1.04 mmol) and caesium carbonate (511 mg, 1.57 mmol) in 15 ml of acetonitrile was added 1-(bromomethyl)-4-(trifluoromethyl)cyclohexane (diastereomer mixture; 2 isomers) (307 mg, 1.25 mmol), then the reaction mixture was stirred at room temperature overnight, then for a further 24 h. For further conversion, there were two more additions of 1-(bromomethyl)-4-(trifluoromethyl)cyclohexane (128 mg, 522 µmol each time) and caesium carbonate (272 mg, 836 µmol each time) and stirring for a further 24 h each time (monitoring of conversion by HPLC). For workup, the mixture was concentrated, and the residue was taken up and extracted with ethyl acetate/water. The aqueous phase was extracted twice more with ethyl acetate. The combined organic phases were washed with saturated sodium chloride solution, dried with sodium sulphate, filtered, and concentrated and dried under reduced pressure. 466 mg (81% purity, 90% of theory) of the title compound were obtained, which was converted further as such.

LC-MS (Method 4): $R_t$=1.08 min; MS (ESIpos): m/z=404 [M+H]$^+$ $^1$H-NMR (400 MHz, DMSO-d6) δ [ppm]: −0.008 (1.25), 1.395 (16.00), 1.406 (2.62), 1.420 (1.08), 1.499 (1.33), 1.508 (0.84), 1.522 (0.93), 1.546 (0.75), 1.595 (0.83), 1.606 (1.20), 1.625 (1.14), 1.643 (1.63), 3.287 (0.76), 3.563 (2.36), 3.581 (2.34).

Intermediate 118 tert-Butyl (5RS)-2-[(4,4-difluorocyclohexyl)methyl]-3-oxo-2,3,5,6,7,8-hexahydro[1,2,4]triazolo[4,3-a]pyridine-5-carboxylate (Racemate)

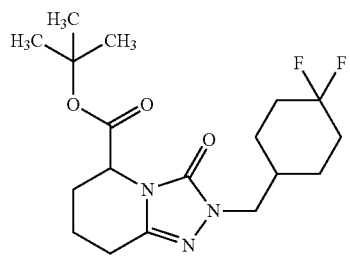 [SMILES: CC(C)(C)OC(=O)C1CCCc2nn(CC3CCC(F)(F)CC3)c(=O)n21]

To tert-butyl (5RS)-3-oxo-2,3,5,6,7,8-hexahydro[1,2,4]triazolo[4,3-a]pyridine-5-carboxylate (racemate) (67.4 mg, 282 µmol) and caesium carbonate (138 mg, 422 µmol) in 4.0 ml of acetonitrile was added 4-(bromomethyl)-1,1-difluorocyclohexane (72.0 mg, 338 µmol), then the reaction mixture was stirred at room temperature over a weekend. For workup, the precipitate present was filtered off, the filtrate was concentrated, and the residue was taken up and extracted with ethyl acetate/water. The aqueous phase was extracted twice more with ethyl acetate. The combined organic phases were washed with saturated sodium chloride solution, dried with sodium sulphate, filtered, and concentrated and dried under reduced pressure. The residue was separated by preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). By combining the product-containing fractions, after removal of the solvents under reduced pressure, 41.0 mg (39% of theory) of the title compound were obtained.

LC-MS (Method 6): $R_t$=1.76 min; MS (ESIpos): m/z=372 [M+H]$^+$ $^1$H-NMR (400 MHz, DMSO-d6) δ [ppm]: 1.396 (16.00), 2.072 (2.01), 3.528 (1.35), 3.545 (1.33), 4.399 (0.62).

Intermediate 119

(5S)-2-[(6-Chloropyridin-3-yl)methyl]-3-oxo-2,5,6,7-tetrahydro-3H-pyrrolo[2,1-c][1,2,4]triazole-5-carboxylic Acid (Enantiomer)

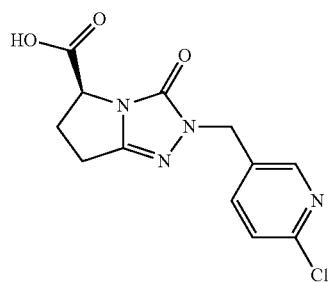 [SMILES: O=C(O)[C@@H]1CCc2nn(Cc3ccc(Cl)nc3)c(=O)n21]

Methyl (5S)-2-[(6-chloropyridin-3-yl)methyl]-3-oxo-2,5,6,7-tetrahydro-3H-pyrrolo[2,1-c][1,2,4]triazole-5-carboxylate (enantiomer) (430 mg, 1.39 mmol) was initially charged in THF (10 ml), and lithium hydroxide (167 mg, 6.96 mmol) dissolved in water was added. After stirring at room temperature overnight, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 185 mg (45% of theory) of the title compound were obtained.

LC-MS (Method 3): $R_t$=0.71 min; MS (ESIpos): m/z=295 [M+H]$^+$

Intermediate 120

(5S)-3-Oxo-2-{[6-(trifluoromethyl)pyridin-3-yl]methyl}-2,5,6,7-tetrahydro-3H-pyrrolo[2,1-c][1,2,4]triazole-5-carboxylic Acid (Enantiomer)

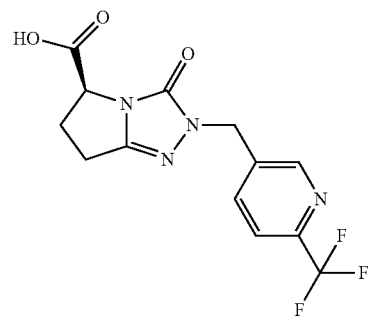 [SMILES: O=C(O)[C@@H]1CCc2nn(Cc3ccc(C(F)(F)F)nc3)c(=O)n21]

Methyl (5S)-3-oxo-2-{[6-(trifluoromethyl)pyridin-3-yl]methyl}-2,5,6,7-tetrahydro-3H-pyrrolo[2,1-c][1,2,4]triazole-5-carboxylate (enantiomer) (441 mg, 1.29 mmol) was initially charged in THF (10 ml), and lithium hydroxide (154 mg, 6.44 mmol) dissolved in water was added. After stirring overnight, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 376 mg (89% of theory) of the title compound were obtained.

LC-MS (Method 3): $R_t$=0.85 min; MS (ESIpos): m/z=329 [M+H]$^+$

Intermediate 121

(5S)-2-(4-Methylbenzyl)-3-oxo-2,5,6,7-tetrahydro-3H-pyrrolo[2,1-c][1,2,4]triazole-5-carboxylic Acid (Enantiomer)

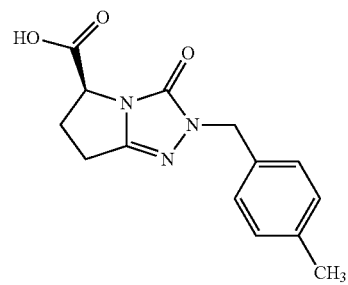 [SMILES: Cc1ccc(Cn2nc3n(c2=O)[C@H](C(=O)O)CC3)cc1]

Methyl (5S)-2-(4-methylbenzyl)-3-oxo-2,5,6,7-tetrahydro-3H-pyrrolo[2,1-c][1,2,4]triazole-5-carboxylate (enantiomer) (280 mg, 975 µmol) was initially charged in THF (4.0 ml), and lithium hydroxide (117 mg, 4.87 mmol) dissolved in water was added. After stirring at room temperature overnight, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 251 mg (94% of theory) of the title compound were obtained.

LC-MS (Method 4): $R_t$=0.59 min; MS (ESIpos): m/z=274 [M+H]$^+$ $^1$H-NMR (400 MHz, DMSO-d6) δ [ppm]: 0.008 (0.73), 1.157 (0.99), 1.174 (2.01), 1.192 (1.01), 1.988 (3.62), 2.274 (10.45), 2.423 (0.43), 2.430 (0.52), 2.439 (0.46), 2.446 (0.46), 2.455 (0.52), 2.463 (0.55), 2.708 (1.26), 2.720 (0.84), 2.730 (2.22), 2.745 (1.81), 2.822 (0.50), 2.841 (0.44), 2.853 (0.62), 2.876 (0.50), 4.020 (0.87), 4.038 (0.87), 4.603 (1.09), 4.610 (1.19), 4.625 (1.25), 4.633 (1.04), 4.708 (0.51), 4.747 (2.97), 4.761 (2.99), 4.800 (0.51), 7.140 (16.00), 13.346 (0.50).

Intermediate 122

(5S)-2-(3-Chloro-4-fluorobenzyl)-3-oxo-2,5,6,7-tetrahydro-3H-pyrrolo[2,1-c][1,2,4]triazole-5-carboxylic Acid (Enantiomer)

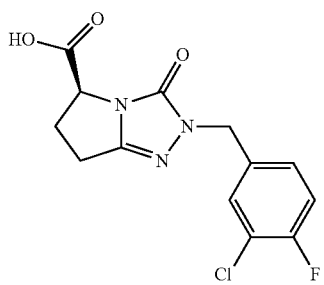 [SMILES: O=C(O)[C@@H]1CCc2nn(Cc3ccc(F)c(Cl)c3)c(=O)n21]

Methyl (5S)-2-(3-chloro-4-fluorobenzyl)-3-oxo-2,5,6,7-tetrahydro-3H-pyrrolo[2,1-c][1,2,4]triazole-5-carboxylate (enantiomer) (460 mg, 1.41 mmol) was initially charged in THF (10 ml), and lithium hydroxide (169 mg, 7.06 mmol) dissolved in water was added. After stirring overnight, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 281 mg (64% of theory) of the title compound were obtained.

LC-MS (Method 3): $R_t$=1.12 min; MS (ESIpos): m/z=312 [M+H]$^+$

Intermediate 123

(5S)-2-[(2-Chloropyridin-4-yl)methyl]-3-oxo-2,5,6,7-tetrahydro-3H-pyrrolo[2,1-c][1,2,4]triazole-5-carboxylic Acid (Enantiomer)

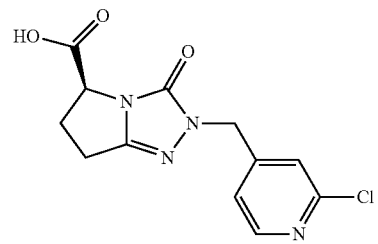 [SMILES: O=C(O)[C@@H]1CCc2nn(Cc3ccnc(Cl)c3)c(=O)n21]

Methyl (5S)-2-[(2-chloropyridin-4-yl)methyl]-3-oxo-2,5,6,7-tetrahydro-3H-pyrrolo[2,1-c][1,2,4]triazole-5-carboxylate (enantiomer) (250 mg, 810 µmol) was initially charged in THF (7.5 ml), and lithium hydroxide (97.0 mg, 4.05 mmol) dissolved in water was added. After stirring overnight, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 230 mg (96% of theory) of the title compound were obtained.

LC-MS (Method 4): $R_t$=0.43 min; MS (ESIpos): m/z=295 [M+H]$^+$ $^1$H-NMR (400 MHz, DMSO-d6) δ [ppm]: −0.149 (0.93), 0.145 (0.82), 2.371 (1.71), 2.715 (1.98), 2.758 (4.35), 2.781 (8.27), 2.795 (7.03), 2.838 (1.67), 2.861 (2.25), 2.891 (2.91), 2.915 (1.98), 4.532 (0.78), 4.662 (3.88), 4.670 (4.35), 4.685 (4.43), 4.692 (3.88), 4.887 (0.78), 4.931 (16.00), 7.253 (5.63), 7.266 (5.79), 7.340 (10.10), 8.377 (7.65), 8.389 (7.61), 11.255 (1.01).

Intermediate 124

(5S)-3-Oxo-2-[3-(trifluoromethyl)benzyl]-2,5,6,7-tetrahydro-3H-pyrrolo[2,1-c][1,2,4]triazole-5-carboxylic Acid (Enantiomer)

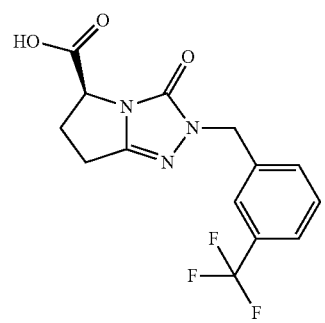 [SMILES: O=C(O)[C@@H]1CCc2nn(Cc3cccc(C(F)(F)F)c3)c(=O)n21]

Methyl (5S)-3-oxo-2-[3-(trifluoromethyl)benzyl]-2,5,6,7-tetrahydro-3H-pyrrolo[2,1-c][1,2,4]triazole-5-carboxylate (enantiomer) (150 mg, 440 µmol) was initially charged in THF (4.5 ml), and lithium hydroxide (52.6 mg, 2.20 mmol)

dissolved in water was added. After stirring overnight, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 129 mg (90% of theory) of the title compound were obtained.

LC-MS (Method 4): $R_t$=0.70 min; MS (ESIpos): m/z=328 [M+H]$^+$

Intermediate 125

(5RS)-2-(4-Methylbenzyl)-3-oxo-2,3,5,6,7,8-hexahydro[1,2,4]triazolo[4,3-a]pyridine-5-carboxylic Acid (Racemate)

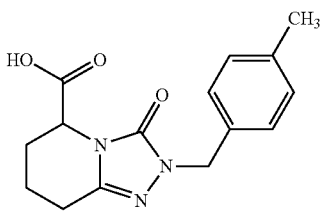 [SMILES: Cc1ccc(Cn2nc3n(c2=O)C(C(=O)O)CCC3)cc1]

Variant a)
Methyl (5RS)-2-(4-methylbenzyl)-3-oxo-2,3,5,6,7,8-hexahydro[1,2,4]triazolo[4,3-a]pyridine-5-carboxylate (racemate) (854 mg, 95% purity, 2.69 mmol) was initially charged in 20 ml of THF/water (3:1), lithium hydroxide (322 mg, 13.5 mmol) was added and the reaction mixture was stirred at room temperature overnight. For workup, the mixture was diluted with water, acidified with 1 N hydrochloric acid, dichloromethane and a little saturated sodium chloride solution were added, and the mixture was extracted. The aqueous phase was extracted twice more with dichloromethane, and the combined organic phases were washed with saturated sodium chloride solution, dried over sodium sulphate, concentrated and dried under reduced pressure. This gave 436 mg (56% of theory) of the title compound.

LC-MS (Method 3): $R_t$=1.15 min; MS (ESIpos): m/z=288 [M+H]$^+$ $^1$H-NMR (400 MHz, DMSO-d6) δ[ppm]: 2.075 (0.98), 2.084 (0.97), 2.092 (0.92), 2.272 (9.23), 4.458 (1.29), 4.770 (4.43), 7.128 (16.00).

Variant b)
To a solution of tert-butyl (5RS)-2-(4-methylbenzyl)-3-oxo-2,3,5,6,7,8-hexahydro[1,2,4]triazolo[4,3-a]pyridine-5-carboxylate (7.14 g, 20.8 mmol) in 100 ml of dichloromethane were added 10 ml (130 mmol) of trifluoroacetic acid, and the mixture was stirred at room temperature overnight. After addition of a further 5 ml (65 mmol) of trifluoroacetic acid and stirring at room temperature for a further day, the mixture was admixed with 14 ml of 3 N NaOH while cooling with an ice bath and stirring vigorously, diluted with dichloromethane/water and extracted. The aqueous phase was extracted twice more with dichloromethane, and the combined organic phases were washed with saturated sodium chloride solution, dried over sodium sulphate, concentrated and dried under reduced pressure.

The product thus obtained (6.63 g, >100% of theory) was used without further purification.

LC-MS (Method 3): $R_t$=1.18 min; MS (ESIpos): m/z=288 [M+H]$^+$ $^1$H-NMR (400 MHz, DMSO-d6) δ[ppm]: −0.008 (1.24), 0.008 (1.06), 1.397 (0.62), 1.534 (0.77), 2.272 (8.87), 4.459 (1.36), 4.770 (4.02), 7.128 (16.00).

Intermediate 126

(5RS)-2-[4-(tert-Butoxycarbonyl)benzyl]-3-oxo-2,3,5,6,7,8-hexahydro[1,2,4]triazolo[4,3-a]pyridine-5-carboxylic Acid (Racemate)

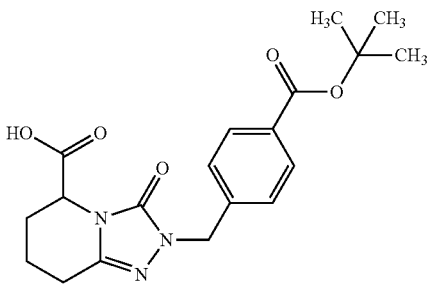 [SMILES: CC(C)(C)OC(=O)c1ccc(Cn2nc3n(c2=O)C(C(=O)O)CCC3)cc1]

Methyl (5RS)-2-[4-(tert-butoxycarbonyl)benzyl]-3-oxo-2,3,5,6,7,8-hexahydro[1,2,4]triazolo[4,3-a]pyridine-5-carboxylate (racemate) (676 mg, 87% purity, 1.52 mmol) was initially charged in 15 ml of THF/water, lithium hydroxide (182 mg, 7.59 mmol) was added and the reaction mixture was stirred at room temperature overnight. For workup, the mixture was adjusted to pH 6 with 1 N hydrochloric acid, admixed with dichloromethane and extracted. The aqueous phase was extracted twice more with dichloromethane, and the combined organic phases were washed with saturated sodium chloride solution, dried over sodium sulphate, concentrated and dried under reduced pressure. This gave a product fraction of 99 mg (71% purity, 12% of theory).

The likewise product-containing aqueous phase was adjusted to pH 3 with 1 N hydrochloric acid, admixed with ethyl acetate and extracted a total of three times. The combined ethyl acetate phases were washed with saturated sodium chloride solution, dried over sodium sulphate, and concentrated and dried under reduced pressure. This gave 147 mg (26% of theory) of the title compound.

LC-MS (Method 3): $R_t$=1.53 min; MS (ESIneg): m/z=372 [M−H]$^-$ $^1$H-NMR (400 MHz, DMSO-d6) δ [ppm]: 1.536 (16.00), 4.911 (2.17), 7.328 (1.14), 7.349 (1.23), 7.846 (1.40), 7.867 (1.28).

Intermediate 127

(5RS)-2-[(1 RS)-1-(4-Chlorophenyl)ethyl]-3-oxo-2,3,5,6,7,8-hexahydro[1,2,4]triazolo[4,3-a]pyridine-5-carboxylic Acid (Diastereomer Mixture; 4 Isomers)

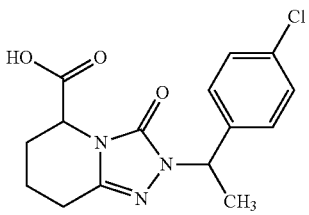 [SMILES: CC(c1ccc(Cl)cc1)n1nc2n(c1=O)C(C(=O)O)CCC2]

To a solution of tert-butyl (5RS)-2-[(1RS)-1-(4-chlorophenyl)ethyl]-3-oxo-2,3,5,6,7,8-hexahydro[1,2,4]triazolo[4,3-a]pyridine-5-carboxylate (diastereomer mixture; 4 isomers) (755 mg, 2.00 mmol) in 10 ml of dichloromethane were added 1.2 ml (16 mmol) of trifluoroacetic acid, and the mixture was stirred at room temperature overnight. After addition of a further 600 µl (7.8 mmol) of trifluoroacetic acid and stirring at room temperature for a further 5 h, the mixture was adjusted to pH 3 with 3 N NaOH while cooling with an ice bath and stirring vigorously, diluted with dichloromethane/water and extracted. The aqueous phase was extracted twice more with dichloromethane, and the combined organic phases were washed with saturated sodium chloride solution, dried over sodium sulphate, concentrated and dried under reduced pressure. In this way, 392 mg (79% purity, 48% of theory) of the title compound were obtained as a diastereomer mixture.

LC-MS (Method 3): $R_t$=1.33 min; MS (ESIpos): m/z=322 [M+H]$^+$; $R_t$=1.36 min; MS (ESIpos): m/z=322 [M+H]$^+$ $^1$H-NMR (400 MHz, DMSO-d6) δ [ppm]: −0.149 (1.83), −0.008 (16.00), 0.008 (13.62), 0.146 (1.78), 1.110 (3.38), 1.288 (4.30), 1.304 (4.30), 1.329 (5.07), 1.406 (11.38), 1.595 (12.57), 1.607 (12.53), 1.613 (13.39), 1.625 (11.70), 2.076 (5.07), 2.580 (3.20), 2.664 (3.47), 2.710 (2.42), 3.286 (7.04), 4.426 (3.15), 4.450 (3.43), 5.326 (3.06), 5.344 (3.29), 7.309 (5.62), 7.319 (4.94), 7.325 (4.75), 7.331 (10.88), 7.340 (10.10), 7.346 (4.25), 7.353 (4.30), 7.355 (14.45), 7.375 (11.93), 7.379 (15.41), 7.385 (4.75), 7.396 (6.86), 7.401 (7.54), 7.484 (4.66).

Intermediate 128

(5RS)-3-Oxo-2-(4-sulphamoylbenzyl)-2,3,5,6,7,8-hexahydro[1,2,4]triazolo[4,3-a]pyridine-5-carboxylic Acid (Racemate)

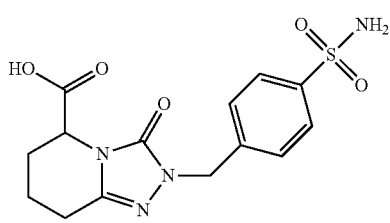 [SMILES: NS(=O)(=O)c1ccc(Cn2nc3n(c2=O)C(C(=O)O)CCC3)cc1]

To a solution of tert-butyl (5RS)-3-oxo-2-(4-sulphamoylbenzyl)-2,3,5,6,7,8-hexahydro[1,2,4]triazolo[4,3-a]pyridine-5-carboxylate (racemate) (35.0 mg, 85.7 µmol) in 5.0 ml of dichloromethane were added 500 µl (6.5 mmol) of trifluoroacetic acid, and the mixture was stirred at room temperature over a weekend. For workup, the mixture was concentrated and dried under reduced pressure. In this way, 30 mg (99% of theory) of the title compound were obtained, which was used further without additional purification.

LC-MS (Method 6): $R_t$=0.66 min; MS (ESIpos): m/z=353 [M+H]$^+$

Intermediate 129

(5RS)-2-[4-(Methylsulphanyl)benzyl]-3-oxo-2,3,5,6,7,8-hexahydro[1,2,4]triazolo[4,3-a]pyridine-5-carboxylic Acid (Racemate)

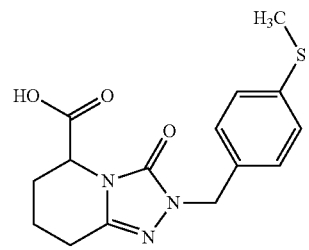 [SMILES: CSc1ccc(Cn2nc3n(c2=O)C(C(=O)O)CCC3)cc1]

To a solution of tert-butyl (5RS)-2-[4-(methylsulphanyl)benzyl]-3-oxo-2,3,5,6,7,8-hexahydro[1,2,4]triazolo[4,3-a]pyridine-5-carboxylate (racemate) (160 mg, 89% purity, 379 µmol) in 5.0 ml of dichloromethane were added 500 µl (6.5 mmol) of trifluoroacetic acid, and the mixture was stirred at room temperature over a weekend. For further conversion, another 100 µl (1.3 mmol) of trifluoroacetic acid were added and the mixture was stirred at room temperature for a further day (monitoring of conversion by HPLC). For workup, the mixture was adjusted to pH 3 with 3 N NaOH while cooling with an ice bath and stirring vigorously, diluted with dichloromethane/water and extracted. The aqueous phase was extracted twice more with dichloromethane, and the combined organic phases were washed with saturated sodium chloride solution, dried over sodium sulphate, concentrated and dried under reduced pressure. 137 mg (109% of theory) of the title compound were obtained, which was converted further as such.

LC-MS (Method 3): $R_t$=1.20 min; MS (ESIpos): m/z=320 [M+H]$^+$ $^1$H-NMR (400 MHz, DMSO-d6) δ [ppm]: −0.008 (2.62), 0.008 (2.24), 1.396 (0.96), 2.452 (16.00), 4.461 (1.33), 4.782 (4.61), 5.754 (0.68), 7.174 (1.26), 7.196 (3.98), 7.215 (4.58), 7.221 (1.06), 7.237 (1.41).

Intermediate 130

(5RS)-2-[(6-Chloropyridin-3-yl)methyl]-3-oxo-2,3,5,6,7,8-hexahydro[1,2,4]triazolo[4,3-a]pyridine-5-carboxylic Acid (Racemate)

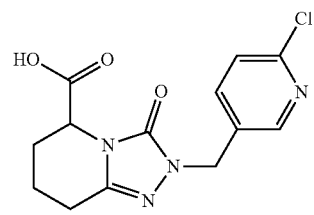 [SMILES: O=C(O)C1CCCc2nn(Cc3ccc(Cl)nc3)c(=O)n21]

To a solution of tert-butyl (5RS)-2-[(6-chloropyridin-3-yl)methyl]-3-oxo-2,3,5,6,7,8-hexahydro[1,2,4]triazolo[4,3-a]pyridine-5-carboxylate (racemate) (1.84 g, 5.04 mmol) in 25 ml of dichloromethane were added 5.0 ml (65 mmol) of trifluoroacetic acid, and the mixture was stirred at room temperature overnight. For workup, the mixture was adjusted to pH 3 with 3 N NaOH while cooling with an ice bath and stirring vigorously, diluted with water and extracted twice with dichloromethane. The combined organic phases were washed with saturated sodium chloride solution, dried over magnesium sulphate, concentrated and dried under reduced pressure. 1.59 g (92% purity, 94% of theory) of the title compound were obtained, which was converted further as such.

LC-MS (Method 3): $R_t$=0.83 min; MS (ESIpos): m/z=309 [M+H]$^+$ $^1$H-NMR (400 MHz, DMSO-d6) δ[ppm]: −0.008 (1.94), 0.008 (1.83), 1.157 (3.09), 1.175 (6.27), 1.193 (3.15), 1.387 (3.56), 1.406 (0.95), 1.506 (0.97), 1.519 (1.00), 1.534 (0.85), 1.795 (0.84), 1.809 (1.23), 1.820 (1.25), 1.830 (1.04), 1.841 (1.01), 1.909 (1.25), 1.988 (11.31), 2.069 (1.57), 2.078 (2.11), 2.084 (2.94), 2.090 (3.28), 2.101 (3.07), 2.113 (1.63), 2.568 (1.70), 2.582 (1.28), 2.614 (1.39), 2.627 (2.10), 2.636 (1.49), 2.656 (0.78), 2.666 (1.09), 4.003 (1.24), 4.021 (3.03), 4.038 (3.02), 4.056 (1.29), 4.218 (0.77), 4.462 (2.60), 4.474 (4.68), 4.487 (2.49), 4.828 (1.17), 4.910 (16.00), 5.093 (0.74), 7.500 (4.57), 7.521 (5.54), 7.703 (3.17), 7.709 (3.32), 7.724 (2.78), 7.730 (2.79), 8.310 (4.06), 8.316 (3.98).

Intermediate 131

(5RS)-2-[(5-Chloropyridin-2-yl)methyl]-3-oxo-2,3,5,6,7,8-hexahydro[1,2,4]triazolo[4,3-a]pyridine-5-carboxylic Acid (Racemate)

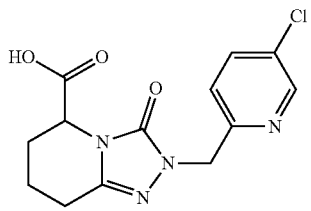 [SMILES: O=C(O)C1CCCc2nn(Cc3ccc(Cl)cn3)c(=O)n21]

To a solution of tert-butyl (5RS)-2-[(5-chloropyridin-2-yl)methyl]-3-oxo-2,3,5,6,7,8-hexahydro[1,2,4]triazolo[4,3-a]pyridine-5-carboxylate (racemate) (268 mg, 82% purity, 602 µmol) in 3.0 ml of dichloromethane were added 600 µl (7.8 mmol) of trifluoroacetic acid, and the mixture was stirred at room temperature overnight. For workup, the mixture was concentrated and dried under reduced pressure. In this way, 220 mg (80% purity, 95% of theory) of the title compound were obtained, which was used further without additional purification.

LC-MS (Method 3): $R_t$=0.87 min; MS (ESIpos): m/z=309 [M+H]$^+$

Intermediate 132

(5RS)-2-[(6-Cyanopyridin-3-yl)methyl]-3-oxo-2,3,5,6,7,8-hexahydro[1,2,4]triazolo[4,3-a]pyridine-5-carboxylic Acid (Racemate)

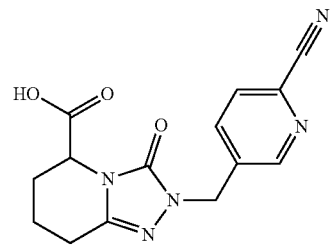 [SMILES: N#Cc1ccc(Cn2nc3n(c2=O)C(C(=O)O)CCC3)cn1]

To a solution of tert-butyl (5RS)-2-[(6-cyanopyridin-3-yl)methyl]-3-oxo-2,3,5,6,7,8-hexahydro[1,2,4]triazolo[4,3-a]pyridine-5-carboxylate (racemate) (303 mg, 853 µmol) in 8.0 ml of dichloromethane were added 1.0 ml (13 mmol) of trifluoroacetic acid, and the mixture was stirred at room temperature overnight. For further conversion, another 200 µl (2.6 mmol) and 100 µl (1.3 mmol) of trifluoroacetic acid were added and the mixture was stirred for a further 3.5 h and 2.5 h respectively. (Monitoring of conversion by HPLC and LC-MS). For workup, the mixture was diluted with dichloromethane/water and extracted. The aqueous phase was extracted twice more with dichloromethane, and the combined organic phases were washed with saturated sodium chloride solution, dried over sodium sulphate, concentrated and dried under reduced pressure. 191 mg (67% purity, 50% of theory) of the title compound were obtained, which was converted further as such.

LC-MS (Method 3): $R_t$=0.72 min; MS (ESIpos): m/z=300 [M+H]$^+$ $^1$H-NMR (400 MHz, DMSO-d6) δ [ppm]: −0.149 (0.84), −0.008 (6.61), 0.008 (6.11), 0.146 (0.76), 1.394 (4.32), 1.400 (16.00), 2.094 (1.18), 2.366 (0.89), 2.665 (0.82), 2.710 (0.84), 4.489 (1.34), 4.985 (1.87), 5.034 (4.55), 5.754 (1.79), 7.851 (0.71), 7.857 (0.76), 7.871 (1.00), 7.876 (0.95), 7.978 (0.74), 8.000 (1.24), 8.023 (1.58), 8.043 (1.26), 8.633 (1.26), 8.638 (1.26).

Intermediate 133

(5RS)-2-[4-Chloro-3-(trifluoromethyl)benzyl]-3-oxo-2,3,5,6,7,8-hexahydro[1,2,4]triazolo[4,3-a]pyridine-5-carboxylic Acid (Racemate)

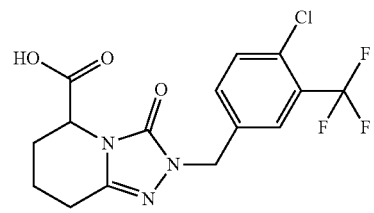 [SMILES: O=C(O)C1CCCc2nn(Cc3ccc(Cl)c(C(F)(F)F)c3)c(=O)n21]

To a solution of tert-butyl (5RS)-2-[4-chloro-3-(trifluoromethyl)benzyl]-3-oxo-2,3,5,6,7,8-hexahydro[1,2,4]triazolo[4,3-a]pyridine-5-carboxylate (racemate) (332 mg, 97% purity, 746 µmol) in 7.0 ml of dichloromethane were added 700 µl (9.1 mmol) of trifluoroacetic acid, and the mixture was stirred at room temperature for 4 h. For further conversion, another 200 µl (2.6 mmol) of trifluoroacetic acid were added and the mixture was stirred further overnight. For workup, the mixture was diluted with dichloromethane/water and extracted. The aqueous phase was extracted twice more with dichloromethane, and the combined organic phases were washed with saturated sodium chloride solution, dried over sodium sulphate, concentrated and dried under reduced pressure. 273 mg (94% of theory) of the title compound were obtained, which was used further as such.

LC-MS (Method 3): $R_t$=1.50 min; MS (ESIpos): m/z=376 [M+H]$^+$ $^1$H-NMR (400 MHz, DMSO-d6) δ[ppm]: −0.149 (0.97), −0.008 (8.63), 0.008 (7.66), 0.146 (0.97), 1.034 (1.14), 1.050 (1.12), 1.377 (3.67), 1.506 (1.07), 1.519 (1.07), 1.534 (0.97), 1.800 (0.90), 1.814 (1.34), 1.824 (1.34), 1.835 (1.09), 1.846 (1.14), 2.076 (1.56), 2.084 (2.31), 2.098 (3.87), 2.108 (3.57), 2.120 (1.92), 2.366 (0.73), 2.519 (2.21), 2.561 (2.04), 2.574 (2.04), 2.588 (1.53), 2.620 (1.53), 2.633 (2.36), 2.643 (1.68), 2.662 (0.97), 2.675 (1.34), 2.685 (0.71), 2.710 (0.75), 3.168 (1.00), 3.508 (2.38), 4.477 (2.63), 4.488 (4.98), 4.501 (2.58), 4.956 (16.00), 7.523 (2.31), 7.529 (2.38), 7.544 (2.99), 7.549 (3.06), 7.706 (5.16), 7.727 (4.21), 7.748 (5.47), 7.754 (5.23), 13.264 (0.73).

Intermediate 134

(5RS)-2-(3-Chlorobenzyl)-3-oxo-2,3,5,6,7,8-hexahydro[1,2,4]triazolo[4,3-a]pyridine-5-carboxylic Acid (Racemate)

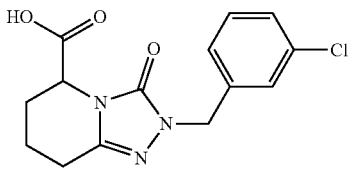 [SMILES: O=C(O)C1CCCc2nn(Cc3cccc(Cl)c3)c(=O)n21]

To a solution of tert-butyl (5RS)-2-(3-chlorobenzyl)-3-oxo-2,3,5,6,7,8-hexahydro[1,2,4]triazolo[4,3-a]pyridine-5-carboxylate (racemate) (284 mg, 84% purity, 656 µmol) in 6.0 ml of dichloromethane were added 600 µl (7.8 mmol) of trifluoroacetic acid, and the mixture was stirred at room temperature for 4 h. For further conversion, another 200 µl (2.6 mmol) of trifluoroacetic acid were added and the mixture was stirred further overnight. For workup, the mixture was diluted with dichloromethane/water and extracted. The aqueous phase was extracted twice more with dichloromethane, and the combined organic phases were washed with saturated sodium chloride solution, dried over sodium sulphate, concentrated and dried under reduced pressure. 224 mg (83% purity, 92% of theory) of the title compound were obtained, which was converted further as such.

LC-MS (Method 3): $R_t$=1.20 min; MS (ESIpos): m/z=308 [M+H]$^+$ $^1$H-NMR (400 MHz, DMSO-d6) δ [ppm]: −0.149 (1.79), −0.008 (16.00), 0.008 (14.92), 0.146 (1.88), 1.147 (1.13), 1.396 (0.56), 2.091 (0.71), 2.323 (0.56), 2.327 (0.89), 2.332 (0.66), 2.366 (1.46), 2.665 (0.80), 2.669 (1.04), 2.674 (0.94), 2.709 (1.55), 3.168 (1.55), 4.486 (0.89), 4.859 (3.48), 7.197 (0.56), 7.214 (0.71), 7.288 (0.99), 7.351 (0.85), 7.356 (2.02), 7.374 (0.89).

Alternative Synthesis:

Methyl (5RS)-2-(3-chlorobenzyl)-3-oxo-2,3,5,6,7,8-hexahydro[1,2,4]triazolo[4,3-a]pyridine-5-carboxylate (racemate) (63.0 mg, 196 µmol) was initially charged in THF (2.5 ml), and lithium hydroxide (23.4 mg, 979 µmol) dissolved in water (2.5 ml) was added. The reaction mixture was stirred at room temperature for 65 h, and then water and 1 N aqueous hydrochloric acid were added. The organic phase was removed and the aqueous phase was extracted repeatedly with ethyl acetate. The combined organic phases were dried over sodium sulphate and filtered, and the filtrate was concentrated. 55.0 mg (91% of theory) of the title compound were obtained.

LC-MS (Method 4): $R_t$=0.68 min; MS (ESIpos): m/z=308 [M+H]$^+$

Intermediate 135

(5RS)-2-(3,4-Dichlorobenzyl)-3-oxo-2,3,5,6,7,8-hexahydro[1,2,4]triazolo[4,3-a]pyridine-5-carboxylic Acid (Racemate)

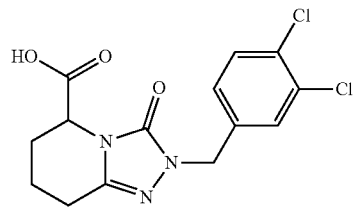 [SMILES: O=C(O)C1CCCc2nn(Cc3ccc(Cl)c(Cl)c3)c(=O)n21]

To a solution of tert-butyl (5RS)-2-(3,4-dichlorobenzyl)-3-oxo-2,3,5,6,7,8-hexahydro[1,2,4]triazolo[4,3-a]pyridine-5-carboxylate (racemate) (330 mg, 78% purity, 646 µmol) in 8.0 ml of dichloromethane were added 900 µl (12 mmol) of trifluoroacetic acid, and the mixture was stirred at room temperature overnight. For further conversion, another 100 µl (1.3 mmol) of trifluoroacetic acid were added and the mixture was stirred further for 5 h. For workup, the mixture was diluted with dichloromethane/water and extracted. The aqueous phase was extracted twice more with dichloromethane, and the combined organic phases were washed with saturated sodium chloride solution, dried over sodium sulphate, concentrated and dried under reduced pressure. 282 mg (80% purity, >100%) of the title compound were obtained, which was converted further as such.

LC-MS (Method 3): $R_t$=1.39 min; MS (ESIpos): m/z=342 [M+H]$^+$ $^1$H-NMR (400 MHz, DMSO-d6) δ [ppm]: −0.008 (0.99), 0.008 (0.93), 1.365 (0.65), 1.392 (6.32), 1.510 (0.93), 1.523 (0.96), 1.535 (1.07), 1.538 (0.85), 1.801 (0.81), 1.811 (1.13), 1.815 (1.18), 1.825 (1.21), 1.836 (1.01), 1.847 (1.01), 2.077 (1.57), 2.086 (2.08), 2.092 (2.91), 2.099 (3.24), 2.108 (3.04), 2.121 (1.63), 2.521 (1.06), 2.563 (1.64), 2.576 (1.70), 2.591 (1.29), 2.621 (1.34), 2.631 (1.97), 2.635 (2.09), 2.644 (1.52), 2.664 (0.79), 2.674 (1.03), 4.475 (2.28), 4.487 (4.46), 4.499 (2.26), 4.706 (0.69), 4.868 (16.00), 5.423 (1.28), 7.221 (2.81), 7.226 (2.94), 7.242 (3.18), 7.247 (3.31), 7.486 (4.76), 7.491 (4.55), 7.603 (7.05), 7.623 (6.45), 7.631 (0.66).

Intermediate 136

(5RS)-2-(3,5-Dichlorobenzyl)-3-oxo-2,3,5,6,7,8-hexahydro[1,2,4]triazolo[4,3-a]pyridine-5-carboxylic Acid Hydrochloride (Racemate)

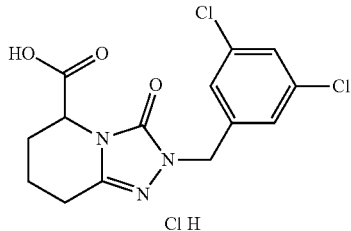

tert-Butyl (5RS)-2-(3,5-dichlorobenzyl)-3-oxo-2,3,5,6,7,8-hexahydro[1,2,4]triazolo[4,3-a]pyridine-5-carboxylate (racemate) (445 mg, 1.12 mmol) was dissolved in 1,4-dioxane (2.0 ml), and hydrochloric acid dissolved in 1,4-dioxane (2.8 ml, 4.0 M, 11 mmol) was added. The reaction mixture was stirred at room temperature for 2 h and then hydrochloric acid dissolved in 1,4-dioxane (2.8 ml, 4.0 M, 11 mmol) was added again. After stirring at room temperature overnight, the solvent was removed under reduced pressure, and 493 mg (79% purity, 92% of theory) of the title compound were obtained.

LC-MS (Method 4): $R_t$=0.80 min; MS (ESIpos): m/z=342 [M+H]$^+$ $^1$H-NMR (400 MHz, DMSO-d6) δ[ppm]: −0.008 (0.80), 0.008 (0.72), 1.175 (0.65), 1.192 (0.78), 1.235 (2.38), 1.395 (4.05), 1.406 (0.88), 1.477 (0.72), 1.496 (1.12), 1.512 (1.51), 1.525 (1.58), 1.540 (1.34), 1.553 (0.93), 1.572 (0.46), 1.808 (1.37), 1.820 (1.91), 1.831 (1.83), 1.842 (1.54), 1.853 (1.50), 1.909 (0.89), 1.988 (0.76), 2.086 (2.68), 2.100 (4.49), 2.107 (4.86), 2.116 (4.43), 2.128 (2.41), 2.560 (3.08), 2.574 (2.23), 2.587 (2.34), 2.602 (1.96), 2.635 (1.94), 2.646 (3.14), 2.656 (2.27), 2.676 (1.29), 2.686 (1.41), 2.698 (0.88), 3.365 (2.96), 3.451 (0.75), 3.463 (0.96), 3.475 (1.00), 3.492 (0.94), 3.504 (0.77), 3.515 (0.42), 3.656 (0.43), 3.667 (0.74), 3.679 (0.85), 3.690 (0.41), 3.699 (0.83), 3.713 (0.61), 4.377 (0.62), 4.490 (3.41), 4.503 (9.30), 4.514 (3.22), 4.768 (0.61), 4.845 (0.78), 4.886 (13.41), 4.931 (0.74), 7.279 (15.72), 7.284 (16.00), 7.299 (0.60), 7.303 (0.53), 7.347 (2.08), 7.352 (2.18), 7.414 (0.50), 7.419 (0.52), 7.451 (1.08), 7.533 (3.64), 7.538 (6.48), 7.543 (3.88), 11.356 (0.56), 13.281 (0.55).

Intermediate 137

(5RS)-3-Oxo-2-{[6-(trifluoromethyl)pyridin-3-yl]methyl}-2,3,5,6,7,8-hexahydro[1,2,4]triazolo[4,3-a]pyridine-5-carboxylic Acid:Trifluoroacetic Acid (Racemate)

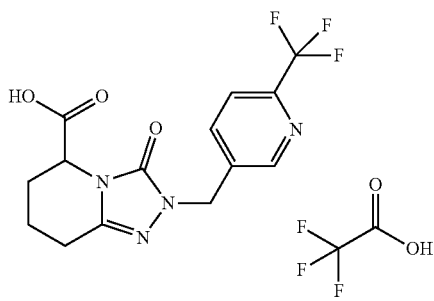 [SMILES: O=C(O)C1CCCc2nn(Cc3ccc(C(F)(F)F)nc3)c(=O)n21 ; O=C(O)C(F)(F)F]

tert-Butyl (5RS)-3-oxo-2-{[6-(trifluoromethyl)pyridin-3-yl]methyl}-2,3,5,6,7,8-hexahydro[1,2,4]triazolo[4,3-a]pyridine-5-carboxylate (racemate) (364 mg, 913 µmol) was dissolved in dichloromethane (10 ml), and trifluoroacetic acid (1.1 ml, 14 mmol) was added at room temperature. After the reaction mixture had been stirred at room temperature overnight, the solvent was removed under reduced pressure. 465 mg (>100%) of the title compound were obtained.

LC-MS (Method 4): $R_t$=0.58 min; MS (ESIpos): m/z=343 [M+H]$^+$

Intermediate 138

(5RS)-2-(3,4-Difluorobenzyl)-3-oxo-2,3,5,6,7,8-hexahydro[1,2,4]triazolo[4,3-a]pyridine-5-carboxylic Acid Hydrochloride (Racemate)

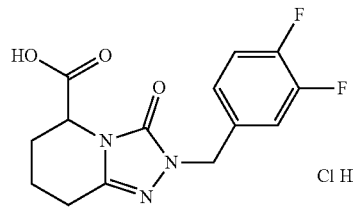

tert-Butyl (5S,R)-2-(3,4-difluorobenzyl)-3-oxo-2,3,5,6,7,8-hexahydro[1,2,4]triazolo[4,3-a]pyridine-5-carboxylate (racemate) (451 mg, 1.23 mmol) was dissolved in 1,4-dioxane (10 ml, 120 mmol), and hydrochloric acid dissolved in 1,4-dioxane (3.1 ml, 4.0 M, 12 mmol) was added. The reaction mixture was stirred at room temperature for 65 h and at 50° C. overnight. Hydrochloric acid dissolved in 1,4-dioxane (3.1 ml, 4.0 M, 12 mmol) was added again, and the mixture was stirred at room temperature for 1 h. The solvent was removed under reduced pressure, and 420 mg (98% of theory) of the title compound were obtained.

$^1$H-NMR (400 MHz, DMSO-d6) δ[ppm]: −0.008 (3.02), 0.008 (2.73), 1.393 (1.69), 1.810 (0.44), 2.098 (1.23), 2.107 (1.13), 2.327 (0.53), 2.562 (0.67), 2.575 (0.60), 2.589 (0.48), 2.621 (0.48), 2.631 (0.77), 2.642 (0.55), 2.670 (0.77), 3.568 (16.00), 4.472 (0.85), 4.484 (1.55), 4.496 (0.75), 4.849 (4.79), 7.101 (0.55), 7.236 (0.48), 7.265 (0.57), 7.285 (0.50), 7.370 (0.55), 7.392 (1.04), 7.398 (0.62), 7.413 (0.59), 7.419 (1.09), 7.440 (0.52).

Intermediate 139

(5RS)-2-(3-Chloro-4-fluorobenzyl)-3-oxo-2,3,5,6,7,8-hexahydro[1,2,4]triazolo[4,3-a]pyridine-5-carboxylic Acid Hydrochloride (Racemate)

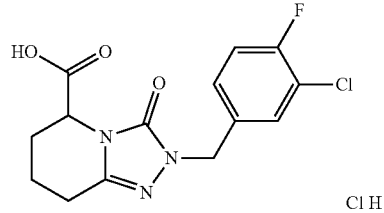 [SMILES: O=C(O)C1CCCc2nn(Cc3ccc(F)c(Cl)c3)c(=O)n21 ; "Cl H"]

tert-Butyl (5RS)-2-(3-chloro-4-fluorobenzyl)-3-oxo-2,3,5,6,7,8-hexahydro[1,2,4]triazolo[4,3-a]pyridine-5-carboxylate (racemate) (391 mg, 1.02 mmol) was dissolved in 1,4-dioxane (10 ml, 120 mmol), and hydrochloric acid dissolved in 1,4-dioxane (2.6 ml, 4.0 M, 10 mmol) was added. The reaction mixture was stirred at room temperature for 65 h and at 50° C. for 3 h. Hydrochloric acid dissolved in 1,4-dioxane (1.3 ml, 4.0 M, 5 mmol) was added again, and the mixture was stirred at 50° C. overnight. The solvent was removed under reduced pressure, and 350 mg (94% of theory) of the title compound were obtained.

$^1$H-NMR (400 MHz, DMSO-d6) δ [ppm]: −0.008 (1.11), 0.008 (1.07), 1.391 (4.37), 1.476 (0.51), 1.492 (0.77), 1.510 (1.08), 1.523 (1.11), 1.538 (0.96), 1.551 (0.66), 1.799 (0.95), 1.812 (1.39), 1.822 (1.40), 1.833 (1.20), 1.844 (1.17), 1.909 (1.18), 2.090 (3.55), 2.097 (3.78), 2.106 (3.58), 2.118 (1.94), 2.519 (1.90), 2.561 (1.92), 2.574 (1.91), 2.589 (1.51), 2.620 (1.53), 2.633 (2.43), 2.643 (1.77), 2.662 (0.94), 2.672 (1.24), 2.685 (0.72), 3.390 (0.80), 3.484 (0.41), 3.492 (0.65), 3.502 (0.60), 3.593 (0.97), 3.671 (0.58), 3.681 (0.64), 3.700 (0.63), 3.709 (0.46), 3.733 (0.41), 3.831 (0.41), 3.840 (0.70), 3.860 (0.72), 4.020 (0.56), 4.189 (0.69), 4.210 (0.69), 4.323 (0.51), 4.329 (0.91), 4.472 (2.61), 4.484 (4.91), 4.496 (2.54), 4.767 (0.52), 4.852 (16.00), 6.348 (0.77), 7.239 (1.31), 7.245 (1.45), 7.251 (1.51), 7.256 (1.74), 7.260 (2.09), 7.266 (2.12), 7.272 (1.95), 7.278 (1.93), 7.368 (3.87), 7.377 (0.46), 7.391 (4.96), 7.413 (2.96), 7.431 (2.61), 7.436 (2.49), 7.448 (2.69), 7.454 (2.57), 8.133 (0.53).

Intermediate 140

(5RS)-2-[(2-Methoxypyridin-4-yl)methyl]-3-oxo-2,3,5,6,7,8-hexahydro[1,2,4]triazolo[4,3-a]pyridine-5-carboxylic Acid Hydrochloride (Racemate)

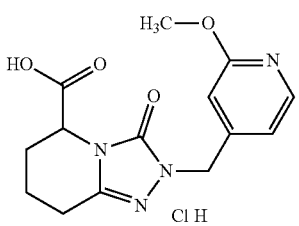

tert-Butyl (5RS)-2-[(2-methoxypyridin-4-yl)methyl]-3-oxo-2,3,5,6,7,8-hexahydro[1,2,4]triazolo[4,3-a]pyridine-5-carboxylate (racemate) (144 mg, 400 μmol) was dissolved in 1,4-dioxane (4.0 ml, 47 mmol), and hydrochloric acid dissolved in 1,4-dioxane (1000 μl, 4.0 M, 4.0 mmol) was added. The reaction mixture was stirred at room temperature for 65 h and at 50° C. overnight. The solvent was removed under reduced pressure, and 165 mg (>100%) of the title compound were obtained.

$^1$H-NMR (400 MHz, DMSO-d6): d [ppm]=1.46-1.60 (m, 2H), 1.79-1.89 (m, 2H), 2.05-2.15 (m, 2H), 3.83 (s, 3H) 4.49 (d, 1H), 4.85 (d, 2H), 6.59 (s, 1H), 6.82 (d, 1H), 8.10 (d, 1H). 1.53 (s, 2H), 1.83 (s, 2H), 2.11 (br s, 5H), 2.63-2.71 (m, 5H), 3.83 (s, 3H), 4.49 (d, 2H), 4.68 (s, 1H), 4.66-4.70 (m, 1H), 4.85 (d, 2H), 6.04 (s, 1H), 6.59 (s, 1H), 6.82 (d, 1H), 7.32 (s, 1H), 8.10 (d, 1H).

Intermediate 141

(5RS)-2-(3-Chloro-4-methoxybenzyl)-3-oxo-2,3,5,6,7,8-hexahydro[1,2,4]triazolo[4,3-a]pyridine-5-carboxylic Acid:Trifluoroacetic Acid (Racemate)

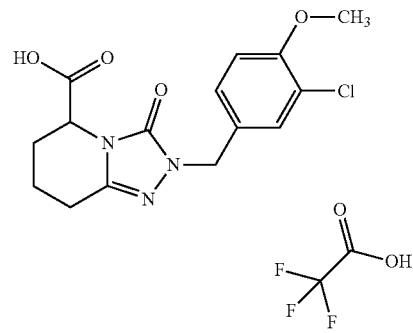 [SMILES: COc1ccc(Cn2nc3n(c2=O)C(C(=O)O)CCC3)cc1Cl ; O=C(O)C(F)(F)F]

tert-Butyl (5RS)-2-(3-chloro-4-methoxybenzyl)-3-oxo-2,3,5,6,7,8-hexahydro[1,2,4]triazolo[4,3-a]pyridine-5-carboxylate (racemate) (365 mg, 925 μmol) was dissolved in dichloromethane (20 ml), and trifluoroacetic acid (710 μl, 9.3 mmol) was added at room temperature. After the reaction mixture had been stirred at room temperature for 48 h, the solvent was removed under reduced pressure. 454 mg (>100%) of the title compound were obtained.

LC-MS (Method 4): $R_t$=0.66 min; MS (ESIpos): m/z=338 [M+H]$^+$ $^1$H-NMR (400 MHz, DMSO-d6) δ[ppm]: −0.008 (0.90), 0.008 (0.79), 1.111 (1.03), 1.157 (0.90), 1.175 (1.82), 1.193 (0.92), 1.228 (0.41), 1.391 (1.94), 1.474 (0.43), 1.488 (0.67), 1.508 (0.88), 1.522 (0.94), 1.535 (2.44), 1.550 (0.56), 1.790 (0.81), 1.802 (1.21), 1.813 (1.21), 1.824 (1.06), 1.835 (1.01), 1.848 (0.68), 1.988 (3.28), 2.067 (1.72), 2.080 (3.10), 2.087 (3.19), 2.096 (2.97), 2.108 (1.57), 2.520 (1.36), 2.563 (1.66), 2.577 (1.26), 2.609 (1.33), 2.620 (2.11), 2.631 (1.48), 2.650 (0.75), 2.661 (1.03), 2.673 (0.66), 2.690 (0.53), 2.731 (2.17), 2.890 (2.79), 4.021 (0.77), 4.039 (0.76), 4.458 (2.30), 4.470 (4.46), 4.482 (2.24), 4.771 (16.00), 5.753 (1.45), 7.094 (4.56), 7.115 (6.97), 7.185 (3.46), 7.190 (3.61), 7.206 (2.20), 7.211 (2.39), 7.298 (5.41), 7.303 (4.82).

Intermediate 142

(5RS)-2-(3-Fluorobenzyl)-3-oxo-2,3,5,6,7,8-hexahydro[1,2,4]triazolo[4,3-a]pyridine-5-carboxylic Acid Hydrochloride (Racemate)

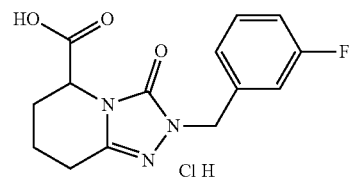

tert-Butyl (5RS)-2-(3-fluorobenzyl)-3-oxo-2,3,5,6,7,8-hexahydro[1,2,4]triazolo[4,3-a]pyridine-5-carboxylate (racemate) (150 mg, 432 μmol) was dissolved in 1,4-dioxane (4.3 ml, 51 mmol), and hydrochloric acid dissolved in 1,4-dioxane (1.1 ml, 4.0 M, 4.3 mmol) was added. The reaction mixture was stirred at room temperature for 65 h. Hydrochloric acid dissolved in 1,4-dioxane (1.1 ml, 4.0 M, 4.3 mmol) was added again, and the mixture was stirred at 50° C. overnight. The solvent was removed under reduced pressure, and 165 mg (89% purity, >100%) of the title compound were obtained.

LC-MS (Method 4): $R_t$=0.59 min; MS (ESIpos): m/z=292 [M+H]$^+$

Intermediate 143

(5RS)-2-(3-Methoxybenzyl)-3-oxo-2,3,5,6,7,8-hexahydro[1,2,4]triazolo[4,3-a]pyridine-5-carboxylic Acid:Trifluoroacetic Acid (Racemate)

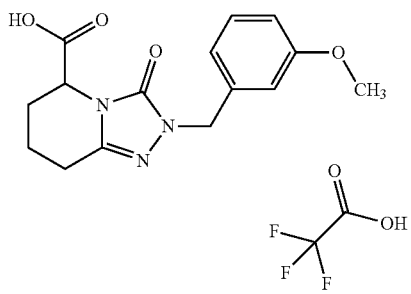 [SMILES: COc1cccc(Cn2nc3n(c2=O)C(C(=O)O)CCC3)c1 ; O=C(O)C(F)(F)F]

tert-Butyl (5RS)-2-(3-methoxybenzyl)-3-oxo-2,3,5,6,7,8-hexahydro[1,2,4]triazolo[4,3-a]pyridine-5-carboxylate (racemate) (340 mg, 947 µmol) was dissolved in dichloromethane (20 ml), and trifluoroacetic acid (730 µl, 9.5 mmol) was added at room temperature. After the reaction mixture had been stirred at room temperature overnight, the solvent was removed under reduced pressure. 435 mg (>100%) of the title compound were obtained.

LC-MS (Method 3): $R_t$=1.04 min; MS (ESIpos): m/z=304 [M+H]$^+$ $^1$H-NMR (400 MHz, DMSO-d6) δ [ppm]: −0.008 (1.85), 0.008 (1.73), 1.111 (1.34), 1.399 (3.15), 1.482 (0.86), 1.515 (1.77), 1.534 (5.41), 1.544 (1.65), 1.557 (1.10), 1.576 (0.53), 1.797 (1.69), 1.810 (2.41), 1.820 (2.43), 1.831 (2.06), 1.843 (1.97), 1.855 (1.32), 1.988 (0.50), 2.047 (0.43), 2.075 (3.45), 2.088 (6.07), 2.095 (6.31), 2.105 (5.87), 2.117 (3.12), 2.328 (0.42), 2.524 (1.98), 2.569 (3.23), 2.583 (2.50), 2.613 (2.67), 2.626 (4.07), 2.636 (2.95), 2.655 (1.45), 2.666 (2.17), 2.678 (1.24), 3.696 (0.64), 3.705 (0.58), 3.750 (0.42), 3.765 (1.85), 4.466 (4.47), 4.477 (8.57), 4.490 (4.32), 4.759 (1.51), 4.799 (16.00), 4.805 (15.56), 4.845 (1.43), 5.398 (0.68), 5.753 (4.67), 6.789 (14.05), 6.809 (6.64), 6.824 (4.19), 6.830 (3.47), 6.845 (4.90), 6.851 (4.14), 7.220 (6.34), 7.240 (8.92), 7.259 (4.69).

Intermediate 144

(5RS)-3-Oxo-2-[3-(trifluoromethyl)benzyl]-2,3,5,6,7,8-hexahydro[1,2,4]triazolo[4,3-a]pyridine-5-carboxylic Acid:Trifluoroacetic Acid (Racemate)

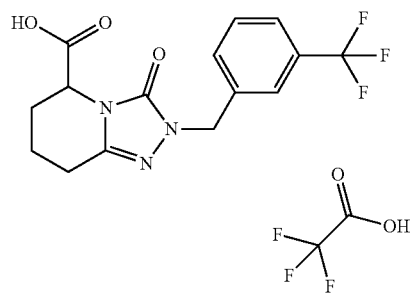 [SMILES: O=C(O)C1CCCc2nn(Cc3cccc(C(F)(F)F)c3)c(=O)n21 ; O=C(O)C(F)(F)F]

tert-Butyl (5RS)-3-oxo-2-[3-(trifluoromethyl)benzyl]-2,3,5,6,7,8-hexahydro[1,2,4]triazolo[4,3-a]pyridine-5-carboxylate (racemate) (388 mg, 975 µmol) was dissolved in dichloromethane (20 ml), and trifluoroacetic acid (750 µl, 9.8 mmol) was added at room temperature. After the reaction mixture had been stirred at room temperature overnight, trifluoroacetic acid (750 µl, 9.8 mmol) was added again. After stirring at 40° C. for 2 h, the solvent was removed under reduced pressure. 534 mg (>100%) of the title compound were obtained.

LC-MS (Method 3): $R_t$=1.34 min; MS (ESIpos): m/z=342 [M+H]$^+$ $^1$H-NMR (400 MHz, DMSO-d6) δ[ppm]: 1.110 (0.81), 1.385 (1.82), 1.535 (3.66), 1.815 (1.57), 2.100 (4.20), 2.328 (0.90), 2.562 (2.17), 2.575 (2.21), 2.590 (1.50), 2.634 (2.53), 2.674 (1.98), 4.482 (2.72), 4.493 (5.55), 4.506 (2.60), 4.958 (16.00), 7.525 (2.56), 7.544 (4.75), 7.569 (2.81), 7.588 (5.17), 7.615 (6.53), 7.649 (4.29), 7.668 (2.58).

Intermediate 145

(5RS)-2-[(1-Methyl-1H-pyrazol-3-yl)methyl]-3-oxo-2,3,5,6,7,8-hexahydro[1,2,4]triazolo[4,3-a]pyridine-5-carboxylic Acid:Trifluoroacetic Acid (Racemate)

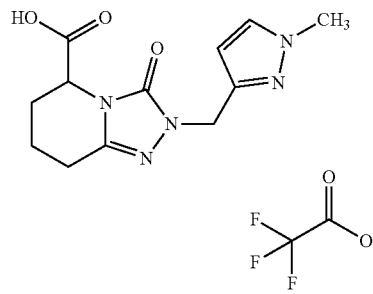

tert-Butyl (5RS)-2-[(1-methyl-1H-pyrazol-3-yl)methyl]-3-oxo-2,3,5,6,7,8-hexahydro[1,2,4]triazolo[4,3-a]pyridine-5-carboxylate (racemate) (150 mg, 450 µmol) was dissolved in dichloromethane (3.0 ml), and trifluoroacetic acid (350 µl, 4.5 mmol) was added at room temperature. The reaction mixture was stirred at room temperature overnight and then trifluoroacetic acid (350 µl, 4.5 mmol) was added again.

After the reaction mixture had been stirred at room temperature overnight, the solvent was removed under reduced pressure. 170 mg (97% of theory) of the title compound were obtained.

LC-MS (Method 4): $R_t$=0.36 min; MS (ESIpos): m/z=278 [M+H]$^+$

Intermediate 146

(5RS)-3-Oxo-2-(5,6,7,8-tetrahydronaphthalen-2-ylmethyl)-2,3,5,6,7,8-hexahydro[1,2,4]triazolo[4,3-a]pyridine-5-carboxylic Acid:Trifluoroacetic Acid (Racemate)

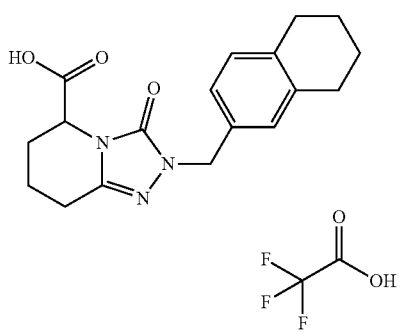 [SMILES: O=C(O)C1CCCc2nn(Cc3ccc4c(c3)CCCC4)c(=O)n21 ; O=C(O)C(F)(F)F]

tert-Butyl (5RS)-3-oxo-2-(5,6,7,8-tetrahydronaphthalen-2-ylmethyl)-2,3,5,6,7,8-hexahydro[1,2,4]triazolo[4,3-a]pyridine-5-carboxylate (racemate) (280 mg, 730 µmol) was dissolved in dichloromethane (5.0 ml), and trifluoroacetic acid (2.0 ml, 26 mmol) was added at room temperature. After the reaction mixture had been stirred at room temperature overnight, the solvent was removed under reduced pressure. 320 mg (94% of theory) of the title compound were obtained.

LC-MS (Method 4): $R_t$=0.81 min; MS (ESIpos): m/z=328 [M+H]$^+$

Intermediate 147

(5RS)-2-[(5-Methyl-1,2-oxazol-3-yl)methyl]-3-oxo-2,3,5,6,7,8-hexahydro[1,2,4]triazolo[4,3-a]pyridine-5-carboxylic Acid (Racemate)

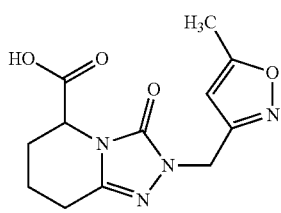 [SMILES: Cc1cc(Cn2nc3n(c2=O)C(C(=O)O)CCC3)no1]

Methyl (5RS)-2-[(5-methyl-1,2-oxazol-3-yl)methyl]-3-oxo-2,3,5,6,7,8-hexahydro[1,2,4]triazolo[4,3-a]pyridine-5-carboxylate (racemate) (412 mg, 1.41 mmol) was initially charged in THF (14 ml), and lithium hydroxide (169 mg, 7.05 mmol) dissolved in water (4.0 ml) was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 136 mg (83% purity, 29% of theory) of the title compound were obtained.

LC-MS (Method 3): $R_t$=0.67 min; MS (ESIpos): m/z=279 [M+H]$^+$ $^1$H-NMR (400 MHz, DMSO-d6) δ [ppm]: 1.157 (1.10), 1.174 (2.26), 1.181 (0.48), 1.192 (1.13), 1.356 (2.56), 1.405 (0.76), 1.499 (0.43), 1.513 (0.60), 1.526 (0.61), 1.541 (0.53), 1.797 (0.52), 1.809 (0.79), 1.820 (0.78), 1.831 (0.66), 1.842 (0.64), 1.908 (2.86), 1.988 (4.00), 2.083 (1.98), 2.089 (2.11), 2.099 (2.04), 2.111 (1.09), 2.201 (1.26), 2.369 (16.00), 2.561 (1.03), 2.573 (1.03), 2.587 (0.81), 2.617 (0.84), 2.629 (1.39), 2.639 (0.93), 2.659 (0.50), 2.670 (0.78), 4.020 (0.97), 4.038 (0.95), 4.426 (0.98), 4.441 (1.01), 4.450 (1.39), 4.462 (2.65), 4.474 (1.38), 4.807 (0.40), 4.847 (6.28), 4.852 (6.39), 4.892 (0.41), 6.069 (3.43), 6.180 (0.58).

Intermediate 148

(5RS)-3-Oxo-2-(pyridin-3-ylmethyl)-2,3,5,6,7,8-hexahydro[1,2,4]triazolo[4,3-a]pyridine-5-carboxylic Acid:Trifluoroacetic Acid (Racemate)

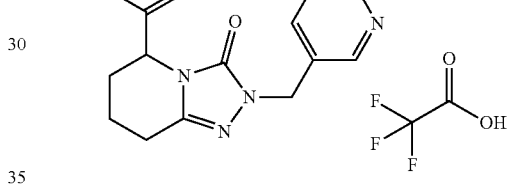

tert-Butyl (5RS)-3-oxo-2-(pyridin-3-ylmethyl)-2,3,5,6,7,8-hexahydro[1,2,4]triazolo[4,3-a]pyridine-5-carboxylate (racemate) (366 mg, 1.11 mmol) was dissolved in dichloromethane (10 ml), and trifluoroacetic acid (1.7 ml, 22 mmol) was added at room temperature. After the reaction mixture had been stirred at room temperature overnight, the solvent was removed under reduced pressure. 442 mg (83% purity, 29% of theory) of the title compound were obtained.

LC-MS (Method 9): $R_t$=3.31 min; MS (ESIpos): m/z=275 [M+H]$^+$

Intermediate 149

(5RS)-3-Oxo-2-(2,4,5-trifluorobenzyl)-2,3,5,6,7,8-hexahydro[1,2,4]triazolo[4,3-a]pyridine-5-carboxylic Acid:Trifluoroacetic Acid (Racemate)

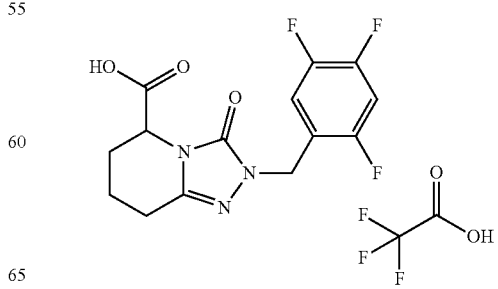

tert-Butyl (5RS)-3-oxo-2-(2,4,5-trifluorobenzyl)-2,3,5,6,7,8-hexahydro[1,2,4]triazolo[4,3-a]pyridine-5-carboxylate (racemate) (390 mg, 1.02 mmol) was dissolved in dichloromethane (8 ml), and trifluoroacetic acid (3.3 ml, 43 mmol) was added at room temperature. After the reaction mixture had been stirred at room temperature overnight, the solvent was removed under reduced pressure. 445 mg (95% of theory) of the title compound were obtained.

LC-MS (Method 3): $R_t$=1.17 min; MS (ESIpos): m/z=328 [M+H]$^+$

Intermediate 150

(5RS)-2-[(2-Chloropyridin-4-yl)methyl]-3-oxo-2,3,5,6,7,8-hexahydro[1,2,4]triazolo[4,3-a]pyridine-5-carboxylic Acid:Trifluoroacetic Acid (Racemate)

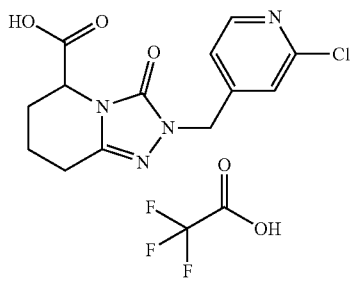

tert-Butyl (5RS)-2-[(2-chloropyridin-4-yl)methyl]-3-oxo-2,3,5,6,7,8-hexahydro[1,2,4]triazolo[4,3-a]pyridine-5-carboxylate (racemate) (490 mg, 1.34 mmol) was dissolved in dichloromethane (12 ml, 190 mmol), and trifluoroacetic acid (1.9 ml, 25 mmol) was added at room temperature. After the reaction mixture had been stirred at room temperature overnight, the solvent was removed under reduced pressure. 581 mg (94% purity, 96% of theory) of the title compound were obtained.

LC-MS (Method 4): $R_t$=0.50 min; MS (ESIpos): m/z=309 [M+H]

Intermediate 151

(5RS)-2-[(5-Chloro-2-thienyl)methyl]-3-oxo-2,3,5,6,7,8-hexahydro[1,2,4]triazolo[4,3-a]pyridine-5-carboxylic Acid:Trifluoroacetic Acid (Racemate)

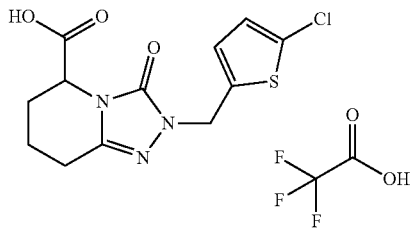 [SMILES: O=C(O)C1CCCc2nn(Cc3ccc(Cl)s3)c(=O)n21 ; O=C(O)C(F)(F)F]

tert-Butyl (5RS)-2-[(5-chloro-2-thienyl)methyl]-3-oxo-2,3,5,6,7,8-hexahydro[1,2,4]triazolo[4,3-a]pyridine-5-carboxylate (racemate) (414 mg, 1.12 mmol) was dissolved in dichloromethane (10 ml, 160 mmol), and trifluoroacetic acid (1.7 ml, 22 mmol) was added at room temperature. After the reaction mixture had been stirred at room temperature for 5 hours, the solvent was removed under reduced pressure. 516 mg (>100%) of the title compound were obtained.

LC-MS (Method 3): $R_t$=1.16 min; MS (ESIpos): m/z=314 [M+H]$^+$ $^1$H-NMR (400 MHz, DMSO-d6) δ[ppm]: 1.110 (1.14), 1.384 (7.34), 1.535 (2.17), 1.568 (1.23), 1.802 (2.23), 1.814 (2.29), 1.824 (1.91), 2.058 (3.54), 2.071 (5.97), 2.081 (5.66), 2.328 (1.63), 2.366 (0.97), 2.565 (2.91), 2.578 (2.97), 2.592 (2.34), 2.623 (2.46), 2.635 (3.91), 2.646 (2.66), 2.675 (2.77), 2.710 (1.09), 4.438 (5.80), 4.451 (9.29), 4.463 (5.60), 4.555 (2.31), 4.906 (1.54), 4.945 (15.09), 4.951 (16.00), 4.986 (2.40), 5.560 (1.09), 6.916 (7.37), 6.926 (10.03), 6.973 (13.74), 6.983 (9.74), 7.020 (0.63), 7.079 (0.63).

Intermediate 152

(5RS)-2-[(4-Methyl-1,2,5-oxadiazol-3-yl)methyl]-3-oxo-2,3,5,6,7,8-hexahydro[1,2,4]triazolo[4,3-a]pyridine-5-carboxylic Acid (Racemate)

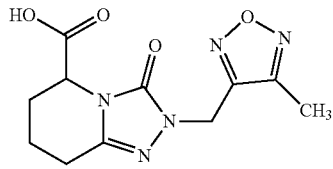 [SMILES: Cc1nonc1Cn1nc2n(c1=O)C(C(=O)O)CCC2]

Methyl (5RS)-2-[(4-methyl-1,2,5-oxadiazol-3-yl)methyl]-3-oxo-2,3,5,6,7,8-hexahydro[1,2,4]triazolo[4,3-a]pyridine-5-carboxylate (racemate) (281 mg, 958 μmol) was initially charged in THF (5.0 ml), and lithium hydroxide (115 mg, 4.79 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 91.0 mg (88% purity, 30% of theory) of the title compound were obtained.

LC-MS (Method 1): $R_t$=0.61 min; MS (ESIpos): m/z=280 [M+H]$^+$

Intermediate 153

(5RS)-2-(2-Methylbenzyl)-3-oxo-2,3,5,6,7,8-hexahydro[1,2,4]triazolo[4,3-a]pyridine-5-carboxylic Acid (Racemate)

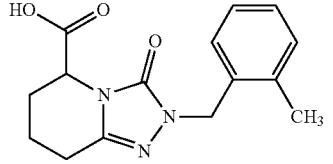 [SMILES: Cc1ccccc1Cn1nc2n(c1=O)C(C(=O)O)CCC2]

Methyl (5RS)-2-(2-methylbenzyl)-3-oxo-2,3,5,6,7,8-hexahydro[1,2,4]triazolo[4,3-a]pyridine-5-carboxylate (racemate) (196 mg, 650 μmol) was initially charged in THF (5.0 ml), and lithium hydroxide (77.9 mg, 3.25 mmol) dissolved in water was added. After stirring at room temperature overnight, the reaction mixture was concentrated

Intermediate 154

(5RS)-2-[4-Fluoro-3-(trifluoromethyl)benzyl]-3-oxo-2,3,5,6,7,8-hexahydro[1,2,4]triazolo[4,3-a]pyridine-5-carboxylic Acid (Racemate)

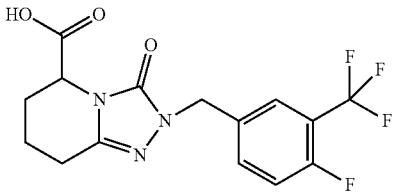 [SMILES: O=C(O)C1CCCc2nn(Cc3ccc(F)c(C(F)(F)F)c3)c(=O)n21]

Methyl (5RS)-2-[4-fluoro-3-(trifluoromethyl)benzyl]-3-oxo-2,3,5,6,7,8-hexahydro[1,2,4]triazolo[4,3-a]pyridine-5-carboxylate (racemate) (569 mg, 1.52 mmol) was initially charged in THF (8.0 ml), and lithium hydroxide (183 mg, 7.62 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 251 mg (94% purity, 43% of theory) of the title compound were obtained.

LC-MS (Method 4): $R_t$=0.77 min; MS (ESIpos): m/z=360 [M+H]$^+$ $^1$H-NMR (400 MHz, DMSO-d6) δ[ppm]: −0.008 (2.89), 0.008 (2.76), 1.157 (2.61), 1.170 (1.52), 1.175 (5.50), 1.193 (2.73), 1.559 (1.10), 1.748 (1.40), 1.905 (1.45), 1.948 (1.17), 1.988 (10.96), 2.129 (1.67), 2.159 (1.21), 2.328 (0.45), 2.458 (0.96), 2.473 (1.31), 2.595 (2.13), 2.634 (1.08), 2.670 (0.46), 3.314 (0.58), 4.003 (0.74), 4.021 (2.44), 4.039 (2.45), 4.056 (0.80), 4.319 (2.46), 4.328 (2.44), 4.549 (0.88), 4.918 (16.00), 7.458 (2.32), 7.480 (3.39), 7.506 (3.05), 7.587 (1.95), 7.600 (2.29), 7.678 (3.14), 7.696 (3.13).

Intermediate 155

(5RS)-2-[2,5-Bis(trifluoromethyl)benzyl]-3-oxo-2,3,5,6,7,8-hexahydro[1,2,4]triazolo[4,3-a]pyridine-5-carboxylic Acid (Racemate)

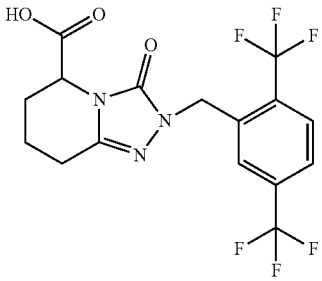 [SMILES: O=C(O)C1CCCc2nn(Cc3cc(C(F)(F)F)ccc3C(F)(F)F)c(=O)n21]

Methyl (5RS)-2-[2,5-bis(trifluoromethyl)benzyl]-3-oxo-2,3,5,6,7,8-hexahydro[1,2,4]triazolo[4,3-a]pyridine-5-carboxylate (racemate) (634 mg, 1.50 mmol) was initially charged in THF (8.0 ml), and lithium hydroxide (179 mg, 7.48 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 242 mg (91% purity, 36% of theory) of the title compound were obtained.

LC-MS (Method 4): $R_t$=0.86 min; MS (ESIpos): m/z=410 [M+H]$^+$ $^1$H-NMR (400 MHz, DMSO-d6) δ[ppm]: −0.149 (0.54), −0.008 (4.55), 0.008 (3.70), 0.146 (0.50), 1.170 (2.38), 1.234 (0.54), 1.573 (1.56), 1.755 (1.93), 1.949 (1.55), 1.988 (2.59), 2.153 (2.28), 2.188 (1.65), 2.328 (1.13), 2.367 (0.71), 2.611 (2.68), 2.666 (1.51), 2.710 (0.66), 3.313 (2.26), 3.405 (1.49), 4.038 (0.40), 4.324 (2.78), 4.746 (1.49), 4.911 (2.40), 5.082 (16.00), 7.649 (8.11), 7.912 (3.70), 7.932 (6.12), 8.013 (7.38), 8.033 (4.99), 8.065 (1.22), 8.098 (0.71).

Intermediate 156

(5RS)-2-[(6-Methylpyridin-3-yl)methyl]-3-oxo-2,3,5,6,7,8-hexahydro[1,2,4]triazolo[4,3-a]pyridine-5-carboxylic Acid (Racemate)

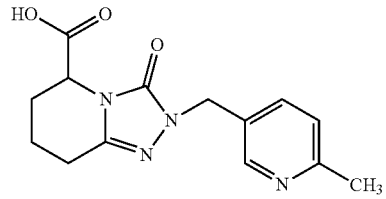 [SMILES: Cc1ccc(Cn2nc3n(c2=O)C(C(=O)O)CCC3)cn1]

Methyl (5RS)-2-[(6-methylpyridin-3-yl)methyl]-3-oxo-2,3,5,6,7,8-hexahydro[1,2,4]triazolo[4,3-a]pyridine-5-carboxylate (racemate) (231 mg, 764 µmol) was initially charged in THF (5.0 ml), and lithium hydroxide (91.5 mg, 3.82 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The aqueous phase was concentrated and suspended with tetrahydrofuran/ethanol (1/1). The solids were removed and the filtrate was concentrated to give the product. 262 mg (>100%) of the title compound were obtained.

LC-MS (Method 4): $R_t$=0.19 min; MS (ESIpos): m/z=288 [M]+

$^1$H-NMR (400 MHz, DMSO-d6) δ[ppm]: −0.149 (0.62), −0.008 (5.32), 0.008 (4.64), 0.146 (0.68), 1.038 (7.69), 1.055 (16.00), 1.072 (8.00), 1.356 (2.60), 1.743 (0.97), 1.760 (2.83), 1.776 (0.99), 2.090 (0.88), 2.328 (0.88), 2.366 (0.48), 2.561 (2.65), 2.620 (0.56), 2.670 (0.90), 2.710 (0.48), 3.413 (3.17), 3.431 (8.60), 3.448 (8.67), 3.466 (3.40), 3.585 (1.73), 3.601 (3.05), 3.618 (1.62), 4.465 (0.59), 4.475 (1.11), 4.936 (1.69), 8.492 (0.70).

Intermediate 157

(5RS)-2-[(6-Methoxypyridin-3-yl)methyl]-3-oxo-2,3,5,6,7,8-hexahydro[1,2,4]triazolo[4,3-a]pyridine-5-carboxylic Acid (Racemate)

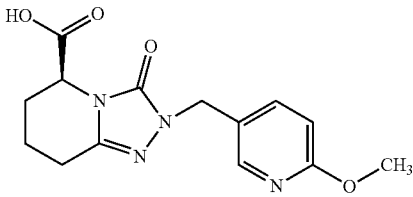 [SMILES: COc1ccc(Cn2nc3n(c2=O)[C@H](C(=O)O)CCC3)cn1]

Methyl (5RS)-2-[(6-methoxypyridin-3-yl)methyl]-3-oxo-2,3,5,6,7,8-hexahydro[1,2,4]triazolo[4,3-a]pyridine-5-carboxylate (racemate) (202 mg, 636 µmol) was initially charged in THF (5.0 ml), and lithium hydroxide (76.1 mg, 3.18 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 45 mg (23% of theory) of the title compound were obtained.

LC-MS (Method 3): $R_t$=0.78 min; MS (ESIpos): m/z=305 [M]$^+$

Intermediate 158

(5RS)-2-[4-Methoxy-3-(trifluoromethyl)benzyl]-3-oxo-2,3,5,6,7,8-hexahydro[1,2,4]triazolo[4,3-a]pyridine-5-carboxylic Acid (Racemate)

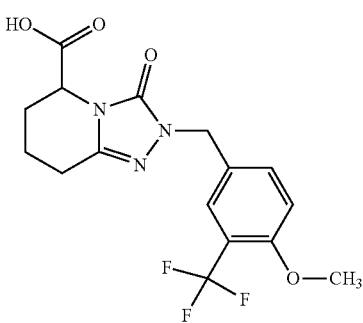 [SMILES: COc1ccc(Cn2nc3n(c2=O)C(C(=O)O)CCC3)cc1C(F)(F)F]

Methyl (5RS)-2-[4-methoxy-3-(trifluoromethyl)benzyl]-3-oxo-2,3,5,6,7,8-hexahydro[1,2,4]triazolo[4,3-a]pyridine-5-carboxylate (racemate) (305 mg, 791 µmol) was initially charged in THF (8.0 ml), and lithium hydroxide (94.8 mg, 3.96 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 151 mg (51% of theory) of the title compound were obtained.

LC-MS (Method 3): $R_t$=1.34 min; MS (ESIpos): m/z=372 [M+H]$^+$ $^1$H-NMR (400 MHz, DMSO-d6) δ [ppm]: −0.008 (1.34), 0.008 (1.63), 1.157 (2.20), 1.175 (4.44), 1.192 (2.26), 1.529 (0.44), 1.785 (0.53), 1.797 (0.50), 1.807 (0.43), 1.819 (0.43), 1.988 (8.02), 2.045 (0.43), 2.079 (1.23), 2.088 (1.19), 2.562 (0.66), 2.598 (0.58), 2.610 (0.95), 2.620 (0.64), 2.650 (0.43), 3.869 (16.00), 4.002 (0.65), 4.020 (1.93), 4.038 (1.92), 4.056 (0.63), 4.419 (0.71), 4.429 (0.98), 4.835 (7.06), 7.223 (1.56), 7.244 (1.81), 7.498 (1.32), 7.520 (4.16).

Intermediate 159

(5RS)-2-[(1-Methyl-1H-benzimidazol-2-yl)methyl]-3-oxo-2,3,5,6,7,8-hexahydro[1,2,4]triazolo[4,3-a]pyridine-5-carboxylic acid (racemate)

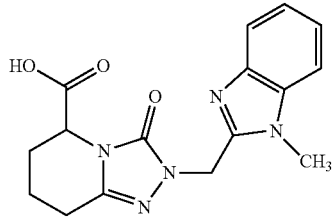 [SMILES: Cn1c(Cn2nc3n(c2=O)C(C(=O)O)CCC3)nc2ccccc21]

Methyl (5RS)-2-[(1-methyl-1H-benzimidazol-2-yl)methyl]-3-oxo-2,3,5,6,7,8-hexahydro[1,2,4]triazolo[4,3-a]pyridine-5-carboxylate (racemate) (137 mg, 401 µmol) was initially charged in THF (3.0 ml), and lithium hydroxide (48.1 mg, 2.01 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 120 mg (91% of theory) of the title compound were obtained.

LC-MS (Method 3): $R_t$=0.60 min; MS (ESIpos): m/z=328 [M+H]$^+$

Intermediate 160

(5RS)-2-[(1-Ethyl-1H-imidazol-2-yl)methyl]-3-oxo-2,3,5,6,7,8-hexahydro[1,2,4]triazolo[4,3-a]pyridine-5-carboxylic Acid (Racemate)

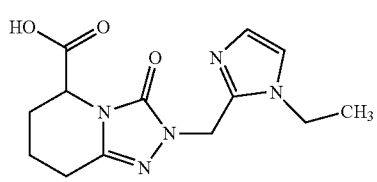 [SMILES: CCn1ccnc1Cn1nc2n(c1=O)C(C(=O)O)CCC2]

Methyl (5RS)-2-[(1-ethyl-1H-imidazol-2-yl)methyl]-3-oxo-2,3,5,6,7,8-hexahydro[1,2,4]triazolo[4,3-a]pyridine-5-carboxylate (racemate) (54.0 mg, 177 µmol) was initially charged in THF (2.0 ml), and lithium hydroxide (21.2 mg, 884 µmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 80.0 mg (60% purity, 93% of theory) of the title compound were obtained.

LC-MS (Method 9): R$_t$=3.44 min; MS (ESIpos): m/z=292 [M+H]$^+$

Intermediate 161

(5RS)-2-[(1-Methyl-1H-indazol-5-yl)methyl]-3-oxo-2,3,5,6,7,8-hexahydro[1,2,4]triazolo[4,3-a]pyridine-5-carboxylic Acid (Racemate)

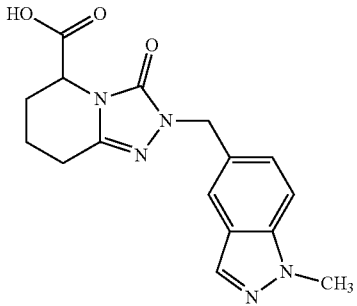 [SMILES: Cn1ncc2cc(Cn3nc4n(c3=O)C(C(=O)O)CCC4)ccc21]

Methyl (5RS)-2-[(1-methyl-1H-indazol-5-yl)methyl]-3-oxo-2,3,5,6,7,8-hexahydro[1,2,4]triazolo[4,3-a]pyridine-5-carboxylate (racemate) (87.0 mg, 98% purity, 250 μmol) was initially charged in THF (2.5 ml), and lithium hydroxide (29.9 mg, 1.25 mmol) dissolved in water was added. After stirring at room temperature overnight, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 67.0 mg (80% of theory) of the title compound were obtained.

LC-MS (Method 3): R$_t$=0.87 min; MS (ESIpos): m/z=328 [M+H]$^+$ $^1$H-NMR (400 MHz, DMSO-d6) δ [ppm]: −0.008 (0.92), 0.008 (0.91), 1.157 (1.12), 1.175 (2.28), 1.192 (1.13), 1.796 (0.45), 1.807 (0.50), 1.908 (0.74), 1.988 (4.27), 2.082 (1.22), 2.327 (0.41), 2.523 (2.15), 2.565 (0.61), 2.596 (0.54), 2.608 (0.89), 2.619 (0.60), 2.648 (0.42), 2.669 (0.50), 4.002 (0.41), 4.021 (16.00), 4.038 (1.11), 4.457 (0.87), 4.468 (1.72), 4.481 (0.89), 4.916 (3.28), 4.921 (3.27), 7.294 (1.26), 7.298 (1.26), 7.316 (1.45), 7.320 (1.49), 7.580 (1.84), 7.608 (2.57), 8.004 (3.39), 13.222 (0.63).

Intermediate 162

(5RS)-3-Oxo-2-({5-[3-(trifluoromethyl)phenyl]-1,2,4-oxadiazol-3-yl}methyl)-2,3,5,6,7,8-hexahydro[1,2,4]triazolo[4,3-a]pyridine-5-carboxylic Acid (Racemate)

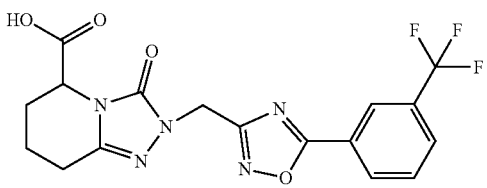 [SMILES: O=C(O)C1CCCc2nn(Cc3noc(-c4cccc(C(F)(F)F)c4)n3)c(=O)n21]

Methyl (5RS)-3-oxo-2-({5-[3-(trifluoromethyl)phenyl]-1,2,4-oxadiazol-3-yl}methyl)-2,3,5,6,7,8-hexahydro[1,2,4]triazolo[4,3-a]pyridine-5-carboxylate (racemate) (640 mg, 1.51 mmol) was initially charged in THF (15 ml), and lithium hydroxide (181 mg, 7.56 mmol) dissolved in water was added. After stirring at room temperature overnight, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 588 mg (88% purity, 84% of theory) of the title compound were obtained.

LC-MS (Method 3): R$_t$=1.42 min; MS (ESIpos): m/z=410 [M+H]$^+$ $^1$H-NMR (400 MHz, DMSO-d6) δ [ppm]: −0.008 (1.41), 0.008 (1.36), 1.094 (1.28), 1.157 (4.33), 1.175 (8.82), 1.193 (4.46), 1.519 (0.93), 1.533 (1.05), 1.546 (1.17), 1.556 (1.03), 1.570 (0.87), 1.582 (0.66), 1.803 (0.93), 1.814 (1.46), 1.825 (1.48), 1.836 (1.29), 1.847 (1.23), 1.861 (0.85), 1.909 (2.18), 1.989 (16.00), 2.084 (2.29), 2.096 (4.23), 2.107 (4.15), 2.120 (2.23), 2.520 (2.12), 2.562 (2.37), 2.577 (1.87), 2.589 (1.95), 2.604 (1.50), 2.631 (1.58), 2.642 (2.66), 2.654 (1.73), 2.673 (1.07), 2.684 (1.24), 2.697 (0.66), 3.396 (0.92), 4.003 (1.25), 4.021 (3.77), 4.039 (3.73), 4.056 (1.23), 4.485 (2.76), 4.498 (5.49), 4.509 (2.71), 4.654 (0.81), 4.936 (1.26), 5.001 (1.44), 5.059 (3.19), 5.099 (10.70), 5.126 (10.72), 5.166 (3.27), 7.875 (2.15), 7.894 (4.91), 7.914 (3.01), 8.100 (3.54), 8.120 (3.11), 8.327 (5.27), 8.391 (3.58), 8.411 (3.46), 13.270 (1.29).

Intermediate 163

(5RS)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic Acid (Racemate)

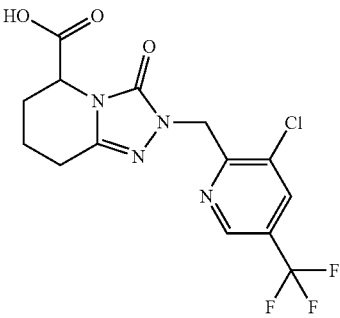 [SMILES: O=C(O)C1CCCc2nn(Cc3ncc(C(F)(F)F)cc3Cl)c(=O)n21]

Methyl (5RS)-2-{[3-chloro-5-(trifluoromethyl)pyridin-2-yl]methyl}-3-oxo-2,3,5,6,7,8-hexahydro[1,2,4]triazolo[4,3-a]pyridine-5-carboxylate (racemate) (293 mg, 750 μmol) was initially charged in THF (6.0 ml), and lithium hydroxide (89.8 mg, 3.75 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 243 mg (86% of theory) of the title compound were obtained.

LC-MS (Method 3): R$_t$=1.16 min; MS (ESIpos): m/z=377 [M+H]$^+$ $^1$H-NMR (400 MHz, DMSO-d6) δ[ppm]: 1.175 (0.73), 1.988 (1.31), 2.079 (0.50), 2.091 (0.90), 2.101 (0.88), 2.107 (0.79), 2.558 (0.47), 2.610 (0.60), 2.621 (0.40), 4.466 (0.65), 4.479 (1.30), 4.491 (0.64), 5.151 (2.36), 5.155 (2.31), 5.753 (16.00), 8.487 (1.31), 8.491 (1.32), 8.903 (1.28), 8.905 (1.29).

Intermediate 164

(5RS)-2-[3-Fluoro-4-(trifluoromethoxy)benzyl]-3-oxo-2,3,5,6,7,8-hexahydro[1,2,4]triazolo[4,3-a]pyridine-5-carboxylic Acid (Racemate)

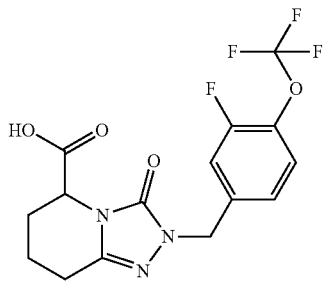 [SMILES: O=C(O)C1CCCc2nn(Cc3ccc(OC(F)(F)F)c(F)c3)c(=O)n21]

Methyl (5RS)-2-[3-fluoro-4-(trifluoromethoxy)benzyl]-3-oxo-2,3,5,6,7,8-hexahydro[1,2,4]triazolo[4,3-a]pyridine-5-carboxylate (racemate) (263 mg, 676 µmol) was initially charged in THF (5.0 ml), and lithium hydroxide (80.9 mg, 3.38 mmol) dissolved in water was added. After stirring at room temperature for 72 hours, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 180 mg (71% of theory) of the title compound were obtained.

LC-MS (Method 3): $R_t$=1.43 min; MS (ESIpos): m/z=376 [M+H]

Intermediate 165

(5RS)-2-[3-Chloro-4-(trifluoromethoxy)benzyl]-3-oxo-2,3,5,6,7,8-hexahydro[1,2,4]triazolo[4,3-a]pyridine-5-carboxylic Acid (Racemate)

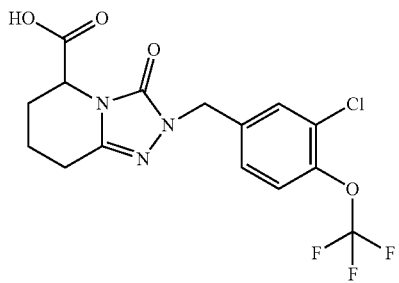 [SMILES: O=C(O)C1CCCc2nn(Cc3ccc(OC(F)(F)F)c(Cl)c3)c(=O)n21]

Methyl (5RS)-2-[3-chloro-4-(trifluoromethoxy)benzyl]-3-oxo-2,3,5,6,7,8-hexahydro[1,2,4]triazolo[4,3-a]pyridine-5-carboxylate (racemate) (293 mg, 99% purity, 715 µmol) was initially charged in THF (7.2 ml), and lithium hydroxide (85.6 mg, 3.57 mmol) dissolved in water was added. After stirring at room temperature for 2 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 85.0 mg (29% of theory) of the title compound were obtained.

LC-MS (Method 3): $R_t$=1.55 min; MS (ESIpos): m/z=391 [M+H]⁺

¹H-NMR (400 MHz, DMSO-d6) δ[ppm]: −0.149 (0.78), −0.008 (7.90), 0.008 (6.70), 0.146 (0.88), 1.038 (0.50), 1.055 (1.00), 1.073 (0.50), 1.157 (1.52), 1.164 (0.90), 1.175 (3.06), 1.182 (1.88), 1.193 (1.64), 1.200 (0.90), 1.235 (0.48), 1.513 (0.96), 1.526 (0.98), 1.819 (1.28), 1.829 (1.24), 1.839 (1.04), 1.851 (1.04), 1.908 (12.72), 1.988 (5.68), 2.102 (3.40), 2.112 (3.14), 2.124 (1.72), 2.328 (0.90), 2.366 (0.68), 2.518 (3.92), 2.523 (3.12), 2.569 (1.76), 2.582 (1.78), 2.596 (1.36), 2.628 (1.36), 2.639 (2.16), 2.650 (1.68), 2.670 (1.68), 2.679 (1.30), 2.692 (0.64), 2.710 (0.66), 3.431 (3.30), 3.449 (3.50), 4.003 (0.46), 4.021 (1.34), 4.038 (1.36), 4.056 (0.50), 4.157 (0.42), 4.164 (0.42), 4.481 (2.44), 4.493 (4.72), 4.505 (2.42), 4.908 (16.00), 7.326 (3.02), 7.332 (2.84), 7.348 (3.62), 7.353 (3.38), 7.531 (5.82), 7.536 (5.94), 7.545 (3.42), 7.549 (3.28), 7.566 (2.76), 7.570 (2.58).

Intermediate 166

(5RS)-2-{[2-Methyl-4-(trifluoromethyl)-1,3-thiazol-5-yl]methyl}-3-oxo-2,3,5,6,7,8-hexahydro[1,2,4]triazolo[4,3-a]pyridine-5-carboxylic Acid (Racemate)

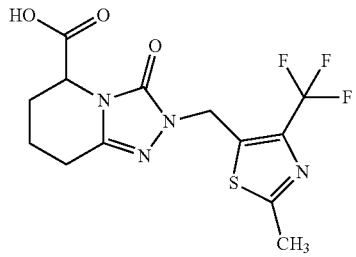 [SMILES: Cc1nc(C(F)(F)F)c(Cn2nc3n(c2=O)C(C(=O)O)CCC3)s1]

Methyl (5RS)-2-{[2-methyl-4-(trifluoromethyl)-1,3-thiazol-5-yl]methyl}-3-oxo-2,3,5,6,7,8-hexahydro[1,2,4]triazolo[4,3-a]pyridine-5-carboxylate (racemate) (380 mg, 1.01 mmol) was initially charged in THF (10 ml), and lithium hydroxide (121 mg, 5.05 mmol) dissolved in water was added. After stirring at room temperature for 3 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 156 mg (41% of theory) of the title compound were obtained.

LC-MS (Method 4): $R_t$=0.61 min; MS (ESIpos): m/z=363 [M+H]

¹H-NMR (400 MHz, DMSO-d6) δ [ppm]: −0.008 (1.08), 0.008 (0.89), 1.157 (2.79), 1.175 (5.61), 1.193 (2.81), 1.356 (0.90), 1.797 (0.50), 1.810 (0.50), 1.820 (0.40), 1.832 (0.41), 1.908 (0.41), 1.988 (10.16), 2.050 (0.44), 2.064 (0.79), 2.075 (1.54), 2.086 (1.45), 2.097 (0.74), 2.343 (0.59), 2.519 (1.18), 2.563 (0.72), 2.576 (0.73), 2.590 (0.59), 2.627 (0.71), 2.643 (16.00), 2.670 (0.82), 2.679 (0.57), 4.003 (0.80), 4.021 (2.41), 4.038 (2.39), 4.056 (0.77), 4.431 (0.85), 4.441 (1.46), 4.455 (0.85), 5.162 (3.10).

Intermediate 167

(5RS)-2-[(3-Methyl-1,2-oxazol-5-yl)methyl]-3-oxo-2,3,5,6,7,8-hexahydro[1,2,4]triazolo[4,3-a]pyridine-5-carboxylic Acid (Racemate)

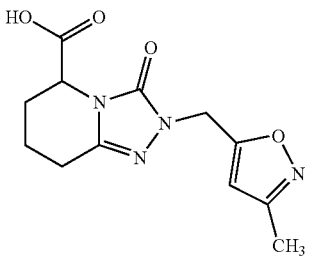

Methyl (5RS)-2-[(3-methyl-1,2-oxazol-5-yl)methyl]-3-oxo-2,3,5,6,7,8-hexahydro[1,2,4]triazolo[4,3-a]pyridine-5-carboxylate (racemate) (259 mg, 86% purity, 762 μmol) was initially charged in THF (7.7 ml), and lithium hydroxide (91.2 mg, 3.81 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 101 mg (90% purity, 43% of theory) of the title compound were obtained.

LC-MS (Method 3): $R_t$=0.64 min; MS (ESIpos): m/z=279 [M+H]$^+$ $^1$H-NMR (400 MHz, DMSO-d6) δ [ppm]: −0.008 (1.37), 0.008 (1.35), 1.157 (0.64), 1.175 (1.32), 1.192 (0.66), 1.812 (0.53), 1.823 (0.54), 1.834 (0.46), 1.845 (0.44), 1.908 (0.48), 1.988 (2.37), 2.071 (0.84), 2.084 (1.48), 2.093 (1.42), 2.100 (1.31), 2.113 (0.67), 2.201 (16.00), 2.226 (0.83), 2.524 (0.85), 2.567 (0.76), 2.580 (0.76), 2.594 (0.61), 2.621 (0.61), 2.633 (0.96), 2.644 (0.67), 2.664 (0.43), 2.674 (0.56), 4.020 (0.57), 4.038 (0.55), 4.455 (1.00), 4.467 (1.96), 4.479 (1.00), 4.495 (0.61), 4.509 (0.60), 4.636 (0.43), 4.973 (4.04), 4.978 (4.07), 6.210 (0.49), 6.234 (3.48).

Intermediate 168

(5RS)-2-[2-Fluoro-3-(trifluoromethyl)benzyl]-3-oxo-2,3,5,6,7,8-hexahydro[1,2,4]triazolo[4,3-a]pyridine-5-carboxylic Acid (Racemate)

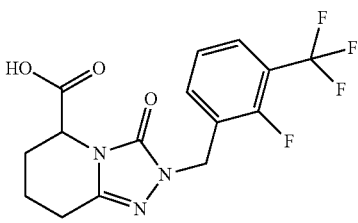 [SMILES: O=C(O)C1CCCc2nn(Cc3cccc(C(F)(F)F)c3F)c(=O)n21]

Methyl (5RS)-2-[2-fluoro-3-(trifluoromethyl)benzyl]-3-oxo-2,3,5,6,7,8-hexahydro[1,2,4]triazolo[4,3-a]pyridine-5-carboxylate (racemate) (184 mg, 493 μmol) was initially charged in THF (3.0 ml), and lithium hydroxide (59.0 mg, 2.46 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 166 mg (94% of theory) of the title compound were obtained.

LC-MS (Method 3): $R_t$=1.35 min; MS (ESIpos): m/z=360 [M+H]$^+$

Intermediate 169

(5RS)-2-[3-Fluoro-5-(trifluoromethyl)benzyl]-3-oxo-2,3,5,6,7,8-hexahydro[1,2,4]triazolo[4,3-a]pyridine-5-carboxylic Acid (Racemate)

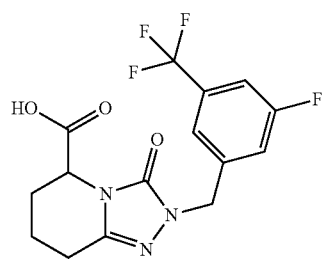 [SMILES: O=C(O)C1CCCc2nn(Cc3cc(F)cc(C(F)(F)F)c3)c(=O)n21]

Methyl (5RS)-2-[3-fluoro-5-(trifluoromethyl)benzyl]-3-oxo-2,3,5,6,7,8-hexahydro[1,2,4]triazolo[4,3-a]pyridine-5-carboxylate (racemate) (154 mg, 413 μmol) was initially charged in THF (3.0 ml), and lithium hydroxide (49.4 mg, 2.06 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 124 mg (84% of theory) of the title compound were obtained.

LC-MS (Method 3): $R_t$=1.39 min; MS (ESIpos): m/z=360 [M+H]

Intermediate 170

(5RS)-3-Oxo-2-[(3,5,6-trimethylpyrazin-2-yl)methyl]-2,3,5,6,7,8-hexahydro[1,2,4]triazolo[4,3-a]pyridine-5-carboxylic Acid (Racemate)

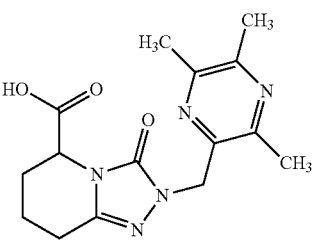 [SMILES: Cc1nc(C)c(Cn2nc3n(c2=O)C(C(=O)O)CCC3)nc1C]

Methyl (5RS)-3-oxo-2-[(3,5,6-trimethylpyrazin-2-yl)methyl]-2,3,5,6,7,8-hexahydro[1,2,4]triazolo[4,3-a]pyridine-5-carboxylate (racemate) (179 mg, 540 μmol) was initially charged in THF (5.0 ml), and lithium hydroxide (64.7 mg, 2.70 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 80.0 mg (47% of theory) of the title compound were obtained.

LC-MS (Method 1): $R_t$=0.65 min; MS (ESIpos): m/z=318 [M+H]

Intermediate 171

(5RS)-2-[(1-Methyl-1H-1,2,4-triazol-3-yl)methyl]-3-oxo-2,3,5,6,7,8-hexahydro[1,2,4]triazolo[4,3-a]pyridine-5-carboxylic Acid (Racemate)

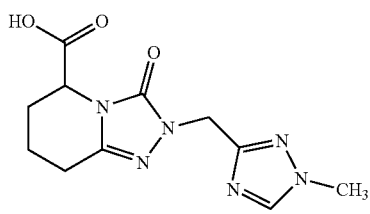 [SMILES: Cn1cnc(Cn2nc3n(c2=O)C(C(=O)O)CCC3)n1]

Methyl (5RS)-2-[(1-methyl-1H-1,2,4-triazol-3-yl)methyl]-3-oxo-2,3,5,6,7,8-hexahydro[1,2,4]triazolo[4,3-a]pyridine-5-carboxylate (racemate) (176 mg, 74% purity, 446 μmol) was initially charged in THF (4.5 ml), and lithium hydroxide (53.4 mg, 2.23 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The aqueous phase was concentrated and 268 mg (76% purity, >100%) of the title compound were thus obtained.

LC-MS (Method 9): $R_t$=3.37 min; MS (ESIpos): m/z=279 [M+H]$^+$ $^1$H-NMR (400 MHz, DMSO-d6) δ [ppm]: −0.149 (0.54), −0.008 (3.90), 0.146 (0.46), 1.592 (0.57), 1.705 (0.76), 1.857 (0.54), 2.119 (0.81), 2.166 (3.04), 2.329 (0.89), 2.368 (0.50), 2.452 (1.14), 2.670 (0.80), 2.712 (0.42), 3.041 (1.56), 3.407 (1.18), 3.815 (16.00), 3.839 (0.43), 3.851 (0.70), 3.924 (2.27), 4.152 (0.95), 4.672 (1.53), 4.688 (0.46), 4.710 (2.53), 4.758 (1.03), 4.815 (2.91), 4.854 (1.76), 8.345 (0.57), 8.360 (3.83), 8.675 (0.64), 11.177 (0.50).

Intermediate 172

(5RS)-3-Oxo-2-{[2-(trifluoromethyl)pyridin-4-yl]methyl}-2,3,5,6,7,8-hexahydro[1,2,4]triazolo[4,3-a]pyridine-5-carboxylic Acid (Enantiomer 1)

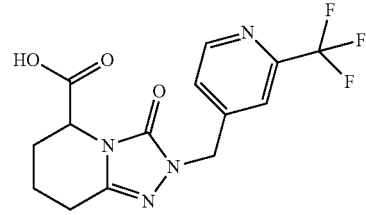 [SMILES: O=C(O)C1CCCc2nn(Cc3ccnc(C(F)(F)F)c3)c(=O)n21]

Methyl (5RS)-3-oxo-2-{[2-(trifluoromethyl)pyridin-4-yl]methyl}-2,3,5,6,7,8-hexahydro[1,2,4]triazolo[4,3-a]pyridine-5-carboxylate (enantiomer 1) (279 mg, 783 μmol) was initially charged in THF (5.0 ml), and lithium hydroxide (93.8 mg, 3.92 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 180 mg (67% of theory) of the title compound were obtained.

LC-MS (Method 3): $R_t$=0.95 min; MS (ESIpos): m/z=343 [M+H]$^+$

The (5S) configuration was assigned on the basis of the crystal structure elucidation for Example 26, 108, 113, 157, 237, 358 and 454.

(5S)-3-Oxo-2-{[2-(trifluoromethyl)pyridin-4-yl]methyl}-2,3,5,6,7,8-hexahydro[1,2,4]triazolo[4,3-a]pyridine-5-carboxylic Acid

Intermediate 173

(5RS)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic Acid (Enantiomer 1)

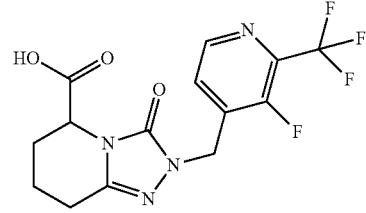 [SMILES: O=C(O)C1CCCc2nn(Cc3ccnc(C(F)(F)F)c3F)c(=O)n21]

Methyl (5RS)-2-{[3-fluoro-2-(trifluoromethyl)pyridin-4-yl]methyl}-3-oxo-2,3,5,6,7,8-hexahydro[1,2,4]triazolo[4,3-a]pyridine-5-carboxylate (enantiomer 1) (181 mg, 484 μmol) was initially charged in THF (3.0 ml), and lithium hydroxide (57.9 mg, 2.42 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 150 mg (86% of theory) of the title compound were obtained.

LC-MS (Method 1): $R_t$=0.89 min; MS (ESIpos): m/z=361 [M+H]+

The (5S) configuration was assigned on the basis of the crystal structure elucidation for Example 26, 108, 113, 157, 237, 358 and 454.

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic Acid Intermediate 174

(5RS)-3-Oxo-2-{[2-(trifluoromethyl)quinolin-4-yl]methyl}-2,3,5,6,7,8-hexahydro[1,2,4]triazolo[4,3-a]pyridine-5-carboxylic Acid (Enantiomer 1)

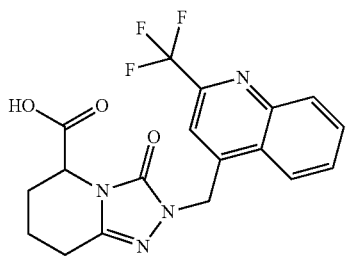 [SMILES: O=C(O)C1CCCc2nn(Cc3cc(C(F)(F)F)nc4ccccc34)c(=O)n21]

Methyl (5RS)-3-oxo-2-{[2-(trifluoromethyl)quinolin-4-yl]methyl}-2,3,5,6,7,8-hexahydro[1,2,4]triazolo[4,3-a]pyridine-5-carboxylate (enantiomer 1) (111 mg, 273 µmol) was initially charged in THF (3.0 ml), and lithium hydroxide (32.7 mg, 1.37 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 94.0 mg (88% of theory) of the title compound were obtained.

LC-MS (Method 4): $R_t$=0.76 min; MS (ESIpos): m/z=393 [M+H]

The (5S) configuration was assigned on the basis of the crystal structure elucidation for Example 26, 108, 113, 157, 237, 358 and 454.

(5S)-3-Oxo-2-{[2-(trifluoromethyl)quinolin-4-yl]methyl}-2,3,5,6,7,8-hexahydro[1,2,4]triazolo[4,3-a]pyridine-5-carboxylic Acid Intermediate 175

(5RS)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic Acid (Enantiomer 1)

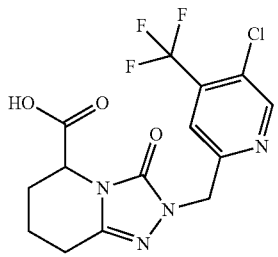 [SMILES: O=C(O)C1CCCc2nn(Cc3cc(C(F)(F)F)c(Cl)cn3)c(=O)n21]

Methyl (5RS)-2-{[5-chloro-4-(trifluoromethyl)pyridin-2-yl]methyl}-3-oxo-2,3,5,6,7,8-hexahydro[1,2,4]triazolo[4,3-a]pyridine-5-carboxylate (enantiomer 1) (269 mg, 688 µmol) was initially charged in THF (3.0 ml), and lithium hydroxide (82.4 mg, 3.44 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 100 mg (39% of theory) of the title compound were obtained.

LC-MS (Method 3): $R_t$=1.29 min; MS (ESIpos): m/z=377 [M+H]

The (5S) configuration was assigned on the basis of the crystal structure elucidation for Example 26, 108, 113, 157, 237, 358 and 454.

(5S)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic Acid Intermediate 176

(5RS)-3-Oxo-2-[(3,5,6-trimethylpyrazin-2-yl)methyl]-2,3,5,6,7,8-hexahydro[1,2,4]triazolo[4,3-a]pyridine-5-carboxylic Acid (Enantiomer 1)

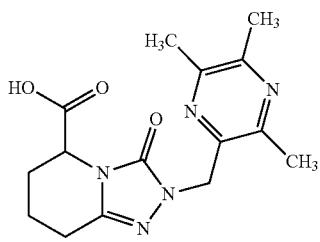 [SMILES: Cc1nc(C)c(Cn2nc3n(c2=O)C(C(=O)O)CCC3)nc1C]

Methyl (5RS)-3-oxo-2-[(3,5,6-trimethylpyrazin-2-yl)methyl]-2,3,5,6,7,8-hexahydro[1,2,4]triazolo[4,3-a]pyridine-5-carboxylate (enantiomer 1) (261 mg, 788 µmol) was initially charged in THF (5.0 ml), and lithium hydroxide (94.3 mg, 3.94 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 124 mg (50% of theory) of the title compound were obtained.

LC-MS (Method 3): $R_t$=0.77 min; MS (ESIpos): m/z=318 [M+H]$^+$

Intermediate 177

(5RS)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic Acid (Enantiomer 1)

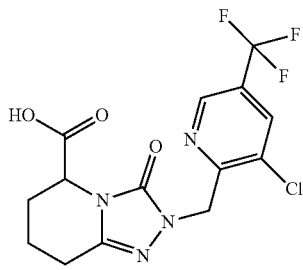 [SMILES: O=C(O)C1CCCc2nn(Cc3ncc(C(F)(F)F)cc3Cl)c(=O)n21]

Methyl (5RS)-2-{[3-chloro-5-(trifluoromethyl)pyridin-2-yl]methyl}-3-oxo-2,3,5,6,7,8-hexahydro[1,2,4]triazolo[4,3-a]pyridine-5-carboxylate (enantiomer 1) (216 mg, 553 µmol) was initially charged in THF (4.0 ml), and lithium hydroxide (66.2 mg, 2.76 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 181 mg (87% of theory) of the title compound were obtained.

LC-MS (Method 3): $R_t$=1.21 min; MS (ESIpos): m/z=377 [M+H]$^+$

Intermediate 178

(5RS)-3-Oxo-2-{[4-(trifluoromethyl)pyridin-2-yl]methyl}-2,3,5,6,7,8-hexahydro[1,2,4]triazolo[4,3-a]pyridine-5-carboxylic Acid (Enantiomer 1)

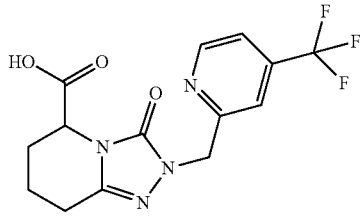 [SMILES: O=C(O)C1CCCc2nn(Cc3cc(C(F)(F)F)ccn3)c(=O)n21]

Methyl (5RS)-3-oxo-2-{[4-(trifluoromethyl)pyridin-2-yl]methyl}-2,3,5,6,7,8-hexahydro[1,2,4]triazolo[4,3-a]pyridine-5-carboxylate (enantiomer 1) (275 mg, 770 µmol) was initially charged in THF (10 ml), and lithium hydroxide (92.2 mg, 3.85 mmol) dissolved in water was added. After stirring at room temperature for 5 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 247 mg (94% of theory) of the title compound were obtained.

LC-MS (Method 4): $R_t$=0.59 min; MS (ESIpos): m/z=343 [M+H]$^+$

The (5S) configuration was assigned on the basis of the crystal structure elucidation for Example 26, 108, 113, 157, 237, 358 and 454.

(5S)-3-Oxo-2-{[4-(trifluoromethyl)pyridin-2-yl]methyl}-2,3,5,6,7,8-hexahydro[1,2,4]triazolo[4,3-a]pyridine-5-carboxylic Acid Intermediate 179

(5RS)-3-Oxo-2-{[2-(trifluoromethyl)pyrimidin-4-yl]methyl}-2,3,5,6,7,8-hexahydro[1,2,4]triazolo[4,3-a]pyridine-5-carboxylic Acid (Enantiomer 1)

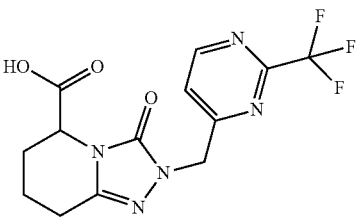 [SMILES: O=C(O)C1CCCc2nn(Cc3ccnc(C(F)(F)F)n3)c(=O)n21]

Methyl (5RS)-3-oxo-2-{[2-(trifluoromethyl)pyrimidin-4-yl]methyl}-2,3,5,6,7,8-hexahydro[1,2,4]triazolo[4,3-a]pyridine-5-carboxylate (enantiomer 1) (49.5 mg, 139 µmol) was initially charged in THF (2.0 ml), and lithium hydroxide (16.6 mg, 693 µmol) dissolved in water was added. After stirring at room temperature for 5 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 45.0 mg (95% of theory) of the title compound were obtained.

LC-MS (Method 4): $R_t$=0.55 min; MS (ESIpos): m/z=344 [M+H]$^+$

The (5S) configuration was assigned on the basis of the crystal structure elucidation for Example 26, 108, 113, 157, 237, 358 and 454.

(5S)-3-Oxo-2-{[2-(trifluoromethyl)pyrimidin-4-yl]methyl}-2,3,5,6,7,8-hexahydro[1,2,4]triazolo[4,3-a]pyridine-5-carboxylic Acid Intermediate 180

(5RS)-3-Oxo-2-(2,4,5-trimethylbenzyl)-2,3,5,6,7,8-hexahydro[1,2,4]triazolo[4,3-a]pyridine-5-carboxylic Acid (Enantiomer 1)

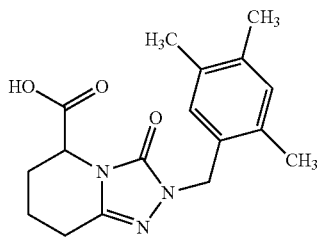 [SMILES: Cc1cc(C)c(Cn2nc3n(c2=O)C(C(=O)O)CCC3)cc1C]

Methyl (5RS)-3-oxo-2-(2,4,5-trimethylbenzyl)-2,3,5,6,7,8-hexahydro[1,2,4]triazolo[4,3-a]pyridine-5-carboxylate (enantiomer 1) (198 mg, 601 μmol) was initially charged in THF (2.0 ml), and lithium hydroxide (72.0 mg, 3.01 mmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 189 mg (99% of theory) of the title compound were obtained.

LC-MS (Method 1): $R_t$=1.05 min; MS (ESIpos): m/z=316 [M+H]$^+$

The (5S) configuration was assigned on the basis of the crystal structure elucidation for Example 26, 108, 113, 157, 237, 358 and 454.

(5S)-3-Oxo-2-(2,4,5-trimethylbenzyl)-2,3,5,6,7,8-hexahydro[1,2,4]triazolo[4,3-a]pyridine-5-carboxylic Acid Intermediate 181

(5RS)-2-(4-Methylbenzyl)-3-oxo-2,3,5,6,7,8-hexahydro[1,2,4]triazolo[4,3-a]pyridine-5-carboxylic Acid (Enantiomer 1)

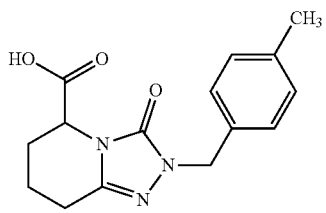 [SMILES: Cc1ccc(Cn2nc3n(c2=O)C(C(=O)O)CCC3)cc1]

Methyl (5RS)-2-(4-methylbenzyl)-3-oxo-2,3,5,6,7,8-hexahydro[1,2,4]triazolo[4,3-a]pyridine-5-carboxylate (enantiomer 1) (1.05 g, 3.48 mmol) was initially charged in THF (29 ml), and lithium hydroxide (417 mg, 17.4 mmol) dissolved in water was added. After stirring overnight, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 733 mg (73% of theory) of the title compound were obtained.

Alternative Synthesis:

tert-Butyl (5RS)-2-(4-methylbenzyl)-3-oxo-2,3,5,6,7,8-hexahydro[1,2,4]triazolo[4,3-a]pyridine-5-carboxylate (enantiomer 1) (2.65 g, 7.72 mmol) was dissolved in dichloromethane (45 ml), and trifluoroacetic acid (45 ml, 580 mmol) was added at room temperature. After the reaction mixture had been stirred at room temperature overnight, the solvent was removed under reduced pressure. The residue was taken up in dichloromethane and admixed with water. The organic phase was removed and the aqueous phase was extracted twice with dichloromethane. The combined organic phases were dried over magnesium sulphate and filtered, and the filtrate was concentrated. 2.16 g (97% of theory) of the title compound were obtained.

LC-MS (Method 1): $R_t$=0.91 min; MS (ESIpos): m/z=288 [M+H]$^+$ $^1$H-NMR (500 MHz, DMSO-d6) δ[ppm]: 1.356 (0.56), 2.065 (0.43), 2.072 (0.54), 2.076 (0.79), 2.082 (0.79), 2.089 (0.76), 2.100 (0.41), 2.271 (8.20), 2.526 (0.56), 2.612 (0.50), 3.321 (0.68), 4.449 (0.65), 4.458 (1.21), 4.468 (0.62), 4.770 (2.95), 7.128 (16.00).

The (5S) configuration was assigned on the basis of the crystal structure elucidation for Example 26, 108, 113, 157, 237, 358 and 454.

(5S)-2-(4-Methylbenzyl)-3-oxo-2,3,5,6,7,8-hexahydro[1,2,4]triazolo[4,3-a]pyridine-5-carboxylic Acid Intermediate 182

(5RS)-5-Methyl-2-(4-methylbenzyl)-3-oxo-2,3,5,6,7,8-hexahydro[1,2,4]triazolo[4,3-a]pyridine-5-carboxylic Acid (Racemate)

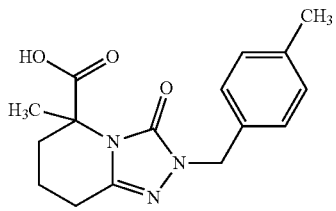

Methyl (5RS)-5-methyl-2-(4-methylbenzyl)-3-oxo-2,3,5,6,7,8-hexahydro[1,2,4]triazolo[4,3-a]pyridine-5-carboxylate (racemate) (32.0 mg, 101 μmol) was initially charged in THF (1.0 ml), and lithium hydroxide (12.1 mg, 507 μmol) dissolved in water was added. After stirring at room temperature for 72 hours, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate

Intermediate 183

(5RS,7RS)-7-Methyl-2-(4-methylbenzyl)-3-oxo-2,3,5,6,7,8-hexahydro[1,2,4]triazolo[4,3-a]pyridine-5-carboxylic Acid (Diastereomer Mixture; 4 Isomers)

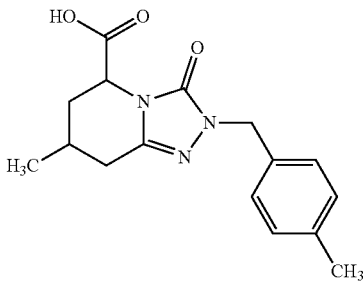

tert-Butyl (5RS,7RS)-7-methyl-3-oxo-2,3,5,6,7,8-hexahydro[1,2,4]triazolo[4,3-a]pyridine-5-carboxylate (diastereomer mixture; 4 isomers) (150 mg, 592 µmol) was initially charged in acetonitrile (6.0 ml). Caesium carbonate (289 mg, 888 µmol) and 1-(bromomethyl)-4-methylbenzene (115 mg, 622 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over magnesium sulphate and filtered, and the filtrate was concentrated. The residue was dissolved in dichloromethane (5 ml), and trifluoroacetic acid (2.5 ml) was added at room temperature. After the reaction mixture had been stirred at room temperature overnight, the solvent was removed under reduced pressure. The residue was purified via preparative HPLC (Method 10). The product-containing fractions were concentrated under reduced pressure, and 120 mg (67% of theory) of the title compound were obtained.

LC-MS (Method 4): $R_t$=0.73 min; MS (ESIpos): m/z=302 [M+H]$^+$ $^1$H-NMR (400 MHz, DMSO-d6) δ [ppm]: −0.008 (0.53), 0.008 (0.47), 1.004 (3.87), 1.021 (4.00), 1.438 (0.57), 1.471 (0.61), 1.785 (0.92), 1.861 (0.40), 2.133 (0.60), 2.162 (0.50), 2.174 (0.69), 2.202 (0.57), 2.244 (0.44), 2.270 (10.91), 2.602 (0.51), 2.609 (0.51), 2.642 (0.45), 2.649 (0.43), 4.233 (0.46), 4.249 (0.53), 4.258 (0.53), 4.275 (0.45), 4.746 (5.02), 4.780 (0.47), 4.795 (0.45), 7.132 (16.00).

Intermediate 184

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers)

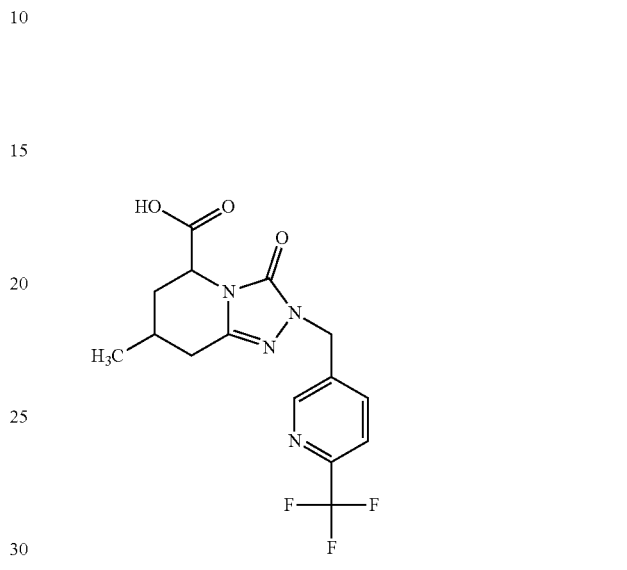

tert-Butyl (5S,7S)-7-methyl-3-oxo-2-{[6-(trifluoromethyl)pyridin-3-yl]methyl}-2,3,5,6,7,8-hexahydro[1,2,4]triazolo[4,3-a]pyridine-5-carboxylate (diastereomer mixture; 4 isomers) (383 mg, 929 µmol) was dissolved in dichloromethane (5.0 ml), and trifluoroacetic acid (5.0 ml, 65 mmol) was added at room temperature. After the reaction mixture had been stirred at room temperature for 2.5 h, the solvent was removed under reduced pressure. The residue was dissolved in dichloromethane and washed with water. The aqueous phase was extracted with dichloromethane, saturated with sodium chloride and extracted once more with dichloromethane. The combined organic phases were dried over magnesium sulphate and filtered, and the filtrate was concentrated. 325 mg (92% of theory) of the title compound were obtained.

LC-MS (Method 3): $R_t$=1.18 min; MS (ESIpos): m/z=357 [M+H]$^+$ $^1$H-NMR (400 MHz, DMSO-d6) δ [ppm]: −0.008 (4.92), 0.008 (2.52), 1.015 (15.45), 1.032 (15.37), 1.237 (0.63), 1.324 (0.45), 1.407 (3.53), 1.444 (1.27), 1.471 (2.46), 1.499 (1.90), 1.504 (2.44), 1.532 (1.40), 1.920 (1.12), 1.927 (1.22), 1.936 (1.30), 1.946 (1.16), 1.954 (1.10), 2.181 (2.72), 2.209 (2.30), 2.221 (3.18), 2.250 (3.93), 2.265 (1.63), 2.282 (1.40), 2.298 (1.26), 2.328 (0.46), 2.519 (2.23), 2.524 (2.06), 2.637 (2.03), 2.643 (2.06), 2.673 (1.93), 2.683 (1.64), 3.566 (1.59), 3.686 (0.42), 4.306 (2.98), 4.322 (3.48), 4.332 (3.20), 4.348 (2.66), 4.835 (1.62), 5.016 (16.00), 5.040 (0.46), 5.754 (1.60), 7.899 (2.66), 7.918 (9.08), 7.919 (8.98), 7.931 (5.18), 7.936 (4.87), 7.952 (1.45), 7.956 (1.45), 8.670 (5.04).

Intermediate 185

(5RS,6RS)-6-Methyl-2-(4-methylbenzyl)-3-oxo-2,3,
5,6,7,8-hexahydro[1,2,4]triazolo[4,3-a]pyridine-5-
carboxylic Acid (Diastereomer Mixture; 4 Isomers)

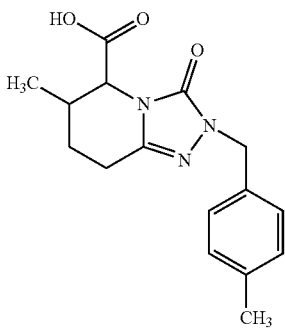 [SMILES: Cc1ccc(Cn2nc3n(c2=O)C(C(=O)O)C(C)CC3)cc1]

Ethyl (5RS,6RS)-6-methyl-2-(4-methylbenzyl)-3-oxo-2, 3,5,6,7,8-hexahydro[1,2,4]triazolo[4,3-a]pyridine-5-carboxylate (diastereomer mixture; 4 isomers) (108 mg, 328 µmol) was initially charged in THF (1.5 ml), and lithium hydroxide (19.6 mg, 820 µmol) dissolved in water (750 µl) was added. After stirring overnight, the reaction mixture was admixed at room temperature with saturated aqueous ammonium chloride solution and 1 N aqueous hydrochloric acid. The organic phase was removed and the aqueous phase was extracted three times with dichloromethane. The combined organic phases were dried over magnesium sulphate and filtered, and the filtrate was concentrated. 95.3 mg (67% purity, 65% of theory) of the title compound were obtained.

LC-MS (Method 8): $R_t$=1.88 min; MS (ESIpos): m/z=302 [M+H]$^+$

Intermediate 186

(5RS,7RS)-2-(4-Methylbenzyl)-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

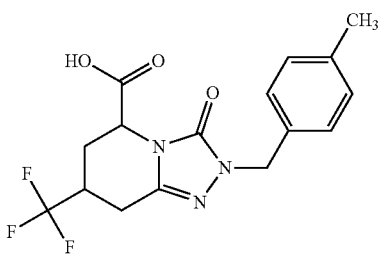 [SMILES: Cc1ccc(Cn2nc3n(c2=O)C(C(=O)O)CC(C(F)(F)F)C3)cc1]

Ethyl (5RS,7RS)2-(4-methylbenzyl)-3-oxo-7-(trifluoromethyl)-2,3,5,6,7,8-hexahydro[1,2,4]triazolo[4,3-a]pyridine-5-carboxylate (diastereomer mixture; 4 isomers) (102 mg, 265 µmol) was initially charged in THF (1.0 ml), and lithium hydroxide (15.9 mg, 663 mol) dissolved in water (500 µl) was added. After stirring overnight, the reaction mixture was admixed at room temperature with saturated aqueous ammonium chloride solution and dichloromethane/i-propanol 1/5. The organic phase was removed and the aqueous phase was extracted twice with dichloromethane/i-propanol 1/5. The aqueous phase was admixed with 1 N aqueous hydrochloric acid and extracted three times with dichloromethane/i-propanol 1/5. The combined organic phases were dried over magnesium sulphate and filtered, and the filtrate was concentrated. 98 mg (82% purity, 83% of theory) of the title compound were obtained.

LC-MS (Method 1): $R_t$=1.06 min; MS (ESIpos): m/z=356 [M+H]$^+$

Intermediate 187

(5RS)-2-[2-(4-Methylphenyl)ethyl]-3-oxo-2,3,5,6,7, 8-hexahydro[1,2,4]triazolo[4,3-a]pyridine-5-carboxylic Acid (Racemate)

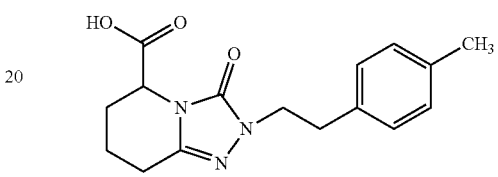

Methyl (5RS)-2-[2-(4-methylphenyl)ethyl]-3-oxo-2,3,5, 6,7,8-hexahydro[1,2,4]triazolo[4,3-a]pyridine-5-carboxylate (racemate) (90.0 mg, 285 µmol) was initially charged in THF (3.0 ml), and lithium hydroxide (34.2 mg, 1.43 mmol) dissolved in water was added. After stirring at room temperature overnight, the reaction mixture was concentrated under reduced pressure at room temperature and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 82.0 mg (95% of theory) of the title compound were obtained.

LC-MS (Method 3): $R_t$=1.27 min; MS (ESIpos): m/z=302 [M+H]$^+$ $^1$H-NMR (400 MHz, DMSO-d6) δ [ppm]: −0.150 (0.41), −0.008 (3.22), 0.008 (2.98), 0.146 (0.44), 1.908 (1.11), 1.988 (0.63), 2.071 (0.92), 2.256 (9.10), 2.327 (0.53), 2.523 (1.85), 2.580 (0.53), 2.643 (0.69), 2.674 (0.63), 2.862 (1.04), 2.881 (2.28), 2.900 (1.16), 3.765 (0.63), 3.783 (1.52), 3.803 (1.33), 3.823 (0.53), 4.389 (0.63), 4.400 (1.22), 4.413 (0.61), 7.084 (16.00), 13.178 (0.58).

Intermediate 188

(5RS)-3-Oxo-2-{[4-(trifluoromethyl)cyclohexyl] methyl}-2,3,5,6,7,8-hexahydro[1,2,4]triazolo[4,3-a] pyridine-5-carboxylic Acid (Diastereomer Mixture; 4 Isomers)

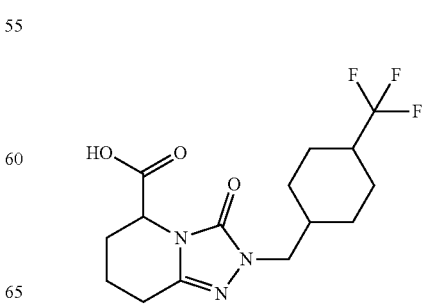

To a solution of tert-butyl (5RS)-3-oxo-2-{[4-(trifluoromethyl)cyclohexyl]methyl}-2,3,5,6,7,8-hexahydro[1,2,4]triazolo[4,3-a]pyridine-5-carboxylate (diastereomer mixture; 4 isomers) (465 mg, 1.15 mmol) in 20 ml of dichloromethane were added 2.0 ml (26 mmol) of trifluoroacetic acid, and the mixture was stirred at room temperature overnight. For workup, the mixture was adjusted to pH 3 with 3 N sodium hydroxide solution while cooling with an ice bath and stirring vigorously, diluted with dichloromethane/water and extracted. The aqueous phase was extracted two more times with dichloromethane. The combined organic phases were washed with saturated sodium chloride solution, dried over sodium sulphate, and concentrated and dried under reduced pressure. 327 mg (82% of theory) of the title compound (as a racemic cis/trans mixture) were obtained, which was converted further as such.

LC-MS (Method 4): $R_t$=0.78 min; MS (ESIpos): m/z=348 [M+H]$^+$ $^1$H-NMR (400 MHz, DMSO-d6) δ [ppm]: −0.149 (1.44), −0.008 (12.24), 0.008 (10.19), 0.146 (1.37), 1.007 (1.88), 1.038 (2.38), 1.061 (1.44), 1.149 (2.53), 1.189 (2.71), 1.220 (2.78), 1.253 (1.77), 1.284 (0.94), 1.395 (6.68), 1.405 (3.32), 1.412 (2.20), 1.479 (7.12), 1.498 (9.86), 1.508 (5.85), 1.521 (7.22), 1.531 (5.74), 1.546 (5.89), 1.561 (4.66), 1.571 (5.81), 1.586 (4.88), 1.595 (5.96), 1.605 (8.52), 1.617 (7.01), 1.624 (7.77), 1.643 (10.76), 1.676 (4.01), 1.804 (3.29), 1.816 (3.72), 1.828 (4.80), 1.859 (3.65), 1.900 (1.95), 2.079 (7.58), 2.088 (6.79), 2.100 (3.68), 2.332 (2.09), 2.366 (1.91), 2.569 (2.93), 2.583 (2.20), 2.619 (2.31), 2.630 (4.01), 2.642 (2.53), 2.670 (2.74), 2.710 (1.48), 3.289 (7.19), 3.427 (2.74), 3.443 (2.85), 3.457 (3.97), 3.462 (4.19), 3.474 (4.19), 3.501 (1.12), 3.519 (0.98), 3.563 (16.00), 3.581 (15.67), 3.609 (3.14), 3.622 (3.61), 3.628 (3.40), 3.642 (3.11), 3.678 (0.61), 4.412 (2.13), 4.424 (5.53), 4.435 (5.16), 4.447 (1.95), 13.170 (3.58).

Intermediate 189

(5RS)-2-[(4,4-Difluorocyclohexyl)methyl]-3-oxo-2,3,5,6,7,8-hexahydro[1,2,4]triazolo[4,3-a]pyridine-5-carboxylic Acid (Racemate)

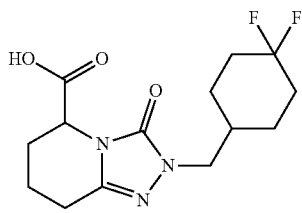 [SMILES: O=C(O)C1CCCc2nn(CC3CCC(F)(F)CC3)c(=O)n21]

To a solution of tert-butyl (5S)-2-[(4,4-difluorocyclohexyl)methyl]-3-oxo-2,3,5,6,7,8-hexahydro[1,2,4]triazolo[4,3-a]pyridine-5-carboxylate (racemate) (41.2 mg, 111 µmol) in 2.0 ml of dichloromethane were added 90 µl (1.2 mmol) of trifluoroacetic acid, and the mixture was stirred at room temperature for 5 h. Subsequently, another 120 µl (1.6 mmol) of trifluoroacetic acid were added and the mixture was stirred further overnight (monitoring of conversion by HPLC). For workup, the mixture was adjusted to pH 3 with 3 N NaOH while cooling with an ice bath and stirring vigorously, diluted with dichloromethane/water and extracted. The aqueous phase was extracted two more times with dichloromethane. The combined organic phases were washed with saturated sodium chloride solution, dried over sodium sulphate, and concentrated and dried under reduced pressure. In this way, 30.5 mg (87% of theory) of the title compound were obtained.

LC-MS (Method 3): $R_t$=1.08 min; MS (ESIpos): m/z=316 [M+H]$^+$ $^1$H-NMR (400 MHz, DMSO-d6) δ[ppm]: −0.149 (1.97), −0.008 (16.00), 0.008 (14.35), 0.146 (1.78), 1.227 (3.20), 1.396 (2.42), 1.515 (1.65), 1.694 (4.48), 1.806 (4.07), 1.975 (2.74), 2.085 (5.12), 2.327 (1.51), 2.366 (1.46), 2.558 (3.84), 2.571 (3.06), 2.634 (3.25), 2.675 (2.51), 2.709 (1.46), 3.286 (9.65), 3.523 (12.53), 3.541 (12.48), 4.417 (3.20), 4.428 (6.13), 4.441 (3.25), 5.754 (1.60), 13.179 (2.88).

Intermediate 190

[2-(Trifluoromethyl)-1,8-naphthyridin-3-yl]methanol

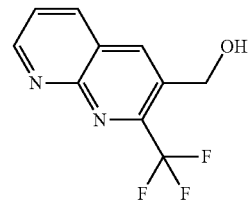 [SMILES: OCc1cc2cccnc2nc1C(F)(F)F]

Ethyl 2-(trifluoromethyl)-1,8-naphthyridine-3-carboxylate (1.00 g, 3.70 mmol) was dissolved in THF (25 ml), and lithium aluminium hydride (1.9 ml, 2.4 M, 4.4 mmol) was added at −20° C. After stirring at −20° C. for 2 hours, the reaction mixture was admixed with saturated aqueous ammonium chloride solution and the THF was removed under reduced pressure. The residue was admixed with ethyl acetate and water. The aqueous phase was extracted three times with ethyl acetate. The combined organic phases were dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 230 mg (26% of theory) of the title compound were obtained.

LC-MS (Method 3): $R_t$=0.90 min; MS (ESIpos): m/z=229 [M+H]$^+$ $^1$H-NMR (400 MHz, DMSO-d6) δ [ppm]: −0.149 (0.86), −0.008 (7.77), 0.008 (6.74), 0.146 (0.86), 2.328 (1.09), 2.367 (0.80), 2.524 (3.56), 2.671 (1.18), 2.711 (0.95), 4.852 (0.43), 4.876 (15.05), 4.890 (15.34), 4.923 (0.52), 5.824 (7.51), 5.838 (15.34), 5.852 (7.14), 7.791 (8.06), 7.801 (8.32), 7.811 (8.49), 7.822 (8.66), 8.679 (8.49), 8.684 (8.66), 8.700 (8.63), 8.704 (8.17), 8.868 (16.00), 9.204 (7.51), 9.209 (7.68), 9.214 (7.80), 9.219 (7.23).

Intermediate 191

3-(Chloromethyl)-2-(trifluoromethyl)-1,8-naphthyridine

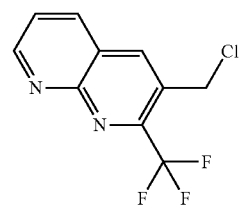 [SMILES: FC(F)(F)c1nc2ncccc2cc1CCl]

[2-(Trifluoromethyl)-1,8-naphthyridin-3-yl]methanol (46.0 mg, 202 µmol) was dissolved in dichloromethane (910 µl), and thionyl dichloride (29 µl, 400 µmol) was added at 0° C. The reaction mixture was stirred at room temperature for 2 hours and then the solvent was removed under reduced pressure. 46.0 mg (93% of theory) of the title compound were obtained.

¹H-NMR (400 MHz, DMSO-d6) δ [ppm]: −0.008 (1.81), 0.008 (1.26), 2.330 (0.40), 2.521 (1.58), 2.526 (1.33), 2.672 (0.57), 2.712 (0.43), 5.126 (16.00), 5.177 (0.78), 5.756 (1.49), 7.026 (0.49), 7.041 (0.66), 7.059 (0.57), 7.853 (3.44), 7.863 (3.55), 7.873 (3.64), 7.883 (3.67), 8.038 (0.42), 8.676 (3.22), 8.681 (3.30), 8.697 (3.06), 8.701 (3.04), 8.995 (9.01), 9.278 (3.59), 9.283 (3.64), 9.288 (3.68), 9.293 (3.40).

Intermediate 192

1-[1-(Bromomethyl)cyclopropyl]-4-(trifluoromethyl)benzene

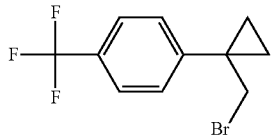 [SMILES: FC(F)(F)c1ccc(C2(CBr)CC2)cc1]

{1-[4-(Trifluoromethyl)phenyl]cyclopropyl}methanol (350 mg, 1.62 mmol) was dissolved in dichloromethane (10 ml), and N,N-diisopropylethylamine (560 µl, 3.2 mmol) and dibromo(triphenyl)phosphorane (854 mg, 96% purity, 1.94 mmol) were added at 0° C. The reaction mixture was stirred at room temperature overnight, and dibromo(triphenyl)phosphorane (854 mg, 96% purity, 1.94 mmol) was added again. After stirring at room temperature overnight, the solvent was removed under reduced pressure, and the residue was purified via column chromatography (silica gel, dichloromethane/ethyl acetate). The product-containing fractions were concentrated under reduced pressure, and 110 mg (23% of theory) of the title compound were obtained.

¹H-NMR (400 MHz, DMSO-d6) δ[ppm]: 1.129 (1.56), 1.136 (1.65), 1.144 (4.59), 1.148 (5.92), 1.157 (3.27), 1.169 (1.19), 1.191 (1.17), 1.202 (3.09), 1.212 (5.74), 1.223 (1.45), 1.231 (1.56), 1.360 (1.16), 1.397 (5.40), 3.915 (16.00), 4.783 (0.41), 7.540 (4.22), 7.561 (5.81), 7.664 (5.75), 7.685 (4.22).

Intermediate 193

Methyl 1-(6-chloropyridin-2-yl)cyclopropanecarboxylate

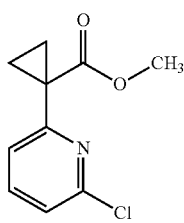

1-(6-Chloropyridin-2-yl)cyclopropanecarboxylic acid (1.00 g, 5.06 mmol) was dissolved in methanol (10 ml), and sulphuric acid (54 µl, 1.0 mmol) was added. The reaction mixture was stirred at 60° C. overnight. The reaction mixture was concentrated under reduced pressure and the residue was dissolved in ethyl acetate and washed with saturated sodium hydrogencarbonate solution. The organic phase was dried over sodium sulphate and filtered and the filtrate was concentrated. 947 mg (87% of theory) of the title compound were obtained.

LC-MS (Method 4): R$_t$=0.83 min; MS (ESIpos): m/z=212 [M+H]⁺

¹H-NMR (400 MHz, DMSO-d6) δ[ppm]: 1.394 (4.13), 1.405 (10.89), 1.414 (14.44), 1.422 (6.17), 1.461 (0.81), 1.484 (0.89), 1.521 (6.34), 1.530 (14.64), 1.539 (10.67), 1.550 (4.00), 2.732 (1.03), 2.892 (1.17), 3.314 (16.00), 3.798 (0.65), 7.384 (6.75), 7.404 (7.47), 7.558 (7.35), 7.577 (8.61), 7.803 (5.32), 7.823 (9.19), 7.842 (4.27).

Intermediate 194

[1-(6-Chloropyridin-2-yl)cyclopropyl]methanol

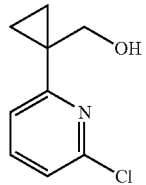 [SMILES: OCC1(c2cccc(Cl)n2)CC1]

Methyl 1-(6-chloropyridin-2-yl)cyclopropanecarboxylate (947 mg, 4.47 mmol) was dissolved in THF (15 ml), and lithium aluminium hydride (2.2 ml, 2.4 M, 5.4 mmol) was added at −78° C. The reaction mixture was stirred at room temperature for 2 hours, and then saturated aqueous ammonium chloride solution was added. The solvent was removed under reduced pressure and the residue was admixed with ethyl acetate and water. The aqueous phase was extracted three times with ethyl acetate. The combined organic phases were dried over sodium sulphate and filtered, and the filtrate was concentrated. 603 mg (92% purity, 68% of theory) of the title compound were obtained.

LC-MS (Method 4): R$_t$=0.68 min; MS (ESIpos): m/z=184 [M+H]⁺

¹H-NMR (400 MHz, DMSO-d6) δ[ppm]: 0.918 (3.81), 0.928 (11.67), 0.933 (14.82), 0.980 (0.54), 1.021 (0.57), 1.058 (5.57), 1.066 (13.62), 1.072 (13.58), 1.082 (4.20), 1.358 (0.67), 1.663 (3.18), 3.718 (15.53), 3.732 (16.00), 4.787 (4.36), 4.800 (8.73), 4.814 (4.16), 7.229 (5.90), 7.248 (6.45), 7.495 (6.83), 7.515 (8.03), 7.695 (0.49), 7.725 (3.88), 7.744 (6.81), 7.764 (3.12), 7.853 (0.40), 9.297 (0.99).

Intermediate 195

2-[1-(Bromomethyl)cyclopropyl]-6-chloropyridine

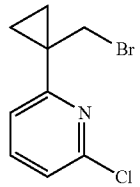 [SMILES: Clc1cccc(C2(CBr)CC2)n1]

[1-(6-Chloropyridin-2-yl)cyclopropyl]methanol (300 mg, 1.63 mmol) was dissolved in dichloromethane (10 ml), and N,N-diisopropylethylamine (570 µl, 3.3 mmol) and dibromo(triphenyl)phosphorane (862 mg, 96% purity, 1.96 mmol) were added at 0° C. The reaction mixture was stirred at room temperature overnight and then concentrated under reduced pressure. The residue was purified via column chromatography (silica gel, dichloromethane/ethyl acetate). The product-containing fractions were concentrated under reduced pressure, and 141 mg (34% of theory) of the title compound were obtained.

GC-MS (Method 2): $R_t$=5.32 min; MS (ESIpos): m/z=213 [M+H]$^+$

Intermediate 196

Ethyl 6-chloro-3-(trifluoromethyl)pyridine-2-carboxylate

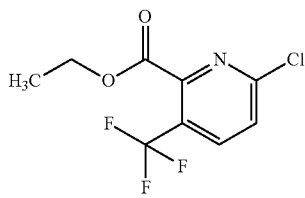 [SMILES: CCOC(=O)c1nc(Cl)ccc1C(F)(F)F]

6-Chloro-3-(trifluoromethyl)pyridine-2-carboxylic acid (2.50 g, 11.1 mmol) was dissolved in ethanol (29 ml), sulphuric acid (710 µl, 13 mmol) was added and the reaction mixture was stirred under reflux overnight. The reaction mixture was concentrated under reduced pressure and the residue was dissolved in ethyl acetate and washed with saturated sodium hydrogencarbonate solution. The organic phase was dried over sodium sulphate and filtered and the filtrate was concentrated. 2.24 g (88% of theory, 70% of theory) of the title compound were obtained and converted further directly.

Intermediate 197

3-Azabicyclo[2.1.1]hexane:trifluoroacetic Acid

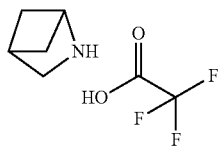

tert-Butyl 2-azabicyclo[2.1.1]hexane-2-carboxylate (70.0 mg, 382 µmol) was dissolved in dichloromethane (10 ml), and trifluoroacetic acid (590 µl, 7.6 mmol) was added at room temperature. After the reaction mixture had been stirred at room temperature overnight, the solvent was removed under reduced pressure. The title compound was obtained. The compound was converted further directly.

Intermediate 198

Ethyl 6-{1-[(benzyloxy)carbonyl]hydrazino}-3-(trifluoromethyl)pyridine-2-carboxylate

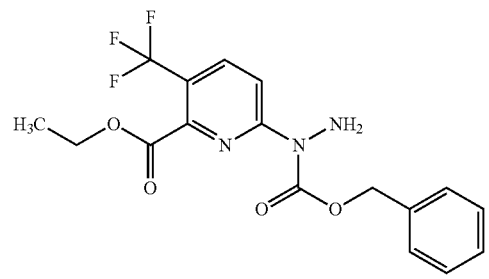 [SMILES: CCOC(=O)c1nc(N(N)C(=O)OCc2ccccc2)ccc1C(F)(F)F]

Under argon, ethyl 6-chloro-3-(trifluoromethyl)pyridine-2-carboxylate (2.24 g, 88% purity, 7.77 mmol) and benzyl hydrazinecarboxylate (1.42 g, 8.55 mmol) were dissolved in toluene (20 ml), and tris(dibenzylideneacetone)dipalladium-chloroform complex (402 mg, 389 µmol), 1,1'-bis(diphenylphosphino)ferrocene (441 mg, 777 µmol) and caesium carbonate (3.04 g, 9.33 mmol) were added. The reaction mixture was stirred at 80° C. for 3 h and then water and ethyl acetate were added. The organic phase was removed and the aqueous phase was extracted with ethyl acetate. The combined organic phases were dried over sodium sulphate and filtered, and the filtrate was concentrated. The residue was purified via column chromatography (silica gel; eluent: isocratic, ethyl acetate/dichloromethane). The product-containing fractions were concentrated under reduced pressure, and 1.80 g (60% of theory) of the title compound were obtained.

LC-MS (Method 4): $R_t$=1.05 min; MS (ESIpos): m/z=384 [M+H]$^+$

Intermediate 199

Ethyl 6-hydrazino-3-(trifluoromethyl)pyridine-2-carboxylate

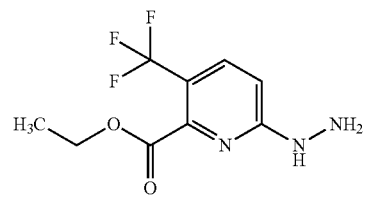 [SMILES: CCOC(=O)c1nc(NN)ccc1C(F)(F)F]

Ethyl 6-{1-[(benzyloxy)carbonyl]hydrazino}-3-(trifluoroethyl)pyridine2-carboxylate (1.80 g, 4.69 mmol) was dissolved in ethanol (10 ml) and converted using a hydrogenation apparatus (H-Cube®, Pd/C 10% palladium, 1 bar, 50° C., flow rate: 1 ml/min). 1.03 g (88% of theory) of the title compound were obtained.

LC-MS (Method 1): $R_t$=0.94 min; MS (ESIpos): m/z=250 [M+H]$^+$

Intermediate 200

Ethyl 3-oxo-6-(trifluoromethyl)-2,3-dihydro[1,2,4]triazolo[4,3-a]pyridine-5-carboxylate

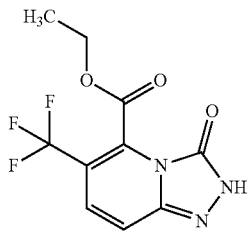 [SMILES: CCOC(=O)c1c(C(F)(F)F)ccc2n[nH]c(=O)n12]

Ethyl 6-hydrazino-3-(trifluoromethyl)pyridine-2-carboxylate (1.11 g, 4.45 mmol) was taken up in THF (15 ml), and di-1H-imidazol-1-ylmethanone (866 mg, 5.34 mmol) was added. The reaction mixture was stirred at room temperature overnight. The reaction mixture was admixed with water and dichloromethane, and admixed with saturated aqueous sodium chloride solution. The organic phase was washed with saturated aqueous sodium chloride solution. The aqueous phase was extracted with dichloromethane. The combined organic phases were dried over sodium sulphate and filtered, and the filtrate was concentrated. 1.22 g (100% of theory) of the title compound were obtained.

LC-MS (Method 4): $R_t$=0.74 min; MS (ESIpos): m/z=276 [M+H]

Intermediate 201

Ethyl (5RS,6RS)-3-oxo-6-(trifluoromethyl)-2,3,5,6,7,8-hexahydro[1,2,4]triazolo[4,3-a]pyridine-5-carboxylate (Diastereomer Mixture; 4 Isomers)

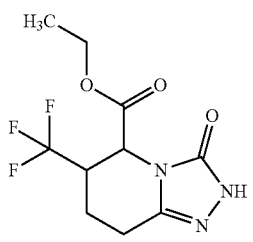 [SMILES: CCOC(=O)C1C(C(F)(F)F)CCc2n[nH]c(=O)n21]

Ethyl 3-oxo-6-(trifluoromethyl)-2,3-dihydro[1,2,4]triazolo[4,3-a]pyridine-5-carboxylate (1.22 g, 4.45 mmol) was dissolved in ethanol (10 ml) and converted using a hydrogenation apparatus (H-Cube®, Pd/C 10% palladium, 1 bar, 80° C., flow rate: 1 ml/min). 1.24 g (100% of theory) of the title compound were obtained.

LC-MS (Method 1): $R_t$=0.88 min; MS (ESIpos): m/z=280 [M+H]$^+$

Intermediate 202

Methyl 6-{1-[(benzyloxy)carbonyl]hydrazino}-5-(trifluoromethyl)pyridine-2-carboxylate

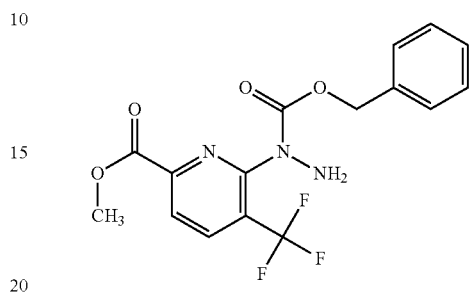

Methyl 6-chloro-5-(trifluoromethyl)pyridine-2-carboxylate (3.00 g, 12.5 mmol), benzyl hydrazinecarboxylate (2.29 g, 13.8 mmol) and tris(dibenzylideneacetone)dipalladium (573 mg, 626 µmol) were suspended in toluene (60 ml) under argon. 1,1'-Bis(diphenylphosphino)ferrocene (694 mg, 1.25 mmol) and caesium carbonate (4.90 g, 15.0 mmol) were added and the reaction mixture was stirred at 80° C. for 3 h. The reaction mixture was admixed with water and ethyl acetate, and the organic phase was removed, washed with water and saturated sodium chloride solution, dried over sodium sulphate, filtered and concentrated. The residue was purified via column chromatography (silica gel; eluent: cyclohexane/ethyl acetate 9:1, 0:1). The product-containing fractions were concentrated under reduced pressure, and 1.87 g (86% purity, 35% of theory) of the title compound were obtained.

LC-MS (Method 1): $R_t$=1.23 min; MS (ESIneg): m/z=368 [M−H]$^-$ $^1$H-NMR (500 MHz, DMSO-d6) δ[ppm]: −0.007 (1.19), 0.006 (0.87), 1.160 (2.79), 1.174 (5.66), 1.189 (2.80), 1.398 (1.98), 1.988 (10.25), 2.518 (0.42), 3.038 (0.55), 3.051 (0.56), 3.852 (16.00), 4.008 (0.77), 4.022 (2.29), 4.037 (2.24), 4.051 (0.73), 4.484 (1.47), 4.496 (1.51), 4.998 (0.87), 5.036 (1.06), 5.085 (0.93), 5.125 (7.85), 5.134 (1.18), 5.146 (1.34), 5.157 (0.63), 7.107 (0.52), 7.195 (0.84), 7.221 (0.64), 7.232 (0.48), 7.238 (0.48), 7.271 (0.56), 7.287 (0.79), 7.309 (5.08), 7.316 (2.18), 7.319 (2.37), 7.326 (1.95), 7.340 (1.80), 7.364 (2.08), 7.380 (3.95), 7.394 (6.93), 7.409 (1.97), 7.416 (1.42), 7.422 (1.02), 7.482 (1.90), 7.498 (2.13), 7.532 (0.42), 8.085 (2.06), 8.101 (1.89), 8.765 (2.66), 8.849 (0.45), 9.009 (0.47), 9.367 (2.77).

Intermediate 203

Methyl 6-hydrazino-5-(trifluoromethyl)pyridine-2-carboxylate

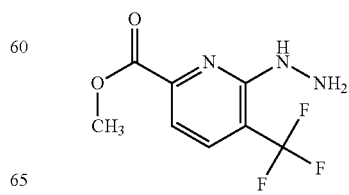

Methyl 6-{1-[(benzyloxy)carbonyl]hydrazino}-5-(trifluoromethyl)pyridine-2-carboxylate (1.87 g, 86% purity, 4.35 mmol) and palladium on charcoal (100 mg, 10% palladium) were suspended in methanol (100 ml) under argon, and the mixture was stirred at room temperature in a hydrogen atmosphere (1 bar) overnight. The reaction mixture was filtered through Celite and washed through with methanol. The filtrate was concentrated under reduced pressure, and 1.09 g (75% purity, 80% of theory) of the title compound were obtained.

LC-MS (Method 3): $R_t$=0.86 min; MS (ESIpos): m/z=236 [M+H]$^+$ $^1$H-NMR (400 MHz, DMSO-d6) δ[ppm]: 3.849 (0.45), 3.875 (16.00), 4.491 (0.97), 4.590 (0.43), 7.244 (0.61), 7.260 (0.47), 7.277 (0.47), 7.291 (1.32), 7.308 (3.01), 7.326 (2.14), 7.956 (2.10), 7.975 (2.01), 8.058 (1.29).

Intermediate 204

Methyl 3-oxo-8-(trifluoromethyl)-2,3-dihydro[1,2,4]triazolo[4,3-a]pyridine-5-carboxylate

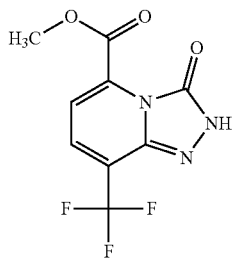

Methyl 6-hydrazino-5-(trifluoromethyl)pyridine-2-carboxylate (1.09 g, 75% purity, 3.48 mmol) was dissolved in THF (30 ml), and 1,1-carbonyldiimidazole (1.01 g, 6.26 mmol) was added at room temperature while stirring. The reaction mixture was stirred at room temperature overnight. The reaction mixture was admixed with water and ethyl acetate, and the organic phase was removed, washed with water and saturated aqueous sodium chloride solution, dried over sodium sulphate, filtered and concentrated. 1.38 g (>100% of theory) of the title compound were obtained.

LC-MS (Method 3): $R_t$=1.07 min; MS (ESIpos): m/z=262 [M+H]$^+$

Intermediate 205 tert-Butyl 6-chloro-5-methylpyridine-2-carboxylate

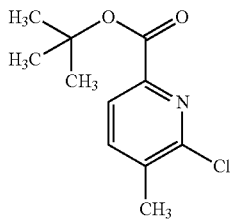

6-Chloro-5-methylpyridine-2-carboxylic acid (2.10 g, 12.2 mmol) was dissolved in pyridine (8.4 ml) and tert-butanol (42 ml, 440 mmol), and 4-methylbenzenesulphonyl chloride (4.67 g, 24.5 mmol) was added. The reaction mixture was stirred at room temperature for 3 h and diluted with saturated aqueous sodium hydrogencarbonate solution and dichloromethane. The organic phase was removed and the aqueous phase was extracted with dichloromethane. The combined organic phases were washed with saturated aqueous sodium chloride solution, dried over sodium sulphate and filtered, and the filtrate was concentrated. 2.50 g (>100%) of the title compound were obtained.

$^1$H-NMR (400 MHz, DMSO-d6) δ [ppm]: 1.552 (16.00), 7.901 (0.52), 7.920 (1.04), 7.959 (0.77), 7.978 (0.43).

Intermediate 206 tert-Butyl 6-{1-[(benzyloxy)carbonyl]hydrazino}-5-methylpyridine-2-carboxylate

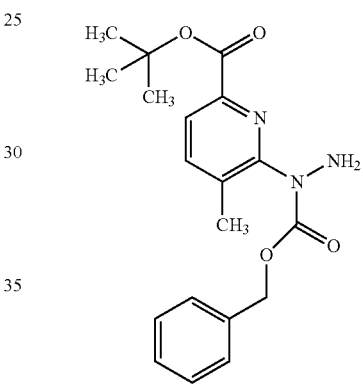

Under argon, tert-butyl 6-chloro-5-methylpyridine-2-carboxylate (2.50 g, 11.0 mmol) and benzyl hydrazinecarboxylate (3.28 g, 19.8 mmol) were dissolved in toluene (50 ml), and tris(dibenzylideneacetone)dipalladium-chloroform complex (568 mg, 549 µmol), caesium carbonate (4.29 g, 13.2 mmol) and 1,1'-bis(diphenylphosphino)ferrocene (609 mg, 1.10 mmol) were added. The reaction mixture was stirred at 80° C. for 4 h and water and ethyl acetate were added. The organic phase was removed and the aqueous phase was extracted three times with ethyl acetate. The combined organic phases were washed with saturated aqueous sodium chloride solution, dried over magnesium sulphate and filtered, and the filtrate was concentrated. The residue was purified via column chromatography (SiO$_2$; eluent: isocratic, ethyl acetate/cyclohexane 30/70). The product-containing fractions were concentrated under reduced pressure, and 1.81 g (46% of theory) of the title compound were obtained.

LC-MS (Method 3): $R_t$=1.91 min; MS (ESIpos): m/z=358 [M+H]$^+$ $^1$H-NMR (400 MHz, DMSO-d6) δ[ppm]: 1.514 (16.00), 2.157 (1.85), 5.112 (1.13), 7.292 (0.85), 7.310 (1.16), 7.377 (0.57), 7.396 (0.48), 7.408 (0.70), 7.446 (0.50), 8.196 (0.45), 9.097 (0.44).

Intermediate 207 tert-Butyl 6-hydrazino-5-methylpyridine-2-carboxylate

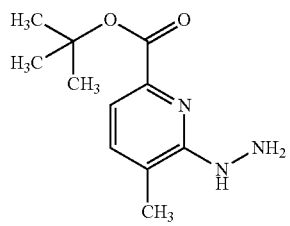 [SMILES: Cc1ccc(C(=O)OC(C)(C)C)nc1NN]

To an initial charge of palladium on charcoal (195 mg, 10% palladium) under argon were added tert-butyl 6-{1-[(benzyloxy)carbonyl]hydrazino}-5-methylpyridine-2-carboxylate (1.30 g, 3.64 mmol) in methanol (60 ml). The reaction mixture was stirred in a hydrogen atmosphere (1 bar) at room temperature for 5 h. The suspension was diluted with methanol and filtered through kieselguhr and washed through with methanol. The solvent was removed under reduced pressure, and 837 mg (99% of theory) of the title compound were obtained.

LC-MS (Method 4): $R_t$=0.50 min; MS (ESIpos): m/z=224 [M+H]

$^1$H-NMR (400 MHz, DMSO-d6) δ[ppm]: 1.527 (16.00), 1.548 (1.20), 2.080 (4.20), 4.258 (1.00), 7.174 (0.76), 7.193 (0.93), 7.343 (0.70), 7.361 (0.59), 7.420 (0.64).

Intermediate 208 tert-Butyl 8-methyl-3-oxo-2,3-dihydro[1,2,4]triazolo[4,3-a]pyridine-5-carboxylate

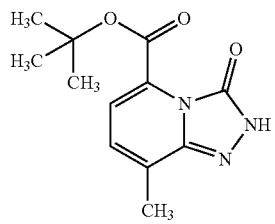

tert-Butyl 6-hydrazino-5-methylpyridine-2-carboxylate (1.18 g, 5.27 mmol) was dissolved in THF (100 ml), and 1,1-carbonyldiimidazole (1.03 g, 6.32 mmol) was added at room temperature while stirring. The reaction mixture was heated under reflux for 1.5 h. The reaction mixture was admixed with water and ethyl acetate, and basified with saturated aqueous sodium hydrogencarbonate solution. The organic phase was removed and the aqueous phase was extracted three times with ethyl acetate. The combined organic phases were washed with saturated aqueous sodium chloride solution, dried over magnesium sulphate and filtered. The filtrate was concentrated and the residue was purified via column chromatography (SiO$_2$; eluent: cyclohexane/ethyl acetate 70:30 to 50:50). The product-containing fractions were concentrated under reduced pressure, and 800 mg (61% of theory) of the title compound were obtained.

LC-MS (Method 4): $R_t$=0.71 min; MS (ESIneg): m/z=248 [M–H]$^-$ $^1$H-NMR (400 MHz, DMSO-d6) δ[ppm]: 1.529 (16.00), 2.245 (3.28), 6.683 (0.78), 6.700 (0.88), 6.940 (0.50), 6.943 (0.51), 6.957 (0.46), 6.960 (0.46), 12.505 (0.46).

Intermediate 209 tert-Butyl (5RS,8RS)-8-methyl-3-oxo-2,3,5,6,7,8-hexahydro[1,2,4]triazolo[4,3-a]pyridine-5-carboxylate (Diastereomer Mixture; 4 Isomers)

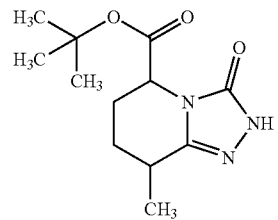 [SMILES: CC1CCC(C(=O)OC(C)(C)C)n2c1n[nH]c2=O]

tert-Butyl 8-methyl-3-oxo-2,3-dihydro[1,2,4]triazolo[4,3-a]pyridine-5-carboxylate (200 mg, 802 μmol) and palladium on charcoal (40 mg, 10% palladium) were suspended in methanol (12 ml), and the mixture was stirred at room temperature in a hydrogen atmosphere (3 bar) for 24 h. The reaction mixture was filtered through kieselguhr and washed with dichloromethane/methanol 9/1. The filtrate was concentrated and the residue was stirred with ethyl acetate for 30 min, then filtered and concentrated. The residue was purified via preparative HPLC (Chromatorex C18, 10 μm, 125 mm×30 mm; eluent: acetonitrile/water gradient). The product-containing fractions were concentrated under reduced pressure, and 150 mg (74% of theory) of the title compound were obtained as a mixture of diastereomers.

LC-MS (Method 4): $R_t$=0.67 min; MS (ESIpos): m/z=254 [M]

$^1$H-NMR (400 MHz, DMSO-d6) δ [ppm]: 1.184 (2.53), 1.201 (2.50), 1.396 (16.00), 1.409 (0.40), 2.096 (0.48), 2.103 (0.44), 2.108 (0.52), 4.363 (0.46), 11.396 (0.58).

Intermediate 210

Methyl (5S)-2-{[3-fluoro-2-(trifluoromethyl)pyridin-4-yl]methyl}-3-oxo-2,5,6,7-tetrahydro-3H-pyrrolo[2,1-c][1,2,4]triazole-5-carboxylate

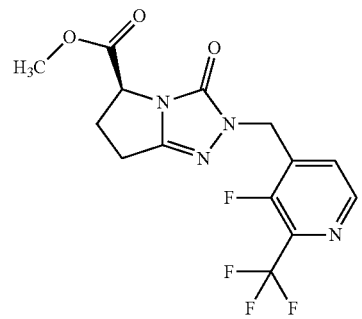 [SMILES: COC(=O)[C@@H]1CCc2nn(Cc3ccnc(C(F)(F)F)c3F)c(=O)n21]

Methyl (5S)-3-oxo-2,5,6,7-tetrahydro-3H-pyrrolo[2,1-c][1,2,4]triazole-5-carboxylate (150 mg, 819 μmol) was initially charged in acetonitrile (8.2 ml). Caesium carbonate (400 mg, 1.23 mmol) and 4-(chloromethyl)-3-fluoro-2-(trifluoromethyl)pyridine hydrochloride (231 mg, 860 µmol) were subsequently added. After stirring at room temperature overnight, water and ethyl acetate were added to the reaction mixture. The organic phase was removed, washed with saturated aqueous sodium chloride solution, dried over sodium sulphate and filtered, and the filtrate was concentrated. 318 mg (75% purity, 81% of theory) of the title compound were obtained.

LC-MS (Method 3): $R_t$=1.39 min; MS (ESIpos): m/z=361 [M+H]$^+$

Intermediate 211 tert-Butyl (5S)-2-(cyclopropylmethyl)-3-oxo-2,3,5,6,7,8-hexahydro[1,2,4]triazolo[4,3-a]pyridine-5-carboxylate

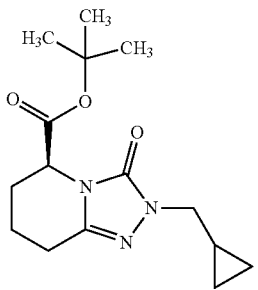 [SMILES: CC(C)(C)OC(=O)[C@@H]1CCCc2nn(CC3CC3)c(=O)n21]

tert-Butyl (5S)-3-oxo-2,3,5,6,7,8-hexahydro[1,2,4]triazolo[4,3-a]pyridine-5-carboxylate (150 mg, 627 µmol) was initially charged in acetonitrile (9.0 ml). Caesium carbonate (633 mg, 1.94 mmol) and (bromomethyl)cyclopropane (130 µl, 1.4 mmol) were subsequently added. After stirring at room temperature over the weekend, the reaction mixture was concentrated under reduced pressure. Water and ethyl acetate were added to the residue. The organic phase was removed and the aqueous phase was extracted three times with ethyl acetate. The combined organic phases were dried over sodium sulphate and filtered, and the filtrate was concentrated. 175 mg (95% of theory) of the title compound were obtained.

LC-MS (Method 4): $R_t$=0.81 min; MS (ESIpos): m/z=294 [M+H]$^+$ $^1$H-NMR (400 MHz, DMSO-d6) δ[ppm]: 0.261 (0.23), 0.273 (0.89), 0.286 (0.95), 0.298 (0.30), 0.323 (0.07), 0.427 (0.26), 0.437 (0.75), 0.441 (0.75), 0.457 (0.80), 0.461 (0.73), 0.472 (0.20), 0.527 (0.08), 0.545 (0.08), 1.055 (0.19), 1.072 (0.29), 1.091 (0.18), 1.241 (0.08), 1.402 (16.00), 1.416 (1.49), 1.491 (0.17), 1.526 (0.18), 1.558 (0.11), 1.807 (0.21), 1.830 (0.18), 1.841 (0.19), 1.988 (0.08), 2.048 (0.56), 2.060 (0.53), 2.070 (0.37), 2.082 (0.20), 2.089 (0.20), 2.097 (0.19), 2.500 (5.48), 2.565 (0.30), 2.578 (0.30), 2.592 (0.24), 2.628 (0.24), 2.639 (0.41), 2.651 (0.25), 2.670 (0.16), 2.681 (0.19), 3.485 (1.60), 3.502 (1.57), 4.379 (0.39), 4.389 (0.43), 4.394 (0.55), 4.404 (0.39).

Intermediate 212

Ethyl (5RS,7RS)-2-[(6-chloropyridin-3-yl)methyl]-3-oxo-7-(trifluoromethyl)-2,3,5,6,7,8-hexahydro[1,2,4]triazolo[4,3-a]pyridine-5-carboxylate (Diastereomer Mixture; 4 Isomers)

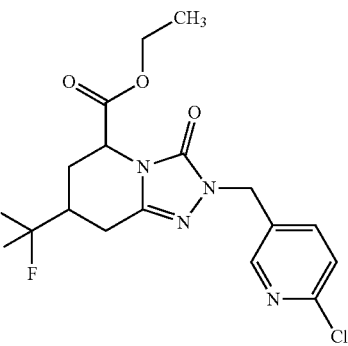

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (1.07 g, 3.83 mmol) was initially charged in acetonitrile (40 ml). Caesium carbonate (1.87 g, 5.75 mmol) and 2-chloro-5-(chloromethyl)pyridine (652 mg, 4.02 mmol) were subsequently added. After stirring at room temperature overnight, the reaction mixture was filtered and ethyl acetate was added. The filtrate was washed with water and saturated aqueous sodium chloride solution, dried over sodium sulphate and filtered, and the filtrate was concentrated. The residue was purified via column chromatography (silica gel, eluent: cyclohexane/ethyl acetate gradient 7/1, 0/1). The product-containing fractions were concentrated under reduced pressure, and 604 mg (89% purity, 34% of theory) of the title compound were obtained.

LC-MS (Method 3): $R_t$=1.67 min; MS (ESIpos): m/z=405 [M+H]$^+$ $^1$H-NMR (400 MHz, DMSO-d6) δ [ppm]: −0.008 (1.54), 0.008 (1.04), 1.164 (7.65), 1.182 (16.00), 1.194 (4.45), 1.199 (8.79), 1.212 (7.15), 1.229 (3.56), 1.305 (0.41), 1.398 (0.87), 1.797 (0.72), 1.828 (0.72), 1.988 (0.50), 2.256 (0.50), 2.275 (1.17), 2.291 (1.41), 2.304 (1.85), 2.318 (3.16), 2.346 (0.60), 2.523 (2.04), 2.678 (1.08), 2.708 (2.69), 2.743 (2.49), 2.760 (1.08), 2.768 (1.27), 2.778 (1.30), 2.808 (1.12), 2.881 (0.66), 2.887 (0.74), 2.921 (0.45), 2.927 (0.46), 2.952 (0.42), 2.978 (1.67), 3.008 (1.40), 3.059 (0.41), 4.114 (0.58), 4.132 (1.58), 4.141 (1.19), 4.150 (1.82), 4.159 (3.29), 4.168 (1.29), 4.177 (3.81), 4.191 (2.65), 4.196 (2.34), 4.208 (3.20), 4.215 (0.99), 4.226 (2.75), 4.235 (1.45), 4.243 (0.95), 4.252 (1.31), 4.270 (0.44), 4.509 (0.78), 4.524 (0.89), 4.537 (0.85), 4.551 (0.71), 4.816 (1.74), 4.822 (2.13), 4.829 (1.91), 4.836 (1.64), 4.910 (1.22), 4.922 (5.15), 4.950 (6.09), 4.959 (5.78), 4.999 (0.74), 5.754 (2.32), 7.521 (4.68), 7.541 (5.67), 7.713 (2.49), 7.719 (2.49), 7.734 (2.52), 7.740 (2.40), 7.751 (0.94), 7.758 (0.91), 8.315 (2.85), 8.321 (2.72), 8.333 (1.28), 8.339 (1.26).

Intermediate 213

Ethyl (5RS,7RS)-3-oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylate (Diastereomer Mixture; 4 Isomers)

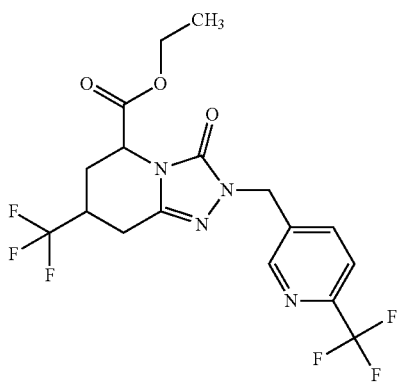 [SMILES: CCOC(=O)C1CC(C(F)(F)F)Cc2nn(Cc3ccc(C(F)(F)F)nc3)c(=O)n21]

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (570 mg, 2.04 mmol) was initially charged in acetonitrile (20 ml). Caesium carbonate (998 mg, 3.06 mmol) and 5-(chloromethyl)-2-(trifluoromethyl)pyridine (419 mg, 2.14 mmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. The residue was purified via column chromatography (silica gel, eluent: cyclohexane/ethyl acetate gradient 4/5, 1/16). The product-containing fractions were concentrated under reduced pressure, and 809 mg (86% of theory) of the title compound were obtained.

LC-MS (Method 1): $R_t$=1.25 min; MS (ESIpos): m/z=439 [M+H]$^+$ $^1$H-NMR (400 MHz, DMSO-d6) δ [ppm]: −0.008 (1.17), 0.008 (1.20), 1.159 (7.54), 1.177 (16.00), 1.192 (8.78), 1.194 (10.17), 1.210 (11.69), 1.228 (5.67), 1.398 (1.08), 1.776 (0.63), 1.806 (1.30), 1.838 (1.33), 1.867 (0.70), 1.908 (3.87), 1.988 (2.50), 2.282 (0.98), 2.298 (1.11), 2.311 (1.39), 2.325 (3.55), 2.366 (0.86), 2.670 (0.70), 2.687 (0.82), 2.717 (2.44), 2.746 (2.57), 2.777 (1.52), 2.787 (1.81), 2.817 (1.77), 2.890 (1.01), 2.896 (1.24), 2.930 (0.63), 2.936 (0.70), 2.986 (1.71), 3.017 (1.46), 4.021 (0.60), 4.038 (0.60), 4.117 (0.41), 4.135 (1.36), 4.144 (0.92), 4.152 (1.52), 4.161 (3.26), 4.176 (3.33), 4.181 (4.21), 4.194 (3.83), 4.199 (3.26), 4.211 (3.58), 4.217 (1.14), 4.229 (2.63), 4.238 (1.36), 4.247 (0.82), 4.256 (1.27), 4.274 (0.41), 4.521 (1.33), 4.536 (1.55), 4.549 (1.52), 4.563 (1.33), 4.831 (1.68), 4.838 (2.12), 4.853 (1.68), 4.931 (2.38), 5.036 (1.05), 5.048 (8.17), 5.077 (5.51), 5.087 (5.39), 5.127 (0.67), 7.913 (1.93), 7.933 (12.67), 7.950 (2.57), 7.954 (2.63), 7.974 (0.82), 8.661 (3.58), 8.679 (2.53).

Intermediate 214

Ethyl (5RS,7RS)-2-{[3-fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylate (Diastereomer Mixture; 4 Isomers)

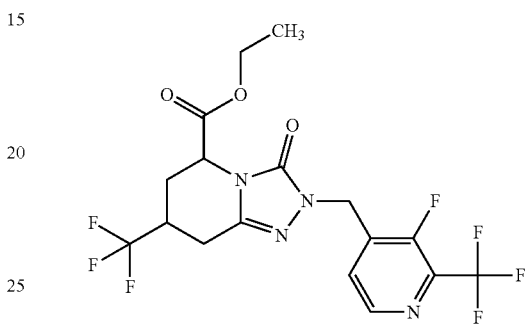

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (500 mg, 83% purity, 1.49 mmol) was initially charged in acetonitrile (15 ml). Caesium carbonate (1.21 g, 3.72 mmol) and 4-(chloromethyl)-3-fluoro-2-(trifluoromethyl)pyridine hydrochloride (420 mg, 1.56 mmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. The residue was purified via column chromatography (silica gel, eluent: cyclohexane/ethyl acetate gradient 7/1, 1/16). The product-containing fractions were concentrated under reduced pressure, and 440 mg (65% of theory) of the title compound were obtained.

LC-MS (Method 3): $R_t$=1.92 min; MS (ESIpos): m/z=457 [M+H]$^+$ $^1$H-NMR (400 MHz, DMSO-d6) δ [ppm]: 0.008 (2.05), 1.157 (4.28), 1.170 (8.73), 1.175 (8.65), 1.187 (16.00), 1.192 (6.64), 1.205 (7.99), 1.210 (4.00), 1.228 (1.75), 1.398 (2.75), 1.819 (0.47), 1.850 (0.50), 1.988 (13.53), 2.253 (0.43), 2.269 (0.50), 2.288 (1.23), 2.303 (1.42), 2.317 (1.87), 2.332 (3.90), 2.365 (0.95), 2.523 (2.37), 2.670 (0.46), 2.696 (0.97), 2.709 (0.48), 2.726 (2.59), 2.762 (2.99), 2.798 (1.01), 2.828 (0.73), 2.908 (0.46), 2.999 (2.03), 3.028 (1.70), 4.003 (1.18), 4.021 (3.36), 4.038 (3.28), 4.056 (1.09), 4.123 (0.48), 4.140 (1.43), 4.149 (1.10), 4.158 (1.74), 4.167 (2.84), 4.175 (1.44), 4.185 (2.86), 4.192 (1.17), 4.199 (1.96), 4.216 (2.83), 4.226 (0.79), 4.234 (2.59), 4.243 (1.39), 4.252 (0.88), 4.261 (1.25), 4.532 (0.48), 4.547 (0.51), 4.560 (0.50), 4.574 (0.43), 4.848 (2.48), 4.857 (2.20), 5.098 (2.28), 5.134 (12.28), 7.594 (1.95), 7.607 (3.49), 7.620 (1.88), 7.638 (0.47), 7.650 (0.81), 7.663 (0.44), 8.581 (4.60), 8.593 (4.39).

Intermediate 215 tert-Butyl (5S)-2-{[6-(difluoromethyl)pyridin-3-yl]methyl}-3-oxo-2,3,5,6,7,8-hexahydro[1,2,4]triazolo[4,3-a]pyridine-5-carboxylate

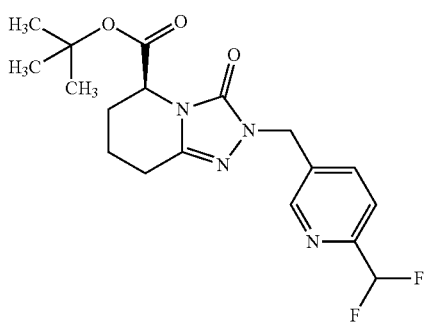 [SMILES: CC(C)(C)OC(=O)[C@@H]1CCCc2nn(Cc3ccc(C(F)F)nc3)c(=O)n21]

tert-Butyl (5S)-3-oxo-2,3,5,6,7,8-hexahydro[1,2,4]triazolo[4,3-a]pyridine-5-carboxylate (239 mg, 999 µmol) was initially charged in acetonitrile (10 ml). Subsequently, caesium carbonate (488 mg, 1.50 mmol) and 5-(chloromethyl)-2-(difluoromethyl)pyridine (186 mg, 1.05 mmol) were added. The reaction mixture was stirred at room temperature overnight. Caesium carbonate (326 mg, 999 µmol) was added again and the mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. 395 mg (83% purity, 86% of theory) of the title compound were obtained.

LC-MS (Method 3): $R_t$=1.58 min; MS (ESIpos): m/z=381 [M+H]$^+$

Intermediate 216

Ethyl (5RS,7RS)-2-[(5-chloro-3-fluoropyridin-2-yl)methyl]-3-oxo-7-(trifluoromethyl)-2,3,5,6,7,8-hexahydro[1,2,4]triazolo[4,3-a]pyridine-5-carboxylate (Diastereomer Mixture; 4 Isomers)

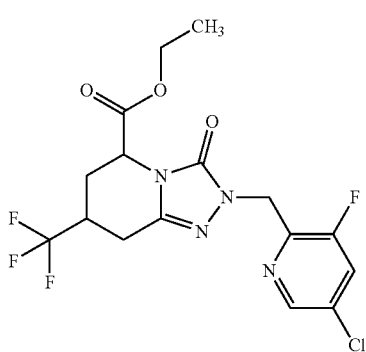 [SMILES: CCOC(=O)C1CC(C(F)(F)F)Cc2nn(Cc3ncc(Cl)cc3F)c(=O)n21]

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (100 mg, 358 µmol) was initially charged in acetonitrile (4.0 ml). Caesium carbonate (175 mg, 537 µmol) and 5-chloro-2-(chloromethyl)-3-fluoropyridine (67.7 mg, 376 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. 135 mg (89% of theory) of the title compound were obtained.

LC-MS (Method 4): $R_t$=0.91 min; MS (ESIpos): m/z=423 [M+H]$^+$

Intermediate 217

Ethyl (5RS,7RS)-2-[(5-chloropyridin-3-yl)methyl]-3-oxo-7-(trifluoromethyl)-2,3,5,6,7,8-hexahydro[1,2,4]triazolo[4,3-a]pyridine-5-carboxylate (Diastereomer Mixture; 4 Isomers)

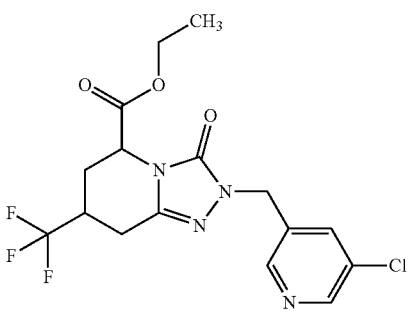 [SMILES: CCOC(=O)C1CC(C(F)(F)F)Cc2nn(Cc3cncc(Cl)c3)c(=O)n21]

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (100 mg, 358 mol) was initially charged in acetonitrile (4.0 ml). Caesium carbonate (175 mg, 537 µmol) and 3-chloro-5-(chloromethyl)pyridine (60.9 mg, 376 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. 128 mg (72% purity, 64% of theory) of the title compound were obtained.

LC-MS (Method 4): $R_t$=0.86 min; MS (ESIpos): m/z=405 [M+H]$^+$

Intermediate 218 tert-Butyl (5S)-2-(4-bromobenzyl)-3-oxo-2,3,5,6,7,8-hexahydro[1,2,4]triazolo[4,3-a]pyridine-5-carboxylate

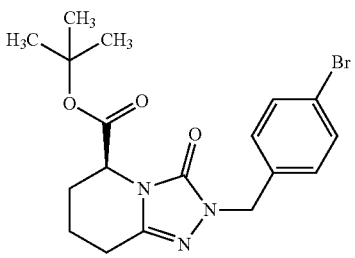 [SMILES: CC(C)(C)OC(=O)[C@@H]1CCCc2nn(Cc3ccc(Br)cc3)c(=O)n21]

tert-Butyl (5S)-3-oxo-2,3,5,6,7,8-hexahydro[1,2,4]triazolo[4,3-a]pyridine-5-carboxylate (150 mg, 627 µmol) was initially charged in acetonitrile (8.0 ml). Caesium carbonate (306 mg, 940 µmol) and 1-bromo-4-(chloromethyl)benzene (135 mg, 658 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. 201 mg (74% of theory) of the title compound were obtained.

LC-MS (Method 3): $R_t$=1.94 min; MS (ESIpos): m/z=408 [M+H]$^+$

Intermediate 219 tert-Butyl (5S)-2-(3-bromobenzyl)-3-oxo-2,3,5,6,7,8-hexahydro[1,2,4]triazolo[4,3-a]pyridine-5-carboxylate

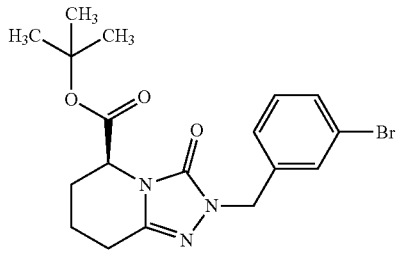 [SMILES: CC(C)(C)OC(=O)[C@@H]1CCCc2nn(Cc3cccc(Br)c3)c(=O)n21]

tert-Butyl (5S)-3-oxo-2,3,5,6,7,8-hexahydro[1,2,4]triazolo[4,3-a]pyridine-5-carboxylate (150 mg, 627 µmol) was initially charged in acetonitrile (8.0 ml). Caesium carbonate (306 mg, 940 µmol) and 1-bromo-3-(chloromethyl)benzene (84 µl, 660 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. 256 mg (94% of theory) of the title compound were obtained.

LC-MS (Method 3): $R_t$=1.94 min; MS (ESIpos): m/z=408 [M+H]$^+$

Intermediate 220 tert-Butyl (5S)-2-(4-bromo-2-fluorobenzyl)-3-oxo-2,3,5,6,7,8-hexahydro[1,2,4]triazolo[4,3-a]pyridine-5-carboxylate

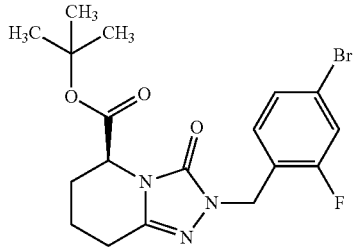 [SMILES: CC(C)(C)OC(=O)[C@@H]1CCCc2nn(Cc3ccc(Br)cc3F)c(=O)n21]

tert-Butyl (5S)-3-oxo-2,3,5,6,7,8-hexahydro[1,2,4]triazolo[4,3-a]pyridine-5-carboxylate (150 mg, 627 µmol) was initially charged in acetonitrile (8.0 ml). Caesium carbonate (306 mg, 940 µmol) and 4-bromo-1-(chloromethyl)-2-fluorobenzene (147 mg, 658 µmol) were subsequently added. The reaction mixture was stirred at room temperature overnight. 4-Bromo-1-(chloromethyl)-2-fluorobenzene (30 mg, 132 µmol) and caesium carbonate (41 mg, 125 µmol) were again added and the mixture was stirred for a further 6 hours. Ethyl acetate was added to the reaction mixture, the organic phase was washed with water and saturated aqueous sodium chloride solution, dried over sodium sulphate and filtered, and the filtrate was concentrated. The residue was purified via column chromatography (silica gel, eluent: cyclohexane/ ethyl acetate gradient 19/1, 0/1). The product-containing fractions were concentrated under reduced pressure, and 135 mg (51% of theory) of the title compound were obtained.

LC-MS (Method 3): $R_t$=2.01 min; MS (ESIpos): m/z=426 [M+H]$^+$ $^1$H-NMR (400 MHz, DMSO-d6) δ [ppm]: −0.174 (0.09), −0.033 (0.69), −0.017 (0.63), 0.121 (0.08), 1.132 (0.07), 1.150 (0.14), 1.167 (0.07), 1.208 (0.08), 1.368 (16.00), 1.445 (0.17), 1.480 (0.18), 1.773 (0.20), 1.795 (0.17), 1.807 (0.17), 1.963 (0.26), 2.029 (0.55), 2.037 (0.48), 2.063 (0.18), 2.071 (0.16), 2.303 (0.07), 2.578 (0.22), 2.589 (0.38), 2.601 (0.24), 2.620 (0.13), 2.631 (0.19), 2.644 (0.16), 3.995 (0.06), 4.013 (0.06), 4.391 (0.38), 4.406 (0.58), 4.416 (0.37), 4.785 (0.08), 4.826 (1.67), 4.867 (0.08), 7.187 (0.37), 7.208 (0.80), 7.228 (0.46), 7.380 (0.50), 7.384 (0.51), 7.401 (0.41), 7.405 (0.42), 7.522 (0.46), 7.527 (0.43), 7.546 (0.47), 7.550 (0.44).

Intermediate 221 tert-Butyl (5S)-3-oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylate (Isomer 1)

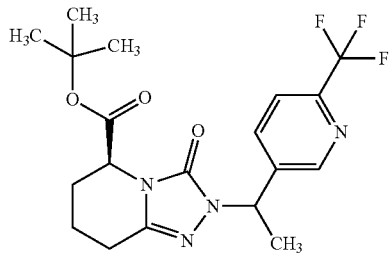 [SMILES: CC(c1ccc(C(F)(F)F)nc1)n1nc2n(c1=O)[C@H](C(=O)OC(C)(C)C)CCC2]

tert-Butyl (5S)-3-oxo-2,3,5,6,7,8-hexahydro[1,2,4]triazolo[4,3-a]pyridine-5-carboxylate (201 mg, 840 µmol) was initially charged in acetonitrile (10 ml). Caesium carbonate (410 mg, 1.26 mmol) and 5-[(1 RS)-1-bromoethyl]-2-(trifluoromethyl)pyridine (320 mg, 70% purity, 882 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. The residue was purified via column chromatography (silica gel, eluent: cyclohexane/ethyl acetate gradient 9/1, 0/1). After the separation, 86.9 mg (24% of theory) of isomer 1, which elutes first, and 97.7 mg (26% of theory) of isomer 2, which elutes later, were isolated.

Isomer 1:

LC-MS (Method 3): $R_t$=1.84 min; MS (ESIpos): m/z=413 [M+H]$^+$ $^1$H-NMR (400 MHz, DMSO-d6) δ [ppm]: −0.149 (0.21), −0.024 (0.08), −0.008 (1.59), 0.008 (1.85), 0.146 (0.21), 1.301 (16.00), 1.382 (0.59), 1.398 (0.12), 1.405 (0.14), 1.457 (0.14), 1.467 (0.17), 1.479 (0.16), 1.489 (0.16), 1.501 (0.17), 1.514 (0.13), 1.527 (0.10), 1.686 (2.25), 1.703 (2.28), 1.820 (0.20), 1.831 (0.19), 1.842 (0.18), 1.852 (0.17), 1.864 (0.15), 1.988 (0.09), 2.057 (0.33), 2.067 (0.63), 2.080 (0.53), 2.099 (0.21), 2.107 (0.17), 2.322 (0.23), 2.327 (0.35), 2.332 (0.25), 2.366 (0.30), 2.522 (0.88), 2.557 (0.36), 2.562 (0.22), 2.572 (0.19), 2.587 (0.39), 2.602 (0.29), 2.614 (0.29), 2.627 (0.22), 2.665 (0.48), 2.669 (0.52), 2.674 (0.60), 2.687 (0.25), 2.710 (0.40), 2.718 (0.20), 2.731 (0.10), 4.432 (0.37), 4.446 (0.62), 4.456 (0.38), 5.520 (0.13), 5.536 (0.46), 5.554 (0.46), 5.572 (0.14), 7.906 (0.63), 7.927 (0.90), 8.015 (0.45), 8.019 (0.46), 8.040 (0.33), 8.699 (0.63), 8.703 (0.63).

Intermediate 222 tert-Butyl (5S)-3-oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylate (Isomer 2)

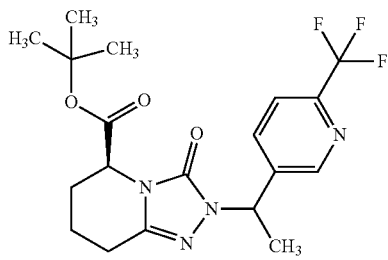

tert-Butyl (5S)-3-oxo-2,3,5,6,7,8-hexahydro[1,2,4]triazolo[4,3-a]pyridine-5-carboxylate (201 mg, 840 μmol) was initially charged in acetonitrile (10 ml). Caesium carbonate (410 mg, 1.26 mmol) and 5-[(1 RS)-1-bromoethyl]-2-(trifluoromethyl)pyridine (320 mg, 70% purity, 882 μmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. The residue was purified via column chromatography (silica gel, eluent: cyclohexane/ethyl acetate gradient 9/1, 0/1). After the separation, 86.9 mg (24% of theory) of isomer 1, which elutes first, and 97.7 mg (26% of theory) of isomer 2, which elutes later, were isolated.

Isomer 2:

LC-MS (Method 3): $R_t$=1.86 min; MS (ESIpos): m/z=413 [M+H]$^+$ $^1$H-NMR (400 MHz, DMSO-d6) δ [ppm]: −0.014 (0.28), 1.152 (0.06), 1.169 (0.13), 1.187 (0.06), 1.240 (0.07), 1.372 (0.22), 1.401 (16.00), 1.480 (0.16), 1.503 (0.17), 1.515 (0.18), 1.529 (0.13), 1.557 (0.09), 1.680 (2.33), 1.698 (2.34), 1.809 (0.19), 1.820 (0.18), 1.831 (0.17), 1.842 (0.17), 1.983 (0.16), 2.049 (0.56), 2.061 (0.46), 2.089 (0.16), 2.322 (0.06), 2.518 (0.24), 2.560 (0.34), 2.575 (0.24), 2.587 (0.25), 2.602 (0.20), 2.659 (0.23), 2.670 (0.39), 2.682 (0.22), 2.712 (0.19), 2.724 (0.10), 3.093 (0.08), 4.399 (0.37), 4.414 (0.62), 4.424 (0.36), 4.635 (0.06), 4.650 (0.07), 5.511 (0.14), 5.529 (0.53), 5.547 (0.48), 5.564 (0.14), 7.881 (0.67), 7.901 (0.90), 8.011 (0.48), 8.016 (0.48), 8.037 (0.36), 8.723 (0.69).

Intermediate 223 tert-Butyl (5S)-3-oxo-2-{[cis/trans-4-(trifluoromethyl)cyclohexyl]methyl}-2,3,5,6,7,8-hexahydro[1,2,4]triazolo[4,3-a]pyridine-5-carboxylate (Diastereomer Mixture; 2 Isomers)

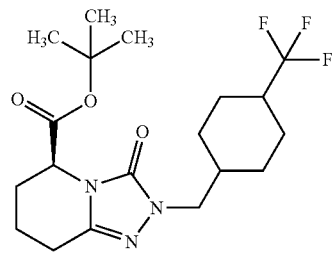 [SMILES: CC(C)(C)OC(=O)[C@@H]1CCCc2nn(CC3CCC(C(F)(F)F)CC3)c(=O)n21]

tert-Butyl (5S)-3-oxo-2,3,5,6,7,8-hexahydro[1,2,4]triazolo[4,3-a]pyridine-5-carboxylate (450 mg, 1.88 mmol) was initially charged in acetonitrile (20 ml). Caesium carbonate (1.90 g, 5.83 mmol) and cis/trans-1-(bromomethyl)-4-(trifluoromethyl)cyclohexane (660 μl, 4.1 mmol) were subsequently added and the reaction mixture was stirred at room temperature overnight. cis/trans-1-(Bromomethyl)-4-(trifluoromethyl)cyclohexane (660 μl, 4.1 mmol) and caesium carbonate (613 mg, 1.88 mmol) were again added and the mixture was stirred over the weekend. The reaction mixture was filtered and ethyl acetate was added. The organic phase was washed with water and saturated aqueous sodium chloride solution, dried over sodium sulphate and filtered, and the filtrate was concentrated. The residue was purified via column chromatography (silica gel; eluent: dichloromethane/methanol 99/1, 9/1). Purification was effected once more via column chromatography (silica gel; eluent: cyclohexane/ethyl acetate 11:1, 1:2). The product-containing fractions were concentrated under reduced pressure, and 112 mg (14% of theory) of the title compound were obtained.

LC-MS (Method 3): $R_t$=2.08 min; MS (ESIpos): m/z=404 [M+H]$^+$

Intermediate 224

(5S)-5-{[(2S)-2-(Hydroxymethyl)pyrrolidin-1-yl]carbonyl}-2-(4-methylbenzyl)-5,6,7,8-tetrahydro[1,2,4]triazolo[4,3-a]pyridin-3(2H)-one

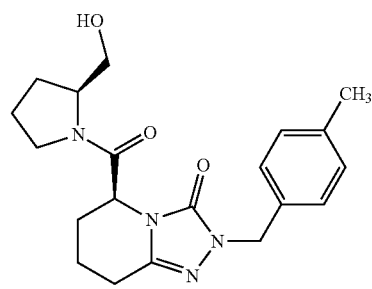 [SMILES: Cc1ccc(Cn2nc3n(c2=O)[C@H](C(=O)N2CCC[C@H]2CO)CCC3)cc1]

(5S)-2-(4-Methylbenzyl)-3-oxo-2,3,5,6,7,8-hexahydro[1,2,4]triazolo[4,3-a]pyridine-5-carboxylic acid (100 mg, 348 µmol) was initially charged in dichloromethane (2.0 ml) and DMF (4.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (85 µl, 490 µmol) were added. After stirring for 15 min, (2S)-pyrrolidin-2-ylmethanol (41 µl, 420 µmol) was added and the reaction mixture was stirred at room temperature for 1.5 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 83.1 mg (64% of theory) of the title compound were obtained.

LC-MS (Method 3): $R_t$=0.93 min; MS (ESIpos): m/z=371 [M+H]$^+$ $^1$H-NMR (400 MHz, DMSO-d6) δ [ppm]: −0.149 (1.74), −0.008 (16.00), 0.008 (12.83), 0.146 (1.58), 2.271 (2.57), 2.327 (2.72), 2.366 (2.42), 2.523 (7.55), 2.669 (2.57), 2.709 (2.42), 4.741 (1.13), 5.753 (3.40), 7.122 (1.66).

Intermediate 225

2-[(2S)-1-{[(5S)-2-(4-Methylbenzyl)-3-oxo-2,3,5,6,7,8-hexahydro[1,2,4]triazolo[4,3-a]pyridin-5-yl]carbonyl}pyrrolidin-2-yl]-2-oxoethyl Acetate

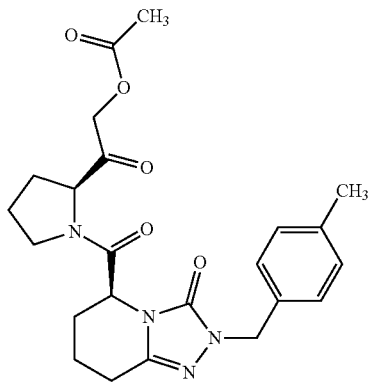 [SMILES: CC(=O)OCC(=O)[C@@H]1CCCN1C(=O)[C@@H]1CCCc2nn(Cc3ccc(C)cc3)c(=O)n21]

tert-Butyl (2S)-2-(acetoxyacetyl)pyrrolidine-1-carboxylate (189 mg, 696 µmol) was dissolved in dichloromethane (1 ml), trifluoroacetic acid (1 ml) was added and the mixture was stirred at room temperature for 1 h, then the volatile organic compounds were removed under reduced pressure. The crude product of (2S)-2-(acetoxyacetyl)pyrrolidine was converted further directly in the next stage.

(5S)-2-(4-Methylbenzyl)-3-oxo-2,3,5,6,7,8-hexahydro[1,2,4]triazolo[4,3-a]pyridine-5-carboxylic acid (100 mg, 348 µmol) was dissolved in dichloromethane (2 ml) and cooled to 0° C. 1-Chloro-N,N,2-trimethylprop-1-en-1-amine (64 µl, 490 µmol) was added and the mixture was stirred at 0° C. for a further 20 min. (2S)-2-(Acetoxyacetyl)pyrrolidine (crude product) was dissolved in dichloromethane (1 ml) and slowly added dropwise to the reaction mixture at 0° C., followed by N,N-diisopropylethylamine (180 µl, 1.0 mmol). After 5 min, the solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 112 mg (73% of theory) of the title compound were obtained.

LC-MS (Method 1): $R_t$=1.05 min; MS (ESIpos): m/z=441 [M+H]$^+$ $^1$H-NMR (400 MHz, DMSO-d6) δ [ppm]: −0.008 (2.75), 0.008 (1.89), 1.580 (0.46), 1.594 (0.46), 1.726 (0.58), 1.759 (0.48), 1.799 (0.53), 1.814 (0.75), 1.832 (0.76), 1.847 (0.76), 1.862 (0.49), 1.912 (0.68), 1.928 (1.30), 1.947 (1.68), 1.960 (1.27), 2.040 (1.43), 2.080 (16.00), 2.096 (4.78), 2.100 (1.50), 2.162 (0.56), 2.183 (0.63), 2.193 (0.66), 2.214 (0.65), 2.269 (11.51), 2.323 (0.52), 2.327 (0.68), 2.366 (0.59), 2.518 (2.35), 2.523 (2.26), 2.567 (1.05), 2.580 (0.71), 2.669 (0.65), 2.710 (0.55), 3.575 (0.79), 3.582 (0.56), 3.599 (0.99), 3.617 (0.43), 3.690 (0.46), 3.750 (0.45), 3.766 (0.94), 3.783 (0.53), 3.791 (0.71), 4.545 (1.05), 4.559 (1.17), 4.566 (1.15), 4.581 (1.01), 4.733 (4.26), 4.766 (0.86), 4.774 (0.45), 4.809 (4.21), 4.822 (5.23), 4.830 (1.60), 4.840 (0.86), 4.865 (1.73), 4.951 (1.12), 4.995 (0.62), 7.093 (0.92), 7.114 (7.45), 7.120 (6.87), 7.141 (0.89).

Intermediate 226

Methyl 3-oxo-8-(trifluoromethyl)-2-{[6-(trifluoromethyl)pyridin-3-yl]methyl}-2,3-dihydro[1,2,4]triazolo[4,3-a]pyridine-5-carboxylate

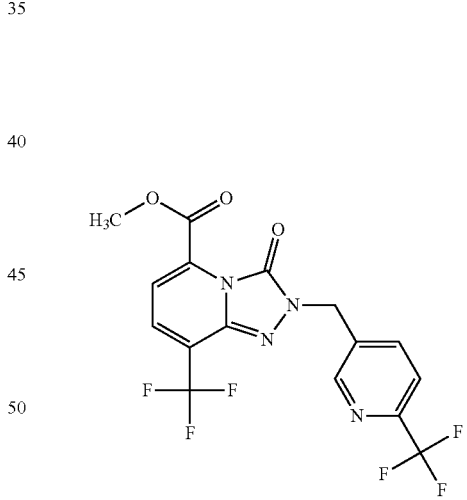

Methyl 3-oxo-8-(trifluoromethyl)-2,3-dihydro[1,2,4]triazolo[4,3-a]pyridine-5-carboxylate (50.0 mg, 191 µmol) was initially charged in acetonitrile (2.0 ml). Caesium carbonate (93.6 mg, 287 µmol) and 5-(chloromethyl)-2-(trifluoromethyl)pyridine (39.3 mg, 201 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. 86.9 mg (77% purity, 83% of theory) of the title compound were obtained.

LC-MS (Method 3): $R_t$=1.80 min; MS (ESIpos): m/z=421 [M+H]$^+$

Intermediate 227

Methyl 2-[(5-chloro-3-fluoropyridin-2-yl)methyl]-3-oxo-8-(trifluoromethyl)-2,3-dihydro[1,2,4]triazolo[4,3-a]pyridine-5-carboxylate

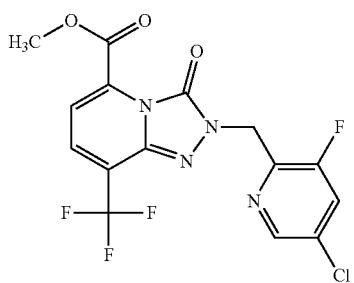 [SMILES: COC(=O)c1ccc(C(F)(F)F)c2nn(Cc3ncc(Cl)cc3F)c(=O)n12]

Methyl 3-oxo-8-(trifluoromethyl)-2,3-dihydro[1,2,4]triazolo[4,3-a]pyridine-5-carboxylate (150 mg, 574 µmol) was initially charged in acetonitrile (5.0 ml). Caesium carbonate (281 mg, 862 µmol) and 5-chloro-2-(chloromethyl)-3-fluoropyridine (109 mg, 603 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. The residue was purified via column chromatography (silica gel, eluent: cyclohexane/ethyl acetate gradient 7/1, 0/1). The product-containing fractions were concentrated under reduced pressure, and 87.5 mg (38% of theory) of the title compound were obtained.

LC-MS (Method 3): $R_t$=1.77 min; MS (ESIpos): m/z=405 [M+H]$^+$ $^1$H-NMR (400 MHz, DMSO-d6) δ[ppm]: −0.150 (0.63), −0.008 (5.70), 0.008 (5.37), 0.146 (0.68), 1.157 (0.41), 1.175 (0.84), 1.398 (1.64), 1.988 (1.53), 2.327 (0.95), 2.670 (1.01), 3.847 (0.65), 3.901 (16.00), 5.334 (4.58), 5.338 (4.66), 6.984 (1.72), 7.001 (1.74), 7.780 (1.39), 7.798 (1.39), 8.146 (1.28), 8.151 (1.34), 8.170 (1.25), 8.175 (1.34), 8.481 (1.50), 8.484 (1.50).

Intermediate 228 tert-Butyl (5RS,8RS)-8-methyl-2-(4-methylbenzyl)-3-oxo-2,3,5,6,7,8-hexahydro[1,2,4]triazolo[4,3-a]pyridine-5-carboxylate (Diastereomer Mixture; 4 Isomers)

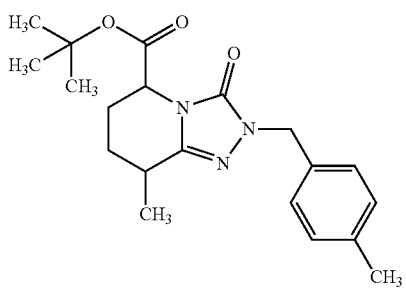 [SMILES: Cc1ccc(Cn2nc3n(c2=O)C(C(=O)OC(C)(C)C)CCC3C)cc1]

tert-Butyl (5RS,8RS)-8-methyl-3-oxo-2,3,5,6,7,8-hexahydro[1,2,4]triazolo[4,3-a]pyridine-5-carboxylate (diastereomer mixture, 4 isomers) (33.4 mg, 132 µmol) was initially charged in acetonitrile (5 ml). Caesium carbonate (51.6 mg, 158 µmol) and 1-(bromomethyl)-4-methylbenzene (25.6 mg, 138 µmol) were subsequently added. The reaction mixture was stirred at room temperature overnight, then 1-(bromomethyl)-4-methylbenzene (5 mg, 2.6 µmol) was added and the mixture was stirred for 2 h. Water and ethyl acetate were added to the reaction mixture. The organic phase was removed and the aqueous phase was extracted three times with ethyl acetate. The combined organic phases were washed with saturated aqueous sodium chloride solution, dried over sodium sulphate and filtered, and the filtrate was concentrated. 39.5 mg (79% of theory) of the title compound were obtained as a mixture of diastereomers.

LC-MS (Method 3): $R_t$=2.02 min; MS (ESIpos): m/z=358 [M+H]$^+$ $^1$H-NMR (400 MHz, DMSO-d6) δ [ppm]: −0.008 (1.06), 0.008 (0.92), 1.153 (0.40), 1.164 (2.69), 1.181 (2.84), 1.194 (0.43), 1.201 (0.63), 1.236 (0.88), 1.259 (0.60), 1.298 (0.42), 1.344 (0.64), 1.350 (0.72), 1.355 (1.41), 1.386 (16.00), 1.396 (3.32), 1.417 (0.68), 1.424 (0.49), 1.428 (0.55), 1.510 (0.69), 1.548 (0.87), 1.562 (0.66), 2.120 (0.63), 2.130 (0.54), 2.272 (5.05), 2.294 (0.49), 2.523 (0.91), 4.447 (0.54), 4.790 (1.10), 4.820 (1.08), 7.129 (6.94).

Intermediate 229 tert-Butyl (5RS,8RS)-8-methyl-3-oxo-2-{[6-(trifluoromethyl)pyridin-3-yl]methyl}-2,3,5,6,7,8-hexahydro[1,2,4]triazolo[4,3-a]pyridine-5-carboxylate (Diastereomer Mixture, 4 Isomers)

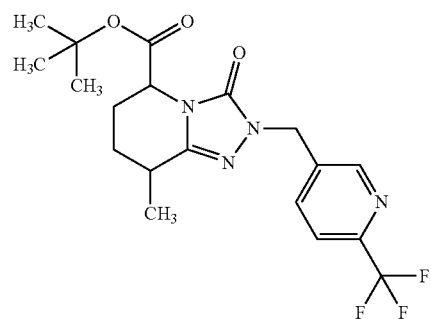 [SMILES: CC1CCC(C(=O)OC(C)(C)C)n2c1nn(Cc1ccc(C(F)(F)F)nc1)c2=O]

tert-Butyl (5RS,8RS)-8-methyl-3-oxo-2,3,5,6,7,8-hexahydro[1,2,4]triazolo[4,3-a]pyridine-5-carboxylate (diastereomer mixture, 4 isomers) (503 mg, 1.98 mmol) was initially charged in acetonitrile (20 ml). Caesium carbonate (970 mg, 2.98 mmol) and 5-(bromomethyl)-2-(trifluoromethyl)pyridine (500 mg, 2.08 mmol) were subsequently added. After stirring at room temperature overnight, the reaction mixture was stirred under reflux for 1 h. Water and ethyl acetate were added to the reaction mixture. The organic phase was removed and the aqueous phase was extracted three times with ethyl acetate. The combined organic phases were washed with saturated aqueous sodium chloride solution, dried over magnesium sulphate and filtered, and the filtrate was concentrated. 854 mg (90% purity, 94% of theory) of the title compound were obtained as a mixture of diastereomers.

LC-MS (Method 4): $R_t$=1.00 min; MS (ESIpos): m/z=413 [M+H]$^+$ $^1$H-NMR (400 MHz, DMSO-d6) δ [ppm]: 1.157 (0.41), 1.177 (3.04), 1.194 (3.00), 1.367 (16.00), 1.548 (0.40), 1.988 (0.72), 2.135 (0.73), 2.145 (0.70), 2.154 (0.41), 4.466 (0.44), 4.475 (0.69), 4.487 (0.44), 5.067 (1.61), 5.074 (1.56), 7.926 (1.76), 8.659 (0.86).

Intermediate 230 tert-Butyl (5S)-2-[(E)-2-(4-fluorophenyl)vinyl]-3-oxo-2,3,5,6,7,8-hexahydro[1,2,4]triazolo[4,3-a]pyridine-5-carboxylate (Enantiomer 1)

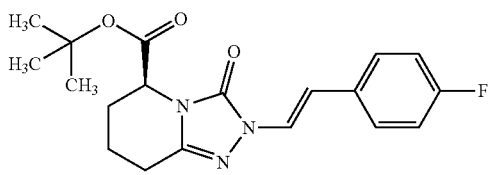 [SMILES: CC(C)(C)OC(=O)[C@@H]1CCCc2nn(/C=C/c3ccc(F)cc3)c(=O)n21]

Molecular sieve (4 Å, 20.0 mg) and [(E)-2-(4-fluorophenyl)vinyl]boric acid (139 mg, 836 μmol) were initially charged in dichloromethane (2.0 ml) at room temperature. Subsequently, triethylamine (120 μl, 840 μmol), copper(II) acetate (85.4 mg, 460 μmol), tert-butyl (5S)-3-oxo-2,3,5,6,7,8-hexahydro[1,2,4]triazolo[4,3-a]pyridine-5-carboxylate (100 mg, 418 μmol) and 2,2,6,6-tetramethylpiperidin-1-yloxyl (71.8 mg, 460 μmol) were added. The reaction mixture was stirred at room temperature overnight. 2 N ammonia in methanol (50 al) were added to the reaction mixture, which was then concentrated. The residue was purified via column chromatography (silica gel, eluent: cyclohexane/ethyl acetate gradient 7/1, 0/1). The product-containing fractions were concentrated under reduced pressure, and 53.1 mg (35% of theory) of the title compound were obtained.

LC-MS (Method 3): $R_t$=2.10 min; MS (ESIpos): m/z=360 [M+H]$^+$ $^1$H-NMR (400 MHz, DMSO-d6) δ [ppm]: −0.008 (1.24), 0.008 (1.17), 1.014 (0.21), 1.098 (0.22), 1.423 (16.00), 1.864 (0.17), 1.872 (0.18), 2.086 (0.17), 2.097 (0.45), 2.107 (0.44), 2.120 (0.25), 2.134 (0.16), 2.141 (0.17), 2.323 (0.20), 2.327 (0.28), 2.332 (0.21), 2.366 (0.25), 2.523 (1.07), 2.636 (0.18), 2.665 (0.54), 2.669 (0.42), 2.674 (0.32), 2.679 (0.38), 2.691 (0.28), 2.710 (0.37), 2.738 (0.21), 2.750 (0.37), 2.762 (0.24), 2.792 (0.17), 4.502 (0.37), 4.511 (0.40), 4.517 (0.53), 4.526 (0.35), 6.753 (0.74), 6.789 (0.85), 7.121 (0.68), 7.143 (1.38), 7.165 (0.75), 7.393 (0.98), 7.429 (0.90), 7.543 (0.70), 7.557 (0.77), 7.565 (0.75), 7.574 (0.30), 7.579 (0.67).

Intermediate 231

Ethyl (5RS,6RS)-2-{[3-fluoro-2-(trifluoromethyl)pyridin-4-yl]methyl}-3-oxo-6-(trifluoromethyl)-2,3,5,6,7,8-hexahydro[1,2,4]triazolo[4,3-a]pyridine-5-carboxylate (Diastereomer Mixture; 4 Isomers)

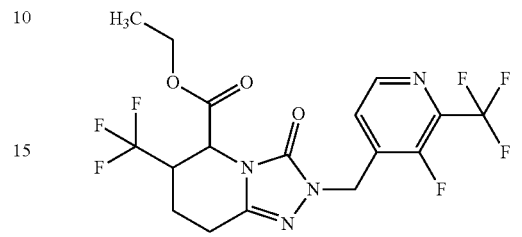

Ethyl (5RS,6RS)-3-oxo-6-(trifluoromethyl)-2,3,5,6,7,8-hexahydro[1,2,4]triazolo[4,3-a]pyridine-5-carboxylate (diastereomer mixture, 4 isomers) (400 mg, 62% purity, 888 μmol) was initially charged in acetonitrile (6.2 ml). Caesium carbonate (579 mg, 1.78 mmol) and 4-(chloromethyl)-3-fluoro-2-(trifluoromethyl)pyridine (199 mg, 933 μmol) were subsequently added. After stirring at room temperature for 48 hours, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 231 mg (73% purity, 42% of theory) of the title compound were obtained.

LC-MS (Method 3): $R_t$=1.82 min; MS (ESIpos): m/z=457 [M+H]$^+$ and $R_t$=1.85 min; MS (ESIpos): m/z=457 [M+H]$^+$ Intermediate 232

Ethyl (5RS,6RS)-3-oxo-6-(trifluoromethyl)-2-{[6-(trifluoromethyl)pyridin-3-yl]methyl}-2,3,5,6,7,8-hexahydro[1,2,4]triazolo[4,3-a]pyridine-5-Carboxylate (Diastereomer Mixture, 4 Isomers)

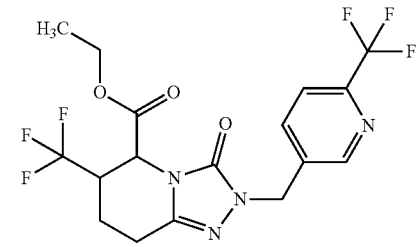 [SMILES: CCOC(=O)C1C(C(F)(F)F)CCc2nn(Cc3ccc(C(F)(F)F)nc3)c(=O)n21]

Ethyl (5RS,6RS)-3-oxo-6-(trifluoromethyl)-2,3,5,6,7,8-hexahydro[1,2,4]triazolo[4,3-a]pyridine-5-carboxylate (diastereomer mixture, 4 isomers) (250 mg, 62% purity, 555 μmol) was initially charged in acetonitrile (3.9 ml). Caesium carbonate (362 mg, 1.11 mmol) and 5-(chloromethyl)-2-(trifluoromethyl)pyridine (114 mg, 583 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 131 mg (54% of theory) of the title compound were obtained.

LC-MS (Method 1): $R_t$=1.23 min; MS (ESIpos): m/z=439 [M+H]$^+$ and $R_t$=1.24 min; MS (ESIpos): m/z=439 [M+H]$^+$ $^1$H-NMR (400 MHz, DMSO-d6) δ [ppm]: −0.149 (1.37), −0.008 (13.25), 0.008 (11.69), 0.146 (1.37), 1.148 (3.00), 1.166 (6.37), 1.185 (9.50), 1.203 (16.00), 1.221 (7.63), 1.833 (0.50), 2.018 (2.69), 2.036 (2.06), 2.052 (0.94), 2.327 (2.19), 2.366 (2.31), 2.523 (6.81), 2.669 (2.50), 2.710 (3.06), 2.764 (1.19), 2.781 (1.88), 2.825 (0.94), 2.869 (0.63), 3.425 (1.00), 4.147 (1.44), 4.154 (1.56), 4.165 (1.62), 4.172 (1.62), 4.179 (2.50), 4.196 (7.44), 4.214 (7.37), 4.232 (2.31), 4.648 (4.00), 4.662 (3.87), 4.815 (1.50), 4.829 (1.62), 5.010 (0.63), 5.058 (9.50), 5.099 (0.69), 7.927 (14.25), 7.930 (11.12), 8.642 (1.69), 8.655 (3.81).

Intermediate 233

Ethyl (5RS,6RS)-2-[(3,5-dichloropyridin-2-yl)methyl]-3-oxo-6-(trifluoromethyl)-2,3,5,6,7,8-hexahydro[1,2,4]triazolo[4,3-a]pyridine-5-Carboxylate (Diastereomer Mixture, 4 Isomers)

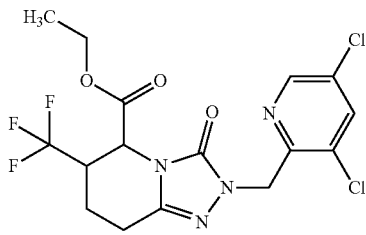 [SMILES: CCOC(=O)C1C(C(F)(F)F)CCc2nn(Cc3ncc(Cl)cc3Cl)c(=O)n21]

Ethyl (5RS,6RS)-3-oxo-6-(trifluoromethyl)-2,3,5,6,7,8-hexahydro[1,2,4]triazolo[4,3-a]pyridine-5-carboxylate (diastereomer mixture, 4 isomers) (566 mg, 2.03 mmol) was initially charged in acetonitrile (15 ml). Caesium carbonate (1.32 g, 4.05 mmol) and 3,5-dichloro-2-(chloromethyl)pyridine (418 mg, 2.13 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 235 mg (86% purity, 23% of theory) of the title compound were obtained.

LC-MS (Method 8): $R_t$=2.82 min; MS (ESIpos): m/z=439 [M+H]$^+$ and $R_t$=2.87 min; MS (ESIpos): m/z=439 [M+H]$^+$ $^1$H-NMR (400 MHz, DMSO-d6) δ[ppm]: −0.149 (1.83), −0.008 (16.00), 0.008 (12.50), 0.146 (1.68), 1.168 (2.67), 1.185 (5.56), 1.201 (8.91), 1.219 (15.85), 1.237 (7.62), 1.831 (0.46), 1.850 (0.46), 2.013 (2.74), 2.028 (2.51), 2.045 (1.22), 2.073 (1.22), 2.327 (1.98), 2.366 (2.44), 2.523 (5.94), 2.621 (0.84), 2.648 (1.07), 2.669 (3.28), 2.710 (2.44), 2.754 (1.98), 2.771 (1.07), 2.797 (0.99), 3.416 (1.07), 4.144 (1.30), 4.155 (1.30), 4.161 (1.37), 4.178 (2.74), 4.195 (7.62), 4.213 (7.47), 4.231 (2.36), 4.616 (4.11), 4.629 (4.04), 4.805 (1.52), 4.819 (1.45), 5.007 (1.22), 5.047 (7.70), 5.055 (6.78), 5.060 (8.15), 5.100 (1.22), 8.259 (3.28), 8.264 (4.11), 8.557 (4.27), 8.562 (4.11).

Intermediate 234

Ethyl (5RS,6RS)-2-[(5-chloro-3-fluoropyridin-2-yl)methyl]-3-oxo-6-(trifluoromethyl)-2,3,5,6,7,8-hexahydro[1,2,4]triazolo[4,3-a]pyridine-5-Carboxylate (Diastereomer Mixture, 4 Isomers)

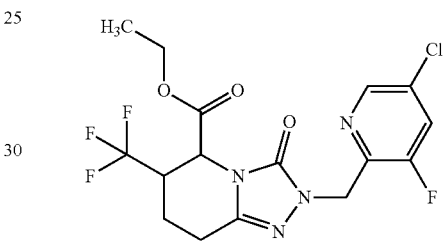

Ethyl (5RS,6RS)-3-oxo-6-(trifluoromethyl)-2,3,5,6,7,8-hexahydro[1,2,4]triazolo[4,3-a]pyridine-5-carboxylate (diastereomer mixture, 4 isomers) (432 mg, 1.55 mmol) was initially charged in acetonitrile (10 ml). Caesium carbonate (1.01 g, 3.09 mmol) and 5-chloro-2-(chloromethyl)-3-fluoropyridine (292 mg, 1.62 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 235 mg (36% of theory) of the title compound were obtained.

LC-MS (Method 4): $R_t$=0.90 min; MS (ESIpos): m/z=423 [M+H]$^+$ $^1$H-NMR (400 MHz, DMSO-d6) δ[ppm]: −0.149 (1.95), −0.008 (16.00), 0.008 (15.09), 0.146 (1.90), 1.164 (2.12), 1.182 (4.63), 1.198 (4.02), 1.216 (5.88), 1.234 (2.85), 2.005 (0.91), 2.020 (0.82), 2.037 (0.48), 2.073 (1.08), 2.327 (0.95), 2.366 (1.08), 2.523 (3.11), 2.617 (0.43), 2.665 (1.08), 2.669 (1.17), 2.674 (1.08), 2.710 (1.21), 2.733 (0.56), 2.747 (0.82), 2.763 (0.61), 2.822 (0.43), 4.133 (0.48), 4.143 (1.08), 4.150 (1.17), 4.161 (1.17), 4.168 (1.08), 4.175 (1.04), 4.192 (2.81), 4.210 (2.72), 4.228 (0.86), 4.607 (1.43), 4.620 (1.43), 4.793 (1.08), 4.807 (1.08), 5.008 (2.68), 5.017 (2.64), 8.104 (1.30), 8.129 (1.38), 8.476 (1.86).

Intermediate 235

Ethyl (5RS,6RS)-2-[(5-chloropyridin-2-yl)methyl]-3-oxo-6-(trifluoromethyl)-2,3,5,6,7,8-hexahydro[1,2,4]triazolo[4,3-a]pyridine-5-Carboxylate (Diastereomer Mixture, 4 Isomers)

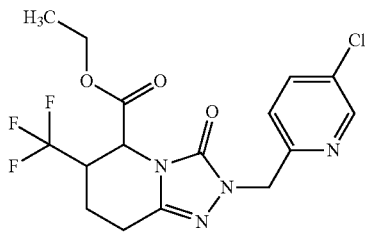 [SMILES: CCOC(=O)C1C(C(F)(F)F)CCc2nn(Cc3ccc(Cl)cn3)c(=O)n21]

Ethyl (5RS,6RS)-3-oxo-6-(trifluoromethyl)-2,3,5,6,7,8-hexahydro[1,2,4]triazolo[4,3-a]pyridine-5-carboxylate (diastereomer mixture, 4 isomers) (400 mg, 1.43 mmol) was initially charged in acetonitrile (7.1 ml). Caesium carbonate (934 mg, 2.87 mmol) and 5-chloro-2-(chloromethyl)pyridine (244 mg, 1.50 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 135 mg (23% of theory) of the title compound were obtained.

LC-MS (Method 3): $R_t$=1.65 min; MS (ESIpos): m/z=405 [M+H]$^+$ and $R_t$=1.68 min; MS (ESIpos): m/z=405 [M+H]$^+$

Intermediate 236 tert-Butyl (5RS,7RS)-2-{[3-fluoro-2-(trifluoromethyl)pyridin-4-yl]methyl}-7-methyl-3-oxo-2,3,5,6,7,8-hexahydro[1,2,4]triazolo[4,3-a]pyridine-5-carboxylate (Diastereomer Mixture, 4 Isomers)

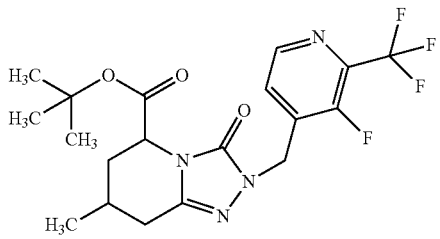 [SMILES: CC1Cc2nn(Cc3ccnc(C(F)(F)F)c3F)c(=O)n2C(C(=O)OC(C)(C)C)C1]

tert-Butyl (5RS,7RS)-7-methyl-3-oxo-2,3,5,6,7,8-hexahydro[1,2,4]triazolo[4,3-a]pyridine-5-carboxylate (diastereomer mixture, 4 isomers) (300 mg, 1.18 mmol) was initially charged in acetonitrile (6.0 ml). Caesium carbonate (965 mg, 2.96 mmol) and 4-(chloromethyl)-3-fluoro-2-(trifluoromethyl)pyridine (266 mg, 1.24 mmol) were subsequently added. After stirring at 60° C. overnight, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 374 mg (73% of theory) of the title compound were obtained.

LC-MS (Method 4): $R_t$=1.02 min; MS (ESIpos): m/z=431 [M+H]$^+$ $^1$H-NMR (400 MHz, DMSO-d6) δ[ppm]: 1.018 (2.06), 1.035 (2.12), 1.354 (5.48), 1.393 (0.48), 1.410 (16.00), 1.911 (0.98), 2.228 (0.46), 2.241 (0.62), 2.269 (0.49), 2.650 (0.42), 4.303 (0.47), 4.313 (0.45), 5.067 (1.13), 5.079 (1.12), 5.133 (0.72), 7.619 (0.77), 7.632 (0.57), 8.569 (0.89), 8.581 (0.89).

Intermediate 237 tert-Butyl (5RS,7RS)-7-methyl-3-oxo-2-{[6-(trifluoromethyl)pyridin-3-yl]methyl}-2,3,5,6,7,8-hexahydro[1,2,4]triazolo[4,3-a]pyridine-5-Carboxylate (Diastereomer Mixture, 4 Isomers)

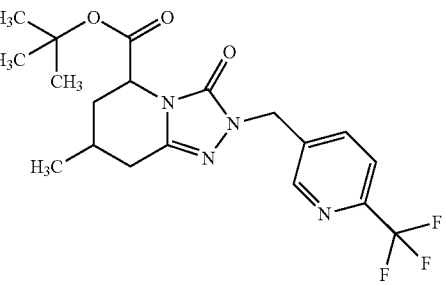

tert-Butyl (5RS,7RS)-7-methyl-3-oxo-2,3,5,6,7,8-hexahydro[1,2,4]triazolo[4,3-a]pyridine-5-carboxylate (diastereomer mixture, 4 isomers) (247 mg, 975 μmol) was initially charged in acetonitrile (5.0 ml). Caesium carbonate (794 mg, 2.44 mmol) and 5-(chloromethyl)-2-(trifluoromethyl)pyridine (200 mg, 1.02 mmol) were subsequently added. After stirring at 60° C. overnight, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 274 mg (68% of theory) of the title compound were obtained.

LC-MS (Method 4): $R_t$=0.98 min; MS (ESIpos): m/z=413 [M+H]$^+$ $^1$H-NMR (400 MHz, DMSO-d6) δ [ppm]: 1.011 (2.18), 1.028 (2.23), 1.337 (5.62), 1.385 (0.63), 1.406 (16.00), 1.905 (1.13), 2.217 (0.52), 2.230 (0.66), 2.258 (0.53), 2.641 (0.48), 4.279 (0.40), 4.295 (0.47), 4.305 (0.45), 5.019 (2.49), 5.077 (0.86), 7.921 (1.40), 7.931 (0.85), 7.936 (0.83), 8.667 (0.73).

Intermediate 238 tert-Butyl (5RS,7RS)-2-(3-chloro-4-fluorobenzyl)-7-methyl-3-oxo-2,3,5,6,7,8-hexahydro[1,2,4]triazolo[4,3-a]pyridine-5-Carboxylate (Diastereomer Mixture, 4 Isomers)

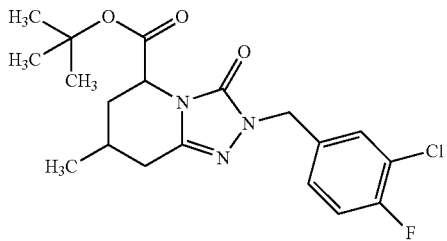 [SMILES: CC1Cc2nn(Cc3ccc(F)c(Cl)c3)c(=O)n2C(C(=O)OC(C)(C)C)C1]

tert-Butyl (5RS,7RS)-7-methyl-3-oxo-2,3,5,6,7,8-hexahydro[1,2,4]triazolo[4,3-a]pyridine-5-carboxylate (diastereomer mixture, 4 isomers) (300 mg, 1.18 mmol) was initially charged in acetonitrile (6.0 ml). Caesium carbonate (965 mg, 2.96 mmol) and 4-(bromomethyl)-2-chloro-1-fluorobenzene (278 mg, 1.24 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 327 mg (70% of theory) of the title compound were obtained.

LC-MS (Method 3): $R_t$=2.09 min; MS (ESIpos): m/z=396 [M+H]

$^1$H-NMR (400 MHz, DMSO-d6) δ [ppm]: −0.008 (0.46), 1.011 (2.15), 1.027 (2.14), 1.348 (0.46), 1.381 (0.71), 1.411 (16.00), 2.186 (0.41), 2.214 (0.51), 2.227 (0.60), 2.255 (0.51), 4.275 (0.41), 4.291 (0.48), 4.302 (0.45), 4.834 (1.64), 7.376 (0.59), 7.399 (0.79), 7.421 (0.44), 7.448 (0.45), 7.453 (0.42), 7.466 (0.45).

Intermediate 239

Ethyl (5RS,7RS)-2-[(5-chloropyridin-2-yl)methyl]-3-oxo-7-(trifluoromethyl)-2,3,5,6,7,8-hexahydro[1,2,4]triazolo[4,3-a]pyridine-5-Carboxylate (Diastereomer Mixture, 4 Isomers)

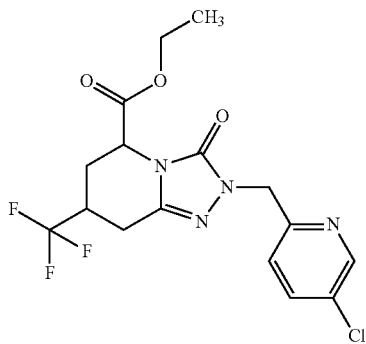 [SMILES: CCOC(=O)C1CC(C(F)(F)F)Cc2nn(Cc3ccc(Cl)cn3)c(=O)n21]

Ethyl (5RS,7RS)-3-oxo-7-(trifluoromethyl)-2,3,5,6,7,8-hexahydro[1,2,4]triazolo[4,3-a]pyridine-5-carboxylate (diastereomer mixture, 4 isomers) (500 mg, 1.70 mmol) was initially charged in acetonitrile (20 ml). Caesium carbonate (1.39 g, 4.25 mmol) and 5-chloro-2-(chloromethyl)pyridine hydrochloride (355 mg, 1.79 mmol) were subsequently added. After stirring overnight, the reaction mixture was concentrated by half and admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 248 mg (36% of theory) of the title compound were obtained.

LC-MS (Method 4): $R_t$=0.89 min; MS (ESIpos): m/z=405 [M+H]

$^1$H-NMR (400 MHz, DMSO-d6) δ [ppm]: −0.149 (0.41), 0.146 (0.41), 1.183 (4.99), 1.201 (15.06), 1.217 (16.00), 1.234 (6.56), 1.780 (0.75), 1.810 (1.63), 1.841 (1.78), 1.871 (0.84), 2.296 (0.77), 2.324 (2.75), 2.336 (2.13), 2.366 (0.42), 2.670 (0.49), 2.686 (0.67), 2.716 (1.72), 2.740 (1.79), 2.753 (1.97), 2.770 (1.78), 2.780 (2.11), 2.810 (2.19), 2.888 (1.32), 2.895 (1.52), 2.929 (0.83), 2.935 (0.84), 2.986 (1.41), 3.015 (1.12), 3.082 (0.72), 4.148 (0.92), 4.162 (2.00), 4.179 (5.57), 4.197 (5.43), 4.217 (2.69), 4.235 (1.82), 4.245 (0.93), 4.253 (0.62), 4.262 (0.85), 4.531 (1.67), 4.546 (1.90), 4.559 (1.81), 4.573 (1.61), 4.824 (1.22), 4.831 (1.64), 4.844 (1.28), 4.948 (11.83), 4.977 (9.93), 7.234 (2.72), 7.256 (2.91), 7.271 (3.45), 7.292 (3.70), 7.929 (3.74), 7.935 (3.92), 7.949 (3.59), 7.956 (3.73), 8.579 (4.25), 8.584 (4.25).

Intermediate 240 tert-Butyl (5RS,8RS)-2-{[3-fluoro-2-(trifluoromethyl)pyridin-4-yl]methyl}-8-methyl-3-oxo-2,3,5,6,7,8-hexahydro[1,2,4]triazolo[4,3-a]pyridine-5-carboxylate (Diastereomer Mixture, 4 Isomers)

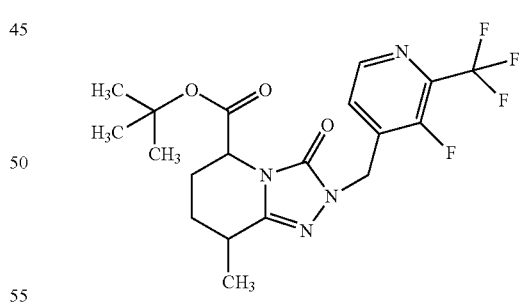

tert-Butyl (5RS,8RS)-8-methyl-3-oxo-2,3,5,6,7,8-hexahydro[1,2,4]triazolo[4,3-a]pyridine-5-carboxylate (diastereomer mixture; 4 isomers) (300 mg, 1.18 mmol) was initially charged in acetonitrile (10 ml). Caesium carbonate (424 mg, 1.30 mmol) and 4-(chloromethyl)-3-fluoro-2-(trifluoromethyl)pyridine (266 mg, 1.24 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 456 mg (89% of theory) of the title compound were obtained.

LC-MS (Method 1): $R_t$=2.09 min; MS (ESIpos): m/z=429 [M−H]$^+$

Intermediate 241 tert-Butyl (5RS,8RS)-2-(3-chloro-4-fluorobenzyl)-8-methyl-3-oxo-2,3,5,6,7,8-hexahydro[1,2,4]triazolo[4,3-a]pyridine-5-Carboxylate (Diastereomer Mixture, 4 Isomers)

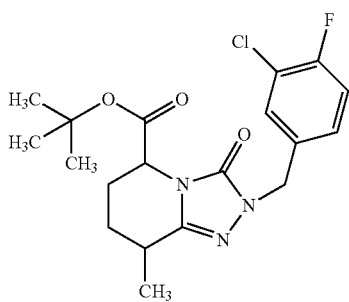 [SMILES: CC1CCC(C(=O)OC(C)(C)C)n2c1nn(Cc1ccc(F)c(Cl)c1)c2=O]

tert-Butyl (5RS,8RS)-8-methyl-3-oxo-2,3,5,6,7,8-hexahydro[1,2,4]triazolo[4,3-a]pyridine-5-carboxylate (diastereomer mixture; 4 isomers) (300 mg, 1.18 mmol) was initially charged in acetonitrile (10 ml). Caesium carbonate (772 mg, 2.37 mmol) and 2-chloro-4-(chloromethyl)-1-fluorobenzene (223 mg, 1.24 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 450 mg (87% of theory) of the title compound were obtained.

LC-MS (Method 3): $R_t$=0.08 min; MS (ESIpos): m/z=340 [M−tBu+H]+

Intermediate 242 tert-Butyl (5RS,8RS)-2-(2,4-difluorobenzyl)-8-methyl-3-oxo-2,3,5,6,7,8-hexahydro[1,2,4]triazolo[4,3-a]pyridine-5-Carboxylate (Diastereomer Mixture, 4 Isomers)

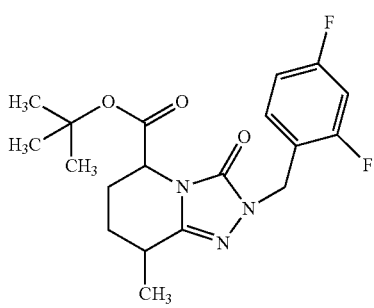 [SMILES: CC1CCC(C(=O)OC(C)(C)C)n2c1nn(Cc1ccc(F)cc1F)c2=O]

tert-Butyl (5RS,8RS)-8-methyl-3-oxo-2,3,5,6,7,8-hexahydro[1,2,4]triazolo[4,3-a]pyridine-5-carboxylate (diastereomer mixture; 4 isomers) (300 mg, 1.18 mmol) was initially charged in acetonitrile (10 ml). Caesium carbonate (772 mg, 2.37 mmol) and 1-(chloromethyl)-2,4-difluorobenzene (202 mg, 1.24 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 400 mg (84% purity, 75% of theory) of the title compound were obtained.

LC-MS (Method 3): $R_t$=1.44 min; MS (ESIpos): m/z=380 [M+H]$^+$

Intermediate 243

Methyl (5S)-2-(2-chloro-4-fluorobenzyl)-3-oxo-2,3,5,6,7,8-hexahydro[1,2,4]triazolo[4,3-a]pyridine-5-carboxylate

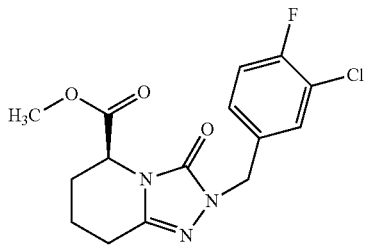 [SMILES: COC(=O)[C@@H]1CCCc2nn(Cc3ccc(F)c(Cl)c3)c(=O)n21]

Methyl (5S)-3-oxo-2,3,5,6,7,8-hexahydro[1,2,4]triazolo[4,3-a]pyridine-5-carboxylate (110 mg, 559 µmol) was initially charged in acetonitrile (2.0 ml, 38 mmol). Caesium carbonate (273 mg, 838 µmol) and 2-chloro-4-(chloromethyl)-1-fluorobenzene (105 mg, 587 µmol) were subsequently added. After stirring overnight, the reaction mixture was admixed at reflux with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 58.5 mg (30% of theory) of the title compound were obtained.

LC-MS (Method 1): $R_t$=1.11 min; MS (ESIpos): m/z=340 [M+H]$^+$

Intermediate 244

Methyl (5S)-3-oxo-2-[3-(trifluoromethyl)benzyl]-2,3,5,6,7,8-hexahydro[1,2,4]triazolo[4,3-a]pyridine-5-carboxylate

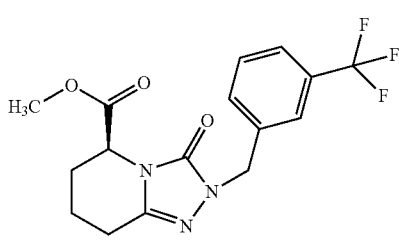 [SMILES: COC(=O)[C@@H]1CCCc2nn(Cc3cccc(C(F)(F)F)c3)c(=O)n21]

Methyl (5S)-3-oxo-2,3,5,6,7,8-hexahydro[1,2,4]triazolo[4,3-a]pyridine-5-carboxylate (300 mg, 1.52 mmol) was initially charged in acetonitrile (6.0 ml). Caesium carbonate (744 mg, 2.28 mmol) and 1-(bromomethyl)-3-(trifluoromethyl)benzene (382 mg, 1.60 mmol) were subsequently added. After stirring overnight, the reaction mixture was admixed under reflux with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 345 mg (64% of theory) of the title compound were obtained.

LC-MS (Method 1): $R_t$=1.15 min; MS (ESIpos): m/z=356 [M+H]$^+$ $^1$H-NMR (400 MHz, DMSO-d6) δ [ppm]: 1.196 (2.01), 1.212 (3.72), 1.226 (2.33), 1.502 (0.44), 1.530 (0.49), 1.802 (0.57), 1.826 (0.49), 1.835 (0.51), 2.078 (0.89), 2.093 (0.89), 2.120 (0.57), 2.131 (0.51), 2.139 (0.55), 2.147 (0.53), 2.328 (0.59), 2.562 (1.35), 2.577 (0.99), 2.589 (0.99), 2.603 (0.80), 2.629 (0.74), 2.641 (1.31), 2.653 (0.76), 2.671 (1.02), 2.711 (0.51), 2.891 (0.42), 3.702 (16.00), 4.622 (1.08), 4.631 (1.23), 4.637 (1.44), 4.647 (1.10), 4.960 (4.25), 4.965 (4.25), 7.101 (5.21), 7.519 (1.04), 7.538 (1.71), 7.584 (0.95), 7.603 (2.01), 7.615 (2.41), 7.658 (1.63), 7.676 (0.87).

Intermediate 245

Methyl (5S)-3-oxo-2-{[5-(trifluoromethyl)pyridin-2-yl]methyl}-2,3,5,6,7,8-hexahydro[1,2,4]triazolo[4,3-a]pyridine-5-carboxylate

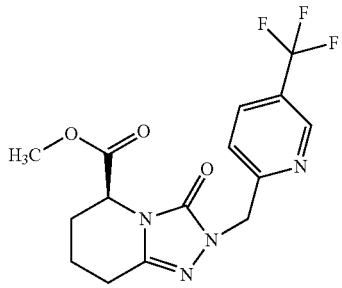 [SMILES: COC(=O)[C@@H]1CCCc2nn(Cc3ccc(C(F)(F)F)cn3)c(=O)n21]

Methyl (5S)-3-oxo-2,3,5,6,7,8-hexahydro[1,2,4]triazolo[4,3-a]pyridine-5-carboxylate (187 mg, 947 µmol) was initially charged in acetonitrile (4.0 ml). Caesium carbonate (463 mg, 1.42 mmol) and 2-(bromomethyl)-5-(trifluoromethyl)pyridine (250 mg, 1.04 mmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 185 mg (55% of theory) of the title compound were obtained.

LC-MS (Method 3): $R_t$=1.34 min; MS (ESIpos): m/z=357 [M+H]$^+$ $^1$H-NMR (400 MHz, DMSO-d6) δ[ppm]: 1.560 (0.40), 1.827 (0.50), 1.841 (0.44), 1.851 (0.42), 2.083 (0.45), 2.092 (0.76), 2.106 (0.76), 2.126 (0.45), 2.135 (0.53), 2.147 (0.47), 2.155 (0.52), 2.163 (0.48), 2.559 (0.44), 2.575 (0.90), 2.589 (0.77), 2.601 (0.78), 2.615 (0.64), 2.637 (0.60), 2.649 (1.13), 2.661 (0.72), 2.691 (0.47), 3.715 (16.00), 4.631 (1.05), 4.641 (1.16), 4.647 (1.36), 4.657 (1.01), 5.063 (5.88), 7.396 (1.64), 7.416 (1.71), 8.223 (1.06), 8.228 (1.09), 8.243 (1.02), 8.249 (1.04), 8.935 (1.74).

Intermediate 246

Methyl (5S)-2-[(5-methyl-1H-pyrazol-3-yl)methyl]-3-oxo-2,3,5,6,7,8-hexahydro[1,2,4]triazolo[4,3-a]pyridine-5-carboxylate

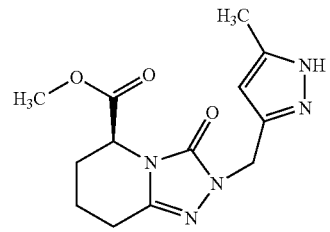 [SMILES: COC(=O)[C@@H]1CCCc2nn(Cc3cc(C)[nH]n3)c(=O)n21]

Methyl (5S)-3-oxo-2,3,5,6,7,8-hexahydro[1,2,4]triazolo[4,3-a]pyridine-5-carboxylate (200 mg, 1.01 mmol) was initially charged in acetonitrile (5.0 ml). Caesium carbonate (364 mg, 1.12 mmol) and 3-(chloromethyl)-5-methyl-1H-pyrazole hydrochloride (178 mg, 1.06 mmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 60.7 mg (21% of theory) of the title compound were obtained.

LC-MS (Method 3): $R_t$=0.85 min; MS (ESIpos): m/z=292 [M+H]$^+$

Intermediate 247

Methyl (5S)-2-{[3-chloro-4-(trifluoromethyl)pyridin-2-yl]methyl}-3-oxo-2,3,5,6,7,8-hexahydro[1,2,4]triazolo[4,3-a]pyridine-5-carboxylate

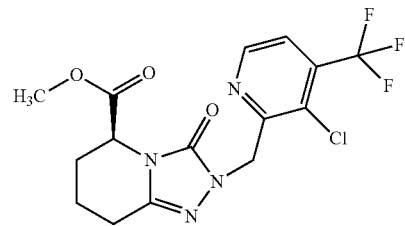 [SMILES: COC(=O)[C@@H]1CCCc2nn(Cc3nccc(C(F)(F)F)c3Cl)c(=O)n21]

Methyl (5S)-3-oxo-2,3,5,6,7,8-hexahydro[1,2,4]triazolo[4,3-a]pyridine-5-carboxylate (150 mg, 761 μmol) was initially charged in acetonitrile (5.0 ml). Caesium carbonate (273 mg, 837 μmol) and 3-chloro-2-(chloromethyl)-4-(trifluoromethyl)pyridine hydrochloride (532 mg, 40% purity, 799 μmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 137 mg (46% of theory) of the title compound were obtained.

LC-MS (Method 1): $R_t$=1.06 min; MS (ESIpos): m/z=391 [M+H]$^+$

Intermediate 248

Methyl (5S)-2-[4-fluoro-3-(trifluoromethyl)benzyl]-3-oxo-2,3,5,6,7,8-hexahydro[1,2,4]triazolo[4,3-a]pyridine-5-carboxylate

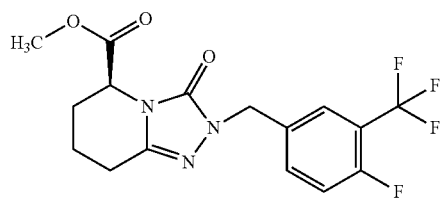 [SMILES: COC(=O)[C@@H]1CCCc2nn(Cc3ccc(F)c(C(F)(F)F)c3)c(=O)n21]

Methyl (5S)-3-oxo-2,3,5,6,7,8-hexahydro[1,2,4]triazolo[4,3-a]pyridine-5-carboxylate (200 mg, 1.01 mmol) was initially charged in acetonitrile (5.0 ml). Caesium carbonate (826 mg, 2.54 mmol) and 4-(bromomethyl)-1-fluoro-2-(trifluoromethyl)benzene (287 mg, 1.12 mmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 370 mg (98% of theory) of the title compound were obtained.

LC-MS (Method 4): $R_t$=0.88 min; MS (ESIpos): m/z=374 [M+H]$^+$

Intermediate 249

Methyl (5S)-3-oxo-2-{[6-(trifluoromethyl)pyridin-3-yl]methyl}-2,3,5,6,7,8-hexahydro[1,2,4]triazolo[4,3-a]pyridine-5-carboxylate

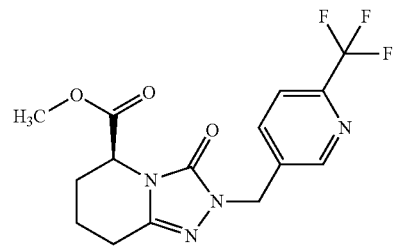 [SMILES: COC(=O)[C@@H]1CCCc2nn(Cc3ccc(C(F)(F)F)nc3)c(=O)n21]

Methyl (5S)-3-oxo-2,3,5,6,7,8-hexahydro[1,2,4]triazolo[4,3-a]pyridine-5-carboxylate (400 mg, 2.03 mmol) was initially charged in acetonitrile (10 ml). Caesium carbonate (991 mg, 3.04 mmol) and 5-(bromomethyl)-2-(trifluoromethyl)pyridine (511 mg, 2.13 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 622 mg (79% of theory) of the title compound were obtained.

LC-MS (Method 4): $R_t$=0.73 min; MS (ESIpos): m/z=357 [M+H]$^+$

Intermediate 250

Methyl (5S)-2-{[6-fluoro-2-(trifluoromethyl)quinolin-4-yl]methyl}-3-oxo-2,3,5,6,7,8-hexahydro[1,2,4]triazolo[4,3-a]pyridine-5-carboxylate

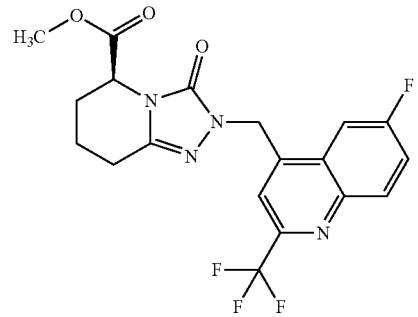 [SMILES: COC(=O)[C@@H]1CCCc2nn(Cc3cc(C(F)(F)F)nc4ccc(F)cc34)c(=O)n21]

Methyl (5S)-3-oxo-2,3,5,6,7,8-hexahydro[1,2,4]triazolo[4,3-a]pyridine-5-carboxylate (200 mg, 1.01 mmol) was initially charged in acetonitrile. Caesium carbonate (826 mg, 2.54 mmol) and 4-(chloromethyl)-6-fluoro-2-(trifluoromethyl)quinoline (453 mg, 62% purity, 1.06 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 59.0 mg (14% of theory) of the title compound were obtained.

LC-MS (Method 1): $R_t$=1.24 min; MS (ESIpos): m/z=425 [M+H]$^+$

Intermediate 251

Methyl (5S)-2-(6,7-dihydro-5H-cyclopenta[c]pyridin-3-ylmethyl)-3-oxo-2,3,5,6,7,8-hexahydro[1,2,4]triazolo[4,3-a]pyridine-5-carboxylate

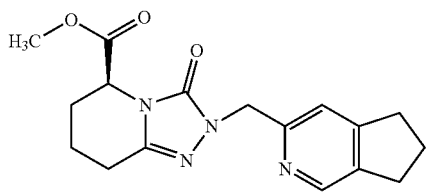 [SMILES: COC(=O)[C@@H]1CCCc2nn(Cc3cc4c(cn3)CCC4)c(=O)n21]

Methyl (5S)-3-oxo-2,3,5,6,7,8-hexahydro[1,2,4]triazolo[4,3-a]pyridine-5-carboxylate (85.5 mg, 433 μmol) was initially charged in acetonitrile (10 ml). Caesium carbonate (353 mg, 1.08 mmol) and 3-(chloromethyl)-6,7-dihydro-5H-cyclopenta[b]pyridine hydrochloride (115 mg, 563 μmol) were subsequently added. After stirring at room temperature overnight and under reflux for a further 3 hours, the reaction mixture was cooled and admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 106 mg (90% purity, 67% of theory) of the title compound were obtained.

LC-MS (Method 3): $R_t$=0.75 min; MS (ESIpos): m/z=329 [M+H]$^+$

Intermediate 252

Methyl (5S)-3-oxo-2-{[5-(trifluoromethyl)pyridin-3-yl]methyl}-2,3,5,6,7,8-hexahydro[1,2,4]triazolo[4,3-a]pyridine-5-carboxylate

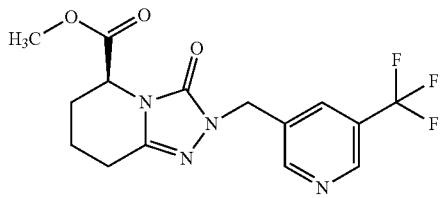 [SMILES: COC(=O)[C@@H]1CCCc2nn(Cc3cncc(C(F)(F)F)c3)c(=O)n21]

Methyl (5S)-3-oxo-2,3,5,6,7,8-hexahydro[1,2,4]triazolo[4,3-a]pyridine-5-carboxylate (90.0 mg, 456 μmol) was initially charged in acetonitrile (10 ml). Caesium carbonate (372 mg, 1.14 mmol) and 3-(chloromethyl)-5-(trifluoromethyl)pyridine (116 mg, 593 μmol) were subsequently added. The reaction mixture was stirred under reflux for 3 hours, at room temperature overnight and then under reflux for another 4 hours. The reaction mixture was cooled to room temperature, and water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 40.9 mg (25% of theory) of the title compound were obtained.

LC-MS (Method 3): $R_t$=1.29 min; MS (ESIpos): m/z=357 [M+H]$^+$

Intermediate 253

Methyl (5S)-3-oxo-2-{[2-(trifluoromethyl)-1,8-naphthyridin-3-yl]methyl}-2,3,5,6,7,8-hexahydro[1,2,4]triazolo[4,3-a]pyridine-5-carboxylate

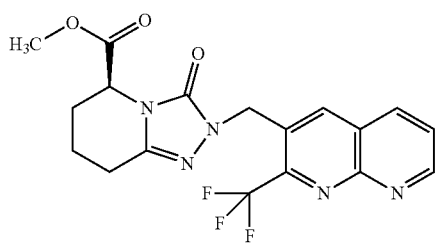 [SMILES: COC(=O)[C@@H]1CCCc2nn(Cc3cc4cccnc4nc3C(F)(F)F)c(=O)n21]

Methyl (5S)-3-oxo-2,3,5,6,7,8-hexahydro[1,2,4]triazolo[4,3-a]pyridine-5-carboxylate (28.3 mg, 143 μmol) was initially charged in acetonitrile (3.0 ml). Caesium carbonate (187 mg, 574 μmol) and 3-(chloromethyl)-2-(trifluoromethyl)-1,8-naphthyridine (46.0 mg, 187 μmol) were subsequently added. After stirring under reflux for 3 hours, the reaction mixture was cooled to room temperature and admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 9.70 mg (17% of theory) of the title compound were obtained.

LC-MS (Method 3): $R_t$=1.23 min; MS (ESIpos): m/z=408 [M+H]$^+$ $^1$H-NMR (400 MHz, DMSO-d6) δ [ppm]: −0.008 (2.26), 0.008 (1.74), 1.572 (0.46), 1.832 (0.55), 1.843 (0.53), 1.857 (0.48), 1.867 (0.48), 2.111 (0.58), 2.135 (1.21), 2.144 (0.85), 2.152 (0.66), 2.164 (0.53), 2.172 (0.55), 2.179 (0.48), 2.327 (0.61), 2.366 (0.52), 2.523 (2.03), 2.561 (0.52), 2.589 (0.90), 2.604 (0.78), 2.616 (0.79), 2.630 (0.66), 2.656 (0.65), 2.667 (1.51), 2.679 (0.84), 2.709 (0.92), 3.732 (16.00), 4.672 (1.05), 4.682 (1.15), 4.688 (1.44), 4.697 (1.01), 5.239 (5.10), 7.818 (1.42), 7.828 (1.44), 7.838 (1.45), 7.849 (1.49), 8.434 (3.29), 8.583 (1.49), 8.588 (1.59), 8.604 (1.46), 8.609 (1.43), 9.248 (1.43), 9.253 (1.53), 9.258 (1.53), 9.263 (1.42).

Intermediate 254 tert-Butyl (5S)-2-[(6-methoxypyridin-3-yl)methyl]-3-oxo-2,3,5,6,7,8-hexahydro[1,2,4]triazolo[4,3-a]pyridine-5-carboxylate

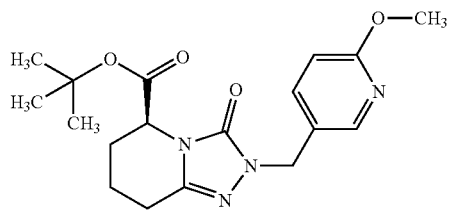 [SMILES: COc1ccc(Cn2nc3n(c2=O)[C@H](C(=O)OC(C)(C)C)CCC3)cn1]

tert-Butyl (5S)-3-oxo-2,3,5,6,7,8-hexahydro[1,2,4]triazolo[4,3-a]pyridine-5-carboxylate (1.33 g, 5.55 mmol) was initially charged in acetonitrile (30 ml). Caesium carbonate (4.52 g, 13.9 mmol), 5-(chloromethyl)-2-methoxypyridine (963 mg, 6.11 mmol) and sodium iodide (5.00 mg, 0.03 mmol) were subsequently added. After stirring for 4 days, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via column chromatography (silica gel, eluent: cyclohexane/ethyl acetate gradient). The product-containing fractions were concentrated under reduced pressure, and 751 mg (37% of theory) of the title compound were obtained.

LC-MS (Method 3): $R_t$=1.56 min; MS (ESIpos): m/z=361 [M+H]$^+$ $^1$H-NMR (400 MHz, DMSO-d6) δ [ppm]: 1.385 (16.00), 2.048 (0.54), 2.058 (0.48), 2.525 (0.41), 3.825 (6.81), 4.424 (0.60), 4.791 (2.68), 6.785 (0.78), 6.807 (0.84), 7.574 (0.51), 7.580 (0.52), 7.595 (0.49), 7.602 (0.50), 8.074 (0.67), 8.080 (0.65).

Intermediate 255 tert-Butyl (5S)-3-oxo-2-{[5-(trifluoromethyl)pyrazin-2-yl]methyl}-2,3,5,6,7,8-hexahydro[1,2,4]triazolo[4,3-a]pyridine-5-carboxylate

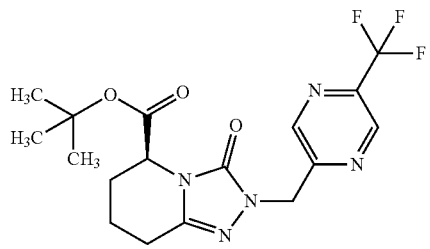 [SMILES: CC(C)(C)OC(=O)[C@@H]1CCCc2nn(Cc3cnc(C(F)(F)F)cn3)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (4.1 ml). Caesium carbonate (1.02 g, 3.13 mmol) and 2-(chloromethyl)-5-(trifluoromethyl)pyrazine (259 mg, 1.32 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 111 mg (22% of theory) of the title compound were obtained.

LC-MS (Method 1): $R_t$=0.83 min; MS (ESIneg): m/z=457 [M−tBu+H]$^+$

Intermediate 256 tert-Butyl (5S)-2-{[3-fluoro-2-(trifluoromethyl)pyridin-4-yl]methyl}-3-oxo-2,3,5,6,7,8-hexahydro[1,2,4]triazolo[4,3-a]pyridine-5-carboxylate

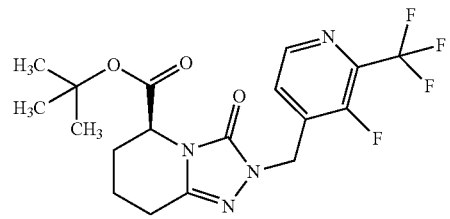 [SMILES: CC(C)(C)OC(=O)[C@@H]1CCCc2nn(Cc3ccnc(C(F)(F)F)c3F)c(=O)n21]

tert-Butyl (5S)-3-oxo-2,3,5,6,7,8-hexahydro[1,2,4]triazolo[4,3-a]pyridine-5-carboxylate (970 mg, 4.05 mmol) was initially charged in acetonitrile (20 ml). Caesium carbonate (3.30 g, 10.1 mmol) and 4-(chloromethyl)-3-fluoro-2-(trifluoromethyl)pyridine (978 mg, 93% purity, 4.26 mmol) were subsequently added. After stirring under reflux for 2 hours and stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 1.37 g (80% of theory) of the title compound were obtained.

LC-MS (Method 3): $R_t$=1.92 min; MS (ESIpos): m/z=417 [M+H]$^+$

Intermediate 257 tert-Butyl (5S)-2-[(1 RS)-1-(4-methylphenyl)ethyl]-3-oxo-2,3,5,6,7,8-hexahydro[1,2,4]triazolo[4,3-a]pyridine-5-carboxylate (Diastereomer Mixture, 2 Isomers)

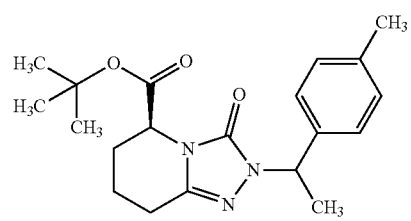 [SMILES: Cc1ccc(C(C)n2nc3n(c2=O)[C@H](C(=O)OC(C)(C)C)CCC3)cc1]

tert-Butyl (5S)-3-oxo-2,3,5,6,7,8-hexahydro[1,2,4]triazolo[4,3-a]pyridine-5-carboxylate (200 mg, 836 µmol) was initially charged in acetonitrile (5.5 ml). Caesium carbonate (681 mg, 2.09 mmol) and 1-[(1RS)-1-chloroethyl]-4-methylbenzene (142 mg, 919 µmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 69.8 mg (23% of theory) of the title compound were obtained.

LC-MS (Method 1): R$_t$=1.35 min; MS (ESIpos): m/z=302 [M+H]$^+$ $^1$H-NMR (400 MHz, DMSO-d6) δ [ppm]: 1.322 (0.75), 1.341 (16.00), 1.587 (2.31), 1.605 (2.28), 2.048 (0.49), 2.059 (0.49), 2.266 (4.00), 2.518 (0.52), 4.407 (0.57), 5.271 (0.49), 5.288 (0.48), 7.111 (0.75), 7.131 (1.46), 7.173 (1.69), 7.193 (0.87).

Intermediate 258 tert-Butyl (5S)-2-[2-(4-methylphenyl)ethyl]-3-oxo-2,3,5,6,7,8-hexahydro[1,2,4]triazolo[4,3-a]pyridine-5-carboxylate

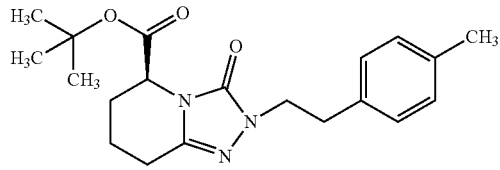 [SMILES: Cc1ccc(CCn2nc3n(c2=O)[C@H](C(=O)OC(C)(C)C)CCC3)cc1]

tert-Butyl (5S)-3-oxo-2,3,5,6,7,8-hexahydro[1,2,4]triazolo[4,3-a]pyridine-5-carboxylate (250 mg, 1.04 mmol) was initially charged in acetonitrile (8.0 ml). Caesium carbonate (851 mg, 2.61 mmol) and 1-(2-bromoethyl)-4-methylbenzene (180 µl, 1.1 mmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 238 mg (64% of theory) of the title compound were obtained.

LC-MS (Method 1): R$_t$=1.35 min; MS (ESIpos): m/z=302 [M+H]$^+$ $^1$H-NMR (400 MHz, DMSO-d6) δ [ppm]: 1.394 (16.00), 2.041 (0.53), 2.051 (0.48), 2.255 (4.71), 2.864 (0.59), 2.883 (1.12), 2.902 (0.64), 3.778 (0.43), 3.783 (0.44), 3.796 (0.81), 3.803 (0.81), 4.373 (0.59), 7.089 (6.23).

Intermediate 259 tert-Butyl (5S)-2-{[3-chloro-4-(trifluoromethyl)pyridin-2-yl]methyl}-3-oxo-2,3,5,6,7,8-hexahydro[1,2,4]triazolo[4,3-a]pyridine-5-carboxylate

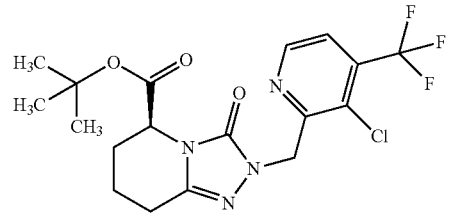 [SMILES: CC(C)(C)OC(=O)[C@@H]1CCCc2nn(Cc3nccc(C(F)(F)F)c3Cl)c(=O)n21]

tert-Butyl (5S)-3-oxo-2,3,5,6,7,8-hexahydro[1,2,4]triazolo[4,3-a]pyridine-5-carboxylate (991 mg, 4.14 mmol) was initially charged in acetonitrile (19 ml). Caesium carbonate (1.48 g, 4.55 mmol) and 3-chloro-2-(chloromethyl)-4-(trifluoromethyl)pyridine (1.00 g, 4.35 mmol) were subsequently added. After stirring overnight, the reaction mixture was admixed under reflux with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 794 mg (42% of theory) of the title compound were obtained.

LC-MS (Method 1): R$_t$=1.28 min; MS (ESIpos): m/z=377 [M−tBu+H]+

Intermediate 260 tert-Butyl (5S)-2-{[1-(4-methylphenyl)cyclopropyl]methyl}-3-oxo-2,3,5,6,7,8-hexahydro[1,2,4]triazolo[4,3-a]pyridine-5-carboxylate

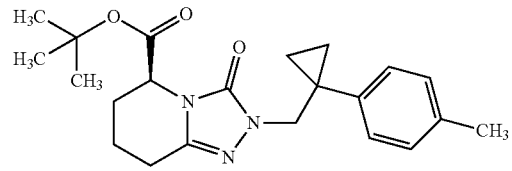 [SMILES: Cc1ccc(C2(Cn3nc4n(c3=O)[C@H](C(=O)OC(C)(C)C)CCC4)CC2)cc1]

tert-Butyl (5S)-3-oxo-2,3,5,6,7,8-hexahydro[1,2,4]triazolo[4,3-a]pyridine-5-carboxylate (120 mg, 500 µmol) was initially charged in acetonitrile (3.0 ml). Caesium carbonate (408 mg, 1.25 mmol) and 1-[1-(bromomethyl)cyclopropyl]-4-methylbenzene (124 mg, 550 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 167 mg (90% purity, 78% of theory) of the title compound were obtained.

LC-MS (Method 3): R$_t$=2.13 min; MS (ESIpos): m/z=384 [M+H]

$^1$H-NMR (400 MHz, DMSO-d6) δ[ppm]: 0.752 (0.63), 0.772 (0.71), 0.977 (1.55), 1.157 (0.59), 1.175 (1.19), 1.192 (0.62), 1.344 (1.25), 1.378 (16.00), 1.405 (1.99), 1.417 (0.84), 1.988 (2.18), 2.016 (0.51), 2.027 (0.54), 2.037 (0.43), 2.232 (4.19), 2.249 (0.42), 2.519 (0.47), 3.755 (0.54), 3.792 (0.96), 3.866 (1.00), 3.902 (0.51), 4.020 (0.51), 4.038 (0.51), 4.322 (0.42), 4.333 (0.42), 4.337 (0.59), 4.347 (0.44), 7.025 (0.89), 7.045 (1.39), 7.119 (1.76), 7.139 (1.14).

Intermediate 261 tert-Butyl (5S)-3-oxo-2-{[2-(trifluoromethyl)-1,8-naphthyridin-3-yl]methyl}-2,3,5,6,7,8-hexahydro[1,2,4]triazolo[4,3-a]pyridine-5-carboxylate

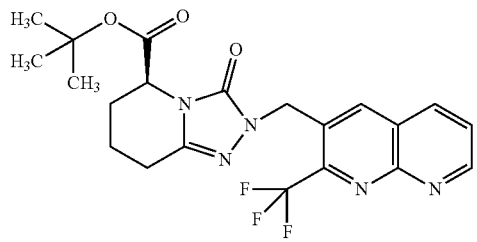 [SMILES: CC(C)(C)OC(=O)[C@@H]1CCCc2nn(Cc3cc4cccnc4nc3C(F)(F)F)c(=O)n21]

tert-Butyl (5S)-3-oxo-2,3,5,6,7,8-hexahydro[1,2,4]triazolo[4,3-a]pyridine-5-carboxylate (208 mg, 868 μmol) was initially charged in acetonitrile (20 ml). Caesium carbonate (1.13 g, 3.47 mmol) and 3-(chloromethyl)-2-(trifluoromethyl)-1,8-naphthyridine (278 mg, 1.13 mmol) were subsequently added. After stirring for 48 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 146 mg (38% of theory) of the title compound were obtained.

LC-MS (Method 3): R$_t$=1.65 min; MS (ESIpos): m/z=450 [M+H]

$^1$H-NMR (400 MHz, DMSO-d6) δ[ppm]: 1.421 (16.00), 2.113 (0.64), 2.125 (0.64), 2.665 (0.41), 4.520 (0.73), 5.235 (1.07), 7.820 (0.54), 7.830 (0.56), 7.840 (0.56), 7.851 (0.57), 8.449 (1.25), 8.564 (0.56), 8.569 (0.57), 8.585 (0.55), 8.589 (0.52), 9.245 (0.61), 9.250 (0.64), 9.256 (0.63), 9.261 (0.57).

Intermediate 262 tert-Butyl (5S)-2-[(6-chloropyridin-3-yl)methyl]-3-oxo-2,3,5,6,7,8-hexahydro[1,2,4]triazolo[4,3-a]pyridine-5-carboxylate

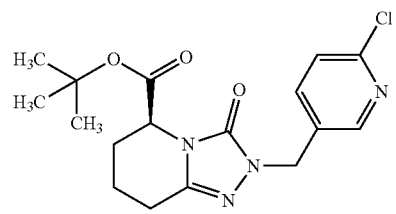 [SMILES: CC(C)(C)OC(=O)[C@@H]1CCCc2nn(Cc3ccc(Cl)nc3)c(=O)n21]

tert-Butyl (5S)-3-oxo-2,3,5,6,7,8-hexahydro[1,2,4]triazolo[4,3-a]pyridine-5-carboxylate (552 mg, 2.31 mmol) was initially charged in acetonitrile (11 ml). Caesium carbonate (1.13 g, 3.46 mmol) and 5-(bromomethyl)-2-chloropyridine (500 mg, 2.42 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 509 mg (93% purity, 56% of theory) of the title compound were obtained.

LC-MS (Method 1): R$_t$=1.13 min; MS (ESIpos): m/z=365 [M+H]$^+$

Intermediate 263 tert-Butyl (5S)-3-oxo-2-{[6-(trifluoromethyl)pyridin-3-yl]methyl}-2,3,5,6,7,8-hexahydro[1,2,4]triazolo[4,3-a]pyridine-5-carboxylate

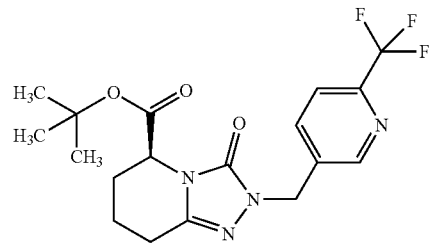 [SMILES: CC(C)(C)OC(=O)[C@@H]1CCCc2nn(Cc3ccc(C(F)(F)F)nc3)c(=O)n21]

tert-Butyl (5S)-3-oxo-2,3,5,6,7,8-hexahydro[1,2,4]triazolo[4,3-a]pyridine-5-carboxylate (1.00 g, 4.18 mmol) was initially charged in acetonitrile (21 ml). Caesium carbonate (2.04 g, 6.27 mmol) and 5-(chloromethyl)-2-(trifluoromethyl)pyridine (858 mg, 4.39 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 1.71 g (100% of theory) of the title compound were obtained.

LC-MS (Method 3): $R_t$=1.73 min; MS (ESIpos): m/z=399 [M+H]$^+$

Intermediate 264 tert-Butyl (5S)-2-{[5-chloro-6-(trifluoromethyl)pyridin-3-yl]methyl}-3-oxo-2,3,5,6,7,8-hexahydro[1,2,4]triazolo[4,3-a]pyridine-5-carboxylate

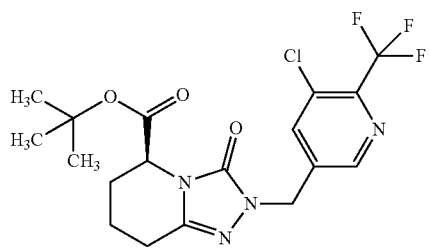 [SMILES: CC(C)(C)OC(=O)[C@@H]1CCCc2nn(Cc3cnc(C(F)(F)F)c(Cl)c3)c(=O)n21]

tert-Butyl (5S)-3-oxo-2,3,5,6,7,8-hexahydro[1,2,4]triazolo[4,3-a]pyridine-5-carboxylate (163 mg, 682 µmol) was initially charged in acetonitrile (5.0 ml). Caesium carbonate (555 mg, 1.70 mmol) and 3-chloro-5-(chloromethyl)-2-(trifluoromethyl)pyridine (549 mg, 30% purity, 716 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 156 mg (72% purity, 38% of theory) of the title compound were obtained.

LC-MS (Method 1): $R_t$=1.35 min; MS (ESIpos): m/z=377 [M−tBu+H]+

Intermediate 265 tert-Butyl (5S)-2-{2-[3-chloro-5-(trifluoromethyl)pyridin-2-yl]ethyl}-3-oxo-2,3,5,6,7,8-hexahydro[1,2,4]triazolo[4,3-a]pyridine-5-carboxylate

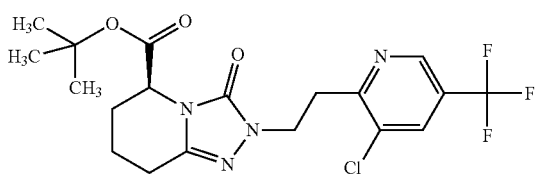 [SMILES: CC(C)(C)OC(=O)[C@@H]1CCCc2nn(CCc3ncc(C(F)(F)F)cc3Cl)c(=O)n21]

tert-Butyl (5S)-3-oxo-2,3,5,6,7,8-hexahydro[1,2,4]triazolo[4,3-a]pyridine-5-carboxylate (95.0 mg, 397 µmol) was initially charged in acetonitrile (3.0 ml). Caesium carbonate (323 mg, 992 µmol) and 3-chloro-2-(2-chloroethyl)-5-(trifluoromethyl)pyridine (113 mg, 94% purity, 437 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 74.5 mg (42% of theory) of the title compound were obtained.

LC-MS (Method 1): $R_t$=1.36 min; MS (ESIpos): m/z=391 [M+H]$^+$ $^1$H-NMR (400 MHz, DMSO-d6) δ[ppm]: −0.008 (2.40), 0.008 (1.82), 1.389 (16.00), 2.034 (0.55), 2.619 (0.43), 2.669 (0.51), 4.058 (0.75), 4.077 (1.16), 4.094 (0.66), 4.361 (0.59), 8.407 (0.85), 8.871 (0.84).

Intermediate 266 tert-Butyl (5S)-3-oxo-2-[3-(trifluoromethyl)benzyl]-2,3,5,6,7,8-hexahydro[1,2,4]triazolo[4,3-a]pyridine-5-carboxylate

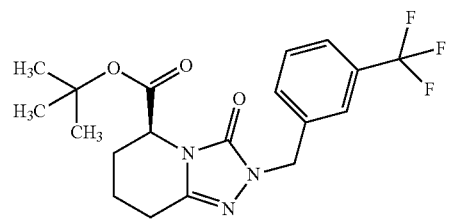 [SMILES: CC(C)(C)OC(=O)[C@@H]1CCCc2nn(Cc3cccc(C(F)(F)F)c3)c(=O)n21]

tert-Butyl (5S)-3-oxo-2,3,5,6,7,8-hexahydro[1,2,4]triazolo[4,3-a]pyridine-5-carboxylate (400 mg, 1.67 mmol) was initially charged in acetonitrile (6.0 ml). Caesium carbonate (817 mg, 2.51 mmol) and 1-(bromomethyl)-3-(trifluoromethyl)benzene (420 mg, 1.76 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 581 mg (87% of theory) of the title compound were obtained.

LC-MS (Method 3): $R_t$=1.98 min; MS (ESIpos): m/z=398 [M+H]$^+$ $^1$H-NMR (400 MHz, DMSO-d6) δ [ppm]: −0.008 (0.69), 0.008 (0.57), 1.384 (16.00), 1.400 (0.78), 2.068 (0.55), 2.077 (0.49), 2.523 (0.41), 4.460 (0.57), 4.949 (1.19), 4.965 (1.15), 7.558 (0.62), 7.575 (0.40), 7.594 (0.64), 7.629 (0.79), 7.652 (0.50).

Intermediate 267 tert-Butyl (5S)-3-oxo-2-(2,4,5-trifluorobenzyl)-2,3,5,6,7,8-hexahydro[1,2,4]triazolo[4,3-a]pyridine-5-carboxylate

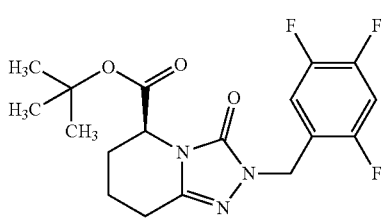 [SMILES: CC(C)(C)OC(=O)[C@@H]1CCCc2nn(Cc3cc(F)c(F)cc3F)c(=O)n21]

tert-Butyl (5S)-3-oxo-2,3,5,6,7,8-hexahydro[1,2,4]triazolo[4,3-a]pyridine-5-carboxylate (400 mg, 1.67 mmol) was initially charged in acetonitrile (10 ml). Caesium carbonate (572 mg, 1.76 mmol) and 1-(chloromethyl)-2,4,5-trifluorobenzene (317 mg, 1.76 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 523 mg (80% of theory) of the title compound were obtained.

LC-MS (Method 3): $R_t$=1.87 min; MS (ESIpos): m/z=328 [M+H]$^+$ $^1$H-NMR (400 MHz, DMSO-d6) δ [ppm]: 1.175 (0.64), 1.394 (16.00), 1.988 (1.17), 2.060 (0.65), 2.069 (0.65), 2.072 (0.65), 2.627 (0.44), 4.428 (0.44), 4.442 (0.62), 4.864 (2.33).

Intermediate 268 tert-Butyl (5S) 2-(3,4-difluorobenzyl)-3-oxo-2,3,5,6,7,8-hexahydro[1,2,4]triazolo[4,3-a]pyridine-5-carboxylate

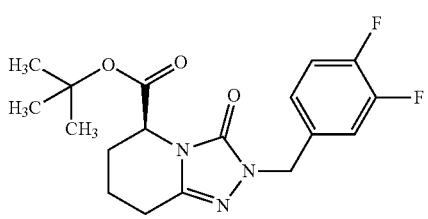 [SMILES: CC(C)(C)OC(=O)[C@@H]1CCCc2nn(Cc3ccc(F)c(F)c3)c(=O)n21]

tert-Butyl (5S)-3-oxo-2,3,5,6,7,8-hexahydro[1,2,4]triazolo[4,3-a]pyridine-5-carboxylate (500 mg, 2.09 mmol) was initially charged in acetonitrile (10 ml). Caesium carbonate (1.70 g, 5.22 mmol) and 4-(bromomethyl)-1,2-difluorobenzene (454 mg, 2.19 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 900 mg (78% purity, 92% of theory) of the title compound were obtained.

LC-MS (Method 1): $R_t$=0.83 min; MS (ESIpos): m/z=310 [M−tBu+H]+

Intermediate 269 tert-Butyl (5S)-2-[3-chloro-4-(trifluoromethyl)benzyl]-3-oxo-2,3,5,6,7,8-hexahydro[1,2,4]triazolo[4,3-a]pyridine-5-carboxylate

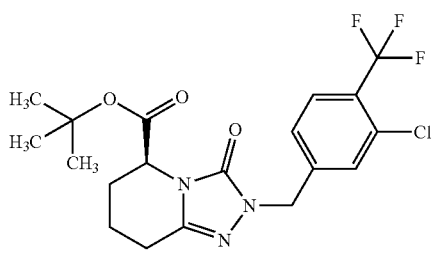 [SMILES: CC(C)(C)OC(=O)[C@@H]1CCCc2nn(Cc3ccc(C(F)(F)F)c(Cl)c3)c(=O)n21]

tert-Butyl (5S)-3-oxo-2,3,5,6,7,8-hexahydro[1,2,4]triazolo[4,3-a]pyridine-5-carboxylate (400 mg, 1.67 mmol) was initially charged in acetonitrile (8.0 ml). Caesium carbonate (1.36 g, 4.18 mmol) and 2-chloro-4-(chloromethyl)-1-(trifluoromethyl)benzene (402 mg, 1.76 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 190 mg (26% of theory) of the title compound were obtained.

LC-MS (Method 3): $R_t$=2.12 min; MS (ESIpos): m/z=454 [M+Na]$^+$ $^1$H-NMR (400 MHz, DMSO-d6) δ [ppm]: −0.008 (0.90), 0.008 (0.82), 1.390 (16.00), 2.075 (0.55), 4.466 (0.60), 4.970 (1.54), 7.404 (0.46), 7.425 (0.49), 7.584 (0.94), 7.844 (0.81), 7.865 (0.75).

Intermediate 270 tert-Butyl (5S)-2-(3-chloro-4-fluorobenzyl)-3-oxo-2,3,5,6,7,8-hexahydro[1,2,4]triazolo[4,3-a]pyridine-5-carboxylate

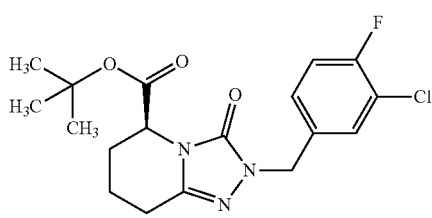 [SMILES: CC(C)(C)OC(=O)[C@@H]1CCCc2nn(Cc3ccc(F)c(Cl)c3)c(=O)n21]

tert-Butyl (5S)-3-oxo-2,3,5,6,7,8-hexahydro[1,2,4]triazolo[4,3-a]pyridine-5-carboxylate (500 mg, 2.09 mmol)

was initially charged in acetonitrile (10 ml). Caesium carbonate (1.70 g, 5.22 mmol) and 4-(bromomethyl)-2-chloro-1-fluorobenzene (490 mg, 2.19 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 600 mg (75% of theory) of the title compound were obtained.

LC-MS (Method 4): $R_t$=1.01 min; MS (ESIpos): m/z=382 [M+H]$^+$

Intermediate 271 tert-Butyl (5S)-2-[3-fluoro-4-(trifluoromethyl)benzyl]-3-oxo-2,3,5,6,7,8-hexahydro[1,2,4]triazolo[4,3-a]pyridine-5-carboxylate

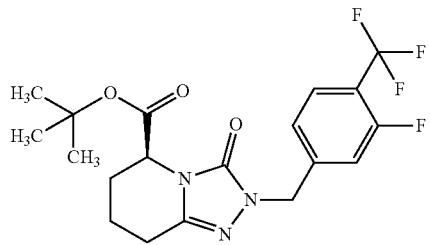 [SMILES: CC(C)(C)OC(=O)[C@@H]1CCCc2nn(Cc3ccc(C(F)(F)F)c(F)c3)c(=O)n21]

tert-Butyl (5S)-3-oxo-2,3,5,6,7,8-hexahydro[1,2,4]triazolo[4,3-a]pyridine-5-carboxylate (500 mg, 2.09 mmol) was initially charged in acetonitrile (10 ml). Caesium carbonate (1.70 g, 5.22 mmol) and 4-(chloromethyl)-2-fluoro-1-(trifluoromethyl)benzene (466 mg, 2.19 mmol) were subsequently added. After stirring for 72 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 707 mg (91% purity, 74% of theory) of the title compound were obtained.

LC-MS (Method 1): $R_t$=0.83 min; MS (ESIpos): m/z=360 [M−tBu+H]+

Intermediate 272 tert-Butyl (5S)-2-{[3-fluoro-2-(trifluoromethyl)pyridin-4-yl]methyl}-3-oxo-2,3,5,6,7,8-hexahydro[1,2,4]triazolo[4,3-a]pyridine-5-carboxylate

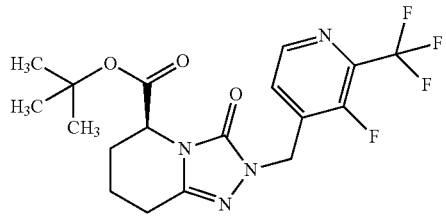 [SMILES: CC(C)(C)OC(=O)[C@@H]1CCCc2nn(Cc3ccnc(C(F)(F)F)c3F)c(=O)n21]

tert-Butyl (5S)-3-oxo-2,3,5,6,7,8-hexahydro[1,2,4]triazolo[4,3-a]pyridine-5-carboxylate (371 mg, 1.55 mmol) was initially charged in acetonitrile (7.0 ml). Caesium carbonate (1.11 g, 3.41 mmol) and 4-(chloromethyl)-3-fluoro-2-(trifluoromethyl)pyridine (348 mg, 1.63 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 420 mg (65% of theory) of the title compound were obtained.

LC-MS (Method 3): $R_t$=1.83 min; MS (ESIpos): m/z=417 [M+H]$^+$ $^1$H-NMR (400 MHz, DMSO-d6) δ [ppm]: 1.228 (0.06), 1.359 (0.10), 1.388 (16.00), 1.471 (0.11), 1.484 (0.16), 1.497 (0.15), 1.506 (0.16), 1.518 (0.17), 1.531 (0.12), 1.545 (0.15), 1.815 (0.19), 1.825 (0.18), 1.837 (0.16), 1.849 (0.16), 2.068 (0.55), 2.081 (0.45), 2.106 (0.17), 2.114 (0.16), 2.322 (0.04), 2.361 (0.04), 2.568 (0.26), 2.581 (0.27), 2.595 (0.21), 2.630 (0.21), 2.641 (0.36), 2.653 (0.23), 2.672 (0.13), 2.683 (0.17), 2.695 (0.09), 4.447 (0.39), 4.461 (0.60), 4.471 (0.37), 4.942 (0.11), 5.083 (2.35), 7.596 (0.35), 7.609 (0.64), 7.622 (0.35), 8.566 (0.73), 8.578 (0.71).

Intermediate 273 tert-Butyl (5S)-2-{[1-(6-chloropyridin-2-yl)cyclopropyl]methyl}-3-oxo-2,3,5,6,7,8-hexahydro[1,2,4]triazolo[4,3-a]pyridine-5-carboxylate

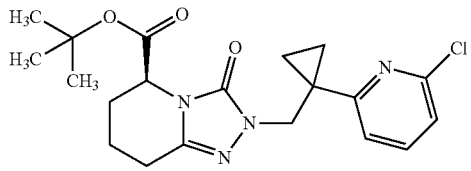 [SMILES: CC(C)(C)OC(=O)[C@@H]1CCCc2nn(CC3(c4cccc(Cl)n4)CC3)c(=O)n21]

tert-Butyl (5S)-3-oxo-2,3,5,6,7,8-hexahydro[1,2,4]triazolo[4,3-a]pyridine-5-carboxylate (129 mg, 541 μmol) was initially charged in acetonitrile (3.0 ml). Caesium carbonate (441 mg, 1.35 mmol) and 2-[1-(bromomethyl)cyclopropyl]-6-chloropyridine (140 mg, 568 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 224 mg (96% of theory) of the title compound were obtained.

LC-MS (Method 3): $R_t$=1.94 min; MS (ESIpos): m/z=405 [M+H]$^+$ $^1$H-NMR (400 MHz, DMSO-d6) δ [ppm]: 1.157 (2.03), 1.161 (1.97), 1.175 (3.58), 1.192 (1.29), 1.253 (0.99), 1.331 (0.71), 1.376 (16.00), 1.406 (3.62), 1.988 (4.27), 2.023 (0.56), 2.036 (0.59), 2.046 (0.41), 2.520 (0.43), 4.020 (0.99), 4.038 (1.01), 4.056 (0.41), 4.096 (2.12), 4.388 (0.40), 4.393 (0.56), 7.245 (0.76), 7.265 (0.83), 7.606 (0.68), 7.625 (0.99), 7.696 (0.72), 7.715 (1.13), 7.735 (0.49).

Intermediate 274 tert-Butyl (5S)-2-{[1-(4-fluorophenyl)cyclopropyl]methyl}-3-oxo-2,3,5,6,7,8-hexahydro[1,2,4]triazolo[4,3-a]pyridine-5-carboxylate

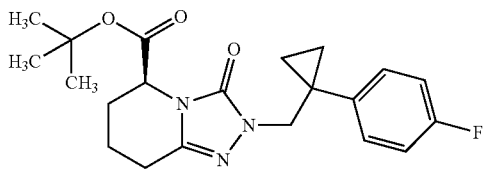 [SMILES: CC(C)(C)OC(=O)[C@@H]1CCCc2nn(CC3(c4ccc(F)cc4)CC3)c(=O)n21]

tert-Butyl (5S)-3-oxo-2,3,5,6,7,8-hexahydro[1,2,4]triazolo[4,3-a]pyridine-5-carboxylate (344 mg, 1.44 mmol) was initially charged in acetonitrile (10 ml). Caesium carbonate (1.17 g, 3.59 mmol) and 1-[1-(bromomethyl)cyclopropyl]-4-fluorobenzene (346 mg, 1.51 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 557 mg (100% of theory) of the title compound were obtained.

LC-MS (Method 3): $R_t$=2.04 min; MS (ESIpos): m/z=388 [M+H]$^+$

Intermediate 275 tert-Butyl (5S)-2-{[1-(4-methoxyphenyl)cyclopropyl]methyl}-3-oxo-2,3,5,6,7,8-hexahydro[1,2,4]triazolo[4,3-a]pyridine-5-carboxylate

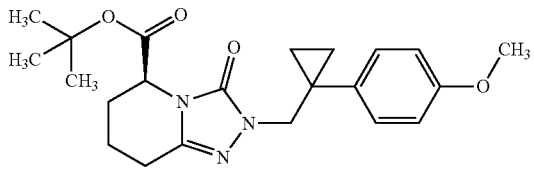 [SMILES: COc1ccc(C2(Cn3nc4n(c3=O)[C@H](C(=O)OC(C)(C)C)CCC4)CC2)cc1]

tert-Butyl (5S)-3-oxo-2,3,5,6,7,8-hexahydro[1,2,4]triazolo[4,3-a]pyridine-5-carboxylate (172 mg, 717 μmol) was initially charged in acetonitrile (4.8 ml). Caesium carbonate (584 mg, 1.79 mmol) and 1-[1-(bromomethyl)cyclopropyl]-4-methoxybenzene (190 mg, 789 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 222 mg (73% of theory) of the title compound were obtained.

LC-MS (Method 3): $R_t$=1.95 min; MS (ESIpos): m/z=344 [M+H]$^+$ $^1$H-NMR (400 MHz, DMSO-d6) δ [ppm]: 0.699 (0.14), 0.724 (0.72), 0.743 (0.79), 0.766 (0.18), 0.839 (0.08), 0.931 (0.17), 0.949 (1.72), 0.971 (0.15), 1.219 (0.07), 1.354 (1.10), 1.380 (16.00), 1.512 (0.20), 1.537 (0.16), 1.780 (0.22), 1.802 (0.20), 1.814 (0.20), 2.019 (0.54), 2.030 (0.56), 2.040 (0.39), 2.327 (0.07), 2.469 (0.14), 2.525 (0.43), 2.595 (0.25), 2.606 (0.42), 2.618 (0.25), 2.637 (0.15), 2.648 (0.21), 2.660 (0.13), 2.709 (0.06), 3.698 (6.61), 3.711 (0.51), 3.726 (0.56), 3.762 (1.00), 3.831 (1.00), 3.867 (0.53), 4.286 (0.06), 4.319 (0.40), 4.334 (0.59), 4.344 (0.39), 6.776 (1.42), 6.798 (1.61), 6.818 (0.10), 6.840 (0.10), 7.142 (1.66), 7.163 (1.47), 7.227 (0.10), 7.248 (0.09).

Intermediate 276 tert-Butyl (5S)-2-{[1-(2,4-difluorophenyl)cyclopropyl]methyl}-3-oxo-2,3,5,6,7,8-hexahydro[1,2,4]triazolo[4,3-a]pyridine-5-carboxylate

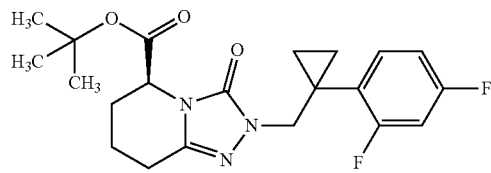 [SMILES: CC(C)(C)OC(=O)[C@@H]1CCCc2nn(CC3(c4ccc(F)cc4F)CC3)c(=O)n21]

tert-Butyl (5S)-3-oxo-2,3,5,6,7,8-hexahydro[1,2,4]triazolo[4,3-a]pyridine-5-carboxylate (313 mg, 1.31 mmol) was initially charged in acetonitrile (8.7 ml). Caesium carbonate (1.06 g, 3.27 mmol) and 1-[1-(bromomethyl)cyclopropyl]-2,4-difluorobenzene (355 mg, 1.44 mmol) were subsequently added. After stirring for 72 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 256 mg (48% of theory) of the title compound were obtained.

LC-MS (Method 1): $R_t$=1.38 min; MS (ESIpos): m/z=350 [M−tBu]$^+$ $^1$H-NMR (400 MHz, DMSO-d6) δ[ppm]: 0.007 (0.24), 0.747 (0.38), 0.759 (1.23), 0.774 (0.45), 0.996 (0.45), 1.007 (1.20), 1.023 (0.37), 1.375 (16.00), 1.466 (0.16), 1.501 (0.17), 1.527 (0.11), 1.764 (0.19), 1.786 (0.17), 1.798 (0.16), 2.005 (0.56), 2.016 (0.45), 2.433 (0.12), 2.448 (0.15), 2.460 (0.14), 2.475 (0.36), 2.563 (0.22), 2.575 (0.38), 2.586 (0.22), 2.605 (0.13), 2.616 (0.19), 3.707 (0.32), 3.743 (1.13), 3.765 (1.16), 3.801 (0.32), 4.278 (0.39), 4.293 (0.62), 4.303 (0.37), 6.882 (0.18), 6.898 (0.37), 6.903 (0.38), 6.918 (0.20), 6.924 (0.21), 7.082 (0.23), 7.089 (0.24), 7.111 (0.34), 7.133 (0.26), 7.138 (0.45), 7.160 (0.46), 7.177 (0.46), 7.198 (0.21).

Intermediate 277 tert-Butyl (5S)-3-oxo-2-({1-[4-(trifluoromethyl)phenyl]cyclopropyl}methyl)-2,3,5,6,7,8-hexahydro[1,2,4]triazolo[4,3-a]pyridine-5-carboxylate

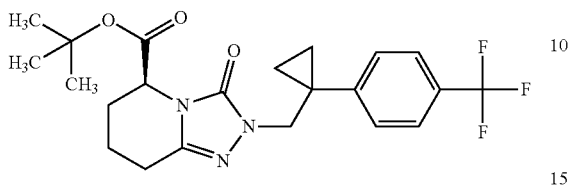

tert-Butyl (5S)-3-oxo-2,3,5,6,7,8-hexahydro[1,2,4]triazolo[4,3-a]pyridine-5-carboxylate (80.4 mg, 336 µmol) was initially charged in acetonitrile (2.0 ml). Caesium carbonate (274 mg, 840 µmol) and 1-[1-(bromomethyl)cyclopropyl]-4-(trifluoromethyl)benzene (110 mg, 94% purity, 370 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 113 mg (74% of theory) of the title compound were obtained.

LC-MS (Method 1): $R_t$=1.47 min; MS (ESIpos): m/z=382 [M−tBu]+

Intermediate 278 tert-Butyl (5S) 2-(2,4-difluorobenzyl)-3-oxo-2,3,5,6,7,8-hexahydro[1,2,4]triazolo[4,3-a]pyridine-5-carboxylate

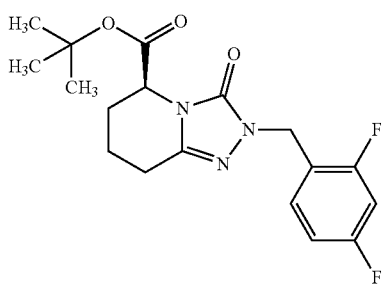 [SMILES: CC(C)(C)OC(=O)[C@@H]1CCCc2nn(Cc3ccc(F)cc3F)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (8.0 ml). Caesium carbonate (1.02 g, 3.13 mmol) and 1-(chloromethyl)-2,4-difluorobenzene (214 mg, 1.32 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 423 mg (92% of theory) of the title compound were obtained.

LC-MS (Method 3): $R_t$=1.81 min; MS (ESIpos): m/z=366 [M+H]+

Intermediate 279 tert-Butyl (5S)-2-(2-chloro-4-fluorobenzyl)-3-oxo-2,3,5,6,7,8-hexahydro[1,2,4]triazolo[4,3-a]pyridine-5-carboxylate

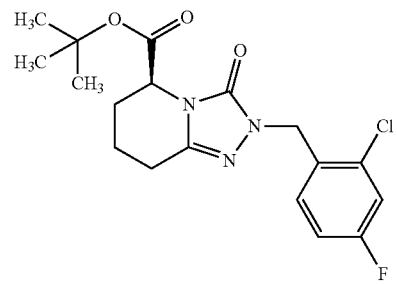 [SMILES: CC(C)(C)OC(=O)[C@@H]1CCCc2nn(Cc3ccc(F)cc3Cl)c(=O)n21]

tert-Butyl (5S)-3-oxo-2,3,5,6,7,8-hexahydro[1,2,4]triazolo[4,3-a]pyridine-5-carboxylate (250 mg, 1.04 mmol) was initially charged in acetonitrile (6.0 ml). Caesium carbonate (851 mg, 2.61 mmol) and 1-(bromomethyl)-2-chloro-4-fluorobenzene (245 mg, 1.10 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 370 mg (88% of theory) of the title compound were obtained.

LC-MS (Method 3): $R_t$=0.83 min; MS (ESIpos): m/z=326 [M−tBu+H]+

Intermediate 280 tert-Butyl (5S)-2-[(5-chloro-6-methoxypyridin-3-yl)methyl]-3-oxo-2,3,5,6,7,8-hexahydro[1,2,4]triazolo[4,3-a]pyridine-5-carboxylate

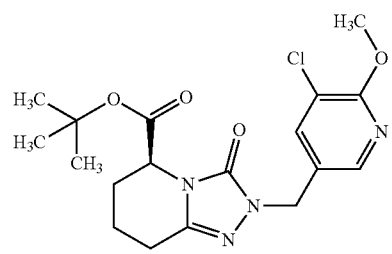 [SMILES: COc1ncc(Cn2nc3n(c2=O)[C@H](C(=O)OC(C)(C)C)CCC3)cc1Cl]

tert-Butyl (5S)-3-oxo-2,3,5,6,7,8-hexahydro[1,2,4]triazolo[4,3-a]pyridine-5-carboxylate (664 mg, 2.78 mmol) was initially charged in acetonitrile (10 ml). Caesium carbonate (1.36 g, 4.17 mmol) and 3-chloro-5-(chloromethyl)-2-methoxypyridine (560 mg, 2.92 mmol) were subsequently added. After stirring overnight, the reaction mixture was admixed at room temperature with water and ethyl acetate.

Intermediate 281 tert-Butyl (5S) 2-(4-fluorobenzyl)-3-oxo-2,3,5,6,7,8-hexahydro[1,2,4]triazolo[4,3-a]pyridine-5-carboxylate

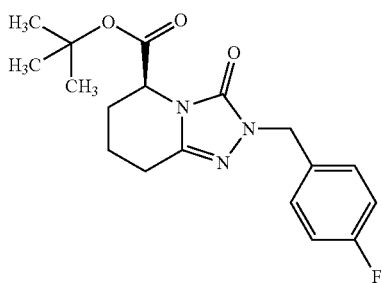 [SMILES: CC(C)(C)OC(=O)[C@@H]1CCCc2nn(Cc3ccc(F)cc3)c(=O)n21]

tert-Butyl (5S)-3-oxo-2,3,5,6,7,8-hexahydro[1,2,4]triazolo[4,3-a]pyridine-5-carboxylate (250 mg, 1.04 mmol) was initially charged in acetonitrile (6.0 ml). Caesium carbonate (851 mg, 2.61 mmol) and 1-(bromomethyl)-4-fluorobenzene (207 mg, 1.10 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 718 mg (90% purity, 59% of theory) of the title compound were obtained.

LC-MS (Method 1): $R_t$=1.25 min; MS (ESIpos): m/z=395 [M+H]$^+$

Intermediate 281 tert-Butyl (5S) 2-(4-fluorobenzyl)-3-oxo-2,3,5,6,7,8-hexahydro[1,2,4]triazolo[4,3-a]pyridine-5-carboxylate tert-Butyl (5S)-3-oxo-2,3,5,6,7,8-hexahydro[1,2,4]triazolo[4,3-a]pyridine-5-carboxylate (250 mg, 1.04 mmol) was initially charged in acetonitrile (6.0 ml). Caesium carbonate (851 mg, 2.61 mmol) and 1-(bromomethyl)-4-fluorobenzene (207 mg, 1.10 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 299 mg (82% of theory) of the title compound were obtained.

LC-MS (Method 3): $R_t$=1.75 min; MS (ESIpos): m/z=348 [M+H]$^+$ $^1$H-NMR (400 MHz, DMSO-d6) δ[ppm]: 1.334 (0.45), 1.392 (16.00), 2.057 (0.50), 2.067 (0.46), 2.073 (0.41), 4.435 (0.57), 4.823 (2.34), 7.143 (0.57), 7.165 (1.32), 7.188 (0.83), 7.276 (0.70), 7.290 (0.77), 7.298 (0.62), 7.312 (0.51).

Intermediate 282 tert-Butyl (5S)-2-[(6-chloropyridin-2-yl)methyl]-3-oxo-2,3,5,6,7,8-hexahydro[1,2,4]triazolo[4,3-a]pyridine-5-carboxylate

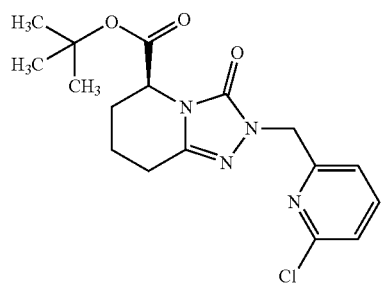 [SMILES: CC(C)(C)OC(=O)[C@@H]1CCCc2nn(Cc3cccc(Cl)n3)c(=O)n21]

tert-Butyl (5S)-3-oxo-2,3,5,6,7,8-hexahydro[1,2,4]triazolo[4,3-a]pyridine-5-carboxylate (266 mg, 1.11 mmol) was initially charged in acetonitrile (10 ml). Caesium carbonate (904 mg, 2.77 mmol) and 2-chloro-6-(chloromethyl)pyridine (189 mg, 1.17 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 372 mg (92% of theory) of the title compound were obtained.

LC-MS (Method 3): $R_t$=1.65 min; MS (ESIpos): m/z=365 [M+H]$^+$ $^1$H-NMR (400 MHz, DMSO-d6) δ[ppm]: −0.009 (0.09), 0.007 (0.09), 0.786 (0.01), 0.805 (0.03), 0.828 (0.02), 0.846 (0.04), 0.865 (0.02), 1.139 (0.04), 1.156 (0.65), 1.174 (1.28), 1.191 (0.66), 1.248 (0.07), 1.372 (0.24), 1.409 (16.00), 1.456 (0.05), 1.469 (0.08), 1.482 (0.12), 1.495 (0.17), 1.507 (0.16), 1.517 (0.17), 1.529 (0.18), 1.542 (0.13), 1.556 (0.10), 1.566 (0.12), 1.823 (0.21), 1.832 (0.19), 1.844 (0.18), 1.856 (0.17), 1.867 (0.13), 1.987 (2.34), 2.044 (0.07), 2.055 (0.08), 2.072 (0.92), 2.081 (0.55), 2.090 (0.52), 2.098 (0.37), 2.109 (0.21), 2.116 (0.19), 2.124 (0.17), 2.136 (0.06), 2.145 (0.05), 2.152 (0.05), 2.160 (0.04), 2.327 (0.02), 2.365 (0.02), 2.573 (0.27), 2.585 (0.28), 2.599 (0.22), 2.630 (0.22), 2.641 (0.38), 2.653 (0.24), 2.672 (0.13), 2.683 (0.18), 2.695 (0.10), 2.808 (0.01), 4.002 (0.19), 4.020 (0.56), 4.037 (0.55), 4.055 (0.18), 4.451 (0.39), 4.461 (0.41), 4.465 (0.58), 4.475 (0.38), 4.737 (0.02), 4.771 (0.08), 4.872 (0.06), 4.915 (2.29), 4.957 (0.06), 5.154 (0.03), 5.169 (0.03), 5.392 (0.02), 5.405 (0.02), 7.163 (0.72), 7.182 (0.77), 7.332 (0.02), 7.350 (0.02), 7.437 (0.62), 7.456 (0.69), 7.482 (0.03), 7.502 (0.03), 7.515 (0.01), 7.558 (0.01), 7.577 (0.01), 7.842 (0.58), 7.861 (1.02), 7.881 (0.51), 7.904 (0.03), 7.918 (0.02).

Intermediate 283

Methyl (5S)-2-[2-(4-fluorophenyl)ethyl]-3-oxo-2,3,5,6,7,8-hexahydro[1,2,4]triazolo[4,3-a]pyridine-5-carboxylate

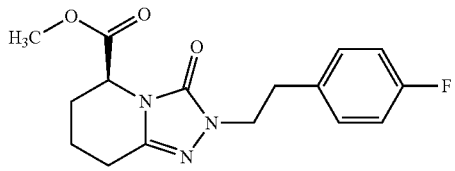 [SMILES: COC(=O)[C@@H]1CCCc2nn(CCc3ccc(F)cc3)c(=O)n21]

Methyl (5S)-3-oxo-2,3,5,6,7,8-hexahydro[1,2,4]triazolo[4,3-a]pyridine-5-carboxylate (224 mg, 1.13 mmol) was initially charged in acetonitrile (8.0 ml). Caesium carbonate (923 mg, 2.83 mmol) and 1-(2-chloroethyl)-4-fluorobenzene (189 mg, 1.19 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 221 mg (61% of theory) of the title compound were obtained.

LC-MS (Method 3): $R_t$=1.43 min; MS (ESIpos): m/z=320 $[M+H]^+$ $^1$H-NMR (400 MHz, DMSO-d6) δ[ppm]: −0.149 (1.81), −0.008 (16.00), 0.008 (13.92), 0.146 (1.74), 1.157 (0.60), 1.175 (1.34), 1.193 (0.74), 1.988 (2.48), 2.073 (0.80), 2.328 (1.81), 2.366 (1.21), 2.523 (5.29), 2.602 (0.54), 2.670 (1.94), 2.710 (1.27), 2.910 (0.54), 2.929 (0.87), 2.947 (0.54), 3.677 (5.42), 3.687 (1.41), 3.808 (0.67), 3.826 (1.00), 3.844 (0.60), 4.021 (0.60), 4.038 (0.60), 4.533 (0.47), 7.067 (0.47), 7.090 (1.14), 7.112 (0.74), 7.208 (0.67), 7.222 (0.74), 7.243 (0.54).

Intermediate 284 tert-Butyl (5S) 2-(4-methoxybenzyl)-3-oxo-2,3,5,6,7,8-hexahydro[1,2,4]triazolo[4,3-a]pyridine-5-carboxylate

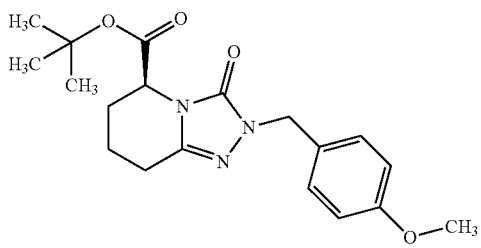 [SMILES: COc1ccc(Cn2nc3n(c2=O)[C@H](C(=O)OC(C)(C)C)CCC3)cc1]

tert-Butyl (5S)-3-oxo-2,3,5,6,7,8-hexahydro[1,2,4]triazolo[4,3-a]pyridine-5-carboxylate (100 mg, 418 μmol) was initially charged in acetonitrile (4.0 ml). Caesium carbonate (272 mg, 836 μmol) and 1-(bromomethyl)-4-methoxybenzene (88.2 mg, 439 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 129 mg (90% purity, 77% of theory) of the title compound were obtained.

LC-MS (Method 1): $R_t$=1.21 min; MS (ESIpos): m/z=304 [M−tBu+H]+

Intermediate 285 tert-Butyl (5S)-2-[(5-chloro-3-fluoropyridin-2-yl)methyl]-3-oxo-2,3,5,6,7,8-hexahydro[1,2,4]triazolo[4,3-a]pyridine-5-carboxylate

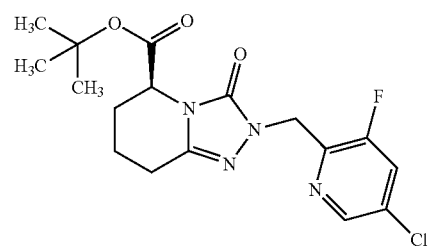 [SMILES: CC(C)(C)OC(=O)[C@@H]1CCCc2nn(Cc3ncc(Cl)cc3F)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (12 ml, 230 mmol). Caesium carbonate (817 mg, 2.51 mmol) and 5-chloro-2-(chloromethyl)-3-fluoropyridine (237 mg, 1.32 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 465 mg (95% of theory) of the title compound were obtained.

LC-MS (Method 4): $R_t$=0.88 min; MS (ESIpos): m/z=383 $[M+H]^+$

Intermediate 286 tert-Butyl (5S)-2-[(5-fluoropyridin-2-yl)methyl]-3-oxo-2,3,5,6,7,8-hexahydro[1,2,4]triazolo[4,3-a]pyridine-5-carboxylate

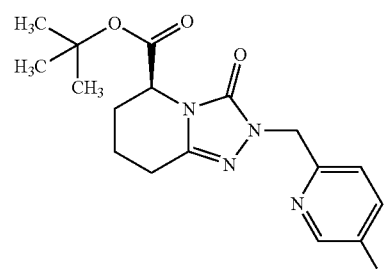

tert-Butyl (5S)-3-oxo-2,3,5,6,7,8-hexahydro[1,2,4]triazolo[4,3-a]pyridine-5-carboxylate (275 mg, 1.15 mmol) was initially charged in acetonitrile (10 ml). Caesium carbonate (936 mg, 2.87 mmol) and 2-(chloromethyl)-5-fluoropyridine hydrochloride (220 mg, 1.21 mmol) were subsequently added. After stirring for 72 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 345 mg (83% of theory) of the title compound were obtained.

LC-MS (Method 3): $R_t$=1.45 min; MS (ESIpos): m/z=349 $[M+H]^+$ $^1$H-NMR (400 MHz, DMSO-d6) δ [ppm]: 1.156 (0.20), 1.174 (0.36), 1.191 (0.20), 1.353 (0.26), 1.408 (16.00), 1.487 (0.22), 1.499 (0.22), 1.510 (0.24), 1.521 (0.25), 1.534 (0.19), 1.814 (0.28), 1.824 (0.28), 1.836 (0.24), 1.847 (0.24), 1.858 (0.18), 1.987 (0.66), 2.049 (0.18), 2.072 (0.93), 2.083 (0.69), 2.107 (0.24), 2.115 (0.20), 2.557 (0.30), 2.570 (0.30), 2.584 (0.24), 2.617 (0.29), 2.628 (0.49), 2.639 (0.29), 2.670 (0.26), 4.440 (0.45), 4.453 (0.67), 4.465 (0.42), 4.928 (1.68), 4.934 (1.63), 7.255 (0.43), 7.266 (0.44), 7.277 (0.49), 7.288 (0.46), 7.701 (0.26), 7.708 (0.25), 7.723 (0.49), 7.730 (0.47), 7.745 (0.24), 7.752 (0.24), 8.513 (0.78), 8.519 (0.73).

Intermediate 287 tert-Butyl (5S)-2-[2-(4-fluorophenyl)ethyl]-3-oxo-2,3,5,6,7,8-hexahydro[1,2,4]triazolo[4,3-a]pyridine-5-carboxylate

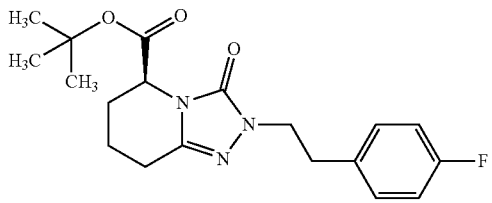 [SMILES: CC(C)(C)OC(=O)[C@@H]1CCCc2nn(CCc3ccc(F)cc3)c(=O)n21]

tert-Butyl (5S)-3-oxo-2,3,5,6,7,8-hexahydro[1,2,4]triazolo[4,3-a]pyridine-5-carboxylate (250 mg, 1.04 mmol) was initially charged in acetonitrile (10 ml). Caesium carbonate (851 mg, 2.61 mmol) and 1-(2-bromoethyl)-4-fluorobenzene (223 mg, 1.10 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 340 mg (83% of theory) of the title compound were obtained.

LC-MS (Method 4): $R_t$=0.98 min; MS (ESIpos): m/z=362 $[M+H]^+$ $^1$H-NMR (400 MHz, DMSO-d6) δ [ppm]: 1.364 (0.43), 1.391 (16.00), 1.406 (2.02), 1.414 (0.60), 2.039 (0.72), 2.049 (0.64), 2.638 (0.44), 2.909 (0.64), 2.927 (1.21), 2.946 (0.68), 3.807 (0.87), 3.825 (1.29), 3.843 (0.76), 4.352 (0.47), 4.366 (0.64), 4.376 (0.41), 7.062 (0.61), 7.084 (1.28), 7.106 (0.77), 7.219 (0.78), 7.233 (0.93), 7.240 (0.73), 7.254 (0.57).

Intermediate 288 tert-Butyl (5S)-2-[(5-chloropyridin-3-yl)methyl]-3-oxo-2,3,5,6,7,8-hexahydro[1,2,4]triazolo[4,3-a]pyridine-5-carboxylate

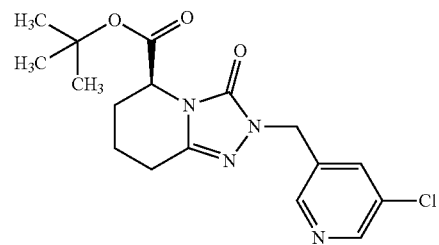 [SMILES: CC(C)(C)OC(=O)[C@@H]1CCCc2nn(Cc3cncc(Cl)c3)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (10 ml). Caesium carbonate (1.02 g, 3.13 mmol) and 3-chloro-5-(chloromethyl)pyridine (213 mg, 1.32 mmol) were subsequently added. After stirring overnight, the reaction mixture was admixed again with 3-chloro-5-(chloromethyl)pyridine (213 mg, 1.32 mmol) and stirred at 60° C. for 4 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 450 mg (98% of theory) of the title compound were obtained.

LC-MS (Method 4): $R_t$=0.84 min; MS (ESIpos): m/z=365 $[M+H]^+$

Intermediate 289 tert-Butyl (5S)-2-(4-chloro-3-fluorobenzyl)-3-oxo-2,3,5,6,7,8-hexahydro[1,2,4]triazolo[4,3-a]pyridine-5-carboxylate

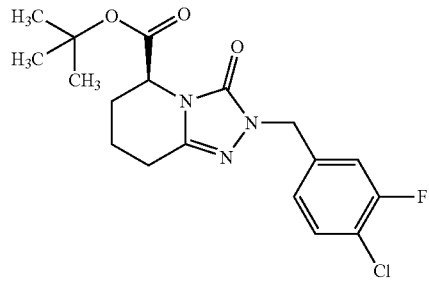 [SMILES: CC(C)(C)OC(=O)[C@@H]1CCCc2nn(Cc3ccc(Cl)c(F)c3)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (5.0 ml). Caesium carbonate (449 mg, 1.38 mmol) and 4-(bromomethyl)-1-chloro-2-fluorobenzene (294 mg, 1.32 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 363 mg (76% of theory) of the title compound were obtained.

LC-MS (Method 8): $R_t$=3.17 min; MS (ESIpos): m/z=382 [M+H]$^+$

Intermediate 290 tert-Butyl (5S)-2-[(5-methoxypyridin-2-yl)methyl]-3-oxo-2,3,5,6,7,8-hexahydro[1,2,4]triazolo[4,3-a]pyridine-5-carboxylate

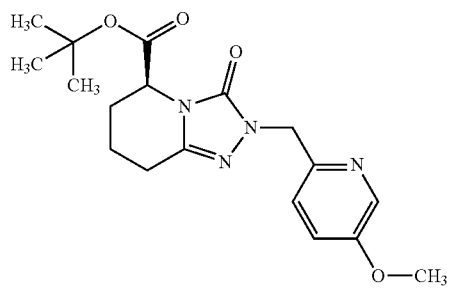 [SMILES: COc1ccc(Cn2nc3n(c2=O)[C@H](C(=O)OC(C)(C)C)CCC3)nc1]

tert-Butyl (5S)-3-oxo-2,3,5,6,7,8-hexahydro[1,2,4]triazolo[4,3-a]pyridine-5-carboxylate (200 mg, 836 μmol) was initially charged in acetonitrile (1.3 ml). Caesium carbonate (545 mg, 1.67 mmol) and 2-(chloromethyl)-5-methoxypyridine (138 mg, 878 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 196 mg (64% of theory) of the title compound were obtained.

LC-MS (Method 3): $R_t$=1.52 min; MS (ESIpos): m/z=361 [M+H]$^+$

Intermediate 291 tert-Butyl (5S)-2-[(3,5-dichloropyridin-2-yl)methyl]-3-oxo-2,3,5,6,7,8-hexahydro[1,2,4]triazolo[4,3-a]pyridine-5-carboxylate

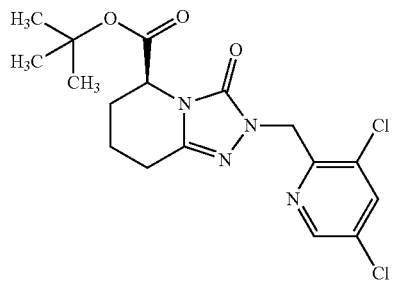 [SMILES: CC(C)(C)OC(=O)[C@@H]1CCCc2nn(Cc3ncc(Cl)cc3Cl)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (5.0 ml). Caesium carbonate (449 mg, 1.38 mmol) and 3,5-dichloro-2-(chloromethyl)pyridine (271 mg, 1.38 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 260 mg (52% of theory) of the title compound were obtained.

LC-MS (Method 4): $R_t$=0.93 min; MS (ESIpos): m/z=399 [M+H]$^+$

Intermediate 292 tert-Butyl (5S)-2-[2-(4-methoxyphenyl)ethyl]-3-oxo-2,3,5,6,7,8-hexahydro[1,2,4]triazolo[4,3-a]pyridine-5-carboxylate

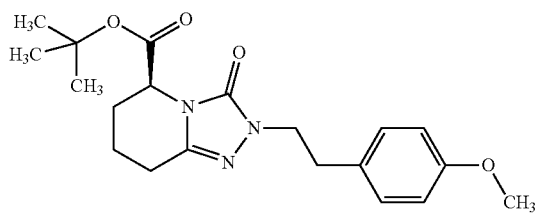 [SMILES: COc1ccc(CCn2nc3n(c2=O)[C@H](C(=O)OC(C)(C)C)CCC3)cc1]

tert-Butyl (5S)-3-oxo-2,3,5,6,7,8-hexahydro[1,2,4]triazolo[4,3-a]pyridine-5-carboxylate (250 mg, 1.04 mmol) was initially charged in acetonitrile (10 ml). Caesium carbonate (851 mg, 2.61 mmol) and 1-(2-bromoethyl)-4-methoxybenzene (170 μl, 1.1 mmol) were subsequently added. After stirring for 4 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 369 mg (87% of theory) of the title compound were obtained.

LC-MS (Method 3): $R_t$=1.86 min; MS (ESIpos): m/z=374 [M+H]$^+$ $^1$H-NMR (400 MHz, DMSO-d6) δ[ppm]: 1.395 (16.00), 1.405 (1.18), 1.417 (0.64), 2.043 (0.56), 2.052 (0.51), 2.844 (0.59), 2.863 (1.09), 2.882 (0.63), 3.713 (6.85), 3.727 (0.83), 3.764 (0.44), 3.768 (0.48), 3.781 (0.80), 3.788 (0.83), 3.801 (0.41), 4.359 (0.41), 4.373 (0.62), 6.827 (1.37), 6.848 (1.63), 7.113 (1.43), 7.135 (1.23).

Intermediate 293 tert-Butyl (5S)-3-oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylate

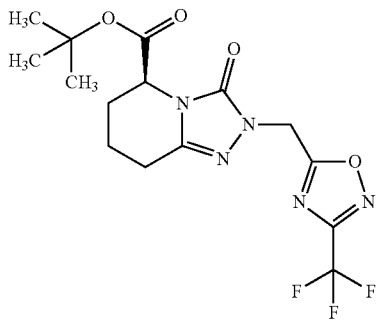 [SMILES: CC(C)(C)OC(=O)[C@@H]1CCCc2nn(Cc3nc(C(F)(F)F)no3)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was dissolved in acetonitrile (10 ml), and caesium carbonate (1.02 g, 3.13 mmol) was added at room temperature. The reaction mixture was stirred at room temperature overnight and at 50° C. for 1 hour. 5-(Chloromethyl)-3-(trifluoromethyl)-1,2,4-oxadiazole (258 mg, 95% purity, 1.32 mmol) was added and the mixture was stirred at 50° C. for 5 hours and at room temperature overnight. 5-(Chloromethyl)-3-(trifluoromethyl)-1,2,4-oxadiazole (94 mg, 95% purity, 0.48 mmol) was added again and the mixture was stirred at 50° C. overnight. 5-(Chloromethyl)-3-(trifluoromethyl)-1,2,4-oxadiazole (94 mg, 95% purity, 0.48 mmol) was added again and the mixture was stirred at 50° C. for 5 hours. The solvent was removed under reduced pressure. The residue was purified via preparative HPLC (Chromatorex C18, 10 µm, 125 mm×30 mm; eluent: acetonitrile/water gradient). The product-containing fractions were concentrated under reduced pressure, and 322 mg (66% of theory) of the title compound were obtained.

LC-MS (Method 3): $R_t$=1.82 min; MS (ESIpos): m/z=334 [M−tBu]+

Intermediate 294 tert-Butyl (5S)-2-[(1-methyl-1H-pyrazolo[3,4-b]pyridin-3-yl)methyl]-3-oxo-2,3,5,6,7,8-hexahydro[1,2,4]triazolo[4,3-a]pyridine-5-carboxylate

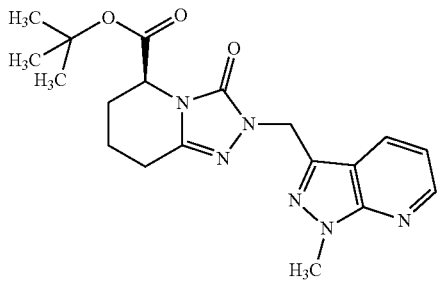 [SMILES: Cn1nc(Cn2nc3n(c2=O)[C@H](C(=O)OC(C)(C)C)CCC3)c2cccnc21]

tert-Butyl (5S)-3-oxo-2,3,5,6,7,8-hexahydro[1,2,4]triazolo[4,3-a]pyridine-5-carboxylate (199 mg, 833 µmol) was initially charged in acetonitrile (7.0 ml). Caesium carbonate (815 mg, 2.50 mmol) and 3-(chloromethyl)-1-methyl-1H-pyrazolo[3,4-b]pyridine (167 mg, 917 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 203 mg (88% purity, 56% of theory) of the title compound were obtained.

LC-MS (Method 4): $R_t$=0.78 min; MS (ESIpos): m/z=385 [M+H]+

$^1$H-NMR (400 MHz, DMSO-d6) δ [ppm]: 0.008 (1.19), 1.175 (0.42), 1.372 (16.00), 1.406 (0.56), 1.988 (0.75), 2.033 (0.53), 2.041 (0.56), 2.524 (0.57), 2.579 (0.42), 4.007 (0.86), 4.028 (5.82), 4.433 (0.40), 4.443 (0.43), 4.448 (0.59), 5.124 (1.50), 5.142 (1.48), 7.178 (0.58), 7.189 (0.61), 7.198 (0.64), 7.209 (0.62), 8.193 (0.63), 8.197 (0.64), 8.213 (0.61), 8.217 (0.60), 8.546 (0.68), 8.550 (0.68), 8.557 (0.64), 8.561 (0.60).

Intermediate 295 tert-Butyl (5S)-2-[(3,5-difluoropyridin-2-yl)methyl]-3-oxo-2,3,5,6,7,8-hexahydro[1,2,4]triazolo[4,3-a]pyridine-5-carboxylate

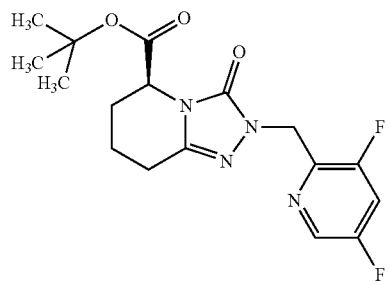 [SMILES: CC(C)(C)OC(=O)[C@@H]1CCCc2nn(Cc3ncc(F)cc3F)c(=O)n21]

tert-Butyl (5S)-3-oxo-2,3,5,6,7,8-hexahydro[1,2,4]triazolo[4,3-a]pyridine-5-carboxylate (258 mg, 1.08 mmol) was initially charged in acetonitrile (10 ml). Caesium carbonate (879 mg, 2.70 mmol) and 2-(chloromethyl)-3,5-difluoropyridine (218 mg, 89% purity, 1.19 mmol) were subsequently added. The reaction mixture was stirred at room temperature for 4 hours, at 50° C. for 8 hours and at room temperature overnight, and then water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 90.1 mg (22% of theory) of the title compound were obtained.

LC-MS (Method 1): $R_t$=1.10 min; MS (ESIpos): m/z=312 [M+H]$^+$ $^1$H-NMR (400 MHz, DMSO-d6) δ[ppm]: 1.404 (16.00), 2.048 (0.56), 2.059 (0.56), 2.517 (0.51), 2.588 (0.42), 4.411 (0.42), 4.421 (0.44), 4.426 (0.58), 4.974 (0.83), 4.977 (0.82), 4.989 (0.82), 8.461 (0.78), 8.467 (0.74).

Intermediate 296 tert-Butyl (5S)-2-[(3-chloropyridin-2-yl)methyl]-3-oxo-2,3,5,6,7,8-hexahydro[1,2,4]triazolo[4,3-a]pyridine-5-carboxylate

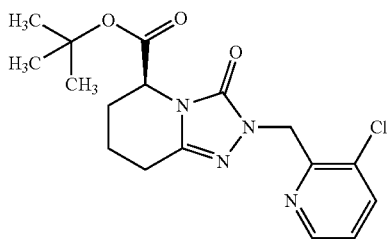 [SMILES: CC(C)(C)OC(=O)[C@@H]1CCCc2nn(Cc3ncccc3Cl)c(=O)n21]

tert-Butyl (5S)-3-oxo-2,3,5,6,7,8-hexahydro[1,2,4]triazolo[4,3-a]pyridine-5-carboxylate (352 mg, 1.47 mmol) was initially charged in acetonitrile (10 ml). Caesium carbonate (1.20 g, 3.68 mmol) and 3-chloro-2-(chloromethyl)pyridine (262 mg, 1.62 mmol) were subsequently added. The reaction mixture was stirred at room temperature for 4 hours, at 50° C. for 4 hours and at room temperature overnight, and then water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 269 mg (88% purity, 44% of theory) of the title compound were obtained.

LC-MS (Method 1): $R_t$=1.10 min; MS (ESIpos): m/z=311 [M+H]$^+$

Intermediate 297 tert-Butyl (5S)-3-oxo-2-{[6-(trifluoromethyl)pyridin-2-yl]methyl}-2,3,5,6,7,8-hexahydro[1,2,4]triazolo[4,3-a]pyridine-5-carboxylate

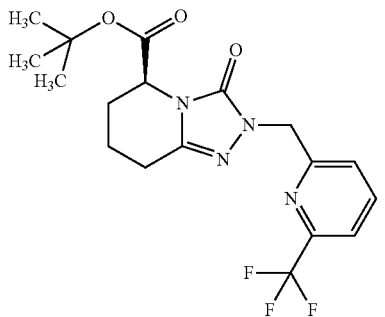 [SMILES: CC(C)(C)OC(=O)[C@@H]1CCCc2nn(Cc3cccc(C(F)(F)F)n3)c(=O)n21]

tert-Butyl (5S)-3-oxo-2,3,5,6,7,8-hexahydro[1,2,4]triazolo[4,3-a]pyridine-5-carboxylate (176 mg, 737 μmol) was initially charged in acetonitrile (5.0 ml, 95 mmol). Caesium carbonate (601 mg, 1.84 mmol) and 2-(chloromethyl)-6-(trifluoromethyl)pyridine (159 mg, 811 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 256 mg (88% purity, 76% of theory) of the title compound were obtained.

LC-MS (Method 4): $R_t$=0.94 min; MS (ESIpos): m/z=399 [M+H]$^+$

Intermediate 298 tert-Butyl (5S)-3-oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylate

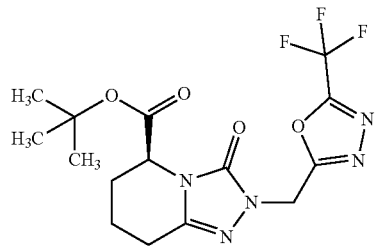 [SMILES: CC(C)(C)OC(=O)[C@@H]1CCCc2nn(Cc3nnc(C(F)(F)F)o3)c(=O)n21]

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (5.0 ml). Caesium carbonate (817 mg, 2.51 mmol) and 2-(chloromethyl)-5-(trifluoromethyl)-1,3,4-oxadiazole (257 mg, 1.38 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 735 mg (66% purity, 99% of theory) of the title compound were obtained.

LC-MS (Method 1): $R_t$=1.18 min; MS (ESIpos): m/z=334 [M−tBu+H]+

Intermediate 299 tert-Butyl (5S)-2-{[1-ethyl-3-(trifluoromethyl)-1H-pyrazol-5-yl]methyl}-3-oxo-2,3,5,6,7,8-hexahydro[1,2,4]triazolo[4,3-a]pyridine-5-carboxylate

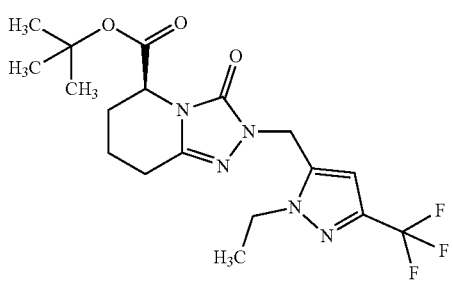 [SMILES: CCn1nc(C(F)(F)F)cc1Cn1nc2n(c1=O)[C@H](C(=O)OC(C)(C)C)CCC2]

tert-Butyl (5S)-3-oxo-2,3,5,6,7,8-hexahydro[1,2,4]triazolo[4,3-a]pyridine-5-carboxylate (174 mg, 725 µmol) was initially charged in acetonitrile (3.0 ml). Caesium carbonate (473 mg, 1.45 mmol) and 5-(chloromethyl)-1-ethyl-3-(trifluoromethyl)-1H-pyrazole (170 mg, 798 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 283 mg (89% purity, 84% of theory) of the title compound were obtained.

LC-MS (Method 1): $R_t$=1.30 min; MS (ESIpos): m/z=360 [M+H]$^+$

Intermediate 300 tert-Butyl (5S)-2-[(5-chloropyridin-2-yl)methyl]-3-oxo-2,3,5,6,7,8-hexahydro[1,2,4]triazolo[4,3-a]pyridine-5-carboxylate

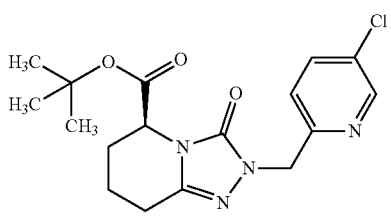

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (5.0 ml). Caesium carbonate (817 mg, 2.51 mmol) and 5-chloro-2-(chloromethyl)pyridine (223 mg, 1.38 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 450 mg (98% of theory) of the title compound were obtained.

LC-MS (Method 3): $R_t$=1.61 min; MS (ESIpos): m/z=365 [M+H]$^+$

Intermediate 301 tert-Butyl (5S)-3-oxo-2-{[2-(trifluoromethyl)-1,3-thiazol-4-yl]methyl}-2,3,5,6,7,8-hexahydro[1,2,4]triazolo[4,3-a]pyridine-5-carboxylate

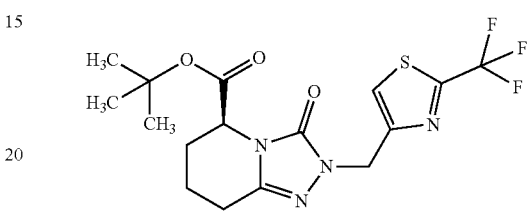

tert-Butyl (5S)-3-oxo-2,3,5,6,7,8-hexahydro[1,2,4]triazolo[4,3-a]pyridine-5-carboxylate (300 mg, 1.25 mmol) was initially charged in acetonitrile (10 ml). Caesium carbonate (817 mg, 2.51 mmol) and 4-(chloromethyl)-2-(trifluoromethyl)-1,3-thiazole (276 mg, 96% purity, 1.32 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 500 mg (98% of theory) of the title compound were obtained.

Intermediate 302 tert-Butyl (5S)-2-{[1-methyl-5-(trifluoromethyl)-1H-pyrazol-3-yl]methyl}-3-oxo-2,3,5,6,7,8-hexahydro[1,2,4]triazolo[4,3-a]pyridine-5-carboxylate

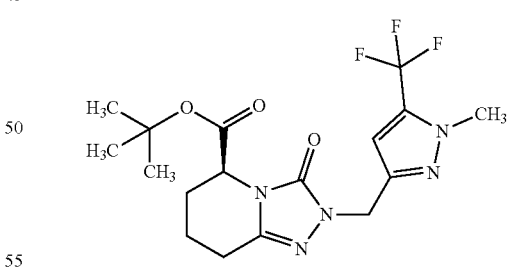

tert-Butyl (5S)-3-oxo-2,3,5,6,7,8-hexahydro[1,2,4]triazolo[4,3-a]pyridine-5-carboxylate (234 mg, 978 µmol) was initially charged in acetonitrile (5.0 ml). Caesium carbonate (638 mg, 1.96 mmol) and 3-(chloromethyl)-1-methyl-5-(trifluoromethyl)-1H-pyrazole (204 mg, 1.03 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sul-

Intermediate 303 tert-Butyl (5S)-2-{[1-benzyl-5-(trifluoromethyl)-1H-pyrazol-3-yl]methyl}-3-oxo-2,3,5,6,7,8-hexahydro[1,2,4]triazolo[4,3-a]pyridine-5-carboxylate

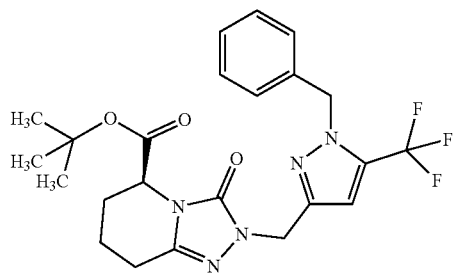 [SMILES: CC(C)(C)OC(=O)[C@@H]1CCCc2nn(Cc3cc(C(F)(F)F)n(Cc4ccccc4)n3)c(=O)n21]

tert-Butyl (5S)-3-oxo-2,3,5,6,7,8-hexahydro[1,2,4]triazolo[4,3-a]pyridine-5-carboxylate (548 mg, 2.29 mmol) was initially charged in acetonitrile (20 ml). Caesium carbonate (1.49 g, 4.58 mmol) and 1-benzyl-3-(chloromethyl)-5-(trifluoromethyl)-1H-pyrazole (728 mg, 95% purity, 2.52 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 781 mg (76% purity, 54% of theory) of the title compound were obtained.

LC-MS (Method 3): $R_t$=2.12 min; MS (ESIpos): m/z=478 [M+H]$^+$

Intermediate 304 tert-Butyl (5S)-2-[(5-bromopyridin-3-yl)methyl]-3-oxo-2,3,5,6,7,8-hexahydro[1,2,4]triazolo[4,3-a]pyridine-5-carboxylate

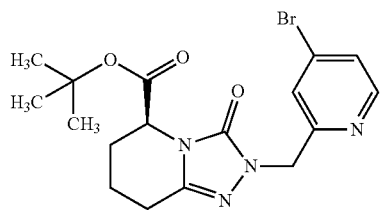 [SMILES: CC(C)(C)OC(=O)[C@@H]1CCCc2nn(Cc3cc(Br)ccn3)c(=O)n21]

tert-Butyl (5S)-3-oxo-2,3,5,6,7,8-hexahydro[1,2,4]triazolo[4,3-a]pyridine-5-carboxylate (396 mg, 1.66 mmol) was initially charged in acetonitrile (6.6 ml). Caesium carbonate (1.08 g, 3.31 mmol) and 3-bromo-5-(chloromethyl)pyridine (376 mg, 1.82 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 146 mg (22% of theory) of the title compound were obtained.

LC-MS (Method 3): $R_t$=1.64 min; MS (ESIpos): m/z=409 [M+H]$^+$ $^1$H-NMR (400 MHz, DMSO-d6) δ[ppm]: 1.390 (16.00), 2.066 (0.53), 2.075 (0.53), 2.640 (0.40), 4.458 (0.61), 4.926 (1.27), 4.939 (1.25), 7.915 (0.87), 8.468 (0.83), 8.472 (0.90), 8.643 (0.71), 8.649 (0.75).

Intermediate 305 tert-Butyl (5S)-2-[(5-bromopyridin-2-yl)methyl]-3-oxo-2,3,5,6,7,8-hexahydro[1,2,4]triazolo[4,3-a]pyridine-5-carboxylate

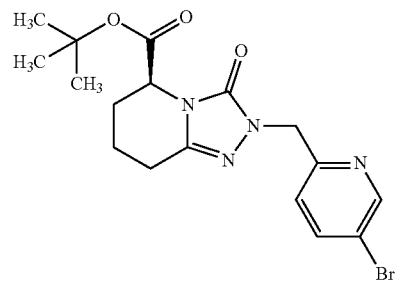 [SMILES: CC(C)(C)OC(=O)[C@@H]1CCCc2nn(Cc3ccc(Br)cn3)c(=O)n21]

tert-Butyl (5S)-3-oxo-2,3,5,6,7,8-hexahydro[1,2,4]triazolo[4,3-a]pyridine-5-carboxylate (309 mg, 1.29 mmol) was initially charged in dichloromethane (7.3 ml). Caesium carbonate (1.05 g, 3.23 mmol) and 5-bromo-2-(chloromethyl)pyridine (347 mg, 1.68 mmol) were subsequently added. After stirring for 5 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 580 mg (>100% of theory) of the title compound were obtained.

LC-MS (Method 3): $R_t$=1.68 min; MS (ESIpos): m/z=409 [M+H]$^+$

Intermediate 306 tert-Butyl (5S)-2-[2-(4-methylphenyl)-2-oxoethyl]-3-oxo-2,3,5,6,7,8-hexahydro[1,2,4]triazolo[4,3-a]pyridine-5-carboxylate

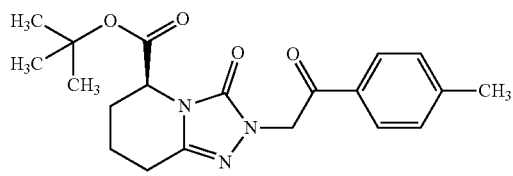 [SMILES: Cc1ccc(C(=O)Cn2nc3n(c2=O)[C@H](C(=O)OC(C)(C)C)CCC3)cc1]

tert-Butyl (5S)-3-oxo-2,3,5,6,7,8-hexahydro[1,2,4]triazolo[4,3-a]pyridine-5-carboxylate (645 mg, 2.70 mmol) was initially charged in acetonitrile (17 ml). Caesium carbonate (2.20 g, 6.74 mmol) and 2-chloro-1-(4-methylphenyl)ethanone (500 mg, 2.97 mmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 605 mg (60% of theory) of the title compound were obtained.

LC-MS (Method 1): $R_t$=1.23 min; MS (ESIpos): m/z=316 [M+H]$^+$

Intermediate 307

(5RS,6RS)-2-{[3-Fluoro-2-(trifluoromethyl)pyridin-4-yl]methyl}-3-oxo-6-(trifluoromethyl)-2,3,5,6,7,8-hexahydro[1,2,4]triazolo[4,3-a]pyridine-5-carboxylic acid (diastereomer mixture; 4 isomers)

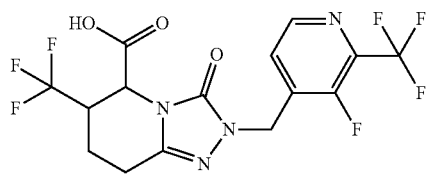 [SMILES: O=C(O)C1C(C(F)(F)F)CCc2nn(Cc3ccnc(C(F)(F)F)c3F)c(=O)n21]

Ethyl (5RS,6RS)-2-{[3-fluoro-2-(trifluoromethyl)pyridin-4-yl]methyl}-3-oxo-6-(trifluoromethyl)-2,3,5,6,7,8-hexahydro[1,2,4]triazolo[4,3-a]pyridine-5-carboxylate (diastereomer mixture, 4 isomers) (231 mg, 506 µmol) was initially charged in THF (5.0 ml), and lithium hydroxide (48.5 mg, 2.02 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 193 mg (89% of theory) of the title compound were obtained.

LC-MS (Method 3): $R_t$=1.38 min; MS (ESIpos): m/z=429 [M+H]$^+$

Intermediate 308

(5RS,6RS)-3-Oxo-6-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture, 4 Isomers)

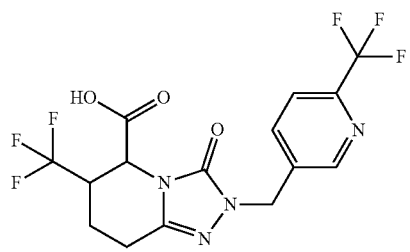 [SMILES: O=C(O)C1C(C(F)(F)F)CCc2nn(Cc3ccc(C(F)(F)F)nc3)c(=O)n21]

Ethyl (5RS,6RS)-3-oxo-6-(trifluoromethyl)-2-{[6-(trifluoromethyl)pyridin-3-yl]methyl}-2,3,5,6,7,8-hexahydro[1,2,4]triazolo[4,3-a]pyridine-5-Carboxylate (Diastereomer Mixture, 4 Isomers) (131 mg, 299 µmol) was initially charged in THF (2.0 ml), and lithium hydroxide (28.6 mg, 1.20 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 109 mg (89% of theory) of the title compound were obtained.

LC-MS (Method 3): $R_t$=1.35 min; MS (ESIpos): m/z=411 [M+H]$^+$ $^1$H-NMR (400 MHz, DMSO-d6) δ[ppm]: −0.149 (0.95), −0.008 (7.81), 0.008 (7.27), 0.146 (0.98), 1.157 (1.55), 1.169 (1.23), 1.175 (3.42), 1.181 (1.45), 1.192 (1.68), 1.236 (0.82), 1.356 (3.51), 1.908 (0.79), 1.946 (1.11), 1.959 (1.33), 1.973 (1.23), 1.988 (6.67), 2.061 (2.06), 2.075 (2.18), 2.097 (1.36), 2.112 (1.26), 2.183 (0.51), 2.328 (1.08), 2.366 (1.33), 2.523 (3.35), 2.600 (0.82), 2.615 (0.82), 2.642 (1.55), 2.669 (2.28), 2.710 (1.36), 2.747 (1.20), 2.761 (2.34), 2.775 (1.30), 2.791 (0.82), 2.804 (1.26), 2.820 (0.66), 3.428 (1.08), 3.439 (1.33), 3.452 (1.58), 3.463 (1.55), 4.002 (0.47), 4.020 (1.39), 4.038 (1.39), 4.564 (5.69), 4.573 (5.50), 5.015 (1.30), 5.056 (8.73), 5.069 (7.91), 5.109 (1.30), 7.900 (0.66), 7.920 (16.00), 8.646 (5.88).

Intermediate 309

(5RS,6RS)-2-[(3,5-Dichloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture, 4 Isomers)

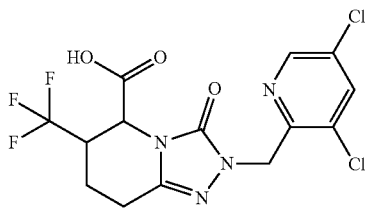

Ethyl (5RS,6RS)-2-[(3,5-dichloropyridin-2-yl)methyl]-3-oxo-6-(trifluoromethyl)-2,3,5,6,7,8-hexahydro[1,2,4]triazolo[4,3-a]pyridine-5-Carboxylate (Diastereomer Mixture, 4 Isomers) (235 mg, 535 µmol) was initially charged in THF (2.0 ml), and lithium hydroxide (51.3 mg, 2.14 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 218 mg (99% of theory) of the title compound were obtained.

LC-MS (Method 4): $R_t$=0.69 min; MS (ESIpos): m/z=411 [M+H]$^+$ $^1$H-NMR (400 MHz, DMSO-d6) δ[ppm]: −0.149 (0.94), −0.008 (13.63), 0.008 (8.92), 0.146 (0.97), 1.157 (0.78), 1.169 (0.80), 1.175 (1.72), 1.181 (1.17), 1.192 (0.80), 1.356 (2.55), 1.908 (0.92), 1.950 (0.97), 1.965 (1.08), 1.974 (1.06), 1.988 (3.47), 2.031 (0.62), 2.044 (1.61), 2.058 (1.72), 2.080 (0.97), 2.094 (0.83), 2.327 (0.80), 2.366 (0.85), 2.523 (5.82), 2.574 (0.99), 2.603 (1.33), 2.619 (1.17), 2.643 (0.83), 2.670 (0.94), 2.710 (1.54), 2.728 (1.79), 2.742 (1.06), 2.758 (0.69), 2.773 (1.01), 3.434 (1.08), 3.445 (1.22), 3.456 (1.20), 4.020 (0.64), 4.038 (0.62), 4.529 (4.25), 4.538 (4.11), 5.056 (16.00), 8.253 (3.70), 8.258 (3.91), 8.553 (4.30), 8.558 (4.14), 13.919 (0.46).

Intermediate 310

(5RS,6RS)-2-[(5-Chloro-3-fluoropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture, 4 Isomers)

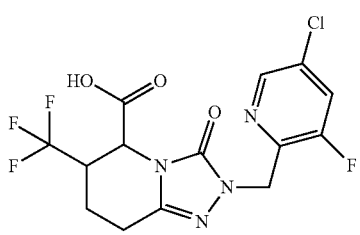 [SMILES: O=C(O)C1C(C(F)(F)F)CCc2nn(Cc3ncc(Cl)cc3F)c(=O)n21]

Ethyl (5RS,6RS)-2-[(5-chloro-3-fluoropyridin-2-yl)methyl]-3-oxo-6-(trifluoromethyl)-2,3,5,6,7,8-hexahydro[1,2,4]triazolo[4,3-a]pyridine-5-Carboxylate (Diastereomer Mixture, 4 Isomers) (235 mg, 556 µmol) was initially charged in THF (3.0 ml), and lithium hydroxide (53.2 mg, 2.22 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 202 mg (92% of theory) of the title compound were obtained.

LC-MS (Method 3): $R_t$=1.17 min; MS (ESIpos): m/z=395 [M+H]$^+$

Intermediate 311

(5RS,6RS)-2-[(5-Chloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture, 4 Isomers)

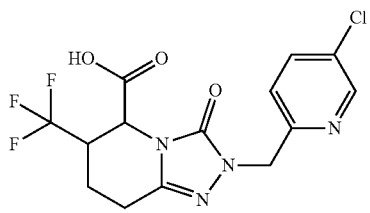 [SMILES: O=C(O)C1C(C(F)(F)F)CCc2nn(Cc3ccc(Cl)cn3)c(=O)n21]

Ethyl (5RS,6RS)-2-[(5-chloropyridin-2-yl)methyl]-3-oxo-6-(trifluoromethyl)-2,3,5,6,7,8-hexahydro[1,2,4]triazolo[4,3-a]pyridine-5-Carboxylate (Diastereomer Mixture, 4 Isomers) (150 mg, 371 µmol) was initially charged in THF (3.0 ml), and lithium hydroxide (35.5 mg, 1.48 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 139 mg (100% of theory) of the title compound were obtained.

LC-MS (Method 3): $R_t$=1.13 min; MS (ESIpos): m/z=377 [M+H]$^+$

Intermediate 312

(5RS,7RS)-2-{[3-Fluoro-2-(trifluoromethyl)pyridin-4-yl]methyl}-7-methyl-3-oxo-2,3,5,6,7,8-hexahydro[1,2,4]triazolo[4,3-a]pyridine-5-carboxylic Acid (Diastereomer Mixture, 4 Isomers)

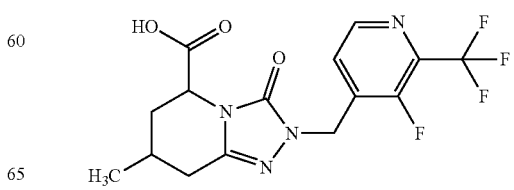

tert-Butyl (5RS,7RS)-2-{[3-fluoro-2-(trifluoromethyl)pyridin-4-yl]methyl}-7-methyl-3-oxo-2,3,5,6,7,8-hexahydro[1,2,4]triazolo[4,3-a]pyridine-5-carboxylate (diastereomer mixture, 4 isomers) (375 mg, 870 µmol) was dissolved in dichloromethane (10 ml), and trifluoroacetic acid (1.3 ml, 17 mmol) was added at room temperature. After the reaction mixture had been stirred at room temperature overnight, the solvent was removed under reduced pressure. 422 mg (90% purity, >100% of theory) of the title compound were obtained.

LC-MS (Method 4): $R_t$=0.71 min; MS (ESIpos): m/z=375 [M+H]$^+$ $^1$H-NMR (400 MHz, DMSO-d6) δ [ppm]: −0.149 (0.49), −0.008 (6.45), 0.008 (2.97), 0.146 (0.43), 1.022 (14.53), 1.039 (14.32), 1.111 (1.07), 1.354 (5.64), 1.385 (0.49), 1.410 (10.08), 1.456 (1.36), 1.484 (2.44), 1.511 (1.83), 1.517 (2.24), 1.535 (0.60), 1.544 (1.24), 1.912 (7.07), 1.932 (1.18), 1.939 (1.27), 1.949 (1.28), 1.966 (1.07), 2.195 (2.45), 2.223 (2.20), 2.235 (3.03), 2.263 (3.53), 2.276 (1.56), 2.294 (1.26), 2.309 (1.13), 2.329 (0.54), 2.367 (0.46), 2.524 (3.54), 2.606 (0.40), 2.650 (3.07), 2.671 (1.00), 2.690 (3.64), 2.696 (2.78), 2.711 (0.81), 2.966 (0.44), 2.987 (0.46), 4.316 (2.81), 4.332 (3.28), 4.342 (3.04), 4.358 (2.54), 4.782 (1.33), 4.801 (1.31), 5.070 (16.00), 5.092 (1.30), 5.134 (3.28), 5.153 (2.60), 5.195 (0.93), 5.535 (0.63), 5.754 (1.36), 6.149 (1.64), 7.567 (0.74), 7.580 (1.34), 7.599 (2.58), 7.612 (4.55), 7.625 (2.75), 8.548 (1.57), 8.564 (5.45), 8.576 (5.15).

Intermediate 313

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture, 4 Isomers)

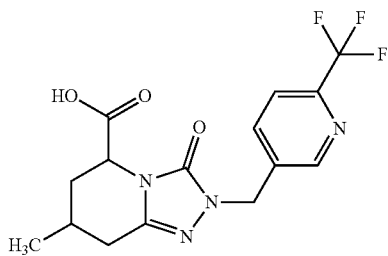 [SMILES: CC1Cc2nn(Cc3ccc(C(F)(F)F)nc3)c(=O)n2C(C(=O)O)C1]

tert-Butyl (5RS,7RS)-7-methyl-3-oxo-2-{[6-(trifluoromethyl)pyridin-3-yl]methyl}-2,3,5,6,7,8-hexahydro[1,2,4]triazolo[4,3-a]pyridine-5-Carboxylate (Diastereomer Mixture, 4 Isomers) (274 mg, 664 µmol) was dissolved in dichloromethane (8.0 ml), and trifluoroacetic acid (1.0 ml, 13 mmol) was added at room temperature. After the reaction mixture had been stirred at room temperature overnight, the solvent was removed under reduced pressure. 438 mg (>100% of theory) of the title compound were obtained.

LC-MS (Method 4): $R_t$=0.66 min; MS (ESIpos): m/z=357 [M+H]$^+$ $^1$H-NMR (400 MHz, DMSO-d6) δ[ppm]: −0.149 (0.46), 0.008 (3.92), 0.146 (0.46), 1.016 (14.93), 1.032 (15.11), 1.111 (1.31), 1.337 (0.57), 1.407 (2.26), 1.444 (1.19), 1.471 (2.41), 1.504 (2.44), 1.532 (1.43), 1.833 (0.54), 1.904 (7.33), 1.927 (1.28), 1.937 (1.34), 1.988 (0.61), 2.073 (0.93), 2.181 (2.59), 2.209 (2.18), 2.222 (3.05), 2.250 (3.80), 2.266 (1.58), 2.283 (1.37), 2.298 (1.24), 2.329 (0.52), 2.367 (0.47), 2.524 (3.38), 2.638 (2.93), 2.642 (2.91), 2.677 (2.32), 2.684 (2.91), 2.711 (0.61), 2.953 (0.46), 2.974 (0.47), 4.306 (2.84), 4.322 (3.29), 4.333 (3.06), 4.348 (2.60), 4.764 (1.36), 4.783 (1.34), 5.016 (16.00), 5.083 (5.43), 5.754 (1.00), 6.132 (2.18), 7.889 (1.01), 7.899 (2.82), 7.909 (3.67), 7.919 (10.17), 7.932 (5.19), 7.936 (5.01), 7.952 (1.48), 8.670 (4.96).

Intermediate 314

(5RS,7RS)-2-(3-Chloro-4-fluorobenzyl)-7-methyl-3-oxo-2,3,5,6,7,8-hexahydro[1,2,4]triazolo[4,3-a]pyridine-5-carboxylic Acid (Diastereomer Mixture, 4 Isomers)

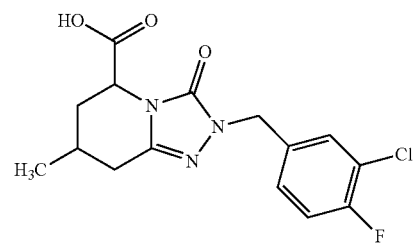 [SMILES: CC1Cc2nn(Cc3ccc(F)c(Cl)c3)c(=O)n2C(C(=O)O)C1]

tert-Butyl (5RS,7RS)-2-(3-chloro-4-fluorobenzyl)-7-methyl-3-oxo-2,3,5,6,7,8-hexahydro[1,2,4]triazolo[4,3-a]pyridine-5-Carboxylate (Diastereomer Mixture, 4 Isomers) (327 mg, 827 µmol) was dissolved in dichloromethane (10 ml), and trifluoroacetic acid (1.3 ml, 17 mmol) was added at room temperature. After the reaction mixture had been stirred at room temperature overnight, the solvent was removed under reduced pressure. 465 mg (>100% of theory) of the title compound were obtained.

LC-MS (Method 1): $R_t$=1.06 min; MS (ESIpos): m/z=340 [M+H]$^+$

Intermediate 315

(5RS,7RS)-2-[(5-Chloropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture, 4 Isomers)

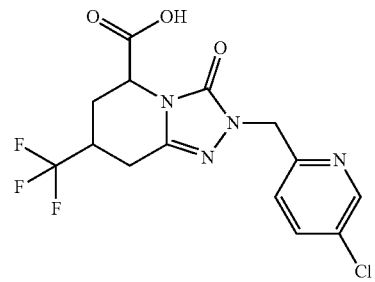 [SMILES: O=C(O)C1CC(C(F)(F)F)Cc2nn(Cc3ccc(Cl)cn3)c(=O)n21]

Ethyl (5RS,7RS)-2-[(5-chloropyridin-2-yl)methyl]-3-oxo-7-(trifluoromethyl)-2,3,5,6,7,8-hexahydro[1,2,4]triazolo[4,3-a]pyridine-5-Carboxylate (Diastereomer Mixture, 4 Isomers)

(248 mg, 612 µmol) was dissolved in THF (8.0 ml), and sodium ethoxide (367 mg, 21% by weight, 1.13 mmol) was added at 0° C. After stirring at 0° C. for 20 minutes and at room temperature overnight, the reaction mixture was admixed with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 206 mg (89% of theory) of the title compound were obtained.

LC-MS (Method 3): $R_t$=1.15 min; MS (ESIpos): m/z=377 [M+H]$^+$ $^1$H-NMR (400 MHz, DMSO-d6) δ [ppm]: −0.149 (1.11), 0.146 (1.07), 1.157 (1.49), 1.169 (3.71), 1.174 (3.55), 1.192 (1.45), 1.235 (0.59), 1.270 (0.59), 1.356 (1.21), 1.371 (0.50), 1.413 (0.52), 1.801 (0.42), 1.908 (2.00), 1.988 (5.04), 2.244 (0.83), 2.279 (2.20), 2.295 (2.52), 2.308 (3.01), 2.327 (7.89), 2.366 (2.38), 2.675 (2.62), 2.705 (6.74), 2.730 (6.62), 2.879 (0.40), 2.954 (0.93), 2.984 (4.62), 3.012 (3.79), 3.039 (0.65), 4.002 (0.44), 4.020 (1.25), 4.038 (1.19), 4.441 (0.42), 4.701 (5.49), 4.711 (4.94), 4.924 (2.18), 4.946 (2.82), 4.965 (16.00), 4.976 (15.98), 5.016 (2.18), 6.578 (0.50), 7.240 (9.06), 7.261 (9.87), 7.277 (0.95), 7.298 (0.83), 7.911 (5.79), 7.917 (6.17), 7.932 (5.93), 7.938 (6.01), 8.579 (7.32), 8.585 (7.57), 13.685 (0.99).

Intermediate 316

(5RS,8RS)-2-{[3-Fluoro-2-(trifluoromethyl)pyridin-4-yl]methyl}-8-methyl-3-oxo-2,3,5,6,7,8-hexahydro[1,2,4]triazolo[4,3-a]pyridine-5-carboxylic Acid (Diastereomer Mixture, 4 Isomers)

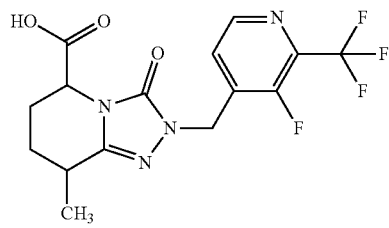 [SMILES: CC1CCC(C(=O)O)n2c1nn(Cc1ccnc(C(F)(F)F)c1F)c2=O]

tert-Butyl (5RS,8RS)-2-{[3-fluoro-2-(trifluoromethyl)pyridin-4-yl]methyl}-8-methyl-3-oxo-2,3,5,6,7,8-hexahydro[1,2,4]triazolo[4,3-a]pyridine-5-carboxylate (diastereomer mixture, 4 isomers) (546 mg, 1.27 mmol) was dissolved in dichloromethane (10 ml), and trifluoroacetic acid (2.0 ml, 25 mmol) was added at room temperature. After the reaction mixture had been stirred at room temperature overnight, the solvent was removed under reduced pressure. 474 mg (94% of theory) of the title compound were obtained.

LC-MS (Method 3): $R_t$=1.29 min; MS (ESIpos): m/z=375 [M+H]$^+$

Intermediate 317

(5RS,8RS)-2-(3-Chloro-4-fluorobenzyl)-8-methyl-3-oxo-2,3,5,6,7,8-hexahydro[1,2,4]triazolo[4,3-a]pyridine-5-carboxylic Acid (Diastereomer Mixture, 4 Isomers)

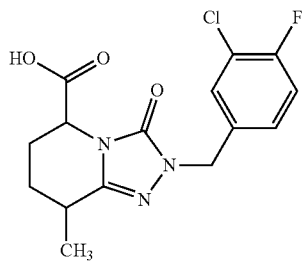 [SMILES: CC1CCC(C(=O)O)n2c1nn(Cc1ccc(F)c(Cl)c1)c2=O]

tert-Butyl (5RS,8RS)-2-(3-chloro-4-fluorobenzyl)-8-methyl-3-oxo-2,3,5,6,7,8-hexahydro[1,2,4]triazolo[4,3-a]pyridine-5-Carboxylate (Diastereomer Mixture, 4 Isomers) (450 mg, 1.14 mmol) was dissolved in dichloromethane (10 ml), and trifluoroacetic acid (1.8 ml, 23 mmol) was added at room temperature. After the reaction mixture had been stirred at room temperature overnight, the solvent was removed under reduced pressure. 470 mg (79% purity, 96% of theory) of the title compound were obtained.

LC-MS (Method 3): $R_t$=1.41 min; MS (ESIpos): m/z=340 [M+H]$^+$

Intermediate 318

(5RS,8RS)-2-(2,4-Difluorobenzyl)-8-methyl-3-oxo-2,3,5,6,7,8-hexahydro[1,2,4]triazolo[4,3-a]pyridine-5-carboxylic Acid (Diastereomer Mixture, 4 Isomers)

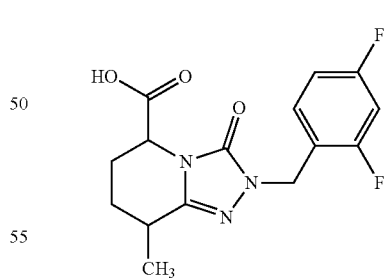

tert-Butyl (5RS,8RS)-2-(2,4-difluorobenzyl)-8-methyl-3-oxo-2,3,5,6,7,8-hexahydro[1,2,4]triazolo[4,3-a]pyridine-5-Carboxylate (Diastereomer Mixture, 4 Isomers) (400 mg, 1.05 mmol) was dissolved in dichloromethane (10 ml), and trifluoroacetic acid (1.6 ml, 21 mmol) was added at room temperature. After the reaction mixture had been stirred at room temperature overnight, the solvent was removed under reduced pressure. 578 mg (87% purity, 148% of theory) of the title compound were obtained.

LC-MS (Method 3): $R_t$=1.26 min; MS (ESIpos): m/z=324 [M+H]$^+$

Intermediate 319

(5RS,8RS)-8-Methyl-3-oxo-2-{[6-(trifluoromethyl) pyridin-3-yl]methyl}-2,3,5,6,7,8-hexahydro[1,2,4] triazolo[4,3-a]pyridine-5-carboxylic Acid (Diastereomer Mixture; 4 Isomers)

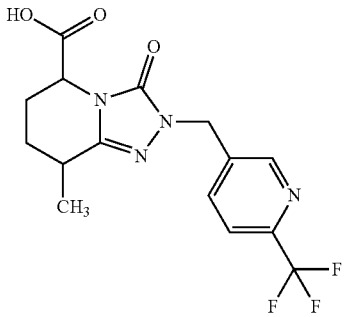 [SMILES: CC1CCC(C(=O)O)n2c1nn(Cc1ccc(C(F)(F)F)nc1)c2=O]

tert-Butyl (5RS,8RS)-8-methyl-3-oxo-2-{[6-(trifluoromethyl)pyridin-3-yl]methyl}-2,3,5,6,7,8-hexahydro[1,2,4]triazolo[4,3-a]pyridine-5-Carboxylate (Diastereomer Mixture, 4 Isomers) (854 mg, 2.07 mmol) was dissolved in dichloromethane (10 ml), and trifluoroacetic acid (10 ml, 130 mmol) was added at room temperature. After the reaction mixture had been stirred at room temperature for 2 h, the solvent was removed under reduced pressure. The residue was admixed with water and dichloromethane. The organic phase was removed and the aqueous phase was extracted three times with dichloromethane. The combined organic phases were washed with saturated aqueous sodium chloride solution, dried over sodium sulphate and filtered, and the filtrate was concentrated. 727 mg (99% of theory) of the title compound were obtained.

LC-MS (Method 3): $R_t$=1.20 min; MS (ESIpos): m/z=357 [M+H]$^+$ $^1$H-NMR (400 MHz, DMSO-d6) δ [ppm]: −0.008 (2.12), 0.008 (1.76), 1.142 (0.42), 1.175 (15.73), 1.192 (16.00), 1.206 (1.64), 1.228 (2.06), 1.239 (1.49), 1.259 (0.64), 1.270 (0.63), 1.320 (0.68), 1.886 (1.20), 1.898 (1.32), 1.908 (1.05), 1.920 (1.15), 2.106 (0.43), 2.119 (1.06), 2.126 (1.10), 2.135 (1.16), 2.142 (1.21), 2.151 (2.06), 2.162 (3.13), 2.168 (3.21), 2.197 (0.61), 2.328 (0.44), 2.524 (1.33), 2.670 (0.41), 2.717 (1.01), 2.731 (1.49), 2.747 (1.88), 2.763 (1.41), 2.778 (0.89), 3.568 (3.56), 4.501 (2.48), 4.507 (3.45), 4.517 (2.38), 4.522 (2.56), 5.023 (1.32), 5.064 (6.79), 5.081 (6.73), 5.122 (1.30), 7.892 (0.60), 7.910 (13.13), 7.912 (13.01), 7.936 (0.51), 8.645 (4.58).

Intermediate 320

(5S)-2-(3-Chloro-4-fluorobenzyl)-3-oxo-2,3,5,6,7,8-hexahydro[1,2,4]triazolo[4,3-a]pyridine-5-carboxylic Acid

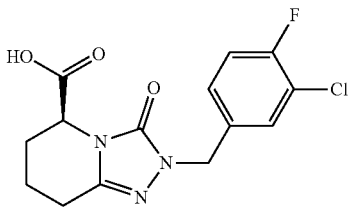 [SMILES: O=C(O)[C@@H]1CCCc2nn(Cc3ccc(F)c(Cl)c3)c(=O)n21]

Methyl (5S)-2-(3-chloro-4-methylbenzyl)-3-oxo-2,3,5,6,7,8-hexahydro[1,2,4]triazolo[4,3-a]pyridine-5-carboxylate (58.5 mg, 172 µmol) was initially charged in THF (570 µl), and lithium hydroxide (20.6 mg, 861 µmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 55.0 mg (98% of theory) of the title compound were obtained.

LC-MS (Method 4): $R_t$=0.70 min; MS (ESIpos): m/z=326 [M+H]$^+$

Intermediate 321

(5S)-3-Oxo-2-[3-(trifluoromethyl)benzyl]-2,3,5,6,7,8-hexahydro[1,2,4]triazolo[4,3-a]pyridine-5-carboxylic Acid

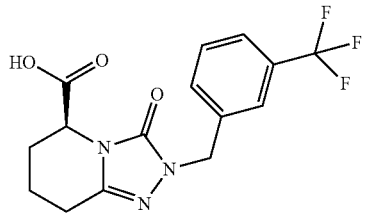 [SMILES: O=C(O)[C@@H]1CCCc2nn(Cc3cccc(C(F)(F)F)c3)c(=O)n21]

Methyl (5S)-3-oxo-2-[3-(trifluoromethyl)benzyl]-2,3,5,6,7,8-hexahydro[1,2,4]triazolo[4,3-a]pyridine-5-carboxylate (336 mg, 947 µmol) was dissolved in THF (10 ml), and trifluoroacetic acid (113 mg, 4.73 mmol) was added at room temperature. After the reaction mixture had been stirred at room temperature for 5 hours, the solvent was removed under reduced pressure. 218 mg (67% of theory) of the title compound were obtained.

LC-MS (Method 1): $R_t$=1.01 min; MS (ESIpos): m/z=342 [M+H]$^+$

Intermediate 322

(5S)-3-Oxo-2-{[4-(trifluoromethyl)pyridin-2-yl]methyl}-2,3,5,6,7,8-hexahydro[1,2,4]triazolo[4,3-a]pyridine-5-carboxylic Acid

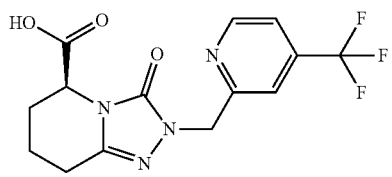 [SMILES: O=C(O)[C@@H]1CCCc2nn(Cc3cc(C(F)(F)F)ccn3)c(=O)n21]

Methyl (5S)-3-oxo-2-{[4-(trifluoromethyl)pyridin-2-yl]methyl}-2,3,5,6,7,8-hexahydro[1,2,4]triazolo[4,3-a]pyridine-5-carboxylate (275 mg, 770 µmol) was initially charged in THF (10 ml), and lithium hydroxide (92.2 mg, 3.85 mmol) dissolved in water was added. After stirring at room temperature for 5 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 247 mg (94% of theory) of the title compound were obtained.

LC-MS (Method 4): $R_t$=0.59 min; MS (ESIpos): m/z=343 [M+H]$^+$

Intermediate 323

(5S)-3-Oxo-2-{[2-(trifluoromethyl)pyrimidin-4-yl]methyl}-2,3,5,6,7,8-hexahydro[1,2,4]triazolo[4,3-a]pyridine-5-carboxylic Acid

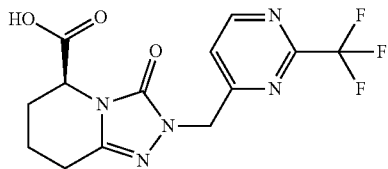 [SMILES: O=C(O)[C@@H]1CCCc2nn(Cc3ccnc(C(F)(F)F)n3)c(=O)n21]

Methyl (5S)-3-oxo-2-{[2-(trifluoromethyl)pyrimidin-4-yl]methyl}-2,3,5,6,7,8-hexahydro[1,2,4]triazolo[4,3-a]pyridine-5-carboxylate (49.5 mg, 139 µmol) was initially charged in THF (2.0 ml), and lithium hydroxide (16.6 mg, 693 µmol) dissolved in water was added. After stirring at room temperature for 5 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 45.0 mg (95% of theory) of the title compound were obtained.

LC-MS (Method 4): $R_t$=0.55 min; MS (ESIpos): m/z=344 [M+H]$^+$

Intermediate 324

(5S)-3-Oxo-2-{[5-(trifluoromethyl)pyridin-2-yl]methyl}-2,3,5,6,7,8-hexahydro[1,2,4]triazolo[4,3-a]pyridine-5-carboxylic Acid

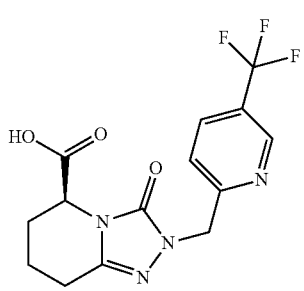 [SMILES: O=C(O)[C@@H]1CCCc2nn(Cc3ccc(C(F)(F)F)cn3)c(=O)n21]

Methyl (5S)-3-oxo-2-{[5-(trifluoromethyl)pyridin-2-yl]methyl}-2,3,5,6,7,8-hexahydro[1,2,4]triazolo[4,3-a]pyridine-5-carboxylate (175 mg, 491 µmol) was initially charged in THF (7.0 ml), and lithium hydroxide (58.8 mg, 2.46 mmol) dissolved in water was added. After stirring at room temperature for 5 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 156 mg (93% of theory) of the title compound were obtained.

LC-MS (Method 3): $R_t$=1.04 min; MS (ESIpos): m/z=343 [M+H]$^+$

Intermediate 325

(5S)-2-[(5-Methyl-1H-pyrazol-3-yl)methyl]-3-oxo-2,3,5,6,7,8-hexahydro[1,2,4]triazolo[4,3-a]pyridine-5-carboxylic Acid

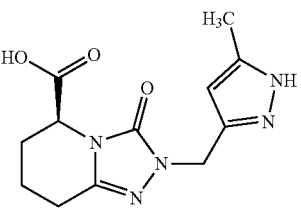 [SMILES: Cc1cc(Cn2nc3n(c2=O)[C@H](C(=O)O)CCC3)n[nH]1]

Methyl (5RS)-2-[(5-methyl-1H-pyrazol-3-yl)methyl]-3-oxo-2,3,5,6,7,8-hexahydro[1,2,4]triazolo[4,3-a]pyridine-5-carboxylate (60.0 mg, 206 µmol) was initially charged in THF (3.0 ml), and lithium hydroxide (24.7 mg, 1.03 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 38.0 mg (67% of theory) of the title compound were obtained.

LC-MS (Method 3): $R_t$=0.57 min; MS (ESIpos): m/z=278 [M+H]$^+$

Intermediate 326

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic Acid

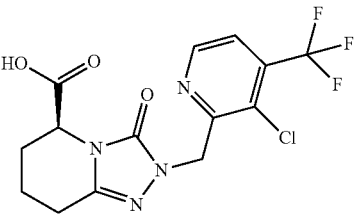 [SMILES: O=C(O)[C@@H]1CCCc2nn(Cc3nccc(C(F)(F)F)c3Cl)c(=O)n21]

Methyl (5S)-2-{[3-chloro-4-(trifluoromethyl)pyridin-2-yl]methyl}-3-oxo-2,3,5,6,7,8-hexahydro[1,2,4]triazolo[4,3-a]pyridine-5-carboxylate (137 mg, 351 µmol) was initially charged in THF (2.0 ml), and lithium hydroxide (42.0 mg, 1.75 mmol) dissolved in water was added. After stirring at room temperature for 72 hours, the reaction mixture was concentrated under reduced pressure and then admixed with water, 1 N aqueous hydrochloric acid and saturated aqueous

Intermediate 327

(5S)-2-[4-Fluoro-3-(trifluoromethyl)benzyl]-3-oxo-2,3,5,6,7,8-hexahydro[1,2,4]triazolo[4,3-a]pyridine-5-carboxylic Acid

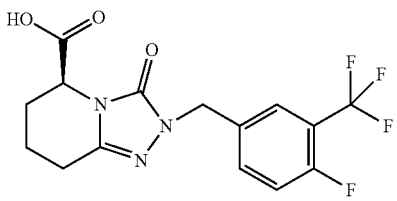

Methyl (5S)-2-[4-fluoro-3-(trifluoromethyl)benzyl]-3-oxo-2,3,5,6,7,8-hexahydro[1,2,4]triazolo[4,3-a]pyridine-5-carboxylate (370 mg, 991 µmol) was initially charged in THF (5.0 ml), and lithium hydroxide (119 mg, 4.96 mmol) dissolved in water was added. After stirring overnight, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 133 mg (37% of theory) of the title compound were obtained.

LC-MS (Method 1): $R_t$=1.03 min; MS (ESIpos): m/z=360 [M+H]$^+$

Intermediate 328

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic Acid

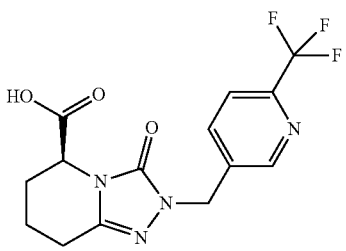 [SMILES: O=C(O)[C@@H]1CCCc2nn(Cc3ccc(C(F)(F)F)nc3)c(=O)n21]

Methyl (5S)-3-oxo-2-{[6-(trifluoromethyl)pyridin-3-yl]methyl}-2,3,5,6,7,8-hexahydro[1,2,4]triazolo[4,3-a]pyridine-5-carboxylate (442 mg, 75% purity, 930 µmol) was initially charged in THF (2.7 ml), and lithium hydroxide (111 mg, 4.65 mmol) dissolved in water was added. After stirring for 72 hours, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. 316 mg (90% of theory) of the title compound were obtained.

LC-MS (Method 1): $R_t$=0.83 min; MS (ESIpos): m/z=343 [M+H]$^+$

Alternative Synthesis:

tert-Butyl (5S)-3-oxo-2-{[6-(trifluoromethyl)pyridin-3-yl]methyl}-2,3,5,6,7,8-hexahydro[1,2,4]triazolo[4,3-a]pyridine-5-carboxylate (411 mg, 1.03 mmol) was dissolved in dichloromethane (5.0 ml), and trifluoroacetic acid (1.6 ml, 21 mmol) was added at 0° C. After the reaction mixture had been stirred at room temperature overnight, the solvent was removed under reduced pressure. 798 mg (90% purity, >100% of theory) of the title compound were obtained.

LC-MS (Method 4): $R_t$=0.60 min; MS (ESIpos): m/z=343 [M+H]$^+$

Intermediate 329

(5S)-2-{[6-Fluoro-2-(trifluoromethyl)quinolin-4-yl]methyl}-3-oxo-2,3,5,6,7,8-hexahydro[1,2,4]triazolo[4,3-a]pyridine-5-carboxylic Acid

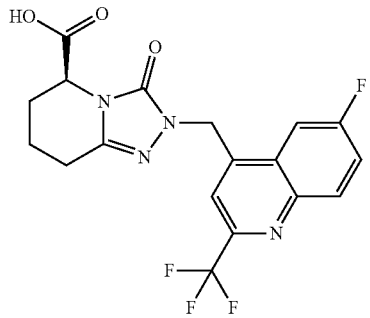 [SMILES: O=C(O)[C@@H]1CCCc2nn(Cc3cc(C(F)(F)F)nc4ccc(F)cc34)c(=O)n21]

Methyl (5S)-2-{[6-fluoro-2-(trifluoromethyl)quinolin-4-yl]methyl}-3-oxo-2,3,5,6,7,8-hexahydro[1,2,4]triazolo[4,3-a]pyridine-5-carboxylate (59.0 mg, 139 µmol) was initially charged in THF (2.0 ml), and lithium hydroxide (16.6 mg, 695 µmol) dissolved in water was added. After stirring at room temperature for 72 hours, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 44.0 mg (77% of theory) of the title compound were obtained.

--- sodium chloride solution. The aqueous phase was extracted three times with ethyl acetate. The combined organic phases were dried over sodium sulphate and filtered, and the filtrate was concentrated. 107 mg (81% of theory) of the title compound were obtained.

LC-MS (Method 3): $R_t$=1.18 min; MS (ESIpos): m/z=377 [M+H]$^+$

LC-MS (Method 3): $R_t$=1.46 min; MS (ESIpos): m/z=411 [M+H]$^+$

Intermediate 330

(5S)-2-(6,7-Dihydro-5H-cyclopenta[c]pyridin-3-ylmethyl)-3-oxo-2,3,5,6,7,8-hexahydro[1,2,4]triazolo[4,3-a]pyridine-5-carboxylic Acid

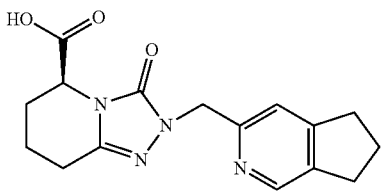 [SMILES: O=C(O)[C@@H]1CCCc2nn(Cc3cc4c(cn3)CCC4)c(=O)n21]

Methyl (5S)-2-(6,7-dihydro-5H-cyclopenta[c]pyridin-3-ylmethyl)-3-oxo-2,3,5,6,7,8-hexahydro[1,2,4]triazolo[4,3-a]pyridine-5-carboxylate (109 mg, 90% purity, 299 µmol) was initially charged in THF (4.0 ml), and lithium hydroxide (35.8 mg, 1.50 mmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 72.0 mg (43% purity, 33% of theory) of the title compound were obtained.

LC-MS (Method 3): $R_t$=0.48 min; MS (ESIpos): m/z=315 [M+H]$^+$ $^1$H-NMR (400 MHz, DMSO-d6) δ[ppm]: 1.645 (7.08), 2.036 (7.44), 2.158 (4.32), 2.859 (16.00), 3.974 (4.21), 4.762 (9.00), 7.462 (5.14), 8.192 (4.78).

Intermediate 331

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic Acid

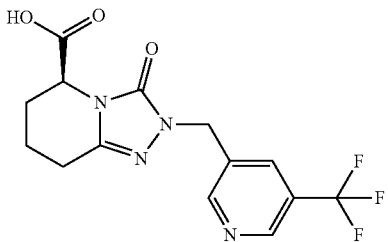 [SMILES: O=C(O)[C@@H]1CCCc2nn(Cc3cncc(C(F)(F)F)c3)c(=O)n21]

Methyl (5S)-3-oxo-2-{[5-(trifluoromethyl)pyridin-3-yl]methyl}-2,3,5,6,7,8-hexahydro[1,2,4]triazolo[4,3-a]pyridine-5-carboxylate (40.9 mg, 115 µmol) was initially charged in THF (3.0 ml, 37 mmol), and lithium hydroxide (13.7 mg, 574 µmol) dissolved in water was added. After stirring at room temperature overnight, the reaction mixture was concentrated under reduced pressure and then admixed with water, 1 N aqueous hydrochloric acid and saturated aqueous sodium chloride solution. The aqueous phase was extracted three times with ethyl acetate. The combined organic phases were dried over sodium sulphate and filtered, and the filtrate was concentrated. 35.4 mg (90% of theory) of the title compound were obtained.

LC-MS (Method 3): $R_t$=0.99 min; MS (ESIpos): m/z=343 [M+H]$^+$

Intermediate 332

(5S)-2-[(6-Methoxypyridin-3-yl)methyl]-3-oxo-2,3,5,6,7,8-hexahydro[1,2,4]triazolo[4,3-a]pyridine-5-carboxylic Acid

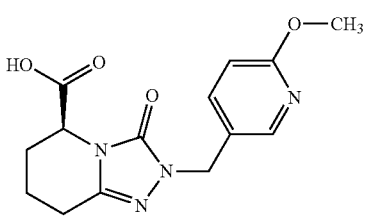 [SMILES: COc1ccc(Cn2nc3n(c2=O)[C@H](C(=O)O)CCC3)cn1]

tert-Butyl (5S)-2-[(6-methoxypyridin-3-yl)methyl]-3-oxo-2,3,5,6,7,8-hexahydro[1,2,4]triazolo[4,3-a]pyridine-5-carboxylate (761 mg, 2.11 mmol) was dissolved in dichloromethane (30 ml), and trifluoroacetic acid (3.3 ml, 42 mmol) was added at room temperature. After the reaction mixture had been stirred at room temperature overnight, the solvent was removed under reduced pressure. 1.97 g (97% of theory) of the title compound were obtained.

LC-MS (Method 3): $R_t$=0.99 min; MS (ESIpos): m/z=305 [M+H]$^+$

Intermediate 333

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic Acid

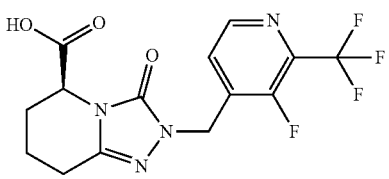 [SMILES: O=C(O)[C@@H]1CCCc2nn(Cc3ccnc(C(F)(F)F)c3F)c(=O)n21]

tert-Butyl (5S)-2-{[3-fluoro-2-(trifluoromethyl)pyridin-4-yl]methyl}-3-oxo-2,3,5,6,7,8-hexahydro[1,2,4]triazolo[4,3-a]pyridine-5-carboxylate (1.37 g, 3.29 mmol) was dissolved in dichloromethane (25 ml), and trifluoroacetic acid (5.1 ml, 66 mmol) was added at room temperature. After the reaction mixture had been stirred at room temperature overnight, the solvent was removed under reduced pressure. 2.07 g (>100% of theory) of the title compound were obtained.

LC-MS (Method 3): $R_t$=1.11 min; MS (ESIpos): m/z=361 [M+H]

Intermediate 334

(5S)-2-[2-(4-Methylphenyl)ethyl]-3-oxo-2,3,5,6,7,8-hexahydro[1,2,4]triazolo[4,3-a]pyridine-5-carboxylic Acid

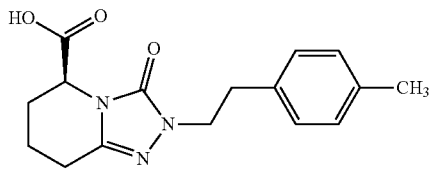 [SMILES: Cc1ccc(CCn2nc3n(c2=O)[C@H](C(=O)O)CCC3)cc1]

tert-Butyl (5S)-2-[2-(4-methylphenyl)ethyl]-3-oxo-2,3,5,6,7,8-hexahydro[1,2,4]triazolo[4,3-a]pyridine-5-carboxylate (238 mg, 665 µmol) was dissolved in dichloromethane (6.7 ml), and trifluoroacetic acid (800 µl, 10 mmol) was added at room temperature. After the reaction mixture had been stirred at room temperature overnight, the solvent was removed under reduced pressure. 325 mg (>100% of theory) of the title compound were obtained.

LC-MS (Method 1): $R_t$=0.98 min; MS (ESIpos): m/z=302 [M+H]

¹H-NMR (400 MHz, DMSO-d6) δ[ppm]: 0.008 (1.06), 1.111 (0.44), 1.228 (0.60), 1.534 (1.02), 1.805 (0.42), 1.816 (0.43), 2.066 (1.03), 2.072 (1.19), 2.082 (1.11), 2.094 (0.64), 2.257 (9.22), 2.524 (0.71), 2.568 (0.54), 2.580 (0.54), 2.594 (0.41), 2.633 (0.41), 2.645 (0.71), 2.656 (0.54), 2.863 (1.16), 2.882 (2.43), 2.900 (1.28), 3.766 (0.67), 3.784 (1.69), 3.804 (1.53), 3.824 (0.62), 4.390 (0.71), 4.402 (1.44), 4.415 (0.79), 7.084 (16.00), 7.093 (1.84).

Intermediate 335

(5S)-2-[(1R)-1-(4-Methylphenyl)ethyl]-3-oxo-2,3,5,6,7,8-hexahydro[1,2,4]triazolo[4,3-a]pyridine-5-carboxylic Acid (Diastereomer Mixture, 2 Isomers)

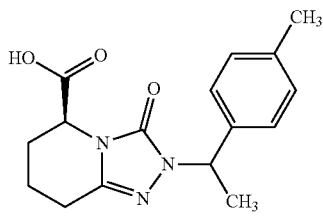 [SMILES: Cc1ccc(C(C)n2nc3n(c2=O)[C@H](C(=O)O)CCC3)cc1]

tert-Butyl (5S)-2-[(1 RS)-1-(4-methylphenyl)ethyl]-3-oxo-2,3,5,6,7,8-hexahydro[1,2,4]triazolo[4,3-a]pyridine-5-carboxylate (69.8 mg, 195 µmol) was dissolved in dichloromethane (2.5 ml), and trifluoroacetic acid (300 µl, 3.9 mmol) was added at room temperature. After the reaction mixture had been stirred at room temperature overnight, the solvent was removed under reduced pressure. 73.1 mg (>100% of theory) of the title compound were obtained.

LC-MS (Method 1): $R_t$=0.98 min; MS (ESIneg): m/z=300 [M−H]⁻

¹H-NMR (400 MHz, DMSO-d6) δ[ppm]: −0.149 (0.62), −0.008 (6.44), 0.008 (6.37), 0.146 (0.65), 1.055 (0.44), 1.291 (0.56), 1.309 (1.08), 1.326 (0.54), 1.532 (0.71), 1.584 (8.87), 1.602 (8.75), 1.799 (0.87), 1.810 (0.79), 1.822 (0.73), 1.832 (0.73), 2.058 (1.44), 2.070 (2.60), 2.081 (2.58), 2.267 (16.00), 2.280 (1.58), 2.327 (1.15), 2.366 (0.85), 2.561 (1.98), 2.576 (1.25), 2.589 (1.21), 2.603 (0.87), 2.632 (0.94), 2.643 (1.50), 2.654 (1.08), 2.669 (1.40), 2.674 (1.37), 2.709 (0.87), 4.414 (0.56), 4.426 (1.52), 4.439 (2.79), 4.450 (1.65), 5.251 (0.56), 5.268 (1.98), 5.286 (1.92), 5.303 (0.54), 7.109 (2.96), 7.129 (5.87), 7.171 (6.58), 7.191 (3.38).

Intermediate 336

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic Acid

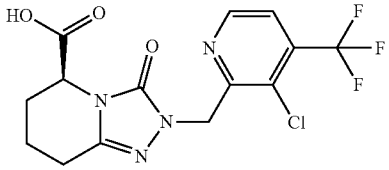

tert-Butyl (5S)-2-{[3-chloro-4-(trifluoromethyl)pyridin-2-yl]methyl}-3-oxo-2,3,5,6,7,8-hexahydro[1,2,4]triazolo[4,3-a]pyridine-5-carboxylate (794 mg, 94% purity, 1.72 mmol) was dissolved in dichloromethane (28 ml), and trifluoroacetic acid (2.7 ml, 34 mmol) was added at room temperature. After the reaction mixture had been stirred at room temperature for 72 hours, the solvent was removed under reduced pressure. 800 mg (78% purity, 96% of theory) of the title compound were obtained.

LC-MS (Method 1): $R_t$=0.91 min; MS (ESIpos): m/z=377 [M+H]⁺

Intermediate 337

(5S)-2-{[1-(4-Methylphenyl)cyclopropyl]methyl}-3-oxo-2,3,5,6,7,8-hexahydro[1,2,4]triazolo[4,3-a]pyridine-5-carboxylic Acid

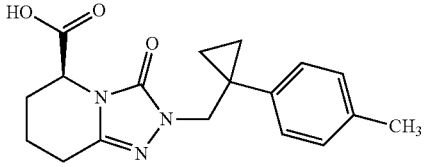 [SMILES: Cc1ccc(C2(Cn3nc4n(c3=O)[C@H](C(=O)O)CCC4)CC2)cc1]

tert-Butyl (5S)-2-{[1-(4-methylphenyl)cyclopropyl]methyl}-3-oxo-2,3,5,6,7,8-hexahydro[1,2,4]triazolo[4,3-a]pyridine-5-carboxylate (167 mg, 436 µmol) was dissolved in dichloromethane (10 ml), and trifluoroacetic acid (670 µl, 8.7 mmol) was added at room temperature. After the reaction mixture had been stirred at room temperature overnight, the solvent was removed under reduced pressure. 228 mg (83% purity, >100% of theory) of the title compound were obtained.

LC-MS (Method 1): $R_t$=1.06 min; MS (ESIpos): m/z=328 [M+H]⁺

¹H-NMR (400 MHz, DMSO-d6) δ[ppm]: −0.008 (2.90), 0.008 (2.46), 0.708 (0.68), 0.729 (1.89), 0.756 (0.50), 0.783

(2.19), 0.806 (0.89), 0.978 (5.27), 1.110 (1.47), 1.175 (0.42), 1.378 (1.96), 1.406 (0.45), 1.535 (3.25), 1.782 (0.88), 1.988 (0.80), 2.051 (2.35), 2.063 (2.37), 2.074 (1.57), 2.206 (0.47), 2.235 (16.00), 2.328 (0.54), 2.524 (2.40), 2.606 (1.64), 2.615 (0.98), 2.646 (0.76), 2.671 (0.54), 3.729 (2.03), 3.765 (3.10), 3.877 (3.00), 3.913 (1.98), 4.363 (1.59), 4.374 (3.00), 4.387 (1.53), 5.754 (0.48), 7.024 (3.37), 7.044 (5.39), 7.106 (6.44), 7.126 (3.93), 11.356 (0.45).

Intermediate 338

(5S)-3-Oxo-2-{[2-(trifluoromethyl)-1,8-naphthyridin-3-yl]methyl}-2,3,5,6,7,8-hexahydro[1,2,4]triazolo[4,3-a]pyridine-5-carboxylic Acid

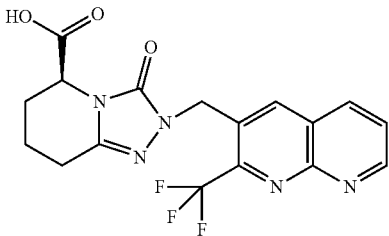 [SMILES: O=C(O)[C@@H]1CCCc2nn(Cc3cc4cccnc4nc3C(F)(F)F)c(=O)n21]

tert-Butyl (5S)-3-oxo-2-{[2-(trifluoromethyl)-1,8-naphthyridin-3-yl]methyl}-2,3,5,6,7,8-hexahydro[1,2,4]triazolo[4,3-a]pyridine-5-carboxylate (146 mg, 326 µmol) was dissolved in dichloromethane (7.0 ml), and trifluoroacetic acid (500 µl, 6.5 mmol) was added at 0° C. After the reaction mixture had been stirred at room temperature overnight, trifluoroacetic acid (500 µl, 6.5 mmol) was added again and the mixture was stirred at room temperature overnight. The solvent was then removed under reduced pressure. 252 mg (>100% of theory) of the title compound were obtained.

LC-MS (Method 4): $R_t$=0.56 min; MS (ESIpos): m/z=394 [M+H]$^+$ $^1$H-NMR (400 MHz, DMSO-d6) δ [ppm]: −0.149 (0.50), −0.008 (3.97), 0.008 (3.74), 0.146 (0.43), 1.111 (2.70), 1.228 (1.92), 1.421 (1.89), 1.535 (16.00), 1.738 (0.70), 1.856 (1.29), 1.890 (1.12), 2.073 (0.69), 2.147 (3.40), 2.160 (3.42), 2.329 (0.91), 2.367 (0.76), 2.585 (2.04), 2.599 (1.53), 2.612 (1.60), 2.627 (1.27), 2.671 (3.07), 2.711 (1.61), 4.550 (2.27), 4.560 (3.95), 4.573 (2.30), 5.243 (10.56), 7.075 (0.58), 7.815 (3.47), 7.825 (3.54), 7.835 (3.67), 7.846 (3.64), 8.380 (7.71), 8.549 (3.54), 8.554 (3.61), 8.570 (3.57), 8.575 (3.38), 9.247 (3.83), 9.252 (4.07), 9.257 (3.95), 9.262 (3.69).

Intermediate 339

(5S)-2-[(6-Chloropyridin-3-yl)methyl]-3-oxo-2,3,5,6,7,8-hexahydro[1,2,4]triazolo[4,3-a]pyridine-5-carboxylic Acid

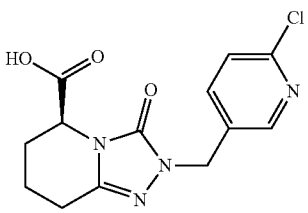 [SMILES: O=C(O)[C@@H]1CCCc2nn(Cc3ccc(Cl)nc3)c(=O)n21]

tert-Butyl (5S)-2-[(6-chloropyridin-3-yl)methyl]-3-oxo-2,3,5,6,7,8-hexahydro[1,2,4]triazolo[4,3-a]pyridine-5-carboxylate (509 mg, 93% purity, 1.30 mmol) was dissolved in dichloromethane (20 ml), and trifluoroacetic acid (2.0 ml, 26 mmol) was added at 0° C. After the reaction mixture had been stirred at room temperature overnight, the solvent was removed under reduced pressure. 850 mg (>100% of theory) of the title compound were obtained.

LC-MS (Method 3): $R_t$=0.85 min; MS (ESIpos): m/z=309 [M+H]$^+$ $^1$H-NMR (400 MHz, DMSO-d6) δ [ppm]: −0.008 (4.68), 0.008 (2.69), 1.030 (0.43), 1.045 (0.45), 1.110 (0.93), 1.387 (0.65), 1.505 (1.01), 1.519 (1.03), 1.534 (2.22), 1.809 (1.24), 1.819 (1.24), 1.830 (1.04), 1.841 (0.96), 2.090 (3.32), 2.100 (3.06), 2.112 (1.60), 2.328 (0.73), 2.367 (0.65), 2.519 (3.99), 2.524 (3.96), 2.568 (1.63), 2.582 (1.27), 2.614 (1.34), 2.626 (2.05), 2.636 (1.46), 2.656 (0.81), 2.666 (1.46), 2.669 (1.44), 2.710 (0.57), 4.461 (2.42), 4.473 (4.35), 4.486 (2.19), 4.827 (0.51), 4.909 (16.00), 5.067 (0.79), 5.075 (0.79), 5.088 (0.82), 5.097 (0.79), 5.445 (0.78), 7.500 (4.15), 7.510 (0.76), 7.520 (5.05), 7.703 (3.14), 7.709 (3.08), 7.723 (2.67), 7.730 (2.53), 8.309 (3.43), 8.314 (3.14).

Intermediate 340

(5S)-2-{[5-Chloro-6-(trifluoromethyl)pyridin-3-yl]methyl}-3-oxo-2,3,5,6,7,8-hexahydro[1,2,4]triazolo[4,3-a]pyridine-5-carboxylic Acid

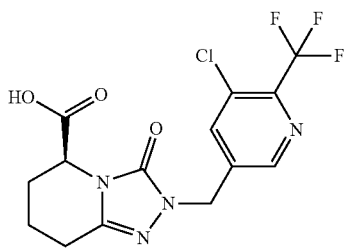 [SMILES: O=C(O)[C@@H]1CCCc2nn(Cc3cnc(C(F)(F)F)c(Cl)c3)c(=O)n21]

tert-Butyl (5S)-2-{[5-chloro-6-(trifluoromethyl)pyridin-3-yl]methyl}-3-oxo-2,3,5,6,7,8-hexahydro[1,2,4]triazolo[4,3-a]pyridine-5-carboxylate (156 mg, 360 µmol) was dissolved in dichloromethane (3.0 ml), and trifluoroacetic acid (560 µl, 7.2 mmol) was added at 0° C. After the reaction mixture had been stirred at room temperature overnight, the solvent was removed under reduced pressure. 156 mg (66% purity, 76% of theory) of the title compound were obtained.

LC-MS (Method 1): $R_t$=0.99 min; MS (ESIpos): m/z=377 [M+H]$^+$

Intermediate 341

(5S)-2-(3,4-Difluorobenzyl)-3-oxo-2,3,5,6,7,8-hexahydro[1,2,4]triazolo[4,3-a]pyridine-5-carboxylic Acid

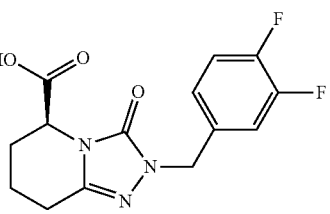

tert-Butyl (5S)-2-(3,4-difluorobenzyl)-3-oxo-2,3,5,6,7,8-hexahydro[1,2,4]triazolo[4,3-a]pyridine-5-carboxylate (900 mg, 78% purity, 1.92 mmol) was dissolved in dichloromethane (10 ml), and trifluoroacetic acid (3.0 ml, 38 mmol) was added at 0° C. After the reaction mixture had been stirred at room temperature overnight, the solvent was removed under reduced pressure. 590 mg (92% of theory) of the title compound were obtained.

LC-MS (Method 3): $R_t$=1.14 min; MS (ESIpos): m/z=310 [M+H]$^+$

Intermediate 342

(5S)-3-Oxo-2-(2,4,5-trifluorobenzyl)-2,3,5,6,7,8-hexahydro[1,2,4]triazolo[4,3-a]pyridine-5-carboxylic Acid

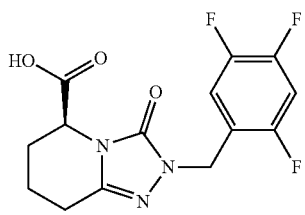 [SMILES: O=C(O)[C@@H]1CCCc2nn(Cc3cc(F)c(F)cc3F)c(=O)n21]

tert-Butyl (5S)-3-oxo-2-(2,4,5-trifluorobenzyl)-2,3,5,6,7,8-hexahydro[1,2,4]triazolo[4,3-a]pyridine-5-carboxylate (523 mg, 1.36 mmol) was dissolved in dichloromethane (10 ml), and trifluoroacetic acid (2.1 ml, 27 mmol) was added at 0° C. After the reaction mixture had been stirred at room temperature overnight, the solvent was removed under reduced pressure. 774 mg (>100% of theory) of the title compound were obtained.

LC-MS (Method 3): $R_t$=1.14 min; MS (ESIpos): m/z=328 [M+H]$^+$ $^1$H-NMR (400 MHz, DMSO-d6) δ[ppm]: −0.008 (0.82), 0.008 (0.68), 1.118 (6.81), 1.129 (0.42), 1.161 (2.13), 1.170 (0.42), 1.179 (4.32), 1.186 (0.44), 1.197 (2.17), 1.236 (1.91), 1.399 (0.56), 1.469 (0.47), 1.484 (1.04), 1.497 (1.48), 1.511 (1.77), 1.521 (2.46), 1.537 (2.89), 1.548 (2.11), 1.561 (1.23), 1.568 (1.17), 1.582 (0.67), 1.756 (0.53), 1.807 (2.09), 1.820 (2.94), 1.830 (2.93), 1.841 (2.39), 1.852 (2.37), 1.914 (1.15), 1.990 (7.81), 2.055 (0.59), 2.060 (0.54), 2.073 (1.51), 2.082 (3.23), 2.090 (5.04), 2.104 (8.58), 2.115 (7.88), 2.126 (4.11), 2.563 (3.78), 2.576 (3.69), 2.591 (2.87), 2.626 (3.11), 2.638 (4.92), 2.648 (3.42), 2.668 (1.70), 2.679 (2.33), 2.690 (1.39), 4.008 (0.60), 4.025 (1.83), 4.043 (1.80), 4.061 (0.58), 4.477 (5.29), 4.488 (10.00), 4.501 (5.14), 4.757 (1.78), 4.831 (1.52), 4.872 (16.00), 4.878 (15.58), 4.918 (1.43), 7.264 (6.52), 7.282 (7.05), 7.287 (7.36), 7.291 (7.18), 7.304 (7.27), 7.308 (7.32), 7.313 (6.92), 7.331 (6.44), 7.523 (4.17), 7.540 (4.34), 7.548 (5.42), 7.565 (5.28), 7.574 (4.10), 7.591 (3.71), 7.621 (1.61), 7.648 (1.44), 7.673 (1.15), 7.694 (1.09), 7.711 (1.06), 7.733 (1.00), 7.761 (0.87), 7.832 (0.71), 8.138 (0.92).

Intermediate 343

(5S)-2-{2-[3-Chloro-5-(trifluoromethyl)pyridin-2-yl]ethyl}-3-oxo-2,3,5,6,7,8-hexahydro[1,2,4]triazolo[4,3-a]pyridine-5-carboxylic Acid

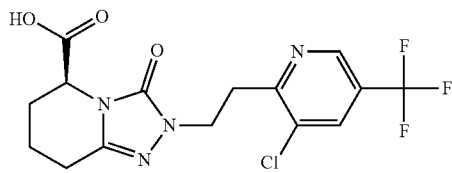 [SMILES: O=C(O)[C@@H]1CCCc2nn(CCc3ncc(C(F)(F)F)cc3Cl)c(=O)n21]

tert-Butyl (5S)-2-{2-[3-chloro-5-(trifluoromethyl)pyridin-2-yl]ethyl}-3-oxo-2,3,5,6,7,8-hexahydro[1,2,4]triazolo[4,3-a]pyridine-5-carboxylate (120 mg, 269 μmol) was dissolved in dichloromethane (4.0 ml), and trifluoroacetic acid (410 μl, 5.4 mmol) was added at 0° C. After the reaction mixture had been stirred at room temperature overnight, trifluoroacetic acid (300 μl, 3.9 mmol) was added again and the mixture was stirred overnight. The solvent was then removed under reduced pressure. 153 mg (>100% of theory) of the title compound were obtained.

LC-MS (Method 1): $R_t$=0.99 min; MS (ESIpos): m/z=391 [M+H]$^+$ $^1$H-NMR (400 MHz, DMSO-d6) δ [ppm]: −0.150 (0.75), 0.146 (0.75), 0.833 (0.43), 1.038 (0.57), 1.056 (1.21), 1.073 (0.60), 1.110 (2.01), 1.157 (0.57), 1.176 (0.83), 1.236 (1.38), 1.291 (3.19), 1.309 (6.41), 1.327 (3.25), 1.390 (1.90), 1.538 (2.30), 1.566 (1.41), 1.783 (2.07), 1.793 (3.13), 1.805 (3.02), 1.815 (2.61), 1.827 (2.53), 2.047 (4.51), 2.060 (8.10), 2.076 (7.58), 2.089 (3.88), 2.328 (1.64), 2.366 (1.32), 2.522 (9.65), 2.563 (3.56), 2.606 (3.36), 2.618 (5.69), 2.629 (3.53), 2.648 (1.92), 2.660 (3.30), 2.671 (3.02), 2.710 (1.35), 3.291 (7.47), 3.309 (16.00), 3.328 (8.53), 3.432 (0.63), 3.449 (0.69), 4.004 (1.58), 4.022 (2.90), 4.039 (5.49), 4.057 (9.91), 4.081 (9.13), 4.099 (5.34), 4.116 (2.82), 4.135 (1.58), 4.384 (6.49), 4.396 (12.67), 4.408 (6.69), 4.415 (4.71), 4.433 (4.22), 4.450 (2.56), 4.729 (2.82), 8.414 (9.91), 8.881 (10.08).

Intermediate 344

(5S)-2-[3-Chloro-4-(trifluoromethyl)benzyl]-3-oxo-2,3,5,6,7,8-hexahydro[1,2,4]triazolo[4,3-a]pyridine-5-carboxylic Acid

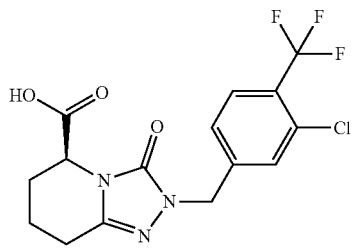 [SMILES: O=C(O)[C@@H]1CCCc2nn(Cc3ccc(C(F)(F)F)c(Cl)c3)c(=O)n21]

tert-Butyl (5S)-2-[3-chloro-4-(trifluoromethyl)benzyl]-3-oxo-2,3,5,6,7,8-hexahydro[1,2,4]triazolo[4,3-a]pyridine-5-carboxylate (523 mg, 1.21 mmol) was dissolved in dichloromethane (10 ml), and trifluoroacetic acid (1.9 ml, 24 mmol) was added at 0° C. After the reaction mixture had been stirred at room temperature overnight, the solvent was removed under reduced pressure. 175 mg (37% of theory) of the title compound were obtained.

LC-MS (Method 1): $R_t$=1.09 min; MS (ESIpos): m/z=376 [M+H]$^+$ $^1$H-NMR (400 MHz, DMSO-d6) δ [ppm]: −0.008 (2.69), 0.008 (2.18), 0.018 (0.56), 0.837 (0.57), 1.227 (0.51), 1.235 (0.42), 1.460 (0.42), 1.515 (1.26), 1.527 (1.23), 1.543 (1.10), 1.822 (1.58), 1.834 (1.53), 1.844 (1.29), 1.855 (1.31), 2.108 (4.38), 2.118 (4.15), 2.130 (2.21), 2.328 (0.63), 2.366 (0.62), 2.524 (2.14), 2.558 (2.84), 2.573 (1.97), 2.586 (2.06), 2.600 (1.62), 2.631 (1.67), 2.643 (2.69), 2.653 (1.89), 2.674 (1.29), 2.683 (1.20), 2.695 (0.72), 2.710 (0.63), 4.107 (0.72), 4.322 (1.38), 4.490 (3.29), 4.501 (5.97), 4.514 (3.19), 4.588 (0.53), 4.973 (16.00), 7.391 (3.50), 7.412 (3.86), 7.561 (7.11), 7.835 (6.26), 7.855 (5.71).

Intermediate 345

(5S)-2-[3-Fluoro-4-(trifluoromethyl)benzyl]-3-oxo-2,3,5,6,7,8-hexahydro[1,2,4]triazolo[4,3-a]pyridine-5-carboxylic Acid

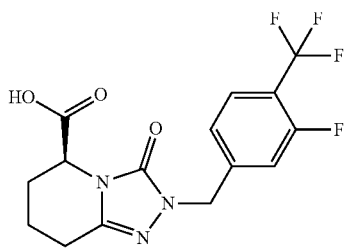 [SMILES: O=C(O)[C@@H]1CCCc2nn(Cc3ccc(C(F)(F)F)c(F)c3)c(=O)n21]

tert-Butyl (5S)-2-[3-fluoro-4-(trifluoromethyl)benzyl]-3-oxo-2,3,5,6,7,8-hexahydro[1,2,4]triazolo[4,3-a]pyridine-5-carboxylate (707 mg, 1.70 mmol) was dissolved in dichloromethane (10 ml), and trifluoroacetic acid (2.6 ml, 34 mmol) was added at 0° C. After the reaction mixture had been stirred at room temperature overnight, the solvent was removed under reduced pressure. 611 mg (96% of theory) of the title compound were obtained.

LC-MS (Method 3): $R_t$=1.42 min; MS (ESIpos): m/z=360 [M+H]$^+$

Intermediate 346

(5S)-2-{[1-(6-Chloropyridin-2-yl)cyclopropyl]methyl}-3-oxo-2,3,5,6,7,8-hexahydro[1,2,4]triazolo[4,3-a]pyridine-5-carboxylic Acid

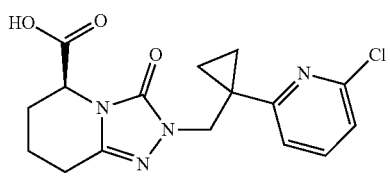 [SMILES: O=C(O)[C@@H]1CCCc2nn(CC3(c4cccc(Cl)n4)CC3)c(=O)n21]

tert-Butyl (5S)-2-{[1-(6-chloropyridin-2-yl)cyclopropyl]methyl}-pyridine-5-carboxylate (224 mg, 554 μmol) was dissolved in dichloromethane (3.0 ml), and trifluoroacetic acid (850 μl, 11 mmol) was added at 0° C. After the reaction mixture had been stirred at room temperature overnight, the solvent was removed under reduced pressure. 330 mg (>100% of theory) of the title compound were obtained.

LC-MS (Method 3): $R_t$=1.20 min; MS (ESIpos): m/z=349 [M+H]$^+$ $^1$H-NMR (400 MHz, DMSO-d6) δ [ppm]: 0.008 (0.48), 1.113 (1.42), 1.143 (0.85), 1.164 (10.97), 1.176 (15.26), 1.194 (2.29), 1.231 (0.88), 1.278 (0.44), 1.299 (0.48), 1.379 (0.87), 1.450 (0.49), 1.468 (0.79), 1.485 (1.13), 1.499 (1.16), 1.513 (1.06), 1.536 (4.67), 1.545 (0.54), 1.600 (0.68), 1.762 (0.79), 1.770 (1.14), 1.779 (1.55), 1.793 (1.54), 1.803 (1.35), 1.815 (1.28), 1.825 (1.00), 1.989 (5.49), 2.063 (4.19), 2.073 (4.25), 2.470 (0.72), 2.484 (1.00), 2.590 (1.40), 2.600 (2.51), 2.612 (1.97), 2.622 (0.54), 2.631 (0.82), 2.642 (1.22), 2.654 (0.82), 3.784 (0.51), 4.005 (0.47), 4.023 (1.38), 4.040 (1.38), 4.058 (0.74), 4.091 (16.00), 4.369 (0.48), 4.381 (0.93), 4.394 (0.53), 4.419 (2.40), 4.431 (4.64), 4.444 (2.31), 7.239 (4.53), 7.259 (4.97), 7.312 (0.46), 7.582 (4.49), 7.601 (6.06), 7.696 (3.81), 7.716 (6.11), 7.735 (2.62), 11.361 (0.58), 12.173 (0.58).

Intermediate 347

(5S)-2-{[1-(4-Fluorophenyl)cyclopropyl]methyl}-3-oxo-2,3,5,6,7,8-hexahydro[1,2,4]triazolo[4,3-a]pyridine-5-carboxylic Acid

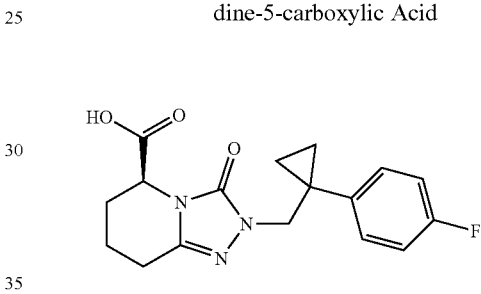

tert-Butyl (5S)-2-{[1-(4-fluorophenyl)cyclopropyl]methyl}-3-oxo-2,3,5,6,7,8-hexahydro[1,2,4]triazolo[4,3-a]pyridine-5-carboxylate (557 mg, 1.44 mmol) was dissolved in dichloromethane (10 ml), and trifluoroacetic acid (2.2 ml, 29 mmol) was added at 0° C. After the reaction mixture had been stirred at room temperature overnight, the solvent was removed under reduced pressure. 743 mg (>100% of theory) of the title compound were obtained.

LC-MS (Method 4): $R_t$=0.73 min; MS (ESIpos): m/z=332 [M+H]$^+$

Intermediate 348

(5S)-2-{[1-(4-Methoxyphenyl)cyclopropyl]methyl}-3-oxo-2,3,5,6,7,8-hexahydro[1,2,4]triazolo[4,3-a]pyridine-5-carboxylic Acid

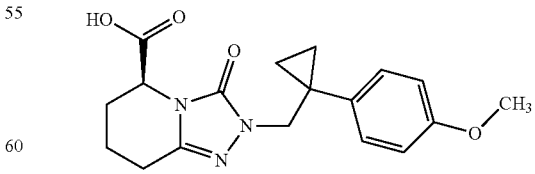

tert-Butyl (5S)-2-{[1-(4-methoxyphenyl)cyclopropyl]methyl}-3-oxo-2,3,5,6,7,8-hexahydro[1,2,4]triazolo[4,3-a]pyridine-5-carboxylate (222 mg, 555 μmol) was dissolved in dichloromethane (3.0 ml), and trifluoroacetic acid (850 μl, 11 mmol) was added at 0° C. After the reaction mixture had been stirred at room temperature overnight, the solvent was removed under reduced pressure. 373 mg (70% purity, >100% of theory) of the title compound were obtained.

LC-MS (Method 1): $R_t$=0.97 min; MS (ESIpos): m/z=344 [M+H]$^+$ $^1$H-NMR (400 MHz, DMSO-d6) δ[ppm]: −0.149 (0.45), −0.008 (3.69), 0.008 (3.61), 0.146 (0.45), 0.678 (1.71), 0.689 (1.42), 0.704 (5.29), 0.726 (1.23), 0.752 (5.96), 0.776 (2.07), 0.916 (1.06), 0.926 (0.88), 0.940 (3.89), 0.950 (14.15), 0.962 (3.42), 0.985 (0.74), 1.045 (0.41), 1.056 (0.73), 1.111 (5.66), 1.116 (0.71), 1.149 (0.79), 1.166 (1.71), 1.184 (0.73), 1.228 (1.91), 1.278 (1.68), 1.291 (4.42), 1.309 (8.19), 1.327 (4.14), 1.381 (0.70), 1.507 (1.73), 1.520 (1.61), 1.535 (1.64), 1.568 (0.69), 1.737 (0.63), 1.775 (1.48), 1.788 (2.14), 1.798 (2.10), 1.809 (1.73), 1.820 (1.70), 2.005 (0.41), 2.032 (2.15), 2.040 (3.48), 2.054 (5.96), 2.065 (5.63), 2.076 (3.11), 2.328 (0.71), 2.367 (0.51), 2.474 (1.41), 2.524 (2.92), 2.558 (2.48), 2.599 (2.19), 2.611 (3.64), 2.622 (2.47), 2.641 (1.28), 2.652 (1.75), 2.665 (1.41), 2.711 (0.54), 3.432 (0.50), 3.653 (0.98), 3.737 (8.71), 3.754 (1.02), 3.764 (0.54), 3.771 (0.63), 3.814 (0.58), 3.836 (8.44), 3.872 (5.20), 4.119 (0.45), 4.132 (0.45), 4.137 (0.42), 4.357 (3.69), 4.369 (6.99), 4.381 (3.73), 4.397 (1.29), 4.415 (3.38), 4.433 (3.32), 4.451 (1.21), 4.463 (0.41), 4.472 (0.41), 5.344 (2.22), 6.767 (1.50), 6.774 (13.78), 6.779 (5.45), 6.791 (5.03), 6.796 (16.00), 7.120 (1.81), 7.127 (15.91), 7.132 (5.25), 7.144 (4.97), 7.149 (14.17), 7.156 (2.15), 11.357 (0.40).

Intermediate 349

(5S)-3-Oxo-2-({1-[4-(trifluoromethyl)phenyl] cyclopropyl}methyl)-2,3,5,6,7,8-hexahydro[1,2,4] triazolo[4,3-a]pyridine-5-carboxylic Acid

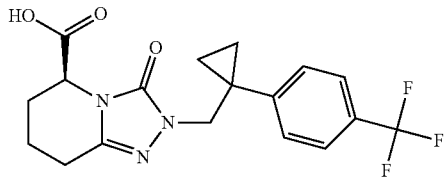 [SMILES: O=C(O)[C@@H]1CCCc2nn(CC3(c4ccc(C(F)(F)F)cc4)CC3)c(=O)n21]

tert-Butyl (5S)-3-oxo-2-({1-[4-(trifluoromethyl)phenyl] cyclopropyl}methyl)-2,3,5,6,7,8-hexahydro[1,2,4]triazolo [4,3-a]pyridine-5-carboxylate (113 mg, 258 μmol) was dissolved in dichloromethane (1.5 ml), and trifluoroacetic acid (400 μl, 5.2 mmol) was added at 0° C. After the reaction mixture had been stirred at room temperature overnight, the solvent was removed under reduced pressure. 115 mg (88% purity, >100% of theory) of the title compound were obtained.

LC-MS (Method 1): $R_t$=1.14 min; MS (ESIpos): m/z=382 [M+H]$^+$ $^1$H-NMR (400 MHz, DMSO-d6) δ[ppm]: −0.150 (0.78), 0.008 (6.17), 0.146 (0.86), 0.866 (2.35), 0.893 (4.18), 0.926 (4.29), 0.951 (2.69), 1.038 (1.78), 1.055 (3.61), 1.073 (1.88), 1.110 (8.13), 1.127 (14.72), 1.227 (4.55), 1.291 (7.84), 1.309 (16.00), 1.327 (8.00), 1.358 (1.25), 1.492 (1.75), 1.736 (1.44), 1.785 (2.20), 1.795 (2.14), 1.817 (1.83), 2.052 (6.41), 2.064 (5.80), 2.327 (1.59), 2.366 (0.94), 2.465 (1.52), 2.601 (3.82), 2.612 (2.54), 2.643 (1.86), 2.670 (1.75), 2.710 (0.97), 3.414 (0.65), 3.431 (1.86), 3.449 (1.83), 3.467 (0.71), 3.859 (1.78), 3.895 (13.78), 3.903 (13.73), 3.940 (1.96), 4.371 (7.48), 4.382 (11.03), 4.396 (8.89), 4.415 (10.17), 4.433 (9.93), 4.451 (5.59), 7.438 (9.57), 7.459 (12.99), 7.569 (13.54), 7.589 (10.01).

Intermediate 350

(5S)-2-{[1-(2,4-Difluorophenyl)cyclopropyl] methyl}-3-oxo-2,3,5,6,7,8-hexahydro[1,2,4]triazolo [4,3-a]pyridine-5-carboxylic Acid

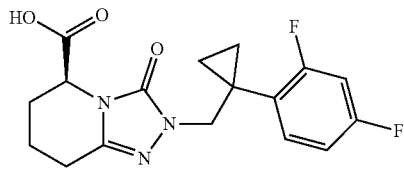 [SMILES: O=C(O)[C@@H]1CCCc2nn(CC3(c4ccc(F)cc4F)CC3)c(=O)n21]

tert-Butyl (5S)-2-{[1-(2,4-difluorophenyl)cyclopropyl] methyl}-3-oxo-2,3,5,6,7,8-hexahydro[1,2,4]triazolo[4,3-a] pyridine-5-carboxylate (256 mg, 630 μmol) was dissolved in dichloromethane (3.7 ml), and trifluoroacetic acid (970 μl, 13 mmol) was added at 0° C. After the reaction mixture had been stirred at room temperature overnight, the solvent was removed under reduced pressure. 391 mg (81% purity, >100% of theory) of the title compound were obtained.

LC-MS (Method 1): $R_t$=1.01 min; MS (ESIpos): m/z=350 [M+H]$^+$

Intermediate 351

(5S)-2-(2,4-Difluorobenzyl)-3-oxo-2,3,5,6,7,8-hexahydro[1,2,4]triazolo[4,3-a]pyridine-5-carboxylic Acid

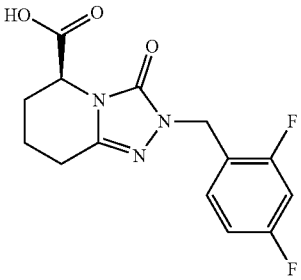 [SMILES: O=C(O)[C@@H]1CCCc2nn(Cc3ccc(F)cc3F)c(=O)n21]

tert-Butyl (5S)-2-(2,4-difluorobenzyl)-3-oxo-2,3,5,6,7,8-hexahydro[1,2,4]triazolo[4,3-a]pyridine-5-carboxylate (443 mg, 1.21 mmol) was dissolved in dichloromethane (10 ml), and trifluoroacetic acid (1.9 ml, 24 mmol) was added at room temperature. After the reaction mixture had been stirred at room temperature overnight, the solvent was removed under reduced pressure. 530 mg (>100% of theory) of the title compound were obtained.

LC-MS (Method 3): $R_t$=1.10 min; MS (ESIpos): m/z=310 [M+H]$^+$ $^1$H-NMR (400 MHz, DMSO-d6) δ [ppm]: −0.149 (0.62), −0.008 (6.71), 0.008 (4.59), 0.146 (0.59), 1.038 (0.42), 1.056 (0.82), 1.110 (1.70), 1.122 (0.42), 1.175 (0.48), 1.181 (0.40), 1.227 (0.42), 1.291 (6.89), 1.309 (13.99), 1.327 (6.97), 1.392 (1.44), 1.475 (1.13), 1.488 (1.88), 1.522 (2.43), 1.534 (3.07), 1.550 (1.54), 1.569 (0.80), 1.787 (2.21), 1.799

(3.27), 1.810 (3.22), 1.821 (2.85), 1.832 (2.72), 1.988 (0.80), 2.063 (4.96), 2.075 (8.83), 2.084 (8.61), 2.092 (8.01), 2.104 (4.30), 2.328 (0.73), 2.367 (0.62), 2.570 (3.82), 2.603 (3.86), 2.614 (5.91), 2.625 (4.13), 2.645 (2.19), 2.656 (2.80), 2.668 (2.25), 2.710 (0.82), 3.432 (0.44), 3.449 (0.44), 4.397 (1.83), 4.415 (5.54), 4.433 (5.58), 4.448 (6.82), 4.460 (11.96), 4.473 (6.07), 4.517 (0.42), 4.783 (0.99), 4.805 (3.20), 4.844 (15.73), 4.860 (16.00), 4.899 (3.40), 5.097 (1.19), 5.127 (1.32), 5.475 (1.65), 5.753 (0.97), 7.047 (2.49), 7.052 (2.65), 7.069 (5.60), 7.074 (5.92), 7.090 (3.24), 7.095 (3.35), 7.221 (3.60), 7.227 (3.42), 7.246 (5.56), 7.251 (5.25), 7.271 (3.80), 7.277 (3.66), 7.290 (3.64), 7.307 (4.64), 7.311 (7.06), 7.328 (6.95), 7.349 (3.11).

Intermediate 352

(5S)-2-(2-Chloro-4-fluorobenzyl)-3-oxo-2,3,5,6,7,8-hexahydro[1,2,4]triazolo[4,3-a]pyridine-5-carboxylic Acid

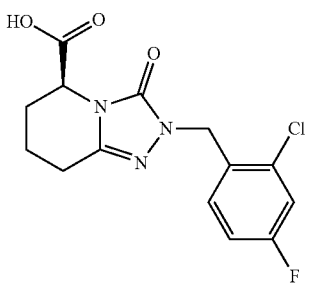 [SMILES: O=C(O)[C@@H]1CCCc2nn(Cc3ccc(F)cc3Cl)c(=O)n21]

tert-Butyl (5S)-2-(2-chloro-4-fluorobenzyl)-3-oxo-2,3,5,6,7,8-hexahydro[1,2,4]triazolo[4,3-a]pyridine-5-carboxylate (371 mg, 970 µmol) was dissolved in dichloromethane (10 ml), and trifluoroacetic acid (1.5 ml, 19 mmol) was added at room temperature. After the reaction mixture had been stirred at room temperature overnight, the solvent was removed under reduced pressure. 580 mg (>100% of theory) of the title compound were obtained.

LC-MS (Method 3): $R_t$=1.19 min; MS (ESIpos): m/z=326 [M+H]$^+$ $^1$H-NMR (400 MHz, DMSO-d6) δ[ppm]: 1.110 (1.55), 1.157 (0.51), 1.175 (1.15), 1.192 (0.58), 1.227 (0.70), 1.404 (1.18), 1.520 (1.43), 1.534 (1.96), 1.548 (1.29), 1.561 (0.93), 1.580 (0.48), 1.802 (1.27), 1.813 (1.85), 1.824 (1.81), 1.836 (1.52), 1.847 (1.48), 1.988 (1.90), 2.073 (4.52), 2.092 (4.73), 2.099 (5.07), 2.108 (4.79), 2.119 (2.69), 2.328 (0.57), 2.366 (0.50), 2.585 (1.84), 2.617 (2.00), 2.628 (3.21), 2.639 (2.14), 2.659 (1.19), 2.670 (2.01), 2.681 (0.96), 2.710 (0.53), 4.021 (0.47), 4.038 (0.48), 4.470 (3.11), 4.482 (5.98), 4.495 (3.09), 4.857 (0.87), 4.898 (16.00), 4.940 (0.98), 5.144 (1.15), 5.158 (1.19), 5.398 (0.94), 5.504 (1.36), 5.753 (0.75), 7.190 (1.16), 7.196 (1.23), 7.211 (3.51), 7.217 (3.73), 7.232 (2.72), 7.238 (2.93), 7.250 (4.64), 7.266 (4.90), 7.287 (2.11), 7.459 (2.87), 7.465 (2.85), 7.481 (2.93), 7.487 (2.91).

Intermediate 353

(5S)-2-[(5-Chloro-6-methoxypyridin-3-yl)methyl]-3-oxo-2,3,5,6,7,8-hexahydro[1,2,4]triazolo[4,3-a]pyridine-5-carboxylic Acid

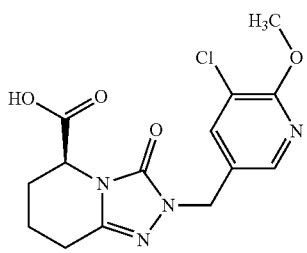 [SMILES: COc1ncc(Cn2nc3n(c2=O)[C@H](C(=O)O)CCC3)cc1Cl]

tert-Butyl (5S)-2-[(5-chloro-6-methoxypyridin-3-yl)methyl]-3-oxo-2,3,5,6,7,8-hexahydro[1,2,4]triazolo[4,3-a]pyridine-5-carboxylate (718 mg, 1.82 mmol) was dissolved in dichloromethane (10 ml), and trifluoroacetic acid (2.8 ml, 36 mmol) was added at room temperature. After the reaction mixture had been stirred at room temperature overnight, the solvent was removed under reduced pressure. 781 mg (>100% of theory) of the title compound were obtained.

LC-MS (Method 3): $R_t$=1.12 min; MS (ESIpos): m/z=339 [M+H]$^+$

Intermediate 354

(5S)-2-(4-Fluorobenzyl)-3-oxo-2,3,5,6,7,8-hexahydro[1,2,4]triazolo[4,3-a]pyridine-5-carboxylic acid

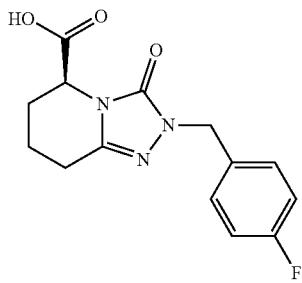 [SMILES: O=C(O)[C@@H]1CCCc2nn(Cc3ccc(F)cc3)c(=O)n21]

tert-Butyl (5S)-2-(4-fluorobenzyl)-3-oxo-2,3,5,6,7,8-hexahydro[1,2,4]triazolo[4,3-a]pyridine-5-carboxylate (299 mg, 862 µmol) was dissolved in dichloromethane (10 ml), and trifluoroacetic acid (1.3 ml, 17 mmol) was added at room temperature. After the reaction mixture had been stirred at room temperature for 4 hours, the solvent was removed under reduced pressure. 397 mg (>100% of theory) of the title compound were obtained.

LC-MS (Method 3): R$_t$=1.02 min; MS (ESIpos): m/z=292 [M+H]$^+$

Intermediate 355

(5S)-2-[(6-Chloropyridin-2-yl)methyl]-3-oxo-2,3,5,6,7,8-hexahydro[1,2,4]triazolo[4,3-a]pyridine-5-carboxylic Acid

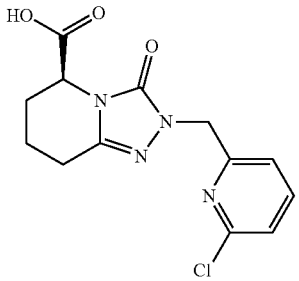 [SMILES: O=C(O)[C@@H]1CCCc2nn(Cc3cccc(Cl)n3)c(=O)n21]

tert-Butyl (5S)-2-[(6-chloropyridin-2-yl)methyl]-3-oxo-2,3,5,6,7,8-hexahydro[1,2,4]triazolo[4,3-a]pyridine-5-carboxylate (372 mg, 1.02 mmol) was dissolved in dichloromethane (10 ml), and trifluoroacetic acid (1.6 ml, 20 mmol) was added at room temperature. After the reaction mixture had been stirred at room temperature overnight, the solvent was removed under reduced pressure. 554 mg (>100% of theory) of the title compound were obtained.

LC-MS (Method 1): R$_t$=0.74 min; MS (ESIpos): m/z=309 [M+H]$^+$

Intermediate 356

(5S)-2-(4-Methoxybenzyl)-3-oxo-2,3,5,6,7,8-hexahydro[1,2,4]triazolo[4,3-a]pyridine-5-carboxylic Acid

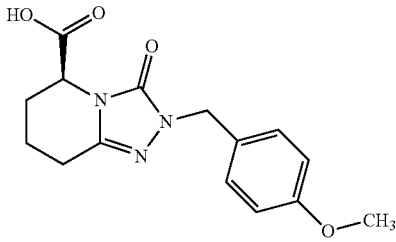 [SMILES: COc1ccc(Cn2nc3n(c2=O)[C@H](C(=O)O)CCC3)cc1]

tert-Butyl (5S)-2-(4-methoxybenzyl)-3-oxo-2,3,5,6,7,8-hexahydro[1,2,4]triazolo[4,3-a]pyridine-5-carboxylate (129 mg, 359 µmol) was dissolved in dichloromethane (3.0 ml), and trifluoroacetic acid (550 µl, 7.2 mmol) was added at room temperature. After the reaction mixture had been stirred at room temperature overnight, the solvent was removed under reduced pressure. 258 mg (50% purity, >100% of theory) of the title compound were obtained.

LC-MS (Method 4): R$_t$=0.58 min; MS (ESIpos): m/z=304 [M+H]$^+$

Intermediate 357

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic Acid

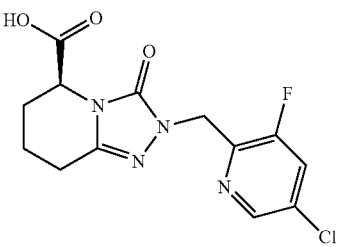 [SMILES: O=C(O)[C@@H]1CCCc2nn(Cc3ncc(Cl)cc3F)c(=O)n21]

tert-Butyl (5S)-2-[(5-chloro-3-fluoropyridin-2-yl)methyl]-3-oxo-2,3,5,6,7,8-hexahydro[1,2,4]triazolo[4,3-a]pyridine-5-carboxylate (465 mg, 1.21 mmol) was dissolved in dichloromethane (10 ml), and trifluoroacetic acid (1.9 ml, 24 mmol) was added at room temperature. After the reaction mixture had been stirred at room temperature overnight, trifluoroacetic acid (0.19 ml, 2.4 mmol) was added again and the mixture was stirred at room temperature for 3 hours. The solvent was then removed under reduced pressure. 813 mg (>100% of theory) of the title compound were obtained.

LC-MS (Method 3): R$_t$=0.96 min; MS (ESIpos): m/z=327 [M+H]$^+$

Intermediate 358

(5S)-2-[(5-Fluoropyridin-2-yl)methyl]-3-oxo-2,3,5,6,7,8-hexahydro[1,2,4]triazolo[4,3-a]pyridine-5-carboxylic Acid

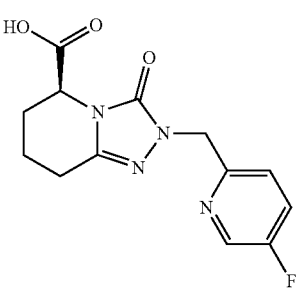 [SMILES: O=C(O)[C@@H]1CCCc2nn(Cc3ccc(F)cn3)c(=O)n21]

tert-Butyl (5S)-2-[(5-fluoropyridin-2-yl)methyl]-3-oxo-2,3,5,6,7,8-hexahydro[1,2,4]triazolo[4,3-a]pyridine-5-carboxylate (345 mg, 989 µmol) was dissolved in dichloromethane (10 ml), and trifluoroacetic acid (1.5 ml, 20 mmol) was added at room temperature. After the reaction mixture had been stirred at room temperature overnight, the solvent was removed under reduced pressure. 549 mg (>100% of theory) of the title compound were obtained.

LC-MS (Method 4): $R_t$=0.42 min; MS (ESIpos): m/z=293 [M+H]$^+$

Intermediate 359

(5S)-2-(4-Chloro-3-fluorobenzyl)-3-oxo-2,3,5,6,7,8-hexahydro[1,2,4]triazolo[4,3-a]pyridine-5-carboxylic Acid

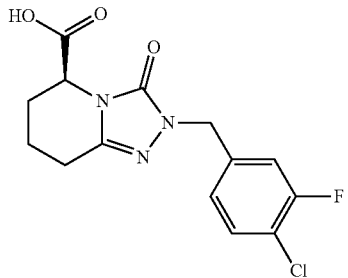 [SMILES: O=C(O)[C@@H]1CCCc2nn(Cc3ccc(Cl)c(F)c3)c(=O)n21]

tert-Butyl (5S)-2-(4-chloro-3-fluorobenzyl)-3-oxo-2,3,5,6,7,8-hexahydro[1,2,4]triazolo[4,3-a]pyridine-5-carboxylate (363 mg, 951 µmol) was dissolved in dichloromethane (8.0 ml), and trifluoroacetic acid (1.5 ml, 19 mmol) was added at room temperature. After the reaction mixture had been stirred at room temperature overnight, the solvent was removed under reduced pressure. 454 mg (>100% of theory) of the title compound were obtained.

LC-MS (Method 4): $R_t$=0.72 min; MS (ESIpos): m/z=326 [M+H]$^+$

Intermediate 360

(5S)-2-[(5-Chloropyridin-3-yl)methyl]-3-oxo-2,3,5,6,7,8-hexahydro[1,2,4]triazolo[4,3-a]pyridine-5-carboxylic Acid

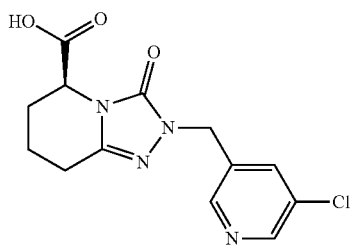 [SMILES: O=C(O)[C@@H]1CCCc2nn(Cc3cncc(Cl)c3)c(=O)n21]

tert-Butyl (5S)-2-[(5-chloropyridin-3-yl)methyl]-3-oxo-2,3,5,6,7,8-hexahydro[1,2,4]triazolo[4,3-a]pyridine-5-carboxylate (450 mg, 1.23 mmol) was dissolved in dichloromethane (12 ml), and trifluoroacetic acid (1.9 ml, 25 mmol) was added at room temperature. After the reaction mixture had been stirred at room temperature overnight, the solvent was removed under reduced pressure. 380 mg (100% of theory) of the title compound were obtained.

LC-MS (Method 4): $R_t$=0.5 min; MS (ESIpos): m/z=309 [M+H]$^+$

Intermediate 361

(5S)-2-[2-(4-Fluorophenyl)ethyl]-3-oxo-2,3,5,6,7,8-hexahydro[1,2,4]triazolo[4,3-a]pyridine-5-carboxylic Acid

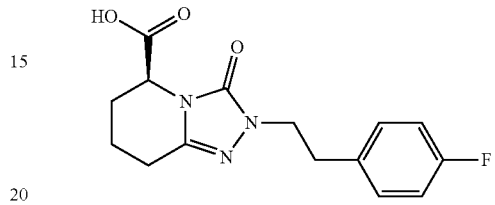

tert-Butyl (5S)-2-[2-(4-fluorophenyl)ethyl]-3-oxo-2,3,5,6,7,8-hexahydro[1,2,4]triazolo[4,3-a]pyridine-5-carboxylate (340 mg, 941 µmol) was dissolved in dichloromethane (10 ml), and trifluoroacetic acid (1.4 ml, 19 mmol) was added at room temperature. After the reaction mixture had been stirred at room temperature overnight, the solvent was removed under reduced pressure. 484 mg (>100% of theory) of the title compound were obtained.

LC-MS (Method 3): $R_t$=1.13 min; MS (ESIpos): m/z=306 [M+H]$^+$

Intermediate 362

(5S)-2-[(5-Methoxypyridin-2-yl)methyl]-3-oxo-2,3,5,6,7,8-hexahydro[1,2,4]triazolo[4,3-a]pyridine-5-carboxylic Acid

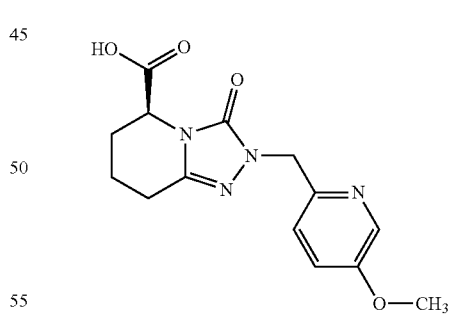

tert-Butyl (5S)-2-[(5-methoxypyridin-2-yl)methyl]-3-oxo-2,3,5,6,7,8-hexahydro[1,2,4]triazolo[4,3-a]pyridine-5-carboxylate (196 mg, 544 µmol) was dissolved in dichloromethane, and trifluoroacetic acid (420 µl, 5.5 mmol) was added at room temperature. After the reaction mixture had been stirred at room temperature overnight, trifluoroacetic acid (840 µl, 11 mmol) was added again and the mixture was stirred for 6 hours. The solvent was then removed under reduced pressure. 302 mg (>100% of theory) of the title compound were obtained.

LC-MS (Method 1): $R_t$=0.53 min; MS (ESIpos): m/z=305 [M+H]$^+$

Intermediate 363

(5S)-2-[(3,5-Dichloropyridin-2-yl)methyl]-3-oxo-2,3,5,6,7,8-hexahydro[1,2,4]triazolo[4,3-a]pyridine-5-carboxylic Acid

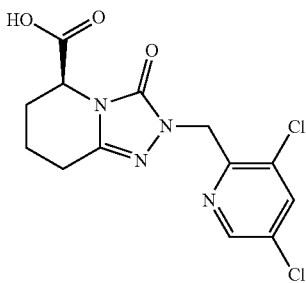 [SMILES: O=C(O)[C@@H]1CCCc2nn(Cc3ncc(Cl)cc3Cl)c(=O)n21]

tert-Butyl (5S)-2-[(3,5-dichloropyridin-2-yl)methyl]-3-oxo-2,3,5,6,7,8-hexahydro[1,2,4]triazolo[4,3-a]pyridine-5-carboxylate (563 mg, 1.41 mmol) was dissolved in dichloromethane (29 ml), and trifluoroacetic acid (2.2 ml, 28 mmol) was added at room temperature. After the reaction mixture had been stirred at room temperature overnight, the solvent was removed under reduced pressure. 823 mg (72% purity, >100% of theory) of the title compound were obtained.

LC-MS (Method 4): $R_t$=0.59 min; MS (ESIpos): m/z=343 [M+H]$^+$ $^1$H-NMR (400 MHz, DMSO-d6) δ[ppm]: −0.008 (1.94), 0.008 (2.31), 1.110 (0.45), 1.228 (0.43), 1.341 (0.41), 1.412 (16.00), 1.522 (0.93), 1.535 (1.80), 1.796 (1.19), 1.807 (1.15), 1.818 (1.05), 1.829 (1.01), 1.988 (0.57), 2.071 (2.07), 2.082 (3.10), 2.092 (2.96), 2.561 (1.34), 2.588 (1.36), 2.599 (2.22), 2.611 (1.52), 2.630 (0.75), 2.641 (1.00), 2.653 (0.60), 2.671 (0.48), 3.914 (1.27), 4.438 (0.62), 4.453 (1.95), 4.466 (3.78), 4.478 (1.88), 4.618 (0.42), 4.855 (1.24), 4.991 (1.12), 5.030 (8.30), 5.041 (9.08), 5.081 (1.19), 6.473 (0.41), 8.250 (4.12), 8.256 (5.12), 8.560 (1.18), 8.567 (5.22), 8.572 (4.55).

Intermediate 364

(5S)-2-[2-(4-Methoxyphenyl)ethyl]-3-oxo-2,3,5,6,7,8-hexahydro[1,2,4]triazolo[4,3-a]pyridine-5-carboxylic Acid

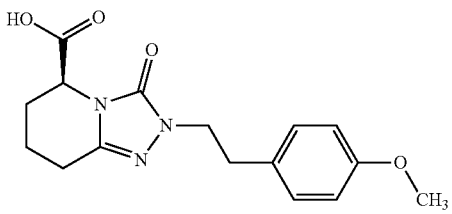 [SMILES: COc1ccc(CCn2nc3n(c2=O)[C@H](C(=O)O)CCC3)cc1]

tert-Butyl (5S)-2-[2-(4-methoxyphenyl)ethyl]-3-oxo-2,3,5,6,7,8-hexahydro[1,2,4]triazolo[4,3-a]pyridine-5-carboxylate (369 mg, 987 μmol) was dissolved in dichloromethane (10 ml), and trifluoroacetic acid (1.5 ml, 20 mmol) was added at room temperature. After the reaction mixture had been stirred at room temperature overnight, the solvent was removed under reduced pressure. 489 mg (85% purity, >100% of theory) of the title compound were obtained.

LC-MS (Method 3): $R_t$=1.11 min; MS (ESIpos): m/z=318 [M+H]$^+$

Intermediate 365

(5S)-2-[(1-Methyl-1H-pyrazolo[3,4-b]pyridin-3-yl)methyl]-3-oxo-2,3,5,6,7,8-hexahydro[1,2,4]triazolo[4,3-a]pyridine-5-carboxylic Acid

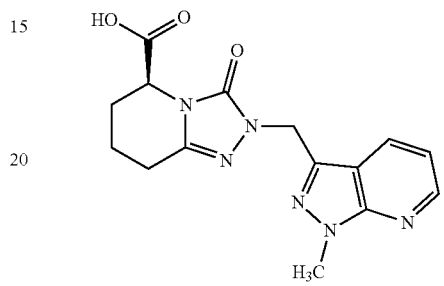

tert-Butyl (5S)-2-[(1-methyl-1H-pyrazolo[3,4-b]pyridin-3-yl)methyl]-3-oxo-2,3,5,6,7,8-hexahydro[1,2,4]triazolo[4,3-a]pyridine-5-carboxylate (203 mg, 88% purity, 465 μmol) was dissolved in dichloromethane (5.0 ml), and trifluoroacetic acid (720 μl, 9.3 mmol) was added at room temperature. After the reaction mixture had been stirred at room temperature overnight, the solvent was removed under reduced pressure. 284 mg (89% purity, >100% of theory) of the title compound were obtained.

LC-MS (Method 1): $R_t$=0.68 min; MS (ESIpos): m/z=329 [M+H]$^+$

Intermediate 366

(5S)-3-Oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylic Acid

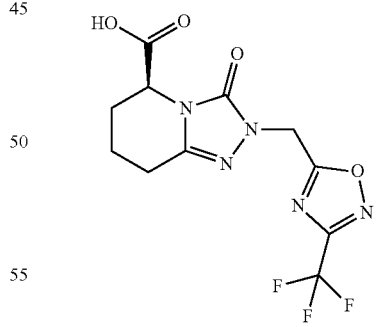

tert-Butyl (5S)-3-oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylate (322 mg, 826 μmol) was dissolved in dichloromethane (7.0 ml), and trifluoroacetic acid (1.3 ml, 17 mmol) was added at room temperature. After the reaction mixture had been stirred at room temperature overnight, the solvent was removed under reduced pressure. 344 mg (82% purity, >100% of theory) of the title compound were obtained.

Intermediate 367

(5S)-2-[(3-Chloropyridin-2-yl)methyl]-3-oxo-2,3,5,6,7,8-hexahydro[1,2,4]triazolo[4,3-a]pyridine-5-carboxylic Acid

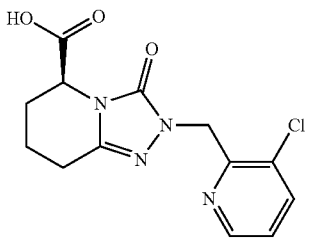 [SMILES: O=C(O)[C@@H]1CCCc2nn(Cc3ncccc3Cl)c(=O)n21]

tert-Butyl (5S)-2-[(3-chloropyridin-2-yl)methyl]-3-oxo-2,3,5,6,7,8-hexahydro[1,2,4]triazolo[4,3-a]pyridine-5-carboxylate (268 mg, 735 μmol) was dissolved in dichloromethane (6.0 ml), and trifluoroacetic acid (1.1 ml, 15 mmol) was added at room temperature. After the reaction mixture had been stirred at room temperature overnight, the solvent was removed under reduced pressure. 409 mg (>100% of theory) of the title compound were obtained.

LC-MS (Method 3): $R_t$=0.79 min; MS (ESIpos): m/z=309 [M+H]$^+$ $^1$H-NMR (400 MHz, DMSO-d6) δ[ppm]: −0.008 (2.47), 0.008 (2.02), 1.111 (1.99), 1.228 (0.41), 1.415 (2.49), 1.513 (1.50), 1.535 (7.93), 1.551 (1.72), 1.564 (1.47), 1.577 (1.09), 1.592 (0.52), 1.787 (1.50), 1.798 (2.36), 1.809 (2.25), 1.820 (2.06), 1.831 (1.96), 1.844 (1.39), 2.074 (3.75), 2.086 (6.76), 2.097 (6.56), 2.110 (3.53), 2.368 (0.55), 2.482 (1.65), 2.524 (4.66), 2.565 (2.75), 2.588 (2.68), 2.600 (4.31), 2.612 (2.90), 2.631 (1.42), 2.641 (1.91), 2.654 (1.08), 2.672 (0.46), 2.712 (0.64), 4.458 (4.22), 4.470 (8.12), 4.482 (4.10), 4.993 (3.18), 5.033 (15.85), 5.050 (16.00), 5.090 (3.22), 5.642 (0.42), 6.764 (0.71), 7.378 (5.76), 7.389 (5.97), 7.398 (6.17), 7.410 (6.32), 7.926 (6.28), 7.929 (6.34), 7.946 (6.01), 7.949 (5.82), 8.468 (6.23), 8.472 (6.05), 8.480 (6.31), 8.483 (5.78).

Intermediate 368

(5S)-2-[(3,5-Difluoropyridin-2-yl)methyl]-3-oxo-2,3,5,6,7,8-hexahydro[1,2,4]triazolo[4,3-a]pyridine-5-carboxylic Acid

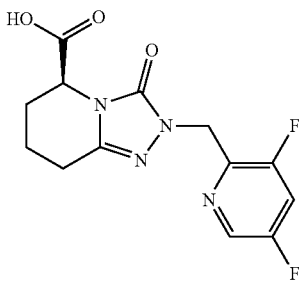 [SMILES: O=C(O)[C@@H]1CCCc2nn(Cc3ncc(F)cc3F)c(=O)n21]

tert-Butyl (5S)-2-[(3,5-difluoropyridin-2-yl)methyl]-3-oxo-2,3,5,6,7,8-hexahydro[1,2,4]triazolo[4,3-a]pyridine-5-carboxylate (90.1 mg, 246 μmol) was dissolved in dichloromethane (2.0 ml), and trifluoroacetic acid (380 μl, 4.9 mmol) was added at room temperature. After the reaction mixture had been stirred at room temperature overnight, the solvent was removed under reduced pressure. 103 mg (90% purity, >100% of theory) of the title compound were obtained.

LC-MS (Method 1): $R_t$=0.64 min; MS (ESIpos): m/z=311 [M+H]$^+$

Intermediate 369

(5S)-3-Oxo-2-{[6-(trifluoromethyl)pyridin-2-yl]methyl}-2,3,5,6,7,8-hexahydro[1,2,4]triazolo[4,3-a]pyridine-5-carboxylic Acid

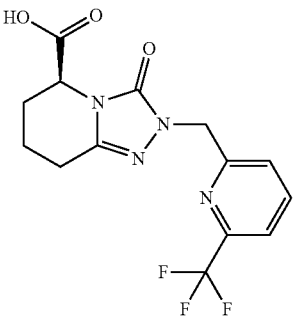 [SMILES: O=C(O)[C@@H]1CCCc2nn(Cc3cccc(C(F)(F)F)n3)c(=O)n21]

tert-Butyl (5S)-3-oxo-2-{[6-(trifluoromethyl)pyridin-2-yl]methyl}-2,3,5,6,7,8-hexahydro[1,2,4]triazolo[4,3-a]pyridine-5-carboxylate (256 mg, 89% purity, 571 μmol) was dissolved in dichloromethane (5.0 ml), and trifluoroacetic acid (880 μl, 11 mmol) was added at room temperature. After the reaction mixture had been stirred at room temperature overnight, the solvent was removed under reduced pressure. 256 mg (85% purity, >100% of theory) of the title compound were obtained.

LC-MS (Method 4): $R_t$=0.61 min; MS (ESIpos): m/z=343 [M+H]$^+$

Intermediate 370

(5S)-3-Oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylic Acid

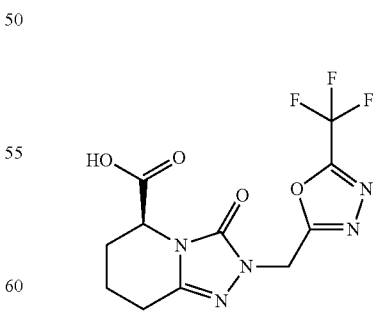

tert-Butyl (5S)-3-oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylate (735 mg, 66% purity, 1.25 mmol) was dissolved in dichloromethane (10 ml), and trifluoroacetic acid (1.9 ml, 25 mmol) was added at room temperature. After the reaction mixture had been stirred at room temperature for 4 days, the solvent was removed under reduced pressure. 415 mg (80% purity, 80% of theory) of the title compound were obtained.

LC-MS (Method 1): $R_t$=0.71 min; MS (ESIpos): m/z=334 [M+H]$^+$ Intermediate 371

(5S)-2-{[1-Ethyl-3-(trifluoromethyl)-1H-pyrazol-5-yl]methyl}-3-oxo-2,3,5,6,7,8-hexahydro[1,2,4]triazolo[4,3-a]pyridine-5-carboxylic Acid

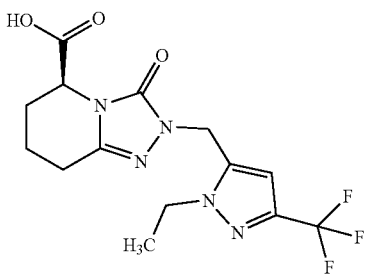 [SMILES: CCn1nc(C(F)(F)F)cc1Cn1nc2n(c1=O)[C@H](C(=O)O)CCC2]

tert-Butyl (5S)-2-{[1-ethyl-3-(trifluoromethyl)-1H-pyrazol-5-yl]methyl}-3-oxo-2,3,5,6,7,8-hexahydro[1,2,4]triazolo[4,3-a]pyridine-5-carboxylate (283 mg, 89% purity, 606 µmol) was dissolved in dichloromethane (5.0 ml), and trifluoroacetic acid (930 µl, 12 mmol) was added at room temperature. After the reaction mixture had been stirred at room temperature overnight, the solvent was removed under reduced pressure. 400 mg (>100% of theory) of the title compound were obtained.

LC-MS (Method 4): $R_t$=0.68 min; MS (ESIpos): m/z=360 [M+H]$^+$

Intermediate 372

(5S)-2-[(5-Chloropyridin-2-yl)methyl]-3-oxo-2,3,5,6,7,8-hexahydro[1,2,4]triazolo[4,3-a]pyridine-5-carboxylic Acid

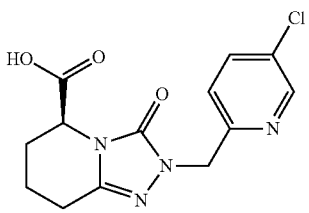 [SMILES: O=C(O)[C@@H]1CCCc2nn(Cc3ccc(Cl)cn3)c(=O)n21]

tert-Butyl (5S)-2-[(5-chloropyridin-2-yl)methyl]-3-oxo-2,3,5,6,7,8-hexahydro[1,2,4]triazolo[4,3-a]pyridine-5-carboxylate (450 mg, 1.23 mmol) was dissolved in dichloromethane (10 ml), and trifluoroacetic acid (1.9 ml, 25 mmol) was added at room temperature. After the reaction mixture had been stirred at room temperature overnight, the solvent was removed under reduced pressure. 380 mg (66% purity, 66% of theory) of the title compound were obtained.

LC-MS (Method 4): $R_t$=0.51 min; MS (ESIpos): m/z=309 [M+H]$^+$

Intermediate 373

(5S)-3-Oxo-2-{[2-(trifluoromethyl)-1,3-thiazol-4-yl]methyl}-2,3,5,6,7,8-hexahydro[1,2,4]triazolo[4,3-a]pyridine-5-carboxylic Acid

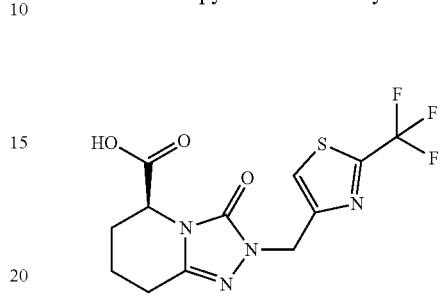

tert-Butyl (5S)-3-oxo-2-{[2-(trifluoromethyl)-1,3-thiazol-4-yl]methyl}-2,3,5,6,7,8-hexahydro[1,2,4]triazolo[4,3-a]pyridine-5-carboxylate (500 mg, 1.24 mmol) was dissolved in dichloromethane (8.0 ml), and trifluoroacetic acid (1.9 ml, 25 mmol) was added at room temperature. After the reaction mixture had been stirred at room temperature overnight, the solvent was removed under reduced pressure. 430 mg (73% purity, 73% of theory) of the title compound were obtained.

LC-MS (Method 4): $R_t$=0.62 min; MS (ESIpos): m/z=349 [M+H]$^+$

Intermediate 374

(5S)-2-{[1-Methyl-5-(trifluoromethyl)-1H-pyrazol-3-yl]methyl}-3-oxo-2,3,5,6,7,8-hexahydro[1,2,4]triazolo[4,3-a]pyridine-5-carboxylic Acid

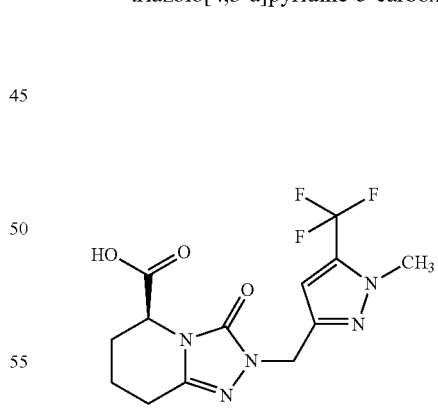

tert-Butyl (5S)-2-{[1-methyl-5-(trifluoromethyl)-1H-pyrazol-3-yl]methyl}-3-oxo-2,3,5,6,7,8-hexahydro[1,2,4]triazolo[4,3-a]pyridine-5-carboxylate (92.0 mg, 229 µmol) was dissolved in dichloromethane (2.0 ml), and trifluoroacetic acid (350 µl, 4.6 mmol) was added at room temperature. After the reaction mixture had been stirred at room temperature for 72 hours, the solvent was removed under reduced pressure. 79.0 mg (70% purity, 100% of theory) of the title compound were obtained.

Intermediate 375

(5S)-2-{[1-Benzyl-5-(trifluoromethyl)-1H-pyrazol-3-yl]methyl}-3-oxo-2,3,5,6,7,8-hexahydro[1,2,4]triazolo[4,3-a]pyridine-5-carboxylic Acid

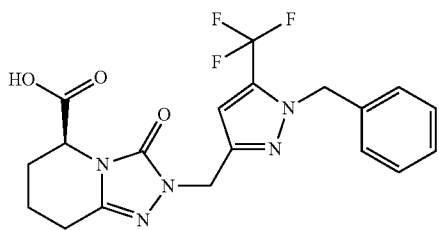 [SMILES: O=C(O)[C@@H]1CCCc2nn(Cc3cc(C(F)(F)F)n(Cc4ccccc4)n3)c(=O)n21]

tert-Butyl (5S)-2-{[1-benzyl-5-(trifluoromethyl)-1H-pyrazol-3-yl]methyl}-3-oxo-2,3,5,6,7,8-hexahydro[1,2,4]triazolo[4,3-a]pyridine-5-carboxylate (781 mg, 75% purity, 1.23 mmol) was dissolved in dichloromethane (10 ml), and trifluoroacetic acid (1.9 ml, 25 mmol) was added at room temperature. After the reaction mixture had been stirred at room temperature for 72 hours, trifluoroacetic acid (1.0 ml, 12.4 mmol) was added again and the reaction mixture was stirred at 40° C. for 2 hours. The solvent was then removed under reduced pressure. 976 mg (70% purity, >100% of theory) of the title compound were obtained.

LC-MS (Method 1): $R_t$=1.11 min; MS (ESIpos): m/z=422 [M+H]

Intermediate 376

(5S)-2-[(5-Bromopyridin-2-yl)methyl]-3-oxo-2,3,5,6,7,8-hexahydro[1,2,4]triazolo[4,3-a]pyridine-5-carboxylic Acid

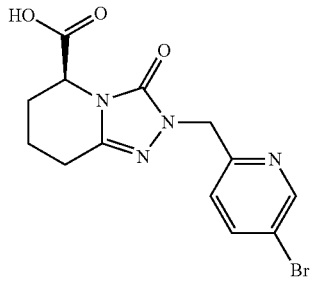 [SMILES: O=C(O)[C@@H]1CCCc2nn(Cc3ccc(Br)cn3)c(=O)n21]

tert-Butyl (5S)-2-[(5-bromopyridin-2-yl)methyl]-3-oxo-2,3,5,6,7,8-hexahydro[1,2,4]triazolo[4,3-a]pyridine-5-carboxylate (580 mg, 1.42 mmol) was dissolved in dichloromethane (91 al), and trifluoroacetic acid (2.2 ml, 28 mmol) was added at room temperature. After the reaction mixture had been stirred at room temperature overnight, the solvent was removed under reduced pressure. 1.01 g (>100% of theory) of the title compound were obtained.

LC-MS (Method 3): $R_t$=0.90 min; MS (ESIpos): m/z=353 [M+H]$^+$ $^1$H-NMR (400 MHz, DMSO-d6) δ[ppm]: −0.149 (1.03), 0.146 (1.10), 1.110 (0.61), 1.176 (0.61), 1.192 (0.61), 1.227 (0.49), 1.409 (2.10), 1.535 (2.52), 1.819 (2.50), 1.830 (2.38), 1.841 (2.08), 1.852 (2.01), 1.988 (0.79), 2.098 (6.34), 2.107 (6.48), 2.328 (1.12), 2.367 (0.79), 2.564 (3.17), 2.577 (3.13), 2.591 (2.47), 2.619 (2.64), 2.630 (4.34), 2.641 (2.94), 2.661 (1.68), 2.671 (2.99), 2.711 (0.82), 4.473 (4.15), 4.485 (8.00), 4.498 (4.10), 4.528 (0.72), 4.769 (4.73), 4.867 (2.29), 4.908 (15.70), 4.919 (16.00), 4.960 (2.43), 5.224 (0.98), 5.831 (1.91), 7.162 (8.61), 7.183 (9.17), 7.532 (0.89), 7.552 (0.98), 8.024 (5.67), 8.030 (5.78), 8.045 (5.62), 8.051 (5.67), 8.102 (0.70), 8.117 (0.65), 8.654 (7.14), 8.659 (7.02), 8.697 (0.63).

Intermediate 377

(5S)-2-[(5-Bromopyridin-3-yl)methyl]-3-oxo-2,3,5,6,7,8-hexahydro[1,2,4]triazolo[4,3-a]pyridine-5-carboxylic Acid

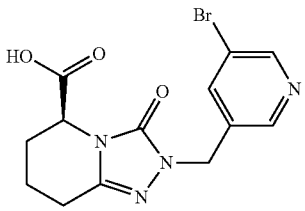 [SMILES: O=C(O)[C@@H]1CCCc2nn(Cc3cncc(Br)c3)c(=O)n21]

tert-Butyl (5S)-2-[(5-bromopyridin-3-yl)methyl]-3-oxo-2,3,5,6,7,8-hexahydro[1,2,4]triazolo[4,3-a]pyridine-5-carboxylate (146 mg, 357 µmol) was dissolved in dichloromethane (2.9 ml), and trifluoroacetic acid (550 µl, 7.1 mmol) was added at room temperature. After the reaction mixture had been stirred at room temperature overnight, the solvent was removed under reduced pressure. 199 mg (89% purity, >100% of theory) of the title compound were obtained.

LC-MS (Method 4): $R_t$=0.52 min; MS (ESIpos): m/z=353 [M+H]$^+$ $^1$H-NMR (400 MHz, DMSO-d6) δ[ppm]: −0.008 (2.87), 0.008 (2.73), 1.111 (0.85), 1.226 (0.54), 1.244 (2.70), 1.260 (2.67), 1.274 (1.67), 1.391 (9.28), 1.509 (1.14), 1.522 (1.13), 1.535 (3.08), 1.815 (1.43), 1.825 (1.40), 1.836 (1.22), 1.847 (1.20), 2.093 (3.51), 2.100 (3.75), 2.109 (3.48), 2.121 (1.86), 2.328 (0.61), 2.524 (2.13), 2.568 (1.92), 2.581 (1.92), 2.595 (1.53), 2.627 (1.61), 2.639 (2.57), 2.650 (1.73), 2.670 (1.47), 2.679 (1.38), 2.692 (0.70), 4.479 (2.53), 4.491 (4.87), 4.503 (2.51), 4.893 (0.40), 4.934 (16.00), 4.974 (0.48), 5.839 (1.06), 7.703 (0.95), 7.893 (3.04), 7.897 (5.36), 7.903 (3.24), 7.919 (0.56), 8.465 (5.32), 8.469 (5.56), 8.643 (4.66), 8.649 (4.90), 9.090 (0.42).

Intermediate 378

(5S)-2-[2-(4-Methylphenyl)-2-oxoethyl]-3-oxo-2,3,5,6,7,8-hexahydro[1,2,4]triazolo[4,3-a]pyridine-5-carboxylic Acid

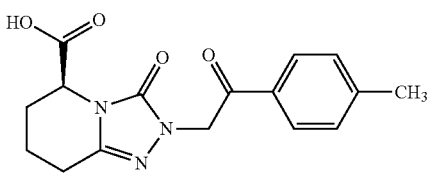 [SMILES: Cc1ccc(C(=O)Cn2nc3n(c2=O)[C@H](C(=O)O)CCC3)cc1]

tert-Butyl (5S)-2-[2-(4-methylphenyl)-2-oxoethyl]-3-oxo-2,3,5,6,7,8-hexahydro[1,2,4]triazolo[4,3-a]pyridine-5-carboxylate (226 mg, 99% purity, 603 µmol) was dissolved in dichloromethane (9.0 ml), and trifluoroacetic acid (930 µl, 12 mmol) was added at room temperature. After the reaction mixture had been stirred at room temperature overnight, the solvent was removed under reduced pressure. 190 mg (100% of theory) of the title compound were obtained.

LC-MS (Method 1): $R_t$=0.86 min; MS (ESIpos): m/z=316 [M+H]$^+$ $^1$H-NMR (400 MHz, DMSO-d6) δ[ppm]: 0.008 (2.13), 1.110 (1.66), 1.419 (0.45), 1.535 (2.08), 1.566 (0.73), 1.577 (0.67), 1.828 (0.81), 1.861 (0.67), 1.988 (0.60), 2.098 (1.30), 2.109 (2.54), 2.121 (2.51), 2.328 (0.50), 2.366 (0.49), 2.398 (16.00), 2.580 (1.52), 2.594 (1.27), 2.607 (1.36), 2.621 (1.07), 2.635 (1.10), 2.647 (1.65), 2.658 (1.19), 2.687 (0.71), 2.710 (0.63), 4.466 (1.43), 4.480 (2.76), 4.491 (1.53), 5.221 (11.53), 7.359 (4.46), 7.380 (5.04), 7.912 (5.54), 7.933 (5.39).

Intermediate 379

(5RS,8RS)-8-Methyl-2-(4-methylbenzyl)-3-oxo-2,3,5,6,7,8-hexahydro[1,2,4]triazolo[4,3-a]pyridine-5-carboxylic Acid (Diastereomer Mixture; 4 Isomers)

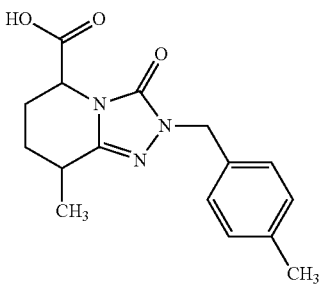 [SMILES: Cc1ccc(Cn2nc3n(c2=O)C(C(=O)O)CCC3C)cc1]

tert-Butyl (5RS,8RS)-8-methyl-2-(4-methylbenzyl)-3-oxo-2,3,5,6,7,8-hexahydro[1,2,4]triazolo[4,3-a]pyridine-5-carboxylate (diastereomer mixture; 4 isomers) (39.5 mg, 111 µmol) was dissolved in dichloromethane (2.0 ml), and trifluoroacetic acid (2.0 ml, 26 mmol) was added at room temperature. After the reaction mixture had been stirred at room temperature overnight, the solvent was removed under reduced pressure. The residue was admixed with water and dichloromethane. The organic phase was removed and the aqueous phase was extracted three times with dichloromethane. The combined organic phases were washed with saturated aqueous sodium chloride solution, dried over sodium sulphate and filtered, and the filtrate was concentrated. 27.2 mg (82% of theory) of the title compound were obtained.

LC-MS (Method 3): $R_t$=1.33 min; MS (ESIpos): m/z=302 [M+H]$^+$ $^1$H-NMR (400 MHz, DMSO-d6) δ [ppm]: −0.008 (4.03), 0.008 (2.37), 0.854 (0.43), 1.162 (6.13), 1.179 (6.09), 1.194 (1.00), 1.200 (0.78), 1.210 (0.80), 1.235 (3.03), 1.259 (1.66), 1.298 (1.05), 1.878 (0.53), 1.888 (0.41), 1.900 (0.43), 2.074 (0.43), 2.110 (0.53), 2.141 (1.26), 2.148 (1.20), 2.245 (0.73), 2.271 (11.10), 2.327 (0.46), 2.518 (2.94), 2.523 (2.66), 2.669 (0.61), 2.674 (0.46), 2.685 (0.45), 2.700 (0.64), 2.709 (0.70), 2.716 (0.77), 2.731 (0.58), 4.471 (0.92), 4.478 (1.27), 4.487 (0.82), 4.492 (0.88), 4.739 (0.98), 4.778 (2.39), 4.825 (2.35), 4.864 (1.01), 5.754 (2.62), 7.105 (0.61), 7.127 (16.00), 7.145 (0.72).

Intermediate 380

(5S)-2-(Cyclopropylmethyl)-3-oxo-2,3,5,6,7,8-hexahydro[1,2,4]triazolo[4,3-a]pyridine-5-carboxylic Acid

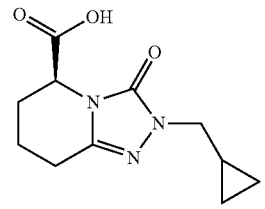 [SMILES: O=C(O)[C@@H]1CCCc2nn(CC3CC3)c(=O)n21]

tert-Butyl (5S)-2-(cyclopropylmethyl)-3-oxo-2,3,5,6,7,8-hexahydro[1,2,4]triazolo[4,3-a]pyridine-5-carboxylate (174 mg, 593 µmol) was dissolved in dichloromethane (6.0 ml), and trifluoroacetic acid (3.0 ml, 39 mmol) was added while cooling with ice. After the reaction mixture had been stirred at room temperature overnight, the solvent was removed under reduced pressure. 231 mg (>100% of theory) of the title compound were obtained.

LC-MS (Method 3): $R_t$=0.73 min; MS (ESIpos): m/z=238 [M+H]$^+$ $^1$H-NMR (400 MHz, DMSO-d6) δ [ppm]: 0.008 (2.18), 0.262 (1.91), 0.274 (8.08), 0.285 (8.53), 0.297 (2.52), 0.313 (0.57), 0.427 (1.63), 0.438 (8.30), 0.442 (7.40), 0.458 (8.82), 0.475 (1.47), 0.488 (0.45), 1.034 (0.65), 1.039 (0.94), 1.051 (1.82), 1.059 (1.78), 1.071 (2.90), 1.083 (1.70), 1.088 (1.77), 1.101 (0.92), 1.111 (3.14), 1.403 (1.07), 1.493 (0.71), 1.513 (1.50), 1.527 (1.76), 1.540 (1.95), 1.550 (1.73), 1.564 (1.44), 1.578 (1.34), 1.590 (0.60), 1.806 (2.26), 1.817 (2.13), 1.828 (2.01), 1.839 (1.90), 1.852 (1.35), 2.060 (3.96), 2.072 (7.12), 2.083 (6.87), 2.097 (3.54), 2.105 (1.98), 2.558 (4.03), 2.572 (2.98), 2.585 (3.06), 2.599 (2.54), 2.628 (2.55), 2.639 (4.08), 2.651 (2.76), 2.670 (1.62), 2.681 (1.95), 2.693 (1.10), 3.482 (16.00), 3.499 (15.83), 4.377 (0.51), 4.409 (3.82), 4.422 (7.29), 4.434 (3.82), 11.357 (0.41).

Intermediate 381

(5S)-2-[(E)-2-(4-Fluorophenyl)vinyl]-3-oxo-2,3,5,6,7,8-hexahydro[1,2,4]triazolo[4,3-a]pyridine-5-carboxylic Acid

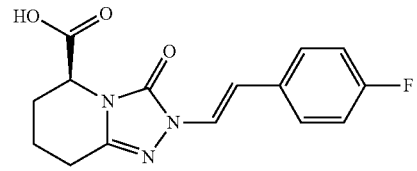 [SMILES: O=C(O)[C@@H]1CCCc2nn(/C=C/c3ccc(F)cc3)c(=O)n21]

tert-Butyl (5S)-2-[(E)-2-(4-fluorophenyl)vinyl]-3-oxo-2,3,5,6,7,8-hexahydro[1,2,4]triazolo[4,3-a]pyridine-5-carboxylate (150 mg, 417 µmol) was dissolved in dichloromethane (5.0 ml), and trifluoroacetic acid (500 µl, 6.5 mmol) was added at room temperature. After the reaction mixture had been stirred at room temperature overnight, the solvent was removed under reduced pressure. 198 mg (>100% of theory) of the title compound were obtained.

LC-MS (Method 3): $R_t$=1.37 min; MS (ESIpos): m/z=304 [M+H]$^+$ $^1$H-NMR (400 MHz, DMSO-d6) δ[ppm]: −0.149 (0.58), −0.008 (5.47), 0.008 (4.55), 0.146 (0.64), 1.030 (0.46), 1.045 (0.49), 1.106 (2.56), 1.110 (3.05), 1.176 (0.43), 1.235 (0.52), 1.311 (2.50), 1.326 (2.02), 1.338 (2.38), 1.423 (1.31), 1.505 (0.82), 1.535 (12.52), 1.554 (1.92), 1.566 (1.80), 1.744 (0.46), 1.865 (2.23), 1.875 (2.20), 1.887 (1.98), 1.897 (1.86), 1.909 (1.40), 2.111 (3.66), 2.123 (6.38), 2.133 (6.11), 2.328 (1.16), 2.367 (1.25), 2.524 (3.18), 2.625 (1.16), 2.640 (1.50), 2.652 (1.25), 2.668 (4.21), 2.683 (2.81), 2.695 (2.90), 2.710 (3.30), 2.739 (2.38), 2.751 (3.97), 2.762 (2.63), 2.782 (1.28), 2.793 (1.83), 2.806 (0.95), 4.114 (3.30), 4.525 (5.50), 4.538 (9.65), 4.550 (5.16), 5.754 (1.40), 6.751 (8.85), 6.788 (9.83), 7.121 (7.97), 7.143 (16.00), 7.166 (8.61), 7.384 (11.48), 7.420 (10.23), 7.542 (8.09), 7.556 (9.16), 7.564 (8.52), 7.578 (7.27).

Intermediate 382

(5S)-2-{[6-(Difluoromethyl)pyridin-3-yl]methyl}-3-oxo-2,3,5,6,7,8-hexahydro[1,2,4]triazolo[4,3-a]pyridine-5-carboxylic Acid

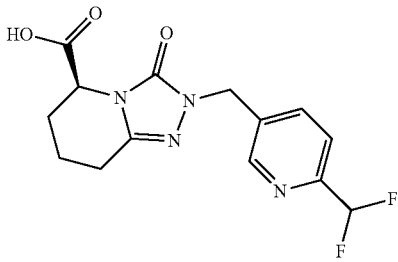 [SMILES: O=C(O)[C@@H]1CCCc2nn(Cc3ccc(C(F)F)nc3)c(=O)n21]

tert-Butyl (5S)-2-{[6-(difluoromethyl)pyridin-3-yl]methyl}-3-oxo-2,3,5,6,7,8-hexahydro[1,2,4]triazolo[4,3-a]pyridine-5-carboxylate (200 mg, 86% purity, 452 μmol) was dissolved in dichloromethane (4.5 ml), and trifluoroacetic acid (2.0 ml, 26 mmol) was added at room temperature. After the reaction mixture had been stirred at room temperature for 3.5 hours, the solvent was removed under reduced pressure. 615 mg (25% purity, >100% of theory) of the title compound were obtained.

LC-MS (Method 3): $R_t$=0.87 min; MS (ESIpos): m/z=325 [M+H]$^+$

Intermediate 383

(5S)-2-(4-Bromobenzyl)-3-oxo-2,3,5,6,7,8-hexahydro[1,2,4]triazolo[4,3-a]pyridine-5-carboxylic Acid

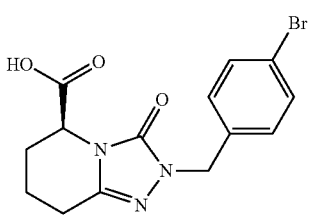 [SMILES: O=C(O)[C@@H]1CCCc2nn(Cc3ccc(Br)cc3)c(=O)n21]

tert-Butyl (5S)-2-(4-bromobenzyl)-3-oxo-2,3,5,6,7,8-hexahydro[1,2,4]triazolo[4,3-a]pyridine-5-carboxylate (201 mg, 74% purity, 365 μmol) was dissolved in dichloromethane (3.7 ml), and trifluoroacetic acid (500 μl, 6.5 mmol) was added at room temperature. After the reaction mixture had been stirred at room temperature overnight, the solvent was removed under reduced pressure. 268 mg (47% purity, 98% of theory) of the title compound were obtained.

LC-MS (Method 4): $R_t$=0.69 min; MS (ESIpos): m/z=352 [M+H]$^+$

Intermediate 384

(5S)-2-(3-Bromobenzyl)-3-oxo-2,3,5,6,7,8-hexahydro[1,2,4]triazolo[4,3-a]pyridine-5-carboxylic Acid

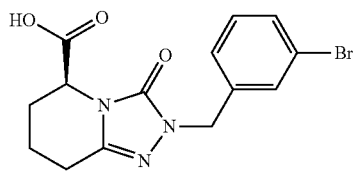 [SMILES: O=C(O)[C@@H]1CCCc2nn(Cc3cccc(Br)c3)c(=O)n21]

tert-Butyl (5S)-2-(3-bromobenzyl)-3-oxo-2,3,5,6,7,8-hexahydro[1,2,4]triazolo[4,3-a]pyridine-5-carboxylate (256 mg, 590 μmol) was dissolved in dichloromethane (4.5 ml), and trifluoroacetic acid (500 μl, 6.5 mmol) was added at room temperature. After the reaction mixture had been stirred at room temperature overnight, the solvent was removed under reduced pressure. 346 mg (59% purity, 98% of theory) of the title compound were obtained.

LC-MS (Method 4): $R_t$=0.69 min; MS (ESIpos): m/z=352 [M+H]$^+$

Intermediate 385

(5S)-2-(4-Bromo-2-fluorobenzyl)-3-oxo-2,3,5,6,7,8-hexahydro[1,2,4]triazolo[4,3-a]pyridine-5-carboxylic Acid

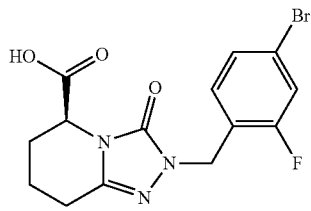 [SMILES: O=C(O)[C@@H]1CCCc2nn(Cc3ccc(Br)cc3F)c(=O)n21]

tert-Butyl (5S)-2-(4-bromo-2-fluorobenzyl)-3-oxo-2,3,5,6,7,8-hexahydro[1,2,4]triazolo[4,3-a]pyridine-5-carboxylate (135 mg, 317 μmol) was dissolved in dichloromethane (3.0 ml), and trifluoroacetic acid (300 μl, 3.9 mmol) was added at room temperature. After the reaction mixture had been stirred at room temperature overnight, the solvent was removed under reduced pressure. 174 mg (>100% of theory) of the title compound were obtained.

LC-MS (Method 3): $R_t$=1.31 min; MS (ESIpos): m/z=370 [M+H]$^+$

Intermediate 386

(5S)-3-Oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylic Acid (Isomer 1)

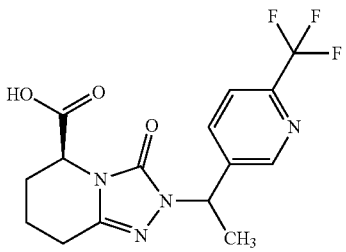 [SMILES: CC(c1ccc(C(F)(F)F)nc1)n1nc2n(c1=O)[C@H](C(=O)O)CCC2]

tert-Butyl (5S)-3-oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylate (isomer 1) (97.0 mg, 235 µmol) was dissolved in dichloromethane (2.0 ml), and trifluoroacetic acid (200 µl, 2.6 mmol) was added at room temperature. After the reaction mixture had been stirred at room temperature overnight, the solvent was removed under reduced pressure. 154 mg (>100% of theory) of the title compound were obtained.

LC-MS (Method 3): $R_t$=1.21 min; MS (ESIpos): m/z=357 [M+H]$^+$

Intermediate 387

(5S)-3-Oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylic Acid (Isomer 2)

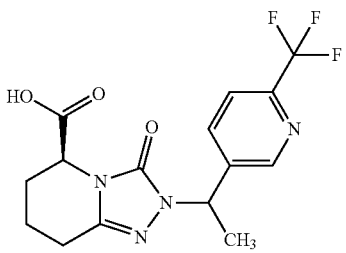

tert-Butyl (5S)-3-oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylate (isomer 2) (86.0 mg, 209 µmol) was dissolved in dichloromethane (2.0 ml), and trifluoroacetic acid (200 µl, 2.6 mmol) was added at room temperature. After the reaction mixture had been stirred at room temperature overnight, the solvent was removed under reduced pressure. 133 mg (>100% of theory) of the title compound were obtained.

LC-MS (Method 3): $R_t$=1.19 min; MS (ESIpos): m/z=357 [M+H]$^+$

Intermediate 388

(5S)-3-Oxo-2-{[cis/trans-4-(trifluoromethyl)cyclohexyl]methyl}-2,3,5,6,7,8-hexahydro[1,2,4]triazolo[4,3-a]pyridine-5-carboxylic Acid (Diastereomer Mixture; 2 Isomers)

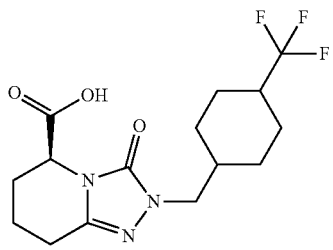 [SMILES: O=C(O)[C@@H]1CCCc2nn(CC3CCC(C(F)(F)F)CC3)c(=O)n21]

tert-Butyl (5S)-3-oxo-2-{[cis/trans-4-(trifluoromethyl)cyclohexyl]methyl}-2,3,5,6,7,8-hexahydro[1,2,4]triazolo[4,3-a]pyridine-5-carboxylate (diastereomer mixture, 2 isomers) (112 mg, 264 µmol) was dissolved in dichloromethane (5.0 ml), and trifluoroacetic acid (500 µl, 6.5 mmol) was added at room temperature. After the reaction mixture had been stirred at room temperature overnight, the solvent was removed under reduced pressure. 153 mg (>100% of theory) of the title compound were obtained.

LC-MS (Method 3): $R_t$=1.41 min; MS (ESIpos): m/z=348 [M+H]$^+$ $^1$H-NMR (400 MHz, DMSO-d6) δ[ppm]: −0.150 (1.53), −0.008 (16.00), 0.008 (13.04), 0.147 (1.83), 1.030 (2.72), 1.110 (9.48), 1.191 (2.96), 1.249 (3.95), 1.395 (3.01), 1.491 (10.32), 1.535 (8.54), 1.685 (3.56), 1.828 (5.53), 2.079 (9.98), 2.328 (2.17), 2.366 (1.78), 2.524 (6.22), 2.569 (4.20), 2.583 (3.11), 2.631 (5.33), 2.670 (3.90), 3.457 (4.64), 3.474 (4.79), 3.609 (5.04), 3.622 (5.68), 3.642 (4.54), 4.424 (8.54), 4.436 (8.69), 4.448 (4.00), 4.970 (3.75).

Intermediate 389

(5S)-2-{[3-Fluoro-2-(trifluoromethyl)pyridin-4-yl]methyl}-3-oxo-2,5,6,7-tetrahydro-3H-pyrrolo[2,1-c][1,2,4]triazole-5-carboxylic Acid

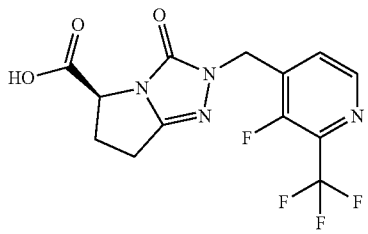 [SMILES: O=C(O)[C@@H]1CCc2nn(Cc3ccnc(C(F)(F)F)c3F)c(=O)n21]

Methyl (5S)-2-{[3-fluoro-2-(trifluoromethyl)pyridin-4-yl]methyl}-3-oxo-2,5,6,7-tetrahydro-3H-pyrrolo[2,1-c][1,2,4]triazole-5-carboxylate (243 mg, 75% purity, 506 µmol) was initially charged in THF (2.5 ml) and water (2.5 ml), and lithium hydroxide (60.6 mg, 2.53 mmol) was added. After stirring for 90 min, the reaction mixture was admixed at room temperature with 1 N aqueous hydrochloric acid. The solvent was concentrated, and the aqueous phase was extracted three times with ethyl acetate. The combined organic phases were dried over sodium sulphate and filtered, and the filtrate was concentrated. 264 mg (>100% of theory) of the title compound were obtained.

LC-MS (Method 4): $R_t$=0.60 min; MS (ESIpos): m/z=347 [M+H]

Intermediate 390

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

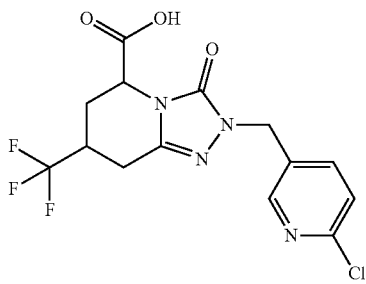 [SMILES: O=C(O)C1CC(C(F)(F)F)Cc2nn(Cc3ccc(Cl)nc3)c(=O)n21]

Ethyl (5RS,7RS)-2-[(6-chloropyridin-3-yl)methyl]-3-oxo-7-(trifluoromethyl)-2,3,5,6,7,8-hexahydro[1,2,4]triazolo[4,3-a]pyridine-5-carboxylate (diastereomer mixture; 4 isomers) (500 mg, 1.24 mmol) was initially charged in THF (10 ml), and sodium ethoxide (850 μl, 21% in ethanol, 2.3 mmol) was added. The reaction mixture was stirred at 0° C. for 15 min and overnight at room temperature. Water was added, and the mixture was acidified with 1 N aqueous hydrochloric acid. The aqueous phase was extracted with ethyl acetate and the organic phase was dried over sodium sulphate and filtered, and the filtrate was concentrated. 479 mg (>100% of theory) of the title compound were obtained.

LC-MS (Method 4): $R_t$=0.64 min; MS (ESIpos): m/z=377 [M+H]

$^1$H-NMR (400 MHz, DMSO-d6) δ [ppm]: 1.094 (0.28), 1.157 (2.06), 1.170 (1.54), 1.175 (4.26), 1.193 (2.09), 1.240 (0.19), 1.271 (0.24), 1.786 (0.19), 1.817 (0.21), 1.908 (2.01), 1.988 (7.50), 2.224 (0.42), 2.240 (0.55), 2.259 (1.12), 2.275 (1.16), 2.288 (1.30), 2.304 (1.30), 2.319 (2.92), 2.352 (1.02), 2.667 (0.88), 2.696 (3.39), 2.720 (3.41), 2.749 (0.95), 2.874 (0.20), 2.951 (0.48), 2.977 (2.16), 3.005 (1.87), 3.034 (0.37), 4.002 (0.61), 4.021 (1.81), 4.038 (1.78), 4.056 (0.60), 4.394 (0.20), 4.409 (0.23), 4.421 (0.22), 4.437 (0.19), 4.689 (2.91), 4.700 (2.65), 4.921 (1.26), 4.948 (16.00), 7.507 (4.76), 7.515 (0.69), 7.527 (5.86), 7.715 (3.26), 7.721 (3.37), 7.735 (3.05), 7.742 (3.13), 7.756 (0.28), 8.317 (4.42), 8.322 (4.42), 8.336 (0.48), 13.683 (0.28).

Intermediate 391

(5RS,7RS)-3-Oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture, 4 Isomers)

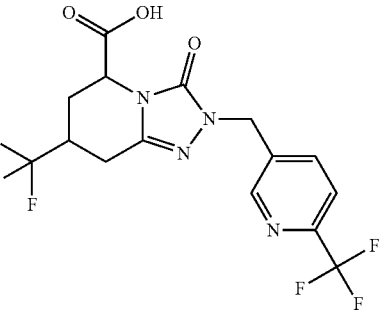

Ethyl (5RS,7RS)-3-oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylate (diastereomer mixture; 4 isomers) (480 mg, 1.10 mmol) was initially charged in THF (20 ml), and sodium ethoxide (760 μl, 21% in ethanol, 2.0 mmol) was added. The reaction mixture was stirred at 0° C. for 20 min and overnight at room temperature. Ice-water was added, and the mixture was acidified with 1 N aqueous hydrochloric acid. The aqueous phase was extracted with ethyl acetate and the organic phase was dried over sodium sulphate and filtered, and the filtrate was concentrated. 577 mg (88% purity, >100% of theory) of the title compound were obtained.

LC-MS (Method 4): $R_t$=0.73 min; MS (ESIpos): m/z=411 [M+H]$^+$ $^1$H-NMR (400 MHz, DMSO-d6) δ [ppm]: −0.008 (0.57), 0.008 (0.56), 1.157 (4.39), 1.169 (1.76), 1.175 (9.00), 1.192 (4.46), 1.908 (1.38), 1.988 (16.00), 2.266 (0.42), 2.283 (0.44), 2.296 (0.49), 2.311 (0.46), 2.328 (1.28), 2.366 (0.50), 2.524 (0.59), 2.675 (0.40), 2.706 (1.29), 2.729 (1.28), 2.986 (0.84), 3.014 (0.71), 4.003 (1.29), 4.021 (3.80), 4.038 (3.75), 4.056 (1.23), 4.701 (0.89), 4.706 (1.09), 4.717 (0.99), 5.047 (0.49), 5.076 (5.23), 7.900 (0.82), 7.920 (2.75), 7.933 (1.79), 7.937 (1.59), 7.954 (0.60), 7.958 (0.60), 8.659 (1.66).

Intermediate 392

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

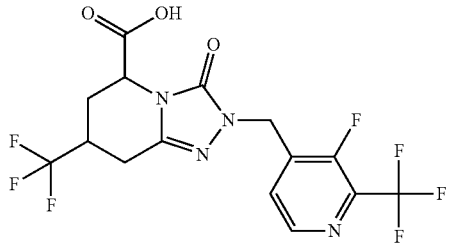 [SMILES: O=C(O)C1CC(C(F)(F)F)Cc2nn(Cc3ccnc(C(F)(F)F)c3F)c(=O)n21]

Ethyl (5RS,7RS)-2-{[3-fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylate (diastereomer mixture, 4 isomers) (440 mg, 964 µmol) was initially charged in THF (5.0 ml) and water (5.0 ml), and lithium hydroxide (69.3 mg, 2.89 mmol) was added. After stirring overnight, the reaction mixture was admixed at room temperature with 1 N aqueous hydrochloric acid. The aqueous phase was extracted with ethyl acetate and the organic phase was dried over sodium sulphate and filtered, and the filtrate was concentrated. 372 mg (90% of theory) of the title compound were obtained.

LC-MS (Method 4): $R_t$=0.78 min; MS (ESIpos): m/z=429 [M+H]$^+$ $^1$H-NMR (400 MHz, DMSO-d6) δ [ppm]: −0.149 (0.91), −0.008 (8.08), 0.008 (7.23), 0.146 (0.98), 1.106 (2.33), 1.110 (1.68), 1.157 (4.28), 1.175 (8.94), 1.193 (4.49), 1.236 (0.42), 1.839 (0.46), 1.908 (14.96), 1.988 (16.00), 2.239 (0.66), 2.254 (0.89), 2.273 (1.85), 2.289 (1.87), 2.303 (2.06), 2.319 (2.18), 2.337 (4.86), 2.367 (1.97), 2.523 (2.97), 2.670 (1.10), 2.689 (1.29), 2.718 (5.76), 2.742 (5.61), 2.770 (1.75), 2.800 (0.73), 2.896 (0.48), 2.974 (0.81), 2.999 (3.66), 3.027 (3.18), 3.055 (0.71), 3.077 (0.89), 4.003 (1.29), 4.021 (3.82), 4.038 (3.78), 4.056 (1.25), 4.417 (0.48), 4.432 (0.54), 4.444 (0.52), 4.459 (0.44), 4.717 (4.76), 4.728 (4.45), 5.085 (1.45), 5.098 (2.93), 5.126 (12.20), 5.136 (12.34), 5.177 (1.39), 5.754 (0.75), 7.583 (3.57), 7.595 (6.94), 7.608 (3.91), 7.631 (0.54), 7.644 (0.87), 7.658 (0.46), 8.562 (7.88), 8.574 (8.27), 8.589 (1.12), 13.733 (0.56).

Intermediate 393

(5RS,7RS)-2-[(5-Chloro-3-fluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

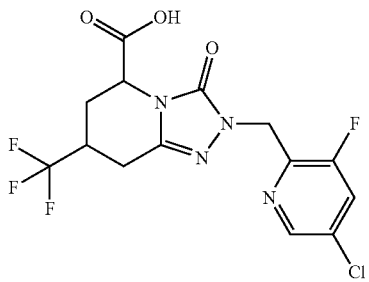 [SMILES: O=C(O)C1CC(C(F)(F)F)Cc2nn(Cc3ncc(Cl)cc3F)c(=O)n21]

Ethyl (5RS,7RS)-2-[(5-chloro-3-fluoropyridin-2-yl)methyl]-3-oxo-7-(trifluoromethyl)-2,3,5,6,7,8-hexahydro[1,2,4]triazolo[4,3-a]pyridine-5-Carboxylate (Diastereomer Mixture, 4 Isomers) (133 mg, 315 µmol) was initially charged in THF (1.5 ml) and water (1.5 ml), and lithium hydroxide (22.6 mg, 944 µmol) was added. After stirring overnight, the reaction mixture was admixed at room temperature with 1 N aqueous hydrochloric acid. The aqueous phase was extracted with ethyl acetate and the organic phase was dried over sodium sulphate and filtered, and the filtrate was concentrated. 113 mg (91% of theory) of the title compound were obtained.

LC-MS (Method 3): $R_t$=1.26 min; MS (ESIpos): m/z=395 [M+H]$^+$

Intermediate 394

(5RS,7RS)-2-[(5-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

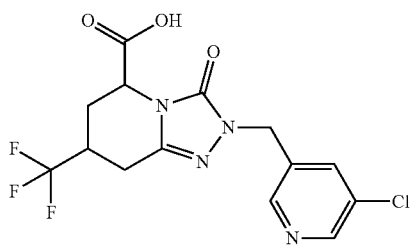 [SMILES: O=C(O)C1CC(C(F)(F)F)Cc2nn(Cc3cncc(Cl)c3)c(=O)n21]

Ethyl (5RS,7RS)-2-[(5-chloropyridin-3-yl)methyl]-3-oxo-7-(trifluoromethyl)-2,3,5,6,7,8-hexahydro[1,2,4]triazolo[4,3-a]pyridine-5-Carboxylate (Diastereomer Mixture, 4 Isomers) (55.0 mg, 136 µmol) was initially charged in THF (1.0 ml) and water (1.0 ml), and lithium hydroxide (9.76 mg, 408 µmol) was added. After stirring overnight, the reaction mixture was admixed at room temperature with 1 N aqueous hydrochloric acid. The aqueous phase was extracted with ethyl acetate and the organic phase was dried over sodium sulphate and filtered, and the filtrate was concentrated. 71.7 mg (75% purity, >100% of theory) of the title compound were obtained.

LC-MS (Method 4): $R_t$=0.64 min; MS (ESIpos): m/z=377 [M+H]$^+$

Intermediate 395

3-Oxo-8-(trifluoromethyl)-2-{[6-(trifluoromethyl)pyridin-3-yl]methyl}-2,3-dihydro[1,2,4]triazolo[4,3-a]pyridine-5-carboxylic Acid

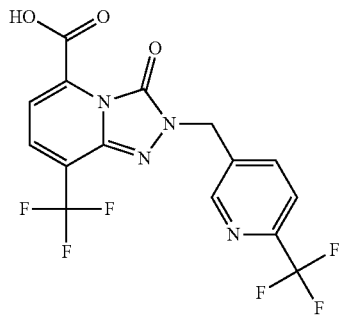 [SMILES: O=C(O)c1ccc(C(F)(F)F)c2nn(Cc3ccc(C(F)(F)F)nc3)c(=O)n12]

Methyl 3-oxo-8-(trifluoromethyl)-2-{[6-(trifluoromethyl)pyridin-3-yl]methyl}-2,3-dihydro[1,2,4]triazolo[4,3-a]pyridine-5-carboxylate (85.0 mg, 77% purity, 156 µmol) was initially charged in THF (1.0 ml) and water (1.0 ml), and lithium hydroxide (7.46 mg, 311 µmol) was added. After stirring overnight, the reaction mixture was admixed at room temperature with 1 N aqueous hydrochloric acid. The aqueous phase was extracted with ethyl acetate and the organic phase was dried over sodium sulphate and filtered, and the filtrate was concentrated. 113 mg (>100% of theory) of the title compound were obtained.

LC-MS (Method 1): $R_t$=0.98 min; MS (ESIpos): m/z=407 [M+H]

Intermediate 396

2-[(5-Chloro-3-fluoropyridin-2-yl)methyl]-3-oxo-8-(trifluoromethyl)-2,3-dihydro[1,2,4]triazolo[4,3-a]pyridine-5-carboxylic Acid

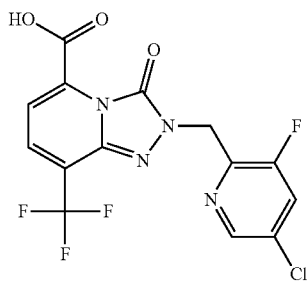 [SMILES: O=C(O)c1ccc(C(F)(F)F)c2nn(Cc3ncc(Cl)cc3F)c(=O)n12]

Methyl 2-[(5-chloro-3-fluoropyridin-2-yl)methyl]-3-oxo-8-(trifluoromethyl)-2,3-dihydro[1,2,4]triazolo[4,3-a]pyridine-5-carboxylate (86.0 mg, 212 µmol) was initially charged in THF (1.0 ml) and water (1.0 ml), and lithium hydroxide (10.2 mg, 425 mol) was added. After stirring overnight, the reaction mixture was admixed at room temperature with 1 N aqueous hydrochloric acid. The aqueous phase was extracted with ethyl acetate and the organic phase was dried over sodium sulphate and filtered, and the filtrate was concentrated. 85.4 mg (96% of theory) of the title compound were obtained.

LC-MS (Method 4): $R_t$=0.68 min; MS (ESIpos): m/z=391 [M+H]

Intermediate 397

5-{[(3R,4S)-3,4-Difluoropyrrolidin-1-yl]carbonyl}-8-(trifluoromethyl)-2-{[6-(trifluoromethyl)pyridin-3-yl]methyl}[1,2,4]triazolo[4,3-a]pyridin-3(2H)-one

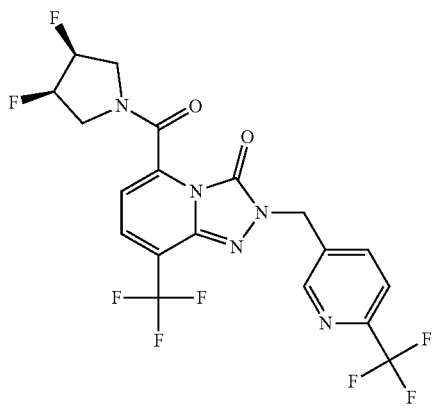 [SMILES: O=C(c1ccc(C(F)(F)F)c2nn(Cc3ccc(C(F)(F)F)nc3)c(=O)n12)N1C[C@@H](F)[C@@H](F)C1]

3-Oxo-8-(trifluoromethyl)-2-{[6-(trifluoromethyl)pyridin-3-yl]methyl}-2,3-dihydro[1,2,4]triazolo[4,3-a]pyridine-5-carboxylic acid (110 mg, 249 µmol) was initially charged in THF (3.0 ml) at room temperature. Subsequently, HBTU (123 mg, 324 mol) and N,N-diisopropylethylamine (220 µl, 1.2 mmol) were added. After stirring for 5 min, (3R,4S)-3, 4-difluoropyrrolidine hydrochloride (42.9 mg, 299 µmol) was added and the reaction mixture was stirred at room temperature for 4 hours. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via column chromatography (silica gel, eluent: dichloromethane/methanol gradient I/O, 98/2). The product-containing fractions were concentrated under reduced pressure, and 23.0 mg (87% purity, 16% of theory) of the title compound were obtained.

LC-MS (Method 3): $R_t$=1.71 min; MS (ESIpos): m/z=496 [M+H]$^+$ $^1$H-NMR (400 MHz, DMSO-d6) δ[ppm]: −0.149 (0.99), −0.009 (8.81), 0.007 (7.55), 0.146 (0.99), 1.237 (0.90), 1.949 (0.36), 2.322 (1.80), 2.327 (2.52), 2.331 (1.80), 2.366 (0.63), 2.522 (5.30), 2.623 (0.36), 2.664 (2.16), 2.669 (2.88), 2.674 (2.25), 2.689 (16.00), 2.709 (0.90), 2.741 (0.27), 3.356 (1.08), 3.390 (0.63), 3.408 (0.54), 3.428 (0.45), 3.473 (0.45), 3.496 (0.45), 3.614 (0.45), 3.636 (0.45), 3.648 (0.45), 3.676 (0.54), 3.723 (0.45), 3.768 (0.27), 3.867 (0.36), 3.906 (0.63), 3.920 (0.54), 3.938 (0.36), 3.953 (0.36), 4.482 (0.27), 4.497 (0.27), 5.320 (1.62), 5.369 (0.27), 5.449 (0.27), 5.472 (0.27), 5.803 (0.27), 6.694 (0.27), 6.723 (0.36), 6.791 (0.36), 6.807 (0.36), 7.268 (0.45), 7.307 (0.81), 7.320 (0.36), 7.777 (0.63), 7.910 (1.08), 7.929 (1.53), 8.026 (0.81), 8.046 (0.63), 8.772 (0.99), 14.278 (0.27).

Intermediate 398

5-{[(3S)-3-Fluoropyrrolidin-1-yl]carbonyl}-8-(trifluoromethyl)-2-{[6-(trifluoromethyl)pyridin-3-yl]methyl}[1,2,4]triazolo[4,3-a]pyridin-3(2H)-one

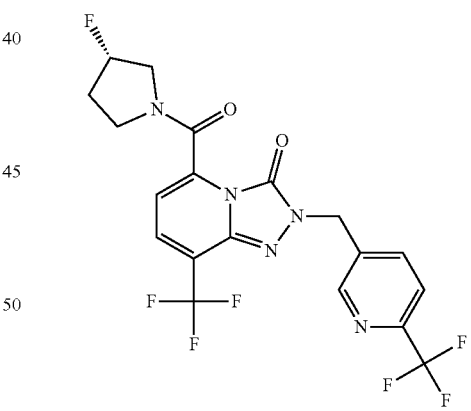

3-Oxo-8-(trifluoromethyl)-2-{[6-(trifluoromethyl)pyridin-3-yl]methyl}-2,3-dihydro[1,2,4]triazolo[4,3-a]pyridine-5-carboxylic acid (127 mg, 300 µmol) was initially charged in THF (5.0 ml) at room temperature. Subsequently, HBTU (148 mg, 390 mol) and N,N-diisopropylethylamine (260 µl, 1.5 mmol) were added. After stirring for 5 min, (3S)-3-fluoropyrrolidine hydrochloride (45.2 mg, 360 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. 167 mg (60% purity, 70% of theory) of the title compound were obtained.

LC-MS (Method 3): $R_t$=1.64 min; MS (ESIpos): m/z=478 [M+H]$^+$

Intermediate 399

2-[(5-Chloro-3-fluoropyridin-2-yl)methyl]-5-{[(3S)-3-fluoropyrrolidin-1-yl]carbonyl}-8-(trifluoromethyl)[1,2,4]triazolo[4,3-a]pyridin-3(2H)-one

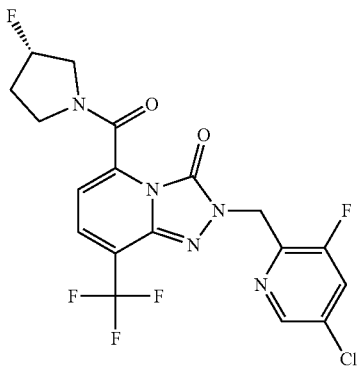 [SMILES: O=C(c1ccc(C(F)(F)F)c2nn(Cc3ncc(Cl)cc3F)c(=O)n12)N1CC[C@H](F)C1]

2-[(5-Chloro-3-fluoropyridin-2-yl)methyl]-3-oxo-8-(trifluoromethyl)-2,3-dihydro[1,2,4]triazolo[4,3-a]pyridine-5-carboxylic acid (42.0 mg, 100 µmol) was initially charged in THF (2.0 ml) at room temperature. Subsequently, HBTU (49.3 mg, 130 µmol) and N,N-diisopropylethylamine (87 µl, 500 µmol) were added. After stirring for 5 min, (3S)-3-fluoropyrrolidine hydrochloride (15.1 mg, 120 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. 51.2 mg (62% purity, 69% of theory) of the title compound were obtained.

LC-MS (Method 3): $R_t$=1.65 min; MS (ESIpos): m/z=462 [M+H]$^+$

Intermediate 400

2-[(5-Chloro-3-fluoropyridin-2-yl)methyl]-5-{[(3R,4S)-3,4-difluoropyrrolidin-1-yl]carbonyl}-8-(trifluoromethyl)[1,2,4]triazolo[4,3-a]pyridin-3(2H)-one

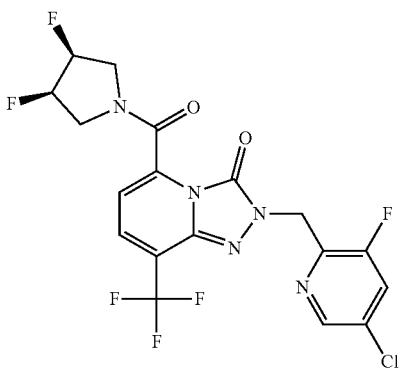 [SMILES: O=C(c1ccc(C(F)(F)F)c2nn(Cc3ncc(Cl)cc3F)c(=O)n12)N1C[C@@H](F)[C@@H](F)C1]

2-[(5-Chloro-3-fluoropyridin-2-yl)methyl]-3-oxo-8-(trifluoromethyl)-2,3-dihydro[1,2,4]triazolo[4,3-a]pyridine-5-carboxylic acid (42.0 mg, 100 µmol) was initially charged in THF (2.0 ml) at room temperature. Subsequently, HBTU (49.3 mg, 130 µmol) and N,N-diisopropylethylamine (87 µl, 500 µmol) were added. After stirring for 5 min, (3R,4S)-3,4-difluoropyrrolidine hydrochloride (17.2 mg, 120 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. 95.2 mg (47% purity, 92% of theory) of the title compound were obtained.

LC-MS (Method 3): $R_t$=1.70 min; MS (ESIpos): m/z=480 [M+H]$^+$

Intermediate 401

(5S)-2-[(5-Chloropyridin-2-yl)methyl]-5-{[(3S)-3-fluoropyrrolidin-1-yl]carbonyl}-6,7-dihydro[1,2,4]triazolo[4,3-a]pyridine-3,8(2H,5H)-dione

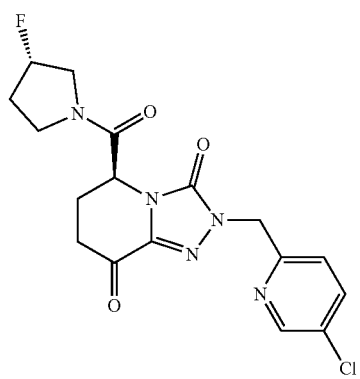 [SMILES: O=C1CC[C@@H](C(=O)N2CC[C@H](F)C2)n2c1nn(Cc1ccc(Cl)cn1)c2=O]

(5S,8RS)-2-[(5-Chloropyridin-2-yl)methyl]-5-{[(3S)-3-fluoropyrrolidin-1-yl]carbonyl}-8-hydroxy-5,6,7,8-tetrahydro[1,2,4]triazolo[4,3-a]pyridin-3(2H)-one (Diastereomer Mixture; 2 Isomers) (39.0 mg, 92.6 µmol) was initially charged in dichloromethane (940 µl) at room temperature and the reaction mixture was cooled to 0° C. Subsequently, Dess-Martin periodinane (98.2 mg, 232 µmol) was added and the reaction mixture was stirred at 0° C. for 15 min and at room temperature overnight. The reaction mixture was admixed with diethyl ether and a solution of sodium thiosulphate (350 mg) in saturated aqueous sodium hydrogencarbonate solution. The organic phase was removed and the aqueous phase was extracted with diethyl ether. The combined organic phases were dried over sodium sulphate and filtered, and the filtrate was concentrated. 12.7 mg (90% purity, 31% of theory) of the title compound were obtained.

LC-MS (Method 1): $R_t$=0.86 min; MS (ESIpos): m/z=394 [M+H]$^+$

Intermediate 402

(5S)-2-[(5-Chloro-3-fluoropyridin-2-yl)methyl]-5-{[(3S)-3-fluoropyrrolidin-1-yl]carbonyl}-6,7-dihydro[1,2,4]triazolo[4,3-a]pyridine-3,8(2H,5H)-dione

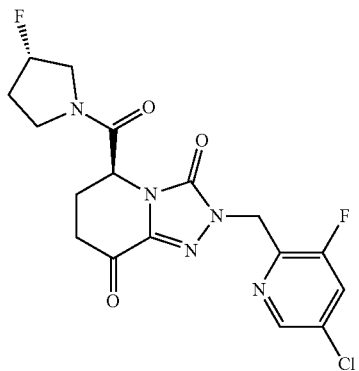 [SMILES: O=C1CC[C@@H](C(=O)N2CC[C@H](F)C2)n2c1nn(Cc1ncc(Cl)cc1F)c2=O]

(5S,8RS)-2-[(5-Chloro-3-fluoropyridin-2-yl)methyl]-5-{[(3S)-3-fluoropyrrolidin-1-yl]carbonyl}-8-hydroxy-5,6,7,8-tetrahydro[1,2,4]triazolo[4,3-a]pyridin-3(2H)-one (diastereomer mixture; 2 isomers) (51.7 mg, 86% purity, 107 µmol) was initially charged in dichloromethane (1.1 ml) at room temperature and the reaction mixture was cooled to 0° C. Subsequently, Dess-Martin periodinane (114 mg, 269 µmol) was added and the reaction mixture was stirred at 0° C. for 15 min and at room temperature overnight. The reaction mixture was admixed with diethyl ether and a solution of sodium thiosulphate (350 mg) in saturated aqueous sodium hydrogencarbonate solution and stirred. The organic phase was removed and the aqueous phase was extracted with diethyl ether and three times with ethyl acetate. The combined organic phases were dried over sodium sulphate and filtered, and the filtrate was concentrated. 25.8 mg (75% purity, 46% of theory) of the title compound were obtained.

LC-MS (Method 1): $R_t$=0.89 min; MS (ESIpos): m/z=412 [M+H]$^+$

Intermediate 403

(5S)-2-[(6-Chloropyridin-3-yl)methyl]-5-[(3,3-difluoropyrrolidin-1-yl)carbonyl]-6,7-dihydro[1,2,4]triazolo[4,3-a]pyridine-3,8(2H,5H)-dione

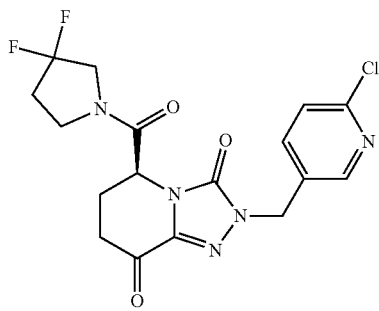 [SMILES: O=C1CC[C@@H](C(=O)N2CCC(F)(F)C2)n2c1nn(Cc1ccc(Cl)nc1)c2=O]

(5S,8RS)-2-[(6-Chloropyridin-3-yl)methyl]-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers) (66.9 mg, 90% purity, 146 µmol) was dissolved in dichloromethane (6.0 ml, 94 mmol), and manganese(IV) oxide (254 mg, 2.92 mmol) was added at room temperature. The reaction mixture was stirred at room temperature overnight. The suspension was filtered through Celite and the filtrate was concentrated under reduced pressure. 47.3 mg (79% of theory) of the title compound were obtained.

LC-MS (Method 4): $R_t$=0.69 min; MS (ESIpos): m/z=412 [M+H]$^+$

Intermediate 404 tert-Butyl (5S)-3-oxo-2-{[2-(trifluoromethyl)pyrimidin-5-yl]methyl}-2,3,5,6,7,8-hexahydro[1,2,4]triazolo[4,3-a]pyridine-5-carboxylate

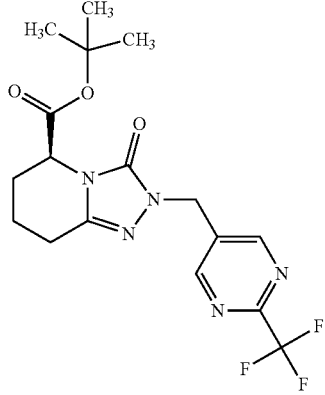 [SMILES: CC(C)(C)OC(=O)[C@@H]1CCCc2nn(Cc3cnc(C(F)(F)F)nc3)c(=O)n21]

tert-Butyl (5S)-3-oxo-2,3,5,6,7,8-hexahydro[1,2,4]triazolo[4,3-a]pyridine-5-carboxylate (16.2 mg, 67.8 µmol) was initially charged in acetonitrile (1.0 ml). Caesium carbonate (33.2 mg, 102 µmol) and 5-(chloromethyl)-2-(trifluoromethyl)pyrimidine (14.0 mg, 71.2 µmol) were subsequently added. After stirring at room temperature overnight, ethyl acetate was added to the reaction mixture. The organic phase was washed with water and saturated aqueous sodium chloride solution, dried over sodium sulphate and filtered, and the filtrate was concentrated. 22 mg (11% purity, 8% of theory) of the title compound were obtained.

LC-MS (Method 3): $R_t$=1.88 min; MS (ESIpos): m/z=400 [M+H]$^+$

Intermediate 405

(5S)-3-Oxo-2-{[2-(trifluoromethyl)pyrimidin-5-yl]methyl}-2,3,5,6,7,8-hexahydro[1,2,4]triazolo[4,3-a]pyridine-5-carboxylic Acid

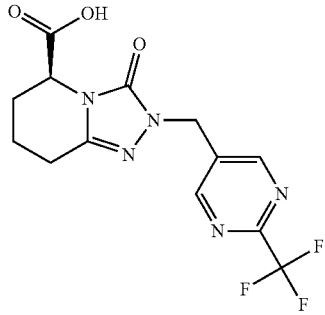 [SMILES: O=C(O)[C@@H]1CCCc2nn(Cc3cnc(C(F)(F)F)nc3)c(=O)n21]

tert-Butyl (5S)-3-oxo-2-{[2-(trifluoromethyl)pyrimidin-5-yl]methyl}-2,3,5,6,7,8-hexahydro[1,2,4]triazolo[4,3-a]pyridine-5-carboxylate (22.0 mg, 11% purity, 6 µmol) was dissolved in 1,4-dioxane (200 µl), and hydrochloric acid dissolved in 1,4-dioxane (140 µl, 4.0 M, 550 µmol) was added. After the reaction mixture had been stirred at room temperature overnight, the solvent was removed under reduced pressure. 22 mg (11% purity, >100% of theory) of the title compound were obtained.

LC-MS (Method 3): $R_t$=0.98 min; MS (ESIpos): m/z=344 [M+H]$^+$

Intermediate 406

Ethyl (5RS,7RS)-2-{[3-chloro-5-(trifluoromethyl)pyridin-2-yl]methyl}-3-oxo-7-(trifluoromethyl)-2,3,5,6,7,8-hexahydro[1,2,4]triazolo[4,3-a]pyridine-5-carboxylate (Diastereomer Mixture; 4 Isomers)

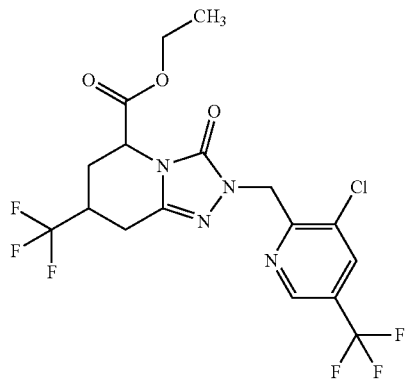 [SMILES: CCOC(=O)C1CC(C(F)(F)F)Cc2nn(Cc3ncc(C(F)(F)F)cc3Cl)c(=O)n21]

Ethyl (5S,7R)-3-oxo-7-(trifluoromethyl)-2,3,5,6,7,8-hexahydro[1,2,4]triazolo[4,3-a]pyridine-5-carboxylate (diastereomer mixture, 4 isomers) (500 mg, 1.79 mmol) was initially charged in acetonitrile (16 ml). Caesium carbonate (1.46 g, 4.48 mmol) and 3-chloro-2-(chloromethyl)-5-(trifluoromethyl)pyridine (432 mg, 1.88 mmol) were subsequently added. The reaction mixture was stirred at room temperature for 72 hours, and then water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. 859 mg (96% of theory) of the title compound were obtained.

LC-MS (Method 4): $R_t$=0.99 min; MS (ESIpos): m/z=473 [M+H]$^+$

Intermediate 407 tert-Butyl (5S)-2-[(5-chloro-3-fluoropyridin-2-yl)methyl]-3-oxo-2,3,5,6,7,8-hexahydro[1,2,4]triazolo[4,3-a]pyridine-5-carboxylate

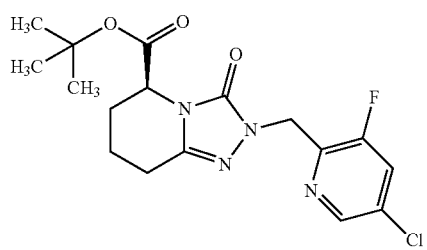 [SMILES: CC(C)(C)OC(=O)[C@@H]1CCCc2nn(Cc3ncc(Cl)cc3F)c(=O)n21]

tert-Butyl (5S)-3-oxo-2,3,5,6,7,8-hexahydro[1,2,4]triazolo[4,3-a]pyridine-5-carboxylate (500 mg, 2.09 mmol) was initially charged in acetonitrile (15 ml). Caesium carbonate (1.36 g, 4.18 mmol) and 5-chloro-2-(chloromethyl)-3-fluoropyridine (395 mg, 2.19 mmol) were subsequently added. The reaction mixture was stirred at room temperature for 72 hours, and then water and ethyl acetate were added. The organic phase was removed and the aqueous phase was extracted three times with ethyl acetate. The combined organic phases were washed with saturated aqueous sodium chloride solution, dried over sodium sulphate and filtered, and the filtrate was concentrated. 793 mg (99% of theory) of the title compound were obtained.

LC-MS (Method 4): $R_t$=0.86 min; MS (ESIpos): m/z=383 [M+H]$^+$

Intermediate 408 tert-Butyl (5S)-2-[(3-chloro-5-fluoropyridin-2-yl)methyl]-3-oxo-2,3,5,6,7,8-hexahydro[1,2,4]triazolo[4,3-a]pyridine-5-carboxylate

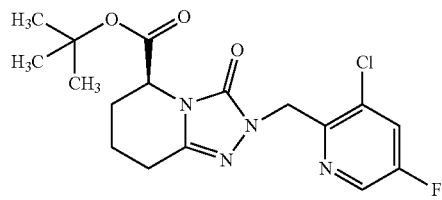 [SMILES: CC(C)(C)OC(=O)[C@@H]1CCCc2nn(Cc3ncc(F)cc3Cl)c(=O)n21]

tert-Butyl (5S)-3-oxo-2,3,5,6,7,8-hexahydro[1,2,4]triazolo[4,3-a]pyridine-5-carboxylate (452 mg, 1.89 mmol) was initially charged in acetonitrile (41 ml). Caesium carbonate (1.54 g, 4.72 mmol) and 3-chloro-2-(chloromethyl)-5-fluoropyridine (476 mg, 2.65 mmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 842 mg (78% purity, 91% of theory) of the title compound were obtained.

LC-MS (Method 3): $R_t$=1.66 min; MS (ESIpos): m/z=383 [M+H]$^+$

Intermediate 409

(5RS,7RS)-2-{[3-Chloro-5-(trifluoromethyl)pyridin-2-yl]methyl}-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

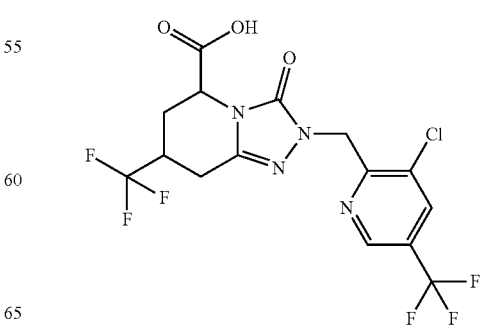

Ethyl (5RS,7RS)-2-{[3-chloro-5-(trifluoromethyl)pyridin-2-yl]methyl}-3-oxo-7-(trifluoromethyl)-2,3,5,6,7,8-hexahydro[1,2,4]triazolo[4,3-a]pyridine-5-carboxylate (diastereomer mixture, 4 isomers) (859 mg, 1.82 mmol) was initially charged in THF (21 ml), and sodium ethoxide solution (1.09 g, 3.36 mmol, 21% by weight) was added. The reaction mixture was stirred at 0° C. for 20 min and overnight at room temperature. The reaction mixture was admixed with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 846 mg (>100% of theory) of the title compound were obtained.

LC-MS (Method 3): $R_t$=1.50 min; MS (ESIpos): m/z=445 [M+H]$^+$

Intermediate 410

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic Acid

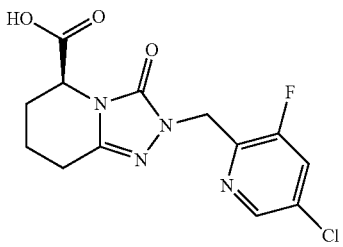 [SMILES: O=C(O)[C@@H]1CCCc2nn(Cc3ncc(Cl)cc3F)c(=O)n21]

tert-Butyl (5S)-2-[(5-chloro-3-fluoropyridin-2-yl)methyl]-3-oxo-2,3,5,6,7,8-hexahydro[1,2,4]triazolo[4,3-a]pyridine-5-carboxylate (793 mg, 2.07 mmol) was dissolved in dichloromethane (15 ml), and trifluoroacetic acid (3.2 ml, 41 mmol) was added at room temperature. After the reaction mixture had been stirred at room temperature overnight, trifluoroacetic acid (0.64 ml, 8.2 mmol) was added again and the reaction mixture was stirred at room temperature for a further 1.5 hours. The solvent was removed under reduced pressure. 676 mg (89% purity, 89% of theory) of the title compound were obtained.

LC-MS (Method 4): $R_t$=0.56 min; MS (ESIpos): m/z=327 [M+H]$^+$

Intermediate 411

(5S)-2-[(3-Chloro-5-fluoropyridin-2-yl)methyl]-3-oxo-2,3,5,6,7,8-hexahydro[1,2,4]triazolo[4,3-a]pyridine-5-carboxylic Acid

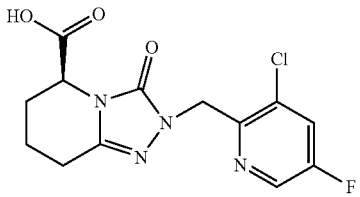 [SMILES: O=C(O)[C@@H]1CCCc2nn(Cc3ncc(F)cc3Cl)c(=O)n21]

tert-Butyl (5S)-2-[(3-chloro-5-fluoropyridin-2-yl)methyl]-3-oxo-2,3,5,6,7,8-hexahydro[1,2,4]triazolo[4,3-a]pyridine-5-carboxylate (842 mg, 2.20 mmol) was dissolved in dichloromethane (14.1 ml), and trifluoroacetic acid (3.4 ml, 44 mmol) was added at room temperature. After the reaction mixture had been stirred at room temperature overnight, the solvent was removed under reduced pressure. 1.45 g (58% purity, 117% of theory) of the title compound were obtained.

LC-MS (Method 4): $R_t$=0.53 min; MS (ESIpos): m/z=327 [M+H]$^+$

Intermediate 412

Ethyl-(5RS,7RS)-2-[(3-chloro-5-fluoropyridin-2-yl)methyl]-3-oxo-7-(trifluoromethyl)-2,3,5,6,7,8-hexahydro[1,2,4]triazolo[4,3-a]pyridine-5-carboxylate (Diastereomer Mixture; 4 Isomers)

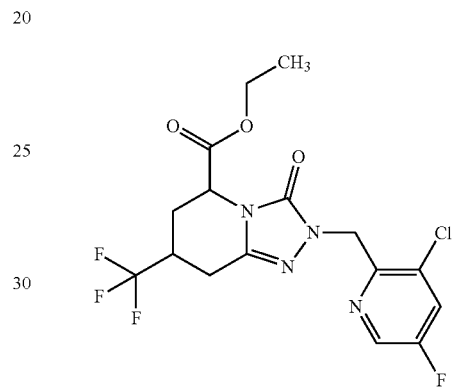

Ethyl-(5RS,7RS)-3-oxo-7-(trifluoromethyl)-2,3,5,6,7,8-hexahydro[1,2,4]triazolo[4,3-a]pyridine-5-Carboxylate (Diastereomer Mixture, 4 Isomers) (300 mg, 1.07 mmol) was initially charged in acetonitrile (10 ml). Caesium carbonate (700 mg, 2.15 mmol) and 3-chloro-2-(chloromethyl)-5-fluoropyridinehydrochloride (254 mg, 96% purity, 1.13 mmol) were subsequently added. The reaction mixture was stirred at room temperature overnight. Additional 3-chloro-2-(chloromethyl)-5-fluoropyridinehydrochloride (254 mg, 96% purity, 1.13 mmol) was then added and heated at 60° C. overnight. To the reaction mixture, water and ethyl acetate were added and the organic phase was separated. The aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 348 mg (75% of theory) of the title compound were obtained.

LC-MS (Method 3): $R_t$=1.67 min; MS (ESIpos): m/z=423 [M+H]$^+$ $^1$H-NMR (400 MHz, DMSO-d6) δ [ppm]: 1.187 (1.01), 1.199 (7.45), 1.204 (2.57), 1.216 (16.00), 1.234 (7.55), 1.769 (0.74), 1.799 (1.54), 1.830 (1.61), 1.860 (0.83), 2.073 (0.42), 2.482 (0.94), 2.521 (0.84), 2.716 (1.04), 2.746 (1.26), 2.756 (1.70), 2.786 (1.98), 2.867 (1.23), 2.873 (1.39), 2.877 (1.27), 2.902 (0.68), 2.907 (0.77), 2.913 (0.75), 3.056 (0.40), 3.069 (0.55), 3.077 (0.63), 3.087 (0.58), 3.098 (0.57), 4.145 (0.51), 4.154 (1.19), 4.159 (1.36), 4.171 (3.77), 4.177 (3.81), 4.189 (3.90), 4.195 (3.66), 4.207 (1.35), 4.213 (1.28), 4.222

(0.43), 4.525 (1.71), 4.539 (1.98), 4.553 (1.89), 4.567 (1.64), 4.982 (1.78), 5.021 (4.32), 5.069 (5.20), 5.109 (1.75), 8.118 (2.64), 8.124 (2.83), 8.139 (2.69), 8.145 (2.80), 8.543 (0.91), 8.548 (5.70), 8.555 (5.07).

Intermediate 413

Ethyl-(5RS,7RS)-2-[(3,5-difluoropyridin-2-yl)methyl]-3-oxo-7-(trifluoromethyl)-2,3,5,6,7,8-hexahydro[1,2,4]triazolo[4,3-a]pyridine-5-carboxylate (Diastereomer Mixture; 4 Isomers)

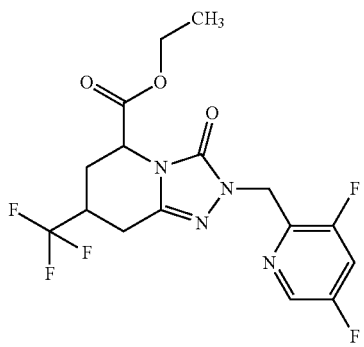 [SMILES: CCOC(=O)C1CC(C(F)(F)F)Cc2nn(Cc3ncc(F)cc3F)c(=O)n21]

Ethyl-(5RS,7RS)-3-oxo-7-(trifluoromethyl)-2,3,5,6,7,8-hexahydro[1,2,4]triazolo[4,3-a]pyridine-5-Carboxylate (Diastereomer Mixture, 4 Isomers) (600 mg, 2.15 mmol) was initially charged in acetonitrile (10 ml). Caesium carbonate (1.75 g, 5.37 mmol) and 2-(chloromethyl)-3,5-difluoropyridine (387 mg, 2.36 mmol) were subsequently added. The reaction mixture was stirred at room temperature overnight and then at 60° C. overnight. Additional 2-(chloromethyl)-3,5-difluoropyridine (100 mg, 0.61 mmol) was then added and the reaction mixture was heated at 60° C. for 1 hour, and then at room temperature for 48 hours. To the reaction mixture, water and ethyl acetate were added and the organic phase was separated. The aqueous phase was extracted three times with ethyl acetate. The combined organic phases were washed with saturated aqueous sodium chloride solution, dried over sodium sulphate and filtered, and the filtrate was concentrated. 734 mg (79% of theory) of the title compound were obtained.

LC-MS (Method 4): $R_t$=0.82 min; MS (ESIpos): m/z=407 [M+H]$^+$

Intermediate 414 tert-Butyl-(5S)-3-oxo-2-{[5-(trifluoromethyl)pyridin-3-yl]methyl}-2,3,5,6,7,8-hexahydro[1,2,4]triazolo[4,3-a]pyridine-5-carboxylate

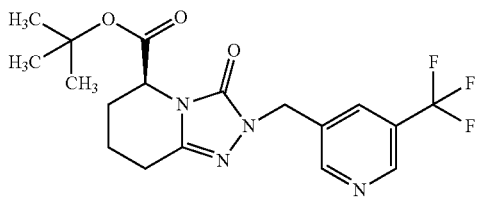 [SMILES: CC(C)(C)OC(=O)[C@@H]1CCCc2nn(Cc3cncc(C(F)(F)F)c3)c(=O)n21]

tert-Butyl-(5S)-3-oxo-2,3,5,6,7,8-hexahydro[1,2,4]triazolo[4,3-a]pyridine-5-carboxylate (154 mg, 645 μmol) was dissolved in acetonitrile (14 ml). Caesium carbonate (525 mg, 1.61 mmol) and 3-(chloromethyl)-5-(trifluoromethyl)pyridine (164 mg, 838 μmol) were added and stirred at 50° C. for 5 hours and at room temperature overnight. The majority of solvent was removed under reduced pressure and water and ethyl acetate were added and the organic phase was separated. The aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 26.4 mg (83% purity, 9% of theory) of the title compound were obtained.

LC-MS (Method 3): $R_t$=1.72 min; MS (ESIpos): m/z=399 [M+H]$^+$

Intermediate 415

(5RS,7RS)-2-[(3-Chloro-5-fluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

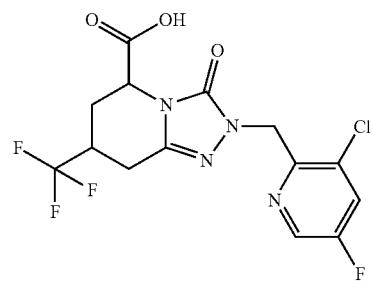 [SMILES: O=C(O)C1CC(C(F)(F)F)Cc2nn(Cc3ncc(F)cc3Cl)c(=O)n21]

Ethyl-(5RS,7RS)-2-[(3-chloro-5-fluoropyridin-2-yl)methyl]-3-oxo-7-(trifluoromethyl)-2,3,5,6,7,8-hexahydro[1,2,4]triazolo[4,3-a]pyridine-5-Carboxylate (Diastereomer Mixture, 4 Isomers) (348 mg, 824 μmol) was initially charged in THF (10 ml), and sodium ethoxide solution (494 mg, 1.52 mmol, 21% by weight in ethanol) was added. The reaction mixture was stirred at room temperature overnight. The reaction mixture was admixed with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 289 mg (87% of theory) of the title compound were obtained.

LC-MS (Method 3): $R_t$=1.14 min; MS (ESIpos): m/z=395 [M+H]$^+$

Intermediate 416

(5RS,7RS)-2-[(3,5-Difluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers)

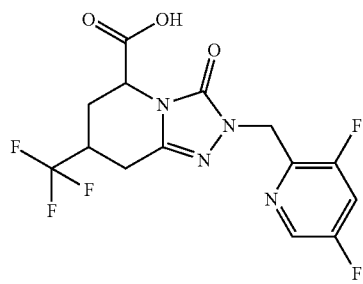 [SMILES: O=C(O)C1CC(C(F)(F)F)Cc2nn(Cc3ncc(F)cc3F)c(=O)n21]

Ethyl-(5RS,7RS)-2-[(3,5-difluoropyridin-2-yl)methyl]-3-oxo-7-(trifluoromethyl)-2,3,5,6,7,8-hexahydro[1,2,4]triazolo[4,3-a]pyridine-5-Carboxylate (Diastereomer Mixture, 4 Isomers) (734 mg, 93% purity, 1.69 mmol) was initially charged in THF (20 ml), and sodium ethoxide solution (1.01 g, 3.12 mmol, 21% by weight in ethanol) was added. The reaction mixture was stirred at 0° C. for 20 min and then at room temperature overnight. The reaction mixture was admixed with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 213 mg (32% of theory) of the title compound were obtained.

LC-MS (Method 3): $R_t$=1.04 min; MS (ESIpos): m/z=379 [M+H]$^+$ $^1$H-NMR (400 MHz, DMSO-d6) δ [ppm]: 1.309 (1.32), 1.324 (2.78), 1.341 (1.44), 1.774 (0.56), 1.804 (0.56), 2.064 (0.56), 2.072 (0.41), 2.096 (0.40), 2.169 (0.58), 2.224 (1.06), 2.240 (1.22), 2.259 (2.88), 2.275 (3.39), 2.301 (9.72), 2.332 (2.28), 2.455 (0.76), 2.636 (2.41), 2.666 (8.01), 2.701 (8.02), 2.743 (1.91), 2.785 (0.63), 2.849 (0.55), 2.949 (5.55), 2.979 (4.61), 3.848 (0.90), 4.073 (0.62), 4.090 (1.31), 4.108 (1.11), 4.113 (1.20), 4.391 (0.55), 4.405 (0.62), 4.418 (0.62), 4.433 (0.53), 4.665 (5.53), 4.671 (7.00), 4.680 (5.72), 4.685 (5.62), 4.836 (0.65), 4.857 (0.88), 4.874 (0.78), 4.898 (1.52), 4.964 (3.41), 4.998 (11.30), 5.030 (10.17), 5.066 (2.90), 7.468 (0.68), 7.495 (0.65), 7.937 (3.94), 7.943 (4.33), 7.962 (6.26), 7.966 (6.71), 7.984 (4.12), 7.990 (4.32), 8.051 (1.42), 8.420 (0.48), 8.468 (14.61), 8.473 (16.00), 13.619 (0.72).

Intermediate 417

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic Acid

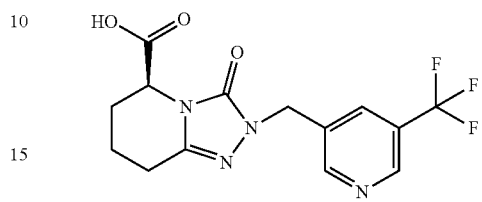

tert-Butyl-(5S)-3-oxo-2-{[5-(trifluoromethyl)pyridin-3-yl]methyl}-2,3,5,6,7,8-hexahydro[1,2,4]triazolo[4,3-a]pyridine-5-carboxylate (1.13 g, 2.83 mmol) was dissolved in dichloromethane (180 μl), and trifluoroacetic acid (4.4 ml, 57 mmol) was added at room temperature. After the reaction mixture had been stirred at room temperature overnight, the solvent was removed under reduced pressure. 980 mg (101% of theory) of the title compound were obtained.

LC-MS (Method 3): $R_t$=1.01 min; MS (ESIpos): m/z=343 [M+H]

Intermediate 418

(5S)-2-{[3-Chloro-5-(trifluoromethyl)pyridin-2-yl]methyl}-5-[(3,3-difluoropyrrolidin-1-yl)carbonyl]-6,7-dihydro[1,2,4]triazolo[4,3-a]pyridine-3,8(2H,5H)-dione

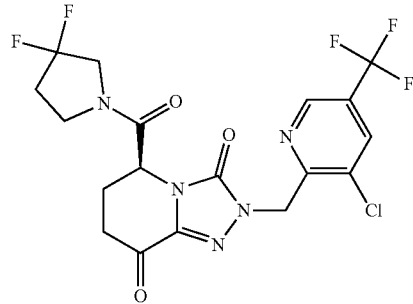 [SMILES: O=C1CC[C@@H](C(=O)N2CCC(F)(F)C2)n2c1nn(Cc1ncc(C(F)(F)F)cc1Cl)c2=O]

(5S,8RS)-2-{[3-Chloro-5-(trifluoromethyl)pyridin-2-yl]methyl}-5-[(3,3-difluoropyrrolidin-1-yl)carbonyl]-8-hydroxy-5,6,7,8-tetrahydro[1,2,4]triazolo[4,3-a]pyridine-3(2H)-one (diastereomer mixture; 2 isomers) (58.0 mg, 120 μmol) was dissolved in dichloromethane (10 ml), and manganese(IV) oxide (209 mg, 2.41 mmol) was added at room temperature. The reaction mixture was stirred at room temperature overnight. The suspension was filtered through Celite and the filtrate was concentrated under reduced pressure. 49.4 mg (86% of theory) of the title compound were obtained.

LC-MS (Method 3): $R_t$=1.55 min; MS (ESIpos): m/z=480 [M+H]$^+$

Intermediate 419

(5S)-2-[(5-Chloropyridin-2-yl)methyl]-5-[(3,3-difluoropyrrolidin-1-yl)carbonyl]-6,7-dihydro[1,2,4]triazolo[4,3-a]pyridine-3,8(2H,5H)-dione

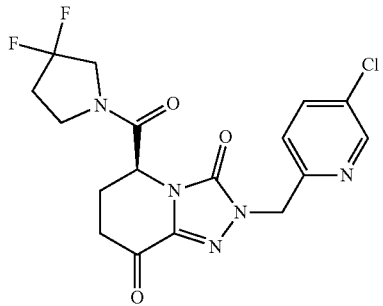 [SMILES: O=C1CC[C@@H](C(=O)N2CCC(F)(F)C2)n2c1nn(Cc1ccc(Cl)cn1)c2=O]

(5S,8RS)-2-[(5-Chloropyridin-2-yl)methyl]-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers) (103 mg, 85% purity, 211 µmol) was dissolved in dichloromethane (8.7 ml), and manganese(IV) oxide (366 mg, 4.21 mmol) was added at room temperature. The reaction mixture was stirred at room temperature overnight. The suspension was filtered through Celite and the filtrate was concentrated under reduced pressure. 79.4 mg (88% purity, 81% of theory) of the title compound were obtained.

LC-MS (Method 3): $R_t$=1.25 min; MS (ESIpos): m/z=412 [M+H]$^+$

Intermediate 420

(5S)-2-[(5-Chloropyridin-2-yl)methyl]-5-[(3-fluoroazetidin-1-yl)carbonyl]-6,7-dihydro[1,2,4]triazolo[4,3-a]pyridine-3,8(2H,5H)-dione

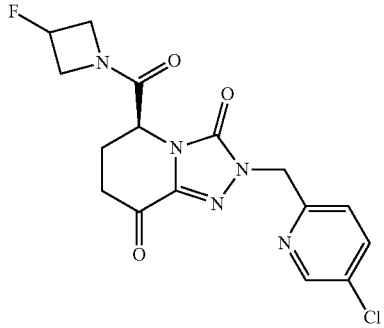 [SMILES: O=C1CC[C@@H](C(=O)N2CC(F)C2)n2c1nn(Cc1ccc(Cl)cn1)c2=O]

(5S,8RS)-2-[(5-Chloropyridin-2-yl)methyl]-5-[(3-fluoroazetidin-1-yl)carbonyl]-8-hydroxy-5,6,7,8-tetrahydro[1,2,4]triazolo[4,3-a]pyridin-3(2H)-one (diastereomer mixture; 2 isomers) (48.1 mg, 86% purity, 108 µmol) was dissolved in dichloromethane (800 µl), and manganese(IV) oxide (188 mg, 2.17 mmol) was added at room temperature. The reaction mixture was stirred at room temperature overnight. The suspension was filtered through Celite and the filtrate was concentrated under reduced pressure. 37.1 mg (63% purity, 57% of theory) of the title compound were obtained.

LC-MS (Method 1): $R_t$=0.83 min; MS (ESIpos): m/z=380 [M+H]$^+$

Intermediate 421

(5S)-2-[(3,5-Difluoropyridin-2-yl)methyl]-5-[(3,3-difluoropyrrolidin-1-yl)carbonyl]-6,7-dihydro[1,2,4]triazolo[4,3-a]pyridine-3,8(2H,5H)-dione

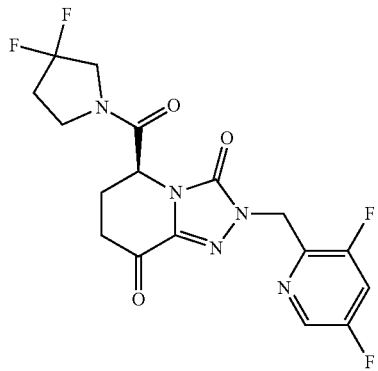 [SMILES: O=C1CC[C@@H](C(=O)N2CCC(F)(F)C2)n2c1nn(Cc1ncc(F)cc1F)c2=O]

(5S,8RS)-2-[(3,5-Difluoropyridin-2-yl)methyl]-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers) (112 mg, 270 µmol) was dissolved in dichloromethane (10 ml), and manganese(IV) oxide (469 mg, 5.39 mmol) was added at room temperature. The reaction mixture was stirred at room temperature overnight. The suspension was filtered through Celite and the filtrate was concentrated under reduced pressure. 61.3 mg (55% of theory) of the title compound were obtained.

LC-MS (Method 4): $R_t$=0.64 min; MS (ESIpos): m/z=414 [M+H]$^+$

Intermediate 422

(5S)-5-{[(3S)-3-Fluoropyrrolidin-1-yl]carbonyl}-2-{[6-(trifluoromethyl)pyridin-3-yl]methyl}-6,7-dihydro[1,2,4]triazolo[4,3-a]pyridine-3,8(2H,5H)-dione (Isomer 1)

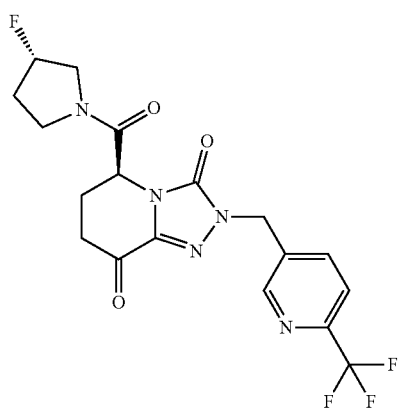 [SMILES: O=C1CC[C@@H](C(=O)N2CC[C@H](F)C2)n2c1nn(Cc1ccc(C(F)(F)F)nc1)c2=O]

(5S,8RS)-5-{[(3S)-3-Fluoropyrrolidin-1-yl]carbonyl}-8-hydroxy-2-{[6-(trifluoromethyl)pyridin-3-yl]methyl}-5,6,7,8-tetrahydro[1,2,4]triazolo[4,3-a]pyridin-3(2H)-one (diastereomer mixture; 2 isomers) (30.0 mg, 69.9 µmol) was initially charged in dichloromethane (180 µl) at room temperature and the reaction mixture was cooled to 0° C. Subsequently, Dess-Martin periodinane (35.6 mg, 83.8 µmol) was added and the reaction mixture was stirred at 0° C. for 15 min and at room temperature for 2 hours. Dess-Martin periodinane (35.6 mg, 83.8 mol) was added again and the mixture was stirred overnight. The reaction mixture was admixed with diethyl ether and a solution of sodium thiosulphate in saturated aqueous sodium hydrogencarbonate solution until the two phases were homogeneous. The organic phase was dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 1.60 mg (5% of theory) of the title compound were obtained.

LC-MS (Method 3): $R_t$=1.28 min; MS (ESIpos): m/z=428 [M+H]$^+$ $^1$H-NMR (400 MHz, DMSO-d6) δ [ppm]: −0.150 (1.86), −0.044 (0.28), −0.035 (0.39), −0.033 (0.39), −0.029 (0.51), −0.027 (0.51), −0.024 (0.56), −0.022 (0.85), −0.020 (1.01), −0.016 (1.69), −0.009 (16.00), 0.007 (14.08), 0.013 (2.08), 0.015 (1.18), 0.018 (0.85), 0.020 (0.56), 0.023 (0.56), 0.025 (0.45), 0.029 (0.34), 0.146 (1.75), 2.113 (0.34), 2.135 (0.34), 2.151 (0.39), 2.193 (0.28), 2.238 (0.45), 2.266 (0.56), 2.292 (0.39), 2.323 (1.35), 2.327 (1.86), 2.331 (1.46), 2.366 (2.37), 2.396 (0.45), 2.424 (0.23), 2.431 (0.28), 2.453 (0.34), 2.523 (4.73), 2.525 (3.66), 2.558 (1.58), 2.612 (0.68), 2.622 (0.62), 2.646 (0.28), 2.664 (1.46), 2.669 (1.80), 2.674 (1.35), 2.709 (2.08), 3.364 (0.56), 3.391 (0.34), 3.400 (0.34), 3.418 (0.28), 3.435 (0.34), 3.507 (0.28), 3.534 (0.34), 3.544 (0.34), 3.651 (0.62), 3.673 (0.56), 3.681 (0.68), 3.702 (0.51), 3.711 (0.56), 3.749 (0.34), 3.792 (0.23), 3.815 (0.34), 3.841 (0.68), 3.889 (0.39), 3.919 (0.39), 3.948 (0.34), 5.029 (0.68), 5.068 (0.45), 5.081 (0.85), 5.185 (0.51), 5.224 (2.14), 5.239 (1.52), 5.245 (1.86), 5.285 (0.73), 5.417 (0.51), 5.541 (0.28), 7.928 (0.96), 7.948 (2.93), 7.965 (1.52), 7.987 (0.51), 8.535 (0.45), 8.699 (1.75).

Intermediate 423

(5S)-2-{[3-Chloro-5-(trifluoromethyl)pyridin-2-yl]methyl}-5-{[(3S)-3-fluoropyrrolidin-1-yl]carbonyl}-6,7-dihydro[1,2,4]triazolo[4,3-a]pyridine-3,8(2H,5H)-dione

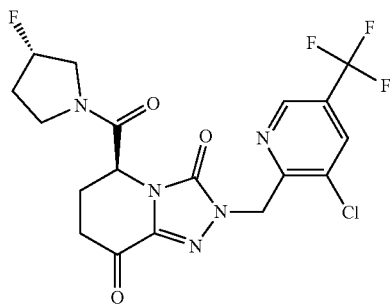 [SMILES: O=C1CC[C@@H](C(=O)N2CC[C@H](F)C2)n2c1nn(Cc1ncc(C(F)(F)F)cc1Cl)c2=O]

(5S,8SR)-2-{[3-Chloro-5-(trifluoromethyl)pyridin-2-yl]methyl}-5-{[(3S)-3-fluoropyrrolidin-1-yl]carbonyl}-8-hydroxy-5,6,7,8-tetrahydro[1,2,4]triazolo[4,3-a]pyridin-3(2H)-one (diastereomer mixture; 2 isomers) (93.0 mg, 201 µmol) was dissolved in dichloromethane (2.0 ml), and manganese(IV) oxide (349 mg, 4.01 mmol) was added at room temperature. The reaction mixture was stirred at room temperature overnight. The suspension was filtered through Celite and the filtrate was concentrated under reduced pressure. 75.5 mg (82% of theory) of the title compound were obtained.

LC-MS (Method 3): $R_t$=1.39 min; MS (ESIpos): m/z=462 [M+H]$^+$

Working Examples

Example 1

(5RS)-5-(Pyrrolidin-1-ylcarbonyl)-2-[4-(trifluoromethyl)benzyl]-5,6,7,8-tetrahydro[1,2,4]triazolo[4,3-a]pyridin-3(2H)-one (racemate)

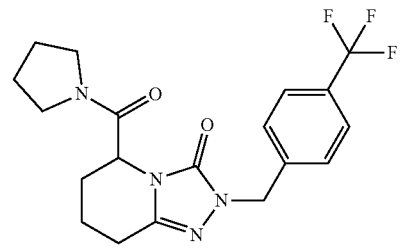 [SMILES: O=C(C1CCCc2nn(Cc3ccc(C(F)(F)F)cc3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (70.0 mg, 296 µmol) was dissolved in 5.0 ml of acetonitrile, then caesium carbonate (145 mg, 444 µmol) and 1-(bromomethyl)-4-(trifluoromethyl)benzene (85.0 mg, 356 µmol) was added and the mixture was stirred at room temperature overnight. For workup, the mixture was stirred with 1 ml of water and separated via preparative HPLC (GromSil 120 ODS-4HE, 250×30 mm 10 µm. Flow rate: 50 ml/min. Gradient (A=water+0.1% formic acid, B=acetonitrile): 0 min 0% B, 6 min 10% B, 27 min 95% B, 38 min 95% B, 40 min 0% B. Run time per separation 40 min. Detection: 210 nm). The product fractions were combined, concentrated and lyophilized. In this way, 92 mg (79% of theory) of the title compound were obtained.

LC-MS (Method 3): $R_t$=1.52 min; MS (ESIpos): m/z=395 [M+H]$^+$

1H-NMR (400 MHz, DMSO-d6): δ [ppm]=1.61-1.84 (m, 4H), 1.86-2.11 (m, 4H), 2.45-2.68 (m, 2H, partially covered by solvent signal), 3.21-3.41 (m, 2H, partially overlapped by water signal), 3.47 (dt, 1H), 3.62 (dt, 1H), 4.75 (dd, 1H), 4.92 (s, 2H), 7.41-7.47 (m, 2H), 7.68-7.74 (m, 2H).

Example 2

(5RS)-2-(4-tert-Butylbenzyl)-5-(pyrrolidin-1-ylcarbonyl)-5,6,7,8-tetrahydro[1,2,4]triazolo[4,3-a]pyridin-3(2H)-one (Racemate)

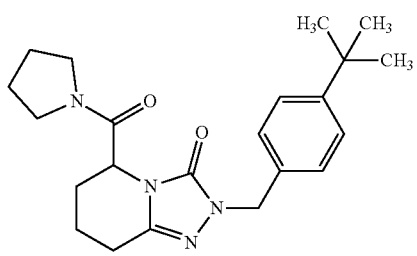 [SMILES: CC(C)(C)c1ccc(Cn2nc3n(c2=O)C(C(=O)N2CCCC2)CCC3)cc1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 μmol) was dissolved in 3.0 ml of acetonitrile, then caesium carbonate (103 mg, 317 μmol) and 1-(bromomethyl)-4-tert-butylbenzene (47 μl, 250 μmol) was added and the mixture was stirred at room temperature overnight. For workup, the mixture was stirred with 1 ml of water and separated via preparative HPLC (GromSil 120 ODS-4HE, 250×30 mm 10 μm. Flow rate: 50 ml/min. Gradient (A=water+0.1% formic acid, B=acetonitrile): 0 min 0% B, 6 min 10% B, 27 min 95% B, 38 min 95% B, 40 min 0% B. Run time per separation 40 min. Detection: 210 nm). The product fractions were combined, concentrated and lyophilized. In this way, 63 mg (81% of theory) of the title compound were obtained.

LC-MS (Method 3): $R_t$=1.75 min; MS (ESIpos): m/z=383 [M+H]$^+$ $^1$H-NMR (400 MHz, DMSO-d$_6$): δ [ppm]=1.26 (s, 9H), 1.61-1.84 (m, 4H), 1.87-2.10 (m 4H), 2.46-2.65 (m, 2H, partially covered by solvent signal), 3.21-3.41 (m, 2H, partially overlapped by water signal), 3.47 (dt, 1H), 3.62 (dt, 1H), 4.70-4.73 (m, 3H), 7.13-7.18 (m, 2H), 7.31-7.37 (m, 2H).

Example 3

(5RS)-2-[(1 RS)-1-(4-Chlorophenyl)ethyl]-5-(pyrrolidin-1-ylcarbonyl)-5,6,7,8-tetrahydro[1,2,4]triazolo[4,3-a]pyridin-3(2H)-one (Diastereomer Mixture; 4 Isomers)

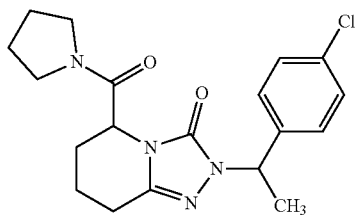

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 μmol) was dissolved in 3.0 ml of acetonitrile, then caesium carbonate (103 mg, 317 μmol) and 1-[(1RS)-1-bromoethyl]-4-chlorobenzene (racemate) (55.7 mg, 254 μmol) was added and the mixture was stirred at room temperature overnight. For workup, the mixture was stirred with 1 ml of water and separated via preparative HPLC (GromSil 120 ODS-4HE, 250×30 mm 10 μm. Flow rate: 50 ml/min. Gradient (A=water+0.1% formic acid, B=acetonitrile): 0 min 0% B, 6 min 10% B, 27 min 95% B, 38 min 95% B, 40 min 0% B. Run time per separation 40 min. Detection: 210 nm). The product fractions were combined, concentrated and lyophilized. In this way, 56 mg (71% of theory) of the title compound were obtained as a diastereomer mixture.

LC-MS (Method 3): $R_t$=1.52 min; MS (ESIpos): m/z=375 [M+H]$^+$ $^1$H-NMR (400 MHz, DMSO-d$_6$): δ [ppm]=1.57-1.64 (m, 3H), 1.64-1.82 (m, 4H), 1.86-2.10 (m, 4H), 2.50-2.69 (m, 2H, partially covered by solvent signal), 3.18-3.39 (m, 2H, partially overlapped by water signal), 3.41-3.50 (m, 1H), 3.56-3.65 (m, 1H), 4.67-4.75 (td, 1H), 5.25-5.33 (m, 1H), 7.28-7.41 (m, 4H).

In a further batch of the same title compound, (5RS)-2-[(1RS)-1-(4-chlorophenyl)ethyl]-3-oxo-2,3,5,6,7,8-hexahydro[1,2,4]triazolo[4,3-a]pyridine-5-carboxylic acid (diastereomer mixture; 4 isomers) (392 mg, 90% purity, 1.10 mmol) were dissolved in 12 ml of THF. Triethylamine (310 μl, 2.2 mmol), HATU (542 mg, 1.43 mmol) and pyrrolidine (110 μl, 1.3 mmol) were added and the mixture was stirred under argon at room temperature for 2 h. For workup, the mixture was diluted with water and then substantially concentrated under reduced pressure. The residue was taken up in ethyl acetate/water. After extraction and removal of the organic phase, the aqueous phase was extracted twice more with ethyl acetate. The organic phases were washed with saturated aqueous sodium chloride solution and dried over sodium sulphate. The residue that remained after concentration and drying under reduced pressure was dissolved in acetonitrile/water and separated in 2 batches via preparative HPLC (column: Kromasil C18, 125×30 mm, 10 μm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). The combined product-containing fractions were concentrated under reduced pressure and dried.

In this way, 293 mg 56 mg (98% purity, 70% of theory) of the title compound were obtained as a racemic diastereomer mixture.

Example 4

(5RS)-2-[(1 RS)-1-(4-Chlorophenyl)ethyl]-5-(pyrrolidin-1-ylcarbonyl)-5,6,7,8-tetrahydro[1,2,4]triazolo[4,3-a]pyridin-3(2H)-one (Isomer 3)

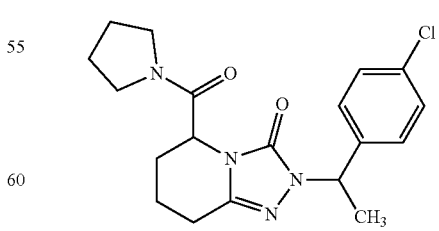

(5RS)-2-[(1 RS)-1-(4-Chlorophenyl)ethyl]-5-(pyrrolidin-1-ylcarbonyl)-5,6,7,8-tetrahydro[1,2,4]triazolo[4,3-a]pyridin-3(2H)-one (diastereomer mixture; 4 isomers) was separated by two preparative liquid chromatography operations on a chiral phase. Firstly, stereoisomer 4 was separated by preparative liquid chromatography on a chiral phase [sample preparation: 392 mg dissolved in 10 ml of ethanol; injection volume: 2.0 ml; column: Daicel Chiralcel® OX-H 5 µm, 250×50 mm; eluent: ethanol, flow rate: 15.0 ml/min; temperature 50° C.; UV detection: 220 nm]. This gave 61 mg of the stereoisomer 4 which elutes last.

In the second step, the combined fractions of the remaining three stereoisomers were dissolved and separated again [sample in 10 ml of ethanol; injection volume: 0.4 ml; column: Daicel Chiralcel® OX-H 5 µm, 250×50 mm; eluent: water/ethanol:isocratic 50% ethanol; flow rate: 15.0 ml/min; temperature 50° C.; UV detection: 220 nm]. This gave, in the sequence of elution, 51 mg of isomer 1, 62 mg of isomer 2 and 53 mg of isomer 3.

Isomer 3:

Specific rotation: −145.16 (589 nm, 0.2450 g/100 cm³ MeOH)

Analytical chiral HPLC: $R_t$=4.74 min, d.e./e.e. =100% [column: Daicel Chiralcel® OX-H 250×4.6 mm; eluent: ethanol; flow rate: 1 ml/min; 50° C.; UV detection: 220 nm].

LC-MS (Method 4): $R_t$=0.82 min; MS (ESIpos): m/z=375 [M+H]$^+$ $^1$H-NMR (500 MHz, DMSO-d$_6$): b [ppm]=1.61 (d, 3H), 1.68-1.74 (m, 2H); 1.74-1.83 (m, 2H), 1.87-1.98 (m, 3H), 1.98-2.07 (m, 1H), 2.50-2.59 (m, 1H, partially covered by solvent signal), 2.65 (dt, 1H), 3.21-3.39 (m, 2H, partially overlapped by water signal), 3.45 (dt, 1H), 3.60 (dt, 1H), 4.70 (dd, 1H), 5.28 (q, 1H), 7.30-7.34 (m, 2H), 7.36-7.40 (m, 2H).

Example 5

(5RS)-2-[(1 RS)-1-(4-Chlorophenyl)ethyl]-5-(pyrrolidin-1-ylcarbonyl)-5,6,7,8-tetrahydro[1,2,4]triazolo[4,3-a]pyridin-3(2H)-one (Isomer 4)

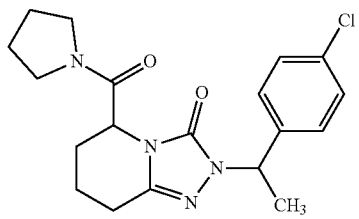 [SMILES: CC(c1ccc(Cl)cc1)n1nc2n(c1=O)C(C(=O)N1CCCC1)CCC2]

(5RS)-2-[(1 RS)-1-(4-Chlorophenyl)ethyl]-5-(pyrrolidin-1-ylcarbonyl)-5,6,7,8-tetrahydro[1,2,4]triazolo[4,3-a]pyridin-3(2H)-one (diastereomer mixture; 4 isomers) was separated by two preparative liquid chromatography operations on a chiral phase. Firstly, stereoisomer 4 was separated by preparative liquid chromatography on a chiral phase [sample preparation: 392 mg dissolved in 10 ml of ethanol; injection volume: 2.0 ml; column: Daicel Chiralcel® OX-H 5 µm, 250×50 mm; eluent: ethanol, flow rate: 15.0 ml/min; temperature 50° C.; UV detection: 220 nm]. This gave 61 mg of the stereoisomer 4 which elutes last.

In the second step, the combined fractions of the remaining three stereoisomers were dissolved and separated again [sample in 10 ml of ethanol; injection volume: 0.4 ml; column: Daicel Chiralcel® OX-H 5 µm, 250×50 mm; eluent: water/ethanol:isocratic 50% ethanol; flow rate: 15.0 ml/min; temperature 50° C.; UV detection: 220 nm]. This gave, in the sequence of elution, 51 mg of isomer 1, 62 mg of isomer 2 and 53 mg of isomer 3.

Isomer 4:

Analytical chiral HPLC: $R_t$=12.6 min, d.e./e.e. =100% [column: Daicel Chiralcel® OX-H 250×4.6 mm; eluent: ethanol; flow rate: 1 ml/min; 50° C.; UV detection: 220 nm].

Specific rotation: +134.80 (589 nm, 0.2500 g/100 cm³ MeOH)

LC-MS (Method 4): $R_t$=0.81 min; MS (ESIpos): m/z=375 [M+H]$^+$

1H-NMR (500 MHz, DMSO-d6): 5 [ppm]=1.60 (d, 3H), 1.63-1.82 (m, 4H), 1.85-2.09 (m, 4H), 2.50-2.61 (m, 1H, partially covered by solvent signal), 2.65 (dt, 1H), 3.23 (dt, 1H), 3.28-3.36 (m, 1H, partially overlapped by water signal), 3.45 (dt, 1H), 3.60 (dt, 1H), 4.72 (dd, 1H), 5.29 (q, 1H), 7.29-7.33 (m, 2H), 7.37-7.41 (m, 2H).

Example 6

(5RS)-2-[4-(Methylsulphonyl)benzyl]-5-(pyrrolidin-1-ylcarbonyl)-5,6,7,8-tetrahydro[1,2,4]triazolo[4,3-a]pyridin-3(2H)-one (Racemate)

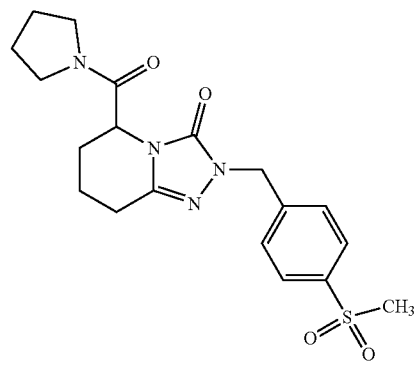 [SMILES: CS(=O)(=O)c1ccc(Cn2nc3n(c2=O)C(C(=O)N2CCCC2)CCC3)cc1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 µmol) was dissolved in 3.0 ml of acetonitrile, then caesium carbonate (103 mg, 317 µmol) and 1-(bromomethyl)-4-(methylsulphonyl)benzene (68.5 mg, 275 µmol) was added and the mixture was stirred at room temperature under argon overnight. For workup, the mixture was stirred with 1 ml of water and separated via preparative HPLC (GromSil 120 ODS-4HE, 250×30 mm 10 µm. Flow rate: 50 ml/min. Gradient (A=water+0.1% formic acid, B=acetonitrile): 0 min 0% B, 6 min 10% B, 27 min 95% B, 38 min 95% B, 40 min 0% B. Run time per separation 40 min. Detection: 210 nm). The product fractions were combined, concentrated and lyophilized. In this way, 71 mg (82% of theory) of the title compound were obtained.

LC-MS (Method 3): $R_t$=0.96 min; MS (ESIpos): m/z=405 [M+H]$^+$

1H-NMR (400 MHz, DMSO-d6): 5 [ppm]=1.61-1.84 (m, 4H), 1.87-2.12 (m, 4H), 2.47-2.69 (m, 2H, partially covered by solvent signal), 3.20 (s, 3H), 3.22-3.40 (m, 2H, partially overlapped by water signal), 3.47 (dt, 1H), 3.62 (dt, 1H), 4.76 (dd, 1H), 4.94 (s, 2H), 7.45-7.51 (m, 2H), 7.87-7.92 (m, 2H).

Example 7

(5RS)-2-[4-(Difluoromethoxy)benzyl]-5-(pyrrolidin-1-ylcarbonyl)-5,6,7,8-tetrahydro[1,2,4]triazolo[4,3-a]pyridin-3(2H)-one (Racemate)

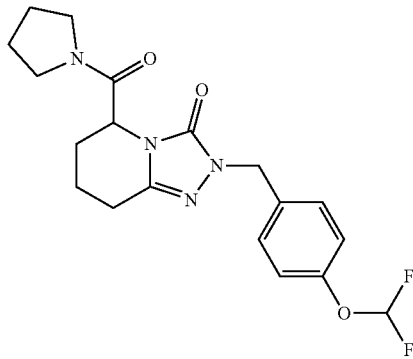 [SMILES: O=C(C1CCCc2nn(Cc3ccc(OC(F)F)cc3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 µmol) was dissolved in 3.0 ml of acetonitrile, then caesium carbonate (103 mg, 317 µmol) and 1-(bromomethyl)-4-(difluoromethoxy)benzene (60.2 mg, 254 µmol) was added and the mixture was stirred at room temperature under argon overnight. For workup, the mixture was stirred with 1 ml of water and separated via preparative HPLC (GromSil 120 ODS-4HE, 250×30 mm 10 µm. Flow rate: 50 ml/min. Gradient (A=water+0.1% formic acid, B=acetonitrile): 0 min 0% B, 6 min 10% B, 27 min 95% B, 38 min 95% B, 40 min 0% B. Run time per separation 40 min. Detection: 210 nm). The product fractions were combined, concentrated and lyophilized. The product obtained was purified for a second time by preparative HPLC as above. In this way, after reconcentration and lyophilization, 29 mg (35% of theory) of the title compound were obtained.

LC-MS (Method 6): $R_t$=1.39 min; MS (ESIpos): m/z=393 [M+H]$^+$

1H-NMR (400 MHz, DMSO-d6): δ [ppm]=1.61-1.84 (m, 4H), 1.87-2.11 (m, 4H), 2.46-2.66 (m, 2H, partially covered by solvent signal), 3.21-3.40 (m, 2H, partially overlapped by water signal), 3.47 (dt, 1H), 3.62 (dt, 1H), 4.73 (dd, 1H), 4.80 (s, 2H), 7.11-7.17 (m, 2H), 7.20 (s, 1H) 7.25-7.31 (m, 2H).

Example 8

(5RS)-2-(3-Methylbenzyl)-5-(pyrrolidin-1-ylcarbonyl)-5,6,7,8-tetrahydro[1,2,4]triazolo[4,3-a]pyridin-3(2H)-one (Racemate)

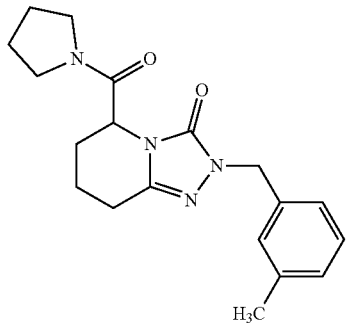 [SMILES: Cc1cccc(Cn2nc3n(c2=O)C(C(=O)N2CCCC2)CCC3)c1]

(5RS)-5-(Pyrrolidin-1-ylcarbonyl)-5,6,7,8-tetrahydro[1,2,4]triazolo[4,3-a]pyridin-3(2H)-one (racemate) (45.0 mg, 190 µmol) and caesium carbonate (93.1 mg, 286 mol) were suspended in 3.0 ml of acetonitrile, then 1-(bromomethyl)-3-methylbenzene (31 µl, 230 µmol) was added and the mixture was stirred at room temperature at first for 2 h, then further overnight. For workup, the mixture was diluted with ethyl acetate and water, and the organic phase was removed. The aqueous phase was extracted twice more with ethyl acetate. The combined organic phases were washed with saturated aqueous sodium chloride solution, and then dried over sodium sulphate. The residue obtained after filtration and concentration under reduced pressure was dissolved in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). The product fractions were combined, concentrated and lyophilized, and subjected to further drying under reduced pressure. In this way, 35.1 mg (54% of theory) of the title compound were obtained.

LC-MS (Method 4): $R_t$=0.77 min; MS (ESIpos): m/z=341 [M+H]$^+$ $^1$H-NMR (500 MHz, DMSO-d$_6$): b [ppm]=1.63-1.84 (m, 4H), 1.88-2.09 (m, 4H), 2.28 (s, 3H), 2.45-2.65 (m, 2H, partially covered by solvent signal), 3.26 (dt, 1H) 3.36 (dt, 1H) 3.40-3.66 (m, 2H, partially overlapped by water signal), 4.70-4.79 (m, 3H), 6.99-7.10 (m, 3H), 7.21 (t, 1H).

Example 9

(5RS)-2-[4-(3-Methyl-1,2,4-oxadiazol-5-yl)benzyl]-5-(pyrrolidin-1-ylcarbonyl)-5,6,7,8-tetrahydro[1,2,4]triazolo[4,3-a]pyridin-3(2H)-one (Racemate)

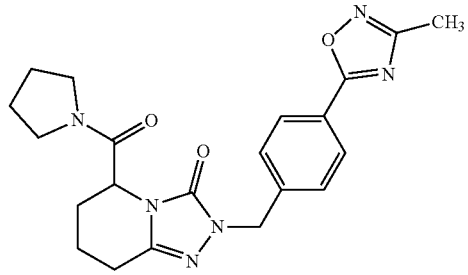 [SMILES: Cc1noc(-c2ccc(Cn3nc4n(c3=O)C(C(=O)N3CCCC3)CCC4)cc2)n1]

(5RS)-5-(Pyrrolidin-1-ylcarbonyl)-5,6,7,8-tetrahydro[1,2,4]triazolo[4,3-a]pyridin-3(2H)-one (racemate) (55.0 mg, 233 µmol) and caesium carbonate (114 mg, 349 µmol) were suspended in 3.0 ml of acetonitrile, then 5-[4-(bromomethyl)phenyl]-3-methyl-1,2,4-oxadiazole (70.7 mg, 279 µmol) was added and the mixture was stirred at room temperature at first for 2 h, then further overnight. For workup, the precipitate present was filtered off with suction and washed with acetonitrile. The filtrate was concentrated, taken up in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). The product fractions were combined, concentrated and dried under reduced pressure. In this way, 42.0 mg (44% of theory) of the title compound were obtained.

LC-MS (Method 3): $R_t$=1.26 min; MS (ESIpos): m/z=409 [M+H]$^+$ $^1$H-NMR (400 MHz, DMSO-d$_6$): b [ppm]=1.64-1.85 (m, 4H), 1.88-2.12 (m, 4H), 2.42 (s, 3H), 2.45-2.70 (m, 2H, partially covered by solvent signal), 3.20-3.57 (m, 3H, partially overlapped by water signal), 3.63 (dt, 1H), 4.73-4.78 (m, 1H), 4.93 (s, 2H), 7.44-7.48 (m, 2H), 8.04-8.08 (m, 2H).

Example 10

(5RS)-2-[4-(5-Methyl-1,2,4-oxadiazol-3-yl)benzyl]-5-(pyrrolidin-1-ylcarbonyl)-5,6,7,8-tetrahydro[1,2,4]triazolo[4,3-a]pyridin-3(2H)-one (Racemate)

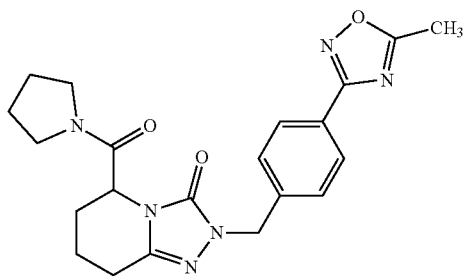 [SMILES: Cc1nc(-c2ccc(Cn3nc4n(c3=O)C(C(=O)N3CCCC3)CCC4)cc2)no1]

(5RS)-5-(Pyrrolidin-1-ylcarbonyl)-5,6,7,8-tetrahydro[1,2,4]triazolo[4,3-a]pyridin-3(2H)-one (racemate) (60.0 mg, 254 µmol) and caesium carbonate (124 mg, 381 µmol) were suspended in 3.0 ml of acetonitrile, then 5-[4-(bromomethyl)phenyl]-3-methyl-1,2,4-oxadiazole (70.7 mg, 279 µmol) was added and the mixture was stirred at room temperature over a weekend. For workup, the precipitate present was filtered off with suction and the filtrate was concentrated. Drying under reduced pressure was followed by purification by chromatography (instrument: Waters Prep LC/MS System, column: Phenomenex Kinetex C18 5 µm 100×30 mm; eluent A: water, eluent B: acetonitrile, flow rate: 65 ml/min plus 5 ml of 2% formic acid in water, room temperature, wavelength 200-400 nm, at-column injection (complete injection); gradient profile: 0 to 2 min 10% eluent B, 2 to 2.2 min to 20% eluent B, 2.2 to 7 min to 60% eluent B, 7 to 7.5 min to 92% eluent B, 7.5 to 9 min at 92% B). The product fraction was lyophilized. This gave 57.6 mg (54% of theory) of the title compound.

LC-MS (Method 3): $R_t$=1.18 min; MS (ESIpos): m/z=409 [M+H]$^+$ $^1$H-NMR (400 MHz, DMSO-d$_6$): b [ppm]=1.62-1.85 (m, 4H), 1.88-2.12 (m, 4H), 2.48-2.72 (m, 2H, partially covered by solvent signal), 2.86 (s, 3H), 3.22-3.41 (m, 2H, partially overlapped by water signal), 3.47 (dt, 1H), 3.63 (dt, 1H), 4.76 (dd, 1H), 4.84-4.95 (m, 2H), 7.38-7.43 (m, 2H), 7.93-7.98 (m, 2H).

Example 11

(5RS)-2-(2,3-Dihydro-1H-inden-5-ylmethyl)-5-(pyrrolidin-1-ylcarbonyl)-5,6,7,8-tetrahydro[1,2,4]triazolo[4,3-a]pyridin-3(2H)-one (Racemate)

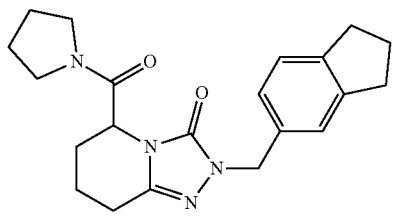 [SMILES: O=C(C1CCCc2nn(Cc3ccc4c(c3)CCC4)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (75.4 mg, 316 µmol) and caesium carbonate (154 mg, 474 µmol) were suspended in 3.0 ml of acetonitrile, then 5-(bromomethyl)indane (100 mg, about 80% purity, about 379 µmol) was added, the mixture was stirred at room temperature for 1.5 h and then left to stand over a weekend at room temperature. For further conversion, caesium carbonate (206 mg, 632 µmol) and 5-(bromomethyl)indane (100 mg, about 80% purity, about 379 µmol) were added once again and the mixture was stirred at room temperature for 4 h. For workup, the precipitate present was filtered off with suction and discarded. The filtrate was concentrated, taken up in acetonitrile/DMSO/water and separated via preparative HPLC (column: Kromasil C18, 250×30 mm, 10 µm, eluent: acetonitrile (B)/water+0.1% TFA (A), gradient: 0 min 90% A, 6 min 90% A, 27 min 5% A, 38 min 5% A, 38 min 5% A, 39 min 90% A; flow rate: 50 ml/min, detector: 210 nm). Product-containing fractions were combined, concentrated and dried under reduced pressure. In this way, 77.2 mg (67% of theory) of the title compound were obtained.

LC-MS (Method 4): $R_t$=0.82 min; MS (ESIpos): m/z=367 [M+H]$^+$ $^1$H-NMR (400 MHz, DMSO-d$_6$): b [ppm]=1.64-1.74 (m, 2H), 1.79 (quint; 2H) 1.88-2.09 (m, 6H), 2.46-2.64 (m, 2H, partially covered by solvent signal), 2.81 (t, 4H), 3.25 (dt, 1H), 3.36 (dt, 1H), 3.42-3.68 (m, 2H, partially overlapped by water signal), 4.67-4.79 (m, 3H), 6.99 (d, 1H), 7.09 (s, 1H), 7.16 (d, 1H).

Example 12

(5RS)-2-[(5-Methyl-1,2,4-oxadiazol-3-yl)methyl]-5-(pyrrolidin-1-ylcarbonyl)-5,6,7,8-tetrahydro[1,2,4]triazolo[4,3-a]pyridin-3(2H)-one (Racemate)

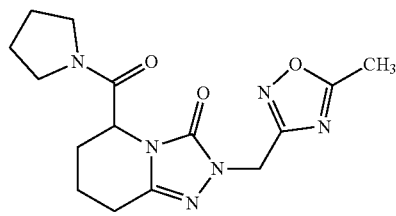 [SMILES: Cc1nc(Cn2nc3n(c2=O)C(C(=O)N2CCCC2)CCC3)no1]

(5RS)-5-(Pyrrolidin-1-ylcarbonyl)-5,6,7,8-tetrahydro[1,2,4]triazolo[4,3-a]pyridin-3(2H)-one (racemate) (30.0 mg, 127 µmol) was initially charged in acetonitrile (2.0 ml). Caesium carbonate (62.1 mg, 190 µmol) and 3-(bromomethyl)-5-methyl-1,2,4-oxadiazole (23.6 mg, 133 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 19.0 mg (45% of theory) of the title compound were obtained.

LC-MS (Method 4): $R_t$=0.48 min; MS (ESIpos): m/z=333 [M+H]$^+$ $^1$H-NMR (500 MHz, DMSO-d6) δ [ppm]: 1.701 (0.70), 1.713 (0.92), 1.717 (0.99), 1.727 (0.86), 1.776 (1.37), 1.789

(2.33), 1.803 (1.73), 1.817 (0.51), 1.899 (0.57), 1.913 (1.61), 1.926 (2.10), 1.940 (1.46), 1.952 (0.51), 1.969 (0.52), 1.979 (0.49), 2.023 (0.40), 2.040 (0.41), 2.052 (0.41), 2.518 (0.65), 2.522 (0.41), 2.568 (3.66), 2.573 (16.00), 2.590 (1.04), 2.598 (1.52), 2.866 (2.48), 3.247 (0.78), 3.256 (0.75), 3.260 (0.64), 3.270 (1.32), 3.284 (1.11), 3.310 (3.45), 3.324 (2.02), 3.338 (1.66), 3.348 (0.84), 3.352 (0.93), 3.362 (0.92), 3.376 (0.44), 3.460 (0.74), 3.466 (0.54), 3.474 (0.47), 3.480 (0.91), 3.494 (0.41), 3.599 (0.41), 3.613 (0.84), 3.619 (0.43), 3.626 (0.48), 3.633 (0.70), 4.494 (1.93), 4.720 (0.77), 4.727 (0.88), 4.732 (0.99), 4.740 (0.78), 4.857 (1.33), 4.889 (3.17), 4.928 (3.18), 4.960 (1.36).

Example 13

(5RS)-2-[(3-Methyl-1,2-oxazol-5-yl)methyl]-5-(pyrrolidin-1-ylcarbonyl)-5,6,7,8-tetrahydro[1,2,4]triazolo[4,3-a]pyridin-3(2H)-one (Racemate)

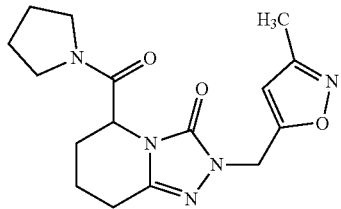 [SMILES: Cc1cc(Cn2nc3n(c2=O)C(C(=O)N2CCCC2)CCC3)on1]

(5RS)-5-(Pyrrolidin-1-ylcarbonyl)-5,6,7,8-tetrahydro[1,2,4]triazolo[4,3-a]pyridin-3(2H)-one (racemate) (40.0 mg, 169 µmol) was initially charged in acetonitrile (2.0 ml). Caesium carbonate (82.7 mg, 254 µmol) and 5-(bromomethyl)-3-methyl-1,2-oxazole (32.8 mg, 186 µmol) were subsequently added. After stirring at room temperature for 2 days, the reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 18.6 mg (33% of theory) of the title compound were obtained.

LC-MS (Method 3): $R_t$=0.89 min; MS (ESIpos): m/z=332 [M+H]$^+$ $^1$H-NMR (400 MHz, DMSO-d6) δ [ppm]: −0.008 (0.87), 0.008 (0.76), 1.686 (0.49), 1.709 (0.99), 1.720 (1.17), 1.732 (0.87), 1.753 (0.57), 1.772 (1.53), 1.789 (2.62), 1.806 (2.01), 1.822 (0.60), 1.892 (0.62), 1.909 (1.85), 1.925 (2.33), 1.942 (1.50), 1.959 (0.66), 1.972 (0.52), 1.983 (0.78), 1.995 (0.71), 2.004 (0.63), 2.014 (0.50), 2.019 (0.48), 2.030 (0.68), 2.039 (0.56), 2.046 (0.46), 2.055 (0.49), 2.201 (16.00), 2.215 (0.69), 2.417 (0.49), 2.523 (1.09), 2.565 (0.86), 2.580 (0.74), 2.590 (0.68), 2.602 (1.21), 2.615 (0.66), 2.643 (0.48), 3.242 (0.75), 3.254 (0.74), 3.271 (1.33), 3.288 (0.70), 3.322 (0.97), 3.339 (1.33), 3.351 (0.50), 3.357 (0.70), 3.369 (0.78), 3.454 (0.86), 3.462 (0.63), 3.471 (0.53), 3.479 (1.08), 3.496 (0.47), 3.589 (0.50), 3.606 (1.03), 3.614 (0.52), 3.623 (0.59), 3.631 (0.79), 3.703 (0.42), 4.495 (0.41), 4.510 (0.41), 4.723 (0.92), 4.732 (1.05), 4.738 (1.20), 4.747 (0.90), 4.940 (4.70), 4.982 (0.54), 6.223 (3.16).

Example 14

(5RS)-2-[3-Fluoro-4-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

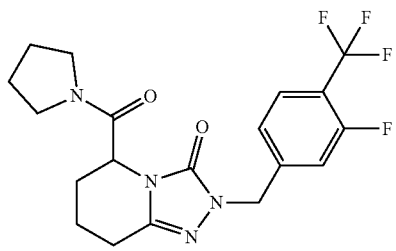 [SMILES: O=C(C1CCCc2nn(Cc3ccc(C(F)(F)F)c(F)c3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (40.0 mg, 169 µmol) was initially charged in acetonitrile (2.0 ml). Caesium carbonate (82.7 mg, 254 µmol) and 4-(bromomethyl)-2-fluoro-1-(trifluoromethyl)benzene (47.9 mg, 186 µmol) were subsequently added. After stirring for 48 h, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. 48.9 mg (70% of theory) of the title compound were obtained.

LC-MS (Method 3): $R_t$=1.55 min; MS (ESIpos): m/z=413 [M+H]

$^1$H-NMR (400 MHz, DMSO-d6) δ[ppm]: −0.008 (3.00), 0.008 (1.79), 1.235 (0.49), 1.681 (1.63), 1.695 (1.81), 1.706 (1.87), 1.719 (2.35), 1.731 (2.76), 1.743 (2.21), 1.756 (2.58), 1.774 (5.53), 1.792 (8.57), 1.809 (6.54), 1.819 (2.30), 1.826 (3.06), 1.837 (3.80), 1.845 (1.54), 1.854 (1.49), 1.893 (2.04), 1.910 (5.29), 1.926 (6.37), 1.943 (3.93), 1.960 (1.38), 1.975 (1.13), 1.987 (1.15), 2.000 (1.81), 2.020 (3.43), 2.045 (1.84), 2.056 (1.54), 2.063 (1.50), 2.071 (1.41), 2.080 (0.76), 2.091 (0.52), 2.327 (0.60), 2.519 (4.26), 2.563 (2.70), 2.573 (2.53), 2.588 (2.17), 2.602 (2.17), 2.614 (3.60), 2.626 (2.07), 2.644 (1.03), 2.656 (1.47), 2.669 (1.30), 2.710 (0.51), 3.097 (1.58), 3.233 (1.25), 3.250 (2.51), 3.262 (2.74), 3.279 (4.78), 3.297 (3.97), 3.328 (2.43), 3.346 (4.21), 3.358 (1.68), 3.364 (2.26), 3.376 (2.38), 3.393 (1.08), 3.443 (1.37), 3.460 (2.81), 3.468 (2.17), 3.478 (1.79), 3.485 (3.40), 3.502 (1.52), 3.593 (1.77), 3.610 (3.23), 3.618 (1.80), 3.627 (1.95), 3.635 (2.43), 3.652 (1.15), 3.711 (0.75), 4.755 (3.09), 4.764 (3.43), 4.769 (4.01), 4.779 (2.85), 4.948 (16.00), 4.985 (0.48), 7.248 (3.78), 7.268 (4.07), 7.296 (3.67), 7.326 (3.62), 7.755 (2.93), 7.775 (5.28), 7.794 (2.72).

Example 15

(5RS)-2-[(2-Methylpyridin-4-yl)methyl]-5-(pyrrolidin-1-ylcarbonyl)-5,6,7,8-tetrahydro[1,2,4]triazolo[4,3-a]pyridin-3(2H)-one (Racemate)

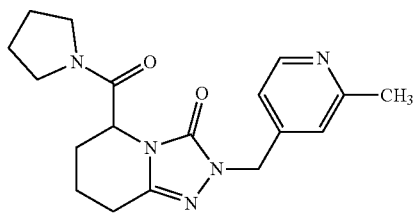 [SMILES: Cc1cc(Cn2nc3n(c2=O)C(C(=O)N2CCCC2)CCC3)ccn1]

(5RS)-5-(Pyrrolidin-1-ylcarbonyl)-5,6,7,8-tetrahydro[1,2,4]triazolo[4,3-a]pyridin-3(2H)-one (40.0 mg, 169 µmol) was initially charged in acetonitrile (2.0 ml). Caesium carbonate (82.7 mg, 254 µmol) and 4-(chloromethyl)-2-methylpyridine hydrochloride (33.2 mg, 186 µmol) were subsequently added. The reaction mixture was stirred at room temperature overnight and further at 85° C. for 24 h. After cooling to room temperature, water and ethyl acetate were added to the reaction mixture. The organic phase was removed and the aqueous phase was extracted three times with ethyl acetate. The aqueous phases were adjusted to pH 7 with sodium hydrogencarbonate. The solvent was removed under reduced pressure and the residue was suspended in ethanol. The mixture was filtered and the filtrate was concentrated. 51.6 mg (94% purity, 84% of theory) of the title compound were obtained.

LC-MS (Method 3): $R_t$=0.51 min; MS (ESIpos): m/z=342 [M+H]

$^1$H-NMR (400 MHz, DMSO-d6) δ[ppm]: −0.149 (1.03), −0.008 (8.61), 0.008 (8.84), 0.146 (0.99), 1.038 (4.77), 1.055 (9.73), 1.072 (4.87), 1.355 (0.51), 1.679 (0.92), 1.692 (1.03), 1.704 (0.90), 1.763 (1.74), 1.780 (3.17), 1.797 (5.03), 1.814 (3.79), 1.833 (1.56), 1.912 (1.91), 1.920 (2.09), 1.927 (2.48), 1.935 (2.30), 1.945 (1.86), 1.952 (1.54), 2.055 (2.57), 2.328 (1.26), 2.366 (0.94), 2.523 (4.09), 2.568 (1.54), 2.583 (1.35), 2.594 (1.42), 2.609 (1.19), 2.618 (1.26), 2.629 (1.81), 2.642 (1.29), 2.673 (16.00), 2.698 (2.66), 2.710 (1.22), 3.087 (0.44), 3.247 (0.78), 3.264 (1.52), 3.277 (1.38), 3.293 (2.27), 3.310 (1.08), 3.335 (1.19), 3.352 (2.36), 3.370 (1.38), 3.382 (1.33), 3.399 (0.76), 3.413 (1.97), 3.431 (5.39), 3.449 (5.39), 3.459 (1.01), 3.466 (2.18), 3.476 (1.77), 3.484 (1.45), 3.501 (2.20), 3.518 (1.19), 3.593 (1.65), 3.610 (2.43), 3.626 (1.86), 3.634 (2.11), 3.652 (1.56), 3.725 (1.54), 4.020 (1.93), 4.753 (0.46), 4.791 (1.58), 4.805 (2.59), 4.815 (1.52), 4.930 (0.85), 5.057 (0.48), 5.101 (4.04), 5.112 (3.93), 5.157 (0.48), 7.543 (1.58), 7.555 (1.61), 7.575 (2.75), 7.833 (0.57), 8.664 (0.57), 8.679 (0.73), 8.703 (2.85), 8.717 (2.53).

Example 16

(5RS)-2-(3-Fluorobenzyl)-5-(pyrrolidin-1-ylcarbonyl)-5,6,7,8-tetrahydro[1,2,4]triazolo[4,3-a]pyridin-3(2H)-one (Racemate)

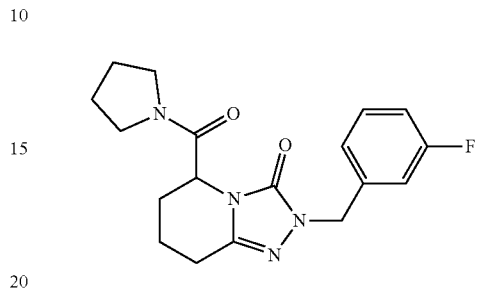

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 µmol) was initially charged in acetonitrile (3.0 ml). Caesium carbonate (103 mg, 317 µmol) and 1-(bromomethyl)-3-fluorobenzene (42.0 mg, 222 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 48.0 mg (66% of theory) of the title compound were obtained.

LC-MS (Method 4): $R_t$=0.68 min; MS (ESIpos): m/z=345 [M+H]

$^1$H-NMR (400 MHz, DMSO-d6) δ[ppm]: −0.149 (0.74), −0.008 (6.59), 0.008 (5.85), 0.146 (0.74), 1.673 (0.74), 1.685 (1.06), 1.699 (1.41), 1.709 (1.99), 1.722 (2.31), 1.733 (1.90), 1.746 (0.96), 1.755 (1.35), 1.773 (3.66), 1.791 (6.30), 1.808 (4.79), 1.824 (1.38), 1.893 (1.48), 1.910 (4.24), 1.926 (5.17), 1.943 (3.15), 1.960 (1.38), 1.983 (1.03), 1.994 (1.80), 2.005 (1.73), 2.021 (1.22), 2.036 (1.48), 2.047 (1.06), 2.053 (1.03), 2.062 (1.06), 2.072 (3.92), 2.088 (0.42), 2.322 (0.58), 2.327 (0.84), 2.332 (0.61), 2.366 (0.64), 2.518 (3.63), 2.522 (3.05), 2.564 (2.02), 2.579 (1.61), 2.593 (1.51), 2.605 (2.80), 2.617 (1.54), 2.636 (0.71), 2.647 (1.09), 2.660 (0.84), 2.665 (0.80), 2.669 (0.93), 2.674 (0.71), 2.709 (0.74), 3.230 (0.90), 3.247 (1.83), 3.259 (1.90), 3.276 (3.31), 3.294 (2.38), 3.328 (2.60), 3.346 (3.44), 3.357 (1.29), 3.364 (1.73), 3.375 (1.96), 3.393 (0.93), 3.439 (1.00), 3.457 (2.12), 3.464 (1.54), 3.474 (1.22), 3.482 (2.70), 3.499 (1.19), 3.595 (1.22), 3.611 (2.41), 3.619 (1.19), 3.628 (1.41), 3.636 (1.86), 3.653 (0.84), 4.740 (2.22), 4.750 (2.47), 4.756 (2.89), 4.765 (2.18), 4.836 (16.00), 7.005 (1.77), 7.031 (1.90), 7.036 (1.70), 7.057 (2.86), 7.076 (3.37), 7.087 (0.96), 7.103 (1.86), 7.110 (1.67), 7.124 (1.09), 7.131 (1.03), 7.356 (1.83), 7.372 (2.09), 7.376 (2.70), 7.391 (2.67), 7.396 (1.67), 7.411 (1.41).

Example 17

(5RS)-2-(3,4-Difluorobenzyl)-5-(pyrrolidin-1-ylcarbonyl)-5,6,7,8-tetrahydro[1,2,4]triazolo[4,3-a]pyridin-3(2H)-one (Racemate)

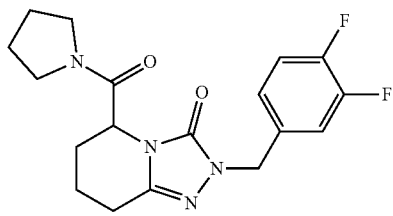 [SMILES: O=C(C1CCCc2nn(Cc3ccc(F)c(F)c3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 μmol) was initially charged in acetonitrile (3.0 ml). Caesium carbonate (103 mg, 317 μmol) and 4-(bromomethyl)-1,2-difluorobenzene (46.0 mg, 222 mol) were subsequently added. After stirring overnight, the reaction mixture was admixed at room temperature with water, aqueous 1 N hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 51.4 mg (67% of theory) of the title compound were obtained.

LC-MS (Method 3): $R_t$=1.29 min; MS (ESIpos): m/z=363 [M+H]$^+$ $^1$H-NMR (400 MHz, DMSO-d6) δ [ppm]: −0.008 (1.10), 0.008 (0.79), 1.659 (0.87), 1.666 (0.94), 1.678 (1.26), 1.692 (1.49), 1.720 (2.53), 1.730 (1.97), 1.744 (1.22), 1.755 (1.63), 1.773 (4.14), 1.791 (6.91), 1.808 (5.24), 1.824 (1.51), 1.893 (1.74), 1.909 (4.73), 1.926 (5.77), 1.942 (3.55), 1.960 (1.63), 1.983 (1.35), 1.994 (2.27), 2.007 (2.54), 2.016 (1.71), 2.034 (1.69), 2.044 (1.27), 2.051 (1.22), 2.060 (1.18), 2.069 (0.65), 2.079 (0.40), 2.519 (2.58), 2.561 (2.09), 2.576 (1.78), 2.591 (1.72), 2.603 (3.08), 2.615 (1.71), 2.633 (0.78), 2.645 (1.17), 2.657 (0.59), 3.229 (1.01), 3.246 (2.10), 3.258 (2.34), 3.275 (4.13), 3.293 (3.31), 3.325 (2.59), 3.343 (3.64), 3.355 (1.42), 3.361 (1.92), 3.373 (2.02), 3.391 (0.93), 3.438 (1.10), 3.456 (2.33), 3.463 (1.76), 3.473 (1.45), 3.480 (2.91), 3.497 (1.27), 3.592 (1.40), 3.609 (2.74), 3.617 (1.46), 3.625 (1.61), 3.633 (2.09), 3.650 (0.96), 4.737 (2.62), 4.746 (2.87), 4.752 (3.26), 4.761 (2.48), 4.816 (16.00), 7.061 (1.51), 7.067 (1.55), 7.072 (1.61), 7.077 (1.78), 7.083 (1.77), 7.087 (1.69), 7.093 (1.61), 7.230 (1.48), 7.235 (1.43), 7.249 (1.57), 7.255 (1.72), 7.258 (1.78), 7.264 (1.49), 7.278 (1.47), 7.283 (1.38), 7.373 (1.70), 7.394 (3.23), 7.400 (1.93), 7.415 (1.77), 7.421 (3.17), 7.442 (1.48).

Example 18

(5RS)-2-(3-Chloro-4-fluorobenzyl)-5-(pyrrolidin-1-ylcarbonyl)-5,6,7,8-tetrahydro[1,2,4]triazolo[4,3-a]pyridin-3(2H)-one (Racemate)

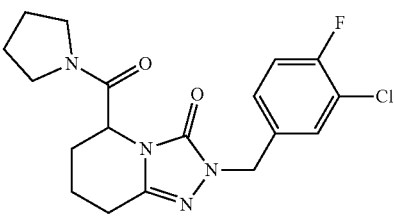 [SMILES: O=C(C1CCCc2nn(Cc3ccc(F)c(Cl)c3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 μmol) was initially charged in acetonitrile (3.0 ml). Caesium carbonate (103 mg, 317 μmol) and 4-(bromomethyl)-2-chloro-1-fluorobenzene (49.7 mg, 222 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 57.0 mg (70% of theory) of the title compound were obtained.

LC-MS (Method 3): $R_t$=1.43 min; MS (ESIpos): m/z=379 [M+H]$^+$ $^1$H-NMR (400 MHz, DMSO-d6) δ[ppm]: −0.008 (1.11), 1.666 (0.83), 1.679 (1.17), 1.692 (1.58), 1.703 (2.12), 1.717 (2.65), 1.727 (2.06), 1.755 (1.33), 1.773 (4.00), 1.790 (6.78), 1.807 (5.21), 1.824 (1.52), 1.892 (1.58), 1.909 (4.70), 1.926 (5.86), 1.942 (3.78), 1.960 (1.52), 1.978 (1.20), 1.989 (2.08), 2.001 (2.02), 2.016 (1.38), 2.031 (1.61), 2.042 (1.22), 2.049 (1.16), 2.057 (1.13), 2.067 (0.64), 2.084 (0.41), 2.328 (0.44), 2.561 (2.11), 2.576 (1.68), 2.590 (1.62), 2.602 (3.04), 2.614 (1.70), 2.632 (0.75), 2.644 (1.17), 2.656 (0.60), 2.670 (0.54), 2.710 (0.50), 3.226 (0.91), 3.243 (1.93), 3.256 (1.96), 3.273 (3.44), 3.290 (2.06), 3.326 (2.63), 3.344 (3.57), 3.356 (1.39), 3.362 (1.83), 3.374 (2.03), 3.391 (0.92), 3.436 (1.07), 3.453 (2.27), 3.461 (1.71), 3.471 (1.36), 3.478 (2.85), 3.495 (1.24), 3.591 (1.30), 3.608 (2.66), 3.616 (1.36), 3.625 (1.55), 3.633 (2.06), 3.649 (0.94), 4.737 (2.43), 4.746 (2.77), 4.752 (3.15), 4.761 (2.37), 4.818 (16.00), 7.219 (1.38), 7.225 (1.49), 7.231 (1.52), 7.241 (2.09), 7.246 (2.05), 7.252 (1.89), 7.258 (1.86), 7.371 (3.67), 7.394 (4.98), 7.415 (2.94), 7.430 (2.84), 7.435 (2.61), 7.448 (2.75), 7.453 (2.63).

Example 19

(5RS)-5-(Pyrrolidin-1-ylcarbonyl)-2-[3-(trifluoromethyl)benzyl]-5,6,7,8-tetrahydro[1,2,4]triazolo[4,3-a]pyridin-3(2H)-one (Racemate)

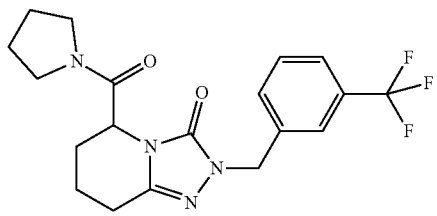 [SMILES: O=C(C1CCCc2nn(Cc3cccc(C(F)(F)F)c3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 µmol) was initially charged in acetonitrile (3.0 ml). Caesium carbonate (103 mg, 317 µmol) and 1-(bromomethyl)-3-(trifluoromethyl)benzene (53.1 mg, 222 µmol) were subsequently added. After stirring overnight, the reaction mixture was admixed at room temperature with water, aqueous 1 N hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 60.6 mg (72% of theory) of the title compound were obtained.

LC-MS (Method 3): $R_t$=1.50 min; MS (ESIpos): m/z=395 [M+H]$^+$ $^1$H-NMR (600 MHz, DMSO-d6) δ[ppm]: 1.664 (0.98), 1.668 (0.95), 1.678 (1.17), 1.682 (1.23), 1.691 (0.96), 1.722 (1.76), 1.728 (1.61), 1.737 (1.14), 1.744 (0.88), 1.768 (1.18), 1.779 (4.61), 1.791 (7.62), 1.802 (5.64), 1.813 (1.54), 1.903 (1.45), 1.914 (4.15), 1.925 (5.43), 1.936 (3.45), 1.947 (0.98), 1.970 (0.90), 1.987 (1.15), 1.993 (1.84), 2.002 (1.65), 2.019 (0.96), 2.024 (1.13), 2.029 (1.12), 2.035 (1.30), 2.043 (1.30), 2.048 (1.39), 2.053 (1.22), 2.058 (0.65), 2.067 (0.45), 2.071 (0.45), 2.520 (1.58), 2.566 (1.45), 2.601 (1.51), 2.608 (2.81), 2.616 (1.71), 2.629 (0.89), 2.636 (1.43), 2.645 (0.69), 3.239 (1.12), 3.251 (2.30), 3.259 (1.97), 3.270 (3.23), 3.282 (1.50), 3.346 (3.70), 3.354 (1.55), 3.358 (1.83), 3.365 (2.29), 3.377 (1.04), 3.447 (1.17), 3.459 (2.47), 3.464 (1.70), 3.471 (1.50), 3.476 (2.81), 3.487 (1.25), 3.604 (1.37), 3.615 (2.62), 3.620 (1.48), 3.626 (1.60), 3.631 (2.16), 3.642 (1.05), 4.755 (2.69), 4.761 (2.92), 4.765 (3.15), 4.771 (2.50), 4.926 (16.00), 7.508 (2.83), 7.521 (3.83), 7.579 (2.39), 7.591 (4.65), 7.604 (2.52), 7.624 (5.77), 7.653 (3.72), 7.665 (2.53).

Example 20

(5RS)-2-(3-Methoxybenzyl)-5-(pyrrolidin-1-ylcarbonyl)-5,6,7,8-tetrahydro[1,2,4]triazolo[4,3-a]pyridin-3(2H)-one (Racemate)

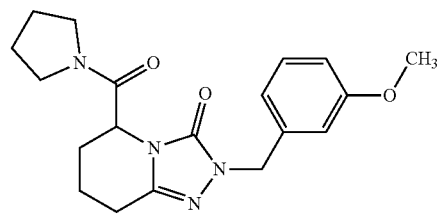 [SMILES: COc1cccc(Cn2nc3n(c2=O)C(C(=O)N2CCCC2)CCC3)c1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 µmol) was initially charged in acetonitrile (2.0 ml). Caesium carbonate (72.4 mg, 222 µmol) and 1-(bromomethyl)-3-methoxybenzene (44.7 mg, 222 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 24.0 mg (32% of theory) of the title compound were obtained.

LC-MS (Method 3): $R_t$=1.21 min; MS (ESIpos): m/z=357 [M+H]$^+$ $^1$H-NMR (400 MHz, DMSO-d6) δ[ppm]: 0.008 (0.70), 1.685 (0.46), 1.717 (0.93), 1.754 (0.42), 1.772 (1.40), 1.789 (2.40), 1.806 (1.85), 1.823 (0.54), 1.893 (0.57), 1.909 (1.70), 1.926 (2.17), 1.942 (1.40), 1.960 (0.57), 1.975 (0.43), 1.987 (0.75), 1.998 (0.72), 2.015 (0.49), 2.030 (0.61), 2.040 (0.43), 2.055 (0.41), 2.568 (0.61), 2.583 (0.58), 2.594 (1.13), 2.606 (0.61), 2.635 (0.43), 3.243 (0.68), 3.256 (0.69), 3.273 (1.24), 3.290 (0.66), 3.339 (1.29), 3.351 (0.48), 3.356 (0.66), 3.368 (0.71), 3.455 (0.80), 3.463 (0.58), 3.473 (0.48), 3.480 (1.01), 3.497 (0.45), 3.595 (0.46), 3.611 (0.97), 3.620 (0.49), 3.628 (0.56), 3.637 (0.76), 3.730 (16.00), 4.732 (0.91), 4.742 (1.03), 4.747 (1.21), 4.757 (1.02), 4.770 (6.44), 6.774 (3.04), 6.777 (2.99), 6.793 (1.49), 6.820 (0.90), 6.824 (0.92), 6.842 (1.08), 6.847 (0.91), 7.218 (1.07), 7.238 (2.10), 7.258 (1.08).

Example 21

(5RS)-2-[(1-Methyl-1H-pyrazol-3-yl)methyl]-5-(pyrrolidin-1-ylcarbonyl)-5,6,7,8-tetrahydro[1,2,4]triazolo[4,3-a]pyridin-3(2H)-one (Racemate)

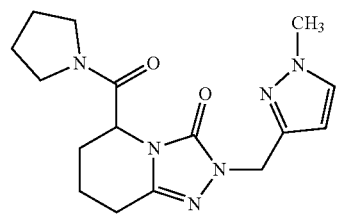 [SMILES: Cn1ccc(Cn2nc3n(c2=O)C(C(=O)N2CCCC2)CCC3)n1]

(5RS)-5-(Pyrrolidin-1-ylcarbonyl)-5,6,7,8-tetrahydro[1,2,4]triazolo[4,3-a]pyridin-3(2H)-one (racemate) (50.0 mg, 212 µmol) was initially charged in acetonitrile (2.0 ml). Caesium carbonate (72.4 mg, 222 µmol) and 3-(bromomethyl)-1-methyl-1H-pyrazole (38.9 mg, 222 µmol) were subsequently added. The reaction mixture was stirred at room temperature overnight and at 90° C. for 1 h. After cooling to room temperature, water, 1 N aqueous hydrochloric acid and ethyl acetate were added to the reaction mixture. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure and separated again by HPLC (Method 11). The product-containing fractions were concentrated under reduced pressure, and 8.00 mg (11% of theory) of the title compound were obtained.

LC-MS (Method 4): $R_t$=0.48 min; MS (ESIpos): m/z=331 [M+H]$^+$ $^1$H-NMR (400 MHz, DMSO-d6) δ [ppm]: −0.008 (3.77), 0.008 (2.98), 1.705 (1.52), 1.717 (1.23), 1.751 (0.50), 1.770 (1.66), 1.787 (2.86), 1.804 (2.19), 1.821 (0.61), 1.891 (0.73), 1.908 (2.10), 1.924 (2.77), 1.941 (1.93), 1.965 (0.96), 2.000 (0.64), 2.011 (0.70), 2.021 (0.58), 2.036 (0.55), 2.327 (1.20), 2.366 (0.96), 2.523 (4.88), 2.574 (1.52), 2.586 (0.82), 2.616 (0.53), 2.669 (1.26), 2.709 (0.85), 3.220 (0.47), 3.236 (0.91), 3.249 (0.93), 3.266 (1.66), 3.334 (2.22), 3.351 (0.99), 3.363 (0.93), 3.380 (0.44), 3.434 (0.47), 3.451 (0.96), 3.458 (0.73), 3.476 (1.23), 3.493 (0.55), 3.590 (0.58), 3.607 (1.17), 3.624 (0.64), 3.633 (0.88), 3.649 (0.41), 3.774 (16.00), 3.796 (0.53), 4.646 (0.58), 4.685 (4.26), 4.696 (4.67), 4.706 (1.49), 4.715 (1.08), 4.735 (0.64), 6.034 (2.42), 6.039 (2.48), 7.569 (2.34), 7.574 (2.34).

Example 22

(5RS)-2-(Pyridin-2-ylmethyl)-5-(pyrrolidin-1-ylcarbonyl)-5,6,7,8-tetrahydro[1,2,4]triazolo[4,3-a]pyridin-3(2H)-one (Racemate)

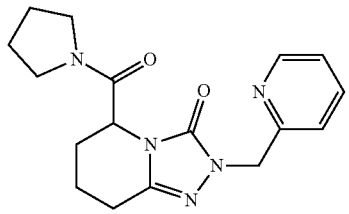 [SMILES: O=C(C1CCCc2nn(Cc3ccccn3)c(=O)n21)N1CCCC1]

(5RS)-5-(Pyrrolidin-1-ylcarbonyl)-5,6,7,8-tetrahydro[1,2,4]triazolo[4,3-a]pyridin-3(2H)-one (50.0 mg, 212 µmol) was initially charged in acetonitrile (2.0 ml). Caesium carbonate (72.4 mg, 222 µmol) and 2-(bromomethyl)pyridine (38.2 mg, 222 µmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure and purified again via preparative HPLC (Chromatorex C18, 10 µm, 125 mm×30 mm; eluent: acetonitrile/water gradient), and 3.00 mg (4% of theory) of the title compound were obtained.

LC-MS (Method 4): $R_t$=0.43 min; MS (ESIpos): m/z=328 [M+H]$^+$ $^1$H-NMR (400 MHz, DMSO-d6) δ [ppm]: −0.149 (0.93), −0.008 (6.95), 0.008 (6.72), 0.146 (0.82), 1.733 (2.39), 1.758 (1.81), 1.775 (4.32), 1.792 (7.12), 1.809 (5.49), 1.825 (1.64), 1.895 (1.58), 1.912 (4.55), 1.928 (5.61), 1.945 (3.45), 1.961 (1.17), 2.019 (2.22), 2.049 (1.69), 2.073 (1.23), 2.327 (2.57), 2.332 (1.87), 2.366 (1.69), 2.523 (8.76), 2.558 (3.09), 2.568 (2.28), 2.583 (1.87), 2.595 (1.69), 2.606 (3.04), 2.620 (1.75), 2.637 (0.88), 2.648 (1.17), 2.665 (2.16), 2.669 (2.80), 2.674 (2.04), 2.709 (1.75), 3.235 (1.11), 3.252 (2.10), 3.265 (2.22), 3.281 (4.09), 3.347 (3.97), 3.365 (1.87), 3.377 (1.99), 3.395 (0.93), 3.449 (1.17), 3.467 (2.28), 3.473 (1.75), 3.491 (2.92), 3.508 (1.46), 3.600 (1.34), 3.617 (2.69), 3.634 (1.64), 3.641 (2.04), 3.659 (0.99), 4.750 (2.34), 4.760 (2.69), 4.765 (3.15), 4.774 (2.63), 4.895 (16.00), 5.114 (0.53), 5.171 (0.53), 7.121 (3.74), 7.140 (4.09), 7.278 (1.81), 7.297 (2.16), 7.311 (2.34), 7.332 (0.58), 7.748 (2.16), 7.753 (2.22), 7.767 (3.85), 7.772 (3.74), 7.787 (1.99), 7.791 (1.93), 8.506 (2.51), 8.520 (2.57).

Example 23

(5RS)-5-(Pyrrolidin-1-ylcarbonyl)-2-{[5-(trifluoromethyl)pyridin-2-yl]methyl}-5,6,7,8-tetrahydro[1,2,4]triazolo[4,3-a]pyridin-3(2H)-one (Racemate)

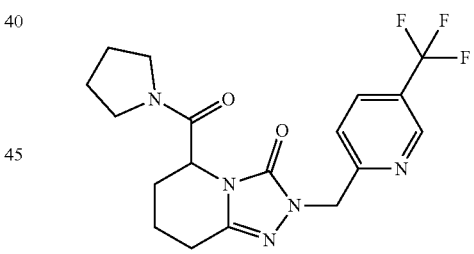

(5RS)-5-(Pyrrolidin-1-ylcarbonyl)-5,6,7,8-tetrahydro[1,2,4]triazolo[4,3-a]pyridin-3(2H)-one (racemate) (40.0 mg, 169 µmol) was initially charged in acetonitrile (2.0 ml). Caesium carbonate (82.7 mg, 254 µmol) and 2-(bromomethyl)-5-(trifluoromethyl)pyridine (44.7 mg, 186 µmol) were subsequently added. After stirring overnight, the reaction mixture was admixed at room temperature with water, 1 N aqueous hydrochloric acid and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 44.6 mg (67% of theory) of the title compound were obtained.

LC-MS (Method 3): $R_t$=1.22 min; MS (ESIpos): m/z=396 [M+H]$^+$ $^1$H-NMR (400 MHz, DMSO-d6) δ[ppm]: −0.149 (0.72), 0.147 (0.71), 1.726 (2.72), 1.738 (3.10), 1.775 (4.76), 1.792 (7.48), 1.809 (5.64), 1.826 (1.77), 1.894 (1.55), 1.911 (4.76), 1.928 (5.91), 1.945 (3.79), 1.962 (1.18), 2.025 (2.84), 2.053 (1.90), 2.328 (0.88), 2.366 (0.64), 2.564 (2.98), 2.574 (2.44), 2.589 (2.03), 2.601 (2.01), 2.613 (3.47), 2.625 (1.98), 2.655 (1.38), 2.669 (1.43), 2.710 (0.77), 3.236 (0.95), 3.253 (1.97), 3.265 (2.17), 3.282 (3.78), 3.329 (2.27), 3.347 (3.67), 3.364 (2.07), 3.377 (2.12), 3.395 (1.00), 3.450 (1.06), 3.467 (2.41), 3.492 (3.06), 3.509 (1.38), 3.599 (1.44), 3.615 (2.87), 3.632 (1.84), 3.640 (2.24), 3.657 (1.00), 4.760 (2.66), 4.775 (3.67), 4.784 (2.76), 5.026 (16.00), 7.383 (4.73), 7.403 (4.96), 8.212 (3.24), 8.233 (3.24), 8.929 (5.73).

Example 24

(5RS)-2-[(5-Methyl-1H-imidazol-4-yl)methyl]-5-(pyrrolidin-1-ylcarbonyl)-5,6,7,8-tetrahydro[1,2,4]triazolo[4,3-a]pyridin-3(2H)-one (Racemate)

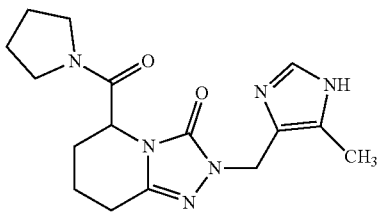 [SMILES: Cc1[nH]cnc1Cn1nc2n(c1=O)C(C(=O)N1CCCC1)CCC2]

(5RS)-5-(Pyrrolidin-1-ylcarbonyl)-5,6,7,8-tetrahydro[1,2,4]triazolo[4,3-a]pyridin-3(2H)-one (racemate) (30.0 mg, 127 μmol) was initially charged in acetonitrile (2.0 ml). Caesium carbonate (165 mg, 508 μmol) and 4-(chloromethyl)-5-methyl-1H-imidazole hydrochloride (25.5 mg, 152 μmol) were subsequently added. After stirring under reflux overnight, the reaction mixture was concentrated under reduced pressure. The residue was purified via preparative HPLC (Method 12). The product-containing fractions were concentrated under reduced pressure, and 1.80 mg (4% of theory) of the title compound were obtained.

LC-MS (Method 3): $R_t$=0.46 min; MS (ESIpos): m/z=331 [M+H]$^+$ $^1$H-NMR (600 MHz, METHANOL-d4) δ [ppm]: 1.814 (0.43), 1.823 (0.63), 1.828 (0.65), 1.833 (0.66), 1.839 (0.65), 1.849 (0.45), 1.856 (0.44), 1.864 (0.53), 1.867 (0.51), 1.872 (0.54), 1.880 (0.52), 1.889 (0.64), 1.895 (0.58), 1.902 (1.23), 1.906 (1.24), 1.913 (1.77), 1.917 (1.61), 1.925 (1.40), 1.928 (1.26), 1.939 (0.67), 2.019 (0.61), 2.029 (1.55), 2.040 (2.38), 2.052 (2.28), 2.063 (1.50), 2.072 (0.63), 2.137 (0.43), 2.143 (0.44), 2.148 (0.46), 2.154 (0.67), 2.161 (0.70), 2.166 (0.75), 2.171 (0.63), 2.178 (0.46), 2.189 (0.40), 2.195 (0.45), 2.217 (0.59), 2.228 (16.00), 2.575 (0.42), 2.584 (0.47), 2.590 (0.45), 2.603 (0.80), 2.613 (0.74), 2.619 (0.77), 2.628 (0.61), 2.681 (0.63), 2.690 (1.26), 2.699 (0.63), 2.709 (0.40), 2.718 (0.74), 3.363 (0.46), 3.374 (0.82), 3.383 (0.74), 3.394 (1.07), 3.406 (0.57), 3.504 (0.62), 3.516 (1.20), 3.524 (0.65), 3.528 (0.81), 3.531 (0.72), 3.536 (1.03), 3.543 (1.03), 3.548 (1.12), 3.554 (0.65), 3.560 (1.06), 3.571 (0.53), 3.756 (0.54), 3.767 (0.99), 3.772 (0.62), 3.778 (0.65), 3.784 (0.84), 3.795 (0.44), 4.630 (0.69), 4.770 (1.70), 4.785 (1.45), 4.796 (4.48), 4.802 (1.53), 4.862 (2.68), 5.491 (5.22), 7.477 (4.91).

Example 25

(5RS)-2-(4-Methylbenzyl)-5-(pyrrolidin-1-ylcarbonyl)-5,6,7,8-tetrahydro[1,2,4]triazolo[4,3-a]pyridin-3(2H)-one (Racemate)

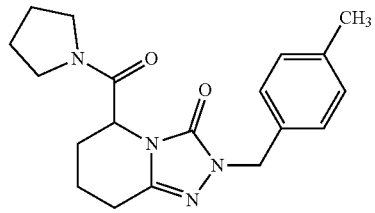 [SMILES: Cc1ccc(Cn2nc3n(c2=O)C(C(=O)N2CCCC2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (436 mg, 1.52 mmol) was dissolved in 10 ml of THF. Triethylamine (420 μl, 3.0 mmol), HATU (865 mg, 2.28 mmol) and pyrrolidine (150 μl, 1.8 mmol) were added and the mixture was stirred under argon at room temperature for 2 h. The reaction mixture was concentrated under reduced pressure, and the residue was dissolved in DMSO/acetonitrile/water and separated in 2 batches via preparative HPLC (column: Kromasil C18, 250×30 mm, 10 μm, eluent: acetonitrile (B)/water+0.1% TFA (A), gradient: 0 min 90% A, 6 min 90% A, 27 min 5% A, 38 min 5% A, 38 min 5% A, 39 min 90% A; flow rate: 50 ml/min, detector: 210 nm). The combined product-containing fractions were concentrated again and dried under reduced pressure. In this way, 430 mg (83% of theory) of the title compound were obtained.

LC-MS (Method 4): $R_t$=0.73 min; MS (ESIpos): m/z=341 [M+H]$^+$ $^1$H-NMR (400 MHz, DMSO-d$_6$): δ [ppm]=1.61-1.83 (m, 4H), 1.86-2.10 (m, 4H), 2.27 (s, 3H), 2.42-2.65 (m, 2H, partially covered by solvent signal), 3.20-3.30 (m, 1H), 3.30-3.41 (m, 1H), 3.47 (dt, 1H), 3.62 (dt, 1H), 4.68-4.79 (m, 3H), 7.07-7.16 (m, 4H).

Example 26

(5RS)-2-(4-Methylbenzyl)-5-(pyrrolidin-1-ylcarbonyl)-5,6,7,8-tetrahydro[1,2,4]triazolo[4,3-a]pyridin-3(2H)-one (Enantiomer 2)

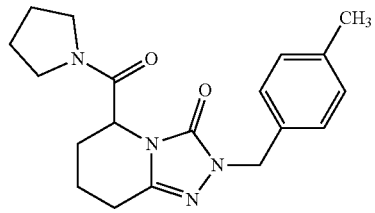 [SMILES: Cc1ccc(Cn2nc3n(c2=O)C(C(=O)N2CCCC2)CCC3)cc1]

(5RS)-2-(4-Methylbenzyl)-5-(pyrrolidin-1-ylcarbonyl)-5,6,7,8-tetrahydro[1,2,4]triazolo[4,3-a]pyridin-3(2H)-one (racemate) was separated by chiral preparative SFC [sample preparation: 1220 mg dissolved in 50 ml of methanol/acetonitrile; injection volume: 2.0 ml; column: Daicel Chiralcel® OD-H 5 μm, 250×50 mm; eluent: CO2/ethanol: isocratic 20% ethanol, flow rate: 80 ml/min; temperature 40°

C.; UV detection: 210 nm]. After the separation, 494 mg of enantiomer 1, which eluted first, and 487 mg of enantiomer 2, which eluted later, were isolated.

Enantiomer 2:

Specific rotation: −25.70 (589 nm, 0.4150 g/100 cm$^3$ MeOH)

Analytical chiral HPLC: R$_t$=4.27 min, e.e. =100% [column: Daicel Chiralcel® ID-3 3 μm 50×4.6 mm; eluent: isohexane/isopropanol 1:1; flow rate: 1 ml/min; UV detection: 220 nm]

LC-MS (Method 3): R$_t$=1.33 min; MS (ESIpos): m/z=341 [M+H]$^+$

1H-NMR (400 MHz, DMSO-d6): δ [ppm]=1.61-1.83 (m, 4H), 1.87-2.10 (m, 4H), 2.27 (s, 3H), 2.47-2.70 (m, 2H, partially covered by solvent signal), 3.21-3.30 (m, 1H), 3.30-3.67 (m, 3H, partially overlapped by water signal), 4.69-4.81 (m, 3H), 7.08-7.16 (m, 4H).

The (5S) configuration was assigned on the basis of crystal structure elucidation for Example 26.

(5S)-2-(4-Methylbenzyl)-5-(pyrrolidin-1-ylcarbonyl)-5,6,7,8-tetrahydro[1,2,4]triazolo[4,3-a]pyridin-3 (2H)-one

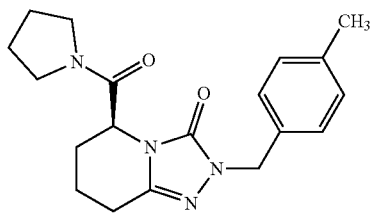 [SMILES: Cc1ccc(Cn2nc3n(c2=O)[C@H](C(=O)N2CCCC2)CCC3)cc1]

Example 27

(5RS)-2-(4-Chlorobenzyl)-5-(pyrrolidin-1-ylcarbonyl)-5,6,7,8-tetrahydro[1,2,4]triazolo[4,3-a]pyridin-3 (2H)-one (Racemate)

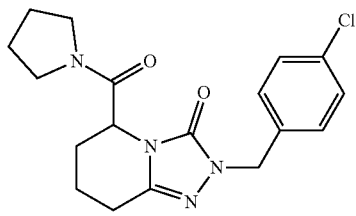 [SMILES: O=C(C1CCCc2nn(Cc3ccc(Cl)cc3)c(=O)n21)N1CCCC1]

Methyl (5RS)-2-(4-chlorobenzyl)-3-oxo-2,3,5,6,7,8-hexahydro[1,2,4]triazolo[4,3-a]pyridine-5-carboxylate (racemate) (77.0 mg, 239 μmol) was initially charged in 1 ml of THF/water, lithium hydroxide (28.7 mg, 1.20 mmol) was added and the reaction mixture was stirred at room temperature over a weekend. For workup, the THF was removed under reduced pressure and the aqueous residue was lyophilized. In this way, 74 mg of the lithium salt of the carboxylic acid were obtained, which was converted further directly. For this purpose, the carboxylic acid was released with aqueous hydrochloric acid and dissolved in 3 ml of THF. Triethylamine (66 μl, 470 μmol), HATU (135 mg, 356 μmol) and pyrrolidine (24 μl, 280 μmol) were added and the mixture was stirred under argon at room temperature overnight. The reaction mixture was concentrated under reduced pressure, and the residue was separated via preparative HPLC (column: Chromatorex, 125×40 mm 10 μm. Flow rate: 50 ml/min. Gradient (A=water+0.1% formic acid, B=acetonitrile): 0 min 10% B, 5 min 10% B, 27 min 98% B, 35 min 98% B, 35.01 min 10% B, 38 min 10% B. Run time per separation 38 min. Detection: 210 nm). The product-containing fractions were concentrated, lyophilized and freed of solvent residues under reduced pressure. In this way, 64.3 mg (75% of theory) of the title compound were obtained.

LC-MS (Method 4): R$_t$=0.76 min; MS (ESIpos): m/z=361 [M+H]$^+$ $^1$H-NMR (400 MHz, DMSO-d$_6$): δ [ppm]=1.61-1.84 (m, 4H), 1.87-2.10 (m, 4H), 2.46-2.66 (m, 2H, partially covered by solvent signal), 3.21-3.40 (m, 2H, partially overlapped by water signal), 3.46 (dt, 1H), 3.62 (dt, 1H), 4.74 (dd, 1H), 4.75-4.85 (m, 2H), 7.22-7.28 (m, 2H), 7.37-7.43 (m, 2H).

Example 28 tert-Butyl 4-{[(5RS)-3-oxo-5-(pyrrolidin-1-ylcarbonyl)-5,6,7,8-tetrahydro[1,2,4]triazolo[4,3-a]pyridin-2 (3H)-yl]methyl}benzoate (Racemate)

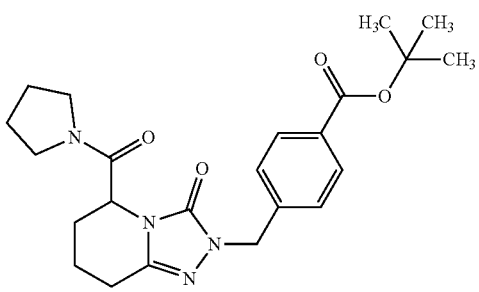 [SMILES: CC(C)(C)OC(=O)c1ccc(Cn2nc3n(c2=O)C(C(=O)N2CCCC2)CCC3)cc1]

(5RS)-2-[4-(tert-Butoxycarbonyl)benzyl]-3-oxo-2,3,5,6,7,8-hexahydro[1,2,4]triazolo[4,3-a]pyridine-5-carboxylic Acid (Racemate) (246 mg, 88% purity, 580 μmol) was dissolved in 6.0 ml of THF. Triethylamine (240 μl, 1.7 mmol), HATU (287 mg, 754 μmol) and pyrrolidine (58 μl, 700 μmol) were added and the mixture was stirred under argon at room temperature overnight. For further conversion, triethylamine (81 μl, 580 μmol), HATU (66.1 mg, 174 μmol) and pyrrolidine (15 μl, 170 μmol) were added once again and the mixture was stirred under the above conditions for a further 2.5 h. For workup, the mixture was diluted with ethyl acetate/water. After extraction and removal of the organic phase, the aqueous phase was extracted twice more with ethyl acetate. The organic phases were washed with saturated aqueous sodium chloride solution and dried over sodium sulphate. The residue that remained after concentration under reduced pressure was dissolved in DMSO/acetonitrile/water and separated in 2 batches via preparative HPLC (column: Kromasil C18, 125×30 mm, 10 μm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). The combined product-containing fractions were concentrated and the crude product was partitioned once again between water and ethyl acetate. From the organic phase, after drying, concentration and drying under reduced pressure, 235 mg (103% of theory) of the title compound were obtained.

LC-MS (Method 4): $R_t$=0.92 min; MS (ESIpos): m/z=427 [M+H]$^+$ $^1$H-NMR (400 MHz, DMSO-d$_6$): δ [ppm]=1.54 (s, 9H), 1.62-1.85 (m, 4H), 1.87-2.10 (m, 4H), 2.47-2.67 (m, 2H, partially covered by solvent signal), 3.22-3.40 (m, 2H, partially overlapped by water signal), 3.47 (dt, 1H), 3.62 (dt, 1H), 4.75 (dd, 1H), 4.88 (s, 2H), 7.30-7.36 (m, 2H), 7.83-7.89 (m, 2H).

Example 29

4-{[(5RS)-3-Oxo-5-(pyrrolidin-1-ylcarbonyl)-5,6,7,8-tetrahydro[1,2,4]triazolo[4,3-a]pyridin-2(3H)-yl]methyl}benzenesulphonamide (Racemate)

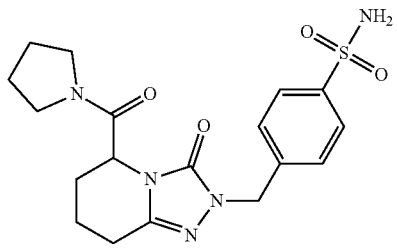 [SMILES: NS(=O)(=O)c1ccc(Cn2nc3n(c2=O)C(C(=O)N2CCCC2)CCC3)cc1]

(5RS)-3-Oxo-2-(4-sulphamoylbenzyl)-2,3,5,6,7,8-hexahydro[1,2,4]triazolo[4,3-a]pyridine-5-carboxylic Acid (Racemate) (30.0 mg, 85.1 μmol) was dissolved in 2.0 ml of DMF. Triethylamine (24 μl, 170 μmol), HATU (48.6 mg, 128 μmol) and pyrrolidine (8.5 μl, 100 μmol) were added and the mixture was stirred under argon at room temperature overnight. For workup and purification, the mixture was separated directly via preparative HPLC (column: Chromatorex, 125×30 mm 10 μm. Flow rate: 50 ml/min. Gradient (A=water+0.1% formic acid, B=acetonitrile). Run time per separation 38 min. 0 min 0% B, 6 min 10% B, 27 min 95% B, 38 min 95% B, 40 min 0% B. Detection: 210 nm). The combined product-containing fractions were lyophilized. In this way, 7.60 mg (22% of theory) of the title compound were obtained.

LC-MS (Method 6): $R_t$=0.99 min; MS (ESIpos): m/z=406 [M+H]$^+$ $^1$H-NMR (400 MHz, DMSO-d$_6$): δ [ppm]=1.60-1.85 (m, 4H), 1.85-2.12 (m, 4H), 2.40-2.69 (m, 2H, partially covered by solvent signal), 3.20-3.31 (m, 1H), 3.31-3.58 (m, 2H, partially overlapped by water signal), 3.62 (dt, 1H), 4.75 (dd, 1H), 4.89 (s, 2H), 7.32 (s, 2H), 7.40 (d, 2H), 7.78 (d, 2H).

Example 30

(5RS)-2-[4-(Methylsulphanyl)benzyl]-5-(pyrrolidin-1-ylcarbonyl)-5,6,7,8-tetrahydro[1,2,4]triazolo[4,3-a]pyridin-3(2H)-one (Racemate)

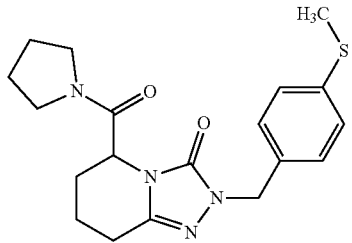 [SMILES: CSc1ccc(Cn2nc3n(c2=O)C(C(=O)N2CCCC2)CCC3)cc1]

(5RS)-2-[4-(Methylsulphanyl)benzyl]-3-oxo-2,3,5,6,7,8-hexahydro[1,2,4]triazolo[4,3-a]pyridine-5-carboxylic acid (racemate) (136 mg, 95% purity, 405 μmol) was dissolved in 4.0 ml of THF. Triethylamine (170 μl, 1.2 mmol), HATU (200 mg, 526 μmol) and pyrrolidine (41 μl, 490 μmol) were added and the mixture was stirred under argon at room temperature over a weekend. The reaction mixture was concentrated under reduced pressure, and the residue was taken up in acetonitrile/water and separated via preparative HPLC (column: Kromasil C18, 125×30 mm, 10 μm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). The product-containing fractions were combined, concentrated and dried under reduced pressure. In this way, 85.0 mg (55% of theory) of the title compound were obtained.

LC-MS (Method 4): $R_t$=0.75 min; MS (ESIpos): m/z=373 [M+H]$^+$ $^1$H-NMR (400 MHz, DMSO-d$_6$): δ [ppm]=1.61-1.84 (m, 4H), 1.88-2.10 (m, 4H), 2.45 (s, 3H), 2.47-2.67 (m, 2H, partially covered by solvent signal), 3.26 (dt, 1H), 3.36 (dt, 1H), 3.47 (dt, 1H), 3.65 (dt, 1H, partially overlapped by water signal), 4.70-4.80 (m, 3H), 7.15-7.25 (m, 4H).

Example 31

(5RS)-2-[(6-Chloropyridin-3-yl)methyl]-5-(pyrrolidin-1-ylcarbonyl)-5,6,7,8-tetrahydro[1,2,4]triazolo[4,3-a]pyridin-3(2H)-one (Racemate)

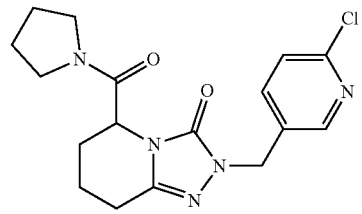 [SMILES: O=C(C1CCCc2nn(Cc3ccc(Cl)nc3)c(=O)n21)N1CCCC1]

(5RS)-2-[(6-Chloropyridin-3-yl)methyl]-3-oxo-2,3,5,6,7,8-hexahydro[1,2,4]triazolo[4,3-a]pyridine-5-carboxylic Acid (Racemate)

(1.59 g, 92% purity, 4.74 mmol) was dissolved in 25 ml of THF. Triethylamine (2.0 ml, 14 mmol), HATU (2.34 g, 6.16 mmol) and pyrrolidine (470 μl, 5.7 mmol) were added and the mixture was stirred at room temperature over a weekend. For workup, the mixture was added to water, saturated with sodium chloride and extracted twice with ethyl acetate. The combined organic phases were dried over magnesium sulphate, filtered and concentrated. The residue was purified by chromatography on silica gel (PuriFlash 100 g silica gel cartridge dichloromethane/methanol 20:1, detector: 214 nm). In this way, 1.11 g (65% of theory) of the title compound were obtained.

LC-MS (Method 3): $R_t$=1.04 min; MS (ESIpos): m/z=362 [M+H]$^+$ $^1$H-NMR (400 MHz, DMSO-d$_6$): δ [ppm]=1.59-1.86 (m, 4H), 1.86-2.10 (m, 4H), 2.53-2.71 (m, 2H, partially covered by solvent signal), 3.21-3.41 (m, 2H, partially overlapped by water signal), 3.47 (dt, 1H), 3.62 (dt, 1H), 4.74 (dd, 1H), 4.88 (s, 2H), 7.51 (d, 1H), 7.70 (dd, 1H), 8.30 (d, 1H). The spectrum shows broad signals for trimethylammonium ions at 1.15 ppm and at 3.05 ppm.

Example 32

(5RS)-2-[(6-Chloropyridin-3-yl)methyl]-5-(pyrrolidin-1-ylcarbonyl)-5,6,7,8-tetrahydro[1,2,4]triazolo[4,3-a]pyridin-3(2H)-one (Enantiomer 2)

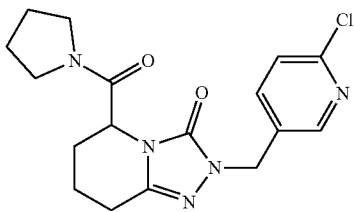 [SMILES: O=C(C1CCCc2nn(Cc3ccc(Cl)nc3)c(=O)n21)N1CCCC1]

(5RS)-2-[(6-Chloropyridin-3-yl)methyl]-5-(pyrrolidin-1-ylcarbonyl)-5,6,7,8-tetrahydro[1,2,4]triazolo[4,3-a]pyridin-3(2H)-one (racemate) was separated by chiral preparative SFC [sample preparation: 400 mg dissolved in 15 ml of ethanol; injection volume: 4.0 ml; column: Daicel Chiralpak® AD SFC 5 µm, 250×50 mm; eluent: CO2/ethanol: isocratic 35% ethanol, flow rate: 80 ml/min; temperature 40° C.; UV detection: 210 nm]. After the separation and lyophilization of the products, 144 mg of enantiomer 1, which eluted first, and 138 mg of enantiomer 2, which eluted later, were isolated.

Enantiomer 2:

Analytical chiral SFC: $R_t$=3.41 min, e.e. =100% [column: Daicel Chiralcel® AD; eluent: CO2/Ethanol 60:40; flow rate: 3 ml ethanol/min; UV detection: 210 nm]

LC-MS (Method 4): $R_t$=0.60 min; MS (ESIpos): m/z=362 [M+H]$^+$

1H-NMR (400 MHz, DMSO-d6): δ [ppm]=1.59-1.85 (m, 4H), 1.87-2.10 (m, 4H), 2.47-2.68 (m, 2H, partially covered by solvent signal), 3.22-3.31 (m, 1H), 3.31-3.40 (m, 1H), 3.47 (dt, 1H), 3.62 (dt, 1H), 4.74 (dd, 1H), 4.88 (s, 2H), 7.51 (d, 1H), 7.70 (dd, 1H), 8.30 (d, 1H).

Example 33

(5RS)-2-[(5-Chloropyridin-2-yl)methyl]-5-(pyrrolidin-1-ylcarbonyl)-5,6,7,8-tetrahydro[1,2,4]triazolo[4,3-a]pyridin-3(2H)-one (Racemate)

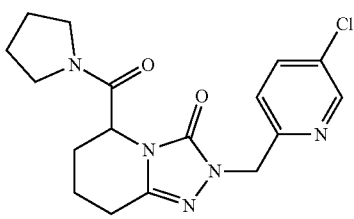 [SMILES: O=C(C1CCCc2nn(Cc3ccc(Cl)cn3)c(=O)n21)N1CCCC1]

(5RS)-2-[(5-Chloropyridin-2-yl)methyl]-3-oxo-2,3,5,6,7,8-hexahydro[1,2,4]triazolo[4,3-a]pyridine-5-carboxylic Acid (Racemate) (220 mg, 81% purity, 574 µmol) was dissolved in 3.0 ml of THF. Triethylamine (400 µl, 2.9 mmol), HATU (284 mg, 746 µmol) and pyrrolidine (57 µl, 690 µmol) were added and the mixture was stirred at room temperature overnight. For workup, the mixture was added to water, saturated with sodium chloride and extracted twice with ethyl acetate. The combined organic phases were dried over magnesium sulphate, filtered and concentrated. The residue was separated via preparative HPLC (column: Chromatorex, 125×30 mm 10 µm. Flow rate: 50 ml/min. Gradient (A=water+0.1% formic acid, B=acetonitrile). Run time per separation 38 min. Detection: 210 nm=>0 min 0% B, 6 min 10% B, 27 min 95% B, 38 min 95% B, 40 min 0% B). In this way, 177 mg (85% of theory) of the title compound were obtained.

LC-MS (Method 3): $R_t$=1.09 min; MS (ESIpos): m/z=362 [M+H]$^+$ $^1$H-NMR (500 MHz, DMSO-d$_6$): δ [ppm]=1.64-1.83 (m, 4H), 1.87-2.11 (m, 4H), 2.46-2.66 (m, 2H, partially covered by solvent signal), 3.22-3.43 (m, 2H, partially overlapped by water signal), 3.48 (dt, 1H), 3.62 (dt, 1H), 4.76 (dd, 1H), 4.87-4.95 (m, 2H), 7.21 (d, 1H), 7.92 (dd, 1H), 8.57 (d, 1H).

Example 34

(5RS)-2-[(5-Chloropyridin-2-yl)methyl]-5-(pyrrolidin-1-ylcarbonyl)-5,6,7,8-tetrahydro[1,2,4]triazolo[4,3-a]pyridin-3(2H)-one (Enantiomer 2)

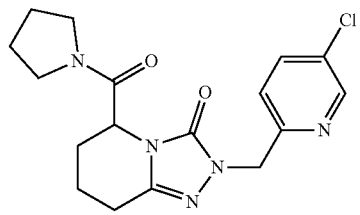

(5RS)-2-[(5-Chloropyridin-2-yl)methyl]-5-(pyrrolidin-1-ylcarbonyl)-5,6,7,8-tetrahydro[1,2,4]triazolo[4,3-a]pyridin-3(2H)-one (racemate) was separated by chiral preparative liquid chromatography [sample preparation: 220 mg dissolved in 12 ml of warm isopropanol; injection volume: 0.5 ml; column: Daicel Chirapak® AS-H 5 µm, 250×50 mm; eluent: isohexane/isopropanol:isocratic 50% isopropanol, flow rate: 15.0 ml/min; temperature 25° C.; UV detection: 210 nm]. After the separation, 69 mg of enantiomer 1, which eluted first, and 66 mg of enantiomer 2, which eluted later, were isolated.

Enantiomer 2:

Analytical chiral HPLC: $R_t$=1.40 min, e.e. =100% [column: Daicel Chiralcel® AS-3 3 µm 50×4.6 mm; eluent: isohexane/isopropanol 1:1; flow rate: 1 ml/min; UV detection: 220 nm]

LC-MS (Method 3): $R_t$=1.06 min; MS (ESIpos): m/z=362 [M+H]$^+$

1H-NMR (400 MHz, DMSO-d6): δ [ppm]=1.62-1.86 (m, 4H), 1.86-2.14 (m, 4H), 2.47-2.69 (m, 2H, partially covered by solvent signal), 3.21-3.42 (m, 2H, partially overlapped by water signal), 3.47 (dt, 1H), 3.62 (dt, 1H), 4.76 (dd, 1H), 4.86-4.96 (m, 2H), 7.21 (d, 1H), 7.92 (dd, 1H), 8.57 (d, 1H).

Example 35

5-{[(5RS)-3-Oxo-5-(pyrrolidin-1-ylcarbonyl)-5,6,7,8-tetrahydro[1,2,4]triazolo[4,3-a]pyridin-2(3H)-yl]methyl}pyridine-2-carbonitrile (Racemate)

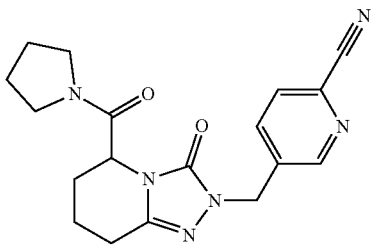 [SMILES: N#Cc1ccc(Cn2nc3n(c2=O)C(C(=O)N2CCCC2)CCC3)cn1]

(5RS)-2-[(6-Cyanopyridin-3-yl)methyl]-3-oxo-2,3,5,6,7,8-hexahydro[1,2,4]triazolo[4,3-a]pyridine-5-carboxylic Acid (Racemate) (190 mg, 70% purity, 444 μmol) was dissolved in 4.0 ml of THF. Triethylamine (190 μl, 1.3 mmol), HATU (220 mg, 578 μmol) and pyrrolidine (45 μl, 530 μmol) were added and the mixture was stirred at room temperature over a weekend. For workup, the mixture was concentrated and the resulting residue was taken up in acetonitrile/water and separated via preparative HPLC (column: Kromasil C18, 125×30 mm, 10 μm, eluent: acetonitrile (B)/water (A, neutral), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. In this way, 80.0 mg (51% of theory) of the title compound were obtained.

LC-MS (Method 4): $R_t$=0.55 min; MS (ESIpos): m/z=353 [M+H]$^+$ $^1$H-NMR (400 MHz, DMSO-d$_6$): δ [ppm]=1.59-1.84 (m, 4H), 1.86-2.11 (m, 4H), 2.46-2.69 (m, 2H, partially covered by solvent signal), 3.22-3.40 (m, 2H, partially overlapped by water signal), 3.47 (dt, 1H), 3.62 (dt, 1H), 4.76 (dd, 1H), 4.95-5.05 (m, 2H), 7.84 (dd, 1H), 8.04 (d, 1H), 8.62 (d, 1H).

Example 36

(5RS)-2-(4-Methoxybenzyl)-5-(pyrrolidin-1-ylcarbonyl)-5,6,7,8-tetrahydro[1,2,4]triazolo[4,3-a]pyridin-3(2H)-one (Racemate)

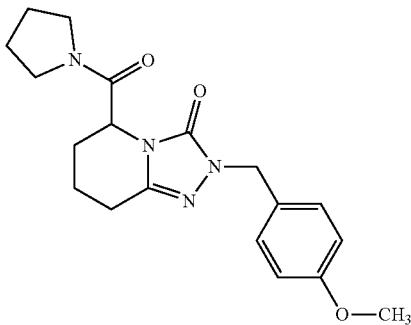 [SMILES: COc1ccc(Cn2nc3n(c2=O)C(C(=O)N2CCCC2)CCC3)cc1]

(5RS)-2-(4-Methoxybenzyl)-3-oxo-2,3,5,6,7,8-hexahydro[1,2,4]triazolo[4,3-a]pyridine-5-carboxylic Acid (Racemate) (1.67 g, 80% purity, 4.40 mmol) was dissolved in DMF (10 ml). Triethylamine (1.2 ml, 8.8 mmol), HATU (2.51 g, 6.61 mmol) and pyrrolidine (440 μl, 5.3 mmol) were added and the mixture was stirred under argon at room temperature overnight. For workup, the mixture was admixed with water, saturated with sodium chloride and extracted three times with 30 ml each time of ethyl acetate. The combined organic phases were dried with magnesium sulphate, filtered and concentrated under reduced pressure. The remaining residue was separated in 3 injections via preparative HPLC (column: Chromatorex, 125×40 mm 10 μm. Flow rate: 50 ml/min. Gradient (A=water+0.1% formic acid, B=acetonitrile). Run time per separation 38 min. Detection: 210 nm=>0 min 0% B, 6 min 10% B, 27 min 95% B, 38 min 95% B, 40 min 0% B=>). By concentrating the product-containing fractions, 830 mg (97% purity, 51% of theory) of the title compound were obtained.

The majority was used further as intermediate without further purification.

About 15 mg were purified once again under the above conditions via preparative HPLC to give 33 mg of the title compound, 100% of theory according to LC-MS.

LC-MS (Method 3): $R_t$=1.16 min; MS (ESIpos): m/z=357 [M+H]$^+$ $^1$H-NMR (400 MHz, DMSO-d$_6$): δ [ppm]=1.62-1.83 (m, 4H), 1.88-2.08 (m, 4H), 2.45-2.64 (m, 2H, partially covered by solvent signal), 3.21-3.40 (m, 2H, partially overlapped by water signal) 3.46 (dt, 1H), 3.62 (dt, 1H), 3.73 (s, 3H), 4.66-4.77 (m, 3H), 6.85-6.91 (m, 2H), 7.13-7.20 (m, 2H).

Example 37

(5RS)-2-[4-Chloro-3-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

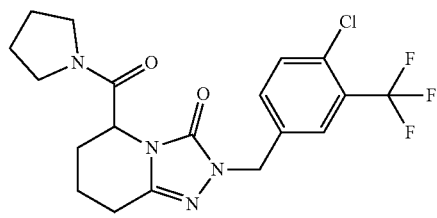 [SMILES: O=C(C1CCCc2nn(Cc3ccc(Cl)c(C(F)(F)F)c3)c(=O)n21)N1CCCC1]

(5RS)-2-[4-Chloro-3-(trifluoromethyl)benzyl]-3-oxo-2,3,5,6,7,8-hexahydro[1,2,4]triazolo[4,3-a]pyridine-5-carboxylic Acid (Racemate) (138 mg, 367 μmol) was dissolved in 4.0 ml of THF. Triethylamine (110 μl, 810 μmol), HATU (182 mg, 477 μmol) and pyrrolidine (37 μl, 440 μmol) were added and the mixture was stirred at room temperature overnight. For workup, the reaction mixture was concentrated and the resulting residue was taken up in acetonitrile/water and separated via preparative HPLC (column: Kromasil C18, 125×30 mm, 10 μm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. In this way, 121 mg (77% of theory) of the title compound were obtained.

LC-MS (Method 3): $R_t$=1.66 min; MS (ESIpos): m/z=429 [M+H]$^+$ $^1$H-NMR (400 MHz, DMSO-d$_6$): δ [ppm]=1.60-1.85 (m, 4H), 1.87-2.11 (m, 4H), 2.47-2.69 (m, 2H, partially covered by solvent signal), 3.21-3.57 (m, 3H, partially overlapped by water signal), 3.62 (dt, 1H), 4.75 (dd, 1H), 4.92 (s, 2H), 7.51 (dd, 1H), 7.72 (d, 1H), 7.76 (d, 1H).

Example 38

(5RS)-2-(3-Chlorobenzyl)-5-(pyrrolidin-1-ylcarbonyl)-5,6,7,8-tetrahydro[1,2,4]triazolo[4,3-a]pyridin-3(2H)-one (Racemate)

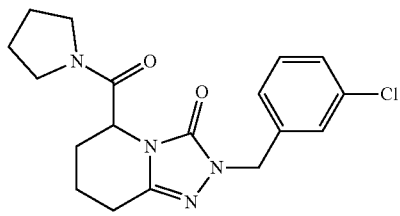 [SMILES: O=C(C1CCCc2nn(Cc3cccc(Cl)c3)c(=O)n21)N1CCCC1]

(5RS)-2-(3-Chlorobenzyl)-3-oxo-2,3,5,6,7,8-hexahydro[1,2,4]triazolo[4,3-a]pyridine-5-carboxylic Acid (Racemate) (110 mg, 83% purity, 297 µmol) was dissolved in 3.5 ml of THF. Triethylamine (91 µl, 650 µmol), HATU (147 mg, 386 µmol) and pyrrolidine (30 µl, 360 µmol) were added and the mixture was stirred at room temperature overnight. For workup, the mixture was concentrated and the resulting residue was taken up in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. This gave 80.3 mg (75% of theory) of the title compound.

LC-MS (Method 3): $R_t$=1.39 min; MS (ESIpos): m/z=361 $[M+H]^+$ $^1$H-NMR (400 MHz, DMSO-$d_6$): δ [ppm]=1.61-1.84 (m, 4H), 1.88-2.11 (m, 4H), 2.47-2.68 (m, 2H, partially covered by solvent signal), 3.26 (dt, 1H), 3.36 (dt, 1H), 3.47 (dt, 1H), 3.62 (dt, 1H, partially overlapped by water signal), 4.75 (dd, 1H), 4.83 (s, 2H), 7.19 (br d, 1H), 7.29 (br s, 1H), 7.32-7.40 (m, 2H).

Example 39

(5RS)-2-(3,4-Dichlorobenzyl)-5-(pyrrolidin-1-ylcarbonyl)-5,6,7,8-tetrahydro[1,2,4]triazolo[4,3-a]pyridin-3(2H)-one (Racemate)

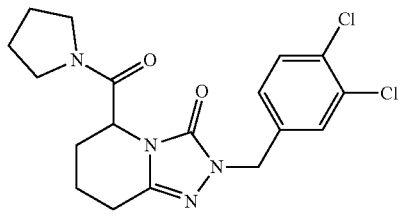

(5RS)-2-(3,4-Dichlorobenzyl)-3-oxo-2,3,5,6,7,8-hexahydro[1,2,4]triazolo[4,3-a]pyridine-5-carboxylic Acid (Racemate) (120 mg, 80% purity, 281 µmol) was dissolved in 3.0 ml of THF. Triethylamine (86 µl, 620 µmol), HATU (139 mg, 365 µmol) and pyrrolidine (28 µl, 340 µmol) were added and the mixture was stirred at room temperature overnight. For workup, the mixture was concentrated and the resulting residue was taken up in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. This gave 113 mg (97% of theory) of the title compound.

LC-MS (Method 4): $R_t$=0.84 min; MS (ESIpos): m/z=395 $[M+H]^+$ $^1$H-NMR (400 MHz, DMSO-$d_6$): δ [ppm]=1.60-1.84 (m, 4H), 1.85-2.10 (m, 4H), 2.45-2.67 (m, 2H, partially covered by solvent signal), 3.21-3.51 (m, 3H, partially overlapped by water signal), 3.62 (dt, 1H), 4.75 (dd, 1H), 4.83 (s, 2H), 7.22 (dd, 1H), 7.49 (d, 1H), 7.62 (d, 1H).

Example 40

(5RS)-5-(Pyrrolidin-1-ylcarbonyl)-2-{[4-(trifluoromethyl)cyclohexyl]methyl}-5,6,7,8-tetrahydro[1,2,4]triazolo[4,3-a]pyridin-3(2H)-one (Diastereomer Mixture; 4 Isomers)

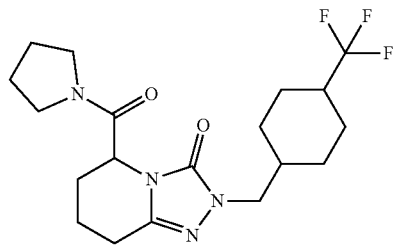 [SMILES: O=C(C1CCCc2nn(CC3CCC(C(F)(F)F)CC3)c(=O)n21)N1CCCC1]

(5RS)-3-Oxo-2-{[4-(trifluoromethyl)cyclohexyl]methyl}-2,3,5,6,7,8-hexahydro[1,2,4]triazolo[4,3-a]pyridine-5-carboxylic acid (diastereomer mixture; 4 isomers) (326 mg, 939 µmol) was dissolved in 10 ml of THF. Triethylamine (260 µl, 1.9 mmol), HATU (464 mg, 1.22 mmol) and pyrrolidine (94 µl, 1.1 mmol) were added and the mixture was stirred at room temperature overnight. For workup, the mixture was admixed with water and then concentrated, and the resulting residue was taken up in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. In this way, 90.2 mg (24% of theory) of the title compound were obtained as a racemic cis/trans mixture.

LC-MS (Method 4): $R_t$=0.90 min; MS (ESIpos): m/z=401 $[M+H]^+$ $^1$H-NMR (400 MHz, DMSO-$d_6$): δ [ppm]=0.89-1.08 (m, 1H), 1.10-1.26 (m, 1H), 1.43-2.10 (m, 15H), 2.11-2.34 (m, 1H), 2.45-2.69 (m, 2H, partially covered by solvent signal), 3.20-3.29 (m, 1H), 3.29-3.72 (m, 5H, partially overlapped by water signal), 4.67-4.74 (m, 1H).

Example 41

(5RS)-2-[(4,4-Difluorocyclohexyl)methyl]-5-(pyrrolidin-1-ylcarbonyl)-5,6,7,8-tetrahydro[1,2,4]triazolo[4,3-a]pyridin-3(2H)-one (Racemate)

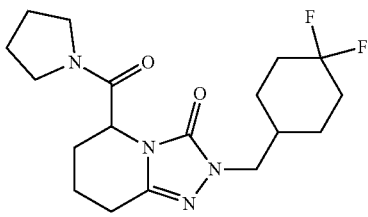 [SMILES: O=C(C1CCCc2nn(CC3CCC(F)(F)CC3)c(=O)n21)N1CCCC1]

(5RS)-2-[(4,4-Difluorocyclohexyl)methyl]-3-oxo-2,3,5,6,7,8-hexahydro[1,2,4]triazolo[4,3-a]pyridine-5-carboxylic Acid (Racemate) (30.5 mg, 96.7 µmol) was dissolved in 1.0 ml of THF. Triethylamine (27 µl, 1.90 µmol), HATU (47.8 mg, 126 µmol) and pyrrolidine (9.7 µl, 120 µmol) were added and the mixture was stirred at room temperature overnight. For workup, the mixture was admixed with water and then concentrated, and the resulting residue was taken up in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. In this way, 17.6 mg (49% of theory) of the title compound were obtained.

LC-MS (Method 4): $R_t$=0.77 min; MS (ESIpos): m/z=369 [M+H]$^+$ $^1$H-NMR (400 MHz, DMSO-d$_6$): δ [ppm]=1.12-1.27 (m, 2H), 1.61-2.09 (m, 15H), 2.47-2.68 (m, 2H, partially covered by solvent signal), 3.25 (dt, 1H), 3.34 (dt, 1H), 3.41-ca. 3.70 (m, 4H, partially overlapped by water signal), 4.70 (dd, 1H).

Example 42

(5RS)-5-[(3,3-Difluoropyrrolidin-1-yl)carbonyl]-2-(4-methylbenzyl)-5,6,7,8-tetrahydro[1,2,4]triazolo[4,3-a]pyridin-3(2H)-one (Racemate)

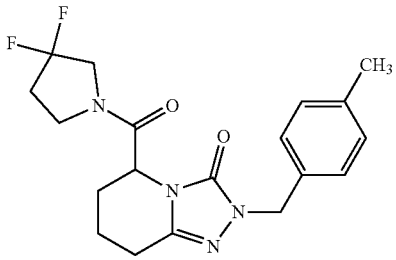 [SMILES: Cc1ccc(Cn2nc3n(c2=O)C(C(=O)N2CCC(F)(F)C2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (36.0 mg, 124 µmol) was dissolved in 1.3 ml of THF. Triethylamine (57 µl, 410 µmol), HATU (70.7 mg, 186 µmol) and 3,3-difluoropyrrolidine hydrochloride (21.4 mg, 149 µmol) were added and the mixture was stirred at room temperature for 3 h. For workup, the mixture was concentrated and the resulting residue was dissolved in DMSO/acetonitrile/water and separated via preparative HPLC (column: Kromasil C18, 250×30 mm, 10 µm, eluent: acetonitrile (B)/water+0.1% TFA (A), gradient: 0 min 90% A, 6 min 90% A, 27 min 5% A, 38 min 5% A, 38 min 5% A, 39 min 90% A; flow rate: 50 ml/min, detector: 210 nm). Product-containing fractions were combined, concentrated and dried. This gave 26.4 mg (57% of theory) of the title compound.

LC-MS ((Method 3): $R_t$=1.46 min; MS (ESIpos): m/z=377 [M+H]$^+$ $^1$H-NMR (400 MHz, DMSO-d$_6$): δ [ppm]=1.59-1.78 (m, 2H), 1.90-2.12 (m, 2H), 2.27 (s, 3H), 2.35-2.66 (m, 4H, partially covered by solvent signal), 3.32-4.24 (m, 4H, partially overlapped by water signal), 4.69-4.85 (m, 3H), 7.09-715 (m, 4H). A rotamer mixture is present.

Example 43

(5RS)-2-[4-Chloro-3-(trifluoromethoxy)benzyl]-5-[(3,3-difluoropyrrolidin-1-yl)carbonyl]-5,6,7,8-tetrahydro[1,2,4]triazolo[4,3-a]pyridin-3(2H)-one (Racemate)

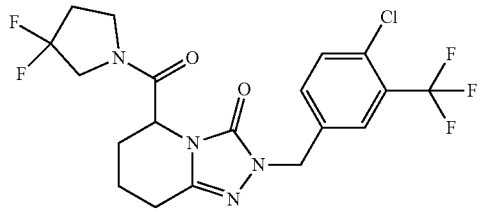 [SMILES: O=C(C1CCCc2nn(Cc3ccc(Cl)c(C(F)(F)F)c3)c(=O)n21)N1CCC(F)(F)C1]

(5RS)-2-[4-Chloro-3-(trifluoromethyl)benzyl]-3-oxo-2,3,5,6,7,8-hexahydro[1,2,4]triazolo[4,3-a]pyridine-5-carboxylic Acid (Racemate) (138 mg, 367 µmol) was dissolved in 4.0 ml of THF. Triethylamine (160 µl, 1.2 mmol), HATU (182 mg, 477 µmol) and 3,3-difluoropyrrolidine hydrochloride (63.3 mg, 441 µmol) were added and the mixture was stirred at room temperature for 3 h. For workup, the mixture was concentrated and the resulting residue was dissolved in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. In this way, 135 mg (79% of theory) of the title compound were obtained.

LC-MS (Method 3): $R_t$=1.76 min; MS (ESIpos): m/z=465 [M+H]$^+$ $^1$H-NMR (400 MHz, DMSO-d$_6$): δ [ppm]=1.58-1.80 (m, 2H), 1.93-2.14 (m, 2H), 2.34-2.69 (m, 4H, partially covered by solvent signal), 3.41-4.26 (m, 4H, partially overlapped by water signal), 4.78 (dd, 0.5H), 4.85 (dd, 0.5H), 4.93 (s, 2H), 7.51 (dd, 1H), 7.72 (d, 1H), 7.76 (d, 1H). A rotamer mixture is present.

Example 44

(5RS)-2-(3-Chlorobenzyl)-5-[(3,3-difluoropyrrolidin-1-yl)carbonyl]-5,6,7,8-tetrahydro[1,2,4]triazolo[4,3-a]pyridin-3(2H)-one (Racemate)

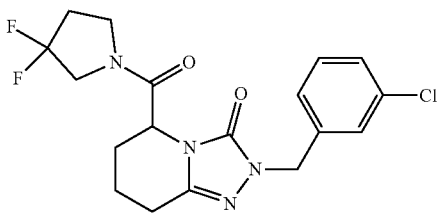 [SMILES: O=C(C1CCCc2nn(Cc3cccc(Cl)c3)c(=O)n21)N1CCC(F)(F)C1]

(5RS)-2-(3-Chlorobenzyl)-3-oxo-2,3,5,6,7,8-hexahydro[1,2,4]triazolo[4,3-a]pyridine-5-carboxylic Acid (Racemate) (110 mg, 83% purity, 297 µmol) was dissolved in 3.5 ml of THF. Triethylamine (130 µl, 950 µmol), HATU (147 mg, 386 µmol) and 3,3-difluoropyrrolidine hydrochloride (51.1 mg, 356 µmol) were added and the mixture was stirred at room temperature overnight. For workup, the mixture was concentrated and the resulting residue was dissolved in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. This gave 89.2 mg (76% of theory) of the title compound.

LC-MS (Method 3): $R_t$=1.52 min; MS (ESIpos): m/z=397 [M+H]$^+$ $^1$H-NMR (400 MHz, DMSO-d$_6$): δ [ppm]=1.59-1.81 (m, 2H), 1.92-2.14 (m, 2H), 2.35-2.69 (m, 4H, partially covered by solvent signal), ca. 3.43-4.25 (m, 4H, partially overlapped by water signal), 4.77 (dd, 0.5H), 4.80-4.89 (m, 2.5H), 7.19 (d, 1H), 7.29 (s, 1H), 7.32-7.42 (m, 2H). A rotamer mixture is present.

Example 45

(5RS)-2-(3,4-Dichlorobenzyl)-5-[(3,3-difluoropyrrolidin-1-yl)carbonyl]-5,6,7,8-tetrahydro[1,2,4]triazolo[4,3-a]pyridin-3(2H)-one (Racemate)

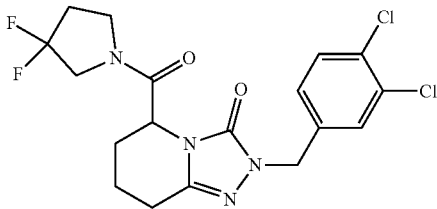 [SMILES: O=C(C1CCCc2nn(Cc3ccc(Cl)c(Cl)c3)c(=O)n21)N1CCC(F)(F)C1]

(5RS)-2-(3,4-Dichlorobenzyl)-3-oxo-2,3,5,6,7,8-hexahydro[1,2,4]triazolo[4,3-a]pyridine-5-carboxylic Acid (Racemate) (120 mg, 80% purity, 281 µmol) was dissolved in 3.5 ml of THF. Triethylamine (125 µl, 900 µmol), HATU (147 mg, 386 µmol) and 3,3-difluoropyrrolidine hydrochloride (48.3 mg, 337 µmol) were added and the mixture was stirred at room temperature overnight. For workup, the mixture was concentrated and the resulting residue was dissolved in acetonitrile/water and separated via preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). Product-containing fractions were combined, concentrated and dried. In this way, 112 mg (90% of theory) of the title compound were obtained.

LC-MS (Method 3): $R_t$=1.68 min; MS (ESIpos): m/z=431 [M+H]$^+$ $^1$H-NMR (400 MHz, DMSO-d$_6$): δ [ppm]=1.59-1.80 (m, 2H), 1.92-2.14 (m, 2H), 2.34-2.69 (m, 4H, partially covered by solvent signal), 3.48-4.25 (m, 4H), 4.77 (dd, 0.5H) 4.81-4.89 (m, 2.5H), 7.22 (dd, 1H), 7.49 (d, 1H), 7.62 (d, 1H). A rotamer mixture is present.

Example 46

(5RS)-2-(3-Chloro-4-methoxybenzyl)-5-(pyrrolidin-1-ylcarbonyl)-5,6,7,8-tetrahydro[1,2,4]triazolo[4,3-a]pyridin-3(2H)-one (Racemate)

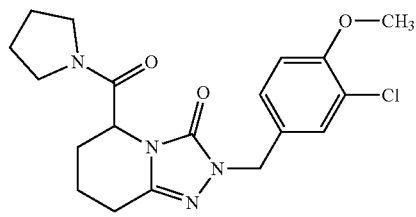 [SMILES: COc1ccc(Cn2nc3n(c2=O)C(C(=O)N2CCCC2)CCC3)cc1Cl]

(5RS)-2-(3-Chloro-4-methoxybenzyl)-3-oxo-2,3,5,6,7,8-hexahydro[1,2,4]triazolo[4,3-a]pyridine-5-carboxylic acid/trifluoroacetic acid (racemate) (70.0 mg, 155 µmol) was initially charged in THF (3.0 ml), and 1-[bis(dimethylamino)methylene]-1H-[1,2,3]triazolo[4,5-b]pyridin-1-ium 3-oxide hexafluorophosphate (76.6 mg, 201 µmol) and triethylamine (110 µl, 770 µmol) were subsequently added. After stirring at room temperature for 15 min, pyrrolidine (16 µl, 190 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 45.3 mg (75% of theory) of the title compound were obtained.

LC-MS (Method 4): $R_t$=0.76 min; MS (ESIpos): m/z=391 [M+H]$^+$ $^1$H-NMR (400 MHz, DMSO-d6) δ [ppm]: 1.399 (1.48), 1.709 (3.03), 1.756 (1.37), 1.773 (4.59), 1.790 (8.04), 1.807 (6.19), 1.824 (1.87), 1.892 (1.96), 1.909 (5.76), 1.925 (7.26), 1.942 (5.02), 1.960 (1.89), 1.977 (2.42), 1.996 (1.92), 2.007 (1.53), 2.022 (1.92), 2.032 (1.45), 2.073 (0.76), 2.328 (0.59), 2.523 (4.16), 2.564 (2.07), 2.577 (1.91), 2.590 (3.62), 2.602 (2.05), 2.621 (0.90), 2.631 (1.41), 2.669 (0.57), 2.865 (0.84), 3.224 (1.07), 3.241 (2.33), 3.254 (2.24), 3.270 (4.01), 3.287 (1.82), 3.326 (1.86), 3.344 (4.00), 3.361 (2.11), 3.373 (2.39), 3.391 (1.09), 3.433 (1.24), 3.451 (2.64), 3.458 (2.04), 3.476 (3.38), 3.493 (1.52), 3.592 (1.52), 3.609 (3.26), 3.625 (1.85), 3.633 (2.56), 3.649 (1.34), 3.729 (0.70), 3.966 (1.62), 4.696 (0.90), 4.724 (3.54), 4.735 (15.25), 4.739 (16.00), 4.779 (0.92), 7.095 (6.08), 7.116 (10.56), 7.167 (5.32), 7.172 (5.46), 7.188 (2.99), 7.193 (3.23), 7.293 (9.06), 7.298 (8.15).

Example 47

(5RS)-5-[(3,3-Difluoropyrrolidin-1-yl)carbonyl]-2-[3-(trifluoromethyl)benzyl]-5,6,7,8-tetrahydro[1,2,4]triazolo[4,3-a]pyridin-3(2H)-one (Racemate)

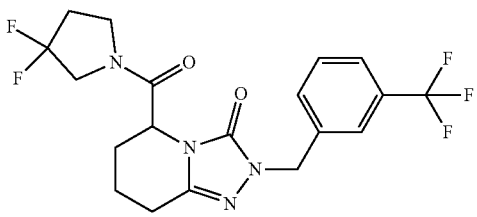 [SMILES: O=C(C1CCCc2nn(Cc3cccc(C(F)(F)F)c3)c(=O)n21)N1CCC(F)(F)C1]

(5RS)-3-Oxo-2-[3-(trifluoromethyl)benzyl]-2,3,5,6,7,8-hexahydro[1,2,4]triazolo[4,3-a]pyridine-5-carboxylic acid/trifluoroacetic acid (racemate) (70.0 mg, 154 µmol) was initially charged in THF (2.6 ml), and 1-[bis(dimethylamino)methylene]-1H-[1,2,3]triazolo[4,5-b]pyridin-1-ium 3-oxide hexafluorophosphate (76.0 mg, 200 µmol) and triethylamine (110 µl, 770 µmol) were subsequently added. After stirring at room temperature for 15 min, 3,3-difluoropyrrolidine hydrochloride (26.5 mg, 184 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.5 mg (70% of theory) of the title compound were obtained.

LC-MS (Method 4): $R_t$=0.86 min; MS (ESIpos): m/z=431 [M+H]$^+$ $^1$H-NMR (400 MHz, DMSO-d6) δ [ppm]: −0.150 (0.90), −0.008 (6.54), 0.008 (6.57), 0.146 (0.79), 1.730 (1.39), 2.012 (1.46), 2.327 (2.25), 2.366 (1.69), 2.523 (8.26), 2.567 (3.00), 2.590 (2.67), 2.609 (3.00), 2.670 (2.59), 2.710 (1.50), 3.537 (1.39), 3.556 (2.07), 3.567 (1.24), 3.671 (1.16), 3.703 (1.43), 3.738 (1.13), 3.770 (1.54), 3.807 (1.80), 3.894 (0.64), 3.913 (1.35), 3.938 (0.94), 3.991 (0.94), 4.180 (0.75), 4.206 (0.75), 4.766 (1.13), 4.783 (1.46), 4.791 (1.13), 4.849 (1.39), 4.931 (16.00), 7.506 (2.37), 7.525 (3.94), 7.572 (2.37), 7.591 (4.39), 7.615 (5.78), 7.648 (3.79), 7.667 (2.22).

Example 48

(5RS)-5-[(3,3-Difluoropyrrolidin-1-yl)carbonyl]-2-(3-methoxybenzyl)-5,6,7,8-tetrahydro[1,2,4]triazolo[4,3-a]pyridin-3(2H)-one (Racemate)

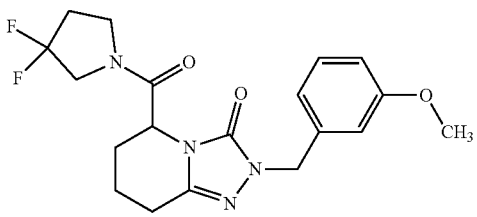 [SMILES: COc1cccc(Cn2nc3n(c2=O)C(C(=O)N2CCC(F)(F)C2)CCC3)c1]

(5RS)-2-(3-Methoxybenzyl)-3-oxo-2,3,5,6,7,8-hexahydro[1,2,4]triazolo[4,3-a]pyridine-5-carboxylic acid/trifluoroacetic acid (racemate) (70.0 mg, 168 µmol) was initially charged in THF (3.0 ml), and 1-[bis(dimethylamino)methylene]-1H-[1,2,3]triazolo[4,5-b]pyridin-1-ium 3-oxide hexafluorophosphate (82.9 mg, 218 µmol) and triethylamine (120 µl, 840 µmol) were subsequently added. After stirring at room temperature for 15 min, 3,3-difluoropyrrolidine hydrochloride (28.9 mg, 201 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 47.1 mg (72% of theory) of the title compound were obtained.

LC-MS (Method 4): $R_t$=0.75 min; MS (ESIpos): m/z=393 [M+H]$^+$ $^1$H-NMR (400 MHz, DMSO-d6) δ [ppm]: 1.176 (0.43), 1.664 (0.83), 1.676 (0.96), 1.688 (1.03), 1.702 (1.17), 1.715 (1.34), 1.724 (1.33), 1.969 (0.80), 1.978 (1.09), 1.992 (1.10), 2.002 (1.22), 2.009 (1.19), 2.026 (0.96), 2.037 (0.90), 2.045 (0.92), 2.052 (0.93), 2.062 (0.88), 2.072 (0.99), 2.080 (0.69), 2.088 (0.63), 2.365 (0.44), 2.380 (0.75), 2.392 (0.57), 2.401 (0.79), 2.409 (0.90), 2.430 (0.86), 2.451 (0.65), 2.472 (0.43), 2.517 (3.02), 2.559 (2.35), 2.569 (2.87), 2.585 (2.57), 2.601 (2.46), 2.612 (1.31), 2.631 (0.48), 2.644 (0.74), 2.669 (0.40), 3.534 (3.05), 3.548 (3.83), 3.554 (3.85), 3.566 (2.82), 3.573 (2.57), 3.635 (0.72), 3.669 (1.32), 3.702 (1.44), 3.769 (1.59), 3.783 (1.02), 3.792 (0.87), 3.802 (1.67), 3.809 (1.48), 3.828 (0.66), 3.894 (0.62), 3.913 (1.29), 3.932 (0.71), 3.939 (0.91), 3.958 (0.48), 3.993 (0.80), 4.021 (0.54), 4.035 (0.71), 4.063 (0.43), 4.147 (0.47), 4.178 (0.68), 4.205 (0.69), 4.750 (1.09), 4.776 (16.00), 4.824 (1.07), 4.834 (1.23), 4.840 (1.38), 4.849 (1.03), 6.773 (6.87), 6.777 (7.30), 6.793 (3.43), 6.823 (2.14), 6.827 (2.29), 6.832 (1.64), 6.845 (2.46), 6.851 (2.14), 7.220 (2.49), 7.241 (5.00), 7.261 (2.64).

Example 49

(5RS)-2-(3-Chloro-4-methoxybenzyl)-5-[(3,3-difluoropyrrolidin-1-yl)carbonyl]-5,6,7,8-tetrahydro[1,2,4]triazolo[4,3-a]pyridin-3(2H)-one (Racemate)

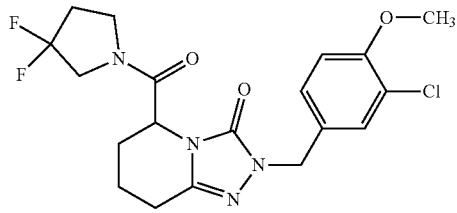 [SMILES: COc1ccc(Cn2nc3n(c2=O)C(C(=O)N2CCC(F)(F)C2)CCC3)cc1Cl]

(5RS)-2-(3-Chloro-4-methoxybenzyl)-3-oxo-2,3,5,6,7,8-hexahydro[1,2,4]triazolo[4,3-a]pyridine-5-carboxylic acid/trifluoroacetic acid (racemate) (70.0 mg, 155 µmol) was initially charged in THF (3.0 ml), and 1-[bis(dimethylamino)methylene]-1H-[1,2,3]triazolo[4,5-b]pyridin-1-ium 3-oxide hexafluorophosphate (76.6 mg, 201 µmol) and triethylamine (110 µl, 770 µmol) were subsequently added. After stirring at room temperature for 15 min, 3,3-difluoropyrrolidine hydrochloride (26.7 mg, 186 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.0 mg (54% of theory) of the title compound were obtained.

LC-MS (Method 4): $R_t$=0.80 min; MS (ESIpos): m/z=427 [M+H]$^+$ $^1$H-NMR (400 MHz, DMSO-d6) δ [ppm]: 1.176 (0.66), 1.669 (0.43), 1.682 (0.48), 1.695 (0.55), 1.707 (0.61), 1.717 (0.61), 1.969 (0.48), 1.981 (0.50), 1.993 (0.57), 2.038 (0.43), 2.045 (0.41), 2.411 (0.41), 2.423 (0.41), 2.565 (1.07), 2.580 (1.02), 2.595 (1.07), 2.607 (0.68), 3.529 (0.46), 3.537 (0.50), 3.546 (0.75), 3.558 (0.84), 3.577 (0.41), 3.666 (0.48), 3.700 (0.55), 3.775 (0.68), 3.806 (1.00), 3.833 (16.00), 3.910 (0.55), 4.745 (4.55), 4.765 (0.50), 4.815 (0.46), 4.825 (0.55), 4.831 (0.59), 4.840 (0.43), 7.097 (1.68), 7.118 (2.94), 7.167 (1.52), 7.172 (1.59), 7.188 (0.84), 7.193 (0.93), 7.292 (2.30), 7.297 (2.12).

Example 50

(5S)-5-(Pyrrolidin-1-ylcarbonyl)-2-{[6-(trifluoromethyl)pyridin-3-yl]methyl}-2,5,6,7-tetrahydro-3H-pyrrolo[2,1-c][1,2,4]triazol-3-one (Enantiomer)

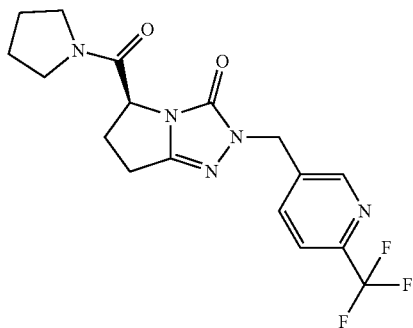 [SMILES: O=C([C@@H]1CCc2nn(Cc3ccc(C(F)(F)F)nc3)c(=O)n21)N1CCCC1]

(5S)-3-Oxo-2-{[6-(trifluoromethyl)pyridin-3-yl]methyl}-2,5,6,7-tetrahydro-3H-pyrrolo[2,1-c][1,2,4]triazole-5-carboxylic acid (enantiomer) (100 mg, 305 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (151 mg, 396 μmol) and triethylamine (170 μl, 1.2 mmol) were added. After stirring for 15 min, pyrrolidine (31 μl, 370 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 50.0 mg (43% of theory) of the title compound were obtained.

LC-MS (Method 3): $R_t$=1.13 min; MS (ESIpos): m/z=382 [M+H]$^+$ $^1$H-NMR (400 MHz, DMSO-d6) δ[ppm]: 1.769 (0.78), 1.784 (3.02), 1.802 (5.93), 1.819 (5.24), 1.835 (1.78), 1.889 (1.56), 1.905 (4.92), 1.922 (6.24), 1.939 (3.71), 1.957 (0.94), 2.367 (1.77), 2.389 (1.77), 2.406 (1.84), 2.416 (1.09), 2.426 (0.84), 2.651 (0.49), 2.674 (1.03), 2.692 (2.10), 2.714 (4.83), 2.724 (2.25), 2.736 (4.61), 2.744 (3.26), 2.754 (1.23), 2.780 (1.92), 2.810 (2.02), 2.832 (1.50), 3.268 (0.55), 3.285 (1.24), 3.298 (2.66), 3.334 (5.63), 3.351 (2.20), 3.364 (1.29), 3.380 (1.63), 3.397 (2.45), 3.404 (1.65), 3.415 (1.42), 3.422 (2.86), 3.439 (1.27), 3.641 (1.30), 3.657 (2.74), 3.666 (1.47), 3.674 (1.51), 3.682 (2.39), 3.699 (1.08), 4.923 (3.04), 4.930 (2.28), 4.944 (3.23), 4.950 (2.23), 5.007 (16.00), 7.902 (2.10), 7.923 (8.79), 7.933 (5.24), 7.957 (1.23), 8.673 (5.78).

Subsequent analyses of Example 175 showed that the 3H-pyrrolo[2,1-c][1,2,4]triazol-3-one systems undergo partial racemization using HATU and are no longer in the form of the pure enantiomer.

Example 51

(5S)-2-(3-Chloro-4-fluorobenzyl)-5-(pyrrolidin-1-ylcarbonyl)-2,5,6,7-tetrahydro-3H-pyrrolo[2,1-c][1,2,4]triazol-3-one (Enantiomer)

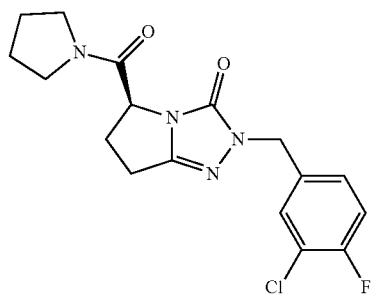 [SMILES: O=C([C@@H]1CCc2nn(Cc3ccc(F)c(Cl)c3)c(=O)n21)N1CCCC1]

(5S)-2-(3-Chloro-4-fluorobenzyl)-3-oxo-2,5,6,7-tetrahydro-3H-pyrrolo[2,1-c][1,2,4]triazole-5-carboxylic acid (enantiomer) (100 mg, 321 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (159 mg, 417 μmol) and triethylamine (180 μl, 1.3 mmol) were added. After stirring for 15 min, pyrrolidine (32 μl, 380 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 65.0 mg (56% of theory) of the title compound were obtained.

LC-MS (Method 4): $R_t$=0.73 min; MS (ESIpos): m/z=365 [M+H]$^+$ $^1$H-NMR (400 MHz, DMSO-d6) δ [ppm]: 1.768 (1.33), 1.784 (5.17), 1.800 (10.32), 1.817 (9.23), 1.833 (3.24), 1.888 (2.78), 1.904 (8.68), 1.921 (10.97), 1.938 (6.38), 1.956 (1.55), 2.327 (1.35), 2.358 (2.20), 2.365 (2.34), 2.379 (3.19), 2.385 (2.61), 2.396 (3.26), 2.407 (1.96), 2.671 (2.13), 2.690 (3.70), 2.712 (7.35), 2.721 (3.63), 2.731 (8.75), 2.739 (5.90), 2.766 (2.80), 2.773 (3.72), 2.803 (3.55), 2.825 (2.63), 2.847 (0.68), 3.265 (1.09), 3.282 (2.37), 3.331 (9.81), 3.349 (3.94), 3.361 (2.22), 3.378 (2.90), 3.395 (4.21), 3.402 (2.85), 3.419 (5.00), 3.437 (2.32), 3.640 (2.37), 3.657 (4.95), 3.665 (2.54), 3.674 (2.66), 3.681 (4.23), 3.698 (1.79), 4.778 (1.21), 4.818 (16.00), 4.823 (15.78), 4.864 (1.11), 4.916 (5.34), 4.923 (3.79), 4.937 (5.68), 4.944 (3.79), 7.250 (2.44), 7.255

(2.66), 7.262 (2.71), 7.271 (4.01), 7.276 (3.79), 7.283 (3.70), 7.289 (3.48), 7.377 (7.40), 7.401 (9.52), 7.422 (5.37), 7.453 (5.78), 7.458 (5.41), 7.471 (5.78), 7.477 (5.32).

Subsequent analyses of Example 175 showed that the 3H-pyrrolo[2,1-c][1,2,4]triazol-3-one systems undergo partial racemization using HATU and are no longer in the form of the pure enantiomer.

Example 52

(5S)-2-[(6-Chloropyridin-3-yl)methyl]-5-(pyrrolidin-1-ylcarbonyl)-2,5,6,7-tetrahydro-3H-pyrrolo[2,1-c][1,2,4]triazol-3-one (Enantiomer)

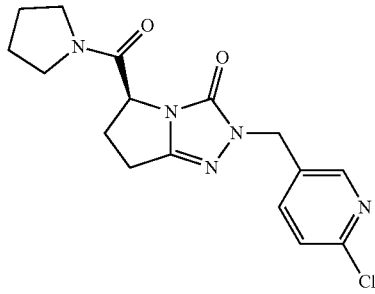 [SMILES: O=C([C@@H]1CCc2nn(Cc3ccc(Cl)nc3)c(=O)n21)N1CCCC1]

(5S)-2-[(6-Chloropyridin-3-yl)methyl]-3-oxo-2,5,6,7-tetrahydro-3H-pyrrolo[2,1-c][1,2,4]triazole-5-carboxylic acid (enantiomer) (80.0 mg, 271 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (134 mg, 353 µmol) and triethylamine (150 µl, 1.1 mmol) were added. After stirring for 15 min, pyrrolidine (27 µl, 330 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 30.0 mg (32% of theory) of the title compound were obtained.

LC-MS (Method 3): $R_t$=0.97 min; MS (ESIpos): m/z=348 [M+H]

$^1$H-NMR (400 MHz, DMSO-d6) δ[ppm]: −0.149 (0.44), 1.782 (2.91), 1.798 (5.45), 1.816 (4.87), 1.832 (1.60), 1.886 (1.48), 1.902 (4.67), 1.919 (5.91), 1.936 (3.46), 1.954 (0.86), 2.328 (0.66), 2.378 (1.73), 2.396 (1.70), 2.681 (1.98), 2.703 (4.30), 2.713 (2.17), 2.724 (4.48), 2.732 (3.11), 2.769 (1.81), 2.799 (1.89), 2.821 (1.40), 3.328 (6.29), 3.346 (2.24), 3.358 (1.33), 3.375 (1.71), 3.392 (2.30), 3.416 (2.65), 3.433 (1.15), 3.636 (1.17), 3.653 (2.62), 3.678 (2.16), 3.694 (0.97), 4.879 (16.00), 4.908 (2.88), 4.929 (3.09), 7.508 (5.17), 7.529 (6.17), 7.716 (3.34), 7.722 (3.44), 7.737 (2.73), 7.743 (2.78), 8.322 (5.32), 8.328 (5.20).

Subsequent analyses of Example 175 showed that the 3H-pyrrolo[2,1-c][1,2,4]triazol-3-one systems undergo partial racemization using HATU and are no longer in the form of the pure enantiomer.

Example 53

(5RS)-2-[(5-Chloro-2-thienyl)methyl]-5-(pyrrolidin-1-ylcarbonyl)-5,6,7,8-tetrahydro[1,2,4]triazolo[4,3-a]pyridin-3(2H)-one (Racemate)

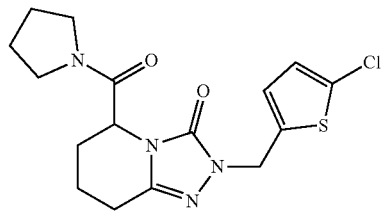 [SMILES: O=C(C1CCCc2nn(Cc3ccc(Cl)s3)c(=O)n21)N1CCCC1]

(5RS)-2-[(5-Chloro-2-thienyl)methyl]-3-oxo-2,3,5,6,7,8-hexahydro[1,2,4]triazolo[4,3-a]pyridine-5-carboxylic acid/trifluoroacetic acid (racemate) (80.0 mg, 187 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (92.4 mg, 243 µmol) and triethylamine (130 µl, 940 µmol) were added. After stirring for 15 min, pyrrolidine (16.0 mg, 224 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 37.9 mg (55% of theory) of the title compound were obtained.

LC-MS (Method 4): $R_t$=0.75 min; MS (ESIpos): m/z=367 [M+H]$^+$ $^1$H-NMR (400 MHz, DMSO-d6) δ[ppm]: 0.008 (1.30), 1.667 (1.13), 1.679 (1.75), 1.702 (3.21), 1.711 (3.57), 1.723 (2.84), 1.753 (1.54), 1.769 (5.20), 1.787 (9.04), 1.804 (6.99), 1.821 (2.02), 1.889 (2.22), 1.906 (6.53), 1.923 (8.49), 1.939 (5.64), 1.958 (2.63), 1.970 (2.76), 1.982 (2.51), 1.991 (2.15), 2.001 (1.70), 2.017 (2.27), 2.027 (1.63), 2.033 (1.49), 2.042 (1.55), 2.052 (0.98), 2.068 (0.58), 2.078 (0.42), 2.327 (0.41), 2.564 (2.63), 2.579 (2.25), 2.592 (2.18), 2.604 (4.23), 2.617 (2.24), 2.634 (0.99), 2.646 (1.58), 2.659 (0.84), 2.669 (0.51), 2.865 (3.48), 3.219 (1.23), 3.236 (2.56), 3.248 (2.58), 3.265 (4.57), 3.282 (2.29), 3.333 (4.95), 3.345 (1.94), 3.350 (2.73), 3.362 (2.79), 3.380 (1.23), 3.428 (1.37), 3.445 (2.98), 3.453 (2.21), 3.462 (1.78), 3.470 (3.82), 3.487 (1.67), 3.586 (1.75), 3.602 (3.65), 3.611 (1.84), 3.619 (2.06), 3.627 (2.82), 3.644 (1.26), 4.707 (3.29), 4.717 (3.82), 4.722 (4.37), 4.732 (3.35), 4.872 (0.79), 4.914 (16.00), 4.957 (0.85), 6.898 (6.58), 6.908 (8.26), 6.973 (11.05), 6.982 (8.62).

Example 54

(5RS)-2-[(5-Chloro-2-thienyl)methyl]-5-[(3,3-difluoropyrrolidin-1-yl)carbonyl]-5,6,7,8-tetrahydro[1,2,4]triazolo[4,3-a]pyridin-3(2H)-one (Racemate)

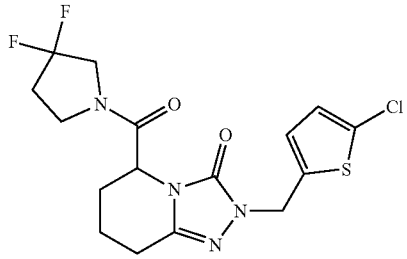 [SMILES: O=C(C1CCCc2nn(Cc3ccc(Cl)s3)c(=O)n21)N1CCC(F)(F)C1]

(5RS)-2-[(5-Chloro-2-thienyl)methyl]-3-oxo-2,3,5,6,7,8-hexahydro[1,2,4]triazolo[4,3-a]pyridine-5-carboxylic acid/trifluoroacetic acid (racemate) (80.0 mg, 187 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (92.4 mg, 243 µmol) and triethylamine (130 µl, 940 µmol) were added. After stirring for 15 min, 3,3-difluoropyrrolidine hydrochloride (32.2 mg, 224 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 42.9 mg (57% of theory) of the title compound were obtained.

LC-MS (Method 4): $R_t$=0.80 min; MS (ESIpos): m/z=403 [M+H]$^+$ $^1$H-NMR (400 MHz, DMSO-d6) δ [ppm]: −0.008 (1.94), 1.718 (1.95), 1.977 (1.59), 1.987 (1.79), 2.032 (1.31), 2.049 (1.24), 2.068 (1.06), 2.327 (0.63), 2.359 (0.64), 2.377 (1.04), 2.406 (1.36), 2.427 (1.37), 2.447 (1.16), 2.569 (3.54), 2.580 (3.06), 2.594 (3.16), 2.610 (3.13), 2.622 (1.69), 2.653 (1.01), 2.669 (0.88), 3.528 (1.74), 3.540 (2.31), 3.548 (2.49), 3.559 (1.40), 3.567 (1.29), 3.626 (0.45), 3.660 (1.48), 3.694 (1.68), 3.731 (0.97), 3.767 (1.92), 3.800 (3.09), 3.818 (0.78), 3.884 (0.83), 3.902 (1.68), 3.928 (1.18), 3.947 (0.61), 3.984 (1.06), 4.012 (0.76), 4.025 (0.96), 4.054 (0.54), 4.138 (0.59), 4.170 (0.95), 4.195 (0.98), 4.226 (0.40), 4.725 (1.42), 4.740 (1.87), 4.749 (1.31), 4.799 (1.40), 4.815 (1.84), 4.824 (1.28), 4.880 (0.62), 4.922 (16.00), 4.964 (0.58), 6.901 (6.08), 6.911 (7.61), 6.975 (10.97), 6.984 (8.41).

Example 55

(5S)-5-(Pyrrolidin-1-ylcarbonyl)-2-[3-(trifluoromethyl)benzyl]-2,5,6,7-tetrahydro-3H-pyrrolo[2,1-c][1,2,4]triazol-3-one (Enantiomer)

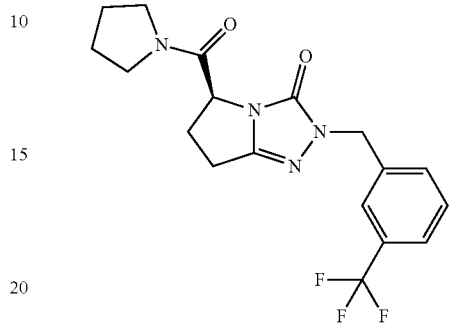

Methyl (5S)-3-oxo-2-[3-(trifluoromethyl)benzyl]-2,5,6,7-tetrahydro-3H-pyrrolo[2,1-c][1,2,4]triazole-5-carboxylate (enantiomer) (129 mg, 378 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (187 mg, 491 µmol) and triethylamine (160 µl, 1.1 mmol) were added. After stirring for 15 min, pyrrolidine (38 µl, 450 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 92.4 mg (64% of theory) of the title compound were obtained.

LC-MS (Method 3): $R_t$=1.42 min; MS (ESIpos): m/z=381 [M+H]$^+$ $^1$H-NMR (400 MHz, DMSO-d6) δ [ppm]: 1.766 (1.04), 1.782 (4.19), 1.799 (7.77), 1.816 (6.67), 1.832 (2.28), 1.887 (2.03), 1.903 (6.44), 1.920 (8.25), 1.937 (4.97), 1.954 (1.24), 2.349 (0.56), 2.360 (1.57), 2.365 (1.56), 2.380 (2.45), 2.387 (1.96), 2.397 (2.42), 2.408 (1.49), 2.417 (1.09), 2.650 (0.53), 2.672 (1.15), 2.691 (2.65), 2.712 (5.74), 2.722 (2.89), 2.733 (6.33), 2.740 (4.71), 2.749 (1.93), 2.767 (2.15), 2.774 (2.86), 2.781 (2.42), 2.797 (1.52), 2.804 (2.59), 2.818 (0.67), 2.826 (1.87), 2.848 (0.50), 3.265 (0.75), 3.282 (1.61), 3.295 (3.42), 3.330 (7.74), 3.348 (2.95), 3.360 (1.63), 3.377 (2.15), 3.394 (3.17), 3.401 (2.24), 3.412 (1.91), 3.419 (3.67), 3.436 (1.66), 3.642 (1.70), 3.659 (3.64), 3.667 (1.93), 3.676 (2.05), 3.684 (3.12), 3.701 (1.38), 4.883 (1.04), 4.923 (16.00), 4.929 (15.45), 4.946 (4.38), 4.953 (3.12), 4.969 (1.11), 7.540 (2.51), 7.559 (5.89), 7.578 (3.43), 7.597 (5.63), 7.616 (2.78), 7.637 (7.35), 7.650 (5.01), 7.669 (2.64).

Subsequent analyses of Example 175 showed that the 3H-pyrrolo[2,1-c][1,2,4]triazol-3-one systems undergo partial racemization using HATU and are no longer in the form of the pure enantiomer.

Example 56

(5RS)-5-[(3,3-Difluoropyrrolidin-1-yl)carbonyl]-2-(3-fluorobenzyl)-5,6,7,8-tetrahydro[1,2,4]triazolo[4,3-a]pyridin-3(2H)-one (Racemate)

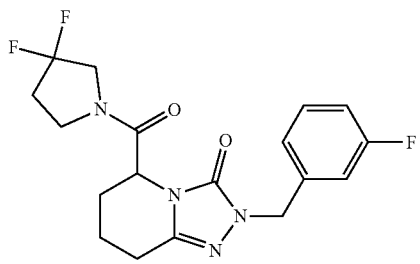 [SMILES: O=C(C1CCCc2nn(Cc3cccc(F)c3)c(=O)n21)N1CCC(F)(F)C1]

(5RS)-2-(3-Fluorobenzyl)-3-oxo-2,3,5,6,7,8-hexahydro[1,2,4]triazolo[4,3-a]pyridine-5-carboxylic acid hydrochloride (racemate) (140 mg, 427 μmol) was initially charged in THF (4.4 ml) at room temperature. Subsequently, 1-[bis(dimethylamino)methylene]-1H-[1,2,3]triazolo[4,5-b]pyridin-1-ium 3-oxide hexafluorophosphate (211 mg, 555 μmol) and triethylamine (300 μl, 2.1 mmol) were added. After stirring for 15 min, 3,3-difluoropyrrolidine hydrochloride (73.6 mg, 513 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 103 mg (63% of theory) of the title compound were obtained.

LC-MS (Method 3): $R_t$=1.36 min; MS (ESIpos): m/z=381 [M+H]$^+$ $^1$H-NMR (400 MHz, DMSO-d6) δ [ppm]: −0.008 (2.16), 0.008 (2.37), 1.676 (0.97), 1.687 (0.91), 1.725 (1.22), 1.989 (1.10), 2.000 (1.15), 2.010 (1.23), 2.044 (0.92), 2.052 (0.94), 2.059 (0.96), 2.069 (0.86), 2.079 (0.71), 2.088 (0.73), 2.095 (0.65), 2.327 (0.76), 2.366 (0.86), 2.382 (0.86), 2.392 (0.62), 2.411 (0.99), 2.430 (0.96), 2.454 (0.79), 2.522 (2.93), 2.580 (2.11), 2.594 (2.22), 2.610 (2.37), 2.624 (1.23), 2.642 (0.57), 2.653 (0.79), 2.669 (1.02), 2.709 (0.62), 3.534 (1.02), 3.541 (1.18), 3.551 (1.70), 3.561 (1.83), 3.570 (1.12), 3.580 (1.01), 3.671 (1.12), 3.705 (1.23), 3.745 (0.68), 3.778 (1.44), 3.792 (0.76), 3.811 (2.30), 3.829 (0.58), 3.893 (0.57), 3.912 (1.20), 3.931 (0.68), 3.939 (0.83), 3.957 (0.42), 3.993 (0.75), 4.022 (0.50), 4.036 (0.68), 4.149 (0.44), 4.180 (0.66), 4.205 (0.68), 4.759 (1.01), 4.769 (1.15), 4.774 (1.33), 4.783 (0.99), 4.843 (16.00), 4.857 (1.28), 7.006 (1.90), 7.030 (1.98), 7.057 (2.87), 7.076 (3.29), 7.090 (1.01), 7.106 (1.95), 7.112 (1.82), 7.128 (1.09), 7.134 (1.04), 7.358 (1.62), 7.374 (1.96), 7.378 (2.58), 7.393 (2.53), 7.413 (1.28).

Example 57

(5RS)-2-[2-(4-Methylphenyl)ethyl]-5-(pyrrolidin-1-ylcarbonyl)-5,6,7,8-tetrahydro[1,2,4]triazolo[4,3-a]pyridin-3(2H)-one (Racemate)

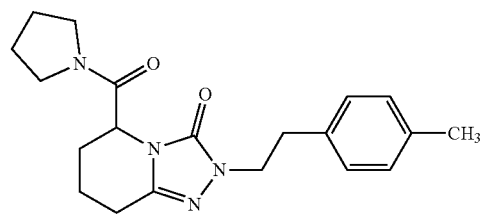 [SMILES: Cc1ccc(CCn2nc3n(c2=O)C(C(=O)N2CCCC2)CCC3)cc1]

(5RS)-2-[2-(4-Methylphenyl)ethyl]-3-oxo-2,3,5,6,7,8-hexahydro[1,2,4]triazolo[4,3-a]pyridine-5-carboxylic Acid (Racemate) (82.0 mg, 100% purity, 272 μmol) was initially charged in THF (2.8 ml), and 1-[bis(dimethylamino)methylene]-1H-[1,2,3]triazolo[4,5-b]pyridin-1-ium 3-oxide hexafluorophosphate (135 mg, 354 μmol) and triethylamine (190 μl, 1.4 mmol) were subsequently added. After stirring at room temperature for 15 min, pyrrolidine (27 μl, 330 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 77.0 mg (80% of theory) of the title compound were obtained.

LC-MS (Method 3): $R_t$=1.42 min; MS (ESIpos): m/z=355 [M+H]$^+$ $^1$H-NMR (400 MHz, DMSO-d6) δ[ppm]: −0.150 (0.41), −0.008 (3.12), 0.008 (3.21), 1.714 (0.99), 1.765 (1.02), 1.781 (1.70), 1.798 (1.31), 1.884 (0.49), 1.899 (1.27), 1.916 (1.68), 1.934 (1.12), 1.961 (0.65), 1.998 (0.53), 2.257 (9.18), 2.327 (0.70), 2.366 (0.43), 2.613 (0.80), 2.669 (0.79), 2.709 (0.41), 2.849 (0.94), 2.868 (1.96), 2.887 (1.03), 3.233 (0.51), 3.263 (0.94), 3.328 (1.09), 3.358 (0.59), 3.440 (0.56), 3.465 (0.70), 3.588 (0.61), 3.613 (0.58), 3.729 (0.63), 3.748 (0.96), 3.766 (0.58), 3.778 (0.91), 3.798 (0.57), 4.660 (0.71), 4.675 (0.82), 4.685 (0.62), 7.085 (16.00).

Example 58

(5RS)-2-(2-Methylbenzyl)-5-(pyrrolidin-1-ylcarbonyl)-5,6,7,8-tetrahydro[1,2,4]triazolo[4,3-a]pyridin-3(2H)-one (Racemate)

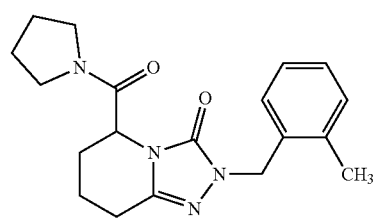 [SMILES: Cc1ccccc1Cn1nc2n(c1=O)C(C(=O)N1CCCC1)CCC2]

(5RS)-2-(2-Methylbenzyl)-3-oxo-2,3,5,6,7,8-hexahydro[1,2,4]triazolo[4,3-a]pyridine-5-carboxylic Acid (Racemate) (80.0 mg, 278 μmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (138 mg, 362 µmol) and triethylamine (78 µl, 560 mol) were added. After stirring for 15 min, pyrrolidine (28 µl, 330 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 42.0 mg (44% of theory) of the title compound were obtained.

LC-MS (Method 3): $R_t$=1.27 min; MS (ESIpos): m/z=341 [M+H]$^+$ $^1$H-NMR (400 MHz, DMSO-d6) δ [ppm]: −0.008 (0.91), 0.008 (0.90), 1.110 (0.57), 1.680 (0.58), 1.703 (1.15), 1.712 (1.23), 1.723 (0.96), 1.756 (0.51), 1.772 (1.74), 1.790 (3.06), 1.807 (2.39), 1.823 (0.69), 1.892 (0.70), 1.909 (2.16), 1.925 (2.75), 1.942 (1.76), 1.959 (0.74), 1.973 (0.55), 1.984 (0.98), 1.996 (1.12), 2.008 (0.75), 2.023 (0.80), 2.034 (0.55), 2.040 (0.50), 2.049 (0.52), 2.293 (16.00), 2.475 (0.40), 2.574 (0.74), 2.585 (1.41), 2.598 (0.79), 2.627 (0.56), 3.226 (0.42), 3.243 (0.89), 3.255 (0.90), 3.272 (1.59), 3.290 (0.88), 3.321 (1.26), 3.340 (1.67), 3.352 (0.61), 3.357 (0.85), 3.369 (0.93), 3.387 (0.43), 3.436 (0.46), 3.454 (1.02), 3.461 (0.74), 3.471 (0.62), 3.479 (1.32), 3.496 (0.58), 3.594 (0.60), 3.610 (1.23), 3.619 (0.61), 3.627 (0.71), 3.635 (0.96), 3.652 (0.42), 4.727 (1.13), 4.736 (1.29), 4.742 (1.50), 4.751 (1.15), 4.778 (8.67), 7.070 (1.24), 7.088 (2.10), 7.117 (0.63), 7.125 (0.62), 7.131 (1.10), 7.139 (1.42), 7.157 (1.70), 7.166 (5.62), 7.180 (1.21), 7.184 (0.89).

Example 59

(5RS)-2-[(2-Chloropyridin-4-yl)methyl]-5-(pyrrolidin-1-ylcarbonyl)-5,6,7,8-tetrahydro[1,2,4]triazolo[4,3-a]pyridin-3(2H)-one (Racemate)

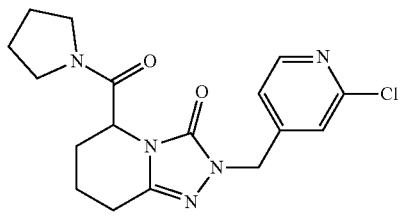 [SMILES: O=C(C1CCCc2nn(Cc3ccnc(Cl)c3)c(=O)n21)N1CCCC1]

(5RS)-2-[(2-Chloropyridin-4-yl)methyl]-3-oxo-2,3,5,6,7,8-hexahydro[1,2,4]triazolo[4,3-a]pyridine-5-carboxylic acid/trifluoroacetic acid (racemate) (110 mg, 94% purity, 245 µmol) was initially charged in THF (2.5 ml) at room temperature. Subsequently, 1-[bis(dimethylamino)methylene]-1H-[1,2,3]triazolo[4,5-b]pyridin-1-ium 3-oxide hexafluorophosphate (121 mg, 318 µmol) and triethylamine (170 µl, 1.2 mmol) were added. After stirring for 15 min, pyrrolidine (25 µl, 290 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 10.0 mg (11% of theory) of the title compound were obtained.

LC-MS (Method 4): $R_t$=0.60 min; MS (ESIpos): m/z=362 [M+H]$^+$ $^1$H-NMR (500 MHz, DMSO-d6) δ [ppm]: −0.120 (0.49), −0.007 (3.51), 0.006 (3.30), 0.117 (0.49), 1.499 (0.65), 1.693 (1.62), 1.740 (2.32), 1.748 (2.11), 1.766 (2.32), 1.778 (6.81), 1.792 (10.92), 1.806 (8.00), 1.820 (2.22), 1.901 (1.95), 1.912 (4.76), 1.925 (6.22), 1.939 (4.00), 1.952 (1.30), 1.997 (1.08), 2.015 (2.59), 2.033 (2.27), 2.040 (1.78), 2.046 (1.73), 2.053 (1.89), 2.062 (1.95), 2.068 (2.05), 2.361 (2.92), 2.365 (2.11), 2.439 (3.14), 2.518 (8.27), 2.522 (6.54), 2.559 (3.51), 2.571 (2.81), 2.580 (2.81), 2.592 (2.27), 2.617 (2.11), 2.627 (4.76), 2.635 (5.08), 2.650 (1.14), 2.660 (1.84), 2.865 (8.59), 3.242 (1.73), 3.256 (3.57), 3.266 (3.41), 3.280 (6.65), 3.338 (3.95), 3.353 (5.62), 3.367 (3.19), 3.376 (3.41), 3.390 (1.62), 3.449 (1.51), 3.463 (3.41), 3.469 (2.54), 3.483 (4.16), 3.497 (1.95), 3.598 (1.89), 3.611 (3.57), 3.625 (2.22), 3.631 (2.92), 3.645 (1.51), 3.700 (4.27), 4.766 (3.68), 4.772 (4.00), 4.778 (4.59), 4.785 (3.57), 4.833 (0.92), 4.878 (0.86), 4.912 (16.00), 4.948 (0.86), 7.209 (5.73), 7.219 (6.11), 7.319 (10.32), 8.342 (0.54), 8.368 (9.30), 8.378 (9.30).

Example 60

(5RS)-2-[(4-Methyl-1,2,5-oxadiazol-3-yl)methyl]-5-(pyrrolidin-1-ylcarbonyl)-5,6,7,8-tetrahydro[1,2,4]triazolo[4,3-a]pyridin-3(2H)-one (Racemate)

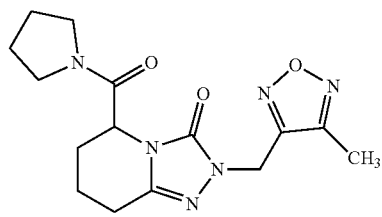 [SMILES: Cc1nonc1Cn1nc2n(c1=O)C(C(=O)N1CCCC1)CCC2]

(5RS)-2-[(4-Methyl-1,2,5-oxadiazol-3-yl)methyl]-3-oxo-2,3,5,6,7,8-hexahydro[1,2,4]triazolo[4,3-a]pyridine-5-carboxylic Acid (Racemate) (91.0 mg, 326 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (161 mg, 424 µmol) and triethylamine (91 µl, 650 µmol) were added. After stirring for 15 min, pyrrolidine (33 µl, 390 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 14.0 mg (13% of theory) of the title compound were obtained.

LC-MS (Method 3): $R_t$=0.97 min; MS (ESIpos): m/z=333 [M+H]$^+$ $^1$H-NMR (400 MHz, DMSO-d6) δ [ppm]: −0.008 (1.20), 0.008 (1.14), 1.711 (0.58), 1.721 (0.49), 1.772 (1.12), 1.790 (2.07), 1.807 (1.67), 1.823 (0.52), 1.891 (0.52), 1.908 (1.52), 1.924 (1.83), 1.941 (1.16), 1.957 (0.46), 1.998 (0.83), 2.023 (0.48), 2.289 (16.00), 2.523 (1.52), 2.565 (0.60), 2.582 (0.53), 2.593 (0.89), 2.606 (0.52), 3.238 (0.56), 3.251 (0.62), 3.268 (1.07), 3.285 (0.55), 3.328 (1.23), 3.345 (0.59), 3.357 (0.61), 3.449 (0.70), 3.456 (0.52), 3.474 (0.90), 3.490 (0.41), 3.588 (0.43), 3.604 (0.83), 3.613 (0.44), 3.621 (0.47), 3.630 (0.66), 4.739 (0.79), 4.748 (0.87), 4.754 (1.02), 4.763 (0.76), 5.087 (4.25), 5.092 (4.25).

Example 61

(5RS)-2-[(5-Methyl-1,2-oxazol-3-yl)methyl]-5-(pyrrolidin-1-ylcarbonyl)-5,6,7,8-tetrahydro[1,2,4]triazolo[4,3-a]pyridin-3(2H)-one (Racemate)

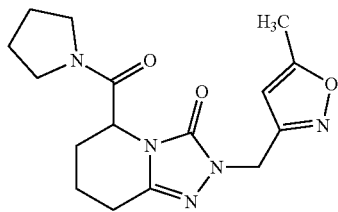 [SMILES: Cc1cc(Cn2nc3n(c2=O)C(C(=O)N2CCCC2)CCC3)no1]

(5RS)-2-[(5-Methyl-1,2-oxazol-3-yl)methyl]-3-oxo-2,3,5,6,7,8-hexahydro[1,2,4]triazolo[4,3-a]pyridine-5-carboxylic Acid (Racemate) (133 mg, 94% purity, 449 µmol) was initially charged in THF (4.7 ml), and 1-[bis(dimethylamino)methylene]-1H-[1,2,3]triazolo[4,5-b]pyridin-1-ium 3-oxide hexafluorophosphate (222 mg, 584 µmol) and triethylamine (310 µl, 2.2 mmol) were subsequently added. After stirring at room temperature for 15 min, pyrrolidine (45 µl, 540 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 18.0 mg (12% of theory) of the title compound were obtained.

LC-MS (Method 4): $R_t$=0.55 min; MS (ESIpos): m/z=332 [M+H]$^+$ $^1$H-NMR (500 MHz, DMSO-d6) δ [ppm]: −0.007 (0.94), 0.006 (0.97), 1.179 (0.41), 1.237 (0.58), 1.717 (1.18), 1.763 (0.56), 1.776 (2.23), 1.790 (3.84), 1.804 (2.83), 1.818 (0.75), 1.899 (0.86), 1.912 (2.55), 1.925 (3.24), 1.939 (2.02), 1.952 (0.90), 1.981 (0.90), 2.007 (0.47), 2.015 (0.60), 2.027 (0.77), 2.036 (0.64), 2.042 (0.66), 2.048 (0.64), 2.201 (1.16), 2.361 (1.31), 2.370 (15.57), 2.371 (16.00), 2.518 (3.75), 2.522 (3.17), 2.567 (0.92), 2.591 (0.79), 2.600 (1.50), 2.610 (0.86), 2.635 (1.63), 2.865 (1.80), 3.232 (0.54), 3.245 (1.12), 3.255 (1.05), 3.269 (1.84), 3.283 (1.07), 3.342 (2.62), 3.352 (1.14), 3.356 (1.29), 3.366 (1.44), 3.380 (0.69), 3.444 (0.60), 3.457 (1.24), 3.463 (0.90), 3.471 (0.75), 3.477 (1.59), 3.491 (0.71), 3.594 (0.69), 3.607 (1.46), 3.614 (0.77), 3.621 (0.86), 3.628 (1.16), 3.641 (0.51), 3.717 (1.24), 4.724 (1.48), 4.729 (1.63), 4.736 (1.35), 4.781 (0.66), 4.813 (5.96), 4.819 (6.01), 4.851 (0.64), 6.062 (4.18).

Example 62

(5RS)-2-[(1-Methyl-1H-benzimidazol-2-yl)methyl]-5-(pyrrolidin-1-ylcarbonyl)-5,6,7,8-tetrahydro[1,2,4]triazolo[4,3-a]pyridin-3(2H)-one (Racemate)

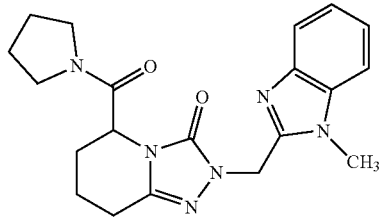 [SMILES: Cn1c(Cn2nc3n(c2=O)C(C(=O)N2CCCC2)CCC3)nc2ccccc21]

(5RS)-2-[(1-Methyl-1H-benzimidazol-2-yl)methyl]-3-oxo-2,3,5,6,7,8-hexahydro[1,2,4]triazolo[4,3-a]pyridine-5-carboxylic Acid (Racemate) (120 mg, 367 µmol) was dissolved in DMF (2.8 ml) at room temperature. Subsequently, 1-[bis(dimethylamino)methylene]-1H-[1,2,3]triazolo[4,5-b]pyridin-1-ium 3-oxide hexafluorophosphate (181 mg, 477 µmol) and triethylamine (200 µl, 1.5 mmol) were added. After stirring for 15 min, pyrrolidine (37 µl, 440 µmol) was added and the reaction mixture was stirred at room temperature overnight. 1-[Bis(dimethylamino)methylene]-1H-[1,2,3]triazolo[4,5-b]pyridin-1-ium 3-oxide hexafluorophosphate (139 mg, 367 µmol) and pyrrolidine (31 µl, 367 µmol) were added again and the mixture was stirred at room temperature for 2 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 46.0 mg (33% of theory) of the title compound were obtained.

LC-MS (Method 3): $R_t$=0.83 min; MS (ESIpos): m/z=381 [M+H]$^+$ $^1$H-NMR (400 MHz, DMSO-d6) δ [ppm]: −0.008 (0.51), 0.008 (0.44), 1.653 (0.44), 1.667 (0.48), 1.677 (0.52), 1.690 (0.67), 1.702 (0.81), 1.712 (0.59), 1.725 (0.41), 1.777 (1.23), 1.795 (2.26), 1.812 (1.88), 1.829 (0.60), 1.897 (0.57), 1.914 (1.73), 1.931 (2.23), 1.947 (1.48), 1.964 (0.58), 1.977 (0.48), 1.987 (0.82), 1.997 (1.01), 2.006 (0.73), 2.022 (0.56), 2.033 (0.46), 2.040 (0.44), 2.048 (0.42), 2.518 (1.12), 2.566 (1.13), 2.578 (0.64), 2.608 (0.40), 3.245 (0.71), 3.258 (0.74), 3.275 (1.21), 3.292 (0.62), 3.324 (0.72), 3.342 (1.30), 3.354 (0.50), 3.360 (0.67), 3.372 (0.73), 3.459 (0.82), 3.466 (0.60), 3.476 (0.51), 3.483 (1.02), 3.501 (0.45), 3.604 (0.47), 3.620 (1.00), 3.628 (0.51), 3.637 (0.58), 3.645 (0.78), 3.755 (16.00), 4.749 (0.91), 4.758 (1.02), 4.764 (1.18), 4.772 (0.87), 5.072 (1.17), 5.111 (3.74), 5.139 (3.71), 5.178 (1.17), 7.172 (0.65), 7.175 (0.66), 7.192 (1.54), 7.209 (1.33), 7.212 (1.19), 7.233 (1.09), 7.236 (1.14), 7.253 (1.60), 7.271 (0.78), 7.273 (0.68), 7.524 (1.79), 7.544 (1.56), 7.582 (1.63), 7.602 (1.52).

Example 63

(5RS)-2-[4-Methoxy-3-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

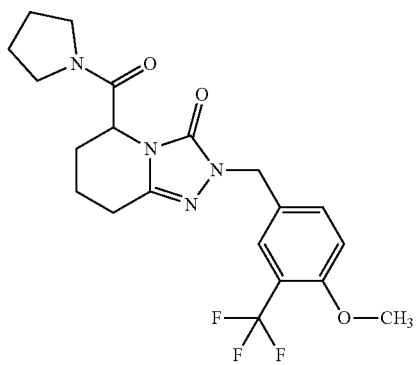 [SMILES: COc1ccc(Cn2nc3n(c2=O)C(C(=O)N2CCCC2)CCC3)cc1C(F)(F)F]

(5RS)-2-[4-Methoxy-3-(trifluoromethyl)benzyl]-3-oxo-2,3,5,6,7,8-hexahydro[1,2,4]triazolo[4,3-a]pyridine-5-carboxylic Acid (Racemate) (75.0 mg, 202 µmol) was initially charged in THF (2.3 ml) at room temperature. Subsequently, 1-[bis(dimethylamino)methylene]-1H-[1,2,3]triazolo[4,5-b]pyridin-1-ium 3-oxide hexafluorophosphate (99.8 mg, 263 mol) and triethylamine (140 µl, 1.0 mmol) were added. After stirring for 15 min, pyrrolidine (20 µl, 240 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 40.0 mg (47% of theory) of the title compound were obtained.

LC-MS (Method 4): $R_t$=0.81 min; MS (ESIpos): m/z=425 [M+H]$^+$ $^1$H-NMR (400 MHz, DMSO-d6) δ [ppm]: −0.008 (1.02), 0.008 (0.93), 1.674 (0.45), 1.697 (0.88), 1.708 (0.99), 1.719 (0.77), 1.755 (0.43), 1.773 (1.40), 1.790 (2.47), 1.807 (1.91), 1.824 (0.55), 1.892 (0.61), 1.909 (1.78), 1.925 (2.25), 1.942 (1.58), 1.960 (0.51), 1.967 (0.47), 1.978 (0.78), 1.990 (0.76), 2.005 (0.53), 2.020 (0.62), 2.030 (0.44), 2.036 (0.41), 2.046 (0.43), 2.073 (0.94), 2.519 (1.40), 2.561 (0.63), 2.576 (0.59), 2.588 (1.12), 2.600 (0.62), 2.630 (0.44), 2.865 (0.45), 3.240 (0.73), 3.253 (0.72), 3.269 (1.28), 3.287 (0.68), 3.322 (1.06), 3.341 (1.35), 3.352 (0.53), 3.358 (0.70), 3.370 (0.77), 3.449 (0.83), 3.457 (0.61), 3.467 (0.49), 3.474 (1.05), 3.491 (0.46), 3.592 (0.48), 3.608 (1.00), 3.616 (0.50), 3.625 (0.57), 3.633 (0.77), 3.871 (16.00), 4.726 (0.91), 4.735 (1.03), 4.741 (1.21), 4.750 (0.90), 4.807 (4.91), 7.227 (1.60), 7.248 (1.89), 7.477 (1.19), 7.498 (1.06), 7.519 (2.24).

Example 64

(5RS)-2-[(1-Methyl-1H-indazol-5-yl)methyl]-5-(pyrrolidin-1-ylcarbonyl)-5,6,7,8-tetrahydro[1,2,4]triazolo[4,3-a]pyridin-3(2H)-one (Racemate)

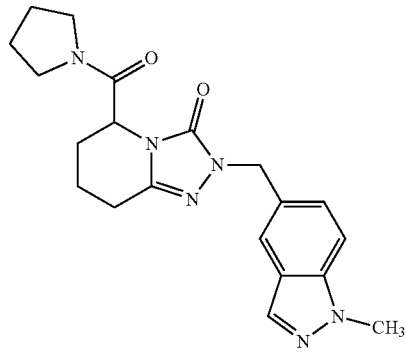 [SMILES: Cn1ncc2cc(Cn3nc4n(c3=O)C(C(=O)N3CCCC3)CCC4)ccc21]

(5RS)-2-[(1-Methyl-1H-indazol-5-yl)methyl]-3-oxo-2,3,5,6,7,8-hexahydro[1,2,4]triazolo[4,3-a]pyridine-5-carboxylic Acid (Racemate) (65.0 mg, 199 µmol) was initially charged in THF (2.3 ml) at room temperature. Subsequently, 1-[bis(dimethylamino)methylene]-1H-[1,2,3]triazolo[4,5-b]pyridin-1-ium 3-oxide hexafluorophosphate (98.2 mg, 258 mol) and triethylamine (140 µl, 990 µmol) were added. After stirring for 15 min, pyrrolidine (20 µl, 240 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 26.0 mg (34% of theory) of the title compound were obtained.

LC-MS (Method 3): $R_t$=1.04 min; MS (ESIpos): m/z=381 [M+H]$^+$ $^1$H-NMR (400 MHz, DMSO-d6) δ [ppm]: −0.008 (1.76), 0.008 (1.67), 1.681 (0.57), 1.691 (0.92), 1.704 (1.22), 1.717 (0.94), 1.775 (1.31), 1.792 (2.33), 1.809 (1.80), 1.826 (0.53), 1.894 (0.59), 1.911 (1.69), 1.928 (2.24), 1.945 (1.49), 1.962 (0.71), 1.972 (0.74), 1.984 (0.67), 1.993 (0.54), 2.007 (0.47), 2.018 (0.55), 2.028 (0.45), 2.043 (0.42), 2.072 (0.79), 2.523 (1.39), 2.567 (0.67), 2.579 (1.17), 2.591 (0.61), 2.621 (0.45), 2.865 (0.91), 3.244 (0.73), 3.257 (0.73), 3.273 (1.25), 3.291 (0.83), 3.331 (0.80), 3.349 (1.31), 3.361 (0.51), 3.367 (0.68), 3.379 (0.74), 3.456 (0.79), 3.463 (0.57), 3.473 (0.48), 3.480 (1.00), 3.497 (0.44), 3.597 (0.45), 3.614 (0.97), 3.622 (0.48), 3.631 (0.54), 3.639 (0.75), 4.021 (16.00), 4.723 (0.86), 4.732 (0.98), 4.739 (1.17), 4.747 (0.84), 4.841 (0.57), 4.879 (2.97), 4.894 (2.98), 4.932 (0.56), 7.280 (1.34), 7.284 (1.16), 7.302 (1.36), 7.305 (1.54), 7.581 (1.86), 7.604 (4.27), 8.009 (2.76).

Example 65

(5RS)-2-[2,5-Bis(trifluoromethyl)benzyl]-5-(pyrrolidin-1-ylcarbonyl)-5,6,7,8-tetrahydro[1,2,4]triazolo[4,3-a]pyridin-3(2H)-one (Racemate)

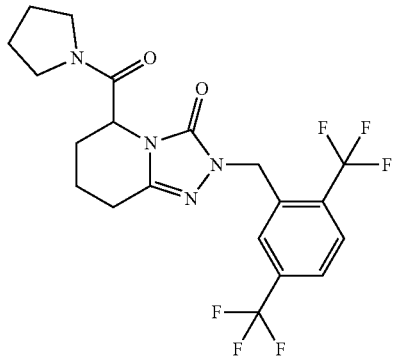 [SMILES: O=C(C1CCCc2nn(Cc3cc(C(F)(F)F)ccc3C(F)(F)F)c(=O)n21)N1CCCC1]

(5RS)-2-[2,5-Bis(trifluoromethyl)benzyl]-3-oxo-2,3,5,6,7,8-hexahydro[1,2,4]triazolo[4,3-a]pyridine-5-carboxylic Acid (Racemate) (50.0 mg, 122 µmol) was initially charged in THF (2.0 ml), and 1-[bis(dimethylamino)methylene]-1H-[1,2,3]triazolo[4,5-b]pyridin-1-ium 3-oxide hexafluorophosphate (60.4 mg, 159 µmol) and triethylamine (51 µl, 370 µmol) were subsequently added. After stirring at room temperature for 15 min, pyrrolidine (10.4 mg, 147 µmol) was added and the reaction mixture was stirred at room temperature for 48 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 18.2 mg (32% of theory) of the title compound were obtained.

LC-MS (Method 3): $R_t$=1.72 min; MS (ESIpos): m/z=463 [M+H]$^+$ $^1$H-NMR (400 MHz, DMSO-d6) δ[ppm]: −0.149 (0.98), −0.008 (11.17), 0.008 (8.68), 0.146 (1.03), 1.697 (1.57), 1.707 (1.63), 1.735 (2.71), 1.756 (2.33), 1.773 (5.59), 1.790 (9.06), 1.807 (6.83), 1.824 (1.95), 1.893 (2.33), 1.909 (6.13), 1.926 (7.38), 1.943 (4.39), 1.960 (1.19), 2.025 (3.74), 2.036 (3.91), 2.078 (1.46), 2.328 (1.79), 2.366 (1.14), 2.524 (6.94), 2.566 (3.04), 2.577 (2.82), 2.592 (2.12), 2.614 (2.06), 2.625 (3.74), 2.638 (2.17), 2.670 (3.15), 2.710 (1.30), 2.865 (3.74), 3.230 (1.25), 3.247 (2.60), 3.260 (2.71), 3.276 (4.99), 3.338 (5.32), 3.356 (2.71), 3.368 (2.82), 3.385 (1.25), 3.441 (1.46), 3.458 (2.98), 3.466 (2.17), 3.483 (3.74), 3.501 (1.68), 3.594 (1.74), 3.611 (3.42), 3.627 (2.01), 3.635 (2.77), 3.652 (1.08), 3.700 (1.19), 3.730 (1.41), 4.749 (0.49), 4.785 (3.15), 4.794 (3.53), 4.800 (4.34), 4.808 (3.04), 5.077 (16.00), 7.654 (7.27), 7.917 (2.98), 7.938 (4.56), 8.013 (6.40), 8.034 (4.23).

Example 66

(5RS)-2-[4-Fluoro-3-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

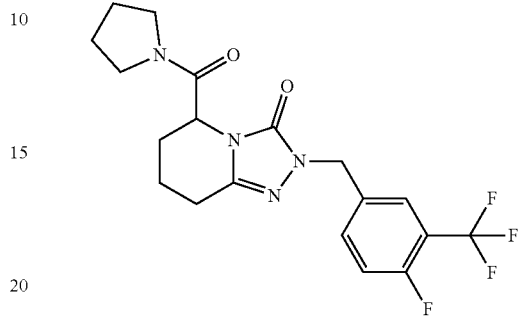

(5RS)-2-[4-Fluoro-3-(trifluoromethyl)benzyl]-3-oxo-2,3,5,6,7,8-hexahydro[1,2,4]triazolo[4,3-a]pyridine-5-carboxylic Acid (Racemate) (50.0 mg, 139 µmol) was initially charged in THF (2.0 ml), and 1-[bis(dimethylamino)methylene]-1H-[1,2,3]triazolo[4,5-b]pyridin-1-ium 3-oxide hexafluorophosphate (68.8 mg, 181 µmol) and triethylamine (58 µl, 420 µmol) were subsequently added. After stirring at room temperature for 15 min, pyrrolidine (11.9 mg, 167 µmol) was added and the reaction mixture was stirred at room temperature overnight. 1-[Bis(dimethylamino)methylene]-1H-[1,2,3]triazolo[4,5-b]pyridin-1-ium 3-oxide hexafluorophosphate (68.8 mg, 181 µmol), pyrrolidine (11.9 mg, 167 µmol) and triethylamine (58 µl, 420 µmol) were added again and the mixture was stirred at room temperature for 48 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 25.6 mg (45% of theory) of the title compound were obtained.

LC-MS (Method 3): $R_t$=1.53 min; MS (ESIpos): m/z=413 [M+H]$^+$ $^1$H-NMR (400 MHz, DMSO-d6) δ [ppm]: −0.149 (0.40), −0.008 (3.74), 0.008 (3.05), 0.146 (0.40), 1.662 (0.79), 1.673 (1.11), 1.686 (1.26), 1.707 (1.77), 1.716 (2.14), 1.726 (1.68), 1.740 (1.04), 1.754 (1.26), 1.773 (3.89), 1.790 (6.75), 1.807 (5.19), 1.824 (1.46), 1.892 (1.79), 1.909 (4.77), 1.925 (5.75), 1.942 (3.51), 1.958 (1.44), 1.982 (1.14), 1.992 (2.02), 2.004 (2.51), 2.014 (1.72), 2.030 (1.46), 2.041 (1.16), 2.048 (1.16), 2.056 (1.11), 2.065 (0.58), 2.323 (0.49), 2.327 (0.67), 2.332 (0.47), 2.366 (0.58), 2.523 (2.42), 2.558 (2.05), 2.572 (1.65), 2.588 (1.58), 2.600 (2.88), 2.613 (1.65), 2.630 (0.75), 2.642 (1.14), 2.654 (0.60), 2.665 (0.58), 2.669 (0.72), 2.674 (0.53), 2.710 (0.63), 2.865 (3.96), 3.225 (0.96), 3.242 (2.02), 3.255 (1.96), 3.272 (3.58), 3.289 (2.11), 3.340 (3.82), 3.351 (1.54), 3.357 (1.98), 3.369 (2.14), 3.387 (0.93), 3.435 (1.04), 3.452 (2.28), 3.460 (1.63), 3.470 (1.35), 3.477 (2.86), 3.494 (1.25), 3.591 (1.32), 3.607 (2.65), 3.615 (1.33), 3.624 (1.53), 3.632 (2.07), 3.649 (0.95), 4.741 (2.49), 4.750 (2.68), 4.756 (3.18), 4.765 (2.39), 4.904 (16.00), 7.478 (1.72), 7.500 (3.12), 7.526 (3.04), 7.561 (1.60), 7.566 (1.77), 7.573 (1.82), 7.579 (2.07), 7.587 (1.23), 7.595 (0.98), 7.600 (1.00), 7.669 (2.53), 7.674 (2.37), 7.687 (2.60).

Example 67

(5RS)-2-[3-Fluoro-4-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

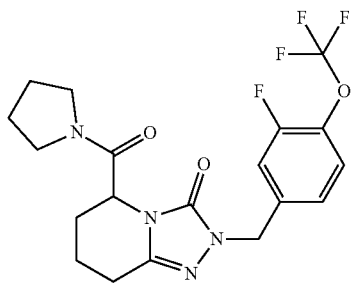 [SMILES: O=C(C1CCCc2nn(Cc3ccc(OC(F)(F)F)c(F)c3)c(=O)n21)N1CCCC1]

(5RS)-2-[3-Fluoro-4-(trifluoromethoxy)benzyl]-3-oxo-2,3,5,6,7,8-hexahydro[1,2,4]triazolo[4,3-a]pyridine-5-carboxylic Acid (Racemate) (80.0 mg, 213 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (105 mg, 277 µmol) and triethylamine (89 µl, 640 µmol) were added. After stirring for 15 min, pyrrolidine (21 µl, 260 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 45.0 mg (49% of theory) of the title compound were obtained.

LC-MS (Method 4): $R_t$=0.88 min; MS (ESIpos): m/z=429 [M+H]$^+$ $^1$H-NMR (400 MHz, DMSO-d6) δ [ppm]: −0.008 (1.37), 0.008 (1.36), 1.662 (0.74), 1.669 (0.77), 1.681 (1.08), 1.695 (1.22), 1.704 (1.35), 1.717 (1.75), 1.728 (2.05), 1.737 (1.56), 1.757 (1.39), 1.774 (4.00), 1.791 (6.45), 1.809 (4.96), 1.818 (1.10), 1.826 (1.95), 1.836 (1.76), 1.844 (0.70), 1.854 (0.69), 1.893 (1.41), 1.910 (4.09), 1.926 (5.10), 1.943 (3.12), 1.960 (1.11), 1.979 (0.73), 1.993 (1.14), 2.003 (2.00), 2.015 (2.49), 2.024 (1.73), 2.040 (1.41), 2.051 (1.14), 2.059 (1.12), 2.066 (1.07), 2.074 (0.68), 2.559 (1.84), 2.570 (1.70), 2.584 (1.52), 2.599 (1.51), 2.611 (2.77), 2.623 (1.59), 2.641 (0.71), 2.653 (1.09), 2.665 (0.70), 3.095 (0.74), 3.232 (0.86), 3.248 (1.81), 3.261 (1.80), 3.278 (3.18), 3.295 (1.57), 3.329 (1.65), 3.346 (3.24), 3.358 (1.22), 3.364 (1.70), 3.376 (1.90), 3.394 (0.86), 3.441 (0.95), 3.459 (2.08), 3.466 (1.55), 3.476 (1.27), 3.484 (2.68), 3.501 (1.19), 3.593 (1.23), 3.610 (2.48), 3.618 (1.30), 3.626 (1.47), 3.634 (1.92), 3.651 (0.90), 4.747 (2.31), 4.756 (2.57), 4.761 (3.04), 4.771 (2.27), 4.879 (16.00), 7.160 (2.64), 7.182 (2.97), 7.303 (2.85), 7.308 (2.71), 7.331 (2.93), 7.336 (2.75), 7.537 (1.68), 7.557 (3.12), 7.577 (1.50).

Example 68

(5RS)-2-{[3-Chloro-5-(trifluoromethyl)pyridin-2-yl]methyl}-5-(pyrrolidin-1-ylcarbonyl)-5,6,7,8-tetrahydro[1,2,4]triazolo[4,3-a]pyridin-3(2H)-one (Racemate)

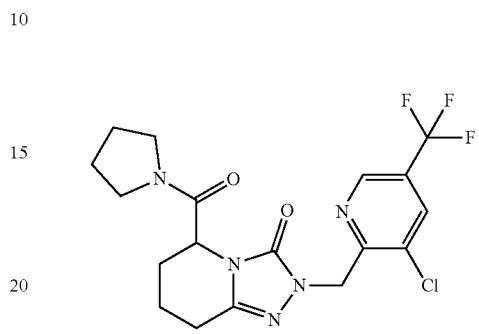

(5RS)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic Acid (Racemate) (80.0 mg, 212 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (105 mg, 276 µmol) and triethylamine (89 µl, 640 mol) were added. After stirring for 15 min, pyrrolidine (21 µl, 250 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated.

The residue was purified via preparative HPLC (Chromatorex C18, 10 µm, 125 mm×30 mm; eluent: acetonitrile/water gradient). The product-containing fractions were concentrated under reduced pressure, and 62.0 mg (68% of theory) of the title compound were obtained.

LC-MS (Method 4): $R_t$=0.75 min; MS (ESIpos): m/z=430 [M+H]$^+$ $^1$H-NMR (400 MHz, DMSO-d6) δ [ppm]: −0.149 (0.57), −0.008 (5.51), 0.008 (4.76), 0.146 (0.58), 1.530 (0.64), 1.678 (1.30), 1.691 (2.52), 1.701 (6.30), 1.714 (8.12), 1.732 (5.69), 1.745 (2.84), 1.753 (2.43), 1.771 (8.48), 1.789 (14.82), 1.806 (11.36), 1.822 (3.36), 1.891 (3.49), 1.908 (10.40), 1.924 (12.93), 1.941 (8.24), 1.959 (3.75), 1.973 (2.58), 1.984 (4.67), 1.995 (4.19), 2.006 (3.22), 2.022 (3.48), 2.036 (2.54), 2.043 (3.25), 2.058 (2.91), 2.078 (1.33), 2.094 (0.70), 2.328 (0.87), 2.366 (0.78), 2.474 (1.94), 2.523 (3.34), 2.567 (3.64), 2.579 (7.40), 2.592 (3.66), 2.609 (1.60), 2.621 (2.75), 2.634 (1.12), 2.670 (0.91), 2.690 (0.54), 2.710 (0.57), 3.229 (1.99), 3.247 (4.27), 3.259 (4.25), 3.276 (7.72), 3.293 (4.00), 3.320 (5.40), 3.338 (7.91), 3.350 (2.84), 3.355 (4.06), 3.367 (4.42), 3.385 (1.97), 3.443 (2.22), 3.460 (4.90), 3.468 (3.60), 3.477 (2.93), 3.485 (6.22), 3.502 (2.73), 3.596 (2.81), 3.612 (5.82), 3.620 (2.96), 3.629 (3.40), 3.637 (4.55), 3.654 (2.03), 4.736 (5.46), 4.745 (6.31), 4.751 (7.34), 4.761 (5.43), 5.063 (4.87), 5.104 (16.00), 5.135 (15.54), 5.175 (4.67), 8.486 (11.75), 8.490 (11.76), 8.903 (11.49), 8.906 (11.69).

Example 69

(5RS)-5-(Pyrrolidin-1-ylcarbonyl)-2-({5-[3-(trifluoromethyl)phenyl]-1,2,4-oxadiazol-3-yl}methyl)-5,6,7,8-tetrahydro[1,2,4]triazolo[4,3-a]pyridin-3(2H)-one (Racemate)

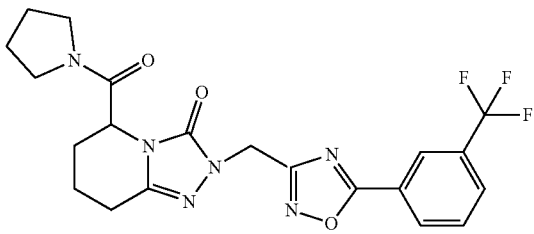

(5RS)-3-Oxo-2-({5-[3-(trifluoromethyl)phenyl]-1,2,4-oxadiazol-3-yl}methyl)-2,3,5,6,7,8-hexahydro[1,2,4]triazolo[4,3-a]pyridine-5-carboxylic Acid (Racemate) (70.0 mg, 88% purity, 151 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (74.7 mg, 197 µmol) and triethylamine (63 µl, 450 µmol) were added. After stirring for 15 min, pyrrolidine (12.9 mg, 181 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 27.6 mg (39% of theory) of the title compound were obtained.

LC-MS (Method 3): $R_t$=1.57 min; MS (ESIpos): m/z=463 [M+H]$^+$ $^1$H-NMR (400 MHz, DMSO-d6) δ[ppm]: -0.149 (1.57), -0.008 (14.76), 0.008 (12.96), 0.146 (1.57), 1.726 (4.98), 1.738 (4.23), 1.760 (1.87), 1.777 (6.00), 1.795 (10.23), 1.812 (7.87), 1.829 (2.32), 1.899 (2.40), 1.915 (7.31), 1.932 (9.52), 1.949 (6.41), 1.964 (2.55), 1.976 (1.84), 1.988 (3.04), 1.999 (2.66), 2.031 (1.99), 2.043 (2.06), 2.053 (2.02), 2.068 (1.95), 2.323 (1.39), 2.327 (1.91), 2.366 (1.12), 2.523 (7.08), 2.566 (3.60), 2.588 (2.66), 2.598 (2.59), 2.610 (5.17), 2.623 (2.62), 2.640 (1.16), 2.652 (1.84), 2.665 (2.21), 2.670 (2.21), 2.674 (1.54), 2.710 (1.16), 3.235 (1.39), 3.252 (3.04), 3.264 (2.96), 3.281 (5.43), 3.329 (2.85), 3.347 (5.47), 3.365 (2.96), 3.377 (3.19), 3.394 (1.46), 3.448 (1.57), 3.466 (3.56), 3.473 (2.51), 3.483 (2.25), 3.490 (4.42), 3.508 (1.95), 3.605 (2.02), 3.622 (4.23), 3.630 (2.10), 3.638 (2.40), 3.647 (3.26), 3.663 (1.42), 4.647 (0.86), 4.662 (0.90), 4.750 (3.78), 4.759 (4.50), 4.765 (5.13), 4.774 (3.78), 5.019 (4.95), 5.060 (16.00), 5.088 (16.00), 5.128 (5.06), 7.876 (3.37), 7.896 (7.46), 7.915 (4.31), 8.100 (5.43), 8.120 (4.53), 8.333 (8.39), 8.394 (5.43), 8.413 (5.17).

Example 70

(5RS)-2-[(1-Ethyl-1H-imidazol-2-yl)methyl]-5-(pyrrolidin-1-ylcarbonyl)-5,6,7,8-tetrahydro[1,2,4]triazolo[4,3-a]pyridin-3(2H)-one (Racemate)

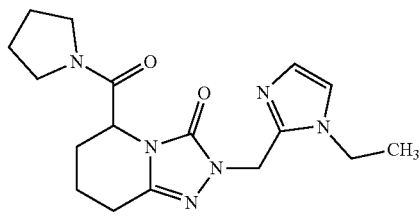 [SMILES: CCn1ccnc1Cn1nc2n(c1=O)C(C(=O)N1CCCC1)CCC2]

(5RS)-2-[(1-Ethyl-1H-imidazol-2-yl)methyl]-3-oxo-2,3,5,6,7,8-hexahydro[1,2,4]triazolo[4,3-a]pyridine-5-carboxylic Acid (Racemate) (80.0 mg, 60% purity, 165 µmol) was initially charged in DMF (2.0 ml), and 1-[bis(dimethylamino)methylene]-1H-[1,2,3]triazolo[4,5-b]pyridin-1-ium 3-oxide hexafluorophosphate (81.4 mg, 214 µmol) and triethylamine (92 µl, 660 µmol) were subsequently added. After stirring at room temperature for 15 min, pyrrolidine (17 µl, 200 µmol) was added and the reaction mixture was stirred at room temperature overnight. 1-[Bis(dimethylamino)methylene]-1H-[1,2,3]triazolo[4,5-b]pyridin-1-ium 3-oxide hexafluorophosphate (63.8 mg, 165 µmol) and pyrrolidine (14 µl, 165 µmol) were added again and the mixture was stirred at room temperature for 2 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 6.00 mg (11% of theory) of the title compound were obtained.

LC-MS (Method 9): $R_t$=3.74 min; MS (ESIpos): m/z=345 [M+H]$^+$ $^1$H-NMR (400 MHz, DMSO-d6) δ [ppm]: -0.008 (3.41), 0.008 (2.88), 1.300 (7.13), 1.319 (16.00), 1.337 (7.18), 1.655 (0.66), 1.666 (0.90), 1.679 (0.96), 1.691 (0.97), 1.705 (1.24), 1.717 (1.47), 1.729 (1.20), 1.757 (1.00), 1.774 (2.92), 1.791 (4.94), 1.808 (3.77), 1.825 (1.17), 1.894 (1.99), 1.910 (3.30), 1.927 (3.65), 1.943 (2.23), 1.961 (1.03), 1.975 (0.56), 1.988 (1.00), 1.999 (2.36), 2.009 (2.34), 2.023 (1.62), 2.034 (0.90), 2.040 (0.83), 2.049 (0.76), 2.072 (0.41), 2.322 (0.52), 2.327 (0.66), 2.332 (0.51), 2.366 (0.54), 2.518 (3.41), 2.523 (2.61), 2.561 (1.55), 2.576 (1.19), 2.592 (1.19), 2.605 (2.17), 2.617 (1.20), 2.634 (0.58), 2.646 (0.89), 2.660 (0.62), 2.665 (0.63), 2.669 (0.75), 2.674 (0.55), 2.689 (0.58), 2.710 (0.54), 2.865 (13.73), 3.219 (0.78), 3.236 (1.55), 3.249 (1.78), 3.266 (3.05), 3.283 (1.95), 3.298 (2.44), 3.315 (4.95), 3.334 (6.17), 3.345 (6.63), 3.445 (0.99), 3.462 (1.79), 3.469 (1.41), 3.479 (1.11), 3.487 (2.22), 3.504 (1.00), 3.581 (1.00), 3.597 (1.93), 3.606 (1.03), 3.614 (1.16), 3.622 (1.45), 3.639 (0.68), 4.145 (1.55), 4.162 (4.11), 4.180 (3.94), 4.183 (3.94), 4.200 (1.38), 4.728 (1.76), 4.738 (2.03), 4.743 (2.55), 4.753 (1.68), 5.163 (1.06), 5.204 (6.89), 5.216 (6.69), 5.257 (1.06), 6.939 (0.66), 7.066 (0.68), 7.194 (0.65), 7.642 (3.94), 7.646 (3.98), 7.776 (4.66), 7.780 (4.28).

Example 71

(5RS)-2-[2-Fluoro-3-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

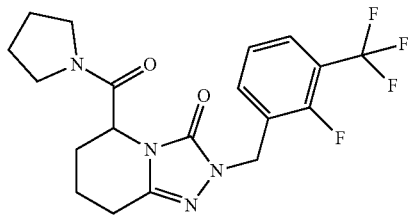 [SMILES: O=C(C1CCCc2nn(Cc3cccc(C(F)(F)F)c3F)c(=O)n21)N1CCCC1]

(5RS)-2-[2-Fluoro-3-(trifluoromethyl)benzyl]-3-oxo-2,3,5,6,7,8-hexahydro[1,2,4]triazolo[4,3-a]pyridine-5-carboxylic Acid (Racemate) (80.0 mg, 223 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (110 mg, 289 μmol) and triethylamine (93 μl, 670 μmol) were added. After stirring for 15 min, pyrrolidine (22 μl, 270 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 55.0 mg (60% of theory) of the title compound were obtained.

LC-MS (Method 3): $R_t$=1.50 min; MS (ESIpos): m/z=413 [M+H]$^+$ $^1$H-NMR (400 MHz, DMSO-d6) δ [ppm]: −0.150 (0.92), 0.008 (8.29), 0.146 (1.03), 1.693 (3.76), 1.704 (5.42), 1.717 (6.38), 1.755 (3.06), 1.773 (9.29), 1.790 (16.00), 1.807 (12.53), 1.824 (3.65), 1.892 (3.91), 1.909 (11.28), 1.926 (14.08), 1.942 (9.14), 1.960 (3.91), 1.988 (5.09), 2.030 (3.91), 2.073 (3.21), 2.328 (2.40), 2.367 (1.18), 2.559 (5.86), 2.573 (4.20), 2.588 (4.06), 2.600 (7.48), 2.613 (4.20), 2.642 (2.91), 2.669 (2.54), 2.690 (1.25), 2.710 (1.40), 3.227 (2.43), 3.243 (4.53), 3.256 (4.57), 3.273 (8.00), 3.290 (4.39), 3.325 (5.31), 3.343 (8.41), 3.361 (4.50), 3.372 (4.94), 3.391 (2.03), 3.436 (2.43), 3.454 (5.05), 3.461 (4.02), 3.479 (6.86), 3.496 (3.02), 3.590 (3.13), 3.607 (6.30), 3.623 (3.76), 3.632 (4.90), 3.649 (2.18), 4.737 (5.82), 4.747 (6.67), 4.752 (8.04), 4.761 (5.68), 4.895 (3.50), 4.935 (15.48), 4.956 (15.48), 4.995 (3.65), 6.509 (1.29), 7.386 (4.68), 7.406 (10.43), 7.425 (6.23), 7.555 (4.72), 7.573 (7.63), 7.590 (3.65), 7.720 (4.13), 7.736 (7.82), 7.756 (3.91).

Example 72

(5RS)-2-[3-Fluoro-5-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

(5RS)-2-[3-Fluoro-5-(trifluoromethyl)benzyl]-3-oxo-2,3,5,6,7,8-hexahydro[1,2,4]triazolo[4,3-a]pyridine-5-carboxylic Acid (Racemate) (80.0 mg, 223 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (110 mg, 289 μmol) and triethylamine (93 μl, 670 μmol) were added. After stirring for 15 min, pyrrolidine (22 μl, 270 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 48.0 mg (52% of theory) of the title compound were obtained.

LC-MS (Method 3): $R_t$=1.55 min; MS (ESIpos): m/z=413 [M+H]

$^1$H-NMR (400 MHz, DMSO-d6) δ [ppm]: −0.008 (3.15), 0.008 (2.63), 1.690 (1.16), 1.701 (1.12), 1.728 (1.86), 1.740 (1.51), 1.755 (1.38), 1.774 (4.07), 1.791 (6.54), 1.809 (5.03), 1.825 (1.42), 1.893 (1.52), 1.910 (4.33), 1.927 (5.32), 1.943 (3.23), 1.961 (1.03), 1.972 (0.74), 2.019 (2.53), 2.028 (1.84), 2.043 (1.33), 2.054 (1.16), 2.062 (1.14), 2.073 (1.44), 2.327 (0.72), 2.563 (2.11), 2.574 (1.91), 2.589 (1.64), 2.604 (1.57), 2.616 (2.72), 2.628 (1.55), 2.646 (0.75), 2.657 (1.15), 2.670 (1.25), 2.710 (0.45), 2.865 (0.60), 3.231 (0.84), 3.247 (1.83), 3.260 (1.90), 3.277 (3.31), 3.294 (1.92), 3.326 (1.93), 3.344 (3.35), 3.361 (1.78), 3.373 (1.90), 3.391 (0.87), 3.439 (0.94), 3.457 (2.17), 3.464 (1.54), 3.482 (2.73), 3.499 (1.19), 3.595 (1.24), 3.611 (2.50), 3.620 (1.31), 3.628 (1.51), 3.636 (1.92), 3.653 (0.88), 4.761 (2.42), 4.770 (2.59), 4.776 (3.10), 4.785 (2.31), 4.959 (16.00), 7.329 (2.37), 7.352 (2.34), 7.502 (5.85), 7.601 (2.38), 7.623 (2.42).

Example 73

(5RS)-2-[3-Chloro-4-(trifluoromethoxy)benzyl]-5-(pyrrolidin-1-ylcarbonyl)-5,6,7,8-tetrahydro[1,2,4]triazolo[4,3-a]pyridin-3(2H)-one (Racemate)

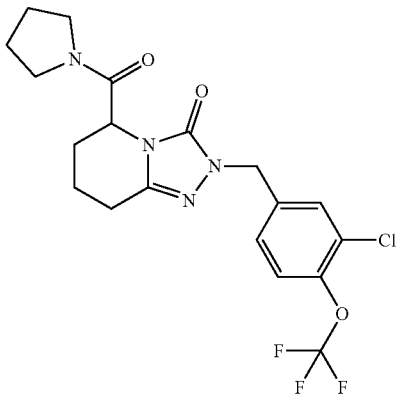 [SMILES: O=C(C1CCCc2nn(Cc3ccc(OC(F)(F)F)c(Cl)c3)c(=O)n21)N1CCCC1]

(5RS)-2-[3-Chloro-4-(trifluoromethoxy)benzyl]-3-oxo-2,3,5,6,7,8-hexahydro[1,2,4]triazolo[4,3-a]pyridine-5-carboxylic Acid (Racemate) (75.0 mg, 95% purity, 182 μmol) was initially charged in THF (2.1 ml) at room temperature. Subsequently, 1-[bis(dimethylamino)methylene]-1H-[1,2,3]triazolo[4,5-b]pyridin-1-ium 3-oxide hexafluorophosphate (89.9 mg, 236 mol) and triethylamine (130 μl, 910 μmol) were added. After stirring for 15 min, pyrrolidine (18 μl, 220 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 41.0 mg (51% of theory) of the title compound were obtained.

LC-MS (Method 3): $R_t$=1.69 min; MS (ESIpos): m/z=445 [M+H]

$^1$H-NMR (400 MHz, DMSO-d6) δ [ppm]: −0.149 (0.80), −0.008 (6.96), 0.008 (5.94), 0.146 (0.78), 1.724 (1.73), 1.756 (1.17), 1.774 (3.10), 1.791 (5.36), 1.808 (4.08), 1.824 (1.15), 1.893 (1.26), 1.909 (3.66), 1.926 (4.36), 1.943 (2.67), 1.960 (1.19), 1.988 (1.32), 1.997 (1.60), 2.010 (1.65), 2.038 (1.17), 2.048 (0.93), 2.063 (1.06), 2.073 (16.00), 2.281 (1.30), 2.327 (1.21), 2.366 (0.71), 2.523 (3.73), 2.558 (1.89), 2.569 (1.54), 2.583 (1.30), 2.597 (1.24), 2.609 (2.28), 2.622 (1.28), 2.639 (0.58), 2.651 (0.93), 2.665 (1.28), 2.669 (1.34), 2.710 (0.59), 2.865 (0.45), 3.229 (0.69), 3.246 (1.58), 3.258 (1.52), 3.275 (2.71), 3.293 (1.56), 3.329 (1.50), 3.347 (2.73), 3.365 (1.47), 3.377 (1.61), 3.394 (0.74), 3.438 (0.78), 3.456 (1.76), 3.464 (1.28), 3.473 (1.06), 3.481 (2.25), 3.498 (0.95), 3.592 (1.02), 3.608 (2.08), 3.617 (1.06), 3.625 (1.23), 3.633 (1.58), 3.650 (0.72), 3.726 (1.63), 4.541 (0.69), 4.745 (1.93), 4.754 (2.10), 4.760 (2.52), 4.769 (1.84), 4.873 (14.14), 7.156 (0.65), 7.306 (2.49), 7.311 (2.54), 7.327 (2.99), 7.332 (3.06), 7.533 (5.10), 7.539 (4.92), 7.547 (2.99), 7.551 (2.88), 7.569 (2.47), 7.572 (2.41).

Example 74

(5RS)-5-(Pyrrolidin-1-ylcarbonyl)-2-{[2-(trifluoromethyl)pyridin-4-yl]methyl}-5,6,7,8-tetrahydro[1,2,4]triazolo[4,3-a]pyridin-3(2H)-one (Enantiomer 1)

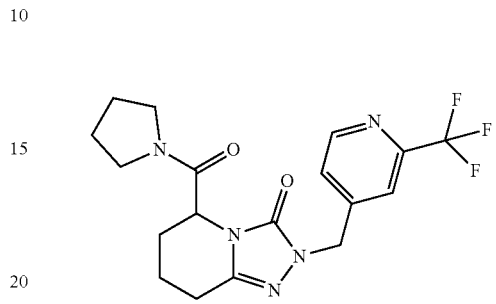

(5RS)-3-Oxo-2-{[2-(trifluoromethyl)pyridin-4-yl]methyl}-2,3,5,6,7,8-hexahydro[1,2,4]triazolo[4,3-a]pyridine-5-carboxylic Acid (Enantiomer 1) (70.0 mg, 205 μmol) was initially charged in THF (2 ml) at room temperature. Subsequently, 1-[bis(dimethylamino)methylene]-1H-[1,2,3]triazolo[4,5-b]pyridin-1-ium 3-oxide hexafluorophosphate (97.1 mg, 255 mol) and triethylamine (82 μl, 590 μmol) were added. After stirring for 15 min, pyrrolidine (20 μl, 240 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 66.0 mg (85% of theory) of the title compound were obtained.

LC-MS (Method 3): $R_t$=1.18 min; MS (ESIpos): m/z=396 [M+H]

$^1$H-NMR (400 MHz, DMSO-d6) δ [ppm]: −0.008 (1.82), 0.008 (1.91), 1.663 (0.97), 1.683 (1.29), 1.696 (1.47), 1.706 (1.28), 1.732 (1.80), 1.741 (2.17), 1.756 (2.12), 1.775 (5.55), 1.792 (8.58), 1.809 (6.36), 1.826 (1.82), 1.894 (1.68), 1.910 (4.88), 1.927 (6.01), 1.943 (3.66), 1.960 (1.07), 1.989 (0.74), 2.000 (0.78), 2.015 (1.44), 2.029 (3.22), 2.038 (3.51), 2.045 (2.41), 2.054 (1.95), 2.066 (1.46), 2.072 (1.43), 2.081 (1.30), 2.108 (0.49), 2.327 (0.55), 2.523 (1.95), 2.558 (2.98), 2.572 (2.50), 2.584 (2.37), 2.598 (1.98), 2.614 (1.90), 2.625 (3.38), 2.637 (2.01), 2.656 (0.92), 2.666 (1.65), 2.679 (0.87), 3.237 (1.07), 3.254 (2.30), 3.266 (2.34), 3.283 (4.24), 3.330 (2.25), 3.347 (4.22), 3.359 (1.53), 3.365 (2.21), 3.377 (2.39), 3.394 (1.07), 3.445 (1.23), 3.462 (2.68), 3.469 (2.01), 3.479 (1.58), 3.487 (3.47), 3.504 (1.50), 3.594 (1.62), 3.611 (3.15), 3.619 (1.64), 3.627 (1.83), 3.636 (2.39), 3.652 (1.14), 4.774 (2.95), 4.783 (3.30), 4.789 (4.07), 4.798 (2.91), 4.980 (0.51), 5.024 (16.00), 5.068 (0.51), 7.473 (4.22), 7.485 (4.38), 7.760 (8.48), 8.726 (6.15), 8.739 (6.08).

The (5S) configuration was assigned on the basis of the crystal structure elucidation for Example 26, 108, 113, 157, 237, 358 and 454.

(5S)-5-(Pyrrolidin-1-ylcarbonyl)-2-{[2-(trifluoromethyl)pyridin-4-yl]methyl}-5,6,7,8-tetrahydro[1,2,4]triazolo[4,3-a]pyridin-3(2H)-one Example 75

(5RS)-2-{[3-Fluoro-2-(trifluoromethyl)pyridin-4-yl]methyl}-5-(pyrrolidin-1-ylcarbonyl)-5,6,7,8-tetrahydro[1,2,4]triazolo[4,3-a]pyridin-3(2H)-one (Enantiomer 1)

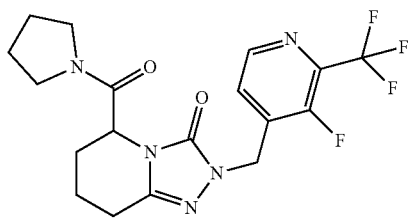 [SMILES: O=C(C1CCCc2nn(Cc3ccnc(C(F)(F)F)c3F)c(=O)n21)N1CCCC1]

(5RS)-2-[[3-Fluoro-2-(trifluoromethyl)-4-pyridyl]methyl]-3-oxo-5,6,7,8-tetrahydro-[1,2,4]triazolo[4,3-a]pyridine-5-carboxylic Acid (Enantiomer 1) (80.0 mg, 214 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (106 mg, 278 µmol) and triethylamine (89 µl, 640 µmol) were added. After stirring for 15 min, pyrrolidine (21 µl, 260 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 67.0 mg (76% of theory) of the title compound were obtained.

LC-MS (Method 3): $R_t$=1.31 min; MS (ESIpos): m/z=414 [M+H]$^+$ $^1$H-NMR (400 MHz, DMSO-d6) δ [ppm]: −0.150 (0.52), 0.008 (3.36), 0.146 (0.57), 1.697 (2.60), 1.708 (2.42), 1.737 (3.98), 1.758 (3.80), 1.774 (8.57), 1.792 (13.17), 1.809 (9.76), 1.825 (2.72), 1.894 (3.04), 1.909 (7.95), 1.926 (9.58), 1.942 (5.78), 1.959 (1.76), 2.025 (5.07), 2.047 (3.06), 2.060 (2.40), 2.067 (2.35), 2.075 (2.15), 2.328 (1.01), 2.366 (0.69), 2.569 (4.00), 2.580 (3.80), 2.594 (3.25), 2.609 (3.31), 2.621 (5.56), 2.633 (3.16), 2.651 (1.53), 2.664 (2.51), 2.710 (0.69), 3.235 (1.85), 3.252 (3.80), 3.264 (4.16), 3.281 (7.27), 3.329 (3.57), 3.347 (6.42), 3.364 (3.45), 3.376 (3.57), 3.394 (1.65), 3.443 (2.03), 3.460 (4.21), 3.468 (3.22), 3.486 (5.21), 3.503 (2.33), 3.592 (2.63), 3.609 (4.96), 3.626 (3.00), 3.634 (3.73), 3.650 (1.62), 4.763 (4.87), 4.772 (5.33), 4.777 (6.22), 4.787 (4.32), 5.015 (1.69), 5.057 (16.00), 5.065 (15.41), 5.107 (1.48), 7.546 (4.85), 7.559 (8.68), 7.571 (4.71), 8.561 (10.29), 8.573 (9.81).

The (5S) configuration was assigned on the basis of the crystal structure elucidation for Example 26, 108, 113, 157, 237, 358 and 454.

(5S)-2-{[3-Fluoro-2-(trifluoromethyl)pyridin-4-yl]methyl}-5-(pyrrolidin-1-ylcarbonyl)-5,6,7,8-tetrahydro[1,2,4]triazolo[4,3-a]pyridin-3(2H)-one Example 76

(5RS)-5-(Pyrrolidin-1-ylcarbonyl)-2-{[2-(trifluoromethyl)quinolin-4-yl]methyl}-5,6,7,8-tetrahydro[1,2,4]triazolo[4,3-a]pyridin-3(2H)-one (Enantiomer 1)

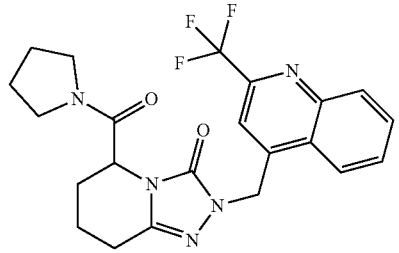 [SMILES: O=C(C1CCCc2nn(Cc3cc(C(F)(F)F)nc4ccccc34)c(=O)n21)N1CCCC1]

(5RS)-3-Oxo-2-{[2-(trifluoromethyl)quinolin-4-yl]methyl}-2,3,5,6,7,8-hexahydro[1,2,4]triazolo[4,3-a]pyridine-5-carboxylic Acid (Enantiomer 1) (94.0 mg, 240 µmol) was initially charged in THF (2.1 ml) at room temperature. Subsequently, 1-[bis(dimethylamino)methylene]-1H-[1,2,3]triazolo[4,5-b]pyridin-1-ium 3-oxide hexafluorophosphate (118 mg, 311 µmol) and triethylamine (100 µl, 720 mol) were added. After stirring for 15 min, pyrrolidine (24 µl, 290 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 57.0 mg (53% of theory) of the title compound were obtained.

LC-MS (Method 3): $R_t$=1.55 min; MS (ESIpos): m/z=446 [M+H]$^+$ $^1$H-NMR (400 MHz, DMSO-d6) δ[ppm]: −0.008 (2.70), 0.008 (2.54), 1.147 (0.45), 1.165 (0.90), 1.183 (0.45), 1.653 (1.17), 1.666 (1.66), 1.678 (1.86), 1.691 (1.77), 1.704 (2.52), 1.717 (3.00), 1.728 (2.29), 1.740 (1.51), 1.751 (1.17), 1.763 (1.72), 1.781 (5.12), 1.799 (9.24), 1.816 (7.40), 1.832 (2.22), 1.899 (2.19), 1.915 (6.75), 1.932 (8.65), 1.949 (5.19), 1.966 (1.61), 1.983 (1.00), 1.998 (1.85), 2.010 (4.50), 2.019 (4.62), 2.034 (2.65), 2.046 (1.72), 2.052 (1.66), 2.061 (1.55), 2.071 (0.74), 2.087 (0.51), 2.096 (0.42), 2.328 (0.56), 2.333 (0.49), 2.342 (1.75), 2.519 (3.00), 2.525 (4.32), 2.567 (2.15), 2.594 (2.16), 2.605 (3.87), 2.617 (2.31), 2.636 (1.19), 2.647 (1.75), 2.660 (1.01), 2.670 (0.71), 3.238 (1.31), 3.255 (2.81), 3.268 (2.72), 3.285 (4.87), 3.340 (2.36), 3.357 (4.92), 3.369 (1.89), 3.375 (2.60), 3.387 (2.96), 3.405 (1.31), 3.440 (1.47), 3.457 (3.21), 3.464 (2.37), 3.474 (1.97), 3.482 (4.04), 3.499 (1.75), 3.606 (1.82), 3.622 (3.91), 3.630 (2.00), 3.639 (2.22), 3.647 (3.07), 3.664 (1.36), 3.803 (0.57), 3.818 (0.56), 4.792 (3.51), 4.801 (3.91), 4.806 (4.95), 4.815 (3.45), 5.408 (3.17), 5.449 (10.04), 5.480 (10.14), 5.521 (3.20), 5.558 (0.51), 6.510 (2.74), 7.293 (0.56), 7.386 (0.63), 7.406 (0.59), 7.750 (16.00), 7.823 (2.56), 7.826 (2.72), 7.844 (5.54), 7.862 (3.75), 7.864 (3.71), 7.943 (3.44), 7.946 (3.64), 7.964 (5.87), 7.967 (4.51), 7.982 (3.21), 7.985 (3.11), 8.214 (6.39), 8.234 (5.46), 8.370 (6.19), 8.390 (5.70).

The (5S) configuration was assigned on the basis of the crystal structure elucidation for Example 26, 108, 113, 157, 237, 358 and 454.

(5S)-5-(Pyrrolidin-1-ylcarbonyl)-2-{[2-(trifluoromethyl)quinolin-4-yl]methyl}-5,6,7,8-tetrahydro[1,2,4]triazolo[4,3-a]pyridin-3(2H)-one Example 77

(5RS)-2-{[2-Methyl-4-(trifluoromethyl)-1,3-thiazol-5-yl]methyl}-5-(pyrrolidin-1-ylcarbonyl)-5,6,7,8-tetrahydro[1,2,4]triazolo[4,3-a]pyridin-3(2H)-one (Racemate)

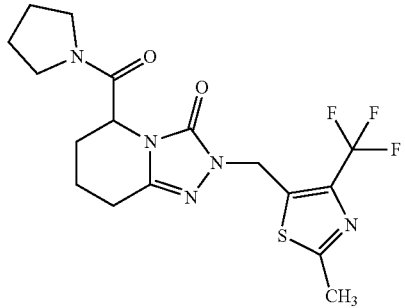 [SMILES: Cc1nc(C(F)(F)F)c(Cn2nc3n(c2=O)C(C(=O)N2CCCC2)CCC3)s1]

(5RS)-2-{[2-Methyl-4-(trifluoromethyl)-1,3-thiazol-5-yl]methyl}-3-oxo-2,3,5,6,7,8-hexahydro[1,2,4]triazolo[4,3-a]pyridine-5-carboxylic Acid (Racemate) (68.0 mg, 188 µmol) was initially charged in THF (2.1 ml) at room temperature. Subsequently, 1-[bis(dimethylamino)methylene]-1H-[1,2,3]triazolo[4,5-b]pyridin-1-ium 3-oxide hexafluorophosphate (92.8 mg, 244 µmol) and triethylamine (78 µl, 560 µmol) were added. After stirring for 15 min, pyrrolidine (19 µl, 230 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 49.0 mg (63% of theory) of the title compound were obtained.

LC-MS (Method 3): $R_t$=1.21 min; MS (ESIpos): m/z=416 [M+H]$^+$ $^1$H-NMR (400 MHz, DMSO-d6) δ [ppm]: −0.008 (2.56), 0.008 (2.06), 1.163 (2.87), 1.181 (6.08), 1.199 (2.98), 1.703 (0.97), 1.714 (1.06), 1.754 (0.51), 1.770 (1.54), 1.787 (2.65), 1.804 (2.06), 1.821 (0.60), 1.889 (0.63), 1.906 (1.90), 1.923 (2.45), 1.939 (1.73), 1.974 (0.84), 1.986 (0.78), 2.003 (0.52), 2.019 (0.67), 2.028 (0.50), 2.327 (0.46), 2.523 (1.51), 2.558 (0.99), 2.568 (0.83), 2.582 (0.68), 2.602 (0.66), 2.613 (1.27), 2.626 (0.75), 2.646 (16.00), 2.669 (0.74), 2.890 (0.45), 3.076 (1.10), 3.089 (1.24), 3.094 (1.13), 3.106 (1.07), 3.236 (0.78), 3.248 (0.79), 3.265 (1.40), 3.282 (0.69), 3.313 (0.78), 3.330 (1.69), 3.428 (0.64), 3.445 (0.98), 3.453 (0.73), 3.470 (1.21), 3.487 (0.56), 3.578 (0.51), 3.595 (1.09), 3.612 (0.63), 3.620 (0.80), 4.713 (0.95), 4.723 (1.09), 4.728 (1.30), 4.738 (0.95), 5.127 (2.30), 5.142 (2.33).

Example 78

(5RS)-2-[(5-Chloropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one (Racemate)

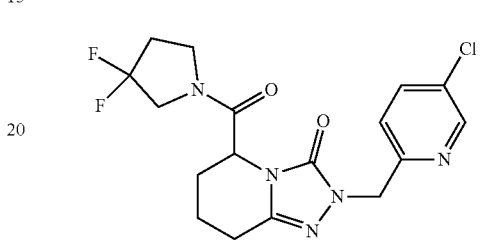

(5RS)-2-[(5-Chloropyridin-2-yl)methyl]-3-oxo-2,3,5,6,7,8-hexahydro[1,2,4]triazolo[4,3-a]pyridine-5-carboxylic Acid (Racemate) (50.0 mg, 162 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (80.1 mg, 211 µmol) and triethylamine (68 µl, 490 µmol) were added. After stirring for 15 min, 3,3-difluoropyrrolidine hydrochloride (27.9 mg, 194 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 25.2 mg (39% of theory) of the title compound were obtained.

LC-MS (Method 4): $R_t$=0.69 min; MS (ESIpos): m/z=398 [M+H]$^+$ $^1$H-NMR (400 MHz, DMSO-d6) δ[ppm]: −0.008 (2.72), 0.008 (2.55), 1.687 (1.41), 1.699 (1.48), 1.726 (1.92), 2.023 (1.76), 2.050 (1.24), 2.064 (1.31), 2.073 (2.50), 2.085 (1.00), 2.101 (0.87), 2.328 (0.75), 2.365 (0.71), 2.381 (1.04), 2.410 (1.31), 2.431 (1.22), 2.569 (4.02), 2.578 (3.03), 2.592 (3.63), 2.607 (3.88), 2.620 (1.88), 2.650 (1.12), 2.665 (1.04), 2.709 (0.48), 3.538 (1.74), 3.557 (2.71), 3.570 (1.44), 3.577 (1.41), 3.638 (0.51), 3.672 (1.50), 3.706 (1.75), 3.740 (1.36), 3.774 (2.31), 3.790 (1.31), 3.798 (1.21), 3.808 (2.23), 3.816 (1.89), 3.835 (0.93), 3.894 (0.74), 3.912 (1.70), 3.931 (0.99), 3.938 (1.22), 3.957 (0.58), 3.972 (0.49), 4.001 (1.06), 4.014 (0.56), 4.030 (0.71), 4.043 (0.99), 4.071 (0.60), 4.147 (0.64), 4.179 (1.00), 4.203 (1.01), 4.235 (0.43), 4.761 (1.40), 4.776 (1.83), 4.785 (1.34), 4.836 (1.45), 4.846 (1.72), 4.851 (1.89), 4.861 (1.45), 4.870 (0.73), 4.914 (16.00), 4.955 (0.69), 7.199 (6.18), 7.220 (6.60), 7.913 (4.28), 7.920 (4.38), 7.934 (4.15), 7.941 (4.23), 8.571 (5.89), 8.577 (5.93).

Example 79

(5RS)-5-[(3,3-Difluoropyrrolidin-1-yl)carbonyl]-2-{[6-(trifluoromethyl)pyridin-3-yl]methyl}-5,6,7,8-tetrahydro[1,2,4]triazolo[4,3-a]pyridin-3(2H)-one (Racemate)

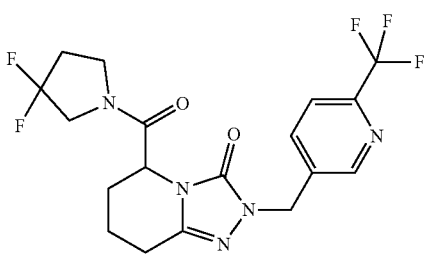 [SMILES: O=C(C1CCCc2nn(Cc3ccc(C(F)(F)F)nc3)c(=O)n21)N1CCC(F)(F)C1]

(5RS)-3-Oxo-2-{[6-(trifluoromethyl)pyridin-3-yl]methyl}-2,3,5,6,7,8-hexahydro[1,2,4]triazolo[4,3-a]pyridine-5-carboxylic acid/trifluoroacetic acid (racemate) (70.0 mg, 153 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (75.8 mg, 199 µmol) and triethylamine (110 µl, 770 µmol) were added. After stirring for 15 min, 3,3-difluoropyrrolidine hydrochloride (26.4 mg, 184 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 37.7 mg (57% of theory) of the title compound were obtained.

LC-MS (Method 4): $R_t$=0.75 min; MS (ESIpos): m/z=432 [M+H]$^+$ $^1$H-NMR (400 MHz, DMSO-d6) δ [ppm]: −0.008 (3.24), 0.008 (3.00), 1.664 (1.10), 1.735 (1.37), 1.908 (1.15), 1.994 (1.34), 2.008 (1.72), 2.018 (1.67), 2.033 (1.58), 2.044 (1.35), 2.052 (1.21), 2.060 (1.13), 2.073 (1.48), 2.080 (0.80), 2.088 (0.84), 2.096 (0.75), 2.328 (0.80), 2.366 (0.81), 2.382 (0.98), 2.411 (1.16), 2.431 (1.11), 2.456 (0.84), 2.569 (3.33), 2.580 (2.48), 2.594 (2.56), 2.610 (2.91), 2.623 (1.48), 2.640 (0.60), 2.653 (0.91), 2.669 (1.06), 2.710 (0.48), 3.534 (1.23), 3.541 (1.45), 3.552 (2.00), 3.561 (2.15), 3.571 (1.27), 3.580 (1.08), 3.670 (1.29), 3.704 (1.47), 3.738 (0.63), 3.749 (0.72), 3.769 (0.56), 3.782 (1.84), 3.794 (0.96), 3.813 (2.64), 3.831 (0.71), 3.891 (0.68), 3.910 (1.45), 3.929 (0.81), 3.936 (1.06), 3.955 (0.49), 3.966 (0.43), 3.995 (0.88), 4.010 (0.45), 4.023 (0.60), 4.038 (0.82), 4.066 (0.49), 4.149 (0.51), 4.182 (0.79), 4.206 (0.79), 4.767 (1.21), 4.776 (1.43), 4.782 (1.63), 4.791 (1.15), 4.838 (1.28), 4.847 (1.44), 4.853 (1.63), 4.862 (1.17), 5.011 (14.35), 7.909 (15.74), 7.913 (16.00), 8.641 (5.64).

Example 80

(5RS)-2-[(6-Chloropyridin-3-yl)methyl]-5-[(3,3-difluoropyrrolidin-1-yl)carbonyl]-5,6,7,8-tetrahydro[1,2,4]triazolo[4,3-a]pyridin-3(2H)-one (Racemate)

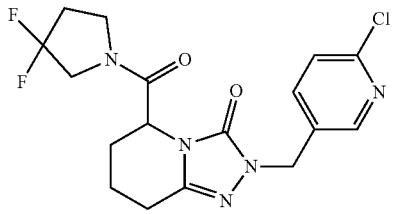 [SMILES: O=C(C1CCCc2nn(Cc3ccc(Cl)nc3)c(=O)n21)N1CCC(F)(F)C1]

(5RS)-2-[(6-Chloropyridin-3-yl)methyl]-3-oxo-2,3,5,6,7,8-hexahydro[1,2,4]triazolo[4,3-a]pyridine-5-carboxylic Acid (Racemate) (350 mg, 15% purity, 170 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (84.1 mg, 221 µmol) and triethylamine (71 µl, 510 µmol) were added. After stirring for 15 min, 3,3-difluoropyrrolidine hydrochloride (29.3 mg, 204 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 46.4 mg (69% of theory) of the title compound were obtained.

LC-MS (Method 4): $R_t$=0.67 min; MS (ESIpos): m/z=398 [M+H]$^+$ $^1$H-NMR (400 MHz, DMSO-d6) δ [ppm]: 1.661 (1.07), 1.726 (1.27), 1.996 (1.45), 2.007 (1.54), 2.043 (1.10), 2.060 (0.88), 2.071 (0.82), 2.327 (0.70), 2.366 (0.54), 2.379 (0.89), 2.408 (1.09), 2.427 (1.04), 2.452 (0.91), 2.560 (2.42), 2.569 (2.97), 2.585 (2.82), 2.602 (2.79), 2.644 (0.79), 2.669 (0.70), 3.537 (1.17), 3.546 (1.77), 3.556 (1.91), 3.565 (1.12), 3.575 (0.94), 3.665 (1.17), 3.700 (1.30), 3.743 (0.64), 3.776 (1.61), 3.807 (2.37), 3.825 (0.62), 3.887 (0.58), 3.906 (1.29), 3.931 (0.92), 3.962 (0.43), 3.991 (0.80), 4.018 (0.57), 4.032 (0.75), 4.063 (0.47), 4.143 (0.51), 4.175 (0.74), 4.200 (0.74), 4.749 (1.05), 4.764 (1.43), 4.773 (1.05), 4.821 (1.16), 4.836 (1.48), 4.846 (1.20), 4.884 (16.00), 7.505 (4.89), 7.525 (6.06), 7.686 (3.27), 7.692 (3.34), 7.707 (2.69), 7.713 (2.73), 8.296 (5.00), 8.301 (4.81).

Example 81

(5RS)-2-(3,5-Dichlorobenzyl)-5-(pyrrolidin-1-ylcarbonyl)-5,6,7,8-tetrahydro[1,2,4]triazolo[4,3-a]pyridin-3(2H)-one (Racemate)

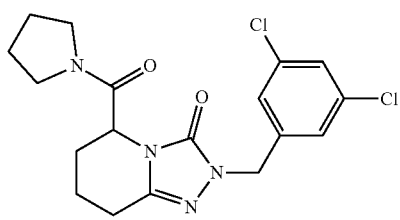

(5RS)-2-(3,5-Dichlorobenzyl)-3-oxo-2,3,5,6,7,8-hexahydro[1,2,4]triazolo[4,3-a]pyridine-5-carboxylic acid hydrochloride (racemate) (70.0 mg, 79% purity, 145 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (71.7 mg, 189 µmol) and triethylamine (100 µl, 730 µmol) were added. After stirring for 15 min, pyrrolidine (12.4 mg, 174 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 21.4 mg (37% of theory) of the title compound were obtained.

LC-MS (Method 3): $R_t$=1.61 min; MS (ESIpos): m/z=395 [M+H]

$^1$H-NMR (400 MHz, DMSO-d6) δ [ppm]: −0.149 (0.96), −0.008 (8.42), 0.008 (7.50), 0.146 (1.00), 1.406 (0.70), 1.725 (1.96), 1.756 (1.37), 1.773 (3.77), 1.791 (6.24), 1.808 (4.80), 1.824 (1.40), 1.893 (1.44), 1.909 (4.25), 1.926 (5.36), 1.943 (3.21), 1.960 (1.44), 1.997 (1.81), 2.015 (1.55), 2.040 (1.29), 2.051 (1.07), 2.058 (1.18), 2.066 (1.07), 2.327 (1.88), 2.366 (1.40), 2.518 (8.61), 2.523 (7.02), 2.565 (2.44), 2.574 (2.00), 2.590 (1.66), 2.603 (1.55), 2.615 (2.77), 2.627 (1.66), 2.644 (0.78), 2.669 (2.48), 2.709 (1.44), 3.228 (0.89), 3.245 (1.88), 3.257 (1.85), 3.274 (3.33), 3.292 (2.25), 3.330 (2.11), 3.348 (3.29), 3.365 (1.74), 3.378 (1.88), 3.395 (0.89), 3.437 (1.00), 3.454 (2.11), 3.461 (1.55), 3.479 (2.66), 3.496 (1.15), 3.593 (1.26), 3.609 (2.40), 3.626 (1.44), 3.634 (1.92), 3.651 (0.81), 4.753 (2.25), 4.762 (2.48), 4.768 (2.77), 4.777 (2.29), 4.851 (16.00), 7.273 (11.16), 7.278 (11.31), 7.533 (2.40), 7.538 (4.25), 7.543 (2.14).

Example 82

(5RS)-2-(3,5-Dichlorobenzyl)-5-[(3,3-difluoropyrrolidin-1-yl)carbonyl]-5,6,7,8-tetrahydro[1,2,4]triazolo[4,3-a]pyridin-3(2H)-one (Racemate)

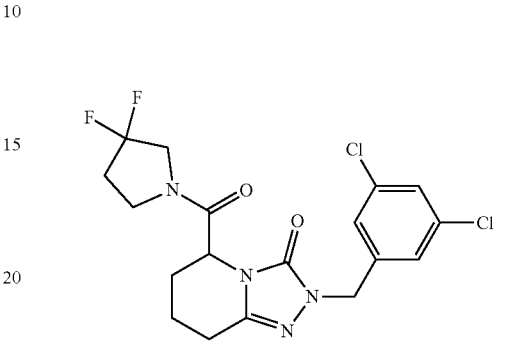

(5RS)-2-(3,5-Dichlorobenzyl)-3-oxo-2,3,5,6,7,8-hexahydro[1,2,4]triazolo[4,3-a]pyridine-5-carboxylic acid hydrochloride (racemate) (70.0 mg, 79% purity, 145 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (71.7 mg, 189 µmol) and triethylamine (100 µl, 730 µmol) were added. After stirring for 15 min, 3,3-difluoropyrrolidine hydrochloride (25.0 mg, 174 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 26.4 mg (94% purity, 40% of theory) of the title compound were obtained.

LC-MS (Method 3): $R_t$=1.73 min; MS (ESIpos): m/z=431 [M+H]

$^1$H-NMR (400 MHz, DMSO-d6) δ [ppm]: −0.008 (3.09), 0.008 (2.90), 1.670 (0.97), 1.734 (1.17), 1.992 (1.13), 2.004 (1.20), 2.013 (1.32), 2.048 (0.92), 2.056 (1.04), 2.063 (1.01), 2.073 (6.09), 2.084 (0.76), 2.091 (0.75), 2.100 (0.66), 2.327 (0.74), 2.366 (0.72), 2.382 (0.91), 2.412 (1.03), 2.424 (0.98), 2.453 (0.85), 2.523 (3.33), 2.565 (2.41), 2.580 (2.09), 2.590 (2.49), 2.605 (2.35), 2.622 (2.34), 2.633 (1.24), 2.665 (1.27), 2.674 (0.86), 2.709 (0.46), 3.533 (1.03), 3.541 (1.15), 3.551 (1.74), 3.562 (1.93), 3.569 (1.05), 3.581 (0.92), 3.672 (1.10), 3.705 (1.28), 3.742 (0.91), 3.764 (0.52), 3.776 (1.52), 3.790 (0.80), 3.808 (2.32), 3.827 (0.59), 3.894 (0.59), 3.912 (1.26), 3.931 (0.71), 3.939 (0.91), 3.958 (0.60), 3.989 (0.78), 4.017 (0.52), 4.032 (0.71), 4.060 (0.42), 4.149 (0.46), 4.183 (0.68), 4.206 (0.70), 4.775 (1.07), 4.784 (1.23), 4.790 (1.41), 4.799 (1.05), 4.858 (16.00), 7.271 (10.23), 7.276 (10.34), 7.536 (2.16), 7.541 (3.82), 7.546 (2.01).

Example 83

(5RS)-2-(3,4-Difluorobenzyl)-5-[(3,3-difluoropyrrolidin-1-yl)carbonyl]-5,6,7,8-tetrahydro[1,2,4]triazolo[4,3-a]pyridin-3(2H)-one (Racemate)

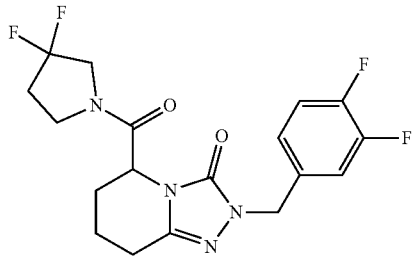 [SMILES: O=C(C1CCCc2nn(Cc3ccc(F)c(F)c3)c(=O)n21)N1CCC(F)(F)C1]

(5RS)-2-(3,4-Difluorobenzyl)-3-oxo-2,3,5,6,7,8-hexahydro[1,2,4]triazolo[4,3-a]pyridine-5-carboxylic acid hydrochloride (racemate) (100 mg, 289 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (143 mg, 376 µmol) and triethylamine (200 µl, 1.4 mmol) were added. After stirring for 15 min, 3,3-difluoropyrrolidine hydrochloride (49.8 mg, 347 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 17.0 mg (15% of theory) of the title compound were obtained.

LC-MS (Method 4): $R_t$=0.78 min; MS (ESIpos): m/z=399 [M+H]$^+$ $^1$H-NMR (400 MHz, DMSO-d6) δ [ppm]: −0.149 (0.64), −0.008 (5.78), 0.008 (4.12), 0.147 (0.54), 1.734 (1.51), 2.012 (1.51), 2.327 (1.54), 2.566 (2.86), 2.591 (2.58), 2.608 (2.98), 2.669 (1.40), 2.709 (0.76), 3.559 (2.11), 3.670 (1.33), 3.704 (1.54), 3.741 (0.97), 3.775 (1.59), 3.809 (2.49), 3.909 (1.33), 3.991 (0.97), 4.178 (0.97), 4.770 (1.68), 4.822 (16.00), 7.083 (1.87), 7.230 (1.68), 7.259 (2.04), 7.278 (1.80), 7.375 (1.75), 7.396 (3.57), 7.402 (2.25), 7.423 (3.55), 7.445 (1.68).

Example 84

(5RS)-5-(Pyrrolidin-1-ylcarbonyl)-2-{[6-(trifluoromethyl)pyridin-3-yl]methyl}-5,6,7,8-tetrahydro[1,2,4]triazolo[4,3-a]pyridin-3(2H)-one (Racemate)

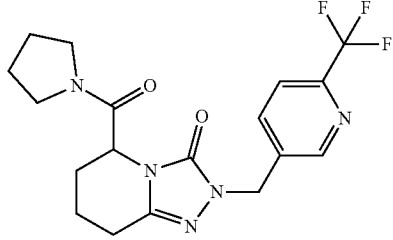 [SMILES: O=C(C1CCCc2nn(Cc3ccc(C(F)(F)F)nc3)c(=O)n21)N1CCCC1]

(5RS)-3-Oxo-2-{[6-(trifluoromethyl)pyridin-3-yl]methyl}-2,3,5,6,7,8-hexahydro[1,2,4]triazolo[4,3-a]pyridine-5-carboxylic acid/trifluoroacetic acid (racemate) (70.0 mg, 153 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (75.8 mg, 199 µmol) and triethylamine (110 µl, 770 µmol) were added. After stirring for 15 min, pyrrolidine (15 µl, 180 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 32.2 mg (53% of theory) of the title compound were obtained.

LC-MS (Method 3): $R_t$=1.23 min; MS (ESIpos): m/z=396 [M+H]$^+$ $^1$H-NMR (400 MHz, DMSO-d6) δ [ppm]: −0.008 (3.63), 0.008 (3.14), 0.146 (0.40), 1.673 (1.10), 1.686 (1.21), 1.696 (1.21), 1.710 (1.60), 1.724 (1.93), 1.736 (1.54), 1.748 (1.13), 1.758 (1.55), 1.774 (4.10), 1.791 (6.82), 1.808 (5.25), 1.825 (1.49), 1.893 (1.46), 1.909 (4.19), 1.926 (5.20), 1.942 (3.16), 1.959 (1.12), 2.013 (2.62), 2.036 (1.46), 2.048 (1.20), 2.055 (1.18), 2.063 (1.13), 2.072 (0.66), 2.327 (0.97), 2.366 (0.58), 2.523 (3.85), 2.564 (2.19), 2.579 (1.70), 2.593 (1.65), 2.605 (2.93), 2.617 (1.70), 2.635 (0.78), 2.646 (1.13), 2.660 (0.89), 2.665 (0.89), 2.669 (1.07), 2.709 (0.62), 3.231 (0.96), 3.247 (1.93), 3.260 (1.93), 3.277 (3.53), 3.295 (2.62), 3.328 (2.30), 3.346 (3.58), 3.363 (1.83), 3.375 (2.02), 3.393 (0.92), 3.440 (0.99), 3.457 (2.20), 3.464 (1.62), 3.474 (1.34), 3.482 (2.82), 3.499 (1.26), 3.592 (1.28), 3.609 (2.61), 3.617 (1.34), 3.626 (1.57), 3.633 (2.02), 3.650 (0.94), 4.747 (2.45), 4.756 (2.74), 4.762 (3.26), 4.771 (2.36), 5.005 (13.36), 7.907 (15.77), 7.910 (16.00), 8.641 (5.00).

Example 85

(5RS)-5-(Pyrrolidin-1-ylcarbonyl)-2-{[6-(trifluoromethyl)pyridin-3-yl]methyl}-5,6,7,8-tetrahydro[1,2,4]triazolo[4,3-a]pyridin-3(2H)-one (Enantiomer 2)

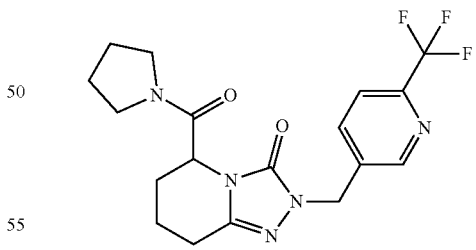

(5RS)-5-(Pyrrolidin-1-ylcarbonyl)-2-{[6-(trifluoromethyl)pyridin-3-yl]methyl}-5,6,7,8-tetrahydro[1,2,4]triazolo[4,3-a]pyridin-3(2H)-one (racemate) was separated by chiral preparative HPLC. [Sample preparation: 75 mg dissolved in 1 ml of ethanol/acetonitrile; injection volume: 0.2 ml; column: Daicel Chiralpak® AD-H 5 µm, 250×20 mm; eluent: n-heptane/ethanol 40:60, flow rate: 20 ml/min; temperature 40° C.; UV detection: 220 nm]. After the separation, 27 mg of enantiomer 1, which eluted first, and 27 mg of enantiomer 2, which eluted later, were isolated.

Enantiomer 2:

Analytical chiral HPLC: $R_t$=3.61 min, e.e. =99.9% [column: Daicel Chiralcel® OJ-3 3 µm 50×4.6 mm; eluent: n-heptane/isopropanol 1:1, 0.2% trifluoroacetic acid, 1% water; flow rate: 1 ml/min; UV detection: 220 nm]

LC-MS (Method 3): $R_t$=1.22 min; MS (ESIpos): m/z=396 [M+H]$^+$ $^1$H-NMR (400 MHz, DMSO-d6) δ[ppm]: 1.61-1.82 (m, 4H). 1.87-1.95 (m, 2H), 1.95-2.10 (m, 2H), 2.56-2.72 (m, 2H), 3.22-3.28 (m, 1H), 3.33-3.39 (m, 1H), 3.47 (dt, 1H), 3.62 (dt, 1H), 4.76 (dd, 1H), 5.00 (s, 2H), 7.91 (d, 2H), 8.64 (s, 1H).

Example 86

(5RS)-2-(3-Chloro-4-fluorobenzyl)-5-[(3,3-difluoropyrrolidin-1-yl)carbonyl]-5,6,7,8-tetrahydro[1,2,4]triazolo[4,3-a]pyridin-3(2H)-one (Racemate)

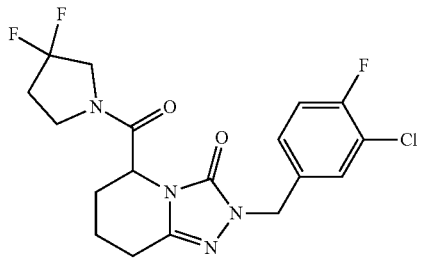 [SMILES: O=C(C1CCCc2nn(Cc3ccc(F)c(Cl)c3)c(=O)n21)N1CCC(F)(F)C1]

(5RS)-2-(3-Chloro-4-fluorobenzyl)-3-oxo-2,3,5,6,7,8-hexahydro[1,2,4]triazolo[4,3-a]pyridine-5-carboxylic acid hydrochloride (racemate) (100 mg, 276 µmol) was initially charged in THF (3.0 ml) at room temperature. Subsequently, 1-[bis(dimethylamino)methylene]-1H-[1,2,3]triazolo[4,5-b]pyridin-1-ium 3-oxide hexafluorophosphate (136 mg, 359 µmol) and triethylamine (190 µl, 1.4 mmol) were added. After stirring for 15 min, 3,3-difluoropyrrolidine hydrochloride (47.6 mg, 331 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 14.0 mg (12% of theory) of the title compound were obtained.

LC-MS (Method 4): $R_t$=0.83 min; MS (ESIpos): m/z=415 [M+H]$^+$ $^1$H-NMR (400 MHz, DMSO-d6) δ [ppm]: −0.149 (0.46), −0.008 (3.79), 0.008 (3.46), 0.146 (0.44), 1.670 (1.08), 1.680 (1.01), 1.694 (0.93), 1.728 (1.34), 1.980 (1.24), 1.995 (1.30), 2.004 (1.45), 2.028 (1.05), 2.038 (1.04), 2.046 (1.10), 2.054 (1.05), 2.063 (0.94), 2.073 (0.88), 2.082 (0.80), 2.089 (0.70), 2.323 (0.61), 2.327 (0.83), 2.332 (0.58), 2.366 (0.83), 2.381 (0.94), 2.391 (0.67), 2.411 (1.10), 2.425 (1.04), 2.452 (0.87), 2.523 (3.60), 2.566 (2.83), 2.576 (2.48), 2.591 (2.76), 2.608 (2.96), 2.619 (1.40), 2.639 (0.57), 2.650 (0.87), 2.665 (0.91), 2.669 (0.93), 2.710 (0.53), 3.531 (1.18), 3.538 (1.34), 3.549 (1.92), 3.559 (2.12), 3.567 (1.21), 3.578 (1.04), 3.668 (1.24), 3.703 (1.42), 3.742 (0.78), 3.764 (0.56), 3.775 (1.64), 3.790 (0.88), 3.808 (2.65), 3.826 (0.68), 3.891 (0.67), 3.909 (1.41), 3.928 (0.77), 3.935 (1.02), 3.954 (0.48), 3.962 (0.46), 3.991 (0.83), 4.005 (0.44), 4.019 (0.60), 4.033 (0.77), 4.061 (0.47), 4.145 (0.53), 4.176 (0.75), 4.201 (0.77), 4.755 (1.15), 4.765 (1.38), 4.771 (1.58), 4.780 (1.20), 4.824 (16.00), 4.838 (1.79), 4.844 (1.77), 4.853 (1.32), 7.220 (1.30), 7.225 (1.47), 7.232 (1.49), 7.241 (2.05), 7.246 (2.01), 7.253 (1.84), 7.258 (1.82), 7.373 (3.89), 7.396 (5.08), 7.418 (3.09), 7.429 (2.86), 7.434 (2.69), 7.447 (2.88), 7.452 (2.65).

Example 87

(5RS)-5-[(3,3-Difluoropyrrolidin-1-yl)carbonyl]-2-(5,6,7,8-tetrahydronaphthalen-2-ylmethyl)-5,6,7,8-tetrahydro[1,2,4]triazolo[4,3-a]pyridin-3(2H)-one (Racemate)

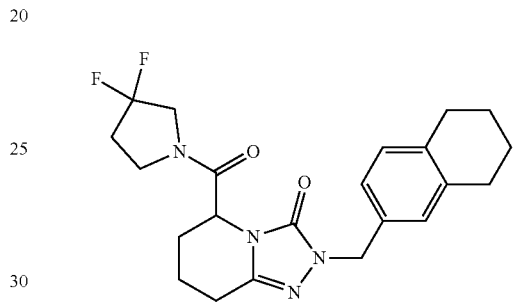

(5RS)-3-Oxo-2-(5,6,7,8-tetrahydronaphthalen-2-ylmethyl)-2,3,5,6,7,8-hexahydro[1,2,4]triazolo[4,3-a]pyridine-5-carboxylic acid/trifluoroacetic acid (racemate) (100 mg, 227 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (112 mg, 295 µmol) and triethylamine (160 µl, 1.1 mmol) were added. After stirring for 15 min, 3,3-difluoropyrrolidine hydrochloride (39.0 mg, 272 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 44.0 mg (47% of theory) of the title compound were obtained.

LC-MS (Method 1): $R_t$=1.25 min; MS (ESIpos): m/z=417 [M+H]$^+$ $^1$H-NMR (400 MHz, DMSO-d6) δ [ppm]: −0.149 (1.52), −0.008 (13.87), 0.008 (12.34), 0.146 (1.37), 1.708 (13.94), 1.996 (2.59), 2.327 (4.65), 2.366 (3.20), 2.523 (15.54), 2.565 (4.80), 2.584 (4.19), 2.598 (3.73), 2.669 (16.00), 2.702 (5.18), 2.718 (5.79), 2.734 (3.05), 3.530 (2.29), 3.554 (3.20), 3.668 (1.75), 3.702 (2.06), 3.736 (1.75), 3.769 (2.13), 3.805 (3.20), 3.910 (1.68), 3.988 (1.37), 4.171 (1.22), 4.685 (5.26), 4.700 (5.64), 4.729 (7.54), 4.740 (8.46), 4.821 (1.83), 6.843 (2.67), 6.860 (3.43), 6.916 (8.15), 6.933 (3.58), 6.979 (4.72), 6.988 (4.88), 7.009 (4.19), 7.028 (4.11), 7.047 (1.60), 7.069 (1.07).

Example 88

(5RS)-5-(Pyrrolidin-1-ylcarbonyl)-2-(5,6,7,8-tetrahydronaphthalen-2-ylmethyl)-5,6,7,8-tetrahydro[1,2,4]triazolo[4,3-a]pyridin-3(2H)-one (Racemate)

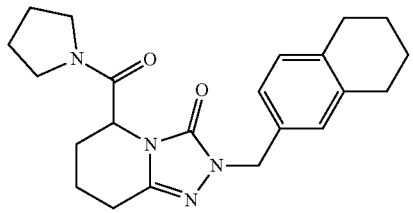 [SMILES: O=C(C1CCCc2nn(Cc3ccc4c(c3)CCCC4)c(=O)n21)N1CCCC1]

(5RS)-3-Oxo-2-(5,6,7,8-tetrahydronaphthalen-2-ylmethyl)-2,3,5,6,7,8-hexahydro[1,2,4]triazolo[4,3-a]pyridine-5-carboxylic acid/trifluoroacetic acid (racemate) (100 mg, 227 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (112 mg, 295 µmol) and triethylamine (160 µl, 1.1 mmol) were added. After stirring for 15 min, pyrrolidine (19.3 mg, 272 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 39.0 mg (45% of theory) of the title compound were obtained.

LC-MS (Method 3): $R_t$=1.60 min; MS (ESIpos): m/z=381 [M+H]$^+$ $^1$H-NMR (400 MHz, DMSO-d6) δ[ppm]: −0.149 (0.77), −0.008 (6.64), 0.008 (5.97), 0.146 (0.77), 1.700 (12.96), 1.708 (16.00), 1.715 (12.30), 1.754 (4.68), 1.772 (7.72), 1.789 (11.63), 1.806 (8.90), 1.822 (2.52), 1.892 (2.73), 1.908 (8.28), 1.925 (10.60), 1.942 (6.89), 1.959 (3.04), 1.983 (3.04), 1.998 (3.14), 2.014 (2.52), 2.025 (2.57), 2.041 (1.90), 2.050 (1.54), 2.061 (0.93), 2.322 (1.49), 2.327 (2.01), 2.332 (1.49), 2.366 (1.23), 2.518 (10.19), 2.523 (9.67), 2.563 (3.24), 2.578 (3.81), 2.590 (4.01), 2.604 (2.11), 2.620 (1.65), 2.632 (1.75), 2.669 (14.05), 2.686 (8.90), 2.703 (6.02), 2.718 (6.07), 2.734 (3.24), 2.865 (1.49), 3.225 (1.13), 3.243 (2.32), 3.255 (2.88), 3.272 (4.12), 3.290 (3.19), 3.339 (5.20), 3.356 (2.78), 3.368 (2.83), 3.386 (1.39), 3.435 (1.65), 3.453 (3.55), 3.460 (2.62), 3.477 (4.48), 3.494 (1.95), 3.593 (1.90), 3.609 (4.12), 3.626 (2.37), 3.634 (3.14), 3.651 (1.49), 4.639 (1.29), 4.677 (6.33), 4.695 (6.28), 4.712 (2.62), 4.722 (10.08), 4.733 (11.37), 4.744 (3.60), 4.753 (2.47), 4.772 (1.18), 6.846 (2.78), 6.862 (3.40), 6.917 (7.97), 6.932 (3.91), 6.969 (2.11), 6.978 (5.09), 6.984 (5.30), 6.998 (2.73), 7.008 (4.32), 7.027 (4.78), 7.045 (1.59).

Example 89

(5RS)-5-(Pyrrolidin-1-ylcarbonyl)-2-(2,4,5-trifluorobenzyl)-5,6,7,8-tetrahydro[1,2,4]triazolo[4,3-a]pyridin-3(2H)-one (Racemate)

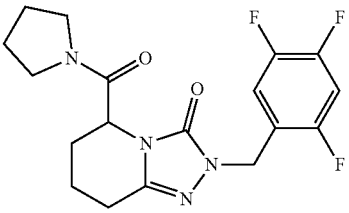 [SMILES: O=C(C1CCCc2nn(Cc3cc(F)c(F)cc3F)c(=O)n21)N1CCCC1]

(5RS)-3-oxo-2-(2,4,5-trifluorobenzyl)-2,3,5,6,7,8-hexahydro[1,2,4]triazolo[4,3-a]pyridine-5-carboxylic acid/trifluoroacetic acid (racemate) (100 mg, 227 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (112 mg, 295 µmol) and triethylamine (160 µl, 1.1 mmol) were added. After stirring for 15 min, pyrrolidine (19.3 mg, 272 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 51.0 mg (59% of theory) of the title compound were obtained.

LC-MS (Method 4): $R_t$=0.75 min; MS (ESIpos): m/z=381 [M+H]$^+$ $^1$H-NMR (400 MHz, DMSO-d6) δ [ppm]: −0.150 (0.92), −0.008 (8.02), 0.008 (7.59), 1.716 (5.33), 1.754 (3.14), 1.773 (9.33), 1.790 (15.97), 1.807 (12.47), 1.824 (3.73), 1.892 (3.99), 1.909 (11.06), 1.925 (13.71), 1.942 (8.61), 2.001 (6.15), 2.028 (3.60), 2.327 (1.80), 2.365 (1.24), 2.571 (4.25), 2.588 (4.06), 2.599 (7.26), 2.611 (4.32), 2.641 (3.21), 2.669 (1.96), 3.226 (2.19), 3.243 (4.71), 3.256 (4.38), 3.272 (8.18), 3.290 (4.32), 3.341 (8.44), 3.358 (4.84), 3.370 (4.74), 3.388 (2.32), 3.435 (2.39), 3.453 (5.37), 3.478 (6.94), 3.495 (2.98), 3.589 (3.11), 3.606 (5.92), 3.631 (4.84), 3.647 (2.32), 4.732 (5.89), 4.747 (7.69), 4.756 (5.73), 4.785 (2.65), 4.825 (16.00), 4.840 (15.90), 4.880 (2.81), 7.259 (3.34), 7.282 (4.22), 7.302 (3.96), 7.325 (3.08), 7.538 (3.66), 7.555 (3.89), 7.565 (5.04), 7.580 (5.24), 7.589 (3.96), 7.606 (3.37).

Example 90

(5RS)-5-[(3,3-Difluoropyrrolidin-1-yl)carbonyl]-2-[(1-methyl-1H-pyrazol-3-yl)methyl]-5,6,7,8-tetrahydro[1,2,4]triazolo[4,3-a]pyridin-3(2H)-one (Racemate)

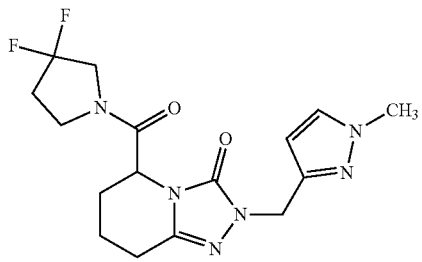 [SMILES: Cn1ccc(Cn2nc3n(c2=O)C(C(=O)N2CCC(F)(F)C2)CCC3)n1]

(5RS)-2-[(1-Methyl-1H-pyrazol-3-yl)methyl]-3-oxo-2,3,5,6,7,8-hexahydro[1,2,4]triazolo[4,3-a]pyridine-5-carboxylic acid/trifluoroacetic acid (racemate) (170 mg, 96% purity, 417 μmol) was initially charged in THF (3.3 ml) at room temperature. Subsequently, 1-[bis(dimethylamino)methylene]-1H-[1,2,3]triazolo[4,5-b]pyridin-1-ium 3-oxide hexafluorophosphate (206 mg, 542 μmol) and triethylamine (290 μl, 2.1 mmol) were added. After stirring for 15 min, 3,3-difluoropyrrolidine hydrochloride (71.9 mg, 500 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 7.00 mg (4% of theory) of the title compound were obtained.

LC-MS (Method 4): $R_t$=0.54 min; MS (ESIpos): m/z=367 [M+H]⁺

¹H-NMR (400 MHz, DMSO-d6) δ [ppm]: −0.008 (1.35), 0.008 (1.13), 1.700 (0.76), 1.982 (0.52), 2.044 (0.44), 2.429 (0.43), 2.566 (1.33), 2.580 (1.08), 3.529 (0.54), 3.549 (0.71), 3.663 (0.43), 3.696 (0.54), 3.730 (0.41), 3.774 (16.00), 3.797 (0.64), 3.908 (0.48), 4.693 (3.32), 4.702 (3.80), 4.741 (0.50), 4.783 (0.41), 4.798 (0.51), 4.807 (0.42), 6.032 (2.54), 6.038 (2.55), 7.571 (2.52), 7.577 (2.49).

Example 91

(5RS)-5-[(3,3-Difluoropyrrolidin-1-yl)carbonyl]-2-(2,4,5-trifluorobenzyl)-5,6,7,8-tetrahydro[1,2,4]triazolo[4,3-a]pyridin-3(2H)-one (Racemate)

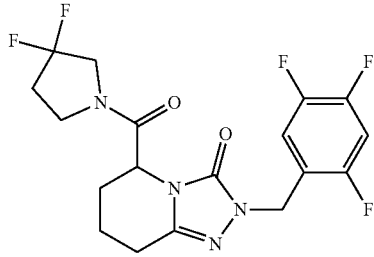 [SMILES: O=C(C1CCCc2nn(Cc3cc(F)c(F)cc3F)c(=O)n21)N1CCC(F)(F)C1]

(5RS)-3-oxo-2-(2,4,5-trifluorobenzyl)-2,3,5,6,7,8-hexahydro[1,2,4]triazolo[4,3-a]pyridine-5-carboxylic acid/trifluoroacetic acid (racemate) (100 mg, 227 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (112 mg, 295 μmol) and triethylamine (160 μl, 1.1 mmol) were added. After stirring for 15 min, 3,3-difluoropyrrolidine hydrochloride (39.0 mg, 272 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 25.0 mg (94% purity, 25% of theory) of the title compound were obtained.

LC-MS (Method 4): $R_t$=0.78 min; MS (ESIpos): m/z=417 [M+H]⁺

¹H-NMR (400 MHz, DMSO-d6) δ [ppm]: −0.149 (0.95), 0.008 (5.95), 1.727 (3.05), 2.007 (3.36), 2.327 (3.00), 2.366 (1.95), 2.560 (5.45), 2.570 (6.68), 2.586 (6.00), 2.604 (6.32), 2.669 (2.68), 3.536 (3.14), 3.556 (4.45), 3.669 (2.59), 3.702 (3.18), 3.738 (2.64), 3.771 (3.36), 3.805 (4.82), 3.888 (1.50), 3.907 (3.09), 3.933 (2.23), 3.989 (1.86), 4.033 (1.91), 4.175 (1.64), 4.201 (1.68), 4.765 (3.45), 4.791 (2.09), 4.831 (15.50), 4.845 (16.00), 4.885 (2.36), 7.263 (2.77), 7.286 (3.82), 7.303 (3.73), 7.330 (3.05), 7.540 (2.95), 7.557 (3.59), 7.564 (4.77), 7.582 (4.55), 7.591 (3.41), 7.608 (3.18).

Example 92

(5RS)-2-[(6-Methoxypyridin-3-yl)methyl]-5-(pyrrolidin-1-ylcarbonyl)-5,6,7,8-tetrahydro[1,2,4]triazolo[4,3-a]pyridin-3(2H)-one (Racemate)

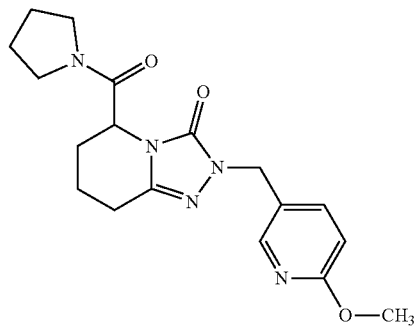 [SMILES: COc1ccc(Cn2nc3n(c2=O)C(C(=O)N2CCCC2)CCC3)cn1]

(5RS)-2-[(6-Methoxypyridin-3-yl)methyl]-3-oxo-2,3,5,6,7,8-hexahydro[1,2,4]triazolo[4,3-a]pyridine-5-carboxylic Acid (Racemate) (44.6 mg, 147 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (72.4 mg, 191 μmol) and triethylamine (61 μl, 440 μmol) were added. After stirring for 15 min, pyrrolidine (12.5 mg, 176 μmol) was added and the reaction mixture was stirred at room temperature for 48 hours. 1-[Bis(dimethylamino)methylene]-1H-[1,2,3]triazolo[4,5-b]pyridin-1-ium 3-oxide hexafluorophosphate (72.4 mg, 191 μmol), triethylamine (61 μl, 440 μmol) and pyrrolidine (12.5 mg, 176 μmol) were added again and the mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 12.7 mg (24% of theory) of the title compound were obtained.

LC-MS (Method 3): $R_t$=0.99 min; MS (ESIpos): m/z=358 [M+H]$^+$ $^1$H-NMR (400 MHz, DMSO-d6) δ[ppm]: −0.008 (2.07), 0.008 (1.18), 1.693 (0.72), 1.705 (0.80), 1.715 (0.62), 1.771 (1.14), 1.789 (2.00), 1.806 (1.55), 1.822 (0.43), 1.891 (0.57), 1.908 (1.48), 1.924 (1.84), 1.941 (1.24), 1.960 (0.57), 1.973 (0.63), 1.985 (0.59), 2.001 (0.43), 2.016 (0.51), 2.523 (1.70), 2.571 (0.63), 2.583 (1.01), 2.595 (0.58), 2.624 (0.41), 2.669 (0.40), 2.865 (1.35), 3.239 (0.63), 3.252 (0.63), 3.269 (1.20), 3.286 (1.14), 3.340 (1.20), 3.352 (0.55), 3.357 (0.67), 3.369 (0.68), 3.449 (0.71), 3.457 (0.53), 3.466 (0.43), 3.474 (0.86), 3.589 (0.42), 3.605 (0.82), 3.614 (0.43), 3.622 (0.47), 3.630 (0.64), 3.826 (16.00), 4.712 (0.78), 4.721 (0.89), 4.727 (1.04), 4.736 (0.82), 4.760 (5.47), 6.783 (1.59), 6.804 (1.70), 7.552 (1.12), 7.558 (1.13), 7.573 (1.08), 7.580 (1.07), 8.050 (1.33), 8.055 (1.26).

Example 93

(5RS)-5-(Pyrrolidin-1-ylcarbonyl)-2-{[4-(trifluoromethyl)pyridin-2-yl]methyl}-5,6,7,8-tetrahydro[1,2,4]triazolo[4,3-a]pyridin-3(2H)-one (Enantiomer 1)

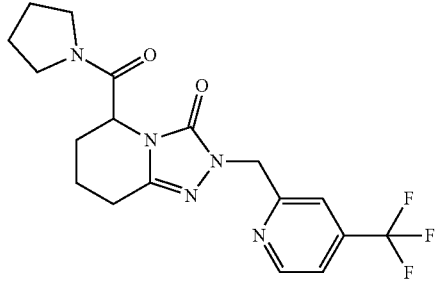 [SMILES: O=C(C1CCCc2nn(Cc3cc(C(F)(F)F)ccn3)c(=O)n21)N1CCCC1]

(5RS)-3-Oxo-2-{[4-(trifluoromethyl)pyridin-2-yl]methyl}-2,3,5,6,7,8-hexahydro[1,2,4]triazolo[4,3-a]pyridine-5-carboxylic Acid (Enantiomer 1) (55.0 mg, 161 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (79.4 mg, 209 μmol) and triethylamine (67 μl, 480 μmol) were added. After stirring for 15 min, pyrrolidine (13.7 mg, 193 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 51.0 mg (80% of theory) of the title compound were obtained.

LC-MS (Method 4): $R_t$=0.68 min; MS (ESIpos): m/z=396 [M+H]$^+$ $^1$H-NMR (400 MHz, DMSO-d6) δ [ppm]: −0.008 (2.19), 0.008 (1.87), 1.681 (1.14), 1.693 (1.55), 1.707 (2.19), 1.718 (3.14), 1.731 (3.80), 1.741 (3.09), 1.755 (2.58), 1.773 (5.88), 1.790 (9.64), 1.807 (7.28), 1.824 (2.17), 1.894 (2.32), 1.910 (6.68), 1.927 (8.29), 1.944 (4.94), 1.962 (1.50), 1.974 (1.07), 1.986 (1.05), 2.000 (1.63), 2.010 (3.01), 2.022 (3.35), 2.034 (2.19), 2.050 (2.32), 2.060 (1.68), 2.067 (1.61), 2.075 (1.61), 2.085 (0.90), 2.096 (0.54), 2.102 (0.54), 2.111 (0.45), 2.328 (0.54), 2.366 (0.41), 2.524 (2.38), 2.559 (3.20), 2.569 (2.81), 2.583 (2.36), 2.597 (2.30), 2.609 (4.19), 2.621 (2.38), 2.639 (1.03), 2.650 (1.59), 2.664 (1.03), 2.670 (0.75), 2.710 (0.49), 2.731 (0.75), 2.865 (1.20), 2.890 (0.97), 3.232 (1.33), 3.249 (2.77), 3.261 (2.75), 3.278 (5.03), 3.296 (3.41), 3.341 (5.30), 3.353 (1.98), 3.358 (2.73), 3.370 (2.83), 3.388 (1.29), 3.445 (1.44), 3.462 (3.18), 3.470 (2.32), 3.479 (1.89), 3.487 (4.06), 3.504 (1.80), 3.597 (1.87), 3.614 (3.82), 3.622 (1.93), 3.630 (2.17), 3.638 (2.94), 3.655 (1.33), 4.764 (3.44), 4.773 (3.82), 4.779 (4.51), 4.788 (3.39), 4.992 (0.86), 5.034 (15.89), 5.037 (16.00), 5.079 (0.88), 7.555 (8.10), 7.701 (4.21), 7.713 (4.40), 8.813 (5.84), 8.826 (5.80).

The (5S) configuration was assigned on the basis of the crystal structure elucidation for Example 26, 108, 113, 157, 237, 358 and 454.

(5S)-5-(Pyrrolidin-1-ylcarbonyl)-2-{[4-(trifluoromethyl)pyridin-2-yl]methyl}-5,6,7,8-tetrahydro[1,2,4]triazolo[4,3-a]pyridin-3(2H)-one Example 94

(5RS)-5-(Pyrrolidin-1-ylcarbonyl)-2-{[2-(trifluoromethyl)pyrimidin-4-yl]methyl}-5,6,7,8-tetrahydro[1,2,4]triazolo[4,3-a]pyridin-3(2H)-one (Enantiomer 1)

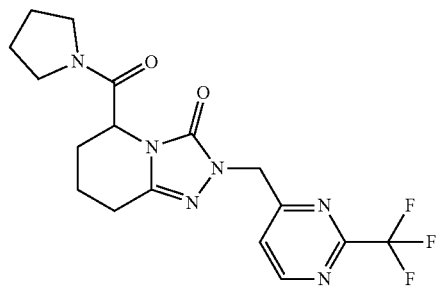 [SMILES: O=C(C1CCCc2nn(Cc3ccnc(C(F)(F)F)n3)c(=O)n21)N1CCCC1]

(5RS)-3-Oxo-2-{[2-(trifluoromethyl)pyrimidin-4-yl]methyl}-2,3,5,6,7,8-hexahydro[1,2,4]triazolo[4,3-a]pyridine-5-carboxylic Acid (Enantiomer 1) (45.0 mg, 131 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (64.8 mg, 170 μmol) and triethylamine (55 μl, 390 μmol) were added. After stirring for 15 min, pyrrolidine (11.2 mg, 157 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent:

acetonitrile/water gradient). The product-containing fractions were concentrated under reduced pressure, and 31.4 mg (100% purity, 60% of theory) of the title compound were obtained.

LC-MS (Method 4): $R_t$=0.65 min; MS (ESIpos): m/z=397 [M+H]$^+$ $^1$H-NMR (400 MHz, DMSO-d6) δ [ppm]: −0.008 (2.47), 0.008 (2.16), 1.699 (1.16), 1.712 (1.27), 1.722 (1.22), 1.757 (2.55), 1.776 (4.88), 1.793 (7.57), 1.810 (5.49), 1.827 (1.56), 1.894 (1.25), 1.911 (3.41), 1.927 (4.31), 1.943 (2.78), 1.960 (0.86), 2.005 (0.61), 2.017 (0.64), 2.030 (1.24), 2.043 (2.93), 2.053 (3.15), 2.068 (1.74), 2.079 (1.22), 2.086 (1.16), 2.094 (1.11), 2.327 (0.73), 2.367 (0.49), 2.523 (2.15), 2.571 (2.36), 2.586 (2.09), 2.597 (2.01), 2.611 (1.69), 2.625 (1.66), 2.636 (2.90), 2.649 (1.72), 2.666 (1.24), 2.679 (1.36), 2.690 (0.68), 2.710 (0.54), 3.242 (1.01), 3.259 (1.98), 3.272 (2.00), 3.288 (3.53), 3.335 (1.77), 3.353 (3.53), 3.364 (1.28), 3.370 (1.84), 3.382 (1.99), 3.400 (0.93), 3.453 (1.01), 3.471 (2.24), 3.478 (1.66), 3.488 (1.33), 3.496 (2.90), 3.513 (1.27), 3.599 (1.36), 3.615 (2.51), 3.624 (1.36), 3.633 (1.62), 3.641 (1.96), 3.657 (0.95), 4.785 (2.52), 4.794 (2.77), 4.799 (3.42), 4.808 (2.43), 5.035 (0.44), 5.080 (16.00), 5.125 (0.42), 7.480 (5.36), 7.493 (5.54), 9.047 (6.50), 9.060 (6.45).

The (5S) configuration was assigned on the basis of the crystal structure elucidation for Example 26, 108, 113, 157, 237, 358 and 454.

(5S)-5-(Pyrrolidin-1-ylcarbonyl)-2-{[2-(trifluoromethyl)pyrimidin-4-yl]methyl}-5,6,7,8-tetrahydro[1,2,4]triazolo[4,3-a]pyridin-3(2H)-one Example 95

(5RS)-2-(3-Chloro-4-fluorobenzyl)-5-[(3-hydroxyazetidin-1-yl)carbonyl]-5,6,7,8-tetrahydro[1,2,4]triazolo[4,3-a]pyridin-3(2H)-one (Racemate)

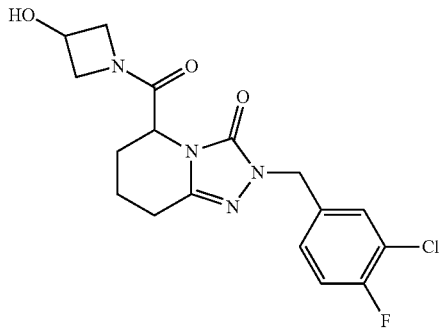 [SMILES: O=C(C1CCCc2nn(Cc3ccc(F)c(Cl)c3)c(=O)n21)N1CC(O)C1]

(5RS)-2-(3-Chloro-4-fluorobenzyl)-3-oxo-2,3,5,6,7,8-hexahydro[1,2,4]triazolo[4,3-a]pyridine-5-carboxylic acid hydrochloride (racemate) (193 mg, 532 µmol) was initially charged in THF (5.0 ml) at room temperature. Subsequently, 1-[bis(dimethylamino)methylene]-1H-[1,2,3]triazolo[4,5-b]pyridin-1-ium 3-oxide hexafluorophosphate (263 mg, 692 µmol) and triethylamine (300 µl, 2.1 mmol) were added. After stirring for 15 min, azetidin-3-ol hydrochloride (70.0 mg, 639 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 63.4 mg (31% of theory) of the title compound were obtained.

LC-MS (Method 3): $R_t$=1.17 min; MS (ESIpos): m/z=381 [M+H]$^+$ $^1$H-NMR (400 MHz, DMSO-d6) δ [ppm]: −0.008 (1.65), 0.008 (1.43), 1.677 (2.01), 1.695 (2.51), 1.709 (2.94), 1.718 (3.05), 1.902 (1.44), 1.927 (2.11), 1.938 (3.11), 1.994 (2.08), 2.004 (2.25), 2.016 (2.08), 2.073 (3.94), 2.327 (0.59), 2.366 (0.45), 2.572 (2.33), 2.580 (3.06), 2.592 (5.37), 2.605 (2.83), 2.622 (1.29), 2.634 (1.98), 2.646 (0.91), 2.669 (0.64), 2.690 (0.67), 2.710 (0.49), 3.596 (1.70), 3.603 (1.93), 3.621 (2.05), 3.629 (2.25), 3.638 (1.86), 3.649 (1.84), 3.664 (1.78), 3.674 (1.75), 3.921 (2.08), 3.932 (2.28), 3.952 (0.58), 4.021 (3.54), 4.045 (3.84), 4.055 (2.17), 4.062 (1.96), 4.105 (1.41), 4.120 (1.77), 4.131 (1.50), 4.146 (1.38), 4.339 (1.43), 4.357 (2.42), 4.378 (1.68), 4.473 (1.22), 4.485 (2.84), 4.502 (5.81), 4.520 (8.36), 4.531 (6.20), 4.546 (2.47), 4.818 (15.96), 4.823 (16.00), 5.789 (3.64), 5.802 (7.82), 5.817 (4.83), 7.223 (2.47), 7.229 (2.57), 7.244 (3.60), 7.250 (3.33), 7.256 (3.17), 7.367 (3.18), 7.371 (3.21), 7.390 (5.20), 7.411 (2.59), 7.416 (2.59), 7.434 (4.30), 7.452 (4.27).

Example 96

(5RS)-5-[(3-Fluoroazetidin-1-yl)carbonyl]-2-{[6-(trifluoromethyl)pyridin-3-yl]methyl}-5,6,7,8-tetrahydro[1,2,4]triazolo[4,3-a]pyridin-3(2H)-one (Racemate)

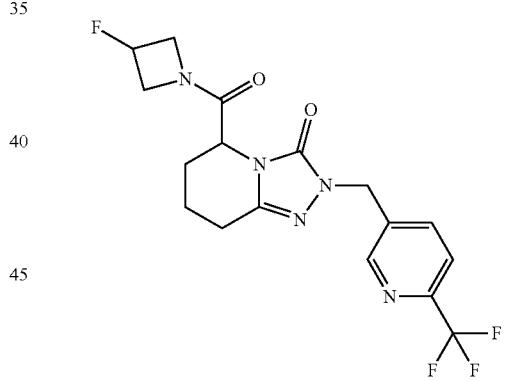

(5RS)-3-Oxo-2-{[6-(trifluoromethyl)pyridin-3-yl]methyl}-2,3,5,6,7,8-hexahydro[1,2,4]triazolo[4,3-a]pyridine-5-carboxylic Acid (Racemate) (60.0 mg, 175 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (86.6 mg, 228 µmol) and triethylamine (73 µl, 530 µmol) were added. After stirring for 15 min, 3-fluoroazetidine hydrochloride (23.5 mg, 210 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10

μm, 125 mm×30 mm; eluent: acetonitrile/water gradient). The product-containing fractions were concentrated under reduced pressure, and 30.0 mg (43% of theory) of the title compound were obtained.

LC-MS (Method 3): $R_t$=1.18 min; MS (ESIpos): m/z=400 [M+H]$^+$ $^1$H-NMR (400 MHz, DMSO-d6) δ [ppm]: −0.150 (0.47), −0.008 (4.45), 0.008 (3.73), 0.146 (0.42), 1.666 (1.19), 1.675 (1.54), 1.690 (1.68), 1.700 (2.17), 1.715 (2.43), 1.968 (1.63), 2.030 (1.47), 2.073 (1.68), 2.366 (0.79), 2.518 (5.13), 2.523 (4.20), 2.560 (2.38), 2.586 (3.13), 2.599 (4.31), 2.613 (2.17), 2.628 (0.84), 2.641 (1.42), 2.655 (0.68), 2.710 (0.84), 3.901 (0.56), 3.930 (1.12), 3.963 (1.21), 3.991 (1.12), 4.026 (0.68), 4.160 (0.49), 4.175 (0.54), 4.228 (1.05), 4.244 (0.98), 4.256 (0.93), 4.277 (1.24), 4.297 (1.10), 4.327 (0.82), 4.366 (0.91), 4.399 (0.72), 4.438 (0.51), 4.460 (0.70), 4.509 (0.54), 4.524 (0.68), 4.557 (2.92), 4.568 (4.36), 4.581 (2.92), 4.638 (0.47), 4.650 (0.56), 4.687 (0.54), 4.704 (0.56), 5.011 (11.69), 5.353 (0.77), 5.408 (0.72), 5.496 (0.75), 5.551 (0.72), 7.912 (16.00), 8.649 (6.27).

Example 97

(5RS)-2-(3-Chloro-4-fluorobenzyl)-5-{[(3S)-3-hydroxypyrrolidin-1-yl]carbonyl}-5,6,7,8-tetrahydro[1,2,4]triazolo[4,3-a]pyridin-3(2H)-one (Enantiomer 1)

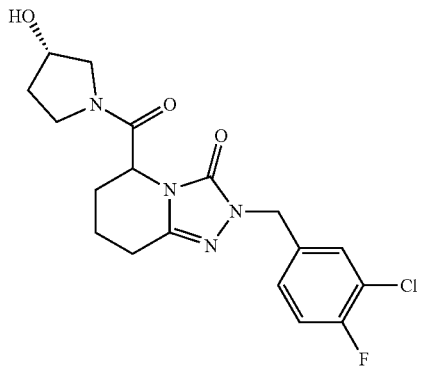 [SMILES: O=C(C1CCCc2nn(Cc3ccc(F)c(Cl)c3)c(=O)n21)N1CC[C@H](O)C1]

(5RS)-2-(3-Chloro-4-fluorobenzyl)-3-oxo-2,3,5,6,7,8-hexahydro[1,2,4]triazolo[4,3-a]pyridine-5-carboxylic acid (enantiomer 1) (55.0 mg, 169 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (83.5 mg, 220 μmol) and triethylamine (71 μl, 510 μmol) were added. After stirring for 15 min, (3S)-pyrrolidin-3-ol hydrochloride (25.0 mg, 203 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 66.0 mg (97% of theory) of the title compound were obtained.

LC-MS (Method 3): $R_t$=1.19 min; MS (ESIpos): m/z=395 [M+H]$^+$ $^1$H-NMR (400 MHz, DMSO-d6) δ[ppm]: −0.008 (2.74), 0.008 (2.46), 1.668 (1.27), 1.681 (1.28), 1.731 (2.93), 1.741 (2.61), 1.754 (2.32), 1.763 (2.04), 1.827 (0.60), 1.839 (0.73), 1.849 (1.61), 1.860 (1.98), 1.872 (1.68), 1.882 (2.15), 1.892 (1.71), 1.904 (1.25), 1.972 (2.44), 1.983 (2.94), 1.994 (2.98), 2.005 (2.63), 2.015 (2.47), 2.023 (2.13), 2.029 (2.09), 2.038 (1.82), 2.050 (1.44), 2.058 (1.57), 2.066 (1.43), 2.073 (5.11), 2.086 (0.54), 2.327 (0.61), 2.366 (0.49), 2.523 (3.02), 2.571 (1.77), 2.580 (1.19), 2.593 (2.23), 2.604 (3.72), 2.616 (2.00), 2.634 (1.06), 2.646 (1.52), 2.660 (0.87), 2.669 (0.81), 2.710 (0.61), 2.731 (3.89), 2.877 (0.63), 2.890 (5.16), 3.199 (1.00), 3.231 (1.38), 3.298 (3.79), 3.339 (2.01), 3.375 (2.71), 3.397 (1.82), 3.415 (0.81), 3.432 (0.70), 3.442 (0.77), 3.454 (1.37), 3.461 (1.36), 3.470 (0.68), 3.483 (1.53), 3.520 (0.41), 3.545 (1.20), 3.562 (1.93), 3.569 (2.22), 3.585 (1.42), 3.640 (1.08), 3.651 (1.61), 3.667 (1.13), 3.678 (1.28), 3.734 (0.54), 3.754 (0.82), 3.774 (0.43), 4.268 (1.82), 4.362 (1.80), 4.687 (0.98), 4.695 (1.13), 4.702 (1.23), 4.710 (0.99), 4.738 (2.01), 4.745 (1.57), 4.794 (1.01), 4.817 (16.00), 4.955 (4.61), 4.964 (4.28), 5.073 (3.17), 5.075 (3.09), 5.082 (3.27), 7.222 (2.22), 7.227 (2.23), 7.238 (2.55), 7.243 (3.00), 7.249 (2.85), 7.255 (2.74), 7.362 (0.47), 7.371 (4.52), 7.394 (6.84), 7.406 (0.56), 7.416 (3.64), 7.430 (3.15), 7.448 (3.23), 7.953 (0.53).

The (5S) configuration was assigned on the basis of the crystal structure elucidation for Example 26, 108, 113, 157, 237, 358 and 454.

(5S)-2-(3-Chloro-4-fluorobenzyl)-5-{[(3S)-3-hydroxypyrrolidin-1-yl]carbonyl}-5,6,7,8-tetrahydro[1,2,4]triazolo[4,3-a]pyridin-3(2H)-one Example 98

(5RS)-5-[(3-Hydroxyazetidin-1-yl)carbonyl]-2-[3-(trifluoromethyl)benzyl]-5,6,7,8-tetrahydro[1,2,4]triazolo[4,3-a]pyridin-3(2H)-one (Enantiomer 1)

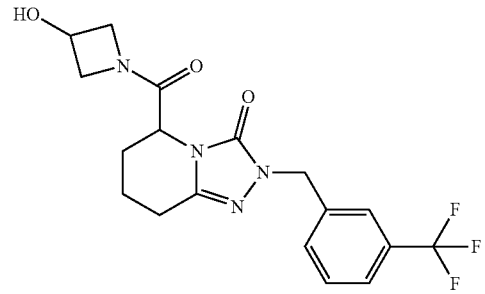 [SMILES: O=C(C1CCCc2nn(Cc3cccc(C(F)(F)F)c3)c(=O)n21)N1CC(O)C1]

(5RS)-3-Oxo-2-[3-(trifluoromethyl)benzyl]-2,3,5,6,7,8-hexahydro[1,2,4]triazolo[4,3-a]pyridine-5-carboxylic acid (enantiomer 1) (55.0 mg, 161 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (79.7 mg, 209 μmol) and triethylamine (67 μl, 480 μmol) were added. After stirring for 15 min, azetidin-3-ol hydrochloride (21.2 mg, 193 mol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 7.90 mg (12% of theory) of the title compound were obtained.

LC-MS (Method 3): $R_t$=1.24 min; MS (ESIpos): m/z=397 [M+H]$^+$ $^1$H-NMR (500 MHz, DMSO-d6) δ [ppm]: 1.666 (2.27), 1.676 (2.26), 1.719 (3.03), 1.920 (1.91), 1.946 (3.45), 2.013 (2.68), 2.020 (2.73), 2.072 (11.94), 2.588 (2.90), 2.597 (5.00), 2.606 (2.91), 2.621 (1.59), 2.631 (2.38), 2.690 (0.66), 3.608 (2.01), 3.623 (2.15), 3.629 (2.19), 3.644 (1.80), 3.652 (1.89), 3.663 (1.89), 3.672 (1.75), 3.928 (2.17), 3.938 (2.46), 3.953 (0.71), 4.029 (3.39), 4.040 (3.81), 4.047 (4.10), 4.059 (2.67), 4.109 (1.41), 4.122 (1.81), 4.130 (1.69), 4.141 (1.49), 4.343 (1.52), 4.358 (2.55), 4.374 (1.66), 4.404 (0.44), 4.495 (3.28), 4.510 (4.92), 4.521 (7.10), 4.533 (5.97), 4.541 (4.89), 4.925 (15.15), 4.931 (16.00), 5.817 (8.02), 7.510 (3.60), 7.524 (5.29), 7.574 (2.93), 7.589 (5.35), 7.604 (3.34), 7.623 (9.33), 7.649 (6.87), 7.664 (4.72).

The (5S) configuration was assigned on the basis of the crystal structure elucidation for Example 26, 108, 113, 157, 237, 358 and 454.

(5S)-5-[(3-Hydroxyazetidin-1-yl)carbonyl]-2-[3-(trifluoromethyl)benzyl]-5,6,7,8-tetrahydro[1,2,4]triazolo[4,3-a]pyridin-3(2H)-one Example 99

(5RS)-5-{[(3S)-3-Hydroxypyrrolidin-1-yl]carbonyl}-2-[3-(trifluoromethyl)benzyl]-5,6,7,8-tetrahydro[1,2,4]triazolo[4,3-a]pyridin-3(2H)-one (Enantiomer 1)

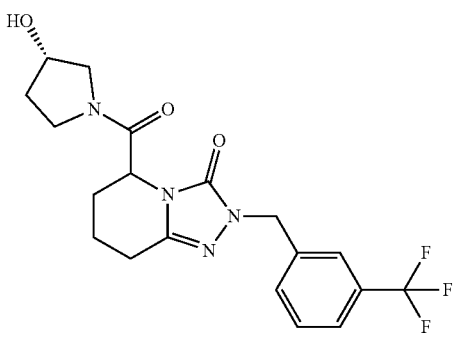 [SMILES: O=C(C1CCCc2nn(Cc3cccc(C(F)(F)F)c3)c(=O)n21)N1CC[C@H](O)C1]

(5RS)-3-Oxo-2-[3-(trifluoromethyl)benzyl]-2,3,5,6,7,8-hexahydro[1,2,4]triazolo[4,3-a]pyridine-5-carboxylic acid (enantiomer 1) (55.0 mg, 161 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (79.7 mg, 209 μmol) and triethylamine (67 μl, 480 μmol) were added. After stirring for 15 min, (3S)-pyrrolidin-3-ol hydrochloride (23.9 mg, 193 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 10.9 mg (16% of theory) of the title compound were obtained.

LC-MS (Method 3): $R_t$=1.26 min; MS (ESIpos): m/z=411 [M+H]$^+$ $^1$H-NMR (500 MHz, DMSO-d6) δ[ppm]: −0.007 (2.44), 0.006 (1.71), 1.677 (1.35), 1.733 (2.92), 1.753 (2.40), 1.835 (0.67), 1.845 (0.79), 1.853 (1.67), 1.862 (2.30), 1.871 (1.79), 1.879 (2.36), 1.888 (1.98), 1.958 (1.81), 1.967 (2.10), 1.976 (2.36), 1.985 (2.86), 1.994 (2.94), 2.003 (2.57), 2.010 (2.04), 2.024 (2.04), 2.031 (2.30), 2.044 (1.74), 2.053 (1.72), 2.060 (1.78), 2.066 (1.45), 2.072 (2.04), 2.087 (0.58), 2.362 (0.62), 2.519 (2.96), 2.563 (1.74), 2.574 (0.72), 2.608 (3.40), 2.640 (1.92), 2.689 (0.42), 2.877 (0.45), 3.205 (1.08), 3.230 (1.45), 3.353 (1.74), 3.369 (2.56), 3.375 (2.51), 3.393 (2.14), 3.400 (1.78), 3.412 (0.69), 3.436 (0.87), 3.444 (0.78), 3.454 (1.01), 3.461 (1.82), 3.484 (1.52), 3.530 (0.41), 3.550 (1.21), 3.563 (2.45), 3.571 (2.19), 3.583 (1.63), 3.647 (1.29), 3.655 (1.90), 3.668 (1.25), 3.677 (1.47), 3.741 (0.57), 3.755 (0.87), 3.772 (0.49), 4.266 (2.09), 4.366 (2.09), 4.392 (0.46), 4.403 (0.66), 4.699 (1.20), 4.705 (1.32), 4.711 (1.42), 4.717 (1.14), 4.742 (1.79), 4.748 (2.20), 4.754 (1.94), 4.806 (0.98), 4.813 (1.09), 4.818 (1.14), 4.825 (0.90), 4.896 (0.42), 4.923 (16.00), 4.968 (1.22), 5.089 (1.29), 7.218 (0.52), 7.507 (2.86), 7.523 (4.44), 7.540 (0.69), 7.574 (3.29), 7.590 (6.42), 7.605 (3.61), 7.621 (6.90), 7.647 (6.52), 7.663 (4.44).

The (5S) configuration was assigned on the basis of the crystal structure elucidation for Example 26, 108, 113, 157, 237, 358 and 454.

(5S)-5-{[(3S)-3-Hydroxypyrrolidin-1-yl]carbonyl}-2-[3-(trifluoromethyl)benzyl]-5,6,7,8-tetrahydro[1,2,4]triazolo[4,3-a]pyridin-3(2H)-one Example 100

(5RS)-5-{[(3R)-3-Fluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (Diastereomer Mixture; 2 Isomers)

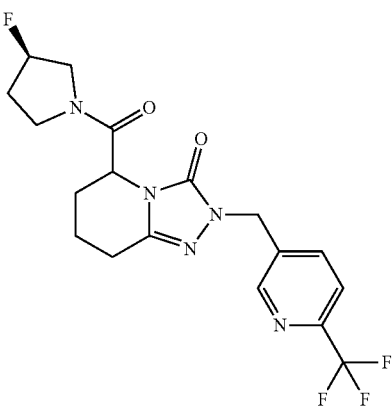 [SMILES: O=C(C1CCCc2nn(Cc3ccc(C(F)(F)F)nc3)c(=O)n21)N1CC[C@@H](F)C1]

(5RS)-3-Oxo-2-{[6-(trifluoromethyl)pyridin-3-yl]methyl}-2,3,5,6,7,8-hexahydro[1,2,4]triazolo[4,3-a]pyridine-5-carboxylic Acid (Racemate) (60.0 mg, 175 μmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (86.6 mg, 228 µmol) and triethylamine (73 µl, 530 µmol) were added. After stirring for 15 min, (3R)-3-fluoropyrrolidine hydrochloride (26.4 mg, 210 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 29.0 mg (40% of theory) of the title compound were obtained.

LC-MS (Method 3): $R_t$=1.21 min; MS (ESIpos): m/z=414 $[M+H]^+$ $^1$H-NMR (400 MHz, DMSO-d6) δ[ppm]: −0.149 (0.59), −0.008 (5.76), 0.008 (4.91), 0.146 (0.59), 1.658 (0.69), 1.736 (1.64), 2.005 (1.91), 2.016 (1.59), 2.067 (1.00), 2.103 (1.54), 2.140 (1.08), 2.270 (0.80), 2.327 (0.74), 2.366 (0.49), 2.518 (3.66), 2.523 (2.83), 2.571 (1.61), 2.599 (1.44), 2.611 (2.42), 2.623 (1.49), 2.653 (0.91), 2.669 (1.07), 2.710 (0.54), 3.369 (0.81), 3.387 (0.58), 3.398 (0.81), 3.524 (1.13), 3.548 (0.97), 3.573 (0.86), 3.600 (1.61), 3.636 (1.07), 3.659 (1.08), 3.681 (1.00), 3.702 (0.56), 3.726 (0.56), 3.747 (1.08), 3.775 (0.80), 3.788 (0.80), 3.856 (1.07), 3.941 (0.74), 4.009 (0.41), 4.694 (0.52), 4.703 (0.64), 4.710 (0.68), 4.719 (0.54), 4.752 (0.69), 4.760 (0.78), 4.767 (0.88), 4.776 (0.66), 4.827 (0.61), 4.839 (1.02), 4.850 (0.58), 4.861 (0.59), 4.876 (0.80), 4.885 (0.61), 5.008 (10.07), 5.261 (0.76), 5.349 (0.49), 5.392 (0.78), 5.482 (0.47), 5.512 (0.41), 7.907 (9.08), 7.911 (16.00), 8.642 (5.57).

Example 101

(5RS)-2-[4-Fluoro-3-(trifluoromethyl)benzyl]-5-{[(3S)-3-hydroxypyrrolidin-1-yl]carbonyl}-5,6,7,8-tetrahydro[1,2,4]triazolo[4,3-a]pyridin-3(2H)-one (Diastereomer Mixture; 2 Isomers)

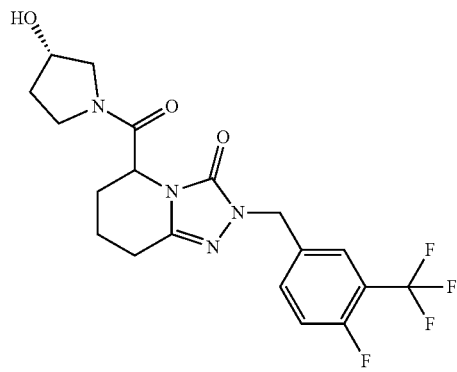 [SMILES: O=C(C1CCCc2nn(Cc3ccc(F)c(C(F)(F)F)c3)c(=O)n21)N1CC[C@H](O)C1]

(5RS)-2-[4-Fluoro-3-(trifluoromethyl)benzyl]-3-oxo-2,3,5,6,7,8-hexahydro[1,2,4]triazolo[4,3-a]pyridine-5-carboxylic Acid (Racemate) (90.0 mg, 250 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (124 mg, 326 µmol) and triethylamine (100 µl, 750 µmol) were added. After stirring for 15 min, (3S)-pyrrolidin-3-ol hydrochloride (37.1 mg, 301 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 34.0 mg (32% of theory) of the title compound were obtained.

LC-MS (Method 3): $R_t$=1.30 min; MS (ESIpos): m/z=429 $[M+H]^+$ $^1$H-NMR (400 MHz, DMSO-d6) δ [ppm]: −0.149 (1.32), −0.008 (12.62), 0.008 (10.09), 0.146 (1.26), 1.676 (1.38), 1.730 (2.98), 1.741 (2.71), 1.826 (0.65), 1.849 (1.75), 1.859 (2.09), 1.871 (1.82), 1.881 (2.34), 1.961 (2.00), 1.971 (2.58), 1.984 (3.11), 1.995 (3.23), 2.005 (3.02), 2.017 (2.65), 2.037 (1.94), 2.056 (1.60), 2.065 (1.42), 2.328 (1.54), 2.366 (0.98), 2.524 (6.71), 2.569 (2.18), 2.603 (3.88), 2.644 (1.60), 2.670 (1.85), 2.710 (0.98), 3.197 (1.05), 3.228 (1.51), 3.338 (2.77), 3.371 (3.54), 3.390 (2.34), 3.426 (0.80), 3.457 (1.72), 3.478 (1.45), 3.545 (1.29), 3.568 (2.28), 3.583 (1.54), 3.639 (1.14), 3.650 (1.72), 3.677 (1.32), 3.706 (1.51), 3.734 (0.62), 3.753 (0.89), 4.266 (2.03), 4.361 (1.97), 4.690 (1.05), 4.698 (1.20), 4.705 (1.29), 4.713 (1.08), 4.742 (2.06), 4.798 (0.92), 4.813 (1.29), 4.821 (0.98), 4.903 (16.00), 4.965 (1.29), 5.074 (1.72), 7.478 (2.49), 7.500 (4.77), 7.526 (4.46), 7.562 (2.74), 7.575 (3.29), 7.671 (3.72), 7.690 (3.82).

Example 102

(5RS)-5-(Pyrrolidin-1-ylcarbonyl)-2-(2,4,5-trimethylbenzyl)-5,6,7,8-tetrahydro[1,2,4]triazolo[4,3-a]pyridin-3(2H)-one (Enantiomer 1)

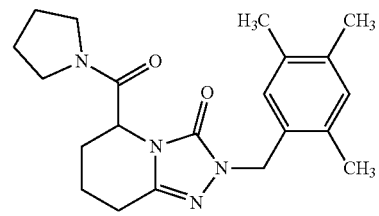 [SMILES: Cc1cc(C)c(Cn2nc3n(c2=O)C(C(=O)N2CCCC2)CCC3)cc1C]

(5RS)-3-Oxo-2-(2,4,5-trimethylbenzyl)-2,3,5,6,7,8-hexahydro[1,2,4]triazolo[4,3-a]pyridine-5-carboxylic acid (enantiomer 1) (93.0 mg, 295 µmol) was initially charged in THF (2.0 ml) at room temperature. Subsequently, 1-[bis(dimethylamino)methylene]-1H-[1,2,3]triazolo[4,5-b]pyridin-1-ium 3-oxide hexafluorophosphate (146 mg, 383 µmol) and triethylamine (120 µl, 880 µmol) were added. After stirring for 15 min, pyrrolidine (30 µl, 350 µmol) was added and the reaction mixture was stirred at room temperature for 72 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 55.0 mg (51% of theory) of the title compound were obtained.

LC-MS (Method 3): R$_t$=1.59 min; MS (ESIpos): m/z=369 [M+H]$^+$ $^1$H-NMR (400 MHz, DMSO-d6) δ [ppm]: −0.008 (0.95), 0.008 (0.80), 1.661 (0.42), 1.673 (0.74), 1.687 (1.21), 1.697 (1.43), 1.710 (1.15), 1.754 (0.47), 1.772 (1.91), 1.790 (3.37), 1.807 (2.63), 1.823 (0.77), 1.892 (0.79), 1.909 (2.45), 1.926 (3.23), 1.942 (2.13), 1.961 (0.95), 1.974 (1.22), 1.985 (1.53), 1.996 (1.03), 2.010 (0.92), 2.020 (0.64), 2.026 (0.58), 2.036 (0.58), 2.046 (0.40), 2.140 (15.41), 2.144 (16.00), 2.205 (14.00), 2.457 (0.40), 2.473 (0.58), 2.523 (1.61), 2.560 (0.86), 2.571 (1.56), 2.583 (0.85), 2.613 (0.63), 3.224 (0.46), 3.240 (0.99), 3.253 (0.98), 3.270 (1.74), 3.287 (0.91), 3.321 (1.38), 3.340 (1.90), 3.352 (0.69), 3.357 (0.94), 3.369 (1.05), 3.387 (0.48), 3.433 (0.53), 3.450 (1.15), 3.458 (0.84), 3.468 (0.69), 3.475 (1.45), 3.492 (0.64), 3.591 (0.67), 3.608 (1.40), 3.616 (0.70), 3.625 (0.78), 3.633 (1.09), 3.649 (0.49), 4.684 (8.43), 4.716 (1.31), 4.725 (1.52), 4.731 (1.73), 4.740 (1.26), 6.890 (4.26), 6.914 (3.98).

The (5S) configuration was assigned on the basis of the crystal structure elucidation for Example 26, 108, 113, 157, 237, 358 and 454.

(5S)-5-(Pyrrolidin-1-ylcarbonyl)-2-(2,4,5-trimethylbenzyl)-5,6,7,8-tetrahydro[1,2,4]triazolo[4,3-a]pyridin-3(2H)-one Example 103

(5RS)-5-(Pyrrolidin-1-ylcarbonyl)-2-[(3,5,6-trimethylpyrazin-2-yl)methyl]-5,6,7,8-tetrahydro[1,2,4]triazolo[4,3-a]pyridin-3(2H)-one (Racemate)

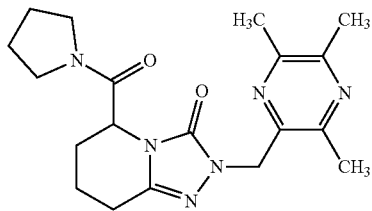 [SMILES: Cc1nc(C)c(Cn2nc3n(c2=O)C(C(=O)N2CCCC2)CCC3)nc1C]

(5RS)-3-Oxo-2-[(3,5,6-trimethylpyrazin-2-yl)methyl]-2,3,5,6,7,8-hexahydro[1,2,4]triazolo[4,3-a]pyridine-5-carboxylic Acid (Racemate) (90.0 mg, 90% purity, 255 μmol) was initially charged in DMF (1.9 ml) at room temperature. Subsequently, 1-[bis(dimethylamino)methylene]-1H-[1,2,3]triazolo[4,5-b]pyridin-1-ium 3-oxide hexafluorophosphate (126 mg, 332 μmol) and triethylamine (110 pal, 770 μmol) were added. After stirring for 15 min, pyrrolidine (26 μl, 310 μmol) was added and the reaction mixture was stirred at room temperature overnight. 1-[Bis(dimethylamino)methylene]-1H-[1,2,3]triazolo[4,5-b]pyridin-1-ium 3-oxide hexafluorophosphate (97 mg, 255 μmol) and triethylamine (36 μl, 255 mol) were added again and the mixture was stirred at room temperature for 1 hour. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 57.0 mg (60% of theory) of the title compound were obtained.

LC-MS (Method 3): R$_t$=0.93 min; MS (ESIpos): m/z=371 [M+H]$^+$ $^1$H-NMR (400 MHz, DMSO-d6) δ [ppm]: 1.649 (0.46), 1.662 (0.81), 1.675 (1.31), 1.685 (1.56), 1.699 (1.24), 1.756 (0.44), 1.773 (1.80), 1.790 (3.21), 1.807 (2.55), 1.824 (0.78), 1.893 (0.77), 1.909 (2.39), 1.926 (3.22), 1.943 (2.22), 1.959 (1.07), 1.969 (1.22), 1.981 (1.37), 1.993 (0.94), 2.007 (0.89), 2.018 (0.64), 2.032 (0.58), 2.384 (14.92), 2.409 (15.08), 2.417 (16.00), 2.450 (0.52), 2.458 (0.45), 2.476 (1.25), 2.574 (0.48), 2.586 (0.61), 3.222 (0.45), 3.239 (0.92), 3.252 (0.96), 3.269 (1.63), 3.286 (0.80), 3.336 (1.71), 3.354 (0.89), 3.366 (0.96), 3.383 (0.44), 3.434 (0.50), 3.451 (1.10), 3.458 (0.82), 3.476 (1.38), 3.493 (0.63), 3.594 (0.64), 3.611 (1.35), 3.619 (0.70), 3.628 (0.78), 3.636 (1.06), 3.652 (0.47), 4.717 (1.21), 4.726 (1.43), 4.732 (1.62), 4.740 (1.19), 4.868 (9.21).

Example 104

(5RS)-5-(Pyrrolidin-1-ylcarbonyl)-2-[(3,5,6-trimethylpyrazin-2-yl)methyl]-5,6,7,8-tetrahydro[1,2,4]triazolo[4,3-a]pyridin-3(2H)-one (Enantiomer 2)

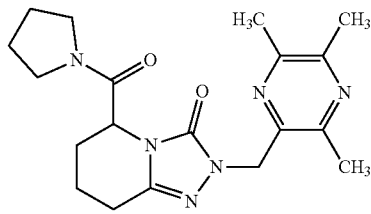 [SMILES: Cc1nc(C)c(Cn2nc3n(c2=O)C(C(=O)N2CCCC2)CCC3)nc1C]

(5RS)-5-(Pyrrolidin-1-ylcarbonyl)-2-[(3,5,6-trimethylpyrazin-2-yl)methyl]-5,6,7,8-tetrahydro[1,2,4]triazolo[4,3-a]pyridin-3(2H)-one (racemate) was separated by chiral preparative HPLC [sample preparation: 46 mg dissolved in 4 ml of ethanol; injection volume: 0.35 ml; column: Daicel Chiralpak® AD-H 5 μm, 250×20 mm; eluent: n-heptane/ethanol: isocratic 60% ethanol, flow rate: 25 ml/min; temperature 25° C.; UV detection: 210 nm]. After the separation, 19 mg of enantiomer 1, which eluted first, and 19 mg (92% purity) of enantiomer 2, which eluted later, were isolated.

Enantiomer 2:

Analytical chiral HPLC: R$_t$=2.11 min, e.e. =99% [column: Daicel Chiralcel® AD-3 3 μm 50×4.6 mm; eluent: n-heptane/ethanol 1:1; flow rate: 1 ml/min; UV detection: 220 nm].

LC-MS (Method 4): R$_t$=0.56 min; MS (ESIpos): m/z=371 [M+H]$^+$ $^1$H-NMR (400 MHz, DMSO-d6) δ [ppm]: 1.63-1.68 (m, 2H), 1.79 (quin, 2H), 1.86-2.07 (m, 4H), 2.38 (s, 3H), 2.41 (d, 6H), 2.44-2.61 (m, 2H, partially covered by solvent signal), 3.14-3.29 (m, 1H), 3.33-3.39 (m, 1H), 3.41-3.52 (m, 1H), 3.57-3.67 (m, 1H), 4.73 (dd, 1H), 4.87 (s, 2H).

Example 105

5(RS)-5-Methyl-2-(4-methylbenzyl)-5-(pyrrolidin-1-ylcarbonyl)-5,6,7,8-tetrahydro[1,2,4]triazolo[4,3-a]pyridin-3(2H)-one (Racemate)

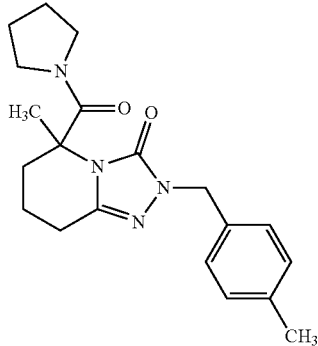 [SMILES: Cc1ccc(Cn2nc3n(c2=O)C(C)(C(=O)N2CCCC2)CCC3)cc1]

(5RS)-5-Methyl-2-(4-methylbenzyl)-3-oxo-2,3,5,6,7,8-hexahydro[1,2,4]triazolo[4,3-a]pyridine-5-carboxylic Acid (Racemate) (30.0 mg, 99.6 μmol) was initially charged in THF (1.0 ml) at room temperature. Subsequently, 1-[bis(dimethylamino)methylene]-1H-[1,2,3]triazolo[4,5-b]pyridin-1-ium 3-oxide hexafluorophosphate (49.2 mg, 129 μmol) and triethylamine (42 μl, 300 μmol) were added. After stirring for 15 min, pyrrolidine (10 μl, 120 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 19.4 mg (55% of theory) of the title compound were obtained.

LC-MS (Method 3): $R_t$=1.46 min; MS (ESIpos): m/z=355 [M+H]$^+$ $^1$H-NMR (400 MHz, DMSO-d6) δ [ppm]: −0.008 (0.46), 0.008 (0.45), 1.155 (0.41), 1.173 (0.84), 1.192 (0.44), 1.202 (0.85), 1.218 (0.84), 1.563 (11.36), 1.715 (1.01), 1.754 (0.66), 1.767 (0.63), 1.781 (0.47), 1.817 (1.45), 1.845 (1.15), 1.958 (0.59), 1.986 (0.75), 2.269 (11.71), 2.599 (0.63), 2.611 (0.73), 2.624 (1.11), 2.635 (1.32), 3.237 (0.41), 4.664 (1.34), 4.702 (2.54), 4.780 (2.48), 4.818 (1.34), 7.127 (16.00).

Example 106

(5RS)-2-{[3-Chloro-5-(trifluoromethyl)pyridin-2-yl]methyl}-5-(pyrrolidin-1-ylcarbonyl)-5,6,7,8-tetrahydro[1,2,4]triazolo[4,3-a]pyridin-3(2H)-one (Enantiomer 1)

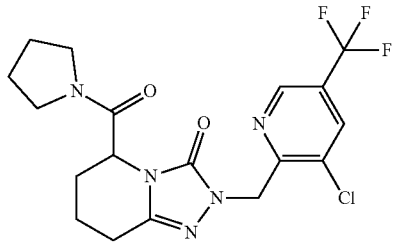 [SMILES: O=C(C1CCCc2nn(Cc3ncc(C(F)(F)F)cc3Cl)c(=O)n21)N1CCCC1]

Methyl (5RS)-2-{[3-chloro-5-(trifluoromethyl)pyridin-2-yl]methyl}-3-oxo-2,3,5,6,7,8-hexahydro[1,2,4]triazolo[4,3-a]pyridine-5-carboxylate (enantiomer 1) (80.0 mg, 205 μmol) was initially charged in THF (1.8 ml) at room temperature. Subsequently, 1-[bis(dimethylamino)methylene]-1H-[1,2,3]triazolo[4,5-b]pyridin-1-ium 3-oxide hexafluorophosphate (101 mg, 266 μmol) and triethylamine (86 μl, 610 mol) were added. After stirring for 15 min, pyrrolidine (21 μl, 250 μmol) was added and the reaction mixture was stirred at room temperature for 72 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 4.20 mg (5% of theory) of the title compound were obtained.

LC-MS (Method 3): $R_t$=1.37 min; MS (ESIpos): m/z=430 [M+H]$^+$ $^1$H-NMR (400 MHz, DMSO-d6) δ [ppm]: −0.149 (1.19), −0.008 (10.74), 0.008 (9.06), 0.146 (1.10), 1.480 (0.71), 1.701 (6.28), 1.714 (8.22), 1.732 (5.79), 1.744 (2.92), 1.753 (2.52), 1.771 (8.44), 1.788 (14.81), 1.805 (11.31), 1.822 (3.31), 1.891 (3.54), 1.908 (10.25), 1.924 (12.95), 1.941 (8.27), 1.958 (3.80), 1.973 (2.70), 1.984 (4.77), 1.995 (4.33), 2.006 (3.23), 2.021 (3.54), 2.042 (3.23), 2.057 (2.92), 2.078 (1.41), 2.327 (2.43), 2.366 (1.81), 2.523 (8.75), 2.566 (4.15), 2.579 (7.65), 2.591 (3.93), 2.609 (1.81), 2.620 (2.70), 2.634 (1.24), 2.670 (2.70), 2.710 (1.77), 3.229 (2.12), 3.246 (4.33), 3.259 (4.51), 3.276 (8.18), 3.337 (8.75), 3.355 (4.33), 3.367 (4.60), 3.384 (2.08), 3.442 (2.34), 3.460 (4.99), 3.467 (3.62), 3.484 (6.32), 3.501 (2.74), 3.595 (2.87), 3.612 (5.88), 3.620 (3.05), 3.629 (3.49), 3.637 (4.69), 3.654 (2.12), 4.735 (5.44), 4.745 (6.32), 4.750 (7.25), 4.760 (5.35), 5.063 (4.82), 5.104 (16.00), 5.134 (15.43), 5.175 (4.64), 8.486 (10.96), 8.489 (11.27), 8.905 (11.09).

The (5S) configuration was assigned on the basis of the crystal structure elucidation for Example 26, 108, 113, 157, 237, 358 and 454.

(5S)-2-{[3-Chloro-5-(trifluoromethyl)pyridin-2-yl]methyl}-5-(pyrrolidin-1-ylcarbonyl)-5,6,7,8-tetrahydro[1,2,4]triazolo[4,3-a]pyridin-3(2H)-one

Example 107

(5RS)-2-{[5-Chloro-4-(trifluoromethyl)pyridin-2-yl]methyl}-5-(pyrrolidin-1-ylcarbonyl)-5,6,7,8-tetrahydro[1,2,4]triazolo[4,3-a]pyridin-3(2H)-one (Enantiomer 1)

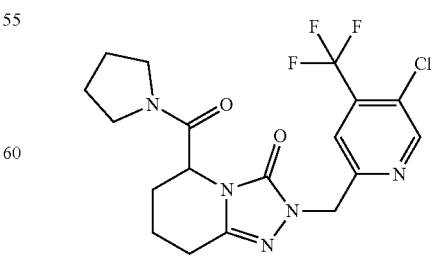

(5RS)-2-{[5-Chloro-4-(trifluoromethyl)pyridin-2-yl]methyl}-3-oxo-2,3,5,6,7,8-hexahydro[1,2,4]triazolo[4,3-a]

pyridine-5-carboxylic Acid (Enantiomer 1) (100 mg, 265 μmol) was initially charged in THF (3.8 ml) at room temperature. Subsequently, 1-[bis(dimethylamino)methylene]-1H-[1,2,3]triazolo[4,5-b]pyridin-1-ium 3-oxide hexafluorophosphate (131 mg, 345 μmol) and triethylamine (110 μl, 800 μmol) were added. After stirring for 15 min, pyrrolidine (27 μl, 320 μmol) was added and the reaction mixture was stirred at room temperature for 72 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 65.0 mg (57% of theory) of the title compound were obtained.

LC-MS (Method 4): $R_t$=0.79 min; MS (ESIpos): m/z=430 [M+H]$^+$ $^1$H-NMR (400 MHz, DMSO-d6) δ [ppm]: −0.008 (2.42), 0.008 (2.12), 1.711 (2.02), 1.724 (2.54), 1.735 (2.04), 1.755 (1.54), 1.772 (4.25), 1.789 (6.89), 1.806 (5.25), 1.823 (1.54), 1.891 (1.57), 1.908 (4.70), 1.925 (5.85), 1.942 (3.54), 1.959 (1.16), 2.005 (2.17), 2.016 (2.70), 2.026 (1.79), 2.043 (1.62), 2.052 (1.21), 2.067 (1.15), 2.328 (0.72), 2.366 (0.47), 2.560 (2.01), 2.575 (1.77), 2.590 (1.68), 2.602 (2.96), 2.614 (1.68), 2.632 (0.81), 2.643 (1.18), 2.670 (0.81), 2.690 (1.16), 2.710 (0.47), 2.731 (0.66), 2.890 (0.73), 3.229 (0.83), 3.246 (1.96), 3.258 (1.95), 3.275 (3.58), 3.293 (1.92), 3.335 (3.62), 3.353 (1.88), 3.365 (1.97), 3.383 (0.88), 3.441 (1.04), 3.458 (2.32), 3.465 (1.61), 3.482 (2.93), 3.500 (1.30), 3.593 (1.31), 3.609 (2.74), 3.626 (1.57), 3.634 (2.05), 3.650 (0.96), 4.755 (2.49), 4.764 (2.73), 4.770 (3.18), 4.779 (2.43), 4.992 (0.41), 5.034 (16.00), 5.076 (0.45), 7.719 (10.56), 8.902 (9.80).

The (5S) configuration was assigned on the basis of the crystal structure elucidation for Example 26, 108, 113, 157, 237, 358 and 454.

(5S)-2-{[5-Chloro-4-(trifluoromethyl)pyridin-2-yl]methyl}-5-(pyrrolidin-1-ylcarbonyl)-5,6,7,8-tetrahydro[1,2,4]triazolo[4,3-a]pyridin-3(2H)-one Example 108

(5RS)-2-(4-Methylbenzyl)-5-(1,3-thiazolidin-3-ylcarbonyl)-5,6,7,8-tetrahydro[1,2,4]triazolo[4,3-a]pyridin-3(2H)-one (Enantiomer 1)

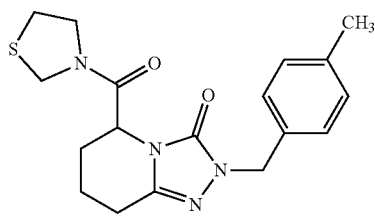 [SMILES: Cc1ccc(Cn2nc3n(c2=O)C(C(=O)N2CCSC2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 μmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 μmol) and N,N-diisopropylethylamine (120 μl, 680 μmol) were added. After stirring for 15 min, 1,3-thiazolidine hydrochloride (39.3 mg, 313 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 44.7 mg (48% of theory) of the title compound were obtained.

LC-MS (Method 4): $R_t$=0.76 min; MS (ESIpos): m/z=359 [M+H]$^+$ $^1$H-NMR (400 MHz, DMSO-d6) δ [ppm]: −0.008 (0.44), 1.647 (0.49), 1.721 (0.75), 1.731 (0.71), 1.952 (0.40), 1.978 (0.57), 1.987 (0.92), 2.039 (0.54), 2.049 (0.59), 2.059 (0.57), 2.272 (16.00), 2.567 (0.97), 2.576 (0.85), 2.588 (1.42), 2.600 (0.79), 2.630 (0.50), 2.999 (0.74), 3.015 (1.56), 3.031 (0.89), 3.128 (1.06), 3.144 (2.19), 3.159 (1.12), 3.624 (0.43), 3.639 (0.56), 3.688 (0.57), 3.768 (0.50), 3.779 (0.46), 3.794 (0.63), 3.941 (0.62), 3.955 (0.43), 3.968 (0.47), 4.367 (0.97), 4.392 (1.26), 4.551 (1.28), 4.577 (1.04), 4.609 (0.73), 4.632 (0.88), 4.749 (6.74), 4.801 (0.89), 4.824 (0.72), 4.845 (0.56), 4.854 (0.68), 4.860 (0.73), 4.868 (0.55), 4.928 (0.45), 4.942 (0.57), 7.101 (0.90), 7.108 (0.56), 7.123 (12.99), 7.125 (12.62), 7.147 (0.89).

The (5S) configuration was assigned on the basis of crystal structure elucidation for Example 108.

(5S)-2-(4-Methylbenzyl)-5-(1,3-thiazolidin-3-ylcarbonyl)-5,6,7,8-tetrahydro[1,2,4]triazolo[4,3-a]pyridin-3(2H)-one

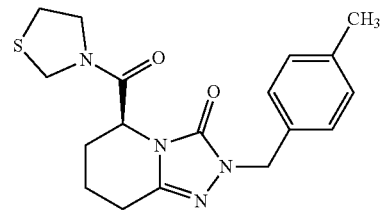 [SMILES: Cc1ccc(Cn2nc3n(c2=O)[C@H](C(=O)N2CCSC2)CCC3)cc1]

Example 109

(2S)-1-{[(5RS)-2-(4-Methylbenzyl)-3-oxo-2,3,5,6,7,8-hexahydro[1,2,4]triazolo[4,3-a]pyridin-5-yl]carbonyl}pyrrolidine-2-carbonitrile (Enantiomer 1)

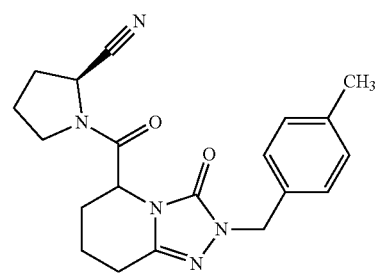 [SMILES: Cc1ccc(Cn2nc3n(c2=O)C(C(=O)N2CCC[C@H]2C#N)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 µmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 µmol) and N,N-diisopropylethylamine (120 µl, 680 µmol) were added. After stirring for 15 min, (2S)-pyrrolidine-2-carbonitrile hydrochloride (41.5 mg, 313 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 35.4 mg (36% of theory) of the title compound were obtained.

LC-MS (Method 1): $R_t$=1.02 min; MS (ESIpos): m/z=366 [M+H]$^+$ $^1$H-NMR (400 MHz, DMSO-d6) δ [ppm]: −0.008 (1.03), 0.008 (0.89), 1.654 (0.52), 1.769 (0.69), 2.027 (1.21), 2.042 (1.71), 2.062 (2.62), 2.078 (2.62), 2.094 (1.23), 2.104 (1.05), 2.115 (0.95), 2.136 (0.93), 2.149 (1.11), 2.159 (0.93), 2.175 (0.45), 2.185 (0.59), 2.204 (1.26), 2.224 (1.18), 2.236 (0.75), 2.244 (0.47), 2.256 (0.74), 2.273 (16.00), 2.327 (0.30), 2.366 (0.18), 2.558 (0.99), 2.569 (0.98), 2.583 (0.79), 2.603 (0.74), 2.616 (1.37), 2.627 (0.79), 2.646 (0.35), 2.658 (0.59), 2.669 (0.49), 2.709 (0.17), 3.672 (2.09), 3.688 (4.23), 3.705 (2.02), 4.749 (8.60), 4.793 (2.28), 4.803 (3.16), 4.813 (2.75), 4.824 (1.44), 7.099 (1.37), 7.120 (9.43), 7.127 (9.47), 7.148 (1.26).

The (5S) configuration was assigned on the basis of the crystal structure elucidation for Example 26, 108, 113, 157, 237, 358 and 454.

(2S)-1-{[(5S)-2-(4-Methylbenzyl)-3-oxo-2,3,5,6,7,8-hexahydro[1,2,4]triazolo[4,3-a]pyridin-5-yl]carbonyl}pyrrolidine-2-carbonitrile Example 110

(5RS)-5-{[(3S)-3-Fluoropyrrolidin-1-yl]carbonyl}-2-(4-methylbenzyl)-5,6,7,8-tetrahydro[1,2,4]triazolo[4,3-a]pyridin-3(2H)-one (Enantiomer 1)

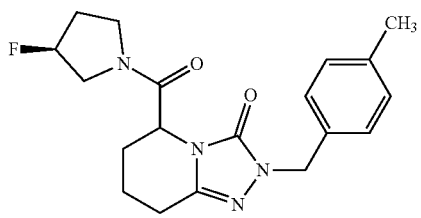 [SMILES: Cc1ccc(Cn2nc3n(c2=O)C(C(=O)N2CC[C@H](F)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 µmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 µmol) and N,N-diisopropylethylamine (120 µl, 680 µmol) were added. After stirring for 15 min, (3S)-3-fluoropyrrolidine hydrochloride (39.3 mg, 313 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 56.2 mg (60% of theory) of the title compound were obtained.

LC-MS (Method 3): $R_t$=1.29 min; MS (ESIpos): m/z=359 [M+H]$^+$ $^1$H-NMR (400 MHz, DMSO-d6) δ [ppm]: −0.008 (0.69), 0.008 (0.65), 1.692 (0.66), 1.706 (1.32), 1.719 (1.54), 1.737 (0.99), 1.750 (0.44), 1.993 (0.51), 2.004 (0.68), 2.017 (0.58), 2.059 (0.73), 2.073 (0.83), 2.085 (0.81), 2.108 (0.79), 2.122 (0.48), 2.133 (0.55), 2.237 (0.43), 2.272 (16.00), 2.522 (1.18), 2.562 (0.69), 2.585 (1.09), 2.590 (1.13), 2.632 (0.42), 3.287 (0.45), 3.633 (1.34), 3.652 (0.99), 3.662 (0.87), 3.679 (0.60), 3.695 (0.51), 3.720 (0.55), 3.740 (0.92), 3.768 (0.67), 3.776 (0.60), 3.784 (0.65), 3.854 (1.17), 4.665 (0.61), 4.674 (0.73), 4.681 (0.78), 4.690 (0.65), 4.698 (0.71), 4.722 (0.84), 4.737 (5.72), 4.746 (3.53), 4.788 (0.47), 5.258 (0.57), 5.381 (0.72), 5.388 (0.75), 5.510 (0.42), 7.102 (0.76), 7.119 (6.24), 7.124 (13.58), 7.146 (0.84).

The (5S) configuration was assigned on the basis of the crystal structure elucidation for Example 26, 108, 113, 157, 237, 358 and 454.

(5S)-5-{[(3S)-3-Fluoropyrrolidin-1-yl]carbonyl}-2-(4-methylbenzyl)-5,6,7,8-tetrahydro[1,2,4]triazolo[4,3-a]pyridin-3(2H)-one Example 111

(5RS)-5-{[(3R)-3-Fluoropyrrolidin-1-yl]carbonyl}-2-(4-methylbenzyl)-5,6,7,8-tetrahydro[1,2,4]triazolo[4,3-a]pyridin-3(2H)-one (Enantiomer 1)

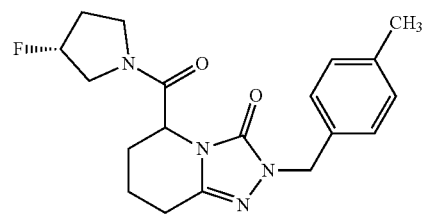 [SMILES: Cc1ccc(Cn2nc3n(c2=O)C(C(=O)N2CC[C@@H](F)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 µmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 µmol) and N,N-diisopropylethylamine (120 µl, 680 µmol) were added. After stirring for 15 min, (3R)-3-fluoropyrrolidine hydrochloride (39.3 mg, 313 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 59.0 mg (63% of theory) of the title compound were obtained.

LC-MS (Method 1): $R_t$=0.98 min; MS (ESIpos): m/z=359 [M+H]$^+$ $^1$H-NMR (400 MHz, DMSO-d6) δ [ppm]: 0.008 (1.25), 1.715 (0.81), 1.979 (1.46), 2.021 (0.58), 2.103 (0.66), 2.135 (0.56), 2.272 (16.00), 2.573 (1.00), 2.585 (1.71), 2.598 (0.96), 2.627 (0.61), 3.359 (0.62), 3.378 (0.56), 3.388 (0.41), 3.503 (0.60), 3.522 (1.39), 3.548 (1.10), 3.569 (0.77), 3.593

(1.76), 3.920 (0.42), 3.942 (1.16), 3.965 (0.46), 4.004 (0.46), 4.746 (7.68), 4.787 (0.75), 4.801 (1.00), 4.811 (0.63), 4.825 (0.70), 4.841 (0.86), 4.850 (0.67), 5.270 (0.57), 5.347 (0.55), 5.398 (0.56), 5.478 (0.52), 7.103 (0.74), 7.125 (14.98), 7.145 (0.79).

The (5S) configuration was assigned on the basis of the crystal structure elucidation for Example 26, 108, 113, 157, 237, 358 and 454.

(5S)-5-{[(3R)-3-Fluoropyrrolidin-1-yl]carbonyl}-2-(4-methylbenzyl)-5,6,7,8-tetrahydro[1,2,4]triazolo[4,3-a]pyridin-3(2H)-one Example 112

(5RS)-5-[(3-Fluoroazetidin-1-yl)carbonyl]-2-(4-methylbenzyl)-5,6,7,8-tetrahydro[1,2,4]triazolo[4,3-a]pyridin-3(2H)-one (Racemate)

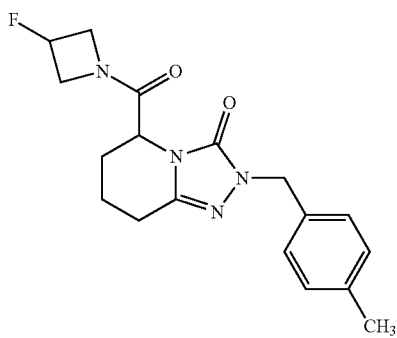

(5RS)-2-(4-Methylbenzyl)-3-oxo-2,3,5,6,7,8-hexahydro[1,2,4]triazolo[4,3-a]pyridine-5-carboxylic Acid (Racemate) (100 mg, 94% purity, 326 µmol) was initially charged together with 3-fluoroazetidine hydrochloride (43.6 mg, 391 µmol) in pyridine/DMF (5/1) (2.0 ml) at room temperature. Subsequently, O-(7-azabenzotriazol-1-yl)-N,N,N',N'-tetramethyluronium hexafluorophosphate (161 mg, 423 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 90.8 mg (80% of theory) of the title compound were obtained.

LC-MS (Method 4): $R_t$=0.69 min; MS (ESIpos): m/z=345 [M+H]$^+$ $^1$H-NMR (400 MHz, DMSO-d6) δ [ppm]: 1.706 (1.68), 1.917 (0.50), 1.930 (0.68), 1.940 (0.74), 2.004 (0.68), 2.017 (0.66), 2.039 (0.48), 2.270 (16.00), 2.522 (1.08), 2.561 (1.51), 2.575 (1.97), 2.588 (0.99), 2.616 (0.62), 3.924 (0.50), 3.953 (0.54), 3.984 (0.49), 4.220 (0.45), 4.235 (0.44), 4.251 (0.59), 4.263 (0.46), 4.277 (0.45), 4.286 (0.50), 4.319 (0.49), 4.515 (1.27), 4.528 (1.95), 4.541 (1.28), 4.745 (6.20), 5.753 (0.52), 7.104 (0.55), 7.125 (15.04), 7.145 (0.54).

Example 113

(5RS)-5-[(3-Fluoroazetidin-1-yl)carbonyl]-2-(4-methylbenzyl)-5,6,7,8-tetrahydro[1,2,4]triazolo[4,3-a]pyridin-3(2H)-one (Enantiomer 2)

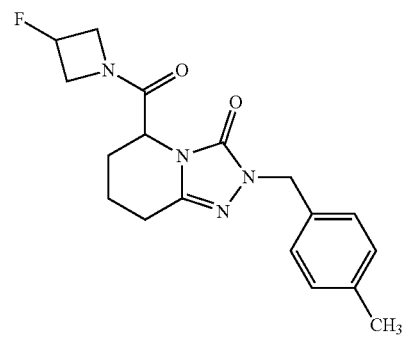

(5RS)-5-[(3-Fluoroazetidin-1-yl)carbonyl]-2-(4-methylbenzyl)-5,6,7,8-tetrahydro[1,2,4]triazolo[4,3-a]pyridin-3(2H)-one (racemate) was separated by chiral preparative HPLC [sample preparation: 69 mg dissolved in 4 ml of ethanol and 4 ml of acetonitrile; injection volume: 0.5 ml; column: Daicel Chiralcel® IA-H 5 µm, 250×20 mm; eluent: n-heptane/ethanol 50:50; flow rate: 15 ml/min; temperature 30° C.; UV detection: 210 nm]. After the separation, 32.3 mg of enantiomer 1, which eluted first, and 32.7 mg of enantiomer 2, which eluted later, were isolated.

Analytical chiral HPLC: $R_t$=2.53 min, d.e.=100% [column: Daicel Chiralcel® IA-3 50×4.6 mm; eluent: n-heptane/ethanol 50:50; flow rate: 1 ml/min; UV detection: 220 nm].

LC-MS (Method 3): $R_t$=1.25 min; MS (ESIpos): m/z=345 [M+H]$^+$ $^1$H-NMR (400 MHz, DMSO-d6) δ [ppm]: 1.702 (1.92), 1.940 (0.86), 2.005 (0.77), 2.017 (0.75), 2.270 (15.01), 2.561 (1.75), 2.575 (2.00), 2.588 (1.08), 2.616 (0.66), 3.921 (0.57), 3.952 (0.62), 3.985 (0.55), 4.219 (0.51), 4.233 (0.50), 4.250 (0.64), 4.286 (0.57), 4.319 (0.52), 4.516 (1.38), 4.528 (2.10), 4.541 (1.39), 4.709 (0.41), 4.745 (6.36), 7.125 (16.00).

The (5S) configuration was assigned on the basis of crystal structure elucidation for Example 113.

(5S)-5-[(3-Fluoroazetidin-1-yl)carbonyl]-2-(4-methylbenzyl)-5,6,7,8-tetrahydro[1,2,4]triazolo[4,3-a]pyridin-3(2H)-one

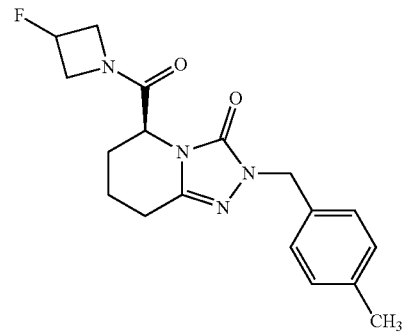

Example 114

(5RS)-5-[(3,3-Difluoroazetidin-1-yl)carbonyl]-2-(4-methylbenzyl)-5,6,7,8-tetrahydro[1,2,4]triazolo[4,3-a]pyridin-3(2H)-one (Racemate)

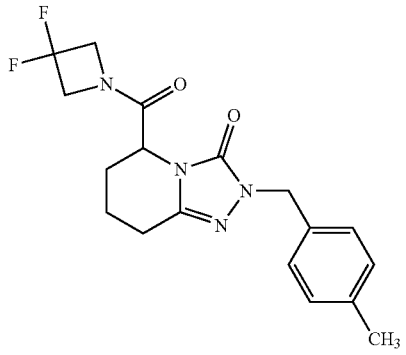

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 μmol) was initially charged together with 3,3-difluoroazetidine hydrochloride (71.0 mg, 548 μmol) in pyridine/DMF (5/1) (2.0 ml) at room temperature. Subsequently, O-(7-azabenzotriazol-1-yl)-N,N,N',N'-tetramethyluronium hexafluorophosphate (218 mg, 574 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 118 mg (62% of theory) of the title compound were obtained.

LC-MS (Method 3): $R_t$=1.42 min; MS (ESIpos): m/z=363 [M+H]$^+$ $^1$H-NMR (400 MHz, DMSO-d6) δ[ppm]: −0.008 (1.26), 0.008 (1.16), 1.697 (0.97), 1.712 (1.59), 1.726 (1.11), 1.959 (0.43), 1.970 (0.74), 1.983 (0.68), 2.029 (0.64), 2.045 (0.67), 2.063 (0.52), 2.271 (12.02), 2.574 (0.83), 2.583 (1.39), 2.598 (0.66), 2.625 (0.40), 4.355 (0.69), 4.384 (0.70), 4.416 (0.41), 4.568 (1.00), 4.583 (1.49), 4.595 (0.96), 4.712 (0.53), 4.752 (5.61), 4.843 (0.47), 7.105 (0.42), 7.127 (16.00), 7.149 (0.40).

Example 115

(5RS)-5-[(3,3-Difluoroazetidin-1-yl)carbonyl]-2-(4-methylbenzyl)-5,6,7,8-tetrahydro[1,2,4]triazolo[4,3-a]pyridin-3(2H)-one (Enantiomer 2)

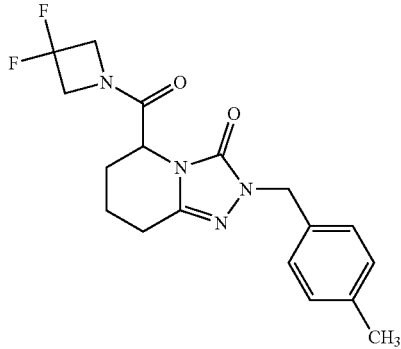 [SMILES: Cc1ccc(Cn2nc3n(c2=O)C(C(=O)N2CC(F)(F)C2)CCC3)cc1]

(5RS)-5-[(3,3-Difluoroazetidin-1-yl)carbonyl]-2-(4-methylbenzyl)-5,6,7,8-tetrahydro[1,2,4]triazolo[4,3-a]pyridin-3(2H)-one (racemate) was separated by chiral preparative HPLC [sample preparation: 105 mg dissolved in 5 ml of ethanol and 5 ml of acetonitrile; injection volume: 0.5 ml; column: Daicel Chiralpak® IB 5 μm, 250×20 mm; eluent: n-heptane/ethanol 50:50; flow rate: 15 ml/min; temperature 40° C.; UV detection: 210 nm]. After the separation, 53.3 mg of enantiomer 1, which eluted first, and 53.2 mg of enantiomer 2, which eluted later, were isolated.

Analytical chiral HPLC: $R_t$=3.04 min, d.e.=99% [column: Daicel Chiraltek® IB-3 50×4.6 mm; eluent: i-hexane/ethanol 50:50; flow rate: 1 ml/min; UV detection: 220 nm].

LC-MS (Method 3): $R_t$=1.39 min; MS (ESIpos): m/z=363 [M+H]$^+$ $^1$H-NMR (400 MHz, DMSO-d6) δ[ppm]: −0.008 (0.65), 0.008 (0.71), 1.697 (1.02), 1.711 (1.66), 1.725 (1.18), 1.742 (0.44), 1.958 (0.42), 1.970 (0.78), 1.982 (0.72), 2.028 (0.68), 2.045 (0.73), 2.062 (0.54), 2.271 (11.98), 2.597 (0.69), 4.355 (0.74), 4.384 (0.75), 4.414 (0.42), 4.567 (0.98), 4.582 (1.51), 4.595 (0.97), 4.712 (0.53), 4.752 (5.92), 4.841 (0.48), 4.872 (0.41), 7.127 (16.00), 7.149 (0.43).

Example 116

(5RS)-5-{[(3S)-3-Hydroxypyrrolidin-1-yl]carbonyl}-2-(4-methylbenzyl)-5,6,7,8-tetrahydro[1,2,4]triazolo[4,3-a]pyridin-3(2H)-one (Enantiomer 1)

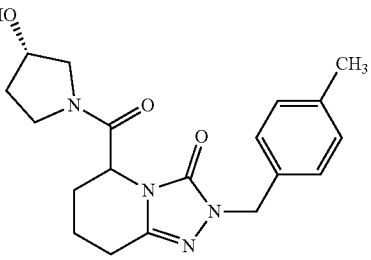

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 μmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 μmol) and N,N-diisopropylethylamine (120 μl, 680 μmol) were added. After stirring for 15 min, (3S)-pyrrolidin-3-ol hydrochloride (38.7 mg, 313 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 54.0 mg (58% of theory) of the title compound were obtained.

LC-MS (Method 1): $R_t$=0.86 min; MS (ESIpos): m/z=357 [M+H]$^+$ $^1$H-NMR (400 MHz, DMSO-d6) δ [ppm]: −0.008 (0.41), 1.705 (1.37), 1.716 (1.38), 1.730 (1.13), 1.752 (0.63), 1.763 (0.58), 1.773 (0.48), 1.782 (0.43), 1.847 (0.72), 1.858 (0.82), 1.869 (0.69), 1.879 (0.90), 1.890 (0.66), 1.903 (0.57), 1.948 (0.77), 1.982 (0.83), 2.000 (1.05), 2.011 (0.90), 2.025 (0.93), 2.035 (0.75), 2.043 (0.63), 2.051 (0.61), 2.061 (0.41), 2.271 (16.00), 2.467 (0.41), 2.524 (1.22), 2.571 (0.77), 2.583 (1.42), 2.594 (0.75), 2.625 (0.59), 3.294 (2.42), 3.304 (3.08), 3.315 (14.88), 3.337 (1.33), 3.356 (0.54), 3.368 (0.86), 3.431 (0.43), 3.439 (0.46), 3.452 (0.54), 3.460 (0.69), 3.560 (0.52), 3.641 (0.79), 3.653 (1.21), 3.669 (0.82), 3.680 (0.94), 4.259 (0.66), 4.267 (0.63), 4.363 (0.76), 4.664 (0.74), 4.672 (0.85), 4.679 (0.94), 4.688 (0.77), 4.695 (0.44), 4.707 (0.69), 4.716 (0.77), 4.722 (0.98), 4.734 (3.46), 4.743 (4.98), 4.782 (0.43), 4.956 (1.20), 4.964 (1.17), 5.074 (1.13), 5.082 (1.11), 7.096 (0.75), 7.102 (0.81), 7.118 (7.66), 7.123 (13.54), 7.144 (0.90).

The (5S) configuration was assigned on the basis of the crystal structure elucidation for Example 26, 108, 113, 157, 237, 358 and 454.

(5S)-5-{[(3S)-3-Hydroxypyrrolidin-1-yl]carbonyl}-2-(4-methylbenzyl)-5,6,7,8-tetrahydro[1,2,4]triazolo[4,3-a]pyridin-3(2H)-one Example 117

(5RS)-5-{[(cis)-6,6-Difluoro-3-azabicyclo[3.1.0]hex-3-yl]carbonyl}-2-(4-methylbenzyl)-5,6,7,8-tetrahydro[1,2,4]triazolo[4,3-a]pyridin-3(2H)-one (Racemate)

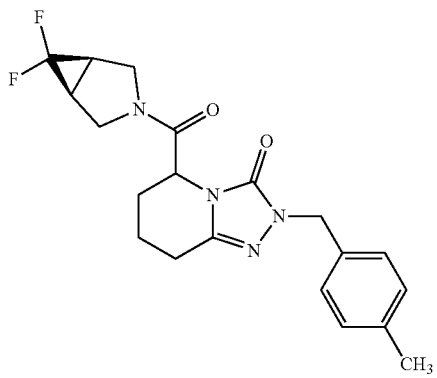 [SMILES: Cc1ccc(Cn2nc3n(c2=O)C(C(=O)N2C[C@@H]4[C@H](C2)C4(F)F)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with (cis)-6,6-difluoro-3-azabicyclo[3.1.0]hexane (65.3 mg, 548 µmol) in pyridine/DMF (5/1) (2.0 ml) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature for 5 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 86.7 mg (43% of theory) of the title compound were obtained.

LC-MS (Method 3): $R_t$=1.48 min; MS (ESIpos): m/z=389 [M+H]$^+$ $^1$H-NMR (400 MHz, DMSO-d6) δ [ppm]: −0.008 (2.15), 0.008 (2.10), 1.697 (0.91), 1.707 (0.84), 1.743 (0.61), 1.980 (0.75), 2.048 (0.40), 2.270 (16.00), 2.327 (0.68), 2.518 (3.43), 2.523 (2.64), 2.563 (1.71), 2.573 (1.66), 2.585 (1.19), 2.602 (0.89), 2.617 (0.68), 2.670 (1.12), 2.709 (0.96), 3.609 (0.51), 3.641 (0.49), 3.651 (0.61), 3.705 (1.31), 3.736 (0.63), 3.773 (0.93), 3.804 (0.68), 3.893 (0.70), 3.921 (1.33), 3.934 (0.58), 3.944 (0.65), 3.957 (0.54), 4.016 (0.82), 4.044 (0.58), 4.668 (0.70), 4.678 (0.89), 4.684 (1.14), 4.694 (0.72), 4.722 (2.45), 4.737 (4.13), 4.741 (4.41), 4.779 (0.58), 7.095 (1.24), 7.117 (10.56), 7.122 (9.65), 7.144 (1.17).

Example 118

(5RS)-2-(4-Methylbenzyl)-5-[(3-oxopyrrolidin-1-yl)carbonyl]-5,6,7,8-tetrahydro[1,2,4]triazolo[4,3-a]pyridin-3(2H)-one (Racemate)

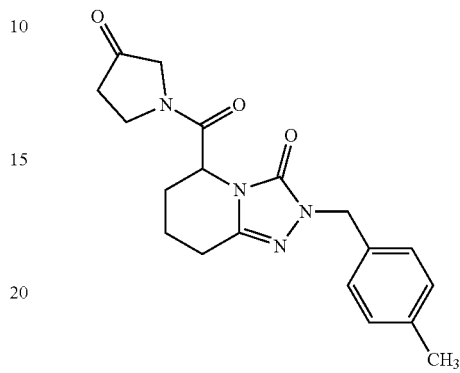

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 94% purity, 489 µmol) was initially charged together with pyrrolidin-3-one hydrochloride (71.3 mg, 586 µmol) in THF (3.0 ml) at room temperature. Subsequently, triethylamine (200 µl, 1.5 mmol) and O-(7-azabenzotriazol-1-yl)-N,N,N',N'-tetramethyluronium hexafluorophosphate (242 mg, 635 µmol) were added and the reaction mixture was stirred at room temperature overnight. The solvent was removed under reduced pressure and the residue was taken up with pyridine (2.5 ml) and DMF (500 µl). After addition of (242 mg, 635 µmol) and pyrrolidin-3-one hydrochloride (71.3 mg, 586 mol), the reaction mixture was stirred at room temperature for 2 h. The reaction mixture was admixed with water and ethyl acetate, and weakly acidified with 10% citric acid. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 80.7 mg (47% of theory) of the title compound were obtained.

LC-MS (Method 4): $R_t$=1.68 min; MS (ESIpos): m/z=355 [M+H]$^+$ $^1$H-NMR (400 MHz, DMSO-d6) δ [ppm]: 1.689 (0.93), 1.705 (1.02), 2.006 (1.17), 2.020 (1.11), 2.050 (0.88), 2.062 (0.79), 2.072 (0.66), 2.272 (16.00), 2.559 (1.50), 2.579 (2.25), 2.599 (1.83), 2.634 (0.49), 2.675 (0.58), 2.694 (0.65), 2.709 (0.82), 2.726 (0.46), 3.659 (0.71), 3.677 (0.70), 3.710 (1.38), 3.744 (1.37), 3.774 (0.70), 3.794 (0.74), 3.942 (0.40), 3.961 (0.45), 4.009 (0.77), 4.054 (1.67), 4.072 (0.42), 4.127 (1.60), 4.171 (0.71), 4.687 (0.61), 4.699 (1.26), 4.711 (0.76), 4.750 (5.78), 4.927 (0.75), 4.938 (0.44), 7.101 (0.97), 7.123 (13.94), 7.148 (0.87).

Example 119

(5RS)-2-(4-Methylbenzyl)-5-[(3-oxopyrrolidin-1-yl) carbonyl]-5,6,7,8-tetrahydro[1,2,4]triazolo[4,3-a] pyridin-3(2H)-one (Enantiomer 2)

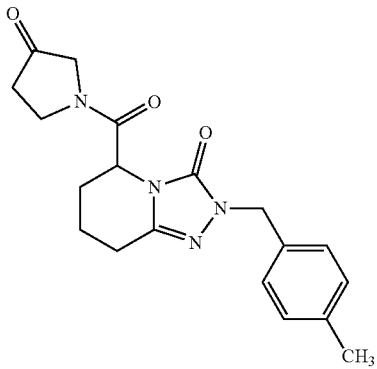 [SMILES: Cc1ccc(Cn2nc3n(c2=O)C(C(=O)N2CCC(=O)C2)CCC3)cc1]

(5RS)-2-(4-Methylbenzyl)-5-[(3-oxopyrrolidin-1-yl)carbonyl]-5,6,7,8-tetrahydro[1,2,4]triazolo[4,3-a]pyridin-3(2H)-one (racemate) was separated by chiral preparative HPLC [sample preparation: 71 mg dissolved in 6 ml of ethanol; injection volume: 0.5 ml; column: Daicel Chiralpak® IC 5 µm, 250×20 mm; eluent: ethanol 100%; flow rate: 15 ml/min; temperature 25° C.; UV detection: 210 nm]. After the separation, 21.8 mg of enantiomer 1, which eluted first, and 20.5 mg of enantiomer 2, which eluted later, were isolated.

Analytical chiral HPLC: $R_t$=2.23 min, d.e.=99% [column: Daicel Chiralpak® IC 50×4.6 mm; eluent: ethanol 100%; flow rate: 1 ml/min; UV detection: 220 nm].

LC-MS (Method 3): $R_t$=1.20 min; MS (ESIpos): m/z=355 [M+H]

$^1$H-NMR (400 MHz, DMSO-d6) δ [ppm]: 1.234 (0.45), 1.652 (0.44), 1.666 (0.63), 1.690 (1.15), 1.704 (1.26), 1.719 (1.03), 1.994 (0.81), 2.007 (1.49), 2.022 (1.37), 2.038 (0.99), 2.051 (1.09), 2.063 (0.98), 2.272 (16.00), 2.579 (2.68), 2.599 (2.22), 2.634 (0.56), 2.677 (0.55), 2.696 (0.79), 2.709 (0.88), 2.726 (0.50), 3.649 (0.48), 3.660 (0.84), 3.678 (0.82), 3.699 (0.51), 3.710 (1.60), 3.744 (1.61), 3.755 (0.54), 3.775 (0.85), 3.785 (0.45), 3.794 (0.86), 3.805 (0.51), 3.942 (0.45), 3.960 (0.52), 4.010 (0.86), 4.055 (1.96), 4.072 (0.56), 4.090 (0.43), 4.127 (1.81), 4.172 (0.85), 4.687 (0.72), 4.699 (1.44), 4.711 (0.88), 4.750 (6.83), 4.914 (0.54), 4.927 (0.90), 4.938 (0.57), 7.102 (0.98), 7.109 (0.75), 7.124 (14.74), 7.147 (0.92).

Example 120

(5RS)-5-[(3-Hydroxyazetidin-1-yl)carbonyl]-2-(4-methylbenzyl)-5,6,7,8-tetrahydro[1,2,4]triazolo[4,3-a]pyridin-3(2H)-one (Racemate)

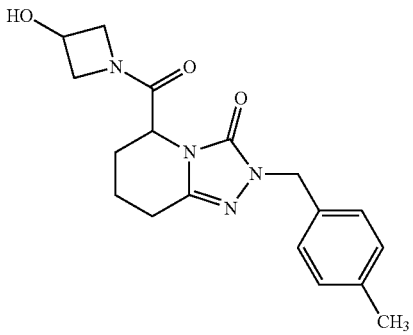 [SMILES: Cc1ccc(Cn2nc3n(c2=O)C(C(=O)N2CC(O)C2)CCC3)cc1]

(5RS)-2-(4-Methylbenzyl)-3-oxo-2,3,5,6,7,8-hexahydro [1,2,4]triazolo[4,3-a]pyridine-5-carboxylic Acid (Racemate) (150 mg, 522 µmol) was initially charged together with azetidin-3-ol hydrochloride (60.1 mg, 548 µmol) in DMF (1.7 ml) and pyridine (330 µl) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 143 mg (80% of theory) of the title compound were obtained.

LC-MS (Method 4): $R_t$=0.62 min; MS (ESIpos): m/z=343 [M+H]

$^1$H-NMR (400 MHz, DMSO-d6) δ [ppm]: −0.008 (0.91), 0.008 (0.71), 1.696 (1.30), 1.706 (1.24), 1.889 (0.47), 1.902 (0.46), 1.913 (0.67), 1.925 (1.00), 1.967 (0.52), 1.980 (0.70), 1.992 (0.73), 2.001 (0.62), 2.270 (16.00), 2.522 (1.16), 2.570 (1.78), 2.582 (0.90), 2.612 (0.63), 3.598 (0.60), 3.617 (0.66), 3.624 (0.70), 3.636 (0.52), 3.648 (0.55), 3.661 (0.60), 3.673 (0.54), 3.917 (0.67), 3.928 (0.77), 4.018 (0.89), 4.032 (1.30), 4.042 (1.18), 4.056 (1.06), 4.103 (0.45), 4.118 (0.53), 4.129 (0.47), 4.144 (0.44), 4.328 (0.49), 4.348 (0.81), 4.368 (0.51), 4.481 (1.32), 4.495 (2.40), 4.504 (2.75), 4.518 (1.96), 4.740 (5.20), 4.745 (4.96), 5.800 (0.90), 7.103 (0.67), 7.123 (13.53), 7.143 (0.69).

Example 121

(5RS)-5-[(3-Hydroxyazetidin-1-yl)carbonyl]-2-(4-methylbenzyl)-5,6,7,8-tetrahydro[1,2,4]triazolo[4,3-a]pyridin-3(2H)-one (Enantiomer 2)

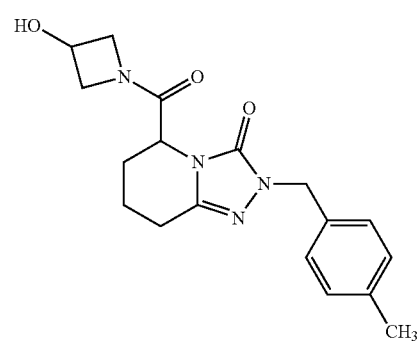 [SMILES: Cc1ccc(Cn2nc3n(c2=O)C(C(=O)N2CC(O)C2)CCC3)cc1]

(5RS)-5-[(3-Hydroxyazetidin-1-yl)carbonyl]-2-(4-methylbenzyl)-5,6,7,8-tetrahydro[1,2,4]triazolo[4,3-a]pyridin-3(2H)-one (racemate) was separated by chiral preparative SFC [sample preparation: 115 mg dissolved in 15 ml of methanol. Injection volume: 0.5 ml; column: Daicel Chiralpak® AD 5 µm, 250×20 mm; eluent: CO$_2$/methanol 80:20; flow rate: 80 ml/min; temperature 40° C.; UV detection: 210 nm]. After the separation, 57.4 mg of enantiomer 1, which eluted first, and 46.4 mg of enantiomer 2, which eluted later, were isolated.

Analytical chiral HPLC (SFC): $R_t$=2.0 min, d.e.=99% [column: Daicel Chiralcel® AD 50×4.6 mm; eluent: CO$_2$/methanol 80:20; flow rate: 3 ml/min; UV detection: 220 nm].

LC-MS (Method 3): $R_t$=1.06 min; MS (ESIpos): m/z=343 [M+H]$^+$ $^1$H-NMR (400 MHz, DMSO-d6) δ [ppm]: 1.696 (1.41), 1.706 (1.35), 1.889 (0.50), 1.901 (0.50), 1.913 (0.71), 1.925

(1.07), 1.980 (0.74), 1.992 (0.78), 2.002 (0.68), 2.270 (16.00), 2.522 (1.52), 2.570 (1.94), 2.583 (1.02), 2.599 (0.46), 2.612 (0.69), 3.598 (0.65), 3.616 (0.70), 3.624 (0.74), 3.634 (0.56), 3.647 (0.59), 3.660 (0.63), 3.673 (0.57), 3.917 (0.71), 3.928 (0.83), 4.018 (0.95), 4.032 (1.37), 4.042 (1.26), 4.056 (1.11), 4.103 (0.46), 4.118 (0.56), 4.129 (0.51), 4.144 (0.49), 4.328 (0.51), 4.348 (0.85), 4.368 (0.55), 4.496 (2.50), 4.504 (3.04), 4.518 (2.20), 4.740 (5.50), 4.745 (5.33), 5.801 (3.34), 7.103 (0.68), 7.123 (13.86).

Example 122

(5RS)-5-{[(3R)-3-Hydroxypyrrolidin-1-yl]carbonyl}-2-(4-methylbenzyl)-5,6,7,8-tetrahydro[1,2,4]triazolo[4,3-a]pyridin-3(2H)-one (Enantiomer 1)

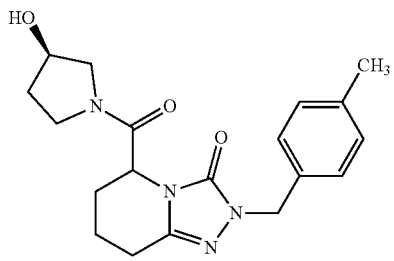 [SMILES: Cc1ccc(Cn2nc3n(c2=O)C(C(=O)N2CC[C@@H](O)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 µmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 µmol) and N,N-diisopropylethylamine (91 µl, 520 µmol) were added. After stirring for 15 min, (3R)-pyrrolidin-3-ol hydrochloride (38.7 mg, 313 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 58.1 mg (62% of theory) of the title compound were obtained.

LC-MS (Method 1): $R_t$=0.86 min; MS (ESIpos): m/z=357 [M+H]$^+$ $^1$H-NMR (400 MHz, DMSO-d6) δ[ppm]: −0.008 (0.58), 0.008 (0.62), 1.649 (0.52), 1.662 (0.50), 1.675 (0.55), 1.689 (0.69), 1.701 (0.85), 1.714 (1.02), 1.721 (1.03), 1.730 (0.92), 1.743 (0.71), 1.754 (0.61), 1.762 (0.56), 1.848 (0.52), 1.859 (0.74), 1.870 (0.56), 1.880 (0.78), 1.891 (0.73), 1.902 (0.55), 1.940 (0.57), 1.971 (1.66), 1.977 (1.57), 1.996 (0.91), 2.003 (0.74), 2.010 (0.72), 2.017 (0.69), 2.027 (0.62), 2.037 (0.43), 2.045 (0.47), 2.052 (0.40), 2.272 (16.00), 2.478 (0.56), 2.518 (1.68), 2.557 (0.61), 2.569 (0.78), 2.582 (1.40), 2.593 (0.73), 2.624 (0.54), 3.199 (0.79), 3.230 (1.12), 3.361 (1.13), 3.372 (1.78), 3.390 (1.59), 3.413 (0.60), 3.454 (0.53), 3.481 (0.81), 3.544 (0.72), 3.560 (1.02), 3.568 (1.26), 3.584 (0.76), 3.595 (0.51), 3.735 (0.41), 3.755 (0.62), 4.264 (0.76), 4.358 (0.65), 4.699 (0.78), 4.708 (0.78), 4.714 (0.96), 4.723 (0.76), 4.741 (4.48), 4.746 (5.17), 4.770 (0.77), 4.779 (0.99), 4.786 (1.01), 4.794 (0.71), 4.956 (0.76), 5.077 (0.89), 5.085 (0.87), 7.102 (0.70), 7.124 (15.25), 7.145 (0.84).

The (5S) configuration was assigned on the basis of the crystal structure elucidation for Example 26, 108, 113, 157, 237, 358 and 454.

(5S)-5-{[(3R)-3-Hydroxypyrrolidin-1-yl]carbonyl}-2-(4-methylbenzyl)-5,6,7,8-tetrahydro[1,2,4]triazolo[4,3-a]pyridin-3(2H)-one Example 123

(5RS)-5-{[3-(Difluoromethoxy)azetidin-1-yl]carbonyl}-2-(4-methylbenzyl)-5,6,7,8-tetrahydro[1,2,4]triazolo[4,3-a]pyridin-3(2H)-one (Racemate)

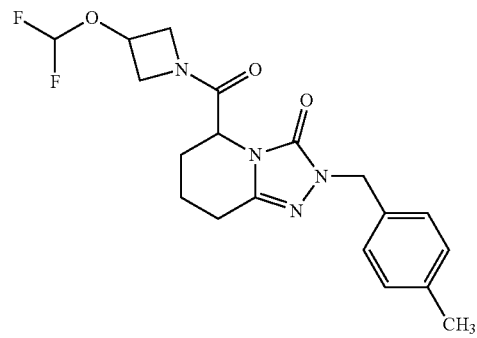 [SMILES: Cc1ccc(Cn2nc3n(c2=O)C(C(=O)N2CC(OC(F)F)C2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with 3-(difluoromethoxy)azetidine (67.5 mg, 548 µmol) in pyridine/DMF (5/1) (3.0 ml) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 27.3 mg (13% of theory) of the title compound were obtained.

LC-MS (Method 1): $R_t$=1.06 min; MS (ESIpos): m/z=393 [M+H]$^+$ $^1$H-NMR (400 MHz, DMSO-d6) δ [ppm]: 0.008 (0.44), 1.701 (1.79), 1.714 (1.40), 1.941 (0.73), 2.003 (0.73), 2.017 (0.62), 2.271 (16.00), 2.327 (0.48), 2.366 (0.48), 2.518 (2.87), 2.559 (1.81), 2.573 (1.95), 2.587 (0.96), 2.602 (0.45), 2.615 (0.71), 2.670 (0.52), 2.710 (0.51), 3.701 (1.17), 3.840 (0.45), 3.858 (0.92), 3.867 (0.93), 3.885 (0.56), 3.895 (0.52), 4.175 (0.85), 4.189 (0.83), 4.201 (0.93), 4.253 (0.42), 4.271 (0.51), 4.281 (0.47), 4.300 (0.73), 4.327 (0.54), 4.336 (0.52), 4.530 (1.75), 4.553 (0.42), 4.651 (0.41), 4.669 (0.55), 4.691 (0.42), 4.746 (6.96), 4.774 (0.68), 5.004 (0.62), 5.050 (0.56), 6.587 (0.54), 6.600 (0.58), 6.773 (1.10), 6.786 (1.21), 6.960 (0.54), 6.972 (0.58), 7.105 (0.65), 7.126 (14.23).

Example 124

(5RS)-2-(4-Methylbenzyl)-5-{[3-(trifluoromethyl)azetidin-1-yl]carbonyl}-5,6,7,8-tetrahydro[1,2,4]triazolo[4,3-a]pyridin-3(2H)-one (Racemate)

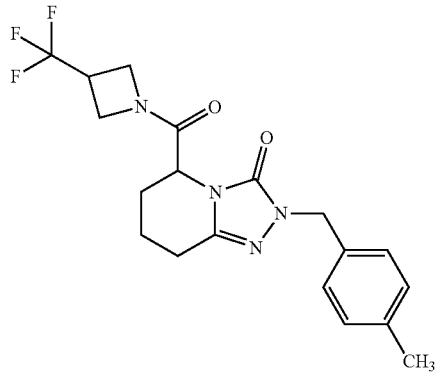 [SMILES: Cc1ccc(Cn2nc3n(c2=O)C(C(=O)N2CC(C(F)(F)F)C2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with 3-(trifluoromethyl)azetidine hydrochloride (92.8 mg, 574 µmol) in pyridine/DMF (5/1) (3.0 ml) at room temperature. Subsequently, O-(7-azabenzotriazol-1-yl)-N,N,N',N'-tetramethyluronium hexafluorophosphate (208 mg, 548 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 139 mg (68% of theory) of the title compound were obtained.

LC-MS (Method 1): $R_t$=1.12 min; MS (ESIpos): m/z=395 [M+H]$^+$ $^1$H-NMR (400 MHz, DMSO-d6) δ[ppm]: 1.694 (1.05), 1.707 (1.44), 1.720 (1.08), 2.003 (0.41), 2.014 (0.44), 2.027 (0.47), 2.271 (12.27), 2.501 (8.74), 2.567 (0.81), 2.575 (0.93), 3.845 (0.41), 3.871 (0.47), 3.934 (0.49), 3.948 (0.43), 4.081 (0.45), 4.105 (0.66), 4.160 (0.44), 4.184 (0.67), 4.207 (0.70), 4.219 (0.41), 4.230 (0.45), 4.386 (0.53), 4.401 (0.48), 4.430 (0.50), 4.453 (0.73), 4.522 (0.44), 4.536 (0.73), 4.548 (0.83), 4.560 (0.69), 4.572 (0.48), 4.584 (0.42), 4.607 (0.74), 4.750 (5.64), 7.104 (0.48), 7.125 (16.00), 7.147 (0.48).

Example 125

(5RS)-5-[(3-Methoxyazetidin-1-yl)carbonyl]-2-(4-methylbenzyl)-5,6,7,8-tetrahydro[1,2,4]triazolo[4,3-a]pyridin-3(2H)-one (Racemate)

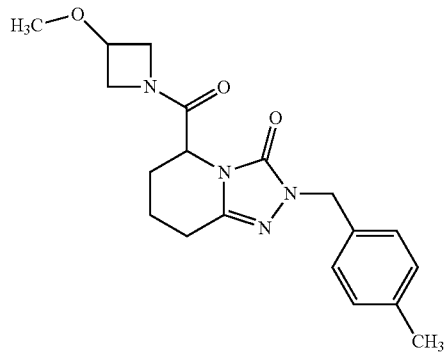

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with 3-methoxyazetidine (47.8 mg, 548 µmol) in pyridine/DMF (5/1) (3.0 ml) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 123 mg (66% of theory) of the title compound were obtained.

LC-MS (Method 3): $R_t$=1.25 min; MS (ESIpos): m/z=357 [M+H]$^+$ $^1$H-NMR (400 MHz, DMSO-d6) δ [ppm]: −0.008 (1.40), 0.008 (1.18), 1.674 (0.74), 1.686 (1.12), 1.697 (1.34), 1.928 (0.77), 1.989 (0.59), 1.999 (0.64), 2.024 (0.45), 2.270 (14.99), 2.522 (1.34), 2.571 (1.48), 2.584 (0.75), 2.613 (0.47), 3.223 (14.06), 3.663 (0.43), 3.671 (0.43), 3.688 (0.50), 3.700 (0.80), 3.712 (0.47), 3.729 (0.51), 3.737 (0.51), 4.007 (0.82), 4.027 (0.89), 4.051 (0.44), 4.087 (0.43), 4.104 (0.57), 4.115 (0.77), 4.128 (0.73), 4.148 (0.57), 4.216 (0.43), 4.226 (0.61), 4.242 (0.49), 4.252 (0.47), 4.259 (0.44), 4.269 (0.62), 4.341 (0.53), 4.364 (0.53), 4.509 (1.78), 4.525 (0.92), 4.742 (6.60), 7.102 (0.59), 7.124 (16.00), 7.145 (0.52).

Example 126

(5RS)-5-[(cis)-3-Azabicyclo[3.1.0]hex-3-ylcarbonyl]-2-(4-methylbenzyl)-5,6,7,8-tetrahydro[1,2,4]triazolo[4,3-a]pyridin-3(2H)-one (Racemate)

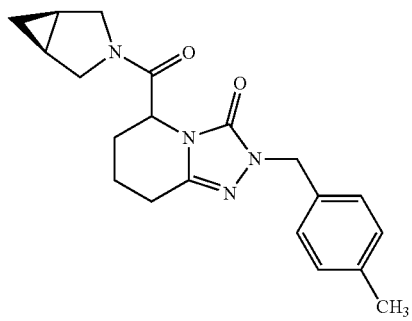 [SMILES: Cc1ccc(Cn2nc3n(c2=O)C(C(=O)N2C[C@H]4C[C@H]4C2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with (cis)-3-azabicyclo[3.1.0]hexane hydrochloride (65.6 mg, 548 µmol) in pyridine/DMF (5/1) (3.0 ml) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 133 mg (72% of theory) of the title compound were obtained.

LC-MS (Method 4): $R_t$=0.78 min; MS (ESIpos): m/z=353 [M+H]$^+$ $^1$H-NMR (400 MHz, DMSO-d6) δ[ppm]: 0.049 (0.40), 0.060 (1.02), 0.071 (1.06), 0.081 (0.51), 0.096 (0.86), 0.107 (0.86), 0.689 (0.74), 0.701 (0.76), 0.707 (0.73), 0.713 (0.71), 0.725 (0.66), 1.515 (0.51), 1.524 (0.73), 1.534 (0.65), 1.543

(0.64), 1.550 (0.53), 1.559 (0.62), 1.568 (0.49), 1.612 (0.56), 1.621 (0.73), 1.630 (0.94), 1.639 (0.89), 1.649 (0.99), 1.659 (1.14), 1.674 (1.73), 1.684 (1.79), 1.695 (1.24), 1.922 (0.50), 1.935 (0.45), 1.976 (0.46), 1.994 (0.46), 2.002 (0.51), 2.019 (0.42), 2.270 (16.00), 2.518 (1.36), 2.559 (1.36), 2.571 (0.70), 2.601 (0.44), 3.203 (0.62), 3.214 (0.65), 3.232 (0.74), 3.243 (0.72), 3.335 (1.10), 3.346 (0.84), 3.497 (1.56), 3.526 (1.22), 3.533 (0.66), 3.544 (0.63), 3.560 (0.73), 3.570 (0.68), 3.659 (2.48), 3.667 (1.15), 3.692 (1.81), 3.722 (1.49), 3.840 (1.36), 3.867 (1.16), 4.618 (0.59), 4.627 (0.72), 4.633 (0.74), 4.643 (0.58), 4.679 (0.57), 4.718 (2.71), 4.729 (2.94), 4.738 (4.39), 4.778 (0.70), 7.094 (1.14), 7.116 (9.92), 7.121 (9.92), 7.142 (1.16).

Example 127

2-(4-Methylbenzyl)-(5RS)-{[(2S)-2-methylpyrrolidin-1-yl]carbonyl}-5,6,7,8-tetrahydro[1,2,4]triazolo[4,3-a]pyridin-3(2H)-one (Enantiomer 1)

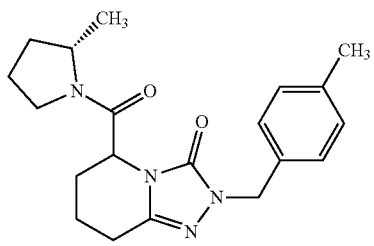 [SMILES: Cc1ccc(Cn2nc3n(c2=O)C(C(=O)N2CCC[C@@H]2C)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 µmol) was initially charged in dichloromethane (1.5 ml) and DMF (3.0 ml) at room temperature. Subsequently, 1-[bis(dimethylamino)methylene]-1H-benzotriazol-1-ium 3-oxide hexafluorophosphate (129 mg, 339 µmol) and N,N-diisopropylethylamine (64 µl, 370 µmol) were added. After stirring for 15 min, (2S)-2-methylpyrrolidine (26.7 mg, 313 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 56.3 mg (61% of theory) of the title compound were obtained.

LC-MS (Method 3): $R_t$=1.45 min; MS (ESIpos): m/z=355 [M+H]$^+$ $^1$H-NMR (400 MHz, DMSO-d6) δ [ppm]: 1.083 (4.23), 1.098 (4.29), 1.166 (1.19), 1.182 (1.20), 1.515 (0.43), 1.522 (0.45), 1.544 (0.43), 1.676 (0.49), 1.688 (0.88), 1.702 (1.05), 1.718 (0.90), 1.730 (0.42), 1.862 (0.51), 1.870 (0.56), 1.887 (0.78), 1.905 (1.14), 1.924 (0.88), 1.939 (1.13), 1.950 (1.08), 1.969 (0.74), 1.995 (0.83), 2.015 (0.71), 2.031 (0.56), 2.270 (12.19), 2.524 (0.87), 2.569 (1.14), 2.581 (0.54), 3.432 (0.49), 3.456 (0.49), 3.669 (0.44), 3.676 (0.51), 3.992 (0.54), 4.669 (0.86), 4.679 (1.59), 4.684 (0.95), 4.694 (0.68), 4.706 (0.71), 4.717 (1.84), 4.746 (0.81), 4.777 (1.77), 4.816 (0.82), 7.122 (16.00).

The (5S) configuration was assigned on the basis of the crystal structure elucidation for Example 26, 108, 113, 157, 237, 358 and 454.

2-(4-Methylbenzyl)-(5S)-{[(2S)-2-methylpyrrolidin-1-yl]carbonyl}-5,6,7,8-tetrahydro[1,2,4]triazolo[4,3-a]pyridin-3(2H)-one

Example 128

(5RS)-{[(3RS)-1,1-Difluoro-5-azaspiro[2.4]hept-5-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

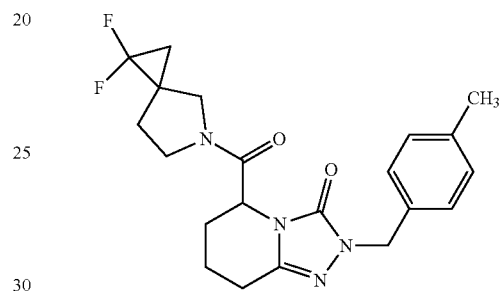

(5RS)-2-(4-Methylbenzyl)-3-oxo-2,3,5,6,7,8-hexahydro[1,2,4]triazolo[4,3-a]pyridine-5-carboxylic acid (enantiomer 1) (200 mg, 696 µmol) was initially charged in dichloromethane (4.0 ml) and DMF (8.0 ml) at room temperature. Subsequently, 1-[bis(dimethylamino)methylene]-1H-benzotriazol-1-ium 3-oxide hexafluorophosphate (343 mg, 905 µmol) and N,N-diisopropylethylamine (320 µl, 1.8 mmol) were added. After stirring for 15 min, (3RS)-1,1-difluoro-5-azaspiro[2.4]heptane hydrochloride (142 mg, 835 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 218 mg (78% of theory) of the title compound were obtained.

LC-MS (Method 3): $R_t$=1.56 min; MS (ESIpos): m/z=403 [M+H]$^+$ $^1$H-NMR (400 MHz, DMSO-d6) δ [ppm]: −0.008 (1.41), 0.008 (1.27), 1.069 (0.81), 1.159 (0.77), 1.601 (0.42), 1.614 (0.52), 1.648 (1.24), 1.668 (1.35), 1.694 (1.64), 1.710 (1.47), 2.008 (1.15), 2.099 (0.56), 2.115 (0.57), 2.161 (0.53), 2.271 (15.89), 2.572 (0.75), 2.584 (1.31), 2.625 (0.49), 3.455 (1.29), 3.497 (0.60), 3.552 (0.59), 3.582 (0.47), 3.640 (0.47), 3.666 (0.52), 3.718 (0.52), 3.751 (0.73), 3.764 (0.69), 3.805 (0.46), 4.710 (0.65), 4.719 (0.61), 4.742 (3.92), 4.794 (0.69), 7.101 (0.69), 7.125 (16.00), 7.146 (0.68). (Mixture of diastereomers)

The (5S) configuration was assigned on the basis of the crystal structure elucidation for Example 26, 108, 113, 157, 237, 358 and 454.

(5S)-{[(3RS)-1,1-Difluoro-5-azaspiro[2.4]hept-5-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

Example 129

(5RS)-{[(3RS)-1,1-Difluoro-5-azaspiro[2.4]hept-5-yl]carbonyl}-2-(4-methylbenzyl)-5,6,7,8-tetrahydro[1,2,4]triazolo[4,3-a]pyridin-3(2H)-one (Isomer 2)

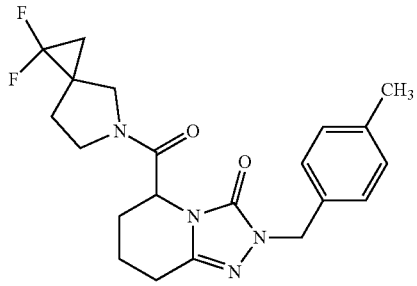 [SMILES: Cc1ccc(Cn2nc3n(c2=O)C(C(=O)N2CCC4(C2)CC4(F)F)CCC3)cc1]

(5RS)-{[(3RS)-1,1-Difluoro-5-azaspiro[2.4]hept-5-yl]carbonyl}-2-(4-methylbenzyl)-5,6,7,8-tetrahydro[1,2,4]triazolo[4,3-a]pyridin-3(2H)-one (diastereomer mixture; 2 isomers) was separated by chiral preparative HPLC [sample preparation: 210 mg dissolved in 4 ml of acetonitrile; injection volume: 0.2 ml; column: Daicel Chiralpak® ID 5 μm, 250×20 mm; eluent: methyl tert-butyl ether/acetonitrile 50:50; flow rate: 15 ml/min; temperature 40° C.; UV detection: 210 nm]. After the separation, 99.0 mg of enantiomer 1, which eluted first, and 101.0 mg of enantiomer 2, which eluted later, were isolated.

Analytical chiral HPLC: $R_t$=10.49 min, d.e.=99% [column: Daicel Chiralcel® ID 250×4.6 mm; eluent: methyl tert-butyl ether/acetonitrile 50:50; flow rate: 1 ml/min; UV detection: 220 nm].

LC-MS (Method 4): $R_t$=0.84 min; MS (ESIpos): m/z=403 [M+H]$^+$ $^1$H-NMR (400 MHz, DMSO-d6) δ [ppm]: −0.008 (1.53), 0.008 (1.55), 1.604 (0.44), 1.617 (0.64), 1.637 (0.89), 1.654 (1.26), 1.669 (1.51), 1.689 (1.60), 1.702 (1.64), 1.710 (1.61), 1.721 (1.32), 2.008 (1.66), 2.025 (1.55), 2.051 (0.73), 2.070 (0.51), 2.084 (0.52), 2.102 (0.51), 2.115 (0.48), 2.165 (0.55), 2.181 (0.52), 2.272 (15.03), 2.561 (0.81), 2.572 (0.83), 2.584 (1.54), 2.596 (0.83), 2.626 (0.57), 3.455 (2.27), 3.478 (0.59), 3.486 (0.60), 3.497 (1.15), 3.515 (0.61), 3.640 (0.76), 3.647 (0.80), 3.665 (0.96), 3.804 (0.82), 3.831 (0.61), 3.881 (0.48), 3.895 (0.42), 4.710 (0.54), 4.725 (0.81), 4.743 (5.21), 4.750 (2.79), 4.783 (0.76), 4.798 (0.93), 4.808 (0.62), 7.101 (0.75), 7.123 (16.00), 7.147 (0.72).

Example 130

(5RS)-{[(3S)-3-Methoxypyrrolidin-1-yl]carbonyl}-2-(4-methylbenzyl)-5,6,7,8-tetrahydro[1,2,4]triazolo[4,3-a]pyridin-3(2H)-one (Enantiomer 1)

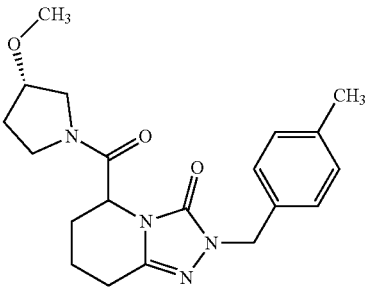 [SMILES: CO[C@H]1CCN(C(=O)C2CCCc3nn(Cc4ccc(C)cc4)c(=O)n32)C1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 μmol) was initially charged in DMF (3.1 ml) and dichloromethane (1.5 ml) at room temperature. Subsequently, 1-[bis(dimethylamino)methylene]-1H-benzotriazol-1-ium 3-oxide hexafluorophosphate (129 mg, 339 μmol) and N,N-diisopropylethylamine (120 μl, 680 μmol) were added. After stirring for 15 min, (3S)-3-methoxypyrrolidine hydrochloride (43.1 mg, 313 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 40.8 mg (42% of theory) of the title compound were obtained.

LC-MS (Method 1): $R_t$=0.96 min; MS (ESIpos): m/z=371 [M+H]$^+$ $^1$H-NMR (400 MHz, DMSO-d6) δ [ppm]: −0.008 (2.98), 0.008 (2.66), 1.644 (0.58), 1.656 (0.64), 1.668 (0.67), 1.702 (0.97), 1.712 (0.97), 1.723 (0.75), 1.860 (0.43), 1.884 (0.68), 1.894 (0.70), 1.906 (0.55), 1.918 (0.89), 1.931 (0.91), 1.940 (0.92), 1.981 (1.60), 1.993 (1.41), 2.003 (1.20), 2.017 (0.89), 2.038 (0.66), 2.065 (0.57), 2.272 (16.00), 2.567 (0.89), 2.578 (1.51), 2.590 (0.88), 2.621 (0.54), 3.235 (12.99), 3.269 (13.24), 3.362 (1.64), 3.384 (0.55), 3.392 (0.75), 3.405 (1.07), 3.416 (1.20), 3.438 (0.53), 3.449 (0.86), 3.455 (0.70), 3.473 (0.65), 3.556 (0.51), 3.567 (0.57), 3.585 (0.78), 3.596 (0.75), 3.709 (0.94), 3.737 (0.69), 3.768 (0.42), 3.787 (0.61), 3.956 (0.89), 4.044 (0.83), 4.742 (6.80), 4.765 (0.83), 4.779 (1.64), 4.788 (1.54), 4.797 (0.73), 7.100 (0.86), 7.123 (14.91), 7.145 (0.90).

The (5S) configuration was assigned on the basis of the crystal structure elucidation for Example 26, 108, 113, 157, 237, 358 and 454.

433

(5S)-{[(3S)-3-Methoxypyrrolidin-1-yl]carbonyl}-2-(4-methylbenzyl)-5,6,7,8-tetrahydro[1,2,4]triazolo[4,3-a]pyridin-3(2H)-one Example 131

(5RS)-{[3-Hydroxy-3-(trifluoromethyl)azetidin-1-yl]carbonyl}-2-(4-methylbenzyl)-5,6,7,8-tetrahydro[1,2,4]triazolo[4,3-a]pyridin-3(2H)-one (Racemate)

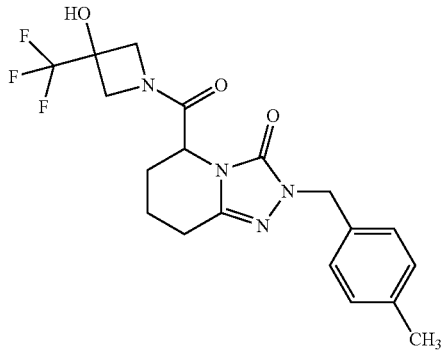 [SMILES: Cc1ccc(Cn2nc3n(c2=O)C(C(=O)N2CC(O)(C(F)(F)F)C2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with 3-(trifluoromethyl)azetidin-3-ol hydrochloride (97.3 mg, 548 µmol) in pyridine/DMF (5/1) (3.0 ml) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 147 mg (68% of theory) of the title compound were obtained.

LC-MS (Method 4): $R_t$=0.76 min; MS (ESIpos): m/z=411 [M+H]$^+$ $^1$H-NMR (400 MHz, DMSO-d6) δ [ppm]: −0.008 (0.49), 0.008 (0.45), 1.704 (1.35), 1.715 (1.20), 2.019 (0.55), 2.027 (0.58), 2.036 (0.57), 2.271 (16.00), 2.518 (0.75), 2.567 (1.09), 2.575 (1.21), 2.587 (1.01), 2.598 (0.45), 3.857 (0.57), 3.885 (0.67), 3.933 (0.61), 3.961 (0.86), 4.081 (1.14), 4.108 (0.81), 4.164 (0.94), 4.192 (1.19), 4.222 (0.65), 4.351 (0.56), 4.376 (0.89), 4.454 (1.17), 4.479 (0.74), 4.558 (0.60), 4.573 (0.90), 4.585 (0.67), 4.593 (0.61), 4.609 (0.77), 4.621 (1.19), 4.647 (0.77), 4.741 (2.29), 4.747 (2.82), 4.754 (4.40), 7.103 (0.62), 7.125 (13.60), 7.145 (0.56), 7.545 (1.60).

434

Example 132

(5RS)-2-(4-Methylbenzyl)-{[(2R)-2-methylpyrrolidin-1-yl]carbonyl}-5,6,7,8-tetrahydro[1,2,4]triazolo[4,3-a]pyridin-3(2H)-one (Enantiomer 1)

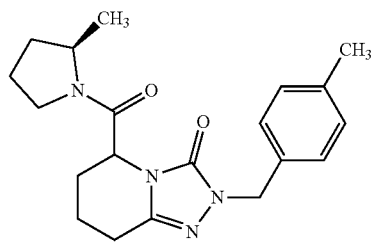 [SMILES: Cc1ccc(Cn2nc3n(c2=O)C(C(=O)N2CCC[C@H]2C)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 µmol) was initially charged in dichloromethane (1.3 ml) and DMF (2.9 ml) at room temperature. Subsequently, 1-[bis(dimethylamino)methylene]-1H-benzotriazol-1-ium 3-oxide hexafluorophosphate (129 mg, 339 µmol) and N,N-diisopropylethylamine (64 µl, 370 µmol) were added. After stirring for 15 min, (2R)-2-methylpyrrolidine (26.7 mg, 313 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.4 mg (50% of theory) of the title compound were obtained.

LC-MS (Method 3): $R_t$=1.47 min; MS (ESIpos): m/z=355 [M+H]$^+$ $^1$H-NMR (400 MHz, DMSO-d6) δ[ppm]: −0.008 (1.50), 0.008 (1.44), 1.057 (6.00), 1.073 (6.07), 1.265 (2.61), 1.281 (2.63), 1.497 (0.42), 1.508 (0.57), 1.517 (0.66), 1.526 (0.56), 1.650 (0.63), 1.659 (0.58), 1.679 (0.60), 1.694 (0.82), 1.714 (1.10), 1.724 (0.98), 1.859 (0.74), 1.870 (0.72), 1.876 (0.73), 1.886 (0.73), 1.897 (1.06), 1.915 (1.11), 1.924 (0.87), 1.933 (1.01), 1.945 (1.27), 1.963 (1.63), 1.977 (1.11), 1.997 (0.92), 2.005 (0.85), 2.015 (0.70), 2.025 (0.74), 2.033 (0.69), 2.042 (0.64), 2.062 (0.48), 2.272 (16.00), 2.583 (1.13), 2.595 (0.65), 2.625 (0.44), 3.247 (0.43), 3.379 (0.41), 3.516 (0.46), 3.523 (0.68), 3.541 (0.68), 3.552 (0.42), 3.566 (0.43), 3.584 (0.85), 3.602 (0.48), 3.609 (0.46), 4.022 (0.62), 4.030 (0.60), 4.038 (0.47), 4.107 (0.46), 4.691 (0.89), 4.700 (1.13), 4.707 (1.26), 4.715 (1.20), 4.739 (6.57), 7.099 (1.02), 7.120 (11.38), 7.124 (11.23), 7.145 (0.99).

The (5S) configuration was assigned on the basis of the crystal structure elucidation for Example 26, 108, 113, 157, 237, 358 and 454.

(5S)-2-(4-Methylbenzyl)-{[(2R)-2-methylpyrrolidin-1-yl]carbonyl}-5,6,7,8-tetrahydro[1,2,4]triazolo[4,3-a]pyridin-3(2H)-one Example 133

(5RS)-2-(4-Methylbenzyl)-5-[(3-oxoazetidin-1-yl)carbonyl]-5,6,7,8-tetrahydro[1,2,4]triazolo[4,3-a]pyridin-3(2H)-one (Racemate)

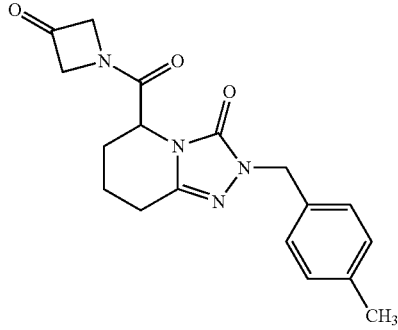 [SMILES: Cc1ccc(Cn2nc3n(c2=O)C(C(=O)N2CC(=O)C2)CCC3)cc1]

(5RS)-2-(4-Methylbenzyl)-3-oxo-2,3,5,6,7,8-hexahydro[1,2,4]triazolo[4,3-a]pyridine-5-carboxylic Acid (Racemate) (150 mg, 522 µmol) was initially charged together with azetidin-3-one (39.0 mg, 548 µmol) in pyridine/DMF (5/1) (3.0 ml) at room temperature. Subsequently, O-(7-azabenzotriazol-1-yl)-N,N,N',N'-tetramethyluronium hexafluorophosphate (218 mg, 574 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 72.2 mg (41% of theory) of the title compound were obtained.

LC-MS (Method 1): $R_t$=0.89 min; MS (ESIpos): m/z=341 [M+H]$^+$ $^1$H-NMR (400 MHz, DMSO-d6) δ [ppm]: 1.710 (0.41), 1.721 (0.65), 1.731 (0.63), 1.743 (0.59), 2.059 (0.86), 2.072 (1.04), 2.085 (0.67), 2.271 (10.99), 2.517 (0.67), 2.559 (0.57), 2.590 (0.46), 2.603 (0.95), 2.616 (0.48), 4.662 (0.54), 4.675 (1.04), 4.688 (0.55), 4.743 (0.87), 4.758 (4.04), 4.766 (1.64), 7.128 (16.00).

Example 134

(5RS,7RS)-5-[(3-Hydroxyazetidin-1-yl)carbonyl]-7-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

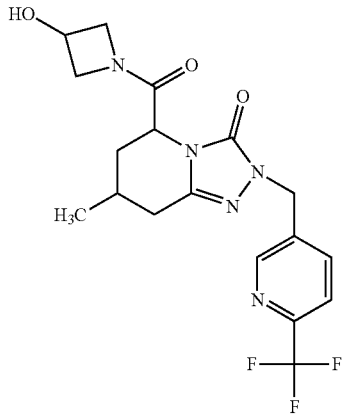 [SMILES: CC1Cc2nn(Cc3ccc(C(F)(F)F)nc3)c(=O)n2C(C(=O)N2CC(O)C2)C1]

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic (diastereomer mixture; 4 isomers) (100 mg, 281 µmol) was initially charged in dichloromethane (1.0 ml) and DMF (2.0 ml) at room temperature. Subsequently, 1-[bis(dimethylamino)methylene]-1H-benzotriazol-1-ium 3-oxide hexafluorophosphate (138 mg, 365 µmol) and N,N-diisopropylethylamine (130 µl, 730 mol) were added. After stirring for 15 min, azetidin-3-ol hydrochloride (36.9 mg, 337 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 85.4 mg (74% of theory) of the title compound were obtained.

LC-MS (Method 1): $R_t$=0.87 min; MS (ESIpos): m/z=412 [M+H]$^+$ $^1$H-NMR (400 MHz, DMSO-d6) δ [ppm]: −0.008 (2.42), 0.008 (2.61), 1.010 (8.92), 1.020 (11.30), 1.026 (11.21), 1.036 (9.74), 1.308 (0.59), 1.339 (1.81), 1.370 (2.83), 1.400 (2.12), 1.433 (0.76), 1.876 (1.61), 2.142 (3.55), 2.174 (4.35), 2.206 (1.62), 2.213 (1.69), 2.327 (0.64), 2.366 (0.41), 2.622 (2.64), 2.669 (2.68), 2.690 (0.68), 2.710 (0.45), 2.731 (6.01), 2.890 (7.03), 3.578 (1.58), 3.585 (1.51), 3.604 (1.66), 3.643 (1.32), 3.655 (1.35), 3.668 (1.47), 3.680 (1.39), 3.903 (1.92), 3.914 (1.76), 4.002 (1.25), 4.021 (1.65), 4.045 (2.41), 4.058 (1.45), 4.067 (1.50), 4.079 (1.42), 4.112 (1.16), 4.126 (1.43), 4.137 (1.26), 4.153 (1.15), 4.325 (1.22), 4.344 (2.16), 4.355 (1.88), 4.370 (3.12), 4.387 (2.44), 4.398 (2.75), 4.414 (1.49), 4.507 (4.97), 4.521 (3.48), 4.986 (16.00), 5.754 (1.00), 5.779 (4.75), 5.793 (4.89), 7.899 (1.61), 7.919 (11.72), 7.951 (1.52), 8.669 (7.52).

Example 135

(5RS,7RS)-5-[(3-Hydroxyazetidin-1-yl)carbonyl]-7-methyl-2-{[6-(trifluoromethyl)pyridin-3-yl]methyl}-5,6,7,8-tetrahydro[1,2,4]triazolo[4,3-a]pyridin-3(2H)-one (Isomer 1)

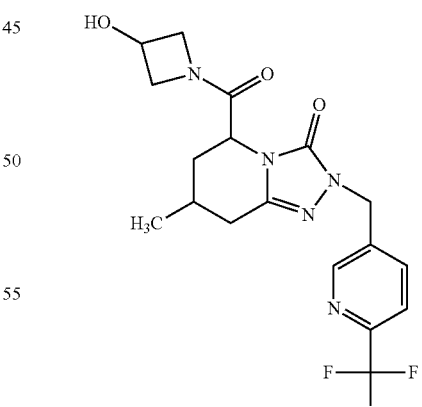

(5RS,7RS)-5-[(3-Hydroxyazetidin-1-yl)carbonyl]-7-methyl-2-{[6-(trifluoromethyl)pyridin-3-yl]methyl}-5,6,7,8-tetrahydro[1,2,4]triazolo[4,3-a]pyridin-3(2H)-one (diastereomer mixture; 4 isomers) was separated by chiral preparative HPLC [sample preparation: 80 mg dissolved in 4 ml of ethanol; injection volume: 0.3 ml; column: Daicel Chiralpak® IC 5 µm, 250×20 mm; eluent: n-heptane/ethanol 50:50; flow rate: 15 ml/min; temperature 40° C.; UV detection: 220 nm]. After the separation, 32.0 mg of isomer 1, which eluted first, and 35.0 mg of isomer 2, which eluted later, were isolated.

Isomer 1:

Analytical chiral HPLC: $R_t$=5.13 min, d.e.=95% [column: Daicel Chiralcel® IAC 250×4.6 mm; eluent: i-hexane/ethanol 50:50; flow rate: 1 ml/min; UV detection: 220 nm].

LC-MS (Method 4): $R_t$=0.63 min; MS (ESIpos): m/z=412 $[M+H]^+$ $^1$H-NMR (600 MHz, DMSO-d6) δ [ppm]: 0.005 (0.61), 1.011 (8.14), 1.022 (16.00), 1.033 (8.42), 1.320 (0.60), 1.340 (1.30), 1.354 (0.89), 1.361 (1.38), 1.374 (1.45), 1.381 (0.86), 1.394 (1.38), 1.414 (0.70), 1.872 (1.32), 1.876 (1.34), 2.136 (1.59), 2.142 (1.78), 2.148 (2.62), 2.156 (2.85), 2.168 (2.59), 2.176 (2.80), 2.183 (1.75), 2.195 (1.42), 2.203 (1.39), 2.517 (0.80), 2.521 (0.80), 2.524 (0.64), 2.615 (0.44), 2.630 (2.25), 2.633 (2.12), 2.654 (2.01), 2.657 (2.01), 2.660 (1.79), 3.584 (1.49), 3.589 (1.37), 3.601 (1.52), 3.607 (1.32), 3.649 (1.18), 3.657 (1.22), 3.666 (1.31), 3.674 (1.27), 3.907 (1.65), 3.915 (1.54), 4.011 (1.14), 4.023 (1.42), 4.027 (1.24), 4.040 (1.18), 4.051 (1.14), 4.059 (1.27), 4.066 (1.30), 4.074 (1.23), 4.119 (1.10), 4.129 (1.22), 4.135 (1.21), 4.147 (1.04), 4.335 (1.09), 4.347 (1.87), 4.363 (2.11), 4.373 (1.76), 4.381 (3.04), 4.391 (3.07), 4.399 (1.69), 4.410 (1.48), 4.496 (2.30), 4.507 (4.00), 4.518 (2.41), 4.531 (0.73), 4.986 (10.70), 4.991 (10.02), 5.802 (6.92), 5.812 (6.99), 7.905 (1.16), 7.911 (1.30), 7.919 (6.21), 7.924 (8.62), 8.671 (4.90).

Example 136

(5RS,7RS)-5-{[(3S)-3-Fluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

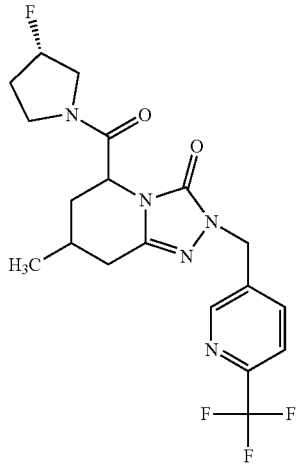 [SMILES: CC1Cc2nn(Cc3ccc(C(F)(F)F)nc3)c(=O)n2C(C(=O)N2CC[C@H](F)C2)C1]

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic (diastereomer mixture; 4 isomers) (100 mg, 281 µmol) was initially charged in dichloromethane (1.0 ml) and DMF (2.0 ml) at room temperature. Subsequently, 1-[bis(dimethylamino)methylene]-1H-benzotriazol-1-ium 3-oxide hexafluorophosphate (138 mg, 365 µmol) and N,N-diisopropylethylamine (130 µl, 730 µmol) were added. After stirring for 15 min, (3S)-3-fluoropyrrolidine hydrochloride (42.3 mg, 337 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 93.0 mg (78% of theory) of the title compound were obtained.

LC-MS (Method 3): $R_t$=1.31 min; MS (ESIpos): m/z=428 $[M+H]^+$ $^1$H-NMR (400 MHz, DMSO-d6) δ [ppm]: −0.149 (0.54), −0.008 (4.36), 0.008 (4.13), 0.146 (0.54), 1.019 (5.78), 1.027 (14.45), 1.035 (7.38), 1.043 (14.30), 1.303 (0.65), 1.333 (1.76), 1.363 (2.31), 1.392 (1.65), 1.411 (0.81), 1.894 (1.42), 2.092 (1.16), 2.115 (1.14), 2.150 (3.60), 2.181 (2.75), 2.191 (3.83), 2.222 (4.36), 2.250 (2.41), 2.328 (0.92), 2.366 (0.52), 2.645 (2.55), 2.680 (2.36), 2.710 (0.54), 3.340 (0.76), 3.353 (0.71), 3.370 (0.92), 3.381 (0.80), 3.408 (0.50), 3.496 (0.64), 3.505 (0.60), 3.550 (1.42), 3.584 (1.94), 3.611 (1.31), 3.648 (1.20), 3.685 (1.45), 3.743 (0.52), 3.759 (0.86), 3.784 (1.49), 3.823 (1.07), 3.888 (1.62), 3.927 (1.07), 3.951 (1.11), 3.988 (0.54), 4.021 (0.40), 4.576 (0.71), 4.592 (0.89), 4.603 (0.84), 4.618 (0.72), 4.641 (0.87), 4.657 (1.35), 4.668 (1.09), 4.674 (0.99), 4.685 (1.27), 4.702 (0.70), 4.722 (0.84), 4.737 (1.00), 4.749 (1.01), 4.764 (0.85), 4.984 (16.00), 5.268 (0.89), 5.340 (0.62), 5.391 (1.04), 5.474 (0.61), 5.513 (0.60), 7.899 (1.19), 7.918 (15.34), 7.942 (0.74), 8.134 (0.60), 8.664 (7.69). (Mixture of diastereomers)

Example 137

(5RS,7RS)-5-{[(3S)-3-Fluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (Isomer 1)

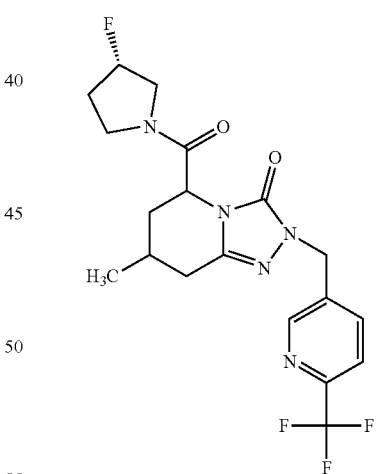

(5RS,7RS)-5-{[(3S)-3-Fluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (diastereomer mixture; 4 isomers) was separated by chiral preparative HPLC [sample preparation: 87 mg dissolved in 3 ml of ethanol; injection volume: 0.1 ml; column: Daicel Chiralcel® OX-H 5 µm, 250×20 mm; eluent: n-heptane/ethanol 50:50; flow rate: 20 ml/min; temperature 25° C.; UV detection: 215 nm]. After the separation, 30.1 mg of isomer 1, which eluted first, and 37.4 mg of isomer 2, which eluted later, were isolated.

Isomer 1:

Analytical chiral HPLC: $R_t$=2.07 min, d.e.=100% [column: Daicel Chiralcel® OX-3 50×4.6 mm; eluent: n-heptane/ethanol 50:50; flow rate: 1 ml/min; UV detection: 220 nm].

LC-MS (Method 4): $R_t$=0.75 min; MS (ESIpos): m/z=428 [M+H]$^+$ $^1$H-NMR (500 MHz, DMSO-d6) δ[ppm]: 0.862 (0.42), 1.021 (8.42), 1.030 (11.85), 1.033 (10.67), 1.043 (9.64), 1.236 (0.53), 1.312 (0.68), 1.336 (1.44), 1.363 (2.05), 1.390 (1.65), 1.414 (0.83), 1.896 (1.37), 1.968 (0.43), 1.990 (0.47), 2.055 (0.44), 2.080 (0.57), 2.103 (1.00), 2.116 (0.94), 2.138 (1.19), 2.159 (2.57), 2.184 (2.56), 2.192 (2.90), 2.214 (3.67), 2.240 (2.57), 2.252 (2.56), 2.278 (1.16), 2.648 (2.43), 2.681 (2.11), 3.333 (1.13), 3.347 (1.49), 3.356 (2.24), 3.370 (2.60), 3.379 (2.36), 3.392 (2.36), 3.467 (0.90), 3.474 (0.87), 3.496 (1.25), 3.503 (1.23), 3.558 (2.68), 3.574 (3.46), 3.580 (3.36), 3.607 (2.29), 3.635 (0.61), 3.701 (0.58), 3.708 (0.66), 3.726 (0.80), 3.733 (0.69), 3.778 (0.56), 3.785 (0.59), 3.803 (0.74), 3.810 (0.68), 3.932 (1.39), 3.949 (2.22), 3.967 (1.42), 3.987 (0.98), 4.012 (0.73), 4.665 (1.30), 4.677 (1.47), 4.686 (1.41), 4.698 (1.25), 4.727 (1.56), 4.739 (1.77), 4.748 (1.71), 4.761 (1.51), 4.986 (16.00), 5.289 (1.44), 5.354 (1.14), 5.394 (1.40), 5.460 (1.13), 7.902 (1.50), 7.918 (12.17), 7.940 (0.91), 8.665 (6.94).

Isomer 2:

Analytical chiral HPLC: $R_t$=2.43 min, d.e.=100% [column: Daicel Chiralcel® OX-3 50×4.6 mm; eluent: n-heptane/ethanol 50:50; flow rate: 1 ml/min; UV detection: 220 nm].

LC-MS (Method 4): $R_t$=0.74 min; MS (ESIpos): m/z=428 [M+H]$^+$ $^1$H-NMR (500 MHz, DMSO-d6) δ [ppm]: 0.847 (0.50), 0.861 (0.56), 1.028 (15.91), 1.041 (16.00), 1.056 (0.79), 1.088 (0.43), 1.101 (0.58), 1.235 (0.87), 1.314 (0.86), 1.336 (1.78), 1.360 (2.56), 1.384 (1.62), 1.406 (0.75), 1.896 (1.43), 1.908 (1.51), 1.963 (0.52), 1.984 (0.55), 2.048 (0.49), 2.070 (0.63), 2.109 (0.83), 2.122 (1.06), 2.158 (3.53), 2.182 (3.07), 2.190 (3.79), 2.214 (3.63), 2.233 (1.72), 2.259 (1.72), 2.273 (1.57), 2.286 (1.33), 2.300 (1.19), 2.313 (0.87), 2.645 (2.47), 2.649 (2.45), 2.677 (2.20), 2.681 (2.08), 3.273 (1.17), 3.288 (1.58), 3.296 (2.22), 3.311 (2.69), 3.319 (2.69), 3.333 (3.51), 3.347 (3.48), 3.387 (2.00), 3.394 (1.81), 3.415 (1.45), 3.423 (1.35), 3.434 (0.69), 3.448 (0.59), 3.465 (0.88), 3.472 (0.89), 3.493 (1.06), 3.501 (0.98), 3.639 (0.74), 3.653 (1.90), 3.658 (1.96), 3.673 (2.34), 3.682 (1.99), 3.694 (2.41), 3.703 (1.33), 3.714 (1.05), 3.733 (0.91), 3.765 (1.34), 3.782 (2.43), 3.801 (1.78), 3.831 (1.27), 3.855 (0.63), 3.880 (2.40), 4.581 (1.40), 4.594 (1.59), 4.603 (1.53), 4.615 (1.36), 4.646 (1.58), 4.658 (1.80), 4.668 (1.73), 4.680 (1.53), 4.982 (14.44), 5.273 (1.35), 5.379 (1.41), 5.387 (1.38), 5.394 (1.28), 5.500 (1.11), 7.901 (1.80), 7.916 (12.89), 7.940 (0.85), 8.664 (6.94).

Example 138

(5RS,7RS)-5-{[(3S)-3-Fluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (Isomer 2)

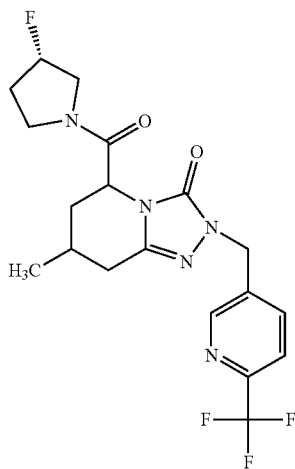 [SMILES: CC1Cc2nn(Cc3ccc(C(F)(F)F)nc3)c(=O)n2C(C(=O)N2CC[C@H](F)C2)C1]

(5RS,7RS)-5-{[(3S)-3-Fluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (diastereomer mixture; 4 isomers) was separated by chiral preparative HPLC [sample preparation: 87 mg dissolved in 3 ml of ethanol; injection volume: 0.1 ml; column: Daicel Chiralcel® OX-H 5 μm, 250×20 mm; eluent: n-heptane/ethanol 50:50; flow rate: 20 ml/min; temperature 25° C.; UV detection: 215 nm]. After the separation, 30.1 mg of isomer 1, which eluted first, and 37.4 mg of isomer 2, which eluted later, were isolated.

Example 139

(5RS,6RS)-6-Methyl-2-(4-methylbenzyl)-5-(pyrrolidin-1-ylcarbonyl)-5,6,7,8-tetrahydro[1,2,4]triazolo[4,3-a]pyridin-3(2H)-one (Isomer 2)

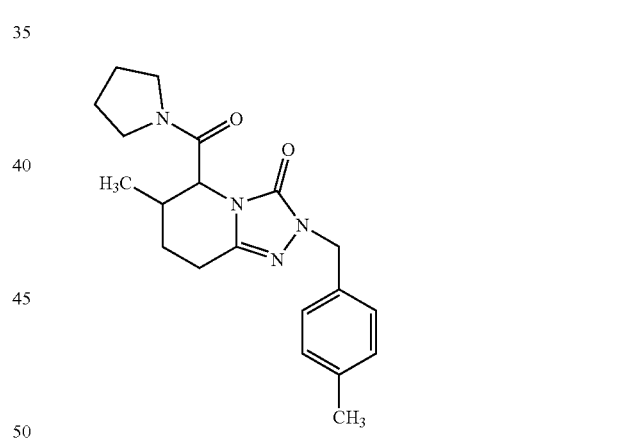

(5RS,6RS)-6-Methyl-2-(4-methylbenzyl)-3-oxo-2,3,5,6,7,8-hexahydro[1,2,4]triazolo[4,3-a]pyridine-5-carboxylic acid (diastereomer mixture) (95.0 mg, 315 μmol) was initially charged together with pyrrolidine (28 μl, 330 μmol) in pyridine/DMF (5/1) (3.0 ml) at room temperature. Subsequently, O-(7-azabenzotriazol-1-yl)-N,N,N',N'-tetramethyluronium hexafluorophosphate (132 mg, 347 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure and subjected directly to a chiral preparative HPLC separation [sample preparation: 35 mg dissolved in 3 ml of ethanol; injection volume: 0.5 ml; column: Daicel Chiralcel® IC 5

μm, 250×20 mm; eluent: n-heptane/ethanol 40:60; flow rate: 15 ml/min; temperature 50° C.; UV detection: 220 nm]. After the separation, 10 mg of isomer 1, which eluted first, and 11 mg of isomer 2, which eluted second, were isolated. Isomer 2:

Analytical chiral HPLC: $R_t$=12.49 min, d.e.=99% [column: Daicel Chiralcel® IC 250×4.6 mm; eluent: i-hexane/ethanol 40:60; flow rate: 1 ml/min; UV detection: 220 nm].

LC-MS (Method 3): $R_t$=1.48 min; MS (ESIpos): m/z=355 [M+H]$^+$ $^1$H-NMR (400 MHz, DMSO-d6) δ [ppm]=0.99 (d, 3H), 1.49-1.62 (m, 1H), 1.70-1.84 (m 2H), 1.84-2.10 (m, 3H), 2.20 (dtd, 1H), 2.27 (s, 3H), 2.55-2.60 (m, 1H), 2.62-2.71 (m, 1H), 3.21-3.29 (m, 1H), 3.32-3.39 (m, 1H), 3.41-3.41 (m, 1H), 3.57 (dt, 1H), 3.77 (dt, 1H), 4.62-4.83 (m, 3H), 7.07-7.19 (m, 4H).

Example 140

(5RS)-5-{[(3S,4S)-3,4-Difluoropyrrolidin-1-yl]carbonyl}-2-(4-methylbenzyl)-5,6,7,8-tetrahydro[1,2,4]triazolo[4,3-a]pyridin-3(2H)-one (Enantiomer 1)

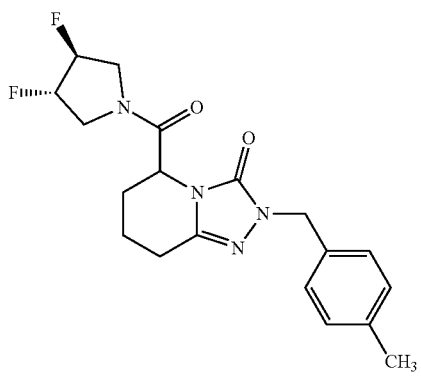 [SMILES: Cc1ccc(Cn2nc3n(c2=O)C(C(=O)N2C[C@H](F)[C@@H](F)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (75.0 mg, 261 μmol) was initially charged in DMF (2.0 ml) and dichloromethane (1.0 ml) at room temperature. Subsequently, 1-[bis(dimethylamino)methylene]-1H-benzotriazol-1-ium 3-oxide hexafluorophosphate (129 mg, 339 μmol) and N,N-diisopropylethylamine (120 μl, 680 μmol) were added. After stirring for 15 min, (3S,4S)-3,4-difluoropyrrolidine hydrochloride (45.0 mg, 313 μmol) was added and the reaction mixture was stirred at room temperature for 2 h. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 53.7 mg (55% of theory) of the title compound were obtained.

LC-MS (Method 4): $R_t$=0.74 min; MS (ESIpos): m/z=377 [M+H]$^+$ $^1$H-NMR (600 MHz, DMSO-d6) δ [ppm]: 1.624 (0.44), 1.629 (0.48), 1.632 (0.47), 1.637 (0.44), 1.642 (0.54), 1.646 (0.55), 1.651 (0.53), 1.722 (0.68), 1.729 (0.74), 1.738 (0.57), 1.744 (0.43), 1.952 (0.45), 1.957 (0.48), 1.962 (0.44), 1.969 (0.54), 1.976 (0.78), 1.980 (0.81), 1.985 (0.70), 2.022 (0.42), 2.027 (0.51), 2.032 (0.49), 2.037 (0.60), 2.040 (0.52), 2.045 (0.67), 2.051 (0.69), 2.056 (0.65), 2.273 (16.00), 2.518 (0.67), 2.563 (0.77), 2.584 (0.76), 2.592 (1.47), 2.600 (0.80), 2.612 (0.47), 2.620 (0.70), 3.647 (2.34), 3.697 (1.29), 3.706 (0.58), 3.711 (0.90), 3.716 (0.50), 3.830 (0.50), 3.853 (0.57), 3.899 (0.49), 3.922 (0.57), 4.152 (0.84), 4.175 (0.78), 4.195 (0.88), 4.217 (0.74), 4.749 (5.23), 4.752 (5.07), 4.873 (1.32), 4.879 (1.49), 4.883 (1.59), 4.890 (1.27), 5.336 (0.63), 5.346 (0.57), 5.429 (0.99), 5.516 (0.64), 7.109 (1.69), 7.123 (9.34), 7.129 (8.38), 7.143 (1.51).

The (5S) configuration was assigned on the basis of the crystal structure elucidation for Example 26, 108, 113, 157, 237, 358 and 454.

(5S)-5-{[(3S,4S)-3,4-Difluoropyrrolidin-1-yl]carbonyl}-2-(4-methylbenzyl)-5,6,7,8-tetrahydro[1,2,4]triazolo[4,3-a]pyridin-3(2H)-one Example 141

(5RS)-2-(4-Methylbenzyl)-5-{[(1RS)-1-oxido-1,3-thiazolidin-3-yl]carbonyl}-5,6,7,8-tetrahydro[1,2,4]triazolo[4,3-a]pyridin-3(2H)-one (Diastereomer Mixture; 2 Isomers)

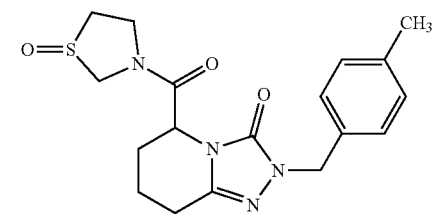 [SMILES: Cc1ccc(Cn2nc3n(c2=O)C(C(=O)N2CCS(=O)C2)CCC3)cc1]

(5RS)-2-(4-Methylbenzyl)-5-(1,3-thiazolidin-3-ylcarbonyl)-5,6,7,8-tetrahydro[1,2,4]triazolo[4,3-a]pyridin-3(2H)-one (enantiomer 1) (80.0 mg, 223 μmol) was initially charged in dichloromethane (3.0 ml) and 3-chlorobenzenecarboperoxoic acid (55.0 mg, 70% purity, 223 μmol) was added. After 4 h at room temperature, saturated aqueous sodium hydrogencarbonate solution was added, and the reaction mixture was extracted with dichloromethane. The combined organic phases were dried over magnesium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 40.0 mg (48% of theory) of the title compound were obtained.

LC-MS (Method 1): $R_t$=0.85 min; MS (ESIpos): m/z=375 [M+H]$^+$ $^1$H-NMR (500 MHz, DMSO-d6) δ [ppm]: 1.627 (0.41), 1.740 (0.62), 1.762 (0.45), 1.987 (0.63), 1.995 (0.76), 2.004 (0.69), 2.022 (0.56), 2.084 (0.42), 2.274 (16.00), 2.514 (0.79), 2.518 (0.79), 2.521 (0.60), 2.568 (0.47), 2.591 (0.73), 2.599 (1.07), 2.634 (0.57), 3.058 (0.50), 3.077 (0.45), 3.097 (0.45), 3.125 (0.46), 3.175 (0.50), 3.262 (0.59), 3.274 (0.75), 3.966 (0.48), 3.974 (0.70), 3.987 (0.64), 3.994 (0.60), 4.088 (0.42), 4.109 (0.64), 4.121 (0.44), 4.287 (0.64), 4.308 (0.49), 4.313 (0.64), 4.342 (0.74), 4.368 (0.88), 4.421 (0.66), 4.446 (0.72), 4.489 (0.59), 4.513 (0.64), 4.610 (0.76), 4.614 (0.82), 4.636 (0.60), 4.640 (0.66), 4.755 (5.93), 4.859 (0.41), 4.864 (0.49), 4.983 (0.64), 4.995 (0.55), 5.002 (0.52), 5.008 (0.55), 5.016 (0.87), 5.020 (0.92), 5.045 (0.78), 5.753 (0.47), 7.105 (0.99), 7.122 (5.96), 7.130 (11.47), 7.145 (0.98). (Mixture of diastereomers)

The (5S) configuration was assigned on the basis of the crystal structure elucidation for Example 26, 108, 113, 157, 237, 358 and 454.

(5S)-2-(4-Methylbenzyl)-5-{[(1 RS)-1-oxido-1,3-thiazolidin-3-yl]carbonyl}-5,6,7,8-tetrahydro[1,2,4]triazolo[4,3-a]pyridin-3(2H)-one (Diastereomer Mixture; 2 Isomers)

Example 142

(5RS)-5-[(1,1-Dioxido-1,3-thiazolidin-3-yl)carbonyl]-2-(4-methylbenzyl)-5,6,7,8-tetrahydro[1,2,4]triazolo[4,3-a]pyridin-3(2H)-one (Enantiomer 1)

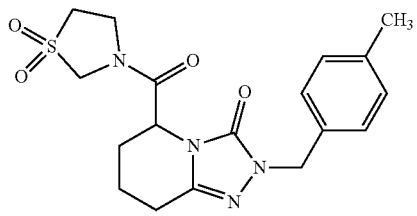 [SMILES: Cc1ccc(Cn2nc3n(c2=O)C(C(=O)N2CCS(=O)(=O)C2)CCC3)cc1]

(5RS)-2-(4-Methylbenzyl)-5-(1,3-thiazolidin-3-ylcarbonyl)-5,6,7,8-tetrahydro[1,2,4]triazolo[4,3-a]pyridin-3(2H)-one (enantiomer 1) (32.0 mg, 89.3 µmol) was initially charged in dichloromethane (2.4 ml) and 3-chlorobenzenecarboperoxoic acid (77.0 mg, 70% purity, 312 µmol) was added. After 4 h at room temperature, saturated aqueous sodium hydrogencarbonate solution was added, and the reaction mixture was extracted with dichloromethane. The combined organic phases were dried over magnesium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 25.5 mg (73% of theory) of the title compound were obtained.

LC-MS (Method 4): $R_t$=0.69 min; MS (ESIpos): m/z=391 [M+H]$^+$ $^1$H-NMR (500 MHz, DMSO-d6) δ[ppm]: 1.583 (0.40), 1.730 (0.58), 1.741 (0.60), 1.962 (0.42), 1.990 (0.89), 1.996 (0.83), 2.015 (0.42), 2.272 (16.00), 2.514 (0.74), 2.518 (0.59), 2.521 (0.48), 2.558 (0.75), 2.569 (0.62), 2.595 (1.12), 2.628 (0.49), 3.423 (0.53), 3.439 (0.95), 3.449 (0.62), 3.455 (0.75), 3.461 (0.76), 3.476 (0.70), 3.580 (0.60), 3.593 (1.14), 3.607 (0.63), 3.850 (0.41), 3.859 (0.62), 3.874 (1.06), 3.884 (0.72), 3.889 (0.69), 3.896 (0.71), 3.901 (0.67), 3.912 (0.60), 4.158 (0.41), 4.247 (0.41), 4.470 (0.46), 4.495 (0.88), 4.544 (0.89), 4.569 (0.47), 4.755 (8.51), 4.844 (1.10), 4.868 (2.16), 4.874 (0.98), 4.880 (0.97), 4.886 (0.71), 4.982 (1.43), 5.006 (1.07), 5.020 (0.41), 5.027 (0.47), 5.032 (0.47), 5.752 (4.50), 7.105 (1.46), 7.122 (9.73), 7.127 (9.02), 7.144 (1.29).

The (5S) configuration was assigned on the basis of the crystal structure elucidation for Example 26, 108, 113, 157, 237, 358 and 454.

(5S)-5-[(1,1-Dioxido-1,3-thiazolidin-3-yl)carbonyl]-2-(4-methylbenzyl)-5,6,7,8-tetrahydro[1,2,4]triazolo[4,3-a]pyridin-3(2H)-one Example 143

(5RS)-5-{[(3S)-3-(Difluoromethyl)pyrrolidin-1-yl]carbonyl}-2-(4-methylbenzyl)-5,6,7,8-tetrahydro[1,2,4]triazolo[4,3-a]pyridin-3(2H)-one (Enantiomer 1)

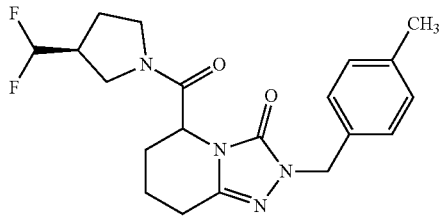 [SMILES: Cc1ccc(Cn2nc3n(c2=O)C(C(=O)N2CC[C@H](C(F)F)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, (3S)-3-(difluoromethyl)pyrrolidine hydrochloride (65.8 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 78.6 mg (58% of theory) of the title compound were obtained.

LC-MS (Method 3): $R_t$=1.47 min; MS (ESIpos): m/z=391 [M+H]$^+$ $^1$H-NMR (500 MHz, DMSO-d6) δ[ppm]: 1.665 (0.43), 1.676 (0.55), 1.709 (1.13), 1.829 (0.41), 1.934 (0.46), 1.943 (0.53), 1.950 (0.75), 1.959 (0.76), 1.984 (0.90), 1.994 (0.95), 2.005 (0.70), 2.013 (0.90), 2.026 (0.70), 2.034 (0.69), 2.041 (0.55), 2.046 (0.49), 2.053 (0.41), 2.115 (0.44), 2.271 (16.00), 2.517 (1.18), 2.574 (0.72), 2.583 (1.40), 2.593 (0.75), 2.617 (0.64), 3.270 (0.49), 3.286 (0.47), 3.295 (0.60), 3.341 (0.43), 3.437 (0.44), 3.454 (0.41), 3.479 (0.49), 3.516 (0.79), 3.533 (0.62), 3.542 (0.59), 3.610 (0.48), 3.647 (0.44), 4.707 (0.48), 4.715 (0.44), 4.722 (0.57), 4.728 (0.96), 4.738 (3.89), 4.745 (3.45), 4.760 (0.44), 4.775 (0.87), 4.780 (0.80), 4.787 (0.40), 6.130 (0.51), 6.139 (0.54), 6.162 (0.52), 7.104 (1.25), 7.120 (10.70), 7.125 (10.23), 7.141 (1.15).

The (5S) configuration was assigned on the basis of the crystal structure elucidation for Example 26, 108, 113, 157, 237, 358 and 454.

445

(5S)-5-{[(3S)-3-(Difluoromethyl)pyrrolidin-1-yl]carbonyl}-2-(4-methylbenzyl)-5,6,7,8-tetrahydro[1,2,4]triazolo[4,3-a]pyridin-3(2H)-one Example 144

(5RS)-5-[(cis)-2-Azabicyclo[3.1.0]hex-2-ylcarbonyl]-2-(4-methylbenzyl)-5,6,7,8-tetrahydro[1,2,4]triazolo[4,3-a]pyridin-3(2H)-one (Diastereomer Mixture; 2 Isomers)

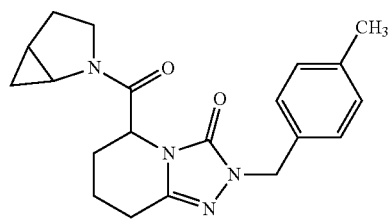 [SMILES: Cc1ccc(Cn2nc3n(c2=O)C(C(=O)N2CCC4CC42)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, cis-2-azabicyclo[3.1.0]hexane hydrochloride (racemate) (49.9 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 92.9 mg (76% of theory) of the title compound were obtained.

LC-MS (Method 3): $R_t$=1.41 min; MS (ESIpos): m/z=353 [M+H]$^+$ $^1$H-NMR (500 MHz, DMSO-d6) δ [ppm]: 0.618 (0.56), 0.623 (0.56), 0.628 (0.79), 0.633 (0.69), 0.639 (0.64), 0.644 (0.61), 0.650 (0.49), 0.654 (0.45), 0.811 (0.53), 0.828 (0.52), 1.567 (0.43), 1.744 (0.75), 1.755 (0.95), 1.767 (1.00), 1.772 (0.92), 1.784 (0.62), 1.860 (0.57), 1.866 (0.43), 1.877 (0.51), 1.884 (0.64), 1.890 (0.41), 1.902 (0.42), 1.908 (0.42), 2.001 (0.55), 2.012 (0.48), 2.019 (0.70), 2.032 (0.79), 2.039 (0.78), 2.047 (0.76), 2.065 (0.53), 2.078 (0.41), 2.145 (0.74), 2.150 (0.68), 2.272 (15.30), 2.518 (0.58), 2.522 (0.77), 2.586 (1.07), 2.596 (0.62), 2.620 (0.47), 2.959 (0.55), 2.984 (0.56), 3.154 (0.42), 3.495 (0.42), 3.499 (0.40), 3.699 (0.42), 3.704 (0.67), 3.711 (0.88), 3.716 (0.65), 3.724 (0.71), 3.729 (0.78), 4.738 (1.92), 4.743 (2.32), 4.753 (3.33), 4.934 (0.45), 4.940 (0.46), 5.070 (0.56), 5.076 (0.65), 5.083 (0.61), 5.089 (0.52), 7.109 (0.79), 7.127 (16.00), 7.144 (0.66).

The (5S) configuration was assigned on the basis of the crystal structure elucidation for Example 26, 108, 113, 157, 237, 358 and 454.

446

(5S)-5-[(cis)-2-Azabicyclo[3.1.0]hex-2-ylcarbonyl]-2-(4-methylbenzyl)-5,6,7,8-tetrahydro[1,2,4]triazolo[4,3-a]pyridin-3(2H)-one (Diastereomer Mixture; 2 Isomers)

Example 145

(5RS)-2-(4-Methylbenzyl)-5-[(3,3,4,4-tetrafluoropyrrolidin-1-yl)carbonyl]-5,6,7,8-tetrahydro[1,2,4]triazolo[4,3-a]pyridin-3(2H)-one (Enantiomer 1)

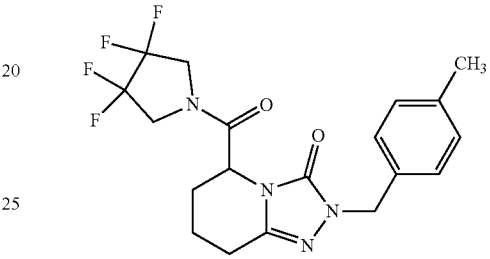

(5RS)-2-(4-Methylbenzyl)-3-oxo-2,3,5,6,7,8-hexahydro[1,2,4]triazolo[4,3-a]pyridine-5-carboxylic acid (enantiomer 1) (50.0 mg, 174 µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (85.8 mg, 226 µmol) and N,N-diisopropylethylamine (79 µl, 450 µmol) were added. After stirring for 15 min, 3,3,4,4-tetrafluoropyrrolidine hydrochloride (37.5 mg, 209 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 11.0 mg (15% of theory) of the title compound were obtained.

LC-MS (Method 3): $R_t$=1.68 min; MS (ESIpos): m/z=413 [M+H]$^+$ $^1$H-NMR (500 MHz, DMSO-d6) δ [ppm]: −0.007 (0.56), 1.141 (2.17), 1.236 (0.42), 1.658 (0.47), 1.665 (0.57), 1.678 (0.56), 1.686 (0.71), 1.697 (0.83), 1.704 (0.92), 1.716 (0.72), 1.726 (0.43), 1.952 (0.43), 1.958 (0.45), 1.964 (0.44), 1.972 (0.62), 1.980 (0.69), 1.986 (0.74), 1.993 (0.62), 2.048 (0.50), 2.054 (0.48), 2.061 (0.69), 2.069 (0.65), 2.076 (0.65), 2.082 (0.64), 2.090 (0.45), 2.116 (0.98), 2.271 (16.00), 2.481 (0.93), 2.514 (0.53), 2.518 (0.54), 2.562 (1.05), 2.568 (1.04), 2.580 (1.52), 2.591 (1.69), 2.601 (0.83), 2.624 (0.53), 4.007 (0.64), 4.037 (0.76), 4.105 (0.74), 4.132 (0.59), 4.411 (0.54), 4.440 (0.52), 4.620 (0.73), 4.646 (0.65), 4.716 (0.43), 4.747 (4.79), 4.752 (4.59), 4.783 (0.41), 4.830 (1.29), 4.838 (1.55), 4.842 (1.66), 4.851 (1.23), 7.104 (1.48), 7.109 (0.84), 7.116 (1.66), 7.121 (10.49), 7.126 (9.73), 7.143 (1.20).

The (5S) configuration was assigned on the basis of the crystal structure elucidation for Example 26, 108, 113, 157, 237, 358 and 454.

447

(5S)-2-(4-Methylbenzyl)-5-[(3,3,4,4-tetrafluoropyrrolidin-1-yl)carbonyl]-5,6,7,8-tetrahydro[1,2,4]triazolo[4,3-a]pyridin-3(2H)-one Example 146

(5RS)-5-{[3-(Fluoromethyl)azetidin-1-yl]carbonyl}-2-(4-methylbenzyl)-5,6,7,8-tetrahydro[1,2,4]triazolo[4,3-a]pyridin-3(2H)-one (Enantiomer 1)

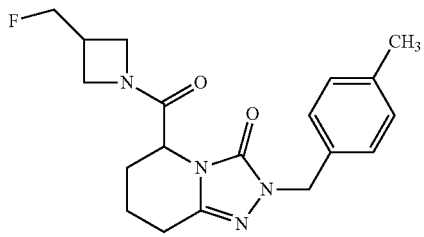 [SMILES: Cc1ccc(Cn2nc3n(c2=O)C(C(=O)N2CC(CF)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (50.0 mg, 174 µmol) was initially charged in DMF (2.0 ml) and dichloromethane (1.0 ml) at room temperature. Subsequently, 1-[bis(dimethylamino)methylene]-1H-benzotriazol-1-ium 3-oxide hexafluorophosphate (85.8 mg, 226 µmol) and N,N-diisopropylethylamine (79 µl, 450 µmol) were added. After stirring for 15 min, 3-(fluoromethyl)azetidine trifluoroacetate (42.4 mg, 209 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 23.2 mg (37% of theory) of the title compound were obtained.

LC-MS (Method 3): $R_t$=1.31 min; MS (ESIpos): m/z=359 [M+H]$^+$ $^1$H-NMR (500 MHz, DMSO-d6) δ [ppm]: −0.007 (0.41), 1.683 (0.67), 1.694 (1.11), 1.705 (1.36), 1.715 (1.05), 1.725 (0.44), 1.911 (0.49), 1.917 (0.52), 1.923 (0.43), 1.986 (0.51), 1.993 (0.63), 2.001 (0.62), 2.005 (0.47), 2.014 (0.63), 2.270 (16.00), 2.514 (0.90), 2.518 (0.75), 2.521 (0.42), 2.526 (0.57), 2.563 (0.66), 2.573 (1.35), 2.584 (0.65), 2.607 (0.56), 3.639 (0.50), 3.650 (0.50), 3.659 (0.56), 3.670 (0.52), 3.704 (0.47), 3.716 (0.48), 3.724 (0.56), 3.735 (0.52), 3.921 (0.43), 3.939 (0.70), 3.963 (0.59), 3.974 (0.57), 3.980 (0.62), 3.991 (0.87), 4.007 (0.80), 4.110 (0.43), 4.122 (0.48), 4.128 (0.56), 4.139 (0.50), 4.252 (0.44), 4.269 (0.79), 4.399 (0.45), 4.416 (0.86), 4.488 (0.61), 4.497 (1.30), 4.500 (1.08), 4.505 (1.00), 4.509 (1.33), 4.518 (1.67), 4.530 (1.10), 4.545 (1.22), 4.556 (1.11), 4.613 (1.09), 4.624 (1.10), 4.639 (1.18), 4.651 (1.12), 4.744 (6.33), 7.107 (0.78), 7.125 (13.27), 7.137 (0.43), 7.142 (0.70).

The (5S) configuration was assigned on the basis of the crystal structure elucidation for Example 26, 108, 113, 157, 237, 358 and 454.

448

(5S)-5-{[3-(Fluoromethyl)azetidin-1-yl]carbonyl}-2-(4-methylbenzyl)-5,6,7,8-tetrahydro[1,2,4]triazolo[4,3-a]pyridin-3(2H)-one Example 147

(5RS)-5-{[(3RS)-3-Fluoro-3-(hydroxymethyl)pyrrolidin-1-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

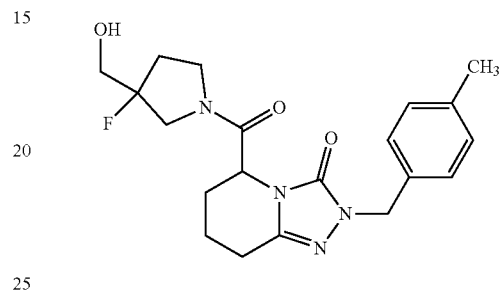

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, [(3RS)-3-fluoropyrrolidin-3-yl]methanol hydrochloride (racemate) (65.0 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 62.8 mg (46% of theory) of the title compound were obtained.

LC-MS (Method 3): $R_t$=1.17 min; MS (ESIpos): m/z=389 [M+H]$^+$ $^1$H-NMR (500 MHz, DMSO-d6) δ [ppm]: −0.007 (0.53), 1.670 (0.41), 1.676 (0.41), 1.685 (0.45), 1.696 (0.56), 1.705 (0.77), 1.716 (1.02), 1.723 (1.05), 1.733 (0.76), 1.973 (0.72), 1.994 (0.76), 2.010 (0.86), 2.023 (0.60), 2.040 (0.73), 2.052 (0.91), 2.064 (0.73), 2.073 (0.74), 2.121 (0.50), 2.132 (0.55), 2.136 (0.56), 2.272 (16.00), 2.514 (0.86), 2.518 (0.81), 2.521 (0.89), 2.577 (0.67), 2.586 (1.31), 2.595 (0.76), 2.619 (0.58), 3.367 (0.42), 3.395 (0.47), 3.437 (0.52), 3.464 (0.64), 3.488 (0.64), 3.516 (0.43), 3.556 (0.83), 3.569 (0.40), 3.584 (0.63), 3.600 (0.63), 3.620 (1.19), 3.656 (1.64), 3.675 (0.69), 3.681 (0.94), 3.697 (0.57), 3.703 (0.49), 3.724 (0.53), 3.737 (0.53), 3.750 (0.57), 3.759 (0.61), 3.773 (0.41), 4.656 (0.40), 4.705 (0.49), 4.725 (0.57), 4.736 (3.09), 4.744 (4.56), 4.753 (1.96), 4.760 (0.52), 4.766 (0.52), 4.773 (0.46), 4.832 (0.44), 4.837 (0.47), 5.241 (0.50), 7.103 (0.89), 7.108 (1.04), 7.120 (7.69), 7.125 (11.68), 7.142 (0.91).

The (5S) configuration was assigned on the basis of the crystal structure elucidation for Example 26, 108, 113, 157, 237, 358 and 454.

449

(5S)-5-{[(3RS)-3-Fluoro-3-(hydroxymethyl)pyrrolidin-1-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

Example 148

(5RS)-5-{[(2S)-2-Methylazetidin-1-yl]carbonyl}-2-(4-methylbenzyl)-5,6,7,8-tetrahydro[1,2,4]triazolo[4,3-a]pyridin-3(2H)-one (Enantiomer 1)

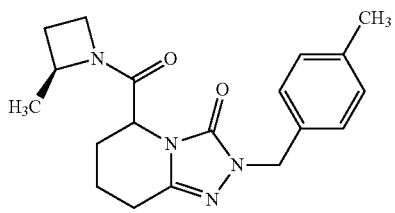

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, (2S)-2-methylazetidine hydrochloride (44.9 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 70.3 mg (59% of theory) of the title compound were obtained.

LC-MS (Method 3): $R_t$=1.36 min; MS (ESIpos): m/z=341 [M+H]$^+$ $^1$H-NMR (500 MHz, DMSO-d6) δ[ppm]: 1.314 (3.24), 1.326 (3.25), 1.349 (1.64), 1.361 (1.62), 1.450 (1.44), 1.462 (1.41), 1.520 (1.03), 1.533 (1.02), 1.706 (1.29), 1.797 (0.63), 1.803 (0.73), 1.815 (0.86), 1.819 (0.85), 1.826 (0.82), 1.838 (0.72), 1.849 (0.51), 1.917 (0.49), 1.924 (0.51), 1.933 (0.42), 1.987 (0.52), 2.001 (0.52), 2.008 (0.53), 2.017 (0.46), 2.270 (16.00), 2.395 (0.54), 2.401 (0.60), 2.413 (0.61), 2.418 (0.61), 2.434 (0.49), 2.517 (0.78), 2.522 (0.97), 2.557 (0.73), 2.567 (1.38), 2.576 (0.76), 2.601 (0.57), 4.120 (0.46), 4.132 (0.46), 4.207 (0.60), 4.220 (0.64), 4.238 (0.42), 4.329 (0.43), 4.340 (0.59), 4.357 (0.58), 4.370 (0.61), 4.423 (0.90), 4.431 (1.03), 4.435 (1.11), 4.443 (0.76), 4.681 (0.41), 4.697 (0.42), 4.712 (0.94), 4.728 (1.99), 4.743 (3.47), 4.756 (0.78), 4.776 (0.69), 7.107 (0.87), 7.126 (13.90), 7.142 (0.72).

The (5S) configuration was assigned on the basis of the crystal structure elucidation for Example 26, 108, 113, 157, 237, 358 and 454.

450

(5S)-5-{[(2S)-2-Methylazetidin-1-yl]carbonyl}-2-(4-methylbenzyl)-5,6,7,8-tetrahydro[1,2,4]triazolo[4,3-a]pyridin-3(2H)-one Example 149

(5RS)-5-{[3-(Difluoromethyl)azetidin-1-yl]carbonyl}-2-(4-methylbenzyl)-5,6,7,8-tetrahydro[1,2,4]triazolo[4,3-a]pyridin-3(2H)-one (Enantiomer 1)

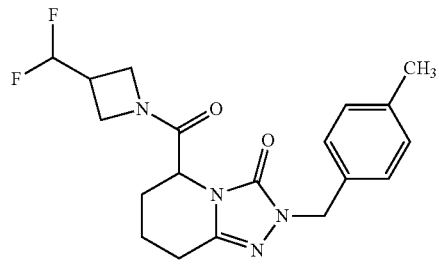 [SMILES: Cc1ccc(Cn2nc3n(c2=O)C(C(=O)N2CC(C(F)F)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (50.0 mg, 174 µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (85.8 mg, 226 µmol) and N,N-diisopropylethylamine (79 µl, 450 µmol) were added. After stirring for 15 min, 3-(difluoromethyl)azetidine hydrochloride (30.0 mg, 209 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 32.3 mg (48% of theory) of the title compound were obtained.

LC-MS (Method 4): $R_t$=0.76 min; MS (ESIpos): m/z=377 [M+H]$^+$ $^1$H-NMR (500 MHz, DMSO-d6) δ[ppm]: 1.676 (0.59), 1.696 (1.28), 1.705 (1.35), 1.714 (1.08), 1.912 (0.46), 1.949 (0.44), 1.984 (0.48), 1.996 (0.65), 2.004 (0.71), 2.012 (0.62), 2.016 (0.60), 2.024 (0.53), 2.270 (16.00), 2.519 (1.23), 2.568 (0.69), 2.577 (1.28), 2.586 (0.71), 2.610 (0.51), 2.689 (1.41), 2.889 (0.42), 3.178 (0.43), 3.186 (0.44), 3.196 (0.46), 3.204 (0.40), 3.775 (0.53), 3.786 (0.55), 3.796 (0.64), 3.806 (0.59), 3.846 (0.43), 3.858 (0.47), 3.866 (0.64), 3.878 (0.59), 3.941 (0.56), 3.959 (0.84), 4.017 (0.59), 4.036 (0.95), 4.055 (0.48), 4.111 (0.55), 4.122 (0.60), 4.129 (0.64), 4.139 (0.56), 4.272 (1.16), 4.275 (1.15), 4.284 (0.93), 4.293 (0.92), 4.434 (0.55), 4.452 (1.03), 4.470 (0.47), 4.518 (1.08), 4.528 (1.66), 4.538 (1.06), 4.746 (7.75), 6.314 (0.51), 6.322 (0.52), 6.352 (0.57), 6.361 (0.56), 7.106 (1.00), 7.124 (14.14), 7.141 (0.85).

The (5S) configuration was assigned on the basis of the crystal structure elucidation for Example 26, 108, 113, 157, 237, 358 and 454.

451

(5S)-5-{[3-(Difluoromethyl)azetidin-1-yl]carbonyl}-2-(4-methylbenzyl)-5,6,7,8-tetrahydro[1,2,4]triazolo[4,3-a]pyridin-3(2H)-one Example 150

(5RS)-5-{[cis-3,4-Difluoropyrrolidin-1-yl]carbonyl}-2-(4-methylbenzyl)-5,6,7,8-tetrahydro[1,2,4]triazolo[4,3-a]pyridin-3(2H)-one (Enantiomer 1)

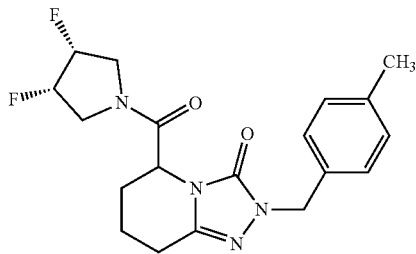 [SMILES: Cc1ccc(Cn2nc3n(c2=O)C(C(=O)N2C[C@@H](F)[C@@H](F)C2)CCC3)cc1]

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (8.0 ml) and dichloromethane (4.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, cis-3,4-difluoropyrrolidine hydrochloride (60.0 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 97.6 mg (75% of theory) of the title compound were obtained.

LC-MS (Method 1): $R_t$=1.03 min; MS (ESIpos): m/z=377 [M+H]$^+$ $^1$H-NMR (400 MHz, DMSO-d6) δ [ppm]: 0.008 (0.52), 1.636 (0.49), 1.643 (0.54), 1.668 (0.75), 1.678 (0.74), 1.695 (0.84), 1.707 (1.04), 1.717 (0.98), 1.730 (0.79), 1.949 (0.69), 1.957 (0.59), 1.974 (0.44), 1.996 (0.88), 2.005 (0.65), 2.022 (0.54), 2.031 (0.62), 2.039 (0.67), 2.047 (0.64), 2.056 (0.56), 2.066 (0.49), 2.074 (0.53), 2.082 (0.46), 2.272 (16.00), 2.522 (1.21), 2.558 (0.95), 2.571 (1.24), 2.585 (1.60), 2.597 (0.90), 2.628 (0.53), 3.485 (0.56), 3.493 (0.47), 3.506 (0.41), 3.514 (0.43), 3.523 (0.49), 3.533 (0.69), 3.541 (0.64), 3.575 (0.43), 3.612 (0.45), 3.626 (0.52), 3.668 (0.51), 3.681 (0.72), 3.688 (0.61), 3.701 (0.94), 3.714 (0.56), 3.724 (0.66), 3.733 (0.53), 3.753 (0.60), 3.766 (0.54), 3.865 (0.45), 3.924 (0.44), 3.938 (0.50), 3.973 (0.48), 3.987 (0.48), 4.172 (0.59), 4.703 (0.41), 4.743 (7.59), 4.750 (3.74), 4.768 (1.29), 4.779 (1.99), 4.789 (1.52), 5.254 (0.49), 5.265 (0.49), 5.275 (0.55), 5.284 (0.44), 5.338 (0.40), 5.349 (0.42), 5.375 (0.53), 5.387 (0.60), 5.398 (0.49), 5.407 (0.49), 5.415 (0.44), 5.457 (0.42), 5.470 (0.40), 5.479 (0.42), 7.096 (0.75), 7.102 (0.98), 7.117 (6.91), 7.123 (13.48), 7.144 (1.02).

The (5S) configuration was assigned on the basis of the crystal structure elucidation for Example 26, 108, 113, 157, 237, 358 and 454.

452

(5S)-5-{[cis-3,4-Difluoropyrrolidin-1-yl]carbonyl}-2-(4-methylbenzyl)-5,6,7,8-tetrahydro[1,2,4]triazolo[4,3-a]pyridin-3(2H)-one Example 151

(5RS)-5-{[(3RS)-3-Fluoro-3-methylpyrrolidin-1-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

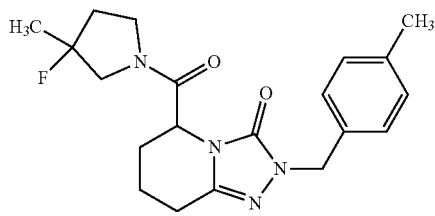

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (8.0 ml) and dichloromethane (4.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, (3RS)-3-fluoro-3-methylpyrrolidine hydrochloride (racemate) (58.3 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 97.9 mg (75% of theory) of the title compound were obtained.

LC-MS (Method 1): $R_t$=1.06 min; MS (ESIpos): m/z=373 [M+H]$^+$ $^1$H-NMR (400 MHz, DMSO-d6) δ [ppm]: −0.008 (0.81), 0.008 (0.67), 1.487 (2.19), 1.496 (2.37), 1.505 (2.23), 1.521 (2.02), 1.539 (2.25), 1.548 (2.39), 1.557 (2.22), 1.573 (1.99), 1.717 (1.18), 1.971 (0.64), 1.983 (0.87), 1.994 (0.92), 2.041 (0.65), 2.065 (0.84), 2.102 (0.67), 2.199 (0.44), 2.222 (0.52), 2.272 (16.00), 2.558 (0.72), 2.583 (1.28), 2.625 (0.46), 3.335 (0.59), 3.354 (0.54), 3.370 (0.45), 3.525 (0.49), 3.552 (0.51), 3.572 (0.69), 3.613 (0.67), 3.631 (0.55), 3.643 (0.63), 3.660 (0.57), 3.679 (0.57), 3.729 (0.64), 3.750 (0.40), 3.951 (0.55), 3.973 (0.40), 4.718 (0.47), 4.724 (0.59), 4.745 (6.15), 4.765 (0.40), 4.824 (0.41), 4.831 (0.44), 7.101 (0.69), 7.124 (13.52), 7.145 (0.82).

The (5S) configuration was assigned on the basis of the crystal structure elucidation for Example 26, 108, 113, 157, 237, 358 and 454.

453

(5S)-5-{[(3RS)-3-Fluoro-3-methylpyrrolidin-1-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

Example 152

(5RS)-5-{[(3RS)-3-Hydroxy-3-(trifluoromethyl)pyrrolidin-1-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

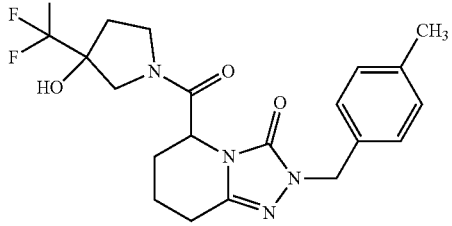

(5RS)-2-(4-Methylbenzyl)-3-oxo-2,3,5,6,7,8-hexahydro[1,2,4]triazolo[4,3-a]pyridine-5-carboxylic acid (enantiomer 1) (100 mg, 348 µmol) was initially charged in DMF (8.0 ml) and dichloromethane (4.0 ml) at room temperature. Subsequently, 1-[bis(dimethylamino)methylene]-1H-benzotriazol-1-ium 3-oxide hexafluorophosphate (172 mg, 452 µmol) and N,N-diisopropylethylamine (160 µl, 900 µmol) were added. After stirring for 15 min, (3RS)-3-(trifluoromethyl)pyrrolidin-3-ol (racemate) (64.8 mg, 418 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 110 mg (73% of theory) of the title compound were obtained.

LC-MS (Method 1): $R_t$=1.06 min; MS (ESIpos): m/z=425 [M+H]$^+$ $^1$H-NMR (400 MHz, DMSO-d6) δ [ppm]: −0.008 (0.70), 0.008 (0.56), 1.664 (0.42), 1.674 (0.50), 1.687 (0.58), 1.719 (1.06), 1.979 (0.80), 1.997 (0.55), 2.015 (0.85), 2.031 (1.20), 2.060 (0.60), 2.077 (0.73), 2.101 (0.91), 2.111 (0.73), 2.124 (0.84), 2.243 (0.48), 2.272 (16.00), 2.299 (0.41), 2.523 (0.93), 2.577 (0.98), 2.588 (1.35), 2.600 (0.67), 2.630 (0.49), 3.444 (0.70), 3.476 (1.14), 3.492 (0.90), 3.539 (1.03), 3.572 (0.71), 3.585 (0.70), 3.617 (0.50), 3.678 (0.77), 3.707 (0.78), 3.733 (0.51), 3.753 (0.43), 3.761 (0.78), 3.778 (0.56), 3.802 (0.94), 3.840 (0.65), 3.868 (0.45), 4.743 (5.23), 4.748 (5.82), 4.769 (0.84), 4.779 (0.40), 4.836 (0.45), 4.842 (0.49), 6.549 (1.70), 6.564 (1.56), 6.615 (1.15), 6.631 (1.25), 7.099 (0.87), 7.124 (12.86), 7.146 (0.94).

The (5S) configuration was assigned on the basis of the crystal structure elucidation for Example 26, 108, 113, 157, 237, 358 and 454.

454

(5S)-5-{[(3RS)-3-Hydroxy-3-(trifluoromethyl)pyrrolidin-1-yl]carbonyl}-2-(4-methylbenzyl)-5,6,7,8-tetrahydro[1,2,4]triazolo[4,3-a]pyridin-3(2H)-one (Diastereomer Mixture; 2 Isomers)

Example 153

(5RS)-5-(Pyrrolidin-1-ylcarbonyl)-2-{[6-(2,2,2-trifluoroethoxy)pyridin-3-yl]methyl}-5,6,7,8-tetrahydro[1,2,4]triazolo[4,3-a]pyridin-3(2H)-one (Racemate)

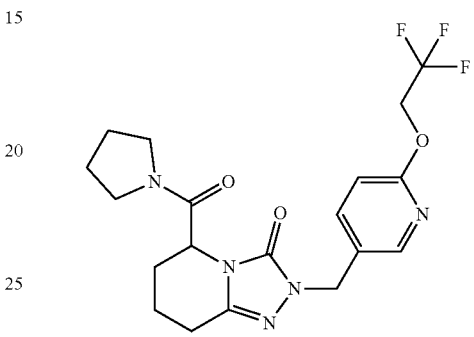

Under argon, 2,2,2-trifluoroethanol (180 µl, 2.5 mmol) were dissolved in 3 ml of DMF (dried over molecular sieve). At 0° C., sodium hydride (101 mg, 60% purity, 2.52 mmol) was added and the mixture was stirred at 0° C. for a further 30 min. After addition of (5RS)-2-[(6-chloropyridin-3-yl)methyl]-5-(pyrrolidin-1-ylcarbonyl)-5,6,7,8-tetrahydro[1,2,4]triazolo[4,3-a]pyridin-3(2H)-one (racemate) (210 mg, 87% purity, 505 µmol), dissolved in 1 ml of DMF, the mixture was stirred at 60° C. for 3 days.

For further conversion, first further 2,2,2-trifluoroethanol (180 µl, 2.5 mmol) was dissolved in 1 ml of DMF, then sodium hydride (101 mg, 60% purity, 2.52 mmol) was added at 0° C. and the mixture was stirred at 0° C. for a further 30 min. The reagent solution thus formed was then added to the main batch solution and the latter was stirred at 60° C. for a further 48 h.

For workup, the cooled mixture was admixed with water, saturated with sodium chloride and extracted repeatedly with ethyl acetate. The combined organic phases were dried over magnesium sulphate, filtered and concentrated. The remaining residue was purified via preparative HPLC (column: Chromatorex, 125×30 mm 10 µm. Flow rate: 50 ml/min. Gradient (A=water+0.1% formic acid, B=acetonitrile). Run time per separation 38 min. Detection: 210 nm=>0 min 0% B, 6 min 10% B, 27 min 95% B, 38 min 95% B, 40 min 0% B=>). By lyophilization of the product-containing fractions, 24.4 mg (11% of theory) of the title compound were obtained.

LC-MS (Method 3): $R_t$=1.47 min; MS (ESIpos): m/z=426 [M+H]$^+$ $^1$H-NMR (400 MHz, DMSO-d$_6$): δ [ppm]=1.59-1.84 (m, 4H), 1.86-2.10 (m, 4H), 2.45-2.65 (m, 2H, partially covered by solvent signal), 3.20-3.41 (m, 2H, partially overlapped by water signal), 3.46 (dt, 1H), 3.62 (dt, 1H), 4.73 (dd, 1H), 4.81 (s, 2H), 4.98 (q, 2H), 6.97 (d, 1H), 7.67 (dd, 1H), 8.08 (d, 1H).

Example 154

4-{[(5RS)-3-Oxo-5-(pyrrolidin-1-ylcarbonyl)-5,6,7,8-tetrahydro[1,2,4]triazolo[4,3-a]pyridin-2(3H)-yl]methyl}benzoic acid (Racemate)

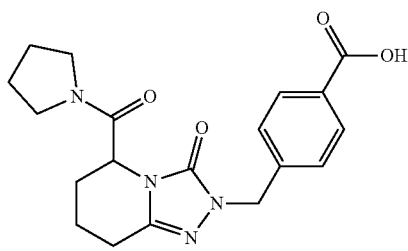 [SMILES: O=C(O)c1ccc(Cn2nc3n(c2=O)C(C(=O)N2CCCC2)CCC3)cc1]

tert-Butyl 4-{[(5RS)-3-oxo-5-(pyrrolidin-1-ylcarbonyl)-5,6,7,8-tetrahydro[1,2,4]triazolo[4,3-a]pyridin-2(3H)-yl]methyl}benzoate (racemate) (245 mg, 574 µmol) was dissolved in 5 ml of dichloromethane. After addition of 750 µl (9.7 mmol) of trifluoroacetic acid, the reaction mixture was stirred at room temperature overnight. For workup, the mixture was admixed with 3 N aqueous sodium hydroxide solution while cooling with an ice bath and stirring vigorously, and was thus adjusted to pH 3. After dilution with dichloromethane/water and extraction, the organic phase was removed, then the aqueous phase was extracted twice with dichloromethane. The combined organic phases were washed with saturated sodium chloride solution, dried over sodium sulphate, and concentrated and freed of residual solvent under reduced pressure. In this way, 195 mg (92% of theory) of the title compound were obtained.

LC-MS (Method 4): $R_t$=0.58 min; MS (ESIpos): m/z=371 [M+H]$^+$ $^1$H-NMR (400 MHz, DMSO-$d_6$): δ [ppm]=1.62-1.84 (m, 4H), 1.89-2.10 (m, 4H), 2.52-2.67 (m, 2H, partially covered by solvent signal), 3.22-3.41 (m, 2H, partially overlapped by water signal), 3.47 (dt, 1H), 3.62 (dt, 1H), 4.75 (dd, 1H), 4.84-4.94 (m, 2H), 7.31-7.36 (m, 2H), 7.88-7.93 (m, 2H), 12.92 (br s, 1H).

Example 155

N-Methyl-4-{[(5RS)-3-oxo-5-(pyrrolidin-1-ylcarbonyl)-5,6,7,8-tetrahydro[1,2,4]triazolo[4,3-a]pyridin-2(3H)-yl]methyl}benzamide (Racemate)

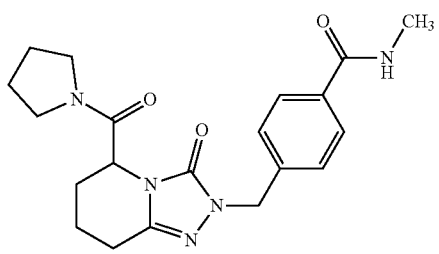 [SMILES: CNC(=O)c1ccc(Cn2nc3n(c2=O)C(C(=O)N2CCCC2)CCC3)cc1]

4-{[(5RS)-3-Oxo-5-(pyrrolidin-1-ylcarbonyl)-5,6,7,8-tetrahydro[1,2,4]triazolo[4,3-a]pyridin-2(3H)-yl]methyl}benzoic acid (racemate) (78.0 mg, 211 µmol) was initially charged in 2.5 ml of dichloromethane, then HATU (160 mg, 421 µmol), N,N-diisopropylethylamine (73 µl, 420 µmol) and methylamine, 33% in ethanol (31 µl, 250 µmol) were added. The mixture was stirred at room temperature overnight. Further methylamine, 33% in ethanol (13 µl, 110 µmol), was added and the mixture was left to stir at room temperature for a further 5 h. For workup, the mixture was diluted with dichloromethane/water, acidified with 1 N aqueous hydrochloric acid and extracted, and the organic phase was removed. The aqueous phase was extracted twice more with dichloromethane, then the combined organic phases were washed with saturated sodium chloride solution, dried over sodium sulphate and concentrated, and residual solvents were removed under reduced pressure. The crude product was separated by preparative HPLC (instrument: Waters Prep LC/MS System, column: Phenomenex Kinetex C18 51 µm 100×30 mm; eluent A: water, eluent B: acetonitrile, flow rate: 65 ml/min plus 5 ml of 2% formic acid in water, room temperature, wavelength 200-400 nm, at-column injection (complete injection); gradient profile: 0 to 2 min 10% eluent B, 2 to 2.2 min to 20% eluent B, 2.2 to 7 min to 60% eluent B, 7 to 7.5 min to 92% eluent B, 7.5 to 9 min at 92% B). By combination of the product-containing lyophilized fractions, 2.00 mg (2.5% of theory) of the title compound were obtained.

LC-MS (Method 12): $R_t$=1.00 min; MS (ESIpos): m/z=384 [M+H]$^+$ $^1$H-NMR (500 MHz, DMSO-$d_6$): δ [ppm]=1.62-1.83 (m, 4H), 1.87-2.11 (m, 4H), 2.47-2.67 (m, 2H, partially covered by solvent signal), 2.62 (dt, 1H), 2.77 (d, 3H), 3.23-3.40 (m, 2H, partially overlapped by water signal), 3.47 (dt, 1H), 3.62 (dt, 1H), 4.75 (dd, 1H), 4.85 (s, 2H), 7.28 (d, 2H), 7.78 (d, 2H), 8.39 (br q, 1H).

Example 156

N,N-Dimethyl-4-{[(5RS)-3-oxo-5-(pyrrolidin-1-ylcarbonyl)-5,6,7,8-tetrahydro[1,2,4]triazolo[4,3-a]pyridin-2(3H)-yl]methyl}benzamide (Racemate)

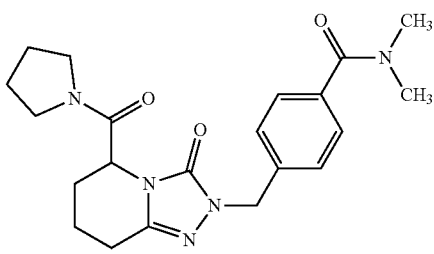 [SMILES: CN(C)C(=O)c1ccc(Cn2nc3n(c2=O)C(C(=O)N2CCCC2)CCC3)cc1]

4-{[(5RS)-3-Oxo-5-(pyrrolidin-1-ylcarbonyl)-5,6,7,8-tetrahydro[1,2,4]triazolo[4,3-a]pyridin-2(3H)-yl]methyl}benzoic acid (racemate) (78.0 mg, 211 µmol) was initially charged in 2.5 ml of dichloromethane, then HATU (160 mg, 421 µmol), N,N-diisopropylethylamine (73 µl, 420 µmol) and dimethylamine, 2 M in THF (126 µl, 252 µmol), were added. The mixture was stirred at room temperature at first for 4 h, then over a weekend. Further dimethylamine, 2 M in THF (105 µl, 210 µmol), was added and the mixture was left to stir at room temperature for a further 54 h. For workup, the mixture was diluted with dichloromethane/water, acidified with 1 N aqueous hydrochloric acid and extracted, and the organic phase was removed. The aqueous phase was extracted twice more with dichloromethane, then the combined organic phases were washed with saturated sodium chloride solution, dried over sodium sulphate and concentrated, and residual solvents were removed under reduced pressure. The crude product was dissolved in acetonitrile/water and separated by preparative HPLC (column: Kromasil C18, 125×30 mm, 10 µm, eluent: acetonitrile (B)/water+0.1% TFA (A), gradient: 0 min 90% A, 6 min 90% A, 18 min 5% A, 20 min 5% A, 21 min 90% A, flow rate: 75 ml/min, detector: 210 nm). By combining the product-containing fractions and removing the solvents under reduced pressure, 36.7 mg (42% of theory) of the title compound were obtained.

LC-MS (Method 3): $R_t$=0.95 min; MS (ESIpos): m/z=398 [M+H]$^+$ $^1$H-NMR (400 MHz, DMSO-d$_6$): δ [ppm]=1.62-1.84 (m, 4H), 1.87-2.11 (m, 4H), 2.46-2.69 (m, 2H, partially covered by solvent signal), 2.90 (br s, 3H), 2.97 (br s, 3H), 3.26 (dt, 1H), 3.36 (dt, 1H), 3.47 (dt, 1H), 3.62 (dt, 1H, partially overlapped by water signal), 4.75 (dd, 1H), 4.85 (s, 2H), 7.24-7.29 (m, 2H), 7.34-7.39 (m, 2H).

Example 157

(5S)-2-(4-Methylbenzyl)-5-(pyrrolidin-1-ylcarbonyl)-2,5,6,7-tetrahydro-3H-pyrrolo[2,1-c][1,2,4]triazol-3-one (Enantiomer)

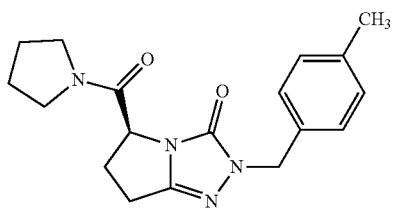 [SMILES: Cc1ccc(Cn2nc3n(c2=O)[C@H](C(=O)N2CCCC2)CC3)cc1]

(5S)-2-(4-Methylbenzyl)-3-oxo-2,5,6,7-tetrahydro-3H-pyrrolo[2,1-c][1,2,4]triazole-5-carboxylic acid (enantiomer) (50.0 mg, 183 µmol) was initially charged in DMF (2.2 ml) and dichloromethane (1.1 ml) at room temperature. Subsequently, 1-[bis(dimethylamino)methylene]-1H-benzotriazol-1-ium 3-oxide hexafluorophosphate (90.2 mg, 238 µmol) and N,N-diisopropylethylamine (64 µl, 370 µmol) were added. After stirring for 15 min, pyrrolidine (15.6 mg, 220 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure. The residue was purified further by chiral preparative HPLC [sample preparation: 37 mg dissolved in 1 ml of acetonitrile; injection volume: 0.20 ml; column: Daicel Chiralpak® AD-H 5 µm, 250×20 mm; eluent: n-heptane/ethanol: 30:70; flow rate: 20 ml/min; temperature 23° C.; UV detection: 220 nm]. 19 mg (31% of theory) of the title compound were obtained.

Analytical chiral HPLC: $R_t$=3.49 min, e.e. =99.9% [column: Daicel Chiralcel® AD-3 3 µm 50×4.6 mm; eluent: n-heptane/i-propanol 1:1, 0.2% trifluoroacetic acid, 1% water; flow rate: 1 ml/min; UV detection: 220 nm LC-MS (Method 4): $R_t$=0.70 min; MS (ESIpos): m/z=327 [M+H]$^+$ $^1$H-NMR (400 MHz, DMSO-d6) δ [ppm]: −0.008 (2.92), 0.008 (2.77), 1.781 (0.76), 1.798 (1.57), 1.816 (1.43), 1.832 (0.52), 1.887 (0.43), 1.903 (1.35), 1.919 (1.69), 1.936 (1.00), 2.274 (9.31), 2.327 (0.50), 2.366 (0.66), 2.377 (0.48), 2.388 (0.45), 2.524 (1.50), 2.670 (1.06), 2.685 (0.85), 2.693 (1.02), 2.706 (1.21), 2.715 (1.32), 2.748 (0.45), 2.755 (0.48), 2.786 (0.55), 2.808 (0.43), 3.291 (0.62), 3.309 (1.49), 3.328 (1.53), 3.345 (0.62), 3.396 (0.72), 3.403 (0.49), 3.414 (0.42), 3.421 (0.84), 3.438 (0.42), 3.527 (1.79), 3.646 (2.87), 3.663 (3.01), 3.688 (2.02), 3.705 (1.07), 4.698 (0.41), 4.736 (2.51), 4.748 (2.52), 4.897 (0.83), 4.905 (0.63), 4.919 (0.97), 4.925 (0.62), 7.137 (16.00).

The (5S) configuration was assigned on the basis of crystal structure elucidation for Example 157.

Example 158

(5RS)-5-(3,6-Dihydropyridin-1 (2H)-ylcarbonyl)-2-(4-methylbenzyl)-5,6,7,8-tetrahydro[1,2,4]triazolo[4,3-a]pyridin-3(2H)-one (Racemate)

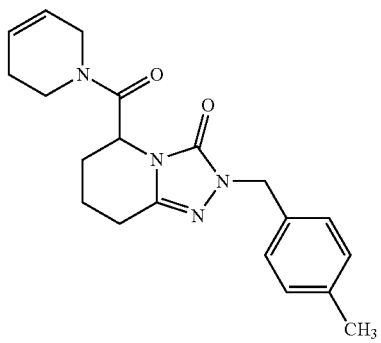 [SMILES: Cc1ccc(Cn2nc3n(c2=O)C(C(=O)N2CC=CCC2)CCC3)cc1]

1,2,3,6-Tetrahydropyridine (8.3 mg, 0.10 mmol) was initially charged in a cavity of a 96-well microtitre plate, and (5RS)-2-(4-methylbenzyl)-3-oxo-2,3,5,6,7,8-hexahydro[1,2,4]triazolo[4,3-a]pyridine-5-carboxylic Acid (Racemate) (28.7 mg, 0.10 mmol) and HATU (49.4 mg, 0.13 mmol), dissolved in 0.8 ml of DMF, were added. 50 µl of 4-methylmorpholine were added, and the microtitre plate was closed and agitated at room temperature overnight. Subsequently, the mixture was filtered and the filtrate was separated by preparative LC-MS.

(MS instrument: Waters, HPLC instrument: Waters (column Waters X-Bridge C18, 19 mm×50 mm, 5 µm, eluent A: water, eluent B: acetonitrile (ULC) with gradient; flow rate: 38.5 ml/min; modifier: aq. ammonia 5%, flow rate: 1.5 ml/min; UV detection: DAD; 210-400 nm)

or:

MS instrument: Waters, HPLC instrument: Waters (column Phenomenex Luna 5µ C18(2) 100 A, AXIA Tech. 50×21.2 mm, eluent A: water, eluent B: acetonitrile (ULC), with gradient; flow rate: 38.5 ml/min; modifier: aq. formic acid 10%, flow rate: 1.5 ml/min; UV detection: DAD; 210-400 nm)

The product-containing fractions were concentrated by means of a centrifugal dryer. The residue of all product fractions was dissolved in a total of 1.8 ml of DMSO, combined and concentrated again. In this way, 19.8 mg (56% of theory) of the title compound were obtained.

LC/MS (Method 13): R$_t$=0.95 min, MS (ESIpos): m/z=353 [M+H]+.

In analogy to Example 158, the example compounds shown in Table 1 were prepared.

TABLE 1

| Example | IUPAC name/structure (Yield) | Analytical data |
|---|---|---|
| Example 159 | (5RS)-2-(4-Methylbenzyl)-5-(morpholin-4-ylcarbonyl)-5,6,7,8-tetrahydro[1,2,4]triazolo[4,3-a]pyridin-3(2H)-one (racemate)<br><br>(19.9 mg, 56% of theory) | LC-MS (Method 13):<br>R$_t$ = 0.85 min<br>MS (ESIpos): m/z = 357<br>[M + H]+ |
| Example 160 | (5RS)-2-(4-Methylbenzyl)-5-[(4-methylpiperidin-1-yl)carbonyl]-5,6,7,8-tetrahydro[1,2,4]triazolo[4,3-a]pyridin-3(2H)-one (racemate)<br><br>(19.9 mg, 54% of theory) | LC-MS (Method 13):<br>R$_t$ = 1.02 min<br>MS (ESIpos): m/z = 369<br>[M + H]+ |
| Example 161 | (5RS)-2-(4-Methylbenzyl)-5-(piperidin-1-ylcarbonyl)-5,6,7,8-tetrahydro[1,2,4]triazolo[4,3-a]pyridin-3(2H)-one (racemate)<br><br>(22.1 mg, 62% of theory) | LC-MS (Method 13):<br>R$_t$ = 0.96 min<br>MS (ESIpos): m/z = 355<br>[M + H]+ |

TABLE 1-continued

| Example | IUPAC name/structure (Yield) | Analytical data |
|---|---|---|
| Example 162 | (5RS)-2-(4-Methylbenzyl)-5-[2(RS)-(2-methylpyrrolidin-1-yl)carbonyl]-5,6,7,8-tetrahydro[1,2,4]triazolo[4,3-a]pyridin-3(2H)-one (4 stereoisomers)<br>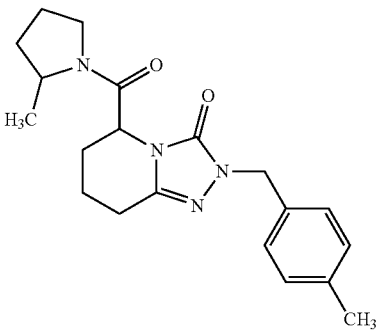 [SMILES: Cc1ccc(Cn2nc3n(c2=O)C(C(=O)N2CCCC2C)CCC3)cc1]<br>(19.4 mg, 55% of theory) | LC-MS (Method 13):<br>Rt = 0.95 min<br>MS (ESIpos): m/z = 355<br>[M + H]+ |

Example 163

(5RS)-2-[(6-Chloropyridin-3-yl)methyl]-5-{[(3S)-3-fluoropyrrolidin-1-yl]carbonyl}-2,5,6,7-tetrahydro-3H-pyrrolo[2,1-c][1,2,4]triazol-3-one (Diastereomer Mixture; 2 Isomers)

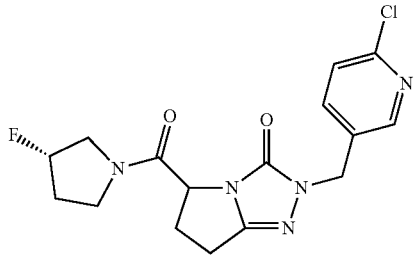 [SMILES: O=C(C1CCc2nn(Cc3ccc(Cl)nc3)c(=O)n21)N1CC[C@H](F)C1]

(5S)-2-[(6-Chloropyridin-3-yl)methyl]-3-oxo-2,5,6,7-tetrahydro-3H-pyrrolo[2,1-c][1,2,4]triazole-5-carboxylic acid (75.0 mg, 78% purity, 199 µmol) was initially charged in THF (2.1 ml) at room temperature. Subsequently, (3S)-3-fluoropyrrolidine hydrochloride (29.9 mg, 238 µmol), HATU (98.1 mg, 258 µmol) and triethylamine (170 µl, 1.2 mmol) were added. The reaction mixture was stirred at room temperature overnight. Triethylamine (55 µl, 400 µmol), (3S)-3-fluoropyrrolidine hydrochloride (12.5 mg, 99.3 µmol) and HATU (37.7 mg, 99.3 µmol) were added again and the mixture was stirred for a further 90 minutes. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 5.91 mg (8% of theory) of the title compound were obtained.

LC-MS (Method 3): $R_t$=0.94 min; MS (ESIpos): m/z=366 [M+H]+

$^1$H-NMR (400 MHz, DMSO-d6) δ[ppm]: −0.008 (1.89), 0.008 (1.61), 2.100 (1.11), 2.115 (1.07), 2.137 (1.07), 2.147 (1.03), 2.161 (0.86), 2.217 (0.84), 2.234 (0.96), 2.264 (1.15), 2.288 (0.52), 2.301 (0.58), 2.307 (0.66), 2.319 (0.78), 2.326 (0.84), 2.334 (0.82), 2.342 (0.82), 2.349 (0.56), 2.357 (0.66), 2.367 (0.62), 2.375 (0.60), 2.383 (0.74), 2.390 (1.01), 2.396 (1.11), 2.403 (0.98), 2.411 (1.03), 2.420 (1.15), 2.430 (0.78), 2.441 (0.66), 2.450 (0.48), 2.671 (1.15), 2.690 (1.41), 2.711 (3.40), 2.719 (3.04), 2.731 (4.98), 2.743 (2.57), 2.752 (4.06), 2.771 (0.86), 2.785 (0.78), 2.792 (1.25), 2.806 (0.64), 2.817 (1.35), 2.825 (1.37), 2.838 (1.27), 2.848 (1.59), 2.859 (1.03), 2.870 (1.01), 2.881 (0.68), 3.342 (1.25), 3.369 (0.74), 3.384 (0.56), 3.393 (0.78), 3.419 (0.66), 3.428 (0.70), 3.468 (0.40), 3.482 (0.72), 3.491 (0.86), 3.516 (1.11), 3.525 (0.74), 3.563 (0.56), 3.573 (0.52), 3.600 (1.29), 3.624 (2.33), 3.646 (1.45), 3.664 (1.89), 3.669 (1.89), 3.685 (2.33), 3.700 (1.55), 3.710 (1.21), 3.726 (1.75), 3.758 (0.58), 3.790 (0.72), 3.832 (0.54), 3.840 (0.62), 3.927 (0.54), 3.935 (0.56), 3.966 (0.74), 3.988 (0.68), 4.013 (0.58), 4.885 (16.00), 4.901 (1.47), 4.939 (1.43), 4.946 (1.55), 4.961 (1.61), 4.967 (1.35), 5.001 (0.46), 5.008 (0.60), 5.018 (0.88), 5.024 (1.17), 5.039 (0.76), 5.045 (0.56), 5.277 (1.37), 5.363 (0.78), 5.372 (0.92), 5.410 (1.37), 5.504 (0.90), 7.511 (6.01), 7.531 (7.46), 7.722 (3.92), 7.743 (3.34), 8.325 (4.96), 8.330 (5.23).

Example 164

(5RS)-5-{[(3S)-3-Fluoropyrrolidin-1-yl]carbonyl}-2-{[6-(trifluoromethyl)pyridin-3-yl]methyl}-2,5,6,7-tetrahydro-3H-pyrrolo[2,1-c][1,2,4]triazol-3-one (Diastereomer Mixture; 2 Isomers)

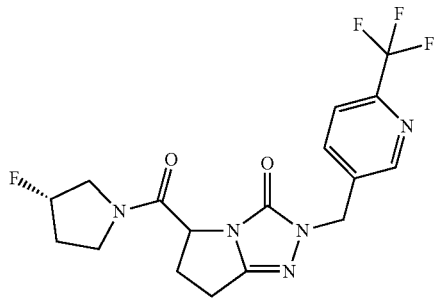 [SMILES: O=C(C1CCc2nn(Cc3ccc(C(F)(F)F)nc3)c(=O)n21)N1CC[C@H](F)C1]

(5S)-3-Oxo-2-{[6-(trifluoromethyl)pyridin-3-yl]methyl}-2,5,6,7-tetrahydro-3H-pyrrolo[2,1-c][1,2,4]triazole-5-carboxylic acid (75.0 mg, 228 µmol) was initially charged in THF (2.4 ml) at room temperature. Subsequently, (3S)-3-fluoropyrrolidine hydrochloride (34.4 mg, 274 µmol), HATU (113 mg, 297 µmol) and triethylamine (190 µl, 1.4 mmol) were added. The reaction mixture was stirred at room temperature for 20 hours. HATU (113 mg, 297 µmol), (3S)-3-fluoropyrrolidine hydrochloride (17.2 mg, 137 µmol) and triethylamine (190 µl, 1.4 mmol) were added again and the mixture was stirred overnight. The reaction mixture was admixed with water and concentrated under reduced pressure. HATU (113 mg, 297 mol), (3S)-3-fluoropyrrolidine hydrochloride (17.2 mg, 137 µmol) and triethylamine (190 µl, 1.4 mmol) were added again and the mixture was stirred at 40° C. overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 39.4 mg (43% of theory) of the title compound were obtained.

LC-MS (Method 4): $R_t$=0.63 min; MS (ESIpos): m/z=400 [M+H]$^+$ $^1$H-NMR (400 MHz, DMSO-d6) δ [ppm]: −0.008 (2.09), 0.008 (1.78), 1.994 (0.41), 2.073 (0.50), 2.101 (1.23), 2.119 (1.08), 2.140 (1.10), 2.150 (1.06), 2.165 (0.94), 2.220 (0.88), 2.238 (1.01), 2.266 (1.21), 2.327 (0.97), 2.333 (0.76), 2.343 (0.61), 2.351 (0.76), 2.358 (0.67), 2.366 (1.12), 2.385 (0.86), 2.393 (0.90), 2.407 (1.42), 2.413 (1.23), 2.422 (0.97), 2.431 (1.21), 2.440 (0.76), 2.451 (0.58), 2.665 (0.68), 2.680 (1.14), 2.700 (1.42), 2.721 (3.08), 2.729 (3.64), 2.741 (5.50), 2.762 (3.84), 2.772 (1.50), 2.782 (1.32), 2.795 (0.92), 2.803 (1.51), 2.827 (1.32), 2.835 (1.30), 2.848 (1.23), 2.858 (1.50), 2.870 (0.94), 2.881 (0.88), 2.893 (0.59), 3.372 (1.39), 3.398 (1.01), 3.424 (0.68), 3.432 (0.72), 3.472 (0.70), 3.488 (0.86), 3.496 (1.10), 3.518 (1.44), 3.541 (0.49), 3.567 (0.92), 3.578 (0.83), 3.605 (2.02), 3.630 (2.74), 3.651 (1.28), 3.669 (1.78), 3.674 (1.66), 3.688 (2.11), 3.704 (1.37), 3.714 (1.06), 3.729 (1.77), 3.761 (0.50), 3.794 (0.61), 3.834 (0.47), 3.843 (0.50), 3.930 (0.45), 3.938 (0.49), 3.969 (0.88), 3.991 (1.12), 4.017 (0.81), 4.053 (0.47), 4.079 (0.56), 4.110 (0.45), 4.886 (0.94), 4.893 (1.03), 4.908 (1.06), 4.915 (0.92), 4.953 (1.19), 4.960 (1.32), 4.975 (1.41), 4.982 (1.23), 5.012 (16.00), 5.032 (1.64), 5.039 (2.07), 5.054 (1.35), 5.060 (0.95), 5.279 (1.44), 5.365 (0.95), 5.374 (0.94), 5.412 (1.44), 5.497 (0.92), 5.506 (0.90), 7.904 (2.50), 7.925 (10.38), 7.937 (6.31), 7.958 (1.66), 8.675 (6.00).

Example 165

(5RS)-2-(3-Chloro-4-fluorobenzyl)-5-{[(3S)-3-fluoropyrrolidin-1-yl]carbonyl}-2,5,6,7-tetrahydro-3H-pyrrolo[2,1-c][1,2,4]triazol-3-one (Diastereomer Mixture; 2 Isomers)

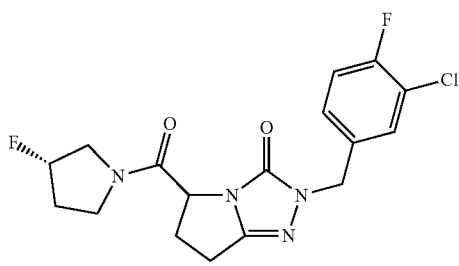 [SMILES: O=C(C1CCc2nn(Cc3ccc(F)c(Cl)c3)c(=O)n21)N1CC[C@H](F)C1]

(5S)-2-(3-Chloro-4-fluorobenzyl)-3-oxo-2,5,6,7-tetrahydro-3H-pyrrolo[2,1-c][1,2,4]triazole-5-carboxylic acid (75.0 mg, 87% purity, 209 µmol) was initially charged in THF (2.2 ml) at room temperature. Subsequently, (3S)-3-fluoropyrrolidine hydrochloride (31.5 mg, 251 µmol), HATU (103 mg, 272 µmol) and triethylamine (180 µl, 1.3 mmol) were added. The reaction mixture was stirred at room temperature overnight. (3S)-3-Fluoropyrrolidine hydrochloride (15.8 mg, 126 µmol), HATU (103 mg, 272 µmol) and triethylamine (180 µl, 1.3 mmol) were added again and the mixture was stirred at 70° C. for 4 hours. The reaction mixture was admixed with water and concentrated under reduced pressure. The residue was purified via preparative HPLC (Chromatorex C18, 10 µm, 125 mm×30 mm; eluent: acetonitrile/water with 0.1% formic acid gradient). The product-containing fractions were concentrated under reduced pressure, and 16.4 mg (20% of theory) of the title compound were obtained.

LC-MS (Method 3): $R_t$=1.37 min; MS (ESIpos): m/z=383 [M+H]$^+$ $^1$H-NMR (400 MHz, DMSO-d6) δ [ppm]: −0.149 (1.85), −0.008 (16.00), 0.008 (13.87), 0.146 (1.80), 2.098 (0.73), 2.266 (0.79), 2.327 (1.91), 2.366 (1.63), 2.396 (0.90), 2.421 (0.84), 2.523 (4.55), 2.670 (1.57), 2.698 (0.90), 2.711 (1.91), 2.727 (2.19), 2.738 (3.59), 2.758 (2.64), 2.799 (0.90), 2.827 (0.95), 2.851 (1.07), 2.874 (0.67), 3.372 (0.79), 3.423 (0.51), 3.495 (0.62), 3.515 (0.90), 3.602 (1.29), 3.628 (1.68), 3.666 (1.07), 3.685 (1.35), 3.727 (4.55), 3.970 (0.56), 3.991 (0.67), 4.015 (0.56), 4.826 (7.92), 4.881 (0.79), 4.903 (0.73), 4.947 (0.79), 4.954 (0.79), 4.970 (0.84), 5.029 (1.01), 5.047 (0.79), 5.277 (0.90), 5.364 (0.56), 5.411 (0.90), 5.503 (0.56), 6.922 (0.45), 7.276 (1.96), 7.288 (1.74), 7.379 (2.86), 7.402 (4.38), 7.424 (2.13), 7.458 (2.19), 7.473 (2.19).

Example 166

(5RS)-2-[(6-Chloropyridin-3-yl)methyl]-5-[(3,3-difluoropyrrolidin-1-yl)carbonyl]-2,5,6,7-tetrahydro-3H-pyrrolo[2,1-c][1,2,4]triazol-3-one (Racemate)

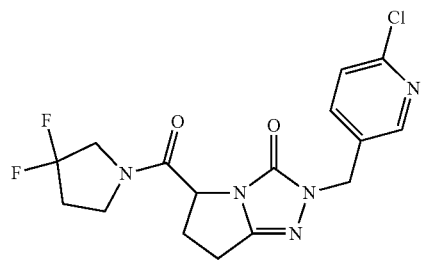 [SMILES: O=C(C1CCc2nn(Cc3ccc(Cl)nc3)c(=O)n21)N1CCC(F)(F)C1]

(5S)-2-[(6-Chloropyridin-3-yl)methyl]-3-oxo-2,5,6,7-tetrahydro-3H-pyrrolo[2,1-c][1,2,4]triazole-5-carboxylic acid (75.0 mg, 78% purity, 199 µmol) was initially charged in THF (2.1 ml) at room temperature. Subsequently, 3,3-difluoropyrrolidine hydrochloride (34.2 mg, 238 µmol), HATU (98.1 mg, 258 µmol) and triethylamine (170 µl, 1.2 mmol) were added. The reaction mixture was stirred at room temperature for 20 hours. 3,3-Difluoropyrrolidine hydrochloride (17.1 mg, 119 µmol), HATU (98.1 mg, 258 µmol) and triethylamine (55 µl, 400 µmol) were added again and the mixture was stirred overnight. The reaction mixture was admixed with water and concentrated under reduced pressure. The residue was purified via preparative HPLC (Chromatorex C18, 10 µm, 125 mm×30 mm; eluent: (acetonitrile/ water with 0.1% formic acid) gradient). The product-containing fractions were concentrated under reduced pressure, and 21.2 mg (28% of theory) of the title compound were obtained.

LC-MS (Method 3): $R_t$=1.11 min; MS (ESIpos): m/z=384 [M+H]$^+$ $^1$H-NMR (400 MHz, DMSO-d6) δ[ppm]: −0.149 (1.41), −0.008 (11.99), 0.008 (10.88), 0.146 (1.35), 2.327 (0.96), 2.366 (0.96), 2.391 (1.02), 2.412 (2.04), 2.424 (2.13), 2.440 (2.52), 2.450 (1.77), 2.459 (1.59), 2.523 (3.45), 2.561 (1.41), 2.578 (0.78), 2.596 (0.42), 2.669 (1.20), 2.675 (1.14), 2.686 (1.05), 2.694 (1.20), 2.716 (2.52), 2.736 (2.79), 2.743 (3.48), 2.751 (1.65), 2.777 (1.92), 2.791 (1.44), 2.820 (1.29), 2.842 (0.75), 3.550 (2.13), 3.569 (3.63), 3.588 (1.86), 3.682 (0.54), 3.699 (1.80), 3.729 (2.31), 3.744 (1.20), 3.763 (0.75), 3.774 (1.65), 3.808 (1.20), 3.895 (0.48), 3.925 (0.96), 3.962 (1.08), 3.976 (1.29), 3.995 (1.08), 4.002 (1.05), 4.021 (0.51), 4.230 (0.48), 4.259 (1.05), 4.291 (1.05), 4.886 (16.00), 4.927 (1.44), 4.934 (1.17), 4.948 (1.53), 5.011 (1.47), 5.018 (1.14), 5.032 (1.59), 5.039 (1.02), 7.510 (4.82), 7.531 (5.96), 7.718 (2.61), 7.723 (2.67), 7.739 (2.25), 7.744 (2.22), 8.324 (4.01), 8.329 (3.93).

Example 167

(5RS)-5-[(3,3-Difluoropyrrolidin-1-yl)carbonyl]-2-{[6-(trifluoromethyl)pyridin-3-yl]methyl}-2,5,6,7-tetrahydro-3H-pyrrolo[2,1-c][1,2,4]triazol-3-one (Racemate)

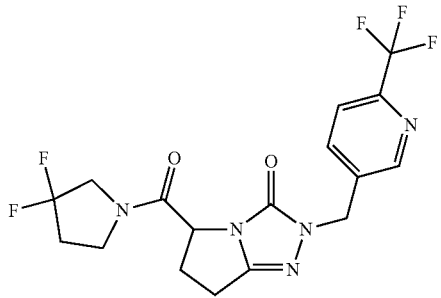 [SMILES: O=C(C1CCc2nn(Cc3ccc(C(F)(F)F)nc3)c(=O)n21)N1CCC(F)(F)C1]

(5S)-3-Oxo-2-{[6-(trifluoromethyl)pyridin-3-yl]methyl}-2,5,6,7-tetrahydro-3H-pyrrolo[2,1-c][1,2,4]triazole-5-carboxylic acid (75.0 mg, 228 μmol) was initially charged in THF (2.4 ml) at room temperature. Subsequently, 3,3-difluoropyrrolidine hydrochloride (39.4 mg, 274 μmol), HATU (113 mg, 297 μmol) and triethylamine (190 μl, 1.4 mmol) were added. The reaction mixture was stirred at room temperature for 20 hours. 3,3-Difluoropyrrolidine hydrochloride (19.7 mg, 137 μmol), HATU (113 mg, 297 μmol) and triethylamine (64 μl, 460 μmol) were added again and the mixture was stirred overnight. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 15.4 mg (16% of theory) of the title compound were obtained.

LC-MS (Method 3): $R_t$=1.30 min; MS (ESIpos): m/z=418 [M+H]$^+$ $^1$H-NMR (400 MHz, DMSO-d6) δ [ppm]: −0.150 (1.95), −0.034 (0.54), −0.009 (16.00), 0.007 (14.34), 0.146 (1.95), 2.327 (1.41), 2.331 (1.16), 2.365 (1.04), 2.408 (0.83), 2.421 (1.16), 2.442 (1.16), 2.460 (1.33), 2.523 (3.69), 2.581 (0.46), 2.669 (1.53), 2.710 (1.08), 2.725 (1.08), 2.747 (1.20), 2.753 (1.37), 2.762 (0.79), 2.787 (0.83), 2.801 (0.58), 2.830 (0.50), 3.556 (0.75), 3.573 (1.41), 3.592 (0.66), 3.702 (0.75), 3.732 (0.87), 3.748 (0.46), 3.770 (0.33), 3.779 (0.62), 3.812 (0.50), 3.929 (0.37), 3.964 (0.46), 3.979 (0.46), 3.998 (0.41), 4.006 (0.41), 4.263 (0.46), 4.293 (0.46), 4.948 (0.46), 4.963 (0.66), 5.012 (5.68), 5.025 (0.79), 5.046 (0.62), 5.053 (0.50), 7.904 (0.75), 7.924 (3.07), 7.935 (1.82), 7.958 (0.54), 8.673 (2.03).

Example 168

(5RS)-2-(3-Chloro-4-fluorobenzyl)-5-[(3,3-difluoropyrrolidin-1-yl)carbonyl]-2,5,6,7-tetrahydro-3H-pyrrolo[2,1-c][1,2,4]triazol-3-one (Racemate)

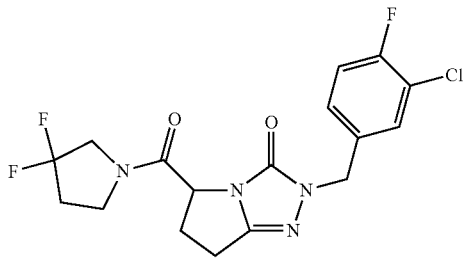 [SMILES: O=C(C1CCc2nn(Cc3ccc(F)c(Cl)c3)c(=O)n21)N1CCC(F)(F)C1]

(5S)-2-(3-Chloro-4-fluorobenzyl)-3-oxo-2,5,6,7-tetrahydro-3H-pyrrolo[2,1-c][1,2,4]triazole-5-carboxylic acid (75.0 mg, 87% purity, 209 μmol) was initially charged in THF (2.2 ml) at room temperature. Subsequently, 3,3-difluoropyrrolidine hydrochloride (36.1 mg, 251 μmol), HATU (103 mg, 272 μmol) and triethylamine (180 μl, 1.3 mmol) were added. The reaction mixture was stirred at room temperature overnight. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 64.0 mg (71% of theory) of the title compound were obtained.

LC-MS (Method 4): $R_t$=0.79 min; MS (ESIpos): m/z=401 [M+H]$^+$ $^1$H-NMR (400 MHz, DMSO-d6) δ [ppm]: −0.150 (1.35), 0.008 (10.27), 0.146 (1.18), 2.327 (2.69), 2.366 (2.86), 2.387 (1.85), 2.410 (3.37), 2.430 (3.54), 2.440 (3.87), 2.460 (2.86), 2.523 (9.60), 2.578 (1.85), 2.669 (3.03), 2.710 (3.54), 2.724 (3.87), 2.744 (5.56), 2.750 (5.73), 2.781 (3.71), 2.797 (2.53), 2.825 (2.02), 2.847 (1.35), 3.552 (3.37), 3.571 (5.73), 3.590 (3.03), 3.701 (3.20), 3.727 (7.58), 3.745 (1.85), 3.776 (2.69), 3.809 (2.02), 3.896 (0.67), 3.926 (1.52), 3.962 (2.02), 3.979 (2.02), 3.996 (1.68), 4.024 (0.84), 4.231 (0.84), 4.260 (1.68), 4.290 (1.68), 4.322 (0.51), 4.785 (1.01), 4.825 (16.00), 4.868 (0.84), 4.934 (1.85), 4.941 (1.85), 4.954 (2.36), 5.018 (2.36), 5.026 (1.68), 5.040 (2.36), 7.270 (3.20), 7.379 (5.22), 7.402 (7.24), 7.424 (3.87), 7.455 (3.87), 7.472 (3.87).

Example 169

(5RS)-2-[(6-Chloropyridin-3-yl)methyl]-5-[(3-fluoroazetidin-1-yl)carbonyl]-2,5,6,7-tetrahydro-3H-pyrrolo[2,1-c][1,2,4]triazol-3-one (Racemate)

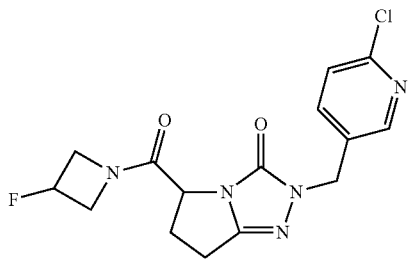 [SMILES: O=C(C1CCc2nn(Cc3ccc(Cl)nc3)c(=O)n21)N1CC(F)C1]

(5S)-2-[(6-Chloropyridin-3-yl)methyl]-3-oxo-2,5,6,7-tetrahydro-3H-pyrrolo[2,1-c][1,2,4]triazole-5-carboxylic acid (75.0 mg, 78% purity, 199 μmol) was initially charged in THF (2.1 ml) at room temperature. Subsequently, 3-fluoroazetidine hydrochloride (26.6 mg, 238 μmol), HATU (98.1 mg, 258 μmol) and triethylamine (170 μl, 1.2 mmol) were added. The reaction mixture was stirred at room temperature overnight. 3-Fluoroazetidine hydrochloride (13.3 mg, 119 μmol), HATU (98.1 mg, 258 μmol) and triethylamine (55 μl, 400 μmol) were added again and the mixture was stirred for a further 5 hours. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 15.4 mg (21% of theory) of the title compound were obtained.

LC-MS (Method 4): $R_t$=0.52 min; MS (ESIpos): m/z=352 [M+H]$^+$ $^1$H-NMR (400 MHz, DMSO-d6) δ[ppm]: −0.149 (0.73), −0.008 (6.62), 0.008 (5.33), 0.146 (0.69), 2.328 (0.95), 2.367 (0.90), 2.390 (0.90), 2.422 (4.13), 2.453 (1.25), 2.524 (2.58), 2.670 (1.38), 2.675 (1.55), 2.690 (1.68), 2.723 (12.26), 3.724 (0.60), 3.929 (1.25), 3.962 (1.55), 3.995 (1.25), 4.024 (1.42), 4.193 (0.69), 4.207 (0.77), 4.225 (1.20), 4.253 (1.72), 4.277 (2.02), 4.293 (1.33), 4.310 (1.46), 4.321 (1.25), 4.343 (0.86), 4.429 (0.60), 4.455 (1.12), 4.489 (1.29), 4.514 (1.55), 4.544 (1.03), 4.557 (1.12), 4.582 (0.39), 4.664 (0.65), 4.679 (0.77), 4.695 (0.77), 4.719 (3.23), 4.731 (4.39), 4.757 (0.69), 4.834 (0.65), 4.877 (16.00), 4.917 (0.77), 5.093 (0.60), 5.343 (0.82), 5.350 (0.99), 5.358 (0.77), 5.374 (0.56), 5.390 (0.77), 5.398 (0.95), 5.486 (0.82), 5.493 (0.99), 5.500 (0.82), 5.532 (0.77), 5.540 (0.90), 7.495 (1.08), 7.506 (6.37), 7.516 (1.55), 7.526 (7.87), 7.720 (4.22), 7.741 (3.61), 8.326 (6.06).

Example 170

(5RS)-5-[(3-Fluoroazetidin-1-yl)carbonyl]-2-{[6-(trifluoromethyl)pyridin-3-yl]methyl}-2,5,6,7-tetrahydro-3H-pyrrolo[2,1-c][1,2,4]triazol-3-one (Racemate)

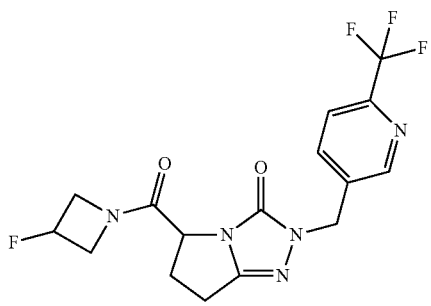 [SMILES: O=C(C1CCc2nn(Cc3ccc(C(F)(F)F)nc3)c(=O)n21)N1CC(F)C1]

(5S)-3-Oxo-2-{[6-(trifluoromethyl)pyridin-3-yl]methyl}-2,5,6,7-tetrahydro-3H-pyrrolo[2,1-c][1,2,4]triazole-5-carboxylic acid (75.0 mg, 228 μmol) was initially charged in THF (2.4 ml) at room temperature. Subsequently, 3-fluoroazetidine hydrochloride (30.6 mg, 274 μmol), HATU (113 mg, 297 μmol) and triethylamine (190 μl, 1.4 mmol) were added. The reaction mixture was stirred at room temperature for 20 hours. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 5.30 mg (6% of theory) of the title compound were obtained.

LC-MS (Method 3): $R_t$=1.12 min; MS (ESIpos): m/z=386 [M+H]$^+$ $^1$H-NMR (400 MHz, DMSO-d6) δ [ppm]: −0.008 (3.13), 0.008 (3.01), 2.328 (0.70), 2.366 (0.52), 2.405 (0.67), 2.432 (3.56), 2.464 (1.22), 2.523 (2.04), 2.670 (0.85), 2.734 (10.77), 3.729 (1.73), 3.938 (1.10), 3.966 (1.37), 3.999 (1.13), 4.028 (1.28), 4.200 (0.64), 4.215 (0.67), 4.230 (1.03), 4.257 (1.52), 4.284 (1.83), 4.296 (1.28), 4.314 (1.16), 4.326 (1.19), 4.348 (0.73), 4.434 (0.46), 4.459 (0.94), 4.494 (1.13), 4.518 (1.37), 4.547 (0.82), 4.561 (0.79), 4.669 (0.55), 4.684 (0.64), 4.746 (3.95), 4.960 (0.43), 5.003 (13.17), 5.043 (0.46), 5.352 (0.88), 5.392 (0.70), 5.400 (0.85), 5.495 (0.88), 5.503 (0.70), 5.543 (0.82), 5.754 (16.00), 7.899 (2.74), 7.919 (9.79), 7.934 (6.11), 7.955 (1.83), 8.674 (6.48).

Example 171

(5RS)-2-(3-Chloro-4-fluorobenzyl)-5-[(3-fluoroazetidin-1-yl)carbonyl]-2,5,6,7-tetrahydro-3H-pyrrolo[2,1-c][1,2,4]triazol-3-one (Racemate)

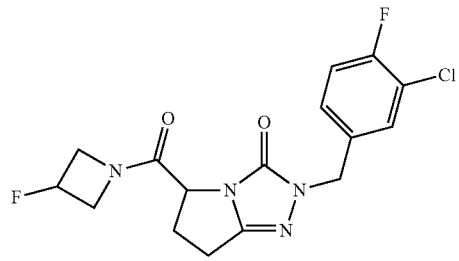 [SMILES: O=C(C1CCc2nn(Cc3ccc(F)c(Cl)c3)c(=O)n21)N1CC(F)C1]

(5S)-2-(3-Chloro-4-fluorobenzyl)-3-oxo-2,5,6,7-tetrahydro-3H-pyrrolo[2,1-c][1,2,4]triazole-5-carboxylic acid (75.0 mg, 87% purity, 209 μmol) was initially charged in THF (2.2 ml) at room temperature. Subsequently, 3-fluoroazetidine hydrochloride (28.0 mg, 251 mol), HATU (103 mg, 272 μmol) and triethylamine (180 μl, 1.3 mmol) were added. The reaction mixture was stirred at room temperature over the weekend. 3-Fluoroazetidine hydrochloride (14.0 mg, 126 μmol), HATU (103 mg, 272 μmol) and triethylamine (180 μl, 1.3 mmol) were added again and the mixture was stirred at 70° C. for 4 hours. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 31.2 mg (40% of theory) of the title compound were obtained.

LC-MS (Method 3): R$_t$=1.34 min; MS (ESIpos): m/z=369 [M+H]$^+$ $^1$H-NMR (400 MHz, DMSO-d6) δ[ppm]: −0.149 (1.75), −0.008 (16.00), 0.146 (1.81), 2.328 (1.81), 2.366 (1.17), 2.423 (4.50), 2.454 (1.58), 2.670 (1.99), 2.731 (14.31), 3.935 (1.46), 3.965 (1.87), 3.996 (1.46), 4.023 (1.87), 4.227 (1.46), 4.254 (2.10), 4.281 (2.57), 4.297 (1.69), 4.309 (1.75), 4.430 (0.70), 4.455 (1.34), 4.487 (1.58), 4.516 (1.81), 4.543 (1.11), 4.557 (1.05), 4.737 (4.96), 4.775 (1.40), 4.816 (12.67), 4.862 (0.93), 5.351 (1.23), 5.398 (1.11), 5.494 (1.11), 5.540 (1.05), 5.753 (1.69), 7.273 (3.62), 7.374 (5.26), 7.397 (7.82), 7.419 (3.68), 7.453 (4.67), 7.470 (4.67).

Example 172

(5RS)-2-[(6-Chloropyridin-3-yl)methyl]-5-{[(3R,4S)-3,4-difluoropyrrolidin-1-yl]carbonyl}-2,5,6,7-tetrahydro-3H-pyrrolo[2,1-c][1,2,4]triazol-3-one (Racemate)

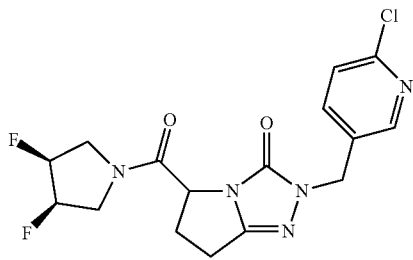 [SMILES: O=C(C1CCc2nn(Cc3ccc(Cl)nc3)c(=O)n21)N1C[C@@H](F)[C@@H](F)C1]

(5S)-2-[(6-Chloropyridin-3-yl)methyl]-3-oxo-2,5,6,7-tetrahydro-3H-pyrrolo[2,1-c][1,2,4]triazole-5-carboxylic acid (75.0 mg, 78% purity, 199 μmol) was initially charged in THF (2.0 ml) at room temperature. Subsequently, (3R,4S)-3,4-difluoropyrrolidine hydrochloride (34.2 mg, 238 μmol), HATU (98.1 mg, 258 μmol) and triethylamine (170 μl, 1.2 mmol) were added. The reaction mixture was stirred at room temperature for 20 hours. HATU (98.1 mg, 258 mol), triethylamine (55 μl, 400 μmol) and (3R,4S)-3,4-difluoropyrrolidine hydrochloride (17.1 mg, 119 μmol) were added again and the mixture was stirred at room temperature overnight. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 45.7 mg (59% of theory) of the title compound were obtained.

LC-MS (Method 3): R$_t$=1.01 min; MS (ESIpos): m/z=384 [M+H]$^+$ $^1$H-NMR (400 MHz, DMSO-d6) δ [ppm]: 2.327 (0.78), 2.350 (0.62), 2.358 (0.83), 2.366 (1.14), 2.384 (1.04), 2.401 (1.27), 2.409 (1.25), 2.418 (1.33), 2.447 (1.17), 2.633 (0.44), 2.674 (1.90), 2.694 (2.26), 2.706 (1.74), 2.722 (2.89), 2.728 (4.29), 2.748 (5.23), 2.783 (2.50), 2.806 (2.06), 2.818 (1.01), 2.828 (1.61), 2.839 (1.27), 2.852 (0.60), 2.862 (0.96), 3.478 (1.04), 3.487 (0.99), 3.512 (1.46), 3.521 (1.59), 3.532 (1.30), 3.567 (1.27), 3.652 (1.35), 3.666 (1.72), 3.687 (1.67), 3.700 (1.87), 3.722 (1.51), 3.734 (0.83), 3.752 (1.27), 3.763 (0.88), 3.784 (0.62), 3.797 (0.62), 3.849 (0.47), 3.862 (0.52), 3.877 (0.94), 3.892 (1.17), 3.926 (1.67), 3.940 (1.40), 3.966 (0.88), 4.181 (0.68), 4.196 (0.78), 4.209 (0.70), 4.223 (1.27), 4.237 (0.81), 4.249 (0.73), 4.265 (0.68), 4.885 (16.00), 4.961 (1.80), 4.968 (1.93), 4.983 (3.69), 4.990 (3.17), 5.004 (2.24), 5.094 (0.60), 5.262 (1.04), 5.274 (1.07), 5.284 (1.04), 5.322 (0.96), 5.344 (0.81), 5.356 (0.86), 5.367 (0.86), 5.383 (0.91), 5.394 (0.96), 5.407 (1.09), 5.420 (1.01), 5.430 (0.99), 5.450 (0.94), 5.458 (0.78), 5.473 (0.86), 5.486 (0.88), 7.511 (5.36), 7.531 (6.56), 7.715 (2.39), 7.720 (4.14), 7.726 (2.60), 7.741 (3.54), 7.746 (2.13), 8.324 (5.18).

Example 173

(5RS)-5-{[(3R,4S)-3,4-Difluoropyrrolidin-1-yl]carbonyl}-2-{[6-(trifluoromethyl)pyridin-3-yl]methyl}-2,5,6,7-tetrahydro-3H-pyrrolo[2,1-c][1,2,4]triazol-3-one (Racemate)

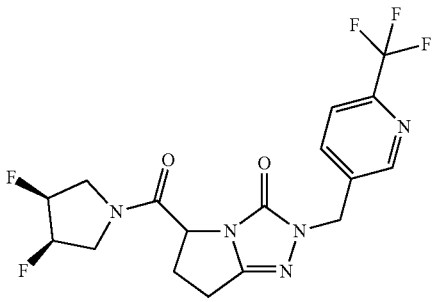 [SMILES: O=C(C1CCc2nn(Cc3ccc(C(F)(F)F)nc3)c(=O)n21)N1C[C@@H](F)[C@@H](F)C1]

(5S)-3-Oxo-2-{[6-(trifluoromethyl)pyridin-3-yl]methyl}-2,5,6,7-tetrahydro-3H-pyrrolo[2,1-c][1,2,4]triazole-5-carboxylic acid (75.0 mg, 228 μmol) was initially charged in THF (2.4 ml) at room temperature. Subsequently, (3R,4S)-3,4-difluoropyrrolidine hydrochloride (39.4 mg, 274 μmol), HATU (113 mg, 297 μmol) and triethylamine (190 μl, 1.4 mmol) were added. The reaction mixture was stirred at room temperature overnight. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 80.3 mg (84% of theory) of the title compound were obtained.

LC-MS (Method 3): R$_t$=1.24 min; MS (ESIpos): m/z=418 [M+H]$^+$ $^1$H-NMR (400 MHz, DMSO-d6) δ[ppm]: −0.149 (0.65), −0.008 (6.58), 0.008 (5.20), 0.146 (0.66), 2.327 (0.78), 2.366 (0.98), 2.428 (0.72), 2.457 (0.73), 2.670 (0.88), 2.682 (0.76), 2.703 (1.20), 2.710 (0.90), 2.715 (0.88), 2.731 (1.59), 2.738 (2.23), 2.758 (2.66), 2.794 (1.35), 2.816 (1.01), 2.838 (0.82), 2.850 (0.69), 2.872 (0.50), 3.364 (16.00), 3.482 (0.98), 3.517 (0.94), 3.525 (0.95), 3.572 (0.75), 3.656 (0.69), 3.670 (0.91), 3.692 (0.87), 3.705 (1.00), 3.726 (0.82), 3.745 (0.44), 3.756 (0.65), 3.768 (0.51), 3.882 (0.50), 3.896 (0.60), 3.930 (0.79), 3.944 (0.72), 3.971 (0.44), 4.199 (0.44), 4.227 (0.66), 4.240 (0.41), 4.975 (0.98), 4.982 (1.03), 4.997 (2.25), 5.012 (8.25), 5.264 (0.53), 5.286 (0.56), 5.324 (0.51), 5.369 (0.44), 5.387 (0.44), 5.409 (0.54), 5.489 (0.48), 7.904 (1.09), 7.924 (4.96), 7.935 (3.27), 7.956 (0.75), 8.672 (3.24).

Example 174

(5RS)-2-(3-Chloro-4-fluorobenzyl)-5-{[(3R,4S)-3,4-difluoropyrrolidin-1-yl)carbonyl]-2,5,6,7-tetrahydro-3H-pyrrolo[2,1-c][1,2,4]triazol-3-one (Racemate)

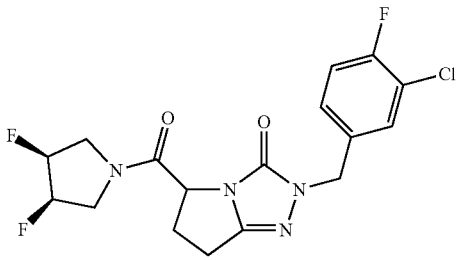 [SMILES: O=C(C1CCc2nn(Cc3ccc(F)c(Cl)c3)c(=O)n21)N1C[C@@H](F)[C@@H](F)C1]

(5S)-2-(3-Chloro-4-fluorobenzyl)-3-oxo-2,5,6,7-tetrahydro-3H-pyrrolo[2,1-c][1,2,4]triazole-5-carboxylic acid (75.0 mg, 87% purity, 209 µmol) was initially charged in THF (2.2 ml) at room temperature. Subsequently, (3R,4S)-3,4-difluoropyrrolidine hydrochloride (36.1 mg, 251 µmol), HATU (103 mg, 272 µmol) and triethylamine (180 µl, 1.3 mmol) were added. The reaction mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 62.9 mg (74% of theory) of the title compound were obtained.

LC-MS (Method 3): $R_t$=1.40 min; MS (ESIpos): m/z=401 [M+H]$^+$ $^1$H-NMR (400 MHz, DMSO-d6) δ[ppm]: −0.150 (0.49), −0.008 (4.42), 0.008 (3.97), 0.146 (0.49), 2.073 (1.28), 2.328 (0.88), 2.351 (0.74), 2.359 (1.01), 2.366 (1.55), 2.378 (1.10), 2.384 (1.24), 2.396 (1.31), 2.402 (1.46), 2.410 (1.42), 2.418 (1.49), 2.435 (0.81), 2.446 (1.28), 2.455 (0.79), 2.524 (2.73), 2.642 (0.58), 2.664 (1.38), 2.670 (1.24), 2.683 (1.76), 2.703 (2.73), 2.713 (2.19), 2.730 (3.31), 2.736 (5.21), 2.745 (3.81), 2.755 (6.60), 2.766 (1.38), 2.773 (1.40), 2.789 (3.58), 2.803 (1.13), 2.810 (2.52), 2.822 (1.20), 2.832 (1.94), 2.844 (1.62), 2.856 (0.74), 2.866 (1.24), 3.480 (1.28), 3.490 (1.29), 3.514 (1.73), 3.523 (1.89), 3.532 (1.56), 3.570 (1.60), 3.655 (1.51), 3.668 (2.03), 3.689 (2.10), 3.703 (2.28), 3.711 (1.82), 3.727 (4.12), 3.738 (1.04), 3.744 (1.01), 3.755 (1.49), 3.766 (1.10), 3.787 (0.79), 3.801 (0.76), 3.851 (0.59), 3.866 (0.68), 3.880 (1.19), 3.894 (1.42), 3.929 (2.01), 3.943 (1.51), 3.968 (1.08), 4.184 (0.83), 4.198 (1.01), 4.212 (0.84), 4.225 (1.55), 4.239 (0.95), 4.252 (0.84), 4.267 (0.77), 4.785 (0.79), 4.826 (16.00), 4.868 (0.67), 4.969 (2.05), 4.977 (2.23), 4.991 (4.24), 4.998 (3.85), 5.011 (2.70), 5.018 (1.64), 5.252 (0.76), 5.261 (1.19), 5.274 (1.24), 5.284 (1.20), 5.323 (1.24), 5.332 (0.97), 5.346 (0.99), 5.355 (1.01), 5.368 (1.06), 5.384 (1.11), 5.395 (1.13), 5.408 (1.28), 5.422 (1.17), 5.445 (0.99), 5.451 (1.11), 5.461 (0.92), 5.475 (1.06), 5.489 (0.99), 5.498 (0.68), 7.247 (1.13), 7.252 (2.10), 7.258 (2.23), 7.264 (2.55), 7.269 (2.79), 7.274 (3.33), 7.280 (3.02), 7.286 (2.98), 7.291 (1.74), 7.380 (4.01), 7.402 (6.63), 7.425 (2.97), 7.455 (3.85), 7.473 (3.87), 8.385 (0.41).

Example 175

(5RS)-5-{[(3R,4S)-3,4-Difluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (Racemate)

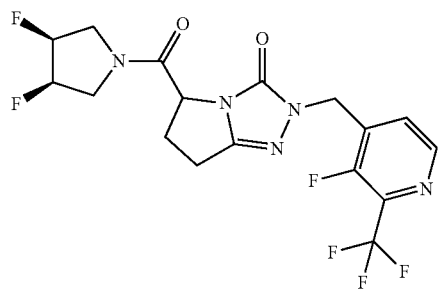 [SMILES: O=C(C1CCc2nn(Cc3ccnc(C(F)(F)F)c3F)c(=O)n21)N1C[C@@H](F)[C@@H](F)C1]

(5S)-2-{[3-Fluoro-2-(trifluoromethyl)pyridin-4-yl]methyl}-3-oxo-2,5,6,7-tetrahydro-3H-pyrrolo[2,1-c][1,2,4]triazole-5-carboxylic acid (66.0 mg, 183 µmol) was initially charged in THF (1.9 ml) at room temperature. Subsequently, (3R,4S)-3,4-difluoropyrrolidine hydrochloride (31.5 mg, 220 µmol), HATU (90.5 mg, 238 µmol) and triethylamine (150 µl, 1.1 mmol) were added. The reaction mixture was stirred at room temperature overnight. HATU (90.5 mg, 238 µmol), triethylamine (150 µl, 1.1 mmol) and (3R,4S)-3,4-difluoropyrrolidine hydrochloride (52.5 mg, 366 µmol) were added again and the mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 53.0 mg (63% of theory) of the title compound were obtained.

LC-MS (Method 4): $R_t$=0.71 min; MS (ESIpos): m/z=436 [M+H]$^+$ $^1$H-NMR (400 MHz, DMSO-d6) δ [ppm]: −0.149 (1.77), −0.008 (15.84), 0.008 (16.00), 0.146 (1.77), 0.854 (1.39), 1.236 (6.21), 1.410 (2.19), 2.327 (2.41), 2.366 (2.62), 2.438 (1.87), 2.670 (2.94), 2.700 (2.09), 2.710 (2.78), 2.719 (3.10), 2.732 (2.62), 2.755 (5.83), 2.775 (6.85), 2.808 (4.76), 2.827 (2.57), 2.850 (2.03), 2.862 (1.93), 2.884 (1.50), 3.487 (1.50), 3.530 (1.98), 3.578 (2.30), 3.675 (2.35), 3.695 (2.52), 3.707 (2.68), 3.730 (2.09), 3.772 (1.55), 3.793 (0.96), 3.805 (0.96), 3.886 (1.44), 3.900 (1.61), 3.936 (2.30), 3.973 (1.34), 4.198 (1.28), 4.225 (1.93), 4.239 (1.28), 4.991 (2.41), 4.999 (2.78), 5.014 (5.24), 5.020 (5.83), 5.035 (3.05), 5.062 (11.99), 5.073 (10.70), 5.113 (1.28), 5.288 (1.50), 5.388 (1.55), 7.607 (3.80), 7.620 (7.44), 7.632 (4.12), 8.573 (8.51), 8.585 (8.56), 10.193 (1.07).

Example 176

(5RS)-5-{[(3R,4S)-3,4-Difluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (Enantiomer 1)

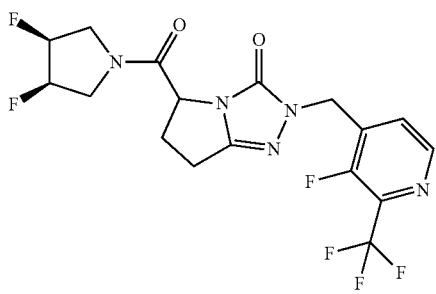 [SMILES: O=C(C1CCc2nn(Cc3ccnc(C(F)(F)F)c3F)c(=O)n21)N1C[C@@H](F)[C@@H](F)C1]

(5RS)-5-{[(3R,4S)-3,4-Difluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (racemate) was separated by chiral preparative HPLC [sample preparation: 53 mg dissolved in 3 ml of acetonitrile and 1 ml of ethanol (warm); injection volume: 0.25 ml; column: Daicel Chiralpak® AS-H 5 µm, 250×20 mm; eluent: n-heptane/ethanol 50:50; flow rate: 15 ml/min; temperature 25° C.; UV detection: 210 nm]. After the separation, 9.2 mg of enantiomer 1, which elutes first, and 12.4 mg of enantiomer 2, which elutes later, were isolated.

Enantiomer 1:

Analytical chiral HPLC: $R_t$=2.22 min, e.e. =99% [column: Daicel Chiraltek® AS, 50×4.6 mm; eluent: i-hexane/ethanol 50:50; flow rate: 1 ml/min; UV detection: 220 nm].

LC-MS (Method 4): $R_t$=0.70 min; MS (ESIpos): m/z=436 [M+H]$^+$ $^1$H-NMR (400 MHz, DMSO-d6) δ [ppm]: −0.149 (7.43), −0.059 (1.78), −0.045 (2.59), −0.029 (4.69), 0.019 (5.82), 0.146 (7.43), 1.238 (2.26), 2.328 (8.08), 2.365 (8.40), 2.425 (4.04), 2.433 (4.36), 2.559 (4.53), 2.670 (7.92), 2.709 (7.11), 2.731 (2.75), 2.753 (7.11), 2.775 (8.08), 2.805 (5.01), 2.825 (2.91), 2.848 (2.26), 3.524 (2.59), 3.580 (2.75), 3.673 (3.39), 3.694 (3.07), 3.708 (3.23), 3.716 (3.07), 3.726 (2.26), 3.760 (2.10), 3.896 (1.94), 3.934 (2.75), 3.980 (1.78), 4.224 (2.10), 4.998 (3.72), 5.017 (7.11), 5.035 (3.88), 5.063 (16.00), 5.114 (2.10), 5.277 (2.26), 5.326 (1.94), 5.373 (2.10), 5.397 (2.26), 5.411 (2.26), 5.454 (1.94), 7.606 (4.69), 7.619 (9.05), 7.631 (4.85), 8.572 (9.70), 8.583 (9.05).

Example 177

(5RS)-5-{[(3R,4S)-3,4-Difluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (Enantiomer 2)

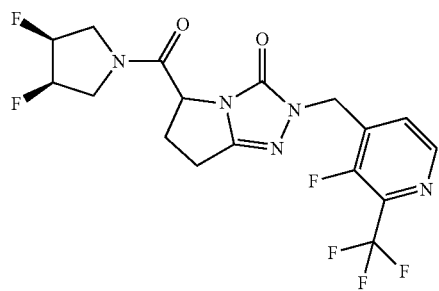 [SMILES: O=C(C1CCc2nn(Cc3ccnc(C(F)(F)F)c3F)c(=O)n21)N1C[C@@H](F)[C@@H](F)C1]

(5RS)-5-{[(3R,4S)-3,4-Difluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (racemate) was separated by chiral preparative HPLC [sample preparation: 53 mg dissolved in 3 ml of acetonitrile and 1 ml of ethanol (warm); injection volume: 0.25 ml; column: Daicel Chiralpak® AS-H 5 µm, 250×20 mm; eluent: n-heptane/ethanol 50:50; flow rate: 15 ml/min; temperature 25° C.; UV detection: 210 nm]. After the separation, 9.2 mg of enantiomer 1, which elutes first, and 12.4 mg of enantiomer 2, which elutes later, were isolated.

Enantiomer 2:

Analytical chiral HPLC: $R_t$=3.86 min, e.e. =98% [column: Daicel Chiraltek® AS, 50×4.6 mm; eluent: i-hexane/ethanol 40:60; flow rate: 1 ml/min; UV detection: 220 nm].

LC-MS (Method 4): $R_t$=0.71 min; MS (ESIpos): m/z=436 [M+H]$^+$ $^1$H-NMR (400 MHz, DMSO-d6) δ [ppm]: −0.149 (1.89), −0.027 (0.41), −0.025 (0.54), −0.022 (0.63), −0.019 (0.99), −0.016 (1.17), −0.015 (1.44), −0.008 (16.00), 0.008 (15.19), 0.014 (1.98), 0.016 (1.26), 0.019 (0.90), 0.021 (0.72), 0.024 (0.50), 0.030 (0.45), 0.146 (1.89), 2.327 (0.90), 2.332 (0.68), 2.366 (0.95), 2.523 (2.52), 2.560 (0.72), 2.669 (1.04), 2.710 (0.99), 2.718 (0.41), 2.755 (0.72), 2.775 (0.90), 2.808 (0.63), 5.021 (0.77), 5.036 (0.41), 5.063 (1.58), 5.072 (1.35), 7.607 (0.50), 7.620 (0.95), 7.632 (0.50), 8.572 (1.08), 8.585 (1.04).

Example 178

(5RS)-5-{[(3S)-3-Fluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (Diastereomer Mixture; 2 Isomers)

(5S)-2-{[3-Fluoro-2-(trifluoromethyl)pyridin-4-yl]methyl}-3-oxo-2,5,6,7-tetrahydro-3H-pyrrolo[2,1-c][1,2,4]triazole-5-carboxylic acid (66.0 mg, 182 µmol) was initially charged in THF (1.9 ml) at room temperature. Subsequently, (3S)-3-fluoropyrrolidine hydrochloride (27.5 mg, 219 µmol), HATU (90.2 mg, 237 µmol) and triethylamine (150 µl, 1.1 mmol) were added. The reaction mixture was stirred at room temperature overnight. (3S)-3-Fluoropyrrolidine hydrochloride (13.7 mg, 109 µmol), HATU (90.2 mg, 237 µmol) and triethylamine (150 µl, 1.1 mmol) were added again and the mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 60.9 mg (78% of theory) of the title compound were obtained.

LC-MS (Method 4): $R_t$=0.69 min; MS (ESIpos): m/z=418 [M+H]$^+$ $^1$H-NMR (400 MHz, DMSO-d6) δ[ppm]: −0.149 (0.93), 0.008 (7.50), 0.146 (0.99), 2.121 (2.67), 2.267 (2.36), 2.327 (3.16), 2.367 (3.29), 2.670 (2.60), 2.698 (2.11), 2.716 (2.91), 2.738 (6.08), 2.745 (5.95), 2.758 (9.67), 2.779 (6.82), 2.815 (2.48), 2.837 (2.36), 2.859 (2.17), 2.868 (2.85), 2.882 (2.29), 3.352 (2.29), 3.376 (1.43), 3.437 (1.18), 3.500 (1.80), 3.519 (2.17), 3.609 (3.04), 3.634 (4.16), 3.654 (2.60), 3.679 (3.47), 3.691 (3.53), 3.732 (3.04), 3.798 (1.18), 3.843 (0.99), 3.938 (1.05), 3.970 (1.49), 3.991 (1.61), 4.014 (0.93), 4.080 (0.81), 4.701 (1.12), 4.715 (0.99), 4.902 (2.05), 4.909 (2.11), 4.924 (2.29), 4.931 (1.80), 4.970 (2.42), 4.977 (2.60), 4.992 (2.79), 5.020 (2.11), 5.061 (15.01), 5.070 (16.00), 5.113 (1.55), 5.281 (2.42), 5.378 (1.74), 5.414 (2.42), 5.500 (1.55), 5.730 (0.68), 7.610 (5.40), 7.622 (9.67), 7.635 (5.21), 8.573 (11.22), 8.585 (10.60).

Example 179

(5RS)-5-{[(3S)-3-Fluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (Isomer 1)

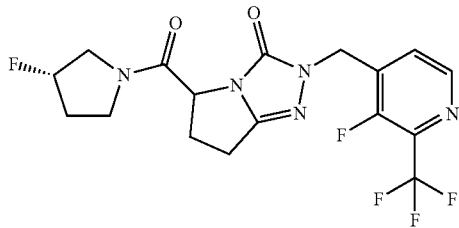 [SMILES: O=C(C1CCc2nn(Cc3ccnc(C(F)(F)F)c3F)c(=O)n21)N1CC[C@H](F)C1]

(5RS)-5-{[(3S)-3-Fluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (diastereomer mixture; 2 isomers) was separated by chiral preparative HPLC [sample preparation: 60 mg dissolved in 3 ml of acetonitrile and 1 ml of ethanol; injection volume: 0.25 ml; column: Daicel Chiralpak® AS-H 5 µm, 250×20 mm; eluent: n-heptane/ethanol 50:50; flow rate: 15 ml/min; temperature 25° C.; UV detection: 210 nm]. After the separation, 10.7 mg of isomer 1, which elutes first, and 15.6 mg of isomer 2, which elutes later, were isolated.

Isomer 1:

Analytical chiral HPLC: $R_t$=2.20 min, d.e.=99% [column: Daicel Chiraltek® AS, 50×4.6 mm; eluent: i-hexane/ethanol 50:50; flow rate: 1 ml/min; UV detection: 220 nm].

LC-MS (Method 4): $R_t$=0.68 min; MS (ESIpos): m/z=418 [M+H]$^+$ $^1$H-NMR (400 MHz, DMSO-d6) δ [ppm]: −0.149 (1.73), −0.008 (15.96), 0.008 (16.00), 0.146 (1.78), 1.100 (0.61), 1.118 (0.61), 1.235 (0.65), 2.104 (0.74), 2.155 (0.56), 2.257 (0.69), 2.327 (1.26), 2.366 (1.47), 2.396 (0.91), 2.417 (1.13), 2.441 (0.65), 2.523 (3.77), 2.665 (1.04), 2.670 (1.39), 2.698 (0.65), 2.710 (1.26), 2.746 (2.12), 2.758 (3.25), 2.764 (2.25), 2.775 (2.60), 2.792 (1.30), 2.814 (0.95), 2.844 (0.78), 2.866 (0.56), 3.345 (0.65), 3.356 (0.82), 3.375 (0.78), 3.386 (0.52), 3.403 (0.43), 3.477 (0.56), 3.502 (0.78), 3.520 (1.21), 3.545 (0.43), 3.572 (0.87), 3.586 (0.74), 3.609 (1.86), 3.635 (1.73), 3.700 (0.39), 3.722 (0.48), 3.969 (0.56), 3.991 (1.04), 4.017 (0.69), 4.058 (0.48), 4.083 (0.52), 4.111 (0.43), 5.023 (0.52), 5.071 (5.46), 5.116 (0.43), 5.278 (0.74), 5.367 (0.61), 5.412 (0.74), 5.498 (0.69), 7.610 (1.21), 7.623 (2.38), 7.635 (1.30), 8.574 (2.95), 8.586 (2.99).

Example 180

(5RS)-5-{[(3S)-3-Fluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (Isomer 2)

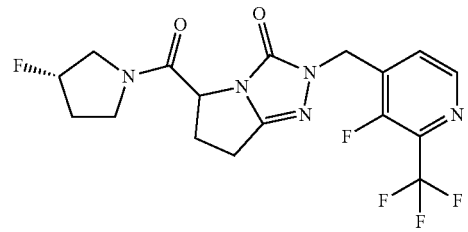 [SMILES: O=C(C1CCc2nn(Cc3ccnc(C(F)(F)F)c3F)c(=O)n21)N1CC[C@H](F)C1]

(5RS)-5-{[(3S)-3-Fluoropyrrolidin-1-yl]carbonyl}-2-{[3-fluoro-2-(trifluoromethyl)pyridin-4-yl]methyl}-2,5,6,7-tetrahydro-3H-pyrrolo[2,1-c][1,2,4]triazol-3-one (diastereomer mixture; 2 isomers) was separated by chiral preparative HPLC [sample preparation: 60 mg dissolved in 3 ml of acetonitrile and 1 ml of ethanol; injection volume: Daicel Chiralpak® AS-H 5 µm, 250×20 mm; eluent: n-heptane/ethanol 50:50; flow rate: 15 ml/min; temperature 25° C.; UV detection: 210 nm]. After the separation, 10.7 mg of isomer 1, which elutes first, and 15.6 mg of isomer 2, which elutes later, were isolated.

Isomer 2:

Analytical chiral HPLC: $R_t$=3.51 min, d.e.=97.4% [column: Daicel Chiraltek® AS, 50×4.6 mm; eluent: i-hexane/ethanol 50:50; flow rate: 1 ml/min; UV detection: 220 nm].

LC-MS (Method 4): $R_t$=0.67 min; MS (ESIpos): m/z=418 [M+H]$^+$ $^1$H-NMR (400 MHz, DMSO-d6) δ [ppm]: −0.149 (1.64), −0.008 (16.00), 0.008 (14.04), 0.146 (1.71), 0.858 (0.44), 1.100 (0.65), 1.118 (0.58), 1.236 (0.91), 1.984 (0.40), 2.010 (0.44), 2.118 (1.20), 2.146 (1.16), 2.215 (0.87), 2.237 (0.98), 2.266 (1.13), 2.327 (1.78), 2.337 (1.13), 2.344 (0.80), 2.354 (0.87), 2.366 (1.53), 2.410 (0.87), 2.433 (1.16), 2.441 (1.31), 2.451 (0.87), 2.463 (1.05), 2.523 (4.33), 2.670 (1.38), 2.674 (1.35), 2.697 (0.95), 2.710 (1.49), 2.716 (1.60), 2.738 (3.67), 2.748 (2.15), 2.759 (4.51), 2.771 (2.80), 2.779 (4.98), 2.818 (1.53), 2.828 (0.84), 2.838 (1.45), 2.847 (1.60), 2.859 (1.82), 2.869 (2.07), 2.882 (1.53), 2.891 (1.31), 2.904 (0.95), 3.333 (2.25), 3.352 (1.56), 3.361 (1.02), 3.379 (0.84), 3.393 (0.80), 3.401 (0.87), 3.428 (0.98), 3.436 (1.05), 3.499 (0.76), 3.525 (1.05), 3.534 (0.91), 3.630 (2.04), 3.655 (2.00), 3.679 (2.73), 3.690 (2.69), 3.706 (2.40), 3.716 (1.78), 3.732 (2.15), 3.739 (1.78), 3.769 (0.80), 3.800 (1.05), 3.844 (0.87), 3.866 (0.55), 3.875 (0.55), 3.931 (0.76), 3.939 (0.84), 3.962 (0.58), 4.902 (1.60), 4.909 (1.75), 4.924 (1.82), 4.931 (1.56), 4.970 (1.85), 4.977 (2.04), 4.992 (2.25), 4.998 (1.82), 5.018 (0.95), 5.061 (7.31), 5.071 (7.53), 5.113 (0.98), 5.282 (1.38), 5.377 (1.09), 5.415 (1.35), 5.510 (1.02), 7.609 (2.69), 7.622 (5.16), 7.635 (2.95), 8.573 (5.60), 8.585 (5.67).

Example 181

(5RS)-5-[(3,3-Difluoropyrrolidin-1-yl)carbonyl]-2-{[3-fluoro-2-(trifluoromethyl)pyridin-4-yl]methyl}-2,5,6,7-tetrahydro-3H-pyrrolo[2,1-c][1,2,4]triazol-3-one (Racemate)

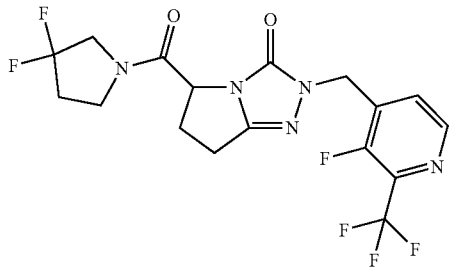 [SMILES: O=C(C1CCc2nn(Cc3ccnc(C(F)(F)F)c3F)c(=O)n21)N1CCC(F)(F)C1]

(5S)-2-{[3-Fluoro-2-(trifluoromethyl)pyridin-4-yl]methyl}-3-oxo-2,5,6,7-tetrahydro-3H-pyrrolo[2,1-c][1,2,4]triazole-5-carboxylic acid (66.0 mg, 182 µmol) was initially charged in THF (1.9 ml) at room temperature. Subsequently, 3,3-difluoropyrrolidine hydrochloride (31.4 mg, 219 µmol), HATU (90.2 mg, 237 µmol) and triethylamine (150 µl, 1.1 mmol) were added. The reaction mixture was stirred at room temperature overnight. 3,3-Difluoropyrrolidine hydrochloride (15.7 mg, 109 µmol), HATU (90.2 mg, 237 µmol) and triethylamine (150 µl, 1.1 mmol) were added again and the mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 38.9 mg (49% of theory) of the title compound were obtained.

LC-MS (Method 4): $R_t$=0.75 min; MS (ESIpos): m/z=436 [M+H]$^+$ $^1$H-NMR (400 MHz, DMSO-d6) δ [ppm]: −0.149 (0.93), −0.008 (7.61), 0.008 (6.67), 0.146 (0.86), 1.410 (1.15), 2.328 (1.87), 2.366 (2.22), 2.392 (1.51), 2.411 (2.51), 2.432 (4.52), 2.440 (3.30), 2.451 (3.66), 2.461 (3.95), 2.469 (3.09), 2.524 (5.96), 2.565 (3.01), 2.583 (1.94), 2.600 (1.08), 2.670 (2.30), 2.694 (1.00), 2.701 (1.08), 2.711 (3.52), 2.720 (2.22), 2.733 (2.44), 2.742 (4.52), 2.749 (3.01), 2.760 (4.66), 2.765 (5.24), 2.771 (5.67), 2.779 (3.52), 2.804 (3.37), 2.813 (3.23), 2.818 (2.94), 2.842 (2.51), 2.864 (1.58), 3.559 (4.09), 3.578 (6.82), 3.597 (3.66), 3.673 (0.65), 3.692 (1.08), 3.708 (3.66), 3.740 (3.73), 3.752 (1.94), 3.782 (3.16), 3.816 (2.15), 3.849 (0.50), 3.904 (0.86), 3.934 (1.72), 3.963 (2.22), 3.973 (1.87), 3.982 (2.51), 4.001 (2.08), 4.007 (2.08), 4.027 (1.00), 4.233 (0.86), 4.262 (1.87), 4.293 (1.79), 4.324 (0.65), 4.957 (2.15), 4.965 (2.22), 4.978 (2.58), 5.021 (1.65), 5.042 (2.73), 5.049 (2.37), 5.063 (16.00), 5.073 (14.28), 5.115 (1.72), 7.610 (2.58), 7.621 (5.09), 7.632 (2.80), 8.572 (8.18), 8.584 (8.18).

Example 182

(5RS)-5-[(3-Fluoroazetidin-1-yl)carbonyl]-2-{[3-fluoro-2-(trifluoromethyl)pyridin-4-yl]methyl}-2,5,6,7-tetrahydro-3H-pyrrolo[2,1-c][1,2,4]triazol-3-one (Racemate)

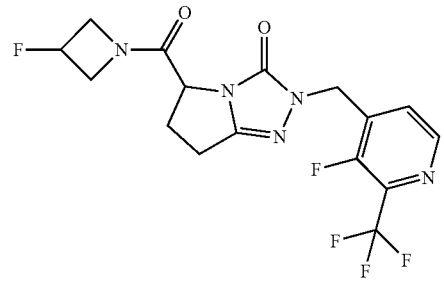 [SMILES: O=C(C1CCc2nn(Cc3ccnc(C(F)(F)F)c3F)c(=O)n21)N1CC(F)C1]

(5S)-2-{[3-Fluoro-2-(trifluoromethyl)pyridin-4-yl]methyl}-3-oxo-2,5,6,7-tetrahydro-3H-pyrrolo[2,1-c][1,2,4]triazole-5-carboxylic acid (66.0 mg, 182 µmol) was initially charged in THF (1.9 ml) at room temperature. Subsequently, 3-fluoroazetidine hydrochloride (24.4 mg, 219 µmol), HATU (90.2 mg, 237 µmol) and triethylamine (150 µl, 1.1 mmol) were added. The reaction mixture was stirred at room temperature overnight. 3-Fluoroazetidine hydrochloride (12.2 mg, 109 µmol), HATU (90.2 mg, 237 µmol) and triethylamine (150 µl, 1.1 mmol) were added again and the mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 39.0 mg (52% of theory) of the title compound were obtained.

LC-MS (Method 4): $R_t$=0.67 min; MS (ESIpos): m/z=404 [M+H]$^+$ $^1$H-NMR (400 MHz, DMSO-d6) δ [ppm]: 0.146 (0.43), 2.328 (1.09), 2.366 (0.75), 2.412 (1.14), 2.444 (4.98), 2.670 (1.11), 2.710 (1.84), 2.749 (16.00), 3.942 (1.73), 3.970 (2.16), 4.003 (1.75), 4.033 (2.11), 4.204 (0.91), 4.221 (1.02), 4.235 (1.70), 4.250 (1.86), 4.263 (2.36), 4.274 (2.30), 4.287 (2.57), 4.300 (2.39), 4.331 (1.86), 4.355 (1.09), 4.434 (0.70), 4.460 (1.45), 4.499 (1.61), 4.515 (2.30), 4.552 (1.16), 4.567 (1.16), 4.668 (0.77), 4.701 (1.64), 4.715 (2.16), 4.750 (4.27), 4.761 (5.57), 5.011 (1.55), 5.053 (11.95), 5.108 (1.18), 5.355 (1.34), 5.401 (1.20), 5.498 (1.27), 5.544 (1.23), 5.733 (0.75), 7.612 (4.61), 7.625 (8.73), 7.638 (4.84), 7.870 (0.66), 8.567 (9.82), 8.579 (9.68).

Example 183

(5S)-5-{[(3R,4R)-3-Fluoro-4-hydroxypyrrolidin-1-yl]carbonyl}-2-(4-methylbenzyl)-5,6,7,8-tetrahydro[1,2,4]triazolo[4,3-a]pyridin-3(2H)-one

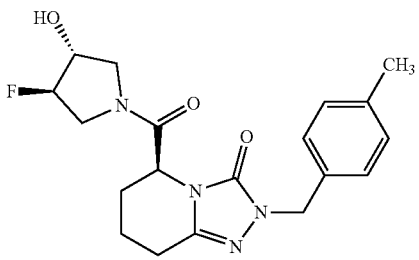 [SMILES: Cc1ccc(Cn2nc3n(c2=O)[C@H](C(=O)N2C[C@@H](O)[C@H](F)C2)CCC3)cc1]

(5S)-2-(4-Methylbenzyl)-3-oxo-2,3,5,6,7,8-hexahydro[1,2,4]triazolo[4,3-a]pyridine-5-carboxylic acid (100 mg, 327 μmol) was initially charged in THF (5.0 ml) at room temperature. Subsequently, HBTU (161 mg, 425 μmol) and N,N-diisopropylethylamine (280 μl, 1.6 mmol) were added. After stirring for 15 min, (3R,4R)-4-fluoropyrrolidin-3-ol hydrochloride (55.6 mg, 393 μmol) was added and the reaction mixture was stirred at room temperature overnight. The reaction mixture was concentrated under reduced pressure. The residue was purified via preparative HPLC (Method 10). The product-containing fractions were concentrated under reduced pressure, and 27.0 mg (22% of theory) of the title compound were obtained. LC-MS (Method 3): $R_t$=1.19 min; MS (ESIpos): m/z=375 [M+H]

$^1$H-NMR (400 MHz, DMSO-d6) δ [ppm]: −0.008 (1.05), 0.008 (0.98), 1.721 (0.88), 1.913 (0.46), 1.950 (0.66), 2.040 (0.52), 2.047 (0.53), 2.056 (0.46), 2.273 (16.00), 2.518 (1.63), 2.522 (1.63), 2.562 (0.77), 2.585 (1.21), 2.628 (0.44), 3.350 (0.47), 3.381 (0.72), 3.457 (0.51), 3.474 (0.47), 3.531 (0.80), 3.557 (0.57), 3.601 (0.59), 3.651 (0.61), 3.690 (1.43), 3.757 (0.46), 4.230 (0.42), 4.338 (0.47), 4.748 (5.25), 4.794 (0.41), 4.809 (0.78), 4.818 (0.72), 4.825 (0.49), 4.903 (0.56), 5.032 (0.53), 5.571 (0.87), 5.580 (0.87), 5.595 (0.49), 5.603 (0.47), 5.662 (0.68), 5.671 (0.71), 5.703 (0.94), 5.712 (0.92), 7.101 (0.88), 7.124 (13.88), 7.147 (0.89).

Example 184

(5S)-2-(Cyclopropylmethyl)-5-{[(3R,4S)-3,4-difluoropyrrolidin-1-yl]carbonyl}-5,6,7,8-tetrahydro[1,2,4]triazolo[4,3-a]pyridin-3(2H)-one

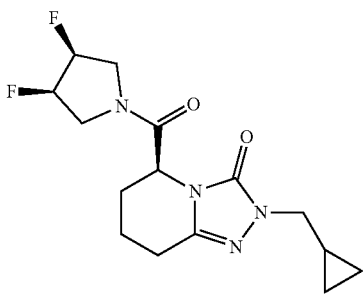 [SMILES: O=C([C@@H]1CCCc2nn(CC3CC3)c(=O)n21)N1C[C@@H](F)[C@@H](F)C1]

Under argon: (5S)-2-(Cyclopropylmethyl)-3-oxo-2,3,5,6,7,8-hexahydro[1,2,4]triazolo[4,3-a]pyridine-5-carboxylic acid (115 mg, 460 μmol) was initially charged in THF (8.5 ml) at room temperature. Subsequently, HATU (228 mg, 599 μmol) and N,N-diisopropylethylamine (240 μl, 1.4 mmol) were added. After stirring for 15 min, (3R,4S)-3,4-difluoropyrrolidine hydrochloride (79.3 mg, 553 μmol) was added and the reaction mixture was stirred at room temperature overnight. The reaction mixture was concentrated under reduced pressure, and the residue was dissolved with water and acetonitrile and purified via preparative HPLC (Chromatorex C18, 10 μm, 125 mm×30 mm; eluent: (acetonitrile/water with 0.1% formic acid) gradient). The product-containing fractions were concentrated under reduced pressure, and 53.3 mg (35% of theory) of the title compound were obtained.

LC-MS (Method 4): $R_t$=0.56 min; MS (ESIpos): m/z=327 [M+H]$^+$ $^1$H-NMR (400 MHz, DMSO-d6) δ [ppm]: 0.261 (12.07), 0.267 (12.21), 0.273 (12.25), 0.437 (10.80), 0.455 (10.86), 1.058 (3.69), 1.715 (5.00), 1.724 (4.78), 1.901 (1.20), 1.936 (2.51), 1.975 (2.53), 1.996 (2.05), 2.005 (1.59), 2.023 (2.13), 2.031 (2.37), 2.040 (2.55), 2.047 (2.47), 2.057 (2.29), 2.067 (1.95), 2.074 (1.97), 2.082 (1.71), 2.328 (0.60), 2.351 (0.50), 2.366 (0.78), 2.567 (3.73), 2.578 (4.58), 2.602 (5.04), 2.612 (6.20), 2.625 (3.47), 2.655 (1.93), 2.669 (1.41), 2.709 (0.42), 3.418 (0.94), 3.454 (14.61), 3.471 (16.00), 3.497 (2.67), 3.510 (2.61), 3.521 (2.53), 3.531 (2.55), 3.540 (1.59), 3.554 (1.24), 3.563 (1.65), 3.604 (1.57), 3.617 (1.89), 3.637 (1.35), 3.651 (1.65), 3.660 (2.07), 3.674 (3.47), 3.690 (3.05), 3.708 (2.67), 3.723 (2.69), 3.740 (2.27), 3.752 (2.17), 3.772 (1.39), 3.786 (1.06), 3.854 (1.63), 3.895 (1.18), 3.921 (1.51), 3.935 (1.67), 3.949 (1.12), 3.969 (1.67), 3.984 (1.63), 3.998 (1.04), 4.013 (0.94), 4.119 (1.06), 4.133 (1.22), 4.147 (1.18), 4.161 (2.13), 4.175 (1.37), 4.189 (1.16), 4.204 (1.02), 4.729 (4.68), 4.741 (6.85), 4.752 (4.56), 5.248 (1.77), 5.259 (1.83), 5.269 (2.07), 5.279 (1.73), 5.290 (1.26), 5.323 (1.55), 5.331 (1.57), 5.344 (1.71), 5.358 (1.65), 5.368 (1.99), 5.381 (2.29), 5.392 (1.87), 5.401 (1.93), 5.434 (1.30), 5.466 (1.55), 5.474 (1.55), 5.487 (1.22), 5.753 (11.24).

Example 185

(5S)-5-(Pyrrolidin-1-ylcarbonyl)-2-{[trans/cis-4-(trifluoromethyl)cyclohexyl]methyl}-5,6,7,8-tetrahydro[1,2,4]triazolo[4,3-a]pyridin-3(2H)-one (Isomer 1)

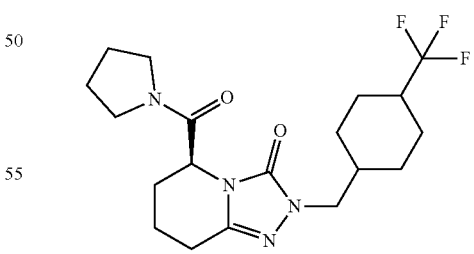

(5S)-3-Oxo-2-{[cis/trans-4-(trifluoromethyl)cyclohexyl]methyl}-2,3,5,6,7,8-hexahydro[1,2,4]triazolo[4,3-a]pyridine-5-carboxylic acid (diastereomer mixture, 2 isomers) (445 mg, 1.26 mmol) was initially charged in THF (13 ml) at room temperature. Subsequently, pyrrolidine (120 μl, 1.5 mmol), HATU (621 mg, 1.63 mmol) and triethylamine (880 μl, 6.3 mmol) were added and the reaction mixture was stirred at room temperature over the weekend. The reaction mixture was admixed with water and concentrated under reduced pressure. The residue was purified via preparative HPLC (Chromatorex C18, 10 μm, 125 mm×40 mm; eluent: (acetonitrile/water with 0.1% formic acid) gradient). The product-containing fractions were concentrated under reduced pressure, and 158 mg (31% of theory) of the diastereomer mixture (2 isomers) were obtained.

(5S)-5-(Pyrrolidin-1-ylcarbonyl)-2-{[trans/cis-4-(trifluoromethyl)cyclohexyl]methyl}-5,6,7,8-tetrahydro[1,2,4]triazolo[4,3-a]pyridin-3(2H)-one (diastereomer mixture; 2 isomers) was separated by chiral preparative HPLC [sample preparation: 158 mg dissolved in 15 ml of methanol; injection volume: 1 ml; column: Daicel Chiralpak® IB 5 μm, 250×30 mm; eluent: carbon dioxide/ethanol 70:30; flow rate: 80 ml/min; temperature 40° C.; UV detection: 210 nm]. After the separation, 56 mg of isomer 1, which elutes first, and 54 mg of isomer 2, which elutes later, were isolated.

Isomer 1:

Analytical chiral HPLC: $R_t$=0.85 min, d.e.=99% [column: Daicel Chiralpak® IB, 50×4.6 mm; eluent: n-heptane/ethanol 70:30; flow rate: 3 ml/min; UV detection: 210 nm].

LC-MS (Method 3): $R_t$=1.53 min; MS (ESIpos): m/z=401 [M+H]

$^1$H-NMR (600 MHz, DMSO-d6) δ [ppm]: 1.465 (2.98), 1.473 (3.40), 1.480 (3.84), 1.487 (4.67), 1.490 (4.53), 1.502 (2.02), 1.507 (1.91), 1.513 (1.33), 1.517 (1.11), 1.524 (1.67), 1.532 (1.52), 1.539 (1.17), 1.549 (1.06), 1.554 (0.73), 1.586 (1.97), 1.591 (2.58), 1.598 (2.08), 1.605 (1.53), 1.612 (1.40), 1.619 (0.96), 1.666 (0.68), 1.679 (0.82), 1.684 (0.90), 1.688 (0.91), 1.693 (0.73), 1.702 (0.78), 1.707 (1.03), 1.711 (1.20), 1.717 (1.36), 1.723 (1.20), 1.733 (0.80), 1.763 (0.70), 1.775 (3.05), 1.786 (5.27), 1.798 (4.12), 1.809 (1.20), 1.899 (1.02), 1.910 (3.13), 1.921 (4.16), 1.932 (2.69), 1.944 (0.83), 1.945 (0.83), 1.954 (0.68), 1.971 (0.80), 1.977 (1.36), 1.986 (1.26), 1.999 (0.71), 2.005 (0.80), 2.009 (0.82), 2.015 (1.00), 2.017 (0.86), 2.023 (0.93), 2.028 (1.06), 2.033 (0.95), 2.047 (0.72), 2.051 (1.08), 2.057 (1.44), 2.064 (1.42), 2.071 (1.20), 2.077 (0.81), 2.265 (0.75), 2.273 (0.73), 2.281 (0.74), 2.512 (0.95), 2.520 (0.72), 2.558 (1.03), 2.603 (1.01), 2.610 (1.93), 2.618 (1.12), 2.630 (0.67), 2.638 (1.12), 3.226 (0.77), 3.237 (1.55), 3.246 (1.41), 3.249 (1.09), 3.257 (2.33), 3.269 (1.10), 3.312 (1.21), 3.324 (2.53), 3.331 (1.48), 3.337 (16.00), 3.343 (1.86), 3.355 (0.76), 3.439 (0.82), 3.450 (1.78), 3.455 (1.23), 3.462 (1.08), 3.467 (2.08), 3.478 (0.95), 3.567 (0.52), 3.580 (0.64), 3.590 (4.31), 3.596 (3.89), 3.604 (4.32), 3.610 (3.99), 3.618 (1.89), 3.629 (0.84), 3.633 (0.57), 4.706 (1.96), 4.711 (2.09), 4.716 (2.32), 4.721 (1.86), 5.759 (13.81).

Example 186

(5S)-5-(Pyrrolidin-1-ylcarbonyl)-2-{[trans/cis-4-(trifluoromethyl)cyclohexyl]methyl}-5,6,7,8-tetrahydro[1,2,4]triazolo[4,3-a]pyridin-3(2H)-one (Isomer 2)

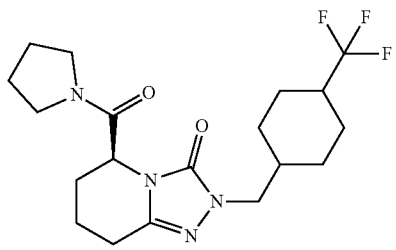 [SMILES: O=C([C@@H]1CCCc2nn(CC3CCC(C(F)(F)F)CC3)c(=O)n21)N1CCCC1]

(5S)-5-(Pyrrolidin-1-ylcarbonyl)-2-{[trans/cis-4-(trifluoromethyl)cyclohexyl]methyl}-5,6,7,8-tetrahydro[1,2,4]triazolo[4,3-a]pyridin-3(2H)-one (diastereomer mixture; 2 isomers) was separated by chiral preparative HPLC [sample preparation: 158 mg dissolved in 15 ml of methanol; injection volume: 1 ml; column: Daicel Chiralpak® IB 5 μm, 250×30 mm; eluent: carbon dioxide/ethanol 70:30; flow rate: 80 ml/min; temperature 40° C.; UV detection: After the separation, 56 mg of isomer 1, which elutes first, and 54 mg of isomer 2, which elutes later, were isolated.

Isomer 2:

Analytical chiral HPLC: $R_t$=1.84 min, d.e.=99% [column: Daicel Chiralpak® IB, 50×4.6 mm; eluent: n-heptane/ethanol 70:30; flow rate: 3 ml/min; UV detection: 210 nm].

LC-MS (Method 3): $R_t$=1.55 min; MS (ESIpos): m/z=401 [M+H]

$^1$H-NMR (400 MHz, DMSO-d6) δ [ppm]: 0.957 (1.26), 0.991 (4.36), 1.023 (5.17), 1.043 (2.00), 1.053 (2.17), 1.147 (2.40), 1.155 (2.66), 1.179 (6.23), 1.186 (6.72), 1.211 (5.99), 1.218 (6.21), 1.243 (2.34), 1.621 (0.98), 1.637 (2.09), 1.647 (2.92), 1.681 (10.46), 1.693 (11.63), 1.706 (11.51), 1.747 (2.77), 1.765 (7.80), 1.782 (12.99), 1.799 (10.09), 1.817 (4.65), 1.832 (7.41), 1.863 (6.74), 1.885 (3.67), 1.902 (9.17), 1.918 (11.87), 1.935 (8.62), 1.952 (3.10), 1.960 (2.94), 1.971 (5.00), 1.983 (5.77), 1.995 (4.03), 2.010 (3.59), 2.020 (2.67), 2.035 (2.39), 2.045 (1.37), 2.057 (0.91), 2.070 (0.68), 2.152 (1.28), 2.160 (1.36), 2.182 (2.42), 2.192 (1.94), 2.204 (2.33), 2.235 (1.10), 2.568 (2.93), 2.588 (3.12), 2.600 (6.14), 2.612 (3.25), 2.629 (1.51), 2.642 (2.49), 2.653 (1.16), 3.212 (1.80), 3.229 (3.63), 3.242 (4.02), 3.258 (6.37), 3.275 (3.12), 3.325 (7.13), 3.343 (3.58), 3.355 (3.72), 3.373 (1.75), 3.390 (0.75), 3.407 (1.01), 3.427 (13.83), 3.443 (16.00), 3.468 (5.79), 3.485 (2.63), 3.578 (2.60), 3.595 (5.41), 3.603 (2.82), 3.611 (3.18), 3.619 (4.08), 3.636 (1.81), 4.682 (4.94), 4.692 (5.90), 4.697 (6.35), 4.706 (4.55), 5.754 (5.05).

Example 187

(5S)-5-(2-Azabicyclo[2.1.1]hex-2-ylcarbonyl)-2-{[3-fluoro-2-(trifluoromethyl)pyridin-4-yl]methyl}-5,6,7,8-tetrahydro[1,2,4]triazolo[4,3-a]pyridin-3(2H)-one

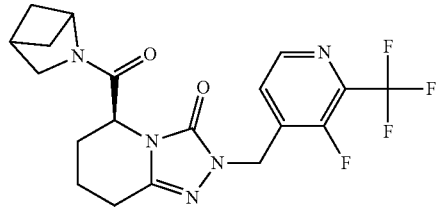 [SMILES: O=C([C@@H]1CCCc2nn(Cc3ccnc(C(F)(F)F)c3F)c(=O)n21)N1CC2CC1C2]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (126 mg, 319 μmol) was initially charged in THF (10 ml) at room temperature. Subsequently, HBTU (157 mg, 414 μmol) and N,N-diisopropylethylamine (560 μl, 3.2 mmol) were added. After stirring for 10 min, 2-(3-azabicyclo[2.1.1]hexane)trifluoroacetic acid (75.4 mg, 382 μmol) was added and the reaction mixture was stirred at room temperature for 30 min. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile with 0.1% formic acid gradient). The product-containing fractions were concentrated under reduced pressure, and 23.6 mg (17% of theory) of the title compound were obtained.

LC-MS (Method 3): $R_t$=1.31 min; MS (ESIpos): m/z=426 [M+H]

$^1$H-NMR (400 MHz, DMSO-d6) δ[ppm]: −0.149 (1.09), −0.008 (10.21), 0.008 (7.21), 0.146 (0.87), 0.942 (1.20), 0.958 (1.04), 1.216 (1.37), 1.233 (1.75), 1.241 (2.51), 1.259 (2.68), 1.305 (3.39), 1.323 (2.84), 1.331 (2.57), 1.357 (5.57), 1.368 (7.10), 1.379 (5.19), 1.405 (1.15), 1.658 (1.80), 1.757 (3.66), 1.768 (3.39), 1.825 (1.91), 1.866 (1.97), 1.932 (3.39), 2.041 (6.44), 2.270 (0.82), 2.327 (2.57), 2.366 (2.35), 2.523 (8.41), 2.558 (4.15), 2.573 (3.71), 2.587 (4.15), 2.608 (4.15), 2.620 (5.84), 2.634 (3.66), 2.665 (3.55), 2.669 (3.49), 2.710 (2.35), 2.861 (2.84), 2.870 (2.78), 2.951 (1.86), 3.234 (3.06), 3.258 (5.41), 3.518 (2.29), 3.538 (3.06), 3.630 (2.84), 3.649 (2.18), 4.557 (2.62), 4.575 (2.57), 4.650 (1.69), 4.665 (2.57), 4.681 (4.04), 4.697 (3.66), 4.912 (2.62), 4.920 (3.11), 4.928 (3.22), 4.935 (2.73), 5.050 (6.23), 5.070 (16.00), 7.128 (0.82), 7.547 (2.57), 7.560 (5.95), 7.574 (5.24), 7.589 (2.02), 8.383 (0.44), 8.564 (9.67), 8.576 (9.72).

Example 188

(5S)-5-[(1 SR,5RS)-2-Azabicyclo[3.1.0]hex-2-ylcarbonyl]-2-(4-methylbenzyl)-5,6,7,8-tetrahydro[1,2,4]triazolo[4,3-a]pyridin-3(2H)-one (Isomer 1)

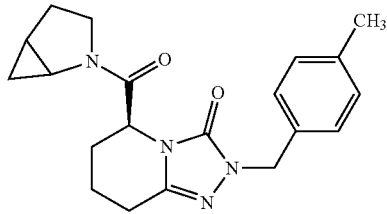 [SMILES: Cc1ccc(Cn2nc3n(c2=O)[C@H](C(=O)N2CCC4CC42)CCC3)cc1]

(5S)-5-[(cis)-2-Azabicyclo[3.1.0]hex-2-ylcarbonyl]-2-(4-methylbenzyl)-5,6,7,8-tetrahydro[1,2,4]triazolo[4,3-a]pyridin-3(2H)-one (diastereomer mixture; 2 isomers) was separated by chiral preparative HPLC [sample preparation: 85 mg dissolved in 5 ml of ethanol; injection volume: 0.4 ml; column: Daicel Chiralpak® AY-H 5 μm, 250×20 mm; eluent: n-heptane/ethanol 20:80; flow rate: 20 ml/min; temperature 25° C.; UV detection: 220 nm]. After the separation, 32.5 mg of isomer 1, which elutes first, and 38.2 mg of isomer 2, which elutes later, were isolated.
Isomer 1:
Analytical chiral HPLC: $R_t$=4.02 min, d.e.=100% [column: Daicel Chiraltrek® AY-3-3 μm 50×6 mm; eluent: n-heptane/ethanol 20:80; flow rate: 1 ml/min; UV detection: 220 nm].

LC-MS (Method 3): $R_t$=1.40 min; MS (ESIpos): m/z=353 [M+H]$^+$ $^1$H-NMR (400 MHz, DMSO-d6) δ[ppm]: 0.615 (0.46), 0.622 (0.54), 0.629 (0.93), 0.635 (0.92), 0.641 (0.61), 0.648 (0.51), 0.809 (0.76), 0.817 (0.50), 0.823 (0.47), 0.831 (0.78), 1.567 (0.43), 1.572 (0.41), 1.588 (0.43), 1.714 (0.42), 1.738 (0.72), 1.752 (0.82), 1.767 (0.82), 1.772 (0.81), 1.788 (0.56), 1.876 (0.40), 1.884 (0.65), 1.892 (0.58), 1.907 (0.57), 1.914 (0.54), 2.006 (0.50), 2.019 (0.71), 2.027 (0.71), 2.039 (0.88), 2.047 (0.75), 2.055 (0.78), 2.062 (0.61), 2.072 (0.55), 2.085 (0.41), 2.147 (0.65), 2.273 (12.38), 2.521 (1.08), 2.563 (0.61), 2.575 (0.60), 2.585 (0.88), 2.597 (0.58), 2.956 (0.78), 2.965 (0.46), 2.978 (0.41), 2.987 (0.84), 3.697 (0.82), 3.703 (0.88), 3.712 (0.99), 3.718 (0.98), 3.729 (1.15), 3.755 (0.41), 4.754 (5.01), 5.069 (0.77), 5.077 (0.94), 5.085 (0.87), 5.092 (0.76), 7.105 (0.41), 7.127 (16.00), 7.149 (0.41).

Example 189

(5S)-5-[(1 SR,5RS)-2-Azabicyclo[3.1.0]hex-2-ylcarbonyl]-2-(4-methylbenzyl)-5,6,7,8-tetrahydro[1,2,4]triazolo[4,3-a]pyridin-3(2H)-one (Isomer 2)

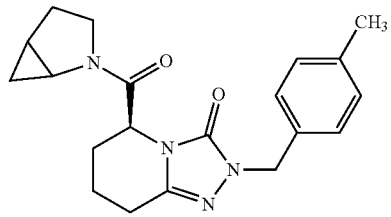 [SMILES: Cc1ccc(Cn2nc3n(c2=O)[C@H](C(=O)N2CCC4CC42)CCC3)cc1]

(5S)-5-[(cis)-2-Azabicyclo[3.1.0]hex-2-ylcarbonyl]-2-(4-methylbenzyl)-5,6,7,8-tetrahydro[1,2,4]triazolo[4,3-a]pyridin-3(2H)-one (diastereomer mixture; 2 isomers) was separated by chiral preparative HPLC [sample preparation: 85 mg dissolved in 5 ml of ethanol; injection volume: 0.4 ml; column: Daicel Chiralpak® AY-H 5 μm, 250×20 mm; eluent: n-heptane/ethanol 20:80; flow rate: 20 ml/min; temperature 25° C.; UV detection: 220 nm]. After the separation, 32.5 mg of isomer 1, which elutes first, and 38.2 mg of isomer 2, which elutes later, were isolated.
Isomer 2:
Analytical chiral HPLC: $R_t$=5.66 min, d.e.=100% [column: Daicel Chiraltrek® AY-3-3 μm 50×6 mm; eluent: n-heptane/ethanol 20:80; flow rate: 1 ml/min; UV detection: 220 nm].

LC-MS (Method 3): $R_t$=1.40 min; MS (ESIpos): m/z=353 [M+H]$^+$ $^1$H-NMR (400 MHz, DMSO-d6) δ [ppm]: 0.614 (0.50), 0.620 (0.50), 0.626 (0.41), 0.635 (0.65), 0.641 (0.60), 0.649 (1.02), 0.655 (1.00), 0.662 (0.63), 0.668 (0.58), 0.882 (0.78), 0.890 (0.52), 0.896 (0.49), 0.904 (0.80), 1.650 (0.44), 1.663 (0.49), 1.675 (0.55), 1.686 (0.65), 1.699 (0.66), 1.711 (0.49), 1.717 (0.46), 1.738 (0.71), 1.752 (1.01), 1.766 (0.91), 1.773 (0.80), 1.787 (0.63), 1.849 (0.41), 1.859 (0.77), 1.869 (0.51), 1.881 (0.53), 1.891 (0.53), 1.931 (0.50), 1.940 (0.52), 1.957 (0.47), 1.974 (0.44), 1.984 (0.56), 1.990 (0.56), 2.008 (0.63), 2.029 (0.60), 2.043 (0.80), 2.057 (0.46), 2.070 (0.43), 2.083 (0.41), 2.117 (0.70), 2.125 (0.46), 2.133 (0.56), 2.145 (0.56), 2.153 (0.61), 2.161 (0.55), 2.272 (15.63), 2.523 (0.89), 2.569 (0.89), 2.584 (1.31), 2.596 (0.68), 2.625 (0.46), 3.130 (0.70), 3.151 (1.03), 3.161 (0.58), 3.171 (0.50), 3.181 (0.88), 3.202 (0.43), 3.480 (0.51), 3.486 (0.56), 3.495 (0.90), 3.501 (0.87), 3.510 (0.57), 3.516 (0.48), 3.578 (0.46), 3.588 (0.49), 3.603 (0.58), 3.612 (0.61), 3.619 (0.51), 3.634 (0.43), 3.677 (0.56), 3.683 (0.53), 3.944 (0.41), 4.710 (0.44), 4.719 (0.51), 4.725 (0.68), 4.742 (5.01), 4.750 (1.90), 4.925 (0.82), 4.934 (0.96), 4.941 (1.03), 4.949 (0.79), 7.104 (0.56), 7.126 (16.00), 7.147 (0.61).

Example 190

(5S)-5-{[(2S)-2-Glycoloylpyrrolidin-1-yl]carbonyl}-2-(4-methylbenzyl)-5,6,7,8-tetrahydro[1,2,4]triazolo[4,3-a]pyridin-3(2H)-one

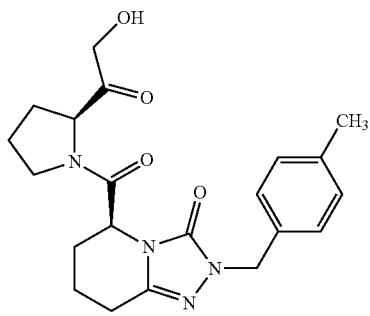 [SMILES: Cc1ccc(Cn2nc3n(c2=O)[C@H](C(=O)N2CCC[C@H]2C(=O)CO)CCC3)cc1]

2-[(2S)-1-{[(5S)-2-(4-Methylbenzyl)-3-oxo-2,3,5,6,7,8-hexahydro[1,2,4]triazolo[4,3-a]pyridin-5-yl]carbonyl}pyrrolidin-2-yl]-2-oxoethyl acetate (124 mg, 282 µmol) was initially charged in THF (1.5 ml) and water (1.5 ml), and lithium hydroxide (16.9 mg, 706 µmol) dissolved in water was added. After stirring for 30 min, the reaction mixture was admixed at room temperature with water, 1 N aqueous hydrochloric acid and saturated aqueous sodium chloride solution. The organic phase was removed and the aqueous phase was extracted three times with ethyl acetate. The combined organic phases were dried over sodium sulphate and filtered, and the filtrate was concentrated. The residue was purified via preparative HPLC (Method 11). The product-containing fractions were concentrated under reduced pressure, and 21.7 mg (19% of theory) of the title compound were obtained.

LC-MS (Method 3): $R_t$=1.16 min; MS (ESIpos): m/z=399 [M+H]$^+$ $^1$H-NMR (400 MHz, DMSO-d6) δ[ppm]: −0.008 (2.58), 0.008 (2.09), 1.569 (0.46), 1.595 (0.59), 1.606 (0.60), 1.632 (0.43), 1.697 (0.48), 1.715 (1.13), 1.730 (1.83), 1.746 (1.66), 1.753 (1.01), 1.762 (1.38), 1.778 (0.83), 1.892 (0.57), 1.910 (1.44), 1.922 (1.77), 1.927 (1.91), 1.939 (1.34), 1.945 (1.40), 2.036 (1.22), 2.047 (2.10), 2.058 (2.01), 2.123 (0.47), 2.140 (0.76), 2.161 (0.86), 2.172 (0.80), 2.193 (0.71), 2.269 (16.00), 2.467 (0.53), 2.523 (1.88), 2.559 (1.48), 2.573 (1.07), 2.601 (0.45), 3.540 (0.50), 3.558 (1.07), 3.565 (0.78), 3.575 (0.71), 3.582 (1.28), 3.600 (0.60), 3.740 (0.62), 3.756 (1.21), 3.765 (0.70), 3.773 (0.74), 3.781 (0.96), 3.797 (0.45), 4.153 (3.51), 4.170 (3.94), 4.559 (1.33), 4.573 (1.48), 4.580 (1.52), 4.595 (1.23), 4.731 (5.31), 4.735 (5.29), 4.808 (1.25), 4.820 (2.25), 4.831 (1.09), 5.177 (1.33), 5.192 (2.83), 5.207 (1.25), 7.090 (1.34), 7.112 (9.45), 7.118 (9.08), 7.125 (4.11), 7.139 (1.22).

Example 191

(5S)-5-[(1,1-Difluoro-5-azaspiro[2.3]hex-5-yl)carbonyl]-2-(4-methylbenzyl)-5,6,7,8-tetrahydro[1,2,4]triazolo[4,3-a]pyridin-3(2H)-one

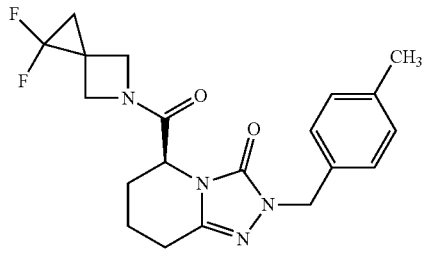 [SMILES: Cc1ccc(Cn2nc3n(c2=O)[C@H](C(=O)N2CC4(C2)CC4(F)F)CCC3)cc1]

(5S)-2-(4-Methylbenzyl)-3-oxo-2,3,5,6,7,8-hexahydro[1,2,4]triazolo[4,3-a]pyridine-5-carboxylic acid (50.0 mg, 174 µmol) was initially charged in dichloromethane (4.0 ml) and DMF (7.0 ml) at room temperature. Subsequently, 1-[bis(dimethylamino)methylene]-1H-benzotriazol-1-ium 3-oxide hexafluorophosphate (85.8 mg, 226 µmol) and N,N-diisopropylethylamine (42 µl, 240 µmol) were added. After stirring for 15 min, 1,1-difluoro-5-azaspiro[2.3]hexane hydrochloride (32.5 mg, 209 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 22.0 mg (30% of theory) of the title compound were obtained.

LC-MS (Method 1): $R_t$=1.10 min; MS (ESIpos): m/z=389 [M+H]$^+$ $^1$H-NMR (400 MHz, DMSO-d6) δ[ppm]: 1.702 (1.18), 1.715 (1.79), 1.728 (1.34), 1.745 (0.60), 1.766 (1.06), 1.787 (1.43), 1.812 (1.15), 1.970 (0.63), 1.982 (0.82), 1.995 (0.85), 2.012 (0.82), 2.029 (0.80), 2.045 (0.53), 2.271 (12.65), 2.567 (1.06), 2.580 (1.02), 3.983 (0.66), 4.007 (1.20), 4.056 (1.17), 4.079 (0.63), 4.363 (0.81), 4.385 (0.86), 4.481 (0.52), 4.510 (0.93), 4.531 (1.39), 4.544 (0.53), 4.574 (0.46), 4.588 (0.69), 4.600 (0.40), 4.753 (5.83), 5.753 (0.46), 7.107 (0.42), 7.128 (16.00), 7.149 (0.45).

Example 192

(5S)-5-[(3-Methylazetidin-1-yl)carbonyl]-2-(4-methylbenzyl)-5,6,7,8-tetrahydro[1,2,4]triazolo[4,3-a]pyridin-3(2H)-one

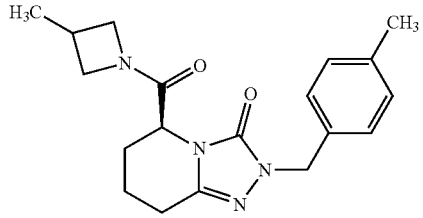

(5S)-2-(4-Methylbenzyl)-3-oxo-2,3,5,6,7,8-hexahydro[1,2,4]triazolo[4,3-a]pyridine-5-carboxylic acid (50.0 mg, 174

µmol) was initially charged in DMF (4.0 ml) and dichloromethane (2.0 ml) at room temperature. Subsequently, 1-[bis(dimethylamino)methylene]-1H-benzotriazol-1-ium 3-oxide hexafluorophosphate (85.8 mg, 226 µmol) and N,N-diisopropylethylamine (79 µl, 450 µmol) were added. After stirring for 15 min, 3-methylazetidine hydrochloride (22.5 mg, 209 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 39.3 mg (63% of theory) of the title compound were obtained.

LC-MS (Method 1): $R_t$=1.02 min; MS (ESIpos): m/z=341 [M+H]$^+$ $^1$H-NMR (400 MHz, DMSO-d6) δ [ppm]: −0.008 (0.45), 0.008 (0.43), 1.183 (4.30), 1.191 (4.27), 1.201 (4.62), 1.208 (4.13), 1.688 (1.31), 1.700 (1.87), 1.715 (1.47), 1.728 (0.65), 1.890 (0.48), 1.902 (0.53), 1.913 (0.79), 1.925 (0.90), 1.935 (0.57), 1.974 (0.74), 1.988 (0.69), 1.994 (0.69), 2.009 (0.68), 2.270 (14.75), 2.568 (1.78), 2.581 (0.90), 2.610 (0.61), 2.688 (0.48), 2.709 (0.62), 2.719 (0.54), 2.733 (0.45), 3.399 (0.56), 3.413 (0.56), 3.423 (0.61), 3.437 (0.57), 3.454 (0.58), 3.469 (0.59), 3.478 (0.65), 3.493 (0.60), 3.696 (0.54), 3.710 (0.60), 3.716 (0.64), 3.730 (0.55), 3.844 (0.53), 3.859 (0.61), 3.865 (0.65), 3.879 (0.56), 3.937 (0.60), 3.959 (0.95), 3.981 (0.54), 4.002 (0.61), 4.024 (0.99), 4.047 (0.54), 4.258 (0.58), 4.278 (1.15), 4.299 (0.52), 4.387 (0.55), 4.408 (1.09), 4.429 (0.52), 4.451 (0.63), 4.464 (1.38), 4.478 (1.38), 4.489 (0.61), 4.741 (6.73), 7.103 (0.54), 7.124 (16.00), 7.145 (0.55).

Example 193

(5S)-2-(4-Methylbenzyl)-5-{[(1 RS)-1-oxido-1,3-thiazolidin-3-yl]carbonyl}-5,6,7,8-tetrahydro[1,2,4]triazolo[4,3-a]pyridin-3(2H)-one (Isomer 1)

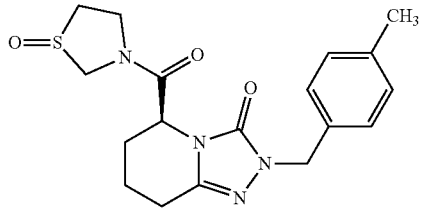 [SMILES: Cc1ccc(Cn2nc3n(c2=O)[C@H](C(=O)N2CCS(=O)C2)CCC3)cc1]

(5S)-2-(4-Methylbenzyl)-5-{[(1 RS)-1-oxido-1,3-thiazolidin-3-yl]carbonyl}-5,6,7,8-tetrahydro[1,2,4]triazolo[4,3-a]pyridin-3(2H)-one (diastereomer mixture; 2 isomers) was separated by chiral preparative HPLC [sample preparation: 24.8 mg dissolved in 1.5 ml of ethanol; injection volume: 1.5 ml; column: Daicel Chiralpak® IA 5 µm, 250×20 mm; eluent: ethanol; flow rate: 15 ml/min; temperature 60° C.; UV detection: 220 nm]. After the separation, 8.0 mg of isomer 1, which elutes first, and 10 mg of isomer 2, which elutes later, were isolated.

Isomer 1:

Analytical chiral HPLC: $R_t$=9.22 min, d.e.=100% [column: Daicel Chiralpak® IA 5 µm, 250×20 mm; eluent: ethanol; flow rate: 15 ml/min; UV detection: 220 nm].

LC-MS (Method 3): $R_t$=1.05 min; MS (ESIpos): m/z=375 [M+H]$^+$ $^1$H-NMR (400 MHz, DMSO-d6) δ [ppm]: 1.617 (0.54), 1.629 (0.55), 1.641 (0.49), 1.703 (0.50), 1.712 (0.48), 1.727 (0.47), 1.736 (0.52), 2.022 (1.00), 2.033 (1.04), 2.044 (0.82), 2.078 (0.73), 2.088 (0.68), 2.274 (16.00), 2.557 (0.73), 2.576 (0.73), 2.589 (1.02), 2.601 (0.86), 2.617 (0.53), 2.630 (0.43), 3.037 (0.51), 3.060 (1.07), 3.082 (1.14), 3.093 (0.85), 3.100 (0.84), 3.117 (0.44), 3.125 (0.49), 3.755 (0.42), 3.770 (0.42), 3.778 (0.77), 3.785 (0.54), 3.800 (0.46), 3.807 (0.42), 4.063 (0.41), 4.082 (0.56), 4.086 (0.53), 4.093 (0.44), 4.105 (0.47), 4.112 (0.48), 4.117 (0.44), 4.162 (0.48), 4.174 (0.85), 4.191 (0.74), 4.198 (0.79), 4.284 (0.75), 4.317 (0.90), 4.418 (1.33), 4.449 (1.48), 4.608 (0.60), 4.613 (0.60), 4.641 (0.49), 4.646 (0.50), 4.753 (7.88), 4.850 (0.71), 4.864 (1.03), 4.874 (0.71), 4.898 (0.46), 4.912 (0.61), 4.921 (0.44), 5.018 (0.94), 5.046 (0.85), 7.103 (0.85), 7.128 (12.94), 7.150 (1.01).

Example 194

(5S)-2-(4-Methylbenzyl)-5-{[(1 RS)-1-oxido-1,3-thiazolidin-3-yl]carbonyl}-5,6,7,8-tetrahydro[1,2,4]triazolo[4,3-a]pyridin-3(2H)-one (Isomer 2)

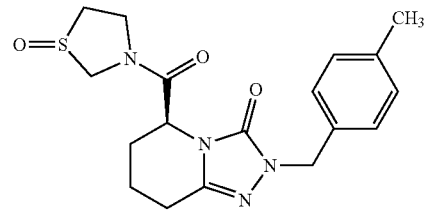 [SMILES: Cc1ccc(Cn2nc3n(c2=O)[C@H](C(=O)N2CCS(=O)C2)CCC3)cc1]

(5S)-2-(4-Methylbenzyl)-5-{[(1 RS)-1-oxido-1,3-thiazolidin-3-yl]carbonyl}-5,6,7,8-tetrahydro[1,2,4]triazolo[4,3-a]pyridin-3(2H)-one (diastereomer mixture; 2 isomers) was separated by chiral preparative HPLC [sample preparation: 24.8 mg dissolved in 1.5 ml of ethanol; injection volume: 1.5 ml; column: Daicel Chiralpak® IA 5 µm, 250×20 mm; eluent: ethanol; flow rate: 15 ml/min; temperature 60° C.; UV detection: 220 nm]. After the separation, 8.0 mg of isomer 1, which elutes first, and 10 mg of isomer 2, which elutes later, were isolated.

Isomer 2:

Analytical chiral HPLC: $R_t$=11.44 min, d.e.=100% [column: Daicel Chiralpak® IA 5 µm, 250×20 mm; eluent: ethanol; flow rate: 15 ml/min; UV detection: 220 nm].

LC-MS (Method 3): $R_t$=1.05 min; MS (ESIpos): m/z=375 [M+H]$^+$ $^1$H-NMR (400 MHz, DMSO-d6) δ [ppm]: 1.739 (0.77), 1.994 (1.34), 2.114 (0.42), 2.274 (16.00), 2.560 (1.09), 2.574 (0.86), 2.598 (1.53), 2.610 (0.98), 2.640 (0.61), 2.938 (0.54), 2.972 (0.59), 3.132 (0.43), 3.160 (0.56), 3.181 (0.77), 3.209 (0.40), 3.273 (0.59), 3.972 (1.19), 3.989 (1.18), 3.997 (1.06), 4.108 (0.72), 4.122 (0.72), 4.135 (0.43), 4.286 (0.52), 4.308 (0.71), 4.338 (1.47), 4.371 (1.58), 4.486 (1.01), 4.516 (1.12), 4.606 (1.00), 4.611 (0.98), 4.644 (0.79), 4.756 (6.31), 4.985 (1.16), 4.994 (1.28), 5.010 (0.98), 5.019 (1.39), 5.050 (0.71), 7.130 (14.05).

Example 195

(5S)-5-[(3-Fluoro-3-methylazetidin-1-yl)carbonyl]-2-(4-methylbenzyl)-5,6,7,8-tetrahydro[1,2,4]triazolo[4,3-a]pyridin-3(2H)-one

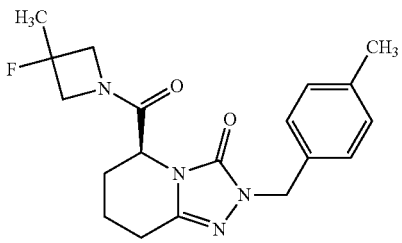 [SMILES: Cc1ccc(Cn2nc3n(c2=O)[C@H](C(=O)N2CC(C)(F)C2)CCC3)cc1]

(5S)-2-(4-Methylbenzyl)-3-oxo-2,3,5,6,7,8-hexahydro[1,2,4]triazolo[4,3-a]pyridine-5-carboxylic acid (50.0 mg, 174 µmol) was initially charged in DMF (2.0 ml) and N,N-diisopropylethylamine (79 µl, 450 µmol) at room temperature. Subsequently, 1-[bis(dimethylamino)methylene]-1H-benzotriazol-1-ium 3-oxide hexafluorophosphate (85.8 mg, 226 µmol) and dichloromethane (1.0 ml) were added. After stirring for 15 min, 3-fluoro-3-methylazetidine hydrochloride (24.0 mg, 191 µmol) was added and the reaction mixture was stirred at room temperature for 2.5 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 23.9 mg (38% of theory) of the title compound were obtained.

LC-MS (Method 3): $R_t$=1.42 min; MS (ESIpos): m/z=359 [M+H]$^+$ $^1$H-NMR (400 MHz, DMSO-d6) δ[ppm]: 1.569 (3.12), 1.577 (3.06), 1.624 (3.10), 1.632 (3.04), 1.712 (1.77), 1.941 (0.71), 2.011 (0.74), 2.024 (0.68), 2.271 (13.50), 2.577 (1.67), 2.620 (0.50), 3.933 (0.54), 3.951 (0.47), 3.980 (1.33), 3.998 (0.90), 4.028 (0.93), 4.043 (0.99), 4.068 (0.41), 4.253 (0.47), 4.301 (0.51), 4.337 (0.49), 4.389 (0.52), 4.403 (0.55), 4.424 (0.65), 4.448 (0.83), 4.474 (0.70), 4.503 (0.81), 4.519 (1.19), 4.533 (1.19), 4.748 (7.16), 7.126 (16.00).

Example 196

(2S)-1-{[(5S)-2-(4-Methylbenzyl)-3-oxo-2,3,5,6,7,8-hexahydro[1,2,4]triazolo[4,3-a]pyridin-5-yl]carbonyl}pyrrolidine-2-carbaldehyde

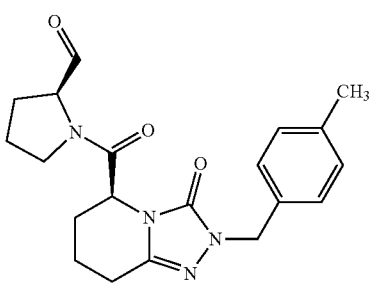 [SMILES: Cc1ccc(Cn2nc3n(c2=O)[C@H](C(=O)N2CCC[C@H]2C=O)CCC3)cc1]

Oxalyl chloride (20 µl, 230 µmol) was initially charged in dichloromethane (2 ml) and cooled to −78° C. Subsequently, a solution of dimethyl sulphoxide (36 µl, 500 µmol) and dichloromethane (1 ml) was added dropwise and the mixture was stirred at −78° C. for 15 min. (5S)-5-{[(2S)-2-(Hydroxymethyl)pyrrolidin-1-yl]carbonyl}-2-(4-methylbenzyl)-5,6,7,8-tetrahydro[1,2,4]triazolo[4,3-a]pyridin-3(2H)-one (77.8 mg, 210 µmol), dissolved in dichloromethane (2 ml), was added dropwise and the reaction mixture was stirred at −78° C. for a further 60 min. Triethylamine (150 µl, 1.1 mmol) of pyridine were added dropwise and the mixture was stirred at −78° C. for a further 20 min. The reaction mixture was brought to room temperature. The reaction mixture was admixed with water. The organic phase was removed and the aqueous phase was extracted three times with dichloromethane. The combined organic phases were washed with saturated aqueous sodium chloride solution, dried over sodium sulphate and filtered, and the filtrate was concentrated. The residue was purified via column chromatography (SiO$_2$; eluent: methanol/dichloromethane 10/90). The product-containing fractions were concentrated under reduced pressure, and 48.9 mg (57% of theory) of the title compound were obtained.

LC-MS (Method 3): $R_t$=1.35 min; MS (ESIpos): m/z=369 [M+H]$^+$ $^1$H-NMR (400 MHz, DMSO-d6) δ [ppm]: −0.008 (3.81), 0.008 (2.35), 1.013 (0.57), 1.091 (0.63), 1.235 (0.83), 1.645 (0.74), 1.657 (0.74), 1.670 (0.86), 1.691 (0.85), 1.705 (0.93), 1.724 (0.92), 1.735 (1.12), 1.748 (1.29), 1.760 (1.25), 1.771 (1.10), 1.782 (0.89), 1.826 (0.52), 1.842 (0.89), 1.858 (1.06), 1.875 (1.07), 1.883 (1.06), 1.892 (1.32), 1.906 (1.40), 1.922 (1.29), 1.937 (1.22), 1.949 (1.42), 1.966 (1.33), 1.985 (1.17), 1.996 (1.25), 2.011 (1.16), 2.020 (1.35), 2.037 (1.48), 2.049 (1.29), 2.064 (1.15), 2.078 (1.20), 2.086 (1.68), 2.099 (1.92), 2.110 (1.86), 2.122 (0.92), 2.233 (0.40), 2.268 (16.00), 2.327 (0.42), 2.518 (2.56), 2.567 (1.27), 2.575 (1.43), 2.587 (1.83), 2.602 (1.80), 2.616 (0.59), 2.628 (0.66), 2.669 (0.42), 3.184 (1.05), 3.211 (1.19), 3.239 (0.57), 3.248 (0.79), 3.266 (1.32), 3.401 (0.42), 3.425 (0.46), 3.576 (0.44), 3.593 (0.86), 3.600 (0.69), 3.618 (1.06), 3.634 (0.49), 3.745 (0.60), 3.763 (0.86), 3.771 (0.74), 3.785 (0.64), 4.323 (0.62), 4.332 (0.73), 4.338 (1.13), 4.344 (0.76), 4.354 (0.60), 4.359 (0.59), 4.709 (0.52), 4.740 (9.55), 4.780 (0.79), 4.792 (0.69), 4.801 (0.52), 4.838 (1.16), 4.849 (1.96), 4.862 (0.99), 5.000 (0.52), 5.007 (0.50), 5.686 (0.85), 5.701 (0.80), 5.753 (1.65), 5.816 (0.77), 5.832 (0.74), 7.090 (1.40), 7.097 (1.38), 7.112 (9.05), 7.118 (13.08), 7.139 (1.38), 9.344 (3.27), 9.349 (3.19).

Example 197

(5S)-5-[(1 RS,5SR)-2-Azabicyclo[3.1.0]hex-2-ylcarbonyl]-2-[(6-chloropyridin-3-yl)methyl]-5,6,7,8-tetrahydro[1,2,4]triazolo[4,3-a]pyridin-3(2H)-one (Isomer 1)

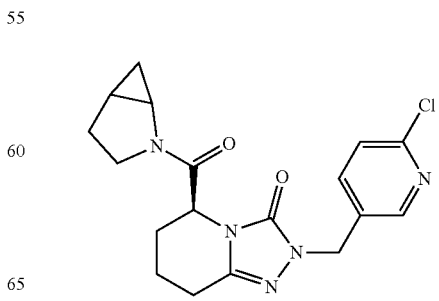

(5S)-2-[(6-Chloropyridin-3-yl)methyl]-3-oxo-2,3,5,6,7,8-hexahydro[1,2,4]triazolo[4,3-a]pyridine-5-carboxylic acid (68.0 mg, 220 µmol) was initially charged in THF (3.7 ml) at room temperature. Subsequently, HATU (109 mg, 286 µmol), (1RS,5SR)-2-azabicyclo[3.1.0]hexane hydrochloride (31.6 mg, 264 µmol) and N,N-diisopropylethylamine (120 µl, 660 µmol) were added. The reaction mixture was stirred at room temperature overnight. The reaction mixture was concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 63.0 mg (77% of theory) of a diastereomer mixture (2 isomers) were obtained.

The diastereomer mixture (2 isomers) was separated by chiral preparative HPLC [sample preparation: 63 mg dissolved in 2 ml of acetonitrile; injection volume: 0.25 ml; column: Daicel Chiralpak® IF 5 µm, 250×20 mm; eluent: n-heptane/ethanol 20:80; flow rate: 20 ml/min; temperature 30° C.; UV detection: 220 nm]. After the separation, 15.3 mg of isomer 1, which elutes first, and 17.2 mg of isomer 2, which elutes later, were isolated.
Isomer 1:
Analytical chiral HPLC: $R_t$=2.91 min, d.e.>99% [column: Daicel Chiralpak® IB, 50×4.6 mm; eluent: n-heptane/ethanol 50:50; flow rate: 1 ml/min; UV detection: 220 nm].

LC-MS (Method 3): $R_t$=1.14 min; MS (ESIpos): m/z=374 $[M+H]^+$ $^1$H-NMR (400 MHz, DMSO-d6) δ [ppm]: −0.149 (1.50), −0.008 (13.97), 0.008 (12.20), 0.146 (1.59), 0.643 (2.92), 0.903 (2.39), 1.755 (2.56), 1.860 (1.94), 1.955 (2.03), 2.044 (2.30), 2.327 (3.18), 2.366 (2.65), 2.523 (9.72), 2.600 (3.54), 2.665 (2.30), 2.670 (3.09), 2.674 (2.56), 2.710 (2.39), 3.148 (2.56), 3.177 (2.56), 3.506 (2.39), 3.610 (1.59), 3.679 (1.50), 3.936 (1.33), 4.743 (1.50), 4.877 (16.00), 4.885 (8.66), 4.934 (2.39), 4.950 (2.74), 4.959 (2.21), 7.504 (6.63), 7.524 (8.49), 7.687 (3.71), 7.693 (5.04), 7.708 (2.74), 7.714 (3.89), 8.296 (5.04), 8.302 (6.72).

Example 198

(5S)-5-[(1 SR,5RS)-2-Azabicyclo[3.1.0]hex-2-ylcarbonyl]-2-[(6-chloropyridin-3-yl)methyl]-5,6,7,8-tetrahydro[1,2,4]triazolo[4,3-a]pyridin-3(2H)-one (Isomer 2)

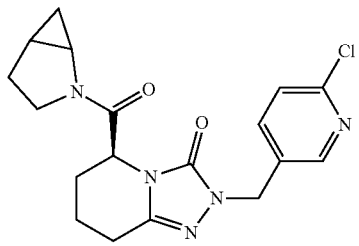 [SMILES: O=C([C@@H]1CCCc2nn(Cc3ccc(Cl)nc3)c(=O)n21)N1CCC2CC21]

(5S)-5-[(1 RS,5SR)-2-Azabicyclo[3.1.0]hex-2-ylcarbonyl]-2-[(6-chloropyridin-3-yl)methyl]-5,6,7,8-tetrahydro[1,2,4]triazolo[4,3-a]pyridin-3(2H)-one (diastereomer mixture; 2 isomers) was separated by chiral preparative HPLC [sample preparation: 63 mg dissolved in 2 ml of acetonitrile; injection volume: 0.25 ml; column: Daicel Chiralpak® IF 5 µm, 250×20 mm; eluent: n-heptane/ethanol 20:80; flow rate: 20 ml/min; temperature 30° C.; UV detection: 220 nm].

After the separation, 15.3 mg of isomer 1, which elutes first, and 17.2 mg of isomer 2, which elutes later, were isolated.
Isomer 2:
Analytical chiral HPLC: $R_t$=4.28 min, d.e.=98% [column: Daicel Chiralpak® IB, 50×4.6 mm; eluent: n-heptane/ethanol 50:50; flow rate: 1 ml/min; UV detection: 220 nm].

LC-MS (Method 3): $R_t$=1.15 min; MS (ESIpos): m/z=374 $[M+H]^+$ $^1$H-NMR (400 MHz, DMSO-d6) δ [ppm]: −0.149 (1.33), −0.008 (16.00), 0.008 (9.33), 0.146 (1.24), 0.562 (0.89), 0.619 (2.22), 0.625 (2.49), 0.632 (4.00), 0.638 (3.91), 0.645 (2.58), 0.651 (2.13), 0.728 (0.80), 0.796 (1.69), 0.811 (3.38), 0.818 (2.22), 0.834 (3.38), 0.847 (1.60), 1.578 (2.04), 1.756 (3.91), 1.791 (2.93), 1.854 (1.42), 1.862 (1.51), 1.876 (2.13), 1.885 (2.76), 1.894 (2.31), 1.908 (2.22), 1.915 (2.13), 2.028 (3.11), 2.038 (3.02), 2.048 (3.38), 2.086 (1.69), 2.163 (2.58), 2.322 (1.69), 2.327 (2.22), 2.332 (1.69), 2.366 (2.04), 2.518 (12.36), 2.523 (11.82), 2.566 (4.18), 2.580 (3.29), 2.600 (4.09), 2.612 (2.76), 2.641 (1.60), 2.665 (1.87), 2.669 (2.31), 2.674 (1.69), 2.709 (2.13), 2.934 (1.51), 2.955 (3.38), 2.964 (2.04), 2.977 (1.78), 2.986 (3.56), 3.008 (1.42), 3.541 (1.24), 3.702 (4.09), 3.711 (4.80), 3.717 (4.18), 3.726 (4.71), 3.732 (5.24), 3.757 (1.87), 3.764 (1.69), 3.802 (0.98), 4.653 (1.07), 4.850 (1.33), 4.882 (7.20), 4.890 (14.22), 4.896 (13.07), 4.936 (1.07), 5.087 (3.38), 5.094 (4.09), 5.102 (3.73), 5.110 (3.20), 7.505 (7.20), 7.525 (8.98), 7.690 (5.96), 7.697 (5.87), 7.711 (4.98), 7.717 (4.80), 8.300 (6.76), 8.306 (6.49).

Example 199

(5S)-5-(2-Azabicyclo[2.1.1]hex-2-ylcarbonyl)-2-{[6-(trifluoromethyl)pyridin-3-yl]methyl}-5,6,7,8-tetrahydro[1,2,4]triazolo[4,3-a]pyridin-3(2H)-one

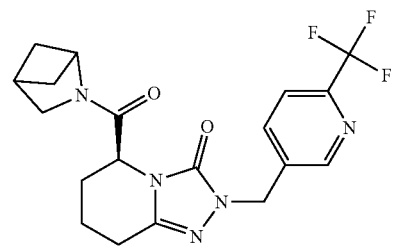 [SMILES: O=C([C@@H]1CCCc2nn(Cc3ccc(C(F)(F)F)nc3)c(=O)n21)N1CC2CC1C2]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (112 mg, 327 µmol) was initially charged in THF (5.0 ml) at room temperature. Subsequently, HATU (161 mg, 425 µmol) and N,N-diisopropylethylamine (570 µl, 3.3 mmol) were added. After stirring for 10 min, 2-(3-azabicyclo[2.1.1]hexane)trifluoroacetic acid (77.4 mg, 393 µmol) was added and the reaction mixture was stirred at room temperature for 60 min. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 24.2 mg (18% of theory) of the title compound were obtained.

LC-MS (Method 4): $R_t$=0.69 min; MS (ESIpos): m/z=408 [M+H]$^+$ $^1$H-NMR (400 MHz, DMSO-d6) δ [ppm]: −0.008 (3.67), 0.008 (3.09), 1.223 (0.73), 1.241 (0.84), 1.249 (1.36), 1.267 (1.47), 1.304 (1.61), 1.321 (1.54), 1.330 (1.47), 1.355 (3.02), 1.369 (4.75), 1.383 (2.69), 1.410 (1.26), 1.647 (0.82), 1.744 (1.96), 1.758 (1.82), 1.815 (0.96), 1.856 (1.05), 1.931 (1.87), 2.036 (3.56), 2.072 (0.98), 2.327 (0.98), 2.366 (0.98), 2.558 (3.13), 2.571 (2.48), 2.593 (2.60), 2.605 (3.58), 2.618 (2.08), 2.635 (0.84), 2.647 (1.24), 2.669 (1.26), 2.710 (1.15), 2.861 (1.59), 2.869 (1.57), 2.877 (1.64), 2.932 (1.01), 2.949 (1.05), 3.228 (1.66), 3.252 (2.90), 3.514 (1.43), 3.534 (1.87), 3.634 (1.78), 3.654 (1.26), 4.555 (1.47), 4.573 (1.50), 4.636 (1.03), 4.651 (1.47), 4.663 (1.10), 4.676 (2.08), 4.693 (2.01), 4.896 (1.50), 4.904 (1.78), 4.911 (1.80), 4.919 (1.47), 4.966 (0.73), 5.001 (7.72), 5.018 (5.08), 5.059 (0.70), 7.913 (16.00), 8.645 (5.01).

Example 200

(5S)-5-[(1 RS,5SR)-2-Azabicyclo[3.1.0]hex-2-ylcarbonyl]-2-{[6-(trifluoromethyl)pyridin-3-yl]methyl}-5,6,7,8-tetrahydro[1,2,4]triazolo[4,3-a]pyridin-3 (2H)-one (Isomer 1)

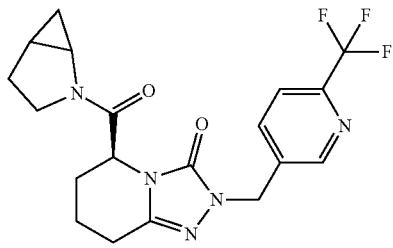 [SMILES: O=C([C@@H]1CCCc2nn(Cc3ccc(C(F)(F)F)nc3)c(=O)n21)N1CCC2CC21]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (251 mg, 733 μmol) was initially charged in THF (12 ml) at room temperature. Subsequently, HATU (362 mg, 953 μmol), (1R,5S)-2-azabicyclo[3.1.0]hexane hydrochloride (105 mg, 880 μmol) and N,N-diisopropylethylamine (380 μl, 2.2 mmol) were added. The reaction mixture was stirred at room temperature overnight. HATU (279 mg, 733 μmol), (1 RS,5SR)-2-azabicyclo[3.1.0]hexane hydrochloride (88 mg, 733 μmol) and N,N-diisopropylethylamine (127 μl, 1.7 mmol) were added again and the mixture was stirred for a further 20 hours. The reaction mixture was concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 54.0 mg (18% of theory) of a diastereomer mixture (2 isomers) were obtained.

The diastereomer mixture (2 isomers) was separated by chiral preparative HPLC [sample preparation: 54 mg dissolved in 20 ml of methanol; injection volume: 1 ml; column: Daicel Chiralpak® IE 5 μm, 250×20 mm; eluent: carbon dioxide/methanol 80:20; flow rate: 80 ml/min; temperature 40° C.; UV detection: 210 nm]. After the separation, 20.2 mg of isomer 1, which elutes first, and 21.3 mg of isomer 2, which elutes later, were isolated.

Isomer 1:

Analytical chiral HPLC: $R_t$=5.41 min, d.e.>99.5% [column: Daicel Chiralpak® IE, 50×4.6 mm; eluent: n-heptane/methanol 80:20; flow rate: 3 ml/min; UV detection: 210 nm].

LC-MS (Method 3): $R_t$=1.32 min; MS (ESIpos): m/z=408 [M+H]$^+$ $^1$H-NMR (400 MHz, DMSO-d6) δ [ppm]: −0.149 (0.66), −0.008 (5.58), 0.008 (5.50), 0.146 (0.59), 0.630 (1.98), 0.637 (1.98), 0.644 (2.57), 0.650 (2.13), 0.657 (1.32), 0.663 (1.17), 0.691 (0.81), 0.711 (0.81), 0.870 (0.81), 0.884 (1.61), 0.906 (1.69), 0.920 (0.73), 1.567 (0.66), 1.651 (0.95), 1.773 (2.13), 1.839 (0.73), 1.862 (1.54), 1.871 (0.95), 1.885 (0.88), 1.894 (0.81), 1.958 (1.47), 1.976 (1.32), 2.029 (1.17), 2.062 (1.83), 2.154 (1.10), 2.323 (1.03), 2.327 (1.39), 2.332 (1.10), 2.366 (1.03), 2.523 (5.43), 2.567 (2.06), 2.578 (1.83), 2.593 (1.98), 2.610 (2.79), 2.651 (1.03), 2.665 (1.47), 2.670 (1.76), 2.674 (1.25), 2.710 (1.17), 3.132 (1.32), 3.152 (1.76), 3.162 (1.69), 3.172 (0.95), 3.183 (1.98), 3.203 (0.81), 3.491 (1.10), 3.497 (1.25), 3.506 (1.91), 3.521 (1.25), 3.584 (1.03), 3.593 (1.10), 3.609 (1.25), 3.619 (1.32), 3.624 (1.10), 3.641 (0.95), 3.649 (0.81), 3.677 (0.73), 3.687 (1.25), 3.693 (1.17), 3.703 (0.73), 3.920 (0.51), 3.943 (0.88), 3.970 (0.51), 4.761 (1.17), 4.769 (0.81), 4.951 (1.69), 4.959 (2.06), 4.965 (2.20), 4.974 (1.76), 5.004 (9.69), 7.908 (10.94), 7.912 (16.00), 8.642 (3.82).

Example 201

(5S)-5-[(1 SR,5RS)-2-Azabicyclo[3.1.0]hex-2-ylcarbonyl]-2-{[6-(trifluoromethyl)pyridin-3-yl]methyl}-5,6,7,8-tetrahydro[1,2,4]triazolo[4,3-a]pyridin-3 (2H)-one (Isomer 2)

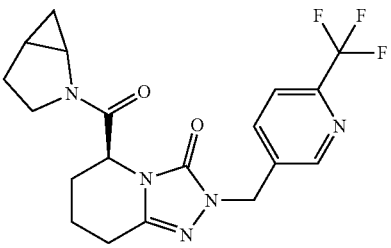 [SMILES: O=C([C@@H]1CCCc2nn(Cc3ccc(C(F)(F)F)nc3)c(=O)n21)N1CCC2CC21]

(5S)-5-[(1 RS,5SR)-2-Azabicyclo[3.1.0]hex-2-ylcarbonyl]-2-{[6-(trifluoromethyl)pyridin-3-yl]methyl}-5,6,7,8-tetrahydro[1,2,4]triazolo[4,3-a]pyridin-3(2H)-one (diastereomer mixture; 2 isomers) was separated by chiral preparative HPLC [sample preparation: 54 mg dissolved in 20 ml of methanol; injection volume: 1 ml; column: Daicel Chiralpak® IE 5 μm, 250×20 mm; eluent: carbon dioxide/methanol 80:20; flow rate: 80 ml/min; temperature 40° C.; UV detection: 210 nm]. After the separation, 20.2 mg of isomer 1, which elutes first, and 21.3 mg of isomer 2, which elutes later, were isolated.

Isomer 2:

Analytical chiral HPLC: $R_t$=6.82 min, d.e.>99.5% [column: Daicel Chiralpak® IE, 50×4.6 mm; eluent: n-heptane/methanol 80:20; flow rate: 3 ml/min; UV detection: 210 nm].

LC-MS (Method 3): $R_t$=1.33 min; MS (ESIpos): m/z=408 [M+H]$^+$ $^1$H-NMR (400 MHz, DMSO-d6) δ[ppm]: −0.149 (0.51), −0.008 (4.45), 0.008 (4.11), 0.146 (0.51), 0.559 (0.56), 0.625 (1.18), 0.630 (1.41), 0.638 (2.42), 0.644 (2.42), 0.651

(1.63), 0.657 (1.30), 0.731 (0.45), 0.751 (0.51), 0.803 (0.96), 0.816 (2.03), 0.838 (2.03), 0.852 (0.96), 1.579 (1.18), 1.745 (1.35), 1.759 (2.37), 1.773 (2.42), 1.794 (2.03), 1.865 (0.90), 1.879 (1.01), 1.889 (1.69), 1.896 (1.35), 1.911 (1.30), 1.918 (1.18), 1.992 (0.90), 2.031 (1.80), 2.039 (1.58), 2.047 (1.58), 2.059 (1.75), 2.185 (1.52), 2.220 (0.90), 2.327 (1.13), 2.332 (0.85), 2.366 (0.79), 2.523 (4.39), 2.563 (2.37), 2.576 (2.03), 2.590 (1.80), 2.609 (2.42), 2.622 (1.63), 2.650 (0.96), 2.665 (1.35), 2.670 (1.41), 2.674 (1.01), 2.710 (0.90), 2.938 (0.90), 2.960 (2.08), 2.970 (1.24), 2.982 (1.01), 2.992 (2.14), 3.014 (0.85), 3.241 (0.51), 3.548 (0.73), 3.554 (0.73), 3.709 (2.42), 3.718 (2.93), 3.725 (2.54), 3.733 (2.76), 3.740 (3.21), 3.764 (1.13), 3.808 (0.51), 4.675 (0.68), 4.975 (0.90), 5.015 (7.21), 5.026 (6.42), 5.067 (0.90), 5.105 (2.03), 5.112 (2.48), 5.120 (2.31), 5.128 (1.97), 7.912 (15.94), 7.915 (16.00), 8.646 (5.41).

Example 202

(5S)-5-[(1 RS,5SR)-2-Azabicyclo[3.1.0]hex-2-ylcarbonyl]-2-(3-chloro-4-fluorobenzyl)-5,6,7,8-tetrahydro[1,2,4]triazolo[4,3-a]pyridin-3(2H)-one (Isomer 1)

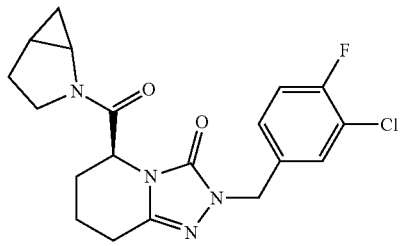 [SMILES: O=C([C@@H]1CCCc2nn(Cc3ccc(F)c(Cl)c3)c(=O)n21)N1CCC2CC21]

(5S)-2-(3-Chloro-4-fluorobenzyl)-3-oxo-2,3,5,6,7,8-hexahydro[1,2,4]triazolo[4,3-a]pyridine-5-carboxylic acid (533 mg, 1.64 mmol) was initially charged in THF (1.5 ml) at room temperature. Subsequently, HATU (809 mg, 2.13 mmol), (1RS,5SR)-2-azabicyclo[3.1.0]hexane hydrochloride (235 mg, 1.96 mmol) and N,N-diisopropylethylamine (860 µl, 4.9 mmol) were added. HATU (622 mg, 1.64 mmol), (1RS,5SR)-2-azabicyclo[3.1.0]hexane hydrochloride (196 mg, 1.63 mmol) and N,N-diisopropylethylamine (287 µl, 1.6 mmol) were added again and the mixture was stirred for a further 20 hours. The reaction mixture was concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 112 mg (18% of theory) of a diastereomer mixture (2 isomers) were obtained.

The diastereomer mixture (2 isomers) was separated by chiral preparative HPLC [sample preparation: 112 mg dissolved in 2 ml of ethanol; injection volume: 0.35 ml; column: Daicel Chiralpak® AY-H 5 µm, 250×20 mm; eluent: n-heptane/ethanol 40:60; flow rate: 15 ml/min; temperature 40° C.; UV detection: 220 nm]. After the separation, 42.1 mg of isomer 1, which elutes first, and 63.6 mg of isomer 2, which elutes later, were isolated.

Isomer 1:

Analytical chiral HPLC: $R_t$=7.43 min, d.e.=99% [column: Daicel Chiralpak® AY-H 5 µm, 250×4.6 mm; eluent: n-heptane/ethanol 50:50; flow rate: 1 ml/min; UV detection: 220 nm].

LC-MS (Method 3): $R_t$=1.49 min; MS (ESIpos): m/z=391 [M+H]$^+$ $^1$H-NMR (400 MHz, DMSO-d6) δ[ppm]: −0.149 (0.75), −0.008 (6.67), 0.008 (5.91), 0.146 (0.75), 0.626 (1.68), 0.633 (2.55), 0.639 (2.55), 0.646 (3.07), 0.652 (3.01), 0.659 (1.86), 0.665 (1.62), 0.676 (0.75), 0.693 (1.22), 0.713 (1.22), 0.727 (0.52), 0.870 (1.16), 0.885 (2.26), 0.892 (1.51), 0.906 (2.38), 0.920 (0.99), 1.548 (0.81), 1.569 (0.99), 1.583 (0.87), 1.657 (1.45), 1.692 (1.51), 1.711 (1.39), 1.756 (3.19), 1.770 (2.84), 1.791 (2.09), 1.830 (0.99), 1.840 (1.04), 1.851 (1.16), 1.861 (2.26), 1.871 (1.51), 1.882 (1.45), 1.893 (1.33), 1.946 (1.68), 1.955 (2.09), 1.988 (1.51), 2.008 (1.91), 2.025 (1.51), 2.051 (2.55), 2.059 (2.43), 2.085 (1.22), 2.131 (1.57), 2.139 (1.39), 2.148 (1.62), 2.159 (1.57), 2.168 (1.45), 2.328 (1.04), 2.366 (0.87), 2.523 (4.52), 2.564 (2.61), 2.575 (2.38), 2.591 (2.67), 2.606 (4.00), 2.619 (2.09), 2.635 (0.99), 2.648 (1.51), 2.665 (1.16), 2.670 (1.28), 2.710 (0.93), 3.106 (0.46), 3.131 (2.09), 3.151 (2.96), 3.161 (1.91), 3.172 (1.39), 3.182 (2.67), 3.202 (1.28), 3.483 (1.57), 3.489 (1.74), 3.499 (2.72), 3.504 (2.67), 3.514 (1.74), 3.519 (1.45), 3.582 (1.33), 3.591 (1.45), 3.607 (1.74), 3.616 (1.86), 3.622 (1.57), 3.638 (1.28), 3.648 (1.16), 3.664 (0.81), 3.670 (0.93), 3.680 (1.74), 3.686 (1.62), 3.696 (0.93), 3.918 (0.70), 3.944 (1.28), 3.967 (0.64), 4.736 (1.16), 4.751 (1.68), 4.760 (1.16), 4.817 (16.00), 4.825 (9.39), 4.942 (2.43), 4.950 (2.84), 4.957 (3.01), 4.966 (2.32), 7.228 (2.03), 7.234 (2.20), 7.243 (2.67), 7.248 (3.01), 7.255 (2.84), 7.260 (2.61), 7.372 (5.62), 7.395 (7.59), 7.417 (4.35), 7.435 (3.71), 7.453 (3.71).

Example 203

(5S)-5-[(1 SR,5RS)-2-Azabicyclo[3.1.0]hex-2-ylcarbonyl]-2-(3-chloro-4-fluorobenzyl)-5,6,7,8-tetrahydro[1,2,4]triazolo[4,3-a]pyridin-3(2H)-one (Isomer 2)

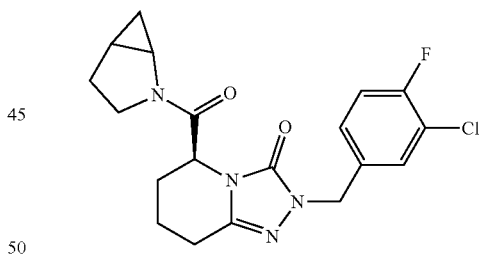

(5S)-5-[(1 SR,5RS)-2-Azabicyclo[3.1.0]hex-2-ylcarbonyl]-2-(3-chloro-4-fluorobenzyl)-5,6,7,8-tetrahydro[1,2,4]triazolo[4,3-a]pyridin-3(2H)-one (diastereomer mixture; 2 isomers) was separated by chiral preparative HPLC [sample preparation: 112 mg dissolved in 2 ml of ethanol; injection volume: 0.35 ml; column: Daicel Chiralpak® AY-H 5 µm, 250×20 mm; eluent: n-heptane/ethanol 40:60; flow rate: 15 ml/min; temperature 40° C.; UV detection: 220 nm]. After the separation, 42.1 mg of isomer 1, which elutes first, and 63.6 mg of isomer 2, which elutes later, were isolated.

Isomer 2:

Analytical chiral HPLC: $R_t$=10.06 min, d.e.=99% [column: Daicel Chiralpak® AY-H 5 µm, 250×4.6 mm; eluent: n-heptane/ethanol 50:50; flow rate: 1 ml/min; UV detection: 220 nm].

LC-MS (Method 3): $R_t$=1.50 min; MS (ESIpos): m/z=391 [M+H]$^+$ $^1$H-NMR (400 MHz, DMSO-d6) δ[ppm]: −0.008 (4.82), 0.008 (3.02), 0.564 (0.72), 0.577 (0.47), 0.619 (1.70), 0.625 (1.95), 0.632 (3.12), 0.638 (3.02), 0.645 (2.02), 0.651 (1.67), 0.729 (0.60), 0.750 (0.60), 0.798 (1.29), 0.813 (2.58), 0.820 (1.70), 0.826 (1.61), 0.834 (2.55), 0.848 (1.13), 1.554 (1.32), 1.567 (1.48), 1.575 (1.42), 1.590 (1.51), 1.726 (1.32), 1.741 (2.27), 1.755 (3.06), 1.770 (2.93), 1.776 (2.83), 1.791 (2.30), 1.806 (0.94), 1.855 (1.07), 1.862 (1.20), 1.877 (1.45), 1.886 (2.14), 1.894 (1.83), 1.909 (1.83), 1.915 (1.73), 1.973 (0.57), 1.994 (1.10), 2.007 (1.39), 2.018 (2.30), 2.026 (2.30), 2.032 (2.30), 2.041 (2.39), 2.053 (2.61), 2.061 (2.39), 2.084 (1.39), 2.099 (1.01), 2.161 (2.08), 2.195 (1.20), 2.328 (0.60), 2.366 (0.54), 2.524 (3.59), 2.559 (2.80), 2.572 (2.46), 2.586 (2.14), 2.597 (2.14), 2.606 (2.93), 2.619 (1.98), 2.638 (0.88), 2.647 (1.07), 2.661 (0.82), 2.670 (0.69), 2.710 (0.50), 2.935 (1.23), 2.957 (2.65), 2.966 (1.57), 2.979 (1.45), 2.989 (2.77), 3.010 (1.13), 3.243 (0.76), 3.528 (0.47), 3.534 (0.50), 3.544 (0.88), 3.549 (0.85), 3.559 (0.47), 3.705 (2.93), 3.714 (3.46), 3.721 (3.31), 3.733 (3.69), 3.758 (1.42), 3.765 (1.23), 3.778 (0.44), 3.805 (0.66), 4.649 (0.69), 4.658 (0.79), 4.664 (0.82), 4.674 (0.60), 4.821 (4.98), 4.833 (16.00), 5.093 (2.68), 5.100 (3.18), 5.108 (2.87), 5.115 (2.46), 7.226 (2.02), 7.232 (2.11), 7.238 (2.20), 7.244 (2.52), 7.248 (2.83), 7.253 (2.68), 7.260 (2.52), 7.265 (2.14), 7.372 (4.63), 7.396 (6.17), 7.417 (3.62), 7.437 (3.94), 7.442 (3.75), 7.455 (3.87), 7.460 (3.53).

Example 204

(5S)-2-[(E)-2-(4-Fluorophenyl)vinyl]-5-(pyrrolidin-1-ylcarbonyl)-5,6,7,8-tetrahydro[1,2,4]triazolo[4,3-a]pyridin-3(2H)-one

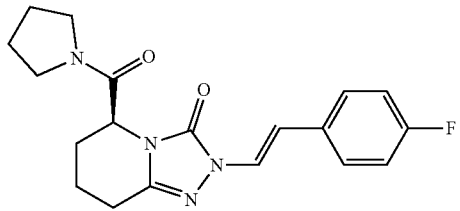 [SMILES: O=C([C@@H]1CCCc2nn(/C=C/c3ccc(F)cc3)c(=O)n21)N1CCCC1]

(5S)-2-[(E)-2-(4-Fluorophenyl)vinyl]-3-oxo-2,3,5,6,7,8-hexahydro[1,2,4]triazolo[4,3-a]pyridine-5-carboxylic acid (195 mg, 643 μmol) was initially charged in THF (6.0 ml) at room temperature. Subsequently, HBTU (317 mg, 836 μmol) and N,N-diisopropylethylamine (560 μl, 3.2 mmol) were added. After stirring for 15 min, pyrrolidine (64 μl, 770 μmol) was added and the reaction mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 μm, 125 mm×40 mm; eluent: acetonitrile with 0.1% formic acid gradient). The product-containing fractions were concentrated under reduced pressure, and 68.5 mg (30% of theory) of the title compound were obtained.

LC-MS (Method 3): $R_t$=1.58 min; MS (ESIpos): m/z=357 [M+H]$^+$ $^1$H-NMR (400 MHz, DMSO-d6) δ [ppm]: −0.149 (0.95), −0.008 (8.77), 0.008 (8.91), 0.146 (1.02), 1.288 (0.66), 1.732 (1.97), 1.743 (1.83), 1.768 (4.16), 1.783 (8.84), 1.800 (12.20), 1.817 (9.42), 1.832 (3.00), 1.893 (1.17), 1.905 (2.63), 1.922 (7.96), 1.938 (10.08), 1.955 (6.06), 1.973 (1.75), 1.988 (1.61), 2.014 (2.05), 2.024 (3.14), 2.047 (2.56), 2.056 (1.97), 2.062 (1.97), 2.072 (2.41), 2.085 (3.43), 2.091 (2.19), 2.099 (1.97), 2.327 (1.39), 2.366 (1.39), 2.523 (5.11), 2.613 (1.32), 2.627 (1.46), 2.638 (1.17), 2.655 (3.58), 2.670 (4.75), 2.680 (3.58), 2.695 (3.00), 2.704 (3.00), 2.716 (5.11), 2.728 (2.92), 2.746 (1.24), 2.758 (1.83), 2.771 (0.88), 3.238 (1.39), 3.256 (3.21), 3.268 (3.51), 3.285 (6.94), 3.344 (7.67), 3.356 (3.21), 3.361 (3.87), 3.374 (3.73), 3.391 (1.90), 3.457 (1.83), 3.474 (3.80), 3.482 (2.85), 3.491 (2.34), 3.499 (4.89), 3.516 (2.19), 3.611 (2.26), 3.627 (4.53), 3.635 (2.34), 3.644 (2.70), 3.652 (3.65), 3.669 (1.61), 4.791 (4.09), 4.800 (4.68), 4.806 (5.33), 4.815 (3.95), 5.754 (1.61), 6.747 (8.77), 6.783 (9.94), 7.121 (7.67), 7.144 (16.00), 7.166 (8.62), 7.330 (11.69), 7.367 (10.37), 7.519 (8.18), 7.533 (9.28), 7.541 (8.99), 7.555 (7.67).

Example 205

(5S)-5-[(1 RS,5SR)-2-Azabicyclo[3.1.0]hex-2-ylcarbonyl]-2-{[3-fluoro-2-(trifluoromethyl)pyridin-4-yl]methyl}-5,6,7,8-tetrahydro[1,2,4]triazolo[4,3-a]pyridin-3(2H)-one (Diastereomer Mixture; 2 Isomers)

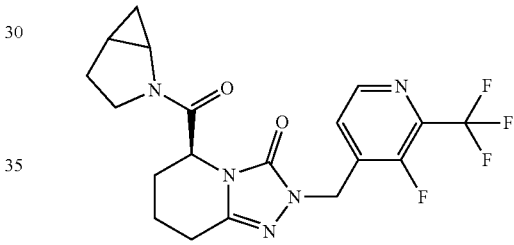

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (52.0 mg, 144 μmol) was initially charged in THF (130 μl) at room temperature. Subsequently, HATU (71.3 mg, 188 μmol), N,N-diisopropylethylamine (76 μl, 430 μmol) and (1 RS,5SR)-2-azabicyclo[3.1.0]hexane hydrochloride (20.7 mg, 173 μmol) were added. The reaction mixture was stirred at room temperature overnight. The reaction mixture was concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 35.0 mg (57% of theory) of the title compound were obtained.

LC-MS (Method 3): $R_t$=1.40 min; MS (ESIpos): m/z=426 [M+H]$^+$ $^1$H-NMR (400 MHz, DMSO-d6) δ[ppm]: −0.149 (1.74), −0.008 (16.00), 0.008 (14.61), 0.146 (1.74), 0.562 (0.63), 0.640 (2.99), 0.728 (0.49), 0.805 (0.90), 0.820 (1.88), 0.842 (1.88), 0.856 (0.83), 0.907 (0.56), 1.595 (1.25), 1.773 (3.20), 1.795 (2.43), 1.861 (1.11), 1.889 (1.67), 1.912 (1.25), 1.991 (1.32), 2.071 (2.02), 2.192 (1.67), 2.327 (2.23), 2.366 (2.16), 2.523 (7.51), 2.563 (2.92), 2.578 (2.37), 2.592 (2.09), 2.625 (2.92), 2.670 (3.27), 2.710 (2.16), 2.942 (0.90), 2.965 (1.81), 2.974 (1.04), 2.996 (2.09), 3.016 (0.83), 3.151 (0.56), 3.512 (0.63), 3.556 (0.63), 3.715 (2.23), 3.740 (2.99), 3.765 (1.04), 3.814 (0.49), 4.682 (0.63), 4.777 (0.42), 4.977 (0.63), 5.076

(9.25), 5.122 (2.23), 5.129 (2.30), 5.138 (2.16), 7.549 (2.50), 7.562 (4.52), 7.575 (2.71), 8.562 (4.94), 8.574 (5.08).

Example 206

(5S)-2-{[6-(Difluoromethyl)pyridin-3-yl]methyl}-5-{[(3S)-3-fluoropyrrolidin-1-yl]carbonyl}-5,6,7,8-tetrahydro[1,2,4]triazolo[4,3-a]pyridin-3(2H)-one

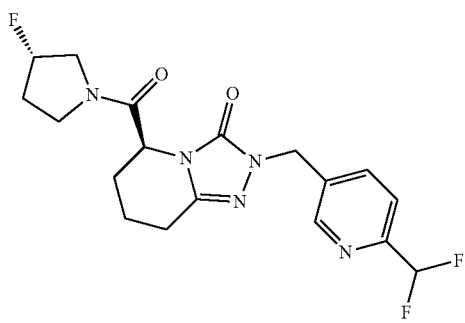 [SMILES: O=C([C@@H]1CCCc2nn(Cc3ccc(C(F)F)nc3)c(=O)n21)N1CC[C@H](F)C1]

(5S)-2-{[6-(Difluoromethyl)pyridin-3-yl]methyl}-3-oxo-2,3,5,6,7,8-hexahydro[1,2,4]triazolo[4,3-a]pyridine-5-carboxylic acid (100 mg, 25% purity, 77.1 μmol) was initially charged in THF (800 μl) at room temperature. Subsequently, (3S)-3-fluoropyrrolidine (8.24 mg, 92.5 μmol), HATU (38.1 mg, 100 μmol) and triethylamine (54 μl, 390 μmol) were added. The reaction mixture was stirred at room temperature overnight. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 15.8 mg (52% of theory) of the title compound were obtained.

LC-MS (Method 3): $R_t$=1.05 min; MS (ESIpos): m/z=396 [M+H]$^+$ $^1$H-NMR (400 MHz, DMSO-d6) δ[ppm]: −0.149 (0.69), 0.146 (0.74), 0.950 (0.66), 1.007 (0.42), 1.732 (3.05), 1.874 (0.54), 1.914 (0.71), 1.998 (2.72), 2.026 (1.96), 2.090 (2.37), 2.106 (2.49), 2.137 (1.90), 2.268 (1.44), 2.327 (1.00), 2.366 (0.80), 2.565 (3.31), 2.605 (4.05), 2.648 (1.58), 2.665 (1.37), 2.710 (0.88), 3.273 (1.54), 3.302 (2.23), 3.320 (2.42), 3.368 (3.38), 3.396 (3.86), 3.406 (3.83), 3.468 (4.74), 3.494 (5.02), 3.523 (5.54), 3.546 (4.81), 3.572 (4.14), 3.599 (4.61), 3.636 (4.12), 3.654 (3.67), 3.679 (3.24), 3.705 (2.27), 3.725 (2.15), 3.745 (3.12), 3.775 (2.34), 3.786 (2.18), 3.857 (2.61), 3.918 (0.97), 3.943 (1.47), 4.008 (0.83), 4.039 (0.69), 4.688 (0.97), 4.698 (1.25), 4.704 (1.28), 4.713 (1.00), 4.746 (1.23), 4.761 (1.63), 4.769 (1.26), 4.818 (0.85), 4.831 (1.23), 4.870 (1.11), 4.955 (16.00), 5.261 (1.33), 5.350 (0.68), 5.392 (1.59), 5.481 (0.69), 5.515 (0.81), 6.807 (4.02), 6.944 (7.57), 7.081 (3.72), 7.682 (5.61), 7.702 (7.55), 7.819 (4.74), 7.839 (3.67), 8.563 (6.89).

Example 207

(5S)-2-{[6-(Difluoromethyl)pyridin-3-yl]methyl}-5-{[(3R,4S)-3,4-difluoropyrrolidin-1-yl]carbonyl}-5,6,7,8-tetrahydro[1,2,4]triazolo[4,3-a]pyridin-3(2H)-one

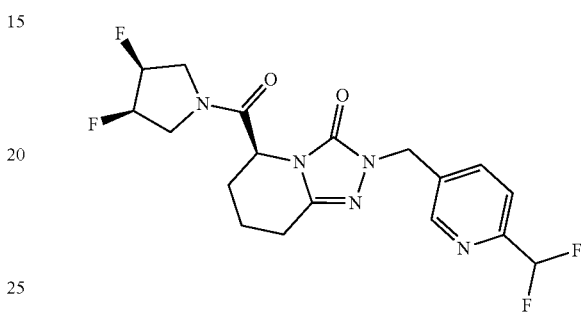

(5S)-2-{[6-(Difluoromethyl)pyridin-3-yl]methyl}-3-oxo-2,3,5,6,7,8-hexahydro[1,2,4]triazolo[4,3-a]pyridine-5-carboxylic acid (100 mg, 25% purity, 77.1 μmol) was initially charged in THF (800 μl) at room temperature. Subsequently, (3R,4S)-3,4-difluoropyrrolidine (9.91 mg, 92.5 μmol), HATU (38.1 mg, 100 μmol) and triethylamine (54 μl, 390 μmol) were added. The reaction mixture was stirred at room temperature overnight. The reaction mixture was admixed with water and concentrated under reduced pressure. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 16.4 mg (49% of theory) of the title compound were obtained.

LC-MS (Method 3): $R_t$=1.13 min; MS (ESIpos): m/z=414 [M+H]$^+$ $^1$H-NMR (400 MHz, DMSO-d6) δ [ppm]: −0.154 (1.88), −0.013 (16.00), 0.141 (1.83), 0.941 (0.39), 1.657 (0.55), 1.729 (0.61), 1.769 (0.33), 1.952 (0.39), 1.966 (0.55), 2.013 (0.66), 2.032 (0.50), 2.055 (0.55), 2.067 (0.50), 2.076 (0.50), 2.089 (0.44), 2.125 (0.33), 2.322 (2.33), 2.327 (1.77), 2.361 (2.05), 2.518 (5.92), 2.561 (1.38), 2.572 (0.94), 2.585 (0.89), 2.598 (1.33), 2.660 (1.83), 2.664 (2.44), 2.705 (1.94), 3.347 (0.39), 3.448 (0.33), 3.486 (0.39), 3.530 (0.50), 3.612 (0.33), 3.665 (0.39), 3.681 (0.55), 3.698 (0.66), 3.723 (0.55), 3.750 (0.44), 3.763 (0.39), 3.921 (0.39), 3.966 (0.33), 3.983 (0.39), 4.170 (0.39), 4.789 (0.89), 4.801 (1.27), 4.952 (5.04), 5.242 (0.39), 5.250 (0.39), 5.282 (0.33), 5.327 (0.44), 5.344 (0.39), 5.359 (0.33), 5.386 (0.44), 5.395 (0.50), 5.412 (0.39), 5.425 (0.33), 5.453 (0.39), 5.491 (0.39), 6.802 (0.94), 6.939 (2.05), 7.076 (1.00), 7.676 (1.38), 7.697 (1.88), 7.812 (1.27), 7.833 (1.00), 8.556 (2.10).

Example 208

(5S)-2-{[6-(Difluoromethyl)pyridin-3-yl]methyl}-5-[(3,3-difluoropyrrolidin-1-yl)carbonyl]-5,6,7,8-tetrahydro[1,2,4]triazolo[4,3-a]pyridin-3(2H)-one

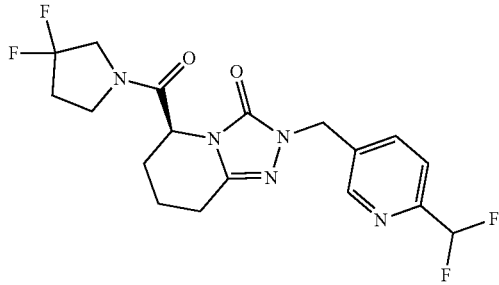 [SMILES: O=C([C@@H]1CCCc2nn(Cc3ccc(C(F)F)nc3)c(=O)n21)N1CCC(F)(F)C1]

(5S)-2-{[6-(Difluoromethyl)pyridin-3-yl]methyl}-3-oxo-2,3,5,6,7,8-hexahydro[1,2,4]triazolo[4,3-a]pyridine-5-carboxylic acid (100 mg, 25% purity, 77.1 µmol) was initially charged in THF (800 µl) at room temperature. Subsequently, 3,3-difluoropyrrolidine (9.91 mg, 92.5 µmol), HATU (38.1 mg, 100 µmol) and triethylamine (54 µl, 390 µmol) were added. The reaction mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 24.3 mg (74% of theory) of the title compound were obtained.

LC-MS (Method 3): $R_t$=1.20 min; MS (ESIpos): m/z=414 [M+H]$^+$ $^1$H-NMR (400 MHz, DMSO-d6) δ[ppm]: −0.149 (1.38), 0.146 (1.30), 1.041 (1.65), 1.673 (1.23), 1.731 (1.69), 2.002 (1.76), 2.012 (1.88), 2.047 (1.38), 2.327 (1.50), 2.366 (1.73), 2.381 (1.04), 2.410 (1.27), 2.431 (1.11), 2.563 (3.80), 2.573 (3.95), 2.588 (3.80), 2.605 (3.84), 2.648 (1.30), 2.670 (2.00), 2.710 (1.92), 2.884 (1.00), 3.533 (1.38), 3.541 (1.61), 3.550 (2.19), 3.560 (2.42), 3.580 (1.19), 3.636 (0.50), 3.668 (1.46), 3.703 (1.69), 3.747 (0.88), 3.782 (2.30), 3.811 (2.57), 3.829 (0.81), 3.891 (0.77), 3.909 (1.61), 3.935 (1.15), 3.953 (0.50), 3.993 (0.96), 4.021 (0.77), 4.037 (0.92), 4.065 (0.61), 4.148 (0.58), 4.179 (0.92), 4.206 (0.92), 4.759 (1.27), 4.774 (1.88), 4.784 (1.38), 4.831 (1.27), 4.846 (1.76), 4.856 (1.27), 4.957 (16.00), 6.806 (3.72), 6.943 (7.10), 7.081 (3.41), 7.682 (4.87), 7.702 (6.71), 7.820 (3.84), 7.840 (2.95), 8.157 (0.81), 8.563 (5.14).

Example 209

(5S)-2-{[6-(Difluoromethyl)pyridin-3-yl]methyl}-5-[(3-fluoroazetidin-1-yl)carbonyl]-5,6,7,8-tetrahydro[1,2,4]triazolo[4,3-a]pyridin-3(2H)-one

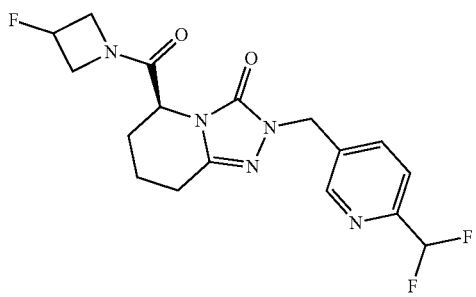 [SMILES: O=C([C@@H]1CCCc2nn(Cc3ccc(C(F)F)nc3)c(=O)n21)N1CC(F)C1]

(5S)-2-{[6-(Difluoromethyl)pyridin-3-yl]methyl}-3-oxo-2,3,5,6,7,8-hexahydro[1,2,4]triazolo[4,3-a]pyridine-5-carboxylic acid (100 mg, 25% purity, 77.1 µmol) was initially charged in THF (800 µl) at room temperature. Subsequently, 3-fluoroazetidine (6.95 mg, 92.5 µmol), HATU (38.1 mg, 100 µmol) and triethylamine (54 µl, 390 µmol) were added. The reaction mixture was stirred at room temperature overnight. The reaction mixture was admixed with water and concentrated under reduced pressure. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 23.2 mg (77% of theory) of the title compound were obtained.

LC-MS (Method 3): $R_t$=1.01 min; MS (ESIpos): m/z=382 [M+H]$^+$ $^1$H-NMR (400 MHz, DMSO-d6) δ[ppm]: −0.149 (1.89), −0.031 (0.40), −0.026 (0.55), −0.024 (0.65), −0.020 (0.84), −0.018 (1.09), −0.015 (1.39), −0.008 (16.00), −0.007 (12.42), 0.008 (15.60), 0.015 (1.74), 0.018 (0.94), 0.021 (0.70), 0.026 (0.45), 0.028 (0.40), 0.033 (0.35), 0.146 (1.94), 0.990 (0.55), 1.701 (1.19), 1.709 (1.24), 1.939 (0.60), 1.949 (0.75), 1.965 (0.80), 1.975 (0.80), 2.008 (0.70), 2.323 (1.64), 2.327 (2.43), 2.332 (1.84), 2.366 (1.79), 2.445 (0.45), 2.464 (0.70), 2.523 (5.42), 2.526 (4.02), 2.558 (2.09), 2.562 (1.94), 2.566 (1.44), 2.569 (1.19), 2.572 (1.19), 2.579 (1.84), 2.594 (2.34), 2.606 (1.29), 2.622 (0.75), 2.636 (0.80), 2.649 (0.45), 2.665 (1.79), 2.670 (2.34), 2.674 (1.84), 2.709 (1.74), 3.930 (0.55), 3.963 (0.60), 3.994 (0.50), 4.023 (0.40), 4.173 (0.40), 4.216 (0.35), 4.225 (0.50), 4.238 (0.50), 4.255 (0.50), 4.273 (0.65), 4.296 (0.55), 4.326 (0.45), 4.367 (0.45), 4.393 (0.35), 4.432 (0.40), 4.459 (0.45), 4.504 (0.40), 4.521 (0.35), 4.548 (1.44), 4.561 (2.14), 4.573 (1.49), 4.688 (0.35), 4.715 (0.35), 4.958 (5.47), 5.351 (0.35), 5.407 (0.40), 5.496 (0.40), 6.805 (1.64), 6.942 (3.03), 7.080 (1.59), 7.680 (1.84), 7.700 (2.48), 7.823 (1.74), 7.842 (1.34), 8.568 (2.68).

Example 210

(5S)-2-(4-Bromobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

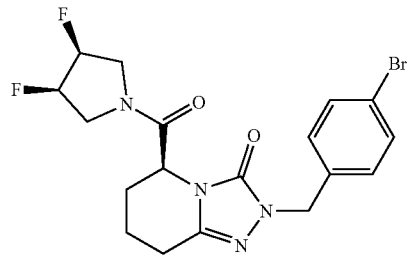 [SMILES: O=C([C@@H]1CCCc2nn(Cc3ccc(Br)cc3)c(=O)n21)N1C[C@@H](F)[C@@H](F)C1]

(5S)-2-(4-Bromobenzyl)-3-oxo-2,3,5,6,7,8-hexahydro[1,2,4]triazolo[4,3-a]pyridine-5-carboxylic acid (134 mg, 47% purity, 179 µmol) was initially charged in THF (2.6 ml) at room temperature. Subsequently, HBTU (88.1 mg, 232 µmol) and N,N-diisopropylethylamine (250 µl, 1.4 mmol) were added. After stirring for 5 min, (3R,4S)-3,4-difluoropyrrolidine hydrochloride (30.8 mg, 214 µmol) was added and the reaction mixture was stirred at room temperature overnight. The reaction mixture was admixed with water and ethyl acetate, and the organic phase was removed. The organic phase was washed with 10% citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 54.3 mg (69% of theory) of the title compound were obtained.

LC-MS (Method 3): $R_t$=1.47 min; MS (ESIpos): m/z=441 [M+H]$^+$ $^1$H-NMR (400 MHz, DMSO-d6) δ [ppm]: 1.174 (0.60), 1.664 (1.05), 1.725 (1.31), 1.925 (0.44), 1.959 (1.00), 1.988 (1.71), 2.004 (1.29), 2.029 (0.82), 2.038 (0.89), 2.046 (0.97), 2.054 (0.92), 2.063 (0.77), 2.073 (0.69), 2.081 (0.76), 2.089 (0.65), 2.328 (0.44), 2.558 (2.09), 2.569 (1.44), 2.583 (1.90), 2.596 (2.49), 2.608 (1.43), 2.628 (0.55), 2.639 (0.85), 2.669 (0.53), 3.452 (0.51), 3.486 (0.85), 3.507 (0.62), 3.524 (0.76), 3.533 (1.02), 3.542 (0.96), 3.566 (0.44), 3.575 (0.63), 3.586 (0.41), 3.612 (0.67), 3.626 (0.77), 3.645 (0.46), 3.659 (0.54), 3.668 (0.75), 3.682 (1.08), 3.701 (1.39), 3.715 (0.85), 3.724 (0.88), 3.733 (0.89), 3.753 (0.84), 3.764 (0.80), 3.786 (0.45), 3.799 (0.43), 3.863 (0.66), 3.905 (0.49), 3.925 (0.65), 3.939 (0.74), 3.953 (0.43), 3.974 (0.70), 3.988 (0.71), 4.003 (0.56), 4.020 (0.50), 4.127 (0.45), 4.142 (0.52), 4.156 (0.50), 4.169 (0.84), 4.183 (0.56), 4.196 (0.49), 4.211 (0.46), 4.789 (16.00), 5.254 (0.70), 5.264 (0.73), 5.275 (0.83), 5.285 (0.70), 5.296 (0.53), 5.310 (0.50), 5.327 (0.60), 5.336 (0.57), 5.349 (0.66), 5.364 (0.57), 5.377 (0.74), 5.387 (0.87), 5.398 (0.73), 5.406 (0.76), 5.416 (0.71), 5.428 (0.49), 5.439 (0.50), 5.448 (0.55), 5.472 (0.61), 5.479 (0.63), 5.492 (0.48), 7.173 (4.16), 7.180 (4.90), 7.194 (5.08), 7.201 (5.37), 7.527 (7.08), 7.545 (5.88), 7.548 (5.94).

Example 211

(5S)-2-(3-Bromobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

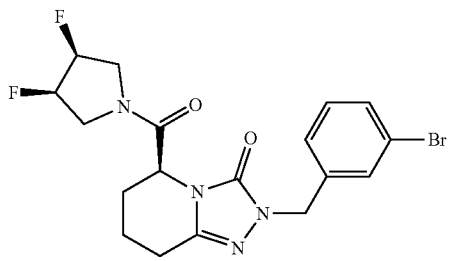 [SMILES: O=C([C@@H]1CCCc2nn(Cc3cccc(Br)c3)c(=O)n21)N1C[C@@H](F)[C@@H](F)C1]

(5S)-2-(3-Bromobenzyl)-3-oxo-2,3,5,6,7,8-hexahydro[1,2,4]triazolo[4,3-a]pyridine-5-carboxylic acid (128 mg, 59% purity, 215 μmol) was initially charged in THF (3.1 ml) at room temperature. Subsequently, HBTU (106 mg, 279 μmol) and N,N-diisopropylethylamine (300 μl, 1.7 mmol) were added. After stirring for 5 min, (3R,4S)-3,4-difluoropyrrolidine hydrochloride (37.0 mg, 258 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 23.2 mg (24% of theory) of the title compound were obtained.

LC-MS (Method 3): $R_t$=1.50 min; MS (ESIpos): m/z=441 [M+H]$^+$ $^1$H-NMR (400 MHz, DMSO-d6) δ [ppm]: 1.670 (1.28), 1.695 (0.91), 1.730 (1.61), 1.928 (0.54), 1.962 (1.20), 2.011 (1.55), 2.019 (1.18), 2.036 (0.94), 2.046 (1.09), 2.054 (1.18), 2.062 (1.15), 2.073 (1.00), 2.081 (0.85), 2.089 (0.96), 2.096 (0.81), 2.327 (0.54), 2.560 (1.83), 2.571 (2.22), 2.582 (1.65), 2.596 (2.31), 2.608 (3.03), 2.620 (1.72), 2.638 (0.65), 2.650 (1.00), 2.665 (0.85), 3.455 (0.57), 3.489 (1.00), 3.510 (0.74), 3.517 (0.80), 3.526 (0.87), 3.537 (1.22), 3.545 (1.15), 3.580 (0.80), 3.616 (0.78), 3.630 (0.91), 3.649 (0.54), 3.671 (0.89), 3.685 (1.24), 3.704 (1.54), 3.718 (0.98), 3.726 (1.29), 3.740 (0.89), 3.757 (1.05), 3.769 (1.07), 3.791 (0.50), 3.803 (0.52), 3.870 (0.80), 3.925 (0.81), 3.939 (0.85), 3.954 (0.50), 3.975 (0.85), 3.989 (0.81), 4.004 (0.52), 4.017 (0.46), 4.133 (0.54), 4.148 (0.59), 4.161 (0.57), 4.175 (0.96), 4.189 (0.65), 4.201 (0.57), 4.217 (0.52), 4.795 (2.35), 4.807 (3.61), 4.823 (16.00), 4.868 (0.41), 5.255 (0.83), 5.266 (0.87), 5.276 (0.98), 5.286 (0.81), 5.299 (0.61), 5.329 (0.70), 5.339 (0.70), 5.351 (0.78), 5.366 (0.68), 5.377 (0.91), 5.389 (1.05), 5.400 (0.83), 5.408 (0.89), 5.417 (0.83), 5.429 (0.59), 5.442 (0.59), 5.459 (0.74), 5.472 (0.72), 5.481 (0.74), 5.495 (0.57), 7.221 (1.92), 7.237 (3.02), 7.288 (2.18), 7.292 (2.61), 7.308 (3.75), 7.311 (4.42), 7.327 (1.78), 7.331 (2.05), 7.435 (5.42), 7.476 (3.16), 7.495 (2.57).

Example 212

(5S)-2-(4-Bromobenzyl)-5-{[(3S)-3-fluoropyrrolidin-1-yl]carbonyl}-5,6,7,8-tetrahydro[1,2,4]triazolo[4,3-a]pyridin-3(2H)-one

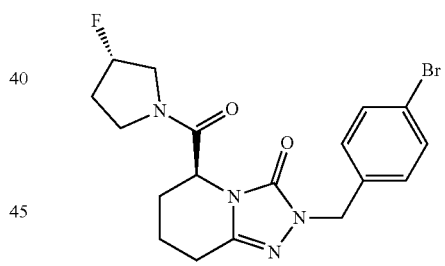

(5S)-2-(4-Bromobenzyl)-3-oxo-2,3,5,6,7,8-hexahydro[1,2,4]triazolo[4,3-a]pyridine-5-carboxylic acid (134 mg, 47% purity, 179 μmol) was initially charged in THF (2.6 ml) at room temperature. Subsequently, HBTU (88.1 mg, 232 μmol) and N,N-diisopropylethylamine (250 μl, 1.4 mmol) were added. After stirring for 5 min, (3S)-3-fluoropyrrolidine hydrochloride (26.9 mg, 214 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 51.7 mg (66% of theory) of the title compound were obtained.

LC-MS (Method 3): $R_t$=1.40 min; MS (ESIpos): m/z=423 [M+H]$^+$ $^1$H-NMR (400 MHz, DMSO-d6) δ[ppm]: −0.149 (1.20), −0.008 (9.55), 0.008 (10.75), 0.146 (1.20), 0.940 (0.85), 0.956 (0.80), 1.728 (4.00), 1.913 (0.90), 2.027 (1.60), 2.085 (2.35), 2.133 (1.70), 2.267 (1.45), 2.327 (1.60), 2.366 (0.85), 2.558 (3.25), 2.573 (2.10), 2.600 (3.30), 2.642 (1.30), 2.670 (1.75), 2.709 (0.90), 3.268 (0.95), 3.287 (2.35), 3.344 (1.60), 3.367 (1.10), 3.392 (1.15), 3.464 (0.90), 3.491 (1.10), 3.606 (0.70), 3.633 (3.60), 3.651 (2.55), 3.657 (2.65), 3.675 (1.95), 3.700 (1.40), 3.722 (1.45), 3.742 (2.65), 3.765 (2.00), 3.786 (1.55), 3.855 (3.20), 4.674 (1.50), 4.684 (1.85), 4.690 (1.95), 4.699 (1.55), 4.731 (1.90), 4.746 (3.25), 4.756 (1.90), 4.785 (16.00), 4.830 (0.70), 5.258 (1.70), 5.389 (2.05), 5.510 (1.10), 7.175 (6.10), 7.181 (8.15), 7.196 (8.05), 7.202 (8.55), 7.520 (1.90), 7.526 (13.45), 7.547 (12.20).

Example 213

(5S)-2-(3-Bromobenzyl)-5-{[(3S)-3-fluoropyrrolidin-1-yl]carbonyl}-5,6,7,8-tetrahydro[1,2,4]triazolo[4,3-a]pyridin-3(2H)-one

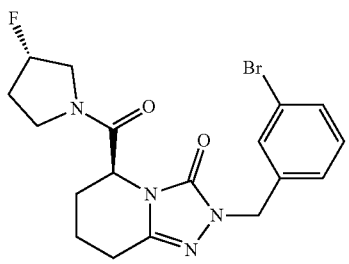 [SMILES: O=C([C@@H]1CCCc2nn(Cc3cccc(Br)c3)c(=O)n21)N1CC[C@H](F)C1]

(5S)-2-(3-Bromobenzyl)-3-oxo-2,3,5,6,7,8-hexahydro[1,2,4]triazolo[4,3-a]pyridine-5-carboxylic acid (128 mg, 59% purity, 215 μmol) was initially charged in THF (3.1 ml) at room temperature. Subsequently, HBTU (106 mg, 279 μmol) and N,N-diisopropylethylamine (300 μl, 1.7 mmol) were added. After stirring for 5 min, (3S)-3-fluoropyrrolidine hydrochloride (32.4 mg, 258 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 55.5 mg (61% of theory) of the title compound were obtained.

LC-MS (Method 3): $R_t$=1.40 min; MS (ESIpos): m/z=423 [M+H]$^+$ $^1$H-NMR (400 MHz, DMSO-d6) δ[ppm]: −0.149 (0.62), 0.146 (0.65), 1.719 (3.49), 1.732 (4.21), 1.871 (0.78), 1.881 (0.75), 1.906 (1.01), 1.995 (1.21), 2.008 (1.21), 2.021 (1.76), 2.064 (1.67), 2.089 (2.48), 2.101 (2.74), 2.126 (1.76), 2.138 (2.02), 2.220 (1.08), 2.242 (1.08), 2.269 (1.47), 2.327 (0.95), 2.366 (0.69), 2.561 (2.45), 2.570 (2.78), 2.587 (2.12), 2.613 (3.46), 2.654 (1.34), 2.669 (1.50), 2.710 (0.82), 3.273 (0.85), 3.347 (1.21), 3.369 (1.14), 3.397 (1.18), 3.405 (1.14), 3.458 (0.85), 3.466 (0.88), 3.494 (1.14), 3.503 (1.08), 3.613 (0.69), 3.638 (3.89), 3.655 (2.61), 3.663 (2.81), 3.680 (2.06), 3.704 (1.50), 3.722 (1.60), 3.742 (3.23), 3.770 (2.06), 3.785 (2.06), 3.856 (3.33), 4.691 (1.53), 4.700 (1.86), 4.706 (1.99), 4.715 (1.57), 4.747 (1.96), 4.756 (2.25), 4.762 (2.58), 4.772 (1.99), 4.819 (16.00), 4.866 (0.88), 5.260 (1.63), 5.390 (2.22), 5.512 (1.21), 7.222 (2.94), 7.241 (4.70), 7.291 (4.70), 7.311 (7.93), 7.330 (3.69), 7.436 (7.09), 7.475 (4.34), 7.495 (3.56).

Example 214

(5S)-2-(4-Bromo-2-fluorobenzyl)-5-{[(3S)-3-fluoropyrrolidin-1-yl]carbonyl}-5,6,7,8-tetrahydro[1,2,4]triazolo[4,3-a]pyridin-3(2H)-one

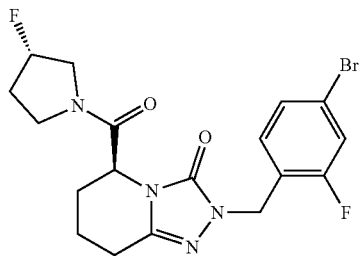 [SMILES: O=C([C@@H]1CCCc2nn(Cc3ccc(Br)cc3F)c(=O)n21)N1CC[C@H](F)C1]

(5S)-2-(4-Bromo-2-fluorobenzyl)-3-oxo-2,3,5,6,7,8-hexahydro[1,2,4]triazolo[4,3-a]pyridine-5-carboxylic acid (85.0 mg, 223 μmol) was initially charged in THF (2.0 ml) at room temperature. Subsequently, HBTU (110 mg, 290 μmol) and N,N-diisopropylethylamine (190 μl, 1.1 mmol) were added. After stirring for 5 min, (3S)-3-fluoropyrrolidine hydrochloride (33.6 mg, 267 μmol) was added and the reaction mixture was stirred at room temperature over the weekend. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 49.1 mg (50% of theory) of the title compound were obtained.

LC-MS (Method 3): $R_t$=1.47 min; MS (ESIpos): m/z=441 [M+H]$^+$ $^1$H-NMR (400 MHz, DMSO-d6) δ[ppm]: −0.149 (2.07), −0.008 (15.92), 0.008 (15.04), 0.146 (1.91), 1.722 (6.61), 1.861 (1.35), 1.895 (1.67), 2.021 (2.87), 2.087 (3.82), 2.135 (2.63), 2.265 (2.31), 2.327 (3.26), 2.366 (2.55), 2.524 (9.47), 2.569 (3.42), 2.597 (5.17), 2.639 (1.99), 2.670 (3.34), 2.710 (2.47), 3.364 (1.67), 3.391 (1.83), 3.462 (1.27), 3.488 (1.83), 3.604 (1.19), 3.630 (6.05), 3.655 (4.38), 3.673 (3.18), 3.693 (2.31), 3.718 (2.55), 3.740 (4.38), 3.764 (3.42), 3.782 (2.79), 3.851 (5.25), 4.669 (2.55), 4.678 (3.34), 4.684 (3.50), 4.693 (2.71), 4.726 (3.18), 4.735 (3.58), 4.741 (4.22), 4.750 (3.18), 4.772 (3.90), 4.811 (16.00), 4.837 (10.27), 4.877 (2.71), 5.257 (2.63), 5.388 (3.42), 5.509 (1.83), 7.188 (3.98), 7.204 (7.08), 7.208 (8.68), 7.224 (4.06), 7.229 (4.70), 7.403 (8.36), 7.408 (8.60), 7.428 (7.24), 7.543 (7.56), 7.547 (7.16), 7.567 (7.72), 7.572 (7.24), 8.559 (0.64).

Example 215

(5S)-2-(4-Bromo-2-fluorobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

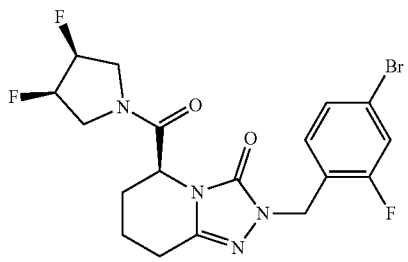 [SMILES: O=C([C@@H]1CCCc2nn(Cc3ccc(Br)cc3F)c(=O)n21)N1C[C@@H](F)[C@@H](F)C1]

(5S)-2-(4-Bromo-2-fluorobenzyl)-3-oxo-2,3,5,6,7,8-hexahydro[1,2,4]triazolo[4,3-a]pyridine-5-carboxylic acid (85.0 mg, 223 µmol) was initially charged in THF (2.0 ml) at room temperature. Subsequently, HBTU (110 mg, 290 µmol) and N,N-diisopropylethylamine (190 µl, 1.1 mmol) were added. After stirring for 5 min, (3R,4S)-3,4-difluoropyrrolidine hydrochloride (38.4 mg, 267 µmol) was added and the reaction mixture was stirred at room temperature over the weekend. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 50.6 mg (49% of theory) of the title compound were obtained.

LC-MS (Method 3): $R_t$=1.54 min; MS (ESIpos): m/z=459 [M+H]$^+$ $^1$H-NMR (400 MHz, DMSO-d6) δ [ppm]: −0.149 (0.70), −0.008 (5.71), 0.008 (5.79), 0.146 (0.63), 1.636 (2.03), 1.661 (2.64), 1.670 (2.35), 1.685 (1.84), 1.699 (2.42), 1.711 (2.93), 1.720 (3.34), 1.734 (2.81), 1.911 (1.09), 1.953 (2.49), 1.962 (2.18), 1.978 (1.62), 1.998 (3.20), 2.022 (2.03), 2.032 (2.28), 2.040 (2.49), 2.048 (2.42), 2.056 (1.91), 2.067 (1.82), 2.073 (2.20), 2.083 (1.69), 2.327 (0.99), 2.366 (0.68), 2.577 (4.65), 2.591 (6.34), 2.603 (3.56), 2.621 (1.36), 2.633 (2.18), 2.646 (1.14), 2.665 (0.92), 2.670 (1.19), 2.674 (0.94), 2.710 (0.80), 3.448 (1.23), 3.457 (0.77), 3.483 (2.13), 3.504 (1.55), 3.511 (1.57), 3.521 (1.84), 3.530 (2.59), 3.538 (2.37), 3.563 (1.09), 3.573 (1.60), 3.583 (1.02), 3.611 (1.67), 3.624 (1.96), 3.643 (1.19), 3.657 (1.33), 3.666 (1.86), 3.680 (2.74), 3.698 (3.46), 3.713 (2.13), 3.722 (2.13), 3.731 (2.32), 3.751 (2.06), 3.761 (2.03), 3.783 (1.16), 3.796 (1.14), 3.825 (0.75), 3.861 (1.65), 3.902 (1.23), 3.921 (1.62), 3.935 (1.89), 3.950 (1.14), 3.971 (1.79), 3.985 (1.84), 4.000 (1.14), 4.013 (1.04), 4.124 (1.14), 4.138 (1.31), 4.152 (1.26), 4.166 (2.15), 4.179 (1.38), 4.192 (1.26), 4.208 (1.14), 4.778 (7.46), 4.785 (7.24), 4.795 (4.72), 4.816 (16.00), 4.830 (9.08), 4.838 (9.27), 4.869 (1.48), 4.877 (2.25), 5.243 (1.14), 5.252 (1.79), 5.265 (1.79), 5.274 (2.03), 5.283 (1.69), 5.295 (1.31), 5.327 (1.48), 5.336 (1.50), 5.348 (1.60), 5.363 (1.43), 5.375 (1.89), 5.386 (2.25), 5.398 (1.86), 5.406 (1.91), 5.414 (1.69), 5.425 (1.23), 5.439 (1.23), 5.456 (1.52), 5.470 (1.57), 5.478 (1.62), 5.492 (1.21), 5.501 (0.80), 7.180 (3.00), 7.188 (3.53), 7.200 (6.70), 7.208 (7.53), 7.221 (3.87), 7.228 (4.16), 7.405 (8.08), 7.425 (6.80), 7.545 (7.07), 7.549 (4.96), 7.569 (7.21), 7.573 (4.99).

Example 216

(5S)-5-{[(3S)-3-Fluoropyrrolidin-1-yl]carbonyl}-2-{(1RS)-1-[6-(trifluoromethyl)pyridin-3-yl]ethyl}-5,6,7,8-tetrahydro[1,2,4]triazolo[4,3-a]pyridin-3(2H)-one (Isomer 1)

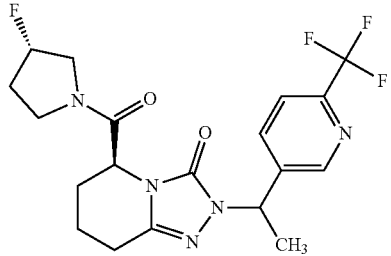 [SMILES: CC(c1ccc(C(F)(F)F)nc1)n1nc2n(c1=O)[C@H](C(=O)N1CC[C@H](F)C1)CCC2]

(5S)-3-Oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylic acid (isomer 1) (75.0 mg, 210 µmol) was initially charged in THF (2.0 ml) at room temperature. Subsequently, HBTU (104 mg, 274 µmol) and N,N-diisopropylethylamine (180 µl, 1.1 mmol) were added. After stirring for 5 min, (3S)-3-fluoropyrrolidine hydrochloride (31.7 mg, 253 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 32.5 mg (36% of theory) of the title compound were obtained.

LC-MS (Method 3): $R_t$=1.36 min; MS (ESIpos): m/z=428 [M+H]$^+$ $^1$H-NMR (400 MHz, DMSO-d6) δ [ppm]: −0.149 (0.57), −0.008 (4.90), 0.008 (5.76), 0.146 (0.57), 1.681 (15.40), 1.699 (16.00), 1.723 (3.24), 1.735 (4.02), 1.747 (3.10), 1.851 (0.68), 1.861 (0.66), 1.887 (0.87), 1.960 (0.90), 1.972 (0.80), 1.985 (1.13), 1.995 (1.46), 2.009 (1.24), 2.061 (1.64), 2.075 (1.83), 2.092 (2.11), 2.126 (1.21), 2.153 (0.79), 2.210 (0.88), 2.231 (0.83), 2.259 (1.15), 2.322 (0.79), 2.327 (1.06), 2.366 (0.60), 2.523 (3.39), 2.569 (1.87), 2.586 (1.53), 2.593 (2.30), 2.609 (1.29), 2.648 (2.28), 2.656 (2.47), 2.669 (2.14), 2.689 (1.02), 2.697 (1.10), 2.710 (1.06), 3.273 (0.63), 3.348 (0.74), 3.361 (0.69), 3.370 (0.74), 3.397 (0.79), 3.405 (0.82), 3.459 (0.61), 3.467 (0.66), 3.494 (0.93), 3.503 (0.87), 3.590 (0.57), 3.616 (1.31), 3.638 (2.46), 3.661 (1.94), 3.689 (0.83), 3.704 (2.09), 3.728 (2.05), 3.750 (1.64), 3.769 (1.31), 3.838 (2.57), 4.644 (1.23), 4.654 (1.51), 4.659 (1.64), 4.669 (1.23), 4.703 (1.53), 4.713 (1.84), 4.719 (2.05), 4.728 (1.56), 5.256 (1.31), 5.388 (1.32), 5.468 (1.95), 5.477 (2.49), 5.486 (2.09), 5.495 (2.76), 7.883 (4.74), 7.903 (6.80), 7.999 (3.75), 8.019 (2.72), 8.705 (5.28).

Example 217

(5S)-5-{[(3S)-3-Fluoropyrrolidin-1-yl]carbonyl}-2-{(1 RS)-1-[6-(trifluoromethyl)pyridin-3-yl]ethyl}-5,6,7,8-tetrahydro[1,2,4]triazolo[4,3-a]pyridin-3(2H)-one (Isomer 2)

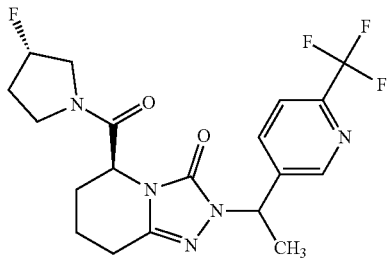 [SMILES: CC(c1ccc(C(F)(F)F)nc1)n1nc2n(c1=O)[C@H](C(=O)N1CC[C@H](F)C1)CCC2]

(5S)-3-Oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylic acid (isomer 2) (65.0 mg, 177 μmol) was initially charged in THF (2.0 ml) at room temperature. Subsequently, HBTU (87.2 mg, 230 μmol) and N,N-diisopropylethylamine (150 μl, 880 μmol) were added. After stirring for 5 min, (3S)-3-fluoropyrrolidine hydrochloride (26.7 mg, 212 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 30.2 mg (40% of theory) of the title compound were obtained.

LC-MS (Method 3): $R_t$=1.35 min; MS (ESIpos): m/z=428 [M+H]$^+$ $^1$H-NMR (400 MHz, DMSO-d6) δ [ppm]: −0.149 (0.56), −0.008 (4.61), 0.008 (4.37), 0.146 (0.49), 1.677 (15.68), 1.694 (16.00), 1.746 (1.65), 1.884 (0.49), 1.924 (0.75), 2.010 (0.61), 2.084 (1.67), 2.104 (1.72), 2.259 (1.02), 2.327 (1.12), 2.367 (0.53), 2.586 (1.62), 2.602 (1.34), 2.612 (1.51), 2.626 (1.26), 2.655 (1.99), 2.665 (1.94), 2.669 (1.96), 2.697 (0.78), 2.710 (0.80), 2.882 (0.51), 3.247 (0.49), 3.275 (0.90), 3.371 (0.65), 3.379 (0.68), 3.441 (0.53), 3.468 (0.77), 3.618 (1.89), 3.634 (1.74), 3.646 (1.36), 3.676 (0.97), 3.715 (1.48), 3.738 (1.51), 3.759 (1.17), 3.777 (1.00), 3.842 (2.06), 4.689 (1.02), 4.698 (1.24), 4.704 (1.33), 4.713 (0.99), 4.746 (1.26), 4.754 (1.46), 4.761 (1.69), 4.770 (1.26), 5.245 (1.06), 5.377 (1.46), 5.489 (1.69), 5.498 (2.54), 5.506 (2.30), 5.515 (2.09), 7.900 (3.88), 7.920 (6.69), 7.974 (2.72), 7.994 (1.62), 8.663 (4.90).

Example 218

(5S)-5-{[(3R,4S)-3,4-Difluoropyrrolidin-1-yl]carbonyl}-2-{(1 RS)-1-[6-(trifluoromethyl)pyridin-3-yl]ethyl}-5,6,7,8-tetrahydro[1,2,4]triazolo[4,3-a]pyridin-3(2H)-one (Isomer 1)

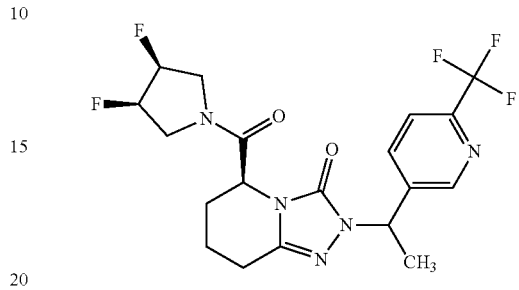

(5S)-3-Oxo-2-{(1R)-1-[6-(trifluoromethyl)pyridin-3-yl]ethyl}-2,3,5,6,7,8-hexahydro[1,2,4]triazolo[4,3-a]pyridine-5-carboxylic acid (isomer 1) (75.0 mg, 210 μmol) was initially charged in THF (2.0 ml) at room temperature. Subsequently, HBTU (104 mg, 274 μmol) and N,N-diisopropylethylamine (180 μl, 1.1 mmol) were added. After stirring for 5 min, (3R,4S)-3,4-difluoropyrrolidine hydrochloride (36.3 mg, 253 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 32.4 mg (35% of theory) of the title compound were obtained.

LC-MS (Method 3): $R_t$=1.43 min; MS (ESIpos): m/z=446 [M+H]$^+$ $^1$H-NMR (400 MHz, DMSO-d6) δ [ppm]: −0.149 (1.11), −0.008 (9.41), 0.008 (9.45), 0.146 (1.07), 1.406 (0.97), 1.679 (15.86), 1.697 (16.00), 1.719 (2.58), 1.943 (1.32), 1.968 (0.93), 1.976 (1.29), 1.990 (1.29), 2.022 (1.15), 2.041 (1.25), 2.048 (1.29), 2.058 (1.22), 2.077 (1.00), 2.322 (1.65), 2.327 (2.29), 2.332 (1.75), 2.523 (6.59), 2.569 (2.04), 2.584 (2.18), 2.595 (2.61), 2.606 (1.93), 2.619 (1.32), 2.652 (2.79), 2.665 (3.15), 2.669 (3.04), 2.674 (2.51), 2.694 (1.36), 2.709 (1.32), 3.491 (1.18), 3.511 (0.89), 3.528 (1.04), 3.537 (1.43), 3.545 (1.32), 3.579 (0.93), 3.617 (0.97), 3.630 (1.11), 3.673 (1.15), 3.687 (1.61), 3.703 (1.79), 3.722 (1.57), 3.736 (1.07), 3.753 (1.25), 3.766 (1.15), 3.801 (0.93), 3.842 (1.04), 3.882 (0.79), 3.915 (0.93), 3.928 (1.15), 3.965 (1.04), 3.978 (1.00), 4.116 (0.79), 4.131 (0.75), 4.146 (1.00), 4.158 (0.79), 4.744 (2.72), 4.758 (3.69), 4.768 (2.51), 5.251 (1.04), 5.262 (1.00), 5.272 (1.07), 5.303 (0.79), 5.312 (0.79), 5.319 (0.89), 5.329 (0.86), 5.342 (0.89), 5.365 (0.89), 5.376 (1.07), 5.385 (1.07), 5.396 (1.07), 5.404 (1.04), 5.418 (1.04), 5.427 (0.79), 5.452 (1.36), 5.470 (2.86), 5.485 (3.19), 5.500 (2.76), 5.516 (0.82), 7.884 (5.37), 7.904 (7.48), 8.002 (4.22), 8.023 (3.11), 8.705 (6.59).

Example 219

(5S)-5-{[(3R,4S)-3,4-Difluoropyrrolidin-1-yl]carbonyl}-2-{(1 RS)-1-[6-(trifluoromethyl)pyridin-3-yl]ethyl}-5,6,7,8-tetrahydro[1,2,4]triazolo[4,3-a]pyridin-3(2H)-one (Isomer 2)

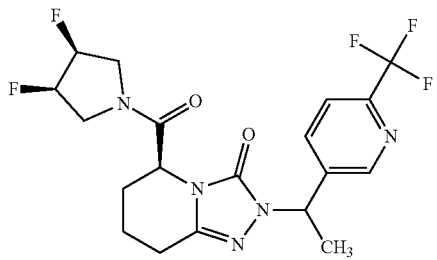 [SMILES: CC(c1ccc(C(F)(F)F)nc1)n1nc2n(c1=O)[C@H](C(=O)N1C[C@@H](F)[C@@H](F)C1)CCC2]

(5S)-3-Oxo-2-{(1 RS)-1-[6-(trifluoromethyl)pyridin-3-yl]ethyl}-2,3,5,6,7,8-hexahydro[1,2,4]triazolo[4,3-a]pyridine-5-carboxylic acid (isomer 2) (65.0 mg, 177 µmol) was initially charged in THF (2.0 ml) at room temperature. Subsequently, HBTU (87.2 mg, 230 µmol) and N,N-diisopropylethylamine (150 µl, 880 µmol) were added. After stirring for 5 min, (3R,4S)-3,4-difluoropyrrolidine hydrochloride (30.5 mg, 212 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 11.6 mg (15% of theory) of the title compound were obtained.

LC-MS (Method 3): $R_t$=1.43 min; MS (ESIpos): m/z=446 [M+H]

$^1$H-NMR (400 MHz, DMSO-d6) δ [ppm]: −0.149 (1.97), −0.050 (0.62), −0.008 (16.00), 0.008 (15.32), 0.018 (0.68), 0.146 (1.66), 1.616 (0.94), 1.652 (1.25), 1.677 (13.66), 1.695 (13.30), 1.741 (1.19), 1.779 (0.83), 1.976 (0.99), 2.017 (1.51), 2.027 (1.51), 2.065 (1.04), 2.093 (0.78), 2.101 (0.78), 2.322 (2.86), 2.327 (3.79), 2.332 (2.81), 2.366 (1.66), 2.392 (0.57), 2.404 (0.62), 2.523 (7.69), 2.567 (0.83), 2.583 (1.09), 2.594 (1.14), 2.609 (1.56), 2.620 (1.14), 2.633 (1.40), 2.651 (2.08), 2.661 (2.44), 2.665 (3.48), 2.669 (4.00), 2.674 (3.01), 2.692 (0.68), 2.710 (1.51), 3.462 (0.73), 3.483 (0.68), 3.501 (0.68), 3.508 (0.94), 3.517 (0.99), 3.605 (0.78), 3.645 (0.68), 3.660 (1.19), 3.673 (0.94), 3.695 (0.99), 3.720 (0.83), 3.737 (0.83), 3.758 (0.62), 3.859 (0.57), 3.897 (0.57), 3.916 (0.78), 3.929 (0.83), 3.958 (0.57), 3.966 (0.78), 3.980 (0.62), 4.145 (0.57), 4.157 (0.78), 4.186 (0.57), 4.796 (1.97), 4.810 (2.49), 4.820 (1.82), 5.247 (0.83), 5.255 (0.78), 5.264 (0.68), 5.311 (0.73), 5.342 (0.73), 5.357 (0.94), 5.368 (0.94), 5.391 (0.88), 5.441 (0.73), 5.476 (1.04), 5.493 (1.66), 5.501 (1.82), 5.511 (1.56), 5.520 (1.66), 7.897 (1.77), 7.901 (2.08), 7.916 (3.32), 7.920 (3.58), 7.966 (1.71), 7.979 (2.18), 7.993 (1.19), 8.551 (0.78), 8.660 (4.26).

Example 220

(5RS,8RS)-5-{[(3S)-3-Fluoropyrrolidin-1-yl]carbonyl}-8-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

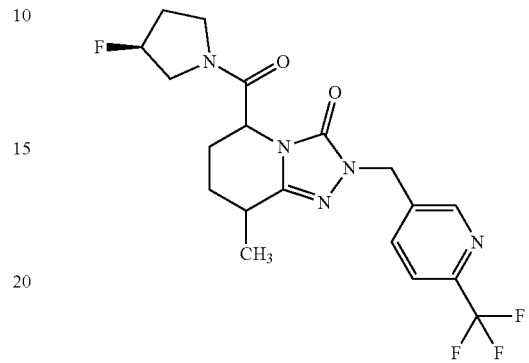

(5RS,8RS)-8-Methyl-3-oxo-2-{[6-(trifluoromethyl)pyridin-3-yl]methyl}octahydro[1,2,4]triazolo[4,3-a]pyridine-5-carboxylic acid (diastereomer mixture; 4 isomers) (100 mg, 279 µmol) was initially charged in dichloromethane (2.0 ml) and DMF (4.0 ml) at room temperature. Subsequently, 1-[bis(dimethylamino)methylene]-1H-benzotriazol-1-ium 3-oxide hexafluorophosphate (138 mg, 363 µmol) and N,N-diisopropylethylamine (120 µl, 670 µmol) were added. After stirring for 15 min, (3S)-3-fluoropyrrolidine hydrochloride (38.5 mg, 307 µmol) was added and the reaction mixture was stirred at room temperature for 30 min. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 76.0 mg (64% of theory) of the title compound were obtained as a diastereomer mixture.

LC-MS (Method 3): $R_t$=1.39 min; MS (ESIpos): m/z=428 [M+H]$^+$ $^1$H-NMR (400 MHz, DMSO-d6) δ [ppm]: −0.008 (0.95), 0.008 (0.84), 1.175 (11.85), 1.181 (12.64), 1.192 (12.80), 1.198 (12.36), 1.345 (0.79), 1.375 (1.07), 1.409 (1.13), 1.442 (0.85), 1.804 (1.52), 1.814 (1.61), 1.824 (1.65), 1.833 (1.39), 1.965 (0.69), 1.999 (1.14), 2.033 (0.60), 2.040 (0.61), 2.078 (3.30), 2.088 (3.09), 2.103 (3.06), 2.111 (3.23), 2.126 (2.92), 2.135 (2.51), 2.153 (1.32), 2.172 (0.58), 2.227 (0.92), 2.237 (0.95), 2.258 (1.26), 2.524 (0.86), 2.707 (1.11), 2.722 (1.74), 2.737 (2.13), 2.752 (1.75), 2.766 (1.08), 3.276 (0.43), 3.357 (0.89), 3.367 (1.05), 3.387 (0.89), 3.397 (0.83), 3.414 (0.46), 3.463 (0.43), 3.490 (0.58), 3.498 (0.58), 3.520 (1.78), 3.543 (1.38), 3.550 (1.09), 3.569 (1.18), 3.599 (2.26), 3.625 (1.34), 3.641 (1.96), 3.648 (1.65), 3.671 (1.54), 3.700 (0.76), 3.714 (0.73), 3.736 (1.85), 3.758 (1.07), 3.766 (1.05), 3.776 (1.17), 3.844 (1.52), 3.910 (0.54), 3.932 (0.99), 3.952 (0.72), 3.980 (0.44), 4.006 (0.53), 4.038 (0.41), 4.725 (0.97), 4.738 (1.03), 4.773 (0.95), 4.782 (1.50), 4.793 (0.96), 4.854 (0.84), 4.860 (1.12), 4.872 (0.97), 4.890 (0.89), 4.902 (1.20), 4.909 (0.81), 5.002 (0.58), 5.052 (13.40), 5.092 (0.56), 5.262 (1.23), 5.269 (1.12), 5.349 (0.69), 5.395 (1.28), 5.481 (0.68), 5.511 (0.56), 7.884 (0.66), 7.908 (16.00), 7.928 (0.87), 8.633 (6.30).

Example 221

(5RS,8RS)-5-{[(3S)-3-Fluoropyrrolidin-1-yl]carbonyl}-8-methyl-2-{[6-(trifluoromethyl)pyridin-3-yl]methyl}-5,6,7,8-tetrahydro[1,2,4]triazolo[4,3-a]pyridin-3(2H)-one (Isomer 1)

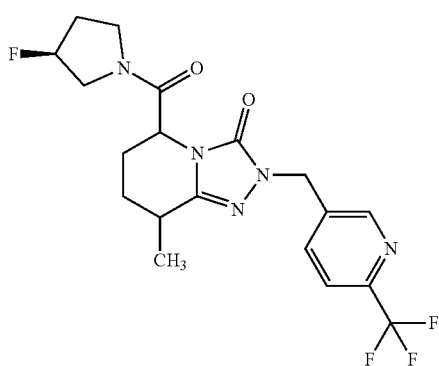 [SMILES: CC1CCC(C(=O)N2CC[C@H](F)C2)n2c1nn(Cc1ccc(C(F)(F)F)nc1)c2=O]

(5RS,8RS)-5-{[(3S)-3-Fluoropyrrolidin-1-yl]carbonyl}-8-methyl-2-{[6-(trifluoromethyl)pyridin-3-yl]methyl}-5,6,7,8-tetrahydro[1,2,4]triazolo[4,3-a]pyridin-3(2H)-one (diastereomer mixture; 4 isomers) was separated by chiral preparative HPLC [sample preparation: 60 mg dissolved in 1 ml of ethanol and 1 ml of acetonitrile; injection volume: 0.25 ml; column: Daicel Chiralpak® IA 5 µm, 250×20 mm; eluent: n-heptane/ethanol 50:50; flow rate: 20 ml/min; temperature 40° C.; UV detection: 220 nm]. After the separation, 18.4 mg of isomer 1, which elutes first, and 18.5 mg of isomer 2, which elutes later, were isolated.

Isomer 1:

Analytical chiral HPLC: $R_t$=1.95 min, d.e.=100% [column: Daicel Chiralcel® ID-3 50×4.6 mm; eluent: n-heptane/ethanol 70:30; flow rate: 1 ml/min; UV detection: 220 nm].

LC-MS (Method 3): $R_t$=1.40 min; MS (ESIpos): m/z=428 [M+H]$^+$ $^1$H-NMR (400 MHz, DMSO-d6) δ [ppm]: −0.008 (2.11), 0.008 (1.73), 1.175 (15.58), 1.191 (16.00), 1.316 (0.40), 1.345 (1.10), 1.373 (1.14), 1.401 (0.52), 1.797 (0.87), 1.821 (1.22), 1.842 (0.80), 1.856 (0.67), 2.003 (0.50), 2.076 (3.92), 2.138 (1.06), 2.153 (0.81), 2.207 (0.68), 2.229 (0.70), 2.245 (0.70), 2.257 (0.97), 2.328 (0.43), 2.670 (0.47), 2.720 (1.03), 2.735 (1.32), 2.744 (1.35), 2.774 (0.60), 3.338 (0.78), 3.356 (0.70), 3.367 (1.10), 3.385 (1.09), 3.395 (0.76), 3.413 (0.61), 3.519 (2.55), 3.542 (1.99), 3.567 (1.70), 3.598 (2.78), 3.647 (0.57), 3.671 (0.60), 3.679 (0.60), 3.745 (0.48), 3.768 (0.62), 3.776 (0.61), 3.909 (0.78), 3.931 (1.41), 3.951 (1.04), 3.978 (0.66), 4.005 (0.77), 4.036 (0.62), 4.858 (1.59), 4.872 (1.35), 4.889 (1.29), 4.901 (1.72), 4.909 (1.15), 5.051 (13.02), 5.269 (0.97), 5.348 (0.97), 5.399 (0.99), 5.480 (0.97), 7.885 (0.47), 7.908 (12.03), 7.928 (0.69), 8.632 (5.68).

Example 222

(5RS,8RS)-5-{[(3S)-3-Fluoropyrrolidin-1-yl]carbonyl}-8-methyl-2-{[6-(trifluoromethyl)pyridin-3-yl]methyl}-5,6,7,8-tetrahydro[1,2,4]triazolo[4,3-a]pyridin-3(2H)-one (Isomer 2)

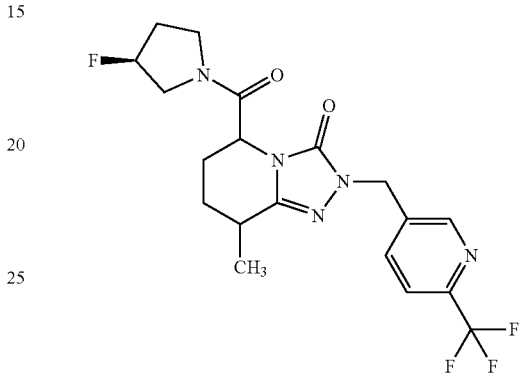

(5RS,8RS)-5-{[(3S)-3-Fluoropyrrolidin-1-yl]carbonyl}-8-methyl-2-{[6-(trifluoromethyl)pyridin-3-yl]methyl}-5,6,7,8-tetrahydro[1,2,4]triazolo[4,3-a]pyridin-3(2H)-one (diastereomer mixture; 4 isomers) was separated by chiral preparative HPLC [sample preparation: 60 mg dissolved in 1 ml of ethanol and 1 ml of acetonitrile; injection volume: 0.25 ml; column: Daicel Chiralpak® IA 5 µm, 250×20 mm; eluent: n-heptane/ethanol 50:50; flow rate: 20 ml/min; temperature 40° C.; UV detection: 220 nm]. After the separation, 18.4 mg of isomer 1, which elutes first, and 18.5 mg of isomer 2, which elutes later, were isolated.

Isomer 2:

Analytical chiral HPLC: $R_t$=2.22 min, d.e.=100% [column: Daicel Chiralcel® ID-3 50×4.6 mm; eluent: n-heptane/ethanol 70:30; flow rate: 1 ml/min; UV detection: 220 nm].

LC-MS (Method 3): $R_t$=1.39 min; MS (ESIpos): m/z=428 [M+H]$^+$ $^1$H-NMR (400 MHz, DMSO-d6) δ [ppm]: −0.008 (1.59), 0.008 (1.32), 1.120 (0.68), 1.181 (15.77), 1.198 (16.00), 1.377 (0.51), 1.391 (0.56), 1.408 (1.21), 1.441 (1.17), 1.464 (0.45), 1.803 (1.39), 1.813 (1.24), 1.824 (1.15), 1.837 (1.13), 1.964 (0.73), 1.999 (1.22), 2.102 (2.42), 2.115 (3.09), 2.126 (3.14), 2.135 (2.50), 2.146 (1.27), 2.170 (0.54), 2.227 (0.65), 2.236 (0.75), 2.271 (0.93), 2.282 (0.84), 2.524 (0.99), 2.707 (1.01), 2.722 (1.52), 2.737 (1.78), 2.752 (1.45), 2.767 (0.89), 3.275 (0.76), 3.294 (1.15), 3.303 (1.69), 3.391 (1.53), 3.400 (1.29), 3.453 (0.67), 3.462 (0.68), 3.489 (0.84), 3.497 (0.79), 3.599 (0.51), 3.624 (1.85), 3.641 (2.31), 3.670 (1.69), 3.698 (1.02), 3.714 (1.01), 3.735 (2.25), 3.757 (1.43), 3.774 (1.16), 3.843 (2.15), 4.724 (1.36), 4.737 (1.44), 4.772 (1.34), 4.781 (2.09), 4.792 (1.37), 5.001 (0.77), 5.042 (8.22), 5.049 (6.72), 5.091 (0.65), 5.260 (1.10), 5.391 (1.28), 5.510 (0.78), 7.883 (0.53), 7.907 (12.15), 7.927 (0.85), 8.632 (4.85).

Example 223

(5RS,8RS)-8-Methyl-2-(4-methylbenzyl)-5-(pyrrolidin-1-ylcarbonyl)-5,6,7,8-tetrahydro[1,2,4]triazolo[4,3-a]pyridin-3(2H)-one (Diastereomer Mixture; 4 Isomers)

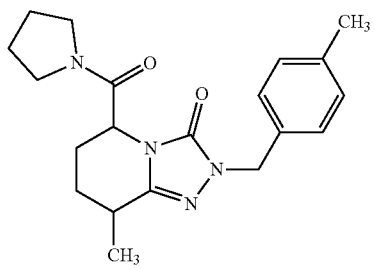 [SMILES: Cc1ccc(Cn2nc3n(c2=O)C(C(=O)N2CCCC2)CCC3C)cc1]

(5RS,8RS)-8-Methyl-2-(4-methylbenzyl)-3-oxo-2,3,5,6,7,8-hexahydro[1,2,4]triazolo[4,3-a]pyridine-5-carboxylic acid (diastereomer mixture; 4 isomers) (27.3 mg, 90.6 μmol) was initially charged in DMF (1.5 ml) and dichloromethane (750 μl) at room temperature.

Subsequently, 1-[bis(dimethylamino)methylene]-1H-benzotriazol-1-ium 3-oxide hexafluorophosphate (44.7 mg, 118 μmol) and N,N-diisopropylethylamine (22 μl, 130 μmol) were added. After stirring for 15 min, pyrrolidine (9.1 μl, 110 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 18.0 mg (55% of theory) of the title compound were obtained as a mixture of diastereomers.

LC-MS (Method 1): $R_t$=1.10 min; MS (ESIpos): m/z=355 [M+H]

$^1$H-NMR (400 MHz, DMSO-d6) δ [ppm]: −0.008 (0.89), 0.008 (0.80), 1.166 (8.74), 1.183 (9.03), 1.380 (0.42), 1.396 (1.31), 1.411 (0.71), 1.432 (0.51), 1.442 (0.50), 1.528 (1.03), 1.755 (1.12), 1.770 (2.91), 1.787 (4.30), 1.804 (3.36), 1.821 (0.86), 1.892 (0.84), 1.908 (2.40), 1.925 (2.98), 1.942 (1.80), 1.958 (0.48), 2.040 (1.84), 2.049 (2.25), 2.058 (1.75), 2.271 (16.00), 2.523 (0.60), 2.663 (0.69), 2.677 (0.96), 2.693 (1.06), 2.708 (0.93), 2.723 (0.55), 3.220 (0.49), 3.237 (1.05), 3.250 (1.04), 3.267 (1.83), 3.284 (0.98), 3.335 (2.01), 3.347 (0.81), 3.353 (1.05), 3.364 (1.12), 3.382 (0.52), 3.428 (0.55), 3.445 (1.19), 3.453 (0.91), 3.463 (0.75), 3.470 (1.52), 3.487 (0.68), 3.578 (0.69), 3.595 (1.41), 3.603 (0.76), 3.611 (0.84), 3.619 (1.12), 3.636 (0.52), 4.707 (1.64), 4.738 (1.56), 4.746 (5.65), 4.757 (1.42), 4.799 (3.57), 4.839 (1.59), 7.097 (1.28), 7.118 (10.61), 7.124 (9.75), 7.145 (1.25).

Example 224

(5RS,7RS)-7-Methyl-2-(4-methylbenzyl)-5-(pyrrolidin-1-ylcarbonyl)-5,6,7,8-tetrahydro[1,2,4]triazolo[4,3-a]pyridin-3(2H)-one (Diastereomer Mixture; 4 Isomers)

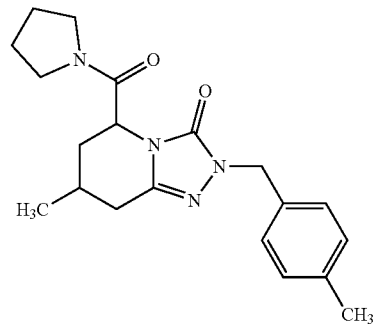 [SMILES: Cc1ccc(Cn2nc3n(c2=O)C(C(=O)N2CCCC2)CC(C)C3)cc1]

(5RS,7RS)-7-Methyl-2-(4-methylbenzyl)-3-oxo-2,3,5,6,7,8-hexahydro[1,2,4]triazolo[4,3-a]pyridine-5-carboxylic acid (60.0 mg, 199 μmol) was initially charged together with pyrrolidine (25 μl, 300 μmol) in pyridine/DMF (5/1) (3.0 ml) at room temperature. Subsequently, O-(7-azabenzotriazol-1-yl)-N,N,N,N-tetramethyluronium hexafluorophosphate (121 mg, 319 μmol) was added and the reaction mixture was stirred at room temperature for 5 h. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 23.0 mg (29% of theory) of the title compound were obtained as a diastereomer mixture.

LC-MS (Method 1): $R_t$=1.06 min; MS (ESIpos): m/z=355 [M+H]

$^1$H-NMR (400 MHz, DMSO-d6) δ [ppm]: 1.013 (3.80), 1.030 (3.91), 1.106 (7.23), 1.329 (0.57), 1.359 (0.58), 1.771 (1.01), 1.788 (1.80), 1.805 (1.54), 1.814 (0.95), 1.860 (0.50), 1.882 (0.68), 1.899 (1.42), 1.916 (1.58), 1.931 (0.91), 2.111 (0.74), 2.141 (0.57), 2.151 (0.79), 2.181 (0.84), 2.270 (10.66), 2.611 (0.49), 2.616 (0.51), 2.646 (0.40), 2.651 (0.45), 2.657 (0.43), 3.076 (2.31), 3.226 (0.41), 3.243 (0.65), 3.256 (0.57), 3.273 (0.92), 3.290 (0.45), 3.339 (0.47), 3.356 (0.93), 3.374 (0.50), 3.386 (0.56), 3.468 (0.59), 3.476 (0.46), 3.493 (0.74), 3.634 (0.73), 3.651 (0.41), 3.659 (0.56), 4.601 (0.62), 4.617 (0.73), 4.628 (0.71), 4.643 (0.61), 4.718 (4.78), 7.128 (16.00).

Example 225

(5RS,7RS)-2-(4-Methylbenzyl)-5-(pyrrolidin-1-ylcarbonyl)-7-(trifluoromethyl)-5,6,7,8-tetrahydro[1,2,4]triazolo[4,3-a]pyridin-3(2H)-one (Diastereomer 1, Racemate)

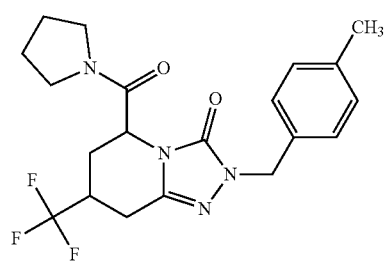 [SMILES: Cc1ccc(Cn2nc3n(c2=O)C(C(=O)N2CCCC2)CC(C(F)(F)F)C3)cc1]

(5RS,7RS)-2-(4-Methylbenzyl)-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (98.0 mg, 276 µmol) was initially charged together with pyrrolidine (25 µl, 300 µmol) in pyridine/DMF (5/1) (2.0 ml) at room temperature. Subsequently, O-(7-azabenzotriazol-1-yl)-N,N,N,N-tetramethyluronium hexafluorophosphate (115 mg, 303 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 37.4 mg (33% of theory) of diastereomer 1 (racemate) and 8.7 mg (8% of theory) of diastereomer 2 (racemate) of the title compound were obtained.

LC-MS (Method 3): $R_t$=1.69 min; MS (ESIpos): m/z=409 [M+H]$^+$ $^1$H-NMR (400 MHz, DMSO-d6) δ [ppm]: −0.008 (0.44), 0.008 (0.45), 1.777 (0.99), 1.794 (1.60), 1.806 (1.64), 1.822 (1.20), 1.839 (0.52), 1.907 (0.75), 1.924 (2.35), 1.941 (3.00), 1.958 (1.73), 1.975 (0.43), 2.167 (0.74), 2.182 (0.75), 2.197 (1.28), 2.210 (2.06), 2.272 (15.46), 2.523 (0.50), 2.643 (0.56), 2.676 (1.24), 2.687 (1.24), 2.719 (0.94), 2.949 (1.79), 2.983 (1.24), 2.993 (0.80), 3.248 (0.42), 3.265 (0.82), 3.277 (0.98), 3.295 (1.74), 3.332 (1.01), 3.349 (1.49), 3.366 (0.94), 3.379 (0.80), 3.396 (0.43), 3.534 (0.43), 3.551 (0.96), 3.559 (0.83), 3.568 (0.62), 3.576 (1.44), 3.593 (0.64), 3.631 (0.66), 3.648 (1.38), 3.655 (0.63), 3.665 (0.77), 3.673 (0.92), 4.723 (0.92), 4.762 (4.01), 4.782 (3.97), 4.820 (0.94), 4.937 (1.52), 4.947 (1.32), 7.104 (0.72), 7.112 (0.47), 7.127 (16.00), 7.150 (0.70).

Example 226

(5RS,7RS)-2-(4-Methylbenzyl)-5-(pyrrolidin-1-ylcarbonyl)-7-(trifluoromethyl)-5,6,7,8-tetrahydro[1,2,4]triazolo[4,3-a]pyridin-3(2H)-one (Diastereomer 2, Racemate)

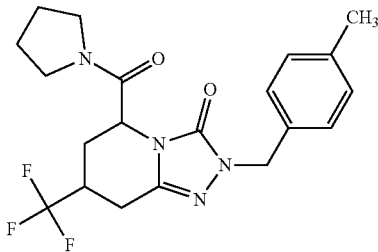 [SMILES: Cc1ccc(Cn2nc3n(c2=O)C(C(=O)N2CCCC2)CC(C(F)(F)F)C3)cc1]

(5RS,7RS)-2-(4-Methylbenzyl)-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (98.0 mg, 276 µmol) was initially charged together with pyrrolidine (25 µl, 300 µmol) in pyridine/DMF (5/1) (2.0 ml) at room temperature. Subsequently, O-(7-azabenzotriazol-1-yl)-N,N,N,N-tetramethyluronium hexafluorophosphate (115 mg, 303 µmol) was added and the reaction mixture was stirred at room temperature for 2 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 37.4 mg (33% of theory) of diastereomer 1 (racemate) and 8.7 mg (8% of theory) of diastereomer 2 (racemate) of the title compound were obtained.

LC-MS (Method 3): $R_t$=1.62 min; MS (ESIpos): m/z=409 [M+H]$^+$ $^1$H-NMR (400 MHz, DMSO-d6) δ[ppm]: −0.008 (0.69), 0.008 (0.74), 1.665 (0.67), 1.692 (0.67), 1.779 (0.59), 1.785 (0.66), 1.797 (0.98), 1.802 (1.02), 1.817 (0.88), 1.910 (1.28), 1.927 (1.65), 1.944 (0.95), 2.274 (9.27), 2.634 (0.46), 2.665 (0.67), 2.674 (0.77), 2.706 (0.77), 2.863 (0.57), 3.263 (0.51), 3.276 (0.51), 3.293 (0.94), 3.354 (0.43), 3.371 (0.81), 3.389 (0.49), 3.401 (0.51), 3.555 (0.51), 3.562 (0.47), 3.579 (0.82), 3.637 (0.80), 3.654 (0.44), 3.661 (0.50), 4.710 (0.65), 4.724 (0.78), 4.745 (4.83), 7.141 (16.00).

Example 227

(5RS,7RS)-2-[(6-Chloropyridin-3-yl)methyl]-5-(pyrrolidin-1-ylcarbonyl)-7-(trifluoromethyl)-5,6,7,8-tetrahydro[1,2,4]triazolo[4,3-a]pyridin-3(2H)-one (Diastereomer 1, Racemate)

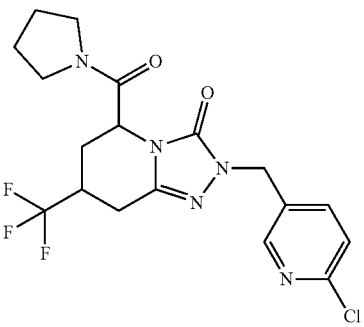 [SMILES: O=C(C1CC(C(F)(F)F)Cc2nn(Cc3ccc(Cl)nc3)c(=O)n21)N1CCCC1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, pyrrolidine (23 µl, 280 µmol) was added and the reaction mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 10.2 mg (10% of theory) of diastereomer 1 (racemate), which elutes first, and 43.7 mg (44% of theory) of diastereomer 2 (racemate), which elutes later, were isolated.

Diastereomer 1, Racemate:

LC-MS (Method 3): $R_t$=1.37 min; MS (ESIpos): m/z=430 [M+H]$^+$ $^1$H-NMR (400 MHz, DMSO-d6) δ [ppm]: −0.149 (1.19), −0.008 (9.63), 0.008 (8.89), 0.146 (1.11), 1.635 (1.26), 1.666 (2.81), 1.693 (2.74), 1.726 (1.48), 1.778 (2.37), 1.785 (2.74), 1.795 (3.93), 1.802 (4.00), 1.818 (3.19), 1.893 (1.56), 1.909 (5.48), 1.926 (6.89), 1.944 (4.00), 2.327 (2.07), 2.366 (1.85), 2.523 (8.67), 2.657 (2.15), 2.669 (2.37), 2.688 (2.52), 2.697 (3.04), 2.710 (2.30), 2.729 (3.41), 2.876 (2.44), 2.911 (1.56), 3.012 (1.19), 3.264 (2.44), 3.276 (2.59), 3.351 (2.52), 3.369 (3.70), 3.386 (2.30), 3.399 (2.37), 3.417 (1.26), 3.569 (2.15), 3.586 (3.63), 3.611 (2.00), 3.627 (3.63), 3.652 (1.93), 4.711 (2.74), 4.725 (3.04), 4.738 (2.81), 4.753 (2.44), 4.884 (16.00), 7.516 (6.22), 7.536 (7.63), 7.720 (4.52), 7.727 (4.44), 7.741 (3.85), 7.747 (3.85), 8.328 (6.00), 8.334 (5.70).

Example 228

(5RS,7RS)-2-[(6-Chloropyridin-3-yl)methyl]-5-(pyrrolidin-1-ylcarbonyl)-7-(trifluoromethyl)-5,6,7,8-tetrahydro[1,2,4]triazolo[4,3-a]pyridin-3(2H)-one (Diastereomer 2, Racemate)

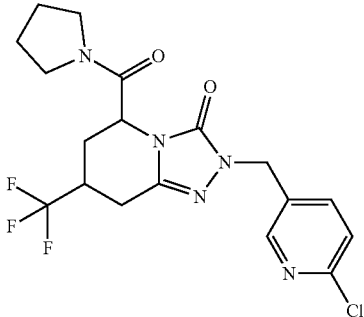 [SMILES: O=C(C1CC(C(F)(F)F)Cc2nn(Cc3ccc(Cl)nc3)c(=O)n21)N1CCCC1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, pyrrolidine (23 µl, 280 µmol) was added and the reaction mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 10.2 mg (10% of theory) of diastereomer 1 (racemate), which elutes first, and 43.7 mg (44% of theory) of diastereomer 2 (racemate), which elutes later, were isolated.

Diastereomer 2, Racemate:

LC-MS (Method 3): $R_t$=1.45 min; MS (ESIpos): m/z=430 [M+H]$^+$ $^1$H-NMR (400 MHz, DMSO-d6) δ [ppm]: −0.149 (0.54), −0.008 (4.44), 0.008 (3.96), 0.146 (0.54), 1.778 (2.01), 1.795 (3.23), 1.805 (3.35), 1.822 (2.59), 1.906 (1.50), 1.923 (4.73), 1.939 (5.81), 1.957 (3.32), 2.173 (1.47), 2.189 (1.53), 2.203 (1.92), 2.218 (4.02), 2.327 (1.02), 2.366 (0.70), 2.523 (3.03), 2.667 (1.95), 2.694 (2.49), 2.705 (2.59), 2.734 (2.08), 2.962 (3.00), 3.000 (1.92), 3.010 (1.47), 3.250 (0.86), 3.268 (1.72), 3.280 (2.27), 3.297 (5.91), 3.331 (3.03), 3.349 (3.32), 3.366 (2.17), 3.377 (1.72), 3.395 (0.99), 3.532 (0.93), 3.549 (1.98), 3.557 (1.79), 3.574 (3.10), 3.591 (1.31), 3.625 (1.44), 3.641 (2.87), 3.658 (1.63), 3.666 (1.85), 3.683 (0.93), 4.914 (16.00), 4.949 (3.26), 4.964 (2.78), 7.510 (5.78), 7.530 (7.41), 7.692 (4.12), 7.699 (4.12), 7.713 (3.32), 7.719 (3.29), 8.299 (5.72), 8.305 (5.52).

Example 229

(5RS,7RS)-2-[(6-Chloropyridin-3-yl)methyl]-5-(pyrrolidin-1-ylcarbonyl)-7-(trifluoromethyl)-5,6,7,8-tetrahydro[1,2,4]triazolo[4,3-a]pyridin-3(2H)-one (Enantiomer 1)

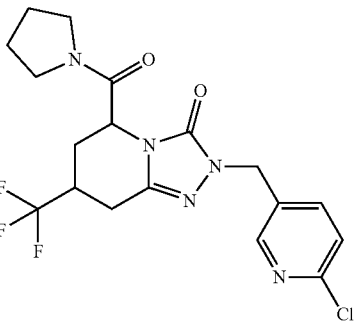

(5RS,7RS)-2-[(6-Chloropyridin-3-yl)methyl]-5-(pyrrolidin-1-ylcarbonyl)-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 42 mg dissolved in 2 ml of ethanol and 2 ml of n-heptane; injection volume: 0.40 ml; column: Daicel Chiralpak® IB 5 µm, 250×20 mm; eluent: n-heptane/ethanol 50:50; flow rate: 15 ml/min; temperature 40° C.; UV detection: 220 nm]. After the separation, 14.7 mg of enantiomer 1, which elutes first, and 16.1 mg of enantiomer 2, which elutes later, were isolated.

Enantiomer 1:

Analytical chiral HPLC: $R_t$=4.99 min, e.e. =99% [column: Daicel Chiralpak® IB, 250×4.6 mm; eluent: i-hexane/ethanol 50:50; flow rate: 1 ml/min; UV detection: 220 nm].

LC-MS (Method 3): $R_t$=1.47 min; MS (ESIpos): m/z=430 [M+H]$^+$ $^1$H-NMR (400 MHz, DMSO-d6) δ[ppm]: −0.149 (1.30), −0.008 (11.16), 0.008 (10.55), 0.146 (1.30), 1.233 (0.61), 1.778 (1.99), 1.794 (3.20), 1.806 (3.29), 1.822 (2.51), 1.906 (1.47), 1.923 (4.58), 1.940 (5.62), 1.957 (3.29), 2.172 (1.47), 2.188 (1.56), 2.202 (1.73), 2.217 (4.06), 2.328 (1.82), 2.366 (1.64), 2.523 (6.49), 2.669 (2.85), 2.694 (2.42), 2.705 (2.51), 2.710 (2.25), 2.734 (2.16), 2.962 (3.11), 2.998 (1.90), 3.010 (1.47), 3.250 (1.12), 3.267 (2.34), 3.279 (2.77), 3.348 (4.67), 3.365 (2.59), 3.377 (2.08), 3.396 (1.21), 3.531 (0.95), 3.549 (2.08), 3.557 (1.73), 3.574 (3.03), 3.591 (1.30), 3.623 (1.38), 3.640 (2.77), 3.658 (1.64), 3.666 (1.99), 3.682 (0.95), 4.914 (16.00), 4.950 (3.20), 4.961 (3.03), 7.510 (4.93), 7.530 (6.23), 7.692 (3.37), 7.698 (3.63), 7.713 (2.85), 7.719 (2.94), 8.298 (4.15), 8.304 (4.24).

Example 230

(5RS,7RS)-2-[(6-Chloropyridin-3-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Diastereomer 2, Racemate)

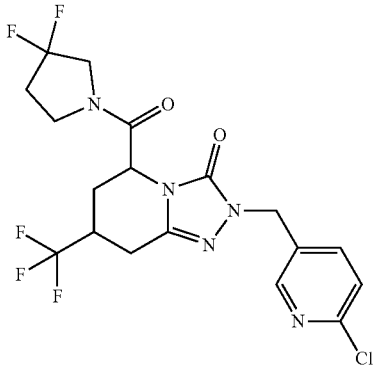 [SMILES: O=C(C1CC(C(F)(F)F)Cc2nn(Cc3ccc(Cl)nc3)c(=O)n21)N1CCC(F)(F)C1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, 3,3-difluoropyrrolidine hydrochloride (40.2 mg, 280 µmol) was added and the reaction mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 10.2 mg of diastereomer 1 (racemate) (9% of theory), which elutes first, and 48 mg (44% of theory) of diastereomer 2 (racemate), which elutes later, were isolated.

Diastereomer 2, Racemate:

LC-MS (Method 3): $R_t$=1.56 min; MS (ESIpos): m/z=466 [M+H]$^+$ $^1$H-NMR (400 MHz, DMSO-d6) δ [ppm]: −0.008 (2.62), 0.008 (2.46), 2.112 (0.44), 2.129 (0.51), 2.148 (1.03), 2.164 (1.01), 2.179 (1.06), 2.189 (1.30), 2.205 (0.97), 2.220 (0.94), 2.236 (0.90), 2.259 (1.65), 2.278 (1.76), 2.311 (0.92), 2.327 (0.61), 2.366 (0.55), 2.374 (0.59), 2.394 (1.16), 2.412 (1.03), 2.424 (1.45), 2.440 (1.32), 2.461 (0.88), 2.523 (1.85), 2.563 (1.83), 2.581 (1.41), 2.601 (0.99), 2.619 (0.50), 2.678 (1.36), 2.686 (1.10), 2.707 (1.76), 2.716 (2.61), 2.725 (1.52), 2.747 (1.89), 2.755 (1.78), 2.901 (1.23), 2.970 (2.55), 3.010 (1.85), 3.534 (0.50), 3.545 (1.25), 3.565 (2.55), 3.578 (1.94), 3.596 (1.23), 3.609 (0.42), 3.710 (1.16), 3.750 (1.54), 3.779 (1.76), 3.814 (1.21), 3.889 (0.72), 3.897 (1.17), 3.914 (2.90), 3.932 (3.03), 3.951 (1.12), 4.130 (1.03), 4.157 (0.84), 4.173 (1.56), 4.200 (1.63), 4.234 (0.97), 4.878 (0.59), 4.920 (16.00), 4.951 (2.06), 4.964 (2.22), 5.029 (1.98), 5.042 (1.91), 7.512 (6.06), 7.532 (7.69), 7.695 (3.71), 7.701 (3.78), 7.715 (3.16), 7.722 (3.16), 8.299 (5.17), 8.305 (5.08).

Example 231

(5RS,7RS)-2-[(6-Chloropyridin-3-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Enantiomer 1)

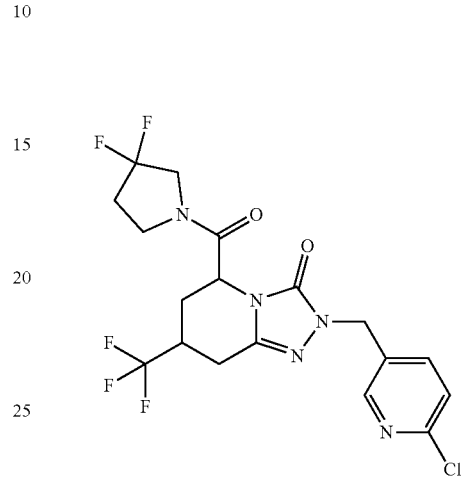

(5RS,7RS)-2-[(6-Chloropyridin-3-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 48 mg dissolved in 2 ml of ethanol and 1.5 ml of n-heptane; injection volume: 0.5 ml; column: Daicel Chiralpak® IE 5 µm, 250×20 mm; eluent: n-heptane/ethanol 40:60; flow rate: 15 ml/min; temperature 40° C.; UV detection: 220 nm]. After the separation, 16.7 mg of enantiomer 1, which elutes first, and 17.5 mg of enantiomer 2, which elutes later, were isolated.

Enantiomer 1:

Analytical chiral HPLC: $R_t$=5.80 min, e.e. =99% [column: Daicel Chiralpak® IE 5 µm, 250×4.6 mm; eluent: i-hexane/ethanol 40:60; flow rate: 1 ml/min; UV detection: 220 nm].

LC-MS (Method 3): $R_t$=1.56 min; MS (ESIpos): m/z=466 [M+H]$^+$ $^1$H-NMR (400 MHz, DMSO-d6) δ[ppm]: −0.149 (1.25), −0.008 (10.99), 0.008 (10.43), 0.146 (1.25), 1.235 (0.77), 2.113 (0.49), 2.128 (0.49), 2.147 (0.97), 2.178 (1.04), 2.190 (1.25), 2.220 (0.97), 2.236 (0.83), 2.257 (1.67), 2.281 (1.74), 2.323 (1.25), 2.328 (1.53), 2.366 (1.32), 2.395 (1.11), 2.424 (1.46), 2.441 (1.25), 2.523 (4.87), 2.563 (2.37), 2.582 (1.67), 2.600 (1.18), 2.665 (1.25), 2.670 (1.67), 2.679 (1.74), 2.687 (1.18), 2.710 (2.50), 2.716 (2.71), 2.726 (1.60), 2.747 (1.88), 2.755 (1.81), 2.911 (1.18), 2.971 (2.50), 3.010 (1.81), 3.545 (1.32), 3.565 (2.64), 3.580 (2.02), 3.596 (1.32), 3.676 (0.42), 3.709 (1.18), 3.751 (1.60), 3.780 (1.81), 3.814 (1.25), 3.896 (1.18), 3.914 (2.92), 3.932 (3.13), 3.951 (1.18), 4.130 (1.04), 4.157 (0.83), 4.173 (1.60), 4.199 (1.60), 4.233 (0.90), 4.879 (0.63), 4.921 (16.00), 4.952 (2.09), 4.964 (2.23), 5.029 (2.02), 5.042 (2.02), 7.512 (6.26), 7.533 (8.00), 7.695 (3.83), 7.701 (3.83), 7.716 (3.20), 7.722 (3.20), 8.299 (5.29), 8.305 (5.08).

Example 232

(5RS,7RS)-2-[(6-Chloropyridin-3-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Enantiomer 2)

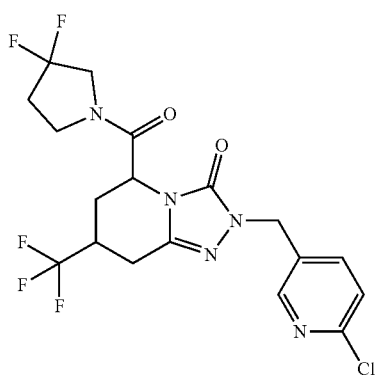 [SMILES: O=C(C1CC(C(F)(F)F)Cc2nn(Cc3ccc(Cl)nc3)c(=O)n21)N1CCC(F)(F)C1]

(5RS,7RS)-2-[(6-Chloropyridin-3-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 48 mg dissolved in 2 ml of ethanol and 1.5 ml of n-heptane; injection volume: 0.5 ml; column: Daicel Chiralpak® IE 5 µm, 250×20 mm; eluent: n-heptane/ethanol 40:60; flow rate: 15 ml/min; temperature 40° C.; UV detection: 220 nm]. After the separation, 16.7 mg of enantiomer 1, which elutes first, and 17.5 mg of enantiomer 2, which elutes later, were isolated.

Enantiomer 2:

Analytical chiral HPLC: $R_t$=6.78 min, e.e. =99% [column: Daicel Chiralpak® IE 5 µm, 250×4.6 mm; eluent: i-hexane/ethanol 40:60; flow rate: 1 ml/min; UV detection: 220 nm].

LC-MS (Method 3): $R_t$=1.56 min; MS (ESIpos): m/z=466 [M+H]$^+$ $^1$H-NMR (400 MHz, DMSO-d6) δ [ppm]: −0.149 (1.77), −0.008 (16.00), 0.008 (12.99), 0.146 (1.77), 1.234 (0.83), 2.189 (0.94), 2.278 (1.25), 2.323 (1.56), 2.328 (1.97), 2.332 (1.35), 2.366 (2.08), 2.424 (1.14), 2.519 (7.90), 2.523 (6.75), 2.580 (1.25), 2.665 (1.66), 2.670 (2.29), 2.675 (1.87), 2.710 (2.81), 2.716 (1.87), 2.747 (1.35), 2.755 (1.25), 2.970 (1.77), 3.009 (1.25), 3.545 (0.94), 3.565 (1.77), 3.580 (1.35), 3.709 (0.83), 3.751 (0.94), 3.779 (1.35), 3.814 (0.94), 3.896 (0.94), 3.913 (1.97), 3.932 (2.18), 3.950 (0.83), 4.129 (0.73), 4.174 (1.14), 4.199 (1.14), 4.920 (10.91), 4.952 (1.35), 4.964 (1.56), 5.030 (1.25), 5.041 (1.35), 7.512 (4.47), 7.533 (5.82), 7.695 (2.70), 7.701 (2.70), 7.716 (2.29), 7.722 (2.29), 8.299 (3.95), 8.305 (3.84).

Example 233

(5RS,7RS)-5-[(3-Hydroxyazetidin-1-yl)carbonyl]-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer 1; 2 Isomers)

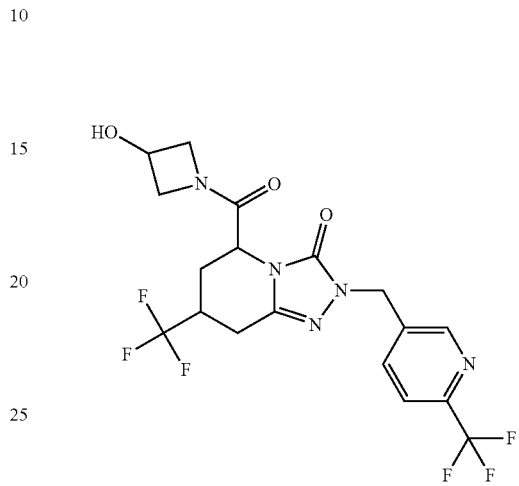

(5RS,7RS)-3-Oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (53.0 mg, 129 µmol) was initially charged in dichloromethane (1.0 ml) and DMF (2.0 ml) at 0° C. Subsequently, 1-[bis(dimethylamino)methylene]-1H-benzotriazol-1-ium 3-oxide hexafluorophosphate (63.7 mg, 168 µmol) and N,N-diisopropylethylamine (59 µl, 340 µmol) were added. After stirring at 0° C. for 60 min, azetidin-3-ol hydrochloride (17.0 mg, 155 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 20.5 mg (34% of theory) of the title compound were obtained.

LC-MS (Method 3): $R_t$=1.32 min; MS (ESIpos): m/z=466 [M+H]$^+$ $^1$H-NMR (400 MHz, DMSO-d6) δ[ppm]: −0.008 (2.82), 0.008 (2.65), 1.236 (0.44), 2.073 (0.95), 2.126 (0.46), 2.145 (1.11), 2.163 (1.78), 2.177 (3.07), 2.190 (4.53), 2.199 (4.11), 2.231 (0.66), 2.328 (0.52), 2.523 (1.78), 2.657 (1.32), 2.666 (1.33), 2.686 (1.72), 2.695 (2.51), 2.704 (1.73), 2.726 (1.98), 2.875 (0.84), 2.905 (1.25), 2.966 (3.44), 2.975 (2.41), 3.005 (2.56), 3.017 (2.01), 3.650 (2.51), 3.659 (1.87), 3.669 (1.95), 3.677 (2.75), 4.027 (1.52), 4.040 (1.57), 4.074 (2.71), 4.089 (2.90), 4.114 (1.38), 4.129 (1.25), 4.144 (1.26), 4.153 (1.29), 4.170 (1.07), 4.461 (0.99), 4.479 (2.15), 4.498 (3.22), 4.520 (2.29), 4.542 (3.24), 4.562 (1.86), 4.579 (0.71), 4.728 (2.11), 4.741 (3.29), 4.749 (2.58), 4.760 (1.45), 5.018 (1.29), 5.043 (10.99), 5.049 (11.28), 5.787 (0.60), 5.801 (0.60), 5.830 (3.51), 5.835 (3.85), 5.844 (4.03), 5.850 (3.07), 7.917 (16.00), 7.948 (0.54), 8.645 (5.51), 8.681 (0.49).

Example 234

(5RS,7RS)-5-[(3-Hydroxyazetidin-1-yl)carbonyl]-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 2)

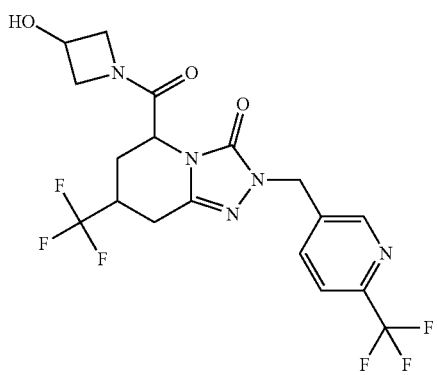 [SMILES: O=C(C1CC(C(F)(F)F)Cc2nn(Cc3ccc(C(F)(F)F)nc3)c(=O)n21)N1CC(O)C1]

(5RS,7RS)-5-[(3-Hydroxyazetidin-1-yl)carbonyl]-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer 1; 2 isomers) was separated by chiral preparative HPLC [sample preparation: 20.5 mg dissolved in 1 ml of ethanol and 1 ml of isopropanol; injection volume: 0.5 ml; column: Daicel Chiralpak® IB 5 µm, 250×20 mm; eluent: n-heptane/ethanol 50:50; flow rate: 20 ml/min; temperature 25° C.; UV detection: 220 nm]. After the separation, 6.1 mg of isomer 1, which elutes first, and 7.4 mg of isomer 2, which elutes later, were isolated.

Isomer 2:

Analytical chiral HPLC: $R_t$=2.34 min, d.e.=100% [column: Daicel Chiralpak® IB-3-3 µm, 50×4.6 mm; eluent: i-hexane/i-propanol 50:50; flow rate: 1 ml/min; UV detection: 220 nm].

LC-MS (Method 3): $R_t$=1.31 min; MS (ESIpos): m/z=466 [M+H]$^+$ $^1$H-NMR (400 MHz, DMSO-d6) δ [ppm]: 1.456 (0.65), 2.145 (1.08), 2.162 (1.77), 2.189 (4.32), 2.230 (0.66), 2.328 (0.77), 2.366 (0.54), 2.657 (1.22), 2.665 (1.38), 2.694 (2.29), 2.704 (1.66), 2.726 (1.80), 2.916 (1.19), 2.965 (3.27), 2.994 (1.08), 3.005 (2.36), 3.017 (1.85), 3.650 (2.33), 3.659 (1.80), 3.677 (2.57), 4.026 (1.47), 4.039 (1.45), 4.073 (2.54), 4.089 (2.75), 4.113 (1.31), 4.129 (1.19), 4.144 (1.21), 4.153 (1.22), 4.170 (1.01), 4.460 (0.89), 4.478 (2.03), 4.498 (3.01), 4.521 (2.19), 4.542 (3.08), 4.561 (1.75), 4.578 (0.70), 4.728 (2.01), 4.740 (3.10), 5.019 (1.22), 5.042 (10.30), 5.049 (10.63), 5.784 (0.61), 5.798 (0.56), 5.831 (4.09), 5.841 (4.20), 7.917 (16.00), 8.645 (6.64), 8.682 (0.65).

Example 235

(5RS,7RS)-5-{[(3S)-3-Fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer Mixture 1; 2 Isomers)

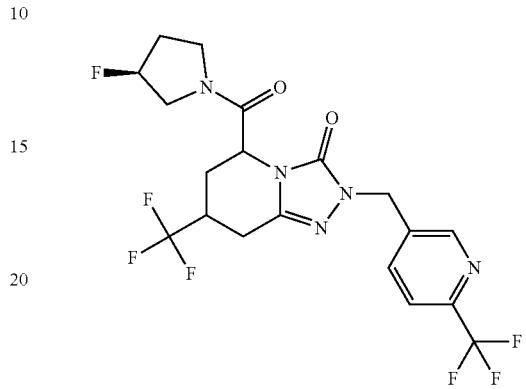

(5RS,7RS)-3-Oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (100 mg, 244 µmol) and (3S)-3-fluoropyrrolidine hydrochloride (33.7 mg, 268 µmol) were initially charged in dichloromethane (2.0 ml) and DMF (4.0 ml) at room temperature. Subsequently, N,N-diisopropylethylamine (100 µl, 580 µmol) and HBTU (120 mg, 317 µmol) were added. After stirring at room temperature for 30 min, saturated aqueous ammonium chloride solution and diethyl ether were added. The organic phase was removed and the aqueous phase was extracted twice with diethyl ether. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 9.5 mg (8% of theory) of diastereomer mixture 1 (2 isomers), which elutes first, and 81.0 mg (69% of theory) of diastereomer mixture 2 (2 isomers), which elutes later, were isolated.

Diastereomer Mixture 1 (2 Isomers):

LC-MS (Method 3): $R_t$=1.52 min; MS (ESIpos): m/z=482 [M+H]$^+$ $^1$H-NMR (400 MHz, DMSO-d6) δ [ppm]: 0.146 (0.42), 1.629 (0.89), 1.660 (1.92), 1.689 (2.14), 1.739 (1.24), 2.096 (1.31), 2.156 (1.24), 2.230 (1.52), 2.260 (1.60), 2.327 (1.24), 2.366 (0.89), 2.679 (2.18), 2.711 (3.02), 2.719 (3.47), 2.751 (3.40), 2.891 (3.33), 2.930 (2.23), 3.027 (1.55), 3.137 (0.61), 3.400 (0.80), 3.440 (0.66), 3.509 (0.80), 3.564 (0.92), 3.611 (1.71), 3.661 (1.60), 3.687 (2.09), 3.714 (1.57), 3.747 (1.20), 3.828 (0.82), 3.855 (0.84), 3.877 (1.66), 3.900 (1.67), 3.932 (1.62), 3.955 (1.78), 3.980 (0.98), 4.011 (0.71), 4.044 (0.52), 4.675 (0.85), 4.689 (0.85), 4.702 (0.96), 4.716 (0.89), 4.726 (0.92), 4.741 (2.04), 4.754 (2.02), 4.768 (1.95), 4.782 (1.10), 4.808 (0.89), 4.822 (0.98), 4.834 (1.01), 4.849 (0.80), 5.015 (16.00), 5.269 (1.05), 5.349 (0.71), 5.402 (1.38), 5.481 (0.75), 5.527 (0.75), 7.908 (3.10), 7.928 (10.34), 7.944 (6.14), 7.963 (1.78), 8.112 (0.42), 8.677 (8.03).

Example 236

(5RS,7RS)-5-{[(3S)-3-Fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer Mixture 2; 2 Isomers)

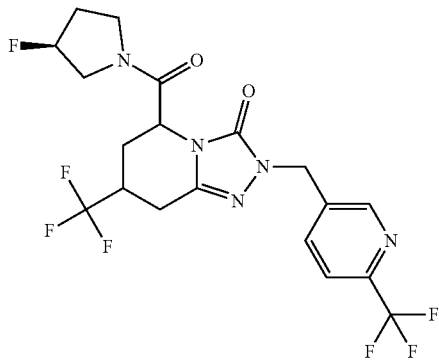 [SMILES: O=C(C1CC(C(F)(F)F)Cc2nn(Cc3ccc(C(F)(F)F)nc3)c(=O)n21)N1CC[C@H](F)C1]

(5RS,7RS)-3-Oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (100 mg, 244 µmol) and (3S)-3-fluoropyrrolidine hydrochloride (33.7 mg, 268 µmol) were initially charged in dichloromethane (2.0 ml) and DMF (4.0 ml) at room temperature. Subsequently, N,N-diisopropylethylamine (100 µl, 580 µmol) and 1-[bis(dimethylamino)methylene]-1H-benzotriazol-1-ium 3-oxide hexafluorophosphate (120 mg, 317 µmol) were added. After stirring at room temperature for 30 min, saturated aqueous ammonium chloride solution and diethyl ether were added. The organic phase was removed and the aqueous phase was extracted twice with diethyl ether. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 9.5 mg (8% of theory) of diastereomer mixture 1 (2 isomers), which elutes first, and 81.0 mg (69% of theory) of diastereomer mixture 2 (2 isomers), which elutes later, were isolated.

Diastereomer Mixture 2 (2 Isomers):

LC-MS (Method 3): $R_t$=1.59 min; MS (ESIpos): m/z=482 [M+H]$^+$ $^1$H-NMR (400 MHz, DMSO-d6) δ [ppm]: −0.008 (1.65), 0.008 (1.33), 2.125 (0.90), 2.141 (1.33), 2.160 (1.40), 2.171 (1.70), 2.205 (1.37), 2.215 (1.80), 2.227 (2.15), 2.236 (2.62), 2.248 (2.33), 2.277 (1.60), 2.293 (1.58), 2.328 (0.94), 2.366 (0.44), 2.518 (1.76), 2.523 (1.38), 2.670 (0.51), 2.675 (0.45), 2.686 (0.78), 2.695 (0.80), 2.710 (1.42), 2.724 (2.01), 2.734 (1.28), 2.755 (1.22), 2.763 (1.34), 2.890 (0.98), 2.925 (0.89), 2.981 (2.29), 3.019 (1.52), 3.354 (0.76), 3.380 (0.82), 3.408 (0.70), 3.434 (0.43), 3.443 (0.41), 3.519 (0.48), 3.530 (0.61), 3.541 (0.44), 3.570 (0.90), 3.592 (0.74), 3.620 (1.36), 3.643 (1.74), 3.672 (1.58), 3.689 (0.92), 3.700 (0.92), 3.738 (0.40), 3.765 (0.48), 3.796 (0.63), 3.831 (0.52), 3.852 (1.09), 3.884 (0.51), 3.892 (0.68), 3.930 (0.43), 3.964 (0.61), 3.990 (1.28), 4.017 (0.63), 4.054 (0.48), 4.922 (0.72), 4.937 (0.76), 4.971 (1.02), 4.986 (1.01), 5.017 (0.52), 5.048 (12.85), 5.073 (0.76), 5.084 (1.10), 5.269 (0.96), 5.358 (0.56), 5.403 (1.14), 5.490 (0.53), 5.524 (0.47), 7.919 (16.00), 8.644 (4.92).

Example 237

(5S,7R)-5-{[(3S)-3-Fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 1)

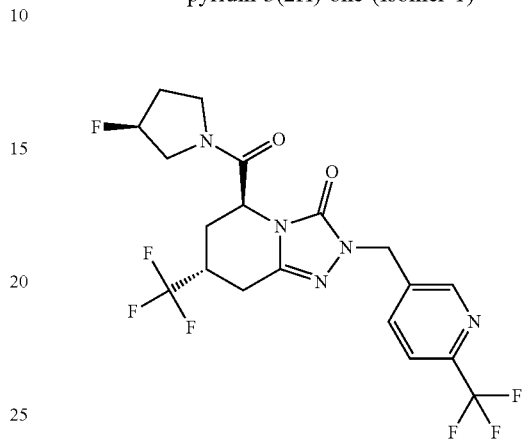

(5RS,7RS)-5-{[(3S)-3-Fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer mixture 2; 2 isomers) was separated by chiral preparative HPLC [sample preparation: 66 mg dissolved in 6 ml of isopropanol; injection volume: 0.5 ml; column: Daicel Chiralpak® IB 5 µm, 250×20 mm; eluent: n-heptane/isopropanol 40:60; flow rate: 15 ml/min; temperature 25° C.; UV detection: 210 nm]. After the separation, 28.8 mg of (5S,7R)-5-{[(3S)-3-fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 1), which elutes first, and 28.8 mg of isomer 2, which elutes later, were isolated.

Isomer 1:

Specific rotation: +42.51 (589 nm, 0.5450 g/100 cm$^3$ MeOH)

Analytical chiral HPLC: $R_t$=1.38 min, d.e.=100% [column: Daicel Chiralpak® IB-3-3 µm, 50×4.6 mm; eluent: i-hexane/i-propanol 50:50; flow rate: 1 ml/min; UV detection: 220 nm].

LC-MS (Method 3): $R_t$=1.59 min; MS (ESIpos): m/z=482 [M+H]$^+$ $^1$H-NMR (400 MHz, DMSO-d6) δ [ppm]: 0.008 (2.13), 1.261 (0.42), 2.108 (0.76), 2.120 (0.83), 2.143 (1.30), 2.172 (2.16), 2.204 (1.57), 2.215 (1.43), 2.235 (1.93), 2.250 (1.89), 2.295 (2.57), 2.328 (1.22), 2.523 (1.13), 2.682 (1.10), 2.697 (0.67), 2.710 (1.91), 2.721 (2.02), 2.735 (1.15), 2.750 (1.64), 2.764 (1.04), 2.925 (1.09), 2.934 (1.13), 2.946 (1.01), 2.954 (0.95), 2.981 (3.14), 3.018 (1.94), 3.029 (1.47), 3.346 (0.77), 3.356 (1.00), 3.375 (0.96), 3.384 (0.72), 3.402 (0.97), 3.434 (0.80), 3.443 (0.80), 3.497 (0.57), 3.505 (0.62), 3.533 (0.87), 3.541 (0.80), 3.623 (0.85), 3.646 (2.19), 3.674 (2.40), 3.691 (1.42), 3.700 (1.79), 3.716 (0.76), 3.738 (0.78), 3.766 (0.41), 3.774 (0.45), 3.799 (0.64), 3.806 (0.65), 3.831 (0.97), 3.853 (1.74), 3.877 (0.84), 3.893 (0.73), 3.901 (0.69), 3.930 (0.83), 3.960 (0.62), 3.987 (0.87), 4.019 (0.51), 4.924 (1.35), 4.937 (1.45), 4.972 (2.03), 4.986 (2.00), 5.004 (0.50), 5.016 (0.79), 5.045 (14.11), 5.269 (1.26), 5.394 (1.60), 5.401 (1.65), 5.524 (0.88), 7.919 (16.00), 7.943 (0.44), 8.644 (5.11).

Example 238

(5RS,7RS)-2-[(6-Chloropyridin-3-yl)methyl]-5-[(3-fluoroazetidin-1-yl)carbonyl]-7-(trifluoromethyl)-5,6,7,8-tetrahydro[1,2,4]triazolo[4,3-a]pyridin-3(2H)-one (Diastereomer 1, Racemate)

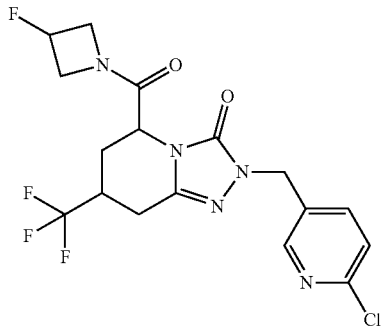 [SMILES: O=C(C1CC(C(F)(F)F)Cc2nn(Cc3ccc(Cl)nc3)c(=O)n21)N1CC(F)C1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, 3-fluoroazetidine hydrochloride (31.3 mg, 280 µmol) was added and the reaction mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 7.90 mg (8% of theory) of diastereomer 1 (racemate), which elutes first, and 31 mg (30% of theory) of diastereomer 2 (racemate), which elutes later, were isolated.

Diastereomer 1, Racemate:

LC-MS (Method 4): $R_t$=0.72 min; MS (ESIpos): m/z=434 [M+H]$^+$ $^1$H-NMR (400 MHz, DMSO-d6) δ [ppm]: −0.149 (1.51), −0.008 (16.00), 0.008 (12.99), 0.146 (1.62), 1.679 (1.16), 1.708 (1.86), 1.739 (1.28), 2.323 (1.86), 2.328 (2.20), 2.332 (1.62), 2.366 (2.43), 2.456 (1.39), 2.523 (7.77), 2.665 (1.97), 2.670 (2.55), 2.675 (2.09), 2.710 (3.94), 2.752 (2.32), 2.867 (2.32), 2.902 (1.28), 2.992 (0.93), 3.969 (0.70), 4.450 (2.67), 4.463 (2.55), 4.478 (2.90), 4.492 (2.09), 4.669 (0.70), 4.902 (6.96), 5.382 (0.70), 5.513 (0.70), 7.517 (3.13), 7.538 (4.06), 7.734 (2.32), 7.754 (1.97), 8.340 (3.36).

Example 239

(5RS,7RS)-2-[(6-Chloropyridin-3-yl)methyl]-5-[(3-fluoroazetidin-1-yl)carbonyl]-7-(trifluoromethyl)-5,6,7,8-tetrahydro[1,2,4]triazolo[4,3-a]pyridin-3(2H)-one (Diastereomer 2, Racemate)

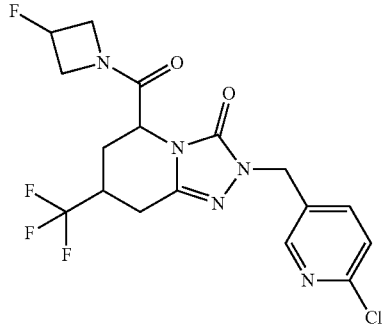 [SMILES: O=C(C1CC(C(F)(F)F)Cc2nn(Cc3ccc(Cl)nc3)c(=O)n21)N1CC(F)C1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, 3-fluoroazetidine hydrochloride (31.3 mg, 280 µmol) was added and the reaction mixture was stirred at room temperature overnight. The reaction mixture was admixed with water and ethyl acetate, and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 7.90 mg (8% of theory) of diastereomer 1 (racemate), which elutes first, and 31 mg (30% of theory) of diastereomer 2 (racemate), which elutes later, were isolated.

Diastereomer 2, Racemate:

LC-MS (Method 4): $R_t$=0.74 min; MS (ESIpos): m/z=434 [M+H]$^+$ $^1$H-NMR (400 MHz, DMSO-d6) δ[ppm]: −0.150 (1.12), −0.008 (9.92), 0.008 (7.26), 0.146 (0.94), 2.187 (2.13), 2.221 (2.54), 2.253 (3.31), 2.327 (1.83), 2.366 (1.59), 2.524 (5.08), 2.670 (2.24), 2.684 (3.19), 2.696 (3.25), 2.710 (1.83), 2.725 (2.60), 2.968 (5.90), 3.003 (3.66), 3.017 (2.36), 3.978 (1.59), 4.039 (1.83), 4.287 (1.71), 4.427 (2.13), 4.460 (1.83), 4.488 (2.07), 4.737 (5.90), 4.751 (5.49), 4.919 (16.00), 5.358 (1.30), 5.502 (1.24), 7.510 (6.85), 7.531 (8.56), 7.701 (5.73), 7.708 (3.31), 7.721 (4.84), 8.307 (9.03).

Example 240

(5RS,7RS)-2-[(6-Chloropyridin-3-yl)methyl]-5-[(3-fluoroazetidin-1-yl)carbonyl]-7-(trifluoromethyl)-5,6,7,8-tetrahydro[1,2,4]triazolo[4,3-a]pyridin-3(2H)-one (Enantiomer 1)

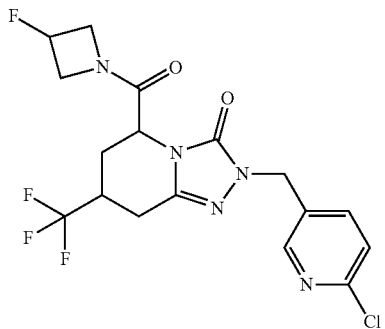 [SMILES: O=C(C1CC(C(F)(F)F)Cc2nn(Cc3ccc(Cl)nc3)c(=O)n21)N1CC(F)C1]

(5RS,7RS)-2-[(6-Chloropyridin-3-yl)methyl]-5-[(3-fluoroazetidin-1-yl)carbonyl]-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 30 mg dissolved in 2.5 ml of ethanol and 1.5 ml of n-heptane; injection volume: 0.7 ml; column: Daicel Chiralpak® IB 5 μm, 250×20 mm; eluent: n-heptane/ethanol 40:60; flow rate: 15 ml/min; temperature 40° C.; UV detection: 220 nm]. After the separation, 8 mg of enantiomer 1, which elutes first, and 8.8 mg of enantiomer 2, which elutes later, were isolated.

Enantiomer 1:

Analytical chiral HPLC: $R_t$=4.56 min, e.e. =99% [column: Daicel Chiralpak® IB 5 μm, 250×4.6 mm; eluent: i-hexane/ethanol 50:50; flow rate: 1 ml/min; UV detection: 220 nm].

LC-MS (Method 3): $R_t$=1.36 min; MS (ESIpos): m/z=434 [M+H]$^+$ $^1$H-NMR (400 MHz, DMSO-d6) δ[ppm]: −0.150 (1.23), 0.008 (9.60), 0.146 (0.98), 1.234 (0.80), 2.104 (0.74), 2.121 (0.98), 2.138 (1.85), 2.155 (2.34), 2.169 (2.22), 2.186 (2.15), 2.223 (2.58), 2.252 (3.32), 2.283 (1.23), 2.327 (2.28), 2.366 (2.15), 2.523 (9.23), 2.610 (0.49), 2.669 (2.71), 2.685 (3.38), 2.695 (3.38), 2.709 (2.65), 2.725 (2.58), 2.934 (1.91), 2.943 (2.09), 2.968 (5.97), 3.002 (3.57), 3.013 (2.40), 3.374 (0.68), 3.402 (0.55), 3.950 (1.29), 3.977 (1.60), 4.006 (1.48), 4.039 (1.91), 4.207 (0.92), 4.219 (0.98), 4.235 (1.60), 4.251 (1.78), 4.261 (1.54), 4.279 (1.42), 4.287 (1.72), 4.304 (1.54), 4.333 (0.68), 4.398 (1.66), 4.423 (2.15), 4.459 (1.72), 4.484 (2.03), 4.621 (0.80), 4.633 (0.98), 4.645 (0.86), 4.671 (1.42), 4.687 (1.60), 4.713 (1.60), 4.736 (6.09), 4.751 (5.29), 4.881 (0.68), 4.919 (16.00), 4.967 (0.68), 5.336 (0.49), 5.359 (1.23), 5.401 (0.92), 5.503 (1.23), 5.550 (1.11), 7.511 (6.46), 7.532 (8.25), 7.701 (5.54), 7.721 (4.49), 7.727 (2.77), 8.307 (8.31).

Example 241

(5RS,7RS)-2-[(6-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture 1; 2 Isomers)

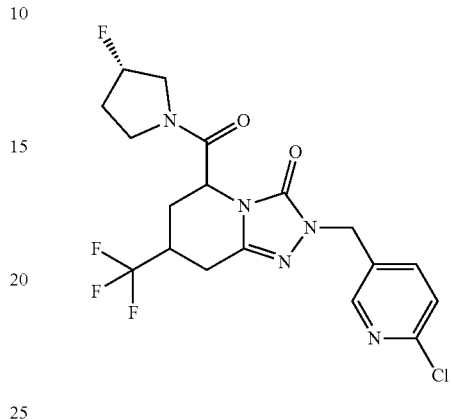

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 μmol) was initially charged in THF (3.0 ml) at room temperature. Subsequently, HBTU (115 mg, 304 μmol) and N,N-diisopropylethylamine (200 μl, 1.2 mmol) were added. After stirring for 15 min, (3S)-3-fluoropyrrolidine hydrochloride (35.2 mg, 280 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). After the separation, 11.2 mg (30% of theory) of diastereomer mixture 1 (2 isomers), which elutes first, and 54 mg (30% of theory) of diastereomer mixture 2 (2 isomers), which elutes later, were isolated.

Diastereomer Mixture 1 (2 Isomers):

LC-MS (Method 4): $R_t$=0.74 min; MS (ESIpos): m/z=448 [M+H]$^+$ $^1$H-NMR (400 MHz, DMSO-d6) δ [ppm]: −0.149 (1.86), −0.033 (0.47), −0.025 (0.56), −0.022 (0.65), −0.008 (16.00), 0.008 (14.19), 0.018 (0.98), 0.146 (1.86), 1.620 (0.42), 1.651 (1.07), 1.664 (0.37), 1.681 (1.07), 1.695 (0.70), 1.704 (0.74), 1.711 (0.60), 1.731 (0.65), 2.051 (0.33), 2.094 (0.65), 2.111 (0.65), 2.124 (0.65), 2.156 (0.56), 2.211 (0.60), 2.226 (0.70), 2.259 (0.79), 2.323 (1.21), 2.327 (1.58), 2.332 (1.16), 2.366 (1.35), 2.523 (5.30), 2.578 (0.60), 2.589 (0.56), 2.594 (0.56), 2.670 (2.70), 2.702 (1.49), 2.710 (3.26), 2.742 (1.86), 2.882 (1.77), 2.922 (1.21), 2.999 (0.74), 3.019 (0.93), 3.043 (0.60), 3.271 (0.51), 3.351 (0.88), 3.368 (0.74), 3.379 (0.47), 3.399 (0.51), 3.426 (0.42), 3.436 (0.37), 3.506 (0.42), 3.514 (0.42), 3.525 (0.42), 3.534 (0.37), 3.556 (0.56), 3.583 (0.47), 3.608 (0.98), 3.622 (0.74), 3.636 (0.65), 3.649 (0.74), 3.656 (0.88), 3.682 (1.07), 3.690 (0.70), 3.707 (0.70), 3.718 (0.60), 3.745 (0.60), 3.792 (0.37), 3.824 (0.60), 3.832 (0.37), 3.849 (0.47), 3.871 (0.74), 3.894 (0.84), 3.910 (0.47), 3.919 (0.70), 3.927 (0.88), 3.954 (0.88), 3.974 (0.51), 4.005 (0.37), 4.664

(0.42), 4.678 (0.51), 4.691 (0.47), 4.706 (0.51), 4.714 (0.60), 4.729 (1.07), 4.743 (1.02), 4.756 (1.07), 4.771 (0.56), 4.796 (0.51), 4.810 (0.56), 4.823 (0.56), 4.838 (0.60), 4.890 (9.02), 4.930 (0.37), 5.269 (0.51), 5.277 (0.56), 5.347 (0.42), 5.400 (0.70), 5.478 (0.37), 5.526 (0.37), 7.516 (3.53), 7.536 (4.42), 7.719 (1.49), 7.726 (2.47), 7.733 (1.81), 7.739 (1.40), 7.746 (2.09), 7.754 (1.44), 8.332 (3.49).

Example 242

(5RS,7RS)-2-[(6-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture 2; 2 Isomers)

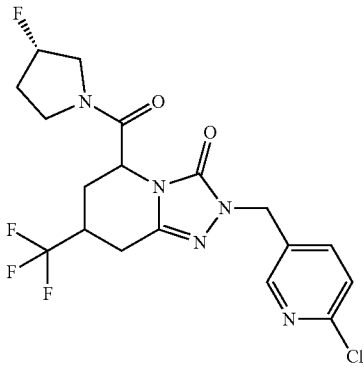 [SMILES: O=C(C1CC(C(F)(F)F)Cc2nn(Cc3ccc(Cl)nc3)c(=O)n21)N1CC[C@H](F)C1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, (3S)-3-fluoropyrrolidine hydrochloride (35.2 mg, 280 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 11.2 mg (30% of theory) of diastereomer mixture 1 (2 isomers), which elutes first, and 54 mg (30% of theory) of diastereomer mixture 2 (2 isomers), which elutes later, were isolated.

Diastereomer Mixture 2 (2 Isomers):
LC-MS (Method 4): $R_t$=0.77 min; MS (ESIpos): m/z=448 [M+H]$^+$ $^1$H-NMR (400 MHz, DMSO-d6) δ [ppm]: −0.149 (0.48), −0.008 (4.34), 0.008 (3.69), 0.146 (0.48), 2.132 (1.45), 2.150 (1.72), 2.161 (2.14), 2.196 (1.69), 2.205 (2.00), 2.226 (3.10), 2.239 (2.31), 2.278 (2.03), 2.322 (1.03), 2.327 (1.07), 2.332 (0.72), 2.366 (0.52), 2.523 (2.31), 2.674 (1.48), 2.685 (0.86), 2.714 (2.38), 2.724 (1.38), 2.744 (1.41), 2.753 (1.45), 2.908 (1.03), 2.973 (2.66), 3.011 (1.69), 3.356 (1.03), 3.373 (1.00), 3.402 (0.83), 3.437 (0.55), 3.512 (0.55), 3.520 (0.62), 3.564 (1.07), 3.586 (0.86), 3.613 (1.62), 3.631 (1.83), 3.667 (1.90), 3.695 (1.14), 3.728 (0.45), 3.761 (0.52), 3.793 (0.66), 3.824 (0.55), 3.847 (1.21), 3.866 (0.62), 3.889 (0.72), 3.925 (0.45), 3.958 (0.59), 3.986 (1.45), 4.012 (0.76), 4.050 (0.55), 4.875 (0.45), 4.921 (16.00), 4.957 (1.34), 4.969 (1.21), 5.013 (1.00), 5.025 (0.97), 5.067 (1.07), 5.265 (1.03), 5.355 (0.62), 5.399 (1.31), 5.487 (0.59), 5.522 (0.52), 7.511 (6.45), 7.532 (8.07), 7.691 (2.24), 7.698 (4.55), 7.705 (2.69), 7.712 (2.00), 7.719 (3.76), 7.725 (2.14), 8.304 (5.21).

Example 243

(5RS,7RS)-2-[(6-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 1)

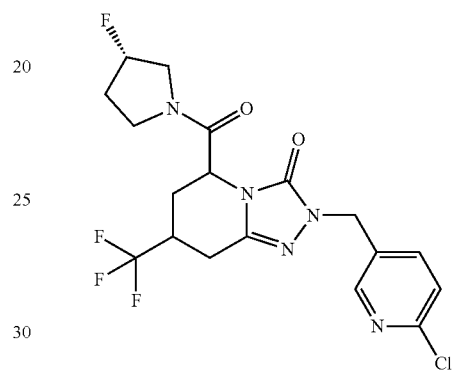

(5RS,7RS)-2-[(6-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture 2; 2 isomers) was separated by chiral preparative HPLC [sample preparation: 54 mg dissolved in 1 ml of ethanol and 1 ml of acetonitrile; injection volume: 0.01 ml; column: Daicel Chiralpak® IE 5 µm, 250×20 mm; eluent: n-heptane/ethanol 50:50; flow rate: 20 ml/min; temperature 30° C.; UV detection: 220 nm]. After the separation, 15.1 mg of isomer 1, which elutes first, and 15.9 mg of isomer 2, which elutes later, were isolated.

Isomer 1:
Analytical chiral HPLC: $R_t$=2.65 min, d.e.=99% [column: Daicel Chiralpak® IE, 50×4.6 mm; eluent: n-heptane/ethanol 50:50; flow rate: 1 ml/min; UV detection: 220 nm].

LC-MS (Method 3): $R_t$=1.44 min; MS (ESIpos): m/z=448 [M+H]$^+$ $^1$H-NMR (400 MHz, DMSO-d6) δ [ppm]: −0.149 (1.26), −0.008 (10.67), 0.008 (11.41), 0.147 (1.43), 0.857 (0.97), 0.877 (0.92), 2.118 (1.43), 2.135 (1.78), 2.165 (3.38), 2.196 (2.24), 2.207 (2.29), 2.225 (2.58), 2.242 (2.70), 2.263 (1.84), 2.282 (3.78), 2.322 (3.50), 2.327 (3.56), 2.332 (2.87), 2.366 (2.29), 2.523 (10.27), 2.670 (4.07), 2.688 (1.26), 2.701 (2.01), 2.710 (4.65), 2.726 (1.72), 2.740 (2.24), 2.755 (1.55), 2.877 (0.92), 2.897 (1.26), 2.940 (1.72), 2.972 (4.36), 3.008 (2.70), 3.020 (2.18), 3.368 (2.12), 3.397 (1.66), 3.427 (1.26), 3.492 (0.97), 3.526 (1.26), 3.537 (1.09), 3.615 (1.26), 3.637 (2.81), 3.667 (3.67), 3.693 (2.92), 3.713 (1.09), 3.732 (1.03), 3.802 (1.03), 3.825 (1.66), 3.845 (2.41), 3.866 (1.55), 3.889 (1.26), 3.896 (1.09), 3.921 (1.09), 3.953 (1.15), 3.979 (1.43), 4.876 (0.97), 4.915 (16.00), 4.957 (3.21), 4.970 (2.92), 5.266 (1.72), 5.391 (2.47), 5.409 (1.38), 5.524 (1.38), 7.511 (9.00), 7.532 (10.67), 7.692 (2.87), 7.698 (6.02), 7.705 (3.73), 7.712 (2.29), 7.719 (5.16), 7.725 (2.92), 8.300 (7.80).

Example 244

(5RS,7RS)-2-[(6-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

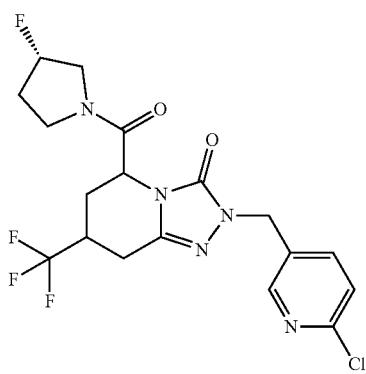 [SMILES: O=C(C1CC(C(F)(F)F)Cc2nn(Cc3ccc(Cl)nc3)c(=O)n21)N1CC[C@H](F)C1]

(5RS,7RS)-2-[(6-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture 2; 2 isomers) was separated by chiral preparative HPLC [sample preparation: 54 mg dissolved in 1 ml of ethanol and 1 ml of acetonitrile; injection volume: 0.01 ml; column: Daicel Chiralpak® IE 5 µm, 250×20 mm; eluent: n-heptane/ethanol 50:50; flow rate: 20 ml/min; temperature 30° C.; UV detection: 220 nm]. After the separation, 15.1 mg of isomer 1, which elutes first, and 15.9 mg of isomer 2, which elutes later, were isolated.

Isomer 2:

Analytical chiral HPLC: $R_t$=3.15 min, d.e.=93% [column: Daicel Chiralpak® IE, 50×4.6 mm; eluent: n-heptane/ethanol 50:50; flow rate: 1 ml/min; UV detection: 220 nm].

LC-MS (Method 3): $R_t$=1.45 min; MS (ESIpos): m/z=448 [M+H]$^+$ $^1$H-NMR (400 MHz, DMSO-d6) δ [ppm]: −0.008 (2.36), 0.008 (2.14), 2.116 (1.14), 2.132 (1.25), 2.150 (1.89), 2.166 (1.40), 2.181 (1.17), 2.196 (1.36), 2.205 (1.97), 2.226 (3.32), 2.239 (2.34), 2.274 (1.40), 2.327 (0.75), 2.366 (0.56), 2.523 (2.11), 2.670 (0.81), 2.675 (1.30), 2.684 (0.93), 2.705 (1.33), 2.715 (2.12), 2.724 (1.17), 2.745 (1.53), 2.753 (1.41), 2.895 (0.95), 2.964 (2.30), 2.975 (1.56), 3.003 (1.68), 3.014 (1.31), 3.355 (2.49), 3.373 (1.63), 3.384 (1.05), 3.401 (0.76), 3.512 (0.76), 3.521 (0.79), 3.564 (1.60), 3.587 (1.26), 3.614 (1.91), 3.630 (1.82), 3.656 (1.02), 3.666 (0.92), 3.682 (0.50), 3.761 (0.51), 3.782 (0.56), 3.791 (0.58), 3.848 (0.48), 3.880 (0.64), 3.888 (0.58), 3.965 (0.74), 3.988 (1.92), 4.012 (0.76), 4.049 (0.84), 4.078 (0.56), 4.922 (16.00), 5.014 (1.53), 5.027 (1.50), 5.067 (1.64), 5.076 (0.99), 5.274 (0.94), 5.356 (0.94), 5.406 (0.90), 5.487 (0.90), 7.512 (4.52), 7.532 (5.71), 7.691 (1.70), 7.698 (3.25), 7.705 (1.96), 7.712 (1.54), 7.719 (2.69), 7.726 (1.59), 8.304 (3.85).

Example 245

(5RS,7RS)-2-[(6-Chloropyridin-3-yl)methyl]-5-{[(3R)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture 2; 2 Isomers)

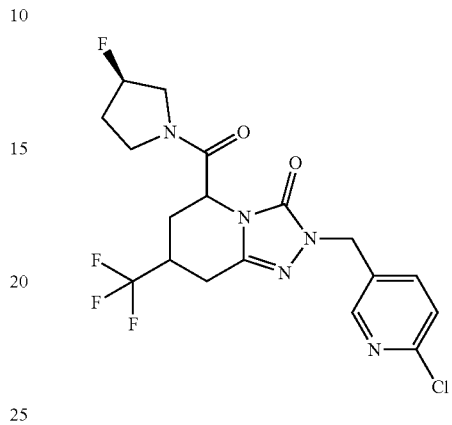

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, (3R)-3-fluoropyrrolidine hydrochloride (35.2 mg, 280 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 20.1 mg (10% of theory) of diastereomer mixture 1 (2 isomers), which elutes first, and 46 mg (44% of theory) of diastereomer mixture 2 (2 isomers), which elutes later, were isolated.

Diastereomer Mixture 2 (2 Isomers):

LC-MS (Method 4): $R_t$=0.77 min; MS (ESIpos): m/z=448 [M+H]$^+$ $^1$H-NMR (400 MHz, DMSO-d6) δ [ppm]: −0.150 (1.12), −0.008 (10.52), 0.008 (7.16), 0.146 (1.12), 2.115 (1.37), 2.162 (2.24), 2.181 (1.43), 2.205 (2.05), 2.227 (3.24), 2.272 (1.99), 2.323 (1.99), 2.328 (2.18), 2.337 (0.93), 2.366 (1.06), 2.523 (4.54), 2.670 (2.30), 2.711 (2.49), 2.724 (1.43), 2.741 (1.43), 2.754 (1.49), 2.895 (1.18), 2.972 (2.61), 3.011 (1.74), 3.372 (1.31), 3.400 (0.93), 3.437 (0.62), 3.487 (0.81), 3.512 (0.75), 3.524 (0.81), 3.564 (1.18), 3.586 (1.00), 3.613 (1.74), 3.633 (1.87), 3.667 (1.99), 3.696 (1.18), 3.713 (0.68), 3.734 (0.62), 3.763 (0.56), 3.793 (0.87), 3.825 (0.56), 3.848 (1.25), 3.867 (0.75), 3.889 (0.68), 3.917 (0.56), 3.966 (0.68), 3.986 (1.56), 4.018 (0.75), 4.047 (0.81), 4.082 (0.56), 4.921 (16.00), 4.958 (1.31), 4.969 (1.25), 5.011 (1.25), 5.026 (1.25), 5.064 (1.06), 5.273 (1.06), 5.345 (0.68), 5.353 (0.75), 5.401 (1.56), 5.493 (0.68), 5.521 (0.68), 7.511 (6.91), 7.532 (8.53), 7.692 (2.24), 7.698 (4.61), 7.705 (2.86), 7.712 (2.12), 7.719 (3.98), 7.725 (2.49), 8.305 (6.16).

Example 246

(5RS,7RS)-2-[(6-Chloropyridin-3-yl)methyl]-5-{[(3R)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 1)

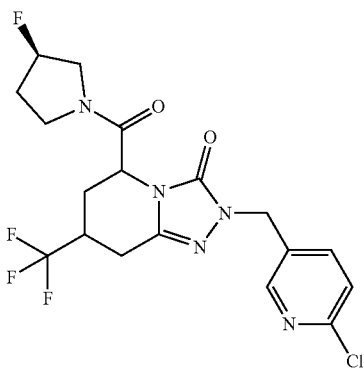 [SMILES: O=C(C1CC(C(F)(F)F)Cc2nn(Cc3ccc(Cl)nc3)c(=O)n21)N1CC[C@@H](F)C1]

(5RS,7RS)-2-[(6-Chloropyridin-3-yl)methyl]-5-{[(3R)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture 2; 2 isomers) was separated by chiral preparative HPLC [sample preparation: 45.8 mg dissolved in 2.5 ml of ethanol, 2.5 ml of n-heptane and 1 ml of dichloromethane; injection volume: 0.4 ml; column: Daicel Chiralpak® IE 5 μm, 250×20 mm; eluent: n-heptane/ethanol 50:50; flow rate: 15 ml/min; temperature 40° C.; UV detection: 220 nm]. After the separation, 19.8 mg of isomer 1, which elutes first, and 16 mg of isomer 2, which elutes later, were isolated.

Isomer 1:

Analytical chiral HPLC: $R_t$=7.02 min, d.e.=99% [column: Daicel Chiralpak® IE 5 μm, 250×4.6 mm; eluent: n-heptane/ethanol 50:50; flow rate: 1 ml/min; UV detection: 220 nm].

LC-MS (Method 3): $R_t$=1.42 min; MS (ESIpos): m/z=448 [M+H]$^+$ $^1$H-NMR (400 MHz, DMSO-d6) δ [ppm]: −0.149 (0.66), −0.008 (6.74), 0.008 (5.83), 0.146 (0.71), 0.846 (0.63), 0.862 (0.58), 1.086 (0.66), 1.102 (0.79), 1.236 (0.76), 2.115 (1.06), 2.131 (1.22), 2.150 (1.80), 2.181 (1.09), 2.204 (1.85), 2.226 (3.25), 2.273 (1.27), 2.327 (1.01), 2.332 (0.71), 2.366 (0.91), 2.523 (3.17), 2.665 (0.89), 2.670 (1.19), 2.674 (1.47), 2.684 (1.01), 2.714 (2.21), 2.723 (1.27), 2.745 (1.62), 2.753 (1.47), 2.887 (0.96), 2.963 (2.33), 3.003 (1.70), 3.014 (1.34), 3.355 (1.09), 3.373 (1.09), 3.383 (0.74), 3.401 (0.61), 3.512 (0.76), 3.520 (0.79), 3.564 (1.62), 3.586 (1.27), 3.614 (1.90), 3.630 (1.83), 3.657 (1.01), 3.665 (0.94), 3.683 (0.51), 3.759 (0.51), 3.783 (0.66), 3.857 (0.48), 3.880 (0.63), 3.964 (0.76), 3.986 (1.93), 4.020 (0.74), 4.046 (0.86), 4.080 (0.61), 4.922 (16.00), 5.014 (1.55), 5.026 (1.52), 5.067 (1.67), 5.274 (0.94), 5.357 (0.91), 5.407 (0.89), 5.489 (0.89), 7.512 (4.74), 7.532 (6.03), 7.691 (1.85), 7.698 (3.37), 7.705 (2.03), 7.712 (1.70), 7.719 (2.87), 7.726 (1.67), 8.304 (4.13).

Example 247

(5RS,7RS)-2-[(6-Chloropyridin-3-yl)methyl]-5-{[(3R)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

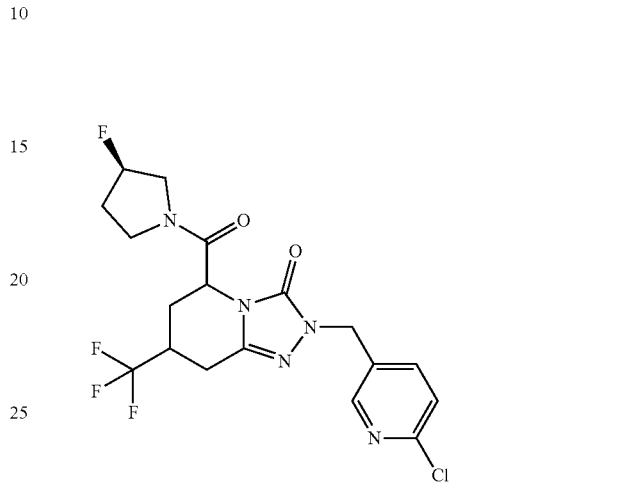

(5RS,7RS)-2-[(6-Chloropyridin-3-yl)methyl]-5-{[(3R)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture 2; 2 isomers) was separated by chiral preparative HPLC [sample preparation: 45.8 mg dissolved in 2.5 ml of ethanol, 2.5 ml of n-heptane and 1 ml of dichloromethane; injection volume: 0.4 ml; column: Daicel Chiralpak® IE 5 μm, 250×20 mm; eluent: n-heptane/ethanol 50:50; flow rate: 15 ml/min; temperature 40° C.; UV detection: 220 nm]. After the separation, 19.8 mg of isomer 1, which elutes first, and 16 mg of isomer 2, which elutes later, were isolated.

Isomer 2:

Analytical chiral HPLC: $R_t$=9.14 min, d.e.=99% [column: Daicel Chiralpak® IE 5 μm, 250×4.6 mm; eluent: n-heptane/ethanol 50:50; flow rate: 1 ml/min; UV detection: 220 nm].

LC-MS (Method 3): $R_t$=1.42 min; MS (ESIpos): m/z=448 [M+H]$^+$ $^1$H-NMR (400 MHz, DMSO-d6) δ [ppm]: −0.149 (1.57), 0.008 (11.20), 0.146 (1.25), 0.857 (0.52), 1.021 (0.73), 1.102 (0.59), 1.234 (1.22), 1.976 (0.70), 2.003 (0.70), 2.082 (0.63), 2.108 (1.22), 2.133 (1.91), 2.167 (3.17), 2.194 (2.37), 2.225 (2.23), 2.233 (2.40), 2.241 (2.71), 2.282 (3.83), 2.327 (2.57), 2.366 (1.46), 2.590 (1.08), 2.672 (3.41), 2.687 (1.22), 2.701 (2.30), 2.711 (3.83), 2.725 (1.81), 2.741 (2.26), 2.755 (1.57), 2.933 (1.67), 2.970 (4.52), 3.010 (2.92), 3.021 (2.23), 3.339 (1.53), 3.350 (1.70), 3.369 (1.53), 3.395 (1.60), 3.427 (1.46), 3.437 (1.25), 3.499 (0.97), 3.526 (1.29), 3.536 (1.32), 3.618 (1.18), 3.641 (2.89), 3.668 (3.65), 3.694 (2.78), 3.712 (1.04), 3.730 (1.43), 3.768 (0.70), 3.795 (0.94), 3.822 (1.46), 3.847 (2.54), 3.869 (1.39), 3.888 (1.01), 3.921 (1.36), 3.956 (0.80), 3.980 (1.36), 4.011 (0.97), 4.875 (1.01), 4.916 (16.00), 4.957 (3.23), 4.971 (3.06), 5.268 (1.74), 5.398 (2.64), 5.521 (1.22), 7.512 (8.10), 7.532 (10.33), 7.698 (5.46), 7.704 (3.72), 7.719 (4.49), 7.725 (2.96), 8.301 (7.48), 17.633 (0.52).

Example 248

(5RS,7RS)-2-[(6-Chloropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Diastereomer 1, Racemate)

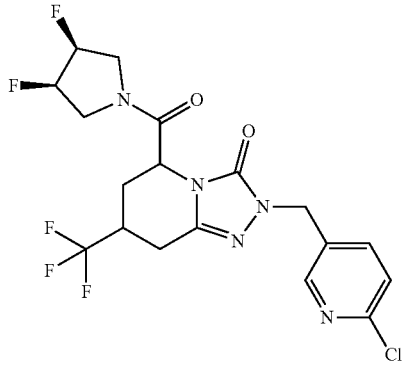 [SMILES: O=C(C1CC(C(F)(F)F)Cc2nn(Cc3ccc(Cl)nc3)c(=O)n21)N1C[C@@H](F)[C@@H](F)C1]

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, (3R,4S)-3,4-difluoropyrrolidine hydrochloride (40.2 mg, 280 µmol) was added and the reaction mixture was stirred at room temperature overnight. The reaction mixture was admixed with water and ethyl acetate, and the organic phase was removed. The organic phase was washed with 10% citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 15.5 mg (13% of theory) of diastereomer 1 (racemate), which elutes first, and 59 mg (54% of theory) of diastereomer 2 (racemate), which elutes later, were isolated.
Diastereomer 1, Racemate:
LC-MS (Method 4): $R_t$=0.77 min; MS (ESIpos): m/z=466 [M+H]$^+$
$^1$H-NMR (400 MHz, DMSO-d6) δ [ppm]: −0.150 (1.14), −0.008 (10.54), 0.007 (8.83), 0.145 (1.14), 1.635 (1.97), 1.663 (2.16), 1.697 (1.84), 1.728 (1.65), 2.327 (1.84), 2.366 (1.40), 2.522 (7.49), 2.559 (3.05), 2.669 (2.16), 2.679 (2.60), 2.711 (4.06), 2.719 (3.43), 2.752 (3.94), 2.884 (3.43), 2.924 (2.41), 2.992 (1.65), 3.002 (1.78), 3.011 (1.84), 3.507 (1.27), 3.517 (1.52), 3.551 (1.71), 3.559 (1.84), 3.570 (1.27), 3.605 (1.33), 3.614 (1.02), 3.638 (1.52), 3.651 (1.46), 3.671 (1.14), 3.684 (1.02), 3.696 (1.40), 3.709 (1.33), 3.729 (1.40), 3.743 (1.40), 3.766 (1.08), 3.779 (1.40), 3.792 (1.59), 3.805 (1.71), 3.818 (1.40), 3.826 (1.46), 3.839 (1.40), 3.867 (1.21), 3.906 (1.08), 4.083 (1.14), 4.097 (1.27), 4.110 (1.65), 4.125 (2.10), 4.143 (1.33), 4.153 (1.97), 4.169 (1.52), 4.709 (2.03), 4.723 (2.60), 4.735 (2.79), 4.751 (2.29), 4.760 (1.59), 4.890 (16.00), 4.920 (3.68), 5.245 (1.27), 5.273 (1.40), 5.283 (1.27), 5.306 (0.95), 5.319 (1.02), 5.325 (1.02), 5.340 (1.08), 5.368 (1.27), 5.378 (1.52), 5.391 (1.40), 5.404 (1.46), 5.413 (1.21), 5.426 (0.89), 5.435 (0.95), 5.449 (1.14), 5.458 (1.02), 5.469 (1.02), 5.483 (0.95), 7.514 (6.16), 7.535 (7.43), 7.698 (0.89), 7.716 (3.05), 7.723 (3.11), 7.727 (3.43), 7.734 (3.75), 7.743 (2.48), 7.748 (2.73), 7.754 (2.54), 8.302 (1.21), 8.325 (3.62), 8.331 (6.92), 8.338 (4.00).

Example 249

(5RS,7RS)-2-[(6-Chloropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Diastereomer 2, Racemate)

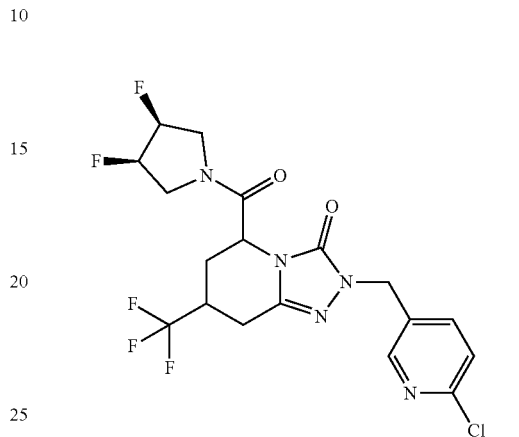

(5RS,7RS)-2-[(6-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (88.0 mg, 234 µmol) was initially charged in THF (3.0 ml) at room temperature. Subsequently, HBTU (115 mg, 304 µmol) and N,N-diisopropylethylamine (200 µl, 1.2 mmol) were added. After stirring for 15 min, (3R,4S)-3,4-difluoropyrrolidine hydrochloride (40.2 mg, 280 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 15.5 mg (13% of theory) of diastereomer 1 (racemate), which elutes first, and 59 mg (54% of theory) of diastereomer 2 (racemate), which elutes later, were isolated.
Diastereomer 2, Racemate:
LC-MS (Method 4): $R_t$=0.80 min; MS (ESIpos): m/z=466 [M+H]$^+$
$^1$H-NMR (400 MHz, DMSO-d6) δ [ppm]: −0.008 (3.00), 0.008 (2.78), 1.030 (0.77), 1.045 (0.77), 2.122 (0.58), 2.138 (0.63), 2.156 (1.24), 2.172 (1.13), 2.187 (1.27), 2.203 (2.42), 2.210 (2.40), 2.219 (2.23), 2.232 (1.38), 2.274 (1.85), 2.305 (1.07), 2.328 (0.55), 2.366 (0.44), 2.670 (0.72), 2.676 (1.60), 2.689 (1.05), 2.706 (1.90), 2.717 (2.84), 2.728 (1.35), 2.746 (2.23), 2.757 (1.62), 2.881 (1.27), 2.963 (3.19), 2.975 (2.18), 3.003 (2.37), 3.015 (1.87), 3.492 (0.83), 3.501 (0.91), 3.534 (1.38), 3.542 (1.27), 3.584 (1.35), 3.643 (0.94), 3.656 (0.85), 3.676 (0.72), 3.689 (0.74), 3.700 (1.57), 3.714 (1.43), 3.733 (1.07), 3.748 (0.99), 3.764 (0.72), 3.777 (0.74), 3.797 (0.55), 3.810 (0.55), 3.840 (0.66), 3.853 (0.94), 3.868 (1.24), 3.888 (1.18), 3.907 (0.99), 4.041 (0.72), 4.055 (0.99), 4.069 (0.63), 4.088 (0.99), 4.103 (0.96), 4.117 (0.66), 4.131 (0.69), 4.152 (0.58), 4.167 (0.63), 4.180 (0.58), 4.195 (1.16), 4.211 (0.69), 4.224 (0.58), 4.240 (0.55), 4.878 (0.61), 4.918 (16.00), 4.963 (0.66), 4.990 (3.00), 5.004 (4.43), 5.259 (0.83), 5.267

(0.94), 5.286 (0.94), 5.294 (0.94), 5.307 (0.55), 5.325 (0.74), 5.341 (0.74), 5.358 (0.74), 5.367 (0.77), 5.383 (1.18), 5.397 (1.10), 5.405 (0.94), 5.415 (1.05), 5.426 (0.96), 5.439 (0.66), 5.455 (0.74), 5.469 (0.74), 5.489 (0.80), 7.512 (5.43), 7.533 (6.88), 7.688 (1.96), 7.695 (2.45), 7.698 (2.97), 7.705 (2.86), 7.709 (2.01), 7.719 (2.51), 7.725 (2.26), 8.295 (2.73), 8.301 (5.34), 8.307 (3.33).

Example 250

(5RS,7RS)-2-[(6-Chloropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Enantiomer 1)

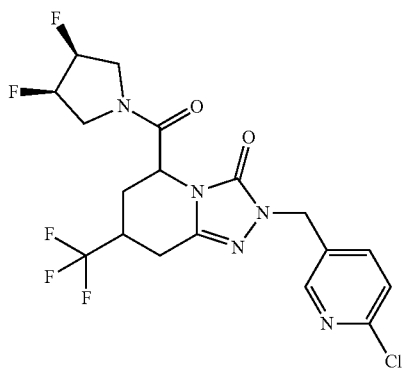 [SMILES: O=C(C1CC(C(F)(F)F)Cc2nn(Cc3ccc(Cl)nc3)c(=O)n21)N1C[C@@H](F)[C@@H](F)C1]

(5RS,7RS)-2-[(6-Chloropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 59 mg dissolved in 3 ml of ethanol; injection volume: 0.05 ml; column: Daicel Chiralpak® IE 5 µm, 250×20 mm; eluent: n-heptane/ethanol 50:50; flow rate: 20 ml/min; temperature 30° C.; UV detection: 220 nm]. After the separation, 13.8 mg of enantiomer 1, which elutes first, and 15.8 mg of enantiomer 2, which elutes later, were isolated.
Enantiomer 1:
Analytical chiral HPLC: $R_t$=1.89 min, e.e. =99% [column: Daicel Chiralpak® IE, 50×4.6 mm; eluent: n-heptane/ethanol 50:50; flow rate: 1 ml/min; UV detection: 220 nm].
LC-MS (Method 3): $R_t$=1.48 min; MS (ESIpos): m/z=466 [M+H]$^+$
$^1$H-NMR (400 MHz, DMSO-d6) δ [ppm]: −0.149 (0.93), −0.008 (9.80), 0.008 (7.71), 0.146 (0.93), 0.859 (0.96), 1.135 (1.58), 1.153 (3.15), 1.171 (1.61), 2.156 (1.16), 2.171 (1.23), 2.187 (1.37), 2.203 (2.50), 2.209 (2.47), 2.218 (2.36), 2.271 (2.06), 2.307 (1.16), 2.327 (1.61), 2.366 (1.37), 2.523 (5.31), 2.669 (1.85), 2.674 (2.02), 2.688 (1.13), 2.709 (2.47), 2.716 (2.81), 2.727 (1.54), 2.746 (2.33), 2.757 (1.68), 2.891 (1.64), 2.910 (2.09), 2.928 (1.51), 2.964 (3.22), 2.976 (2.09), 3.003 (2.50), 3.014 (1.92), 3.491 (0.96), 3.499 (0.99), 3.533 (1.44), 3.582 (1.30), 3.641 (0.93), 3.656 (0.96), 3.700 (1.54), 3.712 (1.44), 3.732 (1.03), 3.745 (1.03), 3.840 (0.89), 3.868 (1.20), 3.888 (1.30), 4.056 (0.99), 4.085 (0.99), 4.102 (1.06), 4.195 (1.23), 4.918 (16.00), 4.990 (3.05), 5.003 (4.52), 5.272 (0.99), 5.283 (1.03), 5.295 (0.99), 5.340 (0.86), 5.384 (1.16), 5.404 (1.03), 5.425 (1.13), 5.504 (0.89), 7.512 (6.17), 7.532 (7.57), 7.688 (2.09), 7.698 (3.19), 7.704 (3.25), 7.719 (2.81), 7.725 (2.57), 8.301 (7.02).

Example 251

(5RS,7RS)-5-[(3,3-Difluoropyrrolidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Diastereomer 2, Racemate)

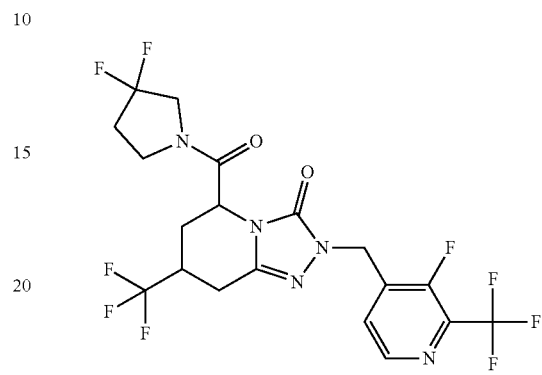

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (93.0 mg, 217 µmol) was initially charged in THF (2.0 ml) at room temperature.
Subsequently, HBTU (107 mg, 282 µmol) and N,N-diisopropylethylamine (190 µl, 1.1 mmol) were added. After stirring for 15 min, 3,3-difluoropyrrolidine hydrochloride (37.4 mg, 261 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 9.3 mg (6% of theory) of diastereomer 1 (racemate), which elutes first, and 75.8 mg (66% of theory) of diastereomer 2 (racemate), which elutes later, were isolated.
LC-MS (Method 3): $R_t$=1.91 min; MS (ESIpos): m/z=518 [M+H]$^+$
$^1$H-NMR (400 MHz, DMSO-d6) δ [ppm]: −0.008 (2.21), 0.008 (2.19), 1.030 (0.81), 1.045 (0.81), 2.073 (0.62), 2.130 (0.89), 2.146 (1.06), 2.165 (2.14), 2.171 (1.67), 2.177 (1.87), 2.182 (2.05), 2.196 (2.25), 2.206 (2.48), 2.212 (2.38), 2.222 (1.95), 2.237 (1.87), 2.252 (1.71), 2.279 (3.19), 2.300 (3.44), 2.328 (2.21), 2.332 (2.35), 2.366 (0.89), 2.377 (1.24), 2.397 (2.11), 2.427 (2.79), 2.443 (2.48), 2.462 (1.67), 2.473 (1.67), 2.523 (2.87), 2.565 (3.40), 2.583 (2.73), 2.603 (1.84), 2.622 (0.92), 2.665 (0.62), 2.670 (0.78), 2.674 (0.62), 2.702 (2.40), 2.709 (2.86), 2.731 (3.35), 2.740 (4.75), 2.749 (3.10), 2.771 (3.90), 2.778 (3.67), 2.920 (2.35), 2.993 (4.94), 3.025 (2.56), 3.033 (3.68), 3.041 (2.21), 3.520 (0.62), 3.539 (1.16), 3.550 (2.35), 3.569 (6.00), 3.589 (4.68), 3.604 (2.37), 3.618 (0.90), 3.636 (0.49), 3.685 (0.67), 3.718 (2.17), 3.755 (3.76), 3.788 (4.03), 3.817 (2.33), 3.851 (0.54), 3.876 (0.54), 3.894 (1.25), 3.902 (2.44), 3.919 (4.70), 3.934 (5.06), 3.953 (2.29), 3.960 (1.38), 3.979 (0.54), 4.105 (0.75), 4.135 (1.98), 4.147 (0.81), 4.163 (1.70), 4.178 (3.27), 4.204 (3.16), 4.236 (1.84), 4.267 (0.52), 4.984 (3.75), 4.997 (3.71), 5.048 (4.57), 5.062 (3.98), 5.074 (4.49), 5.089 (15.44), 5.117 (16.00), 5.158 (4.49), 7.561 (5.02), 7.573 (9.68), 7.586 (5.37), 8.568 (11.97), 8.580 (12.08).

Example 252

(5RS,7RS)-5-[(3,3-Difluoropyrrolidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Enantiomer 2)

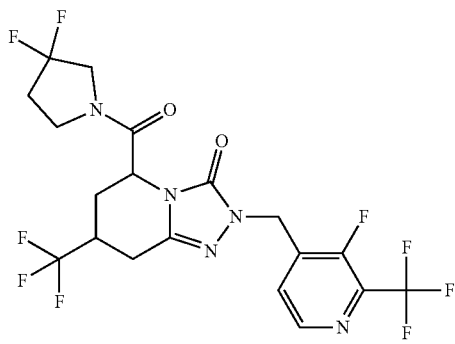 [SMILES: O=C(C1CC(C(F)(F)F)Cc2nn(Cc3ccnc(C(F)(F)F)c3F)c(=O)n21)N1CCC(F)(F)C1]

(5RS,7RS)-5-[(3,3-Difluoropyrrolidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 75.8 mg dissolved in 3 ml of isopropanol in an ultrasound bath, then 3 ml of n-heptane added; injection volume: 0.8 ml; column: Daicel Chiralpak® IA 5 μm, 250×20 mm; eluent: n-heptane/isopropanol 50:50; flow rate: 15 ml/min; temperature 30° C.; UV detection: 220 nm]. After the separation, 11.4 mg of enantiomer 1, which elutes first, and 13.3 mg of enantiomer 2, which elutes later, were isolated.

Enantiomer 2:

Analytical chiral HPLC: $R_t$=7.07 min, e.e. =99% [column: Daicel Chiralpak® IA 5 μm, 250×4.6 mm; eluent: i-hexane/isopropanol 50:50; flow rate: 1 ml/min; UV detection: 220 nm].

LC-MS (Method 3): $R_t$=1.77 min; MS (ESIpos): m/z=518 [M+H]$^+$ $^1$H-NMR (400 MHz, DMSO-d6) δ [ppm]: −0.149 (1.82), −0.008 (16.00), 0.008 (15.76), 0.146 (1.87), 1.260 (0.77), 2.165 (0.72), 2.180 (0.62), 2.205 (0.86), 2.252 (0.57), 2.281 (1.01), 2.296 (1.15), 2.322 (1.87), 2.327 (2.44), 2.332 (1.96), 2.366 (1.72), 2.397 (0.72), 2.409 (0.67), 2.426 (0.96), 2.444 (1.01), 2.523 (5.99), 2.665 (1.58), 2.670 (2.11), 2.674 (1.58), 2.701 (0.81), 2.710 (2.30), 2.731 (1.10), 2.739 (1.49), 2.770 (1.20), 2.778 (1.15), 2.928 (0.81), 2.993 (1.63), 3.033 (1.15), 3.550 (0.77), 3.569 (1.96), 3.588 (1.58), 3.604 (0.77), 3.717 (0.77), 3.756 (1.15), 3.787 (1.29), 3.818 (0.72), 3.903 (0.72), 3.919 (1.49), 3.935 (1.58), 3.951 (0.72), 4.135 (0.62), 4.178 (1.01), 4.204 (1.01), 4.983 (1.25), 4.996 (1.20), 5.047 (1.53), 5.061 (1.20), 5.074 (1.39), 5.089 (4.84), 5.116 (5.08), 5.158 (1.49), 7.560 (1.68), 7.573 (3.16), 7.586 (1.72), 8.568 (4.02), 8.580 (3.98).

Example 253

(5RS,7RS)-5-[(3-Fluoroazetidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Diastereomer 1, Racemate)

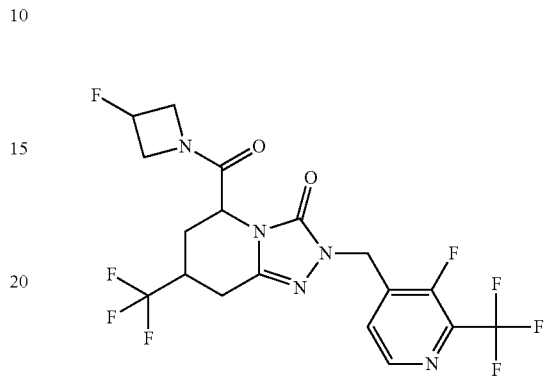

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (93.0 mg, 217 μmol) was initially charged in THF (2.0 ml) at room temperature. Subsequently, HBTU (107 mg, 282 μmol) and N,N-diisopropylethylamine (190 μl, 1.1 mmol) were added. After stirring for 15 min, 3-fluoroazetidine hydrochloride (29.1 mg, 261 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). After the separation, 6.7 mg (6% of theory) of diastereomer 1 (racemate), which elutes first, and 65.5 mg (62% of theory) of diastereomer 2 (racemate), which elutes later, were isolated.

Diastereomer 1, Racemate:

LC-MS (Method 3): $R_t$=1.70 min; MS (ESIpos): m/z=486 [M+H]$^+$ $^1$H-NMR (400 MHz, DMSO-d6) δ[ppm]: −0.150 (1.81), −0.009 (15.15), 0.007 (16.00), 0.146 (1.64), 1.667 (0.62), 1.698 (1.81), 1.728 (2.83), 1.757 (2.04), 1.790 (0.79), 2.327 (2.83), 2.365 (2.54), 2.457 (2.09), 2.522 (8.37), 2.664 (1.87), 2.669 (2.49), 2.709 (2.94), 2.737 (2.37), 2.745 (2.49), 2.776 (2.77), 2.888 (3.11), 2.917 (1.70), 2.928 (1.87), 2.968 (0.62), 3.004 (1.36), 3.017 (1.36), 3.246 (0.51), 3.905 (0.62), 3.943 (1.07), 3.971 (1.36), 4.006 (1.02), 4.041 (0.79), 4.164 (0.73), 4.178 (0.62), 4.190 (0.62), 4.211 (0.79), 4.230 (0.96), 4.255 (0.96), 4.282 (0.73), 4.307 (0.73), 4.321 (0.51), 4.338 (0.62), 4.355 (0.85), 4.384 (1.30), 4.412 (1.24), 4.443 (1.58), 4.471 (3.39), 4.485 (3.00), 4.498 (2.88), 4.512 (2.54), 4.587 (0.57), 4.602 (0.74), 4.639 (1.13), 4.658 (1.24), 4.696 (0.62), 4.727 (0.68), 4.742 (0.51), 5.070 (9.78), 5.079 (10.06), 5.380 (1.24), 5.517 (1.24), 7.635 (3.45), 7.649 (6.05), 7.661 (3.39), 8.579 (5.82), 8.590 (5.48).

Example 254

(5RS,7RS)-5-[(3-Fluoroazetidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Diastereomer 2, Racemate)

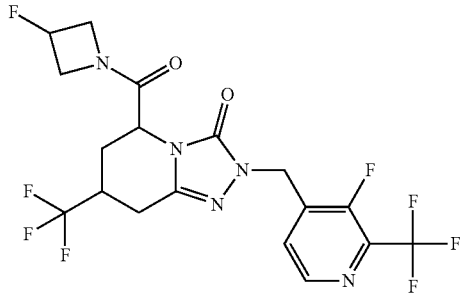 [SMILES: O=C(C1CC(C(F)(F)F)Cc2nn(Cc3ccnc(C(F)(F)F)c3F)c(=O)n21)N1CC(F)C1]

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (93.0 mg, 217 µmol) was initially charged in THF (2.0 ml) at room temperature. Subsequently, HBTU (107 mg, 282 µmol) and N,N-diisopropylethylamine (190 µl, 1.1 mmol) were added. After stirring for 15 min, 3-fluoroazetidine hydrochloride (29.1 mg, 261 µmol) was added and the reaction mixture was stirred at room temperature overnight. The reaction mixture was admixed with water and ethyl acetate, and the organic phase was removed. The organic phase was washed with 10% citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 6.7 mg (6% of theory) of diastereomer 1 (racemate), which elutes first, and 65.5 mg (62% of theory) of diastereomer 2 (racemate), which elutes later, were isolated.

Diastereomer 2, Racemate:

LC-MS (Method 3): $R_t$=1.75 min; MS (ESIpos): m/z=486 [M+H]$^+$ $^1$H-NMR (400 MHz, DMSO-d6) δ[ppm]: −0.149 (0.51), −0.008 (3.67), 0.008 (3.01), 1.030 (0.61), 1.045 (0.71), 2.073 (0.61), 2.137 (1.68), 2.156 (2.90), 2.173 (3.62), 2.187 (3.57), 2.203 (3.16), 2.219 (1.73), 2.240 (3.67), 2.273 (5.10), 2.308 (1.89), 2.328 (1.43), 2.366 (1.12), 2.524 (3.72), 2.679 (2.85), 2.709 (5.76), 2.718 (4.89), 2.748 (4.38), 2.989 (8.76), 3.027 (5.04), 3.036 (3.62), 3.970 (2.55), 4.001 (2.04), 4.031 (2.24), 4.213 (1.27), 4.241 (2.04), 4.270 (2.29), 4.286 (2.70), 4.335 (1.12), 4.403 (2.34), 4.428 (2.75), 4.463 (2.50), 4.490 (3.01), 4.626 (1.17), 4.644 (1.43), 4.671 (2.24), 4.683 (2.50), 4.698 (2.34), 4.710 (2.09), 4.722 (2.19), 4.770 (8.36), 4.785 (7.85), 5.052 (3.72), 5.093 (16.00), 5.110 (9.17), 5.121 (9.27), 5.151 (1.94), 5.163 (2.45), 5.362 (1.78), 5.408 (1.73), 5.505 (1.78), 5.551 (1.68), 7.567 (5.61), 7.579 (10.90), 7.592 (5.91), 8.568 (11.87), 8.580 (11.87).

Example 255

(5RS,7RS)-5-[(3-Fluoroazetidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Enantiomer 2)

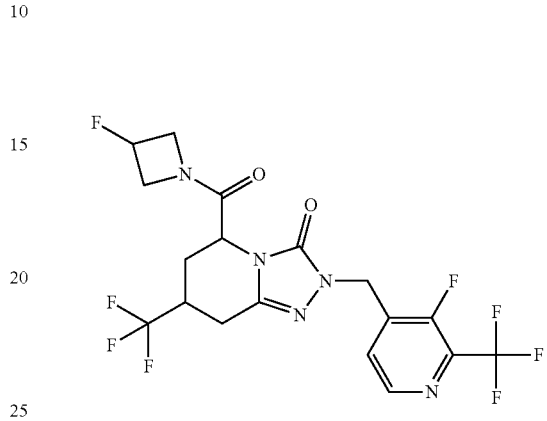

(5RS,7RS)-5-[(3-Fluoroazetidin-1-yl)carbonyl]-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 65.5 mg dissolved in 3 ml of isopropanol, then 1 ml of dichloromethane and 2 ml of n-heptane added; injection volume: 0.4 ml; column: Daicel Chiralpak® IA 5 µm, 250×20 mm; eluent: n-heptane/isopropanol 50:50; flow rate: 15 ml/min; temperature 30° C.; UV detection: 220 nm]. After the separation, 5.7 mg of enantiomer 1, which elutes first, and 5.4 mg of enantiomer 2, which elutes later, were isolated.

Enantiomer 2:

Analytical chiral HPLC: $R_t$=7.09 min, e.e. =99% [column: Daicel Chiralpak® IA 5 µm, 250×4.6 mm; eluent: n-heptane/isopropanol 50:50; flow rate: 1 ml/min; UV detection: 220 nm].

LC-MS (Method 3): $R_t$=1.64 min; MS (ESIpos): m/z=486 [M+H]$^+$ $^1$H-NMR (400 MHz, DMSO-d6) δ[ppm]: −0.150 (1.04), −0.009 (16.00), 0.007 (7.79), 0.017 (0.39), 0.146 (1.01), 0.986 (0.27), 1.002 (0.30), 1.234 (0.42), 2.136 (0.27), 2.155 (0.44), 2.172 (0.54), 2.185 (0.54), 2.201 (0.52), 2.218 (0.32), 2.241 (0.62), 2.272 (0.74), 2.308 (0.30), 2.317 (0.30), 2.322 (0.49), 2.327 (0.57), 2.331 (0.44), 2.366 (0.59), 2.523 (3.72), 2.561 (0.27), 2.563 (0.27), 2.664 (0.57), 2.669 (0.76), 2.674 (0.71), 2.709 (1.26), 2.717 (0.71), 2.747 (0.64), 2.951 (0.44), 2.958 (0.47), 2.988 (1.28), 3.025 (0.74), 3.035 (0.52), 3.967 (0.37), 3.999 (0.32), 4.030 (0.32), 4.053 (0.25), 4.212 (0.25), 4.241 (0.30), 4.256 (0.37), 4.268 (0.37), 4.281 (0.42), 4.308 (0.27), 4.401 (0.35), 4.431 (0.47), 4.461 (0.42), 4.490 (0.42), 4.670 (0.37), 4.683 (0.39), 4.694 (0.42), 4.707 (0.37), 4.721 (0.35), 4.738 (0.27), 4.768 (1.21), 4.783 (1.08), 5.052 (0.54), 5.092 (2.29), 5.109 (1.38), 5.120 (1.33), 5.151 (0.32), 5.161 (0.37), 5.361 (0.27), 5.408 (0.25), 5.505 (0.30), 5.753 (1.97), 7.565 (0.89), 7.578 (1.53), 7.591 (0.84), 8.567 (1.73), 8.579 (1.65).

Example 256

(5RS,7RS)-5-{[(3S)-3-Fluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Diastereomer Mixture 2; 2 Isomers)

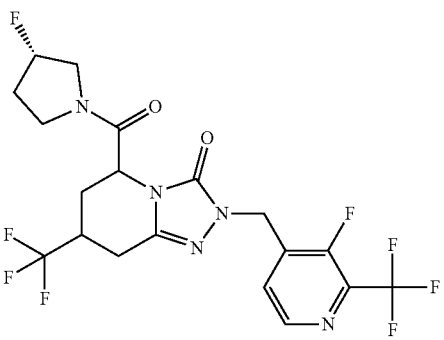 [SMILES: O=C(C1CC(C(F)(F)F)Cc2nn(Cc3ccnc(C(F)(F)F)c3F)c(=O)n21)N1CC[C@H](F)C1]

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (93.0 mg, 217 µmol) was initially charged in THF (2.0 ml) at room temperature. Subsequently, HBTU (107 mg, 282 µmol) and N,N-diisopropylethylamine (190 µl, 1.1 mmol) were added. After stirring for 15 min, (3S)-3-fluoropyrrolidine hydrochloride (32.7 mg, 261 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 8.8 mg (7% of theory) of diastereomer mixture 1 (2 isomers), which elutes first, and 68.3 mg (63% of theory) of diastereomer mixture 2 (2 isomers), which elutes later, were isolated.

Diastereomer Mixture 2, 2 Isomers:

LC-MS (Method 3): $R_t$=1.76 min; MS (ESIpos): m/z=500 [M+H]$^+$ $^1$H-NMR (400 MHz, DMSO-d6) δ [ppm]: −0.149 (0.68), −0.008 (5.73), 0.008 (6.83), 0.146 (0.68), 2.000 (0.94), 2.117 (2.71), 2.149 (4.64), 2.167 (4.38), 2.183 (4.43), 2.213 (4.27), 2.224 (6.57), 2.234 (6.88), 2.245 (8.96), 2.282 (4.59), 2.323 (2.24), 2.328 (2.87), 2.333 (2.76), 2.366 (2.29), 2.523 (7.35), 2.670 (2.35), 2.675 (1.77), 2.700 (2.55), 2.710 (4.59), 2.730 (3.65), 2.738 (6.41), 2.749 (4.07), 2.768 (3.96), 2.778 (4.48), 2.927 (2.97), 2.995 (7.71), 3.033 (5.00), 3.163 (14.80), 3.173 (14.85), 3.360 (8.08), 3.378 (5.73), 3.388 (4.07), 3.406 (3.75), 3.436 (2.14), 3.446 (2.03), 3.508 (1.41), 3.527 (1.93), 3.572 (3.07), 3.596 (2.55), 3.621 (4.74), 3.643 (6.41), 3.662 (3.44), 3.671 (5.32), 3.687 (3.18), 3.696 (3.07), 3.713 (1.30), 3.736 (1.30), 3.763 (1.72), 3.794 (2.14), 3.832 (1.62), 3.853 (3.70), 3.891 (2.24), 3.928 (1.30), 3.963 (2.14), 3.990 (4.38), 4.023 (1.88), 4.087 (4.38), 4.938 (2.29), 4.950 (2.35), 4.986 (3.23), 4.999 (3.13), 5.045 (5.16), 5.087 (11.41), 5.095 (14.85), 5.117 (15.84), 5.159 (4.12), 5.269 (3.13), 5.358 (1.77), 5.402 (3.75), 5.489 (1.72), 5.524 (1.41), 7.562 (5.73), 7.574 (10.32), 7.587 (5.37), 8.136 (13.29), 8.568 (16.00), 8.580 (16.00).

Example 257

(5RS,7RS)-5-{[(3S)-3-Fluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Isomer 1)

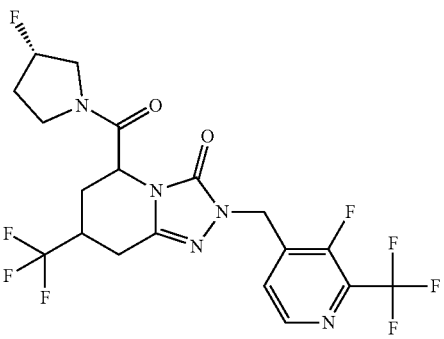 [SMILES: O=C(C1CC(C(F)(F)F)Cc2nn(Cc3ccnc(C(F)(F)F)c3F)c(=O)n21)N1CC[C@H](F)C1]

(5RS,7RS)-5-{[(3S)-3-Fluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (diastereomer mixture 2; 2 isomers) was separated by chiral preparative HPLC [sample preparation: 68.3 mg dissolved in 3 ml of acetonitrile and 2 ml of ethanol (warm); injection volume: 0.25 ml; column: Daicel Chiralpak® IB 5 µm, 250×20 mm; eluent: n-heptane/isopropanol 50:50; flow rate: 15 ml/min; temperature 25° C.; UV detection: 210 nm]. After the separation, 30.7 mg of isomer 1, which elutes first, and 27.2 mg of isomer 2, which elutes later, were isolated.

Isomer 1:

Analytical chiral HPLC: $R_t$=2.17 min, d.e.=99% [column: Daicel Chiraltek® IB 3 µm, 50×4.6 mm; eluent: i-hexane/ethanol 50:50; flow rate: 1 ml/min; UV detection: 220 nm].

LC-MS (Method 4): $R_t$=0.89 min; MS (ESIpos): m/z=500 [M+H]$^+$ $^1$H-NMR (400 MHz, DMSO-d6) δ [ppm]: −0.149 (1.69), −0.008 (15.64), 0.008 (16.00), 0.145 (1.87), 1.235 (1.60), 2.189 (4.18), 2.207 (3.56), 2.243 (4.62), 2.302 (5.60), 2.327 (3.82), 2.332 (3.91), 2.366 (3.56), 2.523 (11.82), 2.669 (4.00), 2.696 (2.93), 2.710 (5.69), 2.724 (4.00), 2.736 (5.24), 2.749 (3.11), 2.765 (4.18), 2.779 (2.84), 2.994 (8.18), 3.032 (4.80), 3.045 (3.64), 3.330 (4.98), 3.350 (2.67), 3.359 (3.38), 3.378 (2.76), 3.406 (2.76), 3.445 (2.22), 3.507 (1.69), 3.534 (2.31), 3.543 (2.13), 3.621 (2.22), 3.640 (4.98), 3.670 (5.96), 3.686 (3.47), 3.696 (4.62), 3.735 (2.13), 3.802 (1.69), 3.832 (2.40), 3.855 (4.80), 3.929 (1.96), 3.962 (1.60), 3.988 (2.31), 4.938 (3.47), 4.950 (3.56), 4.985 (5.16), 4.999 (4.98), 5.042 (4.00), 5.086 (13.60), 5.118 (11.82), 5.159 (3.73), 5.270 (3.29), 5.400 (4.18), 5.523 (2.31), 7.561 (4.89), 7.573 (9.87), 7.587 (5.42), 8.568 (13.42), 8.580 (13.60).

Example 258

(5RS,7RS)-5-{[(3S)-3-Fluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Isomer 2)

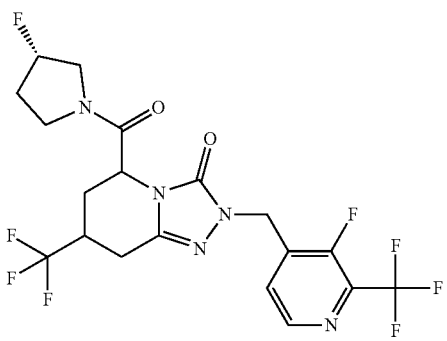 [SMILES: O=C(C1CC(C(F)(F)F)Cc2nn(Cc3ccnc(C(F)(F)F)c3F)c(=O)n21)N1CC[C@H](F)C1]

(5RS,7RS)-5-{[(3S)-3-Fluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (diastereomer mixture 2; 2 isomers) was separated by chiral preparative HPLC [sample preparation: 68.3 mg dissolved in 3 ml of acetonitrile and 2 ml of ethanol (warm); injection volume: 0.25 ml; column: Daicel Chiralpak® IB 5 µm, 250×20 mm; eluent: n-heptane/isopropanol 50:50; flow rate: 15 ml/min; temperature 25° C.; UV detection: 210 nm]. After the separation, 30.7 mg of isomer 1, which elutes first, and 27.2 mg of isomer 2, which elutes later, were isolated.

Isomer 2:

Analytical chiral HPLC: $R_t$=3.68 min, d.e.=97.8% [column: Daicel Chiraltek® IB 3 µm, 50×4.6 mm; eluent: i-hexane/ethanol 50:50; flow rate: 1 ml/min; UV detection: 220 nm].

LC-MS (Method 4): $R_t$=0.89 min; MS (ESIpos): m/z=500 [M+H]$^+$ $^1$H-NMR (400 MHz, DMSO-d6) δ [ppm]: −0.149 (1.67), −0.008 (14.33), 0.008 (12.71), 0.146 (1.67), 1.234 (1.12), 2.148 (3.10), 2.168 (3.16), 2.179 (2.17), 2.197 (2.17), 2.223 (4.71), 2.233 (5.33), 2.244 (6.88), 2.281 (2.91), 2.323 (2.23), 2.327 (2.98), 2.332 (2.29), 2.366 (2.36), 2.523 (8.06), 2.665 (2.05), 2.670 (2.91), 2.674 (2.17), 2.700 (2.11), 2.710 (4.03), 2.730 (2.73), 2.738 (4.22), 2.749 (2.42), 2.770 (3.22), 2.778 (3.10), 2.910 (1.98), 2.987 (4.65), 3.025 (3.41), 3.037 (2.85), 3.361 (2.36), 3.379 (2.29), 3.408 (1.18), 3.518 (1.67), 3.571 (3.16), 3.595 (2.79), 3.620 (3.72), 3.642 (3.72), 3.661 (2.05), 3.764 (1.12), 3.795 (1.24), 3.884 (1.43), 3.965 (1.61), 3.992 (3.60), 4.013 (1.43), 4.053 (1.80), 4.087 (1.24), 5.053 (4.40), 5.095 (16.00), 5.114 (10.67), 5.159 (1.98), 5.275 (2.05), 5.359 (1.98), 5.407 (1.86), 5.490 (1.86), 7.556 (2.67), 7.569 (5.33), 7.576 (5.52), 7.588 (2.79), 8.569 (9.92), 8.581 (9.67).

Example 259

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Diastereomer 1, Racemate)

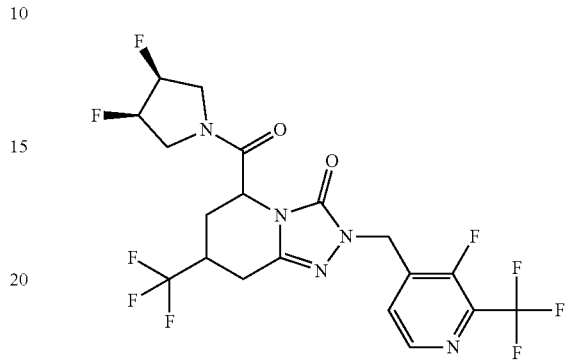

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (93.0 mg, 217 µmol) was initially charged in THF (2.0 ml) at room temperature. Subsequently, HBTU (107 mg, 282 µmol) and N,N-diisopropylethylamine (190 µl, 1.1 mmol) were added. After stirring for 15 min, (3R,4S)-3,4-difluoropyrrolidine hydrochloride (37.4 mg, 261 µmol) was added and the reaction mixture was stirred at room temperature overnight. The reaction mixture was admixed with water and ethyl acetate, and the organic phase was removed. The organic phase was washed with 10% citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 8.5 mg (8% of theory) of diastereomer 1 (racemate), which elutes first, and 72 mg (64% of theory) of diastereomer 2 (racemate), which elutes later, were isolated.

Diastereomer 1, Racemate:

LC-MS (Method 3): $R_t$=1.75 min; MS (ESIpos): m/z=518 [M+H]$^+$ $^1$H-NMR (400 MHz, DMSO-d6) δ [ppm]: −0.150 (2.18), −0.009 (16.00), 0.007 (13.45), 0.145 (2.18), 1.652 (1.09), 1.682 (1.09), 1.713 (1.09), 1.747 (1.09), 2.322 (4.36), 2.327 (6.18), 2.331 (4.36), 2.365 (4.00), 2.412 (1.09), 2.444 (1.82), 2.450 (1.82), 2.523 (14.18), 2.558 (3.27), 2.560 (1.82), 2.564 (2.18), 2.566 (1.82), 2.571 (1.45), 2.576 (1.82), 2.581 (1.45), 2.585 (1.45), 2.592 (1.45), 2.596 (1.45), 2.664 (4.73), 2.669 (5.82), 2.673 (4.00), 2.689 (3.27), 2.709 (4.36), 2.737 (1.82), 2.776 (2.18), 2.906 (2.18), 2.947 (1.45), 2.989 (1.45), 3.024 (1.45), 3.180 (0.73), 3.189 (0.73), 3.201 (1.09), 3.218 (1.82), 3.223 (1.45), 3.234 (1.82), 3.246 (2.55), 3.251 (2.18), 3.358 (0.73), 3.520 (0.73), 3.565 (1.09), 3.639 (0.73), 3.699 (0.73), 3.730 (0.73), 3.788 (1.09), 3.802 (0.73), 3.823 (0.73), 4.139 (1.09), 4.744 (1.45), 4.757 (1.45), 4.764 (1.09), 4.772 (1.45), 5.070 (8.00), 5.249 (0.73), 5.256 (0.73), 5.361 (0.73), 5.394 (1.09), 5.450 (0.73), 5.470 (0.73), 5.753 (13.09), 7.623 (1.82), 7.637 (4.00), 7.650 (2.18), 8.578 (3.64), 8.589 (3.27).

Example 260

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Diastereomer 2, Racemate)

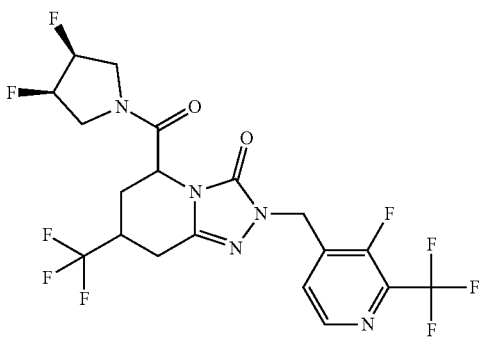 [SMILES: O=C(C1CC(C(F)(F)F)Cc2nn(Cc3ccnc(C(F)(F)F)c3F)c(=O)n21)N1C[C@@H](F)[C@@H](F)C1]

(5RS,7RS)-2-{[3-Fluoro-2-(trifluoromethyl)pyridin-4-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (93.0 mg, 217 μmol) was initially charged in THF (2.0 ml) at room temperature. Subsequently, HBTU (107 mg, 282 μmol) and N,N-diisopropylethylamine (190 μl, 1.1 mmol) were added. After stirring for 15 min, (3R,4S)-3,4-difluoropyrrolidine hydrochloride (37.4 mg, 261 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). After the separation, 8.5 mg (8% of theory) of diastereomer 1 (racemate), which elutes first, and 72 mg (64% of theory) of diastereomer 2 (racemate), which elutes later, were isolated.

Diastereomer 2, Racemate:

LC-MS (Method 3): $R_t$=1.81 min; MS (ESIpos): m/z=518 [M+H]$^+$ $^1$H-NMR (400 MHz, DMSO-d6) δ [ppm]: −0.149 (0.52), −0.008 (6.19), 0.008 (4.22), 0.146 (0.52), 2.137 (1.22), 2.154 (1.44), 2.173 (2.56), 2.189 (2.30), 2.204 (2.67), 2.220 (5.11), 2.230 (4.56), 2.238 (4.56), 2.294 (3.59), 2.328 (3.52), 2.366 (1.59), 2.519 (9.30), 2.524 (8.48), 2.665 (1.37), 2.670 (1.78), 2.675 (1.41), 2.700 (2.89), 2.711 (3.30), 2.729 (3.85), 2.740 (5.56), 2.751 (2.78), 2.769 (4.56), 2.780 (3.37), 2.898 (2.70), 2.986 (6.33), 2.997 (4.70), 3.025 (4.78), 3.036 (3.78), 3.168 (16.00), 3.493 (2.07), 3.502 (3.11), 3.526 (2.63), 3.536 (4.07), 3.545 (3.41), 3.556 (2.52), 3.566 (1.93), 3.588 (2.93), 3.599 (2.07), 3.650 (2.04), 3.665 (1.93), 3.684 (1.70), 3.697 (1.93), 3.707 (3.44), 3.720 (3.26), 3.740 (2.70), 3.754 (2.30), 3.767 (1.56), 3.780 (1.59), 3.801 (1.22), 3.814 (1.22), 3.843 (1.81), 3.871 (2.85), 3.884 (2.52), 3.891 (2.78), 4.046 (1.89), 4.060 (2.70), 4.074 (2.41), 4.091 (3.07), 4.108 (2.52), 4.122 (1.67), 4.136 (1.63), 4.150 (1.26), 4.166 (1.44), 4.180 (1.37), 4.195 (2.37), 4.210 (1.52), 4.224 (1.22), 4.238 (1.19), 5.023 (6.78), 5.034 (8.93), 5.045 (5.93), 5.087 (11.19), 5.110 (8.48), 5.120 (9.63), 5.151 (1.78), 5.161 (3.00), 5.260 (1.96), 5.270 (2.15), 5.285 (2.07), 5.296 (2.07), 5.329 (1.67), 5.337 (1.74), 5.350 (1.81), 5.384 (2.52), 5.407 (2.04), 5.417 (2.19), 5.430 (2.11), 5.440 (1.37), 5.457 (1.74), 5.471 (1.67), 5.479 (1.70), 5.491 (1.85), 7.554 (3.15), 7.566 (6.74), 7.576 (7.70), 7.588 (3.63), 8.167 (0.89), 8.569 (11.81), 8.581 (11.26).

Example 261

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Enantiomer 1)

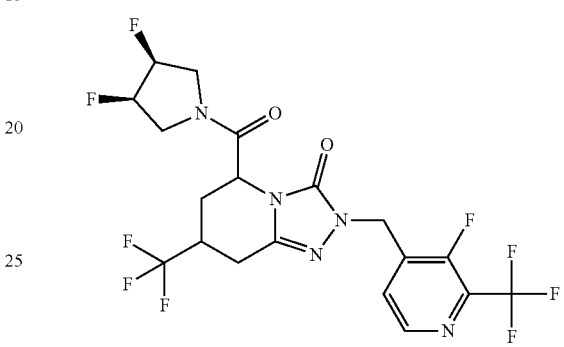

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 72.2 mg dissolved in 3 ml of acetonitrile and 2 ml of ethanol (warm); injection volume: 0.25 ml; column: Daicel Chiralpak® IB 5 μm, 250×20 mm; eluent: n-heptane/ethanol 50:50; flow rate: 15 ml/min; temperature 25° C.; UV detection: 210 nm]. After the separation, 31.3 mg of enantiomer 1, which elutes first, and 31.2 mg of enantiomer 2, which elutes later, were isolated.

Enantiomer 1:

Analytical chiral HPLC: $R_t$=2.08 min, e.e. =99% [column: Daicel Chiraltek® IB, 3 μm, 50×4.6 mm; Laufmittel: i-Hexan/Ethanol 50:50; Fluss: 1 ml/min; UV detection: 220 nm].

LC-MS (Method 4): $R_t$=0.90 min; MS (ESIpos): m/z=518 [M+H]$^+$ $^1$H-NMR (400 MHz, DMSO-d6) δ [ppm]: −0.149 (1.73), −0.008 (16.00), 0.008 (12.80), 0.146 (1.73), 0.852 (0.61), 1.234 (1.30), 2.138 (0.78), 2.153 (0.78), 2.173 (1.56), 2.185 (1.38), 2.204 (1.47), 2.219 (3.03), 2.229 (2.94), 2.238 (2.94), 2.291 (2.42), 2.327 (3.29), 2.366 (2.68), 2.523 (6.66), 2.665 (1.73), 2.670 (2.25), 2.674 (1.64), 2.699 (1.82), 2.710 (3.89), 2.729 (2.42), 2.740 (3.63), 2.752 (1.64), 2.769 (3.03), 2.781 (2.25), 2.898 (1.64), 2.986 (3.98), 2.997 (2.85), 3.025 (3.03), 3.037 (2.51), 3.502 (1.56), 3.535 (2.25), 3.545 (1.99), 3.587 (1.73), 3.650 (1.30), 3.663 (1.12), 3.682 (0.86), 3.707 (2.08), 3.719 (1.99), 3.740 (1.64), 3.753 (1.38), 3.780 (0.86), 3.814 (0.69), 3.872 (1.73), 3.891 (1.64), 4.046 (0.95), 4.059 (1.30), 4.090 (1.30), 4.108 (1.21), 4.137 (0.86), 4.195 (1.47), 4.210 (0.86), 4.224 (0.78), 4.239 (0.69), 5.022 (4.15), 5.034 (5.62), 5.045 (3.72), 5.087 (7.18), 5.110 (5.36), 5.120 (6.49), 5.152 (1.04), 5.161 (1.99), 5.270 (1.47), 5.297 (1.30), 5.329 (0.95), 5.351 (1.04), 5.383 (1.47), 5.417 (1.30), 5.429 (1.30), 5.440

(0.78), 5.470 (1.04), 7.554 (1.73), 7.566 (4.06), 7.576 (4.93), 7.589 (2.25), 8.569 (7.26), 8.581 (7.26).

Example 262

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (Enantiomer 2)

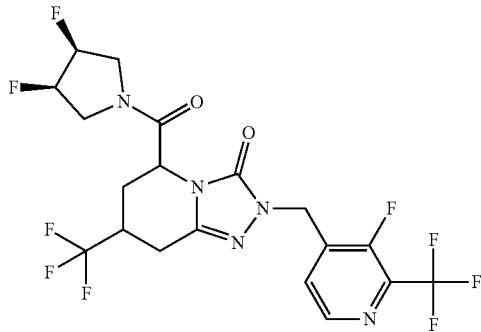 [SMILES: O=C(C1CC(C(F)(F)F)Cc2nn(Cc3ccnc(C(F)(F)F)c3F)c(=O)n21)N1C[C@@H](F)[C@@H](F)C1]

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 72.2 mg dissolved in 3 ml of acetonitrile and 2 ml of ethanol (warm); injection volume: 0.25 ml; column: Daicel Chiralpak® IB 5 µm, 250×20 mm; eluent: n-heptane/ethanol 50:50; flow rate: 15 ml/min; temperature 25° C.; UV detection: 210 nm]. After the separation, 31.3 mg of enantiomer 1, which elutes first, and 31.2 mg of enantiomer 2, which elutes later, were isolated.

Enantiomer 2:

Analytical chiral HPLC: $R_t$=4.11 min, e.e. =99% [column: Daicel Chiraltek® IB 3 µm, 50×4.6 mm; eluent: i-hexane/ethanol 50:50; flow rate: 1 ml/min; UV detection: 220 nm].

LC-MS (Method 4): $R_t$=0.90 min; MS (ESIpos): m/z=518 [M+H]$^+$ $^1$H-NMR (400 MHz, DMSO-d6) δ [ppm]: −0.149 (1.71), 0.008 (15.86), 0.147 (1.71), 0.853 (0.96), 1.234 (2.39), 2.138 (1.78), 2.153 (1.78), 2.173 (3.49), 2.189 (3.21), 2.204 (3.42), 2.221 (6.97), 2.229 (6.63), 2.239 (6.50), 2.293 (5.40), 2.327 (5.40), 2.366 (2.80), 2.519 (10.60), 2.523 (8.27), 2.670 (2.53), 2.700 (3.56), 2.711 (4.79), 2.730 (5.06), 2.741 (7.52), 2.751 (3.76), 2.769 (6.02), 2.781 (4.51), 2.915 (3.42), 2.986 (8.62), 2.997 (6.22), 3.026 (6.56), 3.038 (5.20), 3.502 (3.28), 3.526 (2.67), 3.536 (4.85), 3.546 (4.03), 3.556 (3.01), 3.590 (3.69), 3.650 (2.53), 3.664 (2.46), 3.684 (1.98), 3.707 (4.51), 3.720 (4.44), 3.740 (3.35), 3.753 (3.01), 3.767 (1.98), 3.780 (1.85), 3.802 (1.37), 3.814 (1.44), 3.870 (3.69), 3.892 (3.56), 4.048 (1.85), 4.061 (2.67), 4.075 (1.71), 4.091 (3.01), 4.109 (2.53), 4.122 (1.71), 4.137 (1.78), 4.151 (1.50), 4.166 (1.71), 4.180 (1.64), 4.195 (3.08), 4.210 (1.98), 4.223 (1.50), 4.239 (1.57), 5.023 (9.23), 5.035 (12.51), 5.045 (8.41), 5.087 (15.52), 5.110 (11.56), 5.120 (13.81), 5.152 (2.39), 5.161 (4.31), 5.261 (2.60), 5.271 (2.94), 5.298 (2.87), 5.329 (2.12), 5.350 (2.39), 5.384 (3.35), 5.408 (2.67), 5.418 (2.94), 5.430 (2.80), 5.441 (1.71), 5.457 (2.19), 5.480 (2.26), 5.492 (2.32), 7.555 (3.83), 7.566 (9.37), 7.577 (10.87), 7.589 (5.20), 8.569 (16.00), 8.581 (15.93).

Example 263

(5RS,7RS)-2-[(5-Chloro-3-fluoropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture 1; 2 Isomers)

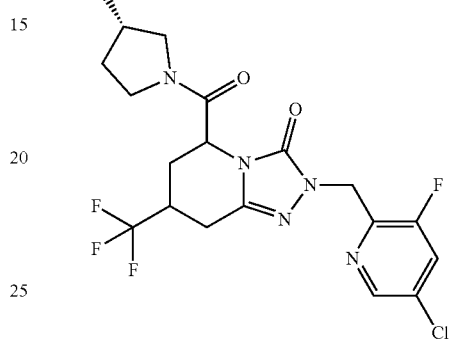

(5RS,7RS)-2-[(5-Chloro-3-fluoropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (55.0 mg, 139 µmol) was initially charged in THF (2.0 ml) at room temperature. Subsequently, HBTU (68.7 mg, 181 µmol) and N,N-diisopropylethylamine (120 µl, 700 mol) were added. After stirring for 5 min, (3S)-3-fluoropyrrolidine hydrochloride (21.0 mg, 167 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 10.5 mg (16% of theory) of diastereomer mixture 1 (2 isomers), which elutes first, and 37 mg (51% of theory) of diastereomer mixture 2 (2 isomers), which elutes later, were isolated.

Diastereomer Mixture 1, 2 Isomers:

LC-MS (Method 1): $R_t$=1.06 min; MS (ESIpos): m/z=466 [M+H]$^+$ $^1$H-NMR (400 MHz, DMSO-d6) δ [ppm]: −0.149 (1.70), −0.033 (0.53), −0.022 (0.95), −0.008 (14.62), 0.008 (16.00), 0.019 (0.95), 0.024 (0.53), 0.026 (0.42), 0.146 (1.70), 1.653 (0.42), 1.682 (0.53), 1.713 (0.53), 1.739 (0.53), 2.097 (0.32), 2.109 (0.32), 2.131 (0.32), 2.212 (0.32), 2.231 (0.32), 2.257 (0.32), 2.323 (1.70), 2.327 (2.33), 2.332 (1.80), 2.366 (1.91), 2.460 (0.32), 2.523 (7.31), 2.559 (2.44), 2.574 (1.27), 2.581 (0.85), 2.586 (0.74), 2.598 (0.74), 2.604 (0.53), 2.637 (0.95), 2.665 (2.44), 2.670 (3.60), 2.674 (2.75), 2.710 (3.18), 2.760 (0.21), 2.862 (1.06), 2.898 (0.74), 2.987 (0.42), 3.011 (0.42), 3.359 (1.59), 3.435 (0.74), 3.468 (0.53), 3.499 (0.64), 3.534 (0.42), 3.554 (0.53), 3.588 (0.53), 3.619 (0.64), 3.636 (0.64), 3.657 (0.64), 3.674 (0.74), 3.703 (0.53), 3.721 (0.42), 3.743 (0.32), 3.787 (0.32), 3.795 (0.32), 3.826 (0.42), 3.859 (0.53), 3.887 (0.42), 3.931 (0.64), 3.957 (0.74), 3.986 (0.42), 4.677

(0.32), 4.690 (0.42), 4.704 (0.32), 4.716 (0.42), 4.731 (0.42), 4.742 (0.42), 4.755 (0.42), 4.767 (0.42), 4.781 (0.32), 4.798 (0.42), 4.812 (0.32), 4.825 (0.32), 4.971 (4.77), 5.284 (0.32), 5.354 (0.32), 5.396 (0.53), 5.417 (0.32), 5.481 (0.32), 5.524 (0.32), 8.104 (1.17), 8.109 (1.27), 8.129 (1.17), 8.133 (1.27), 8.489 (1.70).

Example 264

(5RS,7RS)-2-[(5-Chloro-3-fluoropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture 2; 2 Isomers)

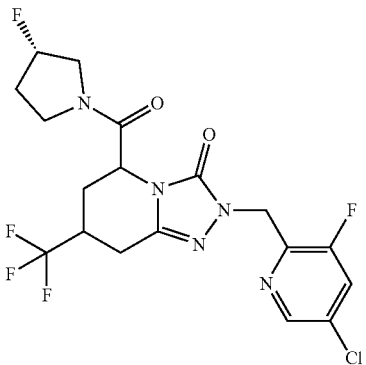 [SMILES: O=C(C1CC(C(F)(F)F)Cc2nn(Cc3ncc(Cl)cc3F)c(=O)n21)N1CC[C@H](F)C1]

(5RS,7RS)-2-[(5-Chloro-3-fluoropyridin-3-yl)methyl]-3-oxo-7-(trifluoromethyl)-2,3,5,678-hexahydro[1,2,4]triazolo[4,3-a]pyridine-5-carboxylic Acid (Diastereomer Mixture; 4 Isomers) (55.0 mg, 139 µmol) was initially charged in THF (2.0 ml) at room temperature. Subsequently, HBTU (68.7 mg, 181 µmol) and N,N-diisopropylethylamine (120 µl, 700 µmol) were added. After stirring for 5 min, (3S)-3-fluoropyrrolidine hydrochloride (21.0 mg, 167 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 10.5 mg (16% of theory) of diastereomer mixture 1 (2 isomers), which elutes first, and 37 mg (51% of theory) of diastereomer mixture 2 (2 isomers), which elutes later, were isolated.
Diastereomer Mixture 2, 2 Isomers:
LC-MS (Method 1): $R_t$=1.10 min; MS (ESIpos): m/z=466 [M+H]$^+$
$^1$H-NMR (400 MHz, DMSO-d6) δ [ppm]: -1.950 (1.23), -1.643 (1.23), -1.565 (0.92), -1.154 (1.23), -0.149 (5.54), -0.039 (1.85), 0.146 (5.23), 1.883 (1.23), 1.954 (1.23), 1.989 (1.54), 1.999 (1.54), 2.039 (1.23), 2.120 (4.31), 2.149 (7.38), 2.186 (6.77), 2.199 (6.46), 2.216 (6.15), 2.268 (5.54), 2.297 (3.69), 2.327 (10.46), 2.367 (6.15), 2.413 (1.54), 2.610 (2.15), 2.635 (3.38), 2.670 (15.38), 2.710 (10.15), 2.801 (1.23), 2.815 (1.23), 2.883 (1.54), 2.948 (9.85), 2.982 (7.08), 3.025 (1.23), 3.084 (1.23), 3.119 (1.23), 3.204 (1.54), 3.361 (5.85), 3.388 (3.38), 3.426 (2.46), 3.474 (1.54), 3.499 (1.85), 3.510 (2.15), 3.524 (1.85), 3.534 (2.15), 3.567 (4.00), 3.597 (4.00), 3.605 (3.08), 3.628 (4.92), 3.668 (4.62), 3.691 (4.00), 3.726 (1.85), 3.762 (1.23), 3.790 (2.46), 3.798 (1.85), 3.820 (2.46), 3.843 (3.08), 3.865 (2.15), 3.887 (2.15), 3.919 (1.85), 3.976 (2.77), 3.996 (3.08), 4.019 (2.77), 4.049 (1.85), 4.076 (1.54), 4.904 (2.46), 4.931 (5.85), 4.970 (16.00), 4.995 (3.69), 5.017 (9.54), 5.056 (6.15), 5.265 (3.08), 5.303 (1.23), 5.355 (2.15), 5.398 (3.69), 5.490 (2.46), 5.522 (1.54), 7.947 (0.92), 8.103 (10.15), 8.107 (10.77), 8.127 (9.85), 8.131 (10.77), 8.201 (1.23), 8.214 (1.54), 8.483 (15.08), 8.698 (0.92), 8.965 (1.23), 10.344 (1.23), 11.406 (0.92), 12.388 (1.23), 12.839 (0.92), 12.989 (1.23), 13.493 (1.23), 15.243 (0.92), 16.225 (0.92).

Example 265

(5RS,7RS)-2-[(5-Chloro-3-fluoropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

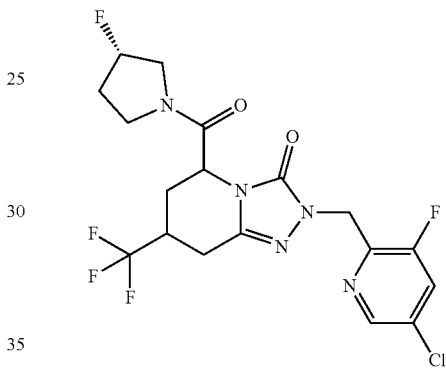

(5RS,7RS)-2-[(5-Chloro-3-fluoropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture 2, 2 isomers) was separated by chiral preparative HPLC [sample preparation: 37 mg dissolved in 2 ml of n-heptane and 2 ml of ethanol; injection volume: 0.9 ml; column: Daicel Chiralpak® IC 5 µm, 250×20 mm; eluent: n-heptane/ethanol 50:50; flow rate: 15 ml/min; temperature 50° C.; UV detection: 220 nm]. After the separation, 14.3 mg of isomer 1, which elutes first, and 15.1 mg of isomer 2, which elutes later, were isolated.
Isomer 2:
Analytical chiral HPLC: $R_t$=6.52 min, d.e.=99% [column: Daicel Chiralpak® IC 5 µm, 250×4.6 mm; eluent: i-hexane/ethanol 50:50; flow rate: 1 ml/min; UV detection: 220 nm].
LC-MS (Method 3): $R_t$=1.49 min; MS (ESIpos): m/z=466 [M+H]$^+$
$^1$H-NMR (400 MHz, DMSO-d6) δ [ppm]: -0.149 (1.56), -0.008 (16.00), 0.008 (15.94), 0.146 (1.50), 1.235 (0.88), 1.971 (0.50), 2.115 (1.50), 2.151 (2.88), 2.185 (2.25), 2.200 (2.12), 2.216 (1.94), 2.231 (1.94), 2.267 (3.25), 2.296 (2.00), 2.327 (2.37), 2.366 (0.69), 2.669 (3.75), 2.678 (3.44), 2.692 (1.62), 2.710 (2.25), 2.948 (4.63), 2.982 (3.75), 3.362 (1.75), 3.390 (1.62), 3.426 (1.25), 3.497 (0.81), 3.523 (1.19), 3.648 (1.81), 3.667 (2.63), 3.692 (2.94), 3.721 (1.25), 3.784 (0.69), 3.818 (1.75), 3.845 (2.25), 3.868 (1.25), 3.916 (1.37), 3.952 (0.75), 3.976 (1.19), 4.009 (0.69), 4.906 (1.75), 4.922 (3.25), 4.966 (8.44), 5.021 (4.12), 5.060 (1.88), 5.266 (1.56), 5.394 (2.37), 5.525 (1.12), 8.102 (4.75), 8.107 (4.81), 8.126 (4.81), 8.131 (4.94), 8.483 (6.12).

Example 266

(5RS,7RS)-2-[(5-Chloro-3-fluoropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Diastereomer 2, Racemate)

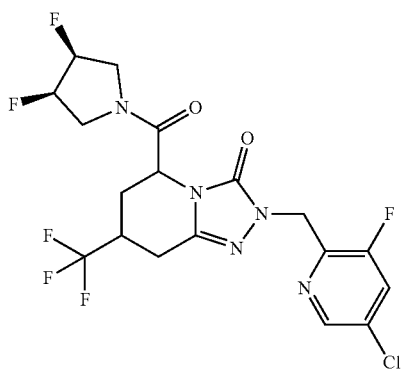 [SMILES: O=C(C1CC(C(F)(F)F)Cc2nn(Cc3ncc(Cl)cc3F)c(=O)n21)N1C[C@@H](F)[C@@H](F)C1]

(5RS,7RS)-2-[(5-Chloro-3-fluoropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (55.0 mg, 139 μmol) was initially charged in THF (2.0 ml) at room temperature. Subsequently, HBTU (68.7 mg, 181 μmol) and N,N-diisopropylethylamine (120 μl, 700 mol) were added. After stirring for 5 min, (3R,4S)-3,4-difluoropyrrolidine hydrochloride (24.0 mg, 167 μmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). After the separation, 23.9 mg (35% of theory) of diastereomer 2 (racemate), which elutes later, were isolated.

LC-MS (Method 1): $R_t$=1.13 min; MS (ESIpos): m/z=484 [M+H]$^+$ $^1$H-NMR (400 MHz, DMSO-d6) δ [ppm]: −0.150 (1.73), −0.031 (0.56), −0.008 (16.00), 0.008 (13.67), 0.146 (1.63), 2.073 (0.42), 2.145 (0.47), 2.161 (0.47), 2.193 (1.17), 2.256 (0.84), 2.295 (0.56), 2.322 (1.45), 2.327 (1.96), 2.332 (1.45), 2.366 (0.56), 2.439 (0.42), 2.648 (0.42), 2.665 (1.77), 2.669 (2.33), 2.684 (1.21), 2.695 (0.65), 2.710 (0.84), 2.728 (0.56), 2.942 (1.77), 2.976 (1.17), 2.988 (0.75), 3.491 (0.37), 3.527 (0.61), 3.535 (0.56), 3.578 (0.61), 3.640 (0.37), 3.653 (0.33), 3.698 (0.56), 3.709 (0.51), 3.729 (0.42), 3.746 (0.37), 3.851 (0.42), 3.870 (0.51), 3.888 (0.51), 3.897 (0.47), 4.058 (0.37), 4.088 (0.47), 4.102 (0.33), 4.201 (0.47), 4.933 (0.89), 4.971 (2.47), 4.993 (1.77), 5.008 (1.21), 5.024 (1.40), 5.028 (1.35), 5.047 (0.47), 5.064 (0.56), 5.267 (0.47), 5.288 (0.47), 5.342 (0.37), 5.382 (0.56), 5.394 (0.47), 5.403 (0.42), 5.426 (0.37), 5.454 (0.33), 5.486 (0.37), 8.103 (1.40), 8.107 (1.49), 8.126 (1.49), 8.131 (1.45), 8.477 (2.19).

Example 267

(5RS,7RS)-2-[(5-Chloro-3-fluoropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Enantiomer 1)

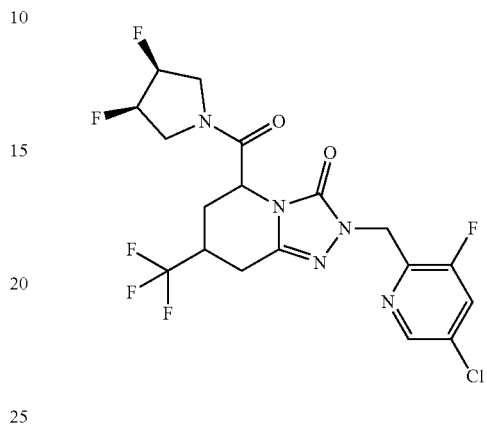

(5RS,7RS)-2-[(5-Chloro-3-fluoropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (diastereomer 2, racemate) was separated by chiral preparative HPLC [sample preparation: 23.9 mg dissolved in 1.5 ml of n-heptane and 2 ml of ethanol; injection volume: 1.2 ml; column: Daicel Chiralpak® IE 5 μm, 250×20 mm; eluent: n-heptane/ethanol 50:50; flow rate: 15 ml/min; temperature 40° C.; UV detection: 220 nm]. After the separation, 8.6 mg of enantiomer 1, which elutes first, and 9.4 mg of enantiomer 2, which elutes later, were isolated.

Enantiomer 1:

Analytical chiral HPLC: $R_t$=1.86 min, e.e. =99% [column: Daicel Chiralpak® IE, 3 μm, 50×4.6 mm; eluent: n-heptane/ethanol 50:50; flow rate: 1 ml/min; UV detection: 220 nm].

LC-MS (Method 3): $R_t$=1.55 min; MS (ESIpos): m/z=484 [M+H]$^+$ $^1$H-NMR (400 MHz, DMSO-d6) δ [ppm]: −0.149 (1.69), −0.008 (16.00), 0.008 (14.89), 0.146 (1.85), 2.128 (0.41), 2.144 (0.82), 2.162 (0.82), 2.193 (2.14), 2.259 (1.40), 2.294 (0.99), 2.323 (1.48), 2.327 (2.18), 2.332 (1.60), 2.366 (1.07), 2.651 (0.70), 2.674 (2.71), 2.683 (2.14), 2.696 (1.07), 2.711 (1.69), 2.941 (3.08), 2.976 (2.06), 2.988 (1.32), 3.488 (0.58), 3.530 (0.95), 3.577 (0.95), 3.641 (0.70), 3.653 (0.58), 3.673 (0.58), 3.697 (0.99), 3.712 (0.99), 3.732 (0.78), 3.746 (0.66), 3.759 (0.45), 3.773 (0.45), 3.837 (0.58), 3.852 (0.78), 3.867 (0.95), 3.911 (0.70), 3.916 (0.70), 4.044 (0.49), 4.056 (0.70), 4.072 (0.53), 4.087 (0.82), 4.104 (0.58), 4.117 (0.45), 4.133 (0.45), 4.170 (0.45), 4.201 (0.78), 4.216 (0.49), 4.231 (0.41), 4.933 (1.69), 4.972 (4.36), 4.977 (3.78), 4.993 (3.13), 5.008 (2.06), 5.024 (2.34), 5.028 (2.39), 5.052 (0.82), 5.064 (1.11), 5.067 (1.03), 5.263 (0.74), 5.292 (0.70), 5.384 (0.95), 5.394 (0.86), 5.414 (0.78), 5.422 (0.66), 5.454 (0.49), 5.474 (0.70), 5.484 (0.66), 8.103 (2.67), 8.108 (2.80), 8.127 (2.76), 8.132 (2.76), 8.477 (4.40), 8.481 (4.40).

Example 268

(5RS,7RS)-2-[(5-Chloropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Diastereomer 1, Racemate)

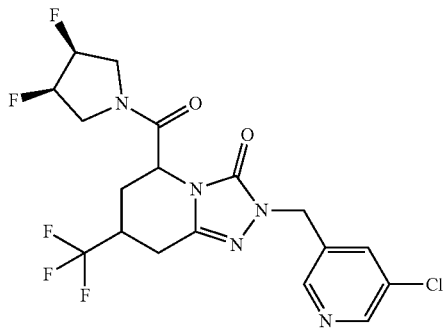 [SMILES: O=C(C1CC(C(F)(F)F)Cc2nn(Cc3cncc(Cl)c3)c(=O)n21)N1C[C@@H](F)[C@@H](F)C1]

(5RS,7RS)-2-[(5-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (70.0 mg, 75% purity, 139 µmol) was initially charged in THF (2.0 ml) at room temperature. Subsequently, HBTU (68.7 mg, 181 µmol) and N,N-diisopropylethylamine (120 µl, 700 mol) were added. After stirring for 5 min, (3R,4S)-3,4-difluoropyrrolidine hydrochloride (24.0 mg, 167 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 12.6 mg (19% of theory) of diastereomer 1 (racemate), which elutes first, and 9 mg (14% of theory) of diastereomer 2 (racemate), which elutes later, were isolated.

Diastereomer 1, Racemate:

LC-MS (Method 3): $R_t$=1.41 min; MS (ESIpos): m/z=466 [M+H]$^+$ $^1$H-NMR (400 MHz, DMSO-d6) δ [ppm]: −0.149 (1.45), −0.020 (0.85), −0.017 (1.09), −0.008 (12.36), 0.008 (16.00), 0.146 (1.58), 1.642 (1.27), 1.670 (1.39), 1.703 (1.27), 1.735 (1.03), 2.323 (1.27), 2.327 (1.76), 2.332 (1.39), 2.366 (1.21), 2.523 (5.52), 2.558 (2.48), 2.564 (2.12), 2.572 (1.76), 2.665 (1.58), 2.669 (2.12), 2.674 (1.64), 2.697 (1.45), 2.710 (1.52), 2.730 (2.00), 2.737 (2.24), 2.769 (2.61), 2.901 (2.18), 2.940 (1.58), 2.996 (1.03), 3.016 (1.09), 3.509 (0.85), 3.521 (0.97), 3.555 (1.15), 3.564 (1.21), 3.572 (0.85), 3.608 (0.85), 3.642 (0.85), 3.655 (1.03), 3.700 (1.03), 3.713 (1.03), 3.735 (0.97), 3.748 (1.21), 3.783 (0.91), 3.797 (0.97), 3.809 (0.97), 3.830 (1.09), 3.844 (0.97), 3.864 (1.03), 3.895 (0.91), 3.910 (0.85), 3.951 (0.79), 4.114 (0.91), 4.130 (1.45), 4.144 (0.97), 4.160 (1.45), 4.174 (1.03), 4.723 (1.21), 4.732 (1.39), 4.737 (1.76), 4.750 (1.70), 4.765 (1.45), 4.773 (1.03), 4.923 (7.94), 4.952 (1.45), 5.248 (0.91), 5.261 (0.85), 5.276 (0.85), 5.287 (0.73), 5.322 (0.73), 5.342 (0.91), 5.354 (0.85), 5.364 (0.91), 5.371 (0.97), 5.383 (0.97), 5.392 (0.97), 5.406 (0.91), 5.415 (0.79), 5.465 (0.79), 5.472 (0.85), 7.796 (3.33), 7.801 (3.64), 8.425 (0.73), 8.446 (2.61), 8.453 (4.12), 8.458 (3.15), 8.576 (3.88), 8.581 (3.45), 9.265 (3.45).

Example 269

(5RS,7RS)-2-[(5-Chloropyridin-3-yl)methyl]-5-{[(3R,4S)-3,4-difluoropyrrolidin-1-yl]carbonyl}-7-(trifluoromethyl)-5,6,7,8-tetrahydro[1,2,4]triazolo[4,3-a]pyridin-3(2H)-one (Diastereomer 2, Racemate)

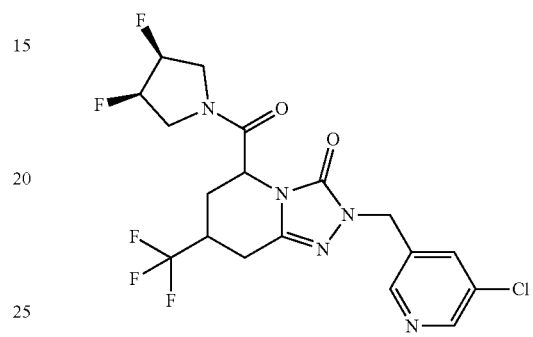

(5RS,7RS)-2-[(5-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (70.0 mg, 75% purity, 139 µmol) was initially charged in THF (2.0 ml) at room temperature. Subsequently, HBTU (68.7 mg, 181 µmol) and N,N-diisopropylethylamine (120 µl, 700 mol) were added. After stirring for 5 min, (3R,4S)-3,4-difluoropyrrolidine hydrochloride (24.0 mg, 167 µmol) was added and the reaction mixture was stirred at room temperature overnight. The reaction mixture was admixed with water and ethyl acetate, and the organic phase was removed. The organic phase was washed with 10% aqueous citric acid solution and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). After the separation, 12.6 mg (19% of theory) of diastereomer 1 (racemate), which elutes first, and 9 mg (14% of theory) of diastereomer 2 (racemate), which elutes later, were isolated.

Diastereomer 2, Racemate:

LC-MS (Method 3): $R_t$=1.46 min; MS (ESIpos): m/z=466 [M+H]$^+$ $^1$H-NMR (400 MHz, DMSO-d6) δ [ppm]: −0.149 (1.95), −0.008 (16.00), 0.008 (14.42), 0.146 (1.86), 2.166 (1.21), 2.182 (1.16), 2.197 (1.44), 2.208 (2.27), 2.218 (2.69), 2.228 (2.13), 2.241 (1.11), 2.277 (1.95), 2.312 (1.16), 2.323 (1.90), 2.327 (2.64), 2.332 (1.90), 2.366 (1.81), 2.523 (5.43), 2.665 (2.04), 2.670 (2.64), 2.674 (1.95), 2.693 (1.44), 2.703 (1.21), 2.710 (2.09), 2.723 (1.95), 2.733 (2.97), 2.743 (1.44), 2.762 (2.37), 2.772 (1.81), 2.889 (1.30), 2.904 (1.25), 2.977 (3.11), 2.988 (2.27), 3.016 (2.27), 3.027 (1.81), 3.500 (1.02), 3.533 (1.58), 3.542 (1.44), 3.552 (1.25), 3.563 (0.74), 3.578 (1.07), 3.586 (1.58), 3.596 (0.97), 3.646 (0.97), 3.660 (0.79), 3.678 (0.79), 3.695 (0.79), 3.703 (1.44), 3.718 (1.53), 3.738 (1.07), 3.752 (1.07), 3.766 (0.79), 3.780 (0.74), 3.800 (0.65), 3.847 (0.83), 3.866 (1.34), 3.895 (1.34), 3.930 (0.70), 4.043 (0.74), 4.057 (0.93), 4.071 (0.65), 4.087 (1.11), 4.104 (0.97), 4.119 (0.70), 4.134 (0.70), 4.157 (0.70), 4.173 (0.74), 4.201 (1.21), 4.230 (0.70), 4.911 (0.74), 4.952 (13.22), 5.007 (3.06), 5.020 (4.31), 5.273 (1.02), 5.296 (1.07), 5.328 (0.65), 5.351 (0.74), 5.386 (1.30), 5.397 (1.16), 5.407 (1.02), 5.418 (1.07), 5.427 (1.07), 5.439 (0.65), 5.458 (0.83), 5.480 (0.83), 5.490 (0.93), 7.750 (1.81), 7.763 (4.50), 8.425 (7.14), 8.429 (4.73), 8.570 (4.87).

Example 270

(5RS,8RS)-5-{[(3R,4S)-3,4-Difluoropyrrolidin-1-yl]carbonyl}-8-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

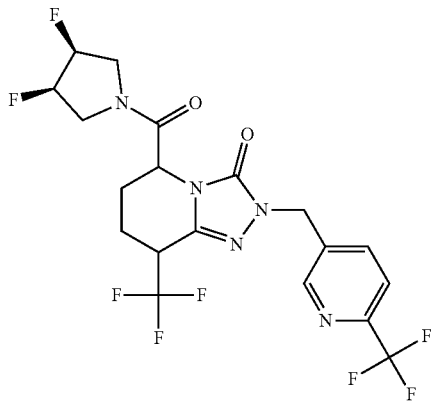 [SMILES: O=C(C1CCC(C(F)(F)F)c2nn(Cc3ccc(C(F)(F)F)nc3)c(=O)n21)N1C[C@@H](F)[C@@H](F)C1]

Under argon: 5-{[(3RS,4RS)-3,4-Difluoropyrrolidin-1-yl]carbonyl}-8-(trifluoromethyl)-2-{[6-(trifluoromethyl)pyridin-3-yl]methyl}[1,2,4]triazolo[4,3-a]pyridin-3(2H)-one (23.0 mg, 46.4 μmol) and palladium on charcoal (50.0 mg, 10% palladium) were suspended in ethanol (5.0 ml) and the mixture was stirred at room temperature in a hydrogen atmosphere (1 atm) overnight. The reaction mixture was filtered through Celite. The filtrate was concentrated and the residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 10.6 mg (46% of theory) of the title compound were obtained.

LC-MS (Method 4): $R_t$=0.85 min; MS (ESIpos): m/z=500 [M+H]$^+$ $^1$H-NMR (400 MHz, DMSO-d6) δ [ppm]: −0.149 (1.36), −0.008 (12.38), 0.008 (12.98), 0.146 (1.36), 1.724 (0.83), 1.755 (1.81), 1.781 (1.89), 1.807 (0.83), 2.067 (1.81), 2.084 (2.34), 2.120 (1.66), 2.167 (3.40), 2.229 (0.83), 2.323 (2.11), 2.327 (2.87), 2.332 (2.19), 2.366 (1.36), 2.665 (2.04), 2.669 (2.72), 2.674 (2.26), 2.710 (1.36), 3.477 (0.98), 3.486 (0.91), 3.498 (0.83), 3.511 (1.58), 3.520 (1.74), 3.532 (1.96), 3.541 (1.21), 3.567 (1.43), 3.574 (1.43), 3.632 (1.06), 3.645 (1.21), 3.666 (0.75), 3.690 (1.43), 3.704 (1.89), 3.726 (1.51), 3.736 (1.58), 3.757 (1.66), 3.771 (1.36), 3.794 (1.06), 3.804 (0.98), 3.840 (0.53), 3.873 (1.06), 3.892 (0.60), 3.909 (0.91), 3.935 (1.06), 3.949 (1.21), 3.964 (0.91), 3.986 (1.21), 4.000 (1.06), 4.015 (0.68), 4.028 (0.60), 4.104 (1.81), 4.136 (1.51), 4.152 (1.13), 4.166 (0.91), 4.179 (1.21), 4.191 (0.98), 4.205 (0.83), 4.220 (0.68), 4.892 (3.92), 4.901 (4.91), 5.065 (2.11), 5.106 (10.57), 5.120 (5.81), 5.126 (6.34), 5.167 (1.43), 5.257 (1.28), 5.270 (1.28), 5.280 (1.43), 5.289 (1.28), 5.300 (0.75), 5.318 (0.91), 5.335 (1.06), 5.346 (0.98), 5.357 (1.06), 5.370 (1.06), 5.381 (1.43), 5.393 (1.43), 5.402 (1.21), 5.412 (1.28), 5.421 (1.13), 5.433 (0.83), 5.447 (0.91), 5.455 (0.91), 5.464 (0.91), 5.479 (0.98), 5.486 (1.06), 5.500 (0.83), 7.922 (16.00), 7.941 (1.28), 8.634 (7.09).

Example 271

(5RS,8RS)-5-{[(3S)-3-Fluoropyrrolidin-1-yl]carbonyl}-8-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

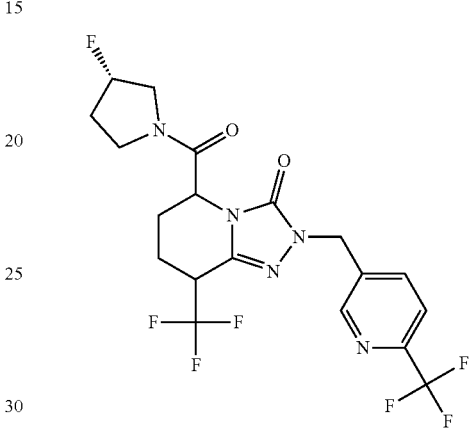

Under argon: 5-{[(3S)-3-Fluoropyrrolidin-1-yl]carbonyl}-8-(trifluoromethyl)-2-{[6-(trifluoromethyl)pyridin-3-yl]methyl}[1,2,4]triazolo[4,3-a]pyridin-3(2H)-one (165 mg, 346 μmol) and palladium on charcoal (50.0 mg, 10% palladium) were suspended in ethanol (29 ml) and stirred at room temperature in a hydrogen atmosphere (1 atm) overnight. The reaction mixture was filtered through Celite. The filtrate was concentrated and the residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 21.3 mg (74% of theory) of the title compound were obtained.

Diastereomer Mixture (4 Isomers):

LC-MS (Method 3): $R_t$=1.51 min; MS (ESIpos): m/z=482 [M+H]$^+$ $^1$H-NMR (400 MHz, DMSO-d6) δ [ppm]: −0.150 (1.89), −0.034 (0.38), −0.009 (16.00), 0.007 (15.87), 0.146 (2.02), 1.742 (0.63), 1.772 (0.76), 1.799 (0.63), 1.827 (0.50), 2.078 (1.51), 2.104 (1.76), 2.152 (1.39), 2.178 (1.76), 2.222 (1.26), 2.251 (0.76), 2.322 (3.15), 2.327 (4.16), 2.331 (3.02), 2.365 (2.39), 2.522 (10.20), 2.587 (0.88), 2.639 (0.50), 2.664 (3.28), 2.669 (4.54), 2.674 (3.28), 2.700 (0.38), 2.709 (2.27), 2.731 (0.50), 2.890 (0.50), 3.366 (1.51), 3.384 (1.39), 3.396 (0.88), 3.412 (1.01), 3.424 (0.50), 3.439 (0.38), 3.467 (0.50), 3.520 (0.76), 3.535 (1.26), 3.559 (1.01), 3.588 (0.88), 3.609 (1.64), 3.629 (1.13), 3.656 (1.01), 3.676 (0.76), 3.737 (0.76), 3.757 (0.76), 3.779 (0.88), 3.804 (0.50), 3.869 (0.88), 3.926 (0.50), 3.948 (0.63), 3.964 (0.63), 4.022 (0.50), 4.053 (0.63), 4.091 (1.01), 4.097 (1.01), 4.778 (0.50), 4.791 (0.63), 4.837 (0.63), 4.846 (0.63), 4.921 (0.76), 4.933 (0.76), 4.956 (0.88), 5.059 (0.63), 5.069 (0.50), 5.099 (2.52), 5.110 (3.02), 5.122 (4.28), 5.162 (0.88), 5.268 (0.88), 5.355 (0.50), 5.402 (0.88), 5.490 (0.63), 7.897 (0.50), 7.921 (9.57), 7.941 (0.63), 8.635 (3.78).

Example 272

(5RS,8RS)-5-{[(3S)-3-Fluoropyrrolidin-1-yl]carbonyl}-8-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 2)

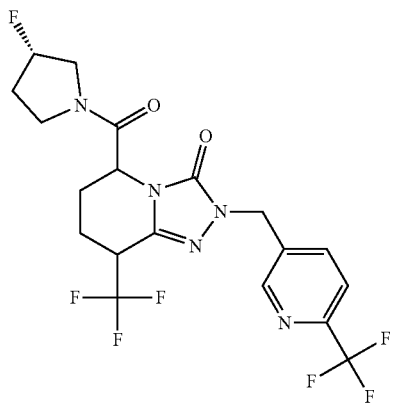 [SMILES: O=C(C1CCC(C(F)(F)F)c2nn(Cc3ccc(C(F)(F)F)nc3)c(=O)n21)N1CC[C@H](F)C1]

(5RS,8RS)-5-{[(3S)-3-Fluoropyrrolidin-1-yl]carbonyl}-8-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer mixture; 4 isomers) was separated by chiral preparative HPLC [sample preparation: 93 mg were dissolved in 3 ml of ethanol and 3 ml of n-heptane; injection volume: 0.58 ml; column: Daicel Chiralpak® IA 5 µm, 250×20 mm; eluent: n-heptane/ethanol 60:40; flow rate: 15 ml/min; temperature 40° C.; UV detection: 220 nm]. After the separation, 46 mg of isomer 1, which elutes first, and 32.7 mg of isomer 2, which elutes later, were isolated.

Isomer 2:

Analytical chiral HPLC: $R_t$=1.95 min, d.e.=98.4% [column: Daicel Chiralpak® IA, 3 µm, 50×4.6 mm; eluent: n-heptane/ethanol 50:50; flow rate: 1 ml/min; UV detection: 220 nm].

LC-MS (Method 3): $R_t$=1.54 min; MS (ESIpos): m/z=482 [M+H]$^+$ $^1$H-NMR (400 MHz, DMSO-d6) δ[ppm]: −0.149 (0.71), −0.008 (6.13), 0.008 (5.87), 0.146 (0.71), 1.806 (1.01), 1.827 (1.52), 1.850 (1.06), 2.078 (2.58), 2.095 (2.28), 2.105 (3.14), 2.142 (2.03), 2.152 (1.92), 2.177 (1.77), 2.192 (1.52), 2.223 (2.38), 2.248 (1.47), 2.274 (1.32), 2.327 (1.77), 2.332 (1.32), 2.367 (1.37), 2.665 (1.16), 2.670 (1.57), 2.674 (1.16), 2.710 (1.27), 3.342 (1.42), 3.360 (0.71), 3.370 (0.81), 3.379 (0.91), 3.406 (0.86), 3.415 (0.81), 3.468 (0.66), 3.475 (0.71), 3.504 (0.81), 3.514 (0.81), 3.633 (2.94), 3.651 (2.18), 3.676 (1.57), 3.699 (1.22), 3.736 (2.03), 3.761 (1.92), 3.781 (1.57), 3.806 (1.16), 3.869 (2.38), 4.089 (1.37), 4.099 (1.37), 4.780 (1.42), 4.791 (1.57), 4.838 (2.18), 4.848 (1.82), 5.059 (1.87), 5.100 (7.90), 5.123 (5.77), 5.164 (1.42), 5.268 (1.42), 5.399 (1.62), 5.520 (0.91), 7.921 (16.00), 7.941 (0.96), 8.637 (7.04).

Example 273

(5RS,8RS)-2-[(3-Fluoropyridin-2-yl)methyl]-5-{[(3S)-3-fluoropyrrolidin-1-yl]carbonyl}-8-(trifluoromethyl)-5,6,7,8-tetrahydro[1,2,4]triazolo[4,3-a]pyridin-3(2H)-one (Diastereomer Mixture; 4 Isomers)

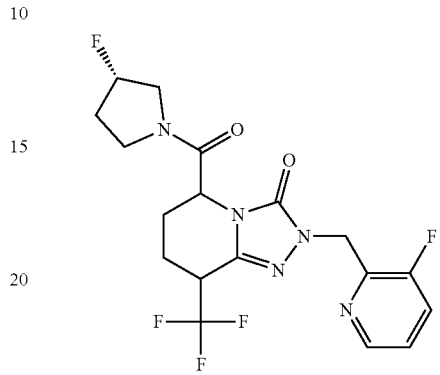

Under argon, 2-[(5-chloro-3-fluoropyridin-2-yl)methyl]-5-{[(3S)-3-fluoropyrrolidin-1-yl]carbonyl}-8-(trifluoromethyl)[1,2,4]triazolo[4,3-a]pyridin-3(2H)-one (50.0 mg, 62% purity, 67.1 µmol) and palladium on charcoal (10.0 mg, 10% palladium) were suspended in ethanol (5.0 ml) and stirred at room temperature in a hydrogen atmosphere (1 atm) over the weekend. The reaction mixture was filtered through Celite. The filtrate was concentrated and the residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 0.5 mg (1.7% of theory) of the title compound were obtained.

LC-MS (Method 3): $R_t$=1.18 min; MS (ESIpos): m/z=432 [M+H]$^+$ $^1$H-NMR (500 MHz, DMSO-d6) δ[ppm]: −0.120 (1.33), −0.009 (5.54), −0.007 (16.00), 0.007 (11.08), 0.117 (1.28), 1.330 (0.87), 1.343 (0.82), 1.768 (1.90), 1.796 (2.56), 1.815 (1.79), 1.823 (2.10), 1.856 (2.36), 1.880 (2.10), 1.901 (0.77), 2.010 (2.82), 2.019 (3.54), 2.027 (3.85), 2.037 (5.03), 2.050 (6.10), 2.072 (4.97), 2.081 (4.26), 2.101 (3.49), 2.121 (4.51), 2.152 (9.44), 2.164 (5.90), 2.182 (4.36), 2.230 (3.18), 2.258 (2.36), 2.271 (2.31), 2.354 (1.18), 2.358 (2.31), 2.361 (3.08), 2.365 (2.21), 2.369 (1.08), 2.518 (5.38), 2.522 (3.79), 2.628 (1.03), 2.631 (2.15), 2.635 (2.97), 2.639 (2.10), 2.643 (0.87), 3.348 (6.56), 3.358 (4.92), 3.371 (3.74), 3.380 (3.13), 3.390 (2.36), 3.411 (1.74), 3.418 (1.69), 3.461 (1.18), 3.468 (1.23), 3.488 (1.95), 3.495 (1.74), 3.516 (1.90), 3.522 (1.95), 3.543 (4.67), 3.563 (4.87), 3.577 (3.03), 3.585 (3.28), 3.590 (3.18), 3.598 (5.03), 3.615 (1.23), 3.633 (3.79), 3.650 (3.95), 3.656 (2.97), 3.670 (2.92), 3.686 (2.72), 3.711 (1.33), 3.738 (2.62), 3.746 (1.54), 3.756 (3.38), 3.764 (2.05), 3.772 (2.05), 3.783 (1.38), 3.789 (1.33), 3.812 (1.59), 3.837 (0.77), 3.861 (3.33), 3.936 (1.59), 3.954 (2.87), 3.972 (2.51), 3.994 (1.28), 4.015 (1.44), 4.041 (1.74), 4.079 (3.95), 4.772 (2.00), 4.776 (2.26), 4.785 (2.36), 4.825 (2.62), 4.830 (3.33), 4.838 (2.72), 4.842 (2.51), 4.896 (2.51), 4.900 (2.97), 4.908 (2.82), 4.912 (2.62), 4.936 (2.51), 4.943 (3.85), 4.953 (2.62), 4.965 (3.90), 4.970 (8.05), 4.973 (7.33), 4.997 (5.59), 5.001 (11.64), 5.005 (10.67), 5.114 (4.26), 5.118 (7.54), 5.122 (6.82), 5.127 (7.74), 5.131 (4.36), 5.146 (2.87), 5.149 (4.97), 5.154 (4.46), 5.159 (5.13), 5.163 (2.77), 5.279 (3.13), 5.285 (2.97), 5.368

(2.05), 5.385 (3.23), 5.393 (3.44), 5.474 (1.85), 5.507 (1.33), 7.422 (6.10), 7.431 (11.08), 7.439 (12.26), 7.448 (12.77), 7.457 (7.08), 7.711 (8.15), 7.713 (6.41), 7.729 (12.10), 7.733 (6.97), 7.748 (7.23), 8.360 (8.05), 8.363 (13.28), 8.369 (8.67), 8.372 (12.87), 8.524 (5.03).

Example 274

(5RS,8RS)-5-{[(3R,4S)-3,4-Difluoropyrrolidin-1-yl]carbonyl}-2-[(3-fluoropyridin-2-yl)methyl]-8-(trifluoromethyl)-5,6,7,8-tetrahydro[1,2,4]triazolo[4,3-a]pyridin-3(2H)-one (Diastereomer Mixture; 4 Isomers)

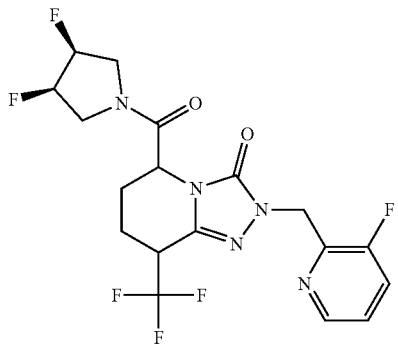 [SMILES: O=C(C1CCC(C(F)(F)F)c2nn(Cc3ncccc3F)c(=O)n21)N1C[C@@H](F)[C@@H](F)C1]

Under argon: 2-[(5-Chloro-3-fluoropyridin-2-yl)methyl]-5-{[(3R,4S)-3,4-difluoropyrrolidin-1-yl]carbonyl}-8-(trifluoromethyl)[1,2,4]triazolo[4,3-a]pyridin-3(2H)-one (95.0 mg, 47% purity, 93.1 µmol) and palladium on charcoal (10.0 mg, 10% palladium) were suspended in ethanol (5.0 ml) and stirred at room temperature in a hydrogen atmosphere (1 atm) overnight. The reaction mixture was filtered through Celite. The filtrate was concentrated and the residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 17 mg (41% of theory) of the title compound were obtained.

LC-MS (Method 3): $R_t$=1.25 min; MS (ESIpos): m/z=450 [M+H]$^+$ $^1$H-NMR (400 MHz, DMSO-d6) δ [ppm]: −0.149 (2.00), 1.747 (1.83), 1.780 (4.50), 1.808 (5.17), 1.839 (2.50), 2.024 (4.67), 2.034 (5.67), 2.049 (5.67), 2.067 (4.67), 2.094 (2.83), 2.133 (9.50), 2.141 (9.33), 2.327 (6.00), 2.366 (3.83), 2.669 (6.17), 2.710 (3.67), 3.471 (3.00), 3.480 (2.83), 3.493 (2.67), 3.504 (4.67), 3.515 (5.50), 3.525 (5.33), 3.534 (3.67), 3.559 (4.17), 3.567 (4.50), 3.626 (2.83), 3.641 (3.33), 3.660 (2.17), 3.674 (2.67), 3.686 (4.17), 3.698 (4.83), 3.720 (4.83), 3.731 (4.50), 3.751 (5.17), 3.765 (3.83), 3.785 (3.33), 3.798 (3.17), 3.855 (2.67), 3.867 (3.00), 3.904 (2.33), 3.933 (2.83), 3.947 (3.00), 3.962 (2.00), 3.983 (3.50), 3.997 (3.17), 4.011 (2.00), 4.026 (1.83), 4.087 (4.83), 4.094 (4.83), 4.102 (5.00), 4.134 (3.67), 4.148 (3.17), 4.164 (2.67), 4.176 (3.67), 4.191 (2.50), 4.204 (2.17), 4.880 (11.50), 4.890 (14.33), 4.971 (9.67), 5.010 (16.00), 5.065 (3.00), 5.114 (9.33), 5.127 (10.00), 5.154 (4.83), 5.168 (6.00), 5.247 (2.50), 5.257 (3.50), 5.268 (3.67), 5.285 (3.50), 5.324 (2.33), 5.337 (3.17), 5.345 (3.00), 5.354 (3.00), 5.366 (3.17), 5.380 (4.17), 5.392 (4.17), 5.403 (3.67), 5.415 (3.67), 5.425 (2.83), 5.443 (2.33), 5.451 (2.33), 5.463 (2.83), 5.475 (3.17), 5.486 (2.83), 5.502 (2.00), 7.419 (5.67), 7.429 (10.67), 7.440 (12.17), 7.450 (12.83), 7.461 (7.00), 7.706 (8.50), 7.731 (13.17), 7.753 (7.83), 8.360 (13.00), 8.371 (12.83).

Example 275

(5S,8RS)-5-{[(3S)-3-Fluoropyrrolidin-1-yl]carbonyl}-8-hydroxy-2-{[6-(trifluoromethyl)pyridin-3-yl]methyl}-5,6,7,8-tetrahydro[1,2,4]triazolo[4,3-a]pyridin-3(2H)-one (Diastereomer Mixture; 2 Isomers)

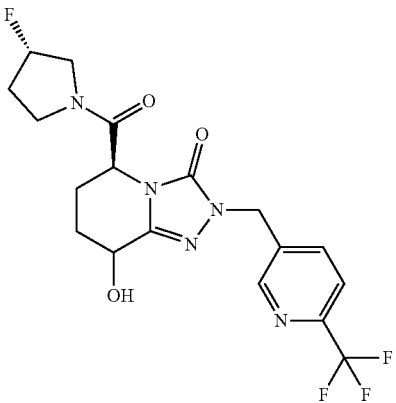 [SMILES: O=C([C@@H]1CCC(O)c2nn(Cc3ccc(C(F)(F)F)nc3)c(=O)n21)N1CC[C@H](F)C1]

(5S)-5-{[(3S)-3-Fluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (150 mg, 363 µmol) was initially charged under argon in dichloromethane (1.5 ml) at room temperature. Subsequently, at 0° C., hydrogen tetrafluoroborate (ethyl ether adduct) (55 µl, 400 µmol) was added dropwise and the reaction mixture was stirred at 0° C. for 30 min and at room temperature for 60 min. The reaction mixture was concentrated and dried under high vacuum overnight. The residue was dissolved in acetonitrile (600 µl) and, at room temperature, a solution of iron(II) (S,S-(2-({(S)-2-[(S)-1-(pyridin-2-ylmethyl)pyrrolidin-2-yl]pyrrolidin-1-yl}methyl)pyridine)(bis-acetonitrile) hexafluoroantimonate (16.9 mg, 18.1 µmol) and acetic acid (10 µl, 180 µmol) in acetonitrile (0.36 ml) was slowly added dropwise. Subsequently, at room temperature, hydrogen peroxide (27 µl, 50% solution in water, 440 µmol) in acetonitrile (3.3 ml) was slowly added dropwise and the mixture was stirred for 10 min. Hydrogen peroxide (27 µl, 50% by weight solution in water, 440 µmol) in acetonitrile (3.3 ml) was again added dropwise and the mixture was stirred for a further 10 minutes. Hydrogen peroxide (27 µl, 50% solution in water, 440 µmol) in acetonitrile (3.3 ml) was once again added dropwise and the mixture was stirred at room temperature for a further 40 minutes. The reaction mixture was admixed with 1 N aqueous sodium hydroxide solution and stirred vigorously at room temperature for 20 min. The mixture was diluted again with 1 N aqueous sodium hydroxide solution and the aqueous phase was extracted with dichloromethane. The organic phase was washed with saturated aqueous sodium chloride solution, dried over sodium sulphate and filtered, and the filtrate was concentrated. The residue was purified via preparative HPLC (Method 11). The product-containing fractions were concentrated under reduced pressure, and 15.0 mg (9% of theory) of the title compound were obtained.

LC-MS (Method 3): $R_t$=1.09 min; MS (ESIpos): m/z=430 [M+H]$^+$ $^1$H-NMR (400 MHz, DMSO-d6) δ [ppm]: −0.149 (1.25), −0.008 (16.00), 0.008 (8.87), 0.015 (0.77), 0.018 (0.60), 0.025 (0.32), 0.146 (1.17), 1.728 (0.85), 1.740 (1.01), 1.751 (1.41), 1.765 (1.49), 1.778 (1.61), 1.800 (0.97), 1.818 (1.17), 1.852 (0.77), 1.884 (0.36), 1.912 (0.52), 1.948 (0.60), 1.999 (0.40), 2.021 (0.36), 2.037 (0.24), 2.105 (1.49), 2.224 (0.60), 2.265 (0.85), 2.323 (1.25), 2.327 (1.53), 2.331 (1.21), 2.366 (2.10), 2.389 (0.97), 2.405 (1.01), 2.425 (0.77), 2.523 (7.70), 2.525 (6.85), 2.558 (1.21), 2.561 (0.77), 2.564 (0.69), 2.566 (0.64), 2.569 (0.56), 2.572 (0.56), 2.576 (0.52), 2.582 (0.40), 2.587 (0.28), 2.594 (0.28), 2.598 (0.28), 2.612 (0.24), 2.651 (0.28), 2.665 (1.29), 2.669 (1.69), 2.673 (1.17), 2.709 (1.69), 3.238 (0.28), 3.361 (0.69), 3.373 (0.40), 3.386 (0.64), 3.397 (0.48), 3.419 (0.32), 3.457 (0.36), 3.484 (0.48), 3.494 (0.52), 3.508 (0.28), 3.516 (0.32), 3.620 (0.85), 3.629 (1.29), 3.636 (1.37), 3.643 (1.45), 3.649 (1.37), 3.667 (1.25), 3.690 (0.85), 3.711 (0.64), 3.730 (1.33), 3.755 (1.21), 3.769 (0.97), 3.776 (1.01), 3.796 (0.60), 3.834 (0.32), 3.861 (1.21), 4.475 (0.36), 4.487 (0.69), 4.501 (0.64), 4.510 (0.77), 4.527 (2.02), 4.538 (1.93), 4.547 (0.77), 4.599 (0.36), 4.610 (0.44), 4.624 (0.24), 4.655 (0.36), 4.670 (0.64), 4.682 (0.40), 4.751 (0.77), 4.762 (0.69), 4.801 (0.89), 4.806 (0.93), 4.817 (0.93), 5.044 (3.83), 5.060 (5.96), 5.101 (0.24), 5.258 (0.93), 5.389 (1.21), 5.513 (0.64), 5.772 (2.66), 5.783 (3.51), 5.796 (1.41), 7.896 (0.60), 7.920 (7.58), 8.650 (2.66), 8.663 (1.37).

Alternative Method:

(5S)-5-{[(3S)-3-Fluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (400 mg, 968 μmol) and cerium(IV) sulphate (1.29 g, 3.87 mmol) were suspended in tert-butanol (1.3 ml) at room temperature. Subsequently, 1 N aqueous sulphuric acid (1.3 ml, 24 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. 270 mg (59% of theory) of the title compound were obtained.

LC-MS (Method 3): $R_t$=1.03 min; MS (ESIpos): m/z=430 [M+H]$^+$

Example 276

(5S)-5-{[(3S)-3-Fluoropyrrolidin-1-yl]carbonyl}-2-{[6-(trifluoromethyl)pyridin-3-yl]methyl}-5,6-dihydro[1,2,4]triazolo[4,3-a]pyridin-3(2H)-one

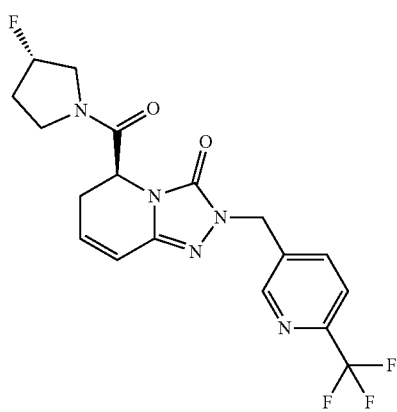 [SMILES: O=C([C@@H]1CC=Cc2nn(Cc3ccc(C(F)(F)F)nc3)c(=O)n21)N1CC[C@H](F)C1]

(5S,8RS)-5-{[(3S)-3-Fluoropyrrolidin-1-yl]carbonyl}-8-hydroxy-2-{[6-(trifluoromethyl)pyridin-3-yl]methyl}-5,6,7,8-tetrahydro[1,2,4]triazolo[4,3-a]pyridin-3(2H)-one (diastereomer mixture; 2 isomers) (200 mg, 70% purity, 326 μmol) was initially charged in THF (4.8 ml) at room temperature. Subsequently, 3,3,3-triethyl-1-(methoxycarbonyl)diazathian-3-ium-1-ide 2,2-dioxide (233 mg, 978 μmol) was added and the mixture was stirred in the microwave at 90° C. for 45 min. 3,3,3-Triethyl-1-(methoxycarbonyl)diazathian-3-ium-1-ide 2,2-dioxide (78 mg, 326 μmol) was added again and the mixture was stirred in the microwave at 90° C. for a further 2 hours. The reaction mixture was concentrated under reduced pressure and the residue was purified via preparative HPLC (Chromatorex C18, 10 μm, 125 mm×40 mm; eluent: acetonitrile/water with 0.1% formic acid gradient). The product-containing fractions were concentrated under reduced pressure, and 9.60 mg (7% of theory) of the title compound were obtained.

LC-MS (Method 3): $R_t$=1.28 min; MS (ESIpos): m/z=412 [M+H]$^+$ $^1$H-NMR (400 MHz, DMSO-d6) δ [ppm]: −0.149 (1.80), −0.032 (0.48), −0.027 (0.60), −0.024 (0.72), −0.019 (0.96), −0.016 (1.20), −0.009 (16.00), 0.007 (15.52), 0.018 (0.96), 0.022 (0.60), 0.027 (0.60), 0.146 (1.80), 2.091 (0.60), 2.116 (0.72), 2.125 (0.72), 2.165 (0.48), 2.239 (0.48), 2.270 (0.60), 2.322 (2.77), 2.327 (3.85), 2.332 (2.77), 2.366 (3.85), 2.394 (0.36), 2.414 (0.36), 2.420 (0.36), 2.434 (0.48), 2.440 (0.48), 2.447 (0.60), 2.451 (0.60), 2.521 (8.66), 2.523 (8.54), 2.526 (6.50), 2.557 (3.61), 2.560 (2.65), 2.562 (2.17), 2.564 (1.80), 2.567 (1.80), 2.569 (1.56), 2.572 (1.32), 2.574 (1.32), 2.577 (1.20), 2.579 (1.20), 2.582 (0.84), 2.584 (0.84), 2.586 (1.08), 2.589 (0.84), 2.601 (0.84), 2.606 (0.96), 2.621 (0.84), 2.628 (0.60), 2.648 (0.48), 2.653 (0.48), 2.665 (3.25), 2.669 (4.33), 2.674 (3.13), 2.709 (4.33), 2.725 (0.60), 2.747 (0.48), 2.753 (0.84), 2.770 (0.60), 2.913 (0.36), 2.943 (0.36), 2.978 (0.60), 2.994 (0.60), 3.008 (0.72), 3.032 (0.48), 3.047 (0.36), 3.055 (0.48), 3.208 (0.36), 3.220 (0.36), 3.246 (0.72), 3.255 (0.72), 3.357 (0.72), 3.372 (0.60), 3.423 (0.48), 3.470 (0.72), 3.496 (0.84), 3.637 (1.08), 3.661 (0.96), 3.688 (0.60), 3.728 (0.96), 3.774 (0.96), 3.847 (0.96), 4.949 (0.60), 4.970 (0.72), 5.004 (1.20), 5.024 (0.96), 5.080 (6.02), 5.259 (0.60), 5.390 (0.84), 5.511 (0.48), 6.248 (0.84), 6.262 (0.96), 6.278 (0.60), 6.307 (1.68), 6.315 (1.80), 6.334 (0.84), 6.340 (0.84), 7.922 (7.58), 8.559 (0.36), 8.664 (2.41), 17.706 (0.36).

Example 278

(5S)-8,8-Difluoro-5-{[(3S)-3-fluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one

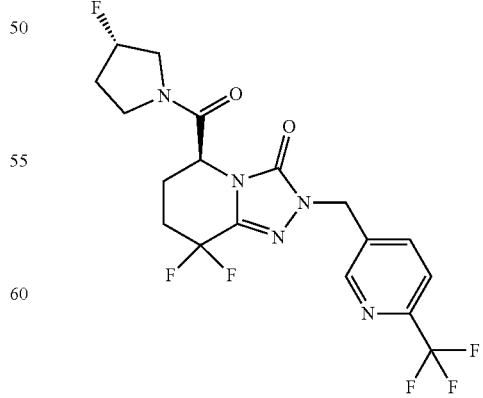

(5S)-5-{[(3S)-3-Fluoropyrrolidin-1-yl]carbonyl}-2-{[6-(trifluoromethyl)pyridin-3-yl]methyl}-6,7-dihydro[1,2,4]

triazolo[4,3-a]pyridine-3,8(2H,5H)-dione (isomer 1) (33.5 mg, 62% purity, 48.6 µmol) was initially charged under argon in dichloromethane (5.0 ml) at room temperature. Subsequently, diethylaminosulphur trifluoride (19 µl, 150 µmol) was added and the mixture was stirred at 40° C. overnight. The reaction mixture was admixed with water and saturated aqueous sodium hydrogencarbonate solution. The aqueous phase was extracted four times with dichloromethane and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 7.10 mg (31% of theory) of the title compound were obtained.

LC-MS (Method 3): $R_t$=1.52 min; MS (ESIpos): m/z=450 [M+H]$^+$ $^1$H-NMR (400 MHz, DMSO-d6) δ [ppm]: −0.149 (1.80), −0.008 (15.78), 0.008 (16.00), 0.027 (0.58), 0.146 (1.66), 1.096 (1.30), 1.113 (3.17), 1.131 (1.51), 2.119 (0.94), 2.148 (1.37), 2.169 (1.01), 2.177 (0.94), 2.237 (1.15), 2.284 (2.02), 2.323 (3.24), 2.327 (3.68), 2.332 (3.10), 2.352 (1.73), 2.366 (3.17), 2.381 (1.37), 2.407 (0.94), 2.435 (1.30), 2.446 (1.08), 2.523 (6.92), 2.568 (0.58), 2.591 (0.58), 2.665 (1.95), 2.670 (2.67), 2.674 (1.95), 2.710 (2.31), 3.184 (0.58), 3.201 (0.65), 3.243 (0.72), 3.346 (1.51), 3.357 (1.08), 3.375 (0.65), 3.395 (0.65), 3.420 (0.58), 3.428 (0.58), 3.518 (0.58), 3.527 (0.65), 3.614 (0.58), 3.655 (1.59), 3.679 (1.66), 3.707 (1.15), 3.758 (0.94), 3.780 (1.37), 3.801 (1.15), 3.825 (0.79), 3.890 (1.51), 4.864 (0.72), 4.878 (1.15), 4.940 (1.51), 5.172 (9.87), 5.277 (1.08), 5.407 (1.15), 5.531 (0.58), 7.946 (14.49), 7.949 (9.37), 8.677 (4.25).

Example 279

(5S,8RS)-2-[(5-Chloropyridin-3-yl)methyl]-5-{[(3S)-3-fluoropyrrolidin-1-yl]carbonyl}-8-hydroxy-5,6,7,8-tetrahydro[1,2,4]triazolo[4,3-a]pyridin-3(2H)-one (Diastereomer Mixture; 2 Isomers)

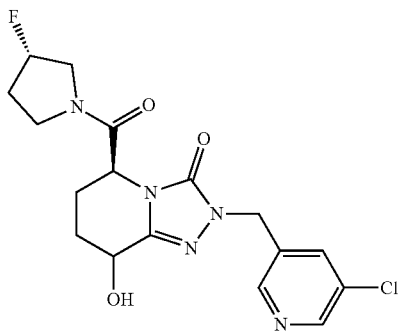 [SMILES: O=C([C@@H]1CCC(O)c2nn(Cc3cncc(Cl)c3)c(=O)n21)N1CC[C@H](F)C1]

(5S)-2-[(5-Chloropyridin-3-yl)methyl]-5-{[(3S)-3-fluoropyrrolidin-1-yl]carbonyl}-5,6,7,8-tetrahydro[1,2,4]triazolo[4,3-a]pyridin-3(2H)-one (15.2 mg, 38.8 µmol) and cerium(IV) sulphate (51.6 mg, 155 µmol) were suspended in tert-butanol (52 µl) at room temperature. Subsequently, 1 N aqueous sulphuric acid (52 µl, 970 µmol) was added and the reaction mixture was stirred at 70° C. overnight. Cerium(IV) sulphate (25.8 mg, 77.6 µmol) was added again and the mixture was stirred once more at 70° C. overnight. The reaction mixture was cooled to room temperature and adjusted to pH 9 with 2 N aqueous sodium hydroxide solution. The solids were filtered off with suction and the filtrate was extracted three times with dichloromethane. The combined organic phases were dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 7.10 mg (46% of theory) of the title compound were obtained.

LC-MS (Method 4): $R_t$=0.48 min; MS (ESIpos): m/z=396 [M+H]$^+$ $^1$H-NMR (600 MHz, DMSO-d6) δ [ppm]: 1.443 (2.53), 1.446 (2.51), 1.727 (1.43), 1.743 (2.23), 1.749 (2.12), 1.757 (2.29), 1.791 (1.45), 1.796 (1.26), 1.811 (2.25), 1.829 (1.28), 1.854 (1.39), 1.907 (2.21), 1.937 (0.93), 1.996 (0.93), 2.012 (1.02), 2.071 (0.87), 2.085 (1.04), 2.103 (2.12), 2.108 (2.12), 2.132 (1.99), 2.156 (1.21), 2.235 (1.28), 2.266 (1.28), 2.383 (2.38), 2.612 (1.34), 3.300 (15.81), 3.310 (16.00), 3.377 (2.90), 3.400 (2.40), 3.423 (1.52), 3.442 (1.30), 3.448 (1.39), 3.465 (1.54), 3.471 (1.45), 3.488 (1.04), 3.626 (1.56), 3.644 (3.44), 3.655 (2.51), 3.662 (2.68), 3.686 (1.65), 3.707 (1.97), 3.725 (1.60), 3.733 (1.52), 3.751 (1.80), 3.766 (1.08), 3.784 (1.95), 3.803 (1.19), 3.830 (1.15), 3.847 (2.25), 4.502 (1.39), 4.537 (3.66), 4.611 (1.00), 4.659 (0.82), 4.669 (1.34), 4.677 (0.89), 4.749 (1.21), 4.757 (1.19), 4.803 (1.34), 4.806 (1.39), 4.813 (1.52), 4.947 (6.52), 4.964 (10.72), 5.280 (1.80), 5.367 (1.75), 5.403 (1.19), 5.490 (1.21), 5.783 (1.47), 7.763 (3.66), 7.782 (2.77), 8.355 (1.36), 8.431 (4.78), 8.446 (3.55), 8.569 (7.77), 8.572 (7.90).

Example 280

(5RS,6RS)-5-{[(3S)-3-Fluoropyrrolidin-1-yl]carbonyl}-2-{[3-fluoro-2-(trifluoromethyl)pyridin-4-yl]methyl}-6-(trifluoromethyl)-5,6,7,8-tetrahydro[1,2,4]triazolo[4,3-a]pyridin-3(2H)-one (Diastereomer Mixture, 2 Isomers)

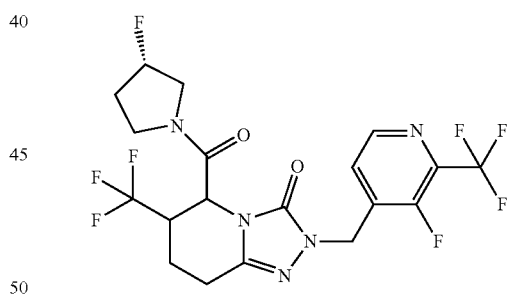

(5RS,6RS)-2-{[3-Fluoro-2-(trifluoromethyl)pyridin-4-yl]methyl}-3-oxo-6-(trifluoromethyl)-2,3,5,6,7,8-hexahydro[1,2,4]triazolo[4,3-a]pyridine-5-carboxylic acid (diastereomer mixture; 4 isomers) (96.0 mg, 224 µmol) was initially charged in THF (2.0 ml), and HBTU (111 mg, 291 µmol) and N,N-diisopropylethylamine (120 µl, 670 µmol) were subsequently added. After stirring at room temperature for 15 min, (3S)-3-fluoropyrrolidine hydrochloride (33.8 mg, 269 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 72.0 mg (64% of theory) of the title compound were obtained.

LC-MS (Method 3): R$_t$=1.64 min; MS (ESIpos): m/z=500 [M+H]$^+$ $^1$H-NMR (400 MHz, DMSO-d6) δ [ppm]: −0.149 (1.82), −0.008 (16.00), 0.008 (13.07), 0.146 (1.70), 2.043 (1.47), 2.248 (0.64), 2.328 (2.23), 2.366 (2.34), 2.523 (6.33), 2.670 (2.81), 2.710 (2.81), 2.782 (1.17), 2.823 (0.70), 3.513 (0.70), 3.538 (1.41), 3.619 (0.70), 3.668 (0.94), 3.768 (0.76), 4.135 (0.70), 4.840 (0.82), 4.855 (0.76), 4.898 (1.11), 4.909 (1.05), 4.942 (0.88), 4.951 (0.82), 4.972 (1.00), 4.986 (0.88), 5.082 (4.10), 5.097 (3.81), 5.278 (0.76), 5.412 (0.88), 7.546 (0.88), 7.558 (1.88), 7.573 (1.70), 7.587 (1.11), 8.572 (3.52), 8.584 (3.40).

Example 281

(5RS,6RS)-5-{[(3S)-3-Fluoropyrrolidin-1-yl]carbonyl}-2-{[3-fluoro-2-(trifluoromethyl)pyridin-4-yl]methyl}-6-(trifluoromethyl)-5,6,7,8-tetrahydro[1,2,4]triazolo[4,3-a]pyridin-3(2H)-one (Isomer 1)

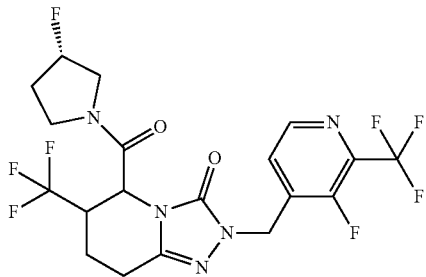 [SMILES: O=C(C1C(C(F)(F)F)CCc2nn(Cc3ccnc(C(F)(F)F)c3F)c(=O)n21)N1CC[C@H](F)C1]

(5RS,6RS)-5-{[(3S)-3-Fluoropyrrolidin-1-yl]carbonyl}-2-{[3-fluoro-2-(trifluoromethyl)pyridin-4-yl]methyl}-6-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 68 mg dissolved in 6 ml of acetonitrile/ethanol (2:1); injection volume: 0.4 ml; column: Daicel Chiralcel® OD-H 5 μm, 250×20 mm; eluent: n-heptane/ethanol 70:30; flow rate: 15 ml/min; temperature 25° C.; UV detection: 210 nm]. After the separation, 26.8 mg of isomer 1, which eluted first, and 27.2 mg of isomer 2, which eluted later, were isolated.

Isomer 1:

Analytical chiral HPLC: R$_t$=10.33 min, d.e.=100% [column: Daicel Chiralcel® OD-3 50×4.6 mm; eluent: n-heptane/ethanol 90:10; flow rate: 1 ml/min; UV detection: 220 nm].

LC-MS (Method 4): R$_t$=0.86 min; MS (ESIpos): m/z=500 [M+H]$^+$ $^1$H-NMR (500 MHz, DMSO-d6) δ [ppm]: −0.120 (0.91), −0.007 (10.14), 0.006 (7.74), 0.117 (0.91), 0.845 (0.57), 1.234 (1.37), 1.961 (2.73), 1.978 (2.79), 1.989 (2.33), 2.036 (3.36), 2.047 (6.89), 2.062 (6.89), 2.073 (3.93), 2.095 (2.11), 2.133 (2.96), 2.159 (2.28), 2.265 (1.82), 2.290 (1.88), 2.361 (2.39), 2.365 (1.71), 2.518 (5.98), 2.522 (4.56), 2.631 (3.87), 2.635 (3.13), 2.649 (2.16), 2.665 (3.42), 2.681 (2.51), 2.703 (1.54), 2.716 (2.22), 2.769 (1.71), 2.785 (3.30), 2.797 (4.61), 2.820 (2.22), 2.831 (2.79), 3.331 (3.70), 3.345 (2.68), 3.394 (1.77), 3.415 (1.77), 3.423 (2.05), 3.465 (1.77), 3.471 (2.16), 3.492 (3.59), 3.500 (3.76), 3.509 (2.51), 3.649 (3.07), 3.667 (4.84), 3.679 (4.38), 3.704 (2.51), 3.724 (5.24), 3.742 (3.07), 3.755 (2.05), 3.785 (1.71), 3.806 (2.73), 3.820 (2.79), 3.840 (1.31), 4.018 (1.37), 4.042 (1.31), 4.092 (1.20), 4.110 (1.14), 4.840 (6.32), 4.853 (6.32), 4.899 (9.00), 4.907 (8.71), 5.034 (1.77), 5.054 (2.28), 5.067 (8.54), 5.082 (10.65), 5.087 (13.04), 5.098 (12.19), 5.115 (1.82), 5.132 (1.94), 5.293 (2.96), 5.399 (3.02), 5.521 (1.99), 5.946 (0.51), 7.549 (3.87), 7.559 (7.12), 7.569 (4.21), 7.575 (3.25), 7.585 (5.41), 7.596 (2.73), 8.572 (16.00), 8.582 (15.43).

Example 282

(5RS,6RS)-2-[(3,5-Dichloropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (Diastereomer Mixture; 2 Isomers)

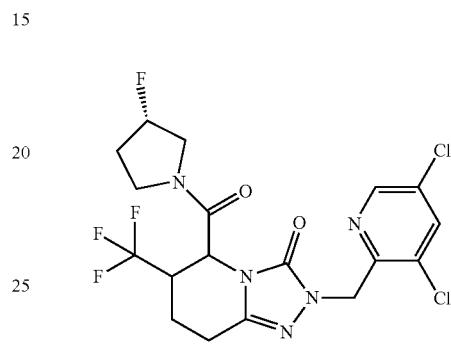

(5RS,6RS)-2-[(3,5-Dichloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 122 μmol) was initially charged in THF (2.0 ml), and HBTU (60.0 mg, 158 μmol) and N,N-diisopropylethylamine (64 μl, 360 μmol) were subsequently added. After stirring at room temperature for 15 min, (3S)-3-fluoropyrrolidine hydrochloride (18.3 mg, 146 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 46.4 mg (79% of theory) of the title compound were obtained.

LC-MS (Method 4): R$_t$=0.84 min; MS (ESIpos): m/z=482 [M+H]$^+$ $^1$H-NMR (400 MHz, DMSO-d6) δ [ppm]: −0.149 (0.64), −0.008 (5.30), 0.008 (4.77), 0.146 (0.64), 1.038 (0.42), 1.055 (0.95), 1.073 (0.53), 1.944 (1.80), 1.964 (1.80), 1.978 (1.48), 2.003 (1.80), 2.026 (2.23), 2.041 (2.75), 2.055 (2.23), 2.073 (5.93), 2.110 (2.23), 2.144 (1.38), 2.244 (1.27), 2.286 (1.27), 2.323 (1.80), 2.327 (2.44), 2.366 (1.70), 2.523 (5.93), 2.575 (1.06), 2.620 (1.91), 2.665 (2.86), 2.670 (3.18), 2.674 (2.65), 2.690 (0.95), 2.710 (2.01), 2.736 (2.75), 2.779 (1.48), 3.347 (2.65), 3.358 (2.01), 3.376 (2.01), 3.405 (1.70), 3.467 (1.17), 3.502 (1.38), 3.530 (3.07), 3.567 (1.17), 3.607 (2.12), 3.652 (1.48), 3.669 (1.91), 3.689 (1.80), 3.714 (1.59), 3.733 (1.38), 3.775 (0.95), 3.803 (0.85), 3.819 (0.95), 3.845 (0.42), 4.004 (0.53), 4.038 (0.42), 4.089 (1.06), 4.122 (1.59), 4.146 (1.80), 4.170 (0.74), 4.816 (2.01), 4.831 (1.91), 4.862 (2.54), 4.871 (2.54), 4.882 (2.23), 4.891 (2.01), 4.930 (2.44), 4.944 (2.33), 4.981 (1.80), 4.987 (1.06), 5.021 (10.91), 5.026 (16.00), 5.045 (6.46), 5.067 (0.74), 5.085 (1.59), 5.279 (1.70), 5.409 (2.01), 5.509 (0.85), 5.945 (0.42), 8.254 (8.26), 8.259 (8.90), 8.558 (6.15), 8.560 (6.78), 8.563 (6.68).

Example 283

(5RS,6RS)-2-[(3,5-Dichloropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (Isomer 1)

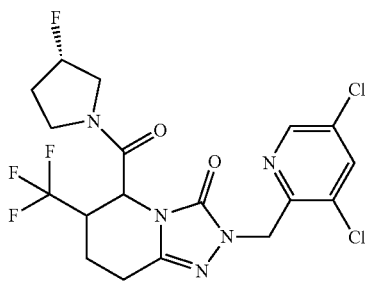 [SMILES: O=C(C1C(C(F)(F)F)CCc2nn(Cc3ncc(Cl)cc3Cl)c(=O)n21)N1CC[C@H](F)C1]

(5RS,7RS)-2-[(3,5-Dichloropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 43 mg dissolved in 5 ml of acetonitrile/isopropanol (3:2); injection volume: 0.5 ml; column: Daicel Chiralcel® OD-H 5 µm, 250×20 mm; eluent: n-heptane/isopropanol 50:50; flow rate: 15 ml/min; temperature 25° C.; UV detection: 210 nm]. After the separation, 19.2 mg of isomer 1, which eluted first, and 18.3 mg of isomer 2, which eluted later, were isolated.

Isomer 1:

Analytical chiral HPLC: $R_t$=3.97 min, d.e.=100% [column: Daicel Chiralcel® ID-3 50×4.6 mm; eluent: n-heptane/isopropanol 50:50; flow rate: 1 ml/min; UV detection: 220 nm].

LC-MS (Method 3): $R_t$=1.61 min; MS (ESIpos): m/z=482 [M+H]$^+$ $^1$H-NMR (400 MHz, DMSO-d6) δ [ppm]: −0.149 (1.20), −0.008 (14.40), 0.008 (9.18), 0.146 (1.16), 1.234 (0.96), 1.909 (0.80), 1.922 (1.36), 1.944 (1.80), 1.957 (1.28), 2.026 (2.85), 2.041 (3.45), 2.055 (2.45), 2.078 (1.88), 2.112 (2.41), 2.147 (1.80), 2.254 (1.28), 2.288 (1.20), 2.327 (1.72), 2.366 (1.44), 2.524 (7.14), 2.576 (1.48), 2.602 (1.72), 2.620 (1.88), 2.670 (2.57), 2.674 (2.73), 2.710 (1.92), 2.745 (2.85), 2.758 (1.84), 2.788 (1.60), 3.404 (1.76), 3.473 (2.25), 3.501 (1.96), 3.509 (2.01), 3.656 (2.81), 3.668 (3.05), 3.690 (3.53), 3.714 (2.93), 3.733 (2.09), 3.749 (2.09), 3.776 (1.16), 3.802 (1.76), 3.820 (1.76), 3.844 (0.88), 4.005 (0.92), 4.036 (0.76), 4.099 (0.88), 4.122 (0.80), 4.816 (3.61), 4.831 (3.61), 4.861 (4.77), 4.871 (4.61), 4.981 (3.09), 5.020 (16.00), 5.027 (8.82), 5.046 (8.82), 5.067 (1.08), 5.085 (2.49), 5.277 (1.80), 5.408 (2.29), 5.529 (1.36), 8.254 (6.50), 8.259 (6.74), 8.557 (6.14), 8.562 (7.06), 8.566 (4.81).

Example 284

(5RS,6RS)-5-{[(3S)-3-Fluoropyrrolidin-1-yl]carbonyl}-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer Mixture; 2 Isomers)

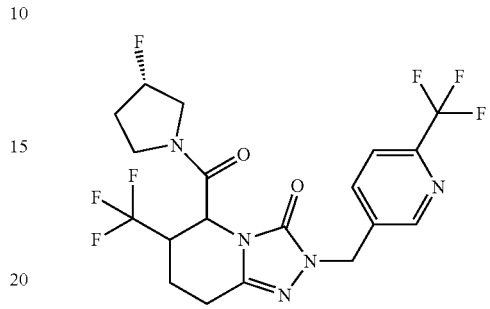

(5RS,6RS)-3-Oxo-6-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (54.0 mg, 132 µmol) was initially charged in THF (2.0 ml), and HBTU (64.9 mg, 171 µmol) and N,N-diisopropylethylamine (69 µl, 390 µmol) were subsequently added. After stirring at room temperature for 15 min, (3S)-3-fluoropyrrolidine hydrochloride (19.8 mg, 158 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 51.4 mg (81% of theory) of the title compound were obtained.

LC-MS (Method 3): $R_t$=1.55 min; MS (ESIpos): m/z=482 [M+H]$^+$

Example 285

(5RS,6RS)-5-{[(3S)-3-Fluoropyrrolidin-1-yl]carbonyl}-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 1)

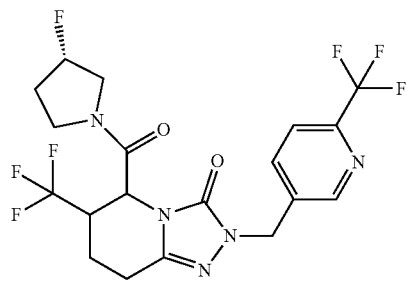 [SMILES: O=C(C1C(C(F)(F)F)CCc2nn(Cc3ccc(C(F)(F)F)nc3)c(=O)n21)N1CC[C@H](F)C1]

(5RS,6RS)-5-{[(3S)-3-Fluoropyrrolidin-1-yl]carbonyl}-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer mixture; 2 isomers) was separated by chiral preparative HPLC [sample preparation: 200 mg dissolved in 5 ml of acetonitrile/isopropanol (1:1); injection volume: 0.15 ml; column: Daicel Chiralcel® IB 5 µm, 250×30 mm; eluent: n-heptane/isopropanol 50:50; flow rate: 60 ml/min; temperature 28° C.; UV detection: 220 nm]. After the separation, 69.8 mg of isomer 1, which eluted first, and 71.7 mg of isomer 2, which eluted later, were isolated.

Isomer 1:

Analytical chiral HPLC: $R_t$=1.79 min, d.e.=100% [column: Daicel Chiralcel® IB-3 50×4.6 mm; eluent: n-heptane/isopropanol 50:50; flow rate: 1 ml/min; UV detection: 220 nm].

LC-MS (Method 3): $R_t$=1.54 min; MS (ESIpos): m/z=482 [M+H]⁺

¹H-NMR (400 MHz, DMSO-d6) δ [ppm]: −0.149 (1.40), −0.008 (16.00), 0.008 (9.77), 0.146 (1.40), 2.052 (1.18), 2.327 (2.15), 2.366 (1.93), 2.669 (2.36), 2.710 (2.15), 2.781 (0.75), 3.509 (0.64), 3.666 (1.07), 4.831 (0.97), 4.847 (0.97), 4.889 (1.29), 4.899 (1.29), 5.018 (2.36), 5.035 (4.08), 5.278 (0.64), 5.405 (0.75), 7.919 (7.30), 8.643 (1.83).

Example 286

(5RS,6RS)-5-{[(3S)-3-Fluoropyrrolidin-1-yl]carbonyl}-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 2)

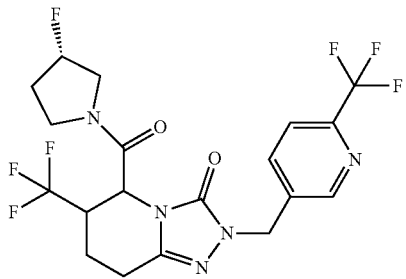 [SMILES: O=C(C1C(C(F)(F)F)CCc2nn(Cc3ccc(C(F)(F)F)nc3)c(=O)n21)N1CC[C@H](F)C1]

(5RS,6RS)-5-{[(3S)-3-Fluoropyrrolidin-1-yl]carbonyl}-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer mixture; 2 isomers) was separated by chiral preparative HPLC [sample preparation: 200 mg dissolved in 5 ml of acetonitrile/isopropanol (1:1); injection volume: 0.15 ml; column: Daicel Chiralcel® IB 5 µm, 250×30 mm; eluent: n-heptane/isopropanol 50:50; flow rate: 60 ml/min; temperature 28° C.; UV detection: 220 nm]. After the separation, 69.8 mg of isomer 1, which eluted first, and 71.7 mg of isomer 2, which eluted later, were isolated.

Isomer 2:

Analytical chiral HPLC: $R_t$=2.10 min, d.e.=100% [column: Daicel Chiralcel® IB-3 50×4.6 mm; eluent: n-heptane/isopropanol 50:50; flow rate: 1 ml/min; UV detection: 220 nm].

LC-MS (Method 3): $R_t$=1.54 min; MS (ESIpos): m/z=482 [M+H]⁺

¹H-NMR (400 MHz, DMSO-d6) δ [ppm]: −0.149 (1.85), −0.008 (16.00), 0.008 (14.32), 0.146 (1.85), 1.967 (1.18), 2.028 (2.36), 2.044 (2.02), 2.327 (3.03), 2.366 (2.36), 2.524 (6.74), 2.587 (0.84), 2.669 (3.87), 2.710 (3.03), 2.767 (1.85), 3.376 (2.19), 3.394 (2.02), 3.422 (1.35), 3.535 (3.54), 3.561 (1.68), 3.589 (1.52), 3.607 (1.68), 3.766 (0.67), 4.099 (0.84), 4.121 (1.18), 4.145 (1.68), 4.187 (0.67), 4.930 (2.36), 4.939 (2.36), 4.963 (2.86), 4.977 (2.69), 5.024 (8.76), 5.036 (4.72), 5.280 (1.01), 5.383 (1.01), 5.413 (1.01), 5.514 (1.01), 7.918 (15.16), 7.921 (16.00), 8.644 (4.04).

Example 287

(5RS,6RS)-2-[(3,5-Dichloropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (Diastereomer 1; Racemate)

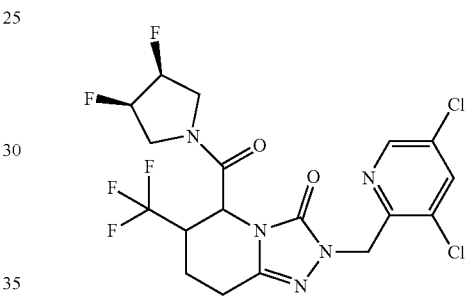

(5RS,6RS)-2-[(3,5-Dichloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 122 µmol) was initially charged in THF (2.0 ml), and HBTU (60.0 mg, 158 mol) and N,N-diisopropylethylamine (64 µl, 360 µmol) were subsequently added. After stirring at room temperature for 15 min, (3R,4S)-3,4-difluoropyrrolidine hydrochloride (20.9 mg, 146 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 41.0 mg (67% of theory) of the title compound were obtained.

LC-MS (Method 3): $R_t$=1.66 min; MS (ESIpos): m/z=500 [M+H]⁺

¹H-NMR (400 MHz, DMSO-d6) δ [ppm]: −0.149 (1.74), −0.008 (16.00), 0.008 (14.26), 0.146 (1.74), 1.937 (1.09), 2.021 (2.29), 2.073 (2.61), 2.328 (3.16), 2.366 (3.16), 2.603 (1.31), 2.625 (1.52), 2.669 (4.03), 2.710 (3.48), 2.740 (2.29), 2.756 (1.52), 3.503 (1.20), 3.650 (1.20), 3.699 (1.09), 3.716 (1.31), 3.818 (1.09), 3.847 (0.87), 4.057 (0.76), 4.398 (0.87), 4.918 (4.14), 4.932 (2.72), 4.989 (1.41), 5.027 (14.59), 5.047 (5.33), 5.087 (1.31), 5.255 (0.98), 5.356 (1.20), 5.462 (0.87), 8.255 (6.10), 8.260 (6.64), 8.557 (5.22).

Example 288

(5RS,6RS)-2-[(3,5-Dichloropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (Enantiomer 2)

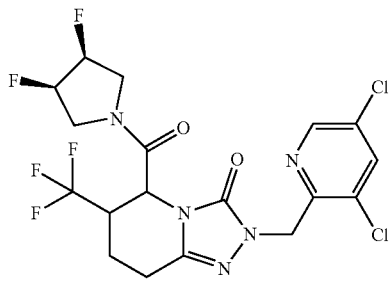 [SMILES: O=C(C1C(C(F)(F)F)CCc2nn(Cc3ncc(Cl)cc3Cl)c(=O)n21)N1C[C@@H](F)[C@@H](F)C1]

(5RS,6RS)-2-[(3,5-Dichloropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (diastereomer 1; racemate) was separated by chiral preparative HPLC [sample preparation: 40 mg dissolved in 3.5 ml of ethanol (in an ultrasound bath); injection volume: 0.80 ml; column: Daicel Chiralcel® OX-H 5 µm, 250×20 mm; eluent: ethanol+0.2% diethylamine; flow rate: 15 ml/min; temperature 55° C.; UV detection: 220 nm]. After the separation, 19.5 mg of enantiomer 1, which eluted first, and 18.4 mg of enantiomer 2, which eluted later, were isolated.

Enantiomer 2:
Analytical chiral HPLC: $R_t$=8.73 min, e.e. =100% [column: Daicel Chiralcel® OX-H-3 250×4.6 mm; eluent: ethanol+0.2% diethylamine; flow rate: 1 ml/min; UV detection: 220 nm].

LC-MS (Method 3): $R_t$=1.70 min; MS (ESIpos): m/z=500 [M+H]$^+$ $^1$H-NMR (400 MHz, DMSO-d6) δ[ppm]: −0.150 (0.79), 0.146 (0.79), 1.234 (0.93), 1.936 (1.08), 2.006 (2.14), 2.022 (2.59), 2.077 (1.22), 2.327 (1.45), 2.366 (1.24), 2.605 (1.53), 2.626 (1.90), 2.670 (2.67), 2.710 (1.61), 2.741 (2.78), 2.756 (1.72), 2.784 (1.48), 3.504 (1.59), 3.524 (1.43), 3.586 (1.24), 3.632 (1.19), 3.651 (1.45), 3.699 (1.27), 3.717 (1.48), 3.732 (1.40), 3.783 (0.90), 3.830 (1.24), 3.848 (0.95), 3.901 (0.85), 4.102 (0.85), 4.396 (1.00), 4.918 (5.32), 4.933 (3.09), 4.989 (1.22), 5.027 (16.00), 5.047 (5.71), 5.086 (1.22), 5.264 (1.19), 5.355 (1.48), 5.447 (1.06), 8.255 (6.88), 8.260 (7.17), 8.559 (6.72).

Example 289

(5RS,6RS)-2-[(3,5-Dichloropyridin-2-yl)methyl]-5-[(3,3-difluoropyrrolidin-1-yl)carbonyl]-6-(trifluoromethyl)-5,6,7,8-tetrahydro[1,2,4]triazolo[4,3-a]pyridin-3(2H)-one (Diastereomer 1, Racemate)

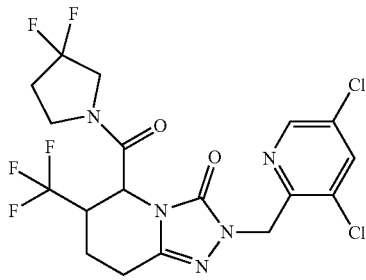 [SMILES: O=C(C1C(C(F)(F)F)CCc2nn(Cc3ncc(Cl)cc3Cl)c(=O)n21)N1CCC(F)(F)C1]

(5RS,6RS)-2-[(3,5-Dichloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 122 µmol) was initially charged in THF (2.0 ml), and HBTU (60.0 mg, 158 µmol) and N,N-diisopropylethylamine (64 µl, 360 µmol) were subsequently added. After stirring at room temperature for 15 min, 3,3-difluoropyrrolidine hydrochloride (20.9 mg, 146 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 43.0 mg (71% of theory) of the title compound were obtained.

LC-MS (Method 3): $R_t$=1.75 min; MS (ESIpos): m/z=500 [M+H]$^+$ $^1$H-NMR (400 MHz, DMSO-d6) δ[ppm]: −0.149 (1.23), −0.008 (10.09), 0.008 (9.95), 0.146 (1.15), 1.939 (1.51), 1.957 (2.16), 1.973 (2.52), 1.991 (2.31), 2.008 (1.59), 2.073 (4.40), 2.328 (2.16), 2.366 (2.52), 2.387 (1.51), 2.416 (1.80), 2.436 (1.73), 2.457 (1.66), 2.573 (2.81), 2.591 (2.45), 2.609 (2.38), 2.638 (2.31), 2.655 (3.10), 2.670 (3.75), 2.710 (2.16), 2.745 (2.81), 2.791 (1.51), 3.406 (2.16), 3.554 (1.66), 3.571 (3.24), 3.588 (3.82), 3.607 (1.59), 3.640 (0.86), 3.675 (3.03), 3.694 (2.16), 3.707 (2.88), 3.720 (2.23), 3.740 (1.73), 3.768 (1.01), 3.801 (2.59), 3.834 (2.31), 3.869 (1.95), 3.909 (1.37), 3.938 (0.72), 4.100 (0.94), 4.119 (2.02), 4.144 (1.87), 4.161 (0.86), 4.365 (0.79), 4.392 (1.30), 4.423 (1.15), 4.453 (0.58), 4.897 (3.82), 4.910 (3.68), 4.948 (4.25), 4.961 (4.18), 4.991 (1.95), 5.031 (16.00), 5.039 (13.91), 5.080 (1.73), 5.489 (0.50), 8.256 (7.86), 8.261 (8.65), 8.557 (9.01), 8.562 (8.86).

Example 290

(5RS,6RS)-2-[(3,5-Dichloropyridin-2-yl)methyl]-5-[(3,3-difluoropyrrolidin-1-yl)carbonyl]-6-(trifluoromethyl)-5,6,7,8-tetrahydro[1,2,4]triazolo[4,3-a]pyridin-3(2H)-one (Enantiomer 2)

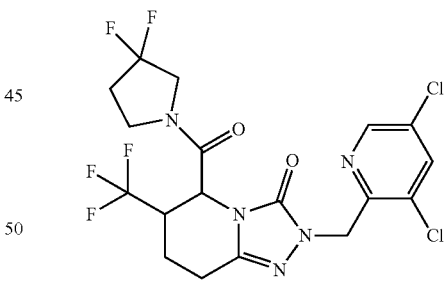

(5RS,6RS)-2-[(3,5-Dichloropyridin-2-yl)methyl]-5-[(3,3-difluoropyrrolidin-1-yl)carbonyl]-6-(trifluoromethyl)-5,6,7,8-tetrahydro[1,2,4]triazolo[4,3-a]pyridin-3(2H)-one (diastereomer 1, racemate) was separated by chiral preparative HPLC [sample preparation: 42 mg dissolved in 3.5 ml of ethanol (in an ultrasound bath); injection volume: 0.80 ml; column: Daicel Chiralcel® OX-H 5 µm, 250×20 mm; eluent: ethanol+0.2% diethylamine; flow rate: 15 ml/min; temperature 55° C.; UV detection: 220 nm]. After the separation, 17.9 mg of enantiomer 1, which eluted first, and 17.0 mg of enantiomer 2, which eluted later, were isolated.

Enantiomer 2:
Analytical chiral HPLC: $R_t$=9.89 min, e.e. =100% [column: Daicel Chiralcel® OZ-H-3 250×4.6 mm; eluent:

n-heptane/ethanol 70:30+0.2% diethylamine; flow rate: 1 ml/min; UV detection: 220 nm].

LC-MS (Method 3): $R_t$=1.74 min; MS (ESIpos): m/z=500 [M+H]+

$^1$H-NMR (400 MHz, DMSO-d6) δ[ppm]: −0.149 (1.99), 0.008 (16.00), 0.146 (2.21), 1.235 (1.40), 1.955 (2.06), 1.974 (2.36), 1.991 (2.36), 2.007 (1.84), 2.057 (2.21), 2.327 (3.24), 2.366 (3.61), 2.573 (2.80), 2.594 (2.29), 2.610 (2.29), 2.637 (2.29), 2.669 (4.87), 2.710 (3.17), 2.742 (2.58), 3.407 (2.14), 3.571 (3.32), 3.588 (3.69), 3.606 (1.55), 3.674 (3.10), 3.707 (2.95), 3.739 (1.84), 3.767 (1.18), 3.800 (2.51), 3.835 (2.43), 3.867 (1.92), 3.909 (1.33), 4.117 (1.92), 4.143 (1.92), 4.395 (1.25), 4.897 (3.47), 4.910 (3.61), 4.947 (4.13), 4.961 (4.13), 4.991 (2.06), 5.030 (15.48), 5.039 (13.20), 5.079 (1.47), 8.256 (8.85), 8.261 (9.00), 8.557 (9.88), 8.562 (9.51).

Example 291

(5RS,6RS)-2-[(5-Chloro-3-fluoropyridin-2-yl) methyl]-5-{[(3R,4S)-3,4-difluoropyrrolidin-1-yl] carbonyl}-6-(trifluoromethyl)-5,6,7,8-tetrahydro[1,2, 4]triazolo[4,3-a]pyridin-3(2H)-one (Diastereomer 1, Racemate)

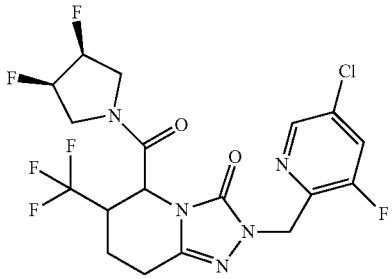 [SMILES: O=C(C1C(C(F)(F)F)CCc2nn(Cc3ncc(Cl)cc3F)c(=O)n21)N1C[C@@H](F)[C@@H](F)C1]

(5RS,6RS)-2-[(5-Chloro-3-fluoropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 127 μmol) was initially charged in THF (2.0 ml), and HBTU (62.5 mg, 165 mol) and N,N-diisopropylethylamine (66 μl, 380 μmol) were subsequently added. After stirring at room temperature for 15 min, (3R,4S)-3,4-difluoropyrrolidine hydrochloride (21.8 mg, 152 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 45.0 mg (73% of theory) of the title compound were obtained.

LC-MS (Method 3): $R_t$=1.56 min; MS (ESIpos): m/z=484 [M+H]

$^1$H-NMR (400 MHz, DMSO-d6) δ [ppm]: −0.149 (1.28), −0.008 (16.00), 0.008 (8.30), 0.146 (1.22), 1.903 (1.42), 1.925 (1.69), 1.938 (1.22), 1.961 (1.01), 1.996 (2.90), 2.012 (3.31), 2.038 (1.35), 2.073 (5.00), 2.327 (2.03), 2.366 (2.36), 2.524 (9.18), 2.573 (1.49), 2.597 (1.42), 2.619 (2.16), 2.635 (1.69), 2.665 (2.70), 2.669 (2.84), 2.674 (2.84), 2.710 (3.38), 2.733 (3.31), 2.748 (2.23), 2.776 (1.76), 3.398 (1.55), 3.466 (1.08), 3.501 (1.69), 3.547 (1.96), 3.599 (1.49), 3.626 (1.22), 3.648 (1.69), 3.662 (1.69), 3.696 (1.62), 3.713 (1.42), 3.736 (1.55), 3.758 (1.01), 3.771 (1.01), 3.789 (1.15), 3.802 (1.22), 3.824 (1.62), 3.839 (1.42), 3.854 (1.08), 3.865 (0.88), 3.880 (0.95), 3.893 (1.15), 3.908 (0.95), 4.054 (0.95), 4.091 (0.95), 4.356 (0.88), 4.372 (1.08), 4.384 (1.15), 4.396 (1.35), 4.410 (1.01), 4.421 (0.88), 4.437 (0.88), 4.902 (5.20), 4.909 (6.01), 4.925 (4.39), 4.940 (1.62), 4.979 (13.37), 4.998 (4.93), 5.002 (4.59), 5.037 (1.28), 5.086 (0.47), 5.260 (1.49), 5.269 (1.49), 5.362 (1.89), 5.392 (1.62), 5.401 (1.62), 5.451 (1.22), 5.480 (1.22), 8.098 (5.60), 8.103 (5.74), 8.122 (5.67), 8.127 (5.60), 8.476 (6.35).

Example 292

(5RS,6RS)-2-[(5-Chloro-3-fluoropyridin-2-yl) methyl]-5-{[(3R,4S)-3,4-difluoropyrrolidin-1-yl] carbonyl}-6-(trifluoromethyl)-5,6,7,8-tetrahydro[1,2, 4]triazolo[4,3-a]pyridin-3(2H)-one (Enantiomer 1)

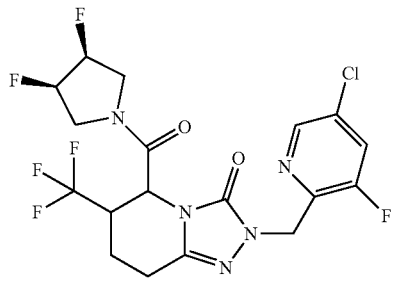 [SMILES: O=C(C1C(C(F)(F)F)CCc2nn(Cc3ncc(Cl)cc3F)c(=O)n21)N1C[C@@H](F)[C@@H](F)C1]

(5RS,6RS)-2-[(5-Chloro-3-fluoropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3 (2H)-one (diastereomer 1, racemate) was separated by chiral preparative HPLC [sample preparation: 44 mg dissolved in 2 ml of acetonitrile/ethanol (1:1)+0.2% diethylamine; injection volume: 0.15 ml; column: Daicel Chiralcel® IB 5 μm, 250×20 mm; eluent: n-heptane/ethanol 50:50; flow rate: 20 ml/min; temperature 30° C.; UV detection: 220 nm]. After the separation, 9.9 mg of enantiomer 1, which eluted first, and 11.9 mg of enantiomer 2, which eluted later, were isolated.

Enantiomer 1:

Analytical chiral HPLC: $R_t$=1.66 min, e.e. =100% [column: Daicel Chiralcel® IE-3 50×4.6 mm; eluent: n-heptane/ethanol 50:50+0.2% diethylamine; flow rate: 1 ml/min; UV detection: 220 nm].

LC-MS (Method 3): $R_t$=1.55 min; MS (ESIpos): m/z=484 [M+H]

$^1$H-NMR (400 MHz, DMSO-d6) δ [ppm]: −0.149 (1.91), 0.008 (16.00), 0.146 (1.91), 1.109 (0.41), 1.236 (0.81), 1.904 (0.93), 1.926 (1.04), 1.961 (0.64), 1.997 (1.86), 2.013 (2.20), 2.057 (0.99), 2.327 (1.86), 2.366 (1.86), 2.596 (0.87), 2.620 (1.33), 2.635 (1.10), 2.670 (2.38), 2.710 (2.55), 2.734 (2.14), 2.749 (1.39), 2.777 (1.22), 3.269 (0.70), 3.399 (0.87), 3.468 (0.58), 3.501 (1.04), 3.556 (1.10), 3.600 (0.93), 3.628 (0.75), 3.650 (1.04), 3.663 (1.10), 3.698 (1.04), 3.713 (0.87), 3.736 (0.93), 3.770 (0.64), 3.790 (0.75), 3.826 (0.99), 3.840 (0.87), 3.854 (0.64), 3.881 (0.58), 3.895 (0.64), 3.908 (0.58), 4.054 (0.64), 4.100 (0.58), 4.356 (0.46), 4.372 (0.70), 4.398 (0.87), 4.410 (0.70), 4.438 (0.52), 4.903 (3.19), 4.909 (4.06), 4.925 (2.84), 4.941 (0.87), 4.979 (9.10), 5.002 (3.19), 5.037 (0.64), 5.260 (0.99), 5.362 (1.16), 5.401 (1.04), 5.481 (0.81), 8.098 (3.36), 8.103 (3.59), 8.122 (3.65), 8.127 (3.54), 8.477 (4.29).

Example 293

(5RS,6RS)-2-[(5-Chloro-3-fluoropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (Enantiomer 2)

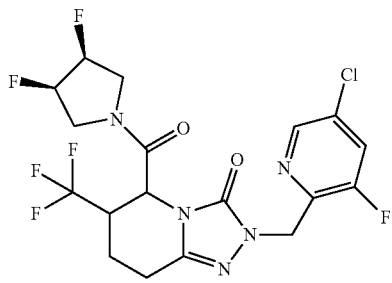 [SMILES: O=C(C1C(C(F)(F)F)CCc2nn(Cc3ncc(Cl)cc3F)c(=O)n21)N1C[C@@H](F)[C@@H](F)C1]

(5RS,6RS)-2-[(5-Chloro-3-fluoropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (diastereomer 1, racemate) was separated by chiral preparative HPLC [sample preparation: 44 mg dissolved in 2 ml of acetonitrile/ethanol (1:1)+0.2% diethylamine; injection volume: 0.15 ml; column: Daicel Chiralcel® IB 5 µm, 250×20 mm; eluent: n-heptane/ethanol 50:50; flow rate: 20 ml/min; temperature 30° C.; UV detection: 220 nm]. After the separation, 9.9 mg of enantiomer 1, which eluted first, and 11.9 mg of enantiomer 2, which eluted later, were isolated.

Enantiomer 2:

Analytical chiral HPLC: $R_t$=1.92 min, e.e. =97% [column: Daicel Chiralcel® IE-3 50×4.6 mm; eluent: n-heptane/ethanol 50:50+0.2% diethylamine; flow rate: 1 ml/min; UV detection: 220 nm].

LC-MS (Method 3): $R_t$=1.55 min; MS (ESIpos): m/z=484 [M+H]$^+$ $^1$H-NMR (400 MHz, DMSO-d6) δ [ppm]: −0.149 (1.80), −0.008 (16.00), 0.008 (14.88), 0.146 (1.80), 1.074 (1.91), 1.091 (3.99), 1.110 (2.08), 1.233 (0.90), 1.904 (1.12), 1.925 (1.46), 1.961 (0.90), 1.997 (2.30), 2.013 (2.75), 2.057 (1.12), 2.327 (1.91), 2.366 (2.36), 2.599 (1.35), 2.619 (1.80), 2.637 (1.40), 2.669 (2.81), 2.710 (3.31), 2.734 (3.14), 2.750 (2.41), 2.776 (2.25), 3.466 (0.95), 3.510 (1.35), 3.556 (1.52), 3.599 (1.35), 3.624 (1.12), 3.649 (1.35), 3.662 (1.40), 3.697 (1.35), 3.713 (1.18), 3.736 (1.35), 3.759 (0.90), 3.770 (0.90), 3.790 (0.90), 3.802 (0.95), 3.825 (1.40), 3.840 (1.18), 3.894 (0.95), 3.908 (0.84), 4.054 (0.79), 4.092 (0.79), 4.356 (0.84), 4.396 (1.07), 4.903 (4.15), 4.912 (5.16), 4.925 (3.59), 4.945 (1.07), 4.979 (11.51), 4.998 (4.10), 5.038 (0.95), 5.270 (1.35), 5.363 (1.52), 5.402 (1.40), 5.481 (1.07), 8.098 (4.94), 8.103 (5.16), 8.122 (5.00), 8.127 (5.33), 8.478 (7.02).

Example 294

(5RS,6RS)-2-[(5-Chloro-3-fluoropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (Diastereomer Mixture; 2 Isomers)

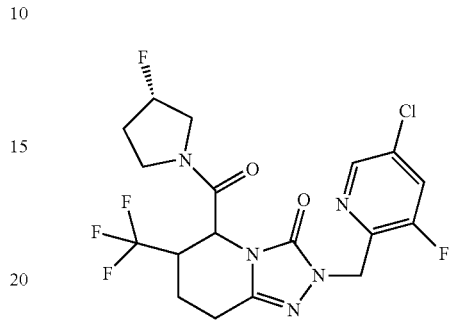

(5RS,6RS)-2-[(5-Chloro-3-fluoropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 127 µmol) was initially charged in THF (2.0 ml), and HBTU (62.5 mg, 165 mol) and N,N-diisopropylethylamine (66 µl, 380 µmol) were subsequently added. After stirring at room temperature for 15 min, (3S)-3-fluoropyrrolidine hydrochloride (19.1 mg, 152 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 39.0 mg (66% of theory) of the title compound were obtained.

LC-MS (Method 3): $R_t$=1.50 min; MS (ESIpos): m/z=466 [M+H]$^+$ $^1$H-NMR (400 MHz, DMSO-d6) δ [ppm]: −0.149 (0.51), −0.008 (4.55), 0.008 (4.09), 0.146 (0.51), 1.250 (1.15), 1.257 (0.72), 1.266 (1.29), 1.271 (1.23), 1.288 (1.07), 1.899 (0.63), 1.913 (1.04), 1.933 (1.73), 1.954 (1.76), 1.968 (1.44), 1.994 (1.69), 2.010 (2.01), 2.018 (2.34), 2.033 (2.50), 2.047 (2.01), 2.068 (1.69), 2.082 (1.73), 2.107 (1.96), 2.148 (1.23), 2.228 (0.88), 2.242 (1.23), 2.288 (1.15), 2.327 (1.18), 2.366 (0.76), 2.524 (2.43), 2.570 (0.90), 2.592 (1.07), 2.614 (1.67), 2.670 (1.94), 2.690 (5.80), 2.710 (1.96), 2.728 (2.56), 2.741 (1.94), 2.770 (1.29), 2.783 (1.02), 3.269 (0.62), 3.298 (1.46), 3.315 (1.66), 3.333 (1.37), 3.343 (1.18), 3.362 (1.53), 3.378 (1.67), 3.391 (1.22), 3.409 (1.37), 3.471 (1.22), 3.498 (1.43), 3.528 (2.82), 3.550 (1.25), 3.565 (1.97), 3.619 (16.00), 3.663 (12.83), 3.793 (1.11), 3.802 (1.18), 3.819 (1.13), 3.845 (0.62), 4.006 (0.48), 4.038 (0.42), 4.090 (0.88), 4.123 (1.48), 4.146 (1.83), 4.170 (0.81), 4.809 (1.87), 4.825 (1.80), 4.854 (2.38), 4.864 (2.40), 4.874 (1.99), 4.884 (1.90), 4.922 (2.36), 4.937 (3.28), 4.976 (11.24), 4.997 (4.44), 5.018 (0.83), 5.034 (1.25), 5.278 (1.60), 5.379 (0.90), 5.411 (1.94), 5.511 (0.78), 5.533 (0.74), 8.097 (5.67), 8.102 (6.01), 8.121 (5.76), 8.126 (6.04), 8.478 (7.30).

Example 295

(5RS,6RS)-2-[(5-Chloro-3-fluoropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (Isomer 1)

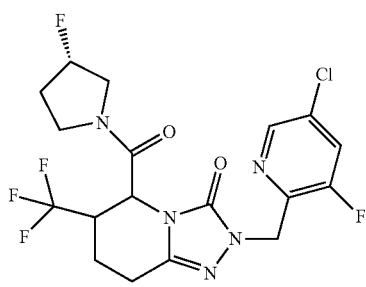 [SMILES: O=C(C1C(C(F)(F)F)CCc2nn(Cc3ncc(Cl)cc3F)c(=O)n21)N1CC[C@H](F)C1]

(5RS,6RS)-2-[(5-Chloro-3-fluoropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 38 mg dissolved in 2 ml of acetonitrile/ethanol (1:1); injection volume: 0.15 ml; column: Daicel Chiralcel® ID 5 μm, 250×20 mm; eluent: n-heptane/ethanol 35:65+0.2% diethylamine; flow rate: 20 ml/min; temperature 25° C.; UV detection: 220 nm]. After the separation, 11.3 mg of isomer 1, which eluted first, and 13.0 mg of isomer 2, which eluted later, were isolated.

Isomer 1:

Analytical chiral HPLC: $R_t$=1.57 min, d.e.=100% [column: Daicel Chiralcel® ID-3 50×4.6 mm; eluent: n-heptane/ethanol 50:50+0.2% diethylamine; flow rate: 1 ml/min; UV detection: 220 nm].

LC-MS (Method 3): $R_t$=1.50 min; MS (ESIpos): m/z=466 [M+H]$^+$ $^1$H-NMR (400 MHz, DMSO-d6) δ [ppm]: −0.149 (1.91), −0.008 (16.00), 0.008 (14.39), 0.146 (1.76), 0.866 (0.88), 0.886 (1.17), 0.904 (0.73), 1.233 (1.61), 1.912 (1.76), 1.933 (2.20), 1.947 (1.91), 2.003 (1.76), 2.018 (4.40), 2.033 (5.14), 2.108 (3.08), 2.242 (1.91), 2.290 (1.61), 2.327 (4.11), 2.366 (3.96), 2.523 (9.39), 2.569 (3.23), 2.595 (2.94), 2.614 (3.23), 2.670 (6.75), 2.710 (5.72), 2.738 (3.96), 2.782 (2.35), 3.366 (2.50), 3.411 (2.35), 3.471 (3.08), 3.497 (2.50), 3.662 (5.87), 3.684 (3.52), 3.717 (3.96), 3.740 (4.55), 3.802 (2.50), 3.819 (2.79), 3.846 (1.32), 3.998 (1.76), 4.039 (1.32), 4.056 (0.73), 4.091 (1.47), 4.124 (1.17), 4.155 (0.88), 4.809 (5.58), 4.824 (5.58), 4.854 (7.05), 4.864 (7.05), 4.932 (2.79), 4.971 (14.39), 4.975 (14.39), 4.996 (7.49), 5.000 (7.49), 5.015 (1.32), 5.039 (2.50), 5.277 (2.79), 5.410 (3.67), 5.532 (1.91), 8.097 (7.93), 8.102 (8.37), 8.121 (8.22), 8.126 (8.51), 8.478 (8.51).

Example 296

(5RS,6RS)-2-[(5-Chloro-3-fluoropyridin-2-yl)methyl]-5-[(3,3-difluoropyrrolidin-1-yl)carbonyl]-6-(trifluoromethyl)-5,6,7,8-tetrahydro[1,2,4]triazolo[4,3-a]pyridin-3(2H)-one (Diastereomer 1, Racemate)

(5RS,6RS)-2-[(5-Chloro-3-fluoropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 127 μmol) was initially charged in THF (1.6 ml), and HBTU (62.5 mg, 165 μmol) and N,N-diisopropylethylamine (66 μl, 380 μmol) were subsequently added. After stirring at room temperature for 15 min, 3,3-difluoropyrrolidine hydrochloride (21.8 mg, 152 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 48.0 mg (78% of theory) of the title compound were obtained.

LC-MS (Method 4): $R_t$=0.86 min; MS (ESIpos): m/z=484 [M+H]$^+$ $^1$H-NMR (400 MHz, DMSO-d6) δ [ppm]: −0.149 (0.59), −0.008 (4.82), 0.008 (4.82), 0.146 (0.57), 1.253 (13.91), 1.269 (16.00), 1.279 (10.17), 1.294 (8.34), 1.928 (0.59), 1.947 (0.89), 1.963 (0.97), 1.981 (0.93), 1.997 (0.65), 2.049 (0.91), 2.073 (2.59), 2.328 (0.75), 2.367 (0.93), 2.389 (0.67), 2.409 (0.63), 2.419 (0.79), 2.439 (0.73), 2.460 (0.69), 2.523 (2.71), 2.576 (1.07), 2.591 (1.01), 2.608 (0.89), 2.632 (0.93), 2.649 (1.24), 2.665 (1.24), 2.670 (1.22), 2.711 (1.01), 2.736 (1.15), 2.781 (0.61), 3.114 (1.28), 3.131 (1.44), 3.143 (1.30), 3.160 (0.43), 3.539 (0.41), 3.552 (0.67), 3.570 (1.66), 3.591 (1.92), 3.603 (1.62), 3.613 (1.76), 3.630 (1.07), 3.672 (1.24), 3.688 (0.97), 3.707 (1.52), 3.733 (0.55), 3.771 (0.47), 3.805 (1.15), 3.838 (1.03), 3.863 (0.67), 3.880 (0.55), 3.904 (0.59), 4.100 (0.43), 4.118 (0.83), 4.144 (0.81), 4.390 (0.49), 4.422 (0.45), 4.888 (1.58), 4.902 (1.56), 4.940 (2.21), 4.953 (1.96), 4.984 (4.23), 4.992 (4.19), 5.031 (0.67), 7.050 (1.40), 7.177 (1.40), 7.304 (1.38), 8.099 (2.31), 8.104 (2.47), 8.123 (2.35), 8.128 (2.53), 8.477 (2.98), 8.481 (2.84).

Example 297

(5RS,6RS)-2-[(5-Chloro-3-fluoropyridin-2-yl)methyl]-5-[(3,3-difluoropyrrolidin-1-yl)carbonyl]-6-(trifluoromethyl)-5,6,7,8-tetrahydro[1,2,4]triazolo[4,3-a]pyridin-3(2H)-one (Enantiomer 2)

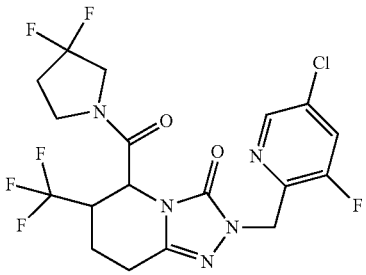 [SMILES: O=C(C1C(C(F)(F)F)CCc2nn(Cc3ncc(Cl)cc3F)c(=O)n21)N1CCC(F)(F)C1]

(5RS,6RS)-2-[(5-Chloro-3-fluoropyridin-2-yl)methyl]-5-[(3,3-difluoropyrrolidin-1-yl)carbonyl]-6-(trifluoromethyl)-5,6,7,8-tetrahydro[1,2,4]triazolo[4,3-a]pyridin-3(2H)-one (diastereomer 1, racemate) was separated by chiral preparative HPLC [sample preparation: 48 mg dissolved in 2 ml of acetonitrile/methanol (1:1); injection volume: 0.20 ml; column: Daicel Chiralcel® IC 5 m, 250×20 mm; eluent: n-heptane/ethanol 50:50; flow rate: 20 ml/min; temperature 30° C.; UV detection: 220 nm]. After the separation, 13.9 mg of enantiomer 1, which eluted first, and 16.2 mg of enantiomer 2, which eluted later, were isolated.
Enantiomer 2:

Analytical chiral HPLC: $R_t$=1.67 min, e.e. =100% [column: Daicel Chiralcel® IC-3 50×4.6 mm; eluent: n-heptane/ethanol 50:50; flow rate: 1 ml/min; UV detection: 220 nm].

LC-MS (Method 3): $R_t$=1.64 min; MS (ESIpos): m/z=484 [M+H]$^+$ $^1$H-NMR (400 MHz, DMSO-d6) δ [ppm]: −0.150 (3.80), 0.146 (2.40), 0.866 (1.00), 0.885 (1.40), 0.904 (0.80), 1.235 (1.00), 1.313 (0.80), 1.946 (1.80), 1.961 (1.80), 1.980 (1.80), 1.998 (1.60), 2.064 (2.20), 2.327 (12.60), 2.365 (16.00), 2.590 (3.00), 2.605 (2.80), 2.626 (2.60), 2.669 (6.80), 2.709 (7.60), 2.736 (2.00), 2.781 (1.20), 3.397 (2.60), 3.569 (2.20), 3.591 (2.00), 3.611 (1.40), 3.640 (1.00), 3.672 (2.00), 3.706 (2.60), 3.773 (1.00), 3.804 (1.80), 3.836 (1.80), 3.861 (1.40), 3.903 (1.20), 3.998 (1.20), 4.117 (1.40), 4.143 (1.40), 4.391 (1.20), 4.415 (1.00), 4.888 (2.60), 4.902 (2.60), 4.941 (3.80), 4.953 (2.60), 4.985 (6.80), 5.031 (1.00), 8.103 (3.00), 8.127 (3.20), 8.482 (3.40).

Example 298

(5RS,6RS)-2-[(5-Chloropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (Diastereomer Mixture; 2 Isomers)

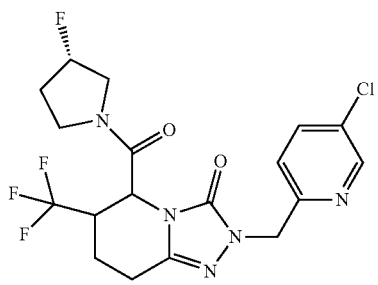 [SMILES: O=C(C1C(C(F)(F)F)CCc2nn(Cc3ccc(Cl)cn3)c(=O)n21)N1CC[C@H](F)C1]

(5RS,6RS)-2-[(5-Chloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (47.0 mg, 125 µmol) was initially charged in THF (2.0 ml), and HBTU (61.5 mg, 162 µmol) and N,N-diisopropylethylamine (65 µl, 370 µmol) were subsequently added. After stirring at room temperature for 15 min, (3S)-3-fluoropyrrolidine hydrochloride (18.8 mg, 150 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 31.0 mg (55% of theory) of the title compound were obtained.

LC-MS (Method 3): $R_t$=1.44 min; MS (ESIpos): m/z=448 [M+H]$^+$ $^1$H-NMR (400 MHz, DMSO-d6) δ [ppm]: −0.149 (1.01), −0.008 (8.66), 0.008 (8.56), 0.146 (1.01), 1.385 (1.47), 1.946 (1.67), 1.968 (2.28), 2.007 (1.67), 2.045 (3.59), 2.060 (3.29), 2.073 (3.14), 2.110 (2.53), 2.144 (1.72), 2.245 (1.52), 2.290 (1.42), 2.328 (2.58), 2.366 (1.87), 2.611 (1.06), 2.669 (3.29), 2.710 (2.73), 2.762 (2.84), 2.805 (1.42), 3.369 (2.28), 3.468 (1.16), 3.509 (1.57), 3.535 (3.34), 3.562 (1.22), 3.615 (1.82), 3.648 (1.57), 3.670 (2.58), 3.740 (1.87), 3.769 (1.42), 3.805 (0.96), 3.824 (1.06), 4.099 (0.96), 4.126 (1.52), 4.150 (1.97), 4.175 (0.86), 4.831 (2.08), 4.847 (2.13), 4.883 (2.94), 4.893 (3.85), 4.915 (6.73), 4.923 (16.00), 4.934 (14.53), 4.954 (3.80), 4.969 (3.24), 4.994 (0.61), 5.142 (0.61), 5.279 (1.82), 5.411 (2.18), 5.513 (0.96), 5.947 (0.51), 7.206 (4.66), 7.218 (3.29), 7.227 (7.80), 7.239 (3.34), 7.249 (3.09), 7.920 (5.57), 7.926 (6.38), 7.941 (5.42), 7.947 (6.08), 8.574 (9.52), 8.580 (8.46).

Example 299

(5RS,6RS)-2-[(5-Chloropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (Isomer 2)

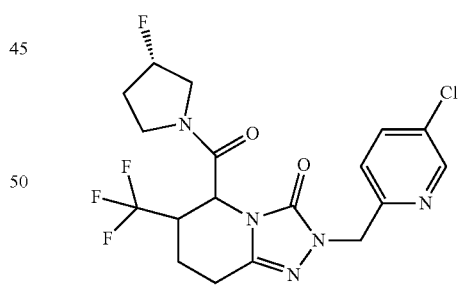

(5RS,7RS)-2-[(5-Chloropyridin-2-yl)methyl]-5-{[(3S)-3-fluoropyrrolidin-1-yl]carbonyl}-6-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 30 mg dissolved in 3 ml of methanol/tert-butyl methyl ether (2:1); injection volume: 1.00 ml; column: Daicel Chiralcel® IB 5 µm, 250×20 mm; eluent: methanol/tert-butyl methyl ether 10:90; flow rate: 20 ml/min; temperature 30° C.; UV detection: 270 nm]. After the separation, 11.1 mg of isomer 1, which eluted first, and 11.3 mg of isomer 2, which eluted later, were isolated.

Isomer 2:

Analytical chiral HPLC: $R_t$=6.44 min, d.e.=100% [column: Daicel Chiralcel® IB 50×4.6 mm; eluent: methanol/tert-butyl methyl ether 10:90; flow rate: 1 ml/min; UV detection: 220 nm].

LC-MS (Method 4): $R_t$=0.77 min; MS (ESIpos): m/z=448 [M+H]$^+$ $^1$H-NMR (400 MHz, DMSO-d6) δ[ppm]: −0.149 (1.82), −0.008 (16.00), 0.008 (15.36), 0.146 (1.87), 1.186 (8.95), 1.427 (2.97), 1.946 (1.36), 1.968 (1.36), 1.981 (1.15), 2.030 (1.40), 2.046 (3.27), 2.060 (3.18), 2.077 (1.91), 2.110 (1.82), 2.126 (1.53), 2.146 (1.49), 2.257 (1.10), 2.292 (1.02), 2.327 (1.49), 2.366 (1.19), 2.524 (2.97), 2.592 (0.64), 2.610 (0.98), 2.633 (1.06), 2.655 (1.87), 2.670 (1.91), 2.689 (0.89), 2.710 (1.78), 2.760 (1.82), 2.775 (2.08), 2.803 (1.02), 2.819 (1.23), 3.370 (1.02), 3.406 (0.98), 3.416 (1.02), 3.469 (1.40), 3.504 (1.70), 3.648 (1.78), 3.670 (3.44), 3.705 (1.70), 3.726 (1.53), 3.744 (2.04), 3.767 (1.32), 3.805 (1.36), 3.824 (1.36), 3.849 (0.59), 4.013 (0.72), 4.036 (0.59), 4.107 (0.68), 4.131 (0.64), 4.831 (3.10), 4.846 (3.06), 4.883 (4.20), 4.892 (4.37), 4.915 (6.49), 4.921 (6.88), 4.932 (11.50), 4.946 (2.38), 4.962 (0.51), 4.974 (0.42), 5.278 (1.53), 5.409 (1.99), 5.532 (1.06), 7.207 (4.20), 7.228 (7.60), 7.249 (3.44), 7.922 (4.12), 7.928 (4.07), 7.943 (3.95), 7.949 (3.90), 8.573 (5.26), 8.579 (5.22).

Example 300

(5RS,6RS)-2-[(5-Chloropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (Diastereomer 1; Racemate)

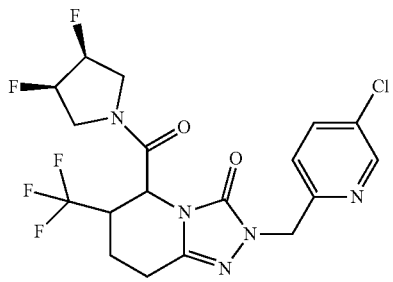 [SMILES: O=C(C1C(C(F)(F)F)CCc2nn(Cc3ccc(Cl)cn3)c(=O)n21)N1C[C@@H](F)[C@@H](F)C1]

(5RS,6RS)-2-[(5-Chloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (47.0 mg, 125 μmol) was initially charged in THF (2.0 ml), and HBTU (61.5 mg, 162 μmol) and N,N-diisopropylethylamine (65 μl, 370 μmol) were subsequently added. After stirring at room temperature for 15 min, (3R,4S)-3,4-difluoropyrrolidine hydrochloride (21.5 mg, 150 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 34.0 mg (59% of theory) of the title compound were obtained.

LC-MS (Method 3): $R_t$=1.50 min; MS (ESIpos): m/z=466 [M+H]$^+$ $^1$H-NMR (400 MHz, DMSO-d6) δ [ppm]: −0.149 (0.67), −0.008 (6.04), 0.008 (5.59), 0.146 (0.67), 1.924 (0.61), 1.938 (1.03), 1.960 (1.34), 1.973 (0.97), 2.006 (1.18), 2.021 (2.58), 2.038 (2.61), 2.053 (1.58), 2.067 (0.94), 2.327 (1.21), 2.366 (1.34), 2.523 (3.25), 2.593 (0.61), 2.613 (0.91), 2.635 (0.91), 2.655 (1.67), 2.669 (2.16), 2.696 (0.94), 2.709 (2.58), 2.725 (0.79), 2.767 (2.37), 2.782 (1.58), 2.811 (1.28), 2.825 (0.70), 3.399 (0.97), 3.411 (1.00), 3.423 (1.00), 3.436 (0.97), 3.473 (0.88), 3.508 (1.28), 3.553 (1.43), 3.563 (1.40), 3.592 (1.15), 3.604 (1.15), 3.633 (0.88), 3.653 (1.24), 3.667 (1.18), 3.686 (0.76), 3.702 (1.21), 3.718 (1.03), 3.727 (1.03), 3.738 (1.31), 3.761 (0.85), 3.774 (0.91), 3.792 (0.85), 3.805 (0.82), 3.828 (1.06), 3.844 (0.85), 3.859 (0.76), 3.871 (0.61), 3.885 (0.64), 3.900 (0.76), 3.914 (0.76), 4.060 (0.67), 4.098 (0.67), 4.365 (0.70), 4.380 (0.76), 4.392 (0.76), 4.403 (0.85), 4.418 (0.76), 4.430 (0.70), 4.446 (0.64), 4.903 (1.03), 4.923 (11.69), 4.935 (16.00), 4.944 (4.98), 4.950 (4.43), 4.978 (0.67), 5.120 (0.49), 5.134 (0.43), 5.244 (0.97), 5.256 (1.09), 5.265 (1.28), 5.273 (1.00), 5.311 (0.76), 5.322 (0.91), 5.358 (1.34), 5.389 (1.09), 5.397 (1.09), 5.462 (0.91), 5.478 (0.91), 7.210 (3.28), 7.225 (3.89), 7.231 (3.83), 7.245 (4.01), 7.923 (3.73), 7.930 (3.58), 7.945 (3.64), 7.948 (3.46), 8.573 (4.61), 8.579 (4.37).

Example 301

(5RS,6RS)-2-[(5-Chloropyridin-2-yl)methyl]-5-{[(3R,4S)-3,4-difluoropyrrolidin-1-yl]carbonyl}-6-(trifluoromethyl)-5,6,7,8-tetrahydro[1,2,4]triazolo[4,3-a]pyridin-3(2H)-one (Enantiomer 2)

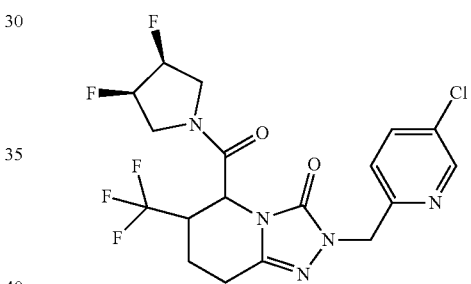

(5RS,6RS)-2-[(5-Chloropyridin-2-yl)methyl]-3-oxo-6-(trifluoromethyl)-2,3,5,6,7,8-hexahydro[1,2,4]triazolo[4,3-a]pyridine-5-carboxylic acid (diastereomer 1, racemate) was separated by chiral preparative HPLC [sample preparation: 34 mg dissolved in 3 ml of methanol/tert-butyl methyl ether (3:1); injection volume: 1.00 ml; column: Daicel Chiralcel® IB 5 μm, 250×20 mm; eluent: methanol/tert-butyl methyl ether 10:90; flow rate: 15 ml/min; temperature 30° C.; UV detection: 270 nm]. After the separation, 15.3 mg of enantiomer 1, which eluted first, and 14.3 mg of enantiomer 2, which eluted later, were isolated.

Enantiomer 2:

Analytical chiral HPLC: $R_t$=5.58 min, e.e. =100% [column: Daicel Chiralcel® IB 50×4.6 mm; eluent: methanol/tert-butyl methyl ether 10:90; flow rate: 1 ml/min; UV detection: 220 nm].

LC-MS (Method 4): $R_t$=0.80 min; MS (ESIpos): m/z=466 [M+H]$^+$ $^1$H-NMR (400 MHz, DMSO-d6) δ[ppm]: −0.149 (1.57), −0.008 (13.32), 0.008 (12.83), 0.146 (1.53), 1.186 (13.39), 1.427 (0.94), 1.925 (0.52), 1.938 (0.87), 1.960 (1.15), 1.973 (0.80), 2.007 (1.08), 2.022 (2.54), 2.038 (2.57), 2.053 (1.57), 2.078 (0.97), 2.327 (1.11), 2.366 (0.90), 2.593 (0.56), 2.612 (0.90), 2.636 (0.90), 2.655 (1.60), 2.670 (2.02), 2.695 (0.90), 2.710 (2.26), 2.769 (2.19), 2.783 (1.43), 2.812 (1.18), 3.423 (0.97), 3.437 (0.90), 3.472 (0.80), 3.508 (1.18), 3.555 (1.25), 3.593 (1.04), 3.632 (0.87), 3.653 (1.18), 3.668 (1.18), 3.687 (0.70), 3.702 (1.11), 3.718 (0.94), 3.727 (0.80), 3.739 (1.22), 3.761 (0.63), 3.774 (0.70), 3.793 (0.80), 3.805 (0.80), 3.828 (1.01), 3.846 (0.80), 3.860 (0.73), 3.885 (0.63), 3.900 (0.80), 3.914 (0.63), 4.061 (0.63), 4.098 (0.66), 4.367 (0.56), 4.380 (0.70), 4.392 (0.70), 4.408 (0.87), 4.418 (0.73), 4.430 (0.70), 4.446 (0.56), 4.923 (11.65), 4.935 (16.00), 4.946 (6.99), 5.244 (0.90), 5.256 (0.97), 5.266 (1.08), 5.322 (0.77), 5.358 (1.25), 5.389 (0.97), 5.440 (0.66), 5.463 (0.87), 5.479 (0.83), 7.211 (3.41), 7.225 (3.58), 7.231 (3.90), 7.246 (3.62), 7.924 (3.44), 7.927 (3.41), 7.930 (3.34), 7.945 (3.27), 7.949 (3.23), 7.951 (3.20), 8.573 (5.39), 8.579 (5.25).

Example 302

(5RS,6RS)-5-[(3-Fluoroazetidin-1-yl)carbonyl]-2-{[3-fluoro-2-(trifluoromethyl)pyridin-4-yl]methyl}-6-(trifluoromethyl)-5,6,7,8-tetrahydro[1,2,4]triazolo[4,3-a]pyridin-3(2H)-one (Diastereomer 1, Racemate)

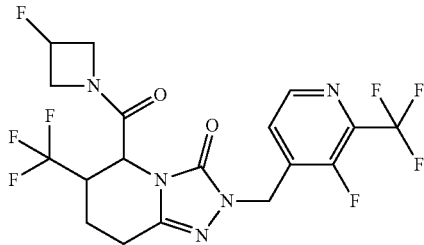 [SMILES: O=C(C1C(C(F)(F)F)CCc2nn(Cc3ccnc(C(F)(F)F)c3F)c(=O)n21)N1CC(F)C1]

(5RS,6RS)-2-{[3-Fluoro-2-(trifluoromethyl)pyridin-4-yl]methyl}-3-oxo-6-(trifluoromethyl)-2,3,5,6,7,8-hexahydro[1,2,4]triazolo[4,3-a]pyridine-5-carboxylic acid (diastereomer mixture; 4 isomers) (96.0 mg, 224 µmol) was initially charged in THF (2.0 ml), and HBTU (111 mg, 291 µmol) and N,N-diisopropylethylamine (120 µl, 670 µmol) were subsequently added. After stirring at room temperature for 15 min, 3-fluoroazetidine hydrochloride (30.0 mg, 269 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 25.0 mg (23% of theory) of the title compound were obtained.

LC-MS (Method 3): $R_t$=1.61 min; MS (ESIpos): m/z=486 [M+H]$^+$ $^1$H-NMR (400 MHz, DMSO-d6) δ [ppm]: −0.149 (1.95), −0.008 (16.00), 0.008 (14.87), 0.146 (2.03), 1.995 (1.95), 2.073 (2.18), 2.327 (3.15), 2.366 (3.00), 2.523 (7.21), 2.670 (3.68), 2.710 (3.31), 2.767 (2.18), 2.783 (1.20), 2.812 (1.05), 3.379 (1.13), 3.973 (1.13), 4.000 (1.20), 4.032 (1.05), 4.229 (1.13), 4.252 (1.43), 4.560 (0.90), 4.654 (2.85), 4.666 (4.36), 4.677 (2.63), 4.867 (0.68), 5.086 (6.91), 5.100 (5.93), 5.371 (0.83), 5.560 (0.90), 7.566 (2.70), 7.579 (5.18), 7.592 (2.70), 8.571 (5.18), 8.583 (5.11).

Example 303

(5RS,6RS)-5-[(3-Fluoroazetidin-1-yl)carbonyl]-2-{[3-fluoro-2-(trifluoromethyl)pyridin-4-yl]methyl}-6-(trifluoromethyl)-5,6,7,8-tetrahydro[1,2,4]triazolo[4,3-a]pyridin-3(2H)-one (Enantiomer 1)

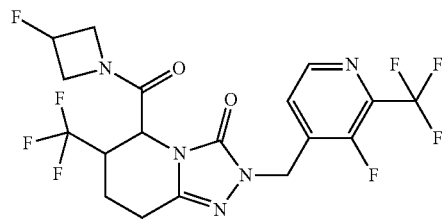 [SMILES: O=C(C1C(C(F)(F)F)CCc2nn(Cc3ccnc(C(F)(F)F)c3F)c(=O)n21)N1CC(F)C1]

(5RS,6RS)-5-[(3-Fluoroazetidin-1-yl)carbonyl]-2-{[3-fluoro-2-(trifluoromethyl)pyridin-4-yl]methyl}-6-(trifluoromethyl)-5,6,7,8-tetrahydro[1,2,4]triazolo[4,3-a]pyridin-3(2H)-one (diastereomer 1, racemate) was separated by chiral preparative HPLC [sample preparation: 23 mg dissolved in isopropanol/dichloromethane/n-heptane (3:1:2); injection volume: 0.50 ml; column: Daicel Chiralcel® IB 5 µm, 250×30 mm; eluent: n-heptane/isopropanol 60:40; flow rate: 60 ml/min; temperature 40° C.; UV detection: 220 nm]. After the separation, 10.5 mg of enantiomer 1, which eluted first, and 11.8 mg of enantiomer 2, which eluted later, were isolated.

Enantiomer 1:

Analytical chiral HPLC: $R_t$=4.70 min, e.e. =100% [column: Daicel Chiralcel® IB-3 50×4.6 mm; eluent: n-heptane/isopropanol 60:40; flow rate: 1 ml/min; UV detection: 220 nm].

LC-MS (Method 3): $R_t$=1.59 min; MS (ESIpos): m/z=486 [M+H]$^+$ $^1$H-NMR (400 MHz, DMSO-d6) δ [ppm]: −0.149 (1.52), −0.008 (16.00), 0.146 (1.68), 1.994 (2.48), 2.047 (2.08), 2.327 (2.96), 2.366 (3.04), 2.670 (4.24), 2.710 (3.76), 2.767 (2.96), 2.811 (1.68), 3.968 (1.44), 3.999 (1.52), 4.030 (1.44), 4.229 (1.60), 4.252 (2.08), 4.567 (1.12), 4.625 (1.04), 4.654 (4.16), 4.666 (5.92), 4.679 (3.44), 4.815 (0.80), 5.087 (9.44), 5.100 (8.16), 5.369 (1.12), 5.560 (0.96), 7.566 (3.52), 7.579 (6.40), 7.592 (3.84), 8.571 (6.48), 8.583 (6.40).

Example 304

(5RS,6RS)-5-[(3-Fluoroazetidin-1-yl)carbonyl]-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer 1, Racemate)

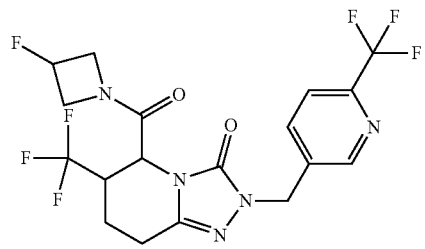 [SMILES: O=C(C1C(C(F)(F)F)CCc2nn(Cc3ccc(C(F)(F)F)nc3)c(=O)n21)N1CC(F)C1]

(5RS,6RS)-3-Oxo-6-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (54.0 mg, 132 μmol) was initially charged in THF (2.0 ml), and HBTU (64.9 mg, 171 mol) and N,N-diisopropylethylamine (69 μl, 390 μmol) were subsequently added. After stirring at room temperature for 15 min, 3-fluoroazetidine hydrochloride (17.6 mg, 158 mol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 47.9 mg (78% of theory) of the title compound were obtained.

LC-MS (Method 3): $R_t$=1.52 min; MS (ESIpos): m/z=468 [M+H]$^+$ $^1$H-NMR (400 MHz, DMSO-d6) δ[ppm]: −0.149 (1.77), −0.008 (16.00), 0.008 (12.72), 0.146 (1.77), 0.886 (0.42), 1.969 (1.43), 1.983 (1.77), 2.040 (1.52), 2.073 (1.43), 2.327 (2.78), 2.366 (3.54), 2.523 (7.75), 2.669 (4.04), 2.710 (3.12), 2.756 (1.85), 2.771 (1.18), 2.797 (0.93), 3.965 (0.93), 3.999 (0.93), 4.028 (0.84), 4.065 (0.67), 4.224 (1.01), 4.246 (1.09), 4.272 (1.18), 4.304 (1.09), 4.569 (0.67), 4.642 (2.53), 4.656 (3.87), 4.666 (2.61), 4.821 (0.51), 5.030 (7.33), 5.044 (7.49), 5.418 (0.67), 5.560 (0.67), 7.921 (12.46), 8.652 (4.63).

Example 305

(5RS,6RS)-5-[(3-Fluoroazetidin-1-yl)carbonyl]-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (Enantiomer 2)

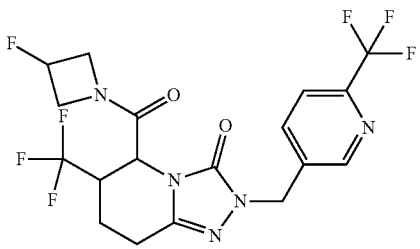 [SMILES: O=C(C1C(C(F)(F)F)CCc2nn(Cc3ccc(C(F)(F)F)nc3)c(=O)n21)N1CC(F)C1]

(5RS,6RS)-5-[(3-Fluoroazetidin-1-yl)carbonyl]-6-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer 1; racemate) was separated by chiral preparative HPLC [sample preparation: 46 mg dissolved in acetonitrile/ethanol (3:1); injection volume: 0.30 ml; column: Daicel Chiralcel® IE 5 μm, 250×30 mm; eluent: n-heptane/ethanol 50:50; flow rate: 15 ml/min; temperature 30° C.; UV detection: 210 nm]. After the separation, 16.9 mg of isomer 1, which eluted first, and 21.7 mg of isomer 2, which eluted later, were isolated.

Enantiomer 2:

Analytical chiral HPLC: $R_t$=2.09 min, e.e. =100% [column: Daicel Chiralcel® IE-3 50×4.6 mm; eluent: n-heptane/ethanol 50:50; flow rate: 1 ml/min; UV detection: 220 nm].

LC-MS (Method 4): $R_t$=0.80 min; MS (ESIpos): m/z=468 [M+H]$^+$ $^1$H-NMR (400 MHz, DMSO-d6) δ[ppm]: −0.149 (0.84), 0.008 (5.48), 0.146 (0.75), 1.100 (0.66), 1.235 (1.33), 1.950 (1.51), 1.968 (1.99), 1.984 (2.44), 2.001 (1.63), 2.040 (1.99), 2.327 (1.45), 2.366 (1.36), 2.524 (6.48), 2.670 (3.22), 2.710 (1.51), 2.738 (1.60), 2.754 (2.71), 2.771 (1.66), 2.797 (1.33), 2.813 (0.69), 3.936 (0.75), 3.967 (1.27), 3.998 (1.36), 4.030 (1.18), 4.061 (0.84), 4.224 (1.39), 4.244 (1.54), 4.274 (1.66), 4.304 (1.51), 4.471 (0.75), 4.485 (0.78), 4.526 (0.72), 4.540 (0.69), 4.567 (0.96), 4.595 (0.72), 4.643 (3.59), 4.655 (5.06), 4.666 (3.28), 4.821 (0.72), 4.849 (0.72), 4.873 (0.66), 5.030 (9.94), 5.045 (9.76), 5.372 (0.90), 5.418 (0.87), 5.515 (0.90), 5.561 (0.87), 7.922 (16.00), 8.653 (6.24).

Example 306

(5RS,6RS)-2-[(3,5-Dichloropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (Diastereomer 1, Racemate)

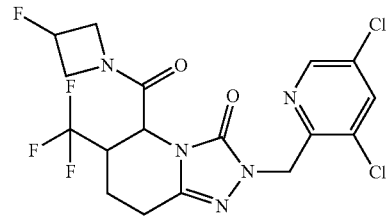 [SMILES: O=C(C1C(C(F)(F)F)CCc2nn(Cc3ncc(Cl)cc3Cl)c(=O)n21)N1CC(F)C1]

(5RS,6RS)-2-[(3,5-Dichloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 122 μmol) was initially charged in THF (2.0 ml), and HBTU (60.0 mg, 158 mol) and N,N-diisopropylethylamine (64 μl, 360 μmol) were subsequently added. After stirring at room temperature for 15 min, 3-fluoroazetidine hydrochloride (16.3 mg, 146 mol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 45.3 mg (80% of theory) of the title compound were obtained.

LC-MS (Method 4): $R_t$=0.82 min; MS (ESIpos): m/z=468 [M+H]$^+$

Example 307

(5RS,6RS)-2-[(3,5-Dichloropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (Enantiomer 1)

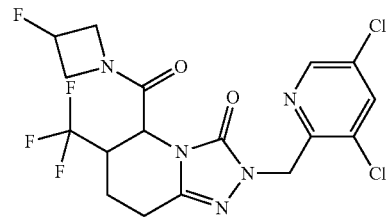 [SMILES: O=C(C1C(C(F)(F)F)CCc2nn(Cc3ncc(Cl)cc3Cl)c(=O)n21)N1CC(F)C1]

(5RS,6RS)-2-[(3,5-Dichloropyridin-2-yl)methyl]-5-[(3-fluoroazetidin-1-yl)carbonyl]-6-(trifluoromethyl)-5,6,7,8- tetrahydro[1,2,4]triazolo[4,3-a]pyridin-3(2H)-one (diastereomer 1; racemate) was separated by chiral preparative HPLC [sample preparation: 40 mg dissolved in acetonitrile/ethanol (3:1); injection volume: 0.40 ml; column: Daicel Chiralcel® IE 5 μm, 250×30 mm; eluent: n-heptane/ethanol 50:50; flow rate: 15 ml/min; temperature 25° C.; UV detection: 210 nm]. After the separation, 17.6 mg of enantiomer 1, which eluted first, and 18.1 mg of enantiomer 2, which eluted later, were isolated.

Enantiomer 1:

Analytical chiral HPLC: $R_t$=2.65 min, e.e. =100% [column: Daicel Chiralcel® IE-3 50×4.6 mm; eluent: n-heptane/ethanol 50:50; flow rate: 1 ml/min; UV detection: 220 nm].

LC-MS (Method 4): $R_t$=0.82 min; MS (ESIpos): m/z=468 [M+H]$^+$ $^1$H-NMR (400 MHz, DMSO-d6) δ [ppm]: −0.149 (1.90), −0.008 (16.00), 0.008 (14.18), 0.146 (1.90), 1.235 (0.78), 1.964 (1.56), 2.064 (1.56), 2.327 (3.46), 2.366 (3.29), 2.523 (7.87), 2.669 (3.37), 2.710 (4.06), 2.728 (2.25), 2.745 (1.21), 2.772 (1.21), 3.958 (1.12), 3.984 (1.04), 4.018 (1.04), 4.243 (1.73), 4.543 (0.86), 4.609 (3.03), 4.623 (3.55), 4.631 (2.77), 4.800 (0.69), 5.037 (9.51), 5.046 (7.26), 5.411 (0.78), 5.548 (0.69), 8.258 (5.97), 8.263 (6.31), 8.556 (4.06).

Example 308

(5RS,6RS)-2-[(5-Chloro-3-fluoropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (Diastereomer 1; Racemate)

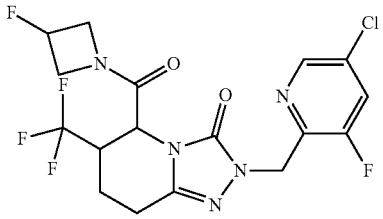 [SMILES: O=C(C1C(C(F)(F)F)CCc2nn(Cc3ncc(Cl)cc3F)c(=O)n21)N1CC(F)C1]

(5RS,6RS)-2-[(5-Chloro-3-fluoropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (50.0 mg, 127 μmol) was initially charged in THF (2.0 ml), and HBTU (62.5 mg, 165 mol) and N,N-diisopropylethylamine (66 μl, 380 μmol) were subsequently added. After stirring at room temperature for 15 min, 3-fluoroazetidine hydrochloride (17.0 mg, 152 mol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 37.0 mg (65% of theory) of the title compound were obtained.

LC-MS (Method 3): $R_t$=1.46 min; MS (ESIpos): m/z=452 [M+H]$^+$ $^1$H-NMR (400 MHz, DMSO-d6) δ [ppm]: −0.149 (1.64), −0.008 (15.18), 0.008 (15.69), 0.146 (1.85), 1.921 (2.87), 1.942 (3.28), 1.956 (4.00), 2.053 (3.28), 2.327 (3.08), 2.366 (2.56), 2.589 (2.36), 2.635 (3.79), 2.650 (4.00), 2.669 (4.31), 2.710 (4.51), 2.720 (5.54), 2.735 (3.49), 2.764 (2.56), 3.925 (1.54), 3.957 (2.46), 3.987 (2.46), 4.017 (2.26), 4.048 (1.44), 4.215 (2.36), 4.240 (2.87), 4.268 (2.77), 4.297 (2.87), 4.465 (1.44), 4.555 (1.74), 4.601 (6.67), 4.610 (8.62), 4.616 (8.82), 4.766 (1.13), 4.779 (1.33), 4.804 (1.44), 4.841 (1.33), 4.856 (1.44), 4.990 (16.00), 5.000 (14.46), 5.415 (1.85), 5.549 (1.74), 8.104 (8.31), 8.129 (8.41), 8.476 (11.59).

Example 309

(5RS,6RS)-2-[(5-Chloro-3-fluoropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (Enantiomer 2)

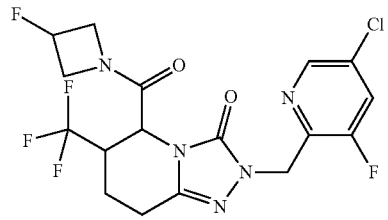 [SMILES: O=C(C1C(C(F)(F)F)CCc2nn(Cc3ncc(Cl)cc3F)c(=O)n21)N1CC(F)C1]

(5RS,6RS)-2-[(5-Chloro-3-fluoropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (diastereomer 1, racemate) was separated by chiral preparative HPLC [sample preparation: 36 mg dissolved in 3 ml of ethanol; injection volume: 0.80 ml; column: Daicel Chiralcel® OX-H 5 μm, 250×20 mm; eluent: ethanol+0.2% diethylamine; flow rate: 15 ml/min; temperature 55° C.; UV detection: 235 nm]. After the separation, 13.7 mg of enantiomer 1, which eluted first, and 11.7 mg of enantiomer 2, which eluted later, were isolated.

Enantiomer 2:

Analytical chiral HPLC: $R_t$=7.56 min, e.e. =100% [column: Daicel Chiralcel® OZ-H 50×4.6 mm; eluent: n-heptane/ethanol 70:30+0.2% diethylamine; flow rate: 1 ml/min; UV detection: 220 nm].

LC-MS (Method 3): $R_t$=1.46 min; MS (ESIpos): m/z=452 [M+H]$^+$ $^1$H-NMR (400 MHz, DMSO-d6) δ [ppm]: −0.149 (1.44), −0.008 (13.25), 0.146 (1.40), 1.236 (0.90), 1.922 (2.61), 1.941 (3.15), 1.956 (3.65), 1.972 (2.25), 2.052 (3.34), 2.327 (2.03), 2.366 (1.94), 2.590 (2.03), 2.634 (3.61), 2.650 (3.70), 2.669 (3.02), 2.703 (2.93), 2.710 (3.65), 2.719 (5.18), 2.735 (3.11), 2.763 (2.52), 2.778 (1.31), 3.870 (0.41), 3.927 (1.22), 3.959 (2.34), 3.986 (2.52), 4.018 (2.16), 4.055 (1.44), 4.172 (1.08), 4.184 (1.26), 4.214 (2.12), 4.238 (2.66), 4.266 (2.75), 4.295 (2.66), 4.314 (1.26), 4.343 (0.90), 4.467 (1.31), 4.481 (1.35), 4.518 (1.26), 4.533 (1.31), 4.552 (1.62), 4.583 (1.08), 4.601 (6.40), 4.610 (8.34), 4.616 (8.88), 4.622 (7.44), 4.790 (0.99), 4.805 (1.17), 4.832 (1.17), 4.856 (1.17), 4.884 (0.95), 4.990 (16.00), 5.000 (14.38), 5.371 (1.53), 5.414 (1.58), 5.513 (1.53), 5.556 (1.49), 8.104 (6.81), 8.128 (6.99), 8.476 (8.16).

Example 310

(5RS,6RS)-2-[(5-Chloropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (Diastereomer 1, Racemate)

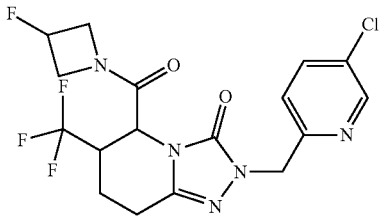 [SMILES: O=C(C1C(C(F)(F)F)CCc2nn(Cc3ccc(Cl)cn3)c(=O)n21)N1CC(F)C1]

(5RS,6RS)-2-[(5-Chloropyridin-2-yl)methyl]-3-oxo-6-(trifluoromethyl)-2,3,5,6,7,8-hexahydro[1,2,4]triazolo[4,3-a]pyridine-5-carboxylic Acid (Diastereomer Mixture; 4 Isomers) (47.0 mg, 125 µmol) was initially charged in THF (2.0 ml), and HBTU (61.5 mg, 162 mol) and N,N-diisopropylethylamine (65 µl, 370 µmol) were subsequently added. After stirring at room temperature for 15 min, 3-fluoroazetidine hydrochloride (16.7 mg, 150 mol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 30.0 mg (55% of theory) of the title compound were obtained.

LC-MS (Method 3): $R_t$=1.40 min; MS (ESIpos): m/z=434 [M+H]$^+$ $^1$H-NMR (400 MHz, DMSO-d6) δ [ppm]: −0.149 (2.09), −0.008 (15.63), 0.008 (16.00), 0.146 (2.02), 1.953 (1.79), 1.973 (2.09), 1.986 (2.54), 2.073 (3.44), 2.327 (2.32), 2.366 (2.09), 2.670 (4.34), 2.710 (2.32), 2.734 (1.87), 2.751 (3.29), 2.768 (2.17), 2.794 (1.72), 2.811 (0.97), 3.935 (0.90), 3.965 (1.57), 3.994 (1.64), 4.023 (1.50), 4.060 (0.82), 4.192 (0.97), 4.224 (1.64), 4.247 (2.09), 4.282 (1.64), 4.304 (1.57), 4.487 (0.90), 4.526 (0.90), 4.542 (0.90), 4.567 (1.20), 4.633 (4.26), 4.642 (4.93), 4.647 (5.23), 4.655 (4.56), 4.780 (1.35), 4.794 (1.72), 4.879 (1.20), 4.931 (13.23), 4.943 (13.08), 4.989 (0.97), 5.412 (1.20), 5.553 (1.12), 7.226 (9.05), 7.248 (9.87), 7.928 (4.64), 7.944 (4.26), 8.575 (7.03), 8.581 (3.96).

Example 311

(5RS,6RS)-2-[(5-Chloropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (Enantiomer 2)

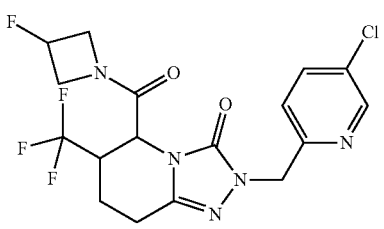 [SMILES: O=C(C1C(C(F)(F)F)CCc2nn(Cc3ccc(Cl)cn3)c(=O)n21)N1CC(F)C1]

(5RS,6RS)-2-[(5-Chloropyridin-2-yl)methyl]-5-[(3-fluoroazetidin-1-yl)carbonyl]-6-(trifluoromethyl)-5,6,7,8-tetrahydro[1,2,4]triazolo[4,3-a]pyridin-3(2H)-one (diastereomer 1; racemate) was separated by chiral preparative HPLC [sample preparation: 30 mg dissolved in 3 ml of ethanol/acetonitrile (1:2); injection volume: 0.25 ml; column: Daicel Chiralcel® IC 5 µm, 250×20 mm; eluent: n-heptane/ethanol (50:50); flow rate: 15 ml/min; temperature 25° C.; UV detection: 210 nm]. After the separation, 12.30 mg of enantiomer 1, which eluted first, and 12.1 mg of enantiomer 2, which eluted later, were isolated.

Enantiomer 2:

Analytical chiral HPLC: $R_t$=2.51 min, e.e. =100% [column: Daicel Chiralcel® IC-3 50×4.6 mm; eluent: n-heptane/ethanol 50:50; flow rate: 1 ml/min; UV detection: 220 nm].

LC-MS (Method 3): $R_t$=140.00 min; MS (ESIpos): m/z=433 [M+H]$^+$ $^1$H-NMR (400 MHz, DMSO-d6) δ [ppm]: −0.149 (0.76), −0.008 (7.47), 0.008 (6.94), 0.146 (0.88), 1.234 (0.53), 1.953 (1.94), 1.971 (2.29), 1.986 (2.82), 2.073 (2.94), 2.327 (2.00), 2.366 (1.53), 2.670 (4.88), 2.710 (1.94), 2.735 (2.18), 2.751 (3.94), 2.767 (2.41), 2.794 (1.94), 3.932 (0.94), 3.964 (1.88), 3.995 (2.06), 4.023 (1.82), 4.058 (1.18), 4.192 (1.00), 4.223 (2.00), 4.247 (2.47), 4.278 (1.82), 4.303 (1.88), 4.475 (1.00), 4.489 (1.06), 4.528 (1.00), 4.563 (1.24), 4.633 (5.24), 4.647 (6.41), 4.655 (5.59), 4.880 (0.94), 4.931 (15.94), 4.943 (16.00), 5.414 (1.18), 5.555 (1.24), 7.227 (10.59), 7.248 (11.29), 7.927 (5.18), 7.947 (4.94), 8.575 (9.65).

Example 312

(5RS,7RS)-5-[(3,3-Difluoropyrrolidin-1-yl)carbonyl]-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer 1; Racemate)

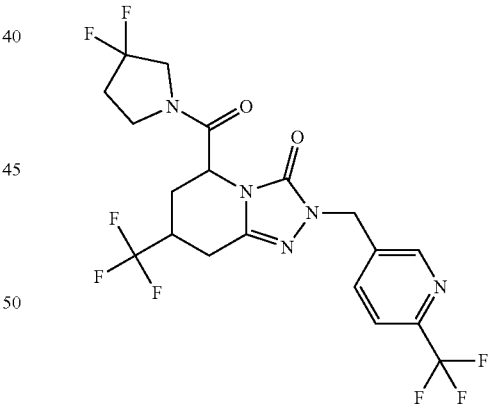

(5RS,7RS)-3-Oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (100 mg, 90% purity, 219 µmol) was initially charged in THF (3.0 ml), and HBTU (108 mg, 285 µmol) and N,N-diisopropylethylamine (110 µl, 660 µmol) were subsequently added. After stirring at room temperature for 15 min, 3,3-difluoropyrrolidine hydrochloride (37.7 mg, 263 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient) and diastereomer 1 was isolated. The product-containing fractions were concentrated under reduced pressure, and 78.2 mg (71% of theory) of the title compound were obtained.

LC-MS (Method 3): $R_t$=1.69 min; MS (ESIpos): m/z=500 [M+H]$^+$ $^1$H-NMR (400 MHz, DMSO-d6) δ [ppm]: −0.149 (0.71), −0.008 (5.74), 0.146 (0.71), 2.138 (0.40), 2.156 (0.79), 2.173 (0.82), 2.198 (0.97), 2.229 (0.73), 2.245 (0.68), 2.270 (1.30), 2.290 (1.46), 2.327 (1.37), 2.366 (0.71), 2.376 (0.51), 2.397 (0.97), 2.427 (1.24), 2.444 (1.13), 2.462 (0.79), 2.565 (1.92), 2.583 (1.48), 2.602 (1.02), 2.670 (0.88), 2.688 (1.06), 2.696 (1.02), 2.717 (1.41), 2.726 (2.30), 2.735 (1.48), 2.757 (1.63), 2.764 (1.68), 2.895 (1.15), 2.927 (1.08), 2.979 (2.12), 3.019 (1.61), 3.541 (0.44), 3.552 (1.04), 3.571 (2.21), 3.586 (2.16), 3.603 (1.28), 3.714 (0.99), 3.756 (1.28), 3.786 (1.52), 3.821 (1.17), 3.901 (1.04), 3.919 (2.36), 3.936 (2.58), 3.955 (1.06), 4.135 (0.88), 4.163 (0.73), 4.178 (1.28), 4.205 (1.35), 4.238 (0.90), 4.968 (1.70), 4.982 (1.63), 5.019 (1.74), 5.048 (16.00), 7.920 (15.23), 7.943 (0.93), 8.642 (5.16), 8.678 (0.77).

Example 313

(5RS,7RS)-5-[(3,3-Difluoropyrrolidin-1-yl)carbonyl]-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Enantiomer 1)

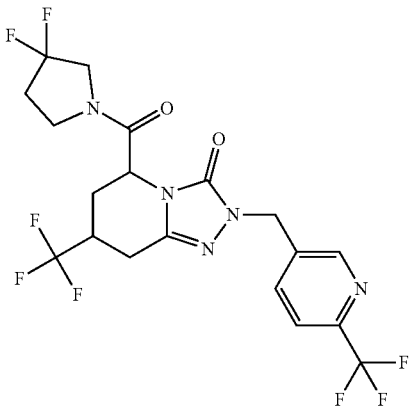 [SMILES: O=C(C1CC(C(F)(F)F)Cc2nn(Cc3ccc(C(F)(F)F)nc3)c(=O)n21)N1CCC(F)(F)C1]

(5RS,7RS)-5-[(3,3-Difluoropyrrolidin-1-yl)carbonyl]-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer 1; racemate) was separated by chiral preparative HPLC [sample preparation: 77 mg dissolved in 2 ml of ethanol; injection volume: 0.50 ml; column: Daicel Chiralcel® OX-H 5 μm, 250×20 mm; eluent: n-heptane/ethanol (50:50); flow rate: 20 ml/min; temperature 40° C.; UV detection: 220 nm]. After the separation, 24.0 mg of isomer 1, which eluted first, and 28.8 mg of isomer 2, which eluted later, were isolated.

Isomer 1:

Analytical chiral HPLC: $R_t$=1.33 min, e.e. =100% [column: Daicel Chiralcel® IE-3 50×4.6 mm; eluent: n-heptane/ethanol 50:50; flow rate: 1 ml/min; UV detection: 220 nm].

LC-MS (Method 3): $R_t$=1.69 min; MS (ESIpos): m/z=500 [M+H]$^+$ $^1$H-NMR (400 MHz, DMSO-d6) δ [ppm]: −0.150 (0.83), −0.008 (6.23), 0.008 (6.13), 0.146 (0.65), 2.156 (0.86), 2.197 (0.99), 2.228 (0.77), 2.244 (0.74), 2.268 (1.33), 2.287 (1.39), 2.327 (2.87), 2.366 (1.20), 2.396 (0.92), 2.425 (1.26), 2.444 (1.26), 2.522 (6.17), 2.565 (1.97), 2.582 (1.29), 2.669 (2.50), 2.674 (1.94), 2.687 (1.05), 2.710 (1.45), 2.716 (1.42), 2.725 (2.16), 2.734 (1.33), 2.756 (1.66), 2.764 (1.45), 2.902 (1.02), 2.979 (2.00), 3.018 (1.48), 3.551 (1.02), 3.570 (2.03), 3.584 (1.54), 3.602 (1.02), 3.714 (0.92), 3.754 (1.11), 3.785 (1.33), 3.820 (1.02), 3.901 (0.96), 3.918 (2.19), 3.936 (2.40), 3.954 (0.92), 4.135 (0.77), 4.163 (0.71), 4.179 (1.17), 4.205 (1.29), 4.237 (0.77), 4.968 (1.54), 4.982 (1.57), 5.047 (16.00), 7.917 (14.49), 7.920 (15.35), 8.642 (5.15).

Example 314

(5RS,7RS)-2-[(5-Chloropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture; 4 Isomers)

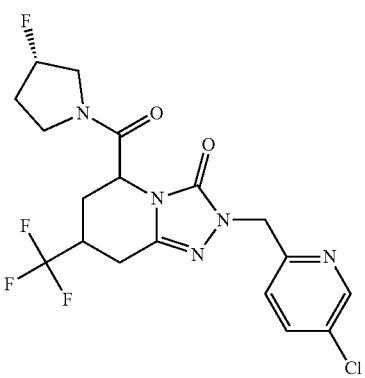 [SMILES: O=C(C1CC(C(F)(F)F)Cc2nn(Cc3ccc(Cl)cn3)c(=O)n21)N1CC[C@H](F)C1]

(5RS,7RS)-2-[(5-Chloropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (206 mg, 546 μmol) was initially charged in THF (8.0 ml), and HBTU (269 mg, 710 μmol) and N,N-diisopropylethylamine (290 μl, 1.6 mmol) were subsequently added. After stirring at room temperature for 15 min, (3S)-3-fluoropyrrolidine hydrochloride (82.3 mg, 656 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 221 mg (90% of theory) of the title compound were obtained.

LC-MS (Method 3): $R_t$=1.44 min; MS (ESIpos): m/z=448 [M+H]$^+$ $^1$H-NMR (400 MHz, DMSO-d6) δ[ppm]: −0.150 (1.37), −0.009 (12.42), 0.007 (13.00), 0.146 (1.37), 1.055 (0.81), 2.072 (16.00), 2.175 (2.57), 2.240 (4.40), 2.291 (2.67), 2.327 (1.82), 2.689 (2.15), 2.709 (2.80), 2.719 (3.42), 2.730 (1.99), 2.748 (2.05), 2.976 (4.40), 3.009 (2.90), 3.353 (1.86), 3.371 (1.79), 3.400 (1.30), 3.442 (0.91), 3.512 (0.81), 3.572 (1.73), 3.618 (1.96), 3.638 (2.84), 3.673 (2.93), 3.691 (1.89), 3.802 (0.98), 3.854 (1.66), 3.897 (1.21), 3.995 (1.99), 4.021 (1.34), 4.890 (1.37), 4.932 (7.20), 4.940 (10.49), 4.947 (10.33), 4.951 (10.20), 4.974 (1.76), 4.991 (2.90), 5.025 (1.43), 5.038 (1.40), 5.081 (1.50), 5.267 (1.60), 5.358 (0.91), 5.401 (1.96), 5.488 (0.88), 7.221 (5.70), 7.242 (6.19), 7.286 (0.85), 7.919 (6.19), 7.925 (6.62), 7.940 (6.00), 7.946 (6.45), 8.574 (6.65), 8.580 (6.71).

Example 315

(5RS,7RS)-2-[(5-Chloropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

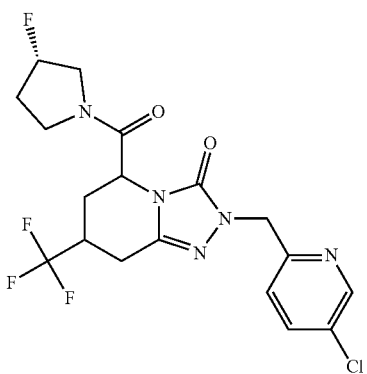 [SMILES: O=C(C1CC(C(F)(F)F)Cc2nn(Cc3ccc(Cl)cn3)c(=O)n21)N1CC[C@H](F)C1]

(5RS,7RS)-2-[(5-Chloropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture; 4 isomers) was separated by chiral preparative HPLC [sample preparation: 218 mg dissolved in 5 ml of ethanol/n-heptane (3:2); injection volume: 0.23 ml; column: Daicel Chiralcel® IC 5 μm, 250×20 mm; eluent: n-heptane/ethanol (50:50); flow rate: 15 ml/min; temperature 40° C.; UV detection: 220 nm]. After the separation, 100 mg of isomer 1, which eluted first, and 90 mg of isomer 2, which eluted later, were isolated.

Isomer 2:

Analytical chiral HPLC: $R_t$=4.14 min, d.e.=100% [column: Daicel Chiralcel® IC-3 50×4.6 mm; eluent: n-heptane/ethanol 50:50; flow rate: 1 ml/min; UV detection: 220 nm].

LC-MS (Method 3): $R_t$=1.44 min; MS (ESIpos): m/z=448 [M+H]$^+$ $^1$H-NMR (400 MHz, DMSO-d6) δ[ppm]: −0.149 (1.94), −0.008 (16.00), 0.008 (15.60), 0.146 (1.94), 1.234 (0.71), 2.002 (0.62), 2.140 (1.85), 2.175 (3.31), 2.211 (2.03), 2.245 (2.95), 2.295 (3.92), 2.327 (3.31), 2.366 (1.41), 2.670 (2.64), 2.709 (2.95), 2.718 (2.95), 2.732 (1.98), 2.748 (1.85), 2.764 (1.45), 2.977 (5.55), 3.011 (3.57), 3.022 (2.25), 3.343 (1.50), 3.355 (1.72), 3.372 (1.59), 3.382 (1.32), 3.399 (1.50), 3.434 (1.32), 3.442 (1.28), 3.495 (0.97), 3.532 (1.28), 3.622 (1.28), 3.647 (2.82), 3.673 (3.83), 3.699 (2.95), 3.718 (1.10), 3.732 (1.19), 3.772 (0.71), 3.812 (1.01), 3.833 (1.45), 3.854 (2.56), 3.876 (1.63), 3.899 (1.15), 3.930 (1.23), 3.964 (0.84), 3.986 (1.32), 4.020 (0.84), 4.891 (2.42), 4.932 (12.52), 4.948 (8.42), 4.952 (9.92), 4.975 (3.31), 4.988 (4.32), 5.268 (1.94), 5.399 (2.56), 5.524 (1.37), 7.222 (6.39), 7.242 (6.96), 7.919 (7.10), 7.926 (7.23), 7.940 (6.74), 7.947 (6.92), 8.574 (7.54), 8.580 (7.58).

Example 316

(5RS,7RS)-2-[(5-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture; 2 Isomers)

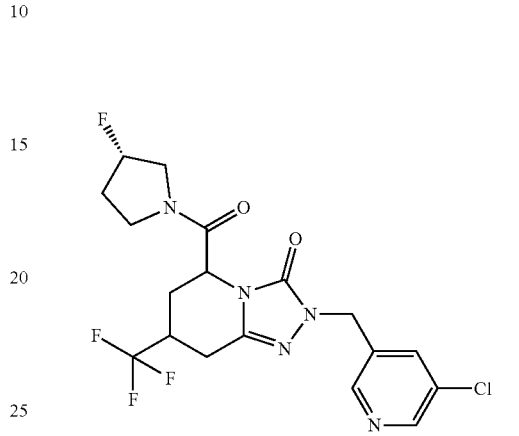

(5RS,7RS)-2-[(5-Chloropyridin-3-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (625 mg, 1.66 mmol) was initially charged in THF (3.0 ml), and HBTU (818 mg, 2.16 mmol) and N,N-diisopropylethylamine (870 μl, 5.0 mmol) were subsequently added. After stirring at room temperature for 15 min, (3S)-3-fluoropyrrolidine hydrochloride (250 mg, 1.99 mmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 296 mg (38% of theory) of the title compound were obtained.

LC-MS (Method 3): $R_t$=1.44 min; MS (ESIpos): m/z=448 [M+H]$^+$ $^1$H-NMR (400 MHz, DMSO-d6) δ[ppm]: −0.149 (1.08), −0.008 (8.89), 0.008 (9.13), 0.146 (1.10), 2.004 (0.47), 2.073 (1.57), 2.171 (2.52), 2.190 (1.50), 2.212 (2.41), 2.235 (3.70), 2.284 (2.39), 2.323 (1.44), 2.327 (1.52), 2.366 (0.68), 2.670 (1.15), 2.691 (1.15), 2.700 (1.08), 2.710 (0.97), 2.729 (2.70), 2.740 (1.60), 2.761 (1.73), 2.769 (1.78), 2.914 (1.23), 2.984 (2.99), 3.023 (2.02), 3.357 (1.10), 3.378 (1.15), 3.406 (0.97), 3.443 (0.63), 3.495 (0.55), 3.505 (0.55), 3.530 (0.89), 3.568 (1.31), 3.590 (1.13), 3.614 (1.78), 3.640 (2.23), 3.674 (1.99), 3.700 (1.36), 3.718 (0.63), 3.733 (0.66), 3.761 (0.58), 3.793 (0.63), 3.829 (0.73), 3.849 (1.50), 3.872 (0.89), 3.896 (0.63), 3.923 (0.58), 3.969 (0.63), 3.994 (1.47), 4.015 (0.81), 4.055 (0.63), 4.087 (0.47), 4.909 (0.68), 4.924 (1.44), 4.956 (16.00), 4.986 (1.39), 5.031 (1.15), 5.043 (1.10), 5.084 (1.18), 5.269 (1.29), 5.358 (0.81), 5.402 (1.55), 5.488 (0.71), 5.524 (0.58), 7.761 (5.30), 7.766 (3.83), 8.428 (6.82), 8.454 (0.50), 8.568 (5.72), 8.574 (5.77).

Example 317

(5RS,7RS)-2-[(5-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 1)

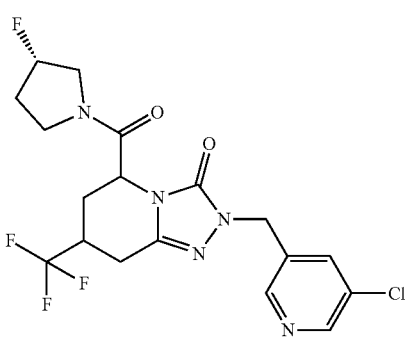 [SMILES: O=C(C1CC(C(F)(F)F)Cc2nn(Cc3cncc(Cl)c3)c(=O)n21)N1CC[C@H](F)C1]

(5RS,7RS)-2-[(5-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 296 mg dissolved in 9 ml of ethanol/n-heptane (7:2); injection volume: 0.20 ml; column: Daicel Chiralcel® IE 5 µm, 250×20 mm; eluent: n-heptane/ethanol (30:70); flow rate: 15 ml/min; temperature 40° C.; UV detection: 220 nm]. After the separation, 110 mg of isomer 1, which eluted first, and 101 mg of isomer 2, which eluted later, were isolated.

Isomer 1:

Analytical chiral HPLC: $R_t$=3.16 min, d.e.=100% [column: Daicel Chiralcel® IE 50×4.6 mm; eluent: n-heptane/ethanol 50:50; flow rate: 1 ml/min; UV detection: 220 nm].

LC-MS (Method 3): $R_t$=1.40 min; MS (ESIpos): m/z=448 [M+H]$^+$ $^1$H-NMR (400 MHz, DMSO-d6) δ[ppm]: −0.149 (1.59), −0.008 (12.81), 0.008 (13.77), 0.146 (1.59), 1.236 (0.64), 2.005 (0.64), 2.137 (2.17), 2.170 (4.08), 2.205 (2.49), 2.235 (3.19), 2.250 (3.19), 2.284 (4.40), 2.327 (3.44), 2.366 (2.49), 2.669 (2.68), 2.689 (1.98), 2.710 (3.12), 2.717 (2.74), 2.729 (3.57), 2.740 (2.10), 2.757 (2.87), 2.770 (1.98), 2.934 (1.85), 2.985 (5.23), 3.023 (3.12), 3.033 (2.42), 3.355 (2.04), 3.373 (1.85), 3.399 (1.85), 3.442 (1.47), 3.504 (1.15), 3.540 (1.40), 3.622 (1.40), 3.647 (2.93), 3.675 (4.21), 3.700 (3.19), 3.718 (1.27), 3.736 (1.34), 3.777 (0.83), 3.809 (1.08), 3.829 (1.66), 3.849 (2.80), 3.871 (1.85), 3.895 (1.15), 3.924 (1.34), 3.954 (0.96), 3.981 (1.59), 4.014 (0.83), 4.908 (1.34), 4.923 (2.55), 4.949 (16.00), 4.972 (3.76), 4.986 (3.44), 5.268 (2.17), 5.400 (2.87), 5.524 (1.47), 7.756 (6.25), 7.761 (7.33), 8.426 (8.67), 8.568 (6.82), 8.574 (6.95).

Example 318

(5RS,7RS)-2-[(5-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

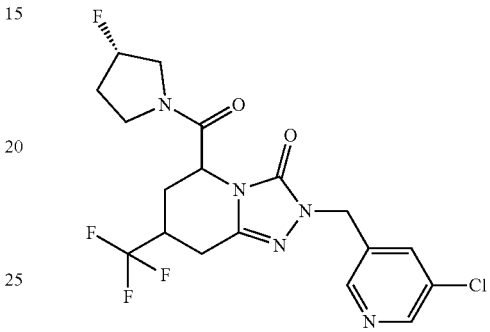

(5RS,7RS)-2-[(5-Chloropyridin-3-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 296 mg dissolved in 9 ml of ethanol/n-heptane (7:2); injection volume: 0.20 ml; column: Daicel Chiralcel® IE 5 µm, 250×20 mm; eluent: n-heptane/ethanol (30:70); flow rate: 15 ml/min; temperature 40° C.; UV detection: 220 nm]. After the separation, 110 mg of isomer 1, which eluted first, and 101 mg of isomer 2, which eluted later, were isolated.

Isomer 1:

Analytical chiral HPLC: $R_t$=4.32 min, d.e.=100% [column: Daicel Chiralcel® IE 50×4.6 mm; eluent: n-heptane/ethanol 50:50; flow rate: 1 ml/min; UV detection: 220 nm].

LC-MS (Method 3): $R_t$=1.40 min; MS (ESIpos): m/z=448 [M+H]$^+$ $^1$H-NMR (400 MHz, DMSO-d6) δ [ppm]: −0.149 (1.14), −0.008 (8.84), 0.008 (8.27), 0.146 (1.03), 2.019 (0.50), 2.159 (1.87), 2.191 (1.18), 2.211 (2.29), 2.233 (3.47), 2.274 (1.45), 2.327 (1.79), 2.366 (1.33), 2.669 (1.71), 2.692 (0.99), 2.699 (0.99), 2.710 (1.60), 2.722 (1.37), 2.731 (2.02), 2.739 (1.30), 2.761 (1.68), 2.768 (1.64), 2.891 (1.03), 2.977 (2.29), 3.016 (1.71), 3.360 (1.14), 3.378 (1.14), 3.406 (0.69), 3.490 (0.46), 3.526 (0.84), 3.567 (1.75), 3.589 (1.37), 3.614 (2.06), 3.633 (1.87), 3.658 (1.03), 3.791 (0.65), 3.858 (0.50), 3.889 (0.69), 3.968 (0.76), 3.994 (1.98), 4.017 (0.76), 4.057 (0.95), 4.087 (0.69), 4.956 (16.00), 5.029 (1.64), 5.044 (1.64), 5.084 (1.75), 5.274 (0.99), 5.358 (0.99), 5.408 (1.03), 5.488 (1.03), 7.761 (4.38), 7.766 (4.50), 8.428 (5.94), 8.568 (4.42), 8.574 (4.42).

Example 319

(5RS,8RS)-2-(3-Chloro-4-fluorobenzyl)-5-{[(3R, 4S)-3,4-difluoropyrrolidin-1-yl]carbonyl}-8-methyl-5,6,7,8-tetrahydro[1,2,4]triazolo[4,3-a]pyridin-3(2H)-one (Diastereomer Mixture; 4 Isomers)

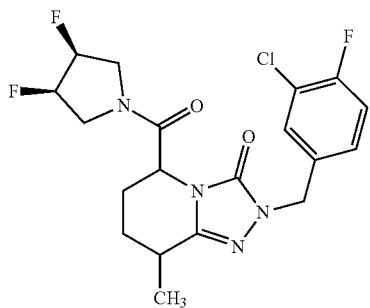 [SMILES: CC1CCC(C(=O)N2C[C@@H](F)[C@@H](F)C2)n2c1nn(Cc1ccc(F)c(Cl)c1)c2=O]

(5RS,8RS)-2-(3-Chloro-4-fluorobenzyl)-8-methyl-3-oxo-2,3,5,6,7,8-hexahydro[1,2,4]triazolo[4,3-a]pyridine-5-carboxylic Acid (Diastereomer Mixture; 4 Isomers) (100 mg, 79% purity, 233 μmol) was initially charged in THF (2.0 ml), and HBTU (115 mg, 302 μmol) and N,N-diisopropylethylamine (120 μl, 700 μmol) were subsequently added. After stirring at room temperature for 15 min, (3R,4S)-3,4-difluoropyrrolidine hydrochloride (40.1 mg, 279 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 44.0 mg (44% of theory) of the title compound were obtained.

LC-MS (Method 4): $R_t$=0.87 min; MS (ESIpos): m/z=429 [M+H]$^+$ $^1$H-NMR (400 MHz, DMSO-d6) δ [ppm]: −0.149 (0.92), −0.008 (7.38), 0.008 (7.15), 0.146 (0.83), 1.173 (15.59), 1.190 (16.00), 1.310 (0.55), 1.341 (1.43), 1.370 (1.57), 1.809 (1.52), 2.014 (0.65), 2.053 (2.35), 2.077 (2.90), 2.327 (1.29), 2.366 (0.88), 2.670 (1.48), 2.710 (1.94), 2.729 (1.80), 2.742 (1.66), 3.453 (0.74), 3.487 (1.20), 3.510 (1.38), 3.534 (1.01), 3.542 (1.15), 3.554 (0.83), 3.565 (0.92), 3.611 (0.92), 3.625 (1.11), 3.644 (0.69), 3.666 (1.24), 3.681 (1.98), 3.695 (1.34), 3.713 (1.94), 3.728 (1.06), 3.745 (1.15), 3.758 (1.15), 3.778 (0.55), 3.792 (0.55), 3.862 (0.92), 3.909 (1.34), 3.922 (1.01), 3.937 (0.60), 3.958 (0.97), 3.973 (1.01), 3.988 (0.60), 4.002 (0.55), 4.125 (0.55), 4.141 (0.69), 4.153 (0.69), 4.168 (0.97), 4.179 (0.74), 4.194 (0.65), 4.208 (0.60), 4.802 (1.61), 4.826 (3.92), 4.842 (7.93), 4.865 (4.29), 4.875 (4.52), 4.906 (0.92), 4.915 (1.52), 5.265 (0.97), 5.276 (1.11), 5.288 (0.92), 5.298 (0.69), 5.314 (0.69), 5.329 (0.78), 5.352 (0.88), 5.366 (0.78), 5.389 (1.15), 5.409 (1.06), 5.429 (0.78), 5.482 (0.78), 7.228 (2.26), 7.234 (2.44), 7.242 (2.31), 7.374 (3.00), 7.395 (4.80), 7.419 (2.72), 7.429 (3.46), 7.447 (3.37).

Example 320

(5RS,8RS)-2-(3-Chloro-4-fluorobenzyl)-5-{[(3S)-3-fluoropyrrolidin-1-yl]carbonyl}-8-methyl-5,6,7,8-tetrahydro[1,2,4]triazolo[4,3-a]pyridin-3(2H)-one (Diastereomer Mixture; 4 Isomers)

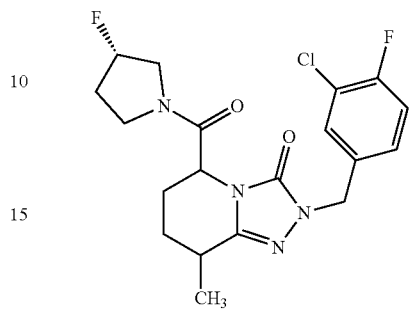

(5RS,8RS)-2-(3-Chloro-4-fluorobenzyl)-8-methyl-3-oxo-2,3,5,6,7,8-hexahydro[1,2,4]triazolo[4,3-a]pyridine-5-carboxylic Acid (Diastereomer Mixture; 4 Isomers) (100 mg, 79% purity, 233 μmol) was initially charged in THF (2.0 ml), and HBTU (115 mg, 302 μmol) and N,N-diisopropylethylamine (120 μl, 700 μmol) were subsequently added. After stirring at room temperature for 15 min, (3S)-3-fluoropyrrolidine hydrochloride (35.0 mg, 279 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 55.0 mg (58% of theory) of the title compound were obtained.

LC-MS (Method 3): $R_t$=1.57 min; MS (ESIpos): m/z=411 [M+H]$^+$ $^1$H-NMR (400 MHz, DMSO-d6) δ [ppm]: −0.149 (1.83), −0.008 (16.00), 0.008 (13.96), 0.146 (1.88), 1.175 (7.42), 1.180 (7.54), 1.192 (7.79), 1.197 (7.46), 1.380 (0.75), 1.813 (1.04), 2.105 (2.08), 2.270 (0.79), 2.327 (2.29), 2.366 (1.33), 2.670 (2.37), 2.710 (2.00), 3.516 (1.17), 3.597 (1.33), 3.643 (1.17), 3.667 (1.04), 3.731 (0.96), 3.840 (0.96), 3.930 (0.63), 4.776 (0.92), 4.799 (0.92), 4.839 (3.08), 4.848 (3.54), 4.871 (3.58), 5.266 (0.71), 5.391 (0.79), 7.245 (1.67), 7.373 (2.58), 7.395 (4.00), 7.418 (2.04), 7.431 (2.04), 7.448 (2.21).

Example 321

(5RS,8RS)-2-(3-Chloro-4-fluorobenzyl)-5-[(3-fluoroazetidin-1-yl)carbonyl]-8-methyl-5,6,7,8-tetrahydro[1,2,4]triazolo[4,3-a]pyridin-3(2H)-one (Diastereomer Mixture; 4 Isomers)

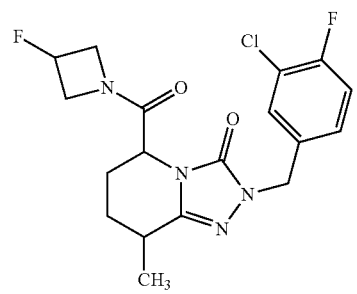 [SMILES: CC1CCC(C(=O)N2CC(F)C2)n2c1nn(Cc1ccc(F)c(Cl)c1)c2=O]

(5RS,8RS)-2-(3-Chloro-4-fluorobenzyl)-8-methyl-3-oxo-2,3,5,6,7,8-hexahydro[1,2,4]triazolo[4,3-a]pyridine-5-carboxylic Acid (Diastereomer Mixture; 4 Isomers) (100 mg, 79% purity, 233 µmol) was initially charged in THF (2.0 ml), and HBTU (115 mg, 302 µmol) and N,N-diisopropylethylamine (120 µl, 700 µmol) were subsequently added. After stirring at room temperature for 15 min, 3-fluoroazetidine hydrochloride (31.1 mg, 279 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 48.0 mg (52% of theory) of the title compound were obtained.

LC-MS (Method 3): $R_t$=1.53 min; MS (ESIpos): m/z=397 [M+H]$^+$ $^1$H-NMR (400 MHz, DMSO-d6) δ [ppm]: −0.149 (0.45), −0.008 (4.06), 0.008 (3.98), 0.146 (0.44), 1.168 (15.72), 1.185 (16.00), 1.244 (0.42), 1.258 (0.43), 1.329 (0.42), 1.358 (0.84), 1.384 (1.02), 1.401 (0.96), 1.431 (0.51), 1.802 (1.14), 1.812 (1.16), 2.037 (2.52), 2.047 (2.73), 2.328 (0.47), 2.523 (1.47), 2.670 (0.54), 2.675 (0.53), 2.695 (0.80), 2.710 (1.63), 2.725 (1.48), 2.738 (1.25), 2.755 (0.72), 3.925 (0.72), 3.987 (0.81), 4.013 (0.55), 4.175 (0.44), 4.216 (0.79), 4.230 (0.84), 4.245 (0.71), 4.266 (0.96), 4.299 (0.86), 4.332 (0.49), 4.357 (0.87), 4.381 (0.59), 4.417 (0.45), 4.444 (0.60), 4.508 (0.40), 4.523 (0.46), 4.562 (0.46), 4.579 (0.51), 4.596 (2.31), 4.605 (3.55), 4.616 (2.39), 4.636 (0.47), 4.667 (0.44), 4.687 (0.44), 4.803 (1.87), 4.843 (6.36), 4.868 (2.98), 4.876 (2.92), 4.916 (0.87), 5.348 (0.55), 5.411 (0.55), 5.490 (0.54), 5.553 (0.53), 7.237 (1.82), 7.371 (2.19), 7.394 (3.62), 7.416 (1.76), 7.433 (2.20), 7.451 (2.21).

Example 322

(5RS,8RS)-5-{[(3R,4S)-3,4-Difluoropyrrolidin-1-yl]carbonyl}-2-{[3-fluoro-2-(trifluoromethyl)pyridin-4-yl]methyl}-8-methyl-5,6,7,8-tetrahydro[1,2,4]triazolo[4,3-a]pyridin-3(2H)-one (Diastereomer Mixture; 4 Isomers)

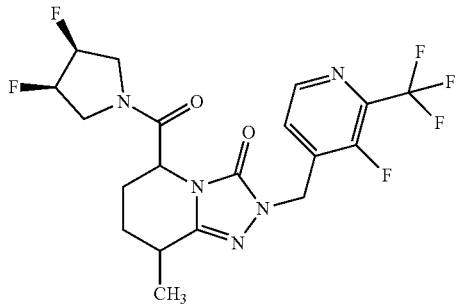 [SMILES: CC1CCC(C(=O)N2C[C@@H](F)[C@@H](F)C2)n2c1nn(Cc1ccnc(C(F)(F)F)c1F)c2=O]

(5RS,8RS)-2-{[3-Fluoro-2-(trifluoromethyl)pyridin-4-yl]methyl}-8-methyl-3-oxo-2,3,5,6,7,8-hexahydro[1,2,4]triazolo[4,3-a]pyridine-5-carboxylic Acid (Diastereomer Mixture; 4 Isomers) (80.0 mg, 214 µmol) was initially charged in THF (2.0 ml), and HBTU (105 mg, 278 µmol) and N,N-diisopropylethylamine (110 µl, 640 µmol) were subsequently added. After stirring at room temperature for 15 min, (3R,4S)-3,4-difluoropyrrolidine hydrochloride (36.8 mg, 256 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 38.0 mg (38% of theory) of the title compound were obtained.

LC-MS (Method 4): $R_t$=0.82 min; MS (ESIpos): m/z=464 [M+H]$^+$ $^1$H-NMR (400 MHz, DMSO-d6) δ [ppm]: −0.149 (1.67), −0.008 (16.00), 0.008 (12.74), 0.146 (1.71), 1.178 (7.16), 1.194 (7.28), 1.345 (0.56), 1.377 (0.60), 1.839 (0.56), 2.107 (1.07), 2.327 (1.19), 2.332 (0.84), 2.366 (1.15), 2.518 (4.34), 2.523 (3.34), 2.665 (0.92), 2.670 (1.23), 2.674 (0.84), 2.710 (1.19), 2.755 (0.68), 2.766 (0.68), 3.496 (0.44), 3.507 (0.44), 3.518 (0.56), 3.526 (0.48), 3.674 (0.48), 3.687 (0.64), 3.720 (0.72), 3.750 (0.44), 3.763 (0.44), 3.913 (0.52), 4.853 (1.43), 4.867 (1.31), 5.048 (0.80), 5.091 (2.75), 5.116 (1.75), 5.124 (1.79), 5.166 (0.56), 7.509 (1.19), 7.518 (1.31), 7.530 (0.64), 8.561 (1.83), 8.573 (1.79).

Example 323

(5RS,8RS)-2-(3-Chloro-4-fluorobenzyl)-5-[(3,3-difluoropyrrolidin-1-yl)carbonyl]-8-methyl-5,6,7,8-tetrahydro[1,2,4]triazolo[4,3-a]pyridin-3(2H)-one (Diastereomer Mixture; 4 Isomers)

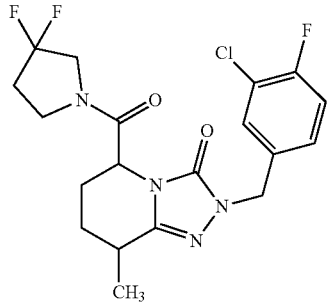 [SMILES: CC1CCC(C(=O)N2CCC(F)(F)C2)n2c1nn(Cc1ccc(F)c(Cl)c1)c2=O]

(5RS,8RS)-2-(3-Chloro-4-fluorobenzyl)-8-methyl-3-oxo-2,3,5,6,7,8-hexahydro[1,2,4]triazolo[4,3-a]pyridine-5-carboxylic Acid (Diastereomer Mixture; 4 Isomers) (100 mg, 79% purity, 233 µmol) was initially charged in THF, and HBTU (115 mg, 302 mol) and N,N-diisopropylethylamine (120 µl, 700 µmol) were subsequently added. After stirring at room temperature for 15 min, 3,3-difluoropyrrolidine hydrochloride (40.1 mg, 279 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 14.0 mg (14% of theory) of the title compound were obtained.

LC-MS (Method 3): $R_t$=1.72 min; MS (ESIpos): m/z=429 [M+H]$^+$ $^1$H-NMR (400 MHz, DMSO-d6) δ [ppm]: −0.149 (1.90), −0.008 (16.00), 0.008 (14.19), 0.146 (1.90), 1.175 (13.05), 1.192 (13.33), 1.370 (1.14), 1.794 (1.62), 2.072 (2.38), 2.327 (2.48), 2.366 (2.29), 2.669 (2.67), 2.710 (2.29), 2.720 (1.52), 2.735 (2.00), 2.751 (1.62), 3.527 (1.52), 3.549 (2.19), 3.665 (1.14), 3.699 (1.43), 3.734 (1.24), 3.769 (2.38), 3.797 (2.00), 3.900 (1.52), 3.969 (0.86), 4.178 (0.86), 4.201 (0.95), 4.802 (3.05), 4.844 (5.71), 4.871 (7.33), 4.912 (1.62), 7.234 (2.19), 7.246 (1.90), 7.373 (3.90), 7.396 (5.33), 7.418 (3.24), 7.427 (3.24), 7.450 (2.95).

Example 324

(5RS,8RS)-2-(2,4-Difluorobenzyl)-5-{[(3R,4S)-3,4-difluoropyrrolidin-1-yl]carbonyl}-8-methyl-5,6,7,8-tetrahydro[1,2,4]triazolo[4,3-a]pyridin-3(2H)-one (Diastereomer Mixture; 4 Isomers)

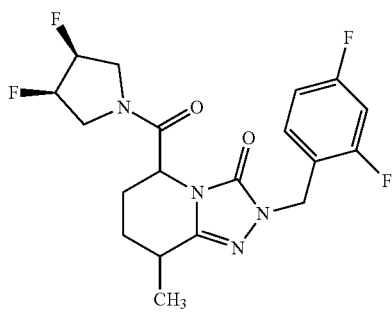 [SMILES: CC1CCC(C(=O)N2C[C@@H](F)[C@@H](F)C2)n2c1nn(Cc1ccc(F)cc1F)c2=O]

(5RS,8RS)-2-(2,4-Difluorobenzyl)-8-methyl-3-oxo-2,3,5,6,7,8-hexahydro[1,2,4]triazolo[4,3-a]pyridine-5-carboxylic acid (diastereomer mixture; 4 isomers) (80.0 mg, 247 µmol) was initially charged in THF (2.0 ml), and HBTU (122 mg, 322 µmol) and N,N-diisopropylethylamine (130 µl, 740 µmol) were subsequently added. After stirring at room temperature for 15 min, (3R,4S)-3,4-difluoropyrrolidine hydrochloride (42.6 mg, 297 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.0 mg (45% of theory) of the title compound were obtained.

LC-MS (Method 4): $R_t$=0.80 min; MS (ESIpos): m/z=413 [M+H]$^+$ $^1$H-NMR (400 MHz, DMSO-d6) δ [ppm]: −0.149 (0.68), −0.008 (6.34), 0.008 (6.42), 0.146 (0.75), 1.165 (15.62), 1.182 (16.00), 1.337 (1.36), 1.370 (1.51), 1.398 (0.68), 1.810 (1.36), 2.041 (2.19), 2.072 (2.72), 2.328 (1.28), 2.366 (0.98), 2.523 (4.60), 2.670 (1.74), 2.700 (1.36), 2.710 (2.42), 2.726 (1.58), 2.742 (1.13), 3.381 (0.83), 3.398 (0.53), 3.448 (0.68), 3.482 (1.13), 3.508 (1.13), 3.519 (1.13), 3.529 (1.06), 3.538 (1.13), 3.562 (0.83), 3.607 (0.83), 3.622 (0.98), 3.640 (0.68), 3.663 (1.13), 3.677 (1.74), 3.695 (1.36), 3.710 (1.66), 3.725 (0.98), 3.742 (1.06), 3.755 (1.13), 3.775 (0.53), 3.856 (0.83), 3.905 (1.28), 3.919 (0.98), 3.934 (0.53), 3.955 (0.91), 3.970 (0.91), 3.985 (0.60), 3.998 (0.53), 4.119 (0.60), 4.135 (0.68), 4.148 (0.60), 4.162 (0.98), 4.174 (0.68), 4.188 (0.68), 4.203 (0.60), 4.788 (2.34), 4.805 (3.25), 4.827 (5.96), 4.884 (3.02), 4.894 (3.40), 4.924 (1.36), 4.934 (1.66), 5.275 (1.06), 5.349 (0.83), 5.385 (1.06), 5.407 (0.91), 5.428 (0.68), 5.440 (0.68), 5.479 (0.75), 7.059 (1.28), 7.081 (2.79), 7.102 (1.58), 7.222 (1.28), 7.251 (3.47), 7.262 (1.89), 7.272 (3.25), 7.289 (1.96), 7.310 (0.91).

Example 325

(5RS,8RS)-5-{[(3R,4S)-3,4-Difluoropyrrolidin-1-yl]carbonyl}-8-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

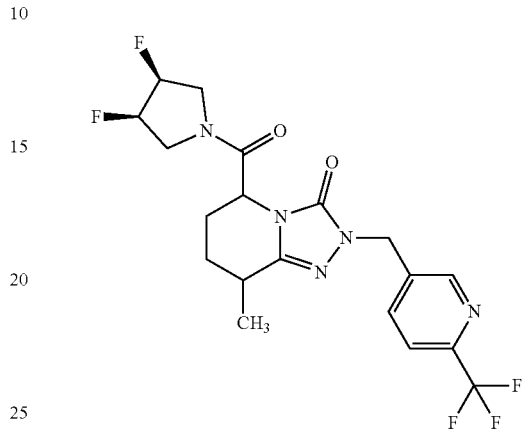

(5RS,8RS)-8-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (80.0 mg, 225 µmol) was initially charged in THF (2.0 ml), and HBTU (111 mg, 292 µmol) and N,N-diisopropylethylamine (120 II, 670 µmol) were subsequently added. After stirring at room temperature for 15 min, (3R,4S)-3,4-difluoropyrrolidine hydrochloride (38.7 mg, 269 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 70.0 mg (70% of theory) of the title compound were obtained.

LC-MS (Method 4): $R_t$=0.78 min; MS (ESIpos): m/z=446 [M+H]$^+$ $^1$H-NMR (400 MHz, DMSO-d6) δ[ppm]: −0.150 (0.54), −0.008 (4.71), 0.008 (5.18), 0.146 (0.58), 1.173 (15.46), 1.190 (16.00), 1.225 (1.08), 1.244 (5.33), 1.259 (6.38), 1.274 (3.52), 1.305 (0.54), 1.337 (1.35), 1.347 (1.04), 1.369 (1.47), 1.399 (0.66), 1.799 (1.00), 1.819 (1.35), 2.072 (2.36), 2.096 (2.67), 2.328 (0.77), 2.366 (0.58), 2.523 (2.67), 2.670 (0.85), 2.690 (0.77), 2.709 (1.12), 2.721 (1.20), 2.737 (1.62), 2.748 (1.55), 2.776 (0.62), 3.129 (0.46), 3.139 (0.50), 3.158 (0.46), 3.457 (0.66), 3.491 (1.04), 3.515 (1.08), 3.527 (1.00), 3.538 (0.93), 3.547 (1.08), 3.560 (0.73), 3.570 (0.77), 3.579 (0.62), 3.616 (1.28), 3.630 (1.31), 3.648 (0.77), 3.663 (0.81), 3.671 (1.16), 3.684 (1.74), 3.696 (1.12), 3.718 (1.74), 3.731 (0.97), 3.750 (1.04), 3.761 (1.04), 3.783 (0.54), 3.795 (0.50), 3.867 (0.85), 3.913 (1.24), 3.926 (0.97), 3.941 (0.50), 3.964 (0.89), 3.977 (0.89), 3.992 (0.54), 4.006 (0.46), 4.128 (0.50), 4.142 (0.58), 4.156 (0.62), 4.167 (0.85), 4.183 (0.66), 4.195 (0.62), 4.210 (0.58), 4.835 (3.32), 4.842 (2.74), 4.849 (3.09), 5.006 (0.54), 5.047 (12.83), 5.093 (0.46), 5.266 (0.93), 5.276 (0.77), 5.288 (0.93), 5.314 (0.70), 5.329 (0.73), 5.353 (0.77), 5.390 (0.97), 5.409 (0.93), 5.420 (0.93), 5.432 (0.62), 5.456 (0.73), 5.464 (0.77), 5.476 (0.73), 7.904 (9.12), 7.908 (11.32), 7.926 (1.00), 8.628 (5.80).

Example 326

(5RS,8RS)-2-(2,4-Difluorobenzyl)-5-{[(3S)-3-fluoropyrrolidin-1-yl]carbonyl}-8-methyl-5,6,7,8-tetrahydro[1,2,4]triazolo[4,3-a]pyridin-3(2H)-one (Diastereomer Mixture; 4 Isomers)

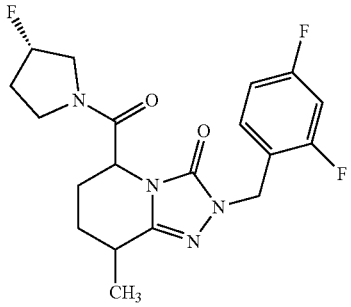 [SMILES: CC1CCC(C(=O)N2CC[C@H](F)C2)n2c1nn(Cc1ccc(F)cc1F)c2=O]

(5RS,8RS)-2-(2,4-Difluorobenzyl)-8-methyl-3-oxo-2,3,5,6,7,8-hexahydro[1,2,4]triazolo[4,3-a]pyridine-5-carboxylic acid (diastereomer mixture; 4 isomers) (80.0 mg, 247 µmol) was initially charged in THF, and HBTU (122 mg, 322 µmol) and N,N-diisopropylethylamine (130 µl, 740 µmol) were subsequently added. After stirring at room temperature for 15 min, (3S)-3-fluoropyrrolidine hydrochloride (37.3 mg, 297 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 50.0 mg (51% of theory) of the title compound were obtained.

LC-MS (Method 3): $R_t$=1.43 min; MS (ESIpos): m/z=395 [M+H]$^+$ $^1$H-NMR (400 MHz, DMSO-d6) δ[ppm]: −0.149 (0.66), −0.008 (6.12), 0.008 (5.45), 0.146 (0.66), 1.168 (15.16), 1.173 (15.96), 1.184 (16.00), 1.190 (15.82), 1.228 (0.49), 1.245 (1.99), 1.261 (2.84), 1.277 (1.42), 1.349 (1.02), 1.380 (1.46), 1.412 (1.51), 1.443 (1.02), 1.787 (1.86), 1.796 (1.95), 1.805 (1.91), 1.934 (0.58), 1.975 (1.06), 2.052 (3.28), 2.092 (3.63), 2.102 (3.59), 2.130 (1.82), 2.221 (1.11), 2.256 (1.42), 2.328 (0.84), 2.366 (0.49), 2.669 (1.24), 2.690 (1.46), 2.700 (2.04), 2.714 (2.53), 2.730 (2.53), 2.743 (1.29), 2.890 (0.80), 3.267 (0.49), 3.356 (1.73), 3.374 (1.20), 3.384 (1.33), 3.402 (0.71), 3.447 (0.58), 3.455 (0.62), 3.481 (0.71), 3.490 (0.80), 3.515 (1.99), 3.542 (1.60), 3.560 (1.37), 3.592 (2.61), 3.619 (1.73), 3.640 (2.13), 3.664 (1.95), 3.687 (0.93), 3.704 (0.93), 3.726 (1.99), 3.752 (1.29), 3.762 (1.55), 3.836 (1.82), 3.904 (0.66), 3.926 (1.24), 3.949 (0.66), 3.969 (0.62), 3.995 (0.66), 4.026 (0.53), 4.697 (1.11), 4.711 (1.20), 4.745 (1.15), 4.754 (1.86), 4.766 (1.20), 4.784 (2.17), 4.792 (2.30), 4.824 (5.67), 4.832 (6.12), 4.872 (1.51), 4.890 (5.81), 4.930 (2.66), 5.258 (1.42), 5.346 (0.84), 5.391 (1.60), 5.477 (0.80), 5.509 (0.66), 5.943 (0.44), 7.054 (1.91), 7.060 (2.04), 7.075 (4.25), 7.081 (4.61), 7.097 (2.39), 7.103 (2.48), 7.220 (2.39), 7.227 (2.39), 7.245 (5.32), 7.252 (5.27), 7.269 (5.36), 7.274 (4.70), 7.284 (2.70), 7.290 (3.50), 7.305 (1.11), 7.312 (1.20).

Example 327

(5RS,8RS)-2-(2,4-Difluorobenzyl)-5-[(3,3-difluoropyrrolidin-1-yl)carbonyl]-8-methyl-5,6,7,8-tetrahydro[1,2,4]triazolo[4,3-a]pyridin-3(2H)-one (Diastereomer Mixture; 4 Isomers)

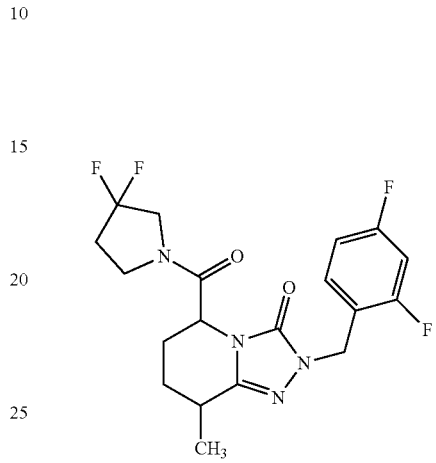

(5RS,8RS)-2-(2,4-Difluorobenzyl)-8-methyl-3-oxo-2,3,5,6,7,8-hexahydro[1,2,4]triazolo[4,3-a]pyridine-5-carboxylic acid (diastereomer mixture; 4 isomers) (80.0 mg, 247 µmol) was initially charged in THF (2.0 ml), and HBTU (122 mg, 322 µmol) and N,N-diisopropylethylamine (130 µl, 740 µmol) were subsequently added. After stirring at room temperature for 15 min, 3,3-difluoropyrrolidine hydrochloride (42.6 mg, 297 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 30.0 mg (29% of theory) of the title compound were obtained.

LC-MS (Method 3): $R_t$=1.57 min; MS (ESIpos): m/z=413 [M+H]$^+$ $^1$H-NMR (400 MHz, DMSO-d6) δ [ppm]: −0.150 (1.37), −0.008 (11.75), 0.008 (10.16), 0.146 (1.30), 1.166 (15.78), 1.183 (16.00), 1.370 (1.30), 1.787 (1.73), 1.820 (1.51), 2.055 (2.67), 2.082 (2.45), 2.092 (2.31), 2.327 (1.66), 2.366 (1.59), 2.377 (1.08), 2.405 (1.37), 2.425 (1.37), 2.447 (1.23), 2.569 (1.87), 2.586 (1.23), 2.670 (1.87), 2.690 (1.44), 2.708 (2.59), 2.720 (2.38), 2.735 (1.80), 2.750 (1.15), 3.525 (1.87), 3.543 (2.59), 3.558 (1.30), 3.626 (0.43), 3.660 (1.51), 3.693 (1.66), 3.731 (1.23), 3.766 (2.67), 3.793 (2.38), 3.812 (0.86), 3.876 (0.79), 3.894 (1.51), 3.921 (1.15), 3.940 (0.94), 3.970 (1.01), 4.013 (1.01), 4.043 (0.65), 4.138 (0.58), 4.168 (0.94), 4.193 (0.94), 4.788 (4.18), 4.828 (6.13), 4.847 (2.45), 4.890 (6.05), 4.930 (2.81), 7.059 (1.59), 7.081 (3.32), 7.102 (1.87), 7.221 (2.09), 7.227 (1.87), 7.247 (4.68), 7.269 (4.97), 7.276 (2.52), 7.285 (3.39), 7.306 (1.37).

Example 328

(5RS,8RS)-5-[(3-Fluoroazetidin-1-yl)carbonyl]-8-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

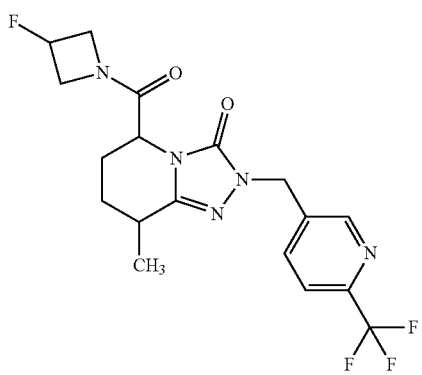 [SMILES: CC1CCC(C(=O)N2CC(F)C2)n2c1nn(Cc1ccc(C(F)(F)F)nc1)c2=O]

(5RS,8RS)-8-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (50.0 mg, 140 µmol) was initially charged in THF (500 µl), and HBTU (69.2 mg, 182 µmol) and N,N-diisopropylethylamine (73 µl, 420 µmol) were subsequently added. After stirring at room temperature for 15 min, 3-fluoroazetidine hydrochloride (18.8 mg, 168 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 35.0 mg (60% of theory) of the title compound were obtained.

LC-MS (Method 3): $R_t$=1.34 min; MS (ESIpos): m/z=414 [M+H]$^+$ $^1$H-NMR (400 MHz, DMSO-d6) δ[ppm]: −0.008 (3.37), 0.008 (3.14), 0.146 (0.42), 1.168 (15.69), 1.185 (16.00), 1.325 (0.46), 1.365 (0.98), 1.385 (1.02), 1.396 (1.08), 1.425 (0.50), 1.813 (1.06), 1.822 (1.08), 2.057 (2.54), 2.328 (0.66), 2.332 (0.52), 2.366 (0.56), 2.523 (2.02), 2.670 (0.75), 2.700 (0.79), 2.711 (1.35), 2.730 (1.41), 2.744 (1.21), 2.759 (0.69), 3.908 (0.44), 3.930 (0.77), 3.958 (0.75), 3.991 (0.83), 4.017 (0.52), 4.177 (0.44), 4.220 (0.71), 4.234 (0.71), 4.275 (0.79), 4.303 (0.77), 4.341 (0.48), 4.363 (0.79), 4.386 (0.56), 4.423 (0.44), 4.448 (0.58), 4.530 (0.44), 4.569 (0.44), 4.584 (0.48), 4.619 (3.03), 4.673 (0.44), 5.004 (0.56), 5.046 (7.13), 5.096 (0.39), 5.349 (0.52), 5.411 (0.52), 5.493 (0.52), 5.554 (0.52), 7.906 (11.32), 8.635 (4.70).

Example 329

(5RS,8RS)-2-(2,4-Difluorobenzyl)-5-[(3-fluoroazetidin-1-yl)carbonyl]-8-methyl-5,6,7,8-tetrahydro[1,2,4]triazolo[4,3-a]pyridin-3(2H)-one (Diastereomer Mixture; 4 Isomers)

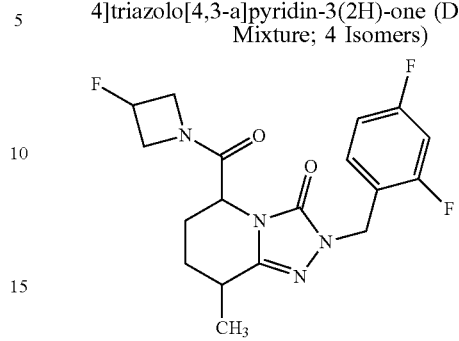

(5RS,8RS)-2-(2,4-Difluorobenzyl)-8-methyl-3-oxo-2,3,5,6,7,8-hexahydro[1,2,4]triazolo[4,3-a]pyridine-5-carboxylic acid (diastereomer mixture; 4 isomers) (80.0 mg, 247 µmol) was initially charged in THF (2.0 ml), and HBTU (122 mg, 322 µmol) and N,N-diisopropylethylamine (130 µl, 740 µmol) were subsequently added. After stirring at room temperature for 15 min, 3-fluoroazetidine hydrochloride (33.1 mg, 297 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 55.0 mg (58% of theory) of the title compound were obtained.

LC-MS (Method 3): $R_t$=1.46 min; MS (ESIpos): m/z=381 [M+H]$^+$ $^1$H-NMR (400 MHz, DMSO-d6) δ[ppm]: −0.149 (1.04), −0.008 (13.04), 0.008 (7.58), 0.146 (1.08), 1.160 (16.00), 1.177 (16.00), 1.334 (0.54), 1.393 (1.18), 1.434 (0.61), 1.805 (1.28), 2.037 (2.96), 2.327 (1.01), 2.366 (0.74), 2.670 (1.55), 2.696 (1.48), 2.710 (2.36), 3.920 (0.91), 3.951 (0.84), 3.984 (0.94), 4.008 (0.61), 4.227 (0.88), 4.263 (1.01), 4.295 (0.94), 4.351 (0.94), 4.410 (0.51), 4.439 (0.64), 4.518 (0.54), 4.583 (3.60), 4.790 (2.49), 4.830 (5.36), 4.886 (2.59), 4.934 (1.21), 5.346 (0.64), 5.408 (0.57), 5.489 (0.57), 5.552 (0.57), 7.057 (1.21), 7.077 (2.39), 7.095 (1.35), 7.226 (1.25), 7.251 (3.20), 7.272 (3.40), 7.290 (2.36), 7.311 (0.94).

Example 330

(5RS,8RS)-5-[(3,3-Difluoropyrrolidin-1-yl)carbonyl]-8-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

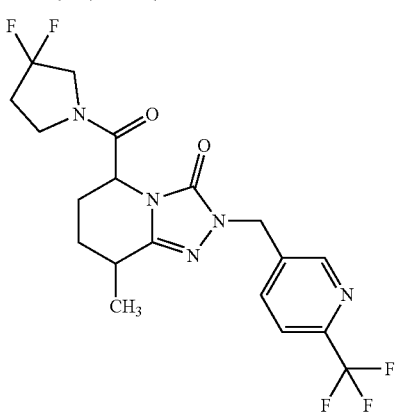

(5RS,8RS)-8-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (100 mg, 281 µmol) was initially charged in THF (2.0 ml), and HBTU (138 mg, 365 µmol) and N,N-diisopropylethylamine (150 µl, 840 µmol) were subsequently added. After stirring at room temperature for 15 min, 3,3-difluoropyrrolidine hydrochloride (48.4 mg, 337 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 60.0 mg (48% of theory) of the title compound were obtained.

LC-MS (Method 4): $R_t$=0.81 min; MS (ESIpos): m/z=446 [M+H]$^+$ $^1$H-NMR (400 MHz, DMSO-d6) δ [ppm]: −0.008 (3.55), 0.008 (3.57), 0.146 (0.46), 1.175 (15.46), 1.191 (16.00), 1.317 (0.44), 1.335 (0.95), 1.349 (1.15), 1.364 (1.25), 1.379 (1.25), 1.395 (0.88), 1.407 (0.64), 1.805 (1.66), 1.817 (1.52), 1.827 (1.39), 1.839 (1.39), 2.073 (3.67), 2.105 (2.42), 2.115 (2.28), 2.328 (0.61), 2.366 (0.76), 2.381 (0.95), 2.390 (0.76), 2.408 (1.25), 2.427 (1.22), 2.451 (0.78), 2.518 (4.01), 2.572 (1.81), 2.589 (1.27), 2.607 (0.66), 2.670 (0.71), 2.696 (0.42), 2.711 (1.52), 2.728 (1.91), 2.743 (2.30), 2.758 (1.81), 2.773 (1.17), 3.533 (1.79), 3.552 (2.69), 3.566 (1.42), 3.573 (1.37), 3.633 (0.46), 3.667 (1.49), 3.701 (1.74), 3.736 (1.03), 3.742 (0.95), 3.756 (0.66), 3.775 (2.98), 3.801 (1.96), 3.807 (1.76), 3.818 (0.91), 3.841 (0.44), 3.882 (0.78), 3.901 (1.64), 3.920 (0.95), 3.927 (1.22), 3.947 (0.93), 3.977 (0.98), 3.992 (0.56), 4.005 (0.71), 4.021 (0.91), 4.048 (0.59), 4.151 (0.61), 4.183 (0.93), 4.206 (0.93), 4.238 (0.46), 4.805 (1.37), 4.812 (1.96), 4.824 (1.49), 4.868 (1.39), 4.875 (2.15), 4.887 (1.47), 5.006 (0.59), 5.050 (12.84), 5.093 (0.66), 7.881 (0.71), 7.906 (15.24), 7.927 (1.35), 8.629 (5.70).

Example 331

(5RS,7RS)-2-(3-Chloro-4-fluorobenzyl)-5-[(3,3-difluoropyrrolidin-1-yl)carbonyl]-7-methyl-5,6,7,8-tetrahydro[1,2,4]triazolo[4,3-a]pyridin-3(2H)-one (Diastereomer Mixture; 4 Isomers)

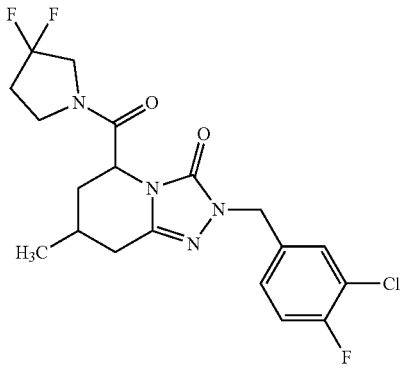 [SMILES: CC1Cc2nn(Cc3ccc(F)c(Cl)c3)c(=O)n2C(C(=O)N2CCC(F)(F)C2)C1]

(5RS,7RS)-2-(3-Chloro-4-fluorobenzyl)-7-methyl-3-oxo-2,3,5,6,7,8-hexahydro[1,2,4]triazolo[4,3-a]pyridine-5-carboxylic Acid (Diastereomer Mixture; 4 Isomers) (70.0 mg, 206 µmol) was initially charged in THF (2.0 ml), and HBTU (102 mg, 268 µmol) and N,N-diisopropylethylamine (110 µl, 620 µmol) were subsequently added. After stirring at room temperature for 15 min, 3,3-difluoropyrrolidine hydrochloride (35.5 mg, 247 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 47.8 mg (54% of theory) of the title compound were obtained.

LC-MS (Method 3): $R_t$=1.69 min; MS (ESIpos): m/z=429 [M+H]$^+$ $^1$H-NMR (400 MHz, DMSO-d6) δ [ppm]: −0.149 (1.30), −0.008 (11.60), 0.008 (9.50), 0.146 (1.20), 1.025 (12.50), 1.041 (12.80), 1.343 (1.20), 1.371 (1.30), 1.873 (1.00), 2.073 (0.90), 2.158 (2.40), 2.188 (2.00), 2.198 (2.80), 2.228 (3.60), 2.327 (2.40), 2.366 (1.70), 2.413 (1.60), 2.651 (2.00), 2.669 (2.40), 2.710 (1.40), 3.555 (2.00), 3.570 (2.20), 3.679 (1.40), 3.712 (1.40), 3.739 (0.90), 3.771 (1.60), 3.803 (1.30), 3.836 (1.70), 3.915 (1.50), 3.941 (1.00), 4.043 (1.00), 4.081 (0.90), 4.110 (1.20), 4.141 (1.20), 4.170 (0.90), 4.591 (1.20), 4.607 (1.40), 4.619 (1.40), 4.633 (1.20), 4.705 (1.20), 4.719 (1.30), 4.730 (1.20), 4.746 (1.10), 4.802 (16.00), 7.240 (1.70), 7.256 (2.50), 7.262 (2.40), 7.268 (2.20), 7.376 (4.10), 7.399 (5.60), 7.421 (3.10), 7.443 (3.20), 7.448 (3.30), 7.461 (3.20), 7.466 (3.10).

Example 332

(5RS,7RS)-5-[(3,3-Difluoropyrrolidin-1-yl)carbonyl]-7-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

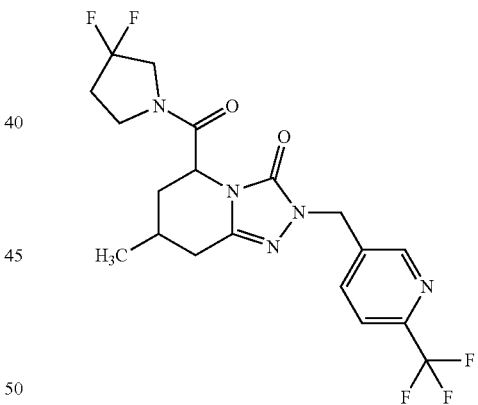

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (100 mg, 281 µmol) was initially charged in THF (2.0 ml), and HBTU (138 mg, 365 µmol) and N,N-diisopropylethylamine (150 µl, 840 µmol) were subsequently added. After stirring at room temperature for 15 min, 3,3-difluoropyrrolidine hydrochloride (48.4 mg, 337 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 106 mg (85% of theory) of the title compound were obtained.

LC-MS (Method 4): $R_t$=0.79 min; MS (ESIpos): m/z=446 [M+H]$^+$ $^1$H-NMR (400 MHz, DMSO-d6) δ[ppm]: −0.149 (0.75), −0.008 (7.11), 0.008 (6.34), 0.146 (0.75), 1.027 (12.01), 1.043 (12.42), 1.318 (0.55), 1.332 (0.57), 1.349 (1.14), 1.361 (1.21), 1.379 (1.21), 1.391 (1.23), 1.410 (0.93), 1.422 (0.62), 1.900 (0.89), 2.073 (0.50), 2.160 (2.26), 2.190 (1.94), 2.201 (2.60), 2.231 (2.85), 2.270 (1.30), 2.328 (1.00), 2.366 (1.09), 2.382 (0.96), 2.400 (0.98), 2.414 (1.39), 2.433 (1.09), 2.453 (0.78), 2.523 (4.67), 2.577 (1.18), 2.595 (0.61), 2.651 (1.98), 2.670 (1.32), 2.686 (1.76), 2.710 (0.93), 3.539 (1.19), 3.557 (2.05), 3.571 (2.33), 3.590 (1.05), 3.648 (0.43), 3.681 (1.25), 3.714 (1.50), 3.740 (0.84), 3.773 (1.53), 3.805 (1.34), 3.818 (1.03), 3.825 (0.96), 3.843 (1.59), 3.861 (0.71), 3.893 (0.73), 3.912 (1.50), 3.938 (1.02), 3.957 (0.43), 4.051 (1.00), 4.089 (0.98), 4.108 (0.73), 4.138 (1.10), 4.170 (0.93), 4.594 (1.10), 4.609 (1.35), 4.621 (1.25), 4.636 (1.10), 4.705 (1.14), 4.720 (1.35), 4.732 (1.23), 4.747 (1.16), 4.988 (16.00), 7.900 (1.03), 7.920 (14.02), 7.946 (0.73), 8.665 (5.02).

Example 333

(5RS,7RS)-5-{[(3R,4S)-3,4-Difluoropyrrolidin-1-yl]carbonyl}-2-{[3-fluoro-2-(trifluoromethyl)pyridin-4-yl]methyl}-7-methyl-5,6,7,8-tetrahydro[1,2,4]triazolo[4,3-a]pyridin-3(2H)-one (Diastereomer Mixture; 4 Isomers)

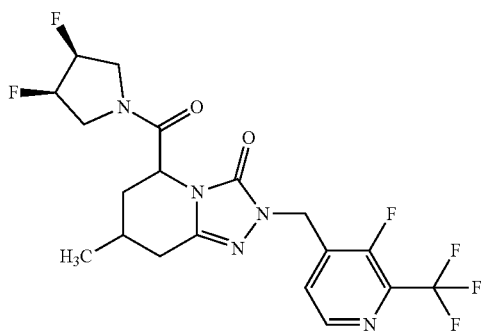 [SMILES: CC1Cc2nn(Cc3ccnc(C(F)(F)F)c3F)c(=O)n2C(C(=O)N2C[C@@H](F)[C@@H](F)C2)C1]

(5RS,7RS)-2-{[3-Fluoro-2-(trifluoromethyl)pyridin-4-yl]methyl}-7-methyl-3-oxo-2,3,5,6,7,8-hexahydro[1,2,4]triazolo[4,3-a]pyridine-5-carboxylic Acid (Diastereomer Mixture; 4 Isomers) (81.4 mg, 90% purity, 196 µmol) was initially charged in THF (2.0 ml), and HBTU (96.5 mg, 254 µmol) and N,N-diisopropylethylamine (100 µl, 590 µmol) were subsequently added. After stirring at room temperature for 15 min, (3R,4S)-3,4-difluoropyrrolidine hydrochloride (33.7 mg, 235 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 41.5 mg (46% of theory) of the title compound were obtained.

LC-MS (Method 3): $R_t$=1.49 min; MS (ESIpos): m/z=464 [M+H]$^+$ $^1$H-NMR (400 MHz, DMSO-d6) δ [ppm]: −0.149 (1.08), −0.008 (9.90), 0.008 (8.58), 0.146 (1.08), 1.029 (12.29), 1.033 (12.77), 1.045 (13.13), 1.050 (12.49), 1.301 (0.76), 1.332 (1.72), 1.364 (2.63), 1.393 (1.84), 1.427 (0.84), 1.892 (1.76), 2.073 (2.95), 2.171 (3.51), 2.201 (2.95), 2.212 (4.07), 2.242 (4.15), 2.259 (1.96), 2.276 (1.72), 2.291 (1.76), 2.327 (1.20), 2.366 (0.88), 2.523 (3.99), 2.661 (3.15), 2.665 (3.27), 2.690 (3.87), 2.697 (2.51), 3.463 (0.84), 3.472 (0.60), 3.497 (1.32), 3.508 (1.28), 3.517 (1.16), 3.533 (0.84), 3.545 (1.48), 3.552 (1.60), 3.597 (1.08), 3.617 (0.96), 3.631 (1.24), 3.652 (0.64), 3.665 (0.88), 3.675 (0.96), 3.690 (1.36), 3.707 (1.52), 3.728 (1.28), 3.741 (1.40), 3.756 (1.52), 3.770 (1.72), 3.792 (1.28), 3.803 (1.60), 3.823 (1.08), 3.872 (0.68), 3.987 (0.84), 4.002 (0.84), 4.015 (0.88), 4.032 (1.20), 4.048 (0.84), 4.061 (0.84), 4.076 (0.60), 4.108 (0.76), 4.123 (0.84), 4.136 (0.80), 4.151 (1.56), 4.167 (0.96), 4.180 (0.84), 4.195 (0.72), 4.662 (2.11), 4.672 (2.39), 4.677 (2.47), 4.684 (2.43), 4.689 (2.31), 4.699 (2.11), 5.040 (16.00), 5.106 (0.44), 5.250 (1.16), 5.260 (1.24), 5.269 (1.20), 5.284 (1.12), 5.306 (0.84), 5.321 (1.04), 5.341 (1.08), 5.356 (0.84), 5.373 (1.20), 5.406 (1.16), 5.436 (0.88), 5.449 (1.04), 5.459 (1.04), 5.471 (0.96), 5.485 (0.76), 5.494 (0.56), 7.589 (3.31), 7.602 (6.26), 7.615 (3.55), 8.568 (5.87), 8.579 (5.67).

Example 334

(5RS,7RS)-5-[(3,3-Difluoropyrrolidin-1-yl)carbonyl]-2-{[3-fluoro-2-(trifluoromethyl)pyridin-4-yl]methyl}-7-methyl-5,6,7,8-tetrahydro[1,2,4]triazolo[4,3-a]pyridin-3(2H)-one (Diastereomer Mixture; 4 Isomers)

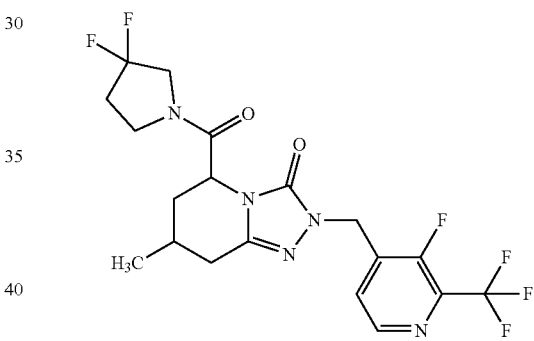

(5RS,7RS)-2-{[3-Fluoro-2-(trifluoromethyl)pyridin-4-yl]methyl}-7-methyl-3-oxo-2,3,5,6,7,8-hexahydro[1,2,4]triazolo[4,3-a]pyridine-5-carboxylic Acid (Diastereomer Mixture; 4 Isomers) (81.4 mg, 90% purity, 196 µmol) was initially charged in THF (2.0 ml), and HBTU (96.5 mg, 254 µmol) and N,N-diisopropylethylamine (100 µl, 590 µmol) were subsequently added. After stirring at room temperature for 15 min, 3,3-difluoropyrrolidine hydrochloride (33.7 mg, 235 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.3 mg (40% of theory) of the title compound were obtained.

LC-MS (Method 3): $R_t$=1.56 min; MS (ESIpos): m/z=464 [M+H]$^+$ $^1$H-NMR (400 MHz, DMSO-d6) δ[ppm]: −0.149 (0.84), −0.008 (7.15), 0.008 (6.47), 0.146 (0.84), 1.033 (11.98), 1.049 (12.26), 1.327 (0.53), 1.342 (0.59), 1.357 (1.11), 1.372 (1.21), 1.387 (1.21), 1.403 (1.21), 1.418 (0.65), 1.432 (0.65), 1.891 (1.21), 2.174 (2.35), 2.204 (2.01), 2.215 (2.75), 2.245 (3.03), 2.283 (1.27), 2.327 (0.99), 2.366 (0.90), 2.381 (0.99), 2.401 (0.99), 2.414 (1.36), 2.432 (1.21), 2.454 (0.87), 2.524 (3.78), 2.559 (1.70), 2.576 (1.05), 2.596 (0.59), 2.665 (2.48), 2.709 (1.83), 3.541 (1.15), 3.550 (1.33), 3.558 (1.98), 3.570 (2.10), 3.589 (1.02), 3.683 (1.21), 3.717 (1.42), 3.738 (0.77), 3.751 (0.68), 3.770 (1.58), 3.803 (1.58), 3.823 (0.93), 3.831 (0.96), 3.848 (1.55), 3.866 (0.68), 3.888 (0.74), 3.908 (1.58), 3.933 (0.96), 3.952 (0.43), 4.056 (0.99), 4.094 (1.02), 4.131 (1.21), 4.165 (0.93), 4.603 (1.15), 4.618 (1.36), 4.630 (1.27), 4.645 (1.11), 4.713 (1.21), 4.728 (1.36), 4.740 (1.30), 4.755 (1.15), 5.042 (16.00), 7.591 (2.54), 7.603 (4.80), 7.616 (2.72), 8.568 (5.29), 8.580 (5.20).

Example 335

(5RS,7RS)-5-[(3-Fluoroazetidin-1-yl)carbonyl]-2-{[3-fluoro-2-(trifluoromethyl)pyridin-4-yl]methyl}-7-methyl-5,6,7,8-tetrahydro[1,2,4]triazolo[4,3-a]pyridin-3(2H)-one (Diastereomer Mixture 1, Racemate)

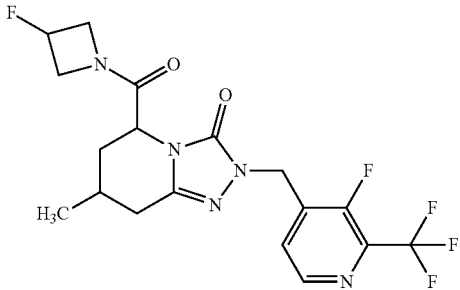 [SMILES: CC1Cc2nn(Cc3ccnc(C(F)(F)F)c3F)c(=O)n2C(C(=O)N2CC(F)C2)C1]

(5RS,7RS)-2-{[3-Fluoro-2-(trifluoromethyl)pyridin-4-yl]methyl}-7-methyl-3-oxo-2,3,5,6,7,8-hexahydro[1,2,4]triazolo[4,3-a]pyridine-5-carboxylic Acid (Diastereomer Mixture; 4 Isomers) (81.4 mg, 90% purity, 196 µmol) was initially charged in THF (2.0 ml), and HBTU (96.5 mg, 254 µmol) and N,N-diisopropylethylamine (100 µl, 590 µmol) were subsequently added. After stirring at room temperature for 15 min, 3-fluoroazetidine hydrochloride (26.2 mg, 235 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 38.9 mg (55% of theory) of the title compound were obtained.

LC-MS (Method 4): $R_t$=0.75 min; MS (ESIpos): m/z=432 [M+H]$^+$ $^1$H-NMR (400 MHz, DMSO-d6) δ[ppm]: −0.149 (1.79), −0.008 (16.00), 0.008 (13.81), 0.146 (1.79), 1.025 (13.71), 1.041 (14.11), 1.388 (1.39), 1.417 (1.59), 1.435 (1.49), 1.467 (0.70), 1.894 (2.09), 2.170 (3.88), 2.200 (2.88), 2.210 (3.78), 2.240 (2.39), 2.327 (2.09), 2.366 (2.19), 2.523 (6.86), 2.648 (2.78), 2.670 (2.39), 2.679 (2.88), 2.710 (2.19), 2.857 (1.29), 3.103 (1.09), 3.880 (0.70), 3.966 (1.09), 4.025 (0.80), 4.153 (0.70), 4.221 (1.09), 4.248 (1.39), 4.273 (1.29), 4.305 (1.29), 4.337 (0.89), 4.396 (3.98), 4.411 (4.37), 4.424 (3.88), 4.439 (3.78), 4.465 (0.80), 4.510 (0.70), 4.561 (0.70), 4.651 (0.70), 5.042 (10.93), 5.107 (0.50), 5.380 (1.19), 5.523 (1.09), 7.603 (3.48), 7.616 (6.56), 7.628 (3.78), 8.567 (6.06), 8.579 (5.96).

Example 336

(5RS,7RS)-5-{[(3R,4S)-3,4-Difluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture 1; Racemate)

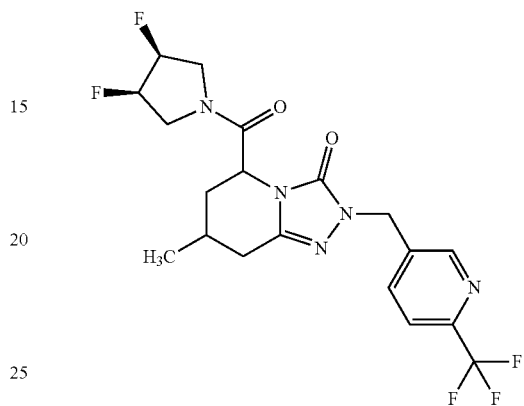

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (78.8 mg, 221 µmol) was initially charged in THF (2.0 ml), and HBTU (109 mg, 288 mol) and N,N-diisopropylethylamine (150 µl, 880 µmol) were subsequently added. After stirring at room temperature for 15 min, (3R,4S)-3,4-difluoropyrrolidine hydrochloride (38.1 mg, 265 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 78.9 mg (80% of theory) of the title compound were obtained.

LC-MS (Method 4): $R_t$=0.76 min; MS (ESIpos): m/z=446 [M+H]$^+$ $^1$H-NMR (400 MHz, DMSO-d6) δ [ppm]: −0.149 (0.58), 0.146 (0.52), 1.023 (10.88), 1.027 (11.14), 1.039 (11.23), 1.290 (0.61), 1.322 (1.50), 1.354 (2.20), 1.385 (1.56), 1.417 (0.75), 1.874 (3.65), 2.157 (2.89), 2.187 (2.52), 2.197 (3.39), 2.228 (3.41), 2.246 (1.76), 2.260 (1.56), 2.278 (1.62), 2.327 (0.78), 2.366 (0.46), 2.642 (2.43), 2.683 (2.20), 2.710 (0.61), 3.461 (0.93), 3.495 (1.24), 3.504 (1.33), 3.513 (1.33), 3.548 (1.68), 3.598 (1.04), 3.617 (0.90), 3.631 (1.13), 3.651 (0.72), 3.664 (0.90), 3.674 (0.98), 3.687 (1.13), 3.697 (1.16), 3.709 (1.42), 3.721 (1.10), 3.731 (1.24), 3.744 (1.22), 3.772 (1.71), 3.807 (1.36), 3.842 (0.81), 3.884 (0.69), 3.982 (0.75), 3.997 (0.84), 4.010 (0.72), 4.027 (1.07), 4.043 (0.72), 4.056 (0.64), 4.070 (0.55), 4.115 (0.67), 4.130 (0.81), 4.143 (0.69), 4.158 (1.36), 4.174 (0.81), 4.187 (0.78), 4.202 (0.78), 4.648 (1.68), 4.654 (1.82), 4.663 (2.05), 4.671 (2.34), 4.682 (1.91), 4.690 (1.74), 4.696 (1.56), 4.986 (16.00), 5.054 (3.27), 5.249 (1.27), 5.260 (1.27), 5.270 (1.30), 5.282 (1.13), 5.322 (1.10), 5.340 (1.04), 5.384 (1.36), 5.407 (1.30), 5.460 (1.16), 5.486 (0.81), 6.088 (0.95), 7.917 (12.88), 8.663 (6.37).

Example 337

(5S,7S)-5-{[(3R,4S)-3,4-Difluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (Enantiomer 1)

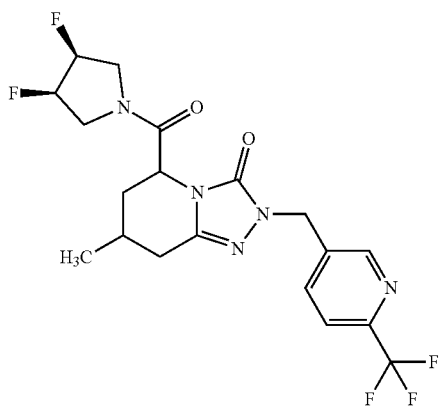 [SMILES: CC1Cc2nn(Cc3ccc(C(F)(F)F)nc3)c(=O)n2C(C(=O)N2C[C@@H](F)[C@@H](F)C2)C1]

(5RS,7RS)-5-{[(3R,4S)-3,4-Difluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (diastereomer 1; racemate) was separated by chiral preparative HPLC [sample preparation: 66.7 mg dissolved in 7 ml of ethanol; injection volume: 0.15 ml; column: Daicel Chiralcel® OD-H 5 μm, 250×20 mm; eluent: n-heptane/ethanol (60:40); flow rate: 15 ml/min; temperature 25° C.; UV detection: 220 nm]. After the separation, 21.7 mg of enantiomer 1, which eluted first, and 26.4 mg of enantiomer 2, which eluted later, were isolated.

Enantiomer 1:

Analytical chiral HPLC: $R_t$=2.78 min, e.e. =100% [column: Daicel Chiralcel® IB-3 50×4.6 mm; eluent: n-heptane/ethanol 50:50; flow rate: 1 ml/min; UV detection: 220 nm].

LC-MS (Method 15): $R_t$=1.31 min; MS (ESIpos): m/z=446 [M+H]$^+$ $^1$H-NMR (400 MHz, DMSO-d6) δ [ppm]: −0.149 (1.09), −0.008 (10.72), 0.008 (11.52), 0.146 (1.20), 1.023 (10.64), 1.028 (11.23), 1.039 (11.52), 1.044 (11.08), 1.236 (1.17), 1.290 (0.77), 1.322 (1.49), 1.354 (2.22), 1.386 (1.57), 1.418 (0.73), 1.875 (3.75), 2.157 (2.95), 2.187 (2.51), 2.198 (3.43), 2.228 (3.43), 2.245 (1.71), 2.263 (1.57), 2.279 (1.57), 2.328 (1.35), 2.643 (2.48), 2.670 (1.86), 2.679 (2.41), 2.710 (0.62), 3.461 (0.95), 3.495 (1.28), 3.504 (1.28), 3.514 (1.31), 3.548 (1.71), 3.598 (1.17), 3.616 (0.95), 3.630 (1.13), 3.650 (0.80), 3.664 (0.95), 3.674 (0.95), 3.688 (1.13), 3.697 (1.13), 3.709 (1.38), 3.721 (1.13), 3.731 (1.24), 3.744 (1.28), 3.772 (1.64), 3.807 (1.38), 3.841 (0.77), 3.934 (0.40), 3.982 (0.80), 3.997 (0.84), 4.010 (0.73), 4.027 (1.13), 4.043 (0.77), 4.056 (0.69), 4.070 (0.51), 4.115 (0.69), 4.130 (0.80), 4.143 (0.69), 4.159 (1.35), 4.173 (0.84), 4.186 (0.80), 4.202 (0.84), 4.648 (1.64), 4.655 (1.75), 4.663 (2.00), 4.670 (2.26), 4.682 (1.97), 4.690 (1.79), 4.697 (1.57), 4.986 (16.00), 5.055 (3.46), 5.249 (1.24), 5.260 (1.28), 5.271 (1.24), 5.322 (1.02), 5.340 (0.98), 5.406 (1.28), 5.461 (1.02), 6.086 (0.98), 7.916 (12.46), 7.919 (12.28), 8.664 (5.94).

Example 338

(5RS,7RS)-5-{[(3R,4S)-3,4-Difluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (Enantiomer 2)

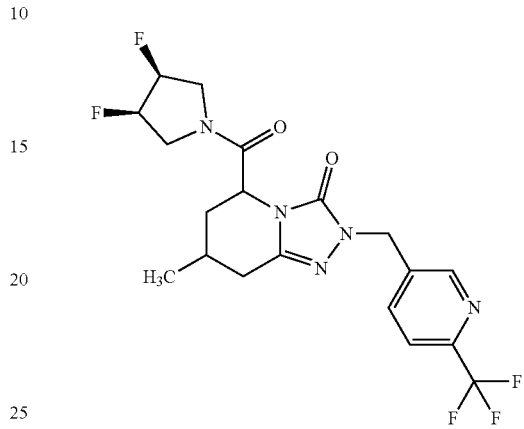

(5RS,7RS)-5-{[(3R,4S)-3,4-Difluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyridin-3(2H)-one (diastereomer 1) was separated by chiral preparative HPLC [sample preparation: 66.7 mg dissolved in 7 ml of ethanol; injection volume: 0.15 ml; column: Daicel Chiralcel® OD-H 5 μm, 250×20 mm; eluent: n-heptane/ethanol (60:40); flow rate: 15 ml/min; temperature 25° C.; UV detection: 220 nm]. After the separation, 21.7 mg of enantiomer 1, which eluted first, and 26.4 mg of enantiomer 2, which eluted later, were isolated.

Enantiomer 2:

Analytical chiral HPLC: $R_t$=2.98 min, e.e. =100% [column: Daicel Chiralcel® IB-3 50×4.6 mm; eluent: n-heptane/ethanol 50:50; flow rate: 1 ml/min; UV detection: 220 nm].

LC-MS (Method 4): $R_t$=0.76 min; MS (ESIpos): m/z=446 [M+H]$^+$ $^1$H-NMR (400 MHz, DMSO-d6) δ [ppm]: −0.149 (1.26), −0.008 (10.77), 0.008 (10.65), 0.146 (1.26), 1.023 (10.81), 1.028 (11.26), 1.039 (11.65), 1.044 (11.19), 1.235 (1.03), 1.290 (0.76), 1.320 (1.49), 1.355 (2.14), 1.388 (1.53), 1.418 (0.73), 1.883 (1.49), 2.157 (3.17), 2.187 (2.60), 2.198 (3.63), 2.228 (3.55), 2.246 (1.76), 2.279 (1.57), 2.327 (1.45), 2.366 (0.42), 2.648 (2.41), 2.670 (1.79), 2.679 (2.33), 2.709 (0.50), 3.460 (0.80), 3.495 (0.99), 3.505 (1.11), 3.514 (1.15), 3.548 (1.53), 3.597 (0.92), 3.617 (0.84), 3.630 (0.99), 3.652 (0.57), 3.674 (0.84), 3.687 (1.03), 3.697 (0.92), 3.709 (1.22), 3.721 (1.03), 3.732 (0.99), 3.744 (0.99), 3.772 (1.41), 3.808 (1.26), 3.983 (0.76), 3.997 (0.80), 4.010 (0.76), 4.028 (1.07), 4.043 (0.76), 4.056 (0.69), 4.072 (0.53), 4.115 (0.65), 4.130 (0.76), 4.144 (0.69), 4.158 (1.26), 4.174 (0.73), 4.187 (0.69), 4.201 (0.65), 4.648 (1.57), 4.655 (1.76), 4.663 (2.06), 4.674 (2.33), 4.681 (2.02), 4.690 (1.76), 4.697 (1.60), 4.986 (16.00), 5.249 (1.07), 5.259 (1.07), 5.270 (1.11), 5.307 (0.76), 5.322 (0.84), 5.372 (1.03), 5.384 (1.11), 5.407 (1.07), 5.459 (0.99), 7.901 (0.95), 7.919 (12.18), 8.663 (6.07).

Example 339

(5RS,7RS)-2-(3-Chloro-4-fluorobenzyl)-5-{[(3R,4S)-3,4-difluoropyrrolidin-1-yl]carbonyl}-7-methyl-5,6,7,8-tetrahydro[1,2,4]triazolo[4,3-a]pyridin-3(2H)-one (Diastereomer Mixture; 4 Isomers)

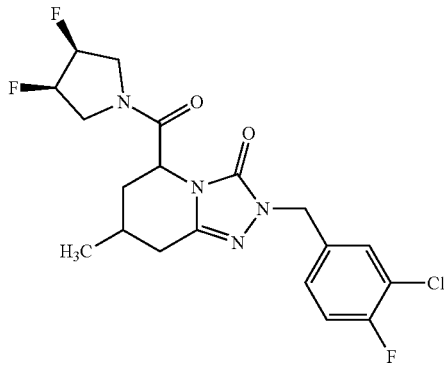 [SMILES: CC1Cc2nn(Cc3ccc(F)c(Cl)c3)c(=O)n2C(C(=O)N2C[C@@H](F)[C@@H](F)C2)C1]

(5RS,7RS)-2-(3-Chloro-4-fluorobenzyl)-7-methyl-3-oxo-2,3,5,6,7,8-hexahydro[1,2,4]triazolo[4,3-a]pyridine-5-carboxylic Acid (Diastereomer Mixture; 4 Isomers) (70.0 mg, 206 µmol) was initially charged in THF (2.0 ml), and HBTU (85.9 mg, 227 µmol) and N,N-diisopropylethylamine (110 µl, 620 µmol) were subsequently added. After stirring at room temperature for 15 min, (3R,4S)-3,4-difluoropyrrolidine hydrochloride (35.5 mg, 247 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 54.2 mg (61% of theory) of the title compound were obtained.

LC-MS (Method 3): $R_t$=1.62 min; MS (ESIpos): m/z=429 [M+H]$^+$ $^1$H-NMR (400 MHz, DMSO-d6) δ [ppm]: −0.149 (1.33), 0.008 (11.11), 0.146 (1.21), 1.026 (10.32), 1.038 (10.57), 1.317 (1.39), 1.348 (1.69), 1.385 (1.39), 1.414 (0.78), 1.885 (1.39), 2.073 (3.68), 2.154 (2.84), 2.185 (2.23), 2.195 (3.26), 2.226 (3.62), 2.328 (2.29), 2.367 (1.39), 2.648 (2.23), 2.670 (2.66), 2.710 (1.51), 3.512 (1.21), 3.548 (1.39), 3.629 (1.03), 3.710 (1.33), 3.759 (1.57), 3.806 (1.27), 3.851 (0.91), 4.020 (1.03), 4.162 (1.33), 4.653 (1.69), 4.673 (2.17), 4.801 (16.00), 5.270 (1.03), 5.406 (1.09), 5.458 (0.97), 7.256 (2.35), 7.377 (2.96), 7.398 (4.35), 7.418 (2.11), 7.444 (3.50), 7.462 (3.50).

Example 340

(5RS,7RS)-2-(3-Chloro-4-fluorobenzyl)-5-[(3-fluoroazetidin-1-yl)carbonyl]-7-methyl-5,6,7,8-tetrahydro[1,2,4]triazolo[4,3-a]pyridin-3(2H)-one (Diastereomer Mixture; 4 Isomers)

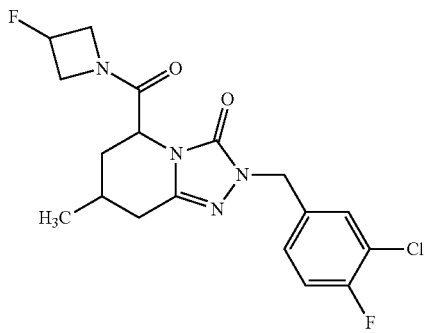 [SMILES: CC1Cc2nn(Cc3ccc(F)c(Cl)c3)c(=O)n2C(C(=O)N2CC(F)C2)C1]

(5RS,7RS)-2-(3-Chloro-4-fluorobenzyl)-7-methyl-3-oxo-2,3,5,6,7,8-hexahydro[1,2,4]triazolo[4,3-a]pyridine-5-carboxylic Acid (Diastereomer Mixture; 4 Isomers) (70.0 mg, 206 µmol) was initially charged in THF (2.0 ml), and HBTU (85.9 mg, 227 µmol) and N,N-diisopropylethylamine (110 µl, 620 µmol) were subsequently added. After stirring at room temperature for 15 min, 3-fluoroazetidine hydrochloride (27.6 mg, 247 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 57.2 mg (69% of theory) of the title compound were obtained.

LC-MS (Method 3): $R_t$=1.53 min; MS (ESIpos): m/z=397 [M+H]$^+$ $^1$H-NMR (400 MHz, DMSO-d6) δ [ppm]: 0.008 (2.93), 1.017 (15.46), 1.033 (16.00), 1.340 (0.54), 1.370 (1.55), 1.400 (1.84), 1.420 (1.72), 1.451 (0.70), 1.876 (1.86), 2.072 (4.68), 2.119 (1.08), 2.152 (4.88), 2.182 (3.65), 2.192 (4.50), 2.223 (2.93), 2.327 (0.62), 2.366 (0.44), 2.630 (3.05), 2.636 (3.11), 2.670 (3.23), 2.709 (0.56), 3.878 (0.75), 3.906 (0.97), 3.936 (1.30), 3.965 (1.55), 3.997 (0.71), 4.026 (0.85), 4.136 (0.63), 4.149 (0.72), 4.165 (0.58), 4.185 (0.85), 4.201 (0.82), 4.233 (1.94), 4.251 (1.38), 4.262 (1.43), 4.291 (1.59), 4.319 (1.46), 4.385 (4.37), 4.400 (4.82), 4.413 (5.10), 4.428 (3.90), 4.448 (0.69), 4.480 (1.31), 4.496 (0.86), 4.533 (0.78), 4.549 (0.82), 4.573 (0.46), 4.644 (0.59), 4.661 (0.68), 4.686 (0.63), 4.698 (0.69), 4.713 (0.73), 4.738 (0.54), 4.806 (14.39), 5.377 (1.22), 5.519 (1.21), 7.264 (3.03), 7.375 (3.36), 7.398 (5.54), 7.420 (2.62), 7.452 (3.55), 7.470 (3.56).

Example 341

(5RS,7RS)-5-[(3-Fluoroazetidin-1-yl)carbonyl]-7-methyl-2-{[6-(trifluoromethyl)pyridin-3-yl]methyl}-5,6,7,8-tetrahydro[1,2,4]triazolo[4,3-a]pyridin-3(2H)-one (Diastereomer Mixture; 4 Isomers)

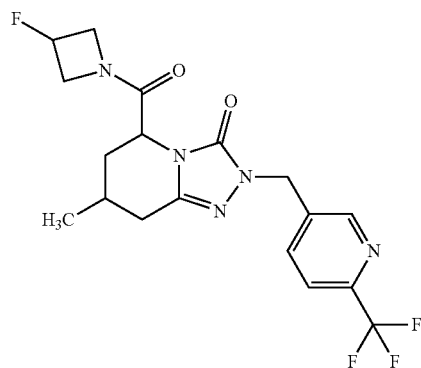 [SMILES: CC1Cc2nn(Cc3ccc(C(F)(F)F)nc3)c(=O)n2C(C(=O)N2CC(F)C2)C1]

(5RS,7RS)-7-Methyl-3-oxo-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (39.8 mg, 112 µmol) was initially charged in THF (2.0 ml), and HBTU (55.1 mg, 145 mol) and N,N-diisopropylethylamine (78 µl, 450 µmol) were subsequently added. After stirring at room temperature for 15 min, 3-fluoroazetidine hydrochloride (15.0 mg, 134 mol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 7.20 mg (16% of theory) of the title compound were obtained.

LC-MS (Method 4): $R_t$=0.71 min; MS (ESIpos): m/z=414 [M+H]$^+$ $^1$H-NMR (400 MHz, DMSO-d6) δ [ppm]: −0.149 (0.80), −0.008 (6.70), 0.008 (6.25), 0.146 (0.88), 1.019 (15.47), 1.035 (16.00), 1.377 (1.52), 1.397 (1.79), 1.407 (1.83), 1.426 (1.71), 1.456 (0.72), 1.883 (1.79), 2.156 (4.65), 2.185 (3.31), 2.195 (4.50), 2.226 (2.93), 2.327 (1.30), 2.366 (0.99), 2.524 (3.89), 2.636 (3.24), 2.671 (3.92), 2.710 (1.14), 3.881 (0.80), 3.913 (0.95), 3.938 (1.26), 3.966 (1.49), 3.994 (0.72), 4.027 (0.84), 4.152 (0.80), 4.185 (0.91), 4.220 (1.22), 4.237 (1.75), 4.271 (1.60), 4.303 (1.41), 4.322 (1.22), 4.388 (4.84), 4.403 (5.60), 4.416 (5.52), 4.430 (4.27), 4.477 (0.99), 4.506 (0.88), 4.541 (0.80), 4.556 (0.80), 4.656 (0.72), 4.712 (0.76), 4.990 (13.22), 5.381 (1.26), 5.515 (1.26), 7.900 (1.98), 7.920 (11.85), 7.949 (1.49), 8.673 (7.35).

Example 342

(5S)-2-{2-[3-Chloro-5-(trifluoromethyl)pyridin-2-yl]ethyl}-5-{[(3S)-3-fluoropyrrolidin-1-yl]carbonyl}-5,6,7,8-tetrahydro[1,2,4]triazolo[4,3-a]pyridin-3(2H)-one

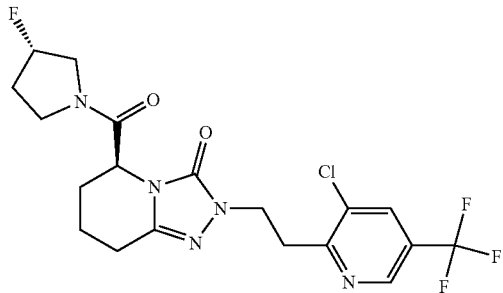 [SMILES: O=C([C@@H]1CCCc2nn(CCc3ncc(C(F)(F)F)cc3Cl)c(=O)n21)N1CC[C@H](F)C1]

(5S)-2-{2-[3-Chloro-5-(trifluoromethyl)pyridin-2-yl]ethyl}-3-oxo-2,3,5,6,7,8-hexahydro[1,2,4]triazolo[4,3-a]pyridine-5-carboxylic acid (75.0 mg, 72% purity, 138 μmol) was initially charged in THF (1.5 ml), and HBTU (99.6 mg, 263 μmol) and N,N-diisopropylethylamine (110 μl, 620 μmol) were subsequently added. After stirring at room temperature for 15 min, (3S)-3-fluoropyrrolidine hydrochloride (29.5 mg, 235 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 50.9 mg (80% of theory) of the title compound were obtained.

LC-MS (Method 3): $R_t$=1.45 min; MS (ESIpos): m/z=462 [M+H]$^+$ $^1$H-NMR (400 MHz, DMSO-d6) δ[ppm]: −0.149 (0.83), −0.008 (7.76), 0.008 (7.06), 0.146 (0.83), 1.723 (3.81), 1.876 (0.90), 1.989 (1.39), 2.060 (2.08), 2.073 (16.00), 2.129 (1.11), 2.256 (1.04), 2.327 (2.15), 2.366 (1.59), 2.523 (7.83), 2.594 (2.35), 2.602 (2.63), 2.645 (1.25), 2.669 (2.29), 2.710 (1.59), 3.282 (5.13), 3.383 (0.97), 3.453 (0.69), 3.480 (0.90), 3.580 (0.69), 3.606 (2.98), 3.631 (2.15), 3.705 (1.87), 3.727 (1.87), 3.751 (1.59), 3.769 (1.25), 3.836 (2.56), 3.975 (0.83), 3.995 (1.45), 4.011 (2.63), 4.028 (4.29), 4.056 (3.39), 4.075 (2.08), 4.091 (1.04), 4.110 (0.62), 4.599 (1.32), 4.609 (1.66), 4.615 (1.66), 4.625 (1.32), 4.657 (1.66), 4.666 (1.87), 4.673 (2.01), 4.681 (1.45), 5.250 (1.25), 5.380 (1.52), 5.502 (0.97), 5.934 (0.48), 8.410 (5.96), 8.877 (5.96).

Example 343

(5S)-2-{2-[3-Chloro-5-(trifluoromethyl)pyridin-2-yl]ethyl}-5-[(3,3-difluoropyrrolidin-1-yl)carbonyl]-5,6,7,8-tetrahydro[1,2,4]triazolo[4,3-a]pyridin-3(2H)-one

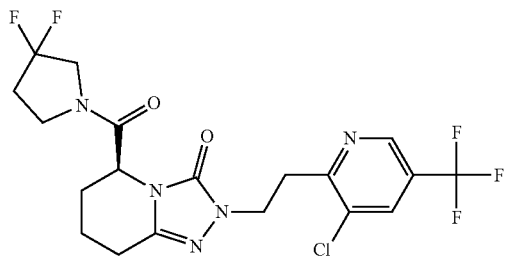 [SMILES: O=C([C@@H]1CCCc2nn(CCc3ncc(C(F)(F)F)cc3Cl)c(=O)n21)N1CCC(F)(F)C1]

(5S)-2-{2-[3-Chloro-5-(trifluoromethyl)pyridin-2-yl]ethyl}-3-oxo-2,3,5,6,7,8-hexahydro[1,2,4]triazolo[4,3-a]pyridine-5-carboxylic acid (65.0 mg, 166 μmol) was initially charged in THF (2.5 ml) at room temperature. Subsequently, HBTU (82.0 mg, 216 mol) and N,N-diisopropylethylamine (87 μl, 500 μmol) were added. After stirring for 15 min, 3,3-difluoropyrrolidine hydrochloride (28.7 mg, 200 μmol) was added and the reaction mixture was stirred at room temperature overnight. HBTU (82.0 mg, 216 μmol) and 3,3-difluoropyrrolidine hydrochloride (28.7 mg, 200 μmol) were added again and the mixture was stirred overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 33.3 mg (42% of theory) of the title compound were obtained.

LC-MS (Method 3): $R_t$=1.59 min; MS (ESIpos): m/z=480 [M+H]$^+$ $^1$H-NMR (400 MHz, DMSO-d6) δ [ppm]: −0.149 (1.01), 0.008 (7.50), 0.146 (0.97), 1.225 (1.31), 1.243 (7.46), 1.258 (8.43), 1.273 (4.85), 1.689 (5.30), 1.702 (7.20), 1.714 (6.68), 1.915 (2.16), 1.947 (3.24), 1.960 (3.10), 1.973 (4.07), 1.988 (3.13), 2.004 (2.39), 2.013 (2.65), 2.028 (2.87), 2.038 (2.91), 2.047 (2.28), 2.063 (2.20), 2.073 (16.00), 2.328 (1.75), 2.350 (1.19), 2.367 (3.32), 2.398 (2.76), 2.418 (2.65), 2.438 (1.79), 2.523 (11.00), 2.565 (5.41), 2.573 (4.03), 2.593 (6.97), 2.639 (2.39), 2.670 (1.94), 2.710 (1.57), 3.130 (0.71), 3.140 (0.75), 3.159 (0.67), 3.280 (8.47), 3.511 (5.45), 3.530 (9.44), 3.549 (5.00), 3.618 (1.42), 3.652 (3.24), 3.686 (3.54), 3.705 (2.01), 3.721 (1.79), 3.738 (3.88), 3.769 (4.92), 3.793 (3.69), 3.811 (1.83), 3.856 (1.83), 3.875 (3.58), 3.895 (2.05), 3.901 (2.46), 3.920 (1.12), 3.953 (1.04), 3.981 (3.66), 4.000 (3.28), 4.017 (6.94), 4.035 (11.93), 4.056 (11.75), 4.075 (5.93), 4.092 (2.80), 4.103 (1.75), 4.131 (2.24), 4.161 (2.09),

Example 344

(5S)-5-{[(3R,4S)-3,4-Difluoropyrrolidin-1-yl]carbonyl}-2-[2-(4-fluorophenyl)ethyl]-5,6,7,8-tetrahydro[1,2,4]triazolo[4,3-a]pyridin-3(2H)-one

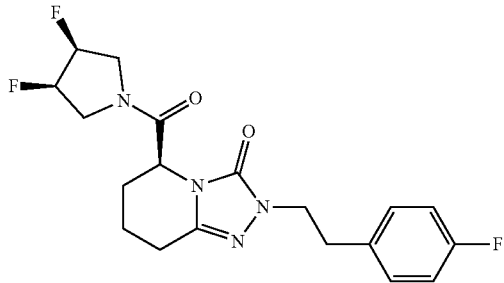 [SMILES: O=C([C@@H]1CCCc2nn(CCc3ccc(F)cc3)c(=O)n21)N1C[C@@H](F)[C@@H](F)C1]

(5S)-2-[2-(4-Fluorophenyl)ethyl]-3-oxo-2,3,5,6,7,8-hexahydro[1,2,4]triazolo[4,3-a]pyridine-5-carboxylic acid (73.1 mg, 240 µmol) was initially charged in THF (2.0 ml), and HBTU (118 mg, 311 µmol) and N,N-diisopropylethylamine (130 µl, 720 µmol) were subsequently added. After stirring at room temperature for 15 min, (3R,4S)-3,4-difluoropyrrolidine hydrochloride (41.3 mg, 287 µmol) was added and the reaction mixture was stirred at room temperature overnight. HBTU (90 mg, 240 µmol), (3R,4S)-3,4-difluoropyrrolidine hydrochloride (34.4 mg, 239 µmol) and N,N-diisopropylethylamine (43 µl, 240 µmol) were added again and the mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 62.3 mg (66% of theory) of the title compound were obtained.

LC-MS (Method 4): $R_t$=0.76 min; MS (ESIpos): m/z=395 [M+H]$^+$ $^1$H-NMR (400 MHz, DMSO-d6) δ [ppm]: −0.149 (1.11), −0.008 (9.50), 0.008 (9.19), 0.146 (1.15), 1.664 (1.94), 1.674 (2.46), 1.687 (3.33), 1.700 (4.32), 1.712 (4.95), 1.723 (4.83), 1.737 (3.13), 1.900 (1.11), 1.940 (2.42), 1.965 (1.74), 1.983 (3.29), 2.008 (2.26), 2.016 (2.22), 2.023 (2.46), 2.031 (2.26), 2.040 (2.02), 2.050 (1.74), 2.057 (1.90), 2.073 (13.15), 2.327 (1.11), 2.366 (1.47), 2.523 (4.55), 2.526 (3.92), 2.557 (4.87), 2.571 (4.36), 2.580 (3.52), 2.605 (3.21), 2.616 (5.98), 2.627 (3.33), 2.647 (1.39), 2.659 (2.46), 2.670 (2.30), 2.710 (1.58), 2.895 (7.80), 2.913 (16.00), 2.931 (8.28), 3.367 (0.59), 3.443 (1.27), 3.453 (0.75), 3.477 (2.14), 3.487 (1.58), 3.498 (2.06), 3.506 (2.26), 3.515 (1.90), 3.524 (1.98), 3.533 (1.98), 3.549 (1.19), 3.558 (1.62), 3.568 (0.99), 3.603 (1.74), 3.617 (1.94), 3.636 (1.27), 3.650 (1.39), 3.659 (2.02), 3.671 (3.13), 3.681 (2.34), 3.691 (2.02), 3.704 (2.77), 3.715 (2.77), 3.732 (3.45), 3.749 (4.00), 3.766 (7.92), 3.784 (12.55), 3.801 (8.75), 3.807 (7.49), 3.817 (4.04), 3.826 (4.24), 3.833 (2.77), 3.841 (3.09), 3.851 (1.47), 3.859 (1.47), 3.880 (1.43), 3.913 (1.62), 3.927 (1.94), 3.942 (1.27), 3.962 (1.90), 3.976 (1.90), 3.990 (1.23), 4.005 (1.15), 4.103 (1.19), 4.118 (1.39), 4.131 (1.27), 4.145 (2.30), 4.160 (1.43), 4.173 (1.27), 4.188 (1.15), 4.706 (5.54), 4.717 (6.65), 4.721 (7.29), 4.731 (5.27), 5.254 (1.86), 5.266 (2.06), 5.276 (1.70), 5.287 (1.31), 5.300 (1.47), 5.314 (1.47), 5.323 (1.35), 5.340 (1.50), 5.358 (1.66), 5.370 (1.86), 5.388 (1.70), 5.397 (1.98), 5.407 (1.82), 5.419 (1.23), 5.429 (1.35), 5.443 (1.54), 5.451 (1.58), 5.462 (1.50), 7.060 (5.35), 7.064 (7.29), 7.082 (13.35), 7.086 (14.61), 7.104 (9.23), 7.109 (8.63), 7.198 (6.34), 7.212 (9.74), 7.221 (10.69), 7.229 (8.44), 7.243 (5.54).

Example 345

(5S)-5-[(3,3-Difluoroazetidin-1-yl)carbonyl]-2-[2-(4-fluorophenyl)ethyl]-5,6,7,8-tetrahydro[1,2,4]triazolo[4,3-a]pyridin-3(2H)-one

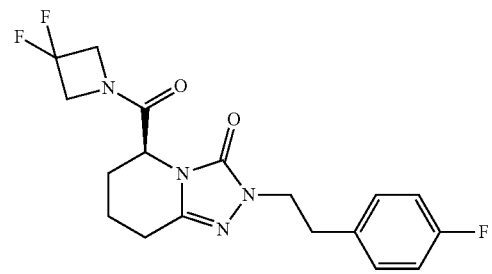 [SMILES: O=C([C@@H]1CCCc2nn(CCc3ccc(F)cc3)c(=O)n21)N1CC(F)(F)C1]

(5S)-2-[2-(4-Fluorophenyl)ethyl]-3-oxo-2,3,5,6,7,8-hexahydro[1,2,4]triazolo[4,3-a]pyridine-5-carboxylic acid (73.1 mg, 240 µmol) was initially charged in THF (2.0 ml), and HBTU (118 mg, 311 µmol) and N,N-diisopropylethylamine (130 µl, 720 µmol) were subsequently added. After stirring at room temperature for 15 min, 3,3-difluoroazetidine hydrochloride (37.2 mg, 287 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 56.0 mg (61% of theory) of the title compound were obtained.

LC-MS (Method 3): $R_t$=1.40 min; MS (ESIpos): m/z=381 [M+H]$^+$ $^1$H-NMR (400 MHz, DMSO-d6) δ[ppm]: −0.149 (1.79), 0.146 (1.90), 1.709 (4.36), 1.721 (6.60), 1.735 (5.71), 1.950 (2.35), 1.961 (3.58), 1.974 (3.36), 1.997 (1.79), 2.012 (2.69), 2.032 (3.02), 2.046 (2.24), 2.073 (6.60), 2.327 (2.80), 2.366 (2.35), 2.523 (10.85), 2.564 (4.36), 2.584 (4.92), 2.600 (5.82), 2.613 (6.83), 2.627 (3.36), 2.642 (1.23), 2.656 (2.24), 2.670 (3.58), 2.710 (2.46), 2.900 (6.94), 2.918 (13.87), 2.937 (7.61), 3.788 (6.60), 3.803 (10.74), 3.808 (11.19), 3.822 (5.26), 4.352 (4.03), 4.499 (4.81), 4.513 (7.94), 4.526 (4.70), 4.662 (2.35), 4.694 (2.69), 4.770 (1.12), 4.799 (2.46), 4.830 (2.24), 7.062 (7.16), 7.084 (16.00), 7.106 (10.29), 7.207 (9.40), 7.221 (10.85), 7.228 (9.17), 7.242 (7.05).

Example 346

(5S)-5-[(3,3-Difluoropyrrolidin-1-yl)carbonyl]-2-[2-(4-methoxyphenyl)ethyl]-5,6,7,8-tetrahydro[1,2,4]triazolo[4,3-a]pyridin-3(2H)-one

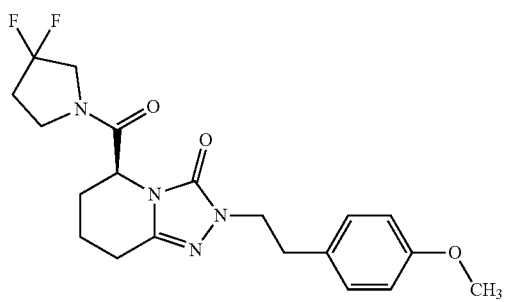 [SMILES: COc1ccc(CCn2nc3n(c2=O)[C@H](C(=O)N2CCC(F)(F)C2)CCC3)cc1]

(5S)-2-[2-(4-Methoxyphenyl)ethyl]-3-oxo-2,3,5,6,7,8-hexahydro[1,2,4]triazolo[4,3-a]pyridine-5-carboxylic acid (92.0 mg, 290 μmol) was initially charged in THF (2.0 ml), and HBTU (143 mg, 377 μmol) and N,N-diisopropylethylamine (150 μl, 870 μmol) were subsequently added. After stirring at room temperature for 15 min, 3,3-difluoropyrrolidine hydrochloride (49.9 mg, 348 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 51.6 mg (92% purity, 40% of theory) of the title compound were obtained.

LC-MS (Method 4): $R_t$=0.75 min; MS (ESIpos): m/z=407 [M+H]$^+$ $^1$H-NMR (400 MHz, DMSO-d6) δ[ppm]: 0.008 (2.58), 1.701 (2.94), 1.713 (4.02), 1.724 (3.77), 1.909 (0.73), 1.957 (1.87), 1.970 (1.77), 1.981 (2.06), 1.995 (2.06), 2.005 (1.63), 2.015 (1.54), 2.031 (1.60), 2.041 (1.55), 2.051 (1.14), 2.066 (1.03), 2.073 (1.41), 2.085 (0.51), 2.328 (0.87), 2.354 (0.71), 2.371 (1.17), 2.403 (1.47), 2.421 (1.42), 2.442 (1.09), 2.523 (4.27), 2.573 (3.78), 2.580 (3.40), 2.596 (2.90), 2.609 (2.10), 2.620 (3.47), 2.631 (1.84), 2.664 (1.65), 2.690 (0.57), 2.710 (0.63), 2.731 (0.98), 2.830 (5.18), 2.849 (10.41), 2.867 (5.46), 2.890 (1.30), 3.519 (15.11), 3.539 (11.03), 3.557 (6.77), 3.659 (1.93), 3.691 (2.71), 3.724 (5.71), 3.743 (6.41), 3.761 (4.83), 3.766 (6.69), 3.787 (4.86), 3.821 (1.36), 3.869 (0.93), 3.887 (1.96), 3.913 (1.36), 3.932 (0.62), 3.956 (0.62), 3.984 (1.22), 3.997 (0.65), 4.013 (0.85), 4.025 (1.11), 4.055 (0.62), 4.119 (0.74), 4.150 (1.12), 4.178 (1.12), 4.208 (0.51), 4.464 (0.46), 4.671 (1.50), 4.687 (2.17), 4.696 (1.57), 4.749 (1.55), 4.758 (1.90), 4.764 (2.10), 4.773 (1.54), 6.826 (13.56), 6.848 (16.00), 7.100 (14.23), 7.121 (12.19).

Example 347

(5S)-5-[(3-Fluoroazetidin-1-yl)carbonyl]-2-[2-(4-methoxyphenyl)ethyl]-5,6,7,8-tetrahydro[1,2,4]triazolo[4,3-a]pyridin-3(2H)-one

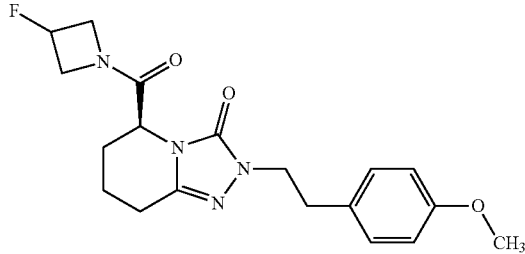 [SMILES: COc1ccc(CCn2nc3n(c2=O)[C@H](C(=O)N2CC(F)C2)CCC3)cc1]

(5S)-2-[2-(4-Methoxyphenyl)ethyl]-3-oxo-2,3,5,6,7,8-hexahydro[1,2,4]triazolo[4,3-a]pyridine-5-carboxylic acid (92.0 mg, 290 μmol) was initially charged in THF (2.0 ml), and HBTU (143 mg, 377 μmol) and N,N-diisopropylethylamine (150 μl, 870 μmol) were subsequently added. After stirring at room temperature for 15 min, 3-fluoroazetidine hydrochloride (38.8 mg, 348 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 58.3 mg (54% of theory) of the title compound were obtained.

LC-MS (Method 4): $R_t$=0.67 min; MS (ESIpos): m/z=375 [M+H]$^+$ $^1$H-NMR (400 MHz, DMSO-d6) δ [ppm]: −0.149 (0.49), 0.146 (0.54), 1.717 (7.02), 1.909 (1.85), 1.922 (2.69), 1.934 (2.88), 1.943 (2.71), 1.955 (2.23), 1.977 (2.25), 1.995 (3.16), 2.012 (2.77), 2.029 (1.85), 2.047 (0.94), 2.072 (7.93), 2.327 (0.82), 2.366 (0.75), 2.572 (5.35), 2.594 (3.84), 2.610 (5.84), 2.624 (3.07), 2.639 (1.24), 2.652 (2.00), 2.665 (1.61), 2.710 (0.97), 2.834 (5.71), 2.852 (11.15), 2.871 (6.06), 3.368 (1.09), 3.531 (6.66), 3.751 (6.68), 3.761 (8.12), 3.769 (6.74), 3.780 (4.30), 3.891 (1.38), 3.906 (1.68), 3.935 (1.59), 3.970 (1.85), 3.994 (1.27), 4.138 (0.90), 4.154 (1.01), 4.168 (0.80), 4.225 (2.17), 4.252 (2.10), 4.282 (1.85), 4.293 (1.55), 4.316 (1.82), 4.345 (1.31), 4.384 (0.88), 4.407 (1.31), 4.430 (1.05), 4.450 (6.06), 4.465 (8.68), 4.476 (6.14), 4.498 (1.18), 4.523 (0.71), 4.601 (0.80), 4.616 (0.94), 4.654 (0.90), 4.670 (0.94), 4.680 (0.88), 4.694 (0.69), 5.327 (1.14), 5.387 (1.14), 5.469 (1.18), 5.530 (1.16), 6.827 (13.64), 6.848 (16.00), 7.105 (10.12), 7.121 (8.80).

Example 348

(5S)-2-{[1-(6-Chloropyrid in-2-yl)cyclopropyl]methyl}-5-[(3-fluoroazetidin-1-yl)carbonyl]-5,6,7,8-tetrahydro[1,2,4]triazolo[4,3-a]pyridin-3(2H)-one

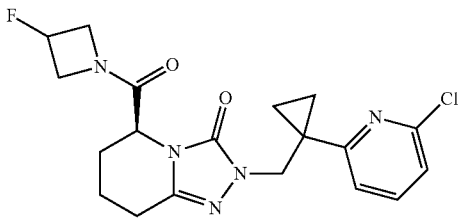 [SMILES: O=C([C@@H]1CCCc2nn(CC3(c4cccc(Cl)n4)CC3)c(=O)n21)N1CC(F)C1]

(5S)-2-{[1-(6-Chloropyrid in-2-yl)cyclopropyl]methyl}-3-oxo-2,3,5,6,7,8-hexahydro[1,2,4]triazolo[4,3-a]pyridine-5-carboxylic acid (60.0 mg, 172 μmol) was initially charged in THF (3.0 ml), and HBTU (84.8 mg, 224 μmol) and N,N-diisopropylethylamine (90 μl, 520 μmol) were subsequently added. After stirring at room temperature for 15 min, 3-fluoroazetidine hydrochloride (23.0 mg, 206 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 12.1 mg (17% of theory) of the title compound were obtained.

LC-MS (Method 3): $R_t$=1.35 min; MS (ESIpos): m/z=406 [M+H]$^+$ $^1$H-NMR (400 MHz, DMSO-d6) δ [ppm]: −0.149 (0.72), −0.008 (6.41), 0.008 (5.61), 0.146 (0.68), 1.107 (0.87), 1.124 (1.74), 1.140 (4.78), 1.166 (16.00), 1.679 (2.92), 1.929 (1.71), 1.991 (1.40), 2.327 (1.21), 2.366 (0.99), 2.523 (5.99), 2.565 (3.94), 2.578 (2.01), 2.594 (0.83), 2.607 (1.33), 2.670 (1.36), 2.690 (0.49), 2.710 (0.99), 3.883 (0.57), 3.914 (1.06), 3.947 (1.18), 3.988 (2.24), 4.033 (3.45), 4.091 (2.73), 4.116 (2.58), 4.129 (1.52), 4.154 (1.90), 4.211 (1.06), 4.227 (1.48), 4.257 (1.21), 4.290 (0.95), 4.310 (0.91), 4.345 (0.49), 4.373 (0.68), 4.410 (0.49), 4.433 (0.68), 4.504 (3.68), 4.623 (0.57), 4.663 (0.53), 5.340 (0.68), 5.401 (0.64), 5.483 (0.61), 5.543 (0.61), 7.243 (5.95), 7.262 (6.60), 7.571 (2.43), 7.578 (2.50), 7.590 (3.30), 7.598 (3.15), 7.699 (1.63), 7.710 (1.78), 7.718 (2.84), 7.729 (2.65), 7.738 (1.33), 7.749 (1.10).

Example 349

(5S)-2-{[1-(6-Chloropyrid in-2-yl)cyclopropyl]methyl}-5-[(3,3-difluoropyrrolidin-1-yl)carbonyl]-5,6,7,8-tetrahydro[1,2,4]triazolo[4,3-a]pyridin-3(2H)-one

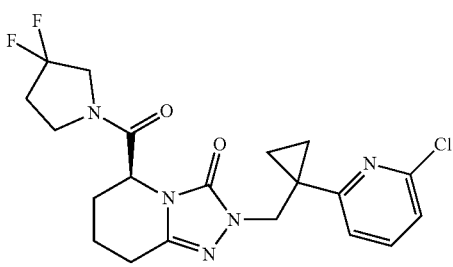 [SMILES: O=C([C@@H]1CCCc2nn(CC3(c4cccc(Cl)n4)CC3)c(=O)n21)N1CCC(F)(F)C1]

(5S)-2-{[1-(6-Chloropyridin-2-yl)cyclopropyl]methyl}-3-oxo-2,3,5,6,7,8-hexahydro[1,2,4]triazolo[4,3-a]pyridine-5-carboxylic acid (60.0 μmg, 172 μmol) was initially charged in THF (3.0 ml), and HBTU (84.8 mg, 224 μmol) and N,N-diisopropylethylamine (90 μl, 520 μmol) were subsequently added. After stirring at room temperature for 15 min, 3,3-difluoropyrrolidine hydrochloride (29.6 mg, 206 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 19.6 mg (26% of theory) of the title compound were obtained.

LC-MS (Method 4): $R_t$=0.81 min; MS (ESIpos): m/z=438 [M+H]$^+$ $^1$H-NMR (400 MHz, DMSO-d6) δ [ppm]: −0.149 (1.50), −0.008 (14.75), 0.008 (12.25), 0.146 (1.75), 1.110 (3.75), 1.128 (5.00), 1.148 (3.50), 1.168 (16.00), 1.699 (2.25), 1.961 (2.25), 2.327 (4.25), 2.366 (3.25), 2.407 (1.75), 2.523 (15.00), 2.563 (5.25), 2.575 (5.25), 2.617 (1.75), 2.670 (4.50), 2.710 (3.25), 3.533 (3.25), 3.544 (3.25), 3.653 (2.00), 3.687 (2.25), 3.729 (1.50), 3.760 (4.00), 3.787 (2.50), 3.899 (2.00), 3.923 (1.50), 3.941 (1.50), 3.965 (5.50), 4.002 (7.75), 4.130 (6.00), 4.163 (4.75), 4.724 (2.50), 4.796 (2.50), 7.242 (8.75), 7.262 (9.75), 7.569 (7.75), 7.589 (10.25), 7.701 (7.00), 7.721 (11.50), 7.740 (5.00).

Example 350

(5S)-2-{[1-(6-Chloropyridin-2-yl)cyclopropyl]methyl}-5-{[(3S)-3-fluoropyrrolidin-1-yl]carbonyl}-5,6,7,8-tetrahydro[1,2,4]triazolo[4,3-a]pyridin-3(2H)-one

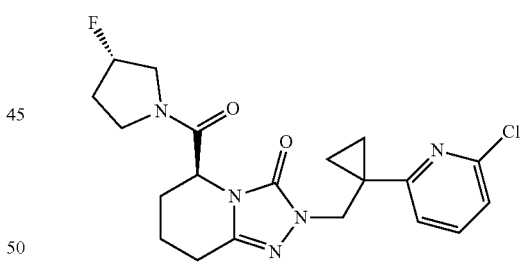

(5S)-2-{[1-(6-Chloropyridin-2-yl)cyclopropyl]methyl}-3-oxo-2,3,5,6,7,8-hexahydro[1,2,4]triazolo[4,3-a]pyridine-5-carboxylic acid (60.0 mg, 172 μmol) was initially charged in THF (3.0 ml), and HBTU (84.8 mg, 224 μmol) and N,N-diisopropylethylamine (90 μl, 520 μmol) were subsequently added. After stirring at room temperature for 15 min, (3S)-3-fluoropyrrolidine hydrochloride (25.9 mg, 206 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 22.5 mg (31% of theory) of the title compound were obtained.

LC-MS (Method 4): R$_t$=0.74 min; MS (ESIpos): m/z=420 [M+H]$^+$ $^1$H-NMR (400 MHz, DMSO-d6) δ [ppm]: −0.149 (1.70), −0.008 (14.64), 0.008 (12.26), 0.146 (1.70), 1.061 (2.04), 1.094 (1.70), 1.108 (4.43), 1.128 (5.45), 1.147 (3.74), 1.167 (12.94), 1.699 (4.43), 1.869 (1.36), 1.997 (2.72), 2.102 (2.04), 2.133 (2.04), 2.261 (1.70), 2.327 (4.43), 2.366 (3.74), 2.395 (0.68), 2.523 (16.00), 2.575 (4.09), 2.620 (1.70), 2.670 (4.77), 2.710 (3.74), 3.233 (1.02), 3.260 (1.70), 3.383 (2.72), 3.453 (1.36), 3.480 (1.70), 3.617 (3.74), 3.642 (3.74), 3.669 (2.38), 3.683 (2.04), 3.703 (2.04), 3.722 (3.40), 3.736 (3.06), 3.764 (3.06), 3.840 (3.74), 3.942 (4.09), 3.958 (3.06), 3.979 (5.45), 3.996 (4.77), 4.122 (4.43), 4.144 (5.79), 4.159 (3.06), 4.182 (4.09), 4.639 (2.04), 4.655 (2.38), 4.665 (1.70), 4.697 (2.38), 4.712 (3.06), 4.722 (2.38), 5.255 (2.04), 5.384 (2.38), 5.506 (1.36), 7.242 (9.53), 7.261 (10.21), 7.344 (0.68), 7.568 (4.09), 7.587 (5.79), 7.602 (6.47), 7.699 (3.74), 7.705 (4.43), 7.719 (5.79), 7.724 (7.49), 7.738 (2.72), 7.744 (3.06).

Example 351

(5S)-5-[(3-Fluoroazetidin-1-yl)carbonyl]-2-{[1-(4-fluorophenyl)cyclopropyl]methyl}-5,6,7,8-tetrahydro[1,2,4]triazolo[4,3-a]pyridin-3(2H)-one

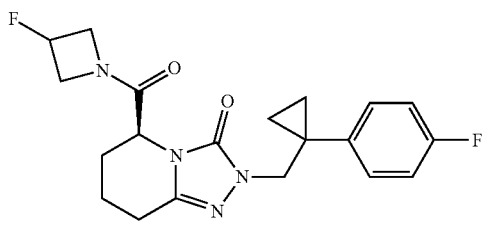 [SMILES: O=C([C@@H]1CCCc2nn(CC3(c4ccc(F)cc4)CC3)c(=O)n21)N1CC(F)C1]

(5S)-2-{[1-(4-Fluorophenyl)cyclopropyl]methyl}-3-oxo-2,3,5,6,7,8-hexahydro[1,2,4]triazolo[4,3-a]pyridine-5-carboxylic acid (80.0 mg, 241 μmol) was initially charged in THF (4.0 ml), and HBTU (119 mg, 314 μmol) and N,N-diisopropylethylamine (130 μl, 720 μmol) were subsequently added. After stirring at room temperature for 15 min, 3-fluoroazetidine hydrochloride (32.3 mg, 290 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 40.8 mg (44% of theory) of the title compound were obtained.

LC-MS (Method 3): R$_t$=1.43 min; MS (ESIpos): m/z=389 [M+H]$^+$ $^1$H-NMR (400 MHz, DMSO-d6) δ[ppm]: −0.149 (1.23), −0.008 (16.00), 0.008 (9.89), 0.146 (1.12), 0.767 (3.30), 0.800 (3.41), 0.825 (1.29), 0.995 (7.97), 1.692 (3.30), 1.931 (1.86), 2.327 (1.66), 2.366 (1.35), 2.524 (8.89), 2.571 (2.64), 2.615 (0.92), 2.670 (1.38), 2.710 (1.09), 3.698 (3.56), 3.735 (5.53), 3.830 (2.12), 3.850 (2.01), 3.865 (1.69), 3.886 (1.81), 3.955 (0.95), 4.182 (1.49), 4.212 (1.35), 4.441 (3.27), 4.618 (0.57), 5.310 (0.66), 5.455 (0.66), 7.015 (2.78), 7.035 (5.30), 7.057 (3.07), 7.229 (3.73), 7.243 (4.79), 7.260 (2.72).

Example 352

(5S)-2-{[1-(4-Fluorophenyl)cyclopropyl]methyl}-5-{[(3S)-3-fluoropyrrolidin-1-yl]carbonyl}-5,6,7,8-tetrahydro[1,2,4]triazolo[4,3-a]pyridin-3(2H)-one

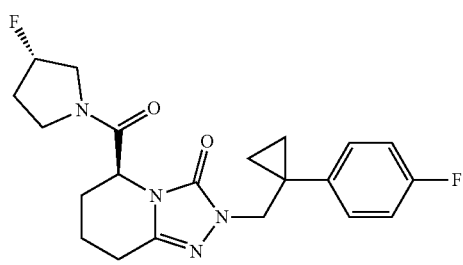 [SMILES: O=C([C@@H]1CCCc2nn(CC3(c4ccc(F)cc4)CC3)c(=O)n21)N1CC[C@H](F)C1]

(5S)-2-{[1-(4-Fluorophenyl)cyclopropyl]methyl}-3-oxo-2,3,5,6,7,8-hexahydro[1,2,4]triazolo[4,3-a]pyridine-5-carboxylic acid (80.0 mg, 241 μmol) was initially charged in THF (4.0 ml), and HBTU (119 mg, 314 μmol) and N,N-diisopropylethylamine (130 μl, 720 μmol) were subsequently added. After stirring at room temperature for 15 min, (3S)-3-fluoropyrrolidine hydrochloride (36.4 mg, 290 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 44.6 mg (46% of theory) of the title compound were obtained.

LC-MS (Method 3): R$_t$=1.47 min; MS (ESIpos): m/z=403 [M+H]$^+$ $^1$H-NMR (400 MHz, DMSO-d6) δ [ppm]: −0.149 (1.34), −0.008 (16.00), 0.008 (9.57), 0.146 (1.23), 0.723 (1.95), 0.750 (3.55), 0.778 (0.77), 0.811 (3.65), 0.835 (1.80), 0.983 (3.09), 0.998 (8.13), 1.710 (4.06), 1.838 (0.82), 1.873 (1.18), 1.997 (2.83), 2.008 (2.42), 2.019 (2.11), 2.033 (2.01), 2.048 (1.80), 2.073 (1.85), 2.125 (1.34), 2.249 (1.39), 2.327 (1.65), 2.366 (1.18), 2.519 (8.64), 2.524 (7.36), 2.586 (3.09), 2.628 (1.34), 2.669 (1.39), 2.710 (1.03), 3.379 (0.98), 3.389 (1.03), 3.450 (0.77), 3.476 (1.03), 3.486 (0.98), 3.563 (0.77), 3.598 (2.62), 3.616 (2.32), 3.633 (2.26), 3.649 (4.63), 3.659 (4.12), 3.685 (6.07), 3.695 (5.30), 3.732 (1.95), 3.753 (1.44), 3.782 (0.57), 3.818 (3.04), 3.859 (3.76), 3.880 (4.32), 3.895 (2.78), 3.916 (3.09), 4.586 (1.59), 4.595 (1.90), 4.602 (1.95), 4.610 (1.59), 4.644 (2.01), 4.654 (2.11), 4.659 (2.57), 4.668 (1.70), 5.247 (1.44), 5.368 (1.44), 5.491 (1.13), 7.015 (5.66), 7.037 (11.63), 7.058 (6.38), 7.221 (4.73), 7.228 (6.23), 7.234 (6.48), 7.242 (8.95), 7.250 (5.86), 7.257 (4.17), 7.264 (4.22).

Example 353

(5S)-5-[(3,3-Difluoropyrrolidin-1-yl)carbonyl]-2-{[1-(4-fluorophenyl)cyclopropyl]methyl}-5,6,7,8-tetrahydro[1,2,4]triazolo[4,3-a]pyridin-3(2H)-one

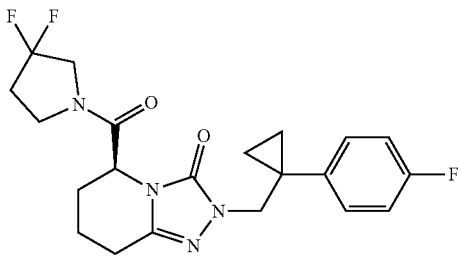

(5RS)-2-{[1-(4-Fluorophenyl)cyclopropyl]methyl}-3-oxo-2,3,5,6,7,8-hexahydro[1,2,4]triazolo[4,3-a]pyridine-5-carboxylic acid (80.0 mg, 241 µmol) was initially charged in THF (4.0 ml), and HBTU (119 mg, 314 µmol) and N,N-diisopropylethylamine (130 µl, 720 µmol) were subsequently added. After stirring at room temperature for 15 min, 3,3-difluoropyrrolidine hydrochloride (41.6 mg, 290 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.1 mg (45% of theory) of the title compound were obtained.

LC-MS (Method 3): $R_t$=1.61 min; MS (ESIpos): m/z=421 [M+H]$^+$ $^1$H-NMR (400 MHz, DMSO-d6) δ [ppm]: −0.149 (0.60), −0.008 (5.39), 0.008 (4.70), 0.146 (0.62), 0.717 (1.43), 0.726 (2.10), 0.753 (4.13), 0.780 (1.04), 0.808 (4.45), 0.833 (2.33), 0.842 (1.75), 0.957 (1.50), 0.966 (1.34), 0.980 (3.94), 0.996 (11.00), 1.013 (3.41), 1.024 (1.20), 1.037 (1.04), 1.649 (1.59), 1.662 (2.05), 1.695 (3.09), 1.705 (3.02), 1.949 (2.90), 1.959 (2.95), 1.974 (3.18), 1.986 (3.07), 2.012 (1.64), 2.021 (1.24), 2.037 (1.08), 2.072 (3.37), 2.327 (0.65), 2.345 (0.81), 2.366 (1.89), 2.385 (1.52), 2.394 (1.68), 2.414 (1.64), 2.434 (1.20), 2.455 (0.71), 2.469 (1.57), 2.568 (3.07), 2.582 (5.12), 2.594 (2.49), 2.612 (1.11), 2.624 (1.78), 2.636 (0.88), 2.670 (0.69), 2.710 (0.71), 3.507 (3.46), 3.526 (5.76), 3.545 (2.88), 3.615 (0.55), 3.648 (2.14), 3.662 (5.37), 3.682 (2.65), 3.699 (7.52), 3.716 (1.41), 3.724 (1.11), 3.738 (3.00), 3.750 (1.54), 3.769 (4.10), 3.787 (1.13), 3.803 (0.55), 3.845 (1.13), 3.870 (8.00), 3.883 (1.54), 3.890 (1.84), 3.906 (5.42), 3.926 (0.76), 3.954 (1.52), 3.968 (0.71), 3.983 (1.06), 3.996 (1.34), 4.024 (0.83), 4.096 (0.85), 4.127 (1.38), 4.154 (1.34), 4.185 (0.55), 4.653 (1.87), 4.667 (2.67), 4.677 (1.84), 4.726 (1.91), 4.735 (2.24), 4.741 (2.58), 4.750 (1.91), 7.014 (7.26), 7.019 (2.61), 7.036 (16.00), 7.058 (9.18), 7.066 (1.08), 7.218 (1.11), 7.226 (9.22), 7.231 (4.54), 7.239 (10.44), 7.247 (8.88), 7.256 (3.53), 7.261 (7.56).

Example 354

(5S)-5-[(3-Hydroxyazetidin-1-yl)carbonyl]-2-{[1-(4-methylphenyl)cyclopropyl]methyl}-5,6,7,8-tetrahydro[1,2,4]triazolo[4,3-a]pyridin-3(2H)-one

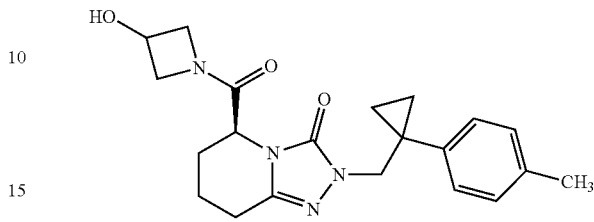

(5S)-2-{[1-(4-Methylphenyl)cyclopropyl]methyl}-3-oxo-2,3,5,6,7,8-hexahydro[1,2,4]triazolo[4,3-a]pyridine-5-carboxylic acid (45.0 mg, 137 µmol) was initially charged in THF (2.0 ml), and HBTU (67.8 mg, 179 µmol) and N,N-diisopropylethylamine (72 µl, 410 µmol) were subsequently added. After stirring at room temperature for 15 min, azetidin-3-ol hydrochloride (18.1 mg, 165 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 19.1 mg (36% of theory) of the title compound were obtained.

LC-MS (Method 3): $R_t$=1.32 min; MS (ESIpos): m/z=383 [M+H]$^+$ $^1$H-NMR (400 MHz, DMSO-d6) δ[ppm]: 0.008 (1.07), 0.711 (0.96), 0.777 (1.56), 0.802 (0.80), 0.930 (0.49), 0.944 (0.73), 0.969 (2.84), 0.984 (1.24), 0.994 (0.48), 1.681 (1.53), 1.691 (1.56), 1.878 (0.47), 1.903 (1.19), 1.914 (1.15), 1.944 (0.79), 1.954 (0.79), 2.236 (16.00), 2.451 (0.40), 2.565 (1.96), 2.577 (1.01), 2.594 (0.50), 2.607 (0.81), 3.572 (0.54), 3.582 (0.58), 3.606 (1.21), 3.618 (0.65), 3.631 (0.67), 3.643 (0.72), 3.654 (1.10), 3.692 (1.94), 3.730 (1.42), 3.879 (1.86), 3.900 (1.83), 3.915 (1.14), 3.936 (1.03), 3.956 (0.55), 3.968 (0.60), 3.979 (0.65), 3.992 (1.11), 4.009 (0.68), 4.036 (0.52), 4.076 (0.51), 4.092 (0.65), 4.116 (0.47), 4.242 (0.53), 4.261 (0.84), 4.281 (0.54), 4.395 (0.64), 4.410 (1.18), 4.418 (1.24), 4.430 (1.31), 4.440 (1.31), 4.456 (1.31), 4.476 (1.35), 5.779 (1.94), 5.793 (1.32), 7.026 (3.34), 7.045 (5.44), 7.103 (3.59), 7.110 (3.97), 7.123 (2.43), 7.130 (2.29).

Example 355

(5S)-5-[(3-Fluoroazetidin-1-yl)carbonyl]-2-{[1-(4-methylphenyl)cyclopropyl]methyl}-5,6,7,8-tetrahydro[1,2,4]triazolo[4,3-a]pyridin-3(2H)-one

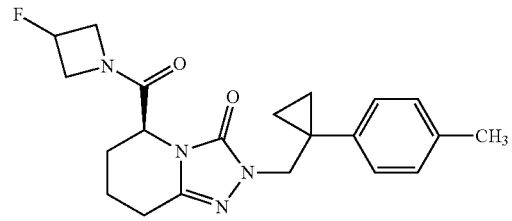 [SMILES: Cc1ccc(C2(Cn3nc4n(c3=O)[C@H](C(=O)N3CC(F)C3)CCC4)CC2)cc1]

(5S)-2-{[1-(4-Methylphenyl)cyclopropyl]methyl}-3-oxo-2,3,5,6,7,8-hexahydro[1,2,4]triazolo[4,3-a]pyridine-5-carboxylic acid (45.0 mg, 137 µmol) was initially charged in THF (2.0 ml), and HBTU (67.8 mg, 179 µmol) and N,N-diisopropylethylamine (72 µl, 410 µmol) were subsequently added. After stirring at room temperature for 15 min, 3-fluoroazetidine hydrochloride (1:1) (18.4 mg, 165 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 17.3 mg (33% of theory) of the title compound were obtained.

LC-MS (Method 3): R$_t$=1.57 min; MS (ESIpos): m/z=385 [M+H]$^+$ $^1$H-NMR (400 MHz, DMSO-d6) δ [ppm]: −0.008 (2.15), 0.008 (1.85), 0.734 (1.36), 0.773 (1.76), 0.798 (0.79), 0.926 (0.52), 0.935 (0.45), 0.966 (3.73), 0.982 (1.21), 0.993 (0.45), 1.690 (1.97), 1.931 (1.03), 1.967 (0.82), 1.982 (0.70), 2.002 (0.48), 2.234 (16.00), 2.327 (0.70), 2.366 (0.52), 2.523 (3.12), 2.570 (1.58), 2.614 (0.58), 2.669 (0.76), 2.709 (0.55), 3.693 (1.12), 3.735 (1.61), 3.874 (2.30), 3.911 (1.61), 3.957 (0.58), 4.187 (0.67), 4.213 (0.70), 4.243 (0.52), 4.255 (0.55), 4.282 (0.67), 4.429 (1.52), 4.443 (2.30), 4.455 (1.55), 7.025 (2.88), 7.044 (4.61), 7.109 (3.64), 7.124 (2.42).

Example 356

(5S)-5-{[(3S)-3-Fluoropyrrolidin-1-yl]carbonyl}-2-({1-[4-(trifluoromethyl)phenyl]cyclopropyl}methyl)-5,6,7,8-tetrahydro[1,2,4]triazolo[4,3-a]pyridin-3(2H)-one

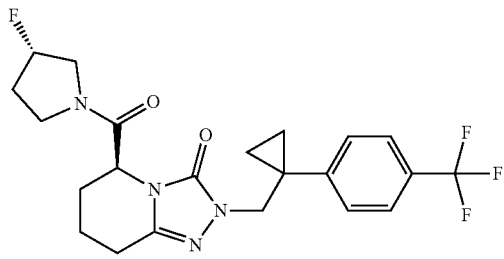 [SMILES: O=C([C@@H]1CCCc2nn(CC3(c4ccc(C(F)(F)F)cc4)CC3)c(=O)n21)N1CC[C@H](F)C1]

(5S)-3-Oxo-2-({1-[4-(trifluoromethyl)phenyl]cyclopropyl}methyl)-2,3,5,6,7,8-hexahydro[1,2,4]triazolo[4,3-a]pyridine-5-carboxylic acid (57.4 mg, 151 µmol) was initially charged in THF (1.4 ml), and HBTU (74.2 mg, 196 µmol) and N,N-diisopropylethylamine (79 µl, 450 µmol) were subsequently added. After stirring at room temperature for 15 min, (3S)-3-fluoropyrrolidine hydrochloride (1:1) (22.7 mg, 181 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 38.5 mg (55% of theory) of the title compound were obtained.

LC-MS (Method 4): R$_t$=0.94 min; MS (ESIpos): m/z=453 [M+H]

$^1$H-NMR (400 MHz, DMSO-d6) δ [ppm]: −0.149 (1.70), −0.008 (16.00), 0.146 (1.70), 0.858 (2.30), 0.939 (1.53), 1.112 (4.68), 1.709 (1.79), 1.871 (0.51), 1.999 (1.28), 2.073 (1.45), 2.251 (0.60), 2.327 (2.64), 2.366 (2.21), 2.589 (1.45), 2.669 (2.81), 2.710 (2.30), 3.491 (0.51), 3.592 (1.45), 3.615 (1.19), 3.688 (0.94), 3.707 (1.02), 3.732 (0.85), 3.763 (1.45), 3.799 (2.21), 3.807 (2.04), 3.920 (1.62), 3.935 (1.87), 3.957 (1.11), 3.971 (1.19), 4.607 (0.77), 4.665 (1.11), 5.247 (0.68), 5.380 (0.68), 5.492 (0.51), 7.430 (2.81), 7.449 (3.66), 7.571 (4.77), 7.592 (3.66).

Example 357

(5S)-5-[(3-Fluoroazetidin-1-yl)carbonyl]-2-{[1-(4-methoxyphenyl)cyclopropyl]methyl}-5,6,7,8-tetrahydro[1,2,4]triazolo[4,3-a]pyridin-3(2H)-one

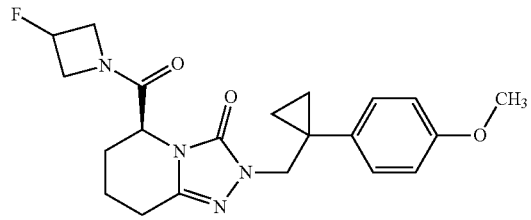 [SMILES: COc1ccc(C2(Cn3nc4n(c3=O)[C@H](C(=O)N3CC(F)C3)CCC4)CC2)cc1]

(5S)-2-{[1-(4-Methoxyphenyl)cyclopropyl]methyl}-3-oxo-2,3,5,6,7,8-hexahydro[1,2,4]triazolo[4,3-a]pyridine-5-carboxylic acid (93.2 mg, 50% purity, 136 µmol) was initially charged in THF (1.2 ml), and HBTU (134 mg, 353 µmol) and N,N-diisopropylethylamine (140 µl, 810 µmol) were subsequently added. After stirring at room temperature for 15 min, 3-fluoroazetidine hydrochloride (18.2 mg, 163 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 38.1 mg (70% of theory) of the title compound were obtained.

LC-MS (Method 4): R$_t$=0.77 min; MS (ESIpos): m/z=401 [M+H]$^+$ $^1$H-NMR (400 MHz, DMSO-d6) δ[ppm]: −0.149 (0.69), −0.008 (6.04), 0.008 (5.43), 0.147 (0.65), 0.705 (0.82), 0.742 (1.16), 0.938 (2.29), 1.696 (1.21), 1.934 (0.65), 2.072 (0.73), 2.328 (1.55), 2.366 (0.99), 2.523 (4.36), 2.670 (1.38), 2.710 (0.99), 3.674 (0.60), 3.700 (16.00), 3.834 (1.29), 3.869 (1.08), 4.281 (0.47), 4.426 (0.95), 4.440 (1.51), 4.451 (0.99), 6.775 (2.20), 6.796 (2.46), 7.131 (1.73), 7.146 (1.60).

Example 358

(5S)-2-{[1-(2,4-Difluorophenyl)cyclopropyl]methyl}-5-{[(3S)-3-fluoropyrrolidin-1-yl]carbonyl}-5,6,7,8-tetrahydro[1,2,4]triazolo[4,3-a]pyridin-3(2H)-one

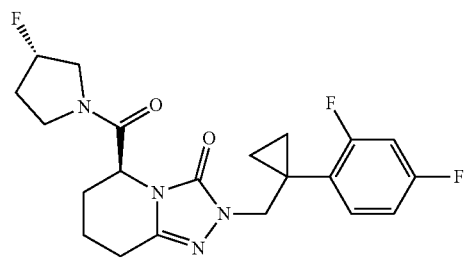 [SMILES: O=C([C@@H]1CCCc2nn(CC3(c4ccc(F)cc4F)CC3)c(=O)n21)N1CC[C@H](F)C1]

(5S)-2-{[1-(2,4-Difluorophenyl)cyclopropyl]methyl}-3-oxo-2,3,5,6,7,8-hexahydro[1,2,4]triazolo[4,3-a]pyridine-5-carboxylic acid (78.0 mg, 223 µmol) was initially charged in THF (2.0 ml), and HBTU (110 mg, 290 μmol) and N,N-diisopropylethylamine (120 μl, 670 μmol) were subsequently added. After stirring at room temperature for 15 min, (3S)-3-fluoropyrrolidine hydrochloride (28.0 mg, 223 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 42.3 mg (45% of theory) of the title compound were obtained.

LC-MS (Method 3): $R_t$=1.52 min; MS (ESIpos): m/z=421 [M+H]$^+$ $^1$H-NMR (400 MHz, DMSO-d6) δ [ppm]: −0.149 (1.76), −0.008 (16.00), 0.008 (12.28), 0.146 (1.76), 0.732 (2.71), 0.765 (2.65), 1.001 (5.42), 1.690 (2.08), 1.995 (1.26), 2.073 (1.39), 2.327 (2.65), 2.366 (1.45), 2.669 (2.83), 2.710 (1.76), 3.606 (2.20), 3.632 (2.65), 3.700 (1.76), 3.805 (3.15), 3.823 (1.95), 3.859 (1.45), 4.626 (1.26), 6.910 (2.08), 7.112 (1.76), 7.134 (1.83).

Example 359

(5S)-2-{[1-(2,4-Difluorophenyl)cyclopropyl]methyl}-5-[(3,3-difluoropyrrolidin-1-yl)carbonyl]-5,6,7,8-tetrahydro[1,2,4]triazolo[4,3-a]pyridin-3(2H)-one

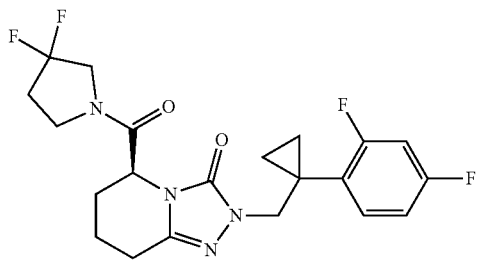 [SMILES: O=C([C@@H]1CCCc2nn(CC3(c4ccc(F)cc4F)CC3)c(=O)n21)N1CCC(F)(F)C1]

(5S)-2-{[1-(2,4-Difluorophenyl)cyclopropyl]methyl}-3-oxo-2,3,5,6,7,8-hexahydro[1,2,4]triazolo[4,3-a]pyridine-5-carboxylic acid (78.0 mg, 100% purity, 223 μmol) was initially charged in THF (2.0 ml), and HBTU (110 mg, 290 μmol) and N,N-diisopropylethylamine (120 μl, 670 μmol) were subsequently added. After stirring at room temperature for 15 min, 3,3-difluoropyrrolidine hydrochloride (32.1 mg, 223 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 42.2 mg (43% of theory) of the title compound were obtained.

LC-MS (Method 3): $R_t$=1.66 min; MS (ESIpos): m/z=439 [M+H]$^+$ $^1$H-NMR (400 MHz, DMSO-d6) δ [ppm]: −0.149 (1.72), −0.008 (16.00), 0.008 (12.30), 0.146 (1.63), 0.712 (1.03), 0.735 (3.44), 0.764 (3.78), 0.788 (1.12), 1.001 (7.83), 1.679 (1.81), 1.969 (1.63), 2.073 (8.09), 2.327 (2.41), 2.366 (2.67), 2.431 (1.20), 2.523 (9.29), 2.591 (1.20), 2.670 (2.49), 2.710 (2.24), 3.493 (1.63), 3.512 (3.10), 3.530 (1.55), 3.604 (1.89), 3.613 (1.72), 3.640 (2.92), 3.649 (2.58), 3.670 (1.20), 3.719 (1.38), 3.731 (1.03), 3.752 (1.46), 3.808 (2.41), 3.819 (2.32), 3.844 (2.15), 3.855 (2.15), 3.946 (0.77), 3.986 (0.69), 4.106 (0.69), 4.138 (0.60), 4.634 (1.29), 4.707 (1.29), 6.889 (1.03), 6.910 (2.24), 6.924 (1.12), 7.085 (1.20), 7.091 (1.20), 7.112 (1.89), 7.134 (1.81), 7.150 (2.06), 7.171 (1.98), 7.189 (0.77).

Example 360

(5S)-2-{[1-Ethyl-3-(trifluoromethyl)-1H-pyrazol-5-yl]methyl}-5-{[(3S)-3-fluoropyrrolidin-1-yl]carbonyl}-5,6,7,8-tetrahydro[1,2,4]triazolo[4,3-a]pyridin-3(2H)-one

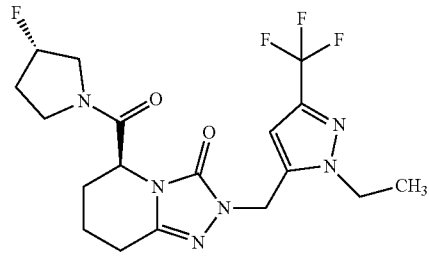 [SMILES: CCn1nc(C(F)(F)F)cc1Cn1nc2n(c1=O)[C@H](C(=O)N1CC[C@H](F)C1)CCC2]

(5S)-2-{[1-Ethyl-3-(trifluoromethyl)-1H-pyrazol-5-yl]methyl}-3-oxo-2,3,5,6,7,8-hexahydro[1,2,4]triazolo[4,3-a]pyridine-5-carboxylic acid (99.9 mg, 91% purity, 254 μmol) was initially charged in THF (2.0 ml), and HBTU (125 mg, 330 μmol) and N,N-diisopropylethylamine (130 μl, 760 μmol) were subsequently added. After stirring at room temperature for 15 min, (3S)-3-fluoropyrrolidine hydrochloride (1:1) (38.2 mg, 304 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 49.2 mg (45% of theory) of the title compound were obtained.

LC-MS (Method 3): $R_t$=1.39 min; MS (ESIpos): m/z=431 [M+H]$^+$ $^1$H-NMR (400 MHz, DMSO-d6) δ [ppm]: −0.008 (2.11), 0.008 (1.84), 1.352 (7.67), 1.370 (16.00), 1.387 (7.75), 1.716 (2.42), 1.729 (2.81), 1.739 (2.10), 1.863 (0.55), 1.874 (0.50), 1.897 (0.67), 1.968 (0.55), 2.002 (0.92), 2.011 (1.11), 2.038 (0.79), 2.054 (1.06), 2.064 (1.33), 2.073 (5.60), 2.084 (1.60), 2.099 (1.51), 2.134 (1.15), 2.170 (0.42), 2.218 (0.70), 2.239 (0.78), 2.267 (0.94), 2.327 (0.51), 2.366 (0.50), 2.565 (1.79), 2.581 (1.33), 2.608 (2.16), 2.650 (0.82), 2.664 (0.58), 2.669 (0.55), 2.710 (0.51), 3.269 (0.51), 3.287 (0.87), 3.343 (0.65), 3.356 (0.58), 3.365 (0.60), 3.392 (0.70), 3.401 (0.73), 3.454 (0.51), 3.463 (0.55), 3.490 (0.74), 3.498 (0.72), 3.623 (1.74), 3.635 (1.32), 3.652 (1.93), 3.662 (1.55), 3.677 (1.11), 3.685 (1.06), 3.721 (1.60), 3.744 (1.68), 3.768 (1.41), 3.776 (1.09), 3.785 (1.18), 3.854 (2.16), 4.186 (2.45), 4.204 (7.35), 4.222 (7.28), 4.240 (2.37), 4.665 (1.06), 4.674 (1.28), 4.681 (1.40), 4.690 (1.09), 4.723 (1.42), 4.732 (1.58), 4.739 (1.87), 4.747 (2.37), 4.787 (10.29), 4.792 (7.03), 4.796 (7.44), 4.835 (0.85), 5.257 (1.08), 5.389 (1.47), 5.511 (0.79), 6.626 (7.19).

Example 361

(5S)-5-{[(3R,4S)-3,4-Difluoropyrrolidin-1-yl]carbonyl}-2-{[1-ethyl-3-(trifluoromethyl)-1H-pyrazol-5-yl]methyl}-5,6,7,8-tetrahydro[1,2,4]triazolo[4,3-a]pyridin-3(2H)-one

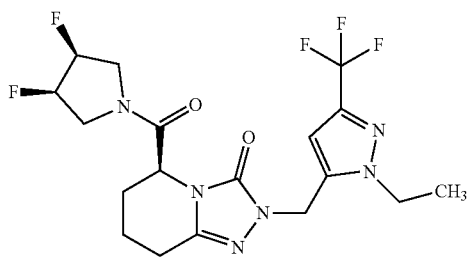 [SMILES: CCn1nc(C(F)(F)F)cc1Cn1nc2n(c1=O)[C@H](C(=O)N1C[C@@H](F)[C@@H](F)C1)CCC2]

(5S)-2-{[1-Ethyl-3-(trifluoromethyl)-1H-pyrazol-5-yl]methyl}-3-oxo-2,3,5,6,7,8-hexahydro[1,2,4]triazolo[4,3-a]pyridine-5-carboxylic acid (99.9 mg, 91% purity, 254 μmol) was initially charged in THF (2.0 ml), and HBTU (125 mg, 330 μmol) and N,N-diisopropylethylamine (130 μl, 760 μmol) were subsequently added. After stirring at room temperature for 15 min, (3R,4S)-3,4-difluoropyrrolidine hydrochloride (43.7 mg, 304 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 45.8 mg (40% of theory) of the title compound were obtained.

LC-MS (Method 3): $R_t$=1.46 min; MS (ESIpos): m/z=449 [M+H]$^+$ $^1$H-NMR (400 MHz, DMSO-d6) δ [ppm]: 0.008 (3.10), 1.244 (0.66), 1.259 (0.70), 1.274 (0.45), 1.351 (7.19), 1.369 (14.93), 1.387 (7.30), 1.669 (1.28), 1.705 (1.30), 1.717 (1.51), 1.726 (1.67), 1.921 (0.54), 1.956 (1.24), 2.002 (1.57), 2.026 (0.97), 2.036 (1.10), 2.044 (1.18), 2.051 (1.10), 2.060 (0.95), 2.071 (0.85), 2.079 (0.97), 2.086 (0.81), 2.327 (0.64), 2.366 (0.85), 2.524 (2.40), 2.566 (2.56), 2.576 (1.78), 2.591 (2.40), 2.603 (3.14), 2.615 (1.76), 2.634 (0.68), 2.645 (1.07), 2.670 (0.79), 2.710 (0.91), 3.484 (2.25), 3.505 (1.69), 3.515 (1.65), 3.524 (1.36), 3.533 (1.30), 3.557 (0.83), 3.566 (1.01), 3.610 (0.97), 3.623 (1.05), 3.643 (0.70), 3.656 (0.76), 3.666 (0.99), 3.679 (1.80), 3.690 (1.16), 3.699 (1.10), 3.712 (1.51), 3.724 (1.36), 3.743 (1.07), 3.755 (1.10), 3.775 (0.89), 3.789 (0.60), 3.865 (0.79), 3.902 (0.60), 3.928 (0.79), 3.941 (0.89), 3.956 (0.58), 3.977 (0.91), 3.991 (0.91), 4.005 (0.62), 4.020 (0.52), 4.128 (0.54), 4.143 (0.62), 4.156 (0.68), 4.169 (1.07), 4.185 (2.79), 4.204 (7.26), 4.222 (7.15), 4.240 (2.40), 4.751 (1.01), 4.767 (2.34), 4.791 (16.00), 4.798 (7.81), 4.838 (0.79), 5.254 (0.87), 5.265 (0.87), 5.274 (1.01), 5.284 (0.97), 5.296 (0.64), 5.311 (0.60), 5.329 (0.74), 5.337 (0.74), 5.351 (0.77), 5.364 (0.74), 5.374 (1.01), 5.387 (1.12), 5.398 (0.87), 5.406 (0.89), 5.427 (0.60), 5.440 (0.62), 5.458 (0.74), 5.472 (0.74), 5.480 (0.77), 5.494 (0.60), 6.619 (5.44), 6.624 (6.20).

Example 362

(5S)-5-[(3,3-Difluoropyrrolidin-1-yl)carbonyl]-2-{[1-ethyl-3-(trifluoromethyl)-1H-pyrazol-5-yl]methyl}-5,6,7,8-tetrahydro[1,2,4]triazolo[4,3-a]pyridin-3(2H)-one

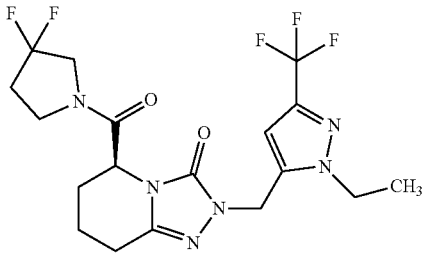 [SMILES: CCn1nc(C(F)(F)F)cc1Cn1nc2n(c1=O)[C@H](C(=O)N1CCC(F)(F)C1)CCC2]

(5S)-2-{[1-Ethyl-3-(trifluoromethyl)-1H-pyrazol-5-yl]methyl}-3-oxo-2,3,5,6,7,8-hexahydro[1,2,4]triazolo[4,3-a]pyridine-5-carboxylic acid (99.9 mg, 91% purity, 254 μmol) was initially charged in THF (2.0 ml), and HBTU (125 mg, 330 μmol) and N,N-diisopropylethylamine (130 μl, 760 μmol) were subsequently added. After stirring at room temperature for 15 min, 3,3-difluoropyrrolidine hydrochloride (43.7 mg, 304 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 49.8 mg (43% of theory) of the title compound were obtained.

LC-MS (Method 3): $R_t$=1.53 min; MS (ESIpos): m/z=449 [M+H]$^+$ $^1$H-NMR (400 MHz, DMSO-d6) δ [ppm]: −0.008 (3.74), 0.008 (1.80), 1.350 (7.76), 1.368 (16.00), 1.386 (7.57), 1.685 (0.98), 1.701 (1.16), 1.714 (1.30), 1.722 (1.30), 1.971 (1.06), 1.984 (1.07), 1.995 (1.23), 2.020 (0.91), 2.030 (0.86), 2.039 (0.91), 2.046 (0.91), 2.056 (0.86), 2.066 (0.68), 2.074 (0.66), 2.082 (0.58), 2.327 (0.54), 2.366 (0.66), 2.379 (0.73), 2.408 (0.88), 2.429 (0.89), 2.563 (2.10), 2.572 (2.36), 2.587 (2.57), 2.604 (2.36), 2.615 (1.11), 2.646 (0.69), 2.670 (0.52), 2.710 (0.45), 3.368 (1.56), 3.527 (1.26), 3.546 (1.89), 3.562 (0.89), 3.568 (0.88), 3.666 (0.91), 3.700 (1.05), 3.731 (0.76), 3.762 (1.37), 3.782 (0.84), 3.793 (1.22), 3.808 (1.07), 3.826 (0.73), 3.889 (0.49), 3.907 (1.08), 3.926 (0.62), 3.934 (0.74), 3.992 (0.69), 4.021 (0.49), 4.034 (0.60), 4.141 (0.43), 4.186 (2.33), 4.204 (6.79), 4.222 (6.20), 4.240 (1.95), 4.731 (0.93), 4.746 (1.32), 4.791 (6.98), 4.797 (8.50), 4.815 (1.25), 4.820 (1.29), 4.830 (0.96), 4.836 (0.88), 6.622 (6.40).

Example 363

(5S)-2-{[1-Ethyl-3-(trifluoromethyl)-1H-pyrazol-5-yl]methyl}-5-[(3-fluoroazetidin-1-yl)carbonyl]-5,6,7,8-tetrahydro[1,2,4]triazolo[4,3-a]pyridin-3(2H)-one

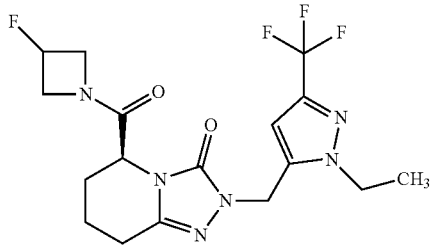 [SMILES: CCn1nc(C(F)(F)F)cc1Cn1nc2n(c1=O)[C@H](C(=O)N1CC(F)C1)CCC2]

(5S)-2-{[1-Ethyl-3-(trifluoromethyl)-1H-pyrazol-5-yl]methyl}-3-oxo-2,3,5,6,7,8-hexahydro[1,2,4]triazolo[4,3-a]pyridine-5-carboxylic acid (99.9 mg, 91% purity, 254 µmol) was initially charged in THF (2.0 ml), and HBTU (125 mg, 330 µmol) and N,N-diisopropylethylamine (130 µl, 760 µmol) were subsequently added. After stirring at room temperature for 15 min, 3-fluoroazetidine hydrochloride (33.9 mg, 304 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 50.6 mg (48% of theory) of the title compound were obtained.

LC-MS (Method 3): $R_t$=1.36 min; MS (ESIpos): m/z=417 [M+H]$^+$ $^1$H-NMR (400 MHz, DMSO-d6) δ [ppm]: −0.149 (0.83), −0.008 (6.74), 0.008 (7.66), 0.146 (0.87), 1.349 (7.70), 1.366 (16.00), 1.384 (8.39), 1.708 (3.48), 1.948 (1.60), 2.022 (1.47), 2.072 (0.69), 2.327 (1.24), 2.366 (1.70), 2.522 (4.08), 2.526 (3.26), 2.580 (3.62), 2.594 (4.58), 2.607 (2.34), 2.622 (1.01), 2.637 (1.51), 2.650 (0.73), 2.665 (1.28), 2.670 (1.60), 2.710 (1.93), 3.922 (1.05), 3.951 (0.96), 3.985 (1.15), 4.008 (0.69), 4.155 (0.64), 4.185 (2.89), 4.203 (7.70), 4.220 (7.89), 4.239 (3.21), 4.257 (1.47), 4.281 (1.19), 4.311 (0.92), 4.346 (0.73), 4.391 (0.73), 4.429 (0.50), 4.455 (0.69), 4.517 (2.70), 4.529 (4.17), 4.541 (2.57), 4.568 (0.60), 4.624 (0.50), 4.636 (0.60), 4.673 (0.55), 4.691 (0.60), 4.715 (0.50), 4.795 (15.08), 5.351 (0.73), 5.403 (0.69), 5.493 (0.69), 5.546 (0.64), 6.632 (7.61).

Example 364

(5S)-5-[(3,3-Difluoropyrrolidin-1-yl)carbonyl]-2-{[2-(trifluoromethyl)-1,3-thiazol-4-yl]methyl}-5,6,7,8-tetrahydro[1,2,4]triazolo[4,3-a]pyridin-3(2H)-one

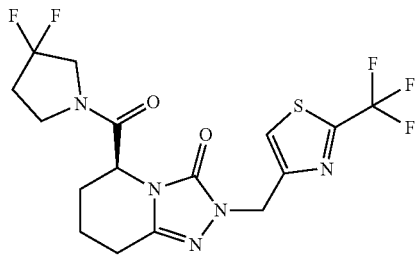 [SMILES: O=C([C@@H]1CCCc2nn(Cc3csc(C(F)(F)F)n3)c(=O)n21)N1CCC(F)(F)C1]

(5S)-3-Oxo-2-{[2-(trifluoromethyl)-1,3-thiazol-4-yl]methyl}-2,3,5,6,7,8-hexahydro[1,2,4]triazolo[4,3-a]pyridine-5-carboxylic acid (50.0 mg, 144 µmol) was initially charged in THF (2.0 ml), and HBTU (70.8 mg, 187 µmol) and N,N-diisopropylethylamine (75 µl, 430 µmol) were subsequently added. After stirring at room temperature for 15 min, 3,3-difluoropyrrolidine hydrochloride (24.7 mg, 172 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 12.0 mg (19% of theory) of the title compound were obtained.

LC-MS (Method 3): $R_t$=1.43 min; MS (ESIpos): m/z=438 [M+H]$^+$ $^1$H-NMR (400 MHz, DMSO-d6) δ [ppm]: −0.149 (1.35), −0.008 (11.66), 0.008 (10.84), 0.146 (1.41), 1.236 (0.59), 1.684 (2.05), 1.733 (2.64), 1.986 (2.23), 2.001 (2.23), 2.012 (2.58), 2.035 (1.99), 2.045 (1.82), 2.054 (1.93), 2.061 (1.93), 2.073 (3.69), 2.081 (1.41), 2.089 (1.41), 2.097 (1.29), 2.327 (1.23), 2.366 (1.99), 2.381 (1.47), 2.410 (1.76), 2.430 (1.64), 2.451 (1.11), 2.573 (6.33), 2.583 (5.16), 2.598 (5.74), 2.612 (5.63), 2.625 (2.99), 2.642 (1.35), 2.654 (1.88), 2.669 (2.17), 2.710 (1.88), 3.538 (2.70), 3.550 (3.69), 3.558 (3.93), 3.568 (2.29), 3.577 (2.17), 3.637 (0.76), 3.670 (2.34), 3.704 (2.75), 3.741 (1.93), 3.774 (3.22), 3.789 (1.99), 3.797 (1.82), 3.807 (3.46), 3.814 (3.05), 3.833 (1.35), 3.895 (1.29), 3.914 (2.64), 3.932 (1.52), 3.940 (1.93), 3.958 (0.94), 3.971 (0.82), 4.000 (1.64), 4.013 (0.94), 4.028 (1.17), 4.042 (1.58), 4.070 (0.88), 4.151 (1.00), 4.182 (1.52), 4.208 (1.47), 4.238 (0.70), 4.758 (2.11), 4.772 (2.93), 4.782 (2.17), 4.831 (2.23), 4.846 (2.87), 4.856 (2.17), 4.957 (2.23), 4.997 (14.01), 5.011 (16.00), 5.051 (2.70), 7.889 (14.07).

Example 365

(5S)-5-{[(3S)-3-Fluoropyrrolidin-1-yl]carbonyl}-2-{[2-(trifluoromethyl)-1,3-thiazol-4-yl]methyl}-5,6,7,8-tetrahydro[1,2,4]triazolo[4,3-a]pyridin-3(2H)-one

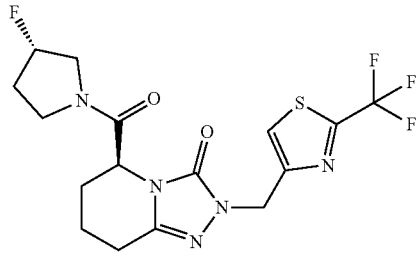 [SMILES: O=C([C@@H]1CCCc2nn(Cc3csc(C(F)(F)F)n3)c(=O)n21)N1CC[C@H](F)C1]

(5S)-3-Oxo-2-{[2-(trifluoromethyl)-1,3-thiazol-4-yl]methyl}-2,3,5,6,7,8-hexahydro[1,2,4]triazolo[4,3-a]pyridine-5-carboxylic acid (100 mg, 287 µmol) was initially charged in THF (2.0 ml), and HBTU (142 mg, 373 µmol) and N,N-diisopropylethylamine (150 µl, 860 µmol) were subsequently added. After stirring at room temperature for 15 min, (3S)-3-fluoropyrrolidine hydrochloride (43.3 mg, 345 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 28.0 mg (23% of theory) of the title compound were obtained.

LC-MS (Method 3): R$_t$=1.29 min; MS (ESIpos): m/z=420 [M+H]$^+$ $^1$H-NMR (400 MHz, DMSO-d6) δ [ppm]: −0.149 (0.75), −0.008 (6.39), 0.008 (6.48), 0.146 (0.77), 1.717 (2.91), 1.727 (4.25), 1.740 (5.22), 1.880 (0.95), 1.890 (0.97), 1.913 (1.23), 1.968 (0.71), 1.994 (1.54), 2.003 (1.43), 2.029 (2.36), 2.086 (3.06), 2.105 (3.66), 2.122 (2.23), 2.137 (2.42), 2.172 (0.75), 2.220 (1.37), 2.240 (1.39), 2.270 (1.85), 2.327 (0.93), 2.366 (0.84), 2.525 (2.78), 2.567 (2.80), 2.577 (3.33), 2.593 (2.73), 2.616 (4.25), 2.659 (1.70), 2.669 (1.48), 2.710 (0.86), 3.274 (1.26), 3.348 (1.26), 3.362 (1.15), 3.370 (1.19), 3.397 (1.34), 3.406 (1.34), 3.459 (0.97), 3.468 (1.04), 3.495 (1.39), 3.504 (1.34), 3.614 (0.90), 3.638 (3.94), 3.657 (4.08), 3.665 (2.84), 3.683 (2.51), 3.698 (1.81), 3.729 (2.27), 3.749 (3.24), 3.774 (2.60), 3.793 (2.12), 3.825 (0.51), 3.862 (4.19), 4.691 (1.98), 4.700 (2.45), 4.707 (2.60), 4.716 (2.03), 4.748 (2.58), 4.757 (3.02), 4.763 (3.37), 4.772 (2.45), 4.953 (2.95), 4.993 (16.00), 5.011 (10.53), 5.050 (1.98), 5.258 (2.01), 5.384 (2.73), 5.390 (2.80), 5.517 (1.48), 5.944 (0.64), 7.887 (12.65).

Example 366

(5S)-5-{[(3R,4S)-3,4-Difluoropyrrolidin-1-yl]carbonyl}-2-{[2-(trifluoromethyl)-1,3-thiazol-4-yl]methyl}-5,6,7,8-tetrahydro[1,2,4]triazolo[4,3-a]pyridin-3(2H)-one

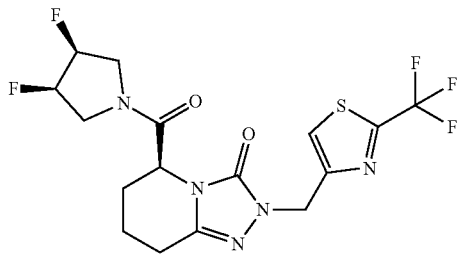 [SMILES: O=C([C@@H]1CCCc2nn(Cc3csc(C(F)(F)F)n3)c(=O)n21)N1C[C@@H](F)[C@@H](F)C1]

(5S)-3-Oxo-2-{[2-(trifluoromethyl)-1,3-thiazol-4-yl]methyl}-2,3,5,6,7,8-hexahydro[1,2,4]triazolo[4,3-a]pyridine-5-carboxylic acid (100 mg, 287 µmol) was initially charged in THF (2.0 ml), and HBTU (142 mg, 373 µmol) and N,N-diisopropylethylamine (150 µl, 860 µmol) were subsequently added. After stirring at room temperature for 15 min, (3R,4S)-3,4-difluoropyrrolidine hydrochloride (49.5 mg, 345 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 25.0 mg (20% of theory) of the title compound were obtained.

LC-MS (Method 3): R$_t$=1.37 min; MS (ESIpos): m/z=438 [M+H]$^+$ $^1$H-NMR (400 MHz, DMSO-d6) δ [ppm]: −0.149 (1.19), −0.008 (10.41), 0.008 (9.40), 0.146 (1.23), 1.673 (1.94), 1.739 (2.42), 1.972 (1.83), 2.017 (2.39), 2.041 (1.53), 2.051 (1.72), 2.058 (1.90), 2.066 (1.79), 2.086 (1.34), 2.094 (1.49), 2.102 (1.27), 2.327 (1.31), 2.366 (1.34), 2.523 (4.21), 2.566 (3.10), 2.577 (3.84), 2.600 (3.92), 2.612 (5.22), 2.624 (3.02), 2.642 (1.08), 2.654 (1.75), 2.669 (1.94), 2.710 (1.49), 3.457 (1.01), 3.482 (1.16), 3.490 (1.94), 3.501 (1.42), 3.512 (1.49), 3.522 (1.53), 3.535 (1.75), 3.545 (1.94), 3.554 (1.12), 3.577 (1.23), 3.616 (1.31), 3.630 (1.49), 3.650 (0.86), 3.663 (1.08), 3.672 (1.38), 3.687 (2.35), 3.702 (2.01), 3.720 (2.09), 3.735 (2.05), 3.752 (1.60), 3.765 (1.75), 3.785 (1.34), 3.799 (0.82), 3.873 (1.27), 3.909 (0.97), 3.932 (1.31), 3.946 (1.45), 3.961 (0.86), 3.981 (1.31), 3.995 (1.34), 4.010 (0.86), 4.024 (0.75), 4.135 (0.90), 4.150 (0.97), 4.164 (0.97), 4.178 (1.57), 4.191 (1.12), 4.204 (1.01), 4.220 (0.90), 4.807 (5.48), 4.957 (2.50), 4.997 (16.00), 5.008 (8.80), 5.013 (9.10), 5.054 (1.60), 5.255 (1.31), 5.266 (1.34), 5.277 (1.57), 5.286 (1.27), 5.297 (1.01), 5.331 (1.16), 5.338 (1.08), 5.352 (1.27), 5.366 (1.08), 5.377 (1.60), 5.389 (1.72), 5.408 (1.49), 5.429 (0.97), 5.474 (1.16), 5.482 (1.23), 5.496 (0.97), 7.880 (8.13), 7.889 (9.14).

Example 367

(2S)-1-{[(5S)-3-Oxo-2-{[2-(trifluoromethyl)-1,3-thiazol-4-yl]methyl}-2,3,5,6,7,8-hexahydro[1,2,4]triazolo[4,3-a]pyridin-5-yl]carbonyl}pyrrolidine-2-carbonitrile

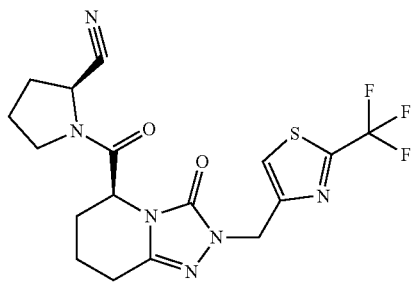 [SMILES: N#C[C@@H]1CCCN1C(=O)[C@@H]1CCCc2nn(Cc3csc(C(F)(F)F)n3)c(=O)n21]

(5S)-3-Oxo-2-{[2-(trifluoromethyl)-1,3-thiazol-4-yl]methyl}-2,3,5,6,7,8-hexahydro[1,2,4]triazolo[4,3-a]pyridine-5-carboxylic acid (50.0 mg, 144 µmol) was initially charged in THF (2.0 ml), and HBTU (70.8 mg, 187 µmol) and N,N-diisopropylethylamine (75 µl, 430 µmol) were subsequently added. After stirring at room temperature for 15 min, (2S)-pyrrolidine-2-carbonitrile hydrochloride (22.8 mg, 172 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 20.0 mg (33% of theory) of the title compound were obtained.

LC-MS (Method 3): R$_t$=1.36 min; MS (ESIpos): m/z=427 [M+H]$^+$ $^1$H-NMR (400 MHz, DMSO-d6) δ [ppm]: −0.149 (0.78), −0.008 (6.45), 0.008 (6.32), 0.146 (0.70), 1.245 (0.52), 1.260 (0.70), 1.396 (0.83), 1.665 (1.66), 1.791 (2.18), 1.805 (1.66), 2.048 (6.84), 2.061 (8.33), 2.080 (8.28), 2.096 (4.45), 2.107 (3.27), 2.117 (3.57), 2.138 (3.05), 2.152 (4.23), 2.163 (3.40), 2.178 (1.44), 2.187 (1.92), 2.207 (4.10), 2.219 (1.40), 2.226 (3.88), 2.238 (2.44), 2.246 (1.35), 2.258 (1.96), 2.278 (0.78), 2.328 (1.57), 2.366 (1.61), 2.523 (3.97), 2.574 (3.62), 2.589 (3.10), 2.600 (3.36), 2.614 (2.57), 2.632 (2.40), 2.644 (4.40), 2.657 (2.66), 2.674 (2.27), 2.686 (1.79), 2.710 (1.79), 3.512 (0.39), 3.679 (6.67), 3.696 (13.47), 3.712 (6.63), 4.788 (4.80), 4.799 (5.06), 4.809 (5.84), 4.819 (6.37), 4.824 (5.01), 4.830 (5.32), 4.839 (3.71), 4.964 (1.40), 5.004 (16.00), 5.010 (15.83), 5.051 (1.35), 7.880 (13.34).

Example 368

(5S)-5-[(3,3-Difluoropyrrolidin-1-yl)carbonyl]-2-{[6-(trifluoromethyl)pyridin-2-yl]methyl}-5,6,7,8-tetrahydro[1,2,4]triazolo[4,3-a]pyridin-3(2H)-one

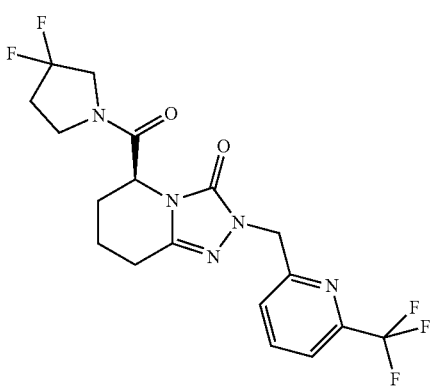 [SMILES: O=C([C@@H]1CCCc2nn(Cc3cccc(C(F)(F)F)n3)c(=O)n21)N1CCC(F)(F)C1]

(5S)-3-Oxo-2-{[6-(trifluoromethyl)pyridin-2-yl]methyl}-2,3,5,6,7,8-hexahydro[1,2,4]triazolo[4,3-a]pyridine-5-carboxylic acid (63.9 mg, 187 µmol) was initially charged in THF (2.0 ml), and HBTU (92.0 mg, 243 µmol) and N,N-diisopropylethylamine (98 µl, 560 µmol) were subsequently added. After stirring at room temperature for 15 min, 3,3-difluoropyrrolidine hydrochloride (32.2 mg, 224 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 35.5 mg (44% of theory) of the title compound were obtained.

LC-MS (Method 3): $R_t$=1.43 min; MS (ESIpos): m/z=432 [M+H]$^+$ $^1$H-NMR (400 MHz, DMSO-d6) δ[ppm]: −0.149 (0.90), −0.008 (8.08), 0.008 (7.97), 0.146 (0.87), 1.695 (1.03), 1.753 (1.26), 1.916 (0.49), 1.981 (0.72), 2.037 (1.38), 2.328 (1.10), 2.366 (1.33), 2.384 (0.82), 2.411 (1.00), 2.431 (0.97), 2.570 (2.74), 2.584 (2.10), 2.594 (2.21), 2.609 (2.18), 2.628 (2.23), 2.669 (1.92), 2.710 (1.00), 3.546 (1.15), 3.557 (1.62), 3.566 (1.72), 3.576 (1.05), 3.585 (0.95), 3.678 (1.08), 3.712 (1.28), 3.749 (0.85), 3.783 (1.44), 3.795 (0.95), 3.821 (1.56), 3.840 (0.56), 3.899 (0.54), 3.918 (1.23), 3.944 (0.87), 3.977 (0.41), 4.006 (0.79), 4.049 (0.69), 4.076 (0.41), 4.156 (0.49), 4.188 (0.74), 4.213 (0.67), 4.788 (1.00), 4.803 (1.41), 4.812 (0.97), 4.859 (0.97), 4.874 (1.41), 4.884 (0.95), 5.012 (16.00), 7.404 (3.54), 7.424 (3.67), 7.829 (4.00), 7.848 (4.72), 8.081 (2.38), 8.101 (4.18), 8.121 (2.05).

Example 369

(5S)-5-[(3-Fluoroazetidin-1-yl)carbonyl]-2-{[6-(trifluoromethyl)pyridin-2-yl]methyl}-5,6,7,8-tetrahydro[1,2,4]triazolo[4,3-a]pyridin-3(2H)-one

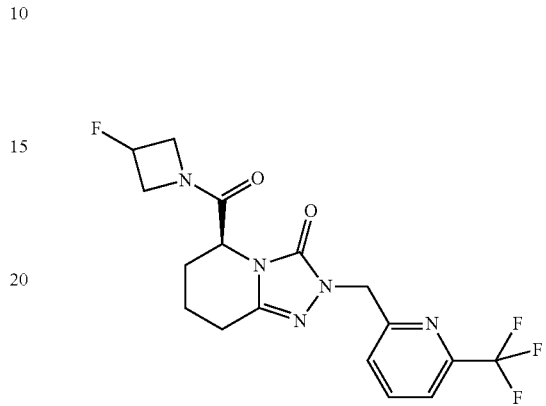

(5S)-3-Oxo-2-{[6-(trifluoromethyl)pyridin-2-yl]methyl}-2,3,5,6,7,8-hexahydro[1,2,4]triazolo[4,3-a]pyridine-5-carboxylic acid (63.9 mg, 187 µmol) was initially charged in THF (2.0 ml), and HBTU (92.0 mg, 243 µmol) and N,N-diisopropylethylamine (98 µl, 560 µmol) were subsequently added. After stirring at room temperature for 15 min, 3-fluoroazetidine hydrochloride (25.0 mg, 224 µmol) was added and the reaction mixture was stirred at room temperature overnight. N,N-Diisopropylethylamine (30 µl, 171 µmol) and 3-fluoroazetidine hydrochloride (10.0 mg, 90 µmol) were added again and the mixture was stirred at room temperature for 2 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 48.0 mg (64% of theory) of the title compound were obtained.

LC-MS (Method 4): $R_t$=0.67 min; MS (ESIpos): m/z=400 [M+H]$^+$ $^1$H-NMR (400 MHz, DMSO-d6) delta [ppm]: −0.149 (0.59), −0.008 (5.08), 0.146 (0.62), 1.689 (1.49), 1.699 (2.17), 1.723 (3.40), 1.733 (3.51), 1.989 (2.24), 2.001 (2.24), 2.050 (1.98), 2.073 (2.86), 2.327 (0.73), 2.366 (0.61), 2.559 (2.89), 2.577 (2.84), 2.603 (3.43), 2.617 (5.09), 2.630 (2.65), 2.647 (0.99), 2.660 (1.92), 2.670 (1.45), 2.710 (0.69), 3.910 (0.73), 3.936 (1.52), 3.965 (1.55), 3.997 (1.55), 4.026 (0.88), 4.166 (0.65), 4.180 (0.75), 4.194 (0.62), 4.231 (1.23), 4.245 (1.23), 4.281 (1.49), 4.312 (1.53), 4.344 (0.86), 4.371 (1.52), 4.396 (1.02), 4.431 (0.73), 4.460 (0.93), 4.516 (0.70), 4.530 (0.83), 4.572 (4.49), 4.586 (6.34), 4.598 (4.31), 4.637 (0.69), 4.654 (0.77), 4.688 (0.73), 4.705 (0.73), 4.730 (0.59), 5.015 (16.00), 5.354 (0.97), 5.405 (0.94), 5.497 (0.96), 5.548 (0.96), 6.957 (0.24), 7.086 (0.29), 7.213 (0.26), 7.419 (6.28), 7.439 (6.67), 7.827 (6.31), 7.847 (7.44), 8.079 (3.43), 8.099 (6.16), 8.118 (2.92), 9.029 (0.16), 9.156 (0.19).

Example 370

(5S)-5-{[(3S)-3-Fluoropyrrolidin-1-yl]carbonyl}-2-{[6-(trifluoromethyl)pyridin-2-yl]methyl}-5,6,7,8-tetrahydro[1,2,4]triazolo[4,3-a]pyridin-3(2H)-one

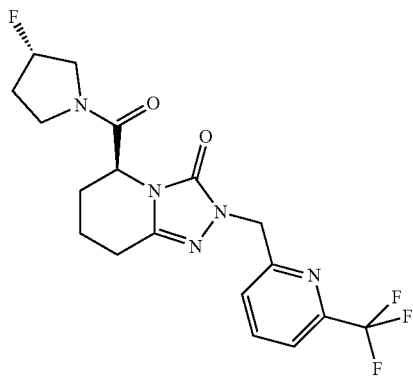 [SMILES: O=C([C@@H]1CCCc2nn(Cc3cccc(C(F)(F)F)n3)c(=O)n21)N1CC[C@H](F)C1]

(5S)-3-Oxo-2-{[6-(trifluoromethyl)pyridin-2-yl]methyl}-2,3,5,6,7,8-hexahydro[1,2,4]triazolo[4,3-a]pyridine-5-carboxylic acid (63.9 mg, 187 µmol) was initially charged in THF (2.0 ml), and HBTU (92.0 mg, 243 µmol) and N,N-diisopropylethylamine (98 µl, 560 µmol) were subsequently added. After stirring at room temperature for 15 min, (3S)-3-fluoropyrrolidine hydrochloride (28.1 mg, 224 µmol) was added and the reaction mixture was stirred at room temperature overnight. N,N-Diisopropylethylamine (30 µl, 171 µmol) and 3-fluoroazetidine hydrochloride (10.0 mg, 90 µmol) were added again and the mixture was stirred at room temperature for 2 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 45.8 mg (58% of theory) of the title compound were obtained.

LC-MS (Method 4): $R_t$=0.69 min; MS (ESIpos): m/z=414 [M+H]$^+$ $^1$H-NMR (400 MHz, DMSO-d6) δ [ppm]: −0.149 (1.00), −0.008 (8.75), 0.008 (7.10), 0.146 (0.96), 1.751 (2.34), 1.901 (0.50), 1.941 (0.73), 2.006 (0.58), 2.063 (1.27), 2.073 (2.26), 2.086 (1.61), 2.106 (1.76), 2.121 (1.61), 2.271 (0.96), 2.327 (1.27), 2.366 (1.50), 2.524 (2.92), 2.562 (1.84), 2.578 (1.46), 2.588 (1.61), 2.603 (1.34), 2.630 (2.30), 2.670 (1.88), 2.710 (1.42), 3.356 (0.54), 3.377 (0.58), 3.404 (0.61), 3.413 (0.65), 3.476 (0.50), 3.502 (0.73), 3.511 (0.65), 3.616 (0.50), 3.641 (2.34), 3.659 (1.76), 3.684 (1.34), 3.705 (0.88), 3.739 (1.34), 3.758 (1.53), 3.782 (1.34), 3.801 (1.04), 3.867 (2.07), 4.715 (1.04), 4.725 (1.30), 4.732 (1.34), 4.740 (1.00), 4.773 (1.34), 4.782 (1.46), 4.788 (1.73), 4.796 (1.27), 5.008 (16.00), 5.261 (1.00), 5.384 (1.34), 5.392 (1.34), 5.514 (0.77), 7.405 (3.84), 7.425 (4.14), 7.828 (4.37), 7.848 (5.06), 8.081 (2.76), 8.101 (4.95), 8.121 (2.34).

Example 371

(5S)-5-{[(3R,4S)-3,4-Difluoropyrrolidin-1-yl]carbonyl}-2-{[6-(trifluoromethyl)pyridin-2-yl]methyl}-5,6,7,8-tetrahydro[1,2,4]triazolo[4,3-a]pyridin-3(2H)-one

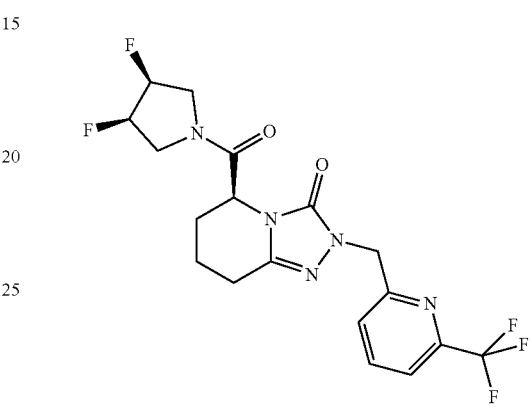

(5S)-3-Oxo-2-{[6-(trifluoromethyl)pyridin-2-yl]methyl}-2,3,5,6,7,8-hexahydro[1,2,4]triazolo[4,3-a]pyridine-5-carboxylic acid (63.9 mg, 187 µmol) was initially charged in THF (2.0 ml), and HBTU (92.0 mg, 243 µmol) and N,N-diisopropylethylamine (98 µl, 560 µmol) were subsequently added. After stirring at room temperature for 15 min, (3R,4S)-3,4-difluoropyrrolidine hydrochloride (32.2 mg, 224 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 35.4 mg (44% of theory) of the title compound were obtained.

LC-MS (Method 4): $R_t$=0.72 min; MS (ESIpos): m/z=432 [M+H]$^+$ $^1$H-NMR (400 MHz, DMSO-d6) δ [ppm]: −0.151 (0.30), −0.010 (2.83), 0.006 (2.53), 0.144 (0.31), 1.680 (0.68), 1.757 (16.00), 1.994 (0.65), 2.041 (1.03), 2.072 (3.14), 2.084 (0.76), 2.327 (0.35), 2.365 (0.46), 2.560 (0.94), 2.575 (0.99), 2.586 (1.23), 2.597 (0.93), 2.612 (1.29), 2.624 (1.74), 2.637 (1.02), 2.668 (0.83), 2.709 (0.47), 3.461 (0.31), 3.496 (0.66), 3.518 (0.57), 3.527 (0.57), 3.551 (0.57), 3.581 (0.40), 3.624 (0.44), 3.638 (0.51), 3.679 (0.48), 3.694 (0.89), 3.709 (0.66), 3.727 (0.71), 3.741 (0.69), 3.760 (0.58), 3.772 (0.56), 3.876 (0.42), 3.938 (0.41), 3.952 (0.47), 3.988 (0.46), 4.002 (0.46), 4.180 (0.57), 4.207 (0.37), 4.611 (2.51), 4.833 (2.42), 5.010 (9.06), 5.276 (0.52), 5.409 (0.53), 5.457 (0.44), 7.401 (2.26), 7.421 (2.43), 7.827 (2.30), 7.846 (2.69), 8.081 (1.33), 8.100 (2.38), 8.120 (1.12).

Example 372

(5S)-2-{[5-Chloro-4-(trifluoromethyl)pyridin-2-yl]methyl}-5-{[(3R,4S)-3,4-difluoropyrrolidin-1-yl]carbonyl}-5,6,7,8-tetrahydro[1,2,4]triazolo[4,3-a]pyridin-3(2H)-one

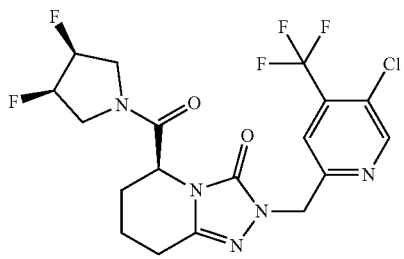 [SMILES: O=C([C@@H]1CCCc2nn(Cc3cc(C(F)(F)F)c(Cl)cn3)c(=O)n21)N1C[C@@H](F)[C@@H](F)C1]

(5S)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic acid (70.0 mg, 186 μmol) was initially charged in THF (3.0 ml), and HBTU (91.6 mg, 242 μmol) and N,N-diisopropylethylamine (97 μl, 560 μmol) were subsequently added. After stirring at room temperature for 15 min, (3R,4S)-3,4-difluoropyrrolidine hydrochloride (32.0 mg, 223 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 53.4 mg (62% of theory) of the title compound were obtained.

LC-MS (Method 3): $R_t$=1.51 min; MS (ESIpos): m/z=466 [M+H]$^+$ $^1$H-NMR (400 MHz, DMSO-d6) δ[ppm]: −0.149 (0.41), −0.008 (3.04), 0.008 (3.60), 1.175 (0.45), 1.669 (1.31), 1.737 (1.59), 1.988 (1.92), 2.028 (1.81), 2.073 (10.98), 2.327 (1.40), 2.366 (0.71), 2.569 (2.50), 2.579 (1.72), 2.593 (2.39), 2.607 (3.34), 2.619 (1.90), 2.649 (1.21), 2.670 (1.51), 2.690 (1.53), 2.710 (0.73), 3.490 (1.03), 3.512 (1.31), 3.554 (0.93), 3.616 (0.86), 3.629 (0.95), 3.672 (1.55), 3.685 (1.90), 3.705 (1.36), 3.719 (1.42), 3.750 (1.21), 3.771 (0.95), 3.869 (0.88), 3.930 (0.90), 3.943 (0.99), 3.979 (0.97), 3.993 (0.84), 4.008 (0.60), 4.021 (0.67), 4.147 (0.67), 4.173 (1.01), 4.187 (0.75), 4.200 (0.62), 4.215 (0.65), 4.810 (2.63), 4.825 (3.36), 4.835 (2.28), 5.040 (16.00), 5.274 (1.01), 5.351 (0.82), 5.388 (1.03), 5.455 (0.82), 7.718 (9.09), 8.901 (8.66).

Example 373

(5S)-2-{[5-Chloro-4-(trifluoromethyl)pyridin-2-yl]methyl}-5-[(3-hydroxyazetidin-1-yl)carbonyl]-5,6,7,8-tetrahydro[1,2,4]triazolo[4,3-a]pyridin-3(2H)-one

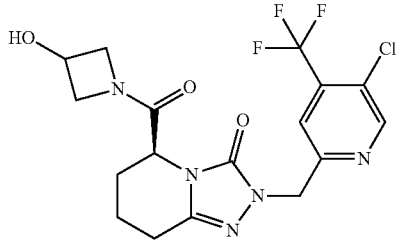 [SMILES: O=C([C@@H]1CCCc2nn(Cc3cc(C(F)(F)F)c(Cl)cn3)c(=O)n21)N1CC(O)C1]

(5S)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic acid (70.0 mg, 186 μmol) was initially charged in THF (3.0 ml), and HBTU (91.6 mg, 242 μmol) and N,N-diisopropylethylamine (97 μl, 560 μmol) were subsequently added. After stirring at room temperature for 15 min, azetidin-3-ol hydrochloride (24.4 mg, 223 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 46.0 mg (57% of theory) of the title compound were obtained.

LC-MS (Method 3): $R_t$=1.20 min; MS (ESIpos): m/z=432 [M+H]$^+$ $^1$H-NMR (400 MHz, DMSO-d6) δ[ppm]: −0.149 (1.32), −0.008 (11.98), 0.008 (10.40), 0.146 (1.38), 1.725 (2.70), 1.919 (1.25), 1.953 (2.77), 2.005 (1.78), 2.015 (1.98), 2.327 (2.50), 2.366 (2.44), 2.523 (9.02), 2.569 (2.30), 2.581 (2.57), 2.594 (4.48), 2.606 (2.44), 2.624 (1.12), 2.636 (1.65), 2.669 (2.63), 2.710 (2.57), 3.606 (1.65), 3.627 (2.90), 3.652 (1.65), 3.663 (1.51), 3.934 (1.65), 3.947 (1.98), 4.021 (2.44), 4.042 (3.29), 4.066 (1.45), 4.091 (1.25), 4.107 (1.58), 4.131 (1.25), 4.349 (1.19), 4.366 (2.04), 4.386 (1.51), 4.495 (4.08), 4.509 (4.48), 4.531 (4.67), 4.546 (4.41), 5.037 (16.00), 5.802 (4.94), 7.731 (14.22), 8.898 (5.99).

Example 374

(5S)-2-{[5-Chloro-4-(trifluoromethyl)pyridin-2-yl]methyl}-5-{[(3S)-3-hydroxypyrrolidin-1-yl]carbonyl}-5,6,7,8-tetrahydro[1,2,4]triazolo[4,3-a]pyridin-3(2H)-one

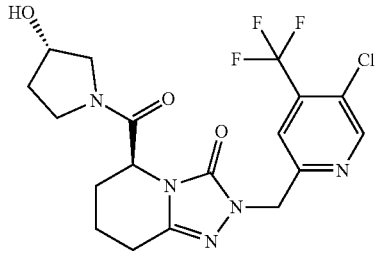 [SMILES: O=C([C@@H]1CCCc2nn(Cc3cc(C(F)(F)F)c(Cl)cn3)c(=O)n21)N1CC[C@H](O)C1]

(5S)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic acid (70.0 mg, 186 μmol) was initially charged in THF (3.0 ml), and HBTU (91.6 mg, 242 μmol) and N,N-diisopropylethylamine (97 μl, 560 μmol) were subsequently added. After stirring at room temperature for 15 min, (3S)-pyrrolidin-3-ol hydrochloride (27.6 mg, 223 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 47.2 mg (57% of theory) of the title compound were obtained.

LC-MS (Method 3): $R_t$=1.22 min; MS (ESIpos): m/z=446 [M+H]$^+$ $^1$H-NMR (400 MHz, DMSO-d6) δ [ppm]: −0.149 (0.73), −0.008 (6.82), 0.008 (5.51), 0.146 (0.70), 1.406 (0.61), 1.739 (3.21), 1.848 (1.56), 1.858 (2.05), 1.879 (2.11), 1.973 (2.36), 1.983 (2.48), 1.995 (3.00), 2.006 (3.18), 2.017 (2.69), 2.068 (1.68), 2.327 (1.38), 2.366 (1.01), 2.523 (5.84), 2.605

(4.10), 2.647 (1.71), 2.669 (1.65), 2.709 (1.13), 2.874 (0.92), 3.201 (1.01), 3.232 (1.44), 3.342 (2.63), 3.368 (3.24), 3.386 (2.36), 3.421 (0.92), 3.431 (0.89), 3.453 (1.62), 3.482 (1.53), 3.549 (1.25), 3.564 (2.17), 3.573 (2.39), 3.588 (1.71), 3.654 (1.96), 3.680 (1.47), 3.697 (0.49), 3.755 (0.92), 4.268 (1.99), 4.360 (2.02), 4.704 (1.16), 4.713 (1.25), 4.720 (1.44), 4.727 (1.10), 4.756 (2.23), 4.762 (1.87), 4.826 (1.22), 4.953 (4.10), 4.961 (3.46), 5.034 (16.00), 5.073 (5.54), 5.082 (5.38), 7.714 (6.70), 7.720 (8.08), 8.902 (11.96).

Example 375

(5S)-2-{[5-Chloro-4-(trifluoromethyl)pyridin-2-yl]methyl}-5-[(3-fluoroazetidin-1-yl)carbonyl]-5,6,7,8-tetrahydro[1,2,4]triazolo[4,3-a]pyridin-3(2H)-one

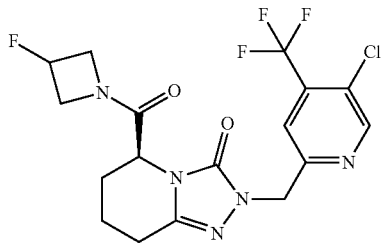 [SMILES: O=C([C@@H]1CCCc2nn(Cc3cc(C(F)(F)F)c(Cl)cn3)c(=O)n21)N1CC(F)C1]

(5S)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic acid (70.0 mg, 186 μmol) was initially charged in THF (3.0 ml), and HBTU (91.6 mg, 242 μmol) and N,N-diisopropylethylamine (97 μl, 560 μmol) were subsequently added. After stirring at room temperature for 15 min, 3-fluoroazetidine hydrochloride (24.9 mg, 223 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 42.0 mg (52% of theory) of the title compound were obtained.

LC-MS (Method 3): $R_t$=1.41 min; MS (ESIpos): m/z=434 [M+H]$^+$ $^1$H-NMR (400 MHz, DMSO-d6) δ [ppm]: −0.149 (0.64), −0.008 (6.01), 0.008 (5.20), 0.146 (0.71), 1.691 (1.93), 1.715 (3.51), 1.970 (1.70), 2.038 (1.49), 2.327 (1.08), 2.366 (0.53), 2.560 (2.77), 2.585 (3.14), 2.598 (4.47), 2.612 (2.34), 2.628 (0.96), 2.641 (1.56), 2.669 (1.24), 2.710 (0.66), 3.908 (0.99), 3.937 (1.21), 3.999 (1.08), 4.174 (0.64), 4.211 (1.05), 4.226 (1.12), 4.259 (1.10), 4.278 (1.21), 4.305 (1.15), 4.335 (0.64), 4.365 (1.17), 4.392 (0.76), 4.431 (0.57), 4.455 (0.71), 4.522 (0.64), 4.557 (2.73), 4.569 (4.40), 4.581 (2.84), 4.639 (0.60), 4.677 (0.60), 5.044 (16.00), 5.355 (0.71), 5.402 (0.73), 5.498 (0.76), 5.546 (0.76), 7.737 (10.15), 8.891 (4.17), 8.902 (4.15).

Example 376

(5S)-2-{[5-Chloro-4-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyridin-3(2H)-one

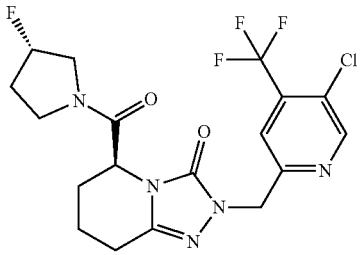 [SMILES: O=C([C@@H]1CCCc2nn(Cc3cc(C(F)(F)F)c(Cl)cn3)c(=O)n21)N1CC[C@H](F)C1]

(5S)-2-{[5-Chloro-4-(trifluoromethyl)pyridin-2-yl]methyl}-3-oxo-2,3,5,6,7,8-hexahydro[1,2,4]triazolo[4,3-a]pyridine-5-carboxylic acid (70.0 mg, 186 μmol) was initially charged in THF (3.0 ml), and HBTU (91.6 mg, 242 μmol) and N,N-diisopropylethylamine (97 μl, 560 μmol) were subsequently added. After stirring at room temperature for 15 min, (3S)-3-fluoropyrrolidine hydrochloride (28.0 mg, 223 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 50.3 mg (60% of theory) of the title compound were obtained.

LC-MS (Method 3): $R_t$=1.44 min; MS (ESIpos): m/z=448 [M+H]$^+$ $^1$H-NMR (400 MHz, DMSO-d6) δ [ppm]: −0.149 (1.07), −0.008 (10.68), 0.008 (7.72), 0.146 (1.11), 1.736 (2.73), 1.929 (0.59), 2.006 (2.25), 2.017 (2.00), 2.073 (4.25), 2.087 (2.03), 2.106 (2.07), 2.137 (1.59), 2.255 (1.15), 2.327 (1.59), 2.366 (1.22), 2.523 (5.73), 2.567 (2.44), 2.583 (1.81), 2.597 (2.11), 2.608 (3.55), 2.620 (2.18), 2.650 (1.33), 2.665 (1.81), 2.670 (1.92), 2.709 (1.33), 3.352 (1.37), 3.371 (1.33), 3.398 (1.00), 3.468 (0.67), 3.495 (1.18), 3.504 (1.22), 3.525 (1.52), 3.554 (1.37), 3.593 (1.92), 3.628 (1.26), 3.652 (1.63), 3.686 (1.15), 3.725 (1.22), 3.747 (1.52), 3.776 (1.29), 3.856 (1.66), 3.920 (0.55), 3.943 (1.03), 3.985 (0.52), 4.009 (0.55), 4.705 (0.85), 4.714 (0.96), 4.721 (1.03), 4.730 (0.78), 4.764 (1.07), 4.779 (1.22), 4.788 (0.92), 4.833 (0.78), 4.846 (1.26), 4.856 (0.74), 4.869 (0.85), 4.884 (1.03), 4.893 (0.81), 5.039 (16.00), 5.258 (1.07), 5.349 (0.70), 5.389 (1.18), 5.481 (0.63), 5.515 (0.63), 7.717 (8.46), 8.903 (7.94).

Example 377

(5S)-2-[(5-Chloropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one

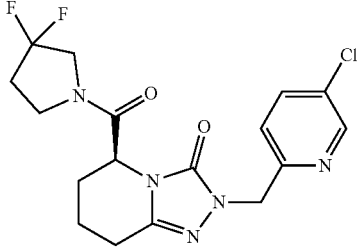 [SMILES: O=C([C@@H]1CCCc2nn(Cc3ccc(Cl)cn3)c(=O)n21)N1CCC(F)(F)C1]

(5S)-2-[(5-Chloropyridin-2-yl)methyl]-3-oxo-2,3,5,6,7,8-hexahydro[1,2,4]triazolo[4,3-a]pyridine-5-carboxylic acid (100 mg, 324 μmol) was initially charged in THF (2.0 ml), and HBTU (160 mg, 421 μmol) and N,N-diisopropylethylamine (170 μl, 970 μmol) were subsequently added. After stirring at room temperature for 15 min, 3,3-difluoropyrrolidine hydrochloride (55.8 mg, 389 μmol) was added and the reaction mixture was stirred at room temperature overnight. N,N-Diisopropylethylamine (170 μl, 970 μmol) was added again and the mixture was stirred at room temperature for 2 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 47.0 mg (36% of theory) of the title compound were obtained.

LC-MS (Method 3): $R_t$=1.24 min; MS (ESIpos): m/z=398 [M+H]$^+$ $^1$H-NMR (400 MHz, DMSO-d6) δ[ppm]: −0.149 (0.69), −0.008 (5.97), 0.008 (5.29), 0.146 (0.69), 1.248 (1.05), 1.265 (1.41), 1.284 (0.90), 1.411 (1.30), 1.699 (1.41), 1.714 (1.52), 1.727 (1.81), 1.917 (0.69), 1.981 (1.63), 1.992 (1.52), 2.021 (1.70), 2.049 (1.23), 2.065 (1.34), 2.074 (1.38), 2.086 (1.12), 2.093 (1.05), 2.328 (1.19), 2.366 (1.67), 2.381 (1.01), 2.411 (1.27), 2.430 (1.27), 2.452 (0.98), 2.569 (4.05), 2.578 (3.08), 2.593 (3.62), 2.608 (3.80), 2.620 (1.85), 2.651 (1.09), 2.665 (1.34), 2.670 (1.38), 2.710 (1.34), 3.538 (1.88), 3.556 (2.82), 3.570 (1.52), 3.577 (1.48), 3.640 (0.51), 3.672 (1.52), 3.705 (1.74), 3.740 (1.38), 3.774 (2.28), 3.791 (1.30), 3.808 (2.14), 3.817 (1.85), 3.835 (0.94), 3.894 (0.83), 3.912 (1.77), 3.931 (0.98), 3.938 (1.27), 3.957 (0.58), 3.973 (0.51), 4.001 (1.09), 4.030 (0.76), 4.044 (1.01), 4.072 (0.62), 4.148 (0.65), 4.180 (0.94), 4.204 (0.94), 4.234 (0.43), 4.761 (1.41), 4.776 (1.92), 4.786 (1.41), 4.836 (1.45), 4.852 (1.92), 4.861 (1.48), 4.914 (16.00), 4.947 (0.47), 4.955 (0.76), 7.199 (6.12), 7.220 (6.66), 7.914 (4.38), 7.920 (4.52), 7.935 (4.24), 7.941 (4.34), 8.572 (5.39), 8.578 (5.29).

Example 378

(5S)-2-[(5-Chloropyridin-2-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

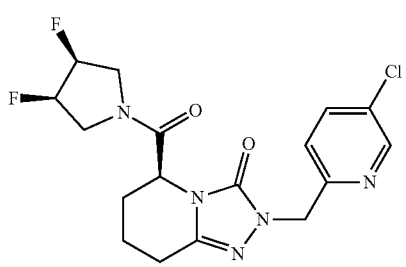 [SMILES: O=C([C@@H]1CCCc2nn(Cc3ccc(Cl)cn3)c(=O)n21)N1C[C@@H](F)[C@@H](F)C1]

(5S)-2-[(5-Chloropyridin-2-yl)methyl]-3-oxo-2,3,5,6,7,8-hexahydro[1,2,4]triazolo[4,3-a]pyridine-5-carboxylic acid (100 mg, 324 μmol) was initially charged in THF (2.0 ml), and HBTU (160 mg, 421 μmol) and N,N-diisopropylethylamine (170 μl, 970 μmol) were subsequently added. After stirring at room temperature for 15 min, (3R,4S)-3,4-difluoropyrrolidine hydrochloride (55.8 mg, 389 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 10.0 mg (8% of theory) of the title compound were obtained.

LC-MS (Method 4): $R_t$=0.64 min; MS (ESIpos): m/z=398 [M+H]$^+$ $^1$H-NMR (400 MHz, DMSO-d6) δ [ppm]: −0.008 (1.28), 0.008 (1.25), 1.656 (0.94), 1.669 (1.15), 1.682 (1.23), 1.692 (1.08), 1.707 (0.89), 1.718 (1.18), 1.729 (1.39), 1.740 (1.56), 1.753 (1.30), 1.936 (0.50), 1.943 (0.52), 1.978 (1.16), 1.986 (1.06), 2.000 (0.81), 2.021 (1.50), 2.045 (0.97), 2.055 (1.06), 2.063 (1.17), 2.073 (2.34), 2.090 (0.84), 2.098 (0.92), 2.106 (0.78), 2.582 (1.56), 2.596 (2.30), 2.608 (3.05), 2.620 (1.71), 2.639 (0.60), 2.650 (0.98), 2.663 (0.53), 3.322 (2.23), 3.449 (0.59), 3.459 (0.81), 3.468 (0.57), 3.483 (0.84), 3.493 (1.38), 3.502 (1.01), 3.514 (1.18), 3.524 (1.17), 3.535 (1.04), 3.547 (1.13), 3.555 (0.73), 3.568 (0.60), 3.578 (0.81), 3.588 (0.54), 3.619 (0.83), 3.633 (0.93), 3.652 (0.59), 3.666 (0.67), 3.674 (0.91), 3.688 (1.62), 3.701 (1.11), 3.707 (1.12), 3.722 (1.44), 3.736 (1.26), 3.753 (1.04), 3.765 (1.10), 3.786 (0.86), 3.799 (0.54), 3.852 (0.50), 3.864 (0.63), 3.871 (0.79), 3.900 (0.51), 3.907 (0.56), 3.912 (0.56), 3.919 (0.49), 3.934 (0.75), 3.947 (0.88), 3.962 (0.53), 3.977 (0.62), 3.984 (0.83), 3.997 (0.85), 4.012 (0.55), 4.026 (0.49), 4.133 (0.53), 4.148 (0.61), 4.162 (0.58), 4.175 (0.98), 4.189 (0.67), 4.202 (0.59), 4.217 (0.54), 4.798 (2.25), 4.811 (3.22), 4.821 (2.12), 4.870 (0.57), 4.911 (16.00), 4.958 (0.47), 5.256 (0.79), 5.265 (0.86), 5.276 (0.95), 5.287 (0.84), 5.299 (0.55), 5.314 (0.65), 5.322 (0.61), 5.329 (0.68), 5.338 (0.66), 5.344 (0.62), 5.353 (0.76), 5.366 (0.68), 5.381 (0.83), 5.388 (1.01), 5.398 (0.80), 5.408 (0.91), 5.418 (0.84), 5.429 (0.64), 5.443 (0.61), 5.451 (0.67), 5.457 (0.67), 5.465 (0.71), 5.475 (0.66), 5.482 (0.62), 5.495 (0.55), 7.197 (3.48), 7.200 (3.78), 7.218 (3.76), 7.220 (4.05), 7.912 (2.52), 7.915 (3.07), 7.918 (2.95), 7.921 (2.92), 7.933 (2.46), 7.935 (2.96), 7.939 (2.85), 7.941 (2.78), 8.215 (0.62), 8.571 (3.84), 8.573 (3.84), 8.577 (3.84).

Example 379

(5S)-2-[(5-Chloropyridin-2-yl)methyl]-5-[(3-fluoroazetidin-1-yl)carbonyl]-5,6,7,8-tetrahydro[1,2,4]triazolo[4,3-a]pyridin-3(2H)-one

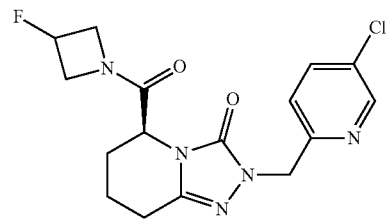 [SMILES: O=C([C@@H]1CCCc2nn(Cc3ccc(Cl)cn3)c(=O)n21)N1CC(F)C1]

(5S)-2-[(5-Chloropyridin-2-yl)methyl]-3-oxo-2,3,5,6,7,8-hexahydro[1,2,4]triazolo[4,3-a]pyridine-5-carboxylic acid (100 mg, 324 μmol) was initially charged in THF (2.0 ml), and HBTU (160 mg, 421 μmol) and N,N-diisopropylethylamine (170 μl, 970 μmol) were subsequently added. After stirring at room temperature for 15 min, 3-fluoroazetidine hydrochloride (43.4 mg, 389 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure and the residue was purified via preparative HPLC (Method 11). The product-containing fractions were concentrated under reduced pressure, and 1.00 mg (1% of theory) of the title compound were obtained.

LC-MS (Method 3): $R_t$=1.04 min; MS (ESIpos): m/z=366 [M+H]$^+$ $^1$H-NMR (400 MHz, DMSO-d6) δ [ppm]: −0.149 (1.02), −0.008 (8.51), 0.008 (5.75), 0.146 (0.64), 1.722 (4.09), 1.969 (2.04), 2.029 (1.71), 2.040 (1.76), 2.328 (1.76), 2.366 (1.97), 2.564 (3.17), 2.584 (3.86), 2.598 (4.65), 2.611 (2.35), 2.626 (0.92), 2.640 (1.46), 2.653 (0.72), 2.670 (0.82), 2.710 (0.66), 3.904 (0.77), 3.929 (1.38), 3.957 (1.30), 3.990 (1.33), 4.017 (0.77), 4.159 (0.69), 4.173 (0.77), 4.237 (1.15), 4.287 (1.38), 4.316 (1.20), 4.343 (0.84), 4.368 (1.35), 4.397 (0.95), 4.432 (0.74), 4.459 (0.89), 4.513 (0.87), 4.559 (4.75), 4.647 (0.74), 4.683 (0.69), 4.700 (0.69), 4.724 (0.54), 4.915 (16.00), 5.356 (0.84), 5.404 (0.87), 5.499 (0.84), 5.546 (0.84), 7.212 (7.00), 7.234 (7.44), 7.912 (3.55), 7.918 (3.65), 7.933 (3.35), 7.938 (3.35), 8.571 (3.40).

Example 380

(5S)-5-{[(3R,4S)-3,4-Difluoropyrrolidin-1-yl]carbonyl}-2-[(5-methoxypyridin-2-yl)methyl]-5,6,7,8-tetrahydro[1,2,4]triazolo[4,3-a]pyridin-3(2H)-one

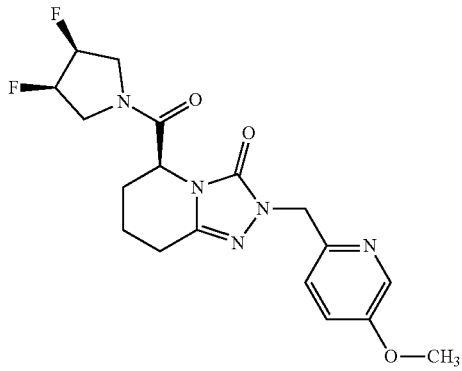 [SMILES: COc1ccc(Cn2nc3n(c2=O)[C@H](C(=O)N2C[C@@H](F)[C@@H](F)C2)CCC3)nc1]

(5S)-2-[(5-Methoxypyridin-2-yl)methyl]-3-oxo-2,3,5,6,7,8-hexahydro[1,2,4]triazolo[4,3-a]pyridine-5-carboxylic acid (45.0 mg, 148 μmol) was initially charged in THF (2.0 ml), and HBTU (72.9 mg, 192 μmol) and N,N-diisopropylethylamine (77 μl, 440 μmol) were subsequently added. After stirring at room temperature for 15 min, (3R,4S)-3,4-difluoropyrrolidine hydrochloride (25.5 mg, 177 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 11.0 mg (19% of theory) of the title compound were obtained.

LC-MS (Method 3): $R_t$=1.15 min; MS (ESIpos): m/z=394 [M+H]$^+$ $^1$H-NMR (400 MHz, DMSO-d6) δ [ppm]: 0.008 (1.72), 1.679 (0.66), 1.720 (0.83), 1.732 (0.84), 1.742 (0.80), 1.968 (0.60), 2.011 (0.73), 2.037 (0.49), 2.047 (0.54), 2.055 (0.57), 2.062 (0.53), 2.071 (0.45), 2.089 (0.43), 2.559 (1.35), 2.569 (0.98), 2.583 (1.23), 2.595 (1.50), 2.607 (0.84), 2.637 (0.50), 3.491 (0.61), 3.501 (0.46), 3.514 (0.51), 3.523 (0.51), 3.535 (0.51), 3.546 (0.56), 3.619 (0.41), 3.632 (0.45), 3.674 (0.46), 3.688 (0.77), 3.704 (0.64), 3.721 (0.66), 3.736 (0.72), 3.754 (0.65), 3.766 (0.66), 3.787 (0.68), 3.810 (16.00), 3.871 (0.41), 3.947 (0.42), 3.983 (0.41), 4.178 (0.46), 4.787 (1.48), 4.797 (1.73), 4.827 (6.88), 5.256 (0.42), 5.267 (0.43), 5.277 (0.49), 5.287 (0.41), 5.378 (0.46), 5.388 (0.53), 5.409 (0.46), 5.418 (0.41), 7.102 (1.50), 7.106 (1.54), 7.124 (1.77), 7.128 (1.82), 7.353 (1.37), 7.357 (1.33), 7.375 (1.17), 7.379 (1.11), 8.209 (1.99), 8.216 (1.83).

Example 381

(5S)-5-[(3,3-Difluoropyrrolidin-1-yl)carbonyl]-2-[(5-methoxypyridin-2-yl)methyl]-5,6,7,8-tetrahydro[1,2,4]triazolo[4,3-a]pyridin-3(2H)-one

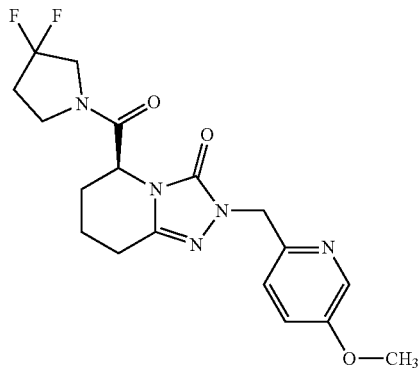 [SMILES: COc1ccc(Cn2nc3n(c2=O)[C@H](C(=O)N2CCC(F)(F)C2)CCC3)nc1]

(5S)-2-[(5-Methoxypyridin-2-yl)methyl]-3-oxo-2,3,5,6,7,8-hexahydro[1,2,4]triazolo[4,3-a]pyridine-5-carboxylic acid (45.0 mg, 148 μmol) was initially charged in THF (2.0 ml), and HBTU (72.9 mg, 192 μmol) and N,N-diisopropylethylamine (77 μl, 440 μmol) were subsequently added. After stirring at room temperature for 15 min, 3,3-difluoropyrrolidine hydrochloride (25.5 mg, 177 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 14.0 mg (23% of theory) of the title compound were obtained.

LC-MS (Method 4): $R_t$=0.57 min; MS (ESIpos): m/z=394 [M+H]$^+$ $^1$H-NMR (400 MHz, DMSO-d6) delta [ppm]: −0.008 (0.99), 0.008 (0.92), 1.675 (0.28), 1.722 (0.51), 1.914 (0.21), 1.981 (0.48), 1.998 (0.36), 2.015 (0.40), 2.031 (0.33), 2.042 (0.30), 2.051 (0.30), 2.057 (0.31), 2.067 (0.31), 2.073 (0.49), 2.085 (0.24), 2.093 (0.21), 2.366 (0.24), 2.382 (0.26), 2.412 (0.29), 2.432 (0.29), 2.452 (0.21), 2.566 (0.80), 2.580 (0.84), 2.597 (0.86), 2.608 (0.55), 2.626 (0.19), 2.639 (0.26), 2.670 (0.19), 2.710 (0.18), 2.893 (0.51), 3.540 (0.40), 3.552 (0.54), 3.560 (0.59), 3.571 (0.34), 3.579 (0.31), 3.673 (0.37), 3.706 (0.40), 3.742 (0.32), 3.774 (0.51), 3.790 (0.33), 3.810 (16.00), 3.835 (0.26), 3.897 (0.20), 3.916 (0.41), 3.935 (0.23), 3.942 (0.29), 4.002 (0.25), 4.031 (0.18), 4.043 (0.23), 4.180 (0.24), 4.207 (0.23), 4.748 (0.34), 4.757 (0.39), 4.763 (0.47), 4.772 (0.33), 4.787 (0.21), 4.827 (3.23), 4.831 (3.75), 4.849 (0.40), 4.871 (0.23), 7.106 (1.41), 7.127 (1.69), 7.352 (1.06), 7.359 (1.08), 7.373 (0.91), 7.381 (0.93), 8.209 (1.75), 8.217 (1.73).

Example 382

(5S)-5-[(3-Fluoroazetidin-1-yl)carbonyl]-2-[(5-methoxypyridin-2-yl)methyl]-5,6,7,8-tetrahydro[1,2,4]triazolo[4,3-a]pyridin-3(2H)-one

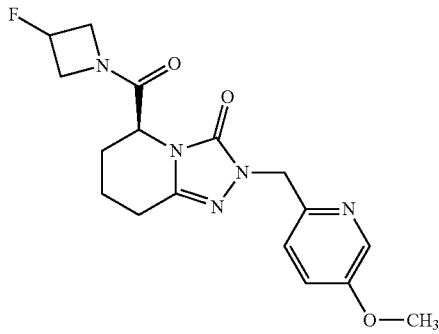 [SMILES: COc1ccc(Cn2nc3n(c2=O)[C@H](C(=O)N2CC(F)C2)CCC3)nc1]

(5S)-2-[(5-Methoxypyridin-2-yl)methyl]-3-oxo-2,3,5,6,7,8-hexahydro[1,2,4]triazolo[4,3-a]pyridine-5-carboxylic acid (45.0 mg, 148 µmol) was initially charged in THF (2.0 ml), and HBTU (72.9 mg, 192 µmol) and N,N-diisopropylethylamine (77 µl, 440 µmol) were subsequently added. After stirring at room temperature for 15 min, 3-fluoroazetidine hydrochloride (19.8 mg, 177 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 14.0 mg (26% of theory) of the title compound were obtained.

LC-MS (Method 4): $R_t$=0.48 min; MS (ESIpos): m/z=362 [M+H]$^+$ $^1$H-NMR (400 MHz, DMSO-d6) delta [ppm]: −0.149 (0.34), −0.008 (3.04), 0.008 (2.32), 0.146 (0.30), 1.720 (1.27), 1.960 (0.60), 2.021 (0.51), 2.032 (0.53), 2.327 (0.48), 2.366 (0.51), 2.523 (1.43), 2.572 (1.15), 2.585 (1.45), 2.598 (0.71), 2.614 (0.27), 2.627 (0.42), 2.641 (0.18), 2.670 (0.46), 2.710 (0.44), 3.809 (16.00), 3.901 (0.21), 3.928 (0.41), 3.956 (0.41), 3.988 (0.46), 4.017 (0.23), 4.157 (0.18), 4.172 (0.21), 4.223 (0.32), 4.239 (0.34), 4.252 (0.30), 4.274 (0.35), 4.305 (0.37), 4.340 (0.21), 4.368 (0.39), 4.395 (0.25), 4.430 (0.18), 4.457 (0.25), 4.534 (0.90), 4.545 (1.45), 4.559 (0.88), 4.577 (0.23), 4.648 (0.21), 4.676 (0.19), 4.701 (0.19), 4.831 (5.32), 5.357 (0.25), 5.405 (0.27), 5.500 (0.25), 5.547 (0.25), 7.118 (2.30), 7.140 (2.76), 7.350 (1.17), 7.358 (1.15), 7.372 (0.97), 7.379 (0.99), 8.210 (1.66).

Example 383

(5S)-2-[(6-Chloropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one

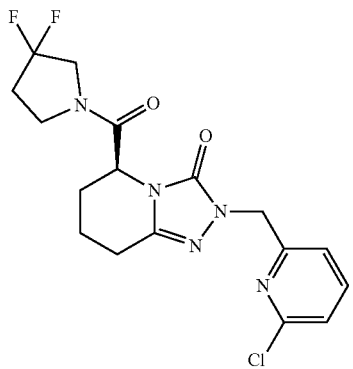 [SMILES: O=C([C@@H]1CCCc2nn(Cc3cccc(Cl)n3)c(=O)n21)N1CCC(F)(F)C1]

(5S)-2-[(6-Chloropyridin-2-yl)methyl]-3-oxo-2,3,5,6,7,8-hexahydro[1,2,4]triazolo[4,3-a]pyridine-5-carboxylic acid (62.9 mg, 204 µmol) was initially charged in THF (2.0 ml), and HBTU (100 mg, 265 µmol) and N,N-diisopropylethylamine (110 µl, 610 µmol) were subsequently added. After stirring at room temperature for 15 min, 3,3-difluoropyrrolidine hydrochloride (35.1 mg, 244 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 52.6 mg (65% of theory) of the title compound were obtained.

LC-MS (Method 3): $R_t$=1.24 min; MS (ESIpos): m/z=398 [M+H]$^+$ $^1$H-NMR (400 MHz, DMSO-d6) δ[ppm]: −0.149 (1.19), −0.008 (10.77), 0.008 (8.41), 0.146 (1.17), 1.483 (6.37), 1.687 (1.00), 1.746 (1.22), 1.980 (0.72), 2.028 (1.32), 2.056 (0.97), 2.072 (1.69), 2.082 (0.85), 2.327 (1.17), 2.366 (1.07), 2.382 (0.85), 2.411 (1.02), 2.430 (0.97), 2.452 (0.80), 2.523 (4.21), 2.566 (2.51), 2.580 (2.14), 2.591 (2.49), 2.605 (2.71), 2.620 (2.34), 2.632 (1.29), 2.665 (1.44), 2.670 (1.47), 2.710 (0.85), 3.541 (1.24), 3.553 (1.74), 3.562 (1.84), 3.572 (1.07), 3.581 (0.97), 3.674 (1.12), 3.707 (1.32), 3.744 (0.87), 3.778 (1.47), 3.791 (0.95), 3.799 (0.82), 3.811 (1.59), 3.836 (0.62), 3.896 (0.60), 3.915 (1.27), 3.941 (0.90), 3.960 (0.42), 4.000 (0.77), 4.030 (0.50), 4.043 (0.72), 4.072 (0.45), 4.153 (0.42), 4.182 (0.72), 4.208 (0.67), 4.776 (1.00), 4.791 (1.37), 4.801 (1.02), 4.848 (1.09), 4.864 (1.52), 4.873 (1.19), 4.892 (16.00), 7.134 (4.18), 7.153 (4.45), 7.433 (3.76), 7.453 (4.18), 7.840 (3.04), 7.860 (5.42), 7.879 (2.69).

Example 384

(5S)-2-[(6-Chloropyridin-2-yl)methyl]-5-[(3-fluoroazetidin-1-yl)carbonyl]-5,6,7,8-tetrahydro[1,2,4]triazolo[4,3-a]pyridin-3(2H)-one

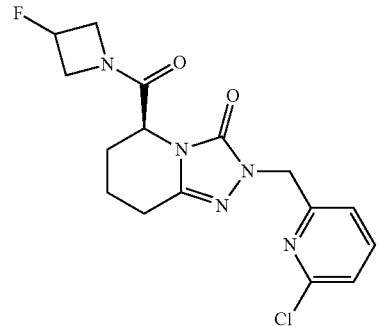 [SMILES: O=C([C@@H]1CCCc2nn(Cc3cccc(Cl)n3)c(=O)n21)N1CC(F)C1]

(5S)-2-[(6-Chloropyridin-2-yl)methyl]-3-oxo-2,3,5,6,7,8-hexahydro[1,2,4]triazolo[4,3-a]pyridine-5-carboxylic acid (62.9 mg, 204 µmol) was initially charged in THF (2.0 ml), and HBTU (100 mg, 265 µmol) and N,N-diisopropylethylamine (110 µl, 610 µmol) were subsequently added. After stirring at room temperature for 15 min, 3-fluoroazetidine hydrochloride (27.3 mg, 244 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 45.5 mg (61% of theory) of the title compound were obtained.

LC-MS (Method 3): R$_t$=1.04 min; MS (ESIpos): m/z=366 [M+H]$^+$ $^1$H-NMR (400 MHz, DMSO-d6) δ [ppm]: −0.149 (1.89), −0.008 (16.00), 0.008 (15.16), 0.146 (1.89), 1.722 (3.70), 1.980 (2.17), 2.044 (1.96), 2.327 (1.75), 2.366 (1.26), 2.574 (3.42), 2.597 (4.33), 2.611 (5.03), 2.625 (2.59), 2.653 (1.68), 2.670 (2.52), 2.710 (1.33), 3.904 (0.84), 3.932 (1.61), 3.962 (1.54), 3.993 (1.54), 4.019 (0.98), 4.175 (0.84), 4.280 (1.33), 4.308 (1.40), 4.368 (1.47), 4.427 (0.77), 4.456 (0.98), 4.559 (4.75), 4.574 (6.57), 4.585 (4.96), 4.652 (0.84), 4.686 (0.77), 4.705 (0.77), 4.893 (15.02), 4.898 (15.09), 5.355 (0.98), 5.405 (0.91), 5.497 (0.98), 5.549 (0.91), 7.150 (4.61), 7.169 (4.89), 7.433 (5.66), 7.452 (6.29), 7.839 (3.42), 7.858 (6.50), 7.877 (3.14).

Example 385

(5S)-2-[(6-Chloropyridin-2-yl)methyl]-5-{[(3R,4S)-3,4-difluoropyrrolidin-1-yl]carbonyl}-5,6,7,8-tetra-hydro[1,2,4]triazolo[4,3-a]pyridin-3(2H)-one

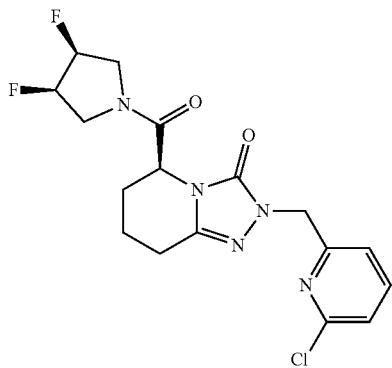 [SMILES: O=C([C@@H]1CCCc2nn(Cc3cccc(Cl)n3)c(=O)n21)N1C[C@@H](F)[C@@H](F)C1]

(5S)-2-[(6-Chloropyridin-2-yl)methyl]-3-oxo-2,3,5,6,7,8-hexahydro[1,2,4]triazolo[4,3-a]pyridine-5-carboxylic acid (62.9 mg, 204 μmol) was initially charged in THF (2.0 ml), and HBTU (100 mg, 265 μmol) and N,N-diisopropylethylamine (110 μl, 610 μmol) were subsequently added. After stirring at room temperature for 15 min, (3R,4S)-3,4-difluoropyrrolidine hydrochloride (35.1 mg, 244 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 60.4 mg (75% of theory) of the title compound were obtained.

LC-MS (Method 3): R$_t$=1.17 min; MS (ESIpos): m/z=398 [M+H]$^+$ $^1$H-NMR (400 MHz, DMSO-d6) δ [ppm]: −0.149 (0.90), −0.008 (7.33), 0.008 (6.93), 0.146 (0.97), 1.677 (1.17), 1.747 (1.40), 1.988 (1.07), 2.029 (1.43), 2.073 (5.97), 2.105 (0.87), 2.327 (0.83), 2.366 (0.83), 2.523 (2.77), 2.558 (1.87), 2.573 (1.70), 2.584 (2.30), 2.608 (2.33), 2.619 (3.17), 2.631 (1.77), 2.665 (1.30), 2.670 (1.30), 2.710 (0.97), 3.458 (0.60), 3.493 (1.23), 3.503 (0.90), 3.516 (1.00), 3.524 (1.00), 3.538 (0.97), 3.548 (1.03), 3.579 (0.77), 3.622 (0.80), 3.635 (0.97), 3.654 (0.63), 3.676 (0.90), 3.691 (1.57), 3.707 (1.33), 3.725 (1.20), 3.738 (1.17), 3.757 (1.00), 3.770 (1.03), 3.789 (0.67), 3.804 (0.57), 3.875 (0.77), 3.915 (0.57), 3.934 (0.77), 3.946 (0.87), 3.961 (0.53), 3.983 (0.80), 3.998 (0.83), 4.011 (0.53), 4.026 (0.50), 4.136 (0.53), 4.151 (0.60), 4.165 (0.67), 4.179 (0.97), 4.193 (0.70), 4.206 (0.60), 4.220 (0.53), 4.824 (3.23), 4.891 (16.00), 5.266 (0.83), 5.276 (0.90), 5.288 (0.83), 5.299 (0.53), 5.314 (0.67), 5.353 (0.80), 5.390 (0.97), 5.409 (0.93), 5.419 (0.87), 5.430 (0.63), 5.452 (0.70), 7.134 (3.47), 7.153 (3.70), 7.433 (4.50), 7.453 (5.13), 7.838 (2.67), 7.842 (2.93), 7.858 (4.63), 7.861 (5.10), 7.878 (2.37), 7.881 (2.57).

Example 386

(5S)-2-[(6-Chloropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

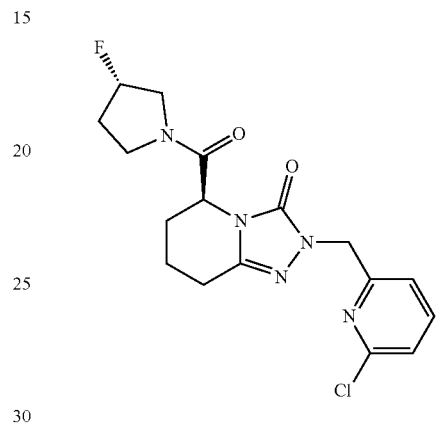

(5S)-2-[(6-Chloropyridin-2-yl)methyl]-3-oxo-2,3,5,6,7,8-hexahydro[1,2,4]triazolo[4,3-a]pyridine-5-carboxylic acid (62.9 mg, 204 μmol) was initially charged in THF (2.0 ml), and HBTU (100 mg, 265 μmol) and N,N-diisopropylethylamine (110 μl, 610 μmol) were subsequently added. After stirring at room temperature for 15 min, (3S)-3-fluoropyrrolidine hydrochloride (30.7 mg, 244 μmol) was added and the reaction mixture was stirred at room temperature overnight. HBTU (38 mg, 102 μmol) and N,N-diisopropylethylamine (18 μl, 102 μmol) were added again and the mixture was stirred overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 53.3 mg (69% of theory) of the title compound were obtained.

LC-MS (Method 3): R$_t$=1.09 min; MS (ESIpos): m/z=380 [M+H]$^+$ $^1$H-NMR (400 MHz, DMSO-d6) δ[ppm]: −0.149 (0.48), −0.008 (4.53), 0.008 (3.45), 0.146 (0.46), 1.747 (2.81), 1.890 (0.58), 1.932 (0.79), 1.968 (0.40), 2.005 (0.79), 2.041 (1.27), 2.073 (2.00), 2.090 (1.79), 2.108 (2.12), 2.139 (1.47), 2.222 (0.79), 2.270 (1.06), 2.327 (0.58), 2.366 (0.46), 2.560 (1.85), 2.575 (1.52), 2.584 (1.79), 2.602 (1.62), 2.622 (2.47), 2.665 (1.25), 2.710 (0.42), 3.278 (0.71), 3.333 (1.04), 3.352 (0.58), 3.365 (0.62), 3.374 (0.66), 3.401 (0.71), 3.409 (0.73), 3.462 (0.56), 3.471 (0.58), 3.498 (0.79), 3.507 (0.73), 3.613 (0.54), 3.638 (2.72), 3.656 (2.06), 3.682 (1.33), 3.701 (1.02), 3.733 (1.35), 3.753 (1.75), 3.774 (1.45), 3.795 (1.18), 3.863 (2.43), 4.706 (1.23), 4.716 (1.66), 4.722 (1.47), 4.732 (1.14), 4.763 (1.47), 4.772 (1.70), 4.778 (1.85), 4.787 (1.37), 4.888 (16.00), 5.260 (1.14), 5.383 (1.50), 5.390 (1.54), 5.514 (0.83), 6.519 (0.96), 7.135 (4.61), 7.154 (4.90), 7.433 (4.78), 7.453 (5.32), 7.841 (3.97), 7.860 (7.07), 7.879 (3.45).

Example 387

(5S)-2-{[3-Chloro-4-(trifluoromethyl)pyridin-2-yl]methyl}-5-[(3,3-difluoropyrrolidin-1-yl)carbonyl]-5,6,7,8-tetrahydro[1,2,4]triazolo[4,3-a]pyridin-3(2H)-one

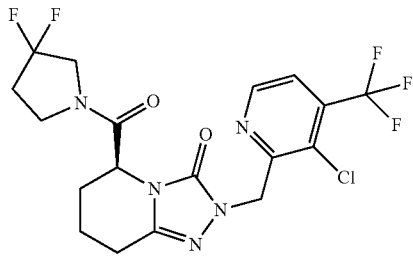 [SMILES: O=C([C@@H]1CCCc2nn(Cc3nccc(C(F)(F)F)c3Cl)c(=O)n21)N1CCC(F)(F)C1]

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (47.0 mg, 125 µmol) was initially charged in THF (2.0 ml) at room temperature. Subsequently, HBTU (61.5 mg, 162 µmol) and N,N-diisopropylethylamine (65 µl, 370 µmol) were added. After stirring for 15 min, 3,3-difluoropyrrolidine hydrochloride (21.5 mg, 150 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 18.5 mg (32% of theory) of the title compound were obtained.

LC-MS (Method 3): $R_t$=1.47 min; MS (ESIpos): m/z=466 [M+H]⁺

¹H-NMR (400 MHz, DMSO-d6) δ[ppm]: −0.149 (1.17), 0.008 (8.40), 0.146 (1.07), 1.711 (4.48), 1.978 (2.57), 2.328 (2.38), 2.366 (2.47), 2.576 (5.46), 2.589 (6.16), 2.603 (3.31), 2.631 (1.54), 2.670 (2.05), 2.710 (1.91), 3.533 (3.17), 3.552 (5.22), 3.573 (2.47), 3.671 (2.33), 3.705 (2.61), 3.736 (2.01), 3.769 (3.27), 3.802 (2.61), 3.813 (2.57), 3.832 (1.73), 3.911 (2.47), 3.939 (1.77), 3.997 (1.73), 4.039 (1.45), 4.143 (1.03), 4.176 (1.45), 4.201 (1.59), 4.769 (2.89), 4.847 (2.71), 4.858 (2.15), 5.104 (3.50), 5.144 (13.62), 5.166 (16.00), 5.207 (3.64), 7.844 (10.78), 7.856 (10.87), 8.735 (9.19), 8.748 (9.00).

Example 388

(5S)-2-{[3-Chloro-4-(trifluoromethyl)pyridin-2-yl]methyl}-5-{[(3R,4S)-3,4-difluoropyrrolidin-1-yl]carbonyl}-5,6,7,8-tetrahydro[1,2,4]triazolo[4,3-a]pyridin-3(2H)-one

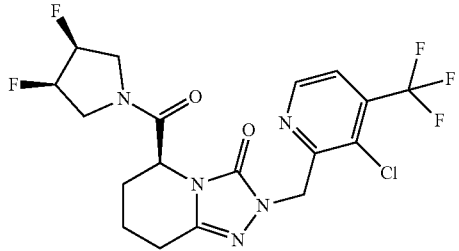 [SMILES: O=C([C@@H]1CCCc2nn(Cc3nccc(C(F)(F)F)c3Cl)c(=O)n21)N1C[C@@H](F)[C@@H](F)C1]

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (50.0 mg, 133 µmol) was initially charged in THF (3.1 ml), and HBTU (65.4 mg, 173 µmol) and N,N-diisopropylethylamine (69 µl, 400 µmol) were subsequently added. After stirring at room temperature for 15 min, (3R,4S)-3,4-difluoropyrrolidine hydrochloride (22.9 mg, 159 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 37.0 mg (60% of theory) of the title compound were obtained.

LC-MS (Method 3): $R_t$=1.40 min; MS (ESIpos): m/z=466 [M+H]⁺

¹H-NMR (400 MHz, DMSO-d6) δ [ppm]: −0.149 (1.23), −0.008 (15.35), 0.008 (9.72), 0.146 (1.36), 1.703 (5.38), 1.715 (5.89), 1.725 (5.77), 1.917 (1.30), 1.958 (2.85), 1.996 (2.91), 2.008 (2.91), 2.040 (2.59), 2.049 (2.79), 2.057 (2.91), 2.065 (2.85), 2.073 (3.50), 2.084 (2.07), 2.092 (2.20), 2.100 (1.94), 2.327 (2.01), 2.332 (1.49), 2.366 (2.20), 2.519 (13.80), 2.524 (12.89), 2.565 (5.51), 2.578 (6.41), 2.589 (8.16), 2.602 (4.66), 2.619 (1.88), 2.632 (2.66), 2.665 (1.94), 2.670 (2.46), 2.674 (1.81), 2.710 (2.46), 3.456 (1.49), 3.490 (2.91), 3.499 (2.07), 3.511 (2.66), 3.520 (2.79), 3.530 (2.40), 3.545 (2.33), 3.562 (1.43), 3.573 (1.88), 3.583 (1.30), 3.616 (2.01), 3.630 (2.20), 3.649 (1.49), 3.663 (1.75), 3.672 (2.40), 3.685 (3.50), 3.695 (2.91), 3.705 (2.66), 3.717 (3.50), 3.731 (2.59), 3.747 (2.59), 3.759 (2.46), 3.780 (2.07), 3.793 (1.30), 3.869 (2.01), 3.905 (1.43), 3.931 (1.88), 3.945 (2.14), 3.959 (1.43), 3.980 (2.20), 3.994 (2.14), 4.009 (1.36), 4.023 (1.23), 4.128 (1.36), 4.143 (1.62), 4.156 (1.49), 4.170 (2.53), 4.184 (1.68), 4.197 (1.49), 4.212 (1.36), 4.791 (6.87), 4.801 (8.10), 4.807 (8.74), 4.816 (6.35), 5.101 (4.28), 5.142 (15.35), 5.146 (14.77), 5.157 (12.96), 5.172 (12.50), 5.198 (2.01), 5.213 (3.95), 5.254 (2.07), 5.262 (2.14), 5.273 (2.46), 5.284 (2.01), 5.297 (1.49), 5.311 (1.68), 5.326 (1.75), 5.335 (1.75), 5.350 (2.07), 5.364 (1.94), 5.387 (2.59), 5.406 (2.33), 5.415 (2.07), 5.426 (1.62), 5.440 (1.55), 5.449 (1.75), 5.463 (1.75), 5.472 (1.68), 5.493 (1.43), 7.844 (15.74), 7.856 (16.00), 8.735 (10.62), 8.748 (10.11).

Example 389

(5S)-2-{[3-Chloro-4-(trifluoromethyl)pyridin-2-yl]methyl}-5-[(3-fluoroazetidin-1-yl)carbonyl]-5,6,7,8-tetrahydro[1,2,4]triazolo[4,3-a]pyridin-3(2H)-one

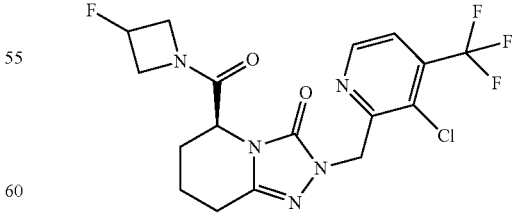

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (50.0 mg, 133 µmol) was initially charged in THF (3.1 ml), and HBTU (65.4 mg, 173 µmol) and N,N-diisopropylethylamine (69 µl, 400 µmol) were subsequently added. After stirring at room temperature for 15 min, 3-fluoroazetidine hydrochloride (17.8 mg, 159 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 30.0 mg (52% of theory) of the title compound were obtained.

LC-MS (Method 3): $R_t$=1.30 min; MS (ESIpos): m/z=434 [M+H]$^+$ $^1$H-NMR (400 MHz, DMSO-d6) δ [ppm]: −0.008 (1.41), 0.008 (1.30), 1.721 (4.73), 1.934 (1.28), 1.946 (1.80), 1.957 (1.88), 1.967 (1.75), 1.979 (1.27), 1.991 (0.90), 2.008 (1.32), 2.026 (1.85), 2.044 (1.66), 2.063 (1.20), 2.073 (0.76), 2.080 (0.64), 2.524 (1.40), 2.572 (3.52), 2.586 (5.17), 2.599 (2.48), 2.614 (0.89), 2.628 (1.52), 2.642 (0.62), 3.895 (0.63), 3.923 (1.28), 3.953 (1.26), 3.985 (1.30), 4.012 (0.73), 4.155 (0.55), 4.169 (0.62), 4.184 (0.51), 4.234 (0.97), 4.286 (1.22), 4.314 (1.22), 4.348 (0.73), 4.368 (1.16), 4.389 (0.84), 4.426 (0.57), 4.453 (0.76), 4.509 (0.60), 4.526 (2.15), 4.537 (3.77), 4.551 (3.73), 4.561 (2.07), 4.576 (0.70), 4.604 (0.47), 4.620 (0.56), 4.635 (0.63), 4.646 (0.55), 4.662 (0.58), 4.671 (0.59), 4.686 (0.62), 4.699 (0.55), 4.713 (0.49), 5.118 (1.66), 5.159 (16.00), 5.171 (5.56), 5.213 (0.81), 5.355 (0.81), 5.370 (0.60), 5.381 (0.64), 5.389 (0.73), 5.396 (0.82), 5.497 (0.78), 5.505 (0.70), 5.512 (0.62), 5.532 (0.71), 5.539 (0.81), 7.845 (8.15), 7.857 (8.51), 8.722 (2.50), 8.734 (4.62), 8.747 (2.37).

Example 390

(5S)-2-{[3-Chloro-4-(trifluoromethyl)pyridin-2-yl]methyl}-5-[(3-hydroxyazetidin-1-yl)carbonyl]-5,6,7,8-tetrahydro[1,2,4]triazolo[4,3-a]pyridin-3(2H)-one

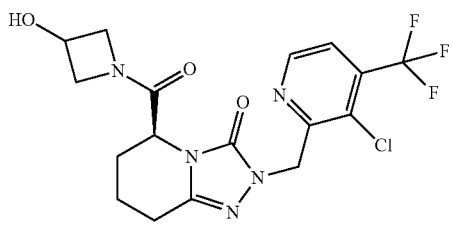 [SMILES: O=C([C@@H]1CCCc2nn(Cc3nccc(C(F)(F)F)c3Cl)c(=O)n21)N1CC(O)C1]

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (50.0 mg, 133 µmol) was initially charged in THF (3.1 ml), and HBTU (65.4 mg, 173 µmol) and N,N-diisopropylethylamine (69 µl, 400 µmol) were subsequently added. After stirring at room temperature for 15 min, azetidin-3-ol hydrochloride (17.4 mg, 159 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 26.0 mg (45% of theory) of the title compound were obtained.

LC-MS (Method 3): $R_t$=1.11 min; MS (ESIpos): m/z=432 [M+H]$^+$ $^1$H-NMR (400 MHz, DMSO-d6) δ [ppm]: −0.149 (1.15), 0.008 (8.71), 0.146 (1.10), 1.706 (7.23), 1.719 (7.18), 1.903 (2.41), 1.915 (2.47), 1.938 (4.55), 1.989 (2.30), 2.001 (3.23), 2.014 (3.01), 2.023 (3.01), 2.038 (2.30), 2.328 (2.30), 2.366 (1.81), 2.523 (9.81), 2.564 (5.48), 2.579 (7.07), 2.592 (3.45), 2.607 (1.48), 2.621 (2.25), 2.670 (2.19), 2.710 (1.75), 3.593 (2.47), 3.601 (2.79), 3.627 (3.78), 3.643 (2.58), 3.658 (2.52), 3.668 (2.47), 3.943 (2.74), 3.954 (3.18), 4.020 (4.82), 4.043 (4.93), 4.061 (2.52), 4.097 (1.97), 4.113 (2.68), 4.137 (1.86), 4.347 (1.92), 4.366 (3.23), 4.387 (2.41), 4.508 (13.21), 5.111 (1.97), 5.152 (16.00), 5.157 (13.97), 5.164 (12.00), 5.204 (1.64), 5.803 (5.42), 7.844 (13.70), 7.857 (14.19), 8.733 (11.29), 8.745 (11.01).

Example 391

(5S)-2-{[3-Chloro-4-(trifluoromethyl)pyridin-2-yl]methyl}-5-{[(3S)-3-hydroxypyrrolidin-1-yl]carbonyl}-5,6,7,8-tetrahydro[1,2,4]triazolo[4,3-a]pyridin-3(2H)-one

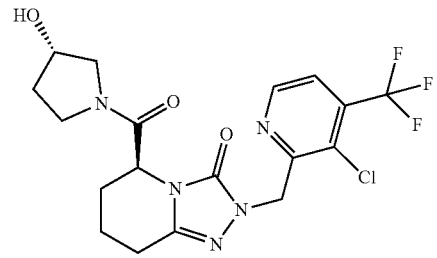 [SMILES: O=C([C@@H]1CCCc2nn(Cc3nccc(C(F)(F)F)c3Cl)c(=O)n21)N1CC[C@H](O)C1]

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (50.0 mg, 133 µmol) was initially charged in THF (2.0 ml), and HBTU (65.4 mg, 173 µmol) and N,N-diisopropylethylamine (69 µl, 400 µmol) were subsequently added. After stirring at room temperature for 15 min, (3S)-pyrrolidin-3-ol hydrochloride (19.7 mg, 159 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 11.0 mg (19% of theory) of the title compound were obtained.

LC-MS (Method 3): $R_t$=1.12 min; MS (ESIpos): m/z=446 [M+H]$^+$ $^1$H-NMR (400 MHz, DMSO-d6) δ [ppm]: −0.150 (1.86), −0.008 (16.00), 0.008 (12.93), 0.146 (1.86), 1.243 (2.08), 1.257 (2.30), 1.728 (6.03), 1.846 (2.63), 1.855 (2.74), 1.877 (3.07), 1.959 (2.85), 2.004 (3.07), 2.044 (3.07), 2.327 (4.60), 2.366 (3.29), 2.585 (5.92), 2.626 (2.63), 2.669 (5.04), 2.689 (1.86), 2.709 (3.51), 3.375 (3.95), 3.435 (2.08), 3.456 (2.85), 3.566 (1.75), 3.644 (3.07), 3.654 (4.49), 3.682 (3.40), 4.262 (2.63), 4.363 (2.85), 4.706 (3.62), 4.714 (2.74), 4.746 (2.52), 5.007 (1.86), 5.036 (1.75), 5.091 (3.95), 5.132 (12.05), 5.159 (10.52), 5.199 (3.07), 7.842 (10.85), 7.855 (11.18), 7.910 (2.30), 8.738 (8.44), 8.750 (8.00).

Example 392

(5S)-2-{[3-Chloro-4-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyridin-3(2H)-one

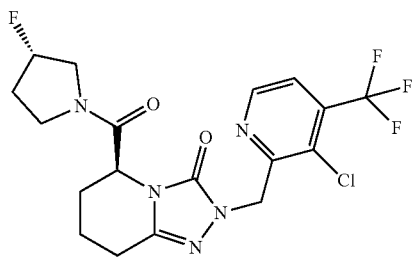 [SMILES: O=C([C@@H]1CCCc2nn(Cc3nccc(C(F)(F)F)c3Cl)c(=O)n21)N1CC[C@H](F)C1]

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (53.0 mg, 141 µmol) was initially charged in THF (2.0 ml) at room temperature. Subsequently, HBTU (69.4 mg, 183 mol) and N,N-diisopropylethylamine (74 µl, 420 µmol) were added. After stirring for 15 min, (3S)-3-fluoropyrrolidine (15.0 mg, 169 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 10). The product-containing fractions were concentrated under reduced pressure, and 11.0 mg (17% of theory) of the title compound were obtained.

LC-MS (Method 3): $R_t$=1.33 min; MS (ESIpos): m/z=448 [M+H]$^+$ $^1$H-NMR (400 MHz, DMSO-d6) δ [ppm]: −0.149 (1.89), −0.008 (16.00), 0.008 (13.03), 0.146 (1.80), 1.734 (6.56), 1.901 (1.62), 1.990 (1.98), 2.016 (2.43), 2.089 (4.22), 2.105 (4.22), 2.122 (2.79), 2.137 (2.61), 2.265 (2.07), 2.327 (3.96), 2.366 (2.61), 2.523 (13.30), 2.570 (3.87), 2.592 (4.85), 2.634 (1.80), 2.669 (4.04), 2.709 (2.52), 3.371 (1.71), 3.406 (1.44), 3.469 (1.08), 3.496 (1.71), 3.629 (4.22), 3.655 (4.31), 3.682 (2.79), 3.692 (2.07), 3.728 (3.33), 3.747 (3.60), 3.771 (2.70), 3.793 (2.25), 3.862 (4.67), 4.693 (2.16), 4.702 (2.70), 4.708 (2.79), 4.717 (2.16), 4.750 (2.70), 4.758 (3.15), 4.765 (3.51), 4.774 (2.61), 5.096 (3.87), 5.137 (12.85), 5.160 (8.54), 5.170 (9.62), 5.200 (2.07), 5.211 (3.24), 5.257 (2.25), 5.388 (2.97), 5.508 (1.62), 7.844 (11.51), 7.856 (12.04), 8.738 (9.17), 8.751 (8.90).

Example 393

(5S)-2-[(3-Chloropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

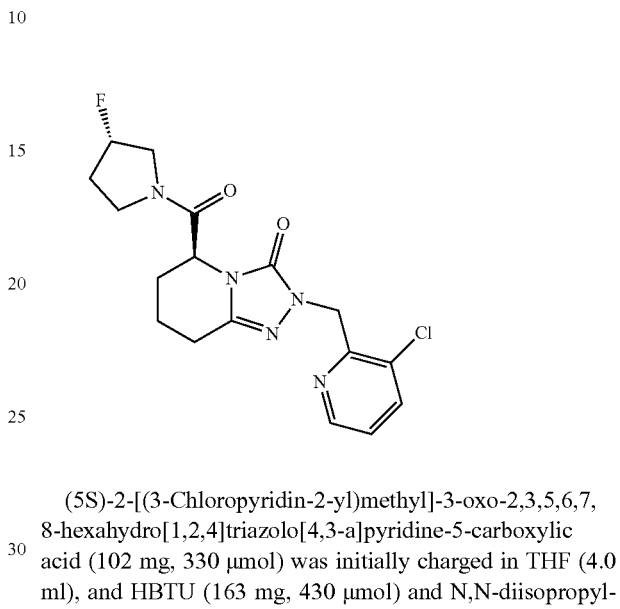

(5S)-2-[(3-Chloropyridin-2-yl)methyl]-3-oxo-2,3,5,6,7,8-hexahydro[1,2,4]triazolo[4,3-a]pyridine-5-carboxylic acid (102 mg, 330 µmol) was initially charged in THF (4.0 ml), and HBTU (163 mg, 430 µmol) and N,N-diisopropylethylamine (170 µl, 990 µmol) were subsequently added. After stirring at room temperature for 15 min, (3S)-3-fluoropyrrolidine hydrochloride (49.8 mg, 396 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 58.1 mg (46% of theory) of the title compound were obtained.

LC-MS (Method 3): $R_t$=0.95 min; MS (ESIpos): m/z=380 [M+H]$^+$ $^1$H-NMR (400 MHz, DMSO-d6) δ[ppm]: −0.149 (1.01), −0.008 (8.13), 0.008 (8.46), 0.146 (1.01), 1.722 (9.21), 1.732 (9.63), 1.861 (1.59), 1.898 (2.43), 1.907 (2.26), 1.974 (2.09), 2.009 (3.60), 2.018 (3.52), 2.045 (2.18), 2.064 (4.10), 2.082 (6.20), 2.098 (5.78), 2.135 (3.69), 2.217 (2.18), 2.237 (2.26), 2.268 (2.85), 2.327 (1.84), 2.366 (1.76), 2.561 (6.45), 2.581 (7.20), 2.624 (2.43), 2.670 (1.93), 2.690 (9.47), 2.710 (1.76), 3.274 (2.01), 3.348 (2.01), 3.363 (1.68), 3.372 (1.93), 3.398 (2.01), 3.407 (2.18), 3.460 (1.51), 3.469 (1.68), 3.496 (2.26), 3.504 (2.09), 3.633 (5.86), 3.642 (3.85), 3.658 (6.03), 3.669 (4.69), 3.685 (3.85), 3.729 (4.69), 3.751 (5.11), 3.776 (4.10), 3.797 (3.35), 3.828 (0.92), 3.865 (6.70), 4.685 (3.35), 4.695 (4.02), 4.701 (4.19), 4.710 (3.27), 4.741 (4.19), 4.750 (4.69), 4.756 (5.36), 4.765 (4.10), 4.947 (6.95), 4.987 (16.00), 4.990 (15.50), 5.034 (11.81), 5.043 (13.82), 5.073 (4.52), 5.083 (6.20), 5.258 (3.18), 5.382 (4.27), 5.389 (4.44), 5.515 (2.43), 5.944 (0.67), 7.374 (10.05), 7.386 (10.39), 7.395 (10.81), 7.406 (11.14), 7.923 (11.23), 7.926 (11.39), 7.943 (10.72), 7.946 (10.47), 8.468 (11.39), 8.479 (11.39).

Example 394

(5S)-2-[(3-Chloropyridin-2-yl)methyl]-5-[(3,3-difluoroazetidin-1-yl)carbonyl]-5,6,7,8-tetrahydro[1,2,4]triazolo[4,3-a]pyridin-3(2H)-one

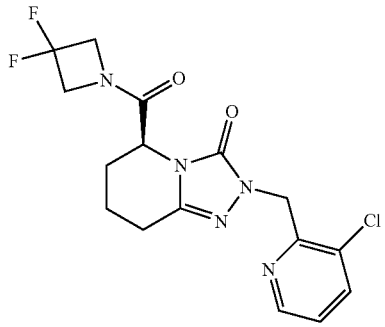 [SMILES: O=C([C@@H]1CCCc2nn(Cc3ncccc3Cl)c(=O)n21)N1CC(F)(F)C1]

(5S)-2-[(3-Chloropyridin-2-yl)methyl]-3-oxo-2,3,5,6,7,8-hexahydro[1,2,4]triazolo[4,3-a]pyridine-5-carboxylic acid (102 mg, 330 µmol) was initially charged in THF (4.0 ml), and HBTU (163 mg, 430 µmol) and N,N-diisopropylethylamine (170 µl, 990 µmol) were subsequently added. After stirring at room temperature for 15 min, 3,3-difluoroazetidine hydrochloride (51.4 mg, 396 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 75.6 mg (60% of theory) of the title compound were obtained.

LC-MS (Method 3): $R_t$=1.07 min; MS (ESIpos): m/z=384 [M+H]$^+$ $^1$H-NMR (400 MHz, DMSO-d6) δ[ppm]: −0.149 (0.48), −0.008 (4.02), 0.008 (4.02), 0.146 (0.48), 1.710 (3.05), 1.726 (4.50), 1.736 (4.27), 1.750 (3.05), 1.770 (1.19), 1.953 (1.29), 1.968 (1.83), 1.979 (2.44), 1.990 (2.25), 2.005 (1.09), 2.030 (1.25), 2.046 (1.83), 2.057 (1.93), 2.066 (2.25), 2.079 (1.83), 2.089 (1.25), 2.104 (0.87), 2.114 (0.58), 2.327 (0.80), 2.366 (0.71), 2.562 (4.56), 2.578 (4.02), 2.588 (6.20), 2.602 (2.96), 2.616 (1.09), 2.630 (1.67), 2.644 (0.74), 2.670 (0.93), 2.710 (0.80), 4.326 (1.73), 4.356 (2.92), 4.378 (2.92), 4.408 (1.80), 4.568 (4.21), 4.583 (6.97), 4.596 (4.18), 4.700 (0.64), 4.728 (1.83), 4.758 (2.22), 4.802 (1.12), 4.834 (2.12), 4.863 (1.80), 4.986 (2.92), 5.026 (16.00), 5.041 (16.00), 5.081 (2.92), 7.378 (5.59), 7.390 (5.78), 7.399 (6.07), 7.410 (6.23), 7.929 (6.71), 7.933 (7.07), 7.949 (6.43), 7.953 (6.43), 8.451 (6.52), 8.455 (6.81), 8.463 (6.68), 8.466 (6.52).

Example 395

(5S)-2-[(3-Chloropyridin-2-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

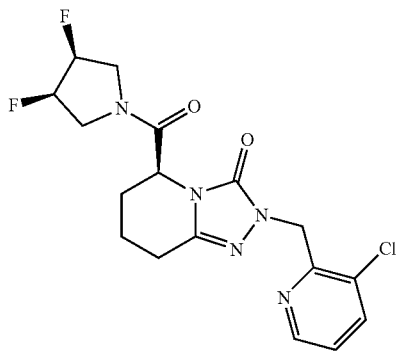 [SMILES: O=C([C@@H]1CCCc2nn(Cc3ncccc3Cl)c(=O)n21)N1C[C@@H](F)[C@@H](F)C1]

(5S)-2-[(3-Chloropyridin-2-yl)methyl]-3-oxo-2,3,5,6,7,8-hexahydro[1,2,4]triazolo[4,3-a]pyridine-5-carboxylic acid (102 mg, 330 µmol) was initially charged in THF (4.0 ml), and HBTU (163 mg, 430 µmol) and N,N-diisopropylethylamine (170 µl, 990 µmol) were subsequently added. After stirring at room temperature for 15 min, (3R,4S)-3,4-difluoropyrrolidine hydrochloride (56.9 mg, 396 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 61.2 mg (47% of theory) of the title compound were obtained.

LC-MS (Method 3): $R_t$=1.05 min; MS (ESIpos): m/z=398 [M+H]$^+$ $^1$H-NMR (400 MHz, DMSO-d6) δ[ppm]: −0.150 (1.35), −0.008 (11.87), 0.008 (10.29), 0.146 (1.35), 1.710 (8.41), 1.721 (7.59), 1.733 (5.11), 1.908 (1.73), 1.952 (3.46), 1.989 (3.61), 2.002 (3.53), 2.017 (2.48), 2.032 (3.08), 2.042 (3.15), 2.049 (3.23), 2.057 (3.38), 2.067 (3.53), 2.072 (7.14), 2.084 (2.63), 2.092 (2.48), 2.102 (1.73), 2.327 (1.65), 2.366 (1.73), 2.518 (9.84), 2.567 (7.66), 2.577 (10.22), 2.589 (5.78), 2.606 (2.10), 2.620 (3.23), 2.632 (1.73), 2.670 (2.10), 2.709 (1.95), 2.890 (0.75), 3.455 (1.95), 3.479 (2.03), 3.488 (3.83), 3.498 (2.70), 3.510 (3.38), 3.520 (3.46), 3.529 (2.93), 3.542 (3.00), 3.563 (1.73), 3.572 (2.40), 3.582 (1.50), 3.616 (2.55), 3.630 (2.85), 3.649 (1.80), 3.663 (2.10), 3.671 (2.78), 3.685 (4.58), 3.696 (3.46), 3.705 (3.08), 3.718 (4.43), 3.730 (2.78), 3.748 (2.85), 3.760 (3.00), 3.781 (2.63), 3.794 (1.65), 3.835 (1.13), 3.870 (2.40), 3.911 (1.73), 3.932 (2.33), 3.946 (2.70), 3.961 (1.65), 3.981 (2.63), 3.995 (2.63), 4.010 (1.65), 4.024 (1.65), 4.131 (1.58), 4.146 (1.80), 4.160 (1.80), 4.174 (3.15), 4.188 (2.18), 4.201 (1.80), 4.216 (1.65), 4.781 (7.96), 4.791 (9.31), 4.797 (10.37), 4.806 (7.51), 4.952 (6.84), 4.959 (4.88), 4.992 (16.00), 4.998 (15.47), 5.029 (14.50), 5.044 (15.02), 5.068 (4.51), 5.083 (6.38), 5.242 (1.80), 5.253 (2.48), 5.263 (2.63), 5.274 (2.93), 5.283 (2.40), 5.296 (1.88), 5.311 (1.73), 5.327 (2.18), 5.336 (2.18), 5.350 (2.48), 5.363 (2.33), 5.375 (2.78), 5.385 (3.23), 5.397 (2.55), 5.406 (2.78), 5.415 (2.85), 5.426 (2.10), 5.440 (1.80), 5.448 (2.10), 5.464 (2.10), 5.472 (2.10), 5.480 (2.18), 5.493 (1.88), 5.502 (1.20), 7.374 (10.44), 7.385 (10.97), 7.394 (11.42), 7.406 (11.72), 7.924 (13.00), 7.944 (12.24), 8.465 (12.85), 8.476 (12.85).

Example 396

(5S)-2-[(3-Chloropyridin-2-yl)methyl]-5-[(3-fluoroazetidin-1-yl)carbonyl]-5,6,7,8-tetrahydro[1,2,4]triazolo[4,3-a]pyridin-3(2H)-one

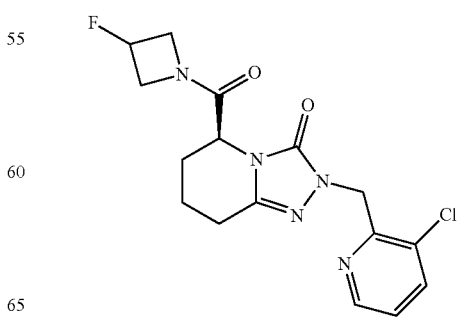

(5S)-2-[(3-Chloropyridin-2-yl)methyl]-3-oxo-2,3,5,6,7,8-hexahydro[1,2,4]triazolo[4,3-a]pyridine-5-carboxylic acid (102 mg, 330 µmol) was initially charged in THF (4.0 ml), and HBTU (163 mg, 430 µmol) and N,N-diisopropylethylamine (170 µl, 990 µmol) were subsequently added. After stirring at room temperature for 15 min, 3-fluoroazetidine hydrochloride (44.2 mg, 396 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 44.7 mg (37% of theory) of the title compound were obtained.

LC-MS (Method 3): $R_t$=0.95 min; MS (ESIpos): m/z=366 [M+H]$^+$ $^1$H-NMR (400 MHz, DMSO-d6) δ[ppm]: −0.008 (1.57), 0.008 (1.11), 1.718 (5.92), 1.928 (1.66), 1.939 (2.29), 1.951 (2.40), 1.961 (2.25), 1.972 (1.69), 1.985 (1.20), 2.002 (1.67), 2.021 (2.41), 2.039 (2.28), 2.056 (1.75), 2.073 (16.00), 2.524 (3.36), 2.561 (4.73), 2.575 (6.55), 2.588 (3.16), 2.603 (1.16), 2.617 (1.86), 2.631 (0.77), 3.894 (0.84), 3.923 (1.64), 3.953 (1.64), 3.984 (1.63), 4.013 (0.91), 4.154 (0.71), 4.168 (0.80), 4.183 (0.68), 4.219 (1.26), 4.233 (1.28), 4.248 (1.10), 4.262 (1.00), 4.286 (1.40), 4.296 (1.38), 4.315 (1.43), 4.359 (1.19), 4.385 (1.41), 4.429 (0.76), 4.454 (0.96), 4.513 (2.81), 4.525 (5.12), 4.538 (4.60), 4.549 (2.31), 4.563 (0.89), 4.579 (0.85), 4.590 (0.66), 4.607 (0.64), 4.618 (0.74), 4.635 (0.82), 4.644 (0.71), 4.662 (0.76), 4.671 (0.81), 4.686 (0.85), 4.697 (0.74), 4.713 (0.61), 4.975 (3.42), 5.015 (15.16), 5.031 (6.48), 5.041 (5.56), 5.071 (1.15), 5.081 (1.50), 5.355 (1.02), 5.362 (0.91), 5.370 (0.85), 5.380 (0.89), 5.388 (0.96), 5.395 (1.04), 5.498 (1.07), 5.513 (0.91), 5.522 (0.87), 5.531 (0.96), 5.539 (1.02), 7.375 (5.78), 7.386 (5.99), 7.395 (6.11), 7.407 (6.15), 7.925 (6.95), 7.929 (6.74), 7.945 (6.47), 7.949 (6.04), 8.453 (3.20), 8.463 (5.44), 8.474 (2.85).

Example 397

(5S)-2-[(3,5-Dichloropyridin-2-yl)methyl]-5-[(3,3-difluoroazetidin-1-yl)carbonyl]-5,6,7,8-tetrahydro[1,2,4]triazolo[4,3-a]pyridin-3(2H)-one

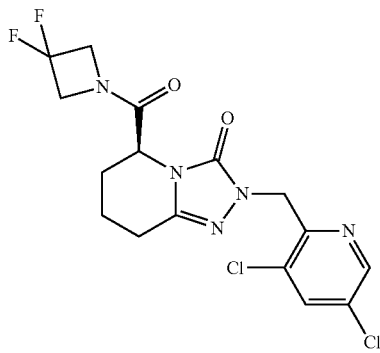 [SMILES: O=C([C@@H]1CCCc2nn(Cc3ncc(Cl)cc3Cl)c(=O)n21)N1CC(F)(F)C1]

(5S)-2-[(3,5-Dichloropyridin-2-yl)methyl]-3-oxo-2,3,5,6,7,8-hexahydro[1,2,4]triazolo[4,3-a]pyridine-5-carboxylic acid (42.1 mg, 123 µmol) was initially charged in THF (1.0 ml), and HBTU (93.1 mg, 245 µmol) and N,N-diisopropylethylamine (85 µl, 490 µmol) were subsequently added. After stirring at room temperature for 15 min, 3,3-difluoroazetidine hydrochloride (23.8 mg, 184 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 43.8 mg (85% of theory) of the title compound were obtained.

LC-MS (Method 3): $R_t$=1.32 min; MS (ESIpos): m/z=418 [M+H]$^+$ $^1$H-NMR (400 MHz, DMSO-d6) δ[ppm]: −0.149 (1.71), −0.008 (16.00), 0.008 (14.02), 0.146 (1.78), 1.720 (2.63), 1.732 (2.50), 1.976 (1.45), 1.990 (1.32), 2.059 (1.25), 2.073 (0.99), 2.327 (2.17), 2.366 (1.98), 2.523 (6.85), 2.569 (2.57), 2.582 (3.42), 2.597 (1.78), 2.625 (0.99), 2.669 (2.17), 2.710 (2.04), 4.356 (1.58), 4.375 (1.65), 4.569 (2.24), 4.584 (3.56), 4.596 (2.04), 4.718 (1.05), 4.747 (1.12), 4.833 (1.19), 4.863 (0.86), 4.980 (1.25), 5.020 (8.63), 5.031 (8.76), 5.071 (1.38), 8.256 (4.81), 8.261 (4.81), 8.552 (5.33), 8.557 (5.20).

Example 398

(5S)-2-[(3,5-Dichloropyridin-2-yl)methyl]-5-[(3-fluoroazetidin-1-yl)carbonyl]-5,6,7,8-tetrahydro[1,2,4]triazolo[4,3-a]pyridin-3(2H)-one

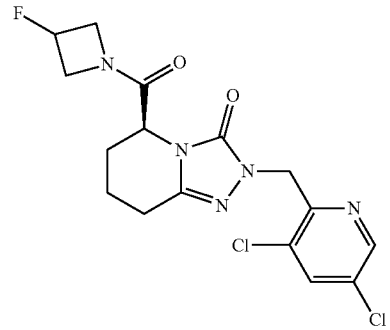 [SMILES: O=C([C@@H]1CCCc2nn(Cc3ncc(Cl)cc3Cl)c(=O)n21)N1CC(F)C1]

(5S)-2-[(3,5-Dichloropyridin-2-yl)methyl]-3-oxo-2,3,5,6,7,8-hexahydro[1,2,4]triazolo[4,3-a]pyridine-5-carboxylic acid (42.1 mg, 123 µmol) was initially charged in THF (1.0 ml), and HBTU (93.1 mg, 245 µmol) and N,N-diisopropylethylamine (85 µl, 490 µmol) were subsequently added. After stirring at room temperature for 15 min, 3-fluoroazetidine hydrochloride (20.5 mg, 184 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 37.5 mg (76% of theory) of the title compound were obtained.

LC-MS (Method 3): $R_t$=1.20 min; MS (ESIpos): m/z=400 [M+H]$^+$ $^1$H-NMR (400 MHz, DMSO-d6) δ [ppm]: 1.713 (6.00), 1.937 (2.24), 1.948 (2.38), 1.957 (2.23), 1.997 (1.64), 2.016 (2.36), 2.034 (2.18), 2.052 (1.51), 2.069 (0.81), 2.328 (0.45), 2.366 (0.45), 2.558 (4.75), 2.572 (5.93), 2.586 (2.94), 2.601 (1.13), 2.614 (1.73), 2.628 (0.76), 2.670 (0.50), 2.710 (0.47), 3.892 (0.81), 3.920 (1.61), 3.950 (1.58), 3.982 (1.66), 4.009 (0.93), 4.152 (0.66), 4.167 (0.78), 4.181 (0.66), 4.224 (1.23), 4.279 (1.56), 4.308 (1.43), 4.338 (0.95), 4.362 (1.56), 4.385 (1.03), 4.423 (0.73), 4.449 (0.98), 4.527 (4.92), 4.571 (0.86), 4.597 (0.58), 4.617 (0.68), 4.633 (0.80), 4.669 (0.76), 4.686

(0.76), 4.710 (0.60), 4.971 (2.86), 5.011 (16.00), 5.021 (6.85), 5.031 (5.96), 5.061 (0.91), 5.071 (1.28), 5.355 (0.98), 5.396 (1.03), 5.498 (0.98), 5.539 (1.00), 8.253 (7.23), 8.258 (7.31), 8.553 (3.19), 8.564 (3.14).

Example 399

(5S)-2-[(3,5-Dichloropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one

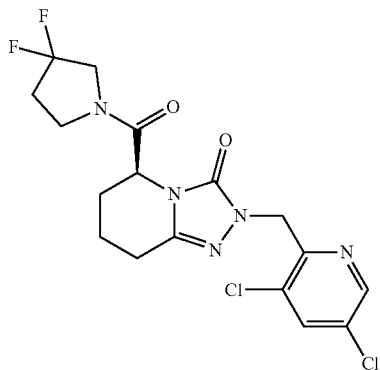 [SMILES: O=C([C@@H]1CCCc2nn(Cc3ncc(Cl)cc3Cl)c(=O)n21)N1CCC(F)(F)C1]

(5S)-2-[(3,5-Dichloropyridin-2-yl)methyl]-3-oxo-2,3,5,6,7,8-hexahydro[1,2,4]triazolo[4,3-a]pyridine-5-carboxylic acid (42.1 mg, 123 µmol) was initially charged in THF (1.0 ml), and HBTU (93.1 mg, 245 µmol) and N,N-diisopropylethylamine (85 µl, 490 µmol) were subsequently added. After stirring at room temperature for 15 min, 3,3-difluoropyrrolidine hydrochloride (26.4 mg, 184 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 34.3 mg (65% of theory) of the title compound were obtained.

LC-MS (Method 4): $R_t$=0.73 min; MS (ESIpos): m/z=432 [M+H]$^+$ $^1$H-NMR (400 MHz, DMSO-d6) δ [ppm]: −0.149 (1.92), −0.008 (16.00), 0.008 (15.60), 0.146 (1.84), 1.704 (4.24), 1.982 (2.24), 2.008 (2.40), 2.046 (1.84), 2.058 (1.92), 2.327 (3.12), 2.366 (2.88), 2.427 (2.16), 2.523 (10.96), 2.562 (5.68), 2.578 (5.36), 2.605 (1.52), 2.620 (1.60), 2.669 (2.96), 2.709 (2.40), 3.530 (2.88), 3.549 (4.64), 3.568 (2.08), 3.667 (2.00), 3.700 (2.32), 3.733 (1.84), 3.764 (3.12), 3.797 (2.40), 3.809 (2.16), 3.829 (1.36), 3.890 (1.04), 3.909 (2.16), 3.934 (1.52), 3.993 (1.36), 4.035 (1.28), 4.064 (0.80), 4.140 (0.88), 4.171 (1.36), 4.196 (1.28), 4.740 (1.84), 4.755 (2.56), 4.764 (1.76), 4.818 (1.84), 4.834 (2.56), 4.844 (1.92), 4.955 (4.56), 4.995 (13.92), 5.027 (15.92), 5.067 (5.28), 8.250 (10.96), 8.255 (11.12), 8.563 (11.76), 8.568 (11.36).

Example 400

(5S)-2-[(3,5-Dichloropyridin-2-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

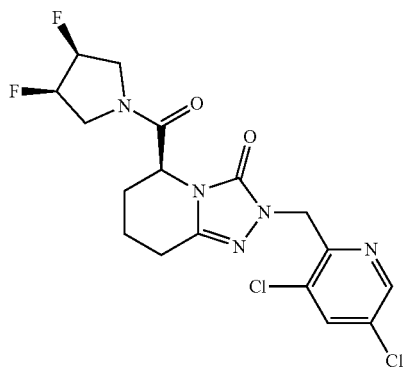 [SMILES: O=C([C@@H]1CCCc2nn(Cc3ncc(Cl)cc3Cl)c(=O)n21)N1C[C@@H](F)[C@@H](F)C1]

(5S)-2-[(3,5-Dichloropyridin-2-yl)methyl]-3-oxo-2,3,5,6,7,8-hexahydro[1,2,4]triazolo[4,3-a]pyridine-5-carboxylic acid (42.1 mg, 123 µmol) was initially charged in THF (1.0 ml), and HBTU (93.1 mg, 245 µmol) and N,N-diisopropylethylamine (85 µl, 490 µmol) were subsequently added. After stirring at room temperature for 15 min, (3R,4S)-3,4-difluoropyrrolidine hydrochloride (26.4 mg, 184 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.2 mg (87% of theory) of the title compound were obtained.

LC-MS (Method 4): $R_t$=0.70 min; MS (ESIpos): m/z=432 [M+H]$^+$ $^1$H-NMR (400 MHz, DMSO-d6) δ [ppm]: −0.149 (1.86), −0.008 (16.00), 0.008 (12.91), 0.146 (1.78), 1.695 (4.33), 1.706 (4.95), 1.718 (4.71), 1.950 (2.24), 1.989 (2.47), 2.000 (2.63), 2.027 (2.09), 2.045 (2.24), 2.052 (2.24), 2.062 (2.16), 2.073 (10.59), 2.328 (2.32), 2.366 (2.24), 2.523 (8.66), 2.564 (5.49), 2.576 (6.72), 2.589 (3.79), 2.607 (1.55), 2.620 (2.24), 2.670 (2.78), 2.710 (2.63), 3.452 (1.31), 3.486 (2.24), 3.507 (2.16), 3.516 (2.16), 3.526 (1.78), 3.541 (1.93), 3.560 (1.24), 3.568 (1.55), 3.613 (1.70), 3.627 (1.86), 3.645 (1.16), 3.660 (1.31), 3.668 (1.86), 3.681 (2.78), 3.691 (2.32), 3.701 (2.01), 3.714 (2.86), 3.726 (2.09), 3.744 (2.01), 3.756 (2.01), 3.776 (1.78), 3.789 (1.08), 3.865 (1.55), 3.902 (1.16), 3.927 (1.47), 3.940 (1.78), 3.956 (1.08), 3.976 (1.70), 3.990 (1.70), 4.005 (1.08), 4.019 (1.08), 4.125 (1.08), 4.139 (1.16), 4.153 (1.08), 4.168 (2.24), 4.182 (1.39), 4.195 (1.16), 4.210 (1.08), 4.778 (5.18), 4.787 (6.34), 4.793 (6.96), 4.802 (5.10), 4.952 (4.17), 4.958 (2.94), 4.992 (11.52), 4.997 (11.21), 5.018 (10.36), 5.033 (10.67), 5.058 (2.55), 5.073 (4.17), 5.152 (0.46), 5.252 (1.78), 5.273 (1.93), 5.295 (1.16), 5.326 (1.55), 5.335 (1.47), 5.349 (1.47), 5.362 (1.55), 5.372 (1.86), 5.385 (2.09), 5.405 (1.78), 5.425 (1.24), 5.479 (1.39), 5.492 (1.24), 7.368 (0.54), 8.251 (8.58), 8.255 (8.50), 8.561 (6.65), 8.564 (8.97), 8.570 (7.42).

Example 401

(5S)-2-{[3-Chloro-5-(trifluoromethyl)pyridin-2-yl]methyl}-5-{[(3R)-3-fluoropyrrolidin-1-yl]carbonyl}-5,6,7,8-tetrahydro[1,2,4]triazolo[4,3-a]pyridin-3(2H)-one

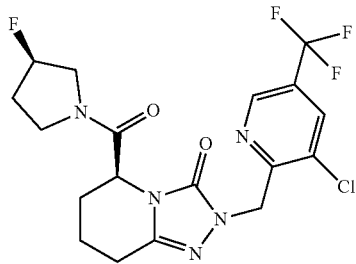 [SMILES: O=C([C@@H]1CCCc2nn(Cc3ncc(C(F)(F)F)cc3Cl)c(=O)n21)N1CC[C@@H](F)C1]

(5S)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic acid (45.0 mg, 119 µmol) was initially charged in THF (2.0 ml) at room temperature. Subsequently, HATU (59.0 mg, 155 mol) and triethylamine (50 µl, 360 µmol) were added. After stirring for 15 min, (3R)-3-fluoropyrrolidine hydrochloride (18.0 mg, 143 µmol) was added and the reaction mixture was stirred at room temperature for 72 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 27.0 mg (50% of theory) of the title compound were obtained.

LC-MS (Method 3): $R_t$=1.35 min; MS (ESIpos): m/z=448 [M+H]$^+$ $^1$H-NMR (400 MHz, DMSO-d6) δ [ppm]: -0.149 (1.64), -0.008 (16.00), 0.008 (12.00), 0.146 (1.33), 1.726 (4.85), 1.990 (5.82), 2.098 (3.27), 2.256 (2.42), 2.327 (3.76), 2.366 (2.30), 2.572 (5.21), 2.585 (7.27), 2.599 (4.36), 2.627 (2.73), 2.669 (4.18), 2.709 (1.88), 3.352 (2.73), 3.370 (2.73), 3.504 (2.36), 3.529 (5.39), 3.554 (4.91), 3.596 (6.36), 3.657 (1.64), 3.682 (1.76), 3.776 (1.58), 3.947 (4.12), 4.009 (1.88), 4.040 (1.33), 4.823 (3.52), 4.861 (3.58), 5.073 (4.06), 5.113 (16.00), 5.133 (9.58), 5.143 (8.67), 5.183 (2.67), 5.268 (2.24), 5.349 (2.18), 5.401 (2.36), 5.482 (2.18), 8.487 (14.30), 8.905 (13.88).

Example 402

(5S)-2-{[3-Chloro-5-(trifluoromethyl)pyridin-2-yl]methyl}-5-[(3-fluoroazetidin-1-yl)carbonyl]-5,6,7,8-tetrahydro[1,2,4]triazolo[4,3-a]pyridin-3(2H)-one

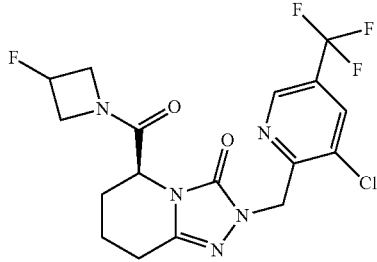 [SMILES: O=C([C@@H]1CCCc2nn(Cc3ncc(C(F)(F)F)cc3Cl)c(=O)n21)N1CC(F)C1]

(5S)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic acid (45.0 mg, 119 µmol) was initially charged in THF (2.0 ml) at room temperature. Subsequently, HATU (59.0 mg, 155 µmol) and triethylamine (50 µl, 360 µmol) were added. After stirring for 15 min, 3-fluoroazetidine hydrochloride (16.0 mg, 143 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 14.0 mg (27% of theory) of the title compound were obtained.

LC-MS (Method 4): $R_t$=0.72 min; MS (ESIpos): m/z=434 [M+H]

$^1$H-NMR (400 MHz, DMSO-d6) δ [ppm]: -0.149 (1.02), -0.008 (10.73), 0.008 (8.00), 0.146 (1.02), 0.976 (1.48), 0.994 (2.62), 1.719 (3.94), 1.804 (1.71), 1.814 (1.93), 1.822 (4.47), 1.830 (1.90), 1.839 (1.67), 1.906 (16.00), 1.945 (1.55), 1.956 (1.67), 2.023 (1.59), 2.040 (1.40), 2.060 (0.99), 2.327 (1.63), 2.366 (1.55), 2.518 (6.60), 2.523 (6.07), 2.568 (3.72), 2.582 (5.23), 2.595 (3.00), 2.624 (1.59), 2.665 (1.29), 2.670 (1.71), 2.674 (1.21), 2.689 (0.87), 2.710 (1.36), 2.731 (1.18), 2.866 (0.87), 2.890 (1.67), 3.056 (1.78), 3.073 (3.98), 3.091 (1.59), 3.893 (0.53), 3.920 (1.06), 3.950 (1.02), 3.984 (1.06), 4.011 (0.57), 4.167 (0.49), 4.226 (0.87), 4.281 (0.99), 4.312 (0.95), 4.369 (0.99), 4.424 (0.45), 4.451 (0.61), 4.534 (3.22), 4.548 (3.03), 4.575 (0.57), 4.633 (0.53), 4.671 (0.53), 4.687 (0.53), 5.089 (1.10), 5.130 (11.11), 5.183 (0.61), 5.356 (0.68), 5.539 (0.68), 6.273 (1.25), 6.510 (1.44), 7.276 (0.53), 8.491 (5.80), 8.494 (5.76), 8.884 (2.62), 8.901 (2.46).

Example 403

(5RS)-2-{[3-Chloro-5-(trifluoromethyl)pyridin-2-yl]methyl}-5-[(3-hydroxyazetidin-1-yl)carbonyl]-5,6,7,8-tetrahydro[1,2,4]triazolo[4,3-a]pyridin-3(2H)-one (Racemate)

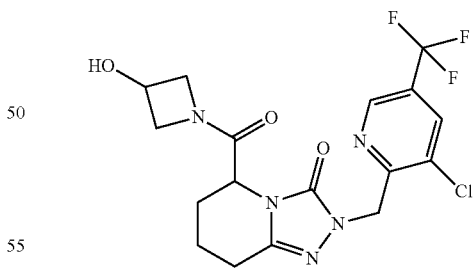

(5RS)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic Acid (Racemate) (45.0 mg, 119 µmol) was initially charged in THF (2.0 ml) at room temperature. Subsequently, HATU (59.0 mg, 155 µmol) and triethylamine (50 µl, 360 µmol) were added. After stirring for 15 min, azetidin-3-ol hydrochloride (15.7 mg, 143 µmol) was added and the reaction mixture was stirred at room temperature for 72 hours. HATU (59.0 mg, 155 µmol) and triethylamine (50 µl, 360 µmol) were added again and the mixture was stirred at room temperature for 3 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 10). The product-containing fractions were concentrated under reduced pressure, and 800 µg (2% of theory) of the title compound were obtained.

LC-MS (Method 3): $R_t$=1.12 min; MS (ESIpos): m/z=432 [M+H]$^+$ $^1$H-NMR (400 MHz, DMSO-d6) δ [ppm]: −0.150 (1.80), −0.009 (16.00), 0.007 (12.68), 0.146 (1.63), 1.723 (1.16), 1.937 (0.93), 2.327 (3.61), 2.365 (2.04), 2.522 (10.53), 2.669 (3.32), 2.709 (2.04), 3.597 (0.76), 3.962 (0.70), 4.022 (0.87), 4.365 (0.64), 4.505 (1.75), 5.081 (0.70), 5.121 (2.44), 5.802 (1.57), 8.487 (2.21), 8.896 (2.44).

Example 404

(5S)-2-{[3-Chloro-5-(trifluoromethyl)pyridin-2-yl]methyl}-5-[(3,3-difluoropyrrolidin-1-yl)carbonyl]-5,6,7,8-tetrahydro[1,2,4]triazolo[4,3-a]pyridin-3(2H)-one

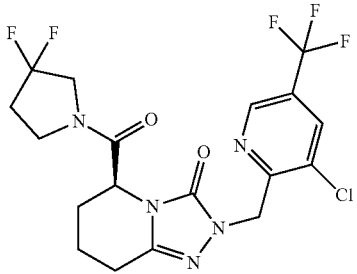 [SMILES: O=C([C@@H]1CCCc2nn(Cc3ncc(C(F)(F)F)cc3Cl)c(=O)n21)N1CCC(F)(F)C1]

(5S)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic acid (35.0 mg, 92.9 µmol) was initially charged in THF (1.0 ml), and HBTU (45.8 mg, 121 µmol) and N,N-diisopropylethylamine (49 µl, 280 µmol) were subsequently added. After stirring at room temperature for 15 min, 3,3-difluoropyrrolidine hydrochloride (16.0 mg, 111 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 33.8 mg (78% of theory) of the title compound were obtained.

LC-MS (Method 3): $R_t$=1.50 min; MS (ESIpos): m/z=466 [M+H]$^+$ $^1$H-NMR (400 MHz, DMSO-d6) δ [ppm]: −0.149 (0.47), −0.008 (4.42), 0.008 (2.91), 1.252 (14.54), 1.268 (16.00), 1.276 (11.71), 1.293 (10.07), 1.686 (2.47), 1.699 (3.85), 1.711 (5.07), 1.724 (4.66), 1.932 (0.91), 1.967 (1.93), 1.982 (2.71), 1.991 (2.60), 2.003 (2.78), 2.016 (2.65), 2.029 (1.98), 2.040 (1.95), 2.055 (2.11), 2.066 (2.11), 2.076 (1.61), 2.091 (1.40), 2.101 (0.83), 2.328 (1.12), 2.366 (1.53), 2.379 (1.77), 2.408 (2.13), 2.429 (2.08), 2.453 (1.85), 2.471 (1.93), 2.524 (6.48), 2.571 (6.61), 2.587 (7.49), 2.600 (3.56), 2.617 (1.20), 2.629 (1.87), 2.642 (0.83), 2.670 (1.14), 2.710 (1.14), 2.895 (9.55), 3.115 (1.48), 3.126 (1.56), 3.133 (1.61), 3.144 (1.53), 3.425 (1.72), 3.444 (1.93), 3.463 (1.20), 3.532 (4.14), 3.551 (6.56), 3.571 (3.43), 3.587 (1.17), 3.604 (1.53), 3.621 (1.82), 3.636 (1.53), 3.649 (1.51), 3.670 (2.63), 3.704 (2.86), 3.736 (2.13), 3.767 (3.30), 3.789 (2.21), 3.798 (3.59), 3.815 (2.89), 3.833 (1.90), 3.870 (0.49), 3.892 (1.33), 3.910 (2.73), 3.930 (1.51), 3.936 (1.95), 3.955 (0.86), 3.970 (0.83), 3.998 (1.74), 4.012 (0.91), 4.028 (1.20), 4.040 (1.64), 4.069 (0.96), 4.142 (1.04), 4.174 (1.61), 4.201 (1.56), 4.231 (0.65), 4.750 (2.19), 4.761 (2.71), 4.766 (3.12), 4.776 (2.26), 4.830 (2.24), 4.840 (2.71), 4.845 (3.10), 4.855 (2.21), 5.076 (3.28), 5.116 (13.61), 5.139 (14.33), 5.166 (0.68), 5.180 (3.51), 8.492 (9.52), 8.902 (9.42), 8.987 (0.62).

Example 405

(5S)-2-{[3-Chloro-5-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyridin-3(2H)-one

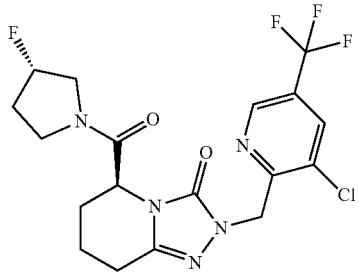 [SMILES: O=C([C@@H]1CCCc2nn(Cc3ncc(C(F)(F)F)cc3Cl)c(=O)n21)N1CC[C@H](F)C1]

(5S)-2-{[3-Chloro-5-(trifluoromethyl)pyridin-2-yl]methyl}-3-oxo-2,3,5,6,7,8-hexahydro[1,2,4]triazolo[4,3-a]pyridine-5-carboxylic acid (35.0 mg, 92.9 µmol) was initially charged in THF (1.0 ml), and HBTU (45.8 mg, 121 µmol) and N,N-diisopropylethylamine (49 µl, 280 µmol) were subsequently added. After stirring at room temperature for 15 min, (3S)-3-fluoropyrrolidine hydrochloride (14.0 mg, 111 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 25.0 mg (61% of theory) of the title compound were obtained.

LC-MS (Method 3): $R_t$=1.36 min; MS (ESIpos): m/z=448 [M+H]$^+$ $^1$H-NMR (400 MHz, DMSO-d6) δ[ppm]: −0.149 (1.09), −0.008 (13.31), 0.008 (8.11), 0.146 (1.09), 1.725 (8.34), 1.734 (8.63), 1.868 (1.37), 1.904 (2.11), 1.913 (1.89), 1.990 (2.91), 2.016 (3.49), 2.069 (4.23), 2.084 (5.66), 2.102 (5.26), 2.120 (3.66), 2.136 (3.37), 2.217 (2.06), 2.265 (2.51), 2.327 (2.46), 2.523 (15.49), 2.566 (4.86), 2.586 (6.51), 2.632 (2.34), 2.669 (2.63), 2.710 (2.11), 3.348 (1.77), 3.371 (1.83), 3.398 (1.94), 3.406 (1.83), 3.460 (1.37), 3.468 (1.43), 3.495 (2.06), 3.504 (2.00), 3.628 (5.26), 3.653 (5.14), 3.680 (3.37), 3.689 (2.69), 3.729 (4.00), 3.749 (4.23), 3.776 (3.37), 3.795 (2.69), 3.828 (0.91), 3.861 (5.43), 4.690 (2.80), 4.699 (3.31), 4.705 (3.43), 4.715 (2.69), 4.747 (3.66), 4.755 (4.06), 4.762 (4.51), 4.771 (3.26), 5.068 (4.69), 5.109 (16.00), 5.133 (9.49), 5.143 (10.46), 5.174 (2.46), 5.184 (3.43), 5.258 (2.74), 5.388 (3.66), 5.511 (2.06), 5.944 (0.86), 8.491 (12.97), 8.904 (13.03).

Example 406

(5S)-2-[(5-Chloro-3-fluoropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one

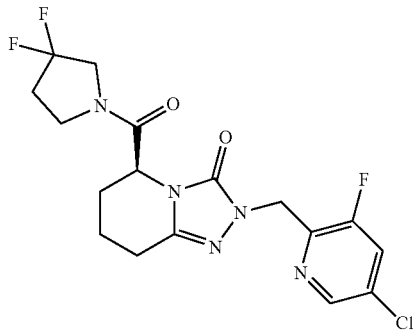 [SMILES: O=C([C@@H]1CCCc2nn(Cc3ncc(Cl)cc3F)c(=O)n21)N1CCC(F)(F)C1]

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (79.3 mg, 243 µmol) was initially charged in THF (2.0 ml), and HBTU (120 mg, 316 µmol) and N,N-diisopropylethylamine (130 µl, 730 µmol) were subsequently added. After stirring at room temperature for 15 min, 3,3-difluoropyrrolidine hydrochloride (41.8 mg, 291 µmol) was added and the reaction mixture was stirred at room temperature overnight. HBTU (120 mg, 316 µmol), 3,3-difluoropyrrolidine hydrochloride (41.8 mg, 291 µmol) and N,N-diisopropylethylamine (130 µl, 730 µmol) were added again and the mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 71.0 mg (70% of theory) of the title compound were obtained.

LC-MS (Method 3): $R_t$=1.32 min; MS (ESIpos): m/z=416 [M+H]$^+$ $^1$H-NMR (400 MHz, DMSO-d6) δ [ppm]: -0.150 (1.61), -0.008 (16.00), 0.008 (12.15), 0.146 (1.57), 1.668 (2.08), 1.693 (4.13), 1.910 (1.34), 1.958 (2.12), 1.970 (2.24), 1.980 (2.75), 1.996 (2.00), 2.012 (1.57), 2.023 (1.77), 2.038 (1.81), 2.048 (1.89), 2.073 (7.90), 2.327 (1.69), 2.366 (2.04), 2.378 (1.61), 2.407 (1.97), 2.429 (1.89), 2.449 (1.77), 2.523 (7.23), 2.568 (6.96), 2.583 (3.50), 2.610 (1.61), 2.669 (1.69), 2.709 (1.61), 3.528 (2.59), 3.548 (3.97), 3.563 (1.97), 3.630 (0.51), 3.665 (1.93), 3.698 (2.20), 3.733 (1.93), 3.765 (2.79), 3.779 (1.69), 3.788 (1.57), 3.798 (2.95), 3.805 (2.44), 3.824 (1.14), 3.888 (0.98), 3.906 (2.32), 3.931 (1.53), 3.952 (0.67), 3.962 (0.67), 3.990 (1.42), 4.020 (0.94), 4.033 (1.30), 4.061 (0.86), 4.137 (0.86), 4.168 (1.26), 4.194 (1.30), 4.227 (0.59), 4.724 (1.89), 4.740 (2.52), 4.750 (1.89), 4.804 (1.97), 4.814 (2.36), 4.820 (2.56), 4.829 (1.85), 4.901 (2.91), 4.939 (7.55), 4.984 (7.90), 4.988 (7.98), 5.023 (3.07), 5.027 (3.07), 8.089 (5.07), 8.094 (5.27), 8.113 (5.31), 8.118 (5.35), 8.476 (6.64), 8.480 (6.41).

Example 407

(5S)-2-[(5-Chloro-3-fluoropyridin-2-yl)methyl]-5-[(3-fluoroazetidin-1-yl)carbonyl]-5,6,7,8-tetrahydro[1,2,4]triazolo[4,3-a]pyridin-3(2H)-one (5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (79.3 mg, 243 µmol) was initially charged in THF (2.0 ml), and HBTU (120 mg, 316 µmol) and N,N-diisopropylethylamine (130 µl, 730 µmol) were subsequently added. After stirring at room temperature for 15 min, 3-fluoroazetidine hydrochloride (32.5 mg, 291 µmol) was added and the reaction mixture was stirred at room temperature overnight. HBTU (120 mg, 316 µmol), 3-fluoroazetidine hydrochloride (32.5 mg, 291 µmol) and N,N-diisopropylethylamine (130 µl, 730 µmol) were added again and the mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 64.1 mg (69% of theory) of the title compound were obtained.

LC-MS (Method 3): $R_t$=1.13 min; MS (ESIpos): m/z=384 [M+H]$^+$ $^1$H-NMR (400 MHz, DMSO-d6) δ [ppm]: -0.149 (0.90), -0.008 (8.03), 0.008 (7.55), 0.146 (0.90), 1.406 (0.80), 1.702 (10.07), 1.911 (2.84), 1.924 (3.75), 1.935 (3.96), 1.945 (3.69), 1.968 (1.91), 1.986 (2.79), 2.005 (3.99), 2.021 (3.59), 2.040 (2.58), 2.059 (1.44), 2.073 (6.46), 2.327 (0.98), 2.366 (0.90), 2.561 (10.79), 2.575 (5.21), 2.590 (1.91), 2.603 (3.19), 2.617 (1.38), 2.670 (1.12), 2.690 (0.98), 2.710 (1.01), 3.892 (1.36), 3.919 (2.74), 3.951 (2.71), 3.982 (2.71), 4.009 (1.59), 4.150 (1.17), 4.165 (1.28), 4.180 (1.06), 4.216 (2.10), 4.229 (2.15), 4.244 (1.91), 4.265 (2.71), 4.295 (2.63), 4.311 (1.38), 4.327 (1.59), 4.355 (2.50), 4.387 (1.67), 4.421 (1.25), 4.446 (1.65), 4.517 (8.93), 4.550 (1.49), 4.566 (1.46), 4.594 (0.93), 4.617 (1.14), 4.634 (1.33), 4.670 (1.25), 4.687 (1.36), 4.697 (1.22), 4.711 (1.01), 4.915 (4.60), 4.919 (4.62), 4.954 (16.00), 4.958 (15.95), 4.981 (8.43), 4.987 (8.05), 5.026 (2.39), 5.353 (1.67), 5.398 (1.70), 5.496 (1.65), 5.541 (1.67), 8.091 (8.53), 8.095 (8.96), 8.115 (8.77), 8.119 (9.09), 8.469 (5.93), 8.478 (5.95).

Example 408

(5S)-2-[(5-Chloro-3-fluoropyridin-2-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

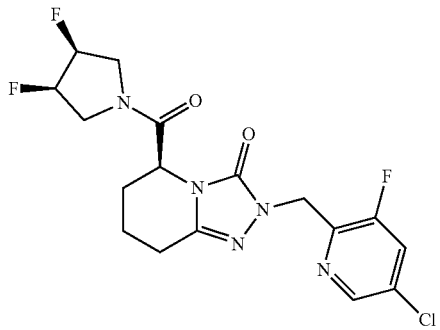 [SMILES: O=C([C@@H]1CCCc2nn(Cc3ncc(Cl)cc3F)c(=O)n21)N1C[C@@H](F)[C@@H](F)C1]

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (79.3 mg, 243 μmol) was initially charged in THF (2.0 ml), and HBTU (120 mg, 316 μmol) and N,N-diisopropylethylamine (130 μl, 730 mol) were subsequently added. After stirring at room temperature for 15 min, (3R,4S)-3,4-difluoropyrrolidine hydrochloride (41.8 mg, 291 μmol) was added and the reaction mixture was stirred at room temperature overnight. HBTU (120 mg, 316 μmol), (3R,4S)-3,4-difluoropyrrolidine hydrochloride (41.8 mg, 291 μmol) and N,N-diisopropylethylamine (130 μl, 730 μmol) were added again and the mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 61.7 mg (61% of theory) of the title compound were obtained.

LC-MS (Method 3): $R_t$=1.25 min; MS (ESIpos): m/z=416 [M+H]$^+$ $^1$H-NMR (400 MHz, DMSO-d6) δ [ppm]: −0.150 (0.54), −0.008 (5.15), 0.008 (5.00), 0.146 (0.58), 1.405 (0.52), 1.650 (1.84), 1.660 (2.36), 1.675 (3.11), 1.685 (4.35), 1.697 (5.00), 1.708 (4.91), 1.911 (1.80), 1.922 (1.29), 1.939 (2.40), 1.966 (1.56), 1.979 (2.94), 1.990 (2.55), 2.003 (1.82), 2.019 (2.17), 2.028 (2.27), 2.036 (2.38), 2.044 (2.38), 2.053 (2.21), 2.063 (1.95), 2.073 (16.00), 2.088 (1.14), 2.327 (0.60), 2.366 (0.67), 2.465 (0.99), 2.567 (6.16), 2.580 (3.43), 2.598 (1.22), 2.610 (1.93), 2.623 (0.97), 2.670 (0.73), 2.690 (0.88), 2.710 (0.71), 2.885 (0.86), 3.440 (0.66), 3.450 (1.18), 3.459 (0.79), 3.475 (1.42), 3.484 (2.55), 3.494 (1.95), 3.506 (1.99), 3.516 (2.06), 3.528 (2.14), 3.538 (2.38), 3.547 (1.44), 3.560 (1.07), 3.570 (1.56), 3.580 (0.97), 3.611 (1.61), 3.625 (1.84), 3.644 (1.18), 3.658 (1.37), 3.666 (1.87), 3.681 (3.58), 3.695 (2.36), 3.714 (2.90), 3.727 (2.66), 3.744 (2.14), 3.757 (2.21), 3.778 (1.70), 3.791 (1.11), 3.827 (0.77), 3.843 (1.05), 3.862 (1.63), 3.903 (1.14), 3.925 (1.54), 3.938 (1.78), 3.953 (1.11), 3.973 (1.74), 3.987 (1.72), 4.002 (1.12), 4.016 (1.01), 4.124 (1.09), 4.139 (1.24), 4.152 (1.22), 4.166 (2.15), 4.180 (1.39), 4.194 (1.24), 4.209 (1.09), 4.764 (5.23), 4.778 (6.95), 4.788 (4.87), 4.902 (4.40), 4.941 (11.19), 4.977 (5.60), 4.981 (5.96), 4.989 (6.24), 4.993 (6.07), 5.015 (1.99), 5.020 (2.08), 5.028 (2.66), 5.032 (2.59), 5.242 (1.22), 5.251 (1.87), 5.263 (1.82), 5.273 (1.93), 5.294 (1.20), 5.308 (1.11), 5.316 (1.20), 5.328 (1.50), 5.336 (1.50), 5.348 (1.61), 5.362 (1.52), 5.374 (2.12), 5.385 (2.19), 5.396 (1.82), 5.405 (1.67), 5.410 (1.65), 5.439 (1.09), 5.446 (1.20), 5.457 (1.56), 5.470 (1.50), 5.479 (1.56), 5.492 (1.18), 5.502 (0.75), 8.090 (6.39), 8.114 (6.56), 8.478 (9.27).

Example 409

(5S)-2-[(5-Chloro-3-fluoropyridin-2-yl)methyl]-5-[(3,3-difluoroazetidin-1-yl)carbonyl]-5,6,7,8-tetrahydro[1,2,4]triazolo[4,3-a]pyridin-3(2H)-one

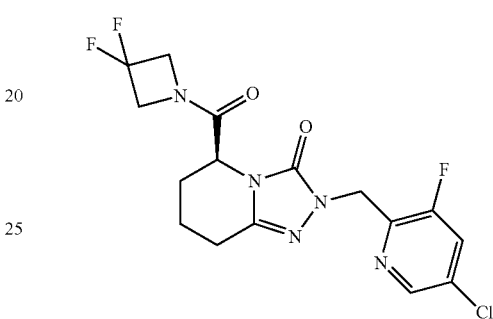

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (79.3 mg, 243 μmol) was initially charged in THF (2.0 ml), and HBTU (120 mg, 316 μmol) and N,N-diisopropylethylamine (130 μl, 730 μmol) were subsequently added. After stirring at room temperature for 15 min, 3,3-difluoroazetidine hydrochloride (37.7 mg, 291 μmol) was added and the reaction mixture was stirred at room temperature overnight. HBTU (120 mg, 316 μmol), 3,3-difluoroazetidine hydrochloride (37.7 mg, 291 μmol) and N,N-diisopropylethylamine (130 μl, 730 μmol) were added again and the mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 78.3 mg (80% of theory) of the title compound were obtained.

LC-MS (Method 3): $R_t$=1.19 min; MS (ESIpos): m/z=402 [M+H]$^+$ $^1$H-NMR (400 MHz, DMSO-d6) δ [ppm]: −0.149 (1.72), −0.008 (16.00), 0.008 (14.28), 0.146 (1.61), 1.405 (0.77), 1.695 (5.71), 1.708 (8.45), 1.722 (7.26), 1.952 (2.97), 1.964 (4.40), 1.976 (4.04), 2.014 (1.96), 2.029 (3.27), 2.049 (4.10), 2.063 (3.03), 2.073 (6.48), 2.327 (2.14), 2.366 (1.96), 2.557 (7.26), 2.571 (9.99), 2.586 (4.88), 2.599 (1.78), 2.613 (2.68), 2.669 (2.44), 2.709 (2.02), 2.891 (0.48), 4.324 (2.97), 4.355 (4.82), 4.376 (4.76), 4.407 (2.86), 4.557 (6.72), 4.572 (10.83), 4.585 (6.42), 4.713 (3.03), 4.741 (3.45), 4.772 (1.61), 4.805 (1.61), 4.833 (3.39), 4.861 (2.91), 4.926 (3.51), 4.931 (3.39), 4.965 (14.16), 4.969 (13.86), 4.987 (14.22), 4.991 (14.28), 5.026 (3.33), 5.030 (3.39), 8.094 (9.16), 8.099 (9.52), 8.118 (9.40), 8.123 (9.64), 8.469 (12.61), 8.473 (12.97).

Example 410

(5S)-2-[(3,5-Difluoropyridin-2-yl)methyl]-5-[(3-fluoroazetidin-1-yl)carbonyl]-5,6,7,8-tetrahydro[1,2,4]triazolo[4,3-a]pyridin-3(2H)-one

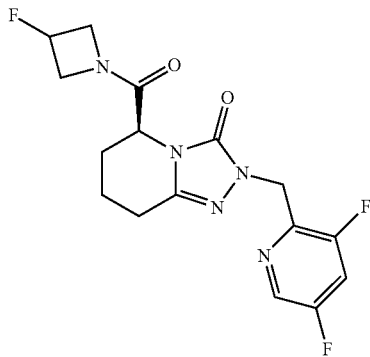 [SMILES: O=C([C@@H]1CCCc2nn(Cc3ncc(F)cc3F)c(=O)n21)N1CC(F)C1]

(5S)-2-[(3,5-Difluoropyridin-2-yl)methyl]-3-oxo-2,3,5,6,7,8-hexahydro[1,2,4]triazolo[4,3-a]pyridine-5-carboxylic acid (34.2 mg, 90% purity, 99.2 μmol) was initially charged in THF (1.0 ml), and HBTU (48.9 mg, 129 μmol) and N,N-diisopropylethylamine (52 μl, 300 μmol) were subsequently added. After stirring at room temperature for 15 min, 3-fluoroazetidine hydrochloride (13.3 mg, 119 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 25.9 mg (71% of theory) of the title compound were obtained.

LC-MS (Method 3): $R_t$=0.95 min; MS (ESIpos): m/z=368 [M+H]$^+$ $^1$H-NMR (400 MHz, DMSO-d6) δ[ppm]: −0.149 (2.23), 0.146 (2.23), 1.699 (11.85), 1.933 (4.77), 2.003 (4.62), 2.021 (4.46), 2.327 (4.54), 2.365 (3.85), 2.559 (12.31), 2.572 (5.54), 2.586 (2.08), 2.602 (3.00), 2.669 (4.31), 2.709 (3.31), 3.826 (1.15), 3.844 (1.69), 3.892 (1.85), 3.921 (3.15), 3.949 (3.23), 3.981 (3.15), 4.009 (2.08), 4.262 (3.46), 4.292 (2.92), 4.353 (2.69), 4.390 (2.00), 4.425 (2.08), 4.449 (2.15), 4.515 (10.92), 4.636 (1.69), 4.906 (4.54), 4.945 (16.00), 4.971 (9.31), 5.016 (2.62), 5.354 (2.08), 5.495 (2.08), 6.950 (6.23), 7.078 (6.69), 7.206 (6.31), 7.926 (4.38), 7.932 (4.69), 7.952 (8.23), 7.974 (4.69), 8.458 (9.00).

Example 411

(5S)-2-[(3,5-Difluoropyridin-2-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

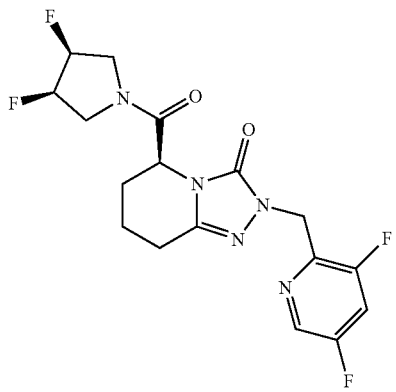 [SMILES: O=C([C@@H]1CCCc2nn(Cc3ncc(F)cc3F)c(=O)n21)N1C[C@@H](F)[C@@H](F)C1]

(5S)-2-[(3,5-Difluoropyridin-2-yl)methyl]-3-oxo-2,3,5,6,7,8-hexahydro[1,2,4]triazolo[4,3-a]pyridine-5-carboxylic acid (34.2 mg, 90% purity, 99.2 μmol) was initially charged in THF (1.0 ml), and HBTU (48.9 mg, 129 μmol) and N,N-diisopropylethylamine (52 μl, 300 μmol) were subsequently added. After stirring at room temperature for 15 min, (3R,4S)-3,4-difluoropyrrolidine hydrochloride (17.1 mg, 119 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 19.7 mg (50% of theory) of the title compound were obtained.

LC-MS (Method 3): $R_t$=1.06 min; MS (ESIpos): m/z=400 [M+H]$^+$ $^1$H-NMR (400 MHz, DMSO-d6) δ[ppm]: −0.149 (1.87), −0.008 (16.00), 0.008 (14.04), 0.146 (1.77), 1.695 (3.14), 1.707 (2.94), 1.936 (1.37), 1.977 (1.57), 2.018 (1.37), 2.035 (1.37), 2.327 (2.85), 2.366 (2.65), 2.563 (4.91), 2.609 (1.57), 2.669 (3.24), 2.710 (2.94), 3.449 (1.18), 3.483 (1.77), 3.495 (1.37), 3.505 (1.47), 3.528 (1.57), 3.538 (1.57), 3.570 (1.08), 3.610 (1.18), 3.625 (1.28), 3.644 (0.88), 3.666 (1.18), 3.681 (2.26), 3.695 (1.77), 3.714 (1.77), 3.727 (1.67), 3.745 (1.47), 3.756 (1.37), 3.778 (1.18), 3.845 (1.87), 3.926 (0.98), 3.938 (1.08), 3.973 (1.08), 3.988 (1.08), 4.168 (1.47), 4.182 (0.88), 4.195 (0.79), 4.762 (3.04), 4.777 (3.93), 4.787 (2.75), 4.893 (2.45), 4.932 (5.99), 4.968 (3.14), 4.980 (3.34), 5.020 (1.47), 5.274 (1.18), 5.348 (0.98), 5.374 (1.37), 5.457 (0.98), 7.928 (1.67), 7.950 (3.14), 7.973 (1.57), 8.465 (5.60).

Example 412

(5S)-2-[(3,5-Difluoropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one

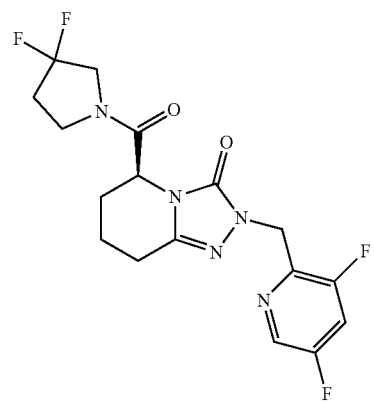 [SMILES: O=C([C@@H]1CCCc2nn(Cc3ncc(F)cc3F)c(=O)n21)N1CCC(F)(F)C1]

(5S)-2-[(3,5-Difluoropyridin-2-yl)methyl]-3-oxo-2,3,5,6,7,8-hexahydro[1,2,4]triazolo[4,3-a]pyridine-5-carboxylic acid (34.2 mg, 90% purity, 99.2 μmol) was initially charged in THF (1.0 ml), and HBTU (48.9 mg, 129 μmol) and N,N-diisopropylethylamine (52 μl, 300 μmol) were subsequently added. After stirring at room temperature for 15 min, 3,3-difluoropyrrolidine hydrochloride (17.1 mg, 119 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 19.9 mg (50% of theory) of the title compound were obtained.

Specific rotation: −19.10 (589 nm, 0.5200 g/100 cm³ chloroform)

Analytical chiral HPLC: $R_t$=3.77 min, e.e. =98.5% [column: Daicel Chiralpak® AZ-3 3 ym, 50×4.6 mm; eluent: i-hexane/i-propanol 50:50; flow rate: 1 ml/min; UV detection: 220 nm].

LC-MS (Method 3): $R_t$=1.14 min; MS (ESIpos): m/z=400 [M+H]⁺

¹H-NMR (400 MHz, DMSO-d6) δ[ppm]: −0.149 (1.80), 0.008 (16.00), 0.146 (1.69), 1.693 (3.83), 1.957 (2.03), 2.086 (3.61), 2.328 (3.27), 2.366 (4.06), 2.566 (6.20), 2.670 (3.27), 2.710 (3.49), 3.530 (2.25), 3.550 (3.27), 3.666 (1.69), 3.700 (1.92), 3.734 (1.69), 3.765 (2.37), 3.800 (2.48), 3.845 (1.46), 3.890 (0.90), 3.907 (1.92), 3.933 (1.46), 3.991 (1.24), 4.033 (1.13), 4.168 (1.24), 4.198 (1.13), 4.739 (2.37), 4.749 (1.58), 4.819 (2.14), 4.895 (2.59), 4.933 (6.42), 4.978 (6.31), 5.015 (2.48), 7.925 (2.37), 7.930 (2.37), 7.949 (3.72), 7.972 (2.25), 7.978 (2.25), 8.463 (7.89), 8.469 (7.66).

Example 413

(5S)-5-[(3,3-Difluoropyrrolidin-1-yl)carbonyl]-2-[(1-methyl-1H-pyrazolo[3,4-b]pyridin-3-yl)methyl]-5,6,7,8-tetrahydro[1,2,4]triazolo[4,3-a]pyridin-3(2H)-one

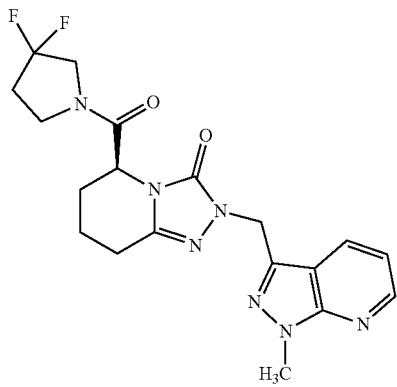 [SMILES: Cn1nc(Cn2nc3n(c2=O)[C@H](C(=O)N2CCC(F)(F)C2)CCC3)c2cccnc21]

(5S)-2-[(1-Methyl-1H-pyrazolo[3,4-b]pyridin-3-yl)methyl]-3-oxo-2,3,5,6,7,8-hexahydro[1,2,4]triazolo[4,3-a]pyridine-5-carboxylic acid (38.0 mg, 116 μmol) was initially charged in THF (2.0 ml), and HBTU (57.1 mg, 150 μmol) and N,N-diisopropylethylamine (60 μl, 350 μmol) were subsequently added. After stirring at room temperature for 15 min, 3,3-difluoropyrrolidine hydrochloride (19.9 mg, 139 μmol) was added and the reaction mixture was stirred at room temperature overnight. HBTU (57.1 mg, 150 μmol) and 3,3-difluoropyrrolidine hydrochloride (19.9 mg, 139 μmol) were added again. After stirring for 6 hours, N,N-diisopropylethylamine (60 μl, 350 μmol) was added and the mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 38.9 mg (93% purity, 75% of theory) of the title compound were obtained.

LC-MS (Method 4): $R_t$=0.61 min; MS (ESIpos): m/z=418 [M+H]⁺

¹H-NMR (400 MHz, DMSO-d6) δ[ppm]: −0.149 (0.81), −0.008 (6.99), 0.008 (5.93), 0.146 (0.77), 1.160 (3.00), 1.178 (6.33), 1.196 (3.08), 1.405 (1.06), 1.686 (0.59), 1.983 (0.62), 2.327 (1.35), 2.366 (1.50), 2.523 (4.58), 2.670 (1.32), 2.710 (1.43), 3.064 (0.51), 3.083 (1.72), 3.095 (1.76), 3.101 (1.68), 3.113 (1.65), 3.131 (0.51), 3.549 (0.84), 3.567 (0.99), 3.670 (0.48), 3.703 (0.55), 3.783 (0.81), 3.807 (0.55), 3.928 (0.51), 4.027 (16.00), 4.767 (0.66), 4.828 (0.48), 4.836 (0.55), 5.111 (7.91), 7.186 (1.61), 7.197 (1.68), 7.206 (1.79), 7.217 (1.76), 8.151 (1.50), 8.170 (1.46), 8.544 (1.72), 8.548 (1.76), 8.555 (1.83), 8.559 (1.68).

Example 414

(5S)-5-{[(3R,4S)-3,4-Difluoropyrrolidin-1-yl]carbonyl}-2-[(1-methyl-1H-pyrazolo[3,4-b]pyridin-3-yl)methyl]-5,6,7,8-tetrahydro[1,2,4]triazolo[4,3-a]pyridin-3(2H)-one

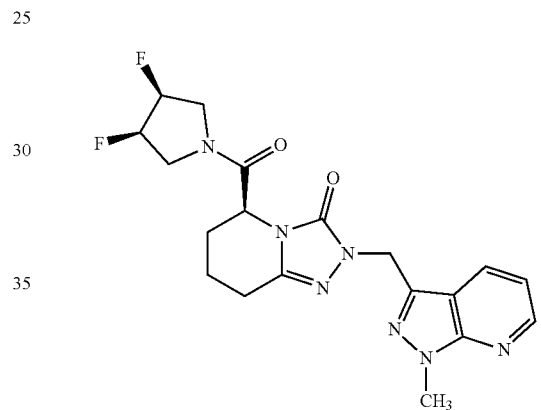

(5S)-2-[(1-Methyl-1H-pyrazolo[3,4-b]pyridin-3-yl)methyl]-3-oxo-2,3,5,6,7,8-hexahydro[1,2,4]triazolo[4,3-a]pyridine-5-carboxylic acid (38.0 mg, 116 μmol) was initially charged in THF (2.0 ml), and HBTU (57.1 mg, 150 μmol) and N,N-diisopropylethylamine (60 μl, 350 μmol) were subsequently added. After stirring at room temperature for 15 min, (3R,4S)-3,4-difluoropyrrolidine hydrochloride (19.9 mg, 139 μmol) was added and the reaction mixture was stirred at room temperature overnight. HBTU (57.1 mg, 150 μmol) and 3,3-difluoropyrrolidine hydrochloride (19.9 mg, 139 μmol) were added again. After stirring for 6 hours, N,N-diisopropylethylamine (60 μl, 350 μmol) was added and the mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 33.6 mg (70% of theory) of the title compound were obtained.

LC-MS (Method 4): $R_t$=0.58 min; MS (ESIpos): m/z=418 [M+H]⁺

¹H-NMR (400 MHz, DMSO-d6) δ [ppm]: −0.149 (1.77), −0.008 (16.00), 0.008 (9.91), 0.146 (1.20), 1.699 (0.68), 1.989 (0.80), 2.327 (3.59), 2.366 (4.10), 2.523 (14.98), 2.670 (2.39), 2.710 (1.88), 3.545 (0.74), 3.700 (0.80), 3.928 (0.74), 4.028 (13.27), 4.185 (0.57), 4.798 (1.37), 5.111

(6.78), 5.289 (0.51), 7.182 (1.02), 7.188 (1.20), 7.193 (1.08), 7.199 (1.37), 7.208 (1.37), 7.213 (1.08), 7.219 (1.14), 8.147 (1.08), 8.153 (1.20), 8.167 (1.08), 8.173 (1.14), 8.548 (1.94), 8.555 (1.99), 8.559 (1.94).

Example 415

(5S)-5-[(3,3-Difluoroazetidin-1-yl)carbonyl]-2-[(1-methyl-1H-pyrazolo[3,4-b]pyridin-3-yl)methyl]-5,6,7,8-tetrahydro[1,2,4]triazolo[4,3-a]pyridin-3(2H)-one

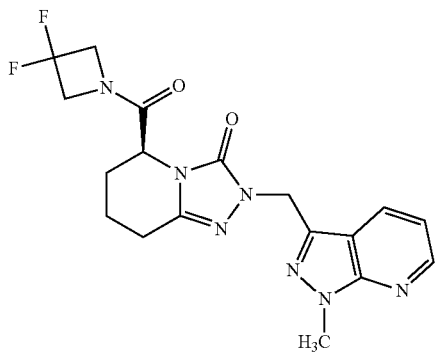 [SMILES: Cn1nc(Cn2nc3n(c2=O)[C@H](C(=O)N2CC(F)(F)C2)CCC3)c2cccnc21]

(5S)-2-[(1-Methyl-1H-pyrazolo[3,4-b]pyridin-3-yl)methyl]-3-oxo-2,3,5,6,7,8-hexahydro[1,2,4]triazolo[4,3-a]pyridine-5-carboxylic acid (38.0 mg, 116 µmol) was initially charged in THF (2.0 ml), and HBTU (57.1 mg, 150 µmol) and N,N-diisopropylethylamine (60 µl, 350 µmol) were subsequently added. After stirring at room temperature for 15 min, 3,3-difluoroazetidine hydrochloride (18.0 mg, 139 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 11.8 mg (25% of theory) of the title compound were obtained.

LC-MS (Method 3): $R_t$=1.05 min; MS (ESIpos): m/z=404 [M+H]$^+$ $^1$H-NMR (400 MHz, DMSO-d6) δ [ppm]: −0.149 (0.90), 0.008 (6.58), 0.146 (0.85), 1.689 (1.45), 1.968 (0.80), 2.033 (0.65), 2.366 (1.55), 2.523 (4.93), 2.559 (2.04), 2.602 (0.45), 2.710 (1.50), 4.026 (16.00), 4.368 (0.80), 4.395 (0.75), 4.595 (1.00), 4.609 (1.50), 4.621 (1.05), 4.717 (0.50), 4.744 (0.55), 4.861 (0.60), 5.122 (7.13), 7.191 (1.60), 7.202 (1.74), 7.211 (1.69), 7.222 (1.64), 8.153 (1.74), 8.157 (1.79), 8.173 (1.74), 8.177 (1.60), 8.545 (1.79), 8.549 (1.79), 8.556 (1.74), 8.560 (1.64).

Example 416

(5RS)-5-{[(3S)-3-Fluoropyrrolidin-1-yl]carbonyl}-2-[(3-methyl-1,2-oxazol-5-yl)methyl]-5,6,7,8-tetrahydro[1,2,4]triazolo[4,3-a]pyridin-3(2H)-one (Racemate)

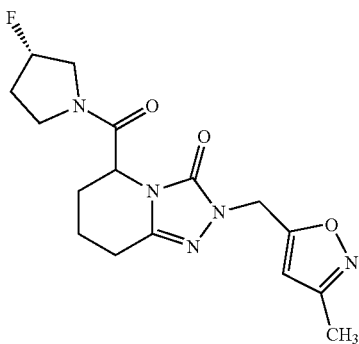 [SMILES: Cc1cc(Cn2nc3n(c2=O)C(C(=O)N2CC[C@H](F)C2)CCC3)on1]

(5RS)-2-[(3-Methyl-1,2-oxazol-5-yl)methyl]-3-oxo-2,3,5,6,7,8-hexahydro[1,2,4]triazolo[4,3-a]pyridine-5-carboxylic Acid (Racemate) (60.0 mg, 216 µmol) was initially charged in THF (3.0 ml) at room temperature. Subsequently, HBTU (123 mg, 323 µmol) and triethylamine (90 µl, 650 µmol) were added. After stirring for 15 min, (3S)-3-fluoropyrrolidine (28.8 mg, 323 µmol) was added and the reaction mixture was stirred at room temperature for 48 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 24.3 mg (32% of theory) of the title compound were obtained.

LC-MS (Method 3): $R_t$=0.88 min; MS (ESIpos): m/z=350 [M+H]$^+$ $^1$H-NMR (400 MHz, DMSO-d6) δ [ppm]: −0.008 (1.93), 0.008 (1.11), 1.721 (0.98), 1.733 (1.10), 1.988 (1.00), 2.040 (0.46), 2.073 (1.80), 2.104 (0.82), 2.136 (0.64), 2.203 (16.00), 2.238 (0.46), 2.268 (0.50), 2.300 (0.64), 2.303 (0.68), 2.327 (0.41), 2.523 (1.89), 2.571 (1.07), 2.595 (1.09), 2.608 (1.43), 2.620 (0.83), 2.650 (0.49), 2.665 (0.50), 2.669 (0.49), 3.345 (0.40), 3.357 (0.54), 3.501 (0.52), 3.508 (0.55), 3.522 (0.69), 3.550 (0.56), 3.569 (0.49), 3.595 (0.91), 3.632 (0.66), 3.653 (0.72), 3.677 (0.52), 3.743 (0.66), 3.775 (0.51), 3.783 (0.46), 3.854 (0.61), 3.940 (0.52), 4.739 (0.43), 4.745 (0.46), 4.812 (0.49), 4.845 (0.42), 4.851 (0.45), 4.946 (5.75), 5.259 (0.41), 5.389 (0.47), 6.226 (2.65).

Example 417

(5RS)-5-[(3-Fluoroazetidin-1-yl)carbonyl]-2-[(3-methyl-1,2-oxazol-5-yl)methyl]-5,6,7,8-tetrahydro[1,2,4]triazolo[4,3-a]pyridin-3(2H)-one (Racemate)

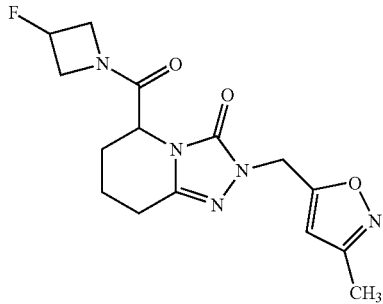 [SMILES: Cc1cc(Cn2nc3n(c2=O)C(C(=O)N2CC(F)C2)CCC3)on1]

(5RS)-2-[(3-Methyl-1,2-oxazol-5-yl)methyl]-3-oxo-2,3,5,6,7,8-hexahydro[1,2,4]triazolo[4,3-a]pyridine-5-carboxylic Acid (Racemate) (60.0 mg, 216 µmol) was initially charged in THF (3.0 ml) at room temperature. Subsequently, HBTU (123 mg, 323 µmol) and triethylamine (90 µl, 650 µmol) were added. After stirring for 15 min, 3-fluoroazetidine hydrochloride (36.1 mg, 323 µmol) was added and the reaction mixture was stirred at room temperature for 48 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 19.2 mg (27% of theory) of the title compound were obtained.

LC-MS (Method 3): $R_t$=0.83 min; MS (ESIpos): m/z=336 [M+H]$^+$ $^1$H-NMR (400 MHz, DMSO-d6) δ [ppm]: 1.714 (1.68), 1.949 (0.76), 2.029 (0.69), 2.072 (0.96), 2.201 (16.00), 2.293 (1.37), 2.585 (1.67), 2.598 (2.00), 2.612 (1.02), 2.639 (0.61), 2.670 (0.45), 3.928 (0.55), 3.954 (0.54), 3.988 (0.53), 4.269 (0.58), 4.300 (0.50), 4.364 (0.45), 4.528 (1.44), 4.541 (2.10), 4.554 (1.49), 4.950 (5.39), 6.234 (3.50), 6.924 (0.44).

Example 418

(5S)-5-[(3,3-Difluoropyrrolidin-1-yl)carbonyl]-2-{[2-(trifluoromethyl)-1,8-naphthyridin-3-yl]methyl}-5,6,7,8-tetrahydro[1,2,4]triazolo[4,3-a]pyridin-3(2H)-one

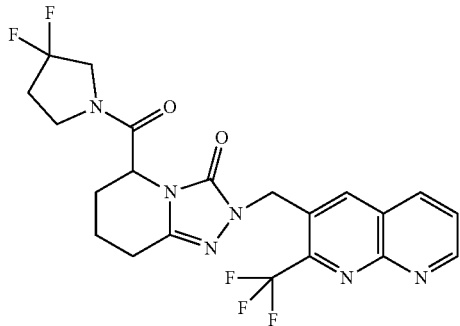 [SMILES: O=C(C1CCCc2nn(Cc3cc4cccnc4nc3C(F)(F)F)c(=O)n21)N1CCC(F)(F)C1]

(5S)-3-Oxo-2-{[2-(trifluoromethyl)-1,8-naphthyridin-3-yl]methyl}-2,3,5,6,7,8-hexahydro[1,2,4]triazolo[4,3-a]pyridine-5-carboxylic acid (50.0 mg, 127 µmol) was initially charged in THF (3.0 ml), and HBTU (62.7 mg, 165 µmol) and N,N-diisopropylethylamine (66 µl, 380 µmol) were subsequently added. After stirring at room temperature for 15 min, 3,3-difluoropyrrolidine hydrochloride (21.9 mg, 153 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 23.1 mg (38% of theory) of the title compound were obtained.

LC-MS (Method 3): $R_t$=1.28 min; MS (ESIpos): m/z=483 [M+H]$^+$ $^1$H-NMR (400 MHz, DMSO-d6) δ [ppm]: −0.149 (1.63), −0.008 (16.00), 0.008 (12.96), 0.146 (1.63), 1.690 (1.01), 1.783 (1.30), 2.060 (1.95), 2.073 (2.17), 2.092 (2.06), 2.327 (1.23), 2.366 (1.27), 2.445 (1.16), 2.523 (4.45), 2.564 (2.39), 2.584 (2.79), 2.599 (2.57), 2.612 (1.92), 2.625 (1.41), 2.639 (1.48), 2.650 (2.46), 2.664 (1.88), 2.690 (1.09), 2.709 (1.23), 3.578 (1.85), 3.597 (3.00), 3.616 (1.48), 3.722 (1.16), 3.756 (1.34), 3.790 (0.76), 3.813 (2.28), 3.839 (1.52), 3.913 (0.58), 3.931 (1.30), 3.957 (0.87), 3.993 (0.43), 4.020 (0.76), 4.064 (0.69), 4.092 (0.47), 4.174 (0.47), 4.202 (0.76), 4.230 (0.80), 4.855 (1.05), 4.868 (1.70), 4.877 (1.01), 4.922 (1.12), 4.937 (1.67), 4.946 (1.01), 5.218 (10.28), 7.815 (2.68), 7.825 (2.79), 7.835 (2.75), 7.846 (2.79), 8.377 (4.16), 8.385 (4.02), 8.560 (3.40), 8.564 (3.44), 8.580 (3.29), 8.585 (3.11), 9.242 (3.73), 9.247 (3.95), 9.252 (3.87), 9.257 (3.55).

Example 419

(5S)-5-{[(3S)-3-Fluoropyrrolidin-1-yl]carbonyl}-2-{[2-(trifluoromethyl)-1,8-naphthyridin-3-yl]methyl}-5,6,7,8-tetrahydro[1,2,4]triazolo[4,3-a]pyridin-3(2H)-one

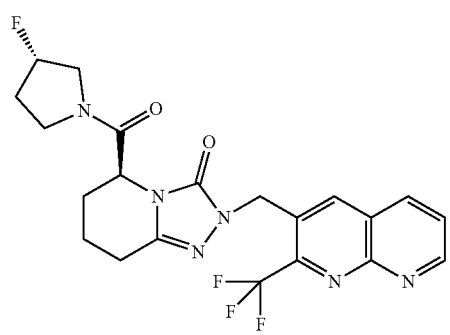 [SMILES: O=C([C@@H]1CCCc2nn(Cc3cc4cccnc4nc3C(F)(F)F)c(=O)n21)N1CC[C@H](F)C1]

(5S)-3-Oxo-2-{[2-(trifluoromethyl)-1,8-naphthyridin-3-yl]methyl}-2,3,5,6,7,8-hexahydro[1,2,4]triazolo[4,3-a]pyridine-5-carboxylic acid (50.0 mg, 127 µmol) was initially charged in THF (3.0 ml), and HBTU (62.7 mg, 165 µmol) and N,N-diisopropylethylamine (66 µl, 380 µmol) were subsequently added. After stirring at room temperature for 15 min, (3S)-3-fluoropyrrolidine hydrochloride (1:1) (19.2 mg, 153 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.2 mg (61% of theory) of the title compound were obtained.

LC-MS (Method 3): $R_t$=1.14 min; MS (ESIpos): m/z=465 [M+H]$^+$ $^1$H-NMR (400 MHz, DMSO-d6) δ [ppm]: −0.149 (1.73), −0.008 (16.00), 0.008 (12.57), 0.146 (1.73), 1.782 (0.41), 2.109 (0.72), 2.323 (0.90), 2.327 (1.17), 2.366 (1.13), 2.518 (4.56), 2.523 (3.76), 2.581 (0.45), 2.669 (1.51), 2.710 (1.24), 3.453 (11.33), 3.669 (0.72), 3.780 (0.53), 3.880 (0.53), 4.849 (0.49), 5.217 (2.30), 7.817 (0.90), 7.827 (0.90), 7.838 (0.87), 7.848 (0.90), 8.368 (1.69), 8.570 (0.79), 8.590 (0.72), 9.242 (0.87), 9.246 (0.90), 9.252 (0.87), 9.257 (0.79).

Example 420

(5S)-5-[(3-Fluoroazetidin-1-yl)carbonyl]-2-{[2-(trifluoromethyl)-1,8-naphthyridin-3-yl]methyl}-5,6,7,8-tetrahydro[1,2,4]triazolo[4,3-a]pyridin-3(2H)-one

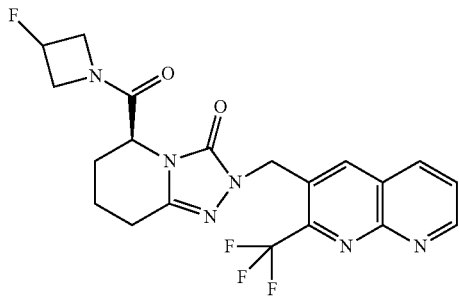 [SMILES: O=C([C@@H]1CCCc2nn(Cc3cc4cccnc4nc3C(F)(F)F)c(=O)n21)N1CC(F)C1]

(5S)-3-Oxo-2-{[2-(trifluoromethyl)-1,8-naphthyridin-3-yl]methyl}-2,3,5,6,7,8-hexahydro[1,2,4]triazolo[4,3-a]pyridine-5-carboxylic acid (50.0 mg, 127 μmol) was initially charged in THF (3.0 ml), and HBTU (62.7 mg, 165 μmol) and N,N-diisopropylethylamine (66 μl, 380 μmol) were subsequently added. After stirring at room temperature for 15 min, 3-fluoroazetidine hydrochloride (17.0 mg, 153 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 20.0 mg (35% of theory) of the title compound were obtained.

LC-MS (Method 3): $R_t$=1.09 min; MS (ESIpos): m/z=451 [M+H]$^+$ $^1$H-NMR (400 MHz, DMSO-d6) δ[ppm]: −0.149 (1.80), −0.008 (16.00), 0.008 (14.79), 0.146 (1.84), 1.759 (1.34), 2.045 (1.72), 2.328 (1.59), 2.366 (1.55), 2.639 (2.64), 2.651 (1.51), 2.669 (2.14), 2.710 (1.51), 3.976 (0.96), 4.280 (0.88), 4.640 (2.26), 4.654 (3.35), 4.665 (2.18), 5.217 (8.00), 5.406 (0.63), 5.549 (0.63), 7.814 (3.18), 7.824 (3.18), 7.835 (3.35), 7.845 (3.31), 8.384 (3.77), 8.558 (2.35), 8.579 (2.30), 9.241 (3.39), 9.246 (3.64), 9.252 (3.73), 9.257 (3.35).

Example 421

(5S)-2-[(6-Chloropyridin-3-yl)methyl]-5-[(3-fluoroazetidin-1-yl)carbonyl]-5,6,7,8-tetrahydro[1,2,4]triazolo[4,3-a]pyridin-3(2H)-one

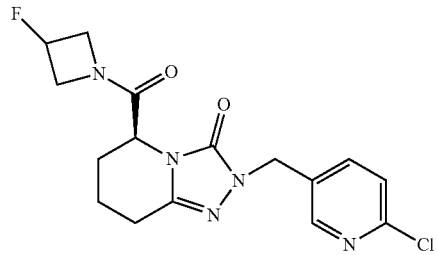 [SMILES: O=C([C@@H]1CCCc2nn(Cc3ccc(Cl)nc3)c(=O)n21)N1CC(F)C1]

(5S)-2-[(6-Chloropyridin-3-yl)methyl]-3-oxo-2,3,5,6,7,8-hexahydro[1,2,4]triazolo[4,3-a]pyridine-5-carboxylic acid (50.0 mg, 162 μmol) was initially charged in THF (3.0 ml), and HBTU (79.8 mg, 211 μmol) and N,N-diisopropylethylamine (85 μl, 490 μmol) were subsequently added. After stirring at room temperature for 15 min, 3-fluoroazetidine hydrochloride (21.7 mg, 194 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 21.0 mg (35% of theory) of the title compound were obtained.

LC-MS (Method 3): $R_t$=0.99 min; MS (ESIpos): m/z=366 [M+H]$^+$ $^1$H-NMR (400 MHz, DMSO-d6) δ [ppm]: −0.149 (0.64), −0.008 (6.53), 0.008 (4.72), 0.146 (0.64), 1.648 (1.11), 1.662 (1.43), 1.672 (2.04), 1.696 (3.22), 1.707 (3.33), 1.719 (3.12), 1.956 (2.12), 1.966 (1.95), 2.002 (1.74), 2.012 (1.71), 2.023 (1.87), 2.327 (0.49), 2.523 (1.99), 2.576 (3.91), 2.590 (5.43), 2.604 (2.71), 2.619 (1.02), 2.632 (1.76), 2.646 (0.72), 2.670 (0.52), 3.897 (0.69), 3.926 (1.46), 3.957 (1.54), 3.989 (1.43), 4.020 (0.85), 4.154 (0.63), 4.169 (0.72), 4.185 (0.58), 4.208 (0.80), 4.223 (1.29), 4.238 (1.27), 4.253 (1.21), 4.270 (1.58), 4.291 (1.46), 4.322 (1.18), 4.360 (1.07), 4.394 (0.93), 4.429 (0.66), 4.456 (0.89), 4.503 (0.67), 4.518 (0.83), 4.538 (3.62), 4.551 (5.54), 4.564 (3.58), 4.598 (0.52), 4.632 (0.61), 4.646 (0.69), 4.659 (0.63), 4.684 (0.69), 4.700 (0.72), 4.724 (0.53), 4.883 (16.00), 5.351 (0.91), 5.406 (0.93), 5.494 (0.89), 5.541 (0.77), 5.548 (0.89), 6.515 (0.69), 7.503 (5.54), 7.523 (6.98), 7.694 (4.39), 7.714 (3.70), 8.305 (5.65).

Example 422

(5S)-2-[(6-Chloropyridin-3-yl)methyl]-5-{[(3S)-3-fluoropyrrolidin-1-yl]carbonyl}-5,6,7,8-tetrahydro[1,2,4]triazolo[4,3-a]pyridin-3(2H)-one

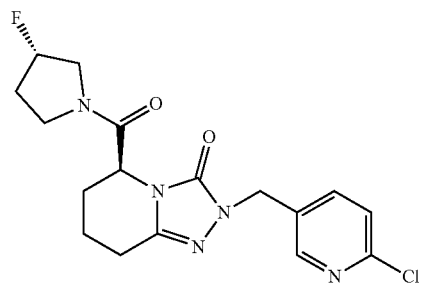 [SMILES: O=C([C@@H]1CCCc2nn(Cc3ccc(Cl)nc3)c(=O)n21)N1CC[C@H](F)C1]

(5S)-2-[(6-Chloropyridin-3-yl)methyl]-3-oxo-2,3,5,6,7,8-hexahydro[1,2,4]triazolo[4,3-a]pyridine-5-carboxylic acid (50.0 mg, 162 μmol) was initially charged in THF (3.0 ml), and HBTU (79.8 mg, 211 μmol) and N,N-diisopropylethylamine (85 μl, 490 μmol) were subsequently added. After stirring at room temperature for 15 min, (3S)-3-fluoropyrrolidine hydrochloride (24.4 mg, 194 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 32.1 mg (52% of theory) of the title compound were obtained.

LC-MS (Method 3): $R_t$=1.05 min; MS (ESIpos): m/z=380 [M+H]$^+$ $^1$H-NMR (400 MHz, DMSO-d6) δ [ppm]: 0.008 (1.05), 1.720 (2.57), 1.727 (2.64), 1.870 (0.64), 1.894 (0.61), 1.904 (0.81), 1.968 (0.58), 1.993 (1.05), 2.020 (1.59), 2.042 (1.32), 2.058 (1.52), 2.074 (1.86), 2.085 (2.16), 2.094 (2.00), 2.101 (2.00), 2.121 (1.39), 2.135 (1.42), 2.217 (0.95), 2.237 (0.88), 2.266 (1.15), 2.519 (3.96), 2.524 (4.19), 2.563 (1.96), 2.578 (1.66), 2.602 (2.47), 2.646 (0.91), 2.670 (0.41), 3.344 (1.01), 3.357 (0.85), 3.365 (0.81), 3.393 (0.81), 3.401 (0.78), 3.454 (0.64), 3.464 (0.64), 3.490 (0.85), 3.499 (0.74), 3.606 (0.74), 3.632 (2.77), 3.649 (2.27), 3.655 (2.06), 3.675 (1.76), 3.697 (1.22), 3.721 (1.32), 3.740 (2.10), 3.764 (1.69), 3.783 (1.22), 3.850 (2.40), 4.678 (1.32), 4.687 (1.52), 4.694 (1.56), 4.703 (1.25), 4.736 (1.69), 4.745 (1.83), 4.751 (1.89), 4.760 (1.35), 4.880 (16.00), 5.257 (1.18), 5.380 (1.52), 5.388 (1.49), 5.509 (0.88), 7.504 (4.87), 7.524 (5.92), 7.683 (2.23), 7.690 (3.92), 7.696 (2.44), 7.704 (1.83), 7.710 (3.11), 7.717 (1.76), 8.296 (4.06), 8.302 (3.55).

Example 423

(5S)-2-[(6-Chloropyridin-3-yl)methyl]-5-[(3,3-difluoropyrrolidin-1-yl)carbonyl]-5,6,7,8-tetrahydro[1,2,4]triazolo[4,3-a]pyridin-3(2H)-one

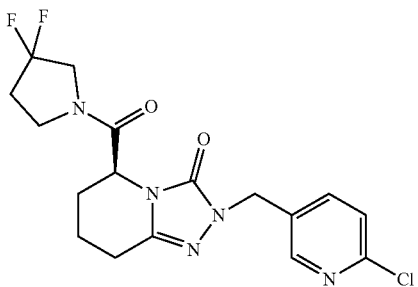 [SMILES: O=C([C@@H]1CCCc2nn(Cc3ccc(Cl)nc3)c(=O)n21)N1CCC(F)(F)C1]

(5S)-2-[(6-Chloropyridin-3-yl)methyl]-3-oxo-2,3,5,6,7,8-hexahydro[1,2,4]triazolo[4,3-a]pyridine-5-carboxylic acid (50.0 mg, 162 μmol) was initially charged in THF (3.0 ml), and HBTU (79.8 mg, 211 μmol) and N,N-diisopropylethylamine (85 μl, 490 μmol) were subsequently added. After stirring at room temperature for 15 min, 3,3-difluoropyrrolidine hydrochloride (27.9 mg, 194 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 32.2 mg (50% of theory) of the title compound were obtained.

LC-MS (Method 4): $R_t$=0.66 min; MS (ESIpos): m/z=398 [M+H]$^+$ $^1$H-NMR (400 MHz, DMSO-d6) δ [ppm]: −0.149 (0.50), −0.008 (4.74), 0.008 (4.04), 0.146 (0.47), 1.660 (1.02), 1.727 (1.22), 1.996 (1.41), 2.007 (1.46), 2.043 (1.07), 2.050 (1.07), 2.059 (0.97), 2.073 (7.86), 2.328 (0.72), 2.366 (0.64), 2.380 (0.87), 2.409 (1.04), 2.424 (0.99), 2.451 (0.82), 2.560 (2.51), 2.569 (3.00), 2.585 (2.75), 2.602 (2.68), 2.645 (0.77), 2.670 (0.69), 2.710 (0.47), 3.529 (1.07), 3.535 (1.14), 3.546 (1.74), 3.556 (1.89), 3.565 (1.12), 3.575 (0.99), 3.665 (1.14), 3.699 (1.29), 3.742 (0.62), 3.776 (1.54), 3.807 (2.41), 3.825 (0.60), 3.886 (0.57), 3.906 (1.24), 3.931 (0.87), 3.951 (0.45), 3.990 (0.79), 4.018 (0.52), 4.034 (0.72), 4.061 (0.42), 4.144 (0.47), 4.175 (0.72), 4.200 (0.72), 4.749 (1.07), 4.764 (1.44), 4.773 (1.04), 4.821 (1.12), 4.836 (1.46), 4.845 (1.19), 4.884 (16.00), 7.505 (4.99), 7.525 (6.28), 7.686 (3.32), 7.692 (3.40), 7.707 (2.70), 7.713 (2.73), 8.296 (4.94), 8.302 (4.79).

Example 424

(5S)-2-[(6-Chloropyridin-3-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

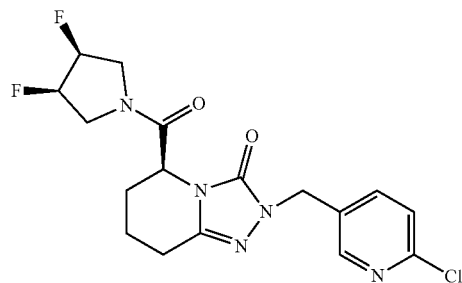 [SMILES: O=C([C@@H]1CCCc2nn(Cc3ccc(Cl)nc3)c(=O)n21)N1C[C@@H](F)[C@@H](F)C1]

(5S)-2-[(6-Chloropyridin-3-yl)methyl]-3-oxo-2,3,5,6,7,8-hexahydro[1,2,4]triazolo[4,3-a]pyridine-5-carboxylic acid (70.0 mg, 227 μmol) was initially charged in THF (4.0 ml), and HBTU (112 mg, 295 μmol) and N,N-diisopropylethylamine (120 μl, 680 μmol) were subsequently added. After stirring at room temperature for 15 min, (3R,4S)-3,4-difluoropyrrolidine hydrochloride (39.1 mg, 272 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 66.6 mg (74% of theory) of the title compound were obtained.

LC-MS (Method 3): $R_t$=1.10 min; MS (ESIpos): m/z=398 [M+H]$^+$ $^1$H-NMR (400 MHz, DMSO-d6) δ[ppm]: −0.149 (1.29), −0.008 (12.08), 0.008 (10.65), 0.146 (1.38), 1.656 (1.21), 1.729 (1.51), 1.968 (1.25), 2.013 (1.73), 2.073 (3.54), 2.327 (1.60), 2.366 (1.12), 2.563 (2.59), 2.588 (2.33), 2.601 (2.93), 2.644 (1.08), 2.669 (1.73), 2.710 (1.25), 3.532 (1.25), 3.577 (0.82), 3.626 (0.99), 3.683 (1.51), 3.700 (1.51), 3.731 (1.29), 3.752 (1.21), 3.866 (0.78), 3.937 (0.95), 3.973 (0.86), 3.988 (0.91), 4.170 (0.91), 4.797 (3.19), 4.884 (16.00), 5.274 (0.95), 5.349 (0.91), 5.389 (1.16), 7.506 (4.27), 7.526 (5.13), 7.680 (1.94), 7.688 (3.15), 7.695 (2.42), 7.709 (2.59), 7.716 (1.90), 8.297 (5.65).

Example 425

(5S)-5-{[(3S)-3-Hydroxypyrrolidin-1-yl]carbonyl}-2-{[6-(trifluoromethyl)pyridin-3-yl]methyl}-5,6,7,8-tetrahydro[1,2,4]triazolo[4,3-a]pyridine-3(2H)-one

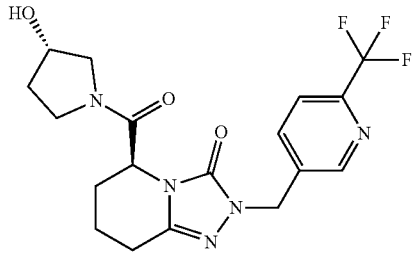 [SMILES: O=C([C@@H]1CCCc2nn(Cc3ccc(C(F)(F)F)nc3)c(=O)n21)N1CC[C@H](O)C1]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (60.0 mg, 175 µmol) was initially charged in THF (2.0 ml), and HATU (86.6 mg, 228 µmol) and triethylamine (73 µl, 530 µmol) were subsequently added. After stirring at room temperature for 15 min, (3S)-pyrrolidin-3-ol hydrochloride (26.0 mg, 210 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 10). The product-containing fractions were concentrated under reduced pressure, and 1.00 mg (92% purity, 1% of theory) of the title compound were obtained.

LC-MS (Method 3): $R_t$=0.99 min; MS (ESIpos): m/z=412 [M+H]$^+$ $^1$H-NMR (400 MHz, DMSO-d6) δ [ppm]: −0.008 (0.69), 0.008 (0.58), 1.637 (0.77), 1.644 (0.75), 1.650 (0.83), 1.663 (1.03), 1.677 (0.98), 1.689 (0.86), 1.736 (2.05), 1.751 (1.94), 1.774 (1.47), 1.783 (1.06), 1.828 (0.46), 1.840 (0.61), 1.851 (1.28), 1.862 (1.57), 1.873 (1.33), 1.883 (1.65), 1.894 (1.33), 1.905 (0.93), 1.939 (0.53), 1.973 (1.71), 1.985 (1.87), 1.997 (2.24), 2.007 (2.18), 2.019 (2.06), 2.029 (1.92), 2.036 (1.50), 2.045 (1.31), 2.057 (1.10), 2.065 (1.19), 2.073 (1.20), 2.523 (1.16), 2.561 (1.75), 2.575 (1.29), 2.597 (1.55), 2.608 (2.72), 2.619 (1.46), 2.638 (0.72), 2.650 (1.08), 2.661 (0.60), 3.204 (0.72), 3.236 (1.03), 3.343 (1.75), 3.369 (1.82), 3.379 (2.23), 3.397 (1.40), 3.419 (0.57), 3.434 (0.59), 3.443 (0.61), 3.457 (1.07), 3.464 (1.17), 3.473 (0.55), 3.485 (1.17), 3.550 (0.84), 3.567 (1.42), 3.573 (1.63), 3.589 (1.08), 3.599 (0.79), 3.640 (0.94), 3.651 (1.41), 3.667 (0.92), 3.678 (1.09), 3.756 (0.58), 4.270 (1.41), 4.363 (1.43), 4.696 (0.83), 4.705 (0.97), 4.712 (1.06), 4.720 (0.84), 4.739 (1.24), 4.752 (1.60), 4.761 (1.16), 4.806 (0.64), 4.815 (0.73), 4.821 (0.85), 4.830 (0.66), 4.964 (2.61), 5.005 (10.49), 5.078 (2.55), 5.087 (2.46), 7.909 (16.00), 8.640 (4.92).

Example 426

(5S)-5-[(3,3-Difluoropyrrolidin-1-yl)carbonyl]-2-{[6-(trifluoromethyl)pyridin-3-yl]methyl}-5,6,7,8-tetrahydro[1,2,4]triazolo[4,3-a]pyridine-3(2H)-one

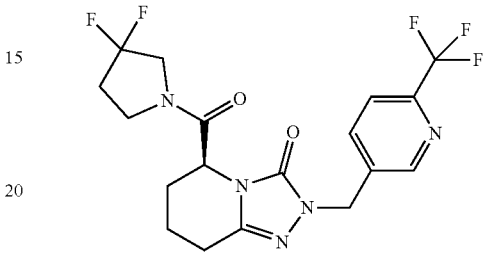

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (100 mg, 85% purity, 248 µmol) was initially charged in THF (2.0 ml), and HBTU (122 mg, 323 µmol) and N,N-diisopropylethylamine (130 µl, 750 µmol) were subsequently added. After stirring at room temperature for 15 min, 3,3-difluoropyrrolidine hydrochloride (42.8 mg, 298 µmol) was added and the reaction mixture was stirred at room temperature overnight. HBTU (122 mg, 323 µmol) and 3,3-difluoropyrrolidine hydrochloride (42.8 mg, 298 µmol) were added again. After stirring at room temperature for 48 hours, N,N-diisopropylethylamine (130 µl, 750 µmol) was added and the mixture was stirred overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 79.6 mg (72% of theory) of the title compound were obtained.

LC-MS (Method 1): $R_t$=1.01 min; MS (ESIpos): m/z=432 [M+H]$^+$ $^1$H-NMR (400 MHz, DMSO-d6) δ [ppm]: −0.150 (0.48), −0.008 (6.41), 0.008 (3.51), 0.146 (0.45), 1.375 (0.48), 1.405 (1.49), 1.663 (1.24), 1.673 (1.15), 1.736 (1.52), 1.753 (1.60), 1.879 (0.96), 1.973 (1.38), 2.008 (1.88), 2.018 (1.83), 2.033 (1.72), 2.043 (1.49), 2.051 (1.35), 2.059 (1.24), 2.073 (1.86), 2.087 (0.90), 2.327 (0.59), 2.366 (0.93), 2.382 (1.12), 2.410 (1.77), 2.430 (2.33), 2.524 (3.77), 2.569 (3.63), 2.579 (2.76), 2.593 (2.87), 2.610 (3.09), 2.623 (1.63), 2.641 (0.70), 2.653 (1.01), 2.665 (0.96), 2.710 (0.53), 3.534 (1.38), 3.541 (1.55), 3.551 (2.11), 3.561 (2.17), 3.570 (1.29), 3.580 (1.07), 3.637 (0.45), 3.670 (1.32), 3.704 (1.52), 3.738 (0.79), 3.747 (0.93), 3.782 (1.97), 3.813 (2.59), 3.830 (0.70), 3.847 (0.42), 3.891 (0.76), 3.910 (1.49), 3.928 (0.84), 3.936 (1.04), 3.954 (0.53), 3.965 (0.51), 3.994 (0.93), 4.009 (0.51), 4.023 (0.70), 4.038 (0.84), 4.065 (0.51), 4.149 (0.59), 4.180 (0.84), 4.205 (0.87), 4.767 (1.35), 4.781 (1.69), 4.791 (1.21), 4.837 (1.32), 4.847 (1.52), 4.853 (1.63), 4.862 (1.15), 4.970 (0.56), 5.011 (14.23), 7.909 (16.00), 7.912 (15.38), 8.641 (5.34).

Example 427

(5S)-5-{[(3S)-3-Fluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one

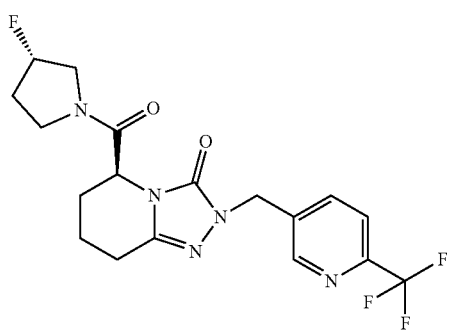 [SMILES: O=C([C@@H]1CCCc2nn(Cc3ccc(C(F)(F)F)nc3)c(=O)n21)N1CC[C@H](F)C1]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (1000 mg, 2.92 mmol) was initially charged in THF (18 ml) at room temperature. Subsequently, HBTU (1.44 g, 3.80 mmol) and N,N-diisopropylethylamine (1.5 ml, 8.8 mmol) were added. After stirring for 15 min, (3S)-3-fluoropyrrolidine hydrochloride (404 mg, 3.21 mmol) was added and the reaction mixture was stirred at room temperature overnight. N,N-Diisopropylethylamine (1.5 ml, 8.8 mmol) was added again and the mixture was stirred again at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 797 mg (66% of theory) of the title compound were obtained.

LC-MS (Method 3): $R_t$=1.23 min; MS (ESIpos): m/z=414 [M+H]$^+$ $^1$H-NMR (400 MHz, DMSO-d6) δ[ppm]: −0.008 (1.38), 0.008 (1.26), 1.701 (1.17), 1.712 (1.38), 1.726 (2.00), 1.736 (2.23), 1.883 (0.48), 1.906 (0.51), 1.923 (0.69), 1.997 (0.78), 2.005 (0.71), 2.022 (0.83), 2.032 (1.29), 2.053 (1.08), 2.073 (2.09), 2.088 (1.68), 2.104 (2.05), 2.124 (1.15), 2.139 (1.40), 2.173 (0.41), 2.221 (0.76), 2.243 (0.69), 2.256 (0.74), 2.270 (1.03), 2.327 (0.53), 2.366 (0.55), 2.519 (2.48), 2.523 (2.09), 2.562 (1.54), 2.566 (1.52), 2.572 (1.59), 2.588 (1.33), 2.614 (2.30), 2.657 (0.90), 2.670 (0.87), 2.710 (0.53), 3.275 (0.69), 3.350 (0.62), 3.362 (0.60), 3.371 (0.64), 3.398 (0.74), 3.407 (0.74), 3.459 (0.55), 3.468 (0.57), 3.495 (0.78), 3.504 (0.74), 3.610 (0.51), 3.637 (2.16), 3.654 (1.86), 3.661 (1.86), 3.681 (1.54), 3.703 (0.97), 3.727 (1.06), 3.746 (1.89), 3.769 (1.36), 3.775 (1.40), 3.789 (1.15), 3.857 (2.28), 4.694 (1.10), 4.703 (1.33), 4.710 (1.38), 4.719 (1.10), 4.752 (1.43), 4.761 (1.56), 4.767 (1.82), 4.776 (1.36), 5.008 (14.51), 5.260 (1.13), 5.383 (1.33), 5.391 (1.40), 5.511 (0.78), 7.911 (16.00), 7.914 (10.30), 8.642 (4.76).

Example 428

(5S)-5-[(3-Hydroxyazetidin-1-yl)carbonyl]-2-{[6-(trifluoromethyl)pyridin-3-yl]methyl}-5,6,7,8-tetrahydro[1,2,4]triazolo[4,3-a]pyridin-3(2H)-one

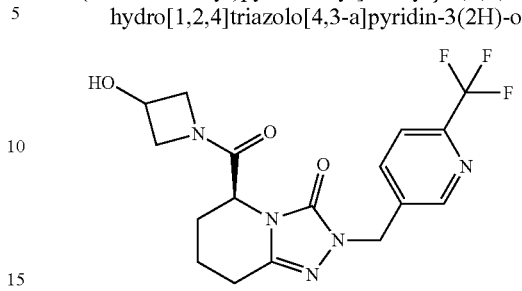

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (65.0 mg, 190 µmol) was initially charged in THF at room temperature. Subsequently, HATU (93.9 mg, 247 µmol) and triethylamine (79 µl, 570 µmol) were added. After stirring for 15 min, azetidin-3-ol hydrochloride (25.0 mg, 228 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 10). The product-containing fractions were concentrated under reduced pressure, and 1.00 mg (1% of theory) of the title compound were obtained.

LC-MS (Method 3): $R_t$=0.98 min; MS (ESIpos): m/z=398 [M+H]$^+$ $^1$H-NMR (400 MHz, DMSO-d6) δ[ppm]: −0.149 (2.09), −0.008 (15.61), 0.008 (16.00), 0.146 (2.16), 2.327 (4.71), 2.366 (2.16), 2.669 (4.41), 2.709 (2.40), 4.534 (2.09), 5.010 (4.48), 5.803 (1.93), 7.908 (5.87), 8.644 (3.25).

Example 429

(5S)-5-[(3-Fluoroazetidin-1-yl)carbonyl]-2-{[6-(trifluoromethyl)pyridin-3-yl]methyl}-5,6,7,8-tetrahydro[1,2,4]triazolo[4,3-a]pyridin-3(2H)-one

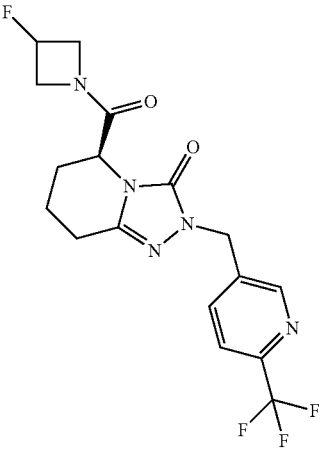 [SMILES: O=C([C@@H]1CCCc2nn(Cc3ccc(C(F)(F)F)nc3)c(=O)n21)N1CC(F)C1]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (100 mg, 292 µmol) was initially charged in THF (2.0 ml), and HBTU (144 mg, 380 µmol) and N,N-diisopropylethylamine (150 µl, 880 µmol) were subsequently added. After stirring at room temperature for 15 min, 3-fluoroazetidine hydrochloride (39.1 mg, 351 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 74.0 mg (63% of theory) of the title compound were obtained.

LC-MS (Method 1): $R_t$=0.90 min; MS (ESIpos): m/z=400 [M+H]$^+$ $^1$H-NMR (400 MHz, DMSO-d6) δ [ppm]: 1.658 (1.45), 1.670 (1.85), 1.683 (2.02), 1.694 (2.48), 1.708 (2.77), 1.961 (1.98), 1.975 (1.90), 2.004 (1.65), 2.025 (1.68), 2.359 (0.41), 2.579 (3.40), 2.593 (4.36), 2.606 (2.24), 2.622 (0.89), 2.635 (1.39), 2.648 (0.64), 2.662 (0.41), 3.898 (0.65), 3.925 (1.33), 3.956 (1.38), 3.986 (1.29), 4.017 (0.76), 4.153 (0.58), 4.168 (0.66), 4.181 (0.58), 4.206 (0.78), 4.222 (1.20), 4.236 (1.17), 4.250 (1.09), 4.269 (1.43), 4.290 (1.27), 4.321 (0.95), 4.359 (1.03), 4.393 (0.82), 4.429 (0.61), 4.455 (0.79), 4.505 (0.69), 4.518 (0.83), 4.550 (3.29), 4.562 (4.78), 4.575 (3.11), 4.597 (0.48), 4.630 (0.56), 4.646 (0.65), 4.681 (0.63), 4.699 (0.62), 4.724 (0.46), 5.004 (12.79), 5.347 (0.79), 5.401 (0.77), 5.489 (0.79), 5.543 (0.75), 7.905 (16.00), 8.642 (6.38).

Example 430

(5S)-5-{[(3S)-3-Fluoropyrrolidin-1-yl]carbonyl}-2-[(6-methoxypyridin-3-yl)methyl]-5,6,7,8-tetrahydro[1,2,4]triazolo[4,3-a]pyridin-3(2H)-one

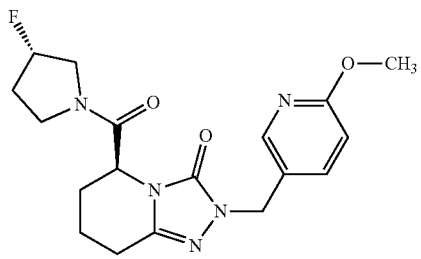 [SMILES: COc1ccc(Cn2nc3n(c2=O)[C@H](C(=O)N2CC[C@H](F)C2)CCC3)cn1]

(5S)-2-[(6-Methoxypyridin-3-yl)methyl]-3-oxo-2,3,5,6,7,8-hexahydro[1,2,4]triazolo[4,3-a]pyridine-5-carboxylic acid (390 mg, 1.28 mmol) was initially charged in THF (5.0 ml), and HBTU (632 mg, 1.67 mmol) and N,N-diisopropylethylamine (670 µl, 3.8 mmol) were subsequently added. After stirring at room temperature for 15 min, (3S)-3-fluoropyrrolidine hydrochloride (193 mg, 1.54 mmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 98.9 mg (20% of theory) of the title compound were obtained.

LC-MS (Method 4): $R_t$=0.57 min; MS (ESIpos): m/z=376 [M+H]$^+$ $^1$H-NMR (400 MHz, DMSO-d6) δ [ppm]: -0.008 (1.34), 0.008 (1.26), 1.706 (0.98), 1.718 (1.14), 2.003 (0.53), 2.048 (0.45), 2.073 (0.60), 2.083 (0.66), 2.108 (0.58), 2.134 (0.43), 2.524 (1.18), 2.565 (0.60), 2.593 (0.91), 3.632 (1.01), 3.650 (0.75), 3.677 (0.48), 3.718 (0.42), 3.736 (0.77), 3.765 (0.54), 3.781 (0.53), 3.827 (16.00), 3.851 (0.91), 4.661 (0.43), 4.671 (0.50), 4.677 (0.55), 4.686 (0.45), 4.719 (0.57), 4.727 (0.67), 4.734 (0.76), 4.743 (0.60), 4.762 (5.88), 5.258 (0.42), 5.389 (0.56), 6.784 (2.23), 6.806 (2.39), 7.551 (0.72), 7.557 (1.53), 7.563 (0.93), 7.572 (0.71), 7.578 (1.46), 7.584 (0.86), 8.054 (1.92).

Example 431

(5S)-5-{[(3R,4S)-3,4-Difluoropyrrolidin-1-yl]carbonyl}-2-[(6-methoxypyridin-3-yl)methyl]-5,6,7,8-tetrahydro[1,2,4]triazolo[4,3-a]pyridin-3(2H)-one

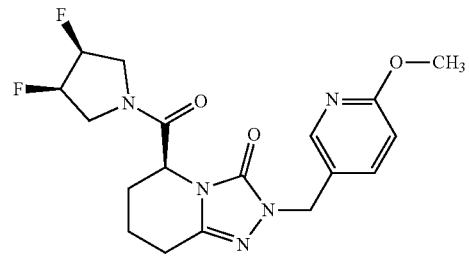 [SMILES: COc1ccc(Cn2nc3n(c2=O)[C@H](C(=O)N2C[C@@H](F)[C@@H](F)C2)CCC3)cn1]

(5S)-2-[(6-Methoxypyridin-3-yl)methyl]-3-oxo-2,3,5,6,7,8-hexahydro[1,2,4]triazolo[4,3-a]pyridine-5-carboxylic acid (390 mg, 1.28 mmol) was initially charged in THF (5.0 ml), and HBTU (632 mg, 1.67 mmol) and N,N-diisopropylethylamine (670 µl, 3.8 mmol) were subsequently added. After stirring at room temperature for 15 min, (3R,4S)-3,4-difluoropyrrolidine hydrochloride (221 mg, 1.54 mmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 111 mg (22% of theory) of the title compound were obtained.

LC-MS (Method 4): $R_t$=0.61 min; MS (ESIpos): m/z=394 [M+H]$^+$ $^1$H-NMR (400 MHz, DMSO-d6) δ [ppm]: -0.008 (0.88), 0.008 (0.85), 1.657 (0.55), 1.695 (0.52), 1.707 (0.63), 1.716 (0.71), 1.730 (0.60), 1.948 (0.53), 1.956 (0.47), 1.994 (0.68), 2.003 (0.53), 2.018 (0.42), 2.029 (0.48), 2.037 (0.53), 2.045 (0.50), 2.052 (0.41), 2.073 (0.81), 2.525 (0.94), 2.575 (0.99), 2.588 (1.28), 2.599 (0.72), 2.630 (0.43), 3.482 (0.43), 3.491 (0.41), 3.532 (0.52), 3.539 (0.47), 3.625 (0.42), 3.666 (0.41), 3.679 (0.56), 3.686 (0.47), 3.699 (0.72), 3.713 (0.46), 3.722 (0.55), 3.752 (0.47), 3.764 (0.45), 3.825 (14.71), 3.828 (16.00), 3.935 (0.40), 4.169 (0.44), 4.766 (8.26), 5.275 (0.42), 5.376 (0.42), 5.386 (0.47), 5.398 (0.40), 6.785 (1.86), 6.806 (2.01), 7.547 (0.88), 7.555 (1.43), 7.562 (1.08), 7.569 (0.92), 7.576 (1.40), 7.583 (1.01), 8.054 (2.30).

Example 432

(2S)-1-({(5S)-2-[(6-Methoxypyridin-3-yl)methyl]-3-oxo-2,3,5,6,7,8-hexahydro[1,2,4]triazolo[4,3-a]pyridin-5-yl}carbonyl)pyrrolidine-2-carbonitrile

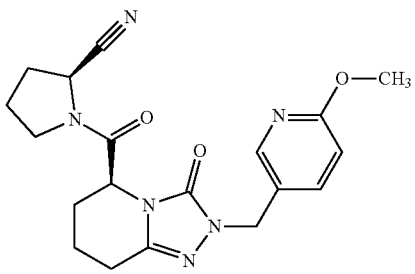 [SMILES: COc1ccc(Cn2nc3n(c2=O)[C@H](C(=O)N2CCC[C@H]2C#N)CCC3)cn1]

(5S)-2-[(6-Methoxypyridin-3-yl)methyl]-3-oxo-2,3,5,6,7,8-hexahydro[1,2,4]triazolo[4,3-a]pyridine-5-carboxylic acid (390 mg, 1.28 mmol) was initially charged in THF (5.0 ml), and HBTU (632 mg, 1.67 mmol) and N,N-diisopropylethylamine (670 µl, 3.8 mmol) were subsequently added. After stirring at room temperature for 15 min, (2S)-pyrrolidine-2-carbonitrile hydrochloride (204 mg, 1.54 mmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 109 mg (18% of theory) of the title compound were obtained.

LC-MS (Method 4): $R_t$=0.60 min; MS (ESIpos): m/z=383 [M+H]$^+$ $^1$H-NMR (400 MHz, DMSO-d6) δ [ppm]: −0.008 (0.93), 0.008 (0.87), 1.988 (0.50), 2.027 (0.70), 2.045 (0.98), 2.059 (1.43), 2.076 (1.42), 2.093 (0.73), 2.104 (0.58), 2.115 (0.48), 2.135 (0.50), 2.148 (0.61), 2.159 (0.53), 2.206 (0.71), 2.225 (0.67), 2.237 (0.42), 2.562 (0.56), 2.573 (0.59), 2.587 (0.46), (0.67), 2.608 (0.41), 2.620 (0.75), 2.632 (0.43), 2.899 (0.83), 3.670 (1.14), 3.686 (2.31), 3.703 (1.10), 3.828 (16.00), 4.767 (3.05), 4.772 (2.80), 4.786 (0.78), 4.793 (1.36), 4.803 (1.54), 4.813 (1.53), 4.823 (0.80), 6.788 (1.71), 6.810 (1.83), 7.550 (1.02), 7.556 (1.09), 7.571 (1.03), 7.577 (1.07), 8.051 (1.46), 8.056 (1.52).

Example 433

(5S)-5-[(3-Fluoroazetidin-1-yl)carbonyl]-2-[(6-methoxypyridin-3-yl)methyl]-5,6,7,8-tetrahydro[1,2,4]triazolo[4,3-a]pyridin-3(2H)-one

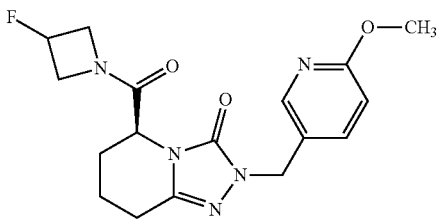 [SMILES: COc1ccc(Cn2nc3n(c2=O)[C@H](C(=O)N2CC(F)C2)CCC3)cn1]

(5S)-2-[(6-Methoxypyridin-3-yl)methyl]-3-oxo-2,3,5,6,7,8-hexahydro[1,2,4]triazolo[4,3-a]pyridine-5-carboxylic acid (390 mg, 1.28 mmol) was initially charged in THF (5.0 ml), and HBTU (632 mg, 1.67 mmol) and N,N-diisopropylethylamine (670 µl, 3.8 mmol) were subsequently added. After stirring at room temperature for 15 min, 3-fluoroazetidine hydrochloride (172 mg, 1.54 mmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 82.9 mg (18% of theory) of the title compound were obtained.

LC-MS (Method 4): $R_t$=0.55 min; MS (ESIpos): m/z=362 [M+H]$^+$ $^1$H-NMR (400 MHz, DMSO-d6) δ [ppm]: −0.008 (0.77), 0.008 (0.79), 1.697 (1.16), 1.940 (0.55), 2.002 (0.46), 2.013 (0.50), 2.524 (1.06), 2.564 (1.20), 2.578 (1.49), 2.591 (0.77), 2.620 (0.48), 3.825 (16.00), 3.955 (0.41), 4.252 (0.44), 4.517 (0.94), 4.529 (1.44), 4.542 (0.94), 4.769 (4.35), 6.783 (1.53), 6.804 (1.66), 7.561 (1.13), 7.582 (1.11), 8.061 (1.73).

Example 434

(5S)-5-[(3,3-Difluoropyrrolidin-1-yl)carbonyl]-2-[(6-methoxypyridin-3-yl)methyl]-5,6,7,8-tetrahydro[1,2,4]triazolo[4,3-a]pyridin-3(2H)-one

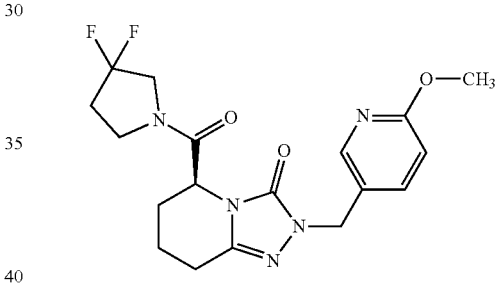

(5S)-2-[(6-Methoxypyridin-3-yl)methyl]-3-oxo-2,3,5,6,7,8-hexahydro[1,2,4]triazolo[4,3-a]pyridine-5-carboxylic acid (390 mg, 1.28 mmol) was initially charged in THF (5.0 ml), and HBTU (632 mg, 1.67 mmol) and N,N-diisopropylethylamine (670 µl, 3.8 mmol) were subsequently added. After stirring at room temperature for 15 min, 3,3-difluoropyrrolidine hydrochloride (221 mg, 1.54 mmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 113 mg (22% of theory) of the title compound were obtained.

LC-MS (Method 4): $R_t$=0.64 min; MS (ESIpos): m/z=394 [M+H]$^+$ $^1$H-NMR (400 MHz, DMSO-d6) δ[ppm]: −0.008 (0.54), 0.008 (0.53), 1.688 (0.41), 1.711 (0.48), 1.970 (0.42), 1.978 (0.42), 1.988 (0.48), 1.996 (0.44), 2.003 (0.43), 2.571 (1.03), 2.587 (1.08), 2.602 (0.57), 3.535 (0.42), 3.544 (0.64), 3.555 (0.70), 3.663 (0.41), 3.697 (0.46), 3.776 (0.65), 3.805 (0.80), 3.826 (16.00), 3.906 (0.47), 4.728 (0.41), 4.737 (0.47), 4.743 (0.54), 4.752 (0.49), 4.766 (6.00), 4.802 (0.43), 4.812 (0.47), 4.817 (0.53), 6.784 (1.80), 6.806 (1.94), 7.553 (1.14), 7.559 (1.17), 7.574 (1.11), 7.580 (1.14), 8.052 (1.50), 8.058 (1.50).

Example 435

(5S)-2-[(5-Chloropyridin-3-yl)methyl]-5-[(3,3-difluoropyrrolidin-1-yl)carbonyl]-5,6,7,8-tetrahydro[1,2,4]triazolo[4,3-a]pyridin-3(2H)-one

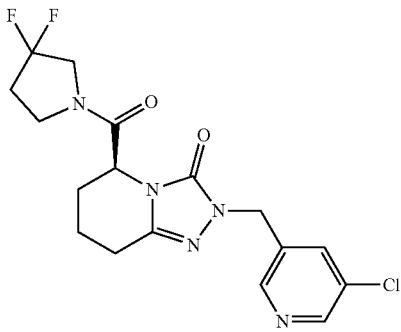 [SMILES: O=C([C@@H]1CCCc2nn(Cc3cncc(Cl)c3)c(=O)n21)N1CCC(F)(F)C1]

(5S)-2-[(5-Chloropyridin-3-yl)methyl]-3-oxo-2,3,5,6,7,8-hexahydro[1,2,4]triazolo[4,3-a]pyridine-5-carboxylic acid (80.3 mg, 260 µmol) was initially charged in THF (2.0 ml), and HBTU (128 mg, 338 µmol) and N,N-diisopropylethylamine (140 µl, 780 µmol) were subsequently added. After stirring at room temperature for 15 min, 3,3-difluoropyrrolidine hydrochloride (44.8 mg, 312 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 32.0 mg (31% of theory) of the title compound were obtained.

LC-MS (Method 4): $R_t$=0.64 min; MS (ESIpos): m/z=398 [M+H]$^+$ $^1$H-NMR (400 MHz, DMSO-d6) δ [ppm]: −0.149 (1.81), −0.008 (16.00), 0.008 (13.78), 0.146 (1.81), 1.672 (0.93), 1.733 (1.14), 1.882 (1.08), 1.975 (1.60), 2.072 (1.08), 2.327 (2.12), 2.366 (2.01), 2.572 (2.84), 2.583 (2.22), 2.598 (2.01), 2.616 (2.22), 2.669 (2.43), 2.709 (1.91), 3.550 (1.55), 3.561 (1.65), 3.670 (0.98), 3.704 (1.19), 3.744 (0.72), 3.777 (1.34), 3.809 (2.01), 3.893 (0.62), 3.911 (1.19), 3.937 (0.83), 3.990 (0.72), 4.033 (0.72), 4.182 (0.72), 4.204 (0.72), 4.765 (0.98), 4.780 (1.34), 4.852 (1.29), 4.917 (13.42), 7.757 (4.34), 8.421 (4.44), 8.562 (4.03), 8.568 (3.77).

Example 436

(5S)-2-[(5-Chloropyridin-3-yl)methyl]-5-[(3-fluoroazetidin-1-yl)carbonyl]-5,6,7,8-tetrahydro[1,2,4]triazolo[4,3-a]pyridin-3(2H)-one

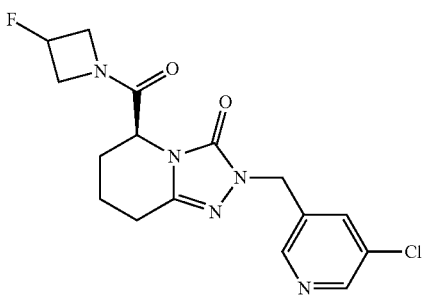 [SMILES: O=C([C@@H]1CCCc2nn(Cc3cncc(Cl)c3)c(=O)n21)N1CC(F)C1]

(5S)-2-[(5-Chloropyridin-3-yl)methyl]-3-oxo-2,3,5,6,7,8-hexahydro[1,2,4]triazolo[4,3-a]pyridine-5-carboxylic acid (80.3 mg, 260 µmol) was initially charged in THF (2.0 ml), and HBTU (128 mg, 338 µmol) and N,N-diisopropylethylamine (140 µl, 780 µmol) were subsequently added. After stirring at room temperature for 15 min, 3-fluoroazetidine hydrochloride (34.8 mg, 312 µmol) was added and the reaction mixture was stirred at room temperature overnight. HBTU (49 mg, 130 µmol) and N,N-diisopropylethylamine (23 µl, 125 µmol) were added again and the mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 49.1 mg (52% of theory) of the title compound were obtained.

LC-MS (Method 4): $R_t$=0.57 min; MS (ESIpos): m/z=366 [M+H]

$^1$H-NMR (400 MHz, DMSO-d6) δ [ppm]: −0.008 (0.83), 0.008 (0.80), 1.651 (0.61), 1.665 (0.79), 1.675 (1.03), 1.690 (1.16), 1.700 (1.51), 1.714 (1.68), 1.723 (1.58), 1.909 (0.49), 1.953 (0.99), 1.963 (1.10), 1.972 (1.01), 1.986 (0.90), 1.995 (0.74), 2.012 (0.88), 2.022 (0.90), 2.032 (0.99), 2.057 (0.66), 2.074 (16.00), 2.520 (1.07), 2.524 (0.97), 2.566 (1.41), 2.573 (1.38), 2.591 (2.03), 2.605 (2.84), 2.618 (1.45), 2.634 (0.55), 2.646 (0.92), 2.660 (0.43), 2.690 (0.60), 3.932 (0.79), 3.962 (0.80), 3.994 (0.79), 4.023 (0.46), 4.215 (0.43), 4.228 (0.70), 4.243 (0.67), 4.257 (0.64), 4.274 (0.83), 4.297 (0.77), 4.327 (0.60), 4.366 (0.55), 4.400 (0.50), 4.461 (0.51), 4.524 (0.43), 4.556 (2.02), 4.568 (2.95), 4.581 (2.13), 4.921 (8.65), 5.192 (0.68), 5.347 (0.77), 5.354 (0.83), 5.402 (0.67), 5.410 (0.72), 5.490 (0.53), 5.497 (0.60), 5.545 (0.50), 5.552 (0.56), 7.775 (2.69), 8.432 (4.55), 8.572 (3.67), 8.577 (3.79).

Example 437

(5S)-2-[(5-Chloropyridin-3-yl)methyl]-5-[(3,3-difluoroazetidin-1-yl)carbonyl]-5,6,7,8-tetrahydro[1,2,4]triazolo[4,3-a]pyridin-3(2H)-one

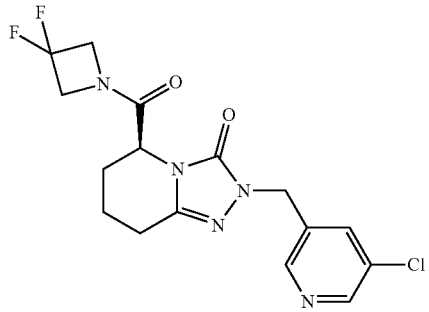 [SMILES: O=C([C@@H]1CCCc2nn(Cc3cncc(Cl)c3)c(=O)n21)N1CC(F)(F)C1]

(5S)-2-[(5-Chloropyridin-3-yl)methyl]-3-oxo-2,3,5,6,7,8-hexahydro[1,2,4]triazolo[4,3-a]pyridine-5-carboxylic acid (80.3 mg, 260 µmol) was initially charged in THF (2.0 ml), and HBTU (128 mg, 338 µmol) and N,N-diisopropylethylamine (140 µl, 780 µmol) were subsequently added. After stirring at room temperature for 15 min, 3,3-difluoroazetidine hydrochloride (40.4 mg, 312 µmol) was added and the reaction mixture was stirred at room temperature for 72 hours. HBTU (49 mg, 130 µmol) and N,N-diisopropylethylamine (23 µl, 125 µmol) were added again and the mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 46.8 mg (47% of theory) of the title compound were obtained.

LC-MS (Method 3): $R_t$=1.31 min; MS (ESIpos): m/z=384 [M+H]

$^1$H-NMR (400 MHz, DMSO-d6) δ [ppm]: −0.149 (0.59), −0.008 (5.47), 0.008 (4.69), 0.146 (0.60), 1.695 (1.59), 1.710 (2.35), 1.720 (2.72), 1.734 (1.99), 1.958 (0.72), 1.970 (0.76), 1.981 (1.13), 1.995 (1.53), 2.027 (0.83), 2.036 (1.05), 2.051 (1.54), 2.061 (1.18), 2.073 (1.96), 2.087 (0.63), 2.327 (0.67), 2.366 (0.54), 2.523 (2.30), 2.565 (1.83), 2.580 (2.04), 2.587 (2.00), 2.600 (2.59), 2.613 (3.34), 2.626 (1.60), 2.641 (0.58), 2.654 (0.92), 2.669 (1.03), 2.710 (0.51), 4.339 (1.04), 4.367 (1.75), 4.390 (1.76), 4.421 (1.05), 4.607 (2.34), 4.622 (3.64), 4.634 (2.33), 4.728 (1.10), 4.758 (1.26), 4.790 (0.59), 4.822 (0.57), 4.851 (1.25), 4.882 (1.12), 4.924 (16.00), 7.768 (5.18), 7.773 (3.13), 8.428 (5.44), 8.432 (5.42), 8.565 (4.90), 8.571 (4.84).

Example 438

(5S)-2-[(5-Chloropyridin-3-yl)methyl]-5-{[(3S)-3-fluoropyrrolidin-1-yl]carbonyl}-5,6,7,8-tetrahydro[1,2,4]triazolo[4,3-a]pyridine-3(2H)-one

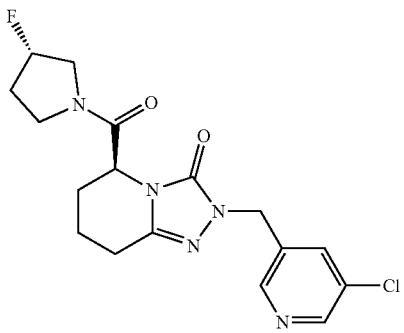 [SMILES: O=C([C@@H]1CCCc2nn(Cc3cncc(Cl)c3)c(=O)n21)N1CC[C@H](F)C1]

(5S)-2-[(5-Chloropyridin-3-yl)methyl]-3-oxo-2,3,5,6,7,8-hexahydro[1,2,4]triazolo[4,3-a]pyridine-5-carboxylic acid (80.3 mg, 260 μmol) was initially charged in THF (2.0 ml), and HBTU (128 mg, 338 μmol) and N,N-diisopropylethylamine (140 μl, 780 μmol) were subsequently added. After stirring at room temperature for 15 min, (3S)-3-fluoropyrrolidine hydrochloride (39.2 mg, 312 μmol) was added and the reaction mixture was stirred at room temperature overnight. HBTU (49 mg, 130 μmol) and N,N-diisopropylethylamine (23 μl, 125 μmol) were added again and the mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 45.6 mg (46% of theory) of the title compound were obtained.

LC-MS (Method 3): $R_t$=1.16 min; MS (ESIpos): m/z=380 [M+H]$^+$ $^1$H-NMR (400 MHz, DMSO-d6) δ [ppm]: −0.008 (1.20), 0.008 (0.99), 1.177 (0.44), 1.410 (0.46), 1.700 (1.25), 1.711 (1.50), 1.725 (2.19), 1.734 (2.40), 1.877 (0.52), 1.911 (0.70), 1.997 (0.86), 2.029 (1.30), 2.051 (0.98), 2.067 (1.28), 2.078 (1.62), 2.088 (1.79), 2.103 (2.22), 2.138 (1.51), 2.221 (0.81), 2.242 (0.75), 2.270 (1.07), 2.524 (1.52), 2.566 (1.62), 2.570 (1.54), 2.576 (1.72), 2.592 (1.47), 2.619 (2.43), 2.661 (1.02), 2.670 (0.75), 2.891 (0.42), 3.274 (0.51), 3.293 (0.65), 3.303 (0.97), 3.321 (1.00), 3.331 (0.68), 3.349 (0.59), 3.362 (0.61), 3.371 (0.69), 3.398 (0.80), 3.406 (0.81), 3.460 (0.67), 3.468 (0.69), 3.495 (0.93), 3.504 (0.91), 3.613 (0.95), 3.637 (3.39), 3.655 (3.06), 3.660 (3.02), 3.681 (3.39), 3.705 (3.85), 3.723 (4.42), 3.743 (5.52), 3.770 (4.46), 3.778 (4.07), 3.816 (2.19), 3.855 (3.39), 4.695 (1.16), 4.704 (1.42), 4.710 (1.48), 4.719 (1.18), 4.752 (1.50), 4.761 (1.71), 4.768 (1.94), 4.776 (1.44), 4.915 (16.00), 5.260 (1.18), 5.384 (1.48), 5.391 (1.55), 5.512 (0.86), 7.756 (4.66), 7.761 (5.11), 8.422 (6.31), 8.564 (5.64), 8.569 (5.61).

Example 439

(5S)-2-[(5-Chloropyridin-3-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

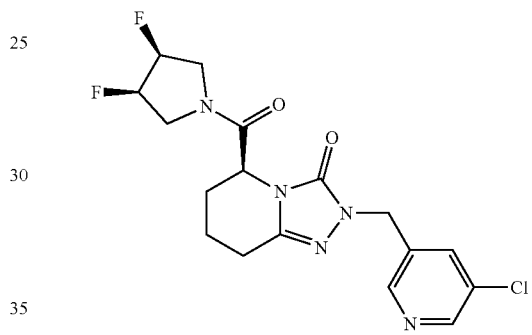

(5S)-2-[(5-Chloropyridin-3-yl)methyl]-3-oxo-2,3,5,6,7,8-hexahydro[1,2,4]triazolo[4,3-a]pyridine-5-carboxylic acid (80.3 mg, 260 μmol) was initially charged in THF (2.0 ml), and HBTU (128 mg, 338 μmol) and N,N-diisopropylethylamine (140 μl, 780 μmol) were subsequently added. After stirring at room temperature for 15 min, (3R,4S)-3,4-difluoropyrrolidine hydrochloride (44.8 mg, 312 μmol) was added and the reaction mixture was stirred at room temperature overnight. HBTU (49 mg, 130 μmol) and N,N-diisopropylethylamine (23 μl, 125 mol) were added again and the mixture was stirred at room temperature for 72 hours. 1-[Bis(dimethylamino)methylene]-1H-benzotriazol-1-ium 3-oxide hexafluorophosphate (49 mg, 130 μmol), N,N-diisopropylethylamine (23 μl, 125 μmol) and (3R,4S)-3,4-difluoropyrrolidine hydrochloride (19 mg, 130 μmol) were added again and the mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 15.1 mg (15% of theory) of the title compound were obtained.

LC-MS (Method 3): $R_t$=1.18 min; MS (ESIpos): m/z=398 [M+H]$^+$ $^1$H-NMR (400 MHz, DMSO-d6) δ [ppm]: −0.149 (0.42), −0.008 (4.20), 0.008 (3.95), 0.146 (0.45), 1.659 (1.27), 1.685 (0.73), 1.732 (1.72), 1.938 (0.60), 1.972 (1.30), 1.994 (1.06), 2.014 (1.71), 2.038 (1.11), 2.049 (1.17), 2.056 (1.27), 2.064 (1.29), 2.073 (3.97), 2.084 (0.91), 2.091 (0.96), 2.099

(0.83), 2.327 (0.49), 2.366 (0.60), 2.523 (2.56), 2.561 (1.97), 2.565 (1.88), 2.576 (2.48), 2.586 (1.71), 2.591 (1.64), 2.600 (2.40), 2.614 (3.24), 2.626 (1.90), 2.645 (0.71), 2.656 (1.13), 2.669 (1.04), 2.709 (0.60), 2.829 (0.45), 2.849 (0.88), 2.867 (0.47), 3.456 (0.56), 3.481 (0.65), 3.490 (1.14), 3.501 (0.87), 3.524 (1.00), 3.536 (1.37), 3.545 (1.36), 3.555 (0.84), 3.568 (0.57), 3.578 (0.75), 3.588 (0.49), 3.618 (0.81), 3.631 (0.91), 3.650 (0.57), 3.664 (0.71), 3.673 (0.92), 3.687 (1.51), 3.704 (1.64), 3.714 (6.37), 3.725 (1.80), 3.741 (1.11), 3.756 (1.34), 3.768 (1.56), 3.789 (0.84), 3.802 (0.68), 3.871 (0.84), 3.890 (0.49), 3.913 (0.73), 3.925 (0.89), 3.939 (0.91), 3.954 (0.54), 3.975 (0.88), 3.989 (0.94), 4.004 (0.58), 4.018 (0.54), 4.133 (0.54), 4.148 (0.71), 4.161 (0.62), 4.175 (1.03), 4.188 (0.69), 4.201 (0.58), 4.216 (0.57), 4.801 (2.22), 4.813 (3.34), 4.823 (2.17), 4.917 (16.00), 5.255 (0.84), 5.266 (0.88), 5.276 (1.00), 5.287 (0.83), 5.298 (0.62), 5.312 (0.61), 5.330 (0.73), 5.338 (0.71), 5.351 (0.76), 5.366 (0.69), 5.379 (0.91), 5.389 (1.06), 5.399 (0.85), 5.408 (0.95), 5.417 (0.85), 5.429 (0.65), 5.442 (0.64), 5.451 (0.68), 5.458 (0.71), 5.473 (0.76), 5.481 (0.75), 5.495 (0.62), 6.826 (1.08), 6.847 (1.30), 7.099 (1.17), 7.121 (1.00), 7.753 (3.97), 7.758 (4.19), 8.419 (5.98), 8.564 (4.00).

Example 440

(5S)-2-{[5-Chloro-6-(trifluoromethyl)pyridin-3-yl]methyl}-5-{[(3R,4S)-3,4-difluoropyrrolidin-1-yl]carbonyl}-5,6,7,8-tetrahydro[1,2,4]triazolo[4,3-a]pyridin-3(2H)-one

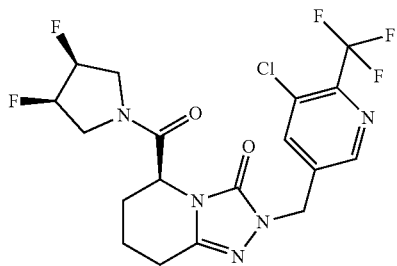 [SMILES: O=C([C@@H]1CCCc2nn(Cc3cnc(C(F)(F)F)c(Cl)c3)c(=O)n21)N1C[C@@H](F)[C@@H](F)C1]

(5S)-2-{[5-Chloro-6-(trifluoromethyl)pyridin-3-yl]methyl}-3-oxo-2,3,5,6,7,8-hexahydro[1,2,4]triazolo[4,3-a]pyridine-5-carboxylic acid (35.0 mg, 92.9 µmol) was initially charged in THF (2.0 ml), and HBTU (45.8 mg, 121 µmol) and N,N-diisopropylethylamine (49 µl, 280 µmol) were subsequently added. After stirring at room temperature for 15 min, (3R,4S)-3,4-difluoropyrrolidine hydrochloride (16.0 mg, 111 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 25.0 mg (58% of theory) of the title compound were obtained.

LC-MS (Method 3): $R_t$=1.53 min; MS (ESIpos): m/z=466 [M+H]$^+$ $^1$H-NMR (400 MHz, DMSO-d6) δ [ppm]: −0.150 (1.49), −0.008 (13.42), 0.008 (10.58), 0.146 (1.49), 1.640 (1.49), 1.752 (1.90), 2.032 (2.58), 2.073 (2.31), 2.328 (4.34), 2.366 (2.98), 2.523 (12.20), 2.583 (2.85), 2.622 (3.39), 2.670 (4.88), 2.710 (3.12), 3.494 (1.63), 3.621 (1.22), 3.691 (2.17), 3.930 (1.08), 3.979 (1.08), 4.176 (1.22), 4.826 (3.80), 5.041 (16.00), 5.390 (1.36), 7.035 (9.63), 8.066 (6.10), 8.538 (8.14).

Example 441

(5S)-2-{[5-Chloro-6-(trifluoromethyl)pyridin-3-yl]methyl}-5-[(3,3-difluoropyrrolidin-1-yl)carbonyl]-5,6,7,8-tetrahydro[1,2,4]triazolo[4,3-a]pyridin-3(2H)-one

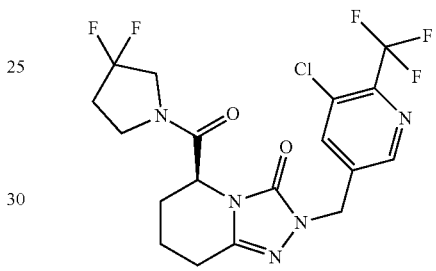

(5S)-2-{[5-Chloro-6-(trifluoromethyl)pyridin-3-yl]methyl}-3-oxo-2,3,5,6,7,8-hexahydro[1,2,4]triazolo[4,3-a]pyridine-5-carboxylic acid (35.0 mg, 92.9 µmol) was initially charged in THF (2.0 ml), and HBTU (45.8 mg, 121 µmol) and N,N-diisopropylethylamine (49 µl, 280 µmol) were subsequently added. After stirring at room temperature for 15 min, 3,3-difluoropyrrolidine hydrochloride (16.0 mg, 111 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 27.0 mg (62% of theory) of the title compound were obtained.

LC-MS (Method 3): $R_t$=1.60 min; MS (ESIpos): m/z=466 [M+H]$^+$ $^1$H-NMR (400 MHz, DMSO-d6) δ [ppm]: −0.149 (1.15), −0.008 (10.01), 0.008 (8.29), 0.146 (1.04), 1.656 (1.27), 1.746 (1.61), 2.020 (2.07), 2.327 (2.65), 2.366 (3.57), 2.383 (1.15), 2.411 (1.50), 2.432 (1.50), 2.452 (1.38), 2.523 (11.28), 2.564 (4.14), 2.579 (3.22), 2.590 (3.68), 2.604 (2.99), 2.623 (3.34), 2.665 (3.11), 2.669 (3.34), 2.709 (2.99), 3.542 (1.84), 3.563 (2.65), 3.573 (1.50), 3.582 (1.38), 3.676 (1.61), 3.709 (1.73), 3.745 (1.38), 3.778 (1.96), 3.813 (2.99), 3.831 (0.81), 3.894 (0.92), 3.912 (1.73), 3.939 (1.15), 3.996 (1.15), 4.038 (1.04), 4.067 (0.69), 4.154 (0.58), 4.186 (0.92), 4.210 (0.92), 4.242 (0.46), 4.781 (1.38), 4.795 (1.96), 4.805 (1.38), 4.849 (1.50), 4.864 (1.96), 4.873 (1.38), 5.040 (16.00), 8.068 (5.99), 8.538 (5.87).

Example 442

(5S)-2-[(5-Chloro-6-methoxypyridin-3-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

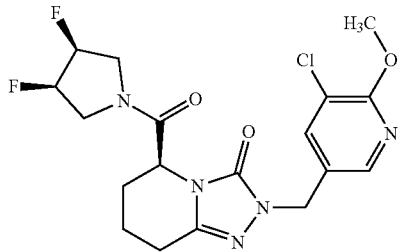 [SMILES: COc1ncc(Cn2nc3n(c2=O)[C@H](C(=O)N2C[C@@H](F)[C@@H](F)C2)CCC3)cc1Cl]

(5S)-2-[(5-Chloro-6-methoxypyridin-3-yl)methyl]-3-oxo-2,3,5,6,7,8-hexahydro[1,2,4]triazolo[4,3-a]pyridine-5-carboxylic acid (80.0 mg, 236 μmol) was initially charged in THF (2.0 ml), and HBTU (116 mg, 307 μmol) and N,N-diisopropylethylamine (120 μl, 710 μmol) were subsequently added. After stirring at room temperature for 15 min, (3R,4S)-3,4-difluoropyrrolidine hydrochloride (40.7 mg, 283 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 37.0 mg (37% of theory) of the title compound were obtained.

LC-MS (Method 4): $R_t$=0.72 min; MS (ESIpos): m/z=428 [M+H]$^+$ $^1$H-NMR (400 MHz, DMSO-d6) δ [ppm]: −0.008 (2.46), 0.008 (2.19), 1.654 (0.57), 1.723 (0.70), 1.956 (0.53), 2.001 (0.70), 2.024 (0.45), 2.035 (0.49), 2.043 (0.55), 2.051 (0.51), 2.060 (0.43), 2.073 (2.65), 2.562 (1.13), 2.572 (0.79), 2.586 (1.04), 2.599 (1.36), 2.611 (0.79), 2.642 (0.49), 2.670 (0.45), 3.486 (0.49), 3.523 (0.43), 3.532 (0.57), 3.541 (0.57), 3.626 (0.43), 3.668 (0.43), 3.682 (0.62), 3.700 (0.74), 3.721 (0.62), 3.734 (0.42), 3.751 (0.49), 3.765 (0.51), 3.924 (14.47), 3.926 (16.00), 3.972 (0.42), 3.985 (0.43), 4.171 (0.48), 4.792 (1.87), 4.804 (8.38), 5.254 (0.42), 5.266 (0.43), 5.276 (0.47), 5.375 (0.45), 5.388 (0.51), 5.399 (0.42), 5.407 (0.40), 7.739 (1.63), 7.745 (2.99), 7.750 (1.89), 8.015 (1.65), 8.021 (3.08), 8.026 (1.76).

Example 443

(5S)-2-[(5-Chloro-6-methoxypyridin-3-yl)methyl]-5-[(3,3-difluoropyrrolidin-1-yl)carbonyl]-5,6,7,8-tetrahydro[1,2,4]triazolo[4,3-a]pyridin-3(2H)-one

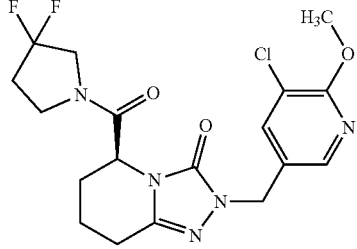 [SMILES: COc1ncc(Cn2nc3n(c2=O)[C@H](C(=O)N2CCC(F)(F)C2)CCC3)cc1Cl]

(5S)-2-[(5-Chloro-6-methoxypyridin-3-yl)methyl]-3-oxo-2,3,5,6,7,8-hexahydro[1,2,4]triazolo[4,3-a]pyridine-5-carboxylic acid (80.0 mg, 236 μmol) was initially charged in THF (2.0 ml), and HBTU (116 mg, 307 μmol) and N,N-diisopropylethylamine (120 μl, 710 mol) were subsequently added. After stirring at room temperature for 15 min, 3,3-difluoropyrrolidine hydrochloride (40.7 mg, 283 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 35.0 mg (35% of theory) of the title compound were obtained.

LC-MS (Method 3): $R_t$=1.41 min; MS (ESIpos): m/z=428 [M+H]$^+$ $^1$H-NMR (400 MHz, DMSO-d6) δ [ppm]: −0.008 (2.15), 0.008 (1.91), 1.722 (0.45), 1.972 (0.71), 1.996 (0.50), 2.073 (0.45), 2.328 (0.43), 2.524 (1.63), 2.569 (1.20), 2.586 (1.03), 2.601 (1.03), 2.670 (0.49), 3.528 (0.41), 3.537 (0.45), 3.546 (0.65), 3.557 (0.73), 3.667 (0.43), 3.700 (0.49), 3.775 (0.64), 3.805 (0.84), 3.909 (0.58), 3.925 (16.00), 4.759 (0.54), 4.769 (0.41), 4.805 (6.06), 4.832 (0.60), 4.842 (0.49), 7.744 (2.13), 7.749 (2.24), 8.020 (1.96), 8.025 (1.94).

Example 444

(5S)-5-{[(3S)-3-Fluoropyrrolidin-1-yl]carbonyl}-2-[3-(trifluoromethyl)benzyl]-5,6,7,8-tetrahydro[1,2,4]triazolo[4,3-a]pyridin-3(2H)-one

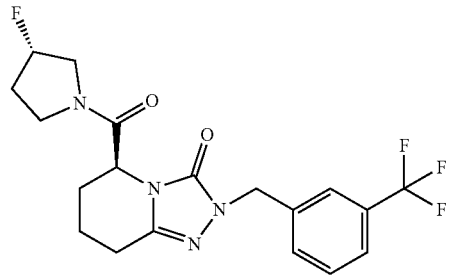 [SMILES: O=C([C@@H]1CCCc2nn(Cc3cccc(C(F)(F)F)c3)c(=O)n21)N1CC[C@H](F)C1]

(5S)-3-Oxo-2-[3-(trifluoromethyl)benzyl]-2,3,5,6,7,8-hexahydro[1,2,4]triazolo[4,3-a]pyridine-5-carboxylic acid (70.0 mg, 205 μmol) was initially charged in THF (3.0 ml), and HATU (101 mg, 267 μmol) and triethylamine (86 μl, 620 μmol) were subsequently added. After stirring at room temperature for 15 min, (3S)-3-fluoropyrrolidine hydrochloride (30.9 mg, 246 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 36.9 mg (44% of theory) of the title compound were obtained.

LC-MS (Method 3): $R_t$=1.49 min; MS (ESIpos): m/z=413 [M+H]$^+$ $^1$H-NMR (400 MHz, DMSO-d6) δ [ppm]: −0.008 (1.84), 0.008 (1.64), 1.163 (0.63), 1.633 (0.62), 1.642 (0.77), 1.655 (0.92), 1.667 (1.04), 1.681 (0.99), 1.707 (1.53), 1.719 (2.14), 1.731 (2.70), 1.741 (2.21), 1.909 (0.49), 1.968 (0.74), 1.997 (2.63), 2.027 (1.41), 2.037 (1.44), 2.049 (1.05), 2.065 (1.42), 2.072 (3.24), 2.080 (1.67), 2.089 (1.84), 2.101 (2.01), 2.137 (1.51), 2.174 (0.50), 2.220 (0.91), 2.257 (1.10), 2.269 (1.15), 2.327 (0.55), 2.366 (0.43), 2.523 (2.43), 2.567 (2.31), 2.584 (1.52), 2.597 (1.92), 2.609 (3.44), 2.621 (2.07), 2.639 (0.82), 2.650 (1.26), 2.665 (0.98), 2.710 (0.48), 3.274 (0.47), 3.352 (0.69), 3.363 (1.15), 3.381 (0.87), 3.393 (0.71), 3.407 (0.80), 3.468 (0.52), 3.494 (0.59), 3.505 (1.14), 3.524 (1.79), 3.552 (1.39), 3.570 (1.09), 3.596 (2.27), 3.613 (0.45), 3.638 (1.50), 3.655 (1.92), 3.681 (1.22), 3.696 (0.75), 3.724 (0.78), 3.744 (1.50), 3.772 (1.20), 3.784 (1.18), 3.855 (1.53), 3.922 (0.58), 3.946 (1.15), 3.969 (0.53), 3.983 (0.47), 4.011 (0.55), 4.043 (0.44), 4.698 (0.75), 4.706 (0.90), 4.713 (0.96), 4.722 (0.74), 4.754 (0.99), 4.763 (1.08), 4.770 (1.21), 4.779 (0.91), 4.824 (0.79), 4.838 (1.28), 4.848 (0.82), 4.861 (0.92), 4.869 (1.02), 4.876 (1.13), 4.885 (1.03), 4.930 (16.00), 5.261 (1.04), 5.270 (1.03), 5.348 (0.69), 5.393 (1.16), 5.481 (0.68), 5.512 (0.56), 7.508 (2.41), 7.527 (4.04), 7.572 (2.77), 7.591 (5.41), 7.620 (5.71), 7.648 (4.73), 7.667 (2.61).

Example 445

(5S)-5-{[(3R,4S)-3,4-Difluoropyrrolidin-1-yl]carbonyl}-2-[3-(trifluoromethyl)benzyl]-5,6,7,8-tetrahydro[1,2,4]triazolo[4,3-a]pyridin-3(2H)-one

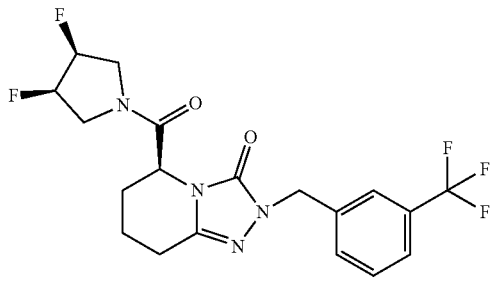 [SMILES: O=C([C@@H]1CCCc2nn(Cc3cccc(C(F)(F)F)c3)c(=O)n21)N1C[C@@H](F)[C@@H](F)C1]

(5S)-3-Oxo-2-[3-(trifluoromethyl)benzyl]-2,3,5,6,7,8-hexahydro[1,2,4]triazolo[4,3-a]pyridine-5-carboxylic acid (60.0 mg, 176 µmol) was initially charged in THF (3.0 ml), and HBTU (86.7 mg, 229 µmol) and N,N-diisopropylethylamine (92 µl, 530 µmol) were subsequently added. After stirring at room temperature for 15 min, (3R,4S)-3,4-difluoropyrrolidine hydrochloride (30.3 mg, 211 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 41.9 mg (55% of theory) of the title compound were obtained.

LC-MS (Method 4): $R_t$=0.85 min; MS (ESIpos): m/z=431 [M+H]$^+$ $^1$H-NMR (400 MHz, DMSO-d6) δ [ppm]: −0.149 (0.53), −0.008 (5.75), 0.008 (4.69), 0.146 (0.53), 1.244 (0.79), 1.259 (0.86), 1.274 (0.53), 1.667 (1.25), 1.731 (1.52), 1.937 (0.51), 1.971 (1.17), 2.012 (1.57), 2.036 (1.01), 2.054 (1.16), 2.063 (1.11), 2.073 (2.67), 2.090 (0.92), 2.327 (0.74), 2.366 (0.63), 2.523 (3.53), 2.570 (2.56), 2.580 (1.83), 2.594 (2.36), 2.608 (3.14), 2.620 (1.85), 2.651 (1.14), 2.665 (1.16), 2.669 (1.07), 2.710 (0.78), 3.033 (0.43), 3.403 (0.58), 3.455 (0.63), 3.490 (1.27), 3.499 (0.92), 3.512 (1.11), 3.521 (1.12), 3.532 (0.99), 3.544 (1.06), 3.565 (0.56), 3.574 (0.79), 3.616 (0.86), 3.630 (0.96), 3.649 (0.56), 3.671 (0.94), 3.685 (1.75), 3.699 (1.24), 3.719 (1.37), 3.732 (1.22), 3.751 (0.99), 3.762 (1.02), 3.785 (0.59), 3.797 (0.51), 3.871 (0.81), 3.926 (0.79), 3.941 (0.89), 3.955 (0.56), 3.976 (0.89), 3.990 (0.88), 4.005 (0.53), 4.018 (0.48), 4.134 (0.54), 4.149 (0.61), 4.162 (0.59), 4.176 (0.99), 4.190 (0.68), 4.202 (0.63), 4.218 (0.58), 4.803 (2.28), 4.816 (3.22), 4.825 (2.15), 4.930 (16.00), 5.266 (0.86), 5.277 (0.99), 5.298 (0.64), 5.330 (0.73), 5.339 (0.71), 5.352 (0.79), 5.366 (0.71), 5.376 (0.92), 5.390 (1.06), 5.400 (0.86), 5.409 (0.94), 5.443 (0.63), 5.473 (0.73), 5.482 (0.76), 5.495 (0.59), 7.505 (1.73), 7.524 (2.86), 7.572 (1.90), 7.591 (3.72), 7.614 (6.46), 7.648 (3.85), 7.668 (2.18).

Example 446

(5S)-5-[(3,3-Difluoropyrrolidin-1-yl)carbonyl]-2-[3-(trifluoromethyl)benzyl]-5,6,7,8-tetrahydro[1,2,4]triazolo[4,3-a]pyridin-3(2H)-one

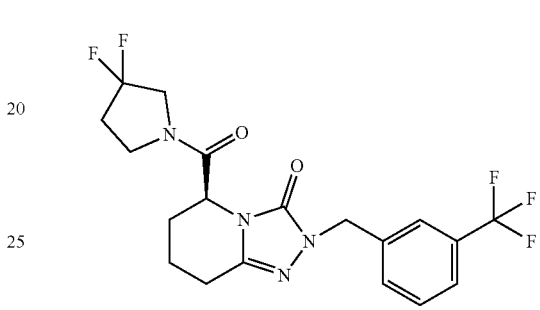

(5S)-3-Oxo-2-[3-(trifluoromethyl)benzyl]-2,3,5,6,7,8-hexahydro[1,2,4]triazolo[4,3-a]pyridine-5-carboxylic acid (60.0 mg, 176 µmol) was initially charged in THF (3.0 ml), and HBTU (86.7 mg, 229 µmol) and N,N-diisopropylethylamine (92 µl, 530 µmol) were subsequently added. After stirring at room temperature for 15 min, 3,3-difluoropyrrolidine hydrochloride (30.3 mg, 211 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 38.0 mg (50% of theory) of the title compound were obtained.

LC-MS (Method 3): $R_t$=1.62 min; MS (ESIpos): m/z=431 [M+H]$^+$ $^1$H-NMR (400 MHz, DMSO-d6) δ [ppm]: −0.008 (3.35), 0.008 (3.36), 0.146 (0.40), 1.672 (1.05), 1.681 (0.96), 1.695 (0.89), 1.720 (1.32), 1.731 (1.28), 1.872 (0.59), 1.972 (1.05), 1.986 (1.17), 2.001 (1.31), 2.013 (1.47), 2.041 (1.03), 2.049 (1.03), 2.057 (1.00), 2.066 (0.92), 2.072 (0.98), 2.085 (0.76), 2.092 (0.66), 2.327 (0.56), 2.366 (0.78), 2.381 (0.85), 2.410 (1.01), 2.430 (0.96), 2.452 (0.79), 2.523 (2.83), 2.576 (2.41), 2.591 (2.53), 2.608 (2.78), 2.620 (1.36), 2.640 (0.54), 2.652 (0.84), 2.665 (0.79), 2.710 (0.57), 3.537 (1.29), 3.549 (1.82), 3.557 (1.97), 3.568 (1.11), 3.576 (1.01), 3.648 (1.56), 3.670 (1.23), 3.703 (1.36), 3.738 (1.12), 3.772 (1.54), 3.783 (1.03), 3.791 (0.84), 3.808 (1.83), 3.828 (0.65), 3.839 (0.48), 3.894 (0.62), 3.913 (1.56), 3.932 (0.75), 3.939 (0.96), 3.958 (0.61), 3.991 (0.82), 4.005 (0.42), 4.019 (0.56), 4.033 (0.75), 4.061 (0.45), 4.149 (0.46), 4.181 (0.73), 4.208 (0.71), 4.767 (1.12), 4.776 (1.31), 4.782 (1.45), 4.792 (1.06), 4.840 (1.14), 4.850 (1.29), 4.855 (1.47), 4.865 (1.09), 4.931 (16.00), 7.506 (2.20), 7.525 (3.60), 7.572 (2.11), 7.591 (4.15), 7.616 (5.26), 7.648 (3.33), 7.668 (1.87).

Example 447

(5S)-5-[(3-Fluoroazetidin-1-yl)carbonyl]-2-[3-(trifluoromethyl)benzyl]-5,6,7,8-tetrahydro[1,2,4]triazolo[4,3-a]pyridin-3(2H)-one

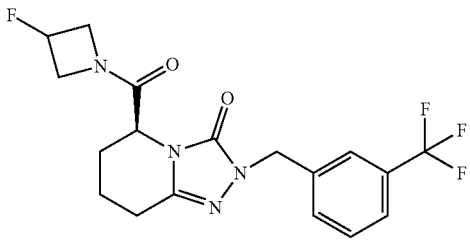 [SMILES: O=C([C@@H]1CCCc2nn(Cc3cccc(C(F)(F)F)c3)c(=O)n21)N1CC(F)C1]

(5S)-3-Oxo-2-[3-(trifluoromethyl)benzyl]-2,3,5,6,7,8-hexahydro[1,2,4]triazolo[4,3-a]pyridine-5-carboxylic acid (60.0 mg, 176 μmol) was initially charged in THF (3.0 ml), and HBTU (86.7 mg, 229 μmol) and N,N-diisopropylethylamine (92 μl, 530 μmol) were subsequently added. After stirring at room temperature for 15 min, 3-fluoroazetidine hydrochloride (23.5 mg, 211 mol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 30.5 mg (44% of theory) of the title compound were obtained.

LC-MS (Method 4): $R_t$=0.80 min; MS (ESIpos): m/z=399 [M+H]$^+$ $^1$H-NMR (400 MHz, DMSO-d6) δ [ppm]: −0.149 (1.79), −0.008 (16.00), 0.008 (13.70), 0.146 (1.87), 1.708 (2.94), 1.961 (1.58), 2.327 (2.73), 2.366 (2.51), 2.523 (9.47), 2.584 (3.52), 2.599 (4.52), 2.613 (2.44), 2.641 (1.65), 2.669 (3.16), 2.709 (2.80), 3.928 (1.15), 3.959 (1.22), 3.990 (1.22), 4.266 (1.29), 4.290 (1.22), 4.463 (0.72), 4.554 (2.87), 4.566 (4.23), 4.931 (12.77), 5.353 (0.79), 5.495 (0.79), 7.511 (2.44), 7.529 (4.23), 7.572 (2.22), 7.590 (4.30), 7.621 (5.88), 7.649 (4.66), 7.669 (2.65).

Example 448

(5S)-5-{[(3S)-3-Fluoropyrrolidin-1-yl]carbonyl}-2-[4-fluoro-3-(trifluoromethyl)benzyl]-5,6,7,8-tetrahydro[1,2,4]triazolo[4,3-a]pyridin-3(2H)-one

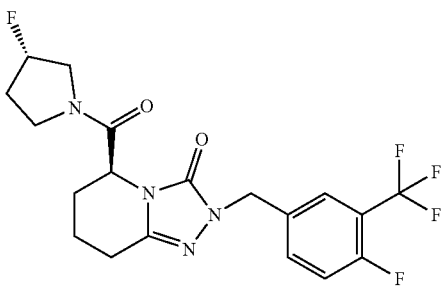 [SMILES: O=C([C@@H]1CCCc2nn(Cc3ccc(F)c(C(F)(F)F)c3)c(=O)n21)N1CC[C@H](F)C1]

(5S)-2-[4-Fluoro-3-(trifluoromethyl)benzyl]-3-oxo-2,3,5,6,7,8-hexahydro[1,2,4]triazolo[4,3-a]pyridine-5-carboxylic acid (61.0 mg, 170 μmol) was initially charged in THF (2.1 ml) at room temperature. Subsequently, HATU (83.9 mg, 221 μmol) and triethylamine (71 μl, 510 μmol) were added. After stirring for 15 min, (3S)-3-fluoropyrrolidine hydrochloride (25.6 mg, 204 μmol) was added and the reaction mixture was stirred at room temperature for 72 hours. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 38.0 mg (52% of theory) of the title compound were obtained.

LC-MS (Method 3): $R_t$=1.53 min; MS (ESIpos): m/z=431 [M+H]$^+$ $^1$H-NMR (400 MHz, DMSO-d6) δ [ppm]: −0.150 (1.93), −0.008 (16.00), 0.008 (15.16), 0.146 (2.01), 1.727 (1.51), 2.077 (1.26), 2.327 (5.70), 2.366 (3.43), 2.523 (15.58), 2.606 (1.76), 2.669 (5.78), 2.710 (2.85), 3.652 (1.09), 3.852 (0.84), 4.908 (7.71), 5.400 (0.84), 7.481 (1.26), 7.502 (2.18), 7.528 (1.93), 7.577 (1.42), 7.685 (1.68).

Example 449

(5S)-2-[4-Fluoro-3-(trifluoromethyl)benzyl]-5-[(3-hydroxyazetidin-1-yl)carbonyl]-5,6,7,8-tetrahydro[1,2,4]triazolo[4,3-a]pyridin-3(2H)-one

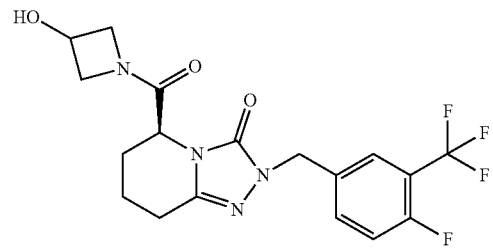 [SMILES: O=C([C@@H]1CCCc2nn(Cc3ccc(F)c(C(F)(F)F)c3)c(=O)n21)N1CC(O)C1]

(5S)-2-[4-Fluoro-3-(trifluoromethyl)benzyl]-3-oxo-2,3,5,6,7,8-hexahydro[1,2,4]triazolo[4,3-a]pyridine-5-carboxylic acid (60.0 mg, 167 μmol) was initially charged in THF at room temperature. Subsequently, HBTU (82.3 mg, 217 μmol) and N,N-diisopropylethylamine (87 μl, 500 μmol) were added. After stirring for 15 min, azetidin-3-ol hydrochloride (22.0 mg, 200 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 32.0 mg (46% of theory) of the title compound were obtained.

LC-MS (Method 3): R$_t$=1.29 min; MS (ESIpos): m/z=415 [M+H]$^+$ $^1$H-NMR (400 MHz, DMSO-d6) δ[ppm]: −0.008 (2.18), 0.008 (1.77), 1.662 (1.86), 1.710 (2.59), 1.719 (2.65), 1.732 (2.18), 1.906 (1.39), 1.919 (1.36), 1.931 (2.08), 1.942 (3.09), 1.954 (2.81), 1.964 (1.67), 1.993 (1.96), 2.003 (2.15), 2.012 (1.89), 2.029 (1.51), 2.328 (0.66), 2.367 (0.50), 2.519 (3.50), 2.524 (3.94), 2.566 (2.08), 2.580 (2.81), 2.592 (5.24), 2.605 (2.75), 2.621 (1.23), 2.634 (1.93), 2.646 (0.85), 2.670 (0.73), 2.675 (0.57), 2.710 (0.54), 3.596 (1.61), 3.603 (1.89), 3.621 (2.05), 3.630 (2.65), 3.646 (1.86), 3.660 (1.74), 3.671 (1.74), 3.920 (2.05), 3.932 (2.34), 3.952 (0.57), 4.021 (3.63), 4.045 (3.85), 4.054 (2.08), 4.062 (1.93), 4.101 (1.39), 4.116 (1.74), 4.127 (1.45), 4.142 (1.33), 4.339 (1.45), 4.357 (2.43), 4.378 (1.67), 4.485 (2.62), 4.502 (5.08), 4.515 (6.28), 4.526 (6.94), 4.537 (5.24), 4.551 (2.21), 4.905 (16.00), 4.910 (15.78), 5.791 (2.78), 5.803 (6.75), 5.817 (3.47), 7.476 (1.86), 7.501 (4.51), 7.525 (3.22), 7.565 (2.97), 7.570 (3.16), 7.577 (3.50), 7.598 (1.80), 7.674 (4.45), 7.691 (4.45).

Example 450

(5S)-5-{[(3S)-3-Fluoropyrrolidin-1-yl]carbonyl}-2-{[2-(trifluoromethyl)pyridin-4-yl]methyl}-5,6,7,8-tetrahydro[1,2,4]triazolo[4,3-a]pyridin-3(2H)-one

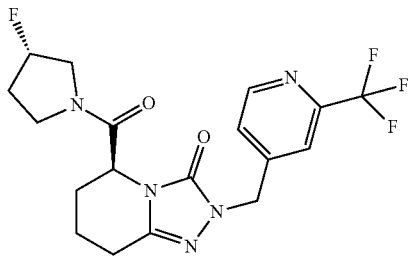 [SMILES: O=C([C@@H]1CCCc2nn(Cc3ccnc(C(F)(F)F)c3)c(=O)n21)N1CC[C@H](F)C1]

(5S)-3-Oxo-2-{[2-(trifluoromethyl)pyridin-4-yl]methyl}-2,3,5,6,7,8-hexahydro[1,2,4]triazolo[4,3-a]pyridine-5-carboxylic acid (100 mg, 292 µmol) was initially charged in DMF (3.3 ml) at room temperature. Subsequently, HBTU (144 mg, 380 µmol) and N,N-diisopropylethylamine (150 µl, 880 µmol) were added. After stirring for 15 min, (3S)-3-fluoropyrrolidine hydrochloride (44.0 mg, 351 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 65.8 mg (54% of theory) of the title compound were obtained.

LC-MS (Method 3): R$_t$=1.18 min; MS (ESIpos): m/z=414 [M+H]$^+$ $^1$H-NMR (400 MHz, DMSO-d6) δ [ppm]: −0.149 (1.51), −0.008 (16.00), 0.008 (10.48), 0.146 (1.36), 1.751 (1.65), 1.952 (0.65), 2.104 (1.79), 2.271 (1.00), 2.323 (3.01), 2.328 (3.80), 2.366 (3.16), 2.518 (15.50), 2.523 (12.84), 2.565 (1.79), 2.580 (1.29), 2.607 (1.15), 2.634 (2.01), 2.670 (4.16), 2.710 (2.94), 3.413 (0.72), 3.474 (0.43), 3.502 (0.65), 3.637 (1.79), 3.654 (1.72), 3.679 (1.22), 3.703 (0.79), 3.753 (1.29), 3.777 (1.22), 3.790 (0.93), 3.857 (1.87), 4.722 (0.93), 4.731 (1.22), 4.780 (1.15), 4.795 (1.51), 5.027 (12.27), 5.261 (1.00), 5.383 (1.15), 5.512 (0.72), 7.486 (2.44), 7.752 (5.31), 8.729 (3.87), 8.741 (3.95).

Example 451

(5S)-5-[(3,3-Difluoropyrrolidin-1-yl)carbonyl]-2-(4-fluorobenzyl)-5,6,7,8-tetrahydro[1,2,4]triazolo[4,3-a]pyridin-3(2H)-one

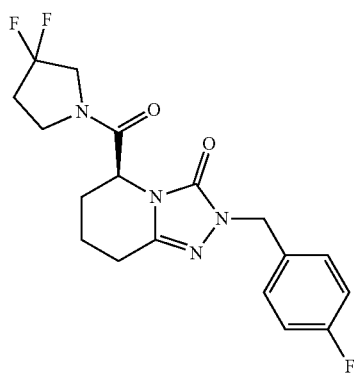 [SMILES: O=C([C@@H]1CCCc2nn(Cc3ccc(F)cc3)c(=O)n21)N1CCC(F)(F)C1]

(5S)-2-(4-Fluorobenzyl)-3-oxo-2,3,5,6,7,8-hexahydro[1,2,4]triazolo[4,3-a]pyridine-5-carboxylic acid (62.8 mg, 215 µmol) was initially charged in THF (2.0 ml, 25 mmol), and HBTU (106 mg, 280 µmol) and N,N-diisopropylethylamine (110 µl, 650 µmol) were subsequently added. After stirring at room temperature for 15 min, 3,3-difluoropyrrolidine hydrochloride (37.1 mg, 259 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 34.6 mg (42% of theory) of the title compound were obtained.

LC-MS (Method 3): R$_t$=1.38 min; MS (ESIpos): m/z=381 [M+H]$^+$ $^1$H-NMR (400 MHz, DMSO-d6) δ[ppm]: −0.149 (1.79), −0.008 (16.00), 0.008 (12.60), 0.146 (1.70), 1.710 (1.61), 1.995 (1.52), 2.042 (1.07), 2.327 (1.97), 2.366 (1.70), 2.380 (0.98), 2.410 (1.16), 2.565 (3.40), 2.580 (2.86), 2.597 (2.86), 2.638 (1.07), 2.670 (2.23), 2.709 (1.61), 3.536 (1.34), 3.547 (2.06), 3.557 (2.15), 3.575 (1.07), 3.665 (1.25), 3.700 (1.43), 3.743 (0.72), 3.775 (1.70), 3.807 (2.59), 3.889 (0.72), 3.907 (1.52), 3.934 (1.07), 3.991 (0.89), 4.035 (0.80), 4.063 (0.54), 4.172 (0.80), 4.198 (0.80), 4.738 (1.16), 4.747 (1.43), 4.798 (15.28), 4.828 (1.61), 4.838 (1.43), 7.141 (4.11), 7.163 (9.56), 7.185 (6.08), 7.256 (5.27), 7.270 (5.90), 7.277 (4.38), 7.291 (3.66).

Example 452

(5S)-5-{[(3R,4S)-3,4-Difluoropyrrolidin-1-yl]carbonyl}-2-(4-fluorobenzyl)-5,6,7,8-tetrahydro[1,2,4]triazolo[4,3-a]pyridin-3(2H)-one

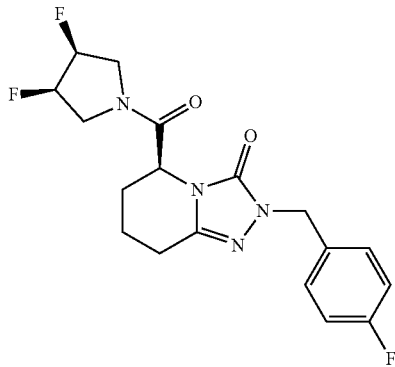 [SMILES: O=C([C@@H]1CCCc2nn(Cc3ccc(F)cc3)c(=O)n21)N1C[C@@H](F)[C@@H](F)C1]

(5S)-2-(4-Fluorobenzyl)-3-oxo-2,3,5,6,7,8-hexahydro[1,2,4]triazolo[4,3-a]pyridine-5-carboxylic acid (62.8 mg, 215 μmol) was initially charged in THF (2.0 ml), and HBTU (106 mg, 280 mol) and N,N-diisopropylethylamine (110 μl, 650 μmol) were subsequently added. After stirring at room temperature for 15 min, (3R,4S)-3,4-difluoropyrrolidine hydrochloride (37.1 mg, 259 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 63.3 mg (77% of theory) of the title compound were obtained.

LC-MS (Method 3): $R_t$=1.30 min; MS (ESIpos): m/z=381 [M+H]$^+$ $^1$H-NMR (400 MHz, DMSO-d6) delta [ppm]: −0.149 (1.91), −0.008 (16.00), 0.008 (12.70), 0.146 (1.74), 1.722 (1.04), 2.002 (1.04), 2.072 (2.43), 2.327 (2.61), 2.366 (1.91), 2.523 (7.65), 2.582 (1.91), 2.595 (2.43), 2.638 (0.87), 2.670 (2.78), 2.710 (1.91), 3.533 (1.04), 3.576 (0.70), 3.626 (0.70), 3.669 (0.70), 3.681 (1.04), 3.701 (1.22), 3.724 (0.87), 3.865 (0.70), 3.940 (0.70), 3.973 (0.70), 3.987 (0.70), 4.171 (0.70), 4.796 (13.22), 5.273 (0.70), 5.388 (0.87), 7.142 (2.43), 7.164 (5.39), 7.183 (3.30), 7.251 (2.26), 7.258 (2.96), 7.264 (3.30), 7.272 (4.35), 7.279 (2.43), 7.287 (1.91), 7.293 (1.74).

Example 453

(5S)-5-{[(3R,4S)-3,4-Difluoropyrrolidin-1-yl]carbonyl}-2-(4-methoxybenzyl)-5,6,7,8-tetrahydro[1,2,4]triazolo[4,3-a]pyridin-3(2H)-one

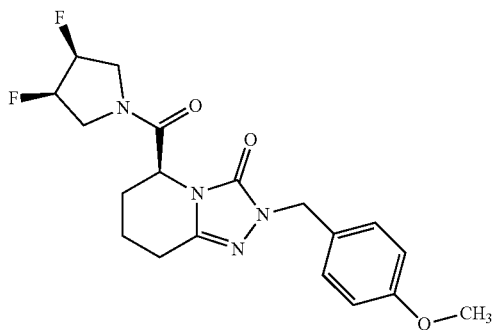 [SMILES: COc1ccc(Cn2nc3n(c2=O)[C@H](C(=O)N2C[C@@H](F)[C@@H](F)C2)CCC3)cc1]

(5S)-2-(4-Methoxybenzyl)-3-oxo-2,3,5,6,7,8-hexahydro[1,2,4]triazolo[4,3-a]pyridine-5-carboxylic acid (258 mg, 50% purity, 425 μmol) was initially charged in THF (5.0 ml), and HBTU (210 mg, 553 μmol) and N,N-diisopropylethylamine (220 μl, 1.3 mmol) were subsequently added. After stirring at room temperature for 15 min, (3R,4S)-3,4-difluoropyrrolidine hydrochloride (73.3 mg, 510 μmol) was added and the reaction mixture was stirred at room temperature for 72 hours. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 45.0 mg (27% of theory) of the title compound were obtained.

LC-MS (Method 4): $R_t$=0.70 min; MS (ESIpos): m/z=393 [M+H]$^+$ $^1$H-NMR (400 MHz, DMSO-d6) δ[ppm]: −0.008 (1.34), 0.008 (1.31), 1.251 (0.81), 1.261 (0.45), 1.268 (0.91), 1.274 (0.75), 1.291 (0.69), 1.642 (1.22), 1.666 (1.72), 1.676 (1.72), 1.692 (1.93), 1.704 (2.38), 1.714 (2.23), 1.728 (1.80), 1.909 (1.09), 1.927 (0.81), 1.944 (1.55), 1.970 (0.99), 1.980 (1.58), 1.993 (1.98), 2.001 (1.45), 2.018 (1.24), 2.028 (1.43), 2.036 (1.54), 2.043 (1.48), 2.052 (1.30), 2.063 (1.13), 2.071 (1.21), 2.079 (1.07), 2.088 (0.60), 2.519 (2.90), 2.570 (2.85), 2.583 (3.73), 2.595 (2.10), 2.615 (0.77), 2.626 (1.27), 2.637 (0.61), 2.689 (1.56), 3.441 (0.48), 3.450 (0.85), 3.459 (0.56), 3.483 (1.47), 3.493 (1.43), 3.505 (1.30), 3.514 (1.58), 3.567 (7.32), 3.576 (7.76), 3.586 (7.42), 3.612 (8.16), 3.625 (7.94), 3.644 (6.37), 3.666 (4.04), 3.681 (3.25), 3.688 (2.58), 3.701 (2.92), 3.714 (2.10), 3.754 (1.71), 3.766 (1.50), 3.787 (0.85), 3.800 (0.81), 3.816 (0.49), 3.829 (0.56), 3.835 (0.54), 3.845 (0.73), 3.858 (0.89), 3.864 (1.10), 3.883 (0.53), 3.893 (0.71), 3.906 (1.04), 3.925 (1.06), 3.938 (1.20), 3.953 (0.74), 3.967 (0.87), 3.974 (1.15), 3.988 (1.16), 4.002 (0.75), 4.017 (0.68), 4.130 (0.73), 4.144 (0.83), 4.158 (0.79), 4.171 (1.38), 4.186 (0.90), 4.198 (0.79), 4.214 (0.73), 4.679 (1.11), 4.719 (16.00), 4.727 (8.38), 4.766 (3.94), 4.772 (4.71), 4.777 (3.27), 5.244 (0.73), 5.254 (1.15), 5.266 (1.15), 5.276 (1.25), 5.285 (1.01), 5.296 (0.78), 5.309 (0.68), 5.318 (0.74), 5.329 (0.93), 5.338 (0.94), 5.350 (0.98), 5.365 (0.88), 5.377 (1.23), 5.387 (1.39), 5.399 (1.14), 5.408 (1.13), 5.414 (1.01), 5.427 (0.75), 5.439 (0.71), 5.448 (0.78), 5.458 (0.98), 5.467 (0.94), 5.471 (0.95), 5.480 (1.00), 5.494 (0.74), 5.503 (0.49), 6.871 (7.75), 6.875 (9.87), 6.893 (10.64), 6.896 (10.38), 7.023 (0.51), 7.150 (8.24), 7.158 (9.24), 7.172 (7.28), 7.179 (7.47), 7.278 (0.53).

Example 454

(5S)-2-(3-Chloro-4-fluorobenzyl)-5-{[(3S)-3-fluoropyrrolidin-1-yl]carbonyl}-5,6,7,8-tetrahydro[1,2,4]triazolo[4,3-a]pyridin-3(2H)-one

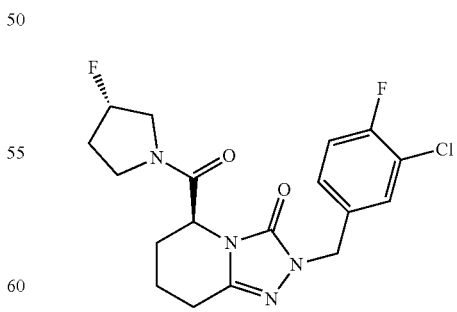

(5S)-2-(3-Chloro-4-fluorobenzyl)-3-oxo-2,3,5,6,7,8-hexahydro[1,2,4]triazolo[4,3-a]pyridine-5-carboxylic acid (60.0 mg, 184 μmol) was initially charged in THF (2.0 ml), and HBTU (90.8 mg, 239 μmol) and N,N-diisopropylethylamine (96 μl, 550 μmol) were subsequently added. After stirring at room temperature for 15 min, (3S)-3-fluoropyrrolidine hydrochloride (27.8 mg, 221 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 39.0 mg (53% of theory) of the title compound were obtained.

LC-MS (Method 3): $R_t$=1.44 min; MS (ESIpos): m/z=397 [M+H]$^+$ $^1$H-NMR (400 MHz, DMSO-d6) δ [ppm]: −0.149 (1.96), −0.008 (16.00), 0.008 (13.73), 0.146 (1.86), 1.728 (2.22), 1.906 (0.57), 2.088 (1.34), 2.266 (0.77), 2.327 (2.74), 2.366 (2.01), 2.523 (8.52), 2.609 (2.12), 2.669 (3.05), 2.710 (1.96), 3.395 (0.72), 3.493 (0.67), 3.635 (1.91), 3.652 (1.55), 3.719 (0.98), 3.742 (1.50), 3.768 (1.14), 3.853 (1.81), 4.702 (1.08), 4.759 (1.50), 4.820 (10.48), 5.260 (0.88), 5.390 (1.14), 5.515 (0.77), 7.245 (1.70), 7.251 (1.75), 7.373 (2.84), 7.396 (4.34), 7.417 (2.32), 7.431 (2.48), 7.449 (2.43).

Example 455

(5S)-2-(3-Chloro-4-fluorobenzyl)-5-[(3,3-difluoropyrrolidin-1-yl)carbonyl]-5,6,7,8-tetrahydro[1,2,4]triazolo[4,3-a]pyridin-3(2H)-one

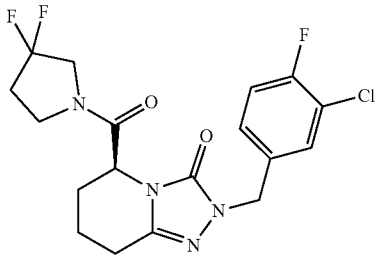 [SMILES: O=C([C@@H]1CCCc2nn(Cc3ccc(F)c(Cl)c3)c(=O)n21)N1CCC(F)(F)C1]

(5S)-2-(3-Chloro-4-fluorobenzyl)-3-oxo-2,3,5,6,7,8-hexahydro[1,2,4]triazolo[4,3-a]pyridine-5-carboxylic acid (60.0 mg, 184 µmol) was initially charged in THF (2.0 ml), and HBTU (90.8 mg, 239 µmol) and N,N-diisopropylethylamine (96 µl, 550 µmol) were subsequently added. After stirring at room temperature for 15 min, 3,3-difluoropyrrolidine hydrochloride (31.7 mg, 221 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 58.0 mg (76% of theory) of the title compound were obtained.

LC-MS (Method 3): $R_t$=1.58 min; MS (ESIpos): m/z=415 [M+H]$^+$ $^1$H-NMR (400 MHz, DMSO-d6) δ [ppm]: −0.008 (2.55), 0.008 (1.32), 1.670 (1.23), 1.680 (1.17), 1.692 (1.09), 1.718 (1.53), 1.728 (1.49), 1.980 (1.43), 1.995 (1.50), 2.005 (1.65), 2.011 (1.56), 2.028 (1.19), 2.039 (1.16), 2.047 (1.23), 2.054 (1.17), 2.064 (1.10), 2.073 (2.24), 2.082 (0.88), 2.090 (0.75), 2.366 (0.60), 2.381 (1.02), 2.392 (0.77), 2.410 (1.20), 2.430 (1.27), 2.453 (1.50), 2.524 (3.13), 2.576 (2.70), 2.591 (2.97), 2.607 (3.10), 2.620 (1.50), 2.637 (0.64), 2.650 (0.89), 2.664 (0.57), 3.519 (0.50), 3.531 (1.37), 3.538 (1.52), 3.549 (2.11), 3.559 (2.19), 3.567 (1.25), 3.578 (1.06), 3.669 (1.29), 3.702 (1.46), 3.742 (0.87), 3.764 (0.74), 3.775 (1.80), 3.790 (1.00), 3.808 (2.63), 3.826 (0.68), 3.891 (0.72), 3.910 (1.44), 3.928 (0.83), 3.936 (1.00), 3.954 (0.54), 3.961 (0.49), 3.990 (0.91), 4.005 (0.49), 4.019 (0.64), 4.033 (0.81), 4.061 (0.48), 4.145 (0.56), 4.177 (0.81), 4.202 (0.81), 4.756 (1.32), 4.765 (1.56), 4.771 (1.70), 4.780 (1.35), 4.824 (16.00), 4.838 (1.92), 4.844 (1.80), 4.853 (1.29), 7.220 (1.53), 7.226 (1.67), 7.232 (1.69), 7.241 (2.18), 7.247 (2.07), 7.253 (1.88), 7.258 (1.76), 7.373 (3.79), 7.396 (5.05), 7.418 (3.12), 7.429 (3.04), 7.434 (2.80), 7.447 (2.95), 7.452 (2.59).

Example 456

(5S)-2-(3-Chloro-4-fluorobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

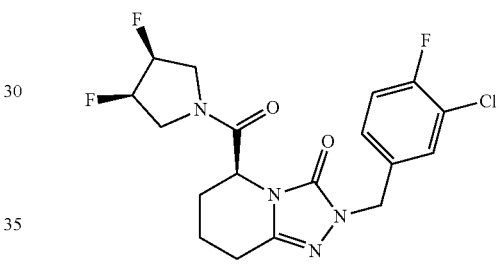

(5S)-2-(3-Chloro-4-fluorobenzyl)-3-oxo-2,3,5,6,7,8-hexahydro[1,2,4]triazolo[4,3-a]pyridine-5-carboxylic acid (60.0 mg, 184 µmol) was initially charged in THF (2.0 ml), and HBTU (90.8 mg, 239 µmol) and N,N-diisopropylethylamine (96 µl, 550 µmol) were subsequently added. After stirring at room temperature for 15 min, (3R,4S)-3,4-difluoropyrrolidine hydrochloride (31.7 mg, 221 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 53.0 mg (69% of theory) of the title compound were obtained.

LC-MS (Method 3): $R_t$=1.47 min; MS (ESIpos): m/z=415 [M+H]$^+$ $^1$H-NMR (400 MHz, DMSO-d6) δ [ppm]: −0.150 (0.55), −0.008 (5.05), 0.008 (4.28), 0.146 (0.63), 1.665 (1.23), 1.729 (1.60), 1.971 (1.16), 2.008 (1.55), 2.051 (1.26), 2.073 (4.71), 2.327 (0.99), 2.366 (0.67), 2.569 (2.20), 2.594 (2.20), 2.607 (2.83), 2.649 (0.94), 2.669 (1.09), 2.709 (0.70), 3.489 (1.14), 3.535 (1.14), 3.545 (1.11), 3.577 (0.70), 3.614 (0.85), 3.629 (0.89), 3.684 (1.33), 3.702 (1.48), 3.723 (1.28), 3.755 (1.01), 3.868 (0.84), 3.926 (0.78), 3.939 (0.87), 3.974 (0.78), 3.989 (0.85), 4.172 (0.92), 4.198 (0.67), 4.804 (3.62), 4.823 (16.00), 5.276 (1.02), 5.388 (1.06), 7.235 (2.20), 7.241 (2.32), 7.370 (2.59), 7.374 (2.87), 7.395 (4.42), 7.419 (2.37), 7.430 (3.75), 7.448 (3.63).

Example 457

(5S)-2-(3-Chloro-4-fluorobenzyl)-5-[(3-fluoroazetidin-1-yl)carbonyl]-5,6,7,8-tetrahydro[1,2,4]triazolo[4,3-a]pyridin-3(2H)-one

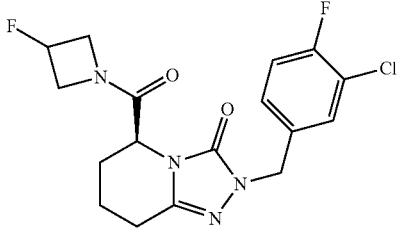 [SMILES: O=C([C@@H]1CCCc2nn(Cc3ccc(F)c(Cl)c3)c(=O)n21)N1CC(F)C1]

(5S)-2-(3-Chloro-4-fluorobenzyl)-3-oxo-2,3,5,6,7,8-hexahydro[1,2,4]triazolo[4,3-a]pyridine-5-carboxylic acid (60.0 mg, 184 µmol) was initially charged in THF (2.0 ml), and HBTU (90.8 mg, 239 µmol) and N,N-diisopropylethylamine (96 µl, 550 µmol) were subsequently added. After stirring at room temperature for 15 min, 3-fluoroazetidine hydrochloride (24.7 mg, 221 mol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 38.0 mg (54% of theory) of the title compound were obtained.

LC-MS (Method 3): $R_t$=1.37 min; MS (ESIpos): m/z=383 [M+H]$^+$ $^1$H-NMR (400 MHz, DMSO-d6) δ [ppm]: −0.149 (0.57), 0.008 (3.84), 0.146 (0.49), 1.258 (0.93), 1.681 (2.36), 1.704 (3.76), 1.957 (2.08), 2.028 (1.83), 2.327 (0.80), 2.366 (0.82), 2.523 (4.91), 2.558 (3.01), 2.583 (3.84), 2.597 (5.04), 2.610 (2.50), 2.626 (0.97), 2.639 (1.59), 2.653 (0.69), 2.670 (0.82), 2.710 (0.77), 3.901 (0.73), 3.928 (1.44), 3.958 (1.46), 3.990 (1.41), 4.018 (0.80), 4.158 (0.62), 4.172 (0.71), 4.185 (0.60), 4.225 (1.30), 4.239 (1.30), 4.257 (1.41), 4.267 (1.53), 4.290 (1.46), 4.323 (1.22), 4.352 (0.88), 4.395 (0.88), 4.433 (0.66), 4.457 (0.86), 4.504 (0.75), 4.519 (0.91), 4.544 (3.87), 4.557 (5.50), 4.570 (3.62), 4.597 (0.49), 4.634 (0.62), 4.647 (0.75), 4.684 (0.71), 4.701 (0.64), 4.727 (0.51), 4.824 (16.00), 5.353 (0.88), 5.406 (0.88), 5.496 (0.86), 5.550 (0.82), 7.248 (2.87), 7.372 (3.29), 7.394 (5.26), 7.417 (2.67), 7.437 (3.31), 7.455 (3.12).

Example 458

(5S)-2-[3-Chloro-4-(trifluoromethyl)benzyl]-5-{[(3R,4S)-3,4-difluoropyrrolidin-1-yl]carbonyl}-5,6,7,8-tetrahydro[1,2,4]triazolo[4,3-a]pyridin-3(2H)-one

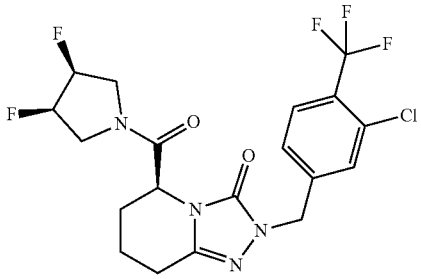 [SMILES: O=C([C@@H]1CCCc2nn(Cc3ccc(C(F)(F)F)c(Cl)c3)c(=O)n21)N1C[C@@H](F)[C@@H](F)C1]

(5S)-2-[3-Chloro-4-(trifluoromethyl)benzyl]-3-oxo-2,3,5,6,7,8-hexahydro[1,2,4]triazolo[4,3-a]pyridine-5-carboxylic acid (43.8 mg, 117 µmol) was initially charged in THF (2.0 ml), and HBTU (57.5 mg, 152 µmol) and N,N-diisopropylethylamine (61 µl, 350 µmol) were subsequently added. After stirring at room temperature for 15 min, (3R,4S)-3,4-difluoropyrrolidine hydrochloride (20.1 mg, 140 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 34.5 mg (64% of theory) of the title compound were obtained.

LC-MS (Method 4): $R_t$=0.93 min; MS (ESIpos): m/z=465 [M+H]$^+$ $^1$H-NMR (400 MHz, DMSO-d6) δ [ppm]: −0.149 (0.42), −0.008 (3.58), 0.008 (3.09), 1.226 (0.51), 1.244 (2.93), 1.259 (3.14), 1.274 (1.91), 1.644 (1.11), 1.668 (1.31), 1.689 (0.71), 1.741 (1.61), 1.908 (0.42), 1.947 (0.57), 1.982 (1.26), 2.003 (0.99), 2.020 (1.73), 2.027 (1.86), 2.045 (1.14), 2.062 (1.35), 2.073 (10.23), 2.089 (0.92), 2.098 (1.01), 2.106 (0.86), 2.328 (0.72), 2.366 (0.69), 2.523 (2.61), 2.570 (1.65), 2.581 (2.21), 2.591 (1.59), 2.605 (2.33), 2.618 (3.14), 2.630 (1.74), 2.649 (0.63), 2.661 (1.28), 2.670 (1.10), 2.690 (0.47), 2.710 (0.62), 3.459 (1.13), 3.484 (1.37), 3.493 (1.94), 3.504 (1.68), 3.516 (1.88), 3.527 (2.12), 3.538 (2.52), 3.549 (2.94), 3.558 (2.70), 3.581 (3.49), 3.590 (3.41), 3.619 (4.21), 3.633 (4.46), 3.652 (4.12), 3.666 (4.31), 3.674 (4.64), 3.689 (5.20), 3.705 (4.91), 3.721 (4.10), 3.756 (3.02), 3.769 (2.58), 3.790 (1.77), 3.803 (1.52), 3.831 (1.04), 3.871 (1.29), 3.909 (0.90), 3.929 (1.08), 3.943 (1.17), 3.958 (0.75), 3.979 (1.08), 3.994 (1.05), 4.008 (0.68), 4.022 (0.63), 4.133 (0.65), 4.148 (0.69), 4.161 (0.68), 4.175 (1.07), 4.188 (0.77), 4.201 (0.69), 4.216 (0.62), 4.810 (2.43), 4.822 (3.53), 4.832 (2.28), 4.944 (16.00), 5.266 (0.95), 5.276 (1.04), 5.288 (0.89), 5.299 (0.62), 5.314 (0.71), 5.330 (0.74), 5.338 (0.74), 5.353 (0.83), 5.367 (0.75), 5.389 (1.10), 5.400 (0.87), 5.409 (0.99), 5.419 (0.92), 5.430 (0.71), 5.443 (0.68), 5.452 (0.72), 5.466 (0.74), 5.475 (0.72), 5.482 (0.69), 5.496 (0.60), 7.372 (2.48), 7.391 (2.67), 7.563 (5.75), 7.841 (4.19), 7.861 (3.82).

Example 459

(5S)-2-[3-Chloro-4-(trifluoromethyl)benzyl]-5-[(3-fluoroazetidin-1-yl)carbonyl]-5,6,7,8-tetrahydro[1,2,4]triazolo[4,3-a]pyridin-3(2H)-one

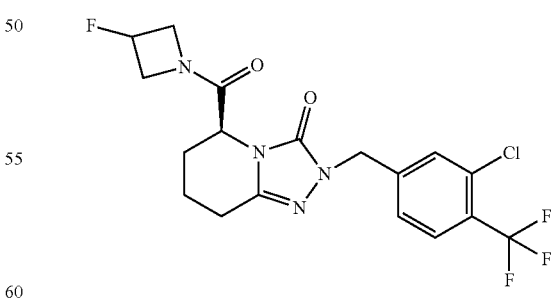

(5S)-2-[3-Chloro-4-(trifluoromethyl)benzyl]-3-oxo-2,3,5,6,7,8-hexahydro[1,2,4]triazolo[4,3-a]pyridine-5-carboxylic acid (43.8 mg, 117 µmol) was initially charged in THF (2.0 ml), and HBTU (57.5 mg, 152 µmol) and N,N-diisopropylethylamine (61 µl, 350 mol) were subsequently added. After stirring at room temperature for 15 min, 3-fluoroazetidine hydrochloride (15.6 mg, 140 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 30.2 mg (58% of theory) of the title compound were obtained.

LC-MS (Method 4): $R_t$=0.89 min; MS (ESIpos): m/z=433 [M+H]$^+$ $^1$H-NMR (400 MHz, DMSO-d6) δ [ppm]: −0.149 (0.53), 0.146 (0.51), 1.708 (3.04), 1.722 (3.28), 1.971 (2.07), 2.038 (1.83), 2.073 (2.00), 2.327 (0.95), 2.366 (0.68), 2.576 (2.89), 2.594 (3.71), 2.608 (5.08), 2.621 (2.63), 2.637 (1.10), 2.650 (1.74), 2.665 (1.38), 2.710 (0.77), 3.907 (0.79), 3.933 (1.42), 3.963 (1.48), 3.995 (1.47), 4.020 (0.91), 4.175 (0.70), 4.228 (1.29), 4.275 (1.60), 4.295 (1.38), 4.324 (0.95), 4.366 (1.12), 4.400 (0.97), 4.437 (0.73), 4.462 (0.95), 4.524 (0.79), 4.563 (3.93), 4.577 (5.79), 4.589 (3.84), 4.651 (0.74), 4.704 (0.74), 4.945 (16.00), 5.354 (0.91), 5.409 (0.92), 5.497 (0.91), 5.550 (0.92), 7.376 (4.42), 7.396 (4.84), 7.569 (8.14), 7.838 (5.78), 7.859 (5.38).

Example 460

(5S)-2-[3-Chloro-4-(trifluoromethyl)benzyl]-5-[(3,3-difluoropyrrolidin-1-yl)carbonyl]-5,6,7,8-tetrahydro[1,2,4]triazolo[4,3-a]pyridin-3(2H)-one

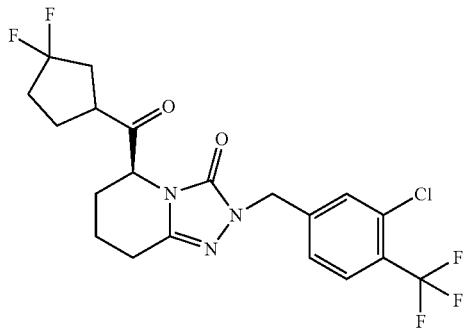 [SMILES: O=C(C1CCC(F)(F)C1)[C@@H]1CCCc2nn(Cc3ccc(C(F)(F)F)c(Cl)c3)c(=O)n21]

(5S)-2-[3-Chloro-4-(trifluoromethyl)benzyl]-3-oxo-2,3,5,6,7,8-hexahydro[1,2,4]triazolo[4,3-a]pyridine-5-carboxylic acid (43.8 mg, 117 µmol) was initially charged in THF (2.0 ml), and HBTU (57.5 mg, 152 µmol) and N,N-diisopropylethylamine (61 µl, 350 mol) were subsequently added. After stirring at room temperature for 15 min, 3,3-difluoropyrrolidine hydrochloride (20.1 mg, 140 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 35.4 mg (65% of theory) of the title compound were obtained.

LC-MS (Method 4): $R_t$=0.96 min; MS (ESIpos): m/z=465 [M+H]$^+$ $^1$H-NMR (400 MHz, DMSO-d6) δ [ppm]: −0.008 (2.40), 0.008 (2.34), 1.244 (0.81), 1.259 (0.99), 1.273 (0.51), 1.673 (1.17), 1.682 (1.09), 1.696 (0.85), 1.740 (1.46), 1.997 (1.18), 2.012 (1.69), 2.022 (1.79), 2.037 (1.61), 2.049 (1.29), 2.057 (1.23), 2.064 (1.17), 2.073 (1.49), 2.085 (0.85), 2.093 (0.87), 2.100 (0.77), 2.281 (0.61), 2.328 (0.48), 2.366 (0.80), 2.382 (0.99), 2.393 (0.73), 2.411 (1.18), 2.430 (1.12), 2.454 (0.87), 2.519 (3.66), 2.562 (2.91), 2.576 (2.85), 2.587 (3.07), 2.602 (2.51), 2.619 (2.89), 2.631 (1.54), 2.650 (0.62), 2.661 (1.10), 2.670 (0.87), 2.690 (0.52), 2.710 (0.48), 2.885 (1.28), 3.535 (1.31), 3.542 (1.47), 3.553 (2.09), 3.562 (2.29), 3.571 (1.29), 3.582 (1.16), 3.639 (0.45), 3.673 (1.35), 3.707 (1.54), 3.726 (0.90), 3.745 (0.94), 3.779 (1.78), 3.786 (1.32), 3.795 (0.96), 3.812 (2.75), 3.831 (0.74), 3.893 (0.70), 3.911 (1.53), 3.930 (0.84), 3.938 (1.09), 3.956 (0.52), 3.966 (0.48), 3.995 (0.94), 4.009 (0.48), 4.023 (0.66), 4.037 (0.85), 4.065 (0.52), 4.150 (0.56), 4.182 (0.85), 4.207 (0.83), 4.541 (0.47), 4.776 (1.25), 4.785 (1.47), 4.791 (1.72), 4.800 (1.24), 4.847 (1.27), 4.856 (1.53), 4.862 (1.75), 4.871 (1.39), 4.945 (16.00), 7.371 (3.29), 7.392 (3.62), 7.564 (5.98), 7.839 (6.03), 7.860 (5.60).

Example 461

(5S)-2-[3-Chloro-4-(trifluoromethyl)benzyl]-5-{[(3S)-3-fluoropyrrolidin-1-yl]carbonyl}-5,6,7,8-tetrahydro[1,2,4]triazolo[4,3-a]pyridin-3(2H)-one

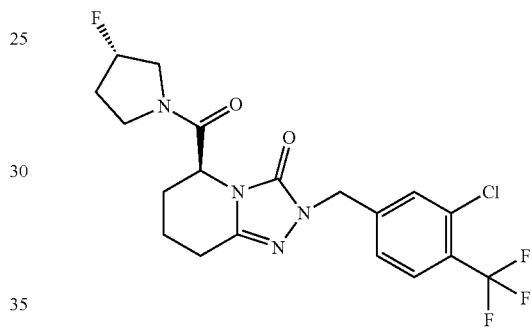

(5S)-2-[3-Chloro-4-(trifluoromethyl)benzyl]-3-oxo-2,3,5,6,7,8-hexahydro[1,2,4]triazolo[4,3-a]pyridine-5-carboxylic acid (43.8 mg, 117 µmol) was initially charged in THF (2.0 ml) at room temperature. Subsequently, HATU (57.6 mg, 152 µmol) and triethylamine (49 µl, 350 µmol) were added. After stirring for 15 min, (3S)-3-fluoropyrrolidine hydrochloride (17.6 mg, 140 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 44.7 mg (86% of theory) of the title compound were obtained.

LC-MS (Method 4): $R_t$=0.90 min; MS (ESIpos): m/z=447 [M+H]$^+$ $^1$H-NMR (400 MHz, DMSO-d6) δ [ppm]: 0.008 (2.72), 1.733 (2.50), 1.741 (2.71), 1.885 (0.64), 1.920 (0.84), 1.970 (0.43), 2.005 (0.84), 2.036 (1.45), 2.047 (1.38), 2.073 (5.69), 2.085 (2.04), 2.108 (2.42), 2.125 (1.59), 2.140 (1.69), 2.222 (0.93), 2.242 (0.83), 2.256 (0.88), 2.270 (1.25), 2.327 (0.64), 2.366 (0.49), 2.523 (2.19), 2.570 (1.75), 2.580 (1.91), 2.595 (1.62), 2.621 (2.69), 2.665 (1.42), 2.710 (0.48), 3.276 (0.75), 3.351 (0.78), 3.363 (0.72), 3.372 (0.77), 3.398 (0.88), 3.407 (0.88), 3.460 (0.65), 3.469 (0.68), 3.496 (0.90), 3.505 (0.85), 3.611 (0.59), 3.637 (2.74), 3.655 (2.24), 3.661 (2.19), 3.681 (1.85), 3.703 (1.17), 3.726 (1.26), 3.747 (2.22), 3.770 (1.72), 3.788 (1.39), 3.857 (2.72), 4.703 (1.29), 4.712 (1.56), 4.719 (1.59), 4.728 (1.26), 4.761 (1.69), 4.769 (1.88), 4.776 (2.09), 4.785 (1.56), 4.941 (16.00), 5.260 (1.32), 5.391 (1.77), 5.512 (0.96), 7.372 (2.79), 7.393 (3.03), 7.564 (5.99), 7.839 (5.89), 7.859 (5.50).

Example 462

(5S)-2-(4-Chloro-3-fluorobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

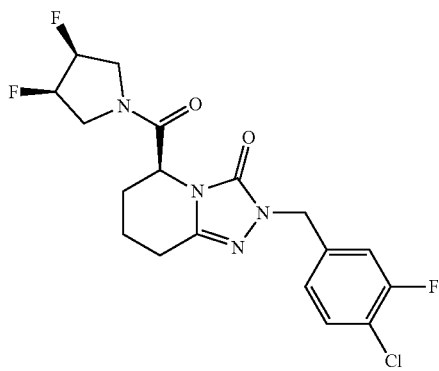 [SMILES: O=C([C@@H]1CCCc2nn(Cc3ccc(Cl)c(F)c3)c(=O)n21)N1C[C@@H](F)[C@@H](F)C1]

(5S)-2-(4-Chloro-3-fluorobenzyl)-3-oxo-2,3,5,6,7,8-hexahydro[1,2,4]triazolo[4,3-a]pyridine-5-carboxylic acid (80.0 mg, 233 µmol) was initially charged in THF (2.0 ml), and HBTU (115 mg, 303 µmol) and N,N-diisopropylethylamine (120 µl, 700 µmol) were subsequently added. After stirring at room temperature for 15 min, (3R,4S)-3,4-difluoropyrrolidine hydrochloride (40.2 mg, 280 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 58.0 mg (60% of theory) of the title compound were obtained.

LC-MS (Method 3): $R_t$=1.48 min; MS (ESIpos): m/z=415 [M+H]$^+$ $^1$H-NMR (400 MHz, DMSO-d6) δ [ppm]: −0.149 (0.47), −0.008 (4.35), 0.008 (4.00), 0.146 (0.45), 1.665 (1.17), 1.699 (0.65), 1.736 (1.42), 1.940 (0.53), 1.973 (1.13), 2.020 (1.52), 2.038 (0.97), 2.048 (1.03), 2.056 (1.13), 2.063 (1.09), 2.073 (1.78), 2.083 (0.83), 2.091 (0.87), 2.099 (0.77), 2.328 (0.69), 2.366 (0.87), 2.523 (2.79), 2.558 (1.86), 2.572 (2.14), 2.582 (1.44), 2.597 (2.04), 2.610 (2.73), 2.621 (1.50), 2.640 (0.57), 2.652 (0.91), 2.665 (0.91), 2.710 (0.81), 3.490 (3.44), 3.500 (2.45), 3.512 (2.10), 3.522 (1.82), 3.533 (1.58), 3.545 (1.54), 3.567 (0.83), 3.576 (0.99), 3.586 (0.75), 3.617 (0.91), 3.630 (1.01), 3.650 (0.63), 3.664 (0.73), 3.672 (0.99), 3.686 (1.56), 3.702 (1.40), 3.719 (1.13), 3.734 (1.11), 3.755 (1.01), 3.765 (0.91), 3.788 (0.55), 3.800 (0.51), 3.868 (0.75), 3.904 (0.57), 3.927 (0.73), 3.941 (0.87), 3.955 (0.49), 3.977 (0.81), 3.991 (0.83), 4.005 (0.51), 4.019 (0.47), 4.131 (0.53), 4.146 (0.59), 4.159 (0.57), 4.172 (0.89), 4.186 (0.63), 4.199 (0.57), 4.214 (0.51), 4.806 (3.42), 4.848 (16.00), 5.265 (0.83), 5.276 (0.93), 5.287 (0.81), 5.298 (0.55), 5.312 (0.63), 5.329 (0.67), 5.337 (0.65), 5.351 (0.75), 5.365 (0.65), 5.388 (0.99), 5.407 (0.91), 5.417 (0.81), 5.428 (0.63), 5.441 (0.59), 5.464 (0.65), 5.472 (0.63), 5.482 (0.65), 5.494 (0.53), 6.947 (0.61), 7.075 (2.08), 7.081 (2.65), 7.101 (2.89), 7.202 (0.65), 7.219 (2.81), 7.244 (2.93), 7.547 (1.88), 7.551 (2.10), 7.567 (3.46), 7.571 (3.84), 7.587 (1.78), 7.591 (2.00).

Example 463

(5S)-2-(4-Chloro-3-fluorobenzyl)-5-[(3-fluoroazetidin-1-yl)carbonyl]-5,6,7,8-tetrahydro[1,2,4]triazolo[4,3-a]pyridin-3(2H)-one

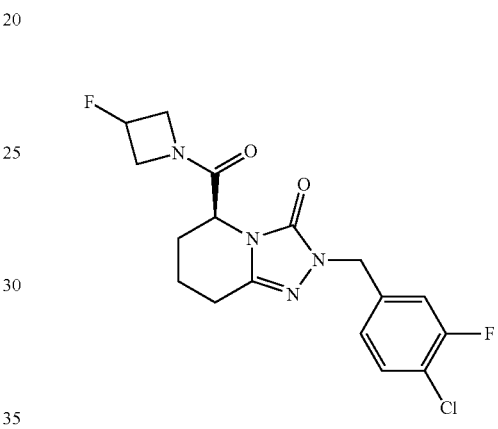

(5S)-2-(4-Chloro-3-fluorobenzyl)-3-oxo-2,3,5,6,7,8-hexahydro[1,2,4]triazolo[4,3-a]pyridine-5-carboxylic acid (80.0 mg, 233 µmol) was initially charged in THF (2.0 ml), and HBTU (115 mg, 303 µmol) and N,N-diisopropylethylamine (120 µl, 700 µmol) were subsequently added. After stirring at room temperature for 15 min, 3-fluoroazetidine hydrochloride (31.2 mg, 280 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.0 mg (40% of theory) of the title compound were obtained.

LC-MS (Method 3): $R_t$=1.38 min; MS (ESIpos): m/z=383 [M+H]$^+$ $^1$H-NMR (400 MHz, DMSO-d6) δ [ppm]: −0.149 (0.92), −0.008 (8.11), 0.146 (0.92), 1.680 (1.99), 1.704 (3.16), 1.715 (3.24), 1.964 (2.03), 2.029 (1.81), 2.327 (1.35), 2.366 (1.49), 2.523 (5.80), 2.560 (3.34), 2.585 (3.95), 2.599 (5.08), 2.612 (2.70), 2.627 (1.03), 2.641 (1.64), 2.669 (1.49), 2.710 (1.49), 3.899 (0.71), 3.932 (1.42), 3.961 (1.46), 3.989 (1.42), 4.019 (0.85), 4.158 (0.64), 4.172 (0.71), 4.224 (1.21), 4.241 (1.24), 4.271 (1.60), 4.292 (1.42), 4.322 (1.14), 4.360 (0.96), 4.395 (0.85), 4.433 (0.64), 4.459 (0.89), 4.548 (3.52), 4.561 (5.48), 4.573 (3.70), 4.676 (0.75), 4.701 (0.68), 4.849 (16.00), 5.352 (0.89), 5.406 (0.85), 5.495 (0.89), 5.548 (0.89), 7.069 (0.57), 7.086 (4.05), 7.106 (4.41), 7.197 (0.46), 7.226 (3.80), 7.252 (3.95), 7.548 (2.74), 7.568 (5.23), 7.588 (2.60).

Example 464

(5S)-2-(4-Chloro-3-fluorobenzyl)-5-[(3,3-difluoro-pyrrolidin-1-yl)carbonyl]-5,6,7,8-tetrahydro[1,2,4]triazolo[4,3-a]pyridin-3(2H)-one

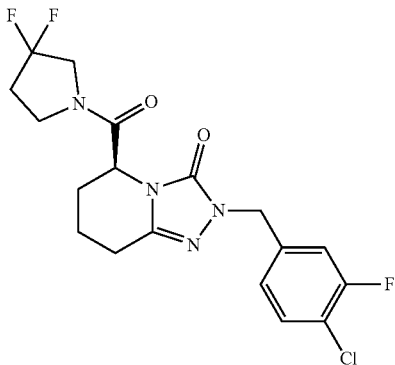 [SMILES: O=C([C@@H]1CCCc2nn(Cc3ccc(Cl)c(F)c3)c(=O)n21)N1CCC(F)(F)C1]

(5S)-2-(4-Chloro-3-fluorobenzyl)-3-oxo-2,3,5,6,7,8-hexahydro[1,2,4]triazolo[4,3-a]pyridine-5-carboxylic acid (80.0 mg, 246 μmol) was initially charged in THF, and HBTU (121 mg, 319 μmol) and N,N-diisopropylethylamine (130 μl, 740 μmol) were subsequently added. After stirring at room temperature for 15 min, 3,3-difluoropyrrolidine hydrochloride (42.3 mg, 295 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 32.0 mg (31% of theory) of the title compound were obtained.

LC-MS (Method 3): $R_t$=1.56 min; MS (ESIpos): m/z=415 [M+H]$^+$ $^1$H-NMR (400 MHz, DMSO-d6) δ [ppm]: −0.149 (0.96), 0.146 (0.93), 1.736 (1.42), 2.013 (1.56), 2.366 (1.99), 2.593 (2.02), 2.609 (2.29), 2.709 (1.46), 3.557 (1.72), 3.670 (1.16), 3.703 (1.19), 3.742 (0.80), 3.774 (1.49), 3.809 (2.12), 3.909 (1.16), 3.935 (0.86), 3.992 (0.86), 4.035 (0.70), 4.178 (0.80), 4.202 (0.73), 4.768 (1.36), 4.848 (16.00), 7.081 (2.72), 7.102 (3.08), 7.217 (2.82), 7.243 (2.78), 7.549 (2.78), 7.569 (5.04), 7.589 (2.45).

Example 465

(5S)-2-(4-Chloro-3-fluorobenzyl)-5-[(3,3-difluoro-azetidin-1-yl)carbonyl]-5,6,7,8-tetrahydro[1,2,4]triazolo[4,3-a]pyridin-3(2H)-one

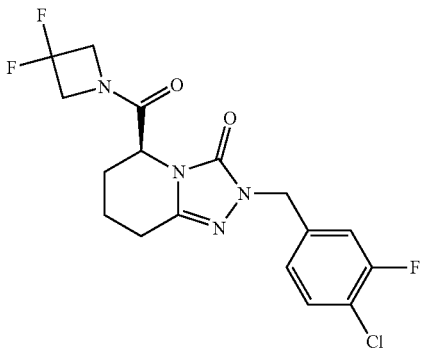 [SMILES: O=C([C@@H]1CCCc2nn(Cc3ccc(Cl)c(F)c3)c(=O)n21)N1CC(F)(F)C1]

(5S)-2-(4-Chloro-3-fluorobenzyl)-3-oxo-2,3,5,6,7,8-hexahydro[1,2,4]triazolo[4,3-a]pyridine-5-carboxylic acid (80.0 mg, 246 μmol) was initially charged in THF, and HBTU (121 mg, 319 μmol) and N,N-diisopropylethylamine (130 μl, 740 μmol) were subsequently added. After stirring at room temperature for 15 min, 3,3-difluoroazetidine hydrochloride (38.2 mg, 295 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 69.0 mg (70% of theory) of the title compound were obtained.

LC-MS (Method 3): $R_t$=1.51 min; MS (ESIpos): m/z=401 [M+H]$^+$ $^1$H-NMR (400 MHz, DMSO-d6) δ [ppm]: 1.701 (1.56), 1.711 (2.31), 1.723 (2.92), 1.736 (2.21), 1.960 (0.70), 1.971 (0.73), 1.982 (1.08), 1.995 (1.51), 2.008 (1.34), 2.019 (0.71), 2.026 (0.80), 2.037 (1.03), 2.051 (1.34), 2.061 (1.12), 2.075 (1.16), 2.096 (0.45), 2.561 (1.86), 2.577 (2.07), 2.582 (2.02), 2.596 (2.35), 2.608 (3.23), 2.621 (1.55), 2.635 (0.56), 2.650 (0.89), 2.664 (0.59), 4.336 (0.99), 4.365 (1.68), 4.388 (1.71), 4.419 (1.03), 4.601 (2.22), 4.616 (3.49), 4.628 (2.18), 4.725 (1.04), 4.755 (1.19), 4.785 (0.54), 4.817 (0.56), 4.854 (16.00), 4.875 (1.28), 7.091 (2.53), 7.112 (2.77), 7.228 (2.62), 7.233 (2.47), 7.254 (2.69), 7.258 (2.54), 7.550 (2.83), 7.570 (5.03), 7.590 (2.63).

Example 466

(5S)-2-(3,4-Difluorobenzyl)-5-{[(3S)-3-fluoropyrrolidin-1-yl]carbonyl}-5,6,7,8-tetrahydro[1,2,4]triazolo[4,3-a]pyridin-3(2H)-one

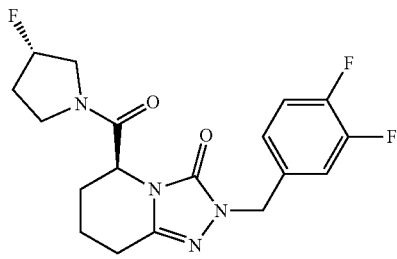 [SMILES: O=C([C@@H]1CCCc2nn(Cc3ccc(F)c(F)c3)c(=O)n21)N1CC[C@H](F)C1]

(5S)-2-(3,4-Difluorobenzyl)-3-oxo-2,3,5,6,7,8-hexahydro[1,2,4]triazolo[4,3-a]pyridine-5-carboxylic acid (60.0 mg, 194 μmol) was initially charged in THF (2.0 ml), and HBTU (95.6 mg, 252 μmol) and N,N-diisopropylethylamine (100 μl, 580 μmol) were subsequently added. After stirring at room temperature for 15 min, (3S)-3-fluoropyrrolidine hydrochloride (29.2 mg, 233 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 42.0 mg (57% of theory) of the title compound were obtained.

LC-MS (Method 4): $R_t$=0.74 min; MS (ESIpos): m/z=381 [M+H]

$^1$H-NMR (400 MHz, DMSO-d6) δ [ppm]: −0.008 (1.32), 0.008 (1.00), 1.705 (1.55), 1.731 (2.78), 1.874 (0.56), 1.909 (0.73), 1.969 (0.40), 1.995 (0.87), 2.023 (1.36), 2.048 (1.03), 2.064 (1.30), 2.074 (1.68), 2.090 (1.82), 2.100 (2.07), 2.126 (1.27), 2.136 (1.45), 2.220 (0.82), 2.269 (1.10), 2.328 (0.48), 2.523 (1.88), 2.560 (1.65), 2.570 (1.83), 2.585 (1.51), 2.613 (2.42), 2.654 (0.91), 2.665 (0.74), 3.273 (0.64), 3.292 (0.87), 3.302 (1.28), 3.320 (1.58), 3.330 (1.65), 3.458 (0.74), 3.466 (0.76), 3.493 (0.93), 3.502 (0.85), 3.610 (0.57), 3.634 (2.77), 3.653 (2.15), 3.678 (1.49), 3.697 (1.09), 3.724 (1.18), 3.745 (1.94), 3.768 (1.62), 3.785 (1.30), 3.855 (2.49), 4.686 (1.18), 4.695 (1.42), 4.701 (1.48), 4.710 (1.16), 4.743 (1.56), 4.752 (1.74), 4.758 (1.95), 4.767 (1.44), 4.819 (16.00), 5.259 (1.23), 5.382 (1.53), 5.390 (1.58), 5.511 (0.86), 7.075 (1.88), 7.080 (1.96), 7.091 (1.90), 7.233 (1.60), 7.257 (2.00), 7.281 (1.62), 7.375 (1.67), 7.396 (3.27), 7.402 (1.91), 7.417 (1.81), 7.423 (3.19), 7.444 (1.51).

Example 467

(5S)-2-(3,4-Difluorobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

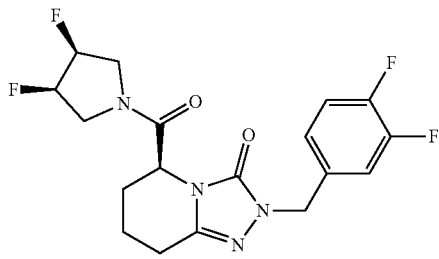 [SMILES: O=C([C@@H]1CCCc2nn(Cc3ccc(F)c(F)c3)c(=O)n21)N1C[C@@H](F)[C@@H](F)C1]

(5S)-2-(3,4-Difluorobenzyl)-3-oxo-2,3,5,6,7,8-hexahydro[1,2,4]triazolo[4,3-a]pyridine-5-carboxylic acid (60.0 mg, 194 μmol) was initially charged in THF (2.0 ml), and HBTU (95.6 mg, 252 μmol) and N,N-diisopropylethylamine (100 μl, 580 μmol) were subsequently added. After stirring at room temperature for 15 min, (3R,4S)-3,4-difluoropyrrolidine hydrochloride (33.4 mg, 233 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 65.0 mg (84% of theory) of the title compound were obtained.

LC-MS (Method 4): $R_t$=0.77 min; MS (ESIpos): m/z=399 [M+H]

$^1$H-NMR (400 MHz, DMSO-d6) δ [ppm]: −0.150 (0.90), −0.008 (10.40), 0.008 (5.42), 0.146 (0.81), 1.652 (1.36), 1.731 (1.54), 1.977 (1.36), 2.010 (2.08), 2.054 (1.54), 2.327 (2.62), 2.366 (3.34), 2.523 (11.66), 2.570 (2.98), 2.580 (2.17), 2.594 (2.53), 2.608 (3.16), 2.650 (1.27), 2.670 (2.44), 2.710 (1.90), 3.456 (0.90), 3.490 (1.45), 3.513 (1.18), 3.545 (1.27), 3.576 (0.90), 3.616 (0.99), 3.630 (0.99), 3.685 (1.63), 3.701 (1.63), 3.724 (1.36), 3.754 (1.18), 3.868 (0.90), 3.940 (0.99), 3.976 (0.90), 3.990 (0.99), 4.174 (0.99), 4.802 (4.07), 4.822 (16.00), 5.276 (0.99), 5.388 (1.18), 7.073 (1.90), 7.230 (1.45), 7.251 (1.81), 7.279 (1.54), 7.377 (1.18), 7.398 (2.53), 7.421 (2.35), 7.447 (0.99).

Example 468

(5S)-2-(3,4-Difluorobenzyl)-5-[(3,3-difluoropyrrolidin-1-yl)carbonyl]-5,6,7,8-tetrahydro[1,2,4]triazolo[4,3-a]pyridin-3(2H)-one

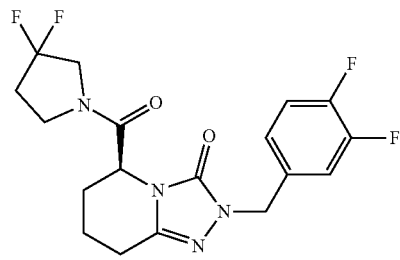 [SMILES: O=C([C@@H]1CCCc2nn(Cc3ccc(F)c(F)c3)c(=O)n21)N1CCC(F)(F)C1]

(5S)-2-(3,4-Difluorobenzyl)-3-oxo-2,3,5,6,7,8-hexahydro[1,2,4]triazolo[4,3-a]pyridine-5-carboxylic acid (60.0 mg, 194 μmol) was initially charged in THF (2.0 ml), and HBTU (95.6 mg, 252 μmol) and N,N-diisopropylethylamine (100 μl, 580 μmol) were subsequently added. After stirring at room temperature for 15 min, 3,3-difluoropyrrolidine hydrochloride (33.4 mg, 233 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 45.0 mg (58% of theory) of the title compound were obtained.

LC-MS (Method 4): $R_t$=0.81 min; MS (ESIpos): m/z=399 [M+H]$^+$ $^1$H-NMR (400 MHz, DMSO-d6) δ [ppm]: −0.149 (0.73), 0.146 (0.65), 1.243 (1.06), 1.258 (1.14), 1.273 (0.65), 1.670 (1.14), 1.731 (1.39), 2.012 (1.55), 2.328 (1.80), 2.366 (2.29), 2.380 (0.98), 2.408 (1.14), 2.426 (1.14), 2.523 (7.59), 2.567 (3.76), 2.591 (3.02), 2.609 (3.18), 2.669 (2.20), 2.710 (2.12), 3.538 (1.47), 3.559 (2.20), 3.578 (1.14), 3.635 (0.57), 3.670 (1.39), 3.703 (1.55), 3.743 (0.98), 3.774 (1.80), 3.809 (2.61), 3.826 (0.73), 3.889 (0.73), 3.909 (1.47), 3.935 (1.06), 3.954 (0.57), 3.992 (0.98), 4.035 (0.82), 4.061 (0.57), 4.145 (0.65), 4.177 (0.82), 4.203 (0.82), 4.700 (0.41), 4.770 (1.71), 4.779 (1.22), 4.822 (16.00), 4.852 (1.39), 7.082 (1.80), 7.230 (1.39), 7.257 (1.80), 7.283 (1.47), 7.376 (1.47), 7.396 (2.86), 7.423 (2.94), 7.445 (1.39).

Example 469

(5S)-2-(3,4-Difluorobenzyl)-5-[(3-fluoroazetidin-1-yl)carbonyl]-5,6,7,8-tetrahydro[1,2,4]triazolo[4,3-a]pyridin-3(2H)-one

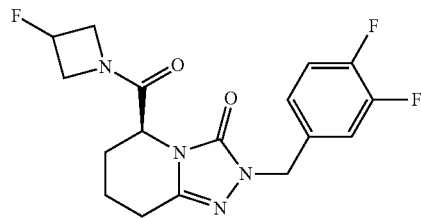 [SMILES: O=C([C@@H]1CCCc2nn(Cc3ccc(F)c(F)c3)c(=O)n21)N1CC(F)C1]

(5S)-2-(3,4-Difluorobenzyl)-3-oxo-2,3,5,6,7,8-hexahydro[1,2,4]triazolo[4,3-a]pyridine-5-carboxylic acid (60.0 mg, 194 µmol) was initially charged in THF (2.0 ml), and HBTU (95.6 mg, 252 µmol) and N,N-diisopropylethylamine (100 µl, 580 µmol) were subsequently added. After stirring at room temperature for 15 min, 3-fluoroazetidine hydrochloride (26.0 mg, 233 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.0 mg (65% of theory) of the title compound were obtained.

LC-MS (Method 3): $R_t$=1.28 min; MS (ESIpos): m/z=367 [M+H]$^+$ $^1$H-NMR (400 MHz, DMSO-d6) δ [ppm]: 1.658 (1.01), 1.671 (1.34), 1.682 (1.98), 1.705 (3.24), 1.715 (3.29), 1.961 (1.99), 1.972 (1.82), 2.008 (1.60), 2.019 (1.65), 2.030 (1.77), 2.073 (1.65), 2.559 (2.65), 2.584 (3.64), 2.598 (4.93), 2.611 (2.51), 2.627 (0.98), 2.640 (1.60), 2.653 (0.71), 2.690 (0.79), 3.900 (0.66), 3.931 (1.37), 3.961 (1.45), 3.991 (1.40), 4.023 (0.80), 4.159 (0.60), 4.175 (0.66), 4.188 (0.54), 4.213 (0.76), 4.227 (1.24), 4.241 (1.20), 4.257 (1.32), 4.270 (1.45), 4.293 (1.44), 4.324 (1.20), 4.355 (0.84), 4.372 (0.70), 4.397 (0.86), 4.434 (0.62), 4.460 (0.86), 4.507 (0.64), 4.522 (0.75), 4.546 (3.49), 4.559 (5.42), 4.571 (3.51), 4.601 (0.49), 4.635 (0.58), 4.649 (0.71), 4.685 (0.64), 4.702 (0.66), 4.713 (0.59), 4.728 (0.52), 4.824 (16.00), 5.354 (0.85), 5.399 (0.75), 5.406 (0.83), 5.497 (0.84), 5.549 (0.83), 7.086 (2.60), 7.239 (1.90), 7.263 (2.53), 7.288 (1.94), 7.374 (1.50), 7.396 (3.14), 7.421 (3.10), 7.443 (1.35).

Example 470

(5S)-5-[(3,3-Difluoropyrrolidin-1-yl)carbonyl]-2-[3-fluoro-4-(trifluoromethyl)benzyl]-5,6,7,8-tetrahydro[1,2,4]triazolo[4,3-a]pyridin-3(2H)-one

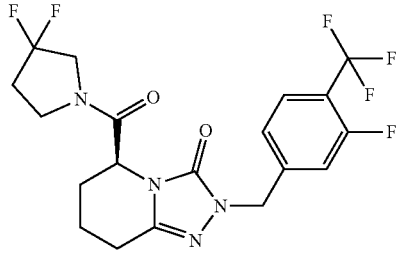 [SMILES: O=C([C@@H]1CCCc2nn(Cc3ccc(C(F)(F)F)c(F)c3)c(=O)n21)N1CCC(F)(F)C1]

(5S)-2-[3-Fluoro-4-(trifluoromethyl)benzyl]-3-oxo-2,3,5,6,7,8-hexahydro[1,2,4]triazolo[4,3-a]pyridine-5-carboxylic acid (60.0 mg, 167 µmol) was initially charged in THF (2.0 ml), and HBTU (82.3 mg, 217 µmol) and N,N-diisopropylethylamine (87 µl, 500 mol) were subsequently added. After stirring at room temperature for 15 min, 3,3-difluoropyrrolidine hydrochloride (28.8 mg, 200 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 37.0 mg (49% of theory) of the title compound were obtained.

LC-MS (Method 4): $R_t$=0.92 min; MS (ESIpos): m/z=449 [M+H]$^+$ $^1$H-NMR (400 MHz, DMSO-d6) δ [ppm]: −0.149 (0.99), 0.008 (7.37), 0.147 (0.91), 1.672 (1.29), 1.743 (1.60), 2.015 (2.03), 2.027 (1.90), 2.051 (1.51), 2.328 (1.55), 2.366 (2.33), 2.383 (1.12), 2.410 (1.38), 2.431 (1.29), 2.563 (3.54), 2.578 (3.11), 2.588 (3.54), 2.604 (3.02), 2.620 (3.19), 2.665 (2.11), 2.670 (2.11), 2.710 (1.90), 3.541 (1.68), 3.561 (2.46), 3.572 (1.38), 3.581 (1.29), 3.641 (0.39), 3.674 (1.42), 3.708 (1.68), 3.744 (1.12), 3.779 (1.98), 3.789 (1.29), 3.813 (2.59), 3.833 (0.82), 3.893 (0.73), 3.912 (1.64), 3.937 (1.12), 3.956 (0.52), 3.997 (0.99), 4.025 (0.73), 4.041 (0.91), 4.069 (0.56), 4.151 (0.65), 4.182 (0.91), 4.206 (0.95), 4.237 (0.43), 4.775 (1.42), 4.789 (1.81), 4.799 (1.38), 4.845 (1.34), 4.861 (1.81), 4.870 (1.29), 4.954 (16.00), 7.248 (3.62), 7.268 (4.05), 7.296 (3.62), 7.326 (3.62), 7.759 (2.72), 7.778 (5.18), 7.798 (2.63).

Example 471

(5S)-5-{[(3S)-3-Fluoropyrrolidin-1-yl]carbonyl}-2-[3-fluoro-4-(trifluoromethyl)benzyl]-5,6,7,8-tetrahydro[1,2,4]triazolo[4,3-a]pyridin-3(2H)-one

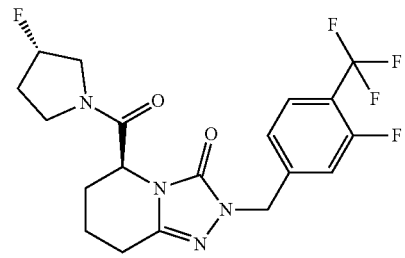 [SMILES: O=C([C@@H]1CCCc2nn(Cc3ccc(C(F)(F)F)c(F)c3)c(=O)n21)N1CC[C@H](F)C1]

(5S)-2-[3-Fluoro-4-(trifluoromethyl)benzyl]-3-oxo-2,3,5,6,7,8-hexahydro[1,2,4]triazolo[4,3-a]pyridine-5-carboxylic acid (60.0 mg, 167 µmol) was initially charged in THF (2.0 ml), and HBTU (82.3 mg, 217 µmol) and N,N-diisopropylethylamine (87 µl, 500 µmol) were subsequently added. After stirring at room temperature for 15 min, (3S)-3-fluoropyrrolidine hydrochloride (25.2 mg, 200 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 44.0 mg (61% of theory) of the title compound were obtained.

LC-MS (Method 4): $R_t$=0.86 min; MS (ESIpos): m/z=431 [M+H]$^+$ $^1$H-NMR (400 MHz, DMSO-d6) δ [ppm]: −0.149 (0.49), −0.008 (4.64), 0.008 (3.55), 0.146 (0.49), 1.709 (1.39), 1.733 (2.38), 1.744 (2.67), 1.890 (0.58), 1.929 (0.83), 1.970 (0.41), 2.005 (0.85), 2.031 (1.00), 2.040 (1.46), 2.075 (1.75), 2.086 (2.02), 2.104 (2.33), 2.110 (2.33), 2.139 (1.65), 2.222 (0.92), 2.271 (1.22), 2.327 (0.92), 2.366 (0.80), 2.523 (2.92), 2.575 (1.68), 2.582 (1.90), 2.597 (1.63), 2.623 (2.65), 2.666 (1.60), 2.710 (0.75), 3.279 (0.83), 3.353 (0.66), 3.364 (0.68), 3.373 (0.75), 3.400 (0.85), 3.409 (0.85), 3.461 (0.63), 3.471 (0.66), 3.497 (0.88), 3.506 (0.85), 3.611 (0.56), 3.637 (2.72), 3.654 (2.26), 3.681 (1.85), 3.702 (1.12), 3.729 (1.31), 3.751 (1.92), 3.776 (1.68), 3.791 (1.31), 3.858 (2.65), 4.702 (1.24), 4.711 (1.53), 4.718 (1.58), 4.727 (1.26), 4.760 (1.63), 4.769 (1.92), 4.775 (2.14), 4.784 (1.53), 4.950 (16.00), 5.261

(1.29), 5.391 (1.70), 5.512 (0.95), 7.248 (2.87), 7.269 (3.14), 7.297 (3.45), 7.326 (3.48), 7.758 (2.72), 7.778 (5.06), 7.797 (2.55).

Example 472

(5S)-5-{[(3R,4S)-3,4-Difluoropyrrolidin-1-yl]carbonyl}-2-[3-fluoro-4-(trifluoromethyl)benzyl]-5,6,7,8-tetrahydro[1,2,4]triazolo[4,3-a]pyridin-3(2H)-one

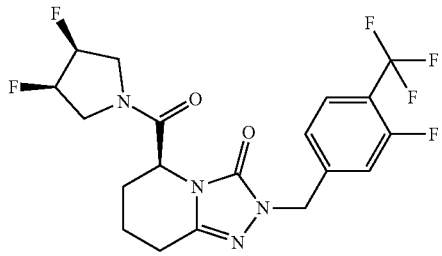 [SMILES: O=C([C@@H]1CCCc2nn(Cc3ccc(C(F)(F)F)c(F)c3)c(=O)n21)N1C[C@@H](F)[C@@H](F)C1]

(5S)-2-[3-Fluoro-4-(trifluoromethyl)benzyl]-3-oxo-2,3,5,6,7,8-hexahydro[1,2,4]triazolo[4,3-a]pyridine-5-carboxylic acid (60.0 mg, 167 µmol) was initially charged in THF (2.0 ml), and HBTU (82.3 mg, 217 µmol) and N,N-diisopropylethylamine (87 µl, 500 µmol) were subsequently added. After stirring at room temperature for 15 min, (3R,4S)-3,4-difluoropyrrolidine hydrochloride (28.8 mg, 200 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 43.0 mg (57% of theory) of the title compound were obtained.

LC-MS (Method 4): R$_t$=0.86 min; MS (ESIpos): m/z=449 [M+H]$^+$ $^1$H-NMR (400 MHz, DMSO-d6) δ [ppm]: −0.149 (1.82), −0.008 (15.01), 0.008 (13.66), 0.146 (1.71), 1.655 (1.45), 1.743 (1.71), 1.982 (1.30), 2.022 (2.03), 2.031 (2.13), 2.064 (1.35), 2.099 (1.14), 2.327 (1.92), 2.366 (2.29), 2.523 (6.13), 2.567 (2.03), 2.582 (2.44), 2.592 (1.71), 2.606 (2.55), 2.619 (3.38), 2.631 (1.92), 2.665 (2.18), 2.670 (2.34), 2.710 (2.18), 3.461 (0.62), 3.495 (1.40), 3.504 (0.94), 3.517 (1.19), 3.526 (1.30), 3.549 (1.09), 3.578 (0.83), 3.620 (0.88), 3.633 (1.04), 3.653 (0.62), 3.675 (1.04), 3.689 (1.97), 3.703 (1.45), 3.723 (1.45), 3.736 (1.40), 3.755 (1.09), 3.766 (1.09), 3.790 (0.62), 3.873 (0.94), 3.908 (0.73), 3.931 (0.88), 3.945 (1.04), 3.960 (0.57), 3.981 (0.94), 3.995 (0.94), 4.010 (0.57), 4.023 (0.57), 4.134 (0.62), 4.149 (0.73), 4.162 (0.68), 4.175 (1.14), 4.189 (0.73), 4.201 (0.68), 4.216 (0.68), 4.821 (3.84), 4.954 (16.00), 5.266 (1.04), 5.276 (1.19), 5.288 (0.99), 5.353 (0.88), 5.389 (1.14), 5.408 (1.14), 5.420 (1.04), 5.431 (0.73), 5.465 (0.83), 7.246 (2.96), 7.267 (3.27), 7.295 (3.27), 7.325 (3.27), 7.760 (2.18), 7.779 (4.05), 7.798 (1.92).

Example 473

(5S)-5-[(3-Fluoroazetidin-1-yl)carbonyl]-2-[3-fluoro-4-(trifluoromethyl)benzyl]-5,6,7,8-tetrahydro[1,2,4]triazolo[4,3-a]pyridin-3(2H)-one

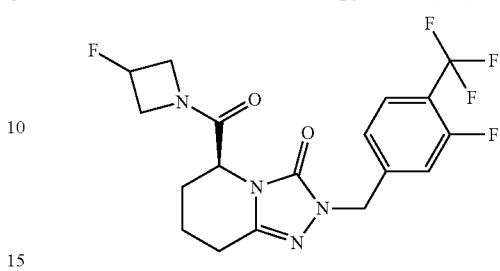

(5S)-2-[3-Fluoro-4-(trifluoromethyl)benzyl]-3-oxo-2,3,5,6,7,8-hexahydro[1,2,4]triazolo[4,3-a]pyridine-5-carboxylic acid (60.0 mg, 167 µmol) was initially charged in THF (2.0 ml), and HBTU (82.3 mg, 217 µmol) and N,N-diisopropylethylamine (87 µl, 500 µmol) were subsequently added. After stirring at room temperature for 15 min, 3-fluoroazetidine hydrochloride (22.4 mg, 200 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 29.0 mg (42% of theory) of the title compound were obtained.

LC-MS (Method 4): R$_t$=0.82 min; MS (ESIpos): m/z=417 [M+H]$^+$ $^1$H-NMR (400 MHz, DMSO-d6) δ[ppm]: −0.149 (1.06), 0.146 (1.06), 1.674 (1.48), 1.698 (2.17), 1.708 (2.70), 1.723 (3.07), 1.977 (2.12), 2.019 (1.87), 2.041 (1.87), 2.086 (4.07), 2.327 (1.23), 2.366 (1.28), 2.570 (3.04), 2.595 (3.93), 2.609 (5.35), 2.622 (2.79), 2.637 (1.09), 2.651 (1.78), 2.665 (1.64), 2.710 (1.45), 3.908 (0.75), 3.935 (1.45), 3.964 (1.48), 3.995 (1.53), 4.023 (0.92), 4.176 (0.75), 4.230 (1.23), 4.243 (1.20), 4.258 (1.09), 4.276 (1.59), 4.306 (1.37), 4.330 (0.89), 4.367 (1.25), 4.400 (0.98), 4.434 (0.67), 4.463 (0.95), 4.515 (0.67), 4.528 (0.81), 4.565 (3.93), 4.578 (5.71), 4.590 (3.71), 4.654 (0.70), 4.689 (0.72), 4.706 (0.72), 4.732 (0.61), 4.954 (16.00), 5.354 (0.89), 5.408 (0.92), 5.498 (0.92), 5.551 (0.86), 7.252 (4.52), 7.272 (4.88), 7.303 (4.29), 7.332 (4.40), 7.757 (2.70), 7.776 (5.16), 7.796 (2.62).

Example 474

(5S)-2-(2-Chloro-4-fluorobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

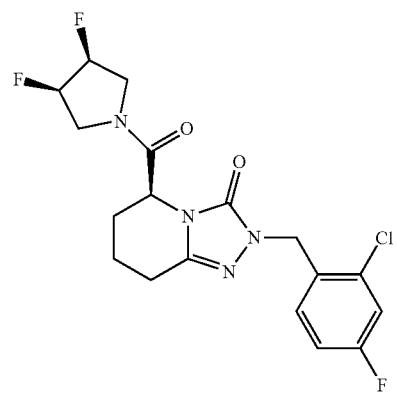 [SMILES: O=C([C@@H]1CCCc2nn(Cc3ccc(F)cc3Cl)c(=O)n21)N1C[C@@H](F)[C@@H](F)C1]

(5S)-2-(2-Chloro-4-fluorobenzyl)-3-oxo-2,3,5,6,7,8-hexahydro[1,2,4]triazolo[4,3-a]pyridine-5-carboxylic acid (63.2 mg, 185 μmol) was initially charged in THF (3.0 ml), and HBTU (91.4 mg, 241 μmol) and N,N-diisopropylethylamine (130 μl, 740 μmol) were subsequently added. After stirring at room temperature for 15 min, (3R,4S)-3,4-difluoropyrrolidine hydrochloride (31.9 mg, 222 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 70.0 mg (91% of theory) of the title compound were obtained.

LC-MS (Method 3): $R_t$=1.43 min; MS (ESIpos): m/z=415 [M+H]$^+$ $^1$H-NMR (400 MHz, DMSO-d6) δ [ppm]: −0.149 (1.38), −0.008 (13.47), 0.008 (11.40), 0.146 (1.38), 1.666 (2.35), 1.736 (2.79), 1.973 (2.17), 2.009 (3.15), 2.019 (3.44), 2.053 (2.14), 2.060 (2.14), 2.073 (5.00), 2.089 (1.70), 2.327 (1.67), 2.366 (1.12), 2.523 (6.84), 2.567 (4.71), 2.577 (3.40), 2.592 (3.95), 2.607 (5.43), 2.618 (3.11), 2.649 (1.88), 2.669 (2.03), 2.709 (1.34), 3.455 (1.19), 3.489 (2.24), 3.498 (1.77), 3.511 (1.88), 3.521 (1.92), 3.544 (1.99), 3.573 (1.45), 3.616 (1.48), 3.630 (1.63), 3.648 (1.05), 3.671 (1.67), 3.685 (3.19), 3.700 (2.46), 3.719 (2.46), 3.733 (2.28), 3.750 (1.95), 3.763 (1.95), 3.798 (1.01), 3.868 (1.48), 3.907 (1.09), 3.926 (1.45), 3.940 (1.63), 3.955 (1.05), 3.975 (1.52), 3.990 (1.63), 4.005 (1.09), 4.018 (0.94), 4.130 (0.98), 4.145 (1.23), 4.159 (1.12), 4.171 (1.85), 4.185 (1.23), 4.198 (0.98), 4.213 (1.05), 4.796 (4.27), 4.808 (5.97), 4.819 (4.16), 4.868 (16.00), 4.875 (9.59), 4.886 (8.65), 4.926 (1.81), 5.264 (1.63), 5.275 (1.85), 5.287 (1.59), 5.297 (1.16), 5.329 (1.41), 5.351 (1.41), 5.388 (1.99), 5.408 (1.63), 5.457 (1.34), 7.201 (1.30), 7.223 (6.33), 7.228 (6.73), 7.238 (9.38), 7.244 (8.36), 7.248 (9.81), 7.254 (6.91), 7.456 (5.36), 7.479 (5.57).

Example 475

(5S)-2-(2-Chloro-4-fluorobenzyl)-5-{[(3S)-3-fluoropyrrolidin-1-yl]carbonyl}-5,6,7,8-tetrahydro[1,2,4]triazolo[4,3-a]pyridin-3(2H)-one

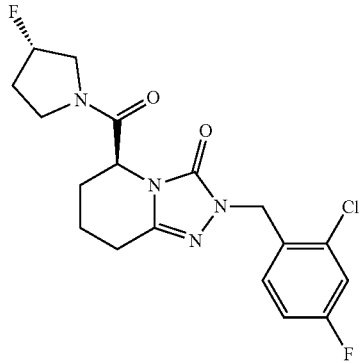 [SMILES: O=C([C@@H]1CCCc2nn(Cc3ccc(F)cc3Cl)c(=O)n21)N1CC[C@H](F)C1]

(5S)-2-(2-Chloro-4-fluorobenzyl)-3-oxo-2,3,5,6,7,8-hexahydro[1,2,4]triazolo[4,3-a]pyridine-5-carboxylic acid (63.2 mg, 185 μmol) was initially charged in THF (3.0 ml), and HBTU (91.4 mg, 241 μmol) and N,N-diisopropylethylamine (130 μl, 740 μmol) were subsequently added. After stirring at room temperature for 15 min, (3S)-3-fluoropyrrolidine hydrochloride (27.9 mg, 222 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 63.6 mg (86% of theory) of the title compound were obtained.

LC-MS (Method 4): $R_t$=0.73 min; MS (ESIpos): m/z=397 [M+H]$^+$ $^1$H-NMR (400 MHz, DMSO-d6) δ [ppm]: −0.149 (1.33), −0.008 (11.31), 0.008 (10.12), 0.146 (1.33), 1.735 (5.83), 1.878 (1.15), 1.911 (1.86), 1.994 (1.64), 2.030 (2.74), 2.064 (2.61), 2.073 (4.69), 2.090 (3.49), 2.101 (3.93), 2.137 (2.78), 2.220 (1.59), 2.268 (2.08), 2.327 (2.03), 2.366 (1.33), 2.558 (4.24), 2.568 (4.15), 2.583 (3.23), 2.612 (4.82), 2.669 (2.78), 2.710 (1.59), 3.272 (1.24), 3.359 (1.46), 3.368 (1.46), 3.395 (1.64), 3.405 (1.68), 3.466 (1.24), 3.493 (1.59), 3.502 (1.55), 3.608 (1.06), 3.633 (4.95), 3.653 (4.24), 3.678 (2.78), 3.695 (2.03), 3.726 (2.48), 3.745 (3.58), 3.768 (2.83), 3.788 (2.43), 3.821 (0.71), 3.855 (4.77), 4.691 (2.30), 4.700 (2.78), 4.706 (2.92), 4.715 (2.30), 4.748 (2.87), 4.757 (3.31), 4.763 (3.76), 4.772 (2.74), 4.823 (3.40), 4.863 (16.00), 4.878 (8.71), 4.885 (9.86), 4.925 (2.21), 5.258 (2.25), 5.390 (2.96), 5.515 (1.72), 5.944 (0.57), 7.199 (1.37), 7.220 (6.81), 7.226 (7.47), 7.241 (8.09), 7.248 (9.15), 7.274 (1.46), 7.456 (5.70), 7.462 (5.57), 7.478 (5.79), 7.483 (5.52).

Example 476

(5S)-2-(2-Chloro-4-fluorobenzyl)-5-[(3-fluoroazetidin-1-yl)carbonyl]-5,6,7,8-tetrahydro[1,2,4]triazolo[4,3-a]pyridin-3(2H)-one

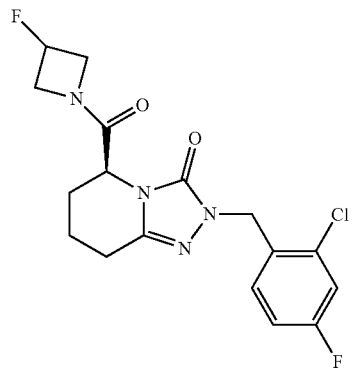 [SMILES: O=C([C@@H]1CCCc2nn(Cc3ccc(F)cc3Cl)c(=O)n21)N1CC(F)C1]

(5S)-2-(2-Chloro-4-fluorobenzyl)-3-oxo-2,3,5,6,7,8-hexahydro[1,2,4]triazolo[4,3-a]pyridine-5-carboxylic acid (63.2 mg, 185 μmol) was initially charged in THF (3.0 ml), and HBTU (91.4 mg, 241 μmol) and N,N-diisopropylethylamine (130 μl, 740 μmol) were subsequently added. After stirring at room temperature for 15 min, 3-fluoroazetidine hydrochloride (24.8 mg, 222 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 57.0 mg (73% of theory) of the title compound were obtained.

LC-MS (Method 4): $R_t$=0.70 min; MS (ESIpos): m/z=383 [M+H]$^+$ $^1$H-NMR (400 MHz, DMSO-d6) δ [ppm]: −0.008 (3.58), 0.008 (2.92), 1.688 (2.51), 1.712 (4.48), 1.721 (4.07), 1.964

(2.44), 1.975 (2.30), 2.008 (1.96), 2.019 (2.00), 2.030 (2.15), 2.073 (5.14), 2.327 (0.53), 2.366 (0.51), 2.523 (2.70), 2.581 (3.90), 2.595 (5.88), 2.609 (3.00), 2.624 (1.16), 2.638 (1.95), 2.651 (0.89), 2.670 (0.66), 2.709 (0.55), 3.898 (0.79), 3.927 (1.67), 3.958 (1.70), 3.991 (1.66), 4.018 (0.96), 4.157 (0.70), 4.171 (0.81), 4.187 (0.66), 4.223 (1.42), 4.239 (1.38), 4.252 (1.29), 4.274 (1.71), 4.302 (1.49), 4.334 (0.93), 4.362 (1.42), 4.394 (1.05), 4.431 (0.75), 4.456 (1.03), 4.506 (0.77), 4.520 (0.88), 4.548 (4.00), 4.560 (6.36), 4.573 (4.15), 4.600 (0.64), 4.635 (0.68), 4.649 (0.81), 4.687 (0.81), 4.702 (0.82), 4.728 (0.62), 4.834 (1.19), 4.874 (16.00), 4.884 (6.86), 4.925 (0.82), 5.353 (1.00), 5.406 (1.00), 5.496 (0.99), 5.549 (1.00), 7.202 (1.12), 7.224 (4.47), 7.242 (10.36), 7.258 (7.49), 7.279 (2.00), 7.455 (3.92), 7.461 (3.86), 7.477 (4.01), 7.483 (3.93).

Example 477

(5S)-2-(2-Chloro-4-fluorobenzyl)-5-[(3,3-difluoro-pyrrolidin-1-yl)carbonyl]-5,6,7,8-tetrahydro[1,2,4]triazolo[4,3-a]pyridin-3(2H)-one

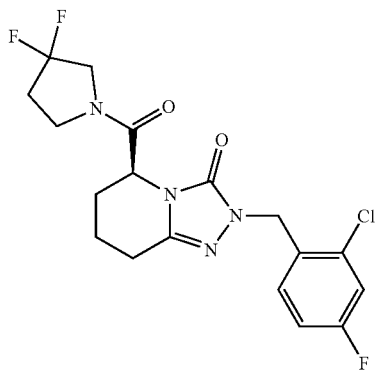 [SMILES: O=C([C@@H]1CCCc2nn(Cc3ccc(F)cc3Cl)c(=O)n21)N1CCC(F)(F)C1]

(5S)-2-(2-Chloro-4-fluorobenzyl)-3-oxo-2,3,5,6,7,8-hexahydro[1,2,4]triazolo[4,3-a]pyridine-5-carboxylic acid (63.2 mg, 185 µmol) was initially charged in THF (3.0 ml), and HBTU (91.4 mg, 241 µmol) and N,N-diisopropylethyl-amine (130 µl, 740 µmol) were subsequently added. After stirring at room temperature for 15 min, 3,3-difluoropyrro-lidine hydrochloride (31.9 mg, 222 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 64.5 mg (84% of theory) of the title compound were obtained.

LC-MS (Method 1): $R_t$=1.09 min; MS (ESIpos): m/z=415 [M+H]

$^1$H-NMR (400 MHz, DMSO-d6) δ[ppm]: −0.149 (1.75), −0.008 (14.84), 0.008 (12.90), 0.146 (1.55), 1.675 (2.23), 1.723 (2.91), 1.911 (0.82), 2.004 (3.30), 2.012 (3.15), 2.039 (2.57), 2.073 (9.41), 2.327 (2.33), 2.366 (2.28), 2.381 (1.89), 2.410 (2.28), 2.430 (2.13), 2.563 (5.62), 2.572 (6.06), 2.587 (5.53), 2.607 (6.01), 2.650 (1.79), 2.670 (2.57), 2.710 (1.99), 3.536 (2.96), 3.556 (4.12), 3.567 (2.33), 3.575 (2.18), 3.636 (0.82), 3.670 (2.47), 3.703 (2.96), 3.740 (1.94), 3.773 (3.25), 3.784 (2.18), 3.809 (4.27), 3.828 (1.21), 3.890 (1.31), 3.909 (2.81), 3.936 (1.99), 3.954 (0.92), 3.993 (1.70), 4.021 (1.31), 4.035 (1.60), 4.063 (0.97), 4.145 (1.12), 4.176 (1.50), 4.201 (1.55), 4.760 (2.47), 4.775 (3.20), 4.785 (2.33), 4.830 (3.35), 4.849 (3.25), 4.868 (15.03), 4.882 (16.00), 4.922 (2.67), 7.199 (1.36), 7.205 (1.36), 7.220 (6.55), 7.226 (7.18), 7.236 (9.31), 7.247 (7.90), 7.252 (9.70), 7.274 (1.65), 7.456 (6.64), 7.462 (6.69), 7.478 (6.50), 7.484 (6.40).

Example 478

(5S)-5-{[(3R)-3-Fluoropyrrolidin-1-yl]carbonyl}-2-{[3-fluoro-2-(trifluoromethyl)pyridin-4-yl]methyl}-5,6,7,8-tetrahydro[1,2,4]triazolo[4,3-a]pyridin-3(2H)-one

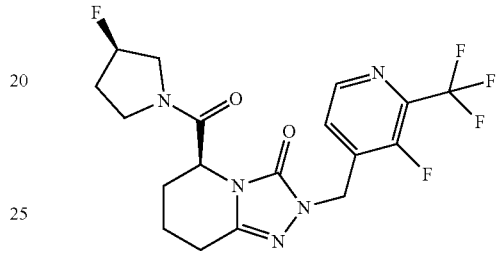

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (60.0 mg, 167 µmol) was initially charged in THF (2.0 ml) at room temperature. Subsequently, HATU (82.3 mg, 217 µmol) and triethylamine (70 µl, 500 µmol) were added. After stirring for 15 min, (3R)-3-fluoro-pyrrolidine hydrochloride (25.1 mg, 200 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sul-phate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 37.0 mg (52% of theory) of the title compound were obtained.

LC-MS (Method 3): $R_t$=1.31 min; MS (ESIpos): m/z=432 [M+H]$^+$ $^1$H-NMR (400 MHz, DMSO-d6) δ [ppm]: −0.149 (0.80), −0.008 (12.00), 0.008 (8.00), 0.146 (0.80), 1.655 (0.80), 1.760 (0.80), 2.016 (2.00), 2.027 (1.60), 2.072 (2.00), 2.101 (0.80), 2.128 (0.80), 2.263 (0.40), 2.324 (1.60), 2.329 (2.40), 2.333 (1.60), 2.367 (2.00), 2.410 (0.40), 2.520 (16.00), 2.524 (14.00), 2.558 (2.80), 2.584 (1.60), 2.595 (1.20), 2.615 (1.20), 2.626 (2.00), 2.638 (1.20), 2.666 (2.40), 2.671 (3.20), 2.711 (2.00), 3.136 (0.40), 3.176 (0.80), 3.209 (0.80), 3.383 (3.20), 3.458 (0.80), 3.528 (2.00), 3.551 (1.60), 3.578 (1.20), 3.603 (2.00), 3.659 (0.80), 3.684 (0.40), 3.748 (0.40), 3.787 (0.40), 3.919 (0.40), 3.942 (0.80), 3.983 (0.40), 4.013 (0.40), 4.043 (0.40), 4.841 (0.80), 4.855 (1.20), 4.866 (0.80), 4.890 (0.80), 5.068 (6.40), 5.272 (0.40), 5.348 (0.40), 5.400 (0.40), 5.481 (0.40), 7.561 (2.00), 8.564 (2.80), 8.575 (2.80).

Example 479

(5S)-2-{[3-Fluoro-2-(trifluoromethyl)pyridin-4-yl]methyl}-5-{[(3S)-3-hydroxypyrrolidin-1-yl]carbonyl}-5,6,7,8-tetrahydro[1,2,4]triazolo[4,3-a]pyridin-3(2H)-one

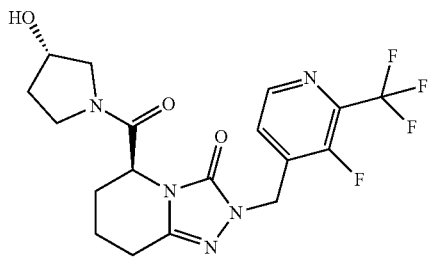 [SMILES: O=C([C@@H]1CCCc2nn(Cc3ccnc(C(F)(F)F)c3F)c(=O)n21)N1CC[C@H](O)C1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (30.0 mg, 83.3 µmol) was initially charged in THF (2.0 ml) at room temperature. Subsequently, HBTU (37.9 mg, 99.9 µmol) and N,N-diisopropylethylamine (44 µl, 250 µmol) were added. After stirring for 15 min, (3S)-pyrrolidin-3-ol (9.43 mg, 108 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 17.0 mg (48% of theory) of the title compound were obtained.

LC-MS (Method 3): $R_t$=1.09 min; MS (ESIpos): m/z=430 [M+H]$^+$ $^1$H-NMR (400 MHz, DMSO-d6) δ [ppm]: −0.149 (1.30), −0.008 (10.80), 0.008 (9.76), 0.146 (1.30), 1.406 (2.34), 1.672 (2.21), 1.750 (4.42), 1.850 (2.47), 1.860 (2.86), 1.872 (2.60), 1.882 (3.25), 1.985 (3.51), 2.008 (3.25), 2.029 (3.90), 2.039 (4.03), 2.075 (2.47), 2.327 (3.64), 2.366 (2.34), 2.518 (16.00), 2.523 (12.88), 2.565 (4.42), 2.576 (4.16), 2.591 (3.12), 2.624 (5.59), 2.665 (5.20), 2.669 (5.20), 2.674 (3.77), 2.710 (2.47), 3.204 (0.91), 3.236 (1.30), 3.346 (4.94), 3.379 (4.42), 3.398 (2.08), 3.433 (1.56), 3.443 (1.56), 3.455 (2.21), 3.463 (2.73), 3.485 (1.95), 3.575 (2.73), 3.593 (1.95), 3.638 (2.47), 3.649 (3.64), 3.665 (2.34), 3.676 (2.86), 3.756 (0.78), 4.270 (2.60), 4.361 (2.86), 4.710 (2.08), 4.719 (2.47), 4.726 (2.60), 4.734 (2.08), 4.752 (2.21), 4.767 (3.38), 4.775 (2.34), 4.834 (0.91), 4.955 (5.07), 4.963 (6.89), 4.972 (2.08), 5.014 (1.17), 5.065 (15.87), 5.078 (7.93), 5.087 (7.02), 5.106 (1.43), 7.542 (4.03), 7.554 (7.93), 7.567 (4.42), 8.562 (9.76), 8.573 (9.76).

Example 480

(5S)-5-{[(3R,4S)-3,4-Difluoropyrrolidin-1-yl]carbonyl}-2-{[3-fluoro-2-(trifluoromethyl)pyridin-4-yl]methyl}-5,6,7,8-tetrahydro[1,2,4]triazolo[4,3-a]pyridin-3(2H)-one

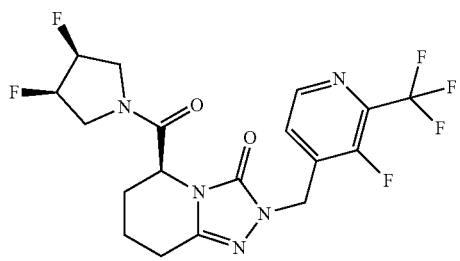 [SMILES: O=C([C@@H]1CCCc2nn(Cc3ccnc(C(F)(F)F)c3F)c(=O)n21)N1C[C@@H](F)[C@@H](F)C1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (1.19 g, 3.15 mmol) was initially charged in THF (25 ml), and HBTU (1.55 g, 4.09 mmol) and N,N-diisopropylethylamine (1.6 ml, 9.4 mmol) were subsequently added. After stirring at room temperature for 15 min, (3R,4S)-3,4-difluoropyrrolidine (371 mg, 3.46 mmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 1.04 g (73% of theory) of the title compound were obtained.

LC-MS (Method 3): $R_t$=1.37 min; MS (ESIpos): m/z=450 [M+H]$^+$ $^1$H-NMR (400 MHz, DMSO-d6) δ[ppm]: −0.149 (0.54), −0.008 (6.70), 0.008 (4.70), 0.146 (0.62), 1.412 (0.79), 1.655 (1.63), 1.747 (1.90), 1.987 (1.56), 2.025 (2.55), 2.034 (2.62), 2.073 (16.00), 2.095 (1.11), 2.102 (1.16), 2.328 (0.62), 2.561 (2.20), 2.576 (2.30), 2.587 (2.97), 2.597 (2.25), 2.612 (3.07), 2.625 (4.03), 2.637 (2.32), 2.669 (1.88), 2.710 (0.47), 3.461 (0.79), 3.495 (1.66), 3.505 (1.19), 3.517 (1.43), 3.527 (1.48), 3.537 (1.26), 3.551 (1.36), 3.581 (0.96), 3.622 (1.04), 3.636 (1.19), 3.655 (0.82), 3.677 (1.24), 3.691 (2.32), 3.704 (1.68), 3.724 (1.88), 3.738 (1.68), 3.755 (1.34), 3.768 (1.43), 3.802 (0.69), 3.873 (1.01), 3.909 (0.84), 3.930 (1.06), 3.944 (1.19), 3.960 (0.74), 3.980 (1.14), 3.995 (1.11), 4.009 (0.72), 4.022 (0.62), 4.131 (0.69), 4.146 (0.79), 4.160 (0.79), 4.172 (1.21), 4.186 (0.91), 4.199 (0.74), 4.214 (0.67), 4.816 (3.24), 4.830 (4.23), 4.840 (2.94), 5.021 (1.34), 5.063 (12.44), 5.074 (6.87), 5.116 (0.89), 5.266 (1.19), 5.276 (1.29), 5.288 (1.16), 5.314 (0.94), 5.329 (0.96), 5.353 (1.01), 5.389 (1.36), 5.408 (1.21), 5.420 (1.21), 5.431 (0.89), 5.444 (0.87), 5.457 (0.99), 7.549 (2.67), 7.561 (4.33), 8.564 (5.98), 8.576 (5.76).

Example 481

(5S)-2-{[3-Fluoro-2-(trifluoromethyl)pyridin-4-yl]methyl}-5-[(3-hydroxyazetidin-1-yl)carbonyl]-5,6,7,8-tetrahydro[1,2,4]triazolo[4,3-a]pyridin-3(2H)-one

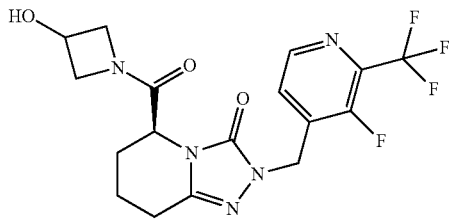 [SMILES: O=C([C@@H]1CCCc2nn(Cc3ccnc(C(F)(F)F)c3F)c(=O)n21)N1CC(O)C1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (30.0 mg, 83.3 µmol) was initially charged in THF (2.0 ml) at room temperature. Subsequently, HBTU (41.1 mg, 108 mol) and N,N-diisopropylethylamine (44 µl, 250 µmol) were added. After stirring for 15 min, azetidin-3-ol hydrochloride (10.9 mg, 99.9 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 10). The product-containing fractions were concentrated under reduced pressure, and 10.0 mg (29% of theory) of the title compound were obtained.

LC-MS (Method 4): $R_t$=0.61 min; MS (ESIpos): m/z=416 [M+H]$^+$ $^1$H-NMR (400 MHz, DMSO-d6) δ [ppm]: −0.149 (1.83), −0.008 (16.00), 0.008 (13.26), 0.146 (1.74), 1.962 (0.46), 2.327 (2.74), 2.366 (2.56), 2.523 (9.05), 2.669 (2.65), 2.710 (2.47), 3.187 (0.55), 4.046 (0.46), 4.523 (0.55), 4.550 (0.64), 5.063 (1.74), 7.561 (0.64), 8.559 (0.64).

Example 482

(5S)-5-[(3,3-Difluoropyrrolidin-1-yl)carbonyl]-2-{[3-fluoro-2-(trifluoromethyl)pyridin-4-yl]methyl}-5,6,7,8-tetrahydro[1,2,4]triazolo[4,3-a]pyridin-3(2H)-one

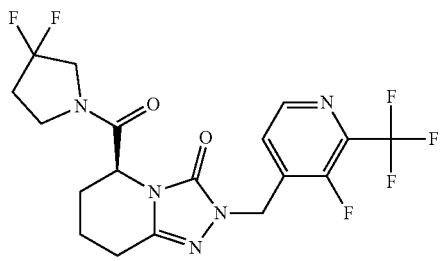 [SMILES: O=C([C@@H]1CCCc2nn(Cc3ccnc(C(F)(F)F)c3F)c(=O)n21)N1CCC(F)(F)C1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (180 mg, 53% purity, 266 µmol) was initially charged in THF (2.4 ml), and HBTU (263 mg, 692 µmol) and N,N-diisopropylethylamine (280 µl, 1.6 mmol) were subsequently added. After stirring at room temperature for 15 min, 3,3-difluoropyrrolidine hydrochloride (91.8 mg, 639 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 106 mg (89% of theory) of the title compound were obtained.

LC-MS (Method 3): $R_t$=1.45 min; MS (ESIpos): m/z=450 [M+H]$^+$ $^1$H-NMR (400 MHz, DMSO-d6) δ [ppm]: −0.149 (0.81), 0.145 (0.69), 1.173 (1.04), 1.191 (0.75), 1.225 (2.76), 1.243 (13.73), 1.259 (16.00), 1.273 (7.74), 1.673 (2.04), 1.748 (2.50), 1.902 (0.95), 1.978 (1.38), 2.019 (3.08), 2.327 (1.53), 2.366 (1.87), 2.382 (1.96), 2.411 (2.36), 2.432 (2.45), 2.455 (2.22), 2.583 (4.23), 2.592 (4.12), 2.608 (4.37), 2.625 (4.72), 2.669 (2.62), 2.710 (0.92), 3.145 (1.27), 3.541 (2.53), 3.560 (3.91), 3.573 (2.13), 3.581 (2.16), 3.641 (1.29), 3.674 (2.27), 3.709 (2.50), 3.744 (1.64), 3.779 (2.91), 3.814 (4.20), 3.833 (1.21), 3.891 (1.21), 3.909 (2.42), 3.936 (1.76), 3.955 (0.83), 3.967 (0.78), 3.997 (1.61), 4.025 (1.12), 4.040 (1.41), 4.067 (0.86), 4.150 (0.83), 4.179 (1.41), 4.205 (1.50), 4.238 (0.55), 4.782 (2.13), 4.797 (2.88), 4.806 (2.07), 4.853 (2.07), 4.868 (2.73), 4.877 (2.13), 5.021 (1.44), 5.063 (13.32), 5.071 (14.39), 5.113 (1.53), 6.513 (0.89), 7.547 (4.03), 7.560 (7.63), 7.573 (4.20), 8.564 (8.86), 8.575 (8.72).

Example 483

(5S)-5-[(3-Fluoroazetidin-1-yl)carbonyl]-2-{[3-fluoro-2-(trifluoromethyl)pyridin-4-yl]methyl}-5,6,7,8-tetrahydro[1,2,4]triazolo[4,3-a]pyridin-3(2H)-one

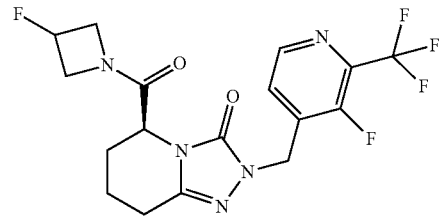 [SMILES: O=C([C@@H]1CCCc2nn(Cc3ccnc(C(F)(F)F)c3F)c(=O)n21)N1CC(F)C1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (30.0 mg, 83.3 µmol) was initially charged in THF (2.0 ml), and HBTU (41.1 mg, 108 µmol) and N,N-diisopropylethylamine (44 µl, 250 µmol) were subsequently added. After stirring at room temperature for 15 min, 3-fluoroazetidine hydrochloride (11.1 mg, 99.9 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 15.0 mg (43% of theory) of the title compound were obtained.

LC-MS (Method 4): $R_t$=0.73 min; MS (ESIpos): m/z=418 [M+H]$^+$ $^1$H-NMR (400 MHz, DMSO-d6) δ [ppm]: −0.150 (0.74), −0.008 (7.63), 0.008 (6.07), 0.146 (0.74), 1.673 (1.71), 1.683 (2.20), 1.698 (2.34), 1.709 (2.72), 1.730 (3.20), 1.982 (2.42), 1.995 (2.49), 2.020 (2.27), 2.327 (1.45), 2.366 (1.38), 2.523 (5.77), 2.574 (3.20), 2.600 (4.24), 2.614 (6.10), 2.627 (3.20), 2.642 (1.30), 2.656 (2.16), 2.669 (2.46), 2.710 (1.60), 3.909 (0.82), 3.935 (1.64), 3.965 (1.64), 3.997 (1.71), 4.023 (1.00), 4.166 (0.71), 4.178 (0.86), 4.194 (0.67), 4.243 (1.34), 4.278 (1.64), 4.309 (1.60), 4.343 (0.93), 4.371 (1.64), 4.398 (1.12), 4.432 (0.82), 4.460 (1.04), 4.516 (0.74), 4.530 (0.89), 4.572 (4.43), 4.585 (6.55), 4.597 (4.24), 4.634 (0.74), 4.649 (0.82), 4.685 (0.78), 4.702 (0.78), 4.726 (0.63), 5.023 (0.78), 5.065 (16.00), 5.115 (0.63), 5.355 (1.00), 5.408 (1.00), 5.497 (1.04), 5.551 (1.04), 7.556 (4.09), 7.569 (7.74), 7.581 (4.28), 8.561 (6.96), 8.573 (7.00).

Example 484

(5S)-5-{[(3S)-3-Fluoropyrrolidin-1-yl]carbonyl}-2-{[3-fluoro-2-(trifluoromethyl)pyridin-4-yl]methyl}-5,6,7,8-tetrahydro[1,2,4]triazolo[4,3-a]pyridin-3(2H)-one

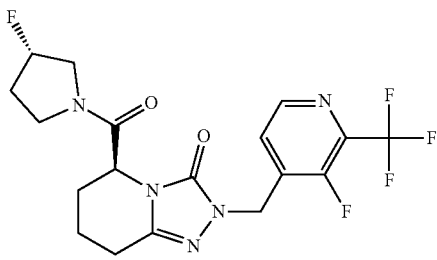 [SMILES: O=C([C@@H]1CCCc2nn(Cc3ccnc(C(F)(F)F)c3F)c(=O)n21)N1CC[C@H](F)C1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (180 mg, 53% purity, 266 μmol) was initially charged in THF (2.4 ml), and HBTU (263 mg, 692 μmol) and N,N-diisopropylethylamine (280 μl, 1.6 mmol) were subsequently added. After stirring at room temperature for 15 min, (3S)-3-fluoropyrrolidine hydrochloride (80.3 mg, 639 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 98.9 mg (86% of theory) of the title compound were obtained.

LC-MS (Method 3): $R_t$=1.31 min; MS (ESIpos): m/z=432 [M+H]$^+$ $^1$H-NMR (400 MHz, DMSO-d6) δ[ppm]: −0.149 (1.74), −0.008 (16.00), 0.008 (13.44), 0.146 (1.64), 1.748 (1.64), 1.934 (0.62), 2.106 (1.64), 2.267 (0.82), 2.327 (2.67), 2.366 (2.15), 2.523 (7.49), 2.587 (1.33), 2.602 (1.13), 2.629 (1.74), 2.669 (3.28), 2.709 (1.95), 3.408 (0.51), 3.462 (0.51), 3.498 (0.62), 3.634 (1.64), 3.652 (1.33), 3.679 (1.13), 3.703 (0.72), 3.751 (1.23), 3.774 (1.13), 3.792 (0.82), 3.857 (1.74), 4.717 (1.13), 4.780 (1.33), 4.790 (1.13), 5.016 (0.92), 5.057 (5.95), 5.071 (4.21), 5.112 (0.62), 5.260 (0.82), 5.393 (1.03), 5.515 (0.62), 7.548 (1.54), 7.561 (3.08), 7.573 (1.74), 8.564 (3.69), 8.575 (3.69).

Example 485

(5S)-2-{[3-Fluoro-2-(trifluoromethyl)pyridin-4-yl]methyl}-5-(1,3-thiazolidin-3-ylcarbonyl)-5,6,7,8-tetrahydro[1,2,4]triazolo[4,3-a]pyridin-3(2H)-one

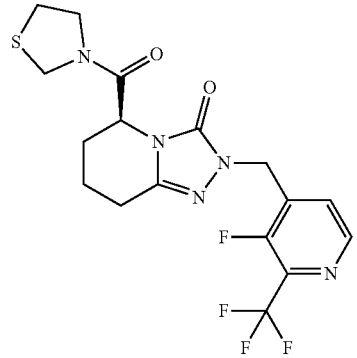 [SMILES: O=C([C@@H]1CCCc2nn(Cc3ccnc(C(F)(F)F)c3F)c(=O)n21)N1CCSC1]

(5S)-2-{[3-Fluoro-2-(trifluoromethyl)pyridin-4-yl]methyl}-3-oxo-2,3,5,6,7,8-hexahydro[1,2,4]triazolo[4,3-a]pyridine-5-carboxylic acid (100 mg, 278 μmol) was initially charged in THF (2.1 ml, 26 mmol), and HBTU (137 mg, 361 μmol) and N,N-diisopropylethylamine (150 μl, 830 μmol) were subsequently added. After stirring at room temperature for 15 min, 1,3-thiazolidine (29.7 mg, 333 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 61.0 mg (51% of theory) of the title compound were obtained.

LC-MS (Method 3): $R_t$=1.40 min; MS (ESIpos): m/z=432 [M+H]$^+$ $^1$H-NMR (400 MHz, DMSO-d6) δ [ppm]: −0.149 (1.81), −0.008 (16.00), 0.008 (14.45), 0.146 (1.94), 1.622 (0.52), 1.764 (0.65), 2.037 (0.90), 2.327 (2.84), 2.366 (2.45), 2.524 (6.32), 2.566 (2.06), 2.581 (1.42), 2.629 (1.29), 2.669 (3.48), 2.710 (2.71), 3.020 (1.42), 3.036 (0.77), 3.130 (0.90), 3.145 (1.81), 3.160 (1.03), 3.643 (0.52), 3.696 (0.52), 3.801 (0.52), 3.945 (0.52), 4.374 (0.90), 4.400 (1.16), 4.556 (1.03), 4.581 (0.90), 4.614 (0.65), 4.637 (0.77), 4.811 (0.77), 4.833 (0.65), 4.904 (0.65), 4.991 (0.52), 5.067 (3.35), 5.075 (3.61), 7.547 (0.90), 7.560 (1.81), 7.574 (0.90), 8.564 (2.06), 8.576 (2.06).

Example 486

(5S)-2-(2,4-Difluorobenzyl)-5-[(3-fluoroazetidin-1-yl)carbonyl]-5,6,7,8-tetrahydro[1,2,4]triazolo[4,3-a]pyridin-3(2H)-one

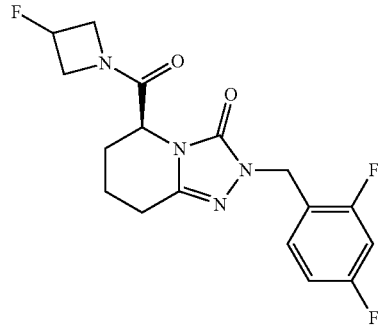 [SMILES: O=C([C@@H]1CCCc2nn(Cc3ccc(F)cc3F)c(=O)n21)N1CC(F)C1]

(5S)-2-(2,4-Difluorobenzyl)-3-oxo-2,3,5,6,7,8-hexahydro[1,2,4]triazolo[4,3-a]pyridine-5-carboxylic acid (60.0 mg, 194 µmol) was initially charged in THF (3.0 ml), and HBTU (95.6 mg, 252 µmol) and N,N-diisopropylethylamine (140 µl, 780 µmol) were subsequently added. After stirring at room temperature for 15 min, 3-fluoroazetidine hydrochloride (26.0 mg, 233 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 53.1 mg (75% of theory) of the title compound were obtained.

LC-MS (Method 3): $R_t$=1.22 min; MS (ESIpos): m/z=367 [M+H]$^+$ $^1$H-NMR (400 MHz, DMSO-d6) δ[ppm]: 0.008 (2.45), 1.702 (7.00), 1.942 (3.26), 2.005 (2.78), 2.016 (2.91), 2.073 (5.89), 2.327 (0.68), 2.366 (0.55), 2.524 (5.41), 2.566 (6.11), 2.580 (8.21), 2.593 (4.09), 2.609 (1.51), 2.622 (2.63), 2.635 (1.12), 2.669 (0.79), 2.710 (0.61), 3.760 (0.96), 3.778 (0.79), 3.894 (1.12), 3.923 (2.21), 3.952 (2.34), 3.985 (2.23), 4.016 (1.34), 4.152 (0.98), 4.167 (1.09), 4.180 (0.90), 4.205 (1.25), 4.220 (2.01), 4.235 (1.97), 4.250 (2.15), 4.264 (2.34), 4.287 (2.30), 4.319 (1.99), 4.348 (1.44), 4.391 (1.40), 4.426 (1.03), 4.450 (1.36), 4.496 (1.09), 4.521 (5.41), 4.533 (8.38), 4.546 (5.32), 4.566 (1.23), 4.591 (0.79), 4.629 (0.96), 4.642 (1.12), 4.681 (1.07), 4.697 (1.07), 4.721 (0.88), 4.784 (2.28), 4.822 (16.00), 4.877 (1.42), 5.351 (1.40), 5.405 (1.38), 5.494 (1.36), 5.548 (1.38), 7.056 (2.78), 7.078 (6.02), 7.097 (3.37), 7.219 (2.93), 7.244 (5.67), 7.268 (3.02), 7.284 (2.85), 7.304 (5.87), 7.322 (5.60), 7.343 (2.34).

Example 487

(5S)-2-(2,4-Difluorobenzyl)-5-[(3,3-difluoropyrrolidin-1-yl)carbonyl]-5,6,7,8-tetrahydro[1,2,4]triazolo[4,3-a]pyridin-3(2H)-one

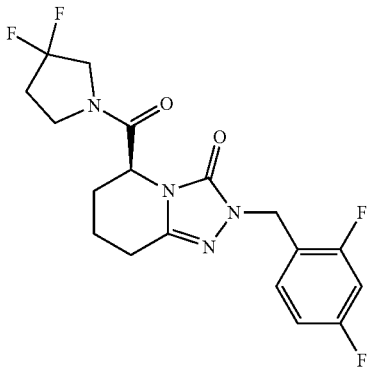 [SMILES: O=C([C@@H]1CCCc2nn(Cc3ccc(F)cc3F)c(=O)n21)N1CCC(F)(F)C1]

(5S)-2-(2,4-Difluorobenzyl)-3-oxo-2,3,5,6,7,8-hexahydro[1,2,4]triazolo[4,3-a]pyridine-5-carboxylic acid (60.0 mg, 194 µmol) was initially charged in THF (3.0 ml), and HBTU (95.6 mg, 252 µmol) and N,N-diisopropylethylamine (140 µl, 780 µmol) were subsequently added. After stirring at room temperature for 15 min, 3,3-difluoropyrrolidine hydrochloride (33.4 mg, 233 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 68.6 mg (89% of theory) of the title compound were obtained.

LC-MS (Method 3): $R_t$=1.42 min; MS (ESIpos): m/z=399 [M+H]$^+$ $^1$H-NMR (400 MHz, DMSO-d6) δ[ppm]: −0.009 (7.97), 1.707 (3.42), 1.991 (3.13), 2.072 (3.13), 2.327 (1.65), 2.365 (1.99), 2.408 (2.33), 2.572 (6.04), 2.590 (6.43), 2.604 (3.99), 2.633 (1.94), 2.669 (1.77), 2.710 (1.77), 3.533 (2.85), 3.544 (4.10), 3.554 (4.38), 3.664 (2.56), 3.697 (2.96), 3.739 (1.59), 3.772 (3.53), 3.804 (5.52), 3.904 (2.90), 3.930 (2.05), 3.989 (1.77), 4.031 (1.59), 4.169 (1.59), 4.196 (1.65), 4.748 (3.19), 4.779 (2.79), 4.817 (16.00), 4.836 (14.92), 4.875 (2.85), 7.059 (2.51), 7.081 (5.47), 7.102 (2.96), 7.218 (3.19), 7.225 (3.07), 7.244 (5.01), 7.268 (3.36), 7.275 (5.07), 7.298 (6.21), 7.315 (5.98), 7.336 (2.62).

Example 488

(5S)-2-(2,4-Difluorobenzyl)-5-{[(3S)-3-fluoropyrrolidin-1-yl]carbonyl}-5,6,7,8-tetrahydro[1,2,4]triazolo[4,3-a]pyridin-3(2H)-one

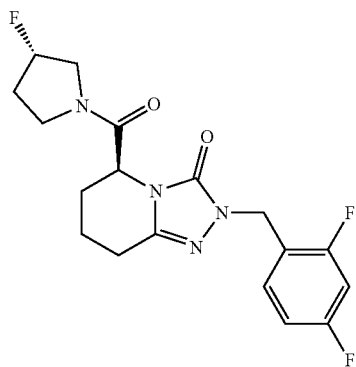 [SMILES: O=C([C@@H]1CCCc2nn(Cc3ccc(F)cc3F)c(=O)n21)N1CC[C@H](F)C1]

(5S)-2-(2,4-Difluorobenzyl)-3-oxo-2,3,5,6,7,8-hexahydro[1,2,4]triazolo[4,3-a]pyridine-5-carboxylic acid (60.0 mg, 194 µmol) was initially charged in THF (3.1 ml), and HBTU (95.6 mg, 252 µmol) and N,N-diisopropylethylamine (140 µl, 780 µmol) were subsequently added. After stirring at room temperature for 15 min, (3S)-3-fluoropyrrolidine hydrochloride (29.2 mg, 233 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 71.0 mg (96% of theory) of the title compound were obtained.

LC-MS (Method 3): $R_t$=1.26 min; MS (ESIpos): m/z=381 [M+H]$^+$ $^1$H-NMR (400 MHz, DMSO-d6) δ [ppm]: −0.149 (0.47), −0.008 (4.61), 0.008 (3.24), 0.146 (0.44), 1.244 (0.93), 1.259 (0.88), 1.274 (0.58), 1.710 (5.63), 1.721 (6.37), 1.858 (1.32), 1.869 (1.26), 1.882 (1.15), 1.892 (1.62), 1.970 (1.59), 1.984 (1.56), 1.996 (2.22), 2.006 (2.91), 2.019 (2.66), 2.050 (2.52), 2.060 (3.16), 2.073 (10.65), 2.086 (3.81), 2.105 (3.24), 2.123 (2.14), 2.134 (2.58), 2.170 (0.93), 2.189 (0.63), 2.217 (1.70), 2.237 (1.81), 2.266 (2.25), 2.323 (0.93), 2.328 (1.07), 2.366 (1.13), 2.519 (4.01), 2.568 (2.96), 2.591 (4.80), 2.596 (4.97), 2.638 (1.87), 2.670 (1.04), 2.690 (1.78), 2.710 (1.04), 2.731 (0.96), 2.890 (1.29), 3.267 (1.13), 3.286 (1.40), 3.296 (2.09), 3.314 (2.11), 3.324 (1.45), 3.342 (1.23), 3.357

(1.26), 3.365 (1.45), 3.369 (1.29), 3.391 (1.67), 3.400 (1.70), 3.453 (1.29), 3.462 (1.34), 3.489 (1.89), 3.498 (1.73), 3.606 (1.23), 3.631 (6.26), 3.649 (4.50), 3.654 (4.12), 3.674 (2.83), 3.693 (2.42), 3.719 (2.61), 3.740 (4.28), 3.766 (3.51), 3.773 (2.74), 3.782 (2.96), 3.814 (0.80), 3.851 (5.46), 4.491 (2.42), 4.668 (4.34), 4.677 (4.78), 4.683 (4.91), 4.693 (4.14), 4.724 (4.69), 4.734 (5.08), 4.740 (5.57), 4.749 (4.36), 4.773 (4.94), 4.812 (16.00), 4.838 (10.21), 4.877 (3.18), 5.258 (2.69), 5.382 (3.35), 5.389 (3.46), 5.510 (1.95), 5.943 (0.63), 6.954 (0.41), 7.054 (2.58), 7.060 (2.74), 7.075 (5.79), 7.081 (6.37), 7.097 (3.27), 7.102 (3.32), 7.218 (3.10), 7.225 (2.94), 7.243 (5.43), 7.249 (5.05), 7.268 (3.29), 7.274 (4.47), 7.280 (2.52), 7.297 (5.52), 7.302 (4.36), 7.314 (3.68), 7.318 (5.46), 7.335 (1.65), 7.340 (1.84).

Example 489

(5S)-2-(2,4-Difluorobenzyl)-5-{[(3R,4S)-3,4-difluoropyrrolidin-1-yl]carbonyl}-5,6,7,8-tetrahydro[1,2,4]triazolo[4,3-a]pyridin-3(2H)-one

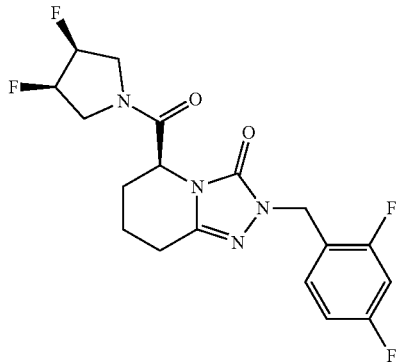 [SMILES: O=C([C@@H]1CCCc2nn(Cc3ccc(F)cc3F)c(=O)n21)N1C[C@@H](F)[C@@H](F)C1]

(5S)-2-(2,4-Difluorobenzyl)-3-oxo-2,3,5,6,7,8-hexahydro[1,2,4]triazolo[4,3-a]pyridine-5-carboxylic acid (60.0 mg, 194 µmol) was initially charged in THF (3.1 ml), and HBTU (95.6 mg, 252 µmol) and N,N-diisopropylethylamine (140 µl, 780 µmol) were subsequently added. After stirring at room temperature for 15 min, (3R,4S)-3,4-difluoropyrrolidine hydrochloride (33.4 mg, 233 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 70.3 mg (91% of theory) of the title compound were obtained.

LC-MS (Method 3): $R_t$=1.34 min; MS (ESIpos): m/z=399 $[M+H]^+$ $^1$H-NMR (400 MHz, DMSO-d6) δ [ppm]: −0.149 (0.55), −0.008 (5.38), 0.008 (5.26), 0.146 (0.55), 1.021 (0.70), 1.038 (0.74), 1.409 (0.50), 1.637 (2.21), 1.661 (2.91), 1.670 (2.58), 1.697 (2.83), 1.709 (3.33), 1.718 (3.71), 1.732 (3.08), 1.909 (1.50), 1.951 (2.82), 1.959 (2.44), 1.975 (1.85), 1.997 (3.57), 2.021 (2.24), 2.032 (2.52), 2.039 (2.71), 2.047 (2.58), 2.056 (2.19), 2.073 (9.63), 2.082 (1.94), 2.110 (0.67), 2.327 (0.77), 2.562 (4.05), 2.577 (5.02), 2.591 (6.66), 2.602 (3.78), 2.621 (1.42), 2.633 (2.28), 2.645 (1.22), 2.670 (0.89), 2.710 (0.67), 3.440 (0.78), 3.449 (1.35), 3.458 (0.84), 3.483 (2.30), 3.504 (1.67), 3.512 (1.74), 3.521 (2.00), 3.530 (2.80), 3.538 (2.63), 3.563 (1.19), 3.573 (1.72), 3.583 (1.09), 3.611 (1.83), 3.625 (2.06), 3.644 (1.28), 3.658 (1.45), 3.666 (2.06), 3.681 (2.99), 3.699 (3.74), 3.714 (2.35), 3.722 (2.38), 3.731 (2.44), 3.751 (2.28), 3.762 (2.16), 3.784 (1.24), 3.797 (1.17), 3.826 (0.81), 3.856 (1.44), 3.862 (1.78), 3.891 (1.17), 3.898 (1.31), 3.922 (1.80), 3.936 (2.03), 3.951 (1.24), 3.965 (1.42), 3.971 (1.92), 3.985 (1.92), 4.000 (1.20), 4.014 (1.11), 4.125 (1.20), 4.140 (1.39), 4.153 (1.36), 4.167 (2.31), 4.181 (1.49), 4.194 (1.33), 4.209 (1.22), 4.780 (9.35), 4.793 (4.99), 4.817 (16.00), 4.831 (9.32), 4.839 (9.45), 4.870 (1.49), 4.879 (2.33), 5.069 (0.81), 5.244 (1.25), 5.253 (1.99), 5.265 (2.00), 5.275 (2.21), 5.283 (1.78), 5.296 (1.38), 5.309 (1.24), 5.317 (1.27), 5.329 (1.60), 5.337 (1.63), 5.349 (1.70), 5.364 (1.55), 5.374 (2.16), 5.387 (2.41), 5.398 (2.00), 5.406 (1.99), 5.414 (1.78), 5.439 (1.24), 5.447 (1.36), 5.457 (1.70), 5.470 (1.64), 5.479 (1.72), 5.493 (1.25), 5.502 (0.83), 7.057 (2.83), 7.060 (2.85), 7.078 (6.16), 7.081 (6.15), 7.100 (3.50), 7.103 (3.46), 7.220 (2.96), 7.246 (5.77), 7.271 (4.75), 7.293 (4.41), 7.301 (4.41), 7.309 (3.89), 7.317 (4.60), 7.330 (1.78), 7.339 (1.81).

Example 490

(5S)-5-[(3,3-Difluoropyrrolidin-1-yl)carbonyl]-2-(2,4,5-trifluorobenzyl)-5,6,7,8-tetrahydro[1,2,4]triazolo[4,3-a]pyridin-3(2H)-one

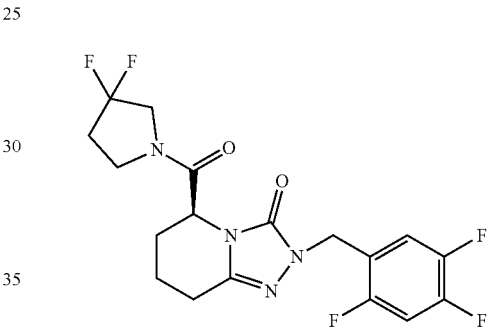

(5S)-3-Oxo-2-(2,4,5-trifluorobenzyl)-2,3,5,6,7,8-hexahydro[1,2,4]triazolo[4,3-a]pyridine-5-carboxylic acid (50.0 mg, 153 µmol) was initially charged in THF (3.0 ml), and HBTU (75.3 mg, 199 µmol) and N,N-diisopropylethylamine (80 µl, 460 µmol) were subsequently added. After stirring at room temperature for 15 min, 3,3-difluoropyrrolidine hydrochloride (26.3 mg, 183 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 34.2 mg (54% of theory) of the title compound were obtained.

LC-MS (Method 3): $R_t$=1.50 min; MS (ESIpos): m/z=417 $[M+H]^+$ $^1$H-NMR (400 MHz, DMSO-d6) δ [ppm]: −0.149 (0.45), −0.008 (4.97), 0.007 (3.87), 0.146 (0.52), 0.966 (0.45), 0.981 (0.45), 1.663 (2.32), 1.688 (1.81), 1.727 (2.84), 1.982 (2.65), 1.995 (3.16), 2.006 (3.42), 2.021 (2.84), 2.034 (2.32), 2.042 (2.39), 2.049 (2.26), 2.059 (2.00), 2.071 (2.00), 2.086 (1.61), 2.327 (1.48), 2.366 (1.74), 2.380 (1.87), 2.409 (2.19), 2.430 (2.19), 2.451 (1.74), 2.560 (5.94), 2.570 (6.97), 2.586 (5.87), 2.604 (6.58), 2.616 (3.16), 2.633 (1.35), 2.646 (2.06), 2.669 (1.81), 2.709 (1.48), 3.530 (2.71), 3.535 (2.90), 3.547 (4.06), 3.556 (4.39), 3.566 (2.52), 3.575 (2.26), 3.636 (0.77), 3.669 (2.39), 3.702 (3.10), 3.737 (2.52), 3.770 (3.42), 3.780 (2.39), 3.788 (1.87), 3.805 (4.65), 3.825 (1.42), 3.835 (0.77), 3.888 (1.35), 3.907 (2.90), 3.925 (1.61), 3.933 (2.06), 3.951

(0.97), 3.961 (0.97), 3.990 (1.87), 4.003 (0.90), 4.018 (1.23), 4.032 (1.68), 4.061 (1.03), 4.143 (1.10), 4.175 (1.68), 4.200 (1.68), 4.230 (0.65), 4.750 (2.39), 4.764 (3.29), 4.774 (2.45), 4.791 (2.19), 4.830 (15.23), 4.845 (16.00), 4.885 (2.52), 7.263 (2.39), 7.280 (2.77), 7.285 (3.16), 7.307 (3.16), 7.312 (2.90), 7.329 (2.45), 7.540 (2.52), 7.556 (2.77), 7.566 (3.87), 7.582 (3.87), 7.591 (2.90), 7.607 (2.65).

Example 491

(5S)-5-[(3-Fluoroazetidin-1-yl)carbonyl]-2-(2,4,5-trifluorobenzyl)-5,6,7,8-tetrahydro[1,2,4]triazolo[4,3-a]pyridin-3(2H)-one

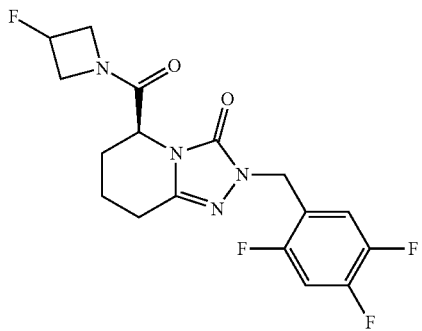 [SMILES: O=C([C@@H]1CCCc2nn(Cc3cc(F)c(F)cc3F)c(=O)n21)N1CC(F)C1]

(5S)-3-Oxo-2-(2,4,5-trifluorobenzyl)-2,3,5,6,7,8-hexahydro[1,2,4]triazolo[4,3-a]pyridine-5-carboxylic acid (50.0 mg, 153 μmol) was initially charged in THF (3.0 ml), and HBTU (75.3 mg, 199 μmol) and N,N-diisopropylethylamine (80 μl, 460 μmol) were subsequently added. After stirring at room temperature for 15 min, 3-fluoroazetidine hydrochloride (20.5 mg, 183 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 27.2 mg (46% of theory) of the title compound were obtained.

LC-MS (Method 3): $R_t$=1.31 min; MS (ESIpos): m/z=385 [M+H]$^+$ $^1$H-NMR (400 MHz, DMSO-d6) δ[ppm]: −0.149 (1.49), −0.008 (13.66), 0.008 (11.22), 0.146 (1.44), 1.675 (2.84), 1.699 (4.55), 1.709 (4.73), 1.956 (2.93), 1.965 (2.75), 2.023 (2.61), 2.073 (1.58), 2.327 (1.49), 2.366 (1.62), 2.523 (5.72), 2.578 (5.18), 2.593 (7.66), 2.606 (3.97), 2.621 (1.58), 2.635 (2.61), 2.648 (1.22), 2.670 (1.67), 2.710 (1.80), 3.899 (0.99), 3.929 (2.03), 3.959 (2.03), 3.991 (2.07), 4.021 (1.22), 4.158 (0.90), 4.171 (1.04), 4.188 (0.86), 4.224 (1.71), 4.238 (1.71), 4.268 (2.30), 4.290 (2.12), 4.321 (1.71), 4.353 (1.35), 4.392 (1.26), 4.429 (0.95), 4.455 (1.31), 4.505 (0.95), 4.538 (4.64), 4.550 (7.62), 4.562 (4.91), 4.600 (0.77), 4.629 (0.81), 4.648 (0.99), 4.682 (0.99), 4.699 (1.04), 4.794 (1.76), 4.834 (16.00), 4.886 (1.17), 5.353 (1.26), 5.406 (1.22), 5.495 (1.22), 5.550 (1.22), 7.272 (1.89), 7.297 (3.15), 7.315 (3.20), 7.339 (1.89), 7.539 (1.89), 7.564 (3.61), 7.581 (3.65), 7.606 (1.98).

Example 492

(5S)-5-{[(3R,4S)-3,4-Difluoropyrrolidin-1-yl]carbonyl}-2-(2,4,5-trifluorobenzyl)-5,6,7,8-tetrahydro[1,2,4]triazolo[4,3-a]pyridin-3(2H)-one

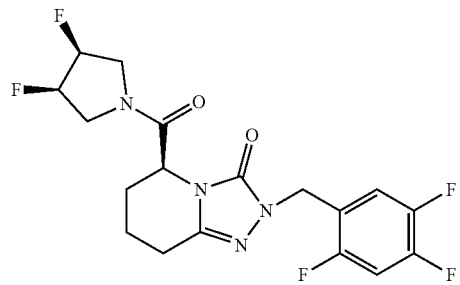 [SMILES: O=C([C@@H]1CCCc2nn(Cc3cc(F)c(F)cc3F)c(=O)n21)N1C[C@@H](F)[C@@H](F)C1]

(5S)-3-Oxo-2-(2,4,5-trifluorobenzyl)-2,3,5,6,7,8-hexahydro[1,2,4]triazolo[4,3-a]pyridine-5-carboxylic acid (50.0 mg, 153 μmol) was initially charged in THF (3.0 ml), and HBTU (75.3 mg, 199 μmol) and N,N-diisopropylethylamine (80 μl, 460 μmol) were subsequently added. After stirring at room temperature for 15 min, (3R,4S)-3,4-difluoropyrrolidine hydrochloride (26.3 mg, 183 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 29.0 mg (46% of theory) of the title compound were obtained.

LC-MS (Method 3): $R_t$=1.41 min; MS (ESIpos): m/z=417 [M+H]$^+$ $^1$H-NMR (400 MHz, DMSO-d6) δ [ppm]: −0.149 (1.81), −0.008 (16.00), 0.008 (13.82), 0.146 (1.81), 1.654 (0.75), 1.728 (0.90), 2.012 (0.94), 2.327 (2.07), 2.366 (1.62), 2.523 (6.70), 2.562 (1.69), 2.603 (1.77), 2.645 (0.68), 2.669 (2.11), 2.709 (1.62), 3.487 (1.28), 3.615 (0.60), 3.685 (1.02), 3.699 (0.83), 3.715 (0.75), 3.937 (0.60), 3.987 (0.53), 4.170 (0.56), 4.795 (2.07), 4.830 (4.10), 4.840 (2.52), 4.888 (0.53), 5.387 (0.64), 7.282 (0.98), 7.307 (1.02), 7.537 (0.56), 7.565 (1.20), 7.581 (1.17), 7.605 (0.56).

Example 493

(5S)-5-{[(3S)-3-Fluoropyrrolidin-1-yl]carbonyl}-2-(2,4,5-trifluorobenzyl)-5,6,7,8-tetrahydro[1,2,4]triazolo[4,3-a]pyridin-3(2H)-one

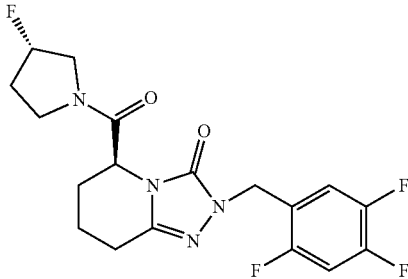 [SMILES: O=C([C@@H]1CCCc2nn(Cc3cc(F)c(F)cc3F)c(=O)n21)N1CC[C@H](F)C1]

(5S)-3-Oxo-2-(2,4,5-trifluorobenzyl)-2,3,5,6,7,8-hexahydro[1,2,4]triazolo[4,3-a]pyridine-5-carboxylic acid (50.0 mg, 153 μmol) was initially charged in THF (3.0 ml), and HBTU (75.3 mg, 199 μmol) and N,N-diisopropylethylamine (80 μl, 460 μmol) were subsequently added. After stirring at room temperature for 15 min, (3S)-3-fluoropyrrolidine hydrochloride (23.0 mg, 183 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 24.7 mg (41% of theory) of the title compound were obtained.

LC-MS (Method 3): $R_t$=1.35 min; MS (ESIpos): m/z=399 [M+H]$^+$ $^1$H-NMR (400 MHz, DMSO-d6) δ [ppm]: −0.149 (1.39), 0.008 (10.78), 0.146 (1.39), 0.934 (0.70), 1.728 (4.52), 1.910 (1.57), 2.073 (4.35), 2.266 (1.91), 2.327 (4.35), 2.366 (4.52), 2.524 (16.00), 2.580 (2.96), 2.609 (4.35), 2.670 (4.52), 2.710 (4.17), 3.395 (1.57), 3.465 (1.04), 3.493 (1.39), 3.631 (4.70), 3.651 (3.83), 3.697 (1.91), 3.741 (3.30), 3.767 (2.78), 3.851 (4.17), 4.695 (2.43), 4.737 (2.61), 4.752 (3.13), 4.761 (2.43), 4.786 (2.26), 4.825 (11.65), 4.846 (7.65), 4.885 (1.91), 5.259 (2.09), 5.390 (2.61), 5.510 (1.57), 7.263 (2.09), 7.284 (2.78), 7.306 (2.96), 7.329 (1.91), 7.540 (1.91), 7.565 (3.30), 7.582 (3.48), 7.607 (2.09).

Example 494

(5S)-5-[(3-Fluoroazetidin-1-yl)carbonyl]-2-{[2-(trifluoromethyl)quinolin-4-yl]methyl}-5,6,7,8-tetrahydro[1,2,4]triazolo[4,3-a]pyridin-3(2H)-one

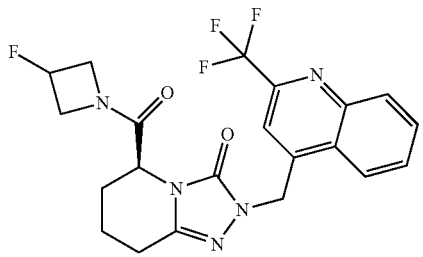 [SMILES: O=C([C@@H]1CCCc2nn(Cc3cc(C(F)(F)F)nc4ccccc34)c(=O)n21)N1CC(F)C1]

(5S)-3-Oxo-2-{[2-(trifluoromethyl)quinolin-4-yl]methyl}-2,3,5,6,7,8-hexahydro[1,2,4]triazolo[4,3-a]pyridine-5-carboxylic acid (60.0 mg, 153 μmol) was initially charged in THF (3.0 ml), and HBTU (69.6 mg, 184 μmol) and N,N-diisopropylethylamine (80 μl, 460 μmol) were subsequently added. After stirring at room temperature for 15 min, 3-fluoroazetidine hydrochloride (25.6 mg, 229 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 63.7 mg (93% of theory) of the title compound were obtained.

LC-MS (Method 3): $R_t$=1.50 min; MS (ESIpos): m/z=450 [M+H]

$^1$H-NMR (400 MHz, DMSO-d6) δ [ppm]: −0.149 (1.76), −0.008 (16.00), 0.008 (14.24), 0.146 (1.92), 1.686 (2.08), 1.710 (2.88), 1.988 (2.72), 2.073 (2.56), 2.327 (3.68), 2.366 (3.84), 2.523 (13.60), 2.586 (3.20), 2.598 (5.60), 2.611 (3.20), 2.628 (1.44), 2.641 (2.24), 2.670 (4.16), 2.710 (4.00), 3.943 (1.28), 4.002 (1.60), 4.272 (1.92), 4.298 (1.60), 4.330 (1.44), 4.358 (0.96), 4.407 (1.12), 4.472 (0.96), 4.524 (0.80), 4.608 (3.52), 4.620 (5.12), 4.632 (3.36), 5.356 (0.96), 5.423 (3.04), 5.463 (13.44), 5.472 (6.24), 5.484 (5.44), 5.513 (1.44), 7.747 (9.12), 7.846 (3.52), 7.863 (2.40), 7.948 (3.84), 7.966 (5.92), 7.984 (3.36), 8.214 (7.04), 8.236 (6.08), 8.368 (4.32), 8.389 (4.00).

Example 495

(5S)-5-[(3-Hydroxyazetidin-1-yl)carbonyl]-2-{[2-(trifluoromethyl)quinolin-4-yl]methyl}-5,6,7,8-tetrahydro[1,2,4]triazolo[4,3-a]pyridin-3(2H)-one

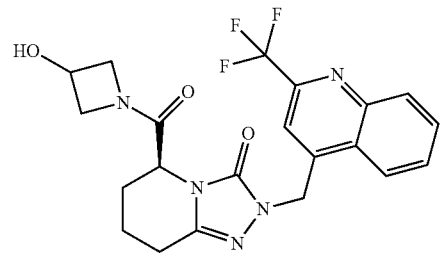 [SMILES: O=C([C@@H]1CCCc2nn(Cc3cc(C(F)(F)F)nc4ccccc34)c(=O)n21)N1CC(O)C1]

(5S)-3-Oxo-2-{[2-(trifluoromethyl)quinolin-4-yl]methyl}-2,3,5,6,7,8-hexahydro[1,2,4]triazolo[4,3-a]pyridine-5-carboxylic acid (60.0 mg, 153 μmol) was initially charged in THF (3.0 ml), and HBTU (75.4 mg, 199 μmol) and N,N-diisopropylethylamine (80 μl, 460 μmol) were subsequently added. After stirring at room temperature for 15 min, azetidin-3-ol hydrochloride (20.1 mg, 184 μmol) was added and the reaction mixture was stirred at room temperature for 6 days. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 41.4 mg (61% of theory) of the title compound were obtained.

LC-MS (Method 3): $R_t$=1.29 min; MS (ESIpos): m/z=448 [M+H]

$^1$H-NMR (400 MHz, DMSO-d6) δ [ppm]: −0.149 (0.53), −0.008 (5.42), 0.008 (4.04), 0.146 (0.53), 1.651 (3.35), 1.717 (4.41), 1.919 (2.45), 1.931 (2.34), 1.944 (3.72), 1.954 (5.95), 1.966 (5.58), 1.998 (3.61), 2.008 (3.72), 2.017 (3.46), 2.073 (1.65), 2.328 (1.17), 2.333 (0.90), 2.367 (1.22), 2.557 (4.04), 2.582 (4.52), 2.594 (8.50), 2.605 (4.62), 2.623 (2.29), 2.635 (3.56), 2.647 (1.65), 2.670 (1.33), 2.711 (1.22), 3.611 (2.82), 3.619 (3.30), 3.637 (3.67), 3.645 (4.47), 3.661 (3.30), 3.676 (3.19), 3.686 (3.14), 3.933 (3.72), 3.945 (4.15), 3.966 (1.01), 4.035 (5.05), 4.054 (6.80), 4.062 (5.48), 4.077 (3.03), 4.115 (2.45), 4.131 (3.03), 4.141 (2.60), 4.156 (2.39), 4.341 (2.50), 4.358 (4.20), 4.379 (2.98), 4.485 (3.03), 4.501 (4.36), 4.518 (7.28), 4.533 (7.44), 4.566 (3.99), 4.582 (8.40), 4.591 (7.71), 4.606 (3.35), 5.413 (2.23), 5.420 (2.18), 5.454 (12.54), 5.461 (13.50), 5.469 (14.41), 5.474 (13.61), 5.510 (2.45), 5.516 (2.34), 5.811 (11.32), 5.826 (5.58), 7.745 (15.63), 7.753 (16.00), 7.829 (3.46), 7.847 (7.97), 7.864 (5.00), 7.945 (7.23), 7.966 (10.79), 7.984 (6.49), 8.214 (13.29), 8.235 (11.48), 8.363 (6.64), 8.373 (7.02), 8.384 (6.43), 8.394 (6.27).

Example 496

(5S)-5-{[(3S)-3-Hydroxypyrrolidin-1-yl]carbonyl}-2-{[2-(trifluoromethyl)quinolin-4-yl]methyl}-5,6,7,8-tetrahydro[1,2,4]triazolo[4,3-a]pyridin-3(2H)-one

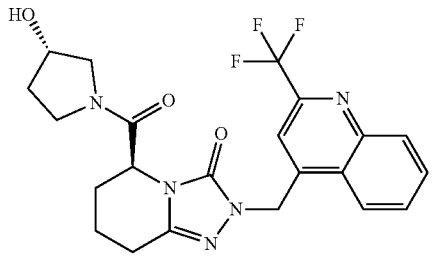 [SMILES: O=C([C@@H]1CCCc2nn(Cc3cc(C(F)(F)F)nc4ccccc34)c(=O)n21)N1CC[C@H](O)C1]

(5S)-3-Oxo-2-{[2-(trifluoromethyl)quinolin-4-yl]methyl}-2,3,5,6,7,8-hexahydro[1,2,4]triazolo[4,3-a]pyridine-5-carboxylic acid (60.0 mg, 153 µmol) was initially charged in THF (3.0 ml, 37 mmol), and HBTU (75.4 mg, 199 µmol) and N,N-diisopropylethylamine (80 µl, 460 µmol) were subsequently added. After stirring at room temperature for 15 min, (3S)-pyrrolidin-3-ol hydrochloride (22.7 mg, 184 µmol) was added and the reaction mixture was stirred at room temperature for 6 days. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 62.3 mg (88% of theory) of the title compound were obtained.

LC-MS (Method 3): $R_t$=1.31 min; MS (ESIpos): m/z=462 [M+H]$^+$ $^1$H-NMR (400 MHz, DMSO-d6) δ [ppm]: −0.008 (3.53), 0.008 (2.56), 1.658 (1.13), 1.670 (1.16), 1.682 (1.13), 1.731 (2.20), 1.741 (2.13), 1.862 (1.43), 1.872 (1.73), 1.884 (1.43), 1.894 (1.83), 1.905 (1.43), 1.928 (0.50), 1.988 (2.20), 2.011 (2.23), 2.021 (2.63), 2.031 (2.56), 2.042 (2.03), 2.054 (1.36), 2.062 (1.56), 2.073 (16.00), 2.328 (0.77), 2.367 (0.57), 2.519 (4.39), 2.523 (4.56), 2.564 (1.66), 2.608 (2.89), 2.620 (1.66), 2.640 (0.96), 2.650 (1.33), 2.665 (1.03), 2.670 (0.96), 2.710 (0.63), 3.209 (0.40), 3.241 (0.60), 3.350 (2.69), 3.379 (2.23), 3.390 (1.20), 3.411 (0.93), 3.443 (0.83), 3.453 (0.86), 3.465 (1.06), 3.473 (1.50), 3.495 (0.93), 3.503 (0.90), 3.569 (1.53), 3.591 (0.93), 3.654 (1.40), 3.665 (2.06), 3.681 (1.50), 3.692 (1.60), 4.276 (1.50), 4.371 (1.60), 4.742 (1.23), 4.750 (1.43), 4.757 (1.53), 4.765 (1.23), 4.783 (1.30), 4.798 (1.70), 4.806 (1.16), 4.864 (0.47), 4.970 (2.10), 5.085 (2.03), 5.406 (1.46), 5.447 (4.79), 5.479 (6.35), 5.520 (1.80), 7.743 (10.31), 7.753 (2.59), 7.758 (1.86), 7.825 (1.53), 7.845 (3.29), 7.863 (2.16), 7.945 (2.96), 7.965 (4.46), 7.984 (2.66), 8.213 (5.52), 8.234 (4.72), 8.366 (2.93), 8.387 (2.79).

Example 497

(5S)-5-{[(3R,4S)-3,4-Difluoropyrrolidin-1-yl]carbonyl}-2-{[2-(trifluoromethyl)quinolin-4-yl]methyl}-5,6,7,8-tetrahydro[1,2,4]triazolo[4,3-a]pyridin-3(2H)-one

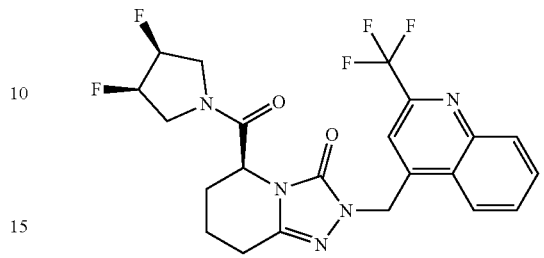

(5S)-3-Oxo-2-{[2-(trifluoromethyl)quinolin-4-yl]methyl}-2,3,5,6,7,8-hexahydro[1,2,4]triazolo[4,3-a]pyridine-5-carboxylic acid (60.0 mg, 153 µmol) was initially charged in THF (3.0 ml), and HBTU (75.4 mg, 199 µmol) and N,N-diisopropylethylamine (80 µl, 460 µmol) were subsequently added. After stirring at room temperature for 15 min, (3R,4S)-3,4-difluoropyrrolidine hydrochloride (26.3 mg, 184 µmol) was added and the reaction mixture was stirred at room temperature for 6 days. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 62.0 mg (84% of theory) of the title compound were obtained.

LC-MS (Method 3): $R_t$=1.60 min; MS (ESIpos): m/z=482 [M+H]$^+$ $^1$H-NMR (400 MHz, DMSO-d6) δ[ppm]: −0.149 (1.71), −0.008 (16.00), 0.008 (11.82), 0.147 (1.50), 1.648 (1.55), 1.733 (1.67), 2.023 (2.46), 2.328 (2.21), 2.367 (1.67), 2.572 (2.42), 2.609 (3.47), 2.670 (2.59), 2.710 (1.75), 3.501 (1.30), 3.522 (1.46), 3.641 (1.09), 3.696 (2.13), 3.729 (2.05), 3.773 (1.30), 3.930 (1.55), 3.978 (1.09), 4.189 (1.09), 4.854 (2.80), 4.867 (3.89), 4.878 (2.92), 5.265 (1.17), 5.357 (1.04), 5.415 (2.42), 5.456 (5.43), 5.464 (5.60), 5.478 (5.35), 5.492 (5.35), 5.534 (1.84), 7.548 (1.17), 7.597 (1.50), 7.627 (1.84), 7.644 (1.09), 7.735 (7.06), 7.743 (8.15), 7.849 (2.92), 7.870 (1.92), 7.946 (3.09), 7.966 (4.89), 7.983 (2.92), 8.215 (6.35), 8.236 (5.31), 8.359 (2.80), 8.367 (3.17), 8.380 (2.76), 8.388 (2.97).

Example 498

(5S)-2-{[6-Fluoro-2-(trifluoromethyl)quinolin-4-yl]methyl}-5-(pyrrolidin-1-ylcarbonyl)-5,6,7,8-tetrahydro[1,2,4]triazolo[4,3-a]pyridin-3(2H)-one

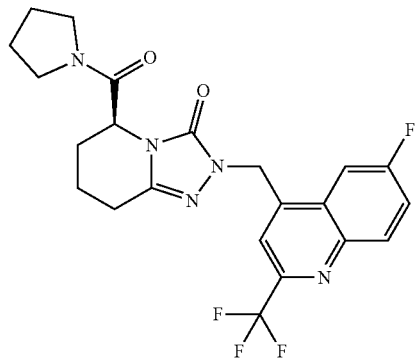 [SMILES: O=C([C@@H]1CCCc2nn(Cc3cc(C(F)(F)F)nc4ccc(F)cc34)c(=O)n21)N1CCCC1]

(5S)-2-{[6-Fluoro-2-(trifluoromethyl)quinolin-4-yl]methyl}-3-oxo-2,3,5,6,7,8-hexahydro[1,2,4]triazolo[4,3-a]pyridine-5-carboxylic acid (44.0 mg, 107 µmol) was initially charged in THF (2.0 ml) at room temperature. Subsequently, HATU (53.0 mg, 139 µmol) and triethylamine (45 µl, 320 µmol) were added. After stirring for 15 min, pyrrolidine (11 µl, 130 µmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 28.6 mg (58% of theory) of the title compound were obtained.

LC-MS (Method 3): $R_t$=1.65 min; MS (ESIpos): m/z=464 [M+H]$^+$ $^1$H-NMR (400 MHz, DMSO-d6) δ[ppm]: −0.150 (1.01), 0.146 (1.06), 1.668 (2.28), 1.719 (3.21), 1.764 (2.32), 1.781 (6.04), 1.799 (10.55), 1.816 (8.53), 1.833 (2.66), 1.899 (2.58), 1.916 (7.89), 1.933 (10.26), 1.949 (6.25), 1.966 (1.98), 2.012 (5.91), 2.022 (5.99), 2.035 (3.80), 2.327 (2.62), 2.366 (1.94), 2.569 (3.29), 2.596 (3.08), 2.606 (4.98), 2.618 (3.17), 2.636 (1.60), 2.647 (2.32), 2.669 (2.96), 2.709 (2.07), 3.234 (1.52), 3.251 (3.29), 3.263 (3.29), 3.280 (5.91), 3.333 (3.55), 3.351 (5.78), 3.368 (3.21), 3.380 (3.42), 3.398 (1.60), 3.438 (1.77), 3.456 (3.67), 3.480 (4.64), 3.497 (2.20), 3.612 (2.07), 3.628 (4.56), 3.645 (2.70), 3.653 (3.63), 3.670 (1.65), 4.797 (4.18), 4.811 (5.87), 4.820 (3.93), 5.374 (2.74), 5.415 (12.37), 5.434 (12.50), 5.475 (2.70), 7.797 (16.00), 7.872 (2.53), 7.879 (2.79), 7.894 (4.18), 7.901 (4.69), 7.916 (3.00), 7.923 (3.04), 8.151 (4.98), 8.158 (5.15), 8.177 (5.11), 8.184 (5.02), 8.295 (4.69), 8.309 (4.90), 8.319 (4.73), 8.333 (4.43).

Example 499

(5S)-5-[(3,3-Difluoroazetidin-1-yl)carbonyl]-2-{[3-(trifluoromethyl)-1,2,4-oxadiazol-5-yl]methyl}-5,6,7,8-tetrahydro[1,2,4]triazolo[4,3-a]pyridin-3(2H)-one

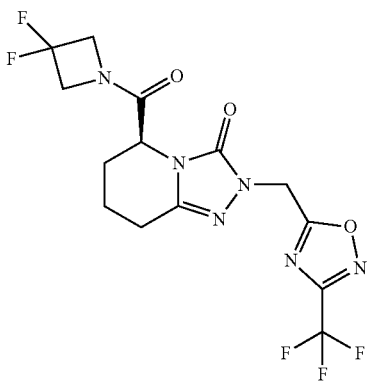 [SMILES: O=C([C@@H]1CCCc2nn(Cc3nc(C(F)(F)F)no3)c(=O)n21)N1CC(F)(F)C1]

(5S)-3-Oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylic acid (85.0 mg, 82% purity, 209 µmol) was initially charged in THF (3.0 ml), and HBTU (103 mg, 272 µmol) and N,N-diisopropylethylamine (110 µl, 630 µmol) were subsequently added. After stirring at room temperature for 15 min, 3,3-difluoroazetidine hydrochloride (32.5 mg, 251 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 46.8 mg (55% of theory) of the title compound were obtained.

LC-MS (Method 4): $R_t$=0.73 min; MS (ESIpos): m/z=409 [M+H]$^+$ $^1$H-NMR (400 MHz, DMSO-d6) δ [ppm]: −0.008 (3.49), 0.008 (2.81), 1.723 (2.72), 1.737 (3.89), 1.753 (2.88), 1.766 (1.17), 1.963 (1.10), 1.975 (1.10), 1.987 (1.10), 1.999 (1.76), 2.012 (1.52), 2.023 (0.68), 2.048 (0.75), 2.063 (1.38), 2.083 (1.48), 2.098 (1.38), 2.117 (0.80), 2.327 (0.63), 2.366 (0.84), 2.523 (1.99), 2.576 (0.82), 2.601 (1.90), 2.619 (3.02), 2.629 (2.08), 2.637 (2.32), 2.643 (3.77), 2.657 (1.80), 2.670 (1.12), 2.686 (0.98), 2.700 (0.45), 2.710 (0.89), 4.339 (1.24), 4.376 (2.11), 4.400 (1.27), 4.620 (2.51), 4.635 (3.98), 4.648 (2.51), 4.727 (1.12), 4.758 (1.31), 4.787 (0.68), 4.803 (0.70), 4.835 (1.41), 4.863 (1.31), 5.392 (0.40), 5.437 (16.00), 5.481 (0.45).

Example 500

(5S)-5-{[(3R,4S)-3,4-Difluoropyrrolidin-1-yl]carbonyl}-2-{[3-(trifluoromethyl)-1,2,4-oxadiazol-5-yl]methyl}-5,6,7,8-tetrahydro[1,2,4]triazolo[4,3-a]pyridin-3(2H)-one

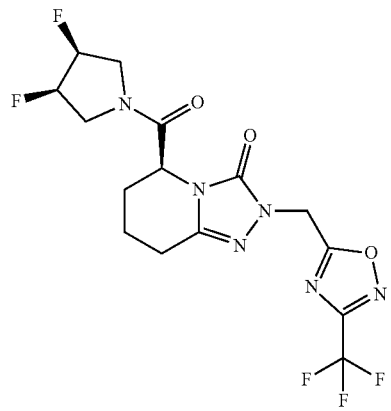 [SMILES: O=C([C@@H]1CCCc2nn(Cc3nc(C(F)(F)F)no3)c(=O)n21)N1C[C@@H](F)[C@@H](F)C1]

(5S)-3-Oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylic acid (85.0 mg, 82% purity, 209 µmol) was initially charged in THF (3.0 ml), and HBTU (103 mg, 272 µmol) and N,N-diisopropylethylamine (110 µl, 630 µmol) were subsequently added. After stirring at room temperature for 15 min, (3R,4S)-3,4-difluoropyrrolidine hydrochloride (36.0 mg, 251 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 49.1 mg (56% of theory) of the title compound were obtained.

LC-MS (Method 4): R$_t$=0.72 min; MS (ESIpos): m/z=423 [M+H]$^+$ $^1$H-NMR (400 MHz, DMSO-d6) δ[ppm]: −0.149 (0.99), −0.008 (9.46), 0.008 (7.63), 0.146 (0.99), 1.690 (1.73), 1.744 (2.14), 1.972 (1.73), 2.012 (1.52), 2.076 (1.78), 2.111 (1.41), 2.327 (1.83), 2.366 (1.73), 2.522 (5.39), 2.602 (2.09), 2.611 (3.03), 2.626 (3.71), 2.638 (4.65), 2.652 (2.41), 2.669 (2.67), 2.690 (1.31), 2.710 (1.93), 3.456 (0.78), 3.519 (1.52), 3.528 (1.31), 3.538 (1.41), 3.571 (1.05), 3.616 (1.10), 3.630 (1.31), 3.648 (0.73), 3.685 (1.93), 3.705 (1.52), 3.717 (1.52), 3.726 (1.57), 3.743 (1.41), 3.757 (1.41), 3.777 (1.15), 3.870 (1.10), 3.905 (0.89), 3.927 (1.20), 3.942 (1.20), 3.957 (0.84), 3.977 (1.20), 3.991 (1.20), 4.007 (0.78), 4.020 (0.84), 4.126 (0.78), 4.141 (0.84), 4.168 (1.36), 4.181 (0.94), 4.193 (0.89), 4.209 (0.73), 4.819 (3.50), 4.829 (4.34), 4.835 (4.55), 4.844 (3.61), 5.266 (1.25), 5.377 (2.14), 5.416 (16.00), 5.419 (13.91), 5.427 (10.88), 5.470 (1.78).

Example 501

(5S)-5-[(3,3-Difluoropyrrolidin-1-yl)carbonyl]-2-{[3-(trifluoromethyl)-1,2,4-oxadiazol-5-yl]methyl}-5,6,7,8-tetrahydro[1,2,4]triazolo[4,3-a]pyridin-3(2H)-one

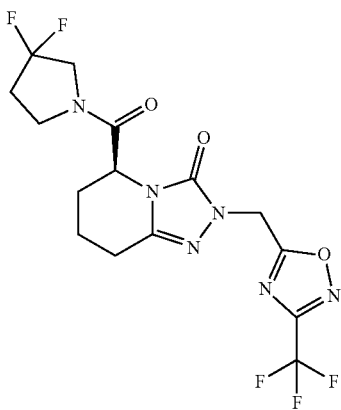 [SMILES: O=C([C@@H]1CCCc2nn(Cc3nc(C(F)(F)F)no3)c(=O)n21)N1CCC(F)(F)C1]

(5S)-3-Oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylic acid (85.0 mg, 82% purity, 209 μmol) was initially charged in THF (3.0 ml), and HBTU (103 mg, 272 μmol) and N,N-diisopropylethylamine (110 μl, 630 μmol) were subsequently added. After stirring at room temperature for 15 min, 3,3-difluoropyrrolidine hydrochloride (36.0 mg, 251 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 69.8 mg (77% of theory) of the title compound were obtained.

LC-MS (Method 3): R$_t$=1.44 min; MS (ESIpos): m/z=423 [M+H]$^+$ $^1$H-NMR (400 MHz, DMSO-d6) δ [ppm]: −0.149 (0.41), −0.008 (3.87), 0.008 (3.12), 0.146 (0.41), 1.704 (1.58), 1.719 (1.84), 1.732 (2.09), 1.741 (2.09), 1.978 (1.42), 1.991 (1.56), 2.002 (1.64), 2.013 (1.44), 2.028 (1.46), 2.052 (1.01), 2.063 (1.30), 2.072 (1.66), 2.078 (1.40), 2.088 (1.34), 2.098 (1.09), 2.107 (1.15), 2.327 (0.79), 2.366 (1.13), 2.380 (1.09), 2.408 (1.40), 2.428 (1.38), 2.450 (1.01), 2.568 (2.17), 2.593 (2.88), 2.608 (3.12), 2.617 (2.94), 2.631 (3.44), 2.640 (3.71), 2.652 (1.94), 2.669 (1.44), 2.683 (1.03), 2.710 (0.95), 3.532 (2.57), 3.551 (4.23), 3.570 (2.05), 3.637 (0.47), 3.670 (1.52), 3.704 (1.66), 3.737 (1.50), 3.768 (2.33), 3.786 (1.36), 3.802 (2.11), 3.811 (1.88), 3.830 (0.97), 3.887 (0.87), 3.906 (1.76), 3.925 (1.03), 3.931 (1.22), 3.950 (0.55), 3.965 (0.57), 3.994 (1.09), 4.007 (0.55), 4.022 (0.83), 4.037 (1.01), 4.065 (0.63), 4.146 (0.69), 4.179 (1.03), 4.202 (0.99), 4.235 (0.47), 4.783 (1.44), 4.793 (1.70), 4.798 (1.88), 4.808 (1.38), 4.858 (1.82), 4.873 (2.27), 4.883 (1.46), 5.375 (0.85), 5.419 (15.23), 5.423 (16.00), 5.467 (1.03), 5.632 (0.45).

Example 502

(5S)-2-[(1 RS)-1-(4-Methylphenyl)ethyl]-5-(pyrrolidin-1-ylcarbonyl)-5,6,7,8-tetrahydro[1,2,4]triazolo[4,3-a]pyridin-3(2H)-one (Diastereomer Mixture, 2 Isomers)

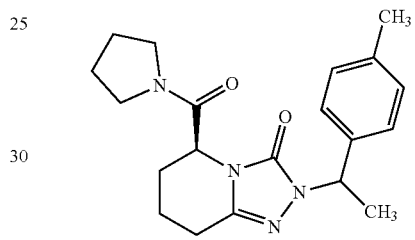

(5S)-2-[(1 RS)-1-(4-Methylphenyl)ethyl]-3-oxo-2,3,5,6,7,8-hexahydro[1,2,4]triazolo[4,3-a]pyridine-5-carboxylic acid (isomer 1) (58.0 mg, 192 μmol) was initially charged in THF (2.3 ml) at room temperature. Subsequently, HBTU (94.9 mg, 250 μmol) and N,N-diisopropylethylamine (130 μl, 770 μmol) were added. After stirring for 15 min, pyrrolidine (19 μl, 230 μmol) was added and the reaction mixture was stirred at room temperature overnight. The reaction mixture was admixed with water and ethyl acetate. The organic phase was removed and the aqueous phase was extracted three times with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 49.8 mg (73% of theory) of the title compound were obtained.

LC-MS (Method 3): R$_t$=1.46 min; MS (ESIpos): m/z=355 [M+H]$^+$ $^1$H-NMR (400 MHz, DMSO-d6) δ [ppm]: −0.149 (1.79), −0.008 (16.00), 0.008 (13.92), 0.146 (1.84), 1.575 (7.98), 1.593 (8.07), 1.710 (1.84), 1.755 (2.17), 1.772 (3.54), 1.789 (2.64), 1.896 (2.31), 1.912 (3.02), 1.929 (2.12), 2.267 (15.10), 2.327 (2.64), 2.366 (1.89), 2.523 (8.12), 2.615 (1.79), 2.670 (2.78), 2.709 (1.98), 3.214 (1.18), 3.226 (1.13), 3.244 (1.94), 3.261 (1.04), 3.343 (1.42), 3.442 (1.23), 3.467 (1.42), 3.592 (1.37), 4.706 (1.60), 4.716 (1.23), 5.225 (1.94), 5.243 (1.75), 7.108 (2.64), 7.128 (5.71), 7.160 (6.75), 7.180 (2.88).

Example 503

(5S)-5-(1,3-Thiazolidin-3-ylcarbonyl)-2-{[6-(trifluoromethyl)pyridin-3-yl]methyl}-5,6,7,8-tetrahydro[1,2,4]triazolo[4,3-a]pyridin-3(2H)-one

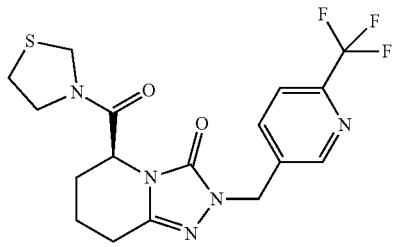 [SMILES: O=C([C@@H]1CCCc2nn(Cc3ccc(C(F)(F)F)nc3)c(=O)n21)N1CCSC1]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (100 mg, 292 µmol) was initially charged in THF (2.0 ml), and HBTU (144 mg, 380 µmol) and N,N-diisopropylethylamine (150 µl, 880 mol) were subsequently added. After stirring at room temperature for 15 min, 1,3-thiazolidine (31.3 mg, 351 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.5 mg (30% of theory) of the title compound were obtained.

LC-MS (Method 1): $R_t$=0.97 min; MS (ESIpos): m/z=414 [M+H]$^+$ $^1$H-NMR (400 MHz, DMSO-d6) δ [ppm]: -0.149 (0.48), -0.008 (3.99), 0.008 (4.42), 0.146 (0.48), 1.619 (0.94), 1.743 (1.45), 1.988 (0.73), 2.020 (1.88), 2.327 (0.94), 2.366 (0.67), 2.567 (2.15), 2.579 (2.06), 2.593 (1.91), 2.613 (2.66), 2.624 (1.54), 2.669 (1.30), 2.710 (0.73), 2.914 (0.42), 3.003 (1.45), 3.019 (3.12), 3.035 (1.72), 3.130 (1.97), 3.146 (4.14), 3.161 (2.21), 3.595 (0.45), 3.611 (0.64), 3.626 (0.82), 3.640 (1.12), 3.655 (0.54), 3.677 (0.60), 3.695 (1.12), 3.712 (0.73), 3.724 (0.60), 3.758 (0.51), 3.773 (0.97), 3.785 (0.88), 3.799 (1.21), 3.814 (0.60), 3.929 (0.57), 3.943 (1.21), 3.958 (0.82), 3.970 (0.94), 3.986 (0.42), 4.371 (1.88), 4.396 (2.42), 4.557 (2.54), 4.583 (2.00), 4.611 (1.42), 4.634 (1.72), 4.809 (1.69), 4.832 (1.42), 4.893 (1.36), 4.972 (1.51), 5.015 (10.37), 5.058 (0.48), 7.910 (15.09), 7.913 (16.00), 8.642 (5.60).

Example 504

(5S)-2-[(5-Bromopyridin-2-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

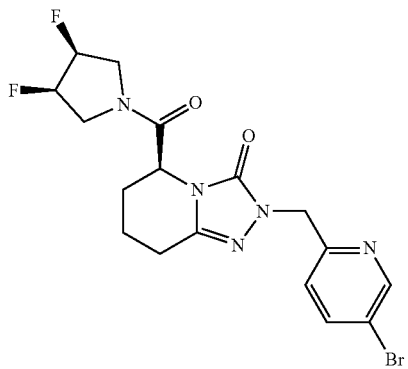 [SMILES: O=C([C@@H]1CCCc2nn(Cc3ccc(Br)cn3)c(=O)n21)N1C[C@@H](F)[C@@H](F)C1]

(5S)-2-[(5-Bromopyridin-2-yl)methyl]-3-oxo-2,3,5,6,7,8-hexahydro[1,2,4]triazolo[4,3-a]pyridine-5-carboxylic acid (100 mg, 283 µmol) was initially charged in THF (23 µl), and (3R,4S)-3,4-difluoropyrrolidine hydrochloride (48.8 mg, 340 µmol) and (200 µl, 1.4 mmol) were subsequently added. After stirring at room temperature for 15 min, HBTU (140 mg, 368 µmol) was added and the reaction mixture was stirred at room temperature for 4 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.5 mg (30% of theory) of the title compound were obtained.

LC-MS (Method 3): $R_t$=0.97 min; MS (ESIpos): m/z=442 [M+H]$^+$ $^1$H-NMR (400 MHz, DMSO-d6) delta [ppm]: -0.149 (1.70), -0.008 (12.77), 0.008 (16.00), 0.146 (1.62), 1.740 (1.45), 2.015 (1.45), 2.073 (2.13), 2.327 (2.89), 2.366 (3.06), 2.571 (2.55), 2.595 (2.30), 2.605 (2.98), 2.648 (1.11), 2.669 (3.06), 2.710 (2.98), 3.491 (1.11), 3.513 (0.94), 3.632 (0.85), 3.687 (1.45), 3.720 (1.19), 3.785 (0.77), 3.946 (0.77), 3.996 (0.68), 4.174 (0.68), 4.808 (2.81), 4.886 (13.53), 5.275 (0.77), 5.385 (0.85), 5.450 (0.60), 7.145 (3.23), 7.165 (3.57), 8.034 (2.64), 8.055 (2.55), 8.650 (3.15).

Example 505

(5S)-2-[(5-Chloropyridin-2-yl)methyl]-5-(1,3-thiazolidin-3-ylcarbonyl)-5,6,7,8-tetrahydro[1,2,4]triazolo[4,3-a]pyridin-3(2H)-one

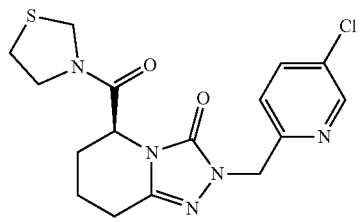 [SMILES: O=C([C@@H]1CCCc2nn(Cc3ccc(Cl)cn3)c(=O)n21)N1CCSC1]

(5S)-2-[(5-Chloropyridin-2-yl)methyl]-3-oxo-2,3,5,6,7,8-hexahydro[1,2,4]triazolo[4,3-a]pyridine-5-carboxylic acid (100 mg, 324 µmol) was initially charged in THF (2.0 ml), and HBTU (160 mg, 421 µmol) and N,N-diisopropylethylamine (170 µl, 970 µmol) were subsequently added. After stirring at room temperature for 15 min, 1,3-thiazolidine (34.7 mg, 389 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 45.0 mg (37% of theory) of the title compound were obtained.

LC-MS (Method 3): $R_t$=1.15 min; MS (ESIpos): m/z=380 [M+H]$^+$ $^1$H-NMR (400 MHz, DMSO-d6) δ [ppm]: -0.008 (2.72), 0.008 (2.67), 1.245 (0.93), 1.261 (1.57), 1.278 (0.76), 1.661 (0.95), 1.746 (1.42), 1.796 (0.77), 1.980 (0.76), 2.016 (1.80), 2.073 (1.11), 2.327 (0.55), 2.524 (1.84), 2.578 (2.03), 2.592 (2.04), 2.610 (2.62), 2.622 (1.51), 2.640 (0.63), 2.652 (0.92), 2.665 (0.84), 2.913 (0.50), 3.002 (1.47), 3.018 (3.08), 3.034 (1.74), 3.130 (2.02), 3.146 (4.22), 3.161 (2.18), 3.596 (0.43), 3.614 (0.67), 3.629 (0.91), 3.644 (1.14), 3.659 (0.60), 3.673 (0.63), 3.690 (1.14), 3.707 (0.71), 3.720 (0.60), 3.761 (0.51), 3.777 (0.94), 3.788 (0.91), 3.803 (1.24), 3.818 (0.61), 3.932 (0.60), 3.947 (1.19), 3.961 (0.83), 3.973 (0.92), 3.989 (0.43), 4.244 (0.93), 4.373 (1.89), 4.399 (2.43), 4.486 (0.45), 4.553 (2.48), 4.578 (1.94), 4.618 (1.41), 4.640 (1.72), 4.808 (1.68), 4.831 (1.34), 4.875 (1.22), 4.891 (1.45), 4.900 (1.35), 4.916 (16.00), 4.958 (1.10), 4.974 (1.11), 7.200 (4.68), 7.221 (5.05), 7.914 (4.06), 7.920 (4.18), 7.935 (3.90), 7.941 (4.01), 8.572 (4.54), 8.578 (4.62).

Example 506

(5S)-2-[(5-Bromopyridin-3-yl)methyl]-5-{[(3R,4S)-3,4-difluoropyrrolidin-1-yl]carbonyl}-5,6,7,8-tetrahydro[1,2,4]triazolo[4,3-a]pyridin-3(2H)-one

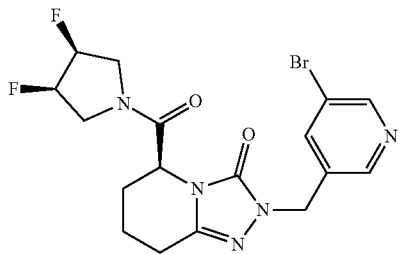 [SMILES: O=C([C@@H]1CCCc2nn(Cc3cncc(Br)c3)c(=O)n21)N1C[C@@H](F)[C@@H](F)C1]

(5S)-2-[(5-Bromopyridin-3-yl)methyl]-3-oxo-2,3,5,6,7,8-hexahydro[1,2,4]triazolo[4,3-a]pyridine-5-carboxylic acid (100 mg, 283 µmol) was initially charged in THF (1.7 ml), and HBTU (140 mg, 368 µmol) and N,N-diisopropylethylamine (250 µl, 1.4 mmol) were subsequently added. After stirring at room temperature for 15 min, (3R,4S)-3,4-difluoropyrrolidine hydrochloride (48.8 mg, 340 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 51.1 mg (41% of theory) of the title compound were obtained.

LC-MS (Method 3): R$_t$=1.19 min; MS (ESIpos): m/z=442 [M+H]$^+$ $^1$H-NMR (400 MHz, DMSO-d6) δ[ppm]: −0.149 (0.64), −0.008 (5.43), 0.008 (5.61), 0.146 (0.67), 1.664 (0.94), 1.732 (1.25), 2.014 (1.37), 2.051 (1.07), 2.067 (0.90), 2.086 (0.77), 2.327 (0.97), 2.366 (0.94), 2.382 (0.97), 2.412 (1.01), 2.431 (0.99), 2.454 (0.88), 2.572 (3.14), 2.583 (2.36), 2.598 (2.26), 2.614 (2.51), 2.669 (1.31), 2.710 (0.71), 3.532 (1.05), 3.541 (1.22), 3.550 (1.83), 3.562 (2.06), 3.580 (0.92), 3.670 (1.18), 3.704 (1.31), 3.746 (0.75), 3.779 (1.91), 3.809 (2.08), 3.826 (0.69), 3.893 (0.60), 3.911 (1.31), 3.937 (0.99), 3.956 (0.54), 3.990 (0.82), 4.018 (0.56), 4.033 (0.77), 4.061 (0.47), 4.149 (0.45), 4.181 (0.75), 4.206 (0.71), 4.765 (1.03), 4.780 (1.44), 4.790 (1.12), 4.837 (1.12), 4.852 (1.50), 4.861 (1.12), 4.905 (16.00), 7.887 (3.24), 7.892 (5.73), 7.897 (3.52), 8.446 (5.61), 8.450 (5.65), 8.639 (5.35), 8.644 (5.37).

Example 507

(5S)-2-[(5-Chloro-3-fluoropyridin-2-yl)methyl]-5-(1,3-thiazolidin-3-ylcarbonyl)-5,6,7,8-tetrahydro[1,2,4]triazolo[4,3-a]pyridin-3(2H)-one

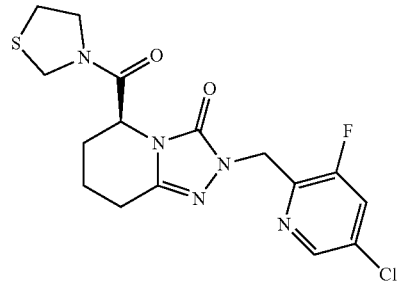 [SMILES: O=C([C@@H]1CCCc2nn(Cc3ncc(Cl)cc3F)c(=O)n21)N1CCSC1]

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (100 mg, 306 µmol) was initially charged in THF (4.6 ml), and HBTU (139 mg, 367 µmol) and N,N-diisopropylethylamine (160 µl, 920 µmol) were subsequently added. After stirring at room temperature for 15 min, 1,3-thiazolidine (35.5 mg, 398 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 40.0 mg (33% of theory) of the title compound were obtained.

LC-MS (Method 3): R$_t$=1.19 min; MS (ESIpos): m/z=398 [M+H]$^+$ $^1$H-NMR (400 MHz, DMSO-d6) δ[ppm]: −0.149 (1.06), −0.008 (9.48), 0.008 (8.72), 0.147 (1.06), 1.653 (2.73), 1.711 (4.09), 1.949 (2.12), 1.983 (4.70), 2.046 (3.03), 2.073 (3.49), 2.327 (2.88), 2.366 (0.76), 2.470 (2.35), 2.525 (8.95), 2.569 (7.73), 2.581 (4.40), 2.599 (1.97), 2.612 (2.65), 2.670 (3.11), 2.710 (1.14), 2.744 (0.76), 2.800 (0.91), 2.998 (3.79), 3.014 (8.27), 3.030 (4.63), 3.128 (5.31), 3.144 (11.37), 3.159 (5.84), 3.610 (1.44), 3.625 (2.27), 3.640 (3.03), 3.663 (1.82), 3.681 (3.11), 3.698 (1.82), 3.711 (1.44), 3.752 (1.36), 3.767 (2.58), 3.780 (2.27), 3.794 (3.18), 3.810 (1.59), 3.924 (1.59), 3.940 (3.18), 3.952 (2.20), 3.966 (2.35), 3.981 (1.14), 4.367 (5.00), 4.392 (6.82), 4.543 (6.67), 4.568 (5.23), 4.609 (3.72), 4.632 (4.40), 4.797 (4.32), 4.820 (3.64), 4.859 (3.79), 4.900 (5.61), 4.905 (5.84), 4.939 (16.00), 4.943 (15.17), 4.991 (11.98), 5.030 (4.85), 8.089 (8.42), 8.094 (8.95), 8.113 (8.87), 8.118 (8.95), 8.478 (9.33), 8.482 (9.25).

Example 508

(5S)-2-[(5-Chloropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

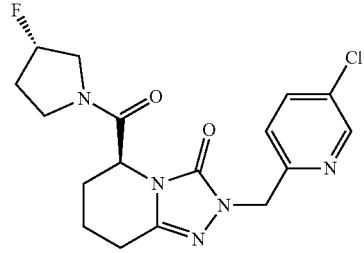 [SMILES: O=C([C@@H]1CCCc2nn(Cc3ccc(Cl)cn3)c(=O)n21)N1CC[C@H](F)C1]

(5S)-2-[(5-Chloropyridin-2-yl)methyl]-3-oxo-2,3,5,6,7,8-hexahydro[1,2,4]triazolo[4,3-a]pyridine-5-carboxylic acid (100 mg, 324 µmol) was initially charged in THF (2.0 ml), and HBTU (160 mg, 421 µmol) and N,N-diisopropylethylamine (280 µl, 1.6 mmol) were subsequently added. After stirring at room temperature for 15 min, (3S)-3-fluoropyrrolidine hydrochloride (48.8 mg, 389 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 67.0 mg (54% of theory) of the title compound were obtained.

LC-MS (Method 3): $R_t$=1.06 min; MS (ESIpos): m/z=380 [M+H]$^+$ $^1$H-NMR (400 MHz, DMSO-d6) δ [ppm]: −0.149 (0.82), −0.008 (6.88), 0.008 (6.28), 0.146 (0.82), 1.743 (4.02), 1.883 (0.88), 1.930 (1.00), 1.997 (1.06), 2.031 (1.66), 2.109 (2.66), 2.138 (2.02), 2.269 (1.42), 2.327 (1.63), 2.366 (0.69), 2.572 (2.81), 2.588 (2.17), 2.612 (3.32), 2.654 (1.30), 2.669 (1.87), 2.709 (0.69), 2.881 (0.42), 3.276 (1.24), 3.350 (1.18), 3.372 (1.03), 3.399 (1.12), 3.407 (1.09), 3.469 (0.91), 3.496 (1.12), 3.505 (1.09), 3.612 (0.72), 3.636 (3.38), 3.655 (2.90), 3.681 (1.87), 3.697 (1.36), 3.732 (2.17), 3.752 (2.35), 3.778 (1.99), 3.794 (1.57), 3.860 (3.29), 4.695 (1.54), 4.704 (1.93), 4.710 (2.14), 4.720 (1.57), 4.752 (2.11), 4.761 (2.32), 4.767 (2.66), 4.776 (1.96), 4.865 (1.21), 4.906 (16.00), 4.913 (11.14), 4.955 (0.91), 5.259 (1.66), 5.389 (2.05), 5.516 (1.09), 5.944 (0.39), 7.200 (6.85), 7.221 (7.37), 7.913 (5.80), 7.920 (5.89), 7.934 (5.40), 7.941 (5.68), 8.572 (6.67), 8.578 (6.70).

Example 509

(5S)-2-[(5-Bromopyridin-3-yl)methyl]-5-{[(3S)-3-fluoropyrrolidin-1-yl]carbonyl}-5,6,7,8-tetrahydro[1,2,4]triazolo[4,3-a]pyridin-3(2H)-one

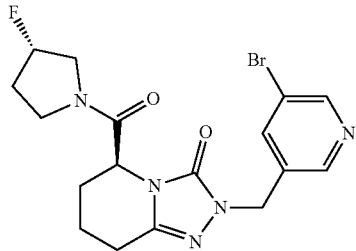 [SMILES: O=C([C@@H]1CCCc2nn(Cc3cncc(Br)c3)c(=O)n21)N1CC[C@H](F)C1]

(5S)-2-[(5-Bromopyridin-3-yl)methyl]-3-oxo-2,3,5,6,7,8-hexahydro[1,2,4]triazolo[4,3-a]pyridine-5-carboxylic acid (100 mg, 283 µmol) was initially charged in THF (1.7 ml), and HBTU (140 mg, 368 µmol) and N,N-diisopropylethylamine (250 µl, 1.4 mmol) were subsequently added. After stirring at room temperature for 15 min, (3S)-3-fluoropyrrolidine hydrochloride (42.7 mg, 340 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 42.7 mg (36% of theory) of the title compound were obtained.

LC-MS (Method 3): $R_t$=1.05 min; MS (ESIpos): m/z=424 [M+H]$^+$ $^1$H-NMR (400 MHz, DMSO-d6) δ [ppm]: −0.149 (1.52), −0.008 (13.23), 0.008 (14.75), 0.146 (1.57), 1.734 (2.39), 1.910 (0.81), 2.027 (1.25), 2.103 (2.17), 2.137 (1.57), 2.270 (1.08), 2.327 (2.22), 2.366 (1.46), 2.565 (2.12), 2.592 (1.63), 2.616 (2.44), 2.669 (2.77), 2.710 (1.46), 3.397 (0.87), 3.468 (0.71), 3.495 (0.87), 3.638 (2.66), 3.662 (2.01), 3.679 (1.63), 3.703 (1.08), 3.723 (1.14), 3.744 (2.44), 3.769 (1.63), 3.854 (2.28), 4.694 (1.14), 4.709 (1.52), 4.719 (1.19), 4.751 (1.46), 4.766 (1.90), 4.775 (1.46), 4.901 (16.00), 5.259 (1.25), 5.390 (1.63), 5.515 (0.87), 7.893 (4.99), 8.448 (5.91), 8.639 (4.72), 8.644 (4.99).

Example 510

(5S)-2-[(5-Bromopyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

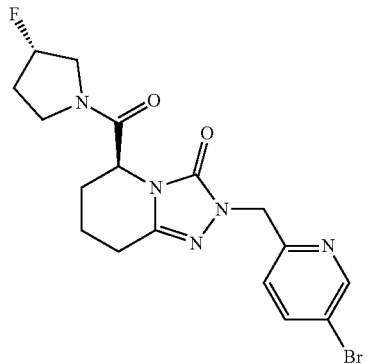 [SMILES: O=C([C@@H]1CCCc2nn(Cc3ccc(Br)cn3)c(=O)n21)N1CC[C@H](F)C1]

(5S)-2-[(5-Bromopyridin-2-yl)methyl]-3-oxo-2,3,5,6,7,8-hexahydro[1,2,4]triazolo[4,3-a]pyridine-5-carboxylic acid (100 mg, 283 µmol) was initially charged in THF (23 µl), and (3S)-3-fluoropyrrolidine hydrochloride (42.7 mg, 340 µmol) and (3S)-3-fluoropyrrolidine hydrochloride (200 µl, 1.4 mmol) were subsequently added. After stirring at room temperature for 15 min, HBTU (140 mg, 368 µmol) was added and the reaction mixture was stirred at room temperature for 4 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 56.0 mg (47% of theory) of the title compound were obtained.

LC-MS (Method 3): $R_t$=1.13 min; MS (ESIpos): m/z=424 [M+H]$^+$ $^1$H-NMR (400 MHz, DMSO-d6) δ [ppm]: −0.149 (0.76), −0.008 (6.64), 0.008 (6.30), 0.146 (0.76), 1.729 (3.63), 1.742 (4.16), 1.882 (0.86), 1.921 (1.05), 1.993 (1.10), 2.034 (1.81), 2.072 (2.05), 2.101 (2.77), 2.138 (2.15), 2.219 (1.19), 2.269 (1.48), 2.327 (1.72), 2.366 (0.91), 2.571 (3.10), 2.586 (2.39), 2.610 (3.58), 2.651 (1.29), 2.669 (2.05), 2.710 (1.10), 3.274 (1.19), 3.349 (1.53), 3.362 (1.29), 3.371 (1.29), 3.398 (1.24), 3.407 (1.29), 3.468 (0.96), 3.495 (1.19), 3.504 (1.15), 3.610 (0.81), 3.635 (3.68), 3.656 (3.06), 3.681 (2.01), 3.701 (1.58), 3.730 (2.24), 3.750 (2.58), 3.778 (2.10), 3.794 (1.67), 3.826 (0.57), 3.860 (3.49), 4.693 (1.72), 4.702 (2.05), 4.708 (2.20), 4.717 (1.72), 4.750 (2.10), 4.759 (2.48), 4.765 (2.77), 4.774 (2.01), 4.841 (1.39), 4.882 (16.00), 4.889 (11.27), 4.930 (1.05), 5.258 (1.62), 5.390 (2.24), 5.515 (1.29), 7.144

(7.02), 7.165 (7.55), 8.032 (5.68), 8.038 (5.83), 8.053 (5.59), 8.059 (5.64), 8.648 (6.83), 8.654 (6.93).

Example 511

(2S)-1-{[(5S)-3-Oxo-2-{[6-(trifluoromethyl)pyridin-3-yl]methyl}-2,3,5,6,7,8-hexahydro[1,2,4]triazolo[4,3-a]pyridin-5-yl]carbonyl}pyrrolidine-2-carbonitrile

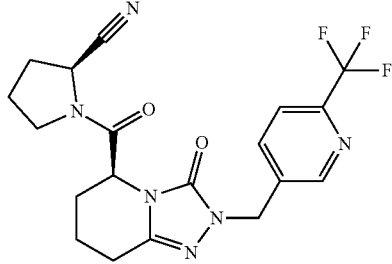 [SMILES: N#C[C@@H]1CCCN1C(=O)[C@@H]1CCCc2nn(Cc3ccc(C(F)(F)F)nc3)c(=O)n21]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (97.0 mg, 283 µmol) was initially charged in THF (2.0 ml), and HBTU (140 mg, 368 µmol) and N,N-diisopropylethylamine (150 µl, 850 µmol) were subsequently added. After stirring at room temperature for 15 min, (2S)-pyrrolidine-2-carbonitrile hydrochloride (45.1 mg, 340 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 36.0 mg (30% of theory) of the title compound were obtained.

LC-MS (Method 1): $R_t$=0.97 min; MS (ESIpos): m/z=421 [M+H]$^+$ $^1$H-NMR (400 MHz, DMSO-d6) δ[ppm]: −0.149 (1.50), 0.146 (1.50), 1.244 (1.05), 1.260 (1.05), 1.641 (1.50), 1.780 (1.64), 2.045 (4.49), 2.061 (6.88), 2.077 (5.98), 2.094 (2.99), 2.117 (2.54), 2.136 (2.39), 2.150 (2.99), 2.161 (2.54), 2.189 (1.35), 2.209 (2.99), 2.228 (2.84), 2.240 (1.79), 2.259 (1.50), 2.327 (3.89), 2.366 (2.84), 2.570 (3.29), 2.586 (2.39), 2.597 (2.39), 2.610 (2.09), 2.646 (3.14), 2.669 (4.34), 2.710 (3.14), 3.676 (4.64), 3.692 (9.27), 3.709 (4.64), 4.798 (2.99), 4.809 (3.44), 4.818 (4.49), 4.830 (4.93), 4.847 (2.54), 4.971 (1.05), 5.011 (9.12), 5.021 (8.52), 5.061 (1.05), 7.915 (16.00), 8.642 (6.13).

Example 512

(2S)-1-({(5S)-2-[(5-Chloropyridin-2-yl)methyl]-3-oxo-2,3,5,6,7,8-hexahydro[1,2,4]triazolo[4,3-a]pyridin-5-yl}carbonyl)pyrrolidine-2-carbonitrile

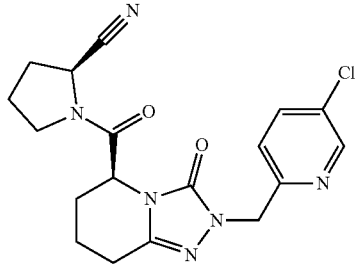 [SMILES: N#C[C@@H]1CCCN1C(=O)[C@@H]1CCCc2nn(Cc3ccc(Cl)cn3)c(=O)n21]

(5S)-2-[(5-Chloropyridin-2-yl)methyl]-3-oxo-2,3,5,6,7,8-hexahydro[1,2,4]triazolo[4,3-a]pyridine-5-carboxylic acid (100 mg, 324 µmol) was initially charged in THF (2.0 ml), and HBTU (160 mg, 421 µmol) and N,N-diisopropylethylamine (170 µl, 970 µmol) were subsequently added. After stirring at room temperature for 15 min, (2S)-pyrrolidine-2-carbonitrile (37.4 mg, 389 µmol) was added and the reaction mixture was stirred at room temperature for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 31.0 mg (25% of theory) of the title compound were obtained.

LC-MS (Method 3): $R_t$=1.16 min; MS (ESIpos): m/z=387 [M+H]$^+$ $^1$H-NMR (400 MHz, DMSO-d6) δ [ppm]: −0.149 (0.55), −0.008 (4.70), 0.008 (4.51), 0.146 (0.56), 1.675 (0.88), 1.791 (1.13), 2.028 (1.26), 2.047 (3.33), 2.063 (4.78), 2.079 (4.08), 2.095 (1.90), 2.106 (1.56), 2.120 (1.82), 2.130 (1.52), 2.137 (1.65), 2.151 (2.09), 2.163 (1.80), 2.177 (0.77), 2.185 (0.98), 2.205 (2.07), 2.225 (2.01), 2.237 (1.20), 2.244 (0.73), 2.256 (0.96), 2.327 (0.85), 2.569 (1.65), 2.584 (1.45), 2.595 (1.58), 2.609 (1.26), 2.628 (1.15), 2.640 (2.16), 2.653 (1.26), 2.670 (1.33), 2.682 (1.02), 3.679 (3.23), 3.695 (6.66), 3.712 (3.27), 4.791 (2.37), 4.802 (2.50), 4.811 (2.76), 4.821 (3.53), 4.828 (2.41), 4.834 (2.61), 4.843 (1.88), 4.915 (16.00), 7.195 (4.32), 7.216 (4.66), 7.921 (3.06), 7.927 (3.05), 7.942 (2.91), 7.949 (2.99), 8.573 (3.80), 8.579 (3.82).

Example 513

(2S)-1-({(5S)-2-[(3,5-Dichloropyridin-2-yl)methyl]-3-oxo-2,3,5,6,7,8-hexahydro[1,2,4]triazolo[4,3-a]pyridin-5-yl}carbonyl)pyrrolidine-2-carbonitrile

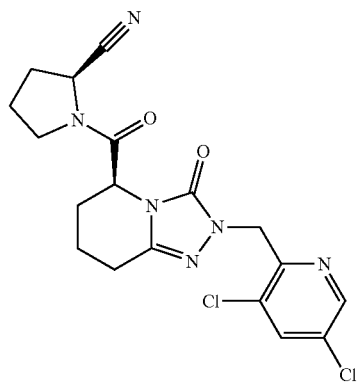 [SMILES: N#C[C@@H]1CCCN1C(=O)[C@@H]1CCCc2nn(Cc3ncc(Cl)cc3Cl)c(=O)n21]

(5S)-2-[(3,5-Dichloropyridin-2-yl)methyl]-3-oxo-2,3,5,6,7,8-hexahydro[1,2,4]triazolo[4,3-a]pyridine-5-carboxylic acid (70.0 mg, 204 µmol) was initially charged in THF (1.7 ml), and HBTU (155 mg, 408 µmol) and N,N-diisopropylethylamine (140 µl, 820 µmol) were subsequently added. After stirring at room temperature for 15 min, (2S)-pyrrolidine-2-carbonitrile hydrochloride (40.6 mg, 306 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 10). The product-containing fractions were concentrated under reduced pressure, and 7.50 mg (94% purity, 8% of theory) of the title compound were obtained.

LC-MS (Method 4): $R_t$=0.70 min; MS (ESIpos): m/z=421 [M+H]$^+$ $^1$H-NMR (400 MHz, DMSO-d6) δ[ppm]: −0.149 (1.95), −0.008 (16.00), 0.008 (15.18), 0.146 (1.88), 1.665 (0.69), 1.759 (0.88), 2.045 (2.07), 2.060 (2.89), 2.077 (2.95), 2.093 (1.63), 2.136 (1.19), 2.149 (1.57), 2.161 (1.19), 2.181 (0.75), 2.201 (1.57), 2.221 (1.44), 2.233 (0.94), 2.252 (0.88), 2.327 (2.38), 2.366 (2.51), 2.577 (1.38), 2.606 (1.88), 2.617 (1.13), 2.669 (2.51), 2.710 (2.45), 3.672 (2.51), 3.689 (5.02), 3.706 (2.32), 4.780 (1.63), 4.791 (1.95), 4.801 (3.39), 4.811 (3.26), 4.826 (1.44), 4.964 (1.19), 5.004 (6.40), 5.018 (6.53), 5.058 (1.25), 8.251 (2.51), 8.256 (2.70), 8.566 (2.89), 8.572 (2.82).

Example 514

(2S)-1-({(5S)-2-[(5-Chloro-3-fluoropyridin-2-yl) methyl]-3-oxo-2,3,5,6,7,8-hexahydro[1,2,4]triazolo [4,3-a]pyridin-5-yl}carbonyl)pyrrolidine-2-carbonitrile

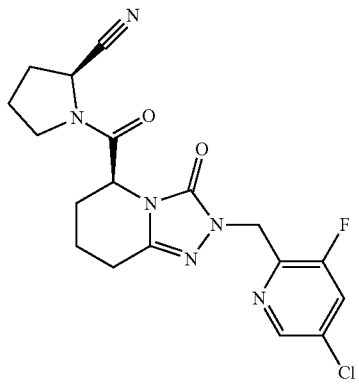 [SMILES: N#C[C@@H]1CCCN1C(=O)[C@@H]1CCCc2nn(Cc3ncc(Cl)cc3F)c(=O)n21]

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (100 mg, 306 µmol) was initially charged in THF (4.6 ml), and HBTU (139 mg, 367 µmol) and N,N-diisopropylethylamine (160 µl, 920 µmol) were subsequently added. After stirring at room temperature for 15 min, (2S)-pyrrolidine-2-carbonitrile (38.3 mg, 398 µmol) was added and the reaction mixture was stirred for 72 hours. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 35.0 mg (28% of theory) of the title compound were obtained.

LC-MS (Method 3): $R_t$=1.19 min; MS (ESIpos): m/z=405 [M+H]$^+$ $^1$H-NMR (400 MHz, DMSO-d6) δ [ppm]: −0.008 (3.01), 0.008 (2.62), 1.247 (1.39), 1.264 (2.35), 1.281 (1.26), 1.655 (2.13), 1.746 (2.54), 1.757 (2.62), 1.772 (1.94), 1.982 (1.68), 2.001 (2.40), 2.017 (3.51), 2.025 (4.06), 2.046 (5.71), 2.059 (9.52), 2.078 (9.69), 2.094 (5.49), 2.104 (3.31), 2.115 (3.01), 2.129 (2.61), 2.137 (3.62), 2.149 (4.47), 2.160 (3.59), 2.176 (1.91), 2.182 (2.56), 2.202 (4.62), 2.214 (1.69), 2.221 (4.22), 2.234 (2.64), 2.241 (1.72), 2.253 (2.06), 2.274 (0.86), 2.287 (0.55), 2.328 (1.08), 2.567 (3.13), 2.584 (3.05), 2.597 (5.37), 2.610 (2.96), 2.627 (1.37), 2.639 (2.19), 2.651 (0.94), 2.665 (0.85), 2.670 (1.04), 3.502 (0.56), 3.521 (0.44), 3.670 (7.94), 3.687 (16.00), 3.703 (7.75), 4.739 (0.60), 4.783 (6.98), 4.786 (5.83), 4.793 (8.96), 4.802 (12.61), 4.812 (9.58), 4.910 (3.03), 4.915 (3.01), 4.949 (10.52), 4.953 (10.25), 4.975 (10.53), 4.979 (10.66), 5.014 (3.03), 5.019 (2.99), 5.040 (0.48), 6.973 (0.87), 7.101 (0.90), 7.229 (0.82), 8.090 (7.00), 8.095 (7.61), 8.114 (7.09), 8.118 (7.72), 8.480 (9.30), 8.483 (9.78).

Example 515

(5S)-5-{[(3S)-3-Fluoropyrrolidin-1-yl]carbonyl}-2-{ [5-(trifluoromethyl)pyridin-3-yl]methyl}-5,6,7,8-tetrahydro[1,2,4]triazolo[4,3-a]pyridin-3(2H)-one

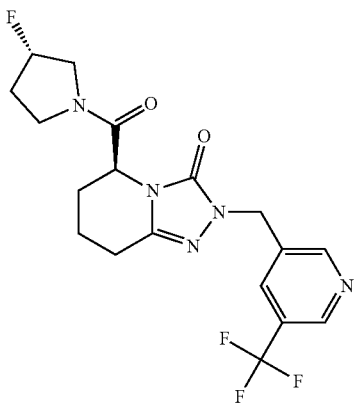 [SMILES: O=C([C@@H]1CCCc2nn(Cc3cncc(C(F)(F)F)c3)c(=O)n21)N1CC[C@H](F)C1]

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic acid (46.5 mg, 136 µmol) was initially charged in THF (11 µl), and (3S)-3-fluoropyrrolidine hydrochloride (20.5 mg, 163 µmol) and (3S)-3-fluoropyrrolidine hydrochloride (95 µl, 680 µmol) were subsequently added. After stirring at room temperature for 15 min, HBTU (67.0 mg, 177 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure and the residue was purified via preparative HPLC (Method 11). The product-containing fractions were concentrated under reduced pressure, and 29.5 mg (53% of theory) of the title compound were obtained.

LC-MS (Method 3): $R_t$=1.16 min; MS (ESIpos): m/z=414 [M+H]$^+$ $^1$H-NMR (400 MHz, DMSO-d6) δ [ppm]: 1.695 (1.26), 1.734 (2.23), 1.888 (0.52), 1.924 (0.76), 1.999 (0.84), 2.034 (1.38), 2.047 (1.33), 2.068 (1.37), 2.088 (1.85), 2.104 (2.27), 2.138 (1.59), 2.221 (0.85), 2.242 (0.78), 2.256 (0.80), 2.270 (1.14), 2.327 (0.56), 2.569 (1.57), 2.577 (1.70), 2.591 (1.48), 2.617 (2.57), 2.660 (1.13), 2.670 (0.97), 3.361 (1.30), 3.371 (1.17), 3.398 (1.01), 3.406 (0.99), 3.460 (0.64), 3.468 (0.71), 3.495 (0.89), 3.504 (0.86), 3.613 (0.59), 3.630 (2.11), 3.637 (2.26), 3.654 (2.41), 3.666 (1.56), 3.681 (1.50), 3.698 (1.11), 3.725 (1.28), 3.746 (1.94), 3.770 (1.64), 3.784 (1.49), 3.855 (2.48), 4.703 (1.17), 4.712 (1.42), 4.719 (1.49), 4.728 (1.18), 4.762 (1.50), 4.770 (1.68), 4.777 (1.93), 4.786 (1.45), 5.017

(16.00), 5.260 (1.25), 5.384 (1.52), 5.391 (1.57), 5.512 (0.89), 8.059 (5.28), 8.742 (5.83), 8.917 (5.45).

Example 516

(5S)-5-{[(3S)-3-Fluoropyrrolidin-1-yl]carbonyl}-2-[2-(4-methylphenyl)-2-oxoethyl]-5,6,7,8-tetrahydro[1,2,4]triazolo[4,3-a]pyridin-3(2H)-one

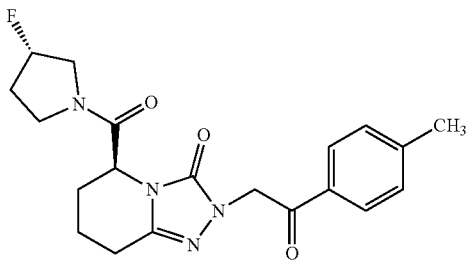 [SMILES: Cc1ccc(C(=O)Cn2nc3n(c2=O)[C@H](C(=O)N2CC[C@H](F)C2)CCC3)cc1]

(5S)-2-[2-(4-Methylphenyl)-2-oxoethyl]-3-oxo-2,3,5,6,7,8-hexahydro[1,2,4]triazolo[4,3-a]pyridine-5-carboxylic acid (121 mg, 383 µmol) was initially charged in THF (7.0 ml), and HBTU (189 mg, 498 µmol) and N,N-diisopropylethylamine (200 µl, 1.1 mmol) were subsequently added. After stirring at room temperature for 15 min, (3S)-3-fluoropyrrolidine hydrochloride (1:1) (57.7 mg, 459 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 77.3 mg (52% of theory) of the title compound were obtained.

LC-MS (Method 3): $R_t$=1.27 min; MS (ESIpos): m/z=387 [M+H]$^+$ $^1$H-NMR (400 MHz, DMSO-d6) δ [ppm]: −0.149 (1.36), −0.008 (16.00), 0.008 (8.62), 0.146 (1.10), 1.760 (1.10), 2.110 (0.79), 2.327 (2.33), 2.366 (3.25), 2.397 (11.03), 2.523 (12.00), 2.577 (0.97), 2.597 (1.23), 2.622 (1.14), 2.669 (1.89), 2.709 (1.76), 3.658 (0.75), 3.757 (0.57), 3.870 (0.75), 4.704 (0.48), 4.758 (0.57), 5.186 (4.75), 5.254 (0.40), 5.384 (0.48), 7.358 (2.46), 7.378 (2.55), 7.908 (2.59), 7.927 (2.37).

Example 517

(5S)-2-[2,2-Difluoro-2-(4-methylphenyl)ethyl]-5-{[(3S)-3-fluoropyrrolidin-1-yl]carbonyl}-5,6,7,8-tetrahydro[1,2,4]triazolo[4,3-a]pyridin-3(2H)-one

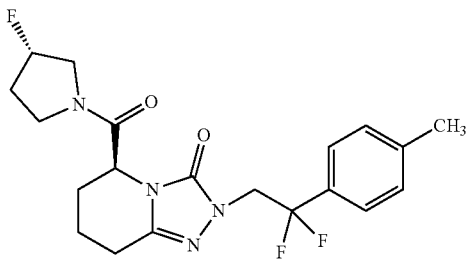 [SMILES: Cc1ccc(C(F)(F)Cn2nc3n(c2=O)[C@H](C(=O)N2CC[C@H](F)C2)CCC3)cc1]

(5S)-5-{[(3S)-3-Fluoropyrrolidin-1-yl]carbonyl}-2-[2-(4-methylphenyl)-2-oxoethyl]-5,6,7,8-tetrahydro[1,2,4]triazolo[4,3-a]pyridin-3(2H)-one (51.5 mg, 133 µmol) was dissolved in 1,2-dichloroethane (2.0 ml), and diethylaminosulphur trifluoride (1.0 ml, 90% purity, 6.8 mmol) and 1 drop of ethanol were added. The reaction mixture was stirred at 70° C. for 3 hours. The reaction mixture was added dropwise to a saturated aqueous sodium hydrogencarbonate solution. Dichloromethane was added and the organic phase was removed. The organic phase was washed with saturated aqueous sodium chloride solution, dried over sodium sulphate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 16.8 mg (31% of theory) of the title compound were obtained.

LC-MS (Method 3): $R_t$=1.49 min; MS (ESIpos): m/z=409 [M+H]$^+$ $^1$H-NMR (400 MHz, DMSO-d6) δ [ppm]: 0.007 (6.14), 1.148 (1.48), 1.729 (2.36), 2.084 (1.37), 2.347 (16.00), 2.365 (1.48), 2.568 (2.08), 2.608 (1.70), 2.669 (1.37), 2.710 (0.99), 3.615 (1.92), 3.640 (1.48), 3.726 (1.32), 3.750 (1.04), 3.839 (1.70), 4.275 (1.26), 4.315 (1.64), 4.658 (0.99), 4.716 (1.26), 5.383 (1.15), 7.288 (3.84), 7.308 (5.81), 7.393 (4.88), 7.413 (3.18).

The following examples 518-546 were prepared as described in Example 517:

Example 518

(5S)-2-{[3-Chloro-5-(trifluoromethyl)pyridin-2-yl]ethyl}-5-[(3-fluoroazetidin-1-yl)carbonyl]-5,6,7,8-tetrahydro[1,2,4]triazolo[4,3-a]pyridin-3(2H)-one

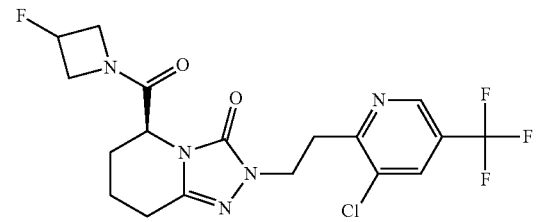 [SMILES: O=C([C@@H]1CCCc2nn(CCc3ncc(C(F)(F)F)cc3Cl)c(=O)n21)N1CC(F)C1]

(5S)-2-{2-[3-Chloro-5-(trifluoromethyl)pyridin-2-yl]ethyl}-3-oxo-2,3,5,6,7,8-hexahydro[1,2,4]triazolo[4,3-a]pyridine-5-carboxylic acid (75.0 mg, 72% purity, 138 µmol), N,N-diisopropylethylamine (110 pal, 620 µmol), HBTU (99.6 mg, 263 µmol), 3-fluoroazetidine hydrochloride (1:1) (26.2 mg, 235 µmol). Stirring at room temperature overnight. After purification, 44.1 mg (71% of theory) of the title compound were obtained.

LC-MS (Method 3): $R_t$=1.43 min; MS (ESIpos): m/z=448 [M+H]$^+$ $^1$H-NMR (400 MHz, DMSO-d6) δ[ppm]: −0.149 (3.72), 0.146 (3.72), 1.707 (9.96), 1.931 (3.82), 1.992 (4.03), 2.072 (3.02), 2.327 (5.53), 2.366 (4.03), 2.584 (7.95), 2.625 (2.72), 2.669 (5.53), 2.709 (3.52), 3.283 (11.07), 3.910 (2.92), 4.024 (5.94), 4.041 (13.08), 4.059 (9.96), 4.235 (3.62), 4.324 (2.72), 4.441 (6.14), 4.454 (9.86), 4.468 (6.44), 4.658 (1.81), 5.385 (1.81), 5.517 (1.81), 8.413 (16.00), 8.876 (14.79).

Example 519

(5S)-5-[(3,3-Difluoropyrrolidin-1-yl)carbonyl]-2-[2-(4-fluorophenyl)ethyl]-5,6,7,8-tetrahydro[1,2,4]triazolo[4,3-a]pyridin-3(2H)-one

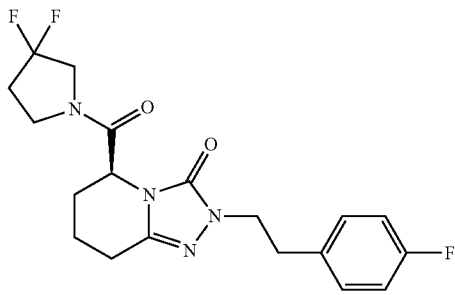 [SMILES: O=C([C@@H]1CCCc2nn(CCc3ccc(F)cc3)c(=O)n21)N1CCC(F)(F)C1]

(5S)-2-[2-(4-Fluorophenyl)ethyl]-3-oxo-2,3,5,6,7,8-hexahydro[1,2,4]triazolo[4,3-a]pyridine-5-carboxylic acid (73.1 mg, 240 µmol), N,N-diisopropylethylamine (130 µl, 720 µmol), HBTU (118 mg, 311 µmol), 3,3-difluoropyrrolidine hydrochloride (1:1) (41.3 mg, 287 µmol). Stirring at room temperature for 72 hours. After purification, 53.2 mg (56% of theory) of the title compound were obtained.

LC-MS (Method 3): $R_t$=1.48 min; MS (ESIpos): m/z=395 [M+H]$^+$ $^1$H-NMR (400 MHz, DMSO-d6) δ[ppm]: 0.008 (2.61), 1.683 (1.93), 1.709 (3.74), 1.891 (1.36), 1.971 (3.06), 2.011 (1.82), 2.026 (1.70), 2.037 (1.82), 2.328 (1.93), 2.353 (0.68), 2.367 (2.16), 2.400 (1.59), 2.523 (7.72), 2.567 (4.43), 2.576 (4.99), 2.591 (3.40), 2.604 (2.50), 2.616 (4.31), 2.660 (2.16), 2.670 (2.84), 2.710 (1.70), 2.895 (5.90), 2.914 (12.26), 2.932 (6.47), 3.518 (3.29), 3.538 (5.22), 3.557 (2.50), 3.623 (0.68), 3.658 (1.93), 3.691 (2.16), 3.721 (1.48), 3.751 (4.20), 3.767 (5.56), 3.785 (13.39), 3.803 (10.55), 3.822 (3.86), 3.838 (2.04), 3.857 (1.13), 3.882 (2.27), 3.909 (1.70), 3.928 (0.79), 3.949 (0.68), 3.979 (1.48), 4.008 (1.02), 4.020 (1.36), 4.050 (0.79), 4.115 (0.79), 4.147 (1.36), 4.174 (1.36), 4.204 (0.57), 4.668 (1.82), 4.683 (2.61), 4.693 (1.82), 4.744 (1.93), 4.759 (2.61), 4.769 (1.82), 7.062 (7.15), 7.085 (16.00), 7.107 (10.33), 7.203 (8.74), 7.217 (9.87), 7.225 (8.17), 7.239 (6.70).

Example 520

(5S)-5-[(3-Fluoroazetidin-1-yl)carbonyl]-2-[2-(4-fluorophenyl)ethyl]-5,6,7,8-tetrahydro[1,2,4]triazolo[4,3-a]pyridin-3(2H)-one

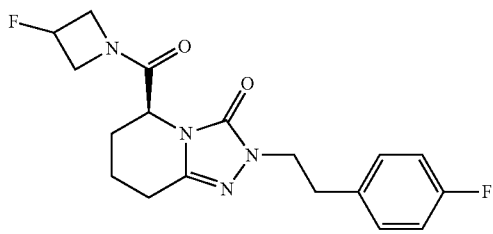 [SMILES: O=C([C@@H]1CCCc2nn(CCc3ccc(F)cc3)c(=O)n21)N1CC(F)C1]

(5S)-2-[2-(4-Fluorophenyl)ethyl]-3-oxo-2,3,5,6,7,8-hexahydro[1,2,4]triazolo[4,3-a]pyridine-5-carboxylic acid (73.1 mg, 240 µmol), N,N-diisopropylethylamine (130 µl, 720 µmol), HBTU (118 mg, 311 µmol), 3-fluoroazetidine hydrochloride (1:1) (32.1 mg, 287 mol). Stirring at room temperature for 72 hours. After purification, 37.7 mg (43% of theory) of the title compound were obtained.

LC-MS (Method 3): $R_t$=1.49 min; MS (ESIpos): m/z=363 [M+H]$^+$ $^1$H-NMR (400 MHz, DMSO-d6) δ [ppm]: −0.149 (2.06), −0.008 (15.54), 0.008 (16.00), 0.146 (2.06), 1.715 (3.20), 1.943 (1.26), 1.972 (1.14), 1.991 (1.37), 2.006 (1.26), 2.328 (2.40), 2.366 (1.94), 2.523 (7.43), 2.567 (2.74), 2.588 (1.83), 2.606 (2.97), 2.619 (1.71), 2.648 (1.03), 2.670 (2.74), 2.710 (1.94), 2.898 (2.74), 2.917 (5.60), 2.935 (3.09), 3.782 (2.17), 3.799 (4.00), 3.969 (0.80), 4.220 (1.14), 4.238 (1.14), 4.277 (0.80), 4.411 (0.57), 4.448 (2.40), 4.462 (3.43), 4.475 (2.17), 4.663 (0.46), 5.332 (0.57), 5.520 (0.57), 7.064 (2.29), 7.085 (5.03), 7.106 (3.09), 7.223 (4.00).

Example 521

(5S)-2-[2-(4-Methylphenyl)ethyl]-5-(pyrrolidin-1-ylcarbonyl)-5,6,7,8-tetrahydro[1,2,4]triazolo[4,3-a]pyridin-3(2H)-one

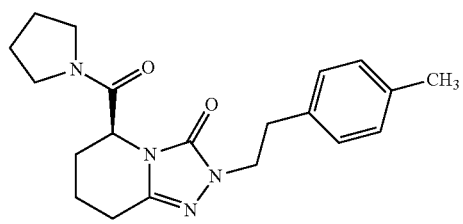 [SMILES: Cc1ccc(CCn2nc3n(c2=O)[C@H](C(=O)N2CCCC2)CCC3)cc1]

(5S)-2-[2-(4-Methylphenyl)ethyl]-3-oxo-2,3,5,6,7,8-hexahydro[1,2,4]triazolo[4,3-a]pyridine-5-carboxylic acid (200 mg, 664 µmol), N,N-diisopropylethylamine (460 µl, 2.7 mmol), HBTU (327 mg, 863 µmol), pyrrolidine (66 µl, 800 µmol). Stirring at room temperature overnight. After purification, 163 mg (69% of theory) of the title compound were obtained.

LC-MS (Method 3): $R_t$=1.45 min; MS (ESIpos): m/z=355 [M+H]$^+$ $^1$H-NMR (400 MHz, DMSO-d6) δ [ppm]: −0.008 (1.86), 0.008 (1.55), 1.703 (0.76), 1.714 (1.01), 1.733 (0.71), 1.746 (0.55), 1.764 (1.00), 1.781 (1.71), 1.798 (1.34), 1.815 (0.41), 1.883 (0.41), 1.900 (1.27), 1.916 (1.67), 1.933 (1.07), 1.951 (0.54), 1.962 (0.61), 1.973 (0.54), 1.982 (0.43), 1.997 (0.44), 2.018 (0.40), 2.257 (9.36), 2.560 (0.68), 2.580 (0.44), 2.602 (0.42), 2.613 (0.87), 2.626 (0.44), 2.848 (1.00), 2.868 (1.97), 2.887 (1.03), 3.233 (0.51), 3.246 (0.52), 3.263 (0.91), 3.280 (0.45), 3.328 (1.08), 3.346 (0.51), 3.357 (0.53), 3.440 (0.58), 3.447 (0.42), 3.465 (0.74), 3.589 (0.70), 3.606 (0.41), 3.613 (0.54), 3.729 (0.62), 3.748 (0.95), 3.758 (0.65), 3.766 (0.59), 3.777 (0.97), 3.797 (0.54), 4.659 (0.65), 4.669 (0.75), 4.675 (0.88), 4.684 (0.64), 7.085 (16.00).

Example 522

(5S)-5-{[(3R,4S)-3,4-Difluoropyrrolidin-1-yl]carbonyl}-2-[2-(4-methoxyphenyl)ethyl]-5,6,7,8-tetrahydro[1,2,4]triazolo[4,3-a]pyridin-3(2H)-one

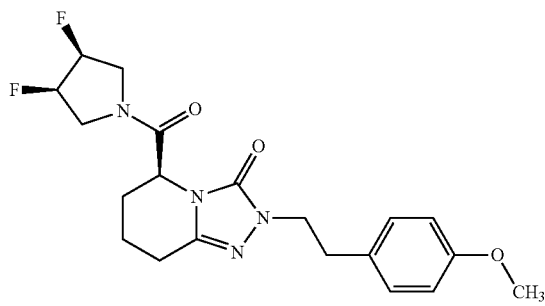 [SMILES: COc1ccc(CCn2nc3n(c2=O)[C@H](C(=O)N2C[C@@H](F)[C@@H](F)C2)CCC3)cc1]

(5S)-2-[2-(4-Methoxyphenyl)ethyl]-3-oxo-2,3,5,6,7,8-hexahydro[1,2,4]triazolo[4,3-a]pyridine-5-carboxylic acid (92.0 mg, 290 µmol), N,N-diisopropylethylamine (150 µl, 870 µmol), HBTU (143 mg, 377 µmol), (3R,4S)-3,4-difluoropyrrolidine hydrochloride (49.9 mg, 348 µmol). Stirring at room temperature for 72 hours. After purification, 71.1 mg (60% of theory) of the title compound were obtained.

LC-MS (Method 4): $R_t$=0.72 min; MS (ESIpos): m/z=407 [M+H]$^+$ $^1$H-NMR (400 MHz, DMSO-d6) δ[ppm]: 1.680 (0.47), 1.704 (0.90), 1.715 (1.09), 1.727 (1.01), 1.939 (0.47), 1.976 (0.55), 1.986 (0.65), 1.998 (0.48), 2.012 (0.44), 2.021 (0.42), 2.028 (0.46), 2.036 (0.44), 2.045 (0.41), 2.073 (1.37), 2.563 (0.77), 2.575 (0.79), 2.586 (0.63), 2.620 (1.09), 2.631 (0.63), 2.663 (0.51), 2.830 (1.48), 2.848 (2.93), 2.867 (1.56), 3.477 (0.48), 3.499 (0.42), 3.509 (0.44), 3.532 (0.49), 3.673 (0.68), 3.689 (0.68), 3.715 (16.00), 3.742 (2.34), 3.750 (1.16), 3.761 (1.70), 3.769 (1.37), 3.782 (0.78), 3.804 (0.47), 4.152 (0.43), 4.710 (0.96), 4.723 (1.33), 4.734 (0.92), 6.828 (2.79), 6.846 (2.98), 6.850 (2.86), 7.095 (2.14), 7.104 (2.47), 7.116 (1.95), 7.125 (2.09).

Example 523

(5S)-5-[(3,3-Difluoroazetidin-1-yl)carbonyl]-2-[2-(4-methoxyphenyl)ethyl]-5,6,7,8-tetrahydro[1,2,4]triazolo[4,3-a]pyridin-3(2H)-one

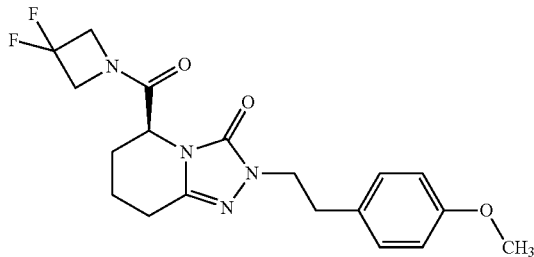 [SMILES: COc1ccc(CCn2nc3n(c2=O)[C@H](C(=O)N2CC(F)(F)C2)CCC3)cc1]

(5S)-2-[2-(4-Methoxyphenyl)ethyl]-3-oxo-2,3,5,6,7,8-hexahydro[1,2,4]triazolo[4,3-a]pyridine-5-carboxylic acid (92.0 mg, 290 µmol), N,N-diisopropylethylamine (150 µl, 870 µmol), HBTU (143 mg, 377 µmol), 3,3-difluoroazetidine hydrochloride (45.1 mg, 348 µmol). Stirring at room temperature for 72 hours. After purification, 64.5 mg (57% of theory) of the title compound were obtained.

LC-MS (Method 3): $R_t$=1.46 min; MS (ESIpos): m/z=393 [M+H]$^+$ $^1$H-NMR (400 MHz, DMSO-d6) δ [ppm]: −0.008 (0.90), 0.008 (0.75), 1.711 (0.65), 1.726 (1.00), 1.738 (0.92), 1.749 (0.63), 1.960 (0.54), 1.971 (0.50), 2.016 (0.41), 2.028 (0.40), 2.037 (0.48), 2.569 (0.65), 2.589 (0.83), 2.605 (0.98), 2.618 (1.19), 2.632 (0.57), 2.835 (1.24), 2.854 (2.48), 2.872 (1.35), 3.713 (16.00), 3.743 (0.87), 3.750 (0.92), 3.760 (1.69), 3.770 (1.68), 3.779 (0.83), 3.789 (0.76), 4.342 (0.64), 4.357 (0.64), 4.501 (0.86), 4.515 (1.44), 4.528 (0.85), 4.700 (0.45), 4.807 (0.43), 6.825 (3.10), 6.847 (3.66), 6.854 (0.44), 7.102 (3.30), 7.123 (2.85).

Example 524

(5S)-5-[(3,3-Difluoropyrrolidin-1-yl)carbonyl]-2-{[1-(4-methylphenyl)cyclopropyl]methyl}-5,6,7,8-tetrahydro[1,2,4]triazolo[4,3-a]pyridin-3(2H)-one

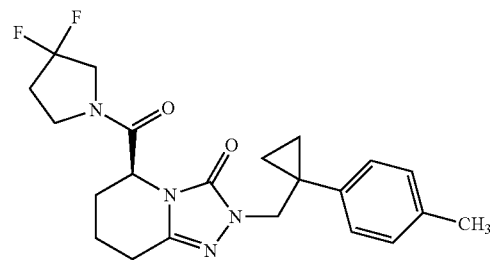 [SMILES: Cc1ccc(C2(Cn3nc4n(c3=O)[C@H](C(=O)N3CCC(F)(F)C3)CCC4)CC2)cc1]

(5S)-2-{[1-(4-Methylphenyl)cyclopropyl]methyl}-3-oxo-2,3,5,6,7,8-hexahydro[1,2,4]triazolo[4,3-a]pyridine-5-carboxylic acid (45.0 mg, 137 µmol), N,N-diisopropylethylamine (72 µl, 410 µmol), HBTU (67.8 mg, 179 µmol), 3,3-difluoropyrrolidine hydrochloride (23.7 mg, 165 µmol). Stirring at room temperature overnight. After purification, 27.3 mg (48% of theory) of the title compound were obtained.

LC-MS (Method 3): $R_t$=1.72 min; MS (ESIpos): m/z=417 [M+H]$^+$ $^1$H-NMR (400 MHz, DMSO-d6) δ[ppm]: −0.008 (2.67), 0.008 (2.32), 0.677 (0.52), 0.687 (0.71), 0.702 (1.17), 0.713 (1.14), 0.720 (0.89), 0.786 (1.23), 0.796 (1.02), 0.811 (0.74), 0.821 (0.61), 0.921 (0.53), 0.931 (0.55), 0.945 (1.24), 0.955 (1.62), 0.966 (2.20), 0.974 (1.56), 0.988 (1.08), 0.998 (0.49), 1.662 (0.70), 1.688 (1.08), 1.958 (0.93), 1.972 (0.93), 1.985 (0.91), 2.012 (0.58), 2.022 (0.44), 2.073 (1.06), 2.235 (16.00), 2.327 (0.53), 2.366 (0.85), 2.393 (0.59), 2.416 (0.56), 2.435 (0.42), 2.467 (0.58), 2.523 (2.70), 2.566 (1.36), 2.580 (1.61), 2.622 (0.61), 2.669 (0.58), 2.710 (0.45), 3.509 (0.99), 3.528 (1.58), 3.549 (0.71), 3.644 (1.67), 3.649 (1.91), 3.680 (2.35), 3.685 (2.14), 3.712 (0.55), 3.744 (1.27), 3.772 (1.06), 3.869 (0.74), 3.895 (0.58), 3.915 (1.88), 3.922 (1.67), 3.951 (1.38), 3.958 (1.74), 4.000 (0.47), 4.133 (0.47), 4.159 (0.42), 4.657 (0.64), 4.671 (0.88), 4.681 (0.62), 4.731 (0.67), 4.747 (0.85), 4.756 (0.62), 7.025 (3.25), 7.045 (5.44), 7.105 (6.96), 7.125 (4.16).

Example 525

(5S)-5-{[(3S)-3-Hydroxypyrrolidin-1-yl]carbonyl}-2-{[1-(4-methylphenyl)cyclopropyl]methyl}-5,6,7,8-tetrahydro[1,2,4]triazolo[4,3-a]pyridin-3(2H)-one

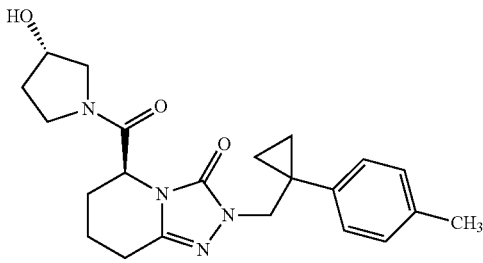 [SMILES: Cc1ccc(C2(Cn3nc4n(c3=O)[C@H](C(=O)N3CC[C@H](O)C3)CCC4)CC2)cc1]

(5S)-2-{[1-(4-Methylphenyl)cyclopropyl]methyl}-3-oxo-2,3,5,6,7,8-hexahydro[1,2,4]triazolo[4,3-a]pyridine-5-carboxylic acid (45.0 mg, 137 µmol), N,N-diisopropylethylamine (72 µl, 410 µmol), HBTU (67.8 mg, 179 µmol), (3S)-pyrrolidin-3-ol hydrochloride (1:1) (20.4 mg, 165 µmol). Stirring at room temperature overnight. After purification, 24.4 mg (45% of theory) of the title compound were obtained.

LC-MS (Method 4): $R_t$=0.74 min; MS (ESIpos): m/z=397 [M+H]$^+$ $^1$H-NMR (400 MHz, DMSO-d6) δ[ppm]: −0.008 (2.87), 0.008 (2.23), 0.683 (0.77), 0.706 (1.23), 0.786 (1.29), 0.809 (0.80), 0.820 (0.58), 0.921 (0.45), 0.933 (0.56), 0.944 (1.00), 0.956 (1.70), 0.966 (2.06), 0.992 (0.79), 1.387 (0.55), 1.692 (1.47), 1.703 (1.54), 1.752 (0.58), 1.762 (0.51), 1.831 (0.77), 1.842 (0.86), 1.853 (0.73), 1.863 (0.91), 1.874 (0.74), 1.930 (0.79), 1.964 (1.45), 1.975 (1.42), 1.987 (1.40), 1.997 (0.95), 2.013 (0.66), 2.072 (1.15), 2.236 (16.00), 2.327 (0.57), 2.366 (0.53), 2.447 (0.64), 2.464 (0.80), 2.523 (1.85), 2.565 (0.86), 2.577 (1.36), 2.619 (0.60), 2.669 (0.51), 2.709 (0.44), 3.243 (0.42), 3.276 (2.35), 3.287 (2.17), 3.297 (1.50), 3.404 (1.13), 3.413 (0.96), 3.427 (0.92), 3.434 (1.00), 3.456 (0.55), 3.464 (0.45), 3.528 (0.58), 3.549 (0.45), 3.606 (0.87), 3.617 (1.32), 3.634 (3.12), 3.644 (1.09), 3.671 (2.81), 3.918 (1.76), 3.928 (1.40), 3.954 (1.38), 3.964 (1.11), 4.251 (0.78), 4.349 (0.85), 4.591 (0.77), 4.599 (0.88), 4.606 (0.95), 4.614 (0.77), 4.633 (0.63), 4.647 (0.81), 4.656 (0.57), 7.026 (3.04), 7.046 (4.91), 7.106 (4.38), 7.112 (4.57), 7.126 (2.87), 7.132 (2.62).

Example 526

(5S)-5-{[(3S)-3-Fluoropyrrolidin-1-yl]carbonyl}-2-{[1-(4-methylphenyl)cyclopropyl]methyl}-5,6,7,8-tetrahydro[1,2,4]triazolo[4,3-a]pyridin-3(2H)-one

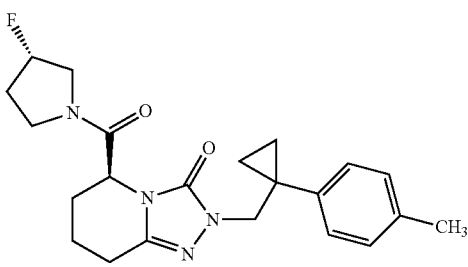 [SMILES: Cc1ccc(C2(Cn3nc4n(c3=O)[C@H](C(=O)N3CC[C@H](F)C3)CCC4)CC2)cc1]

(5S)-2-{[1-(4-Methylphenyl)cyclopropyl]methyl}-3-oxo-2,3,5,6,7,8-hexahydro[1,2,4]triazolo[4,3-a]pyridine-5-carboxylic acid (45.0 mg, 137 µmol), N,N-diisopropylethylamine (72 µl, 410 µmol), HBTU (67.8 mg, 179 µmol), (3S)-3-fluoropyrrolidine hydrochloride (20.7 mg, 165 µmol). Stirring at room temperature overnight. After purification, 21.6 mg (39% of theory) of the title compound were obtained.

LC-MS (Method 3): $R_t$=1.58 min; MS (ESIpos): m/z=399 [M+H]$^+$ $^1$H-NMR (400 MHz, DMSO-d6) δ[ppm]: −0.149 (0.60), −0.008 (5.27), 0.008 (4.23), 0.146 (0.55), 0.674 (0.50), 0.684 (0.73), 0.700 (1.15), 0.707 (1.10), 0.789 (1.04), 0.947 (0.89), 0.966 (1.93), 0.989 (0.86), 1.387 (3.45), 1.708 (1.54), 1.870 (0.42), 1.984 (0.86), 1.994 (0.94), 2.031 (0.73), 2.049 (0.65), 2.077 (0.65), 2.126 (0.50), 2.235 (16.00), 2.327 (0.97), 2.366 (1.07), 2.523 (4.28), 2.580 (1.28), 2.625 (0.65), 2.669 (1.20), 2.709 (1.10), 3.379 (0.47), 3.476 (0.44), 3.603 (0.99), 3.633 (2.01), 3.641 (1.80), 3.670 (2.17), 3.678 (1.54), 3.709 (0.99), 3.733 (0.70), 3.755 (0.57), 3.821 (1.15), 3.911 (1.33), 3.929 (1.54), 3.947 (1.04), 3.965 (1.23), 4.592 (0.57), 4.601 (0.68), 4.608 (0.65), 4.617 (0.57), 4.650 (0.76), 4.665 (0.94), 4.674 (0.70), 4.910 (0.55), 5.247 (0.57), 5.377 (0.63), 5.499 (0.44), 7.026 (2.90), 7.046 (4.72), 7.102 (3.47), 7.108 (4.33), 7.123 (2.35), 7.128 (2.45).

Example 527

(5S)-5-[(3-Fluoroazetidin-1-yl)carbonyl]-2-({1-[4-(trifluoromethyl)phenyl]cyclopropyl}methyl)-5,6,7,8-tetrahydro[1,2,4]triazolo[4,3-a]pyridin-3(2H)-one

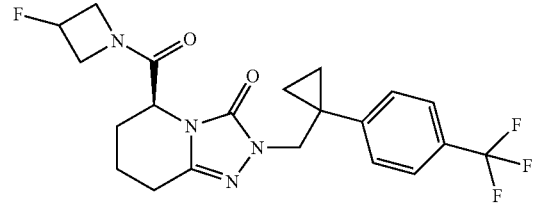 [SMILES: O=C([C@@H]1CCCc2nn(CC3(c4ccc(C(F)(F)F)cc4)CC3)c(=O)n21)N1CC(F)C1]

(5S)-3-Oxo-2-({1-[4-(trifluoromethyl)phenyl]cyclopropyl}methyl)-2,3,5,6,7,8-hexahydro[1,2,4]triazolo[4,3-a]pyridine-5-carboxylic acid (57.4 mg, 151 µmol), N,N-diisopropylethylamine (79 µl, 450 µmol), HBTU (74.2 mg, 196 µmol), 3-fluoroazetidine hydrochloride (20.1 mg, 181 µmol). Stirring at room temperature overnight. After purification, 37.9 mg (57% of theory) of the title compound were obtained.

LC-MS (Method 4): $R_t$=0.92 min; MS (ESIpos): m/z=439 [M+H]$^+$ $^1$H-NMR (400 MHz, DMSO-d6) δ [ppm]: −0.149 (1.76), −0.008 (16.00), 0.008 (14.16), 0.146 (1.84), 0.852 (2.09), 0.877 (6.79), 0.925 (5.03), 0.949 (2.09), 1.078 (1.17), 1.111 (14.24), 1.691 (4.86), 1.932 (2.60), 1.967 (2.09), 2.072 (2.85), 2.327 (2.43), 2.366 (2.76), 2.523 (11.64), 2.569 (4.69), 2.611 (1.76), 2.669 (2.76), 2.710 (2.85), 3.799 (4.94), 3.835 (8.54), 3.877 (1.34), 3.908 (4.77), 3.923 (3.77), 3.946 (2.76), 3.961 (2.93), 4.189 (1.93), 4.219 (1.93), 4.254 (1.34), 4.274 (1.17), 4.321 (1.01), 4.357 (0.75), 4.385 (0.92), 4.449 (5.11), 4.613 (0.84), 5.316 (0.84), 5.370 (0.92), 5.462 (0.84), 5.505 (0.84), 7.434 (8.80), 7.454 (11.81), 7.572 (10.05), 7.592 (7.71).

Example 528

(5S)-5-{[(3S)-3-Fluoropyrrolidin-1-yl]carbonyl}-2-{[1-(4-methoxyphenyl)cyclopropyl]methyl}-5,6,7,8-tetrahydro[1,2,4]triazolo[4,3-a]pyridin-3(2H)-one

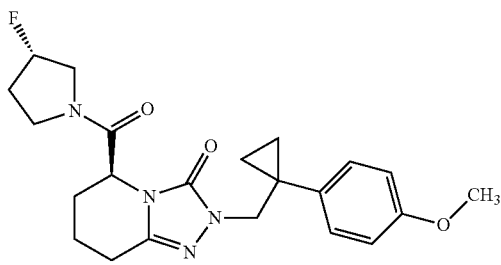 [SMILES: COc1ccc(C2(Cn3nc4n(c3=O)[C@H](C(=O)N3CC[C@H](F)C3)CCC4)CC2)cc1]

(5S)-2-{[1-(4-Methoxyphenyl)cyclopropyl]methyl}-3-oxo-2,3,5,6,7,8-hexahydro[1,2,4]triazolo[4,3-a]pyridine-5-carboxylic acid (93.2 mg, 50% purity, 136 µmol), N,N-diisopropylethylamine (140 µl, 810 µmol), HBTU (134 mg, 353 µmol), (3S)-3-fluoropyrrolidine hydrochloride (1:1) (20.4 mg, 163 µmol). Stirring at room temperature overnight. After purification, 42.9 mg (76% of theory) of the title compound were obtained.

LC-MS (Method 4): R$_t$=0.79 min; MS (ESIpos): m/z=415 [M+H]$^+$ $^1$H-NMR (400 MHz, DMSO-d6) δ [ppm]: −0.008 (1.55), 0.008 (1.21), 0.659 (0.47), 0.676 (0.69), 0.686 (0.80), 0.756 (0.77), 0.780 (0.43), 0.922 (0.63), 0.940 (1.59), 1.712 (1.04), 1.987 (0.54), 1.997 (0.67), 2.009 (0.56), 2.021 (0.47), 2.035 (0.49), 2.050 (0.46), 2.073 (7.98), 2.523 (1.28), 2.591 (0.77), 3.282 (0.42), 3.613 (1.24), 3.621 (1.22), 3.636 (0.59), 3.649 (1.32), 3.657 (1.14), 3.702 (16.00), 3.736 (0.53), 3.821 (0.80), 3.862 (0.89), 3.881 (1.07), 3.898 (0.68), 3.918 (0.80), 4.598 (0.45), 4.605 (0.46), 4.647 (0.48), 4.662 (0.62), 4.670 (0.45), 6.777 (2.71), 6.798 (2.98), 7.123 (1.91), 7.130 (2.47), 7.145 (1.88), 7.152 (2.06).

Example 529

(5S)-5-[(3,3-Difluoropyrrolidin-1-yl)carbonyl]-2-{[1-(4-methoxyphenyl)cyclopropyl]methyl}-5,6,7,8-tetrahydro[1,2,4]triazolo[4,3-a]pyridin-3(2H)-one

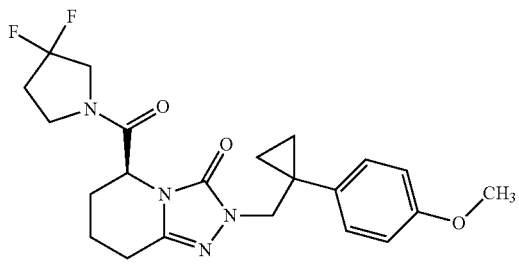 [SMILES: COc1ccc(C2(Cn3nc4n(c3=O)[C@H](C(=O)N3CCC(F)(F)C3)CCC4)CC2)cc1]

(5S)-2-{[1-(4-Methoxyphenyl)cyclopropyl]methyl}-3-oxo-2,3,5,6,7,8-hexahydro[1,2,4]triazolo[4,3-a]pyridine-5-carboxylic acid (93.2 mg, 50% purity, 136 µmol), N,N-diisopropylethylamine (140 µl, 810 µmol), HBTU (134 mg, 353 µmol), 3,3-difluoropyrrolidine hydrochloride (1:1) (23.4 mg, 163 µmol). Stirring at room temperature overnight. After purification, 41.1 mg (70% of theory) of the title compound were obtained.

LC-MS (Method 4): R$_t$=0.86 min; MS (ESIpos): m/z=433 [M+H]$^+$ $^1$H-NMR (400 MHz, DMSO-d6) δ [ppm]: −0.149 (0.44), −0.008 (4.06), 0.008 (3.72), 0.147 (0.48), 0.664 (0.44), 0.685 (0.72), 0.754 (0.78), 0.777 (0.48), 0.919 (0.72), 0.939 (1.64), 0.958 (0.65), 1.693 (0.68), 1.975 (0.61), 2.327 (0.78), 2.366 (1.19), 2.392 (0.41), 2.523 (3.21), 2.584 (1.13), 2.628 (0.44), 2.670 (0.92), 2.710 (0.92), 3.508 (0.65), 3.527 (1.06), 3.547 (0.58), 3.627 (0.89), 3.663 (1.16), 3.682 (0.55), 3.701 (16.00), 3.743 (0.72), 3.771 (0.78), 3.870 (1.36), 3.910 (0.96), 4.668 (0.55), 4.743 (0.55), 4.752 (0.41), 6.776 (3.14), 6.798 (3.58), 7.127 (3.79), 7.149 (3.38).

Example 530

(5S)-2-{[1-(2,4-Difluorophenyl)cyclopropyl]methyl}-5-(pyrrolidin-1-ylcarbonyl)-5,6,7,8-tetrahydro[1,2,4]triazolo[4,3-a]pyridin-3(2H)-one

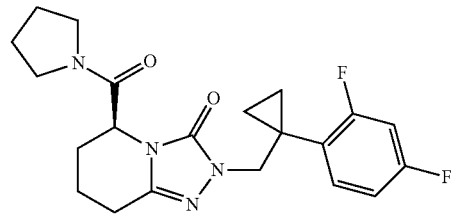 [SMILES: O=C([C@@H]1CCCc2nn(CC3(c4ccc(F)cc4F)CC3)c(=O)n21)N1CCCC1]

(5S)-2-{[1-(2,4-Difluorophenyl)cyclopropyl]methyl}-3-oxo-2,3,5,6,7,8-hexahydro[1,2,4]triazolo[4,3-a]pyridine-5-carboxylic acid (78.0 mg, 223 µmol), N,N-diisopropylethylamine (120 µl, 670 µmol), HBTU (110 mg, 290 µmol), pyrrolidine (22 µl, 270 µmol). Stirring at room temperature overnight. After purification, 9.80 mg (11% of theory) of the title compound were obtained.

LC-MS (Method 3): R$_t$=1.53 min; MS (ESIpos): m/z=403 [M+H]

$^1$H-NMR (400 MHz, DMSO-d6) δ [ppm]: −0.149 (0.71), 0.146 (0.71), 0.705 (1.90), 0.730 (7.14), 0.761 (8.00), 0.786 (2.29), 0.968 (1.24), 1.001 (16.00), 1.036 (0.90), 1.237 (0.71), 1.676 (5.05), 1.684 (5.29), 1.695 (4.43), 1.707 (2.24), 1.732 (1.52), 1.749 (5.90), 1.766 (10.43), 1.783 (8.14), 1.800 (2.48), 1.865 (2.33), 1.881 (6.90), 1.898 (8.90), 1.915 (6.19), 1.939 (6.10), 1.953 (5.67), 1.975 (2.43), 1.990 (1.90), 2.073 (5.00), 2.327 (1.29), 2.367 (1.00), 2.418 (1.19), 2.435 (1.48), 2.459 (3.52), 2.574 (1.67), 2.586 (2.48), 2.670 (1.43), 2.710 (1.10), 3.196 (1.29), 3.213 (2.71), 3.225 (3.05), 3.242 (5.24), 3.259 (2.57), 3.281 (3.24), 3.345 (2.14), 3.388 (1.76), 3.405 (3.52), 3.412 (2.76), 3.430 (4.52), 3.447 (2.05), 3.533 (2.05), 3.550 (4.19), 3.566 (2.48), 3.574 (3.24), 3.600 (7.00), 3.636 (9.14), 3.813 (8.90), 3.849 (6.48), 4.598 (3.76), 4.612 (5.62), 4.622 (3.81), 6.883 (1.90), 6.889 (2.10), 6.904 (4.05), 6.910 (4.43), 6.925 (2.33), 6.932 (2.43), 7.087 (2.14), 7.094 (2.33), 7.116 (3.86), 7.137 (3.90), 7.144 (2.67), 7.156 (5.05), 7.173 (4.71), 7.195 (2.19).

Example 531

(5S)-5-(Pyrrolidin-1-ylcarbonyl)-2-{[5-(trifluoromethyl)pyridin-2-yl]methyl}-5,6,7,8-tetrahydro[1,2,4]triazolo[4,3-a]pyridin-3(2H)-one

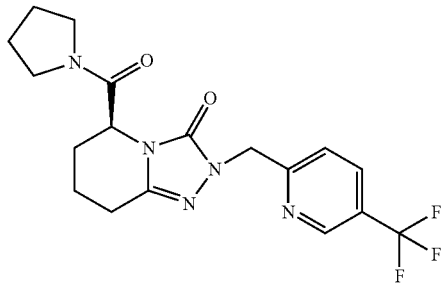 [SMILES: O=C([C@@H]1CCCc2nn(Cc3ccc(C(F)(F)F)cn3)c(=O)n21)N1CCCC1]

(5S)-3-Oxo-2-{[5-(trifluoromethyl)pyridin-2-yl]methyl}-2,3,5,6,7,8-hexahydro[1,2,4]triazolo[4,3-a]pyridine-5-carboxylic acid (60.0 mg, 175 µmol), triethylamine (73 µl, 530 µmol), HATU (86.6 mg, 228 µmol), pyrrolidine (15.0 mg, 210 µmol). Stirring at room temperature overnight. After purification, 51.6 mg (74% of theory) of the title compound were obtained.

LC-MS (Method 3): $R_t$=1.23 min; MS (ESIpos): m/z=396 [M+H]

$^1$H-NMR (400 MHz, DMSO-d6) δ [ppm]: −0.008 (2.08), 0.008 (1.90), 1.154 (3.17), 1.172 (6.53), 1.190 (3.27), 1.689 (0.90), 1.702 (1.25), 1.713 (1.69), 1.725 (2.58), 1.738 (3.07), 1.748 (2.44), 1.756 (2.05), 1.774 (4.73), 1.792 (7.66), 1.809 (5.78), 1.826 (1.71), 1.894 (1.71), 1.909 (6.12), 1.927 (5.83), 1.944 (3.53), 1.961 (1.02), 1.977 (0.83), 1.989 (0.80), 2.002 (1.29), 2.013 (2.31), 2.026 (2.61), 2.038 (1.76), 2.053 (1.85), 2.063 (1.34), 2.070 (1.25), 2.078 (1.22), 2.089 (0.73), 2.104 (0.42), 2.328 (0.69), 2.367 (0.47), 2.523 (3.17), 2.565 (2.44), 2.574 (2.24), 2.589 (1.92), 2.600 (1.83), 2.612 (3.36), 2.624 (1.90), 2.642 (0.85), 2.654 (1.29), 2.666 (1.14), 2.710 (0.56), 2.866 (1.29), 3.008 (1.19), 3.026 (3.44), 3.044 (3.36), 3.062 (1.12), 3.235 (1.08), 3.252 (2.19), 3.265 (2.12), 3.282 (3.95), 3.328 (3.27), 3.347 (4.14), 3.359 (1.61), 3.364 (2.17), 3.376 (2.29), 3.394 (1.03), 3.449 (1.15), 3.467 (2.46), 3.475 (1.83), 3.485 (1.49), 3.492 (3.15), 3.509 (1.42), 3.598 (1.47), 3.615 (2.86), 3.623 (1.51), 3.632 (1.69), 3.640 (2.25), 3.656 (1.05), 4.760 (2.66), 4.769 (2.95), 4.775 (3.56), 4.784 (2.64), 5.026 (16.00), 7.194 (0.95), 7.383 (4.80), 7.404 (5.03), 8.207 (3.02), 8.212 (3.10), 8.228 (2.95), 8.233 (2.97), 8.929 (4.64).

Example 532

(5S)-5-[(3,3-Difluoroazetidin-1-yl)carbonyl]-2-[(5-methoxypyridin-2-yl)methyl]-5,6,7,8-tetrahydro[1,2,4]triazolo[4,3-a]pyridin-3(2H)-one

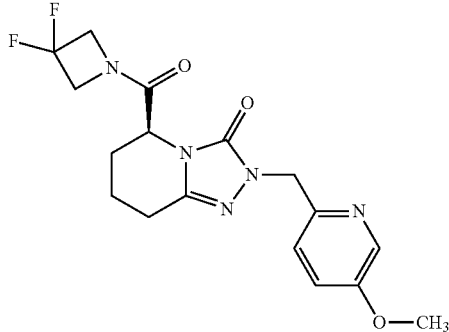 [SMILES: COc1ccc(Cn2nc3n(c2=O)[C@H](C(=O)N2CC(F)(F)C2)CCC3)nc1]

(5S)-2-[(5-Methoxypyridin-2-yl)methyl]-3-oxo-2,3,5,6,7,8-hexahydro[1,2,4]triazolo[4,3-a]pyridine-5-carboxylic acid (45.0 mg, 148 µmol), N,N-diisopropylethylamine (77 µl, 440 µmol), HBTU (72.9 mg, 192 µmol), 3,3-difluoroazetidine hydrochloride (23.0 mg, 177 µmol). Stirring at room temperature for 72 hours. After purification, 20.0 mg (36% of theory) of the title compound were obtained.

LC-MS (Method 4): $R_t$=0.54 min; MS (ESIpos): m/z=380 [M+H]$^+$ $^1$H-NMR (400 MHz, DMSO-d6) δ[ppm]: 1.710 (1.02), 1.725 (1.59), 1.739 (1.12), 1.755 (0.41), 1.977 (0.42), 1.989 (0.76), 2.001 (0.67), 2.043 (0.64), 2.061 (0.68), 2.078 (0.51), 2.524 (0.77), 2.608 (0.64), 3.809 (16.00), 4.331 (0.41), 4.361 (0.69), 4.384 (0.69), 4.414 (0.42), 4.582 (0.92), 4.597 (1.47), 4.610 (0.91), 4.730 (0.43), 4.760 (0.50), 4.838 (6.91), 4.876 (0.46), 7.128 (1.79), 7.149 (2.18), 7.352 (1.38), 7.360 (1.40), 7.374 (1.15), 7.381 (1.19), 8.205 (1.83), 8.212 (1.80).

Example 533

(5S)-2-{[3-Chloro-4-(trifluoromethyl)pyridin-2-yl]methyl}-5-(pyrrolidin-1-ylcarbonyl)-5,6,7,8-tetrahydro[1,2,4]triazolo[4,3-a]pyridin-3(2H)-one

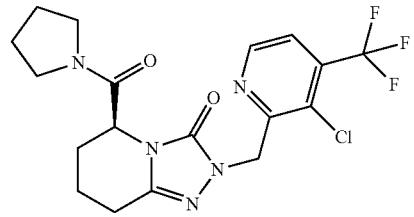 [SMILES: O=C([C@@H]1CCCc2nn(Cc3nccc(C(F)(F)F)c3Cl)c(=O)n21)N1CCCC1]

(5S)-2-{[3-Chloro-4-(trifluoromethyl)pyridin-2-yl]methyl}-3-oxo-2,3,5,6,7,8-hexahydro[1,2,4]triazolo[4,3-a]pyridine-5-carboxylic acid (53.0 mg, 141 µmol), triethylamine (59 µl, 420 µmol), HATU (69.5 mg, 183 µmol), pyrrolidine (14 µl, 170 µmol). Stirring at room temperature overnight. After purification, 40.0 mg (66% of theory) of the title compound were obtained.

LC-MS (Method 4): $R_t$=0.74 min; MS (ESIpos): m/z=430 [M+H]$^+$ $^1$H-NMR (400 MHz, DMSO-d6) δ[ppm]: −0.150 (0.42), −0.008 (3.83), 0.008 (3.11), 0.146 (0.41), 1.171 (0.73), 1.189 (0.45), 1.271 (0.69), 1.289 (0.69), 1.353 (3.47), 1.371 (3.53), 1.677 (1.03), 1.691 (2.06), 1.701 (5.00), 1.714 (6.44), 1.732 (4.67), 1.744 (2.31), 1.753 (1.98), 1.771 (6.88), 1.788 (11.86), 1.806 (9.09), 1.822 (2.66), 1.891 (2.78), 1.908 (8.33), 1.924 (10.44), 1.941 (6.73), 1.958 (3.14), 1.972 (2.09), 1.983 (3.64), 1.994 (3.30), 2.010 (1.77), 2.025 (2.72), 2.039 (2.05), 2.047 (2.56), 2.061 (2.41), 2.082 (1.11), 2.097 (0.59), 2.327 (0.67), 2.366 (0.64), 2.519 (5.92), 2.560 (3.36), 2.569 (3.11), 2.581 (6.08), 2.594 (3.08), 2.611 (1.28), 2.623 (2.17), 2.636 (0.92), 2.669 (0.75), 2.674 (0.58), 2.710 (0.66), 3.229 (1.62), 3.246 (3.50), 3.259 (3.55), 3.276 (6.45), 3.293 (4.66), 3.339 (6.78), 3.351 (2.56), 3.356 (3.48), 3.368 (3.94), 3.386 (1.69), 3.442 (1.84), 3.459 (3.97), 3.466 (2.95), 3.476 (2.39), 3.484 (5.08), 3.501 (2.19), 3.596 (2.28), 3.613 (5.03), 3.621 (2.52), 3.630 (2.78), 3.638 (3.70), 3.653 (2.63), 3.740 (7.44), 3.902 (4.11), 3.921 (0.52), 4.024 (0.61), 4.042 (0.59), 4.099 (0.61), 4.200 (0.53), 4.216 (0.50), 4.738 (4.37), 4.747 (5.06), 4.754 (5.78), 4.763 (4.33), 5.093 (4.67), 5.133 (16.00), 5.161 (15.97), 5.201 (4.61), 7.843 (9.97), 7.855 (10.39), 8.738 (8.03), 8.750 (7.84).

Example 534

(5S)-5-[(3-Fluoroazetidin-1-yl)carbonyl]-2-[(1-methyl-1H-pyrazolo[3,4-b]pyridin-3-yl)methyl]-5,6,7,8-tetrahydro[1,2,4]triazolo[4,3-a]pyridin-3(2H)-one

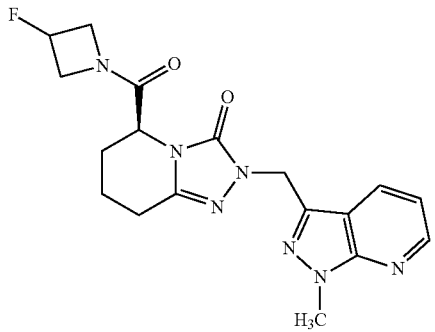 [SMILES: Cn1nc(Cn2nc3n(c2=O)[C@H](C(=O)N2CC(F)C2)CCC3)c2cccnc21]

(5S)-2-[(1-Methyl-1H-pyrazolo[3,4-b]pyridin-3-yl)methyl]-3-oxo-2,3,5,6,7,8-hexahydro[1,2,4]triazolo[4,3-a]pyridine-5-carboxylic acid (38.0 mg, 116 µmol), N,N-diisopropylethylamine (60 µl, 350 µmol), HBTU (57.1 mg, 150 µmol), 3-fluoroazetidine hydrochloride (1:1) (15.5 mg, 139 µmol). Stirring at room temperature overnight. After purification, 24.7 mg (100% purity, 55% of theory) of the title compound were obtained.

LC-MS (Method 3): $R_t$=0.93 min; MS (ESIpos): m/z=386 [M+H]

$^1$H-NMR (400 MHz, DMSO-d6) δ [ppm]: -0.008 (4.40), 0.008 (2.66), 1.677 (1.65), 1.935 (0.83), 2.004 (0.72), 2.327 (0.63), 2.366 (0.74), 2.523 (4.40), 2.562 (1.52), 2.578 (0.60), 2.592 (0.76), 2.665 (0.63), 2.669 (0.72), 2.709 (0.83), 3.931 (0.56), 3.963 (0.60), 4.007 (1.07), 4.025 (16.00), 4.231 (0.51), 4.260 (0.69), 4.287 (0.60), 4.316 (0.51), 4.541 (1.41), 4.553 (2.10), 4.566 (1.39), 5.116 (6.39), 7.190 (1.01), 7.196 (1.14), 7.204 (1.34), 7.216 (1.07), 8.156 (1.72), 8.177 (1.59), 8.543 (2.21), 8.547 (2.23), 8.554 (2.21), 8.558 (2.01).

Example 535

(5S)-5-(Pyrrolidin-1-ylcarbonyl)-2-{[5-(trifluoromethyl)pyridin-3-yl]methyl}-5,6,7,8-tetrahydro[1,2,4]triazolo[4,3-a]pyridin-3(2H)-one

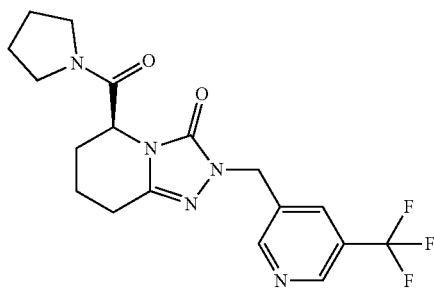 [SMILES: O=C([C@@H]1CCCc2nn(Cc3cncc(C(F)(F)F)c3)c(=O)n21)N1CCCC1]

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic acid (35.4 mg, 103 µmol), triethylamine (43 µl, 310 µmol), HATU (59.0 mg, 155 µmol), pyrrolidine (13 µl, 160 µmol). Stirring at room temperature overnight. After purification, 16.7 mg (41% of theory) of the title compound were obtained.

LC-MS (Method 3): $R_t$=1.20 min; MS (ESIpos): m/z=396 [M+H]

$^1$H-NMR (400 MHz, DMSO-d6) δ [ppm]: -0.149 (0.71), -0.008 (6.63), 0.008 (5.76), 0.146 (0.68), 1.681 (1.20), 1.722 (2.27), 1.739 (2.24), 1.756 (2.05), 1.773 (3.94), 1.791 (6.63), 1.808 (5.19), 1.824 (1.51), 1.893 (1.49), 1.909 (4.48), 1.926 (5.64), 1.943 (3.35), 1.961 (1.04), 2.013 (2.69), 2.036 (1.46), 2.056 (1.20), 2.327 (1.49), 2.366 (0.85), 2.567 (2.19), 2.581 (1.86), 2.597 (1.65), 2.608 (2.93), 2.620 (1.75), 2.650 (1.23), 2.669 (1.53), 2.710 (0.80), 3.228 (1.18), 3.245 (2.27), 3.257 (2.27), 3.274 (3.54), 3.292 (1.94), 3.340 (5.12), 3.358 (2.17), 3.370 (2.17), 3.388 (1.04), 3.437 (1.01), 3.454 (2.15), 3.461 (1.65), 3.479 (2.81), 3.496 (1.16), 3.593 (1.20), 3.610 (2.57), 3.627 (1.49), 3.635 (2.01), 3.652 (1.01), 4.754 (2.38), 4.763 (2.67), 4.769 (3.12), 4.778 (2.34), 5.012 (16.00), 8.063 (5.22), 8.737 (5.29), 8.912 (4.96).

Example 536

(5S)-5-[(3,3-Difluoropyrrolidin-1-yl)carbonyl]-2-[(6-fluoropyridin-3-yl)methyl]-5,6,7,8-tetrahydro[1,2,4]triazolo[4,3-a]pyridin-3(2H)-one

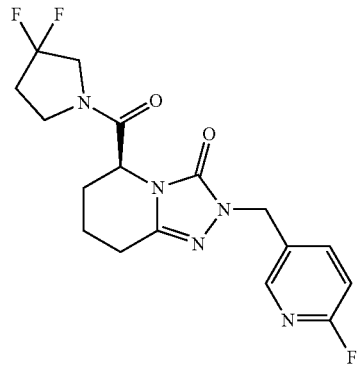 [SMILES: O=C([C@@H]1CCCc2nn(Cc3ccc(F)nc3)c(=O)n21)N1CCC(F)(F)C1]

(5S)-2-[(6-Fluoropyridin-3-yl)methyl]-3-oxo-2,3,5,6,7,8-hexahydro[1,2,4]triazolo[4,3-a]pyridine-5-carboxylic acid (60.0 mg, 205 µmol), N,N-diisopropylethylamine (110 µl, 620 µmol), HBTU (101 mg, 267 µmol), 3,3-difluoropyrrolidine hydrochloride (35.4 mg, 246 µmol). Stirring at room temperature overnight. After purification, 43.3 mg (55% of theory) of the title compound were obtained.

LC-MS (Method 3): $R_t$=1.05 min; MS (ESIpos): m/z=382 [M+H]$^+$ $^1$H-NMR (400 MHz, DMSO-d6) δ [ppm]: -0.149 (0.48), -0.008 (5.78), 0.008 (3.49), 0.146 (0.48), 1.700 (1.48), 1.713 (1.68), 1.725 (1.91), 1.915 (0.89), 1.981 (1.88), 1.992 (1.52), 2.005 (1.58), 2.021 (1.68), 2.049 (1.27), 2.058 (1.32), 2.064 (1.38), 2.073 (3.23), 2.085 (0.96), 2.093 (0.96), 2.100 (0.82), 2.327 (0.71), 2.366 (1.04), 2.381 (1.12), 2.411 (1.37), 2.433 (1.33), 2.519 (5.01), 2.524 (4.66), 2.567 (3.46), 2.576 (3.26), 2.591 (3.81), 2.607 (3.64), 2.619 (1.71), 2.635 (0.71), 2.650 (1.07), 2.665 (0.89), 2.669 (0.87), 2.690 (2.78), 2.710 (0.69), 3.539 (1.68), 3.558 (2.41), 3.571 (1.32), 3.578 (1.27), 3.639 (0.44), 3.673 (1.38), 3.706 (1.63), 3.742 (1.35), 3.774 (2.11), 3.791 (1.29), 3.799 (1.17), 3.809 (2.09), 3.817 (1.76), 3.835 (0.81), 3.844 (0.69), 3.895 (0.77), 3.914 (1.61), 3.933 (0.91), 3.940 (1.10), 3.958 (0.53), 3.973 (0.51), 4.002 (1.02), 4.014 (0.56), 4.029 (0.71), 4.043 (0.89), 4.071 (0.54), 4.149

(0.63), 4.181 (0.89), 4.205 (0.92), 4.760 (1.40), 4.775 (1.75), 4.785 (1.27), 4.835 (1.40), 4.845 (1.61), 4.850 (1.81), 4.860 (1.43), 4.908 (16.00), 4.942 (0.46), 4.949 (0.44), 6.519 (1.88), 7.226 (3.00), 7.237 (3.08), 7.248 (3.35), 7.260 (3.20), 7.698 (1.93), 7.706 (1.99), 7.720 (3.54), 7.728 (3.59), 7.742 (1.73), 7.750 (1.76), 8.512 (5.68), 8.520 (5.44).

Example 537

(5S)-5-[(3,3-Difluoroazetidin-1-yl)carbonyl]-2-[(6-fluoropyridin-3-yl)methyl]-5,6,7,8-tetrahydro[1,2,4]triazolo[4,3-a]pyridin-3(2H)-one

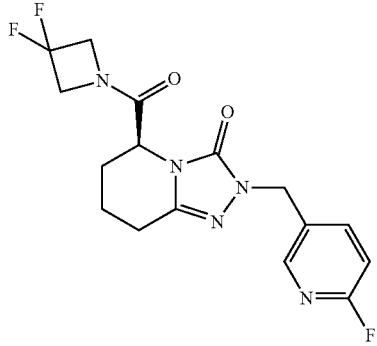 [SMILES: O=C([C@@H]1CCCc2nn(Cc3ccc(F)nc3)c(=O)n21)N1CC(F)(F)C1]

(5S)-2-[(6-Fluoropyridin-3-yl)methyl]-3-oxo-2,3,5,6,7,8-hexahydro[1,2,4]triazolo[4,3-a]pyridine-5-carboxylic acid (60.0 mg, 205 µmol), N,N-diisopropylethylamine (110 µl, 620 µmol), HBTU (101 mg, 267 µmol), 3,3-difluoroazetidine hydrochloride (31.9 mg, 246 µmol). Stirring at room temperature for 72 hours. After purification, 41.5 mg (55% of theory) of the title compound were obtained.

LC-MS (Method 3): $R_t$=1.20 min; MS (ESIpos): m/z=368 [M+H]$^+$ $^1$H-NMR (400 MHz, DMSO-d6) δ[ppm]: –0.008 (1.07), 1.716 (2.85), 1.730 (4.22), 1.745 (2.96), 1.759 (1.15), 1.961 (0.99), 1.974 (1.04), 1.985 (1.17), 1.997 (1.96), 2.009 (1.75), 2.021 (0.75), 2.034 (0.84), 2.050 (1.58), 2.070 (1.74), 2.085 (1.40), 2.103 (0.84), 2.560 (1.95), 2.618 (1.73), 2.632 (0.58), 2.647 (0.96), 2.661 (0.43), 4.333 (1.13), 4.363 (1.88), 4.385 (1.88), 4.416 (1.14), 4.597 (2.54), 4.612 (3.97), 4.624 (2.50), 4.705 (0.40), 4.734 (1.19), 4.763 (1.35), 4.794 (0.66), 4.816 (0.68), 4.847 (1.36), 4.877 (1.28), 4.918 (16.00), 7.251 (2.70), 7.262 (2.75), 7.272 (3.02), 7.283 (2.90), 7.699 (1.82), 7.706 (1.90), 7.721 (3.45), 7.728 (3.55), 7.742 (1.69), 7.750 (1.72), 8.507 (4.62), 8.514 (4.60).

Example 538

(5S)-2-[(6-Methoxypyridin-3-yl)methyl]-5-(pyrrolidin-1-ylcarbonyl)-5,6,7,8-tetrahydro[1,2,4]triazolo[4,3-a]pyridin-3(2H)-one

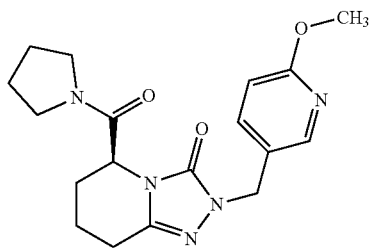 [SMILES: COc1ccc(Cn2nc3n(c2=O)[C@H](C(=O)N2CCCC2)CCC3)cn1]

(5S)-2-[(6-Methoxypyridin-3-yl)methyl]-3-oxo-2,3,5,6,7,8-hexahydro[1,2,4]triazolo[4,3-a]pyridine-5-carboxylic acid (467 mg, 1.53 mmol), N,N-diisopropylethylamine (800 µl, 4.6 mmol), HBTU (757 mg, 2.00 mmol), pyrrolidine (150 µl, 1.8 mmol). Stirring at room temperature overnight. After purification, 40.0 mg (95% purity, 7% of theory) of the title compound were obtained.

LC-MS (Method 4): $R_t$=0.58 min; MS (ESIpos): m/z=358 [M+H]

$^1$H-NMR (400 MHz, DMSO-d6) δ [ppm]: –0.149 (0.63), –0.008 (5.45), 0.008 (4.76), 0.146 (0.63), 1.706 (0.80), 1.772 (1.20), 1.789 (2.01), 1.806 (1.61), 1.823 (0.52), 1.891 (0.69), 1.908 (1.55), 1.924 (1.89), 1.941 (1.20), 1.960 (0.57), 1.971 (0.80), 2.017 (0.52), 2.327 (1.38), 2.366 (1.20), 2.523 (5.10), 2.570 (0.92), 2.583 (1.15), 2.625 (0.46), 2.665 (1.20), 2.670 (1.55), 2.710 (1.26), 2.847 (0.46), 2.865 (0.92), 3.239 (0.69), 3.251 (0.75), 3.269 (1.38), 3.340 (2.24), 3.358 (1.09), 3.369 (0.86), 3.387 (0.52), 3.449 (0.75), 3.474 (0.97), 3.491 (0.46), 3.589 (0.40), 3.606 (0.86), 3.630 (0.69), 3.826 (16.00), 4.711 (0.75), 4.726 (1.03), 4.736 (0.75), 4.760 (5.79), 6.782 (1.72), 6.803 (1.89), 7.552 (1.15), 7.558 (1.15), 7.573 (1.09), 7.580 (1.15), 8.050 (1.43), 8.056 (1.38).

Example 539

(5S)-5-{[(3S)-3-Fluoropyrrolidin-1-yl]carbonyl}-2-{[2-(trifluoromethyl)quinolin-4-yl]methyl}-5,6,7,8-tetrahydro[1,2,4]triazolo[4,3-a]pyridin-3(2H)-one

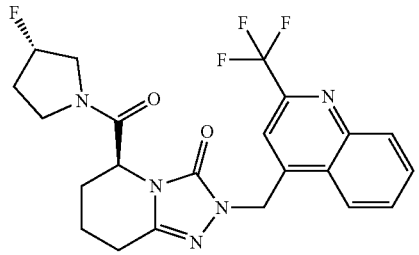 [SMILES: O=C([C@@H]1CCCc2nn(Cc3cc(C(F)(F)F)nc4ccccc34)c(=O)n21)N1CC[C@H](F)C1]

(5S)-3-Oxo-2-{[2-(trifluoromethyl)quinolin-4-yl]methyl}-2,3,5,6,7,8-hexahydro[1,2,4]triazolo[4,3-a]pyridine-5-carboxylic acid (38.5 mg, 98.1 µmol), N,N-diisopropylethylamine (51 µl, 290 µmol), HBTU (48.4 mg, 128 µmol), (3S)-3-fluoropyrrolidine hydrochloride (14.8 mg, 118 µmol). Stirring at room temperature overnight. After purification, 30.9 mg (68% of theory) of the title compound were obtained.

LC-MS (Method 3): $R_t$=1.54 min; MS (ESIpos): m/z=464 [M+H]$^+$ $^1$H-NMR (400 MHz, DMSO-d6) δ[ppm]: –0.149 (1.85), –0.008 (16.00), 0.008 (13.66), 0.146 (1.95), 1.732 (2.93), 2.006 (3.22), 2.327 (4.10), 2.366 (2.34), 2.609 (4.59), 2.670 (4.39), 2.709 (2.24), 3.527 (2.54), 3.554 (2.54), 3.608 (2.54), 3.651 (2.34), 3.748 (2.44), 3.777 (11.02), 3.862 (1.76), 3.960 (1.46), 4.328 (6.54), 4.759 (1.46), 4.810 (1.66), 4.890 (1.76), 5.267 (1.95), 5.408 (3.22), 5.459 (6.15), 5.481 (6.54), 5.522 (2.15), 5.800 (2.24), 6.282 (3.22), 7.741 (7.32), 7.748 (5.56), 7.756 (4.68), 7.847 (4.39), 7.865 (3.02), 7.946 (4.10), 7.966 (6.15), 7.983 (3.90), 8.214 (8.39), 8.235 (7.02), 8.371 (4.10), 8.387 (3.90).

Example 540

(5S)-5-[(3-Fluoroazetidin-1-yl)carbonyl]-2-{[3-(trifluoromethyl)-1,2,4-oxadiazol-5-yl]methyl}-5,6,7,8-tetrahydro[1,2,4]triazolo[4,3-a]pyridin-3(2H)-one

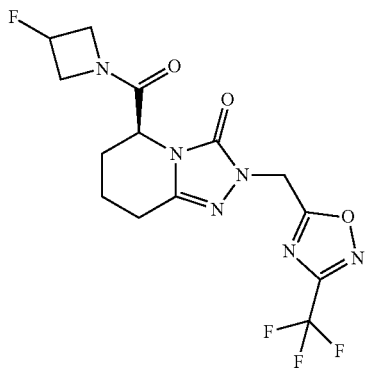 [SMILES: O=C([C@@H]1CCCc2nn(Cc3nc(C(F)(F)F)no3)c(=O)n21)N1CC(F)C1]

(5S)-3-Oxo-2-{[3-(trifluoromethyl)-1,2,4-oxadiazol-5-yl]methyl}-2,3,5,6,7,8-hexahydro[1,2,4]triazolo[4,3-a]pyridine-5-carboxylic acid (85.0 mg, 82% purity, 209 µmol), N,N-diisopropylethylamine (110 µl, 630 µmol), HBTU (103 mg, 272 µmol), 3-fluoroazetidine hydrochloride (28.0 mg, 251 µmol). Stirring at room temperature overnight. After purification, 53.0 mg (65% of theory) of the title compound were obtained.

LC-MS (Method 3): $R_t$=1.24 min; MS (ESIpos): m/z=391 [M+H]$^+$ $^1$H-NMR (400 MHz, DMSO-d6) δ[ppm]: −0.149 (0.75), −0.008 (6.77), 0.008 (6.05), 0.146 (0.77), 1.706 (3.09), 1.728 (5.31), 1.738 (4.23), 1.954 (2.13), 1.967 (2.27), 1.976 (1.96), 2.041 (1.91), 2.053 (2.07), 2.073 (4.26), 2.328 (0.77), 2.366 (0.88), 2.524 (2.07), 2.558 (1.66), 2.586 (2.85), 2.602 (3.73), 2.620 (4.67), 2.632 (6.49), 2.646 (3.21), 2.661 (1.38), 2.675 (2.40), 2.689 (0.88), 2.710 (1.02), 3.926 (1.22), 3.989 (1.44), 4.013 (1.02), 4.160 (0.72), 4.175 (0.80), 4.191 (0.69), 4.215 (1.46), 4.230 (1.46), 4.245 (1.35), 4.261 (1.55), 4.280 (1.52), 4.299 (1.46), 4.338 (0.88), 4.363 (1.60), 4.393 (1.13), 4.428 (0.83), 4.452 (1.02), 4.510 (0.69), 4.527 (0.88), 4.567 (3.76), 4.580 (6.36), 4.593 (3.65), 4.622 (0.80), 4.639 (0.83), 4.676 (0.80), 4.690 (0.80), 4.717 (0.61), 5.349 (1.05), 5.421 (16.00), 5.476 (0.88), 5.492 (1.13), 5.546 (1.05).

Example 541

(5S)-5-[(3,3-Difluoropyrrolidin-1-yl)carbonyl]-2-{[5-(trifluoromethyl)-1,3,4-oxadiazol-2-yl]methyl}-5,6,7,8-tetrahydro[1,2,4]triazolo[4,3-a]pyridin-3(2H)-one

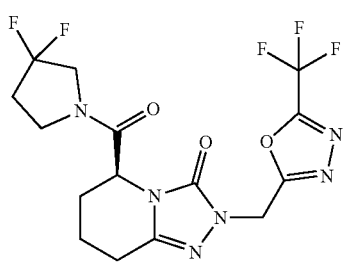 [SMILES: O=C([C@@H]1CCCc2nn(Cc3nnc(C(F)(F)F)o3)c(=O)n21)N1CCC(F)(F)C1]

(5S)-3-Oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylic acid (100 mg, 80% purity, 240 µmol), N,N-diisopropylethylamine (130 µl, 720 µmol), HBTU (118 mg, 312 µmol), 3,3-difluoropyrrolidine hydrochloride (1:1) (41.4 mg, 288 µmol). Stirring at room temperature for 72 hours. After purification, 18.0 mg (18% of theory) of the title compound were obtained.

LC-MS (Method 3): $R_t$=1.27 min; MS (ESIpos): m/z=423 [M+H]$^+$ $^1$H-NMR (400 MHz, DMSO-d6) δ [ppm]: −0.149 (0.80), −0.008 (6.76), 0.008 (5.45), 0.146 (0.80), 1.257 (1.67), 1.726 (2.55), 1.919 (3.78), 1.979 (4.73), 2.015 (2.04), 2.059 (1.75), 2.076 (1.67), 2.327 (2.47), 2.366 (3.05), 2.380 (1.45), 2.409 (1.75), 2.430 (1.82), 2.577 (4.22), 2.591 (4.15), 2.601 (3.93), 2.616 (4.29), 2.631 (4.29), 2.670 (3.56), 2.710 (2.91), 3.529 (3.35), 3.548 (5.38), 3.567 (2.55), 3.669 (1.96), 3.703 (2.11), 3.730 (1.38), 3.765 (2.76), 3.794 (2.62), 3.811 (2.33), 3.827 (2.11), 3.888 (0.95), 3.908 (2.25), 3.934 (1.60), 3.954 (0.80), 3.993 (1.38), 4.035 (1.16), 4.064 (0.73), 4.148 (0.87), 4.173 (1.16), 4.205 (1.24), 4.769 (1.82), 4.785 (2.40), 4.795 (1.82), 4.844 (1.89), 4.860 (2.18), 4.869 (1.67), 5.253 (1.82), 5.295 (15.13), 5.305 (16.00), 5.347 (3.56), 6.510 (0.65).

Example 542

(5S)-5-[(3-Fluoroazetidin-1-yl)carbonyl]-2-{[5-(trifluoromethyl)-1,3,4-oxadiazol-2-yl]methyl}-5,6,7,8-tetrahydro[1,2,4]triazolo[4,3-a]pyridin-3(2H)-one

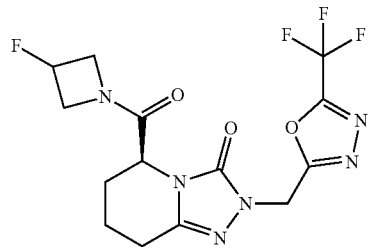 [SMILES: O=C([C@@H]1CCCc2nn(Cc3nnc(C(F)(F)F)o3)c(=O)n21)N1CC(F)C1]

(5S)-3-Oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylic acid (100 mg, 80% purity, 240 µmol), N,N-diisopropylethylamine (130 µl, 720 µmol), HBTU (118 mg, 312 µmol), 3-fluoroazetidine hydrochloride (32.1 mg, 288 µmol). Stirring at room temperature overnight. After purification, 21.0 mg (22% of theory) of the title compound were obtained.

LC-MS (Method 3): $R_t$=1.06 min; MS (ESIpos): m/z=391 [M+H]$^+$ $^1$H-NMR (400 MHz, DMSO-d6) δ [ppm]: −0.149 (0.62), −0.008 (4.52), 0.008 (4.71), 0.146 (0.67), 1.406 (0.72), 1.722 (5.05), 1.962 (2.21), 2.040 (2.07), 2.328 (1.83), 2.366 (1.68), 2.523 (4.85), 2.571 (2.88), 2.588 (3.70), 2.609 (4.56), 2.624 (5.67), 2.636 (3.08), 2.652 (1.25), 2.665 (3.22), 2.710 (1.73), 3.826 (0.82), 3.938 (1.35), 3.987 (1.25), 4.175 (0.77), 4.211 (1.39), 4.228 (1.44), 4.258 (1.44), 4.295 (1.44), 4.334 (0.86), 4.360 (1.35), 4.392 (1.06), 4.430 (0.91), 4.459 (1.01), 4.520 (0.82), 4.555 (3.51), 4.567 (5.67), 4.579 (3.51), 4.642 (0.82), 5.260 (1.01), 5.302 (16.00), 5.311 (7.06), 5.353 (1.44), 5.404 (0.96), 5.493 (1.01), 5.546 (0.96), 6.510 (1.20).

Example 543

(5S)-5-{[(3R,4S)-3,4-Difluoropyrrolidin-1-yl]carbonyl}-2-{[5-(trifluoromethyl)-1,3,4-oxadiazol-2-yl]methyl}-5,6,7,8-tetrahydro[1,2,4]triazolo[4,3-a]pyridin-3(2H)-one

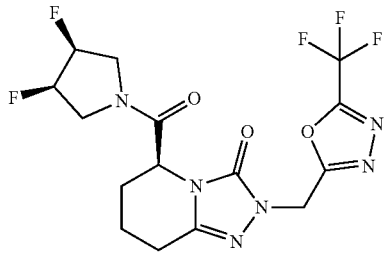 [SMILES: O=C([C@@H]1CCCc2nn(Cc3nnc(C(F)(F)F)o3)c(=O)n21)N1C[C@@H](F)[C@@H](F)C1]

(5S)-3-Oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylic acid (100 mg, 80% purity, 240 µmol), N,N-diisopropylethylamine (130 µl, 720 µmol), HBTU (118 mg, 312 µmol), (3R,4S)-3,4-difluoropyrrolidine hydrochloride (1:1) (41.4 mg, 288 µmol). Stirring at room temperature overnight. After purification, 30.0 mg (30% of theory) of the title compound were obtained.

LC-MS (Method 3): $R_t$=1.23 min; MS (ESIpos): m/z=423 [M+H]$^+$ $^1$H-NMR (400 MHz, DMSO-d6) δ[ppm]: −0.149 (1.10), −0.008 (9.43), 0.008 (8.71), 0.146 (1.14), 1.413 (1.14), 1.684 (1.95), 1.738 (2.57), 1.750 (2.19), 1.919 (1.05), 1.979 (2.00), 2.001 (1.76), 2.045 (1.48), 2.062 (1.86), 2.071 (1.86), 2.080 (1.52), 2.097 (1.43), 2.327 (1.71), 2.366 (1.57), 2.522 (4.71), 2.571 (2.86), 2.584 (2.81), 2.595 (3.67), 2.604 (2.71), 2.618 (3.81), 2.630 (4.95), 2.643 (2.95), 2.670 (3.29), 2.710 (1.86), 3.455 (0.90), 3.489 (1.62), 3.513 (1.67), 3.535 (1.48), 3.545 (1.67), 3.557 (1.10), 3.567 (1.24), 3.614 (1.19), 3.627 (1.43), 3.647 (1.05), 3.670 (1.52), 3.684 (2.14), 3.703 (1.62), 3.717 (1.71), 3.741 (1.52), 3.752 (1.52), 3.772 (1.29), 3.826 (1.00), 3.870 (1.29), 3.927 (1.19), 3.941 (1.48), 3.957 (0.90), 3.977 (1.29), 3.991 (1.38), 4.007 (0.90), 4.021 (0.81), 4.127 (0.81), 4.142 (1.00), 4.155 (0.86), 4.169 (1.62), 4.183 (1.05), 4.196 (0.95), 4.211 (0.90), 4.806 (4.05), 4.816 (4.81), 4.821 (5.48), 4.831 (4.14), 5.253 (3.14), 5.276 (1.67), 5.294 (16.00), 5.309 (10.86), 5.340 (1.86), 5.351 (3.05), 5.365 (1.24), 5.376 (1.67), 5.388 (1.71), 5.407 (1.43), 5.473 (1.24), 5.481 (1.24).

Example 544

(5S)-5-{[(3S)-3-Fluoropyrrolidin-1-yl]carbonyl}-2-{[5-(trifluoromethyl)-1,3,4-oxadiazol-2-yl]methyl}-5,6,7,8-tetrahydro[1,2,4]triazolo[4,3-a]pyridin-3(2H)-one

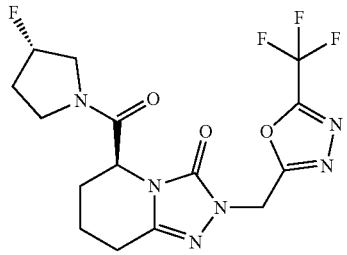 [SMILES: O=C([C@@H]1CCCc2nn(Cc3nnc(C(F)(F)F)o3)c(=O)n21)N1CC[C@H](F)C1]

(5S)-3-Oxo-2-{[5-(trifluoromethyl)-1,3,4-oxadiazol-2-yl]methyl}-2,3,5,6,7,8-hexahydro[1,2,4]triazolo[4,3-a]pyridine-5-carboxylic acid (100 mg, 80% purity, 240 µmol), N,N-diisopropylethylamine (130 µl, 720 µmol), HBTU (118 mg, 312 µmol), (3S)-3-fluoropyrrolidine hydrochloride (36.2 mg, 288 µmol). Stirring at room temperature overnight. After purification, 18.9 mg (19% of theory) of the title compound were obtained.

LC-MS (Method 3): $R_t$=1.16 min; MS (ESIpos): m/z=405 [M+H]$^+$ $^1$H-NMR (400 MHz, DMSO-d6) δ [ppm]: −0.150 (4.07), 0.145 (4.07), 1.740 (4.95), 1.910 (1.45), 2.029 (2.04), 2.110 (3.49), 2.268 (1.75), 2.327 (8.44), 2.366 (9.89), 2.584 (4.95), 2.631 (5.53), 2.669 (10.18), 2.709 (11.35), 3.395 (2.62), 3.501 (1.75), 3.651 (3.20), 3.722 (2.91), 3.745 (3.49), 3.770 (2.91), 3.857 (4.07), 4.715 (2.33), 4.774 (3.20), 5.246 (2.91), 5.288 (16.00), 5.297 (9.02), 5.303 (10.47), 5.346 (1.75), 5.388 (2.91), 5.512 (1.75).

Example 545

(5S)-2-{[5-Chloro-6-(trifluoromethyl)pyridin-3-yl]methyl}-5-(pyrrolidin-1-ylcarbonyl)-5,6,7,8-tetrahydro[1,2,4]triazolo[4,3-a]pyridin-3(2H)-one

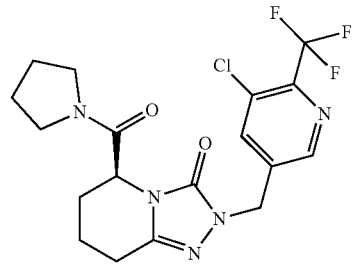 [SMILES: O=C([C@@H]1CCCc2nn(Cc3cnc(C(F)(F)F)c(Cl)c3)c(=O)n21)N1CCCC1]

(5S)-2-{[5-Chloro-6-(trifluoromethyl)pyridin-3-yl]methyl}-3-oxo-2,3,5,6,7,8-hexahydro[1,2,4]triazolo[4,3-a]pyridine-5-carboxylic acid (35.0 mg, 92.9 µmol), N,N-diisopropylethylamine (49 µl, 280 µmol), HBTU (45.8 mg, 121 µmol), pyrrolidine (9.3 µl, 110 µmol). Stirring at room temperature for 72 hours. After purification, 25.0 mg (63% of theory) of the title compound were obtained.

LC-MS (Method 3): $R_t$=1.49 min; MS (ESIpos): m/z=430 [M+H]$^+$ $^1$H-NMR (400 MHz, DMSO-d6) δ [ppm]: −0.008 (3.06), 0.008 (2.74), 1.243 (2.70), 1.259 (3.33), 1.647 (1.15), 1.667 (1.47), 1.681 (1.59), 1.691 (1.31), 1.708 (1.15), 1.734 (2.34), 1.744 (2.18), 1.757 (2.50), 1.775 (5.76), 1.792 (9.37), 1.809 (7.07), 1.826 (1.99), 1.894 (1.91), 1.910 (5.56), 1.927 (6.87), 1.943 (4.17), 1.960 (1.23), 1.979 (0.91), 1.992 (0.87), 2.006 (1.67), 2.019 (3.69), 2.028 (4.01), 2.044 (2.18), 2.056 (1.63), 2.063 (1.67), 2.071 (1.59), 2.328 (0.91), 2.366 (0.67), 2.523 (4.09), 2.564 (3.10), 2.575 (2.78), 2.590 (2.30), 2.605 (2.26), 2.616 (3.93), 2.628 (2.34), 2.646 (1.07), 2.660 (1.67), 2.670 (1.79), 2.690 (0.71), 2.710 (0.79), 2.885 (3.65), 3.033 (1.91), 3.235 (1.23), 3.251 (2.54), 3.264 (2.66), 3.281 (4.96), 3.330 (3.73), 3.348 (4.96), 3.360 (1.99), 3.366 (2.62), 3.378 (2.90), 3.396 (1.67), 3.403 (2.02), 3.442 (1.43), 3.459 (3.06), 3.466 (2.26), 3.476 (1.87), 3.484 (3.89), 3.501 (1.75), 3.593 (1.95), 3.610 (3.77), 3.618 (2.14), 3.627 (2.38), 3.635 (3.06), 3.652 (1.43), 4.760 (3.30), 4.769 (3.73), 4.775 (4.53), 4.784 (3.18), 4.992 (0.60), 5.035 (16.00), 5.078 (0.56), 8.067 (6.83), 8.537 (6.95), 8.541 (6.83).

Example 546

(5S)-5-[(3-Fluoroazetidin-1-yl)carbonyl]-2-(4-fluorobenzyl)-5,6,7,8-tetrahydro[1,2,4]triazolo[4,3-a]pyridin-3(2H)-one

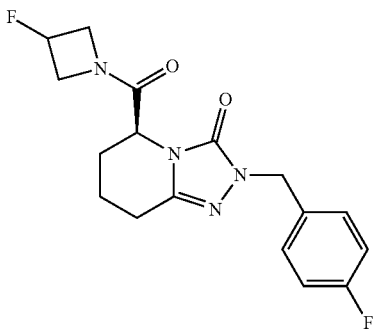 [SMILES: O=C([C@@H]1CCCc2nn(Cc3ccc(F)cc3)c(=O)n21)N1CC(F)C1]

(5S)-2-(4-Fluorobenzyl)-3-oxo-2,3,5,6,7,8-hexahydro[1,2,4]triazolo[4,3-a]pyridine-5-carboxylic acid (62.8 mg, 215 µmol), N,N-diisopropylethylamine (110 µl, 650 µmol), HBTU (106 mg, 280 µmol), 3-fluoroazetidine hydrochloride (1:1) (28.8 mg, 259 µmol). Stirring at room temperature overnight. After purification, 15.9 mg (21% of theory) of the title compound were obtained.

LC-MS (Method 4): $R_t$=0.65 min; MS (ESIpos): m/z=349 [M+H]$^+$ $^1$H-NMR (400 MHz, DMSO-d6) δ [ppm]: −0.150 (0.69), −0.008 (9.17), 0.008 (5.47), 0.146 (0.72), 1.175 (0.67), 1.706 (4.47), 1.908 (2.61), 1.947 (2.08), 1.988 (2.36), 2.010 (1.81), 2.022 (1.89), 2.072 (0.81), 2.327 (0.69), 2.366 (0.61), 2.571 (4.19), 2.585 (5.22), 2.598 (2.61), 2.613 (1.08), 2.627 (1.61), 2.640 (0.72), 2.669 (0.81), 2.709 (0.67), 3.894 (0.78), 3.927 (1.42), 3.954 (1.50), 3.987 (1.39), 4.020 (1.14), 4.152 (0.64), 4.166 (0.75), 4.182 (0.61), 4.222 (1.28), 4.236 (1.28), 4.252 (1.53), 4.264 (1.33), 4.288 (1.42), 4.321 (1.28), 4.346 (0.86), 4.392 (0.89), 4.429 (0.67), 4.455 (0.89), 4.496 (0.86), 4.525 (3.69), 4.538 (5.50), 4.551 (3.61), 4.590 (0.50), 4.633 (0.61), 4.648 (0.72), 4.684 (0.64), 4.697 (0.67), 4.798 (16.00), 5.351 (0.89), 5.404 (0.89), 5.494 (0.89), 5.547 (0.86), 7.140 (4.42), 7.161 (9.78), 7.184 (5.97), 7.263 (5.64), 7.277 (6.94), 7.295 (3.83).

Example 547

(5S,8RS)-2-[(5-Chloropyridin-2-yl)methyl]-5-{[(3S)-3-fluoropyrrolidin-1-yl]carbonyl}-8-hydroxy-5,6,7,8-tetrahydro[1,2,4]triazolo[4,3-a]pyridin-3(2H)-one (Diastereomer Mixture; 2 Isomers)

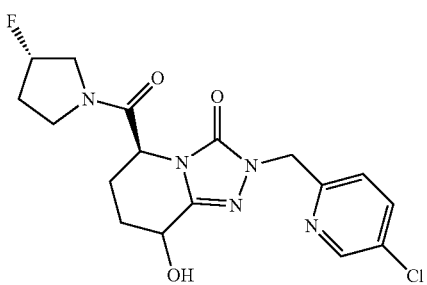 [SMILES: O=C([C@@H]1CCC(O)c2nn(Cc3ccc(Cl)cn3)c(=O)n21)N1CC[C@H](F)C1]

(5S)-2-[(5-Chloropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one (66.6 mg, 175 µmol) and cerium(IV) sulphate (350 mg, 1.05 mmol) were suspended in tert-butanol (230 µl) at room temperature. Subsequently, 1 N aqueous sulphuric acid (230 µl, 4.4 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. 40.4 mg (55% of theory) of the title compound were obtained.

LC-MS (Method 1): $R_t$=0.73 min; MS (ESIpos): m/z=396 [M+H]$^+$ $^1$H-NMR (400 MHz, DMSO-d6) δ[ppm]: −0.008 (3.50), 1.167 (0.78), 1.215 (0.80), 1.236 (1.14), 1.273 (0.68), 1.283 (0.48), 1.352 (0.59), 1.425 (0.57), 1.526 (0.41), 1.743 (1.70), 1.754 (2.02), 1.767 (2.20), 1.780 (2.30), 1.799 (1.41), 1.812 (1.70), 1.822 (2.02), 1.855 (1.40), 1.873 (0.98), 1.906 (1.16), 1.942 (1.08), 1.988 (0.74), 2.026 (0.56), 2.107 (1.89), 2.124 (1.73), 2.132 (1.74), 2.222 (1.05), 2.234 (1.05), 2.270 (1.43), 2.327 (0.99), 2.366 (1.04), 2.391 (1.34), 2.403 (1.29), 2.432 (0.84), 2.669 (0.72), 3.269 (0.74), 3.343 (0.69), 3.361 (0.68), 3.388 (0.77), 3.398 (0.71), 3.451 (0.53), 3.459 (0.60), 3.486 (0.83), 3.495 (0.78), 3.629 (1.85), 3.641 (2.63), 3.657 (2.17), 3.665 (2.21), 3.685 (1.68), 3.738 (1.68), 3.759 (1.83), 3.779 (1.65), 3.801 (1.05), 3.834 (0.50), 3.866 (2.24), 4.488 (0.63), 4.501 (0.59), 4.526 (3.47), 4.537 (3.85), 4.554 (0.99), 4.673 (0.62), 4.742 (1.35), 4.754 (1.28), 4.798 (1.71), 4.809 (1.65), 4.896 (0.56), 4.906 (0.72), 4.937 (2.42), 4.956 (16.00), 4.998 (0.56), 5.258 (1.44), 5.388 (2.08), 5.517 (1.20), 5.754 (6.83), 5.778 (4.87), 5.789 (5.77), 5.802 (1.23), 7.201 (3.74), 7.223 (3.98), 7.236 (1.17), 7.256 (1.19), 7.926 (4.56), 7.932 (4.63), 7.947 (4.21), 7.953 (4.26), 8.582 (4.62), 8.588 (4.12).

Example 548

(5S)-2-[(5-Chloropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (Diastereomer Mixture; 2 Isomers)

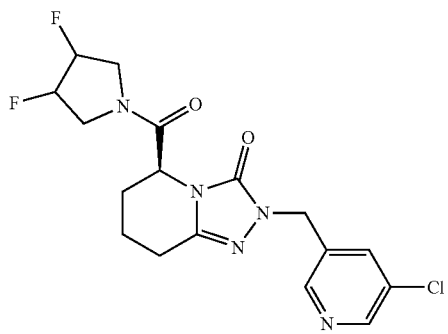 [SMILES: O=C([C@@H]1CCCc2nn(Cc3cncc(Cl)c3)c(=O)n21)N1CC(F)C(F)C1]

(5S)-2-[(5-Chloropyridin-3-yl)methyl]-3-oxo-2,3,5,6,7,8-hexahydro[1,2,4]triazolo[4,3-a]pyridine-5-carboxylic acid (162 mg, 525 µmol) was initially charged in THF (11 ml) at room temperature. Subsequently, HBTU (259 mg, 683 µmol) and N,N-diisopropylethylamine (460 µl, 2.6 mmol) were added. After stirring for 5 min, trans-3,4-difluoropyrrolidine hydrochloride (90.5 mg, 630 µmol) was added and the reaction mixture was stirred at room temperature overnight. HBTU (259 mg, 683 µmol) and N,N-diisopropylethylamine (460 µl, 2.6 mmol) were added again and the mixture was stirred at room temperature overnight. The reaction mixture was then admixed with saturated aqueous sodium hydrogencarbonate solution and extracted twice with ethyl acetate. The combined organic phases were washed with saturated aqueous sodium chloride solution, dried over sodium sulphate and filtered, and the filtrate was concentrated. The residue was purified via preparative HPLC (Method 12). The product-containing fractions were concentrated under reduced pressure, and 2.90 mg (1.4% of theory) of the title compound were obtained.

LC-MS (Method 3): $R_t$=1.09 min; MS (ESIpos): m/z=398 [M+H]$^+$ $^1$H-NMR (400 MHz, DMSO-d6) δ[ppm]: −0.149 (1.68), −0.008 (14.62), 0.008 (11.46), 0.146 (1.68), 1.146 (0.59), 1.735 (2.72), 1.936 (1.14), 2.000 (1.28), 2.073 (1.23), 2.327 (3.01), 2.366 (1.63), 2.564 (3.01), 2.579 (2.72), 2.590 (2.67), 2.604 (3.80), 2.617 (4.15), 2.629 (2.47), 2.670 (3.60), 2.710 (1.73), 3.570 (0.84), 3.637 (3.36), 3.674 (1.09), 3.712 (1.63), 3.733 (1.19), 3.757 (1.43), 3.822 (1.63), 3.860 (1.09), 3.940 (3.60), 4.014 (1.58), 4.138 (1.19), 4.171 (0.94), 4.203 (1.19), 4.236 (0.94), 4.771 (2.12), 4.780 (1.58), 4.916 (16.00), 5.309 (1.78), 5.444 (2.22), 5.537 (0.84), 7.760 (7.85), 8.425 (7.90), 8.564 (7.26), 8.570 (7.26).

Example 549

(5S)-2-[(5-Chloro-3-fluoropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (Diastereomer Mixture; 2 Isomers)

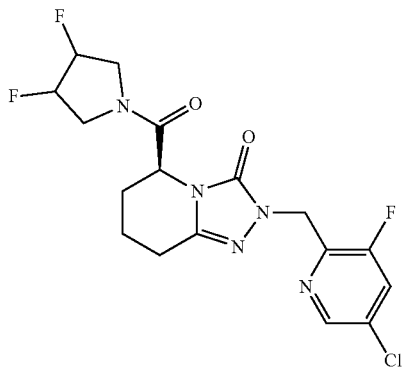 [SMILES: O=C([C@@H]1CCCc2nn(Cc3ncc(Cl)cc3F)c(=O)n21)N1CC(F)C(F)C1]

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (212 mg, 650 µmol) was initially charged in THF (14 ml) at room temperature. Subsequently, HBTU (320 mg, 845 µmol) and N,N-diisopropylethylamine (570 µl, 3.2 mmol) were added. After stirring for 5 min, trans-3,4-difluoropyrrolidine hydrochloride (112 mg, 780 µmol) was added and the reaction mixture was stirred at room temperature overnight. HBTU (320 mg, 845 µmol) and N,N-diisopropylethylamine (570 µl, 3.2 mmol) were added again and the mixture was stirred at room temperature overnight. The reaction mixture was then admixed with saturated aqueous sodium hydrogencarbonate solution and extracted twice with ethyl acetate. The combined organic phases were washed with saturated aqueous sodium chloride solution, dried over sodium sulphate and filtered, and the filtrate was concentrated. The residue was purified via preparative HPLC (Method 12). The product-containing fractions were concentrated under reduced pressure, and 26.5 mg (10% of theory) of the title compound were obtained.

LC-MS (Method 3): $R_t$=1.18 min; MS (ESIpos): m/z=416 [M+H]$^+$ $^1$H-NMR (400 MHz, DMSO-d6) δ[ppm]: −0.149 (2.07), −0.008 (16.00), 0.008 (12.99), 0.146 (1.88), 1.147 (0.75), 1.719 (6.31), 1.731 (4.52), 1.879 (1.41), 1.902 (1.98), 1.914 (1.79), 1.968 (1.79), 2.035 (1.51), 2.055 (1.88), 2.074 (2.35), 2.093 (2.45), 2.110 (1.88), 2.128 (1.13), 2.327 (4.14), 2.366 (2.07), 2.558 (9.13), 2.571 (9.13), 2.584 (4.80), 2.600 (2.07), 2.613 (3.01), 2.669 (4.99), 2.709 (2.45), 3.527 (1.32), 3.563 (1.60), 3.627 (6.12), 3.665 (1.88), 3.711 (4.24), 3.745 (2.45), 3.782 (1.69), 3.813 (3.01), 3.850 (2.35), 3.936 (5.84), 4.015 (3.67), 4.127 (1.88), 4.160 (1.60), 4.190 (1.98), 4.223 (1.69), 4.726 (2.73), 4.737 (3.48), 4.742 (3.67), 4.752 (2.92), 4.855 (2.73), 4.870 (3.58), 4.880 (2.64), 4.902 (4.42), 4.941 (10.82), 4.990 (10.82), 5.029 (4.24), 5.308 (2.73), 5.427 (3.86), 5.441 (3.58), 5.533 (1.51), 5.565 (1.41), 8.089 (6.59), 8.094 (7.25), 8.114 (7.06), 8.118 (7.44), 8.478 (8.19), 8.482 (8.38).

Example 550

(5S)-2-[(6-Chloropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (Diastereomer Mixture; 2 Isomers)

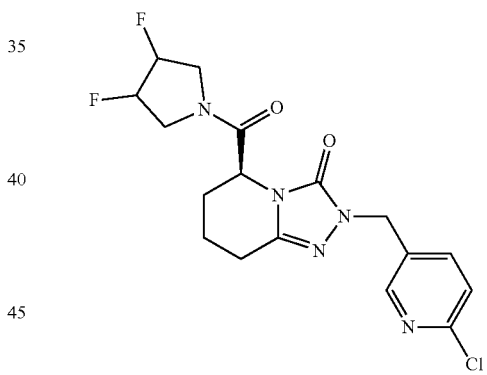

(5S)-2-[(6-Chloropyridin-3-yl)methyl]-3-oxo-2,3,5,6,7,8-hexahydro[1,2,4]triazolo[4,3-a]pyridine-5-carboxylic acid (200 mg, 649 µmol) was initially charged in THF (14 ml) at room temperature. Subsequently, HBTU (320 mg, 843 µmol) and N,N-diisopropylethylamine (570 µl, 3.2 mmol) were added. After stirring for 5 min, trans-3,4-difluoropyrrolidine hydrochloride (112 mg, 779 µmol) was added and the reaction mixture was stirred at room temperature overnight. The suspension was filtered and the filtrate was admixed with saturated aqueous sodium hydrogencarbonate solution and extracted twice with ethyl acetate. The aqueous phase was acidified with 1 N aqueous hydrochloric acid and extracted with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×40 mm; eluent: (acetonitrile/water with 0.1% formic acid) gradient). The product-containing fractions were concentrated under reduced pressure, and 71.5 mg (28% of theory) of the title compound were obtained.

LC-MS (Method 3): $R_t$=1.10 min; MS (ESIpos): m/z=398 [M+H]$^+$ $^1$H-NMR (400 MHz, DMSO-d6) δ [ppm]: −0.149 (0.57), −0.008 (4.53), 0.008 (5.49), 0.146 (0.57), 1.648 (0.77), 1.672 (0.75), 1.720 (2.21), 1.730 (2.59), 1.742 (2.35), 1.887 (0.75), 1.912 (0.77), 1.928 (0.99), 1.959 (0.50), 1.995 (1.10), 2.020 (0.70), 2.030 (0.70), 2.037 (0.68), 2.045 (0.79), 2.057 (0.75), 2.065 (0.88), 2.073 (1.22), 2.082 (0.95), 2.099 (1.10), 2.108 (1.02), 2.116 (0.83), 2.124 (0.84), 2.134 (0.72), 2.327 (0.79), 2.366 (0.75), 2.524 (3.00), 2.566 (2.71), 2.576 (2.64), 2.591 (3.79), 2.604 (4.17), 2.616 (2.26), 2.633 (0.83), 2.646 (1.29), 2.660 (0.77), 2.665 (0.74), 2.669 (0.88), 2.710 (0.74), 3.528 (0.65), 3.565 (0.90), 3.633 (3.32), 3.667 (1.08), 3.709 (1.83), 3.730 (1.33), 3.753 (1.42), 3.766 (0.63), 3.789 (1.08), 3.820 (1.85), 3.845 (0.77), 3.857 (1.15), 3.914 (0.65), 3.936 (3.36), 4.013 (1.96), 4.023 (1.35), 4.132 (1.02), 4.166 (0.88), 4.196 (1.06), 4.230 (0.83), 4.739 (1.67), 4.749 (2.03), 4.755 (2.15), 4.765 (1.63), 4.883 (16.00), 4.907 (1.53), 5.257 (0.41), 5.310 (1.56), 5.399 (0.84), 5.425 (1.87), 5.442 (1.99), 5.533 (0.75), 5.567 (0.74), 7.506 (6.29), 7.527 (7.96), 7.690 (4.02), 7.696 (4.04), 7.710 (3.34), 7.716 (3.29), 8.299 (5.30), 8.304 (5.14).

Example 551

(5S)-2-[(6-Chloropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (Isomer 1)

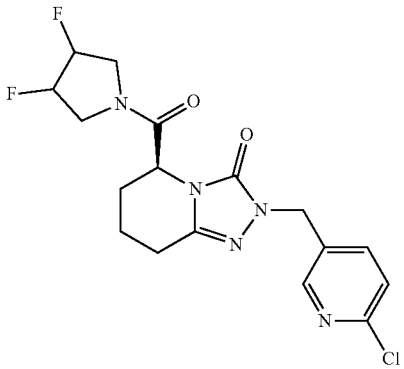 [SMILES: O=C([C@@H]1CCCc2nn(Cc3ccc(Cl)nc3)c(=O)n21)N1CC(F)C(F)C1]

(5S)-2-[(6-Chloropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (diastereomer mixture; 2 isomers) was separated by chiral preparative HPLC [sample preparation: 71.5 mg dissolved in 2 ml of ethanol and 2 ml of dichloromethane; injection volume: 0.3 ml; column: Daicel Chiralpak® IF 5 μm, 250×20 mm; eluent: n-heptane/ethanol 35:65; flow rate: 15 ml/min; temperature 25° C.; UV detection: 210 nm]. After the separation, 19.2 mg of isomer 1, which elutes first, and 20.3 mg of isomer 2, which elutes later, were isolated.

Isomer 1:

Analytical chiral HPLC: $R_t$=2.66 min, d.e.=99% [column: Daicel Chiralpak® IF-3 50×4.6 mm; eluent: n-heptane/ethanol 50:50; flow rate: 1 ml/min; UV detection: 220 nm].

LC-MS (Method 4): $R_t$=0.59 min; MS (ESIpos): m/z=398 [M+H]$^+$ $^1$H-NMR (400 MHz, DMSO-d6) δ[ppm]: −0.149 (0.77), −0.008 (5.90), 0.008 (6.28), 0.146 (0.70), 1.237 (0.41), 1.647 (0.98), 1.732 (1.32), 1.741 (1.34), 1.755 (1.01), 1.958 (0.70), 1.995 (1.68), 2.020 (1.08), 2.029 (1.03), 2.045 (1.15), 2.057 (1.10), 2.065 (1.20), 2.073 (1.08), 2.327 (1.39), 2.366 (0.91), 2.523 (4.61), 2.565 (2.30), 2.576 (2.25), 2.591 (2.95), 2.604 (3.05), 2.616 (1.80), 2.634 (0.72), 2.646 (1.01), 2.669 (1.61), 2.710 (1.03), 3.092 (1.49), 3.633 (4.37), 3.672 (0.67), 3.708 (2.37), 3.729 (1.63), 3.765 (0.41), 3.784 (1.13), 3.811 (0.86), 3.844 (1.10), 3.914 (0.84), 3.947 (1.10), 4.132 (1.54), 4.166 (1.34), 4.196 (1.63), 4.229 (1.25), 4.888 (16.00), 4.907 (2.42), 5.310 (1.15), 5.426 (1.82), 5.532 (1.13), 7.507 (4.56), 7.527 (5.83), 7.688 (3.24), 7.695 (3.33), 7.709 (2.69), 7.715 (2.81), 8.299 (3.72), 8.304 (3.79).

Example 552

(5S)-2-[(6-Chloropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (Isomer 2)

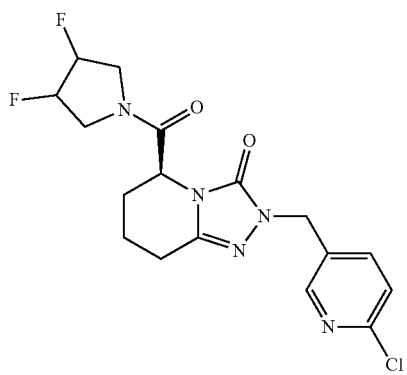 [SMILES: O=C([C@@H]1CCCc2nn(Cc3ccc(Cl)nc3)c(=O)n21)N1CC(F)C(F)C1]

(5S)-2-[(6-Chloropyridin-3-yl)methyl]-5-{[trans-3,4-difluoropyrrolidin-1-yl]carbonyl}-5,6,7,8-tetrahydro[1,2,4]triazolo[4,3-a]pyridin-3(2H)-one (diastereomer mixture; 2 isomers) was separated by chiral preparative HPLC [sample preparation: 71.5 mg dissolved in 2 ml of ethanol and 2 ml of dichloromethane; injection volume: 0.3 ml; column: Daicel Chiralpak® IF 5 μm, 250×20 mm; eluent: n-heptane/ethanol 35:65; flow rate: 15 ml/min; temperature 25° C.; UV detection: 210 nm]. After the separation, 19.2 mg of isomer 1, which elutes first, and 20.3 mg of isomer 2, which elutes later, were isolated.

Isomer 2:

Analytical chiral HPLC: $R_t$=3.85 min, d.e.=99% [column: Daicel Chiralpak® IF-3 50×4.6 mm; eluent: n-heptane/ethanol 50:50; flow rate: 1 ml/min; UV detection: 220 nm].

LC-MS (Method 4): $R_t$=0.60 min; MS (ESIpos): m/z=398 [M+H]$^+$ $^1$H-NMR (400 MHz, DMSO-d6) δ [ppm]: −0.149 (0.56), −0.008 (4.82), 0.008 (5.43), 0.146 (0.58), 1.236 (0.48), 1.719 (2.19), 1.730 (2.33), 1.742 (1.97), 1.889 (0.92), 1.928 (1.31), 2.098 (1.19), 2.108 (1.05), 2.117 (1.01), 2.124 (1.07), 2.134 (0.86), 2.327 (1.15), 2.366 (0.42), 2.567 (2.57), 2.575 (2.43), 2.590 (3.10), 2.604 (3.42), 2.617 (1.87), 2.633 (0.88), 2.646 (1.15), 2.669 (1.57), 2.710 (0.78), 3.092 (1.25), 3.528 (0.86), 3.565 (1.21), 3.630 (0.98), 3.666 (1.19), 3.701 (0.56), 3.733 (0.54), 3.753 (1.89), 3.789 (1.49), 3.821 (1.93), 3.857 (1.29), 3.935 (4.26), 3.979 (0.44), 4.014 (2.75), 4.739 (2.19), 4.749 (2.77), 4.754 (2.93), 4.764 (2.23), 4.883 (16.00), 5.309 (1.19), 5.443 (1.95), 5.568 (1.07), 7.506 (4.64), 7.527 (5.95), 7.690 (3.22), 7.696 (3.46), 7.711 (2.75), 7.717 (2.87), 8.298 (4.10), 8.304 (4.34).

Example 553

(5S)-5-{[trans-3,4-Difluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (Isomer 1)

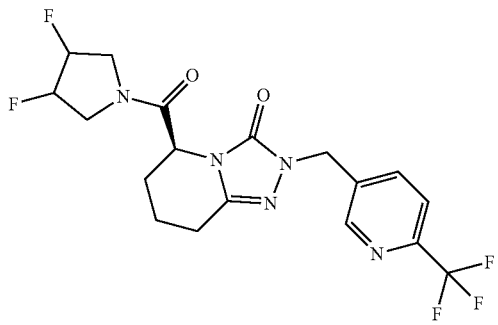 [SMILES: O=C([C@@H]1CCCc2nn(Cc3ccc(C(F)(F)F)nc3)c(=O)n21)N1CC(F)C(F)C1]

(5S)-3-Oxo-2-{[6-(trifluoromethyl)pyridin-3-yl]methyl}-2,3,5,6,7,8-hexahydro[1,2,4]triazolo[4,3-a]pyridine-5-carboxylic acid (389 mg, 88% purity, 1.00 mmol) was initially charged in THF (21 ml) at room temperature. Subsequently, HBTU (493 mg, 1.30 mmol) and N,N-diisopropylethylamine (870 µl, 5.0 mmol) were added. After stirring for 5 min, trans-3,4-difluoropyrrolidine hydrochloride (172 mg, 1.20 mmol) was added and the reaction mixture was stirred at room temperature overnight. The suspension was filtered and the filtrate was admixed with saturated aqueous sodium hydrogencarbonate solution and extracted twice with ethyl acetate. The aqueous phase was acidified with 1 N aqueous hydrochloric acid and extracted with ethyl acetate. The combined organic phases were washed with saturated aqueous sodium chloride solution, dried over sodium sulphate and filtered, and the filtrate was concentrated. The residue was purified via preparative HPLC (Chromatorex C18, 10 µm, 125 mm×40 mm; eluent: (acetonitrile/water with 0.1% formic acid) gradient). The product-containing fractions were concentrated under reduced pressure, and 128.5 mg (84% purity, 25% of theory) of a diastereomer mixture (2 isomers) were obtained.

The diastereomer mixture (2 isomers) was separated by chiral preparative HPLC [sample preparation: 128.5 mg dissolved in 2 ml of ethanol and 2 ml of n-heptane; injection volume: 0.4 ml; column: Daicel Chiralpak® IC 5 µm, 250×20 mm; eluent: n-heptane/ethanol 50:50; flow rate: 15 ml/min; temperature 40° C.; UV detection: 220 nm]. After the separation, 43 mg of isomer 1, which elutes first, and 45.5 mg of isomer 2, which elutes later, were isolated.

Isomer 1:

Analytical chiral HPLC: $R_t$=1.74 min, d.e.=99% [column: Daicel Chiralpak® IC-3 3 µm, 50×4.6 mm; eluent: n-heptane/ethanol 50:50; flow rate: 1 ml/min; UV detection: 220 nm].

LC-MS (Method 3): $R_t$=1.25 min; MS (ESIpos): m/z=432 [M+H]$^+$ $^1$H-NMR (400 MHz, DMSO-d6) δ [ppm]: −0.149 (1.66), −0.008 (13.19), 0.008 (12.41), 0.146 (1.56), 1.196 (0.61), 1.213 (1.39), 1.231 (0.78), 1.651 (1.02), 1.751 (1.36), 2.008 (1.69), 2.031 (1.39), 2.055 (1.15), 2.075 (1.15), 2.327 (1.36), 2.366 (0.68), 2.560 (2.37), 2.575 (2.10), 2.586 (1.97), 2.600 (2.88), 2.613 (2.98), 2.626 (1.73), 2.669 (1.97), 2.710 (0.68), 3.638 (4.24), 3.677 (0.75), 3.713 (2.37), 3.735 (1.56), 3.773 (0.44), 3.815 (0.92), 3.849 (1.05), 3.919 (0.81), 3.952 (1.12), 4.139 (1.59), 4.172 (1.39), 4.202 (1.76), 4.235 (1.25), 4.901 (2.14), 4.916 (2.95), 4.926 (2.10), 4.972 (0.58), 5.013 (9.08), 5.058 (0.58), 5.312 (1.15), 5.427 (1.93), 5.533 (1.19), 7.911 (14.88), 7.915 (16.00), 8.644 (5.59).

Example 554

(5S)-5-{[trans-3,4-Difluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (Isomer 2)

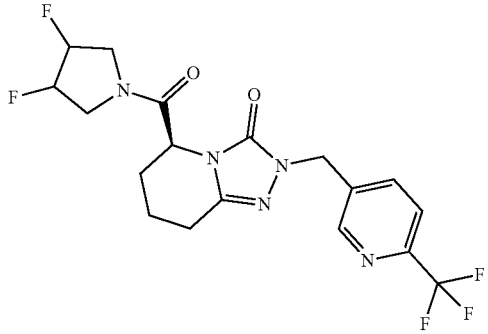 [SMILES: O=C([C@@H]1CCCc2nn(Cc3ccc(C(F)(F)F)nc3)c(=O)n21)N1CC(F)C(F)C1]

(5S)-5-{[trans-3,4-Difluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (diastereomer mixture; 2 isomers) was separated by chiral preparative HPLC [sample preparation: 128.5 mg dissolved in 2 ml of ethanol and 2 ml of n-heptane; injection volume: 0.4 ml; column: Daicel Chiralpak® IC 5 µm, 250×20 mm; eluent: n-heptane/ethanol 50:50; flow rate: 15 ml/min; temperature 40° C.; UV detection: 220 nm]. After the separation, 43 mg of isomer 1, which elutes first, and 45.5 mg of isomer 2, which elutes later, were isolated.

Isomer 2:

Analytical chiral HPLC: $R_t$=2.51 min, d.e.=99% [column: Daicel Chiralpak® IC-3 3 µm, 50×4.6 mm; eluent: n-heptane/ethanol 50:50; flow rate: 1 ml/min; UV detection: 220 nm].

LC-MS (Method 8): $R_t$=1.80 min; MS (ESIpos): m/z=432 [M+H]$^+$ $^1$H-NMR (400 MHz, DMSO-d6) δ [ppm]: −0.149 (1.97), −0.008 (16.00), 0.146 (1.86), 1.726 (1.43), 1.740 (1.55), 1.939 (0.89), 2.108 (0.81), 2.328 (1.66), 2.366 (1.28), 2.576 (1.70), 2.584 (1.55), 2.600 (2.09), 2.613 (2.28), 2.626 (1.20), 2.670 (2.01), 2.710 (1.28), 3.534 (0.58), 3.570 (0.85), 3.635 (0.58), 3.671 (0.81), 3.759 (1.20), 3.796 (0.89), 3.827 (1.24), 3.864 (0.85), 3.940 (2.90), 4.019 (1.97), 4.755 (1.43), 4.770 (1.97), 4.780 (1.51), 5.010 (9.89), 5.310 (0.85), 5.446 (1.35), 5.574 (0.73), 7.912 (8.81), 7.915 (10.01), 8.645 (3.29).

Example 555

(5S)-2-[(5-Chloropyridin-2-yl)methyl]-8,8-difluoro-5-{[(3S)-3-fluoropyrrolidin-1-yl]carbonyl}-5,6,7,8-tetrahydro[1,2,4]triazolo[4,3-a]pyridin-3(2H)-one

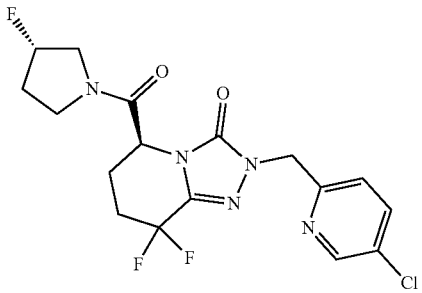 [SMILES: O=C([C@@H]1CCC(F)(F)c2nn(Cc3ccc(Cl)cn3)c(=O)n21)N1CC[C@H](F)C1]

Under argon: (5S)-2-[(5-chloropyridin-2-yl)methyl]-5-{[(3S)-3-fluoropyrrolidin-1-yl]carbonyl}-6,7-dihydro[1,2,4]triazolo[4,3-a]pyridine-3,8(2H,5H)-dione (20.7 mg, 71% purity, 37.2 µmol) was initially charged in dichloromethane (3.8 ml) at room temperature. Subsequently, diethylaminosulphur trifluoride (15 µl, 110 µmol) was added and the mixture was stirred at 40° C. overnight. The reaction mixture was admixed with water and saturated aqueous sodium hydrogencarbonate solution. The aqueous phase was extracted four times with dichloromethane and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 7.00 mg (44% of theory) of the title compound were obtained.

LC-MS (Method 4): $R_t$=0.77 min; MS (ESIpos): m/z=416 [M+H]$^+$ $^1$H-NMR (400 MHz, DMSO-d6) δ[ppm]: −0.149 (1.99), −0.008 (15.19), 0.008 (16.00), 0.146 (1.74), 1.072 (1.31), 1.126 (1.25), 1.146 (1.31), 1.178 (1.56), 1.190 (1.43), 1.364 (0.93), 2.151 (1.06), 2.327 (5.23), 2.366 (3.24), 2.669 (4.86), 2.710 (2.24), 3.526 (0.75), 3.645 (1.43), 3.673 (1.31), 3.700 (1.12), 3.777 (1.18), 3.889 (1.25), 4.896 (0.81), 4.960 (1.12), 5.064 (5.60), 5.078 (3.55), 5.276 (0.75), 5.406 (1.00), 7.282 (2.93), 7.303 (3.18), 7.951 (2.18), 7.957 (2.37), 7.972 (2.24), 7.979 (2.30), 8.440 (0.68), 8.590 (2.49).

Example 556

(5S)-2-[(5-chloro-3-fluoropyridin-2-yl)methyl]-8,8-difluoro-5-{[(3S)-3-fluoropyrrolidin-1-yl]carbonyl}-5,6,7,8-tetrahydro[1,2,4]triazolo[4,3-a]pyridin-3(2H)-one

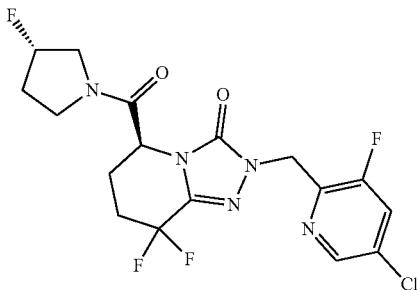 [SMILES: O=C([C@@H]1CCC(F)(F)c2nn(Cc3ncc(Cl)cc3F)c(=O)n21)N1CC[C@H](F)C1]

Under argon: (5S)-2-[(5-chloro-3-fluoropyridin-2-yl)methyl]-5-{[(3S)-3-fluoropyrrolidin-1-yl]carbonyl}-6,7-dihydro[1,2,4]triazolo[4,3-a]pyridine-3,8(2H,5H)-dione (25.8 mg, 79% purity, 49.4 µmol) was initially charged in dichloromethane (5.1 ml) at room temperature. Subsequently, diethylaminosulphur trifluoride (20 µl, 150 µmol) was added and the mixture was stirred at 40° C. overnight. Diethylaminosulphur trifluoride (8 µl, 59 µmol) was added again and the mixture was stirred at 40° C. for 2 hours. The reaction mixture was admixed with water and saturated aqueous sodium hydrogencarbonate solution. The aqueous phase was extracted four times with dichloromethane and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 9.10 mg (42% of theory) of the title compound were obtained.

LC-MS (Method 3): $R_t$=1.42 min; MS (ESIpos): m/z=434 [M+H]$^+$ $^1$H-NMR (400 MHz, DMSO-d6) δ [ppm]: −0.149 (1.72), −0.008 (14.25), 0.008 (16.00), 0.146 (1.68), 1.148 (0.62), 2.144 (1.21), 2.249 (1.13), 2.327 (4.24), 2.366 (2.01), 2.670 (3.11), 2.710 (1.46), 3.416 (0.95), 3.477 (0.69), 3.520 (0.77), 3.611 (0.62), 3.637 (1.86), 3.668 (1.72), 3.698 (1.28), 3.745 (0.99), 3.767 (1.53), 3.790 (1.21), 3.813 (0.88), 3.881 (1.79), 4.893 (1.13), 4.952 (1.46), 5.084 (1.02), 5.123 (4.05), 5.144 (2.63), 5.183 (0.73), 5.273 (0.99), 5.403 (1.21), 5.528 (0.66), 8.136 (2.30), 8.155 (2.23), 8.160 (2.37), 8.501 (3.14).

Example 557

(5S)-2-[(6-Chloropyridin-3-yl)methyl]-5-[(3,3-difluoropyrrolidin-1-yl)carbonyl]-8,8-difluoro-5,6,7,8-tetrahydro[1,2,4]triazolo[4,3-a]pyridin-3(2H)-one

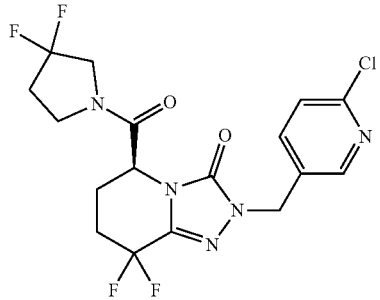 [SMILES: O=C([C@@H]1CCC(F)(F)c2nn(Cc3ccc(Cl)nc3)c(=O)n21)N1CCC(F)(F)C1]

(5S)-2-[(6-Chloropyridin-3-yl)methyl]-5-[(3,3-difluoropyrrolidin-1-yl)carbonyl]-6,7-dihydro[1,2,4]triazolo[4,3-a]pyridine-3,8(2H,5H)-dione (47.3 mg, 115 µmol) was initially charged under argon in dichloromethane (12 ml, 180 mmol) at room temperature. Subsequently, diethylaminosulphur trifluoride (46 µl, 340 µmol) was added and the mixture was stirred at 40° C. overnight. The reaction mixture was admixed with water and saturated aqueous sodium hydrogencarbonate solution. The aqueous phase was extracted four times with dichloromethane and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 40 mg (80% of theory) of the title compound were obtained.

LC-MS (Method 3): $R_t$=1.50 min; MS (ESIpos): m/z=434 [M+H]$^+$ $^1$H-NMR (400 MHz, DMSO-d6) δ [ppm]: −0.149 (0.94), −0.008 (7.23), 0.008 (7.13), 0.146 (0.88), 2.281 (2.47), 2.323 (2.09), 2.327 (2.43), 2.366 (1.18), 2.416 (1.59), 2.442 (1.91), 2.463 (1.83), 2.523 (3.29), 2.564 (1.51), 2.580 (1.04), 2.597 (0.78), 2.617 (0.48), 2.665 (1.00), 2.670 (1.26), 2.710 (0.58), 3.556 (1.97), 3.575 (3.31), 3.595 (1.83), 3.696 (1.10), 3.729 (1.30), 3.760 (0.88), 3.791 (1.35), 3.824 (1.73), 3.843 (1.32), 3.862 (0.80), 3.881 (0.72), 3.900 (1.41), 3.919 (0.78), 3.927 (0.84), 4.042 (0.78), 4.070 (0.52), 4.085 (0.72), 4.112 (0.42), 4.146 (0.50), 4.181 (0.66), 4.204 (0.70), 4.936 (1.59), 5.008 (1.59), 5.045 (16.00), 7.539 (4.94), 7.560 (6.24), 7.724 (3.37), 7.730 (3.41), 7.744 (2.75), 7.750 (2.87), 8.334 (4.38), 8.340 (4.38).

Example 558

(5S)-5-{[(3R,4S)-3,4-Difluoropyrrolidin-1-yl]carbonyl}-2-{[6-(trifluoromethyl)pyridin-3-yl]methyl}-5,6-dihydro[1,2,4]triazolo[4,3-a]pyridin-3(2H)-one

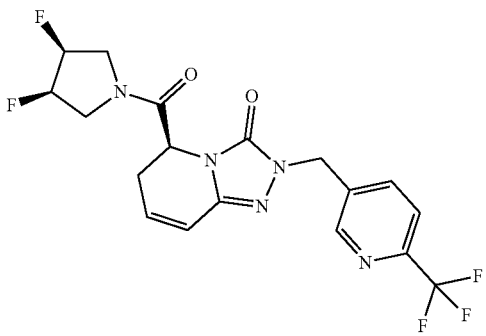 [SMILES: O=C([C@@H]1CC=Cc2nn(Cc3ccc(C(F)(F)F)nc3)c(=O)n21)N1C[C@@H](F)[C@@H](F)C1]

(5S)-5-{[(3R,4S)-3,4-Difluoropyrrolidin-1-yl]carbonyl}-2-{[6-(trifluoromethyl)pyridin-3-yl]methyl}-5,6,7,8-tetrahydro[1,2,4]triazolo[4,3-a]pyridin-3(2H)-one (176 mg, 408 μmol) and cerium(IV) sulphate (542 mg, 1.63 mmol) were suspended in tert-butanol (1.7 ml) at room temperature. Subsequently, 1 N aqueous sulphuric acid (1.7 ml, 32 mmol) was added and the reaction mixture was stirred at 70° C. for 72 hours. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. The residue was purified via preparative HPLC (Chromatorex C18, 10 μm, 125 mm×40 mm; eluent: (acetonitrile/water with 0.1% formic acid) gradient). The product-containing fractions were concentrated under reduced pressure and the residue was separated by chiral preparative HPLC [sample preparation: 34.8 mg dissolved in 3 ml of ethanol; injection volume: 0.3 ml; column: Daicel Chiralcel OX-H 5 μm, 250×20 mm; eluent: n-heptane/ethanol 25:75; flow rate: 15 ml/min; temperature 50° C.; UV detection: 220 nm]. The product-containing fractions were concentrated under reduced pressure, and 11.0 mg (6% of theory) of the title compound were obtained.

LC-MS (Method 1): $R_t$=1.01 min; MS (ESIpos): m/z=430 [M+H]$^+$ $^1$H-NMR (400 MHz, DMSO-d6) δ[ppm]: −0.149 (1.91), −0.008 (15.66), 0.008 (16.00), 0.146 (1.78), 0.996 (3.35), 1.006 (3.56), 1.131 (1.98), 1.150 (3.83), 1.168 (2.05), 1.223 (2.53), 1.240 (2.74), 1.347 (2.87), 1.475 (2.74), 2.287 (7.04), 2.327 (2.46), 2.366 (1.85), 2.670 (2.94), 2.709 (1.85), 2.906 (1.37), 3.777 (0.62), 3.896 (0.62), 3.950 (0.55), 5.087 (4.85), 5.108 (0.82), 6.250 (0.62), 6.316 (1.23), 7.923 (4.72), 8.661 (2.05).

Example 559

(5S)-5-{[(3S)-3-Fluoropyrrolidin-1-yl]carbonyl}-2-{[2-(trifluoromethyl)pyrimidin-5-yl]methyl}-5,6,7,8-tetrahydro[1,2,4]triazolo[4,3-a]pyridin-3(2H)-one

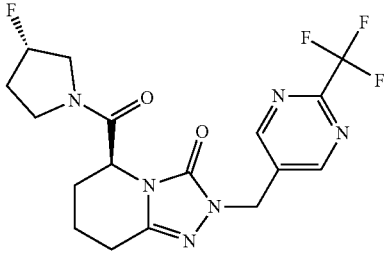 [SMILES: O=C([C@@H]1CCCc2nn(Cc3cnc(C(F)(F)F)nc3)c(=O)n21)N1CC[C@H](F)C1]

(5S)-3-Oxo-2-{[2-(trifluoromethyl)pyrimidin-5-yl]methyl}-2,3,5,6,7,8-hexahydro[1,2,4]triazolo[4,3-a]pyridine-5-carboxylic acid (22.0 mg, 79% purity, 26.9 μmol) was initially charged in THF (2.0 ml) at room temperature. Subsequently, HBTU (31.6 mg, 83.3 μmol) and N,N-diisopropylethylamine (56 μl, 320 μmol) were added. After stirring for 5 min, (3S)-3-fluoropyrrolidine hydrochloride (9.66 mg, 76.9 mol) was added and the reaction mixture was stirred at room temperature overnight. The reaction mixture was admixed with ethyl acetate. The organic phase was washed with saturated sodium hydrogencarbonate solution, water and saturated aqueous sodium chloride solution, dried over sodium sulphate and filtered, and the filtrate was concentrated. The residue was purified via preparative HPLC (Method 14). The product-containing fractions were concentrated under reduced pressure, and 0.4 mg (3.6% of theory) of the title compound were obtained.

LC-MS (Method 3): $R_t$=1.30 min; MS (ESIpos): m/z=415 [M+H]$^+$ $^1$H-NMR (400 MHz, DMSO-d6) δ[ppm]: −0.149 (2.02), −0.008 (16.00), 0.008 (15.11), 0.146 (1.96), 1.148 (0.70), 1.405 (2.85), 2.327 (4.62), 2.366 (1.96), 2.393 (5.82), 2.670 (4.17), 2.710 (1.71), 3.876 (0.57), 9.068 (1.90).

Example 560

(5S)-2-[(3-Chloro-5-fluoropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

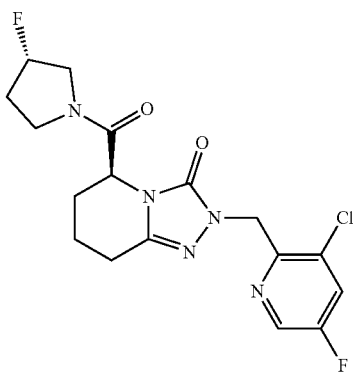 [SMILES: O=C([C@@H]1CCCc2nn(Cc3ncc(F)cc3Cl)c(=O)n21)N1CC[C@H](F)C1]

(5S)-2-[(3-Chloro-5-fluoropyridin-2-yl)methyl]-3-oxo-2,3,5,6,7,8-hexahydro[1,2,4]triazolo[4,3-a]pyridine-5-carboxylic acid (150 mg, 459 μmol) was initially charged in THF (37 μl), and HBTU (226 mg, 597 μmol) and N,N-diisopropylethylamine (240 μl, 1.4 mmol) were subsequently added. After stirring at room temperature for 15 min, (3S)-3-fluoropyrrolidine hydrochloride (63.4 mg, 505 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 42.7 mg (23% of theory) of the title compound were obtained.

LC-MS (Method 3): $R_t$=1.04 min; MS (ESIpos): m/z=398 [M+H]$^+$ $^1$H-NMR (400 MHz, DMSO-d6) δ[ppm]: −0.149 (0.48), −0.008 (3.94), 0.008 (3.64), 0.146 (0.42), 1.243 (0.46), 1.258 (0.46), 1.726 (1.88), 1.894 (0.48), 2.016 (0.71), 2.073 (16.00), 2.094 (1.03), 2.264 (0.57), 2.327 (1.25), 2.366 (0.69), 2.578 (1.45), 2.621 (0.53), 2.669 (1.25), 2.710 (0.67), 3.359 (0.42), 3.405 (0.48), 3.501 (0.46), 3.628 (1.23), 3.651 (1.19), 3.680 (0.77), 3.724 (0.91), 3.746 (1.03), 3.769 (0.83), 3.790 (0.67), 3.857 (1.37), 4.680 (0.65), 4.695 (0.79), 4.705 (0.65), 4.736 (0.79), 4.745 (0.89), 4.751 (1.01), 4.761 (0.77), 4.940 (1.21), 4.980 (3.19), 5.016 (1.88), 5.026 (2.16), 5.056 (0.63), 5.065 (0.87), 5.257 (0.65), 5.388 (0.85), 5.509 (0.51), 8.101 (1.66), 8.107 (1.82), 8.122 (1.78), 8.129 (1.84), 8.546 (3.25), 8.553 (3.19).

Example 561

(5RS)-2-[(6-Chlorpyridin-3-yl)methyl]-5-{[(3S)-3-fluorpyrrolidin-1-yl]carbonyl}-5,6,7,8-tetrahydro[1,2,4]triazolo[4,3-a]pyridin-3(2H)-on (Racemate)

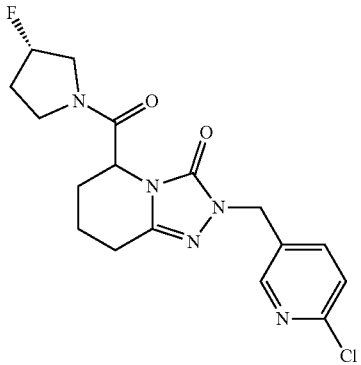 [SMILES: O=C(C1CCCc2nn(Cc3ccc(Cl)nc3)c(=O)n21)N1CC[C@H](F)C1]

(5RS)-2-[(6-Chloropyridin-3-yl)methyl]-3-oxo-2,3,5,6,7,8-hexahydro[1,2,4]triazolo[4,3-a]pyridine-5-carboxylic Acid (Racemate) (130 mg, 421 μmol) was initially charged in THF (34 μl), and 1-[bis(dimethylamino)methylene]-1H-benzotriazol-1-ium 3-oxide hexafluorophosphate (208 mg, 547 μmol) and N,N-diisopropylethylamine (220 μl, 1.3 mmol) were subsequently added. After stirring at room temperature for 15 min, (3S)-3-fluoropyrrolidine hydrochloride (58.2 mg, 463 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 73.6 mg (46% of theory) of the title compound were obtained.

LC-MS (Method 3): $R_t$=1.02 min; MS (ESIpos): m/z=380 [M+H]$^+$ $^1$H-NMR (400 MHz, DMSO-d6) δ[ppm]: −0.149 (1.02), −0.008 (13.52), 0.008 (9.53), 0.146 (1.12), 1.110 (0.63), 1.147 (0.44), 1.727 (2.58), 1.908 (0.63), 1.993 (3.02), 2.102 (2.14), 2.137 (1.70), 2.255 (1.26), 2.366 (1.70), 2.518 (12.01), 2.523 (9.78), 2.558 (3.50), 2.601 (3.84), 2.613 (2.33), 2.644 (1.41), 2.710 (1.80), 2.881 (14.25), 3.391 (1.07), 3.519 (1.70), 3.543 (1.60), 3.568 (1.46), 3.595 (2.67), 3.632 (1.95), 3.654 (1.75), 3.675 (1.51), 3.696 (0.78), 3.717 (0.92), 3.741 (1.75), 3.772 (1.26), 3.781 (1.22), 3.851 (1.60), 3.939 (1.22), 4.002 (0.63), 4.035 (0.39), 4.678 (0.83), 4.687 (0.97), 4.751 (1.26), 4.822 (1.41), 4.860 (1.80), 4.881 (16.00), 5.259 (1.12), 5.349 (0.83), 5.390 (1.22), 5.479 (0.83), 5.510 (0.63), 7.505 (6.42), 7.525 (7.88), 7.683 (3.02), 7.690 (5.45), 7.696 (3.21), 7.704 (2.48), 7.710 (4.38), 7.717 (2.33), 8.297 (5.25).

Example 562

(5RS,7RS)-2-{[3-Chloro-5-(trifluoromethyl)pyridin-2-yl]methyl}-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture, 2 Isomers)

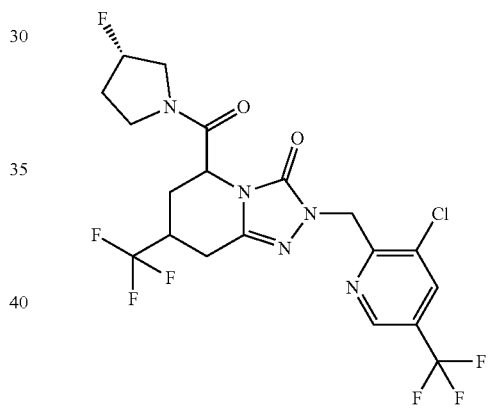

(5RS,7RS)-2-{[3-Chloro-5-(trifluoromethyl)pyridin-2-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (423 mg, 50% purity, 476 μmol) was initially charged in THF (4.5 ml), and HBTU (234 mg, 618 μmol) and N,N-diisopropylethylamine (250 μl, 1.4 mmol) were subsequently added. After stirring at room temperature for 15 min, (3S)-3-fluoropyrrolidine hydrochloride (71.7 mg, 571 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 54.6 mg (22% of theory) of the title compound were obtained.

LC-MS (Method 3): $R_t$=1.70 min; MS (ESIpos): m/z=516 [M+H]$^+$ $^1$H-NMR (400 MHz, DMSO-d6) δ [ppm]: −0.149 (1.14), −0.008 (16.00), 0.008 (8.79), 0.146 (1.14), 1.148 (0.44), 2.166 (1.01), 2.230 (1.31), 2.278 (1.11), 2.327 (2.72), 2.366 (1.34), 2.523 (8.12), 2.669 (3.05), 2.696 (1.07), 2.710 (1.84), 2.729 (0.64), 2.963 (1.61), 2.995 (1.27), 3.572 (0.57), 3.637 (0.84), 3.670 (0.77), 3.853 (0.50), 3.998 (0.57), 4.946 (0.44), 4.982 (0.54), 5.023 (0.50), 5.105 (0.70), 5.147 (2.62), 5.167 (1.88), 5.177 (1.88), 5.218 (0.64), 5.268 (0.54), 5.399 (0.64), 8.501 (2.48), 8.893 (2.55).

Example 563

(5RS,7RS)-2-{[3-Chloro-5-(trifluoromethyl)pyridin-2-yl]methyl}-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

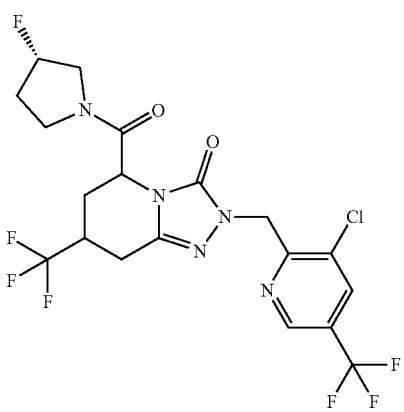

(5RS,7RS)-2-{[3-Chloro-5-(trifluoromethyl)pyridin-2-yl]methyl}-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture; 2 isomers) was separated by chiral preparative HPLC [sample preparation: 55 mg dissolved in 8 ml of acetonitrile; injection volume: 0.9 ml; column: Daicel Chiralpak® AD, 250×20 mm; eluent: $CO_2$/isopropanol 85:15; flow rate: 80 ml/min; temperature 40° C.; UV detection: 210 nm]. After the separation, 17 mg of isomer 1, which eluted first, and 18 mg of isomer 2, which eluted later, were isolated.

Isomer 2:

Analytical chiral HPLC: $R_t$=2.4 min, d.e.=98% [column: Daicel Chiralpak® AD 50×4.6 mm; eluent: $CO_2$/isopropanol 85:15; flow rate: 3 ml/min; UV detection: 210 nm].

LC-MS (Method 3): $R_t$=1.70 min; MS (ESIpos): m/z=516 [M+H]$^+$ $^1$H-NMR (400 MHz, DMSO-d6) δ [ppm]: −0.149 (0.86), −0.008 (6.12), 0.008 (5.73), 0.068 (0.53), 0.146 (0.79), 1.029 (0.66), 1.045 (0.66), 1.146 (0.66), 1.999 (1.05), 2.104 (2.17), 2.137 (3.42), 2.164 (6.45), 2.200 (4.61), 2.215 (4.48), 2.231 (5.40), 2.245 (4.61), 2.280 (6.98), 2.322 (4.48), 2.327 (4.81), 2.366 (1.51), 2.523 (10.01), 2.652 (2.77), 2.669 (5.86), 2.685 (4.41), 2.697 (5.73), 2.710 (5.14), 2.728 (3.75), 2.743 (2.44), 2.967 (9.81), 2.999 (8.36), 3.342 (2.77), 3.353 (2.90), 3.371 (2.90), 3.380 (2.17), 3.399 (2.83), 3.433 (2.37), 3.441 (2.30), 3.503 (1.71), 3.530 (2.37), 3.539 (2.24), 3.576 (5.40), 3.631 (8.95), 3.643 (3.75), 3.670 (4.81), 3.694 (5.40), 3.724 (3.29), 3.786 (1.19), 3.831 (2.70), 3.852 (4.61), 3.874 (2.90), 3.905 (1.98), 3.927 (2.24), 3.960 (1.58), 3.985 (2.50), 4.016 (1.32), 4.933 (3.62), 4.947 (3.88), 4.983 (5.53), 4.997 (5.40), 5.101 (4.48), 5.142 (14.42), 5.167 (9.81), 5.178 (11.98), 5.208 (2.44), 5.218 (4.21), 5.267 (3.49), 5.401 (4.67), 5.525 (2.37), 7.799 (0.99), 7.821 (1.51), 7.946 (1.45), 7.967 (1.25), 8.500 (15.01), 8.504 (16.00), 8.894 (15.54).

Example 564

(5RS,7RS)-2-{[3-Chloro-5-(trifluoromethyl)pyridin-2-yl]methyl}-5-[(3,3-difluoropyrolidin-1-yl)carbonyl]-7-(trifluoromethyl)-5,6,7,8-tetrahydro[1,2,4]triazolo[4,3-a]pyridin-3(2H)-one (Diastereomer 1; Racemate)

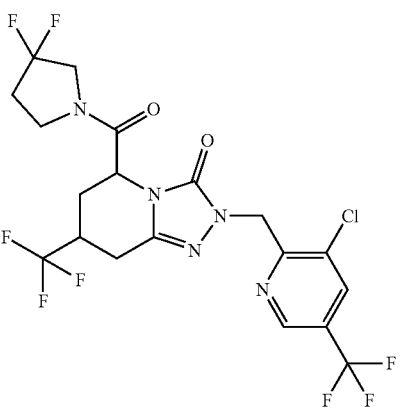

(5RS,7RS)-2-{[3-Chloro-5-(trifluoromethyl)pyridin-2-yl]methyl}-3-oxo-7-(trifluoromethyl)-2,3,5,6,7,8-hexahydro[1,2,4]triazolo[4,3-a]pyridine-5-carboxylic acid (diastereomer mixture; 4 isomers) (423 mg, 951 μmol) was initially charged in THF (9.0 ml), and 1-[bis(dimethylamino)methylene]-1H-benzotriazol-1-ium 3-oxide hexafluorophosphate (469 mg, 1.24 mmol) and N,N-diisopropylethylamine (500 μl, 2.9 mmol) were subsequently added. After stirring at room temperature for 15 min, 3,3-difluoropyrrolidine hydrochloride (164 mg, 1.14 mmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient) and diastereomer 1 was isolated. The product-containing fractions were concentrated under reduced pressure, and 48.0 mg (9% of theory) of the title compound were obtained.

LC-MS (Method 3): $R_t$=1.85 min; MS (ESIpos): m/z=534 [M+H]$^+$ $^1$H-NMR (400 MHz, DMSO-d6) δ [ppm]: −0.149 (0.81), −0.008 (6.61), 0.008 (7.06), 0.146 (0.71), 2.073 (16.00), 2.158 (0.58), 2.194 (0.81), 2.240 (0.58), 2.272 (1.10), 2.323 (1.45), 2.327 (1.74), 2.366 (0.84), 2.424 (0.87), 2.440 (0.87), 2.523 (4.03), 2.669 (2.06), 2.702 (1.32), 2.710 (1.58), 2.734 (0.81), 2.959 (2.10), 2.996 (1.35), 3.540 (0.68), 3.560 (1.32), 3.581 (1.16), 3.601 (0.65), 3.711 (0.61), 3.746 (0.97), 3.781 (1.03), 3.808 (0.61), 3.905 (0.68), 3.921 (1.39), 3.939 (1.48), 3.957 (0.61), 4.137 (0.55), 4.179 (0.90), 4.205 (0.87), 4.238 (0.52), 4.966 (1.06), 4.980 (1.03), 5.050 (1.06), 5.067 (1.00), 5.107 (1.16), 5.148 (4.26), 5.174 (4.48), 5.214 (1.23), 8.505 (3.45), 8.890 (3.42).

Example 565

(5RS,7RS)-2-{[3-Chloro-5-(trifluoromethyl)pyridin-2-yl]methyl}-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Enantiomer 2)

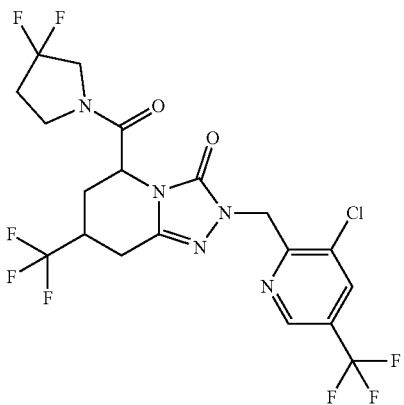

(5RS,7RS)-2-{[3-Chloro-5-(trifluoromethyl)pyridin-2-yl]methyl}-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (diastereomer 1; racemate) was separated by chiral preparative HPLC [sample preparation: 48 mg dissolved in 2.5 ml of ethanol/acetonitrile (1:1); injection volume: 0.15 ml; column: Daicel Chiralcel® OX-H 5 μm, 250×20 mm; eluent: n-heptane/ethanol (10:80)+0.2% diethylamine; flow rate: 30 ml/min; temperature 28° C.; UV detection: 220 nm]. After the separation, 9.9 mg of enantiomer 1, which eluted first, and 9.1 mg of enantiomer 2, which eluted later, were isolated.

Enantiomer 2:

Analytical chiral HPLC: $R_t$=6.38 min, e.e. =100% [column: Daicel Chiralcel® OX-H-3 250×4.6 mm; eluent: heptane/ethanol (1:1)+0.2% diethylamine; flow rate: 1 ml/min; UV detection: 220 nm].

LC-MS (Method 3): $R_t$=1.82 min; MS (ESIpos): m/z=534 [M+H]$^+$ $^1$H-NMR (400 MHz, DMSO-d6) δ [ppm]: −0.149 (2.14), −0.008 (15.25), 0.008 (16.00), 0.146 (1.94), 0.854 (0.45), 1.075 (0.89), 1.141 (1.44), 1.235 (1.49), 2.160 (1.34), 2.194 (2.09), 2.225 (1.19), 2.240 (0.99), 2.274 (2.63), 2.323 (3.43), 2.327 (4.17), 2.366 (2.09), 2.395 (1.44), 2.425 (1.89), 2.669 (5.17), 2.692 (2.34), 2.702 (3.38), 2.710 (4.22), 2.735 (1.94), 2.961 (5.22), 2.994 (3.33), 3.509 (0.84), 3.541 (1.54), 3.561 (3.18), 3.582 (2.78), 3.602 (1.44), 3.712 (1.39), 3.746 (2.34), 3.781 (2.53), 3.808 (1.49), 3.905 (1.64), 3.922 (3.28), 3.939 (3.58), 3.957 (1.49), 4.138 (1.39), 4.180 (2.14), 4.206 (2.04), 4.236 (1.14), 4.965 (2.43), 4.979 (2.43), 5.051 (2.53), 5.065 (2.48), 5.107 (2.78), 5.148 (10.68), 5.174 (11.33), 5.214 (2.93), 8.502 (7.90), 8.890 (7.90).

Example 566

(5RS,7RS)-2-[(5-Chloropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Diastereomer 1; Racemate)

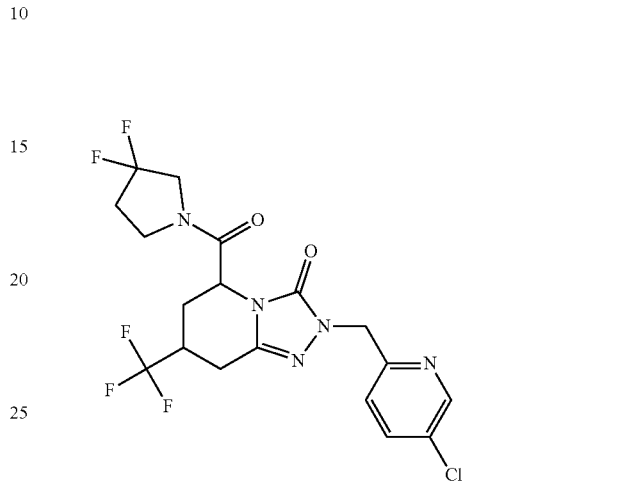

(5RS,7RS)-2-[(5-Chloropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (393 mg, 76% purity, 793 μmol) was initially charged in THF (3.8 ml), and HBTU (391 mg, 1.03 mmol) and N,N-diisopropylethylamine (410 μl, 2.4 mmol) were subsequently added. After stirring at room temperature for 15 min, 3,3-difluoropyrrolidine hydrochloride (137 mg, 951 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 171 mg (45% of theory) of the title compound were obtained.

LC-MS (Method 4): $R_t$=0.87 min; MS (ESIpos): m/z=466 [M+H]$^+$ $^1$H-NMR (400 MHz, DMSO-d6) δ [ppm]: 2.125 (0.60), 2.141 (0.72), 2.161 (1.46), 2.172 (1.67), 2.192 (1.64), 2.206 (2.29), 2.220 (1.51), 2.235 (1.39), 2.251 (1.32), 2.273 (2.84), 2.290 (3.01), 2.327 (2.24), 2.377 (0.97), 2.396 (1.79), 2.426 (2.36), 2.443 (2.27), 2.461 (1.61), 2.565 (2.70), 2.583 (2.16), 2.603 (1.46), 2.686 (1.65), 2.714 (2.61), 2.723 (3.94), 2.732 (2.44), 2.754 (2.45), 2.936 (2.06), 2.972 (5.32), 3.013 (2.95), 3.518 (0.44), 3.538 (0.84), 3.549 (1.85), 3.567 (4.66), 3.586 (3.76), 3.602 (1.90), 3.681 (0.54), 3.714 (1.84), 3.753 (3.10), 3.785 (3.25), 3.816 (1.94), 3.850 (0.49), 3.879 (0.44), 3.905 (1.92), 3.922 (3.99), 3.939 (4.34), 3.957 (1.84), 3.982 (0.44), 4.112 (0.52), 4.141 (1.65), 4.169 (1.47), 4.181 (2.52), 4.211 (2.65), 4.239 (1.52), 4.896 (2.75), 4.937 (14.75), 4.953 (16.00), 4.979 (3.36), 4.993 (3.14), 5.046 (3.20), 5.060 (3.14), 7.221 (8.97), 7.242 (9.62), 7.919 (6.01), 7.926 (6.46), 7.941 (5.80), 7.947 (6.12), 8.574 (8.32), 8.579 (8.50).

Example 567

(5RS,7RS)-2-[(5-Chloropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Enantiomer 2)

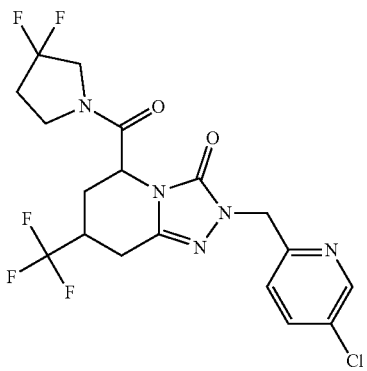 [SMILES: O=C(C1CC(C(F)(F)F)Cc2nn(Cc3ccc(Cl)cn3)c(=O)n21)N1CCC(F)(F)C1]

(5RS,7RS)-2-[(5-Chloropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (diastereomer 1; racemate) was separated by chiral preparative HPLC [sample preparation: 170 mg dissolved in 5 ml of ethanol/n-heptane (3:2); injection volume: 0.5 ml; column: Daicel Chiralpak® ID, 250×20 mm; eluent: n-heptane/ethanol 60:40; flow rate: 15 ml/min; temperature 45° C.; UV detection: 210 nm]. After the separation, 77 mg of isomer 1, which eluted first, and 75 mg of isomer 2, which eluted later, were isolated.

Enantiomer 2:

Analytical chiral HPLC: $R_t$=3.17 min, e.e. =100% [column: Daicel Chiralpak® IC-3 50×4.6 mm; eluent: n-heptane/ethanol 70:30; flow rate: 1 ml/min; UV detection: 220 nm].

LC-MS (Method 3): $R_t$=1.58 min; MS (ESIpos): m/z=466 [M+H]$^+$ $^1$H-NMR (400 MHz, DMSO-d6) δ[ppm]: −0.149 (1.00), −0.008 (7.03), 0.008 (7.68), 0.146 (0.79), 1.149 (0.72), 1.233 (0.50), 2.161 (1.43), 2.176 (1.43), 2.205 (2.01), 2.235 (1.22), 2.250 (1.22), 2.291 (2.58), 2.327 (4.66), 2.366 (2.37), 2.395 (1.65), 2.425 (2.15), 2.441 (2.01), 2.523 (9.54), 2.564 (3.73), 2.582 (2.51), 2.669 (4.23), 2.711 (3.66), 2.723 (3.80), 2.732 (2.51), 2.753 (2.37), 2.972 (4.66), 3.013 (2.73), 3.548 (1.79), 3.567 (4.30), 3.586 (3.37), 3.601 (1.79), 3.680 (0.57), 3.714 (1.72), 3.753 (2.80), 3.784 (2.80), 3.816 (1.72), 3.848 (0.57), 3.904 (1.94), 3.922 (3.52), 3.937 (3.80), 3.956 (1.72), 4.141 (1.51), 4.179 (2.22), 4.209 (2.37), 4.236 (1.36), 4.895 (2.73), 4.936 (14.28), 4.952 (16.00), 4.978 (2.94), 4.993 (3.16), 5.045 (2.87), 5.059 (2.94), 7.220 (8.47), 7.241 (9.26), 7.920 (6.67), 7.926 (6.82), 7.941 (6.39), 7.947 (6.67), 8.574 (5.96), 8.579 (6.10).

Example 568

(5S)-2-[(5-Chloro-3-fluoropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

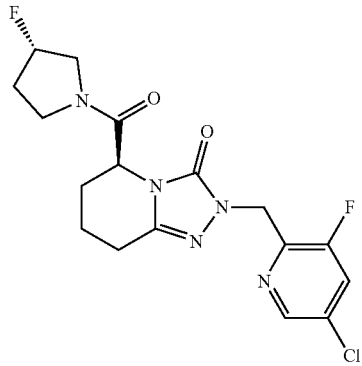 [SMILES: O=C([C@@H]1CCCc2nn(Cc3ncc(Cl)cc3F)c(=O)n21)N1CC[C@H](F)C1]

(5S)-2-[(5-Chloro-3-fluoropyridin-2-yl)methyl]-3-oxo-2,3,5,6,7,8-hexahydro[1,2,4]triazolo[4,3-a]pyridine-5-carboxylic acid (500 mg, 1.53 mmol) was initially charged in THF (10 ml), and HBTU (755 mg, 1.99 mmol) and N,N-diisopropylethylamine (800 μl, 4.6 mmol) were subsequently added. After stirring at room temperature for 15 min, (3S)-3-fluoropyrrolidine hydrochloride (211 mg, 1.68 mmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 224 mg (37% of theory) of the title compound were obtained.

LC-MS (Method 4): $R_t$=0.64 min; MS (ESIpos): m/z=398 [M+H]$^+$ $^1$H-NMR (400 MHz, DMSO-d6) δ [ppm]: −0.149 (0.47), −0.008 (4.50), 0.008 (3.40), 0.146 (0.48), 1.177 (0.66), 1.707 (8.23), 1.716 (9.32), 1.848 (1.55), 1.872 (1.42), 1.884 (2.38), 1.894 (2.16), 1.962 (2.26), 1.996 (3.78), 2.033 (2.11), 2.051 (3.61), 2.069 (5.37), 2.085 (4.80), 2.104 (4.92), 2.120 (2.73), 2.133 (2.92), 2.215 (1.98), 2.236 (2.33), 2.265 (2.73), 2.327 (1.24), 2.366 (0.60), 2.465 (1.95), 2.524 (5.83), 2.567 (6.06), 2.572 (6.32), 2.614 (2.23), 2.670 (1.05), 2.710 (0.41), 2.750 (0.55), 3.268 (1.76), 3.342 (2.24), 3.357 (1.80), 3.366 (1.83), 3.393 (2.05), 3.401 (2.04), 3.455 (1.48), 3.463 (1.61), 3.490 (2.14), 3.499 (2.00), 3.609 (1.40), 3.627 (6.06), 3.652 (6.49), 3.661 (5.02), 3.678 (3.80), 3.688 (2.92), 3.720 (3.38), 3.740 (4.82), 3.768 (3.62), 3.776 (3.09), 3.786 (3.42), 3.819 (0.66), 3.855 (6.40), 4.666 (3.14), 4.675 (3.97), 4.681 (4.07), 4.691 (3.11), 4.722 (4.04), 4.732 (4.63), 4.738 (5.18), 4.747 (3.80), 4.896 (5.44), 4.934 (13.27), 4.978 (6.77), 4.983 (8.22), 4.986 (9.25), 4.991 (8.06), 5.017 (2.71), 5.025 (4.04), 5.030 (3.54), 5.256 (3.12), 5.388 (4.35), 5.510 (2.31), 5.942 (0.72), 8.088 (9.86), 8.093 (9.96), 8.112 (9.86), 8.117 (10.03), 8.135 (5.61), 8.478 (16.00), 8.483 (15.45).

Example 569

(5RS,7RS)-2-[(3,5-Difluoropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture; 4 Isomers)

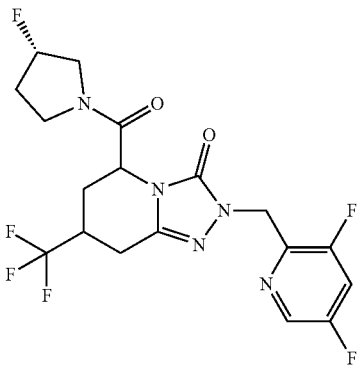 [SMILES: O=C(C1CC(C(F)(F)F)Cc2nn(Cc3ncc(F)cc3F)c(=O)n21)N1CC[C@H](F)C1]

(5RS,7RS)-2-[(3,5-Difluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (123 mg, 96% purity, 312 µmol) was initially charged in THF (10 ml), and HBTU (154 mg, 406 µmol) and N,N-diisopropylethylamine (160 µl, 940 µmol) were subsequently added. After stirring at room temperature for 15 min, (3S)-3-fluoropyrrolidine hydrochloride (47.0 mg, 375 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 92.9 mg (63% of theory) of the title compound were obtained.

LC-MS (Method 4): $R_t$=0.73 min; MS (ESIpos): m/z=450 [M+H]$^+$ $^1$H-NMR (400 MHz, DMSO-d6) δ [ppm]: −0.149 (0.66), −0.008 (5.04), 0.008 (4.55), 0.146 (0.66), 1.312 (0.45), 2.000 (0.83), 2.073 (1.32), 2.118 (3.31), 2.149 (5.50), 2.168 (3.97), 2.185 (5.50), 2.199 (5.37), 2.216 (5.04), 2.262 (4.38), 2.294 (2.81), 2.328 (2.19), 2.366 (0.95), 2.634 (1.90), 2.643 (1.78), 2.666 (5.13), 2.677 (6.82), 2.688 (2.98), 2.709 (4.38), 2.945 (8.19), 2.977 (5.75), 3.332 (2.69), 3.344 (3.22), 3.362 (3.02), 3.373 (2.11), 3.390 (2.36), 3.426 (1.24), 3.434 (1.28), 3.475 (0.79), 3.501 (1.45), 3.511 (1.36), 3.523 (1.32), 3.568 (2.94), 3.597 (2.89), 3.616 (2.85), 3.632 (4.05), 3.641 (3.10), 3.668 (3.93), 3.693 (3.14), 3.724 (1.45), 3.766 (0.95), 3.789 (1.49), 3.820 (2.11), 3.844 (2.94), 3.864 (1.49), 3.885 (1.41), 3.917 (1.57), 3.951 (0.83), 3.976 (2.32), 3.997 (2.36), 4.020 (1.86), 4.050 (1.32), 4.080 (1.03), 4.905 (1.98), 4.919 (5.75), 4.962 (11.66), 4.994 (2.65), 5.010 (9.22), 5.052 (5.37), 5.266 (2.48), 5.274 (2.32), 5.356 (1.57), 5.400 (3.18), 5.489 (1.45), 5.526 (1.20), 7.937 (4.26), 7.943 (4.63), 7.962 (6.78), 7.966 (7.24), 7.985 (4.51), 7.990 (4.80), 8.467 (15.71), 8.472 (16.00).

Example 570

(5RS,7RS)-2-[(3,5-Difluoropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Isomer 2)

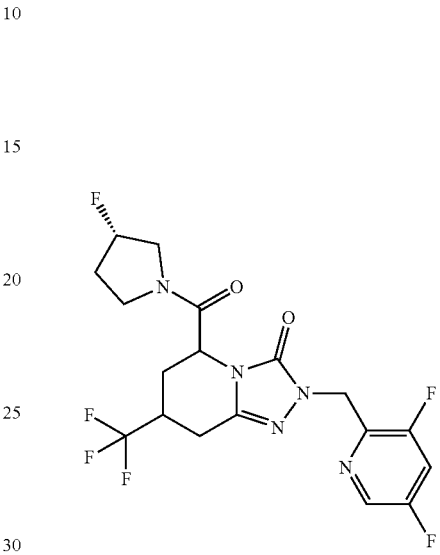

(5RS,7RS)-2-[(3,5-Difluoropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture; 4 isomers) was separated by chiral preparative HPLC [sample preparation: 82.6 mg dissolved in 4 ml of ethanol/acetonitrile (3:1); injection volume: 0.30 ml; column: Daicel Chiralcel® IC 5 µm, 250×20 mm; eluent: n-heptane/ethanol (1:1); flow rate: 15 ml/min; temperature 30° C.; UV detection: 210 nm]. After the separation, 34.4 mg of isomer 1, which eluted first, and 36.6 mg of isomer 2, which eluted later, were isolated.

Isomer 2:

Analytical chiral HPLC: $R_t$=2.237 min, d.e.=100% [column: Daicel Chiralcel® IC-3 50×4.6 mm; eluent: n-heptane/ethanol (1:1); flow rate: 1 ml/min; UV detection: 220 nm].

LC-MS (Method 3): $R_t$=1.35 min; MS (ESIpos): m/z=450 [M+H]$^+$ $^1$H-NMR (400 MHz, DMSO-d6) δ [ppm]: −0.150 (1.82), −0.008 (12.17), 0.008 (12.50), 0.146 (1.68), 2.148 (5.04), 2.186 (3.97), 2.215 (3.56), 2.262 (5.38), 2.296 (3.63), 2.327 (3.03), 2.366 (2.69), 2.665 (5.65), 2.678 (5.51), 2.692 (2.89), 2.710 (5.38), 2.946 (8.07), 2.981 (6.45), 3.390 (2.62), 3.434 (1.95), 3.523 (1.82), 3.646 (3.03), 3.668 (4.64), 3.692 (4.91), 3.722 (2.29), 3.820 (3.23), 3.845 (3.83), 3.867 (2.08), 3.919 (2.62), 3.976 (1.88), 4.917 (7.13), 4.956 (11.83), 5.012 (6.45), 5.052 (3.03), 5.265 (2.62), 5.396 (4.17), 5.530 (1.95), 7.937 (4.10), 7.943 (4.64), 7.967 (6.79), 7.985 (4.37), 7.991 (4.37), 8.467 (16.00), 8.472 (15.93).

Example 571

(5RS,7RS)-2-[(3-Chloro-5-fluoropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (Diastereomer Mixture 1; 2 Isomers)

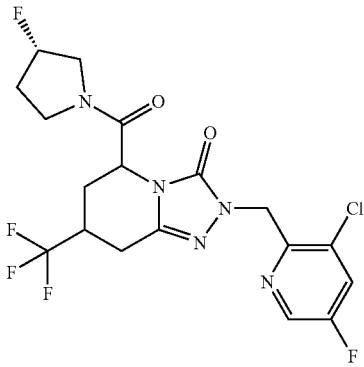 [SMILES: O=C(C1CC(C(F)(F)F)Cc2nn(Cc3ncc(F)cc3Cl)c(=O)n21)N1CC[C@H](F)C1]

(5RS,7RS)-2-[(3-chloro-5-fluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (100 mg, 253 µmol) was initially charged in THF (3.0 ml), and HBTU (125 mg, 329 mol) and N,N-diisopropylethylamine (130 µl, 760 µmol) were subsequently added. After stirring at room temperature for 15 min, (3S)-3-fluoropyrrolidine hydrochloride (38.2 mg, 304 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 85.0 mg (72% of theory) of the title compound were obtained.

LC-MS (Method 3): $R_t$=1.45 min; MS (ESIpos): m/z=466 [M+H]$^+$ $^1$H-NMR (400 MHz, DMSO-d6) δ [ppm]: −0.150 (0.48), −0.008 (4.20), 0.146 (0.46), 1.197 (4.10), 1.213 (4.14), 1.229 (0.78), 1.245 (3.16), 1.260 (4.36), 1.277 (2.13), 1.999 (0.66), 2.073 (6.51), 2.127 (2.51), 2.158 (4.28), 2.195 (4.66), 2.210 (4.58), 2.224 (5.13), 2.270 (4.30), 2.327 (1.21), 2.366 (0.82), 2.643 (1.61), 2.676 (3.50), 2.688 (5.07), 2.699 (2.37), 2.710 (1.65), 2.720 (2.79), 2.730 (1.89), 2.951 (6.59), 2.982 (5.39), 3.345 (2.13), 3.362 (1.95), 3.393 (1.51), 3.437 (0.94), 3.474 (0.54), 3.500 (1.39), 3.527 (1.00), 3.570 (2.35), 3.596 (2.47), 3.633 (3.26), 3.669 (2.89), 3.688 (2.01), 3.723 (1.47), 3.767 (0.68), 3.790 (1.05), 3.822 (1.47), 3.848 (1.99), 3.873 (1.27), 3.887 (1.01), 3.921 (1.05), 3.955 (0.68), 3.980 (1.85), 3.999 (2.01), 4.025 (1.53), 4.053 (1.05), 4.085 (0.76), 4.922 (1.57), 4.935 (1.67), 4.970 (4.56), 4.975 (4.56), 5.015 (10.99), 5.050 (7.88), 5.060 (9.85), 5.089 (2.65), 5.100 (3.48), 5.266 (2.03), 5.356 (1.19), 5.399 (2.57), 5.489 (1.15), 5.524 (1.05), 8.112 (7.30), 8.118 (7.84), 8.133 (7.48), 8.140 (7.86), 8.543 (16.00), 8.549 (15.62).

Example 572

(5RS,7RS)-2-[(3-Chloro-5-fluoropyridin-2-yl)methyl]-5-{[(3S)-3-fluoropyrrolidin-1-yl]carbonyl}-7-(trifluormethyl)-5,6,7,8-tetrahydro[1,2,4]triazolo[4,3-a]pyridin-3(2H)-one (Isomer 2)

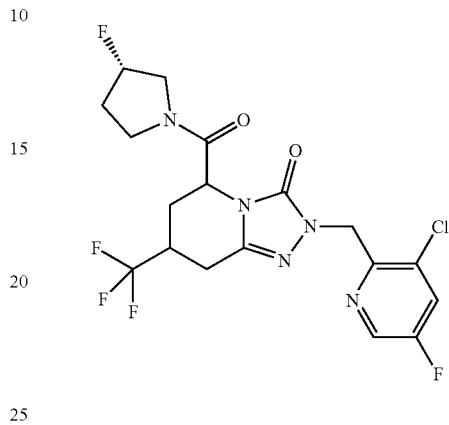

(5RS,7RS)-2-[(3-Chloro-5-fluoropyridin-2-yl)methyl]-5-{[(3S)-3-fluoropyrrolidin-1-yl]carbonyl}-7-(trifluoromethyl)-5,6,7,8-tetrahydro[1,2,4]triazolo[4,3-a]pyridin-3(2H)-one (diastereomer mixture 1; 2 isomers) was separated by chiral preparative HPLC [sample preparation: 83.0 mg dissolved in 5 ml of i-propanol/acetonitrile (1:1); injection volume: 0.30 ml; column: Daicel Chiralcel® IB 5 µm, 250×20 mm; eluent: n-heptane/i-propanol (25:75); flow rate: 15 ml/min; temperature 35° C.; UV detection: 220 nm]. After the separation, 32.5 mg of isomer 1, which eluted first, and 32.6 mg of isomer 2, which eluted later, were isolated.

Isomer 2:

Analytical chiral HPLC: $R_t$=4.109 min, d.e.=100% [column: Daicel Chiralcel® IB-3 50×4.6 mm; eluent: n-heptane/i-propanol (1:1); flow rate: 1 ml/min; UV detection: 220 nm].

LC-MS (Method 3): $R_t$=1.46 min; MS (ESIpos): m/z=466 [M+H]$^+$ $^1$H-NMR (400 MHz, DMSO-d6) δ [ppm]: −0.150 (1.21), −0.008 (9.38), 0.008 (8.11), 0.146 (1.05), 0.852 (0.55), 1.173 (1.38), 1.235 (2.76), 1.973 (0.77), 1.999 (0.88), 2.122 (2.70), 2.159 (5.85), 2.195 (4.36), 2.210 (4.08), 2.225 (4.86), 2.240 (4.14), 2.273 (6.68), 2.297 (2.92), 2.322 (2.37), 2.327 (3.20), 2.366 (2.10), 2.523 (7.12), 2.643 (2.37), 2.660 (2.98), 2.665 (2.92), 2.669 (3.70), 2.675 (5.02), 2.688 (5.02), 2.702 (3.31), 2.709 (3.09), 2.720 (3.53), 2.734 (2.26), 2.943 (4.91), 2.954 (8.61), 2.987 (7.50), 3.338 (1.82), 3.348 (2.43), 3.366 (2.32), 3.376 (1.71), 3.394 (2.59), 3.429 (1.99), 3.438 (1.99), 3.491 (1.38), 3.500 (1.43), 3.527 (2.04), 3.535 (1.93), 3.630 (2.70), 3.642 (3.14), 3.671 (3.86), 3.678 (3.42), 3.695 (3.97), 3.723 (3.20), 3.786 (1.10), 3.821 (2.92), 3.848 (4.14), 3.873 (2.54), 3.907 (1.71), 3.922 (2.15), 3.956 (1.27), 3.981 (2.15), 4.013 (1.16), 4.922 (3.42), 4.934 (3.70), 4.970 (9.71), 4.983 (4.91), 5.010 (11.75), 5.015 (9.82), 5.051 (8.28), 5.060 (10.32), 5.090 (2.76), 5.100 (4.41), 5.266 (2.98), 5.394 (4.25), 5.525 (2.15), 8.113 (8.17), 8.119 (8.77), 8.134 (8.33), 8.140 (8.99), 8.543 (16.00), 8.549 (15.78).

Example 573

(5RS,7RS)-2-[(3,5-Difluoropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Diastereomer 1; Racemate)

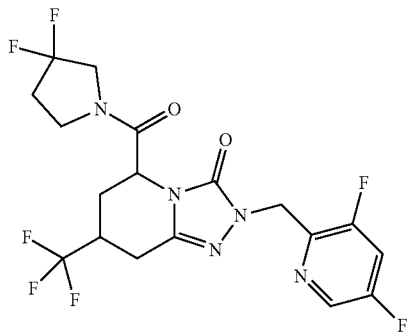 [SMILES: O=C(C1CC(C(F)(F)F)Cc2nn(Cc3ncc(F)cc3F)c(=O)n21)N1CCC(F)(F)C1]

(5RS,7RS)-2-[(3,5-Difluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (90.0 mg, 96% purity, 228 μmol) was initially charged in THF (2.0 ml), and HBTU (113 mg, 297 μmol) and N,N-diisopropylethylamine (120 μl, 690 μmol) were subsequently added. After stirring at room temperature for 15 min, 3,3-difluoropyrrolidine hydrochloride (39.4 mg, 274 μmol) was added and the reaction mixture was stirred at room temperature overnight. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 68.7 mg (62% of theory) of the title compound were obtained.

LC-MS (Method 4): $R_t$=0.83 min; MS (ESIpos): m/z=468 [M+H]$^+$ $^1$H-NMR (400 MHz, DMSO-d6) δ [ppm]: −0.008 (1.74), 1.404 (2.01), 2.098 (1.04), 2.114 (1.19), 2.133 (2.22), 2.144 (2.67), 2.163 (2.48), 2.179 (3.71), 2.194 (2.19), 2.209 (2.15), 2.225 (2.01), 2.257 (4.64), 2.283 (2.63), 2.328 (0.83), 2.375 (1.44), 2.394 (2.76), 2.412 (2.48), 2.424 (3.58), 2.441 (3.18), 2.460 (2.18), 2.469 (1.85), 2.524 (2.66), 2.562 (4.10), 2.582 (3.23), 2.602 (2.30), 2.620 (1.20), 2.639 (1.82), 2.648 (2.48), 2.673 (4.46), 2.683 (6.28), 2.692 (4.09), 2.716 (3.58), 2.724 (3.18), 2.940 (9.27), 2.981 (5.71), 3.512 (0.75), 3.531 (1.47), 3.542 (3.00), 3.560 (7.48), 3.580 (5.90), 3.596 (2.96), 3.609 (1.20), 3.626 (0.72), 3.673 (0.89), 3.707 (2.73), 3.746 (4.58), 3.776 (4.66), 3.808 (2.96), 3.844 (1.14), 3.873 (0.81), 3.892 (1.79), 3.899 (2.90), 3.917 (7.20), 3.936 (7.09), 3.956 (2.73), 3.962 (1.95), 3.982 (0.81), 4.105 (0.92), 4.134 (2.60), 4.146 (0.99), 4.163 (2.09), 4.176 (4.09), 4.204 (3.97), 4.237 (2.24), 4.266 (0.65), 4.925 (5.80), 4.936 (5.21), 4.961 (13.01), 5.015 (15.41), 5.034 (4.96), 5.050 (5.57), 7.938 (4.48), 7.943 (4.78), 7.962 (6.94), 7.966 (7.24), 7.985 (4.63), 7.991 (4.78), 8.465 (16.00), 8.471 (15.52).

Example 574

(5RS,7RS)-2-[(3,5-Difluoropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Enantiomer 1)

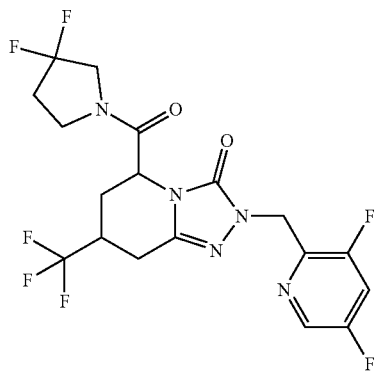 [SMILES: O=C(C1CC(C(F)(F)F)Cc2nn(Cc3ncc(F)cc3F)c(=O)n21)N1CCC(F)(F)C1]

(5RS,7RS)-2-[(3,5-Difluoropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (diastereomer 1; racemate) was separated by chiral preparative HPLC [sample preparation: 59.9 mg dissolved in 4 ml of ethanol/acetonitrile (1:1); injection volume: 0.20 ml; column: Daicel Chiralcel® IC 5 μm, 250×20 mm; eluent: n-heptane/ethanol (1:1); flow rate: 15 ml/min; temperature 30° C.; UV detection: 210 nm]. After the separation, 27.8 mg of enantiomer 1, which eluted first, and 27.2 mg of enantiomer 2, which eluted later, were isolated.

Enantiomer 1:

Analytical chiral HPLC: $R_t$=1.483 min, e.e. =100% [column: Daicel Chiralcel® IC-3 50×4.6 mm; eluent: n-heptane/ethanol (1:1); flow rate: 1 ml/min; UV detection: 220 nm].

LC-MS (Method 3): $R_t$=1.50 min; MS (ESIpos): m/z=468 [M+H]$^+$ $^1$H-NMR (400 MHz, DMSO-d6) δ [ppm]: 0.008 (6.37), 2.179 (2.78), 2.257 (3.92), 2.327 (2.12), 2.366 (2.22), 2.673 (4.20), 2.682 (4.63), 2.710 (3.16), 2.941 (6.80), 2.978 (4.11), 3.541 (2.22), 3.560 (5.90), 3.580 (4.44), 3.707 (2.22), 3.747 (3.40), 3.776 (3.59), 3.809 (1.98), 3.899 (2.31), 3.917 (5.47), 3.936 (5.24), 3.956 (2.03), 4.133 (1.89), 4.177 (2.97), 4.204 (2.97), 4.235 (1.79), 4.924 (4.34), 4.961 (9.82), 5.014 (11.66), 5.034 (3.87), 5.052 (4.20), 7.938 (3.82), 7.944 (4.29), 7.967 (6.18), 7.985 (3.73), 7.991 (4.20), 8.465 (16.00), 8.471 (15.24).

Example 575

(5RS,7RS)-2-[(3-Chloro-5-fluoropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Diastereomer 1; Racemate)

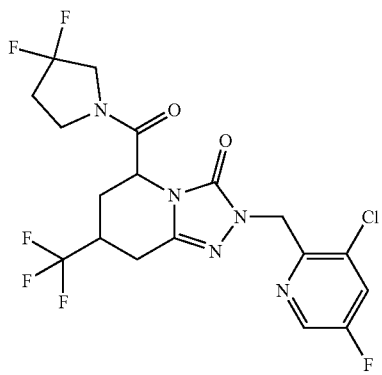 [SMILES: O=C(C1CC(C(F)(F)F)Cc2nn(Cc3ncc(F)cc3Cl)c(=O)n21)N1CCC(F)(F)C1]

(5RS,7RS)-2-[(3-Chloro-5-fluoropyridin-2-yl)methyl]-3-oxo-7-(trifluoromethyl)-2,3,5,6,7,8-hexahydro[1,2,4]triazolo[4,3-a]pyridine-5-carboxylic Acid (Diastereomer Mixture; 4 Isomers) (100 mg, 253 µmol) was initially charged in THF (3.0 ml), and HBTU (125 mg, 329 µmol) and N,N-diisopropylethylamine (130 µl, 760 µmol) were subsequently added. After stirring at room temperature for 15 min, 3,3-difluoropyrrolidine hydrochloride (43.6 mg, 304 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 98.5 mg (80% of theory) of the title compound were obtained.

LC-MS (Method 3): $R_t$=1.60 min; MS (ESIpos): m/z=484 [M+H]$^+$ $^1$H-NMR (400 MHz, DMSO-d6) δ[ppm]: 2.073 (6.45), 2.189 (2.26), 2.257 (2.86), 2.328 (1.53), 2.425 (2.10), 2.693 (3.86), 2.736 (2.40), 2.950 (5.52), 2.983 (3.83), 3.541 (1.70), 3.560 (4.29), 3.581 (3.93), 3.598 (1.83), 3.710 (1.43), 3.745 (2.73), 3.779 (3.03), 3.807 (1.76), 3.920 (4.22), 3.939 (4.29), 3.958 (1.66), 4.134 (1.40), 4.178 (2.49), 4.206 (2.23), 4.238 (1.56), 4.953 (2.89), 4.977 (4.86), 5.017 (12.87), 5.038 (3.29), 5.056 (13.87), 5.097 (4.56), 8.113 (6.82), 8.119 (7.38), 8.134 (6.69), 8.140 (7.32), 8.540 (16.00), 8.546 (15.67).

Example 576

(5RS,7RS)-2-[(3-Chloro-5-fluoropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (Enantiomer 2)

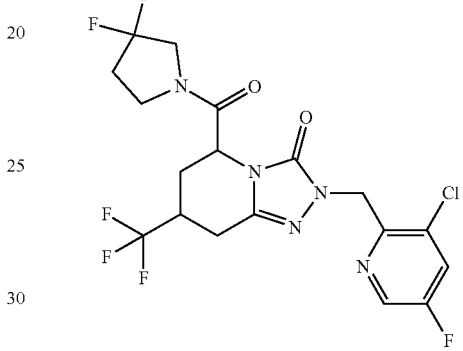

(5RS,7RS)-2-[(3-Chloro-5-fluoropyridin-2-yl)methyl]-5-[(3,3-difluoropyrrolidin-1-yl)carbonyl]-7-(trifluoromethyl)-5,6,7,8-tetrahydro[1,2,4]triazolo[4,3-a]pyridin-3(2H)-one (diastereomer 1; racemate) was separated by chiral preparative HPLC [sample preparation: 93.0 mg dissolved in 4 ml of ethanol/acetonitrile (1:1); injection volume: 0.20 ml; column: Daicel Chiralcel® IC 5 m, 250×20 mm; eluent: n-heptane/ethanol (1:1); flow rate: 15 ml/min; temperature 30° C.; UV detection: 220 nm]. After the separation, 40.9 mg of enantiomer 1, which eluted first, and 38.3 mg of enantiomer 2, which eluted later, were isolated.

Enantiomer 2:

Analytical chiral HPLC: $R_t$=1.874 min, e.e. =100% [column: Daicel Chiralcel® IC-3 50×4.6 mm; eluent: n-heptane/ethanol (1:1); flow rate: 1 ml/min; UV detection: 220 nm].

LC-MS (Method 3): $R_t$=1.60 min; MS (ESIpos): m/z=484 [M+H]$^+$ $^1$H-NMR (400 MHz, DMSO-d6) δ [ppm]: −0.149 (2.11), −0.008 (16.00), 0.008 (13.37), 0.146 (1.89), 2.266 (3.05), 2.327 (7.16), 2.366 (4.95), 2.669 (6.11), 2.694 (2.63), 2.710 (3.79), 2.950 (4.84), 2.983 (3.37), 3.559 (3.58), 3.578 (3.05), 3.745 (2.42), 3.775 (2.53), 3.919 (3.47), 3.937 (3.58), 4.178 (2.42), 4.204 (2.32), 4.976 (4.32), 5.016 (10.53), 5.056 (12.21), 5.096 (3.79), 8.113 (5.89), 8.119 (6.11), 8.134 (5.47), 8.140 (5.89), 8.540 (13.47), 8.546 (12.42).

Example 577

(5S)-5-{[(3S)-3-Fluoropyrrolidin-1-yl]carbonyl}-2-{[5-(trifluoromethyl)pyridin-3-yl]methyl}-5,6,7,8-tetrahydro[1,2,4]triazolo[4,3-a]pyridin-3(2H)-one

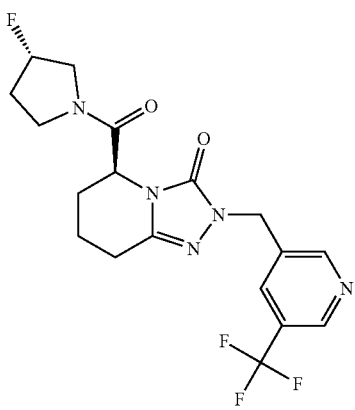 [SMILES: O=C([C@@H]1CCCc2nn(Cc3cncc(C(F)(F)F)c3)c(=O)n21)N1CC[C@H](F)C1]

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic acid (46.5 mg, 136 µmol) was initially charged in THF (1.1 ml), and HBTU (67.0 mg, 177 µmol) and N,N-diisopropylethylamine (95 µl, 680 mol) were subsequently added. After stirring at room temperature for 15 min, (3S)-3-fluoropyrrolidine hydrochloride (20.5 mg, 163 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 29.5 mg (53% of theory) of the title compound were obtained.

LC-MS (Method 3): $R_t$=1.16 min; MS (ESIpos): m/z=414 [M+H]$^+$ $^1$H-NMR (400 MHz, DMSO-d6) δ [ppm]: 1.695 (1.26), 1.734 (2.23), 1.888 (0.52), 1.924 (0.76), 1.999 (0.84), 2.034 (1.38), 2.047 (1.33), 2.068 (1.37), 2.088 (1.85), 2.104 (2.27), 2.138 (1.59), 2.221 (0.85), 2.242 (0.78), 2.256 (0.80), 2.270 (1.14), 2.327 (0.56), 2.569 (1.57), 2.577 (1.70), 2.591 (1.48), 2.617 (2.57), 2.660 (1.13), 2.670 (0.97), 3.361 (1.30), 3.371 (1.17), 3.398 (1.01), 3.406 (0.99), 3.460 (0.64), 3.468 (0.71), 3.495 (0.89), 3.504 (0.86), 3.613 (0.59), 3.630 (2.11), 3.637 (2.26), 3.654 (2.41), 3.666 (1.56), 3.681 (1.50), 3.698 (1.11), 3.725 (1.28), 3.746 (1.94), 3.770 (1.64), 3.784 (1.49), 3.855 (2.48), 4.703 (1.17), 4.712 (1.42), 4.719 (1.49), 4.728 (1.18), 4.762 (1.50), 4.770 (1.68), 4.777 (1.93), 4.786 (1.45), 5.017 (16.00), 5.260 (1.25), 5.384 (1.52), 5.391 (1.57), 5.512 (0.89), 8.059 (5.28), 8.742 (5.83), 8.917 (5.45).

Example 578

(5S)-5-{[(3R,4S)-3,4-Difluoropyrrolidin-1-yl]carbonyl}-2-{[5-(trifluoromethyl)pyridin-3-yl]methyl}-5,6,7,8-tetrahydro[1,2,4]triazolo[4,3-a]pyridin-3(2H)-one

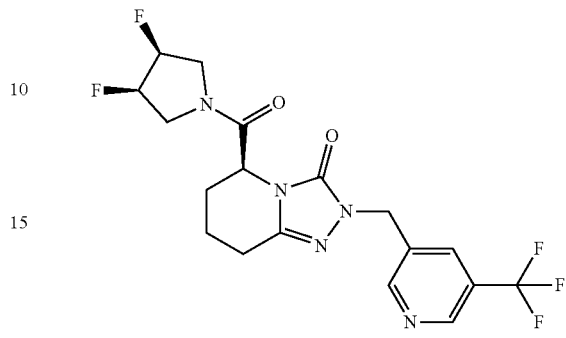

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic acid (130 mg, 380 µmol) was initially charged in THF (3.1 ml), and HBTU (187 mg, 494 µmol) and N,N-diisopropylethylamine (200 µl, 1.1 mmol) were subsequently added. After stirring at room temperature for 15 min, (3R,4S)-3,4-difluoropyrrolidine hydrochloride (60.0 mg, 418 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 28.1 mg (17% of theory) of the title compound were obtained.

LC-MS (Method 4): $R_t$=0.71 min; MS (ESIpos): m/z=432 [M+H]$^+$ $^1$H-NMR (400 MHz, DMSO-d6) δ[ppm]: −0.149 (1.89), −0.008 (14.86), 0.008 (16.00), 0.146 (1.81), 1.739 (0.46), 2.025 (0.59), 2.073 (1.52), 2.327 (1.60), 2.332 (1.26), 2.366 (1.09), 2.523 (5.09), 2.575 (1.14), 2.614 (1.22), 2.670 (2.02), 2.674 (1.52), 2.710 (1.26), 3.684 (0.55), 3.729 (0.46), 4.825 (1.09), 5.020 (5.09), 8.061 (1.56), 8.740 (1.73), 8.915 (1.52).

Example 579

(5S)-5-[(3,3-Difluoropyrrolidin-1-yl)carbonyl]-2-{[5-(trifluoromethyl)pyridin-3-yl]methyl}-5,6,7,8-tetrahydro[1,2,4]triazolo[4,3-a]pyridin-3(2H)-one

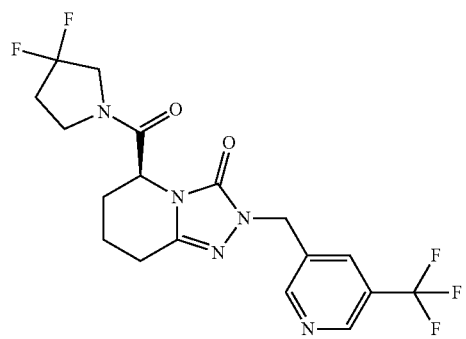 [SMILES: O=C([C@@H]1CCCc2nn(Cc3cncc(C(F)(F)F)c3)c(=O)n21)N1CCC(F)(F)C1]

(5S)-3-Oxo-2-{[5-(trifluoromethyl)pyridin-3-yl]methyl}-2,3,5,6,7,8-hexahydro[1,2,4]triazolo[4,3-a]pyridine-5-carboxylic acid (130 mg, 380 µmol) was initially charged in THF (3.1 ml), and HBTU (187 mg, 494 µmol) and N,N-diisopropylethylamine (200 µl, 1.1 mmol) were subsequently added. After stirring at room temperature for 15 min, 3,3-difluoropyrrolidine hydrochloride (60.0 mg, 418 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 32.6 mg (20% of theory) of the title compound were obtained.

LC-MS (Method 3): $R_t$=1.34 min; MS (ESIpos): m/z=432 [M+H]$^+$ $^1$H-NMR (400 MHz, DMSO-d6) δ [ppm]: −0.149 (1.49), −0.008 (11.08), 0.008 (11.23), 0.146 (1.49), 1.656 (1.12), 1.735 (1.37), 2.009 (1.73), 2.072 (2.13), 2.088 (0.97), 2.327 (2.00), 2.366 (1.46), 2.425 (1.28), 2.571 (3.49), 2.582 (2.49), 2.596 (2.37), 2.615 (2.76), 2.670 (2.31), 2.710 (1.09), 3.534 (1.70), 3.553 (2.55), 3.568 (1.28), 3.670 (1.31), 3.703 (1.49), 3.738 (1.24), 3.769 (1.85), 3.783 (1.12), 3.801 (1.85), 3.827 (0.79), 3.895 (0.64), 3.913 (1.46), 3.939 (1.00), 3.958 (0.76), 3.990 (0.91), 4.032 (0.82), 4.058 (0.52), 4.150 (0.49), 4.184 (0.82), 4.208 (0.88), 4.776 (1.15), 4.792 (1.70), 4.801 (1.15), 4.848 (1.24), 4.863 (1.64), 4.872 (1.18), 5.019 (16.00), 8.060 (5.25), 8.741 (5.22), 8.918 (4.80).

Example 580

(5S)-2-[(3-Chloro-5-fluoropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

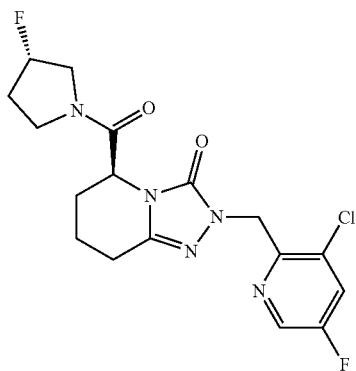 [SMILES: O=C([C@@H]1CCCc2nn(Cc3ncc(F)cc3Cl)c(=O)n21)N1CC[C@H](F)C1]

(5S)-2-[(3-Chlor-5-fluoropyridin-2-yl)methyl]-3-oxo-2,3,5,6,7,8-hexahydro[1,2,4]triazolo[4,3-a]pyridine-5-carboxylic acid (150 mg, 459 µmol) was initially charged in THF (3.4 ml), and HBTU (226 mg, 597 µmol) and N,N-diisopropylethylamine (240 µl, 1.4 mmol) were subsequently added. After stirring at room temperature for 15 min, (3S)-3-fluoropyrrolidine hydrochloride (63.4 mg, 505 µmol) was added and the reaction mixture was stirred at room temperature overnight. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 42.7 mg (23% of theory) of the title compound were obtained.

LC-MS (Method 3): $R_t$=1.04 min; MS (ESIpos): m/z=398 [M+H]$^+$ $^1$H-NMR (400 MHz, DMSO-d6) δ [ppm]: −0.149 (0.48), −0.008 (3.94), 0.008 (3.64), 0.146 (0.42), 1.243 (0.46), 1.258 (0.46), 1.726 (1.88), 1.894 (0.48), 2.016 (0.71), 2.073 (16.00), 2.094 (1.03), 2.264 (0.57), 2.327 (1.25), 2.366 (0.69), 2.578 (1.45), 2.621 (0.53), 2.669 (1.25), 2.710 (0.67), 3.359 (0.42), 3.405 (0.48), 3.501 (0.46), 3.628 (1.23), 3.651 (1.19), 3.680 (0.77), 3.724 (0.91), 3.746 (1.03), 3.769 (0.83), 3.790 (0.67), 3.857 (1.37), 4.680 (0.65), 4.695 (0.79), 4.705 (0.65), 4.736 (0.79), 4.745 (0.89), 4.751 (1.01), 4.761 (0.77), 4.940 (1.21), 4.980 (3.19), 5.016 (1.88), 5.026 (2.16), 5.056 (0.63), 5.065 (0.87), 5.257 (0.65), 5.388 (0.85), 5.509 (0.51), 8.101 (1.66), 8.107 (1.82), 8.122 (1.78), 8.129 (1.84), 8.546 (3.25), 8.553 (3.19).

Example 581

(5S)-2-[(3,5-Difluoropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one

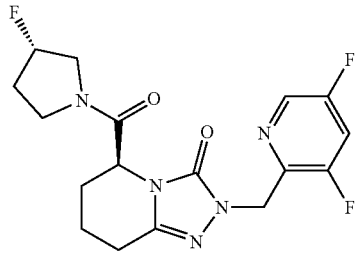 [SMILES: O=C([C@@H]1CCCc2nn(Cc3ncc(F)cc3F)c(=O)n21)N1CC[C@H](F)C1]

(5S)-2-[(3,5-Difluoropyridin-2-yl)methyl]-3-oxo-2,3,5,6,7,8-hexahydro[1,2,4]triazolo[4,3-a]pyridine-5-carboxylic acid (185 mg, 596 µmol) was initially charged in THF (5.0 ml), and HBTU (294 mg, 775 µmol) and N,N-diisopropylethylamine (520 µl, 3.0 mmol) were subsequently added. After stirring at room temperature for 5 min, (S)-(+)-3-fluoropyrrolidine hydrochloride (89.9 mg, 716 µmol) was added and the reaction mixture was stirred at room temperature over a weekend. The reaction mixture was admixed with water and ethyl acetate, and the organic phase was removed. The organic phase was washed with saturated aqueous sodium hydrogencarbonate solution, water and saturated aqueous sodium chloride solution, dried over sodium sulphate and filtered, and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 38.2 mg (17% of theory) of the title compound were obtained.

LC-MS (Method 3): $R_t$=0.96 min; MS (ESIpos): m/z=382 [M+H]

$^1$H-NMR (400 MHz, DMSO-d6) δ [ppm]: 0.008 (2.60), 1.706 (9.68), 1.715 (10.82), 1.847 (1.79), 1.857 (1.68), 1.871 (1.71), 1.883 (2.85), 1.893 (2.55), 1.968 (2.44), 1.994 (4.47), 2.029 (2.47), 2.050 (4.18), 2.067 (6.02), 2.084 (5.61), 2.103 (5.56), 2.120 (2.96), 2.134 (3.42), 2.187 (0.87), 2.220 (2.22), 2.236 (2.79), 2.266 (3.12), 2.328 (1.19), 2.366 (1.08), 2.463 (1.87), 2.565 (7.46), 2.570 (7.65), 2.611 (2.82), 2.670

(1.19), 2.710 (0.98), 2.882 (1.11), 3.268 (1.90), 3.286 (2.96), 3.342 (2.25), 3.357 (2.12), 3.366 (2.25), 3.393 (2.47), 3.401 (2.58), 3.455 (1.84), 3.464 (1.87), 3.490 (2.55), 3.499 (2.52), 3.610 (1.68), 3.628 (7.08), 3.653 (7.89), 3.661 (6.07), 3.679 (4.53), 3.688 (3.47), 3.720 (4.04), 3.741 (5.88), 3.770 (3.93), 3.778 (3.88), 3.785 (4.18), 3.819 (0.81), 3.855 (7.62), 4.664 (3.72), 4.674 (4.66), 4.680 (4.75), 4.690 (3.69), 4.721 (4.61), 4.730 (5.37), 4.736 (6.07), 4.746 (4.61), 4.887 (6.07), 4.925 (14.56), 4.976 (9.90), 5.015 (4.15), 5.257 (3.66), 5.382 (4.91), 5.388 (5.13), 5.510 (2.74), 7.924 (4.47), 7.930 (4.66), 7.948 (7.65), 7.953 (7.86), 7.972 (4.58), 7.978 (4.69), 8.465 (16.00), 8.471 (15.38).

Example 582

(5RS,7RS)-5-{[rel-(3R,4R)-3,4-Difluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Diastereomer Mixture; 8 Isomers)

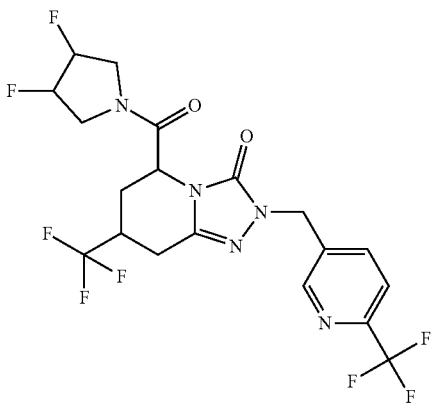 [SMILES: O=C(C1CC(C(F)(F)F)Cc2nn(Cc3ccc(C(F)(F)F)nc3)c(=O)n21)N1CC(F)C(F)C1]

(5RS,7RS)-3-Oxo-7-(trifluoromethyl)-2-{[6-(trifluoromethyl)pyridin-3-yl]methyl}-2,3,5,6,7,8-hexahydro[1,2,4]triazolo[4,3-a]pyridine-5-carboxylic Acid (Diastereomer Mixture; 4 Isomers) (259 mg, 92% purity, 581 µmol) was initially charged in THF (5.3 ml), and HBTU (286 mg, 755 µmol) and N,N-diisopropylethylamine (300 µl, 1.7 mmol) were subsequently added. After stirring at room temperature for 5 min, rel-(3R,4R)-3,4-difluoropyrrolidine hydrochloride (100 mg, 697 µmol) was added and the reaction mixture was stirred at room temperature overnight.

The reaction mixture was admixed with water and ethyl acetate, and the organic phase was removed. The organic phase was washed three times with saturated aqueous sodium hydrogencarbonate solution and 1 N aqueous hydrochloric acid. The water phase was extracted with ethyl acetate and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 311 mg (97% of theory) of the title compound were obtained.

LC-MS (Method 3): $R_t$=1.56 und 1.62 min; MS (ESIpos): m/z=500 [M+H]$^+$ $^1$H-NMR (400 MHz, DMSO-d6) δ [ppm]: −0.008 (1.18), 0.008 (1.10), 1.171 (2.12), 1.194 (15.97), 1.210 (16.00), 2.073 (1.12), 2.200 (0.77), 2.216 (1.54), 2.229 (1.70), 2.254 (1.42), 2.289 (0.48), 2.451 (1.81), 2.489 (6.72), 2.564 (1.85), 2.690 (0.88), 2.701 (0.92), 2.729 (1.49), 2.739 (1.37), 2.769 (1.51), 2.895 (0.95), 2.933 (0.63), 2.975 (1.58), 2.985 (2.01), 3.014 (1.57), 3.023 (1.95), 3.501 (0.87), 3.627 (0.56), 3.661 (0.78), 3.676 (1.06), 3.729 (0.55), 3.754 (2.19), 3.795 (0.53), 3.825 (0.69), 3.863 (0.48), 3.982 (0.54), 4.050 (0.44), 4.094 (1.10), 4.126 (0.41), 4.157 (0.66), 4.192 (0.96), 4.225 (0.54), 4.256 (0.68), 4.289 (0.48), 4.985 (1.04), 5.021 (0.69), 5.052 (8.26), 5.107 (1.17), 5.118 (1.11), 5.322 (0.83), 5.440 (1.32), 5.457 (1.10), 5.549 (0.50), 7.920 (10.95), 7.923 (10.77), 7.945 (0.58), 8.147 (2.92), 8.646 (4.33), 8.678 (0.41).

Example 583

(5RS,7RS)-5-{[rel-(3R,4R)-3,4-Difluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 3)

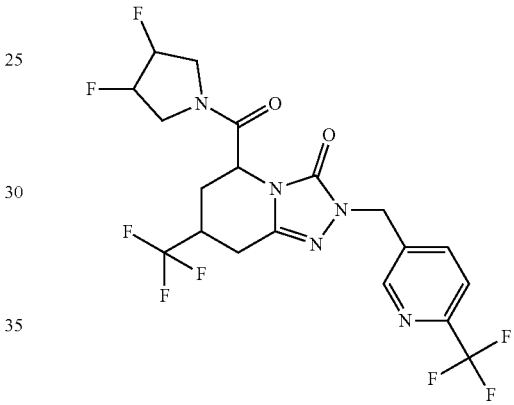

(5RS,7RS)-5-{[rel-(3R,4R)-3,4-Difluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer mixture; 8 isomers) was separated by chiral preparative HPLC [sample preparation: 311 mg dissolved in 5 ml of ethanol/acetonitrile (1:1); injection volume: 0.1 ml; column: Daicel Chiralcel® OX-H 5 µm, 250×20 mm; eluent: n-heptane/ethanol (7:3); flow rate: 40 ml/min; temperature 35° C.; UV detection: 220 nm]. After the separation, 4 major diastereomers were isolated. (82 mg of diastereomeric mixture (isomer 1 and isomer 2), which eluted first, 46.7 mg of isomer 3, which eluted second, and 39.4 mg of isomer 4, which eluted last)
Isomer 3:

Analytical chiral HPLC: $R_t$=2.63 min, d.e.=99% [column: Daicel Chiralpak® IA-3, 50×4.6 mm; eluent: i-hexane/ethanol (1:1); flow rate: 1 ml/min; UV detection: 220 nm].

LC-MS (Method 3): $R_t$=1.62 min; MS (ESIpos): m/z=500 [M+H]$^+$ $^1$H-NMR (400 MHz, DMSO-d6) δ [ppm]: −0.149 (0.84), −0.008 (6.67), 0.008 (6.52), 0.146 (0.70), 1.100 (0.43), 1.243 (3.42), 1.258 (3.30), 1.273 (2.09), 2.163 (0.64), 2.198 (1.62), 2.214 (1.45), 2.228 (1.77), 2.256 (2.75), 2.291 (1.16), 2.327 (1.57), 2.366 (1.16), 2.669 (1.88), 2.700 (1.71), 2.709 (1.19), 2.729 (2.70), 2.739 (2.26), 2.768 (2.75), 2.911 (1.01), 2.974 (2.41), 3.012 (1.65), 3.023 (1.36), 3.675 (2.52), 3.711 (0.52), 3.752 (4.38), 3.947 (0.90), 3.980 (1.10), 4.050 (0.81), 4.083 (1.10), 4.190 (1.71), 4.223 (1.39), 4.255 (1.80), 4.288

(1.19), 5.051 (15.10), 5.105 (3.13), 5.117 (2.84), 5.323 (1.16), 5.439 (2.29), 5.549 (1.13), 7.919 (16.00), 7.923 (15.77), 8.645 (5.74).

Example 584

(5RS,7RS)-5-{[rel-(3R,4R)-3,4-Difluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (Isomer 4)

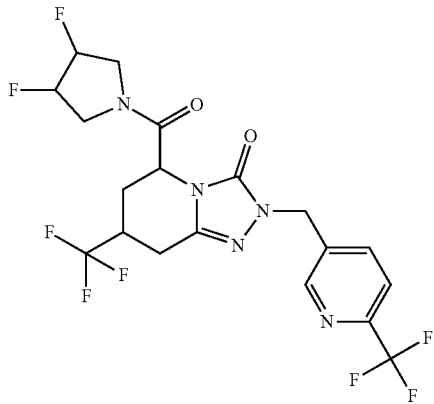 [SMILES: O=C(C1CC(C(F)(F)F)Cc2nn(Cc3ccc(C(F)(F)F)nc3)c(=O)n21)N1CC(F)C(F)C1]

(5RS,7RS)-5-{[rel-(3R,4R)-3,4-Difluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (diastereomer mixture; 8 isomers) was separated by chiral preparative HPLC [sample preparation: 311 mg dissolved in 5 ml of ethanol/acetonitrile (1:1); injection volume: 0.1 ml; column: Daicel Chiralcel® OX-H 5 µm, 250×20 mm; eluent: n-heptane/ethanol (7:3); flow rate: 40 ml/min; temperature 35° C.; UV detection: 220 nm]. After the separation, 4 major diastereomers were isolated. (82 mg of diastereomeric mixture (isomer 1 and isomer 2), which eluted first, 46.7 mg of isomer 3, which eluted second, and 39.4 mg of isomer 4, which eluted last)

Isomer 4:

Analytical chiral HPLC: $R_t$=3.25 min, d.e.=96.7% [column: Daicel Chiralpak® IA-3, 50×4.6 mm; eluent: i-hexane/ethanol (1:1); flow rate: 1 ml/min; UV detection: 220 nm].

LC-MS (Method 3): $R_t$=1.62 min; MS (ESIpos): m/z=500 [M+H]$^+$ $^1$H-NMR (400 MHz, DMSO-d6) δ [ppm]: −0.148 (0.80), −0.008 (5.80), 0.008 (5.01), 0.146 (0.89), 1.243 (4.40), 1.259 (4.16), 1.273 (2.95), 2.224 (3.88), 2.327 (1.96), 2.367 (1.68), 2.670 (2.85), 2.710 (1.82), 2.726 (2.15), 2.736 (2.95), 2.767 (1.73), 2.986 (2.95), 3.022 (2.11), 3.626 (1.50), 3.728 (1.22), 3.755 (1.96), 3.791 (1.08), 3.823 (1.96), 3.860 (1.08), 3.993 (1.22), 4.094 (2.71), 4.125 (1.22), 4.155 (1.92), 4.190 (1.03), 4.983 (2.99), 5.045 (7.77), 5.051 (8.05), 5.322 (1.08), 5.456 (1.73), 5.589 (1.12), 7.919 (16.00), 7.923 (15.20), 8.645 (5.80).

Example 585

(5S,8SR)-2-[(3,5-Difluoropyridin-2-yl)methyl]-5-{[(3S)-3-fluoropyrrolidin-1-yl]carbonyl}-8-hydroxy-5,6,7,8-tetrahydro[1,2,4]triazolo[4,3-a]pyridin-3(2H)-one (Diastereomer Mixture; 2 Isomers)

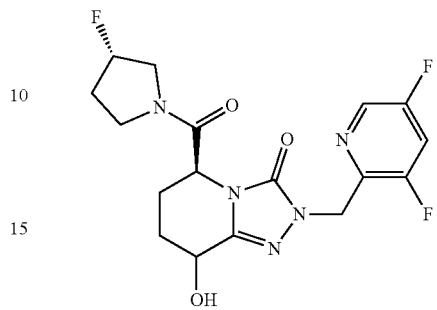

(5S)-2-[(3,5-Difluoropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one (46.0 mg, 121 µmol) and cerium(IV) sulphate (240 mg, 724 µmol) were suspended in tert-butanol (160 µl) at room temperature. Subsequently, 1 N aqueous sulphuric acid (160 µl, 3.0 mmol) was added and the reaction mixture was stirred at 70° C. overnight. Cerium (IV) sulphate (240 mg, 724 µmol) and 1 N aqueous sulphuric acid (160 µl, 3.0 mmol) were added again and the mixture was stirred at 70° C. overnight. The reaction mixture was cooled to room temperature and adjusted to pH 9 with 1 N aqueous sodium hydroxide solution. The suspension was filtered and the filtrate was extracted three times with dichloromethane. The combined organic phases were dried over sodium sulphate and filtered, and the filtrate was concentrated. The residue was purified via preparative HPLC (Phenomenex, 5 µm silica gel, 21.2 mm×100 mm; eluent: acetonitrile/water gradient). The product-containing fractions were concentrated under reduced pressure, and 4.40 mg (9% of theory) of the title compound were obtained.

LC-MS (Method 3): $R_t$=0.76 min; MS (ESIpos): m/z=398 [M+H]$^+$ $^1$H-NMR (400 MHz, DMSO-d6) δ [ppm]: 1.735 (4.24), 2.100 (3.29), 2.327 (11.14), 2.366 (8.63), 2.669 (9.73), 2.709 (6.27), 3.636 (5.65), 3.751 (4.08), 3.770 (4.08), 3.860 (5.33), 4.485 (7.84), 4.717 (3.29), 4.772 (3.92), 4.931 (4.08), 4.971 (10.04), 5.015 (7.53), 5.056 (3.76), 5.256 (2.82), 5.383 (4.86), 5.743 (10.82), 5.755 (11.29), 7.945 (4.55), 7.964 (7.53), 7.993 (3.92), 8.479 (16.00).

Example 586

(5S)-2-[(5-Chloropyridin-2-yl)methyl]-5-[(3,3-difluoropyrrolidin-1-yl)carbonyl]-8,8-difluoro-5,6,7,8-tetrahydro[1,2,4]triazolo[4,3-a]pyridin-3(2H)-one

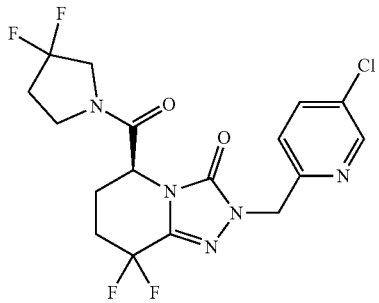 [SMILES: O=C([C@@H]1CCC(F)(F)c2nn(Cc3ccc(Cl)cn3)c(=O)n21)N1CCC(F)(F)C1]

(5S)-2-[(5-Chloropyridin-2-yl)methyl]-5-[(3,3-difluoropyrrolidin-1-yl)carbonyl]-6,7-dihydro[1,2,4]triazolo[4,3-a]

pyridine-3,8(2H,5H)-dione (79.4 mg, 88% purity, 170 µmol) was initially charged in a teflon flask under argon in dichloromethane (3 ml) at room temperature. Subsequently, diethylaminosulphur trifluoride (67 µl, 510 µmol) was added and the mixture was stirred at 40° C. overnight. The reaction mixture was admixed with water and saturated aqueous sodium hydrogencarbonate solution. The aqueous phase was extracted four times with dichloromethane and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 53.6 mg (72% of theory) of the title compound were obtained.

LC-MS (Method 3): $R_t$=1.51 min; MS (ESIpos): m/z=434 [M+H]$^+$ $^1$H-NMR (500 MHz, DMSO-d6) δ [ppm]: −0.120 (1.43), −0.007 (16.00), 0.006 (9.20), 0.116 (1.20), 2.292 (2.63), 2.340 (1.37), 2.358 (2.34), 2.361 (2.74), 2.365 (2.23), 2.440 (2.40), 2.518 (1.89), 2.522 (1.49), 2.566 (1.14), 2.580 (0.86), 2.593 (0.63), 2.631 (1.43), 2.635 (1.94), 2.639 (1.31), 3.563 (2.29), 3.578 (3.77), 3.593 (2.17), 3.705 (1.14), 3.732 (1.26), 3.766 (0.69), 3.792 (1.37), 3.818 (1.20), 3.825 (1.03), 3.831 (0.97), 3.846 (1.66), 3.861 (0.69), 3.893 (0.69), 3.908 (1.54), 3.923 (0.86), 3.929 (0.97), 3.944 (0.40), 4.027 (0.40), 4.050 (0.86), 4.061 (0.46), 4.072 (0.57), 4.085 (0.69), 4.107 (0.46), 4.159 (0.51), 4.183 (0.69), 4.203 (0.74), 4.961 (1.71), 5.036 (2.40), 5.047 (1.37), 5.068 (6.91), 5.078 (10.06), 5.110 (1.49), 7.284 (5.09), 7.301 (5.37), 7.953 (5.37), 7.958 (5.26), 7.970 (4.97), 7.975 (5.03), 8.590 (6.57), 8.594 (6.34).

Example 587

(5S)-2-[(5-Chloropyridin-2-yl)methyl]-8,8-difluoro-5-[(3-fluoroazetidin-1-yl)carbonyl]-5,6,7,8-tetrahydro[1,2,4]triazolo[4,3-a]pyridin-3(2H)-one

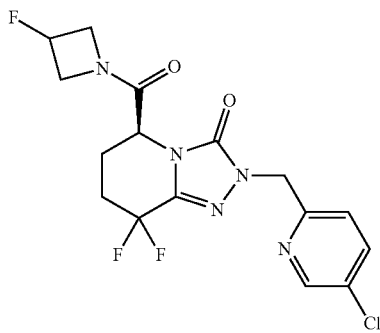 [SMILES: O=C([C@@H]1CCC(F)(F)c2nn(Cc3ccc(Cl)cn3)c(=O)n21)N1CC(F)C1]

(5S)-2-[(5-Chloropyridin-2-yl)methyl]-5-[(3-fluoroazetidin-1-yl)carbonyl]-6,7-dihydro[1,2,4]triazolo[4,3-a]pyridine-3,8(2H,5H)-dione (37.1 mg, 63% purity, 61.5 µmol) was initially charged under argon in dichloromethane (1.7 ml) at room temperature. Subsequently, diethylaminosulphur trifluoride (39 µl, 290 µmol) was added and the mixture was stirred at 40° C. overnight. The reaction mixture was admixed with water and saturated aqueous sodium hydrogencarbonate solution. The aqueous phase was extracted twice with dichloromethane and the combined organic phases were dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 12.4 mg (48% of theory) of the title compound were obtained.

LC-MS (Method 3): $R_t$=1.33 min; MS (ESIpos): m/z=402 [M+H]$^+$ $^1$H-NMR (500 MHz, DMSO-d6) δ [ppm]: −0.120 (1.40), −0.007 (15.46), 0.006 (8.74), 0.117 (1.13), 1.058 (0.72), 1.067 (0.90), 1.072 (1.35), 1.087 (0.77), 1.097 (0.81), 1.104 (0.77), 1.112 (1.26), 1.119 (1.35), 1.126 (1.13), 1.133 (0.95), 1.165 (0.68), 1.179 (0.86), 1.190 (0.86), 1.273 (1.62), 1.345 (0.41), 2.224 (2.07), 2.237 (2.07), 2.303 (3.38), 2.312 (3.29), 2.358 (3.06), 2.361 (3.65), 2.365 (2.66), 2.405 (1.31), 2.428 (2.57), 2.518 (1.94), 2.522 (1.22), 2.631 (1.76), 2.635 (2.52), 2.639 (1.67), 3.313 (10.05), 3.955 (1.58), 3.978 (1.80), 4.003 (1.53), 4.026 (1.58), 4.201 (0.81), 4.216 (0.86), 4.227 (0.77), 4.248 (1.53), 4.260 (1.53), 4.272 (1.40), 4.283 (1.31), 4.302 (0.90), 4.315 (0.77), 4.328 (0.68), 4.360 (0.95), 4.381 (1.76), 4.403 (1.76), 4.430 (1.85), 4.451 (1.04), 4.574 (0.77), 4.589 (0.90), 4.618 (0.81), 4.642 (1.31), 4.654 (1.26), 4.682 (0.90), 4.698 (0.86), 4.705 (0.86), 4.727 (3.43), 4.735 (6.58), 5.040 (1.31), 5.071 (16.00), 5.080 (7.53), 5.112 (0.86), 5.373 (1.13), 5.429 (1.13), 5.487 (1.13), 5.537 (0.99), 5.543 (1.08), 7.292 (7.12), 7.309 (7.44), 7.953 (4.91), 7.956 (4.96), 7.970 (4.64), 7.973 (4.60), 8.288 (15.95), 8.583 (5.09), 8.589 (7.35), 8.595 (4.60).

Example 588

(5S)-2-[(3,5-Difluoropyridin-2-yl)methyl]-5-[(3,3-difluoropyrrolidin-1-yl)carbonyl]-8,8-difluoro-5,6,7,8-tetrahydro[1,2,4]triazolo[4,3-a]pyridin-3(2H)-one

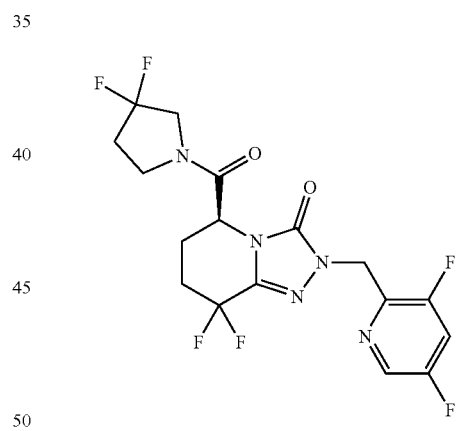

(5S)-2-[(3,5-Difluoropyridin-2-yl)methyl]-5-[(3,3-difluoropyrrolidin-1-yl)carbonyl]-6,7-dihydro[1,2,4]triazolo[4,3-a]pyridine-3,8(2H,5H)-dione (67.3 mg, 163 µmol) was initially charged under argon in dichloromethane (7 ml) at room temperature. Subsequently, diethylaminosulphur trifluoride (86 µl, 650 µmol) was added and the mixture was stirred at 40° C. overnight. Diethylaminosulphur trifluoride (86 µl, 650 µmol) was added again and the mixture was stirred at 40° C. overnight. The reaction mixture was diluted with dichloromethane and washed with saturated aqueous sodium hydrogencarbonate solution and saturated sodium chloride solution. The organic phase was dried over sodium sulphate and filtered and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and dissolved in ethyl acetate. The organic phase was washed with 1 N aqueous hydrochloric acid and water, dried over sodium sulphate and filtered and the filtrate was concentrated. 13.6 mg (19% of theory) of the title compound were obtained.

LC-MS (Method 3): R$_t$=1.42 min; MS (ESIpos): m/z=436 [M+H]

$^1$H-NMR (400 MHz, DMSO-d6) δ[ppm]: −0.150 (2.27), 0.008 (12.80), 1.348 (3.47), 1.504 (5.73), 1.908 (2.27), 2.271 (6.53), 2.327 (7.60), 2.366 (6.13), 2.670 (4.40), 2.710 (4.93), 3.553 (5.33), 3.573 (8.67), 3.591 (4.53), 3.694 (3.07), 3.729 (3.47), 3.783 (4.00), 3.814 (4.27), 3.900 (4.00), 4.035 (2.00), 4.197 (2.00), 4.950 (4.40), 5.028 (3.73), 5.076 (2.27), 5.117 (12.40), 5.133 (12.27), 5.169 (2.67), 7.969 (4.67), 7.975 (4.80), 7.999 (6.40), 8.015 (4.40), 8.484 (16.00), 8.490 (15.07).

Example 589

(5S)-2-{[3-Chloro-5-(trifluoromethyl)pyridin-2-yl]methyl}-8,8-difluoro-5-{[(3S)-3-fluoropyrrolidin-1-yl]carbonyl}-5,6,7,8-tetrahydro[1,2,4]triazolo[4,3-a]pyridin-3(2H)-one

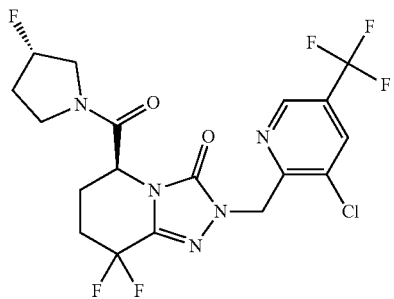 [SMILES: O=C([C@@H]1CCC(F)(F)c2nn(Cc3ncc(C(F)(F)F)cc3Cl)c(=O)n21)N1CC[C@H](F)C1]

(5S)-2-{[3-Chloro-5-(trifluoromethyl)pyridin-2-yl]methyl}-5-{[(3S)-3-fluoropyrrolidin-1-yl]carbonyl}-6,7-dihydro[1,2,4]triazolo[4,3-a]pyridine-3,8(2H,5H)-dione (75.0 mg, 162 µmol) was initially charged in a teflon flask under argon in dichloromethane (10 ml) at room temperature. Subsequently, diethylaminosulphur trifluoride (110 µl, 810 µmol) was added and the mixture was stirred at 40° C. overnight. Saturated aqueous sodium hydrogencarbonate solution was then added and the aqueous phase was extracted with dichloromethane. The organic phase was dried over sodium sulphate and filtered and the filtrate was concentrated. The residue was purified via preparative HPLC (Chromatorex C18, 10 µm, 125 mm×30 mm; eluent: (acetonitrile/water with 0.1% formic acid) gradient). The product-containing fractions were concentrated under reduced pressure, and 55.5 mg (71% of theory) of the title compound were obtained.

LC-MS (Method 4): R$_t$=0.88 min; MS (ESIpos): m/z=484 [M+H]

$^1$H-NMR (400 MHz, DMSO-d6) δ[ppm]: −0.149 (0.66), −0.008 (4.35), 0.008 (3.90), 0.147 (0.51), 1.168 (0.96), 1.185 (1.97), 1.203 (0.91), 1.292 (0.86), 1.310 (1.87), 1.328 (0.81), 2.012 (0.46), 2.117 (1.57), 2.150 (1.92), 2.251 (1.57), 2.282 (2.38), 2.332 (4.56), 2.346 (3.09), 2.366 (3.80), 2.407 (1.37), 2.447 (1.82), 2.524 (4.86), 2.670 (1.77), 2.710 (1.77), 3.349 (1.62), 3.394 (1.11), 3.421 (1.11), 3.483 (0.91), 3.519 (1.11), 3.614 (0.76), 3.639 (3.44), 3.667 (3.49), 3.696 (2.28), 3.732 (1.06), 3.755 (1.52), 3.777 (2.43), 3.799 (2.13), 3.823 (1.47), 3.887 (3.04), 3.900 (1.06), 3.910 (0.96), 3.918 (1.06), 4.925 (2.13), 4.984 (2.63), 5.274 (1.82), 5.299 (16.00), 5.348 (0.76), 5.406 (2.03), 5.527 (1.16), 8.531 (7.49), 8.916 (7.59).

Example 590

(5S)-2-{[3-Chloro-5-(trifluoromethyl)pyridin-2-yl]methyl}-5-[(3,3-difluoropyrrolidin-1-yl)carbonyl]-8,8-difluoro-5,6,7,8-tetrahydro[1,2,4]triazolo[4,3-a]pyridin-3(2H)-one

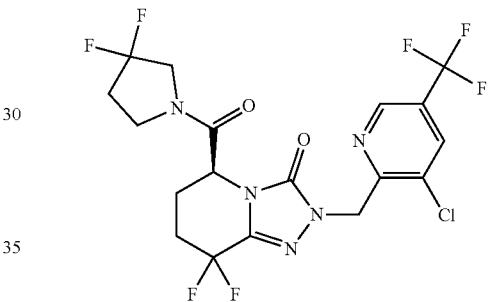

(5S)-2-{[3-Chloro-5-(trifluoromethyl)pyridin-2-yl]methyl}-5-[(3,3-difluoropyrrolidin-1-yl)carbonyl]-6,7-dihydro[1,2,4]triazolo[4,3-a]pyridine-3,8(2H,5H)-dione (65.0 mg, 48% purity, 65.0 µmol) was initially charged in a teflon flask under argon in dichloromethane (2.0 ml) at room temperature. Subsequently, diethylaminosulphur trifluoride (26 µl, 200 mol) was added and the mixture was stirred at 40° C. overnight. Diethylaminosulphur trifluoride (26 µl, 200 µmol) was added again and the mixture was stirred at 40° C. overnight. Diethylaminosulphur trifluoride (86 µl, 650 µmol) was added again and the mixture was stirred at 40° C. overnight. Saturated aqueous sodium hydrogencarbonate solution was then added and the aqueous phase was extracted with dichloromethane. The organic phase was washed with water and saturated sodium chloride solution, dried over sodium sulphate and filtered and the filtrate was concentrated. The residue was purified via preparative HPLC (Method 14). The product-containing fractions were concentrated under reduced pressure, and 4.00 mg (12% of theory) of the title compound were obtained.

LC-MS (Method 3): R$_t$=1.76 min; MS (ESIpos): m/z=502 [M+H]$^+$ $^1$H-NMR (400 MHz, DMSO-d6) δ [ppm]: 0.008 (16.00), 0.146 (3.40), 2.327 (13.00), 2.366 (8.00), 2.669 (12.60), 2.710 (6.60), 3.576 (4.00), 5.305 (13.80), 8.531 (6.80), 8.915 (5.60).

Example 591

(5S,8RS)-2-[(6-Chloropyridin-3-yl)methyl]-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers)

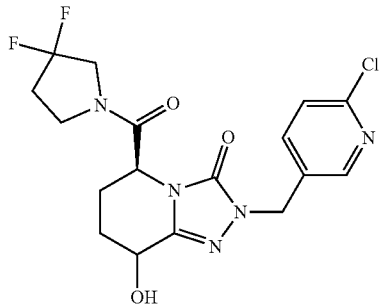 [SMILES: O=C([C@@H]1CCC(O)c2nn(Cc3ccc(Cl)nc3)c(=O)n21)N1CCC(F)(F)C1]

(5S)-2-[(6-Chloropyridin-3-yl)methyl]-5-[(3,3-difluoropyrrolidin-1-yl)carbonyl]-5,6,7,8-tetrahydro[1,2,4]triazolo[4,3-a]pyridin-3(2H)-one (100 mg, 244 μmol) and cerium(IV) sulphate (486 mg, 1.46 mmol) were suspended in tert-butanol (330 μl) at room temperature. Subsequently, 1 N aqueous sulphuric acid (330 μl, 6.1 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. 66.9 mg (90% purity, 60% of theory) of the title compound were obtained.

LC-MS (Method 3): $R_t$=0.98 min; MS (ESIpos): m/z=414 [M+H]$^+$

Example 592

(5S,8RS)-2-[(5-Chloro-3-fluoropyridin-2-yl)methyl]-5-{[(3S)-3-fluoropyrrolidin-1-yl]carbonyl}-8-hydroxy-5,6,7,8-tetrahydro[1,2,4]triazolo[4,3-a]pyridin-3(2H)-one (Diastereomer Mixture; 2 Isomers)

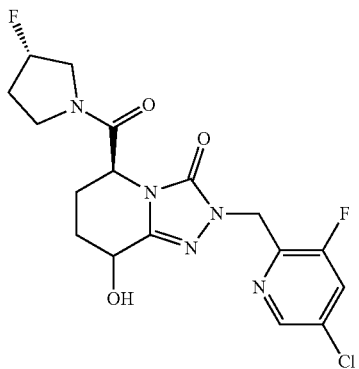 [SMILES: O=C([C@@H]1CCC(O)c2nn(Cc3ncc(Cl)cc3F)c(=O)n21)N1CC[C@H](F)C1]

(5S)-2-[(5-Chloro-3-fluoropyridin-2-yl)methyl]-5-{[(3S)-3-fluoropyrrolidin-1-yl]carbonyl}-5,6,7,8-tetrahydro[1,2,4]triazolo[4,3-a]pyridin-3(2H)-one (95.7 mg, 229 μmol) and cerium(IV) sulphate (456 mg, 1.37 mmol) were suspended in tert-butanol (310 μl) at room temperature. Subsequently, 1 N aqueous sulphuric acid (310 μl, 5.7 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. 51.7 mg (86% purity, 47% of theory) of the title compound were obtained.

LC-MS (Method 1): $R_t$=0.74 min; MS (ESIpos): m/z=414 [M+H]$^+$

Example 593

(5S,8RS)-2-{[3-Chloro-5-(trifluoromethyl)pyridin-2-yl]methyl}-5-{[(3S)-3-fluoropyrrolidin-1-yl]carbonyl}-8-hydroxy-5,6,7,8-tetrahydro[1,2,4]triazolo[4,3-a]pyridin-3(2H)-one (Diastereomer Mixture; 2 Isomers)

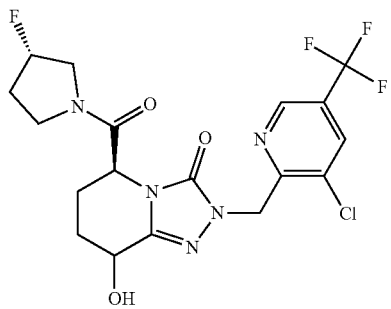 [SMILES: O=C([C@@H]1CCC(O)c2nn(Cc3ncc(C(F)(F)F)cc3Cl)c(=O)n21)N1CC[C@H](F)C1]

(5S)-2-{[3-Chloro-5-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyridin-3(2H)-on (685 mg, 1.53 mmol) and cerium(IV) sulphate (3.05 g, 9.18 mmol) were suspended in tert-butanol (2 ml) at room temperature. Subsequently, 1 N aqueous sulphuric acid (2.0 ml, 38 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. The residue was purified via preparative HPLC (Chromatorex C18, 10 μm, 125 mm×30 mm; eluent: (acetonitrile/water with 0.1% formic acid) gradient). The product-containing fractions were concentrated under reduced pressure, and 93.8 mg (13% of theory) of the title compound were obtained.

LC-MS (Method 4): $R_t$=0.64 min; MS (ESIpos): m/z=464 [M+H]$^+$ $^1$H-NMR (400 MHz, DMSO-d6) δ [ppm]: −0.149 (1.95), −0.008 (11.35), 1.747 (4.47), 1.844 (3.91), 2.136 (3.53), 2.268 (3.44), 2.328 (4.00), 2.365 (5.86), 2.669 (3.26), 2.710 (3.81), 3.485 (2.05), 3.613 (4.09), 3.639 (5.30), 3.655 (5.02), 3.755 (4.00), 3.865 (4.84), 4.502 (7.53), 4.512 (7.26), 4.727 (3.35), 4.783 (4.00), 4.794 (3.72), 5.117 (3.44), 5.156 (15.35), 5.171 (8.47), 5.180 (10.33), 5.221 (3.07), 5.256

(3.35), 5.381 (4.56), 5.513 (2.51), 5.748 (10.05), 5.760 (10.05), 6.606 (1.49), 8.501 (16.00), 8.915 (14.88).

Example 594

(5S,8RS)-2-{[3-Chloro-5-(trifluoromethyl)pyridin-2-yl]methyl}-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers)

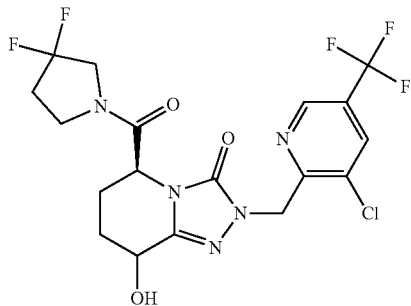 [SMILES: O=C([C@@H]1CCC(O)c2nn(Cc3ncc(C(F)(F)F)cc3Cl)c(=O)n21)N1CCC(F)(F)C1]

(5S)-2-{[3-Chloro-5-(trifluoromethyl)pyridin-2-yl]methyl}-5-[(3,3-difluoropyrrolidin-1-yl)carbonyl]-5,6,7,8-tetrahydro[1,2,4]triazolo[4,3-a]pyridin-3(2H)-on (630 mg, 95% purity, 1.28 mmol) and cerium(IV) sulphate (2.56 g, 7.71 mmol) were suspended in tert-butanol (1.7 ml) at room temperature. Subsequently, 1 N aqueous sulphuric acid (1.7 ml, 32 mmol) was added and the reaction mixture was stirred at 70° C. for 20 hours. Additional 1 N aqueous sulphuric acid (1.7 ml, 32 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were dried over sodium sulphate and filtered, and the filtrate was concentrated. The residue was purified via preparative HPLC (Chromatorex C18, 10 μm, 125 mm×40 mm; eluent: (acetonitrile/water with 0.1% formic acid) gradient). The product-containing fractions were concentrated under reduced pressure, and 58.7 mg (9% of theory) of the title compound were obtained.

LC-MS (Method 3): $R_t$=1.28 min; MS (ESIpos): m/z=482 [M+H]$^+$ $^1$H-NMR (400 MHz, DMSO-d6) δ[ppm]: −0.149 (1.45), −0.008 (10.12), 0.008 (9.85), 1.424 (2.44), 1.445 (1.90), 1.742 (3.98), 1.815 (3.07), 1.898 (2.80), 2.132 (2.26), 2.327 (4.43), 2.366 (5.06), 2.405 (3.25), 2.669 (2.89), 2.709 (3.34), 3.521 (4.16), 3.540 (7.32), 3.560 (4.34), 3.658 (2.44), 3.692 (2.53), 3.725 (2.71), 3.758 (2.89), 3.791 (4.07), 3.819 (3.07), 3.916 (3.07), 3.996 (1.81), 4.188 (2.17), 4.212 (1.90), 4.501 (6.51), 4.797 (3.07), 4.807 (2.98), 4.884 (2.98), 5.123 (2.26), 5.163 (15.82), 5.176 (16.00), 5.217 (2.62), 5.763 (11.30), 5.775 (11.39), 8.505 (14.73), 8.914 (13.02).

Example 595

(5S,8RS)-2-[(5-Chloropyridin-2-yl)methyl]-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers)

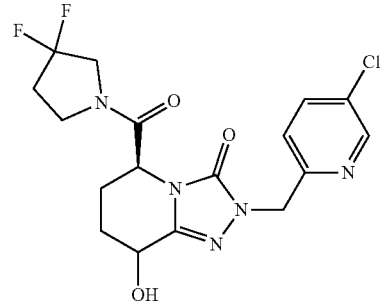 [SMILES: O=C([C@@H]1CCC(O)c2nn(Cc3ccc(Cl)cn3)c(=O)n21)N1CCC(F)(F)C1]

(5S)-2-[(5-Chloropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one (174 mg, 74% purity, 324 μmol) and cerium(IV) sulphate (645 mg, 1.94 mmol) were suspended in tert-butanol (430 μl) at room temperature. Subsequently, 1 N aqueous sulphuric acid (430 μl, 8.1 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were washed with water and saturated aqueous sodium chloride solution, dried over sodium sulphate and filtered, and the filtrate was concentrated. 103 mg (85% purity, 65% of theory) of the title compound were obtained.

LC-MS (Method 1): $R_t$=0.82 min; MS (ESIpos): m/z=414 [M+H]$^+$

Example 596

(5S,8RS)-2-[(5-Chloropyridin-2-yl)methyl]-5-[(3-fluoroazetidin-1-yl)carbonyl]-8-hydroxy-5,6,7,8-tetrahydro[1,2,4]triazolo[4,3-a]pyridin-3(2H)-one (Diastereomer Mixture; 2 Isomers)

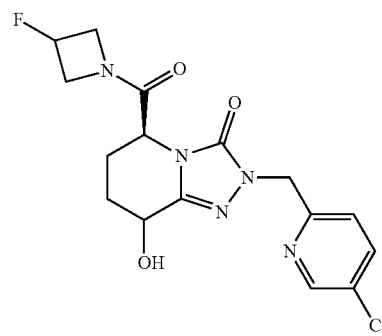

(5S)-2-[(5-Chloropyridin-2-yl)methyl]-5-[(3-fluoroazetidin-1-yl)carbonyl]-5,6,7,8-tetrahydro[1,2,4]triazolo[4,3-a]pyridin-3(2H)-one (166 mg, 98% purity, 445 μmol) and cerium(IV) sulphate (887 mg, 2.67 mmol) were suspended in tert-butanol (590 µl) at room temperature. Subsequently, 1 N aqueous sulphuric acid (590 µl, 11 mmol) was added and the reaction mixture was stirred at 70° C. overnight. The reaction mixture was cooled to room temperature and adjusted to pH 9 with 2 N aqueous sodium hydroxide solution. The suspension was filtered and the filtrate was extracted three times with dichloromethane. The combined organic phases were washed with water and saturated aqueous sodium chloride solution, dried over sodium sulphate and filtered, and the filtrate was concentrated. 48.1 mg (84% purity, 24% of theory) of the title compound were obtained.

LC-MS (Method 3): $R_t$=0.83 min; MS (ESIpos): m/z=382 $[M+H]^+$

Example 597

(5S,8RS)-2-[(3,5-Difluoropyridin-2-yl)methyl]-5-[(3,3-difluoropyrrolidin-1-yl)carbonyl]-8-hydroxy-5,6,7,8-tetrahydro[1,2,4]triazolo[4,3-a]pyridin-3(2H)-one (Diastereomer Mixture; 2 Isomers)

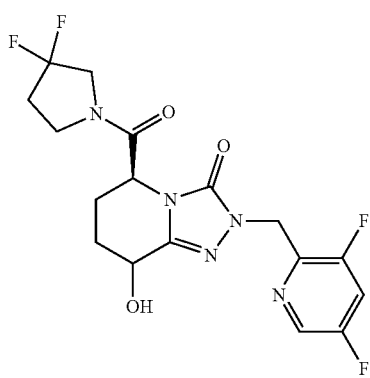 [SMILES: O=C([C@@H]1CCC(O)c2nn(Cc3ncc(F)cc3F)c(=O)n21)N1CCC(F)(F)C1]

(5S)-2-[(3,5-Difluoropyridin-2-yl)methyl]-5-[(3,3-difluoropyrrolidin-1-yl)carbonyl]-5,6,7,8-tetrahydro[1,2,4]triazolo[4,3-a]pyridin-3(2H)-one (226 mg, 567 µmol) and cerium(IV) sulphate (1.13 g, 3.40 mmol) were suspended in tert-butanol (770 µl) at room temperature. Subsequently, 1 N aqueous sulphuric acid (770 µl, 770 µmol) was added and the reaction mixture was stirred at 70° C. overnight. The reaction mixture was cooled to room temperature and adjusted to pH 9 with 2 N aqueous sodium hydroxide solution. The aqueous phase was extracted three times with ethyl acetate and the combined organic phases were dried over sodium sulphate and filtered, and the filtrate was concentrated. 116 mg (49% of theory) of the title compound were obtained.

LC-MS (Method 3): $R_t$=0.91 min; MS (ESIpos): m/z=416 $[M+H]^+$ $^1$H-NMR (400 MHz, DMSO-d6) δ [ppm]: 1.097 (3.87), 1.110 (1.22), 1.135 (4.05), 1.157 (1.27), 1.175 (2.34), 1.193 (1.34), 1.227 (16.00), 1.736 (6.08), 1.768 (0.64), 1.797 (0.65), 1.845 (0.62), 1.858 (0.55), 1.880 (1.03), 1.892 (0.81), 1.939 (0.47), 1.959 (0.47), 1.988 (4.06), 2.328 (0.69), 2.359 (0.53), 2.378 (0.68), 2.407 (0.68), 2.425 (0.68), 2.448 (0.57), 2.570 (0.72), 2.589 (0.50), 3.518 (0.78), 3.538 (1.26), 3.559 (0.77), 3.653 (0.55), 3.687 (0.65), 3.722 (0.49), 3.758 (0.71), 3.790 (0.95), 3.812 (0.72), 3.914 (0.65), 3.940 (0.50), 3.991 (0.42), 4.002 (0.53), 4.021 (1.25), 4.038 (1.17), 4.056 (0.42), 4.186 (0.45), 4.388 (1.59), 4.486 (1.30), 4.495 (1.21), 4.776 (0.62), 4.786 (0.63), 4.853 (0.63), 4.863 (0.64), 4.940 (0.71), 4.978 (2.02), 5.018 (2.18), 5.056 (0.84), 5.280 (0.84), 5.294 (0.72), 5.757 (2.51), 5.769 (2.47), 5.780 (0.44), 5.794 (0.41), 7.940 (0.81), 7.945 (0.83), 7.964 (1.33), 7.968 (1.37), 7.987 (0.86), 7.993 (0.84), 8.446 (0.74), 8.452 (0.75), 8.477 (3.04), 8.483 (2.64).

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

Abbreviations and Acronyms

| | |
|---|---|
| ATP | adenosine triphosphate |
| COPD | chronic obstructive pulmonary disease |
| LPS | lipopolysaccharide |
| PGP | proline-glycine-proline |
| Poly(I:C) | polyinosinic-polycytidylic acid |

B-1 Biochemical Human Prolyl Endopeptidase (PREP) Assay for Identification of Inhibitors of PREP Activity Using a Fluorescently Labelled Substrate Principle of the Assay:

The enzymatic conversion of the fluorescent peptide substrate was observed on the basis of the measurement of the fluorescence intensity. The enzyme activity was determined by the ascertaining of the initial slope in the increase in fluorescence. Compounds that inhibit PREP were identified on the basis of the decrease in the initial slope compared to a reaction mixture without test compound.

Determination of Activity:

$IC_{50}$ values were determined by the plotting of the percentage PREP activity against the concentration of the test substance by interpolation.

Assay Description:

To recombinant full-length human prolyl endopeptidase (PREP, R&D-Systems, 4308-SE; final concentration, for example, 0.4 nM, volume: 25 µl) in reaction buffer (50 mM Tris-HCl, pH 7.5; 150 mM NaCl; 0.13% BSA, 5 mM EDTA, 3 mM GSH, 0.005% Brij-35) was added a test compound (in DMSO, in an appropriate final concentration range from 1 nM to 30 µM, volume: 1 µl) in a well of a 384-well microtitre plate. The reaction was initiated by adding the substrate Z-Gly-Pro-AMC (final concentration 50 µM; Z=carboxybenzyl; AMC=7-amino-4-methylcoumarin, volume: 25 µl). The progress of the PREP reaction was observed by measuring the fluorescence intensity in a Tecan SAFIRE II plate spectrophotometer at 32° C. over a period of 60 min (excitation wavelength: 360 nm, emission wavelength: 465 nm).

Table B-1 below collates the $IC_{50}$ values thus obtained from the human prolyl endopeptidase assay for individual working examples of the invention (some as mean values from multiple independent individual determinations).

TABLE B-1

| Example No. | Prolyl endopeptidase (human) IC$_{50}$ [mol/l] |
|---|---|
| 1 | 1.75E−09 |
| 2 | 1.54E−08 |
| 3 | 6.00E−09 |
| 4 | 2.20E−09 |
| 5 | 8.00E−09 |
| 6 | 1.20E−07 |
| 7 | 8.00E−09 |
| 8 | 9.90E−10 |
| 9 | 3.90E−08 |
| 10 | 2.40E−08 |
| 11 | 7.00E−10 |
| 12 | 9.95E−08 |
| 13 | 5.40E−09 |
| 14 | 3.00E−10 |
| 15 | 8.40E−09 |
| 16 | 2.20E−09 |
| 17 | 1.20E−09 |
| 18 | 5.75E−10 |
| 19 | 5.70E−10 |
| 20 | 1.50E−09 |
| 21 | 6.90E−09 |
| 22 | 4.20E−08 |
| 23 | 4.95E−09 |
| 24 | 4.90E−09 |
| 25 | 7.60E−10 |
| 26 | 7.30E−10 |
| 27 | 1.28E−09 |
| 28 | 2.40E−08 |
| 29 | 1.20E−09 |
| 30 | 1.60E−09 |
| 31 | 2.90E−09 |
| 32 | 1.48E−09 |
| 33 | 7.70E−09 |
| 34 | 7.50E−09 |
| 35 | 1.50E−08 |
| 36 | 3.65E−09 |
| 37 | 8.30E−10 |
| 38 | 1.00E−09 |
| 39 | 5.50E−10 |
| 40 | 5.20E−09 |
| 41 | 1.30E−08 |
| 42 | 1.45E−09 |
| 43 | 1.90E−09 |
| 44 | 2.10E−09 |
| 45 | 1.60E−09 |
| 46 | 9.50E−10 |
| 47 | 1.60E−09 |
| 48 | 5.00E−09 |
| 49 | 1.75E−09 |
| 50 | 1.20E−08 |
| 51 | 8.90E−10 |
| 52 | 4.60E−09 |
| 53 | 7.10E−10 |
| 54 | 1.30E−09 |
| 55 | 1.40E−09 |
| 56 | 5.60E−09 |
| 57 | 4.10E−09 |
| 58 | 4.00E−09 |
| 59 | 1.22E−08 |
| 60 | 1.85E−08 |
| 61 | 1.60E−08 |
| 62 | 2.00E−09 |
| 63 | 7.40E−10 |
| 64 | 9.40E−10 |
| 65 | 1.85E−09 |
| 66 | 3.80E−10 |
| 67 | 8.70E−09 |
| 68 | 3.90E−09 |
| 69 | 2.10E−07 |
| 70 | 1.10E−08 |
| 71 | 7.10E−10 |
| 72 | 8.30E−10 |
| 73 | 1.50E−09 |
| 74 | 4.75E−09 |
| 75 | 1.10E−09 |
| 76 | 3.80E−10 |
| 77 | 4.80E−09 |
| 78 | 6.00E−09 |
| 79 | 6.70E−09 |
| 80 | 1.60E−08 |
| 81 | 8.40E−10 |
| 82 | 1.75E−09 |
| 83 | 2.10E−09 |
| 84 | 5.70E−09 |
| 85 | 2.10E−09 |
| 86 | 1.00E−09 |
| 87 | 1.17E−09 |
| 88 | 2.70E−10 |
| 89 | 1.30E−09 |
| 90 | 9.80E−09 |
| 91 | 2.30E−09 |
| 92 | 3.00E−09 |
| 93 | 6.00E−09 |
| 94 | 5.70E−08 |
| 95 | 9.00E−09 |
| 96 | 7.40E−09 |
| 97 | 6.50E−09 |
| 98 | 2.57E−07 |
| 99 | 1.27E−08 |
| 100 | 7.90E−09 |
| 101 | 3.05E−09 |
| 102 | 2.50E−10 |
| 103 | 1.60E−10 |
| 104 | 4.60E−10 |
| 105 | 1.05E−08 |
| 106 | 1.70E−09 |
| 107 | 2.10E−09 |
| 108 | 1.50E−10 |
| 109 | 2.10E−10 |
| 110 | 3.20E−10 |
| 111 | 4.10E−10 |
| 112 | 1.59E−09 |
| 113 | 4.20E−10 |
| 114 | 1.95E−09 |
| 115 | 1.10E−09 |
| 116 | 3.00E−09 |
| 117 | 3.15E−09 |
| 118 | 5.60E−09 |
| 119 | 1.40E−09 |
| 120 | 9.60E−09 |
| 121 | 4.30E−09 |
| 122 | 1.02E−08 |
| 123 | 1.20E−08 |
| 124 | 1.40E−08 |
| 125 | 2.50E−08 |
| 126 | 2.84E−08 |
| 127 | 4.35E−08 |
| 128 | 4.60E−08 |
| 129 | 1.00E−08 |
| 130 | 5.05E−08 |
| 131 | 1.07E−07 |
| 132 | 1.41E−07 |
| 133 | 1.45E−07 |
| 134 | 7.90E−08 |
| 135 | 3.45E−08 |
| 136 | 1.17E−09 |
| 137 | 1.30E−07 |
| 138 | 1.00E−09 |
| 139 | 8.70E−10 |
| 140 | 1.60E−08 |
| 141 | 8.30E−10 |
| 142 | 2.55E−09 |
| 143 | 1.31E−08 |
| 144 | 1.70E−09 |
| 145 | 1.27E−08 |
| 146 | 9.30E−10 |
| 147 | 7.00E−08 |
| 148 | 2.13E−08 |
| 149 | 2.50E−08 |
| 150 | 5.80E−10 |
| 151 | 2.60E−10 |
| 152 | 3.80E−08 |
| 153 | 3.60E−08 |
| 154 | 7.90E−07 |

TABLE B-1-continued

| Example No. | Prolyl endopeptidase (human) IC$_{50}$ [mol/l] |
|---|---|
| 155 | 2.10E−07 |
| 156 | 6.90E−08 |
| 157 | 1.30E−09 |
| 158 | 8.90E−09 |
| 159 | 1.60E−08 |
| 160 | 3.20E−08 |
| 161 | 3.70E−08 |
| 162 | 1.30E−07 |
| 163 | 2.80E−09 |
| 164 | 3.70E−09 |
| 165 | 8.90E−10 |
| 166 | 2.20E−08 |
| 167 | 5.65E−08 |
| 168 | 4.10E−09 |
| 169 | 3.15E−08 |
| 170 | 9.00E−08 |
| 171 | 6.30E−09 |
| 172 | 6.30E−09 |
| 173 | 5.85E−09 |
| 174 | 1.15E−09 |
| 175 | 7.00E−09 |
| 176 | 4.45E−07 |
| 177 | 6.90E−09 |
| 178 | 1.30E−09 |
| 179 | 6.00E−07 |
| 180 | 3.20E−09 |
| 181 | 2.48E−08 |
| 182 | 3.75E−08 |
| 183 | 1.09E−07 |
| 184 | 4.50E−09 |
| 185 | 3.70E−10 |
| 186 | 1.25E−09 |
| 187 | 1.02E−07 |
| 188 | 9.10E−11 |
| 189 | 3.40E−08 |
| 190 | 1.30E−10 |
| 191 | 2.80E−09 |
| 192 | 3.20E−10 |
| 193 | 4.20E−10 |
| 194 | 3.75E−10 |
| 195 | 6.90E−10 |
| 196 | 4.00E−10 |
| 197 | 2.35E−07 |
| 198 | 1.03E−09 |
| 199 | 5.90E−08 |
| 200 | 4.55E−07 |
| 201 | 5.45E−09 |
| 202 | 1.90E−08 |
| 203 | 8.20E−10 |
| 204 | 3.20E−07 |
| 205 | 1.00E−08 |
| 206 | 1.20E−09 |
| 207 | 4.20E−09 |
| 208 | 1.50E−08 |
| 209 | 5.50E−09 |
| 210 | 2.70E−10 |
| 211 | 1.50E−10 |
| 212 | 4.10E−11 |
| 213 | 7.70E−10 |
| 214 | 2.00E−10 |
| 215 | 5.30E−10 |
| 216 | 5.60E−10 |
| 217 | 1.20E-9 |
| 218 | 3.30E-9 |
| 219 | 7.30E-9 |
| 220 | 1.50E−09 |
| 221 | 9.80E−07 |
| 222 | 1.10E−09 |
| 223 | 4.15E−10 |
| 224 | 5.60E−10 |
| 225 | 2.30E−10 |
| 226 | 3.60E−09 |
| 227 | 2.40E−08 |
| 228 | 2.20E−09 |
| 229 | 3.40E−10 |
| 230 | 2.30E−09 |
| 231 | 4.80E−08 |
| 232 | 4.00E−07 |
| 233 | 2.03E−07 |
| 234 | 1.20E−07 |
| 235 | 6.80E−09 |
| 236 | 1.40E−09 |
| 237 | 9.40E−10 |
| 238 | 7.30E−08 |
| 239 | 1.12E−08 |
| 240 | 4.20E−09 |
| 241 | 5.80E−09 |
| 242 | 2.00E−09 |
| 243 | 6.23E−10 |
| 244 | 1.10E−08 |
| 245 | 6.90E−09 |
| 246 | 1.30E−09 |
| 247 | 9.10E−07 |
| 248 | 1.20E−08 |
| 249 | 8.30E−10 |
| 250 | 9.20E−10 |
| 251 | 3.40E−09 |
| 252 | 3.10E−09 |
| 253 | 1.20E−07 |
| 254 | 3.05E−08 |
| 255 | 1.51E−08 |
| 256 | 1.70E−09 |
| 257 | 5.95E−10 |
| 258 | 9.15E−08 |
| 259 | 1.70E−08 |
| 260 | 2.60E−09 |
| 261 | 1.00E−09 |
| 262 | 7.90E−07 |
| 263 | 2.80E−09 |
| 264 | 2.55E−09 |
| 265 | 1.30E−09 |
| 266 | 5.10E−09 |
| 267 | 2.30E−09 |
| 268 | 2.30E−08 |
| 269 | 4.20E−09 |
| 270 | 2.00E−09 |
| 271 | 1.10E−09 |
| 272 | 6.95E−10 |
| 273 | 7.60E−09 |
| 274 | 5.90E−09 |
| 275 | 1.15E−09 |
| 276 | 3.60E−09 |
| 278 | 3.30E−09 |
| 279 | 4.85E−10 |
| 280 | 3.80E−09 |
| 281 | 2.20E−09 |
| 282 | 1.50E−08 |
| 283 | 6.20E−09 |
| 284 | 3.00E−09 |
| 285 | 1.30E−09 |
| 286 | 9.85E−08 |
| 287 | 2.30E−08 |
| 288 | 1.60E−08 |
| 289 | 1.17E−07 |
| 290 | 8.20E−08 |
| 291 | 9.65E−08 |
| 292 | 3.70E−08 |
| 293 | 8.50E−08 |
| 294 | 2.00E−08 |
| 295 | 1.20E−08 |
| 296 | 1.80E-7 |
| 297 | 1.15E−07 |
| 298 | 2.40E−08 |
| 299 | 3.50E−09 |
| 300 | 1.90E-8 |
| 301 | 1.95E−08 |
| 302 | 4.95E−08 |
| 303 | 3.50E−08 |
| 304 | 3.50E−08 |
| 305 | 1.40E−08 |
| 306 | 2.15E−07 |
| 307 | 9.85E−08 |
| 308 | 1.25E−07 |
| 309 | 6.40E−08 |

TABLE B-1-continued

| Example No. | Prolyl endopeptidase (human) IC$_{50}$ [mol/l] |
|---|---|
| 310 | 1.50E−08 |
| 311 | 3.00E−08 |
| 312 | 8.90E−09 |
| 313 | 4.00E−09 |
| 314 | 1.40E−09 |
| 315 | 1.40E−09 |
| 316 | 2.60E−09 |
| 317 | 4.10E−10 |
| 318 | 5.18E−07 |
| 319 | 6.30E−10 |
| 320 | 6.90E−10 |
| 321 | 9.30E−10 |
| 322 | 9.40E−10 |
| 323 | 9.60E−10 |
| 324 | 1.20E−09 |
| 325 | 1.50E−09 |
| 326 | 1.50E−09 |
| 327 | 1.90E−09 |
| 328 | 4.10E−09 |
| 329 | 4.30E−09 |
| 330 | 4.90E−09 |
| 331 | 6.80E−10 |
| 332 | 3.90E−09 |
| 333 | 2.10E−09 |
| 334 | 2.95E−09 |
| 335 | 1.05E−09 |
| 336 | 6.60E−10 |
| 337 | 7.50E−09 |
| 338 | 1.50E−09 |
| 339 | 4.90E−09 |
| 340 | 4.80E−10 |
| 341 | 3.70E−09 |
| 342 | 1.75E−09 |
| 343 | 7.90E−09 |
| 344 | 5.30E−10 |
| 345 | 6.40E−09 |
| 346 | 4.20E−09 |
| 347 | 4.80E−09 |
| 348 | 3.80E−09 |
| 349 | 1.45E−09 |
| 350 | 3.50E−10 |
| 351 | 1.60E−09 |
| 352 | 3.20E−10 |
| 353 | 2.30E−09 |
| 354 | 1.90E−08 |
| 355 | 1.30E−09 |
| 356 | 3.00E−10 |
| 357 | 4.30E−10 |
| 358 | 6.80E−11 |
| 359 | 1.10E−09 |
| 360 | 8.10E−10 |
| 361 | 1.20E−09 |
| 362 | 1.35E−09 |
| 363 | 2.30E−09 |
| 364 | 2.90E−08 |
| 365 | 2.30E−09 |
| 366 | 2.10E−09 |
| 367 | 4.25E−10 |
| 368 | 9.00E−09 |
| 369 | 1.30E−08 |
| 370 | 1.00E−09 |
| 371 | 1.20E−09 |
| 372 | 1.30E−09 |
| 373 | 1.35E−07 |
| 374 | 5.15E−08 |
| 375 | 2.60E−09 |
| 376 | 4.10E−10 |
| 377 | 6.86E−09 |
| 378 | 2.60E−09 |
| 379 | 2.50E−09 |
| 380 | 2.10E−09 |
| 381 | 5.50E−09 |
| 382 | 5.90E−09 |
| 383 | 8.55E−09 |
| 384 | 1.10E−08 |
| 385 | 1.80E−09 |
| 386 | 9.40E−10 |
| 387 | 3.40E−09 |
| 388 | 5.75E−10 |
| 389 | 1.45E−09 |
| 390 | 1.35E−08 |
| 391 | 8.65E−09 |
| 392 | 4.60E−10 |
| 393 | 1.40E−09 |
| 394 | 2.80E−08 |
| 395 | 1.60E−09 |
| 396 | 6.00E−09 |
| 397 | 6.90E−09 |
| 398 | 1.19E−09 |
| 399 | 1.55E−09 |
| 400 | 4.55E−10 |
| 401 | 3.40E−09 |
| 402 | 2.70E−09 |
| 403 | 1.89E−07 |
| 404 | 2.33E−09 |
| 405 | 2.25E−10 |
| 406 | 3.60E−09 |
| 407 | 1.35E−09 |
| 408 | 4.60E−10 |
| 409 | 1.40E−08 |
| 410 | 7.70E−09 |
| 411 | 2.50E−09 |
| 412 | 3.00E−09 |
| 413 | 1.90E−09 |
| 414 | 7.90E−10 |
| 415 | 5.40E−09 |
| 416 | 3.40E−09 |
| 417 | 1.80E−08 |
| 418 | 2.24E−09 |
| 419 | 8.80E−10 |
| 420 | 1.70E−09 |
| 421 | 9.10E−10 |
| 422 | 6.30E−10 |
| 423 | 1.85E−09 |
| 424 | 3.80E−10 |
| 425 | 3.50E−08 |
| 426 | 6.93E−09 |
| 427 | 1.10E−09 |
| 428 | 5.30E−08 |
| 429 | 3.70E−09 |
| 430 | 1.10E−09 |
| 431 | 9.95E−10 |
| 432 | 1.30E−10 |
| 433 | 3.10E−09 |
| 434 | 2.40E−09 |
| 435 | 2.65E−09 |
| 436 | 4.70E−09 |
| 437 | 7.10E−09 |
| 438 | 1.68E−09 |
| 439 | 2.20E−09 |
| 440 | 7.15E−10 |
| 441 | 2.00E−09 |
| 442 | 1.00E−09 |
| 443 | 6.10E−10 |
| 444 | 1.90E−10 |
| 445 | 7.60E−10 |
| 446 | 7.30E−10 |
| 447 | 1.40E−09 |
| 448 | 6.15E−10 |
| 449 | 5.55E−09 |
| 450 | 1.10E−09 |
| 451 | 1.10E−09 |
| 452 | 1.30E−09 |
| 453 | 3.75E−10 |
| 454 | 6.30E−11 |
| 455 | 7.70E−10 |
| 456 | 2.70E−10 |
| 457 | 1.32E−09 |
| 458 | 5.10E−09 |
| 459 | 2.00E−10 |
| 460 | 1.70E−10 |
| 461 | 6.25E−10 |
| 462 | 2.85E−10 |
| 463 | 2.25E−10 |

TABLE B-1-continued

| Example No. | Prolyl endopeptidase (human) IC$_{50}$ [mol/l] |
|---|---|
| 464 | 5.10E−10 |
| 465 | 2.10E−09 |
| 466 | 4.10E−10 |
| 467 | 4.90E−10 |
| 468 | 1.40E−09 |
| 469 | 7.95E−10 |
| 470 | 8.20E−10 |
| 471 | 4.25E−10 |
| 472 | 2.45E−10 |
| 473 | 1.70E−10 |
| 474 | 3.60E−10 |
| 475 | 3.30E−10 |
| 476 | 7.80E−10 |
| 477 | 2.10E−10 |
| 478 | 2.65E−09 |
| 479 | 2.50E−08 |
| 480 | 5.20E−10 |
| 481 | 2.75E−08 |
| 482 | 2.80E−09 |
| 483 | 2.10E−09 |
| 484 | 2.95E−10 |
| 485 | 4.30E−09 |
| 486 | 4.65E−10 |
| 487 | 7.25E−10 |
| 488 | 1.50E−10 |
| 489 | 1.10E−10 |
| 490 | 3.80E−10 |
| 491 | 4.40E−10 |
| 492 | 5.20E−10 |
| 493 | 3.20E−10 |
| 494 | 9.10E−10 |
| 495 | 1.65E−08 |
| 496 | 1.80E−08 |
| 497 | 1.80E−10 |
| 498 | 4.40E−10 |
| 499 | 1.10E−07 |
| 500 | 5.15E−09 |
| 501 | 2.55E−08 |
| 502 | 4.10E−09 |
| 503 | 2.00E−09 |
| 504 | 1.80E−09 |
| 505 | 1.40E−09 |
| 506 | 1.20E−09 |
| 507 | 9.40E−10 |
| 508 | 9.10E−10 |
| 509 | 7.00E−10 |
| 510 | 5.35E−10 |
| 511 | 3.65E−10 |
| 512 | 1.50E−10 |
| 513 | 1.30E−10 |
| 514 | 6.10E−11 |
| 515 | 5.90E−10 |
| 516 | 4.20E−09 |
| 517 | 9.50E−10 |
| 518 | 1.50E−08 |
| 519 | 1.40E−09 |
| 520 | 1.70E−09 |
| 521 | 4.40E−10 |
| 522 | 1.50E−09 |
| 523 | 2.85E−08 |
| 524 | 2.90E−09 |
| 525 | 1.52E−08 |
| 526 | 3.80E−10 |
| 527 | 1.20E−09 |
| 528 | 7.20E−10 |
| 529 | 9.60E−10 |
| 530 | 2.20E−10 |
| 531 | 3.00E−09 |
| 532 | 3.40E−08 |
| 533 | 4.40E−10 |
| 534 | 1.23E−09 |
| 535 | 5.10E−09 |
| 536 | 9.60E−09 |
| 537 | 8.80E−09 |
| 538 | 8.20E−10 |
| 539 | 8.50E−10 |
| 540 | 2.70E−08 |
| 541 | 6.30E−08 |
| 542 | 9.40E−08 |
| 543 | 3.35E−08 |
| 544 | 4.40E−09 |
| 545 | 6.70E−10 |
| 546 | 5.70E−10 |
| 547 | 4.30E−10 |
| 548 | 3.10E−8 |
| 549 | 3.60E−8 |
| 550 | 1.80E−8 |
| 551 | 4.80E−7 |
| 552 | 6.40E−9 |
| 553 | 5.75E−7 |
| 554 | 1.00E−8 |
| 555 | 5.40E−10 |
| 556 | 6.30E−10 |
| 557 | 3.20E−9 |
| 558 | 1.90E−9 |
| 559 | 3.50E−8 |
| 560 | 4.30E−10 |
| 561 | 3.70E−10 |
| 562 | 1.33E−9 |
| 563 | 3.30E−10 |
| 564 | 4.40E−9 |
| 565 | 1.50E−9 |
| 566 | 4.10E−9 |
| 567 | 2.70E−9 |
| 568 | 6.20E−10 |
| 569 | 8.50E−10 |
| 570 | 5.70E−10 |
| 571 | 1.10E−9 |
| 572 | 1.40E−9 |
| 573 | 5.90E−9 |
| 574 | 5.20E−9 |
| 575 | 7.40E−9 |
| 576 | 8.70E−9 |
| 577 | 5.90E−10 |
| 578 | 2.30E−9 |
| 579 | 1.10E−9 |
| 580 | 4.30E−10 |
| 581 | 3.00E−10 |
| 582 | 1.40E−7 |
| 583 | 9.70E−7 |
| 584 | 5.00E−8 |
| 585 | 4.30E−10 |
| 586 | 1.40E−8 |
| 587 | 6.40E−9 |
| 588 | 1.80E−8 |
| 589 | 3.50E−10 |
| 590 | 3.90E−9 |

B-2 Biochemical Murine Prolyl Endopeptidase (PREP) Assay

Determination of Activity:

IC$_{50}$ values were determined by the plotting of the percentage PREP activity against the concentration of the test substance by interpolation.

Mouse Brain Homogenate Preparation:

Mouse brain from BalbC mice in 0.8 ml of a mixture of 100 mM sodium phosphate (pH 7.0) and 3 mM dithiothreitol was homogenized 4×25 sec in an OmniBead Ruptor. The resultant homogenate was centrifuged at 13 000 rpm and 4° C. for 20 min. The aliquoted supernatant was frozen at −80° C.

Assay Description:

Mouse brain homogenate was diluted 1:100 in a reaction buffer (50 mM Tris-HCl, pH 7.5; 150 mM NaCl; 0.13% BSA, 5 mM EDTA, 3 mM GSH, 0.005% Brij-35) and 25 µl of the solution were introduced into a well of a 384-well microtitre plate. A test compound (in DMSO, in an appropriate final concentration range of, for example, 1 nM to 30 µM, volume: 1 µl) was added. The reaction is initiated by adding the substrate Z-Gly-Pro-AMC (final concentration 50 µM; Z=carboxybenzyl; AMC=7-amino-4-methylcoumarin, volume: 25 µl). The progress of the PREP reaction was observed by measuring the fluorescence intensity in a suitable plate spectrometer at 32° C. over a period of, for example, 60 min (excitation wavelength: 360 nm, emission wavelength: 465 nm).

Table 1 below collates the $IC_{50}$ values thus obtained from the KDR and PDGFR kinase assays for individual working examples of the invention (some as mean values from multiple independent individual determinations).

B-3 Efficacy of PREP Inhibitors in Mice Exposed to Cigarette Smoke

The suitability of the substances of the invention for the treatment/prophylaxis of the disorders mentioned can be shown in the animal model which follows.

Material and Methods:
Mice:
Strain: BALB/C, origin: Charles River Netherlands, sex: male, age: 8 to 10 weeks, weight: 25 g, n=21.
Vehicle:
Solutol, EtOH, water (S: 40%, EtOH 10%, water 50% (v/v))

For the administration of PREP inhibitors by gavage, they were dissolved in the above-described vehicle (c=3750 µg/ml).

The mice were divided into three groups of seven animals each and treated as follows:
Group 1: no smoke exposure (ambient air), two daily doses of 200 µl of vehicle without active ingredient
Group 2: smoke exposure, two daily doses of 200 µl of vehicle without active ingredient
Group 3: smoke exposure, two daily doses of 200 µl of vehicle with active ingredient (30 mg/kg in each case)

Smoke Exposure:
For exposure to cigarette smoke, the animals of groups 2 and 3 (the animals of group 1 did not experience any smoke exposure and remained in the holding cages) were introduced twice daily into an exposure chamber having a total volume of 52 litres that was divided into 16 individual cages by dividing grids. For exposure to smoke, the animals, which were kept in groups (7 animals per cage), were each introduced into a single cage of the exposure chamber (7 animals per cage). Between the two daily exposures, there was a smoke-free period of 5 hours. In total, the animals were exposed to smoke on five successive days. Cigarettes were each burnt in pairs. The mainstream smoke from the cigarettes was introduced into the exposure chamber.

The smoke exposure was conducted according to the following scheme:
Day 1: 1st smoking period: 2×2 cigarettes, 2nd smoking period: 3×2 cigarettes
Day 2: 1st smoking period: 4×2 cigarettes, 2nd smoking period: 5×2 cigarettes
Day 3: 1st smoking period: 6×2 cigarettes, 2nd smoking period: 7×2 cigarettes
Days 4 and 5: 1st and 2nd smoking period: each 7×2 cigarettes The treatment of the animals with PREP inhibitors or vehicle was commenced 15 minutes before the first smoking period on day 1. Subsequently, the animals received two daily doses at an interval of 8 hours of PREP inhibitors or vehicle in the above-described dosage.

On day 6, the animals were sacrificed by the intraperitoneal administration of 150 mg/kg pentobarbital (Euthesate®). The tracheas were exposed and incised for insertion of cannulas. These cannulas were used to purge the lungs four times with physiological saline at 37° C. The cells from these four fractions in each case of the bronchoalveolar lavage fluid (BALF) were centrifuged at 4° C. at 400×g/5 minutes. Subsequently, the cell pellets were combined and resuspended in 150 µl of physiological saline (4° C.) in each case. Following staining with Türk's solution, the total number of cells was counted by light microscopy. For quantification of the neutrophil granulocytes (neutrophils for short), the cells were transferred to microscope slides (Cytospin) and stained with DiffQuick (Dade A. G., Düdingen, Switzerland). Finally, neutrophils, macrophages and lymphocytes were counted and the relative proportions of the total number previously determined was calculated. To determine the PGP concentration in the BALF, 200 µl in each case from the supernatant from the first BALF fraction was admixed with bestatin (final concentration: 1 mM) and stored at −20° C. until analysis.

Quantification of PGP in the Bronchoalveolar Lavage Fluid (BALF)

PGP was determined by the method of Hardison et al. [Hardison et al., *J. Immunol.* 2009, 182:4423-4431] using the following equipment: ESI-LC-MS/MS (Shimadzu HPLC, Columbia, Mass., USA) with a Finnigan TSQ quantum discovery Max quadrupole mass spectrometer in conjunction with electrospray thermal ionization (Thermo Fisher Scientific, San Jose, Calif., USA) and an Atlantis dC18 column (100 mm×2.1 mm, dp=3 µm, Waters Chromatography, Milford, Mass., USA) or an Atlantis pre-column (10 mm×2.1 mm, dp=3 µm, Waters).

B-4 Purification, Crystallization and Single Crystal Structure Determination of PREP (Porcine) in a Complex with Examples 26, 108, 113, 157, 237, 358 and 454

Abbreviations:
GST=glutathione-S-transferases
IPTG=isopropyl-β-D-thiogalactopyranoside
OD600=optical density at 600 nM
TRIS-HCl=tris(hydroxymethyl)aminomethane hydrochloride
EDTA=ethylenediaminetetraacetic acid
DTT=dithiothreitol
PAGE=polyacrylamide gel electrophoresis
TEV=tobacco etch virus
SEC=size exclusion chromatography
FPLC=fast protein liquid chromatography
NaCl=sodium chloride
PEG=polyethylene glycol
MES=2-(N-morpholino)ethanesulphonic acid
DMSO=dimethyl sulphoxide
CCD=charge-coupled device 4.1 Expression and Purification of PREP
Expression System:
Formation of an *E. coli* Expression Vector for Production of GST-PREP (Porcine)—Uniprot Number P23687

The PREP (porcine) expression vector used (based on pET-22b) encodes a fusion protein consisting of GST tag, attB1-5# (Gateway, Invitrogen), TEV cleavage site, PREP (porcine) region (1-710) and attB2-3#, (Gateway, Invitrogen).

*E. coli* Expression in a Bioreactor:
The *E. coli* strain BL21 DE3 was transformed with the above expression vector and a stable strain was established by ampicillin selection. This transformed strain was used for expression in a 10 l bioreactor (Sartorius). The conditions for the bioreactor run were: Circlegrow medium, incubation at 17° C. for 16 h, induction with 500 µM IPTG at OD600, 200 µg/ml ampicillin).

Purification of PREP (Porcine):

The E. coli pellet from 9 l of bioreactor culture was suspended in 200 ml of lysis buffer (50 mM TRIS-HCl pH 7.5; 150 mM NaCl; 5 mM EDTA; 5 mM DTT), 20 µl pf Benzonase (Roche) were added and digestion was effected in a microfluidizer (3×900 bar). The soluble fraction of the lysate (centrifugation 100 000×g 40 min, 4° C.) was used for further chromatographic purification.

In subsequent affinity chromatography, a glutathione matrix (Protino GST/4B) was incubated with the soluble lysate fraction, which resulted in binding of the GST-PREP (porcine) to the matrix, and washed with lysis buffer (50 mM Tris HCl pH 7.5; 150 mM NaCl; 5 mM EDTA; 5 mM DTT) and buffer A (50 mM TRIS-HCl pH 7.5; 150 mM NaCl; 1 mM EDTA; 1 mM DTT). Subsequently, the fusion protein GST-PREP (porcine) was eluted with buffer B (50 mM Tris HCl pH 7.5; 150 mM NaCl; 1 mM EDTA; 15 mM glutathione; 1 mM DTT). The elution fractions were analysed in Coomassie/PAGE and the fractions of the elution peak containing GST-PREP (porcine) were combined. (Yield 172 mg of fusion protein from 9 l of E. coli culture).

To detach the GST tag, an incubation with TEV protease was conducted in solution during the dialysis. For this purpose, the purified GST-PREP (porcine) (172 mg) was admixed with TEV protease (produced in-house) in a TEV: fusion protein ratio of 1:50 w/w and dialysed in a dialysis system (SlideA-Lyzer cutoff 10 000 Da) against 2×2 litres of buffer A (17 h, 6° C.). By means of Coomassie/PAGE, the cleavage mixture was analysed and a 90% conversion was determined.

In a further column affinity chromatography with glutathione matrix (Protino GST/4B), the protein PREP (porcine) (without GST tag) was isolated (110 mg) from the cleavage mixture in the eluate and concentrated by means of an ultrafiltration unit (Amicon Ultra millipore 50 kDa cutoff) for further processing.

Subsequently, size exclusion chromatography was conducted in order to isolate the monomer fraction of PREP (porcine). For this purpose, a Superdex S200 26/60 column (GE) with SEC buffer (50 mM Tris HCl pH 7.5; 150 mM NaCl; 1 mM EDTA; 1 mM DTT) was used. The final samples were aliquoted (1 ml), shock-frozen in liquid nitrogen and stored at −80° C. Storage buffer: 50 mM Tris-Cl pH 7.5; 150 mM NaCl; 1 mM EDTA.

Final concentration of PREP (porcine): 3.24 mg/ml, 20 ml, 64.8 mg total, yield from 9 l of E. coli culture 7.2 mg/l In order to transfer PREP (porcine) from the storage buffer (see above) into the crystallization buffer (10 mM TRIS-HCl pH 7.5; 100 mM NaCl), a trans-buffering operation was conducted by means of an FPLC system with a desalinating column (at 6° C.) and subsequent concentration (Millipore UFC 905096 ultrafiltration unit, 50 000 Da cutoff).

4.2 Complex Formation and Crystallization of PREP (Porcine)

The protein pig PREP was present at a concentration of ∼34 mg/ml in 10 mM Tris at pH=7.5 and 100 mM NaCl. The protein solution was admixed in each case with DMSO solutions of the example compounds, such that there was a final concentration of the example compounds of 4 mM in the protein buffer. The protein complex solution was incubated on an agitator at 4° C. for at least 3 hours and the solution was subsequently centrifuged for 5 minutes. Analysable single crystals were obtainable at 20° C. with the aid of the hanging drop method. For this purpose, equal volumes of the protein solution and the reservoir solution (13-15% PEG8000, 0.2 M magnesium acetate tetrahydrate, 0.1 M MES at pH=6.25) were pipetted together and admixed with crystal seeds of pig PREP. Crystals of pig PREP usually form overnight.

4.3 Data Collection and Processing

A single crystal of good visual appearance was introduced for a very short time into a solution containing 13-15% PEG8000, 0.2 M magnesium acetate tetrahydrate, 0.1 M MES at pH=6.25 and 20% glycerol, and then shock-frozen in liquid nitrogen. The crystals of examples [237, 108, 113] were analysed in a Rigaku 007HF generator from Rigaku at 100 K and a wavelength of 1.5418 Å. The detection instrument used was a Pilatus 2K counter. The data were processed with the HKL3000 program. The crystals of examples [358, 474, 157, 026] have been analysed on a Bruker Proteum System at 100 K and a wavelength of 1.5148 Å. The detection instrument used was a CCD counter. The data were integrated with the SAINT program and scaled with the SADABS program (both part of the Bruker Proteum software package).

The crystals crystallized in the orthorhombic space group P2(1)2(1)2(1) with one molecule in the asymmetric unit.

4.4 Structure Determination and Refinement

It was possible to resolve the structure of PREP (porcine) by the molecular replacement method with a further internal structure as search model and the MOLREP program (CCP4 software package). All examples [xxx] were generated as a 3D model with the aid of the Discovery Studio program, and a parameter file was generated with the PRODRG program. All examples were positioned manually in the respective electron density and minimized in terms of electron density in the COOT program. Further refinement was effected by iterative means with the REFMAC5.5 and COOT programs (both CCP4 software package). Data and refinement statistics for all examples are summarized in Tables B2-8:

TABLE B-2-8

Data collection and refinement statistics for pig PREP in a complex with examples 237, 358, 454, 108, 113, 157 and 26.

| Example | |
|---|---|
| | 237 |
| Wavelength [Å] | 1.5418 |
| Resolution [Å] | 50.00-1.67 |
| Reflections (observed/averaged) | 313006/91758 |
| Completeness [%]$^a$ | 98.4 (94.5) |
| I/s$^a$ | 43.3 (4.2) |
| $R_{merge}$$^{a, b}$ | 0.042 (0.174) |
| Space group | P2(1)2(1)2(1) |
| Cell parameters [Å] | |
| a | 70.844 |
| b | 99.754 |
| c | 111.326 |
| $R_{cryst}$$^c$ | 0.156 |
| $R_{free}$$^d$ | 0.194 |
| Wilson temperature factor [Å$^2$] | 23.1 |
| RMSD of bond lengths [Å]$^e$ | 0.03 |
| RMSD of bond angles [°] | 2.495 |
| | 358 |
| Wavelength [Å] | 1.5418 |
| Resolution [Å] | 74.17-1.72 |
| Reflections (observed/averaged) | 585565/82393 |
| Completeness [%]$^a$ | 97.4 (93.2) |
| I/s$^a$ | 23.1 (2.4) |
| $R_{merge}$$^{a, b}$ | 0.045 (0.419) |
| Space group | P2(1)2(1)2(1) |

TABLE B-2-8-continued

Data collection and refinement statistics for pig PREP in a complex with examples 237, 358, 454, 108, 113, 157 and 26.

| Example | |
|---|---|
| Cell parameters [Å] | |
| a | 70.799 |
| b | 99.485 |
| c | 111.289 |
| $R_{cryst}{}^c$ | 0.177 |
| $R_{free}{}^d$ | 0.215 |
| Wilson temperature factor [Å$^2$] | 29.4 |
| RMSD of bond lengths [Å]$^e$ | 0.029 |
| RMSD of bond angles [°] | 2.41 |
| 454 | |
| Wavelength [Å] | 1.5418 |
| Resolution [Å] | 73.86-1.95 |
| Reflections (observed/averaged) | 521863/56951 |
| Completeness [%]$^a$ | 99.0 (94.4) |
| I/s$^a$ | 21.1 (2.6) |
| $R_{merge}{}^{a,b}$ | 0.061 (0.258) |
| Space group | P2(1)2(1)2(1) |
| Cell parameters [Å] | |
| a | 70.662 |
| b | 98.967 |
| c | 110.958 |
| $R_{cryst}{}^c$ | 0.159 |
| $R_{free}{}^d$ | 0.207 |
| Wilson temperature factor [Å$^2$] | 28.6 |
| RMSD of bond lengths [Å]$^e$ | 0.024 |
| RMSD of bond angles [°] | 2.223 |
| 108 | |
| Wavelength [Å] | 1.5418 |
| Resolution [Å] | 74.88-2.20 |
| Reflections (observed/averaged) | 186219/40375 |
| Completeness [%]$^a$ | 96.9 (88.4) |
| I/s$^a$ | 19.4 (2.9) |
| $R_{merge}{}^{a,b}$ | 0.063 (0.299) |
| Space group | P2(1)2(1)2(1) |
| Cell parameters [Å] | |
| a | 71.542 |
| b | 100.758 |
| c | 111.916 |
| $R_{cryst}{}^c$ | 0.199 |
| $R_{free}{}^d$ | 0.264 |
| Wilson temperature factor [Å$^2$] | 21.7 |
| RMSD of bond lengths [Å]$^e$ | 0.016 |
| RMSD of bond angles [°] | 1.714 |
| 113 | |
| Wavelength [Å] | 1.5418 |
| Resolution [Å] | 74.73-1.80 |
| Reflections (observed/averaged) | 185943/68415 |
| Completeness [%]$^a$ | 91.7 (85.7) |
| I/s$^a$ | 9.7 (3.6) |
| $R_{merge}{}^{a,b}$ | 0.090 (0.312) |
| Space group | P2(1)2(1)2(1) |
| Cell parameters [Å] | |
| a | 71.383 |
| b | 100.533 |
| c | 111.728 |
| $R_{cryst}{}^c$ | 0.248 |
| $R_{free}{}^d$ | 0.289 |
| Wilson temperature factor [Å$^2$] | 24.0 |
| RMSD of bond lengths [Å]$^e$ | 0.028 |
| RMSD of bond angles [°] | 2.536 |
| 157 | |
| Wavelength [Å] | 1.5418 |
| Resolution [Å] | 74.58-1.70 |
| Reflections (observed/averaged) | 440687/86834 |
| Completeness [%]$^a$ | 98.2 (92.0) |
| I/s$^a$ | 16.1 (3.9) |
| $R_{merge}{}^{a,b}$ | 0.063 (0.328) |
| Space group | P2(1)2(1)2(1) |
| Cell parameters [Å] | |
| a | 71.183 |
| b | 100.38 |
| c | 111.434 |
| $R_{cryst}{}^c$ | 0.180 |
| $R_{free}{}^d$ | 0.220 |
| Wilson temperature factor [Å$^2$] | 18.25 |
| RMSD of bond lengths [Å]$^e$ | 0.028 |
| RMSD of bond angles [°] | 2.403 |
| 26 | |
| Wavelength [Å] | 1.5418 |
| Resolution [Å] | 73.92-2.30 |
| Reflections (observed/averaged) | 146137/33493 |
| Completeness [%]$^a$ | 94.7 (67.8) |
| I/s$^a$ | 17.8 (5.5) |
| $R_{merge}{}^{a,b}$ | 0.059 (0.104) |
| Space group | P2(1)2(1)2(1) |
| Cell parameters [Å] | |
| a | 70.675 |
| b | 99.198 |
| c | 110.862 |
| $R_{cryst}{}^c$ | 0.158 |
| $R_{free}{}^d$ | 0.233 |
| Wilson temperature factor [Å$^2$] | 29.37 |
| RMSD of bond lengths [Å]$^e$ | 0.019 |
| RMSD of bond angles [°] | 1.920 |

$^a$The values in brackets are for the outermost resolution shell $^b$R$_{merge}$ = Σhkl |I$_{hkl}$ − <I$_{hkl}$>|/Σhkl <I$_{hkl}$>; I$_{hkl}$ is the intensity of the reflections hkl and <I$_{hkl}$> is the average value of repeatedly measured intensities $^c$R$_{cryst}$ = Σ |F$_{obs}$ − F$_{calc}$|/Σ F$_{obs}$; F$_{obs}$ and F$_{calc}$ are the observed and calculated structure factors $^d$5% test set $^e$RMSD, root mean square deviation of the parameter set of the ideal bond geometry

4.5 Absolute Structure Determination of Example 237 in PREP (Porcine)

The complex of pig PREP with Example 237 crystallizes with one molecule in the asymmetric unit. The stereochemistry of Example 237 is determined unambiguously through the knowledge of the stereochemistry of the protein pig PREP. In Example 237, the S configuration is unambiguously present at the stereocentres C31 and C2, and R configuration is present at C6 (FIG. 1).

Structure from Example 237: (5S,7R)-5-{[(3S)-3-Fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one with the following formula:

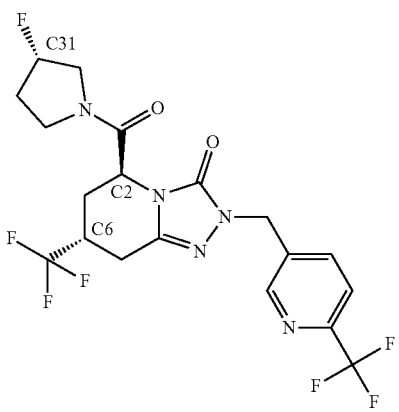

4.6 Absolute Structure Determination of Example 358 in PREP (Porcine)

The complex of pig PREP with Example 358 crystallizes with one molecule in the asymmetric unit. The stereochemistry of Example 358 is determined unambiguously through the knowledge of the stereochemistry of the protein pig PREP. In Example 358, the S configuration is unambiguously present at both stereocentres C26 and C2 (FIG. 2).

Structure from Example 358: (5S)-5-[(3-Fluoroazetidin-1-yl)carbonyl]-2-{[1-(4-methoxyphenyl)cyclopropyl]methyl}-5,6,7,8-tetrahydro[1,2,4]triazolo[4,3-a]pyridin-3(2H)-one with the following formula:

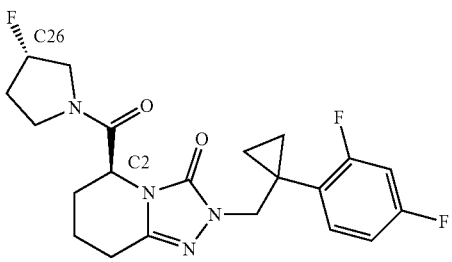

4.7 Absolute Structure Determination of Example 454 in PREP (Porcine)

The complex of pig PREP with Example 454 crystallizes with one molecule in the asymmetric unit. The stereochemistry of Example 454 is determined unambiguously through the knowledge of the stereochemistry of the protein pig PREP. In Example 454, the S configuration is unambiguously present at both stereocentres C25 and C6 (FIG. 3).

Structure from Example 454: (5S)-2-(3-Chloro-4-fluorobenzyl)-5-{[(3S)-3-fluoropyrrolidin-1-yl]carbonyl}-5,6,7,8-tetrahydro[1,2,4]triazolo[4,3-a]pyridin-3(2H)-one with the following formula:

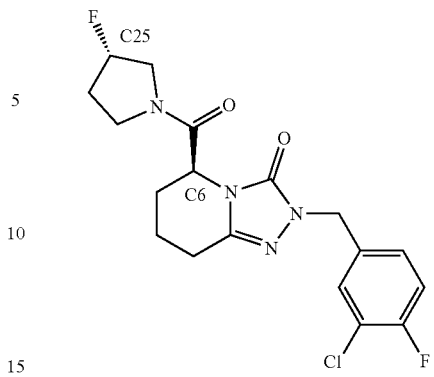

4.8 Absolute Structure Determination of Example 108 in PREP (Porcine)

The complex of pig PREP with Example 108 crystallizes with one molecule in the asymmetric unit. The stereochemistry of Example 108 is determined unambiguously through the knowledge of the stereochemistry of the protein pig PREP. In Example 108, the S configuration is unambiguously present at the stereocentre C8 (FIG. 4).

Structure from Example 108: (2-{[(1 S)-1-(3-chlorophenyl)-2-fluoroethyl]amino}-7-methoxy-1,3-benzoxazol-5-yl)[(2S,5S)-5-(2-hydroxyethyl)-2-methylmorpholin-4-yl]methanone with the following formula:

(5S)-2-(4-Methylbenzyl)-5-(1,3-thiazolidin-3-ylcarbonyl)-5,6,7,8-tetrahydro[1,2,4]triazolo[4,3-a]pyridin-3(2H)-one

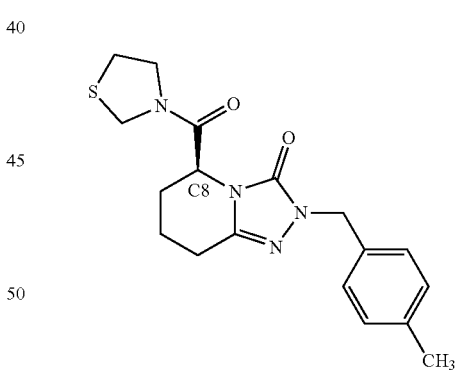

4.9 Absolute Structure Determination of Example 113 in PREP (Porcine)

The complex of pig PREP with Example 113 crystallizes with one molecule in the asymmetric unit. The stereochemistry of Example 113 is determined unambiguously through the knowledge of the stereochemistry of the protein pig PREP. In Example 113, the S configuration is unambiguously present at the stereocentre C3 (FIG. 5).

Structure from Example 113: (5S)-5-[(3-Fluoroazetidin-1-yl)carbonyl]-2-(4-methylbenzyl)-5,6,7,8-tetrahydro[1,2,4]triazolo[4,3-a]pyridin-3(2H)-one with the following formula:

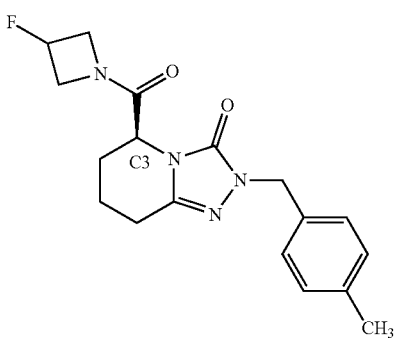

4.10 Absolute Structure Determination of Example 157 in PREP (Porcine)

The complex of pig PREP with Example 157 crystallizes with one molecule in the asymmetric unit. The stereochemistry of Example 157 is determined unambiguously through the knowledge of the stereochemistry of the protein pig PREP. In Example 157, the S configuration is unambiguously present at the stereocentre C1 (FIG. 6).

Structure from Example 157: (5S)-2-(4-Methylbenzyl)-5-(pyrrolidin-1-ylcarbonyl)-2,5,6,7-tetrahydro-3H-pyrrolo[2,1-c][1,2,4]triazol-3-one with the following formula:

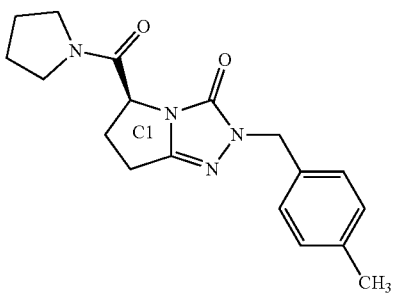

4.11 Absolute Structure Determination of Example 26 in PREP (Porcine)

The complex of pig PREP with Example 26 crystallizes with one molecule in the asymmetric unit. The stereochemistry of Example 26 is determined unambiguously through the knowledge of the stereochemistry of the protein pig PREP. In Example 26, the S configuration is unambiguously present at the stereocentre C3 (FIG. 7).

Structure from Example 26: (5S)-2-(4-Methylbenzyl)-5-(pyrrolidin-1-ylcarbonyl)-5,6,7,8-tetrahydro[1,2,4]triazolo[4,3-a]pyridin-3(2H)-one with the following formula:

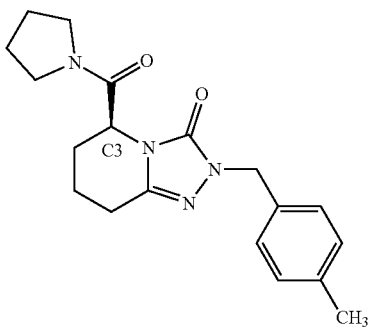

Literature B-4

Emsley P. et al. (2010) Acta Cryst. D66:486-501
Evans P. R, (2005) Acta Cryst. D62, 72-82
Long et al. F (2008) Acta Cryst. D64, 125-132
Murshudo G. N. et al. (1997) Acta Cryst. D53, 240-255

C. WORKING EXAMPLES OF PHARMACEUTICAL COMPOSITIONS

The compounds of the invention can be converted to pharmaceutical preparations as follows:
Tablet:
Composition:
100 mg of the compound according to the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.
Tablet weight 212 mg. Diameter 8 mm, radius of curvature 12 mm.
Production:
The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.
Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound of the invention.
Production:
The Rhodigel is suspended in ethanol; the compound of the invention is added to the suspension. The water is added while stirring. The mixture is stirred for about 6 h until the swelling of the Rhodigel is complete.
Solution for Oral Administration:
Composition: 500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring process is continued until the compound according to the invention has completely dissolved.
i.v. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

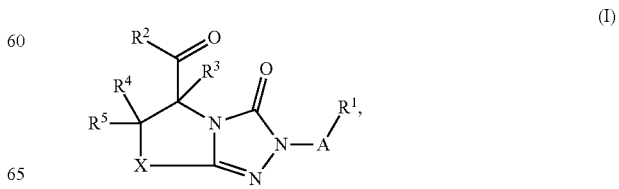

wherein
A is $(C_1-C_4)$-alkylene or $CD_2$,
  wherein $(C_1-C_4)$-alkylene is optionally substituted by hydroxyl and $(C_1-C_4)$-alkoxy and optionally up to pentasubstituted by fluorine;
or
A is a group of the formula

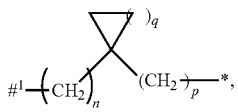

wherein
n is 0 or 1,
P is 0 or 1,
q is 1 or 2,
wherein
$\#^1$ marks the bond to the nitrogen atom of the 5-oxo-4,5-dihydro-1H-1,2,4-triazol-1-yl ring, and
* marks the bond to $R^1$;
X is $-CR^6R^7-$, $\#^2-CR^6R^7-CR^8R^9-$, $\#^2-CR^6=CR^8-$, or
$\#^2-CR^6R^7-CR^8R^9-CR^{10}R^{11}-**$,
wherein $\#^2$ marks the bond to the carbon atom of the $CR^4R^5-$ group, and
wherein ** marks the bond to the carbon atom of the 5-oxo-4,5-dihydro-1H-1,2,4-triazol-1-yl ring;
wherein
$R^6$ is hydrogen, fluorine, $(C_1-C_4)$-alkyl, $(C_1-C_4)$-alkoxy, trifluoromethoxy, hydroxyl, mono-$(C_1-C_4)$-alkylamino, or di-$(C_1-C_4)$-alkylamino,
  wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and optionally up to pentasubstituted by fluorine;
$R^7$ is hydrogen, fluorine, or $(C_1-C_4)$-alkyl,
  wherein $(C_1-C_4)$-alkyl is optionally up to pentasubstituted by fluorine;
or
$R^6$ and $R^7$ together with the carbon atom to which they are bonded form a carbonyl group;
or
$R^6$ and $R^7$ together with the carbon atom to which they are bonded form a cyclopropyl ring, cyclobutyl ring, or cyclopentyl ring;
or
$R^6$ and $R^4$ together with the carbon atom to which they are bonded form a cyclopropyl ring, cyclobutyl ring, or cyclopentyl ring;
$R^8$ is hydrogen, $(C_1-C_4)$-alkyl, $(C_1-C_4)$-alkoxy, fluorine, hydroxyl, mono-$(C_1-C_4)$-alkylamino, or di-$(C_1-C_4)$-alkylamino,
  wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and optionally up to pentasubstituted by fluorine;
$R^9$ is hydrogen, fluorine or $(C_1-C_4)$-alkyl,
  wherein $(C_1-C_4)$-alkyl is optionally up to pentasubstituted by fluorine;
or
$R^8$ and $R^9$ together with the carbon atom to which they are bonded form a cyclopropyl ring, cyclobutyl ring, or cyclopentyl ring;
or
$R^7$ and $R^9$ together with the carbon atoms to which they are bonded form a cyclopropyl ring, cyclobutyl ring, or cyclopentyl ring;
$R^{10}$ is hydrogen, $(C_1-C_4)$-alkyl, $(C_1-C_4)$-alkoxy, fluorine, hydroxyl, mono-$(C_i-C_4)$-alkylamino, or di-$(C_1-C_4)$-alkylamino,
  wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and optionally up to pentasubstituted by fluorine;
$R^{11}$ is hydrogen, fluorine, or $(C_1-C_4)$-alkyl,
  wherein $(C_1-C_4)$-alkyl is optionally up to pentasubstituted by fluorine;
or
$R^{10}$ and $R^{11}$ together with the carbon atom to which they are bonded form a cyclopropyl ring, cyclobutyl ring or cyclopentyl ring;
$R^1$ is $(C_3-C_7)$-cycloalkyl, phenyl or 5- to 6-membered heteroaryl,
  wherein $(C_3-C_7)$-cycloalkyl is optionally substituted by 1 to 3 substituents independently selected from the group consisting of halogen, cyano, trifluoromethyl, $(C_1-C_4)$-alkyl, and $(C_1-C_4)$-alkoxy,
    wherein $(C_1-C_4)$-alkyl is optionally up to pentasubstituted by fluorine;
  wherein phenyl is substituted by 1 to 4 substituents independently selected from the group consisting of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, monofluoromethoxy, difluoromethoxy, trifluoromethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_5)$-cycloalkylaminocarbonyl, $(C_1-C_4)$-alkylsulphanyl, $(C_1-C_4)$-alkylsulphonyl, $(C_1-C_4)$-alkylsulphonimidoyl, $(C_1-C_4)$-cycloalkylsulphonyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino, and di-$(C_1-C_4)$-alkylamino,
or
wherein phenyl is optionally fused to $(C_3-C_7)$-cycloalkyl, $(C_3-C_7)$-heterocyclyl or 5- to 6-membered heteroaryl,
  wherein phenyl is optionally substituted by methyl, ethyl, chlorine, fluorine or methoxy,
  wherein $(C_3-C_7)$-cycloalkyl, $(C_3-C_7)$-heterocyclyl and 5- to 6-membered heteroaryl is optionally substituted by 1 or 2 $(C_1-C_4)$-alkyl substituents,
    wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and optionally up to pentasubstituted by fluorine,
or
wherein 5- to 10-membered heteroaryl is optionally substituted by 1 to 4 substituents independently selected from the group consisting of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, difluoromethoxy, trifluoromethoxy, 2,2,2-trifluoroethoxy, phenyl, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_5)$-cycloalkylaminocarbonyl, $(C_1-C_4)$-alkylsulphanyl, $(C_1-C_4)$-alkylsulphonyl, $(C_1-C_4)$-alkylsulphonimidoyl, $(C_1-C_4)$-cycloalkylsulphonyl, amino sulphonyl, mono-$(C_1-C_4)$-alkylamino sulphonyl, di-$(C_1-C_4)$-alkylaminosulphonyl, $(C_1-C_4)$-alkylsulphinyl, amino, mono-$(C_1-C_4)$-alkylamino, and di-$(C_1-C_4)$-alkylamino,
wherein phenyl is optionally substituted by methyl, ethyl, chlorine, fluorine or methoxy,
or
wherein said 5- to 6-membered heteroaryl of $R^1$ is optionally fused to $(C_3-C_7)$-cycloalkyl, $(C_3-C_7)$-heterocyclyl, phenyl or 5- to 6-membered heteroaryl,
wherein said 5- to 6-membered heteroaryl of $R^1$ is optionally substituted by methyl, ethyl, chlorine, fluorine or methoxy,
wherein $(C_3-C_7)$-cycloalkyl, $(C_3-C_7)$-heterocyclyl, phenyl and 5- to 6-membered heteroaryl fused to said 5- to 6-membered heteroaryl of $R^1$ are optionally substituted by 1 or 2 $(C_1-C_4)$-alkyl substituents,
wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and up to pentasubstituted by fluorine;
$R^2$ is a group of the formula

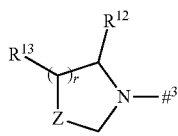

wherein
$^3$ marks the bond to the carbonyl carbon atom,
r is 0 or 1,
Z is O, $NR^{18}$, S, SO, $SO_2$, or $CR^{14A}R^{14B}$,
wherein
$R^{14A}$ is hydrogen, halogen, cyano, $(C_1-C_4)$-alkyl, $(C_3-C_6)$-cycloalkyl, trifluoromethyl, difluoromethyl, fluoromethyl, hydroxyl, $(C_1-C_4)$-alkoxy, $(C_3-C_5)$-cycloalkoxy, difluoromethoxy, trifluoromethoxy, or 2,2,2-trifluoroethoxy,
wherein $(C_1-C_4)$-alkyl is optionally substituted by hydroxyl, amino, mono-$(C_1-C_4)$-alkylamino or di-$(C_1-C_4)$-alkylamino,
$R^{14B}$ is hydrogen, fluorine or $(C_1-C_4)$-alkyl,
wherein $(C_1-C_4)$-alkyl is optionally up to pentasubstituted by fluorine,
or
$R^{14A}$ and $R^{14B}$ together with the carbon atom to which they are bonded form a carbonyl group,
$R^{18}$ is hydrogen or methyl,
$R^{12}$ is hydrogen, cyano, $(C_1-C_4)$-alkyl, acetyl, or formyl,
wherein $(C_1-C_4)$-alkyl is optionally substituted by hydroxyl or up to pentasubstituted by fluorine,
wherein acetyl is optionally substituted by hydroxyl or up to trisubstituted by fluorine,
$R^{13}$ is hydrogen, fluorine or $(C_1-C_4)$-alkyl,
or
$R^{12}$ and $R^{13}$ together with the carbon atoms to which they are bonded form a cyclopropyl or cyclobutyl ring,
wherein the cyclopropyl or cyclobutyl ring is optionally up to disubstituted by fluorine, or
$R^{13}$ and $R^{14A}$ together with the carbon atoms to which they are bonded form a cyclopropyl or cyclobutyl ring,
wherein the cyclopropyl or cyclobutyl ring is optionally up to disubstituted by fluorine,
or
$R^{14A}$ and $R^{14B}$ together with the carbon atom to which they are bonded form a cyclopropyl or cyclobutyl ring,
wherein the cyclopropyl or cyclobutyl ring is optionally up to disubstituted by fluorine,
wherein $R^{13}$, $R^{14A}$ and $R^{14B}$ are hydrogen when $R^{12}$ is not hydrogen,
wherein $R^{12}$ is hydrogen when one of the $R^{13}$, $R^{14A}$ and $R^{14B}$ substituents is not hydrogen;
or
$R^2$ is a group of the formula

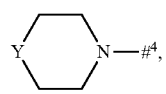

wherein
$^4$ marks the bond to the carbonyl carbon atom,
Y is $NR^{15}$, $CR^{16A}R^{16B}$, oxygen, or sulphur,
wherein
$R^{15}$ is hydrogen or methyl,
$R^{16A}$ is hydrogen or methyl,
$R^{16B}$ is hydrogen or methyl;
$R^3$ is hydrogen or $(C_1-C_4)$-alkyl;
$R^4$ is hydrogen, $(C_1-C_4)$-alkyl, $(C_1-C_4)$-alkoxy, fluorine, hydroxyl, mono-$(C_1-C_4)$-alkylamino, or di-$(C_1-C_4)$-alkylamino,
wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and optionally up to pentasubstituted by fluorine;
$R^5$ is hydrogen or $(C_1-C_4)$-alkyl,
wherein $(C_1-C_4)$-alkyl is optionally up to pentasubstituted by fluorine;
or
$R^4$ and $R^5$ together with the carbon atom to which they are bonded form a carbonyl group;
or
$R^4$ and $R^5$ together with the carbon atom to which they are bonded form a cyclopropyl ring, cyclobutyl ring, or cyclopentyl ring,
or a salt, a solvate, or a solvate of a salt thereof.
2. The compound according to claim 1, wherein
A is $(C_1-C_4)$-alkylene,
wherein $(C_1-C_4)$-alkylene is optionally substituted by hydroxyl and methoxy and is optionally up to trisubstituted by fluorine;
or
A is a group of the formula

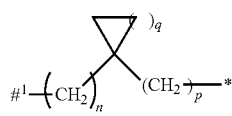

wherein
n is 1,
p is 0,
q is 1,
wherein
$\#^1$ marks the bond to the nitrogen atom of the 5-oxo-4,5-dihydro-1H-1,2,4-triazol-1-yl ring,
* marks the bond to $R^1$;
X is —$CR^6R^7$— or $\#^2$-$CR^6R^7$—$CR^8R^9$—**,
wherein $\#^2$ marks the bond to the carbon atom of the $CR^4R^5$— group,
wherein ** marks the bond to the carbon atom of the 5-oxo-4,5-dihydro-1H-1,2,4-triazol-1-yl ring;
wherein
$R^6$ is hydrogen, fluorine, methyl, ethyl, methoxy, ethoxy, trifluoromethoxy, hydroxyl, mono-$(C_1-C_4)$-alkylamino or di-$(C_1-C_4)$-alkylamino,
wherein methyl and ethyl is optionally up to trisubstituted by fluorine;
$R^7$ is hydrogen, fluorine or methyl,
wherein methyl is optionally up to trisubstituted by fluorine;
or
$R^6$ and $R^7$ together with the carbon atom to which they are bonded form a carbonyl group;
or
$R^6$ and $R^7$ together with the carbon atom to which they are bonded form a cyclopropyl or cyclobutyl ring;
or
$R^6$ and $R^4$ together with the carbon atoms to which they are bonded form a cyclopropyl or cyclobutyl ring;
$R^8$ is hydrogen, fluorine, methyl, ethyl, methoxy, ethoxy, hydroxyl, mono-$(C_1-C_4)$-alkylamino or di-$(C_1-C_4)$-alkylamino,
wherein methyl and ethyl are optionally up to trisubstituted by fluorine;
$R^9$ is hydrogen, fluorine or methyl,
wherein methyl is optionally up to trisubstituted by fluorine;
or
$R^8$ and $R^9$ together with the carbon atom to which they are bonded form a cyclopropyl or cyclobutyl ring;
$R^1$ is $(C_5-C_6)$-cycloalkyl, phenyl or 5 to 6-membered heteroaryl,
wherein $(C_5-C_6)$-cycloalkyl is optionally substituted by 1 to 3 substituents independently selected from the group consisting of fluorine, cyano, trifluoromethyl, methyl, ethyl, methoxy, and ethoxy,
wherein methyl and ethyl are optionally up to trisubstituted by fluorine,
wherein phenyl is substituted by 1 to 4 substituents independently selected from the group consisting of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, monofluoromethoxy, difluoromethoxy, trifluoromethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulphanyl, $(C_1-C_4)$-alkylsulphonyl, $(C_1-C_4)$-alkylsulphonimidoyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino, and di-$(C_1-C_4)$-alkylamino,
or
wherein phenyl is optionally fused to cyclopentyl, cyclohexyl, 5- to 6-membered heterocyclyl or 5- to 6-membered heteroaryl,
wherein phenyl is optionally substituted by methyl, ethyl, chlorine, fluorine or methoxy,
wherein cyclopentyl, cyclohexyl, 5- to 6-membered heterocyclyl and 5- to 6-membered heteroaryl are optionally substituted by 1 or 2 methyl or ethyl substituents,
wherein methyl and ethyl are optionally substituted by methoxy, hydroxyl, monomethylamino or diethylamino and optionally up to trisubstituted by fluorine,
or
wherein 5- to 10-membered heteroaryl is optionally substituted by 1 to 4 substituents independently selected from the group consisting of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, difluoromethoxy, trifluoromethoxy, 2,2,2-trifluoroethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_1-C_4)$-alkylsulphanyl, $(C_1-C_4)$-alkylsulphonyl, $(C_1-C_4)$-alkylsulphonimidoyl, aminosulphonyl, mono-$(C_1-C_4)$-alkylaminosulphonyl, di-$(C_1-C_4)$-alkylaminosulphonyl, $(C_1-C_4)$-alkylsulphinyl, amino, mono-$(C_1-C_4)$-alkylamino, and di-$(C_1-C_4)$-alkylamino,
or
wherein said 5- to 6-membered heteroaryl of $R^1$ is optionally fused to cyclopentyl, cyclohexyl, phenyl or 5- to 6-membered heterocyclyl,
wherein said 5- to 6-membered heteroaryl of $R^1$ is optionally substituted by methyl, ethyl, chlorine, fluorine or methoxy,
wherein the cyclopentyl, cyclohexyl, phenyl and 5- to 6-membered heterocyclyl fused to said 5- to 6-membered heteroaryl of $R^1$ are optionally substituted by 1 or 2 $(C_1-C_4)$-alkyl substituents,
wherein $(C_1-C_4)$-alkyl is optionally substituted by $(C_1-C_4)$-alkoxy, hydroxyl, mono-$(C_1-C_4)$-alkylamino or di-$(C_1-C_4)$-alkylamino and up to pentasubstituted by fluorine;
$R^2$ is a group of the formula

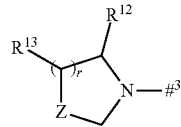

wherein
$\#^3$ marks the bond to the carbonyl carbon atom,
r is 0 or 1,
Z is S, SO, $SO_2$, or $CR^{14A}R^{14B}$,
wherein
$R^{14A}$ is hydrogen, halogen, cyano, $(C_1-C_4)$-alkyl, cyclopropyl, trifluoromethyl, difluoromethyl, fluoromethyl, hydroxyl, methoxy, ethoxy, cyclopropoxy, difluoromethoxy, trifluoromethoxy, 2,2, 2- or trifluoroethoxy, hydroxycarbonyl, aminocarbonyl, or amino,
wherein $(C_1-C_4)$-alkyl is optionally substituted by hydroxyl, amino, mono-$(C_1-C_4)$-alkylamino, or di-$(C_1-C_4)$-alkylamino, R$^{14B}$ is hydrogen, fluorine, methyl or trifluoromethyl,
or
R$^{14A}$ and R$^{14B}$ together with the carbon atom to which they are bonded form a carbonyl group,
R$^{12}$ is hydrogen, cyano, methyl, ethyl, acetyl, or formyl,
wherein methyl is optionally substituted by hydroxyl or up to pentasubstituted by fluorine,
wherein acetyl is substituted by hydroxyl or up to trisubstituted by fluorine,
R$^{13}$ is hydrogen, fluorine or methyl,
or
R$^{12}$ and R$^{13}$ together with the carbon atoms to which they are bonded form a cyclopropyl ring,
wherein the cyclopropyl ring is optionally up to disubstituted by fluorine,
or
R$^{13}$ and R$^{14A}$ together with the carbon atoms to which they are bonded form a cyclopropyl or cyclobutyl ring,
wherein the cyclopropyl or cyclobutyl ring is optionally up to disubstituted by fluorine,
or
R$^{14A}$ and R$^{14B}$ together with the carbon atom to which they are bonded form a cyclopropyl or cyclobutyl ring,
wherein the cyclopropyl or cyclobutyl ring is optionally up to disubstituted by fluorine,
R$^{13}$, R$^{14A}$ and R$^{14B}$ are hydrogen when R$^{12}$ is not hydrogen,
wherein R$^{12}$ is hydrogen when one of the R$^{13}$, R$^{14A}$ and R$^{14B}$ substituents is not hydrogen;
or
R$^2$ is a group of the formula

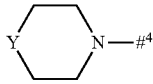

wherein
$^4$ marks the bond to the carbonyl carbon atom,
Y is NR$^{15}$, CR$^{16A}$R$^{B13}$, oxygen, or sulphur,
wherein
R$^{15}$ is hydrogen or methyl,
R$^{16A}$ is hydrogen or methyl,
R$^{16B}$ is hydrogen or methyl;
R$^3$ is hydrogen or methyl;
R$^4$ is hydrogen, fluorine, methyl, ethyl, methoxy, ethoxy, trifluoromethoxy, hydroxyl, mono-(C$_1$-C$_4$)-alkylamino, or di-(C$_1$-C$_4$)-alkylamino,
wherein methyl and ethyl are optionally up to trisubstituted by fluorine;
R$^5$ is hydrogen, or methyl,
wherein methyl is optionally up to trisubstituted by fluorine;
or
R$^4$ and R$^5$ together with the carbon atom to which they are bonded form a cyclopropyl ring,
or a salt, a solvate, or a solvate of a salt thereof.
3. The compound according to claim 1, wherein:
A is —CH$_2$—, —CH(CH$_3$)—, —CH$_2$CH$_2$—, #$^5$—CH$_2$CH(CH$_3$)—*, #$^5$—CH$_2$C(CH$_3$)$_2$—*, #$^5$—CH$_2$CHF—*, or #$^5$—CH$_2$CF$_2$—*, wherein #$^5$ marks the bond to the nitrogen atom of the 5-oxo-4,5-dihydro-1H-1,2,4-triazol-1-yl ring,
wherein *** marks the bond to the R$^1$ group;
X is -#$^2$-CR$^6$R$^7$—CR$^8$R$^9$—**,
wherein #$^2$ marks the bond to the carbon atom of the CR$^4$R$^5$— group,
wherein ** marks the bond to the carbon atom of the 5-oxo-4,5-dihydro-1H-1,2,4-triazol-1-yl ring;
wherein
R$^6$ is hydrogen, fluorine, methyl, trifluoromethyl, or hydroxyl;
R$^7$ is hydrogen, fluorine, or methyl;
or
R$^6$ and R$^7$ together with the carbon atom to which they are bonded form a cyclopropyl ring;
R$^8$ is hydrogen, (C$_1$-C$_4$)-alkyl, (C$_1$-C$_4$)-alkoxy, fluorine, hydroxyl, mono-(C$_1$-C$_4$)-alkylamino, or di-(C$_1$-C$_4$)-alkylamino,
wherein (C$_1$-C$_4$)-alkyl is optionally substituted by (C$_1$-C$_4$)-alkoxy, hydroxyl, mono-(C$_1$-C$_4$)-alkylamino or di-(C$_1$-C$_4$)-alkylamino and optionally up to pentasubstituted by fluorine;
R$^9$ is hydrogen, fluorine or (C$_1$-C$_4$)-alkyl,
wherein (C$_1$-C$_4$)-alkyl is optionally up to pentasubstituted by fluorine;
or
R$^8$ and R$^9$ together with the carbon atom to which they are bonded form a cyclopropyl ring, cyclobutyl ring, or cyclopentyl ring;
or
R$^7$ and R$^9$ together with the carbon atoms to which they are bonded form a cyclopropyl ring, cyclobutyl ring, or cyclopentyl ring;
R$^1$ is phenyl or 5- to 6-membered heteroaryl,
wherein phenyl is substituted by 1 to 3 substituents independently selected from the group consisting of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphonyl, methylsulphonyl, methylsulphonimidoyl, aminosulphonyl, and methylsulphinyl;
or
wherein phenyl is optionally fused to cyclopentyl, cyclohexyl, 5- to 6-membered heterocyclyl or 5- to 6-membered heteroaryl,
wherein cyclopentyl, cyclohexyl, 5 to 6-membered heterocyclyl and 5- to 6-membered heteroaryl are optionally substituted by 1 or 2 methyl or ethyl substituents;
or
wherein 5- to 6-membered heteroaryl is optionally substituted by 1 to 3 substituents independently selected from the group consisting of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, and dimethylaminocarbonyl;
or
wherein said 5- to 6-membered heteroaryl of R$^1$ is optionally fused to cyclopentyl, cyclohexyl, 5- to 6-membered heterocyclyl, phenyl or 5- to 6-membered heteroaryl,
wherein said 5- to 6-membered heteroaryl of R$^1$ is optionally substituted by methyl, ethyl, chlorine, fluorine or methoxy, and wherein the cyclopentyl, cyclohexyl, 5- to 6-membered heterocyclyl, phenyl and 5- to 6-membered heteroaryl fused to said 5- to 6-membered heteroaryl of $R^1$ are optionally substituted by 1 or 2 $(C_1$-$C_4)$-alkyl substituents;

$R^2$ is a group of the formula

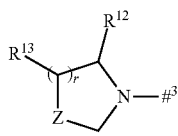

wherein
$\#^3$ marks the bond to the carbonyl carbon atom,
r is 0 or 1,
Z is S or $CR^{14A}R^{14B}$ when r is 0,
Z is S, SO, $SO_2$ or $CR^{14A}R^{14B}$ when r is 1,
in each of which
$R^{14A}$ is hydrogen, fluorine, methyl, trifluoromethyl, difluoromethyl, fluoromethyl, hydroxyl, methoxy, difluoromethoxy, or trifluoromethoxy,
$R^{14B}$ is hydrogen or fluorine,
or
$R^{14A}$ and $R^{14B}$ together with the carbon atom to which they are bonded form a carbonyl group,
$R^{12}$ is hydrogen, cyano, methyl, acetyl, or formyl,
wherein acetyl is substituted by hydroxyl or up to trisubstituted by fluorine,
$R^{13}$ is hydrogen, fluorine, or methyl,
or
$R^{12}$ and $R^{13}$ together with the carbon atoms to which they are bonded form a cyclopropyl ring,
or
$R^{13}$ and $R^{14A}$ together with the carbon atom to which they are bonded form a cyclopropyl ring,
wherein the cyclopropyl ring is optionally up to disubstituted by fluorine,
or
$R^{14A}$ and $R^{14B}$ together with the carbon atom to which they are bonded form a cyclopropyl ring,
wherein the cyclopropyl ring is optionally up to disubstituted by fluorine,
wherein $R^{13}$, $R^{14A}$ and $R^{14B}$ are hydrogen when $R^{12}$ is not hydrogen,
wherein $R^{12}$ is hydrogen when one of the $R^{13}$, $R^{14A}$ and $R^{14B}$ substituents is not hydrogen;
$R^3$ is hydrogen;
$R^4$ is hydrogen, fluorine, or methyl; and
$R^5$ is hydrogen,
or a salt, a solvate, or a solvate of a salt thereof.

4. The compound according to claim 1, wherein:
A is $CH_2$—, —$CH(CH_3)$—, —$CH_2CH_2$—, $\#^5$—$CH_2CH(CH_3)$—*, $\#^5$—$CH_2C(CH_3)_2$—*, $\#^5$—$CH_2CHF$—*, or $\#^5$—$CH_2CF_2$—*,
wherein $\#^5$ marks the bond to the nitrogen atom of the 5-oxo-4,5-dihydro-1H-1,2,4-triazol-1-yl ring,
wherein *** marks the bond to the $R^1$ group;
X is -$\#^2$-$CR^6R^7$—$CR^8R^9$—**,
wherein $\#^2$ marks the bond to the carbon atom of the $CR^4R^5$— group,
wherein ** marks the bond to the carbon atom of the 5-oxo-4,5-dihydro-1H-1,2,4-triazol-1-yl ring;

wherein
$R^6$ is hydrogen, fluorine, methyl, trifluoromethyl, or hydroxyl;
$R^7$ is hydrogen, fluorine, or methyl;
or
$R^6$ and $R^7$ together with the carbon atom to which they are bonded form a cyclopropyl ring;
$R^8$ is hydrogen, fluorine, methyl, or trifluoromethyl;
$R^9$ is hydrogen, fluorine, or methyl;
$R^1$ is phenyl or 5- to 6-membered heteroaryl,
wherein phenyl is substituted by 1 to 3 substituents independently selected from the group consisting of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl, and methylsulphinyl;
or
wherein phenyl is optionally fused to cyclopentyl, cyclohexyl, 5- to 6-membered heterocyclyl or 5- to 6-membered heteroaryl,
wherein cyclopentyl, cyclohexyl, 5- to 6-membered heterocyclyl and 5- to 6-membered heteroaryl are optionally substituted by 1 or 2 methyl or ethyl substituents;
or
wherein 5- to 6-membered heteroaryl is optionally substituted by 1 to 3 substituents independently selected from the group consisting of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, and dimethylaminocarbonyl;
or
wherein said 5- to 6-membered heteroaryl of $R^1$ is optionally fused to cyclopentyl, cyclohexyl, 5- to 6-membered heterocyclyl, phenyl or 5- to 6-membered heteroaryl,
wherein said 5- to 6-membered heteroaryl of $R^1$ is optionally substituted by methyl, ethyl, chlorine, fluorine or methoxy,
wherein the cyclopentyl, cyclohexyl, 5- to 6-membered heterocyclyl, phenyl and 5- to 6-membered heteroaryl fused to said 5- to 6-membered heteroaryl of $R^1$ are optionally substituted by 1 or 2 $(C_1$-$C_4)$-alkyl substituents;
$R^2$ is a group of the formula

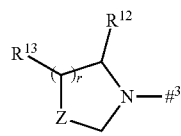

wherein
$\#^3$ marks the bond to the carbonyl carbon atom,
r is 0 or 1,
Z is S or $CR^{14A}R^{14B}$ when r is 0, or
Z is S, SO, $SO_2$ or $CR^{14A}R^{14B}$ when r is 1,
in each of which
$R^{14A}$ is hydrogen, fluorine, methyl, trifluoromethyl, difluoromethyl, fluoromethyl, hydroxyl, methoxy, difluoromethoxy or trifluoromethoxy, $R^{14B}$ is hydrogen or fluorine,
or
$R^{14A}$ and $R^{14B}$ together with the carbon atom to which they are bonded form a carbonyl group,
$R^{12}$ is hydrogen, cyano, methyl, acetyl or formyl,
 wherein acetyl is substituted by hydroxyl or up to trisubstituted by fluorine,
$R^{13}$ is hydrogen, fluorine or methyl,
or
$R^{12}$ and $R^{13}$ together with the carbon atoms to which they are bonded form a cyclopropyl ring,
or
$R^{13}$ and $R^{14A}$ together with the carbon atom to which they are bonded form a cyclopropyl ring,
 wherein the cyclopropyl ring is optionally up to disubstituted by fluorine,
or
$R^{14A}$ and $R^{14B}$ together with the carbon atom to which they are bonded form a cyclopropyl ring,
 wherein the cyclopropyl ring is optionally up to disubstituted by fluorine,
  wherein $R^{13}$, $R^{14A}$ and $R^{14B}$ are hydrogen when $R^{12}$ is not hydrogen,
  wherein $R^{12}$ is hydrogen when one of the $R^{13}$, $R^{14A}$ and $R^{14B}$ substituents is not hydrogen;
$R^3$ is hydrogen;
$R^4$ is hydrogen, fluorine, or methyl; and
$R^5$ is hydrogen,
or a salt, a solvate, or a solvate of a salt thereof.

5. The compound according to claim 1, wherein:
A is —CH$_2$—, —CH(CH$_3$)—, —CH$_2$CH$_2$—, #$^5$—CH$_2$CH(CH$_3$)—*, #$^5$—CH$_2$C(CH$_3$)$_2$—*, #$^5$—CH$_2$CHF—* or #$^5$—CH$_2$CF$_2$—*,
 wherein #$^5$ marks the bond to the nitrogen atom of the 5-oxo-4,5-dihydro-1H-1,2,4-triazol-1-yl ring,
 wherein *** marks the bond to the $R^1$ group;
X is -#$^2$-CR$^6$R$^7$—CR$^8$R$^9$—**,
 wherein #$^2$ marks the bond to the carbon atom of the CR$^4$R$^5$— group,
 wherein ** marks the bond to the carbon atom of the 5-oxo-4,5-dihydro-1H-1,2,4-triazol-1-yl ring;
wherein
$R^6$ is hydrogen, fluorine, methyl, trifluoromethyl, or hydroxyl;
$R^7$ is hydrogen, fluorine, or methyl;
or
 $R^6$ and $R^7$ together with the carbon atom to which they are bonded form a cyclopropyl ring;
$R^8$ is hydrogen, fluorine, methyl or trifluoromethyl;
$R^9$ is hydrogen, fluorine or methyl;
$R^1$ is phenyl, pyrazolyl, imidazolyl, thiazolyl, thiophenyl, oxazolyl, oxadiazolyl, or pyridyl,
 wherein phenyl is substituted by 1 to 3 substituents independently selected from the group consisting of fluorine, chlorine, cyano, methyl, ethyl, trifluoromethyl, methoxy, difluoromethoxy, trifluoromethoxy, hydroxycarbonyl, methoxycarbonyl, ethoxycarbonyl, tert-butoxycarbonyl, methylaminocarbonyl, dimethylaminocarbonyl, methylsulphanyl, methylsulphonyl, methylsulphonimidoyl, aminosulphonyl, and methylsulphinyl;
or
 wherein phenyl is optionally fused to cyclopentyl, cyclohexyl, pyrazolyl, or pyridyl,
  wherein cyclopentyl, cyclohexyl, pyrazolyl or pyridyl is optionally substituted by 1 or 2 methyl or ethyl substituents;
or
 wherein said pyrazolyl, imidazolyl, thiazolyl, thiophenyl, oxazolyl, oxadiazolyl or pyridyl of $R^1$ is optionally substituted by 1 to 3 substituents independently selected from the group consisting of fluorine, chlorine, cyano, methyl, ethyl, trifluoromethyl, methoxy, ethoxy, difluoromethoxy, trifluoromethoxy, 2,2,2-trifluoroethoxy, methylaminocarbonyl, tert-butylaminocarbonyl, and dimethylaminocarbonyl;
or
 wherein said pyrazolyl, imidazolyl, thiazolyl, thiophenyl, oxazolyl, oxadiazolyl or pyridyl of $R^1$ is optionally fused to cyclopentyl, cyclohexyl, phenyl or pyridyl,
  wherein said pyridyl of $R^1$ is optionally substituted by methyl, ethyl, chlorine, fluorine, or methoxy,
   wherein the cyclopentyl, cyclohexyl, phenyl and pyridyl fused to said pyrazolyl, imidazolyl, thiazolyl, thiophenyl, oxazolyl, oxadiazolyl or pyridyl of $R^1$ are optionally substituted by 1 or 2 (C$_1$-C$_4$)-alkyl substituents;
$R^2$ is a group of the formula wherein
$^3$ marks the bond to the carbonyl carbon atom,
r is 0 or 1,
Z is S or CR$^{14A}$R$^{14B}$ when r is 0,
Z is S, SO, SO$_2$ or CR$^{14A}$R$^{14B}$ when r is 1,
 in each of which
  $R^{14A}$ is hydrogen, fluorine, methyl, trifluoromethyl, difluoromethyl, fluoromethyl, hydroxyl, methoxy, difluoromethoxy or trifluoromethoxy,
  $R^{14B}$ is hydrogen or fluorine,
  or
  $R^{14A}$ and $R^{14B}$ together with the carbon atom to which they are bonded form a carbonyl group,
$R^{12}$ is hydrogen, cyano, methyl, acetyl or formyl,
 wherein acetyl is substituted by hydroxyl or up to trisubstituted by fluorine,
$R^{13}$ is hydrogen, fluorine, or methyl,
or
$R^{12}$ and $R^{13}$ together with the carbon atoms to which they are bonded form a cyclopropyl ring,
or
$R^{13}$ and $R^{14A}$ together with the carbon atom to which they are bonded form a cyclopropyl ring,
 wherein the cyclopropyl ring is optionally up to disubstituted by fluorine,
or
$R^{14A}$ and $R^{14B}$ together with the carbon atom to which they are bonded form a cyclopropyl ring,
 wherein the cyclopropyl ring is optionally up to disubstituted by fluorine,
  wherein $R^{13}$, $R^{14A}$ and $R^{14B}$ are hydrogen when $R^{12}$ is not hydrogen,
  wherein $R^{12}$ is hydrogen when one of the $R^{13}$, $R^{14A}$ and $R^{14B}$ substituents is not hydrogen;

R³ is hydrogen;
R⁴ is hydrogen, fluorine, or methyl; and
R⁵ is hydrogen,
or a salt, a solvate, or a solvate of a salt thereof.

6. A process for preparing a compound of formula (I) according to claim 1,

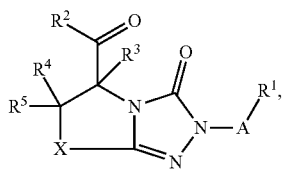
(I)

wherein
A is —CH₂—, —CH(CH₃)—, —CH₂CH₂—, #⁵—CH₂CH(CH₃)—*, #⁵—CH₂C(CH₃)₂—*, #⁵—CH₂CHF—*, or #⁵—CH₂CF₂—*,
wherein #⁵ marks the bond to the nitrogen atom of the 5-oxo-4,5-dihydro-1H-1,2,4-triazol-1-yl ring,
wherein *** marks the bond to the R¹ group, and
wherein R¹, R², R³, R⁴, R⁵ and X are as defined in claim 1,
comprising either
[A] reacting a compound of formula (II)

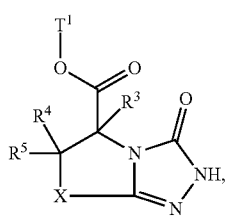
(II)

wherein R³, R⁴, R⁵ and X are as defined in claim 1, and
T¹ is (C₁-C₄)-alkyl or benzyl,
in an inert solvent in the presence of a suitable base with a compound of formula (III)

(III)

wherein
A¹ is —CH₂—, —CH(CH₃)—, —CH₂CH₂—, #⁵—CH₂CH(CH₃)—*, #⁵—CH₂C(CH₃)₂—*, #⁵—CH₂CHF—*, or #⁵—CH₂CF₂—*,
wherein #⁵ marks the bond to the nitrogen atom of the 5-oxo-4,5-dihydro-1H-1,2,4-triazol-1-yl ring,
wherein *** marks the bond to the R¹ group,
R¹ is as defined in claim 1,
and
X¹ is a suitable leaving group,
to give a compound of formula (IV)

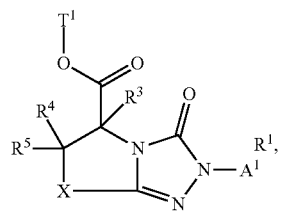
(IV)

wherein A¹, R¹, R³, R⁴, R⁵, X and T¹ are as defined above;
converting the compound of formula (IV) to a compound of formula (V) by removing the "T¹" group in an inert solvent in the presence of a suitable base or acid

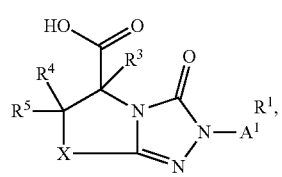
(V)

wherein A¹, R¹, R³, R⁴, R⁵ and X are as defined above;
reacting the compound of formula (V) in an inert solvent under amide coupling conditions with an amine of the formula (VI-A) or (VI-B)

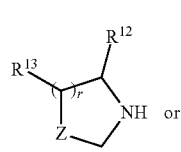
(VI-A)

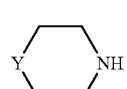
(VI-B)

wherein Y, Z, r, R¹² and R¹³ are as defined in claim 1;
thereby providing the compound of formula (I); and
optionally further converting the compound of formula (I) with the appropriate (i) solvents and/or (ii) acids or bases to the solvate, the salt, or the solvate of the salt thereof;
or
[B] reacting a compound of formula (II)

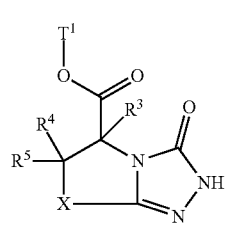
(II)

wherein R³, R⁴, R⁵ and X are as defined in claim 1,
and
T¹ is (C₁-C₄)-alkyl or benzyl,
in an inert solvent in the presence of a suitable base with
an amine of formula (VI-A) or (VI-B)

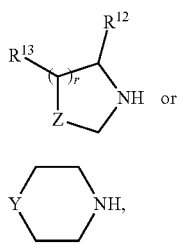
(VI-A)

(VI-B)

wherein Y, Z, r, R¹² and R¹³ are as defined in claim 1,
to give a compound of the formula (XXIII-A) or (XXIII-B)

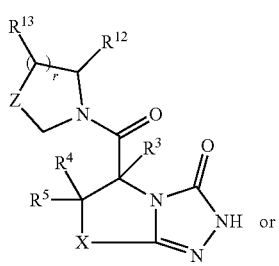
(XXIII-A)

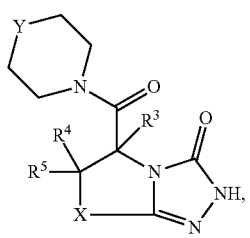
(XXIII-B)

wherein R³, R⁴, R⁵, R¹², R¹³, X, Y, Z, and r are as defined above; reacting the compound of formula (XXIII-A) or the compound of formula (XXIII-B) in an inert solvent in the presence of a suitable base with a compound of the formula (III)

(III)

wherein
A¹ is —CH₂—,—CH(CH₃)—, —CH₂CH₂—, #⁵—CH₂CH(CH₃)—*, #⁵—CH₂C(CH₃)₂—*, #⁵—CH₂CHF—*, or #⁵—CH₂CF₂—*,
wherein #⁵ marks the bond to the nitrogen atom of the 5-oxo-4,5-dihydro-1H-1,2,4-triazol-1-yl ring, wherein *** marks the bond to the R¹ group,
R¹ is as defined in claim 1,
and
X¹ is a suitable leaving group;
thereby providing the compound of formula (I); and optionally further converting the compound of formula (I) with the appropriate (i) solvents and/or (ii) acids or bases to the solvate, the salt, or the solvate of the salt thereof;
or
[C] converting a compound of formula (VII)

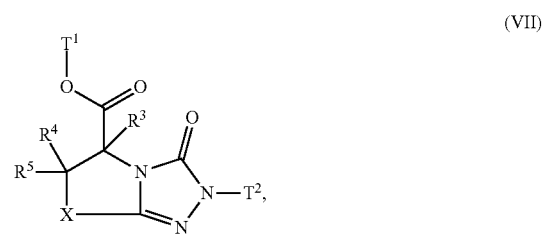
(VII)

wherein R³, R⁴, R⁵ and X are as defined in claim 1, and
T¹ is (C₁-C₄)-alkyl or benzyl,
T² is 4-methoxybenzyl, benzyl, allyl, β-(trimethylsilyl)ethoxymethyl (SEM), methoxymethyl (MOM), or benzyloxymethyl,
by hydrolysis of the ester group in an inert solvent in the presence of a suitable base or acid to a compound of formula (VIII)

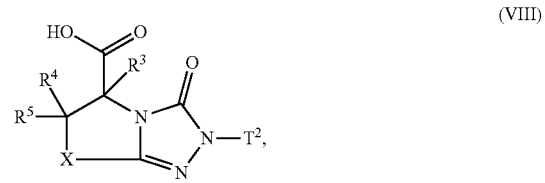
(VIII)

wherein R³, R⁴, R⁵, T² and X are as defined above;
reacting the compound of formula (VIII) in an inert solvent under amide coupling conditions with an amine of formula (VI-A) or formula (VI-B)

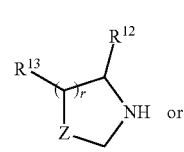
(VI-A)

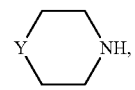
(VI-B)

wherein Y, Z, r, $R^{12}$ and $R^{13}$ are as defined in claim 1, to give a compound of the formula (IX-A) or (IX-B)

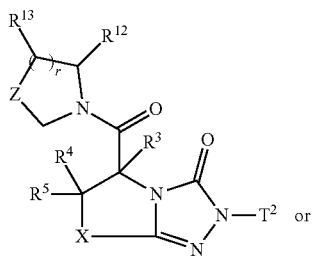

(IX-A)

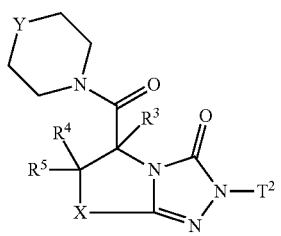

(IX-B)

wherein $R^3$, $R^4$, $R^5$, $R^{12}$, $R^{13}$, $T^2$, X, Y, Z, and r are as defined above;
removing the protecting group "$T^2$" in an inert solvent in the presence of a suitable base or acid or optionally in the presence of a suitable palladium catalyst to provide a compound of formula (X-A) or (X-B)

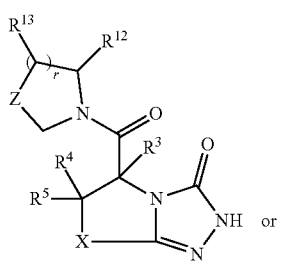

(X-A)

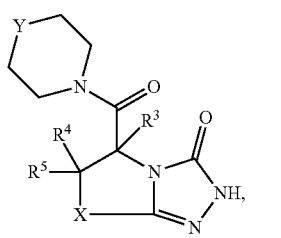

(X-B)

wherein $R^3$, $R^4$, $R^5$, $R^{12}$, $R^{13}$, X, Y, Z, and r are as defined above;
reacting the compound of formula (X-A) or (X-B) in an inert solvent in the presence of a suitable base with a compound of the formula (III)

(III)

wherein
$A^1$ is A,
$R^1$ is as defined in claim 1,
and
$X^1$ is a suitable leaving group;
thereby providing the compound of formula (I); and optionally further converting the compound of formula (I) with the appropriate (i) solvents and/or (ii) acids or bases to the solvate, the salt, or the solvate of the salt thereof.

7. A pharmaceutical composition, comprising a compound according to claim 1 in combination with one or more inert, nontoxic, pharmaceutically suitable excipients.

8. A pharmaceutical combination, comprising a compound according to claim 1 in combination with one or more active ingredients selected from the group consisting of PDE 5 inhibitors, sGC activators, sGC stimulators, prostacyclin analogues, IP receptor agonists, endothelin antagonists, compounds that inhibit the signal transduction cascade, and pirfenidone.

9. A method for treatment of a lung inflammation disorder, comprising administering to a human in need thereof an effective amount of a compound of formula (I) according to claim 1, wherein the lung inflammation disorder is selected from the group consisting of chronic obstructive pulmonary disease (COPD), cystic fibrosis, asthma, idiopathic pulmonary fibrosis (IPF), and bronchiolitis obliterans syndrome (BOS).

10. A method for treatment of a lung inflammation disorder, comprising administering to a human in need thereof an effective amount of a pharmaceutical composition according to claim 7, wherein the lung inflammation disorder is selected from the group consisting of chronic obstructive pulmonary disease (COPD), cystic fibrosis, asthma, idiopathic pulmonary fibrosis (IPF), and bronchiolitis obliterans syndrome (BOS).

11. A method for treatment of a lung inflammation disorder, comprising administering to a human in need thereof an effective amount of a pharmaceutical combination according to claim 8, wherein the lung inflammation disorder is selected from the group consisting of chronic obstructive pulmonary disease (COPD), cystic fibrosis, asthma, idiopathic pulmonary fibrosis (IPF), and bronchiolitis obliterans syndrome (BOS).

12. The process according to claim 6, wherein $X^1$ is chlorine, bromine, iodine, mesylate {(methylsulphonyl)oxy}, triflate {[(trifluoromethyl)sulphonyl]oxy}, nonaflate {[(nonafluorobutyl)sulphonyl]oxy}, nosylate {[(4-nitrophenyl)sulphonyl]oxy} or tosylate {[(4-methylphenyl) sulphonyl] oxy}.

13. The compound according to claim 1, wherein the compound is (5RS,7RS)-2-[(6-chloropyridin-3-yl)methyl]-5-{[(3R,4S)-3,4-difluoropyrrolidin-1-yl] carbonyl}-7-(trifluoromethyl)-5,6,7,8-tetrahydro[1,2,4]triazolo[4,3-a]pyridin-3(2H)-one (enantiomer 1) of the formula

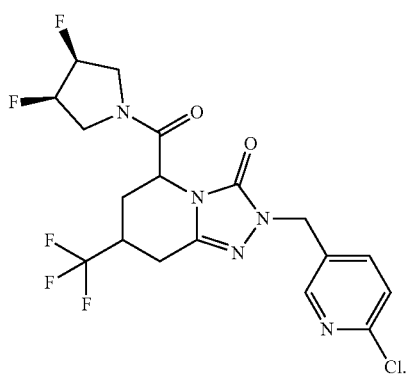 [SMILES: O=C(C1CC(C(F)(F)F)Cc2nn(Cc3ccc(Cl)nc3)c(=O)n21)N1C[C@@H](F)[C@@H](F)C1]

14. The compound according to claim 1, wherein the compound is (5S,7R)-5-{[(3S)-3-fluoropyrrolidin-1-yl]carbonyl}-7-(trifluoromethyl)-2-{[6-(trifluoromethyl)pyridin-3-yl]methyl}-5,6,7,8-tetrahydro[1,2,4]triazolo[4,3-a]pyridin-3(2H)-one (isomer 1) of the formula

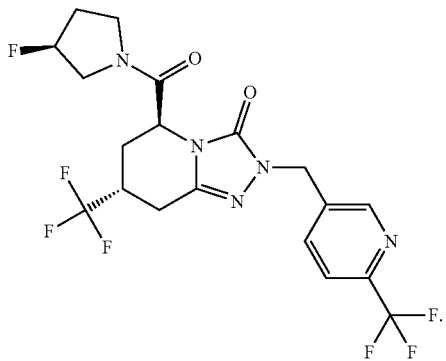 [SMILES: O=C([C@@H]1C[C@@H](C(F)(F)F)Cc2nn(Cc3ccc(C(F)(F)F)nc3)c(=O)n21)N1CC[C@H](F)C1]

15. The compound according to claim 1, wherein the compound is (5S)-5-{[(3R,4S)-3,4-difluoropyrrolidin-1-yl]carbonyl}-2-{[3-fluoro-2-(trifluoromethyl)pyridin-4-yl]methyl}-5,6,7,8-tetrahydro[1,2,4]triazolo[4,3-a]pyridin-3(2H)-one of the formula

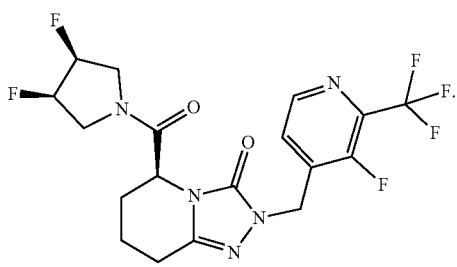 [SMILES: O=C([C@@H]1CCCc2nn(Cc3ccnc(C(F)(F)F)c3F)c(=O)n21)N1C[C@@H](F)[C@@H](F)C1]

16. The compound according to claim 1, wherein the compound is (5S)-5-{[(3S)-3-fluoropyrrolidin-1-yl]carbonyl}-2-{[6-(trifluoromethyl)pyridin-3-yl]methyl}-5,6,7,8-tetrahydro [1,2,4] triazolo[4,3-a]pyridin-3(2H)-one of the formula

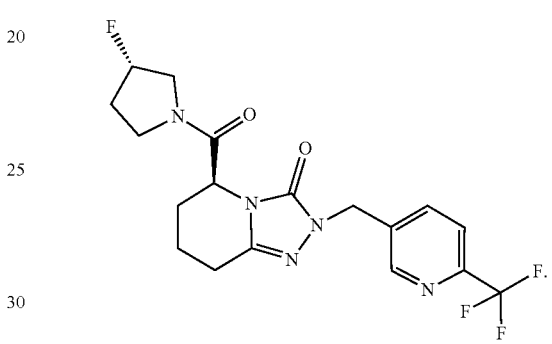

17. The method of claim 9, wherein the chronic obstructive pulmonary disease is pulmonary emphysema, chronic bronchitis, bronchiectasis, pulmonary hypertension in COPD (PH-COPD), or acute exacerbation in COPD (AE-COPD).

18. The method of claim 10, wherein the chronic obstructive pulmonary disease is pulmonary emphysema, chronic bronchitis, bronchiectasis, pulmonary hypertension in COPD (PH-COPD), or acute exacerbation in COPD (AE-COPD).

19. The method of claim 11, wherein the chronic obstructive pulmonary disease is pulmonary emphysema, chronic bronchitis, bronchiectasis, pulmonary hypertension in COPD (PH-COPD), or acute exacerbation in COPD (AE-COPD).

* * * * *